United States Patent
Pena et al.

(10) Patent No.: US 7,108,972 B2
(45) Date of Patent: Sep. 19, 2006

(54) PROTEINS, POLYNUCLEOTIDES ENCODING THEM AND METHODS OF USING THE SAME

(75) Inventors: Carol E. A. Pena, New Haven, CT (US); Richard A. Shimkets, Guilford, CT (US); Li Li, Branford, CT (US); Suresh G. Shenoy, Branford, CT (US); Ramesh Kekuda, Danbury, CT (US); Kimberly A. Spytek, New Haven, CT (US); Corine A. M. Vernet, Branford, CT (US); Uriel M. Malyankar, Branford, CT (US); Xiaojia (Sasha) Guo, Branford, CT (US); Vladimir Y. Gusev, Madison, CT (US); Stacie J. Casman, North Haven, CT (US); Ferenc L. Boldog, North Haven, CT (US); Katarzyna Furtak, Ansonia, CT (US); Velizar T. Tchernev, Branford, CT (US); Meera Patturajan, Branford, CT (US); Esha A. Gangolli, Madison, CT (US); Muralidhara Padigaru, Branford, CT (US); Xiaohong Liu, Branford, CT (US); Jason C. Baumgartner, New Haven, CT (US); Valerie Gerlach, Branford, CT (US); Steven K. Spaderna, Berlin, CT (US); Bryan D. Zerhusen, Branford, CT (US)

(73) Assignee: CuraGen Corporation, New Haven, CT (US)

( * ) Notice: Subject to any disclaimer, the term of this patent is extended or adjusted under 35 U.S.C. 154(b) by 635 days.

(21) Appl. No.: 10/080,334

(22) Filed: Feb. 21, 2002

(65) Prior Publication Data

US 2004/0002584 A1 Jan. 1, 2004

Related U.S. Application Data

(60) Provisional application No. 60/270,523, filed on Feb. 21, 2001, provisional application No. 60/322,712, filed on Sep. 17, 2001, provisional application No. 60/311,980, filed on Aug. 13, 2001, provisional application No. 60/330,307, filed on Oct. 18, 2001, provisional application No. 60/278,796, filed on Mar. 26, 2001, provisional application No. 60/281,521, filed on Apr. 4, 2001, provisional application No. 60/276,677, filed on Mar. 16, 2001, provisional application No. 60/311,595, filed on Aug. 10, 2001, provisional application No. 60/270,220, filed on Feb. 21, 2001, provisional application No. 60/274,295, filed on Mar. 8, 2001, provisional application No. 60/318,526, filed on Sep. 10, 2001, provisional application No. 60/286,548, filed on Apr. 25, 2001, provisional application No. 60/291,765, filed on May 17, 2001, provisional application No. 60/270,797, filed on Feb. 23, 2001, provisional application No. 60/276,400, filed on Mar. 16, 2001, and provisional application No. 60/270,810, filed on Feb. 23, 2001.

(51) Int. Cl.
*C12Q 1/68* (2006.01)

(52) U.S. Cl. .................... 435/6; 435/7.1; 435/69.1; 536/23.2

(58) Field of Classification Search .................. 435/7.1, 435/69.1, 320.1; 536/23.2
See application file for complete search history.

(56) References Cited

U.S. PATENT DOCUMENTS

2002/0177165 A1 * 11/2002 Ashkenazi et al. .......... 435/7.1

FOREIGN PATENT DOCUMENTS

| WO | WO 00/65067 | 11/2000 |
|----|-------------|---------|
| WO | WO 00/71709 | 11/2000 |
| WO | WO 01/90334 | 11/2001 |

OTHER PUBLICATIONS

Rost, B. Enzyme function less conserved than anticipated. 2002. 318(2):595–608.*
GenBank Accession No. AK054835, Dated: Oct. 31, 2001.
GenBank Accession No. AF151840, Dated: Jun. 1, 1999.
Lin, B. et al., (2001) "Prostate short-chain dehydrogenase reductase 1 (PSDR1): A new member of the short-chain steroid dehydrogenase/reductase family highly expressed in normal and neoplastic prostate epithelium." *Cancer Research* 61(4):1611–8.
Oppermann, U.C.T., et al., (2001) "Forms and functions of human SDR enzymes." *Chemico-Biological Interactions* 130–2(1–3):699–705.
Haeseleer, F., et al., (2000) "Short-chain dehydrogenases/reductases in retina." *Methods in Enzymology* 316:372–83.
Kedishvili, N.Y., et al. (2001) "Cloning of the human RoDH-related short chain dehydrogenase gene and analysis of its structure." *Chemico-Biological Interactions* 130–2(1–3):457–67.
Partial International Search Report of PCT/US02/05374, mailed May 8, 2003.
International Search Report of PCT/US02/05374, mailed Jul. 31, 2003.
GenBank Accession No.: A34720 (Aug. 13, 1999).
GenBank Accession No.: A53856 (Mar. 17, 1999).
GenBank Accession No.: A58922 (Dec. 5, 1998).

(Continued)

*Primary Examiner*—Jeffrey Fredman
*Assistant Examiner*—Heather G. Calamita
(74) *Attorney, Agent, or Firm*—Mei Benni; George M. Yahwak

(57) ABSTRACT

Disclosed herein are nucleic acid sequences that encode novel polypeptides. Also disclosed are polypeptides encoded by these nucleic acid sequences, and antibodies, which immunospecifically-bind to the polypeptide, as well as derivatives, variants, mutants, or fragments of the aforementioned polypeptide, polynucleotide, or antibody. The invention further discloses therapeutic, diagnostic and research methods for diagnosis, treatment, and prevention of disorders involving any one of these novel human nucleic acids and proteins.

6 Claims, No Drawings

OTHER PUBLICATIONS

GenBank Accession No.: AAA35748 (Apr. 27, 1993).
GenBank Accession No.: AAA37552 (Aug. 26, 1994).
GenBank Accession No.: AAA50405 (Apr. 4, 2002).
GenBank Accession No.: AAB03850 (Jul. 16, 1996).
GenBank Accession No.: AAB23193 (May 8, 1993).
GenBank Accession No.: AAB61241 (Jun. 15, 1997).
GenBank Accession No.: AAC41765 (Jul. 23, 1995).
GenBank Accession No.: AAD28253 (Apr. 29, 1999).
GenBank Accession No.: AAD28254 (May 3, 2000).
GenBank Accession No.: AAD53310 (Sep. 6, 1999).
GenBank Accession No.: AAF44924 (Mar. 21, 2000).
GenBank Accession No.: AAF51584 (Oct. 4, 2000).
GenBank Accession No.: AAF53442 (Oct. 4, 2000).
GenBank Accession No.: AAF56980 (Oct. 5, 2000).
GenBank Accession No.: AAF89632 (Mar. 22, 2001).
GenBank Accession No.: AAF89690 (Aug. 18, 2000).
GenBank Accession No.: AAG27034 (Jan. 16, 2002).
GenBank Accession No.: AAG27599 (Oct. 30, 2000).
GenBank Accession No.: AAG33986 (May 20, 2002).
GenBank Accession No.: AAH00698 (Jul. 12, 2001).
GenBank Accession No.: AAH01200 (Jul. 12, 2001).
GenBank Accession No.: AAH07201 (Jul. 12, 2001).
GenBank Accession No.: AAH07758 (Jul. 12, 2001).
GenBank Accession No.: AAH08276 (Jul. 12, 2001).
GenBank Accession No.: AAH09754 (Jul. 12, 2001).
GenBank Accession No.: AAH10075 (Jul. 12, 2001).
GenBank Accession No.: AAH11170 (Jul. 30, 2001).
GenBank Accession No.: AAH14814 (Oct. 4, 2001).
GenBank Accession No.: AAH16204 (Nov. 5, 2001).
GenBank Accession No.: AAH18775 (Dec. 11, 2001).
GenBank Accession No.: AAH19999 (Jan. 22, 2002).
GenBank Accession No.: AAK28551 (Apr. 2, 2001).
GenBank Accession No.: AAK57641 (May 30, 2001).
GenBank Accession No.: AAK67316 (Jun. 27, 2001).
GenBank Accession No.: AAL18610 (Dec. 7, 2001).
GenBank Accession No.: AAL18611 (Dec. 7, 2001).
GenBank Accession No.: AAL49494 (Dec. 20, 2001).
GenBank Accession No.: AAL76092 (Feb. 12, 2002).
GenBank Accession No.: AB026497 (Apr. 29, 2000).
GenBank Accession No.: AB047829 (Oct. 11, 2001).
GenBank Accession No.: AB051125 (Oct. 11, 2001).
GenBank Accession No.: AB051503 (Feb. 7, 2001).
GenBank Accession No.: AB051832 (Mar. 23, 2001).
GenBank Accession No.: AB058715 (Jun. 5, 2001).
GenBank Accession No.: AB062939 (Jun. 13, 2001).
GenBank Accession No.: AB071036 (Feb. 7, 2002).
GenBank Accession No.: AE003406 (Mar. 21, 2000).
GenBank Accession No.: AE003416 (Mar. 21, 2000).
GenBank Accession No.: AE003591 (Oct. 4, 2000).
GenBank Accession No.: AE003646 (Oct. 4, 2000).
GenBank Accession No.: AE003772 (Oct. 5, 2000).
GenBank Accession No.: AF003598 (Jun. 15, 1997).
GenBank Accession No.: AF006823 (Oct. 6, 1997).
GenBank Accession No.: AF056022 (Jul. 2, 1998).
GenBank Accession No.: AF056490 (Jun. 4, 1998).
GenBank Accession No.: AF121859 (Sep. 14, 2001).
GenBank Accession No.: AF127764 (Apr. 29, 1999).
GenBank Accession No.: AF127765 (May 3, 2000).
GenBank Accession No.: AF152324 (Jul. 22, 1999).
GenBank Accession No.: AF152336 (Jul. 22, 1999).
GenBank Accession No.: AF152489 (Jul. 14, 1999).
GenBank Accession No.: AF167438 (Mar. 22, 2001).
GenBank Accession No.: AF169693 (Aug. 18, 2000).
GenBank Accession No.: AF177942 (Sep. 6, 1999).
GenBank Accession No.: AF179904 (Mar. 29, 2000).
GenBank Accession No.: AF213884 (Feb. 21, 2000).
GenBank Accession No.: AF224669 (Feb. 21, 2000).
GenBank Accession No.: AF277376 (Oct. 30, 2000).
GenBank Accession No.: AF277452 (May 20, 2002).
GenBank Accession No.: AF312024 (Jan. 10, 2001).
GenBank Accession No.: AF320815 (Dec. 20, 2001).
GenBank Accession No.: AF332653 (May 30, 2001).
GenBank Accession No.: AF339912 (Apr. 2, 2001).
GenBank Accession No.: AF388183 (Dec. 7, 2001).
GenBank Accession No.: AF388184 (Dec. 7, 2001).
GenBank Accession No.: AJ002535 (Sep. 14, 2001).
GenBank Accession No.: AJ002962 (Jan. 8, 1998).
GenBank Accession No.: AJ238248 (Apr. 24, 1999).
GenBank Accession No.: AJ243224 (Nov. 27, 2000).
GenBank Accession No.: AJ310931 (Apr. 26, 2002).
GenBank Accession No.: AJ310932 (Apr. 26, 2002).
GenBank Accession No.: AK004413 (Jan. 19, 2002).
GenBank Accession No.: AK006107 (Jan. 19, 2002).
GenBank Accession No.: AK009450 (Jan. 19, 2002).
GenBank Accession No.: AK016425 (Jan. 19, 2002).
GenBank Accession No.: AK017350 (Jan. 19, 2002).
GenBank Accession No.: AK020927 (Jan. 19, 2002).
GenBank Accession No.: AL078581 (Apr. 17, 2000).
GenBank Accession No.: AL136087 (Sep. 5, 2000).
GenBank Accession No.: AL136125 (Aug. 29, 2000).
GenBank Accession No.: AL354950 (Jun. 21, 2002).
GenBank Accession No.: AL512688 (Jan. 12, 2001).
GenBank Accession No.: AP000509 (Aug. 22, 2001).
GenBank Accession No.: AX041971 (Nov. 23, 2000).
GenBank Accession No.: AX049362 (Jan. 12, 2001).
GenBank Accession No.: AY010111 (Jan. 16, 2002).
GenBank Accession No.: AY077715 (Feb. 12, 2002).
GenBank Accession No.: BAA23324 (Nov. 7, 1997).
GenBank Accession No.: BAA93660 (Apr. 29, 2000).
GenBank Accession No.: BAB12255 (Oct. 11, 2001).
GenBank Accession No.: BAB18151 (Oct. 11, 2001).
GenBank Accession No.: BAB21807 (Feb. 7, 2001).
GenBank Accession No.: BAB23296 (Jan. 19, 2002).
GenBank Accession No.: BAB24412 (Jan. 19, 2002).
GenBank Accession No.: BAB26296 (Jan. 19, 2002).
GenBank Accession No.: BAB30227 (Jan. 19, 2002).
GenBank Accession No.: BAB30702 (Jan. 19, 2002).
GenBank Accession No.: BAB32258 (Jan. 19, 2002).
GenBank Accession No.: BAB39761 (Mar. 23, 2001).
GenBank Accession No.: BAB47441 (Jun. 5, 2001).
GenBank Accession No.: BAB60731 (Jun. 13, 2001).
GenBank Accession No.: BAB84586 (Feb. 7, 2002).
GenBank Accession No.: BC000698 (Jul. 12, 2001).
GenBank Accession No.: BC001200 (Jul. 12, 2001).
GenBank Accession No.: BC007201 (Jul. 12, 2001).
GenBank Accession No.: BC007758 (Jul. 12, 2001).
GenBank Accession No.: BC008276 (Jul. 12, 2001).
GenBank Accession No.: BC009754 (Jul. 12, 2001).
GenBank Accession No.: BC010075 (Jul. 12, 2001).
GenBank Accession No.: BC011170 (Jul. 30, 2001).
GenBank Accession No.: BC014814 (Oct. 4, 2001).
GenBank Accession No.: BC016204 (Nov. 5, 2001).
GenBank Accession No.: BC018775 (Dec. 11, 2001).
GenBank Accession No.: BC019999 (Jan. 22, 2002).
GenBank Accession No.: CAB88114 (Apr. 17, 2000).
GenBank Accession No.: CAC05478 (Aug. 29, 2000).
GenBank Accession No.: CAC07335 (Sep. 5, 2000).

GenBank Accession No.: CAC07336 (Sep. 5, 2000).
GenBank Accession No.: CAC16112 (Nov. 13, 2000).
GenBank Accession No.: CAC16113 (Nov. 13, 20000.
GenBank Accession No.: CAC21646 (Jan. 12, 2001).
GenBank Accession No.: CAC44768 (Sep. 14, 2001).
GenBank Accession No.: CAC70712 (Apr. 26, 2002).
GenBank Accession No.: CAC70714 (Apr. 26, 2002).
GenBank Accession No.: D50373 (Nov. 7, 1997).
GenBank Accession No.: D84307 (Feb. 6, 1999).
GenBank Accession No.: D86970 (Oct. 6, 2001).
GenBank Accession No.: I38005 (May 13, 1997).
GenBank Accession No.: JS0487 (Sep. 6, 1996).
GenBank Accession No. L08375 (Jul. 16, 1996).
GenBank Accession No.: L32179 (Sep. 9, 1994).
GenBank Accession No. L33243 (Jul. 25, 1995).
GenBank Accession No. L43619 (Jul. 23, 1995).
GenBank Accession No.: M19154 (Apr. 4, 2002).
GenBank Accession No.: M21188 (Nov. 8, 1994).
GenBank Accession No.: M22832 (Aug. 26, 1994).
GenBank Accession No.: M30691 (Apr. 27, 1993).
GenBank Accession No.: M34225 (Apr. 27, 1993).
GenBank Accession No.: M68892 (Jan. 6, 1995).
GenBank Accession No.: M86826 (Apr. 27, 1993).
GenBank Accession No.: NM_000070 (Oct. 31, 2000).
GenBank Accession No.: NM_000224 (Oct. 31, 2000).
GenBank Accession No.: NM_000296 (Apr. 24, 2002).
GenBank Accession No.: NM_000889 (Oct. 31, 2000).
GenBank Accession No.: NM_001086 (Oct. 31, 2000).
GenBank Accession No.: NM_001446 (Nov. 16, 2001).
GenBank Accession No.: NM_001859 (Oct. 31, 2000).
GenBank Accession No.: NM_002273 (Oct. 31, 2000).
GenBank Accession No.: NM_002861 (Dec. 10, 2001).
GenBank Accession No.: NM_003238 (Oct. 31, 2000).
GenBank Accession No.: NM_004969 (Nov. 1, 2000).
GenBank Accession No.: NM_005512 (Nov. 1, 2000).
GenBank Accession No.: NM_007044 (May 16, 2002).
GenBank Accession No.: NM_010096 (Jan. 7, 2002).
GenBank Accession No.: NM_011835 (Jan. 7, 2002).
GenBank Accession No.: NM_012287 (Dec. 22, 2001).
GenBank Accession No.: NM_012795 (Nov. 1, 2000).
GenBank Accession No.: NM_013159 (Jul. 23, 2002).
GenBank Accession No.: NM_013566 (Jan. 7, 2002).
GenBank Accession No.: NM_014716 (May 14, 2002).
GenBank Accession No.: NM_016026 (Apr. 8, 2002).
GenBank Accession No.: NM_017117 (Jul. 23, 2002).
GenBank Accession No.: NM_020403 (Jul. 3, 2001).
GenBank Accession No.: NM_022124 (Oct. 29, 2001).
GenBank Accession No.: NM_022843 (Jun. 21, 2002).
GenBank Accession No.: NM_023383 (Jan. 8, 2002).
GenBank Accession No.: NM_024229(Jan. 8, 2002).
GenBank Accession No.: NM_025664(Jan. 7, 2002).
GenBank Accession No.: NM_030649(Nov. 16, 2001).
GenBank Accession No.: NM_031156 (Jan. 8, 2002).
GenBank Accession No.: NM_031460(Jul. 8, 2002).
GenBank Accession No.: NM_032115(Nov. 6, 2001).
GenBank Accession No.: NM_032116(May 14, 2002).
GenBank Accession No.: NP_037291 (Jul. 23, 2002).
GenBank Accession No.: NM_052870(May 14, 2002).
GenBank Accession No.: NM_053568(Nov. 7, 2001).
GenBank Accession No.: NM_053644(Jul. 22, 2002).
GenBank Accession No.: NM_078471(May 16, 2002).
GenBank Accession No.: NM_078483(Dec. 14, 2001).
GenBank Accession No.: NM_080744(May 14, 2002).
GenBank Accession No.: NM_130415(Jan. 30, 2002).
GenBank Accession No.: NM_130796(Feb. 11, 2002).
GenBank Accession No.: NM_130830(Feb. 15, 2002).
GenBank Accession No.: NP_000061(Oct. 31, 2000).
GenBank Accession No.: NP_000215(Oct. 31, 2000).
GenBank Accession No.: NP_000287 (Apr. 24, 2002).
GenBank Accession No.: NP_000880 (Oct. 31, 2000).
GenBank Accession No.: NP_001077(Oct. 31, 2000).
GenBank Accession No.: NP_001437 (Nov. 16, 2001).
GenBank Accession No.: NP_001850(Oct. 31, 2000).
GenBank Accession No.: NP_002264(Oct. 31, 2000).
GenBank Accession No.: NP_002852 (Dec. 10, 2001).
GenBank Accession No.: NP_003229 (Oct. 31, 2000).
GenBank Accession No.: NP_004960 (Nov. 1, 2000).
GenBank Accession No. NP_005503 (Nov. 1, 2000).
GenBank Accession No. NP_008975 (May 16, 2002).
GenBank Accession No. NP_034226(Jan. 7, 2002).
GenBank Accession No.: NP_035965 (Jan. 7, 2002).
GenBank Accession No.: NP_036419 (Dec. 22, 2001).
GenBank Accession No.: NP_036927 (Nov. 1, 2000).
GenBank Accession No.: NP_037291 (Jul. 23, 2002).
GenBank Accession No.: NP_038594 (Jan. 7, 2002).
GenBank Accession No.: NP_057110 (Apr. 8, 2002).
GenBank Accession No.: NP_058813 (Jul. 23, 2002).
GenBank Accession No.: NP_065136 (Jul. 3, 2001).
GenBank Accession No.: NP_071407 (Oct. 29, 2001).
GenBank Accession No.: NP_073754 (Jun. 21, 2002).
GenBank Accession No.: NP_075872 (Jan. 8, 2002).
GenBank Accession No.: NP_077191 (Jan. 8, 2002).
GenBank Accession No.: NP_079940 (Jan. 7, 2002).
GenBank Accession No.: NP_085152 (Nov. 16, 2001).
GenBank Accession No.: NP_112419 (Jan. 8, 2002).
GenBank Accession No.: NP_113648 (Jul. 8, 2002).
GenBank Accession No.: NP_115491 (Nov. 6, 2001).
GenBank Accession No.: NP_115492 (May 14, 2002).
GenBank Accession No.: NP_443102 (May 14, 2002).
GenBank Accession No.: NP_446020 (Nov. 7, 2001).
GenBank Accession No.: $NP_{13}$_446096 (Jul. 22, 2002).
GenBank Accession No.: NP_510880 (May 16, 2002).
GenBank Accession No.: NP_510968 (Dec. 14, 2001).
GenBank Accession No.: NP_542782 (May 14, 2002).
GenBank Accession No.: NP_569099 (Jan. 30, 2002).
GenBank Accession No.: NP_570614 (Feb. 11, 2002).
GenBank Accession No.: NP_570843 (Feb. 15, 2002).
GenBank Accession No.: O08791 (Oct. 16, 2001).
GenBank Accession No.: O15431 (Jun. 15, 2002).
GenBank Accession No.: O15540 (Jun. 15, 2002).
GenBank Accession No.: O60658 (Jun. 15, 2002).
GenBank Accession No.: O73742 (Jun. 15, 2002).
SWALL (SPTR) Accession No.: O75449 (Nov. 1, 1998).
SWALL (SPTR) Accession No.: O75668 (Nov. 1, 1998).
GenBank Accession No.: P05783 (Jun. 15, 2002).
GenBank Accession No.: P05787 (Jun. 15, 2002).
GenBank Accession No.: P08112 (Jun. 15, 2002).
GenBank Accession No.: P09858 (Oct. 16, 2001).
GenBank Accession No.: P20807 (Jun. 15, 2002).
GenBank Accession No.: P26010 (Jun. 15, 2002).
GenBank Accession No.: P26011 (Jun. 15, 2002).
GenBank Accession No.: P35460 (Oct. 16, 2001).
GenBank Accession No.: P98161 (Jun. 15, 2002).
GenBank Accession No.: Q05423 (Oct. 1, 1996).
SWALL (SPTR) Accession No.: Q07822 (Nov. 1, 1996).
GenBank Accession No.: Q14392 (Jun. 15, 2002).
SWALL (SPTR) Accession No.: Q15140 (Nov. 1, 1996).
SWALL (SPTR) Accession No.: Q63318 (Nov. 1, 1996).

SWALL (SPTR) Accession No.: Q92614 (Feb. 1, 1997).
SWALL (SPTR) Accession No.: Q95218 (Feb. 1, 1997).
GenBank Accession No.: Q99447 (Jun. 15, 2002).
GenBank Accession No.: Q9H251 (Jun. 15, 2002).
GenBank Accession No.: Q9H4W6 (Jun. 15, 2002).
SWALL (SPTR) Accession No.: Q9H591 (Mar. 1, 2001).
SWALL (SPTR) Accession No.: Q9HD02 (Mar. 1, 2001).
SWALL (SPTR) Accession No.: Q9JK41 (Oct. 16, 2001).
SWALL (SPTR) Accession No.: Q9NRT9 (Oct. 1, 2000).
SWALL (SPTR) Accession No.: Q9NRW0 (Oct. 1, 2000).
SWALL (SPTR) Accession No.: Q9QZU3 (May 1, 2000).
GenBank Accession No.: Q9UN67 (Jun. 15, 2002).
SWALL (SPTR) Accession No.: Q9UQR3 (May 1, 2000).
SWALL (SPTR) Accession No.: Q9VLM4 (May 1, 2000).
SWALL (SPTR) Accession No.: Q9Y5F8 (Nov. 1, 1999).
SWALL (SPTR) Accession No.: Q9Y5G9 (Nov. 1, 1999).
GenBank Accession No.: Q9Y5X1 (Jun. 15, 2002).
GenBank Accession No.: S06889 (Apr. 12, 1995).
GenBank Accession No.: S44607 (Sep. 20, 1999).
GenBank Accession No.: S56581 (May 3, 1996).
GenBank Accession No.: T30549 (Oct. 22, 1999).
GenBank Accession No.: U42412 (May 30, 1996).
GenBank Accession No.: U85047 (Jul. 11, 2001).
GenBank Accession No.: U87960 (Mar. 4, 1997).
GenBank Accession No.: U92702 (May 29, 1997).
GenBank Accession No.: U92704 (May 29, 1997).
GenBank Accession No.: XM_003002 (May 13, 2002).
GenBank Accession No.: XM_027698 (May 8, 2002).
GenBank Accession No.: XM_029078 (May 13, 2002).
GenBank Accession No.: XM_031413 (Feb. 7, 2002).
GenBank Accession No.: XM_031443 (May 13, 2002).
GenBank Accession No.: XM_051017 (May 13, 2002).
GenBank Accession No.: XM_051153 (May 13, 2002).
GenBank Accession No.: XM_051448 (May 13, 2002).
GenBank Accession No.: XM_054521 (May 13, 2002).
GenBank Accession No.: XM_057519 (May 8, 2002).
GenBank Accession No.: XM_058449 (May 13, 2002).
GenBank Accession No.: XM_059717 (Dec. 10, 2001).
GenBank Accession No.: XM_067453 (May 13, 2002).
GenBank Accession No.: XM_067707 (May 8, 2002).
GenBank Accession No.: XM_079250 (Feb. 1, 2002).
GenBank Accession No.: XM_087161 (May 13, 2002).
GenBank Accession No.: XM_089356 (May 13, 2002).
GenBank Accession No.: XM_093473 (May 8, 2002).
GenBank Accession No.: XM_094815 (Feb. 6, 2002).
GenBank Accession No.: XP_003002 (May 13, 2002).
GenBank Accession No.: XP_027698(May 8, 2002).
GenBank Accession No.: XP_029078 (May 13, 2002).
GenBank Accession No.: XP_031413 (Feb. 7, 2002).
GenBank Accession No. XP_031443 (May 13, 2002).
GenBank Accession No. XP_051017 (May 13, 2002).
GenBank Accession No. XP_051153 (May 13, 2002).
GenBank Accession No. XP_051448 (May 13, 2002).
GenBank Accession No.: XP_054521 (May 13, 2002).
GenBank Accession No.: XP_057519 (May 8, 2002).
GenBank Accession No.: XP_058449 (May 13, 2002).
GenBank Accession No.: XP_059717 (Dec. 10, 2001).
GenBank Accession No. XP_067453 (May 13, 2002).
GenBank Accession No.: XP_067707 (May 8, 2002).
GenBank Accession No.: XP_079250 (Feb. 1, 2002).
GenBank Accession No.: XP_087161 (May 13, 2002).
GenBank Accession No.: XP_089356 (May 13, 2002).
GenBank Accession No.: XP_093473 (May 8, 2002).
GenBank Accession No. XP_094815 (Feb. 6, 2002).

GenBank Accession No.: Y00083 (Mar. 27, 1995).
Al–Awqati et al. (2000). "Phenotypic plasticity and terminal differentiation of the intercalated cell: the hensin pathway." *Exp Nephrol* 8(2): 66–71.
Alderborn et al. (2000). "Determination of single–nucleotide polymorphisms by real–time pyrophosphate DNA sequencing." *Genome Res* 10(8): 1249–1258.
Andrews and Berndt (1998). "Adhesion–dependent signalling and the initiation of haemostasis and thrombosis." *Histol Histopathol* 13(3): 837–844.
Andrews et al. (1999). "The glycoprotein Ib–IX–V complex in platelet adhesion and signaling." *Thromb Haemost* 82(2): 357–364.
Authier et al. (1996). "Insulin–degrading enzyme." *Clin Invest Med* 19(3): 149–160.
Baker et al. (1992). "Mapping of the human integrin beta 7 gene (ITG beta 7) to 12q13.13 by non–isotopic in situ hybridization." *Mamm Genome* 2(4): 272–273.
Barton et al. (1988). "Chromosomal mapping of genes for transforming growth factors beta 2 and beta 3 in man and mouse: dispersion of TGF–beta gene family." *Oncogene Res* 3(4): 323–331.
Battye et al. (2001). "Repellent signaling by Slit requires the leucine–rich repeats." *J. Neurosci* 21(12): 4290–4298.
Berx et al. (1998). "Mutations of the human E–cadherin (CDH1) gene." *Hum Mutat* 12(4): 226–237.
Biswas and Russell (1997). "Expression cloning and characterization of oxidative 17beta– and 3alpha– hydroxysteroid dehydrogenases from rat and human prostate." *J Biol Chem* 272(25): 15959–15966.
Bolz et al. (2001). "Mutation of CDH23, encoding a new member of the cadherin gene family, causes Usher syndrome type 1D." *Nat Genet* 27(1): 108–112.
Bork et al. (2001). "Usher syndrome 1D and nonsyndromic autosomal recessive deafness DFNB12 are caused by allelic mutations of the novel cadherin–like gene CDH23." *Am J Hum Genet* 68(1): 26–37.
Burkman et al. (2001). "Current perspectives on benefits and risks of hormone replacement therapy." *Am J Obstet Gynecol* 185(2 Suppl): S13–S23.
Casanova et al. (1999). "Exocrine pancreatic disorders in transsgenic mice expressing human keratin 8." *J Clin Invest* 103(11): 1587–1595.
Caulin et al. (2000). "Keratin–dependent, epithelial resistance to tumor necrosis factor–induced apoptosis." *J. Cell Biol.* 149(1): 17–22.
Chae et al. (2001). "Calpain 3 gene mutations: genetic and clinico–pathologic findings in limb–girdle muscular dystropy." *Neuromuscul Disord* 11(6–7): 547–555.
Chaib et al. (1996). "Mapping of DFNB12, a gene for a non–syndromal autosomal recessive deafness, to chromosome 10q21–22." *Hum Mol Genet* 5(7): 1061–1064.
Chavez et al. (1999). "TWIK–2, a new weak inward rectifying member of the tandem pore domain potassium channel family." *J Biol Chem* 274(12): 7887–7892.
Cheng et al. (1996). "CRP–ductin: a gene expressed in intestinal crypts and in pancreatic and hepatic ducts." *Anat Rec* 244(3): 327–343.
Chu et al. (1997). "Selection of invasive and metastatic subpopulations from a human lung adenocarcinoma cell line." *Am J Respir Cell Mol Biol* 17(3): 353–360.

Clemetson and Clemetson (1994). "Molecular abnormalities in Glanzmann's thrombasthenia, Bernard–Soulier syndrome, and platelet–type von Willebrand's disease." *Curr Opin Hematol 1*(5): 388–393.

de Martin et al. (1987). "Complementary DNA for human glioblastoma–derived T cell suppressor factor, a novel member of the transforming growth factor–beta gene family." *Embo J 6*(12): 3673–3677.

Di Palma et al. (2001). "Mutation in Cdh23, encoding a new type of cadherin, cause stereocilia disorganization in waltzer, the mouse model for Usher syndrome type 1D." *Nat Genet 27*(1): 103–107.

Di Palma et al. (2001). "Genomic structure, alternative splice forms and normal and mutant alleles of cadherin 23 (Cdh23)." *Cell 281*(1–2): 31–41.

Dickinson et al. (1990). "Chromosomal localization of seven members of the murine TGF–beta superfamily suggests close linkage to several morphogenetic mutant loci." *Genomics 6*(3): 505–520.

Duckworth et al. (1998). "Insulin degradation: progress and potential." *Endocr Rev 19*(5): 608–624.

Edbauer et al. (2002). "Insulin–degrading enzyme rapidly removes the beta–amyloid precursor protein intracellular domain (AICD)." *J Biol Chem 277*(16): 13389–13393.

Engle and Kennett (1994). "Cloning, analysis, and chromosomal localization of myoxin (MYH12), the human homologue to the mouse dilute gene." *Genomics 19*(3): 407–416.

Erle et al. (1991). "Complete amino acid sequence of an integrin beta subunit (beta 7) identified in leukocytes." *J Biol Chem 266*(17): 11009–11016.

Field and Hand (1987). "Secretion of lingual lipase and amylase from rat lingual serous glands." *Am J Physiol. 253*(2 Pt 1): G217–G225.

Gaillard et al. (2001). "Glucocorticoid and type 1 interferon interactions at the blood–brain barrier: relevance for drug therapies for multiple sclerosis." *Neuroreport 12*(10): 2189–2193.

Gerber et al. (1996). "Evidence for a fourth locus in Usher syndrome type I." *J Med Genet 33*(1): 77–79.

German et al. (2002). "Neurodegeneration in the Niemann–Pick C mouse: glial involvement." *Neuroscience 109*(3): 437–450.

Godbout et al. (1998). "Correlation of B–FABP and GFAP expression in malignant glioma." *Oncogene 16*(15): 1955–1962.

Goichberg et al. (2001). "Recruitment of beta–catenin to cadherin–mediated intercellular adhesions is involved in myogenic induction." *J Cell Sci 114*(Pt 7): 1309–1319.

Gumley et al. (1995). "Tissue expression, structure and function of the murine Ly–6 family of molecules." *Immunol Cell Biol 73*(4): 277–296.

Haft et al. (1998). "Identification of a family of sorting nexin molecules and characterization of their association with receptors." *Mol Cell Biol 18*(12): 7278–7287.

Hagman et al. (1993). "Cloning and functional characterization of early B–cell factor, a regulator of lymphocyte–specific gene expression." *Genes Dev 7*(5): 760–773.

Hamosh and Scow (1973). "Lingual lipase and its role in the digestion of dietary lipid." *J Clin Invest 52*(1): 88–95.

Hanks et al. (1988). "Amino acid sequence of the BSC–1 cell growth inhibitor (polyergin) deduced from the nucleotide sequence of the cDNA." *Proc Natl Acad Sci U S A 85*(1): 79–82.

Hartman et al. (1998). "Katanin, a microtubule–severing protein, is a novel AAA ATPase that targets to the centrosome using a WD40–containing subunit." *Cell 93*(2): 277–287.

Hayashi and Suzuki (2000). "Molecular pathogenesis of Bernard–Soulier syndrome." *Semin Thromb Hemost 26*(1): 53–59. Abstract Only.

Hickey et al. (1993). "Human platelet glycoprotein V: characterization of the polypeptide and the related ib–V–IX receptor system of adhesive, leucine–rich glycoproteins." *Proc Natl Acad Sci U S A 90*(18): 8327–8331.

Hiroi et al. (1996). "Expression of a nonmuscle myosin heavy chain in glomerular cell differentiates various types of glomerular disease in rats." *Kidney Int 49*(5): 1231–1241.

Holinka (2001). "Design and conduct of clinical trials in hormone replacement therapy." *Ann N Y Acad Sci 943*: 89–108.

Holmin et al. (1998). "Intracerebral inflammation after human brain contusion." *Neurosurgery 42*(2): 291–298; discussion 298–299.

Howard et al. (1999). "Interaction of the metalloprotease disintegrins MDC9 and MDC15 with two SH3 domain–containing proteins, endophilin I and SH3PX1." *J Biol Chem 274*(44): 31693–31699.

Huang and Wang (2001). "The calpain family and human disease." *Trends Mol Med 7*(8): 355–362.

Jackson et al. (1980). "Formation of cytoskeletal elements during mouse embryogenesis. Intermediate filaments of the cytokeratin type and desmosomes in preimplantation embryos." *Differentiation 17*(3): 161–179.

Jackson et al. (2000). "Cytohesins and centaurins: mediators of PI 3–kinase–regulated Arf signaling." *Trends Biochem Sci 25*(10): 489–495.

Kamijima et al. (1999). "Enhanced embryonic nonmuscle myosin heavy chain isoform and matrix metalloproteinase expression in aortic abdominal aneurysm with rapid progression." *Cardiovasc Pathol 8*(5): 291–295.

Kanemitsu et al. (2000). "Characterization of the promoter of the murine mac25 gene." *Biochem Biophys Res Commun 279*(1): 251–257.

Kato (2000). "A secreted tumor–suppressor, mac25, with activin–binding activity." *Mol Med 6*(2): 126–135.

Kobe and Deisenhofer (1994). "The leucine–rich repeat: a versatile binding motif." *Trends Biochem Sci 19*(10): 415–421.

Kohmura et al. (1998). "Diversity revealed by a novel family of cadherins expressed in neurons at a synaptic complex." *Neuron 20*(6): 1137–1151.

Krissansen et al. (1992). "Chromosomal locations of the genes coding for the integrin beta 6 and beta 7 subunits." *Immunogenetics 35*(1): 58–61.

Kurochkin (2001). "Insulin–degrading enzyme: embarking on amyloid destruction." *Trends Biochem Sci 26*(7): 421–425.

Kurten et al. (1996). "Enhanced degradation of EGF receptors by a sorting nexin, SNX1." *Science 272*(5264): 1008–1010.

LeClair et al. (1986). "Isolation of a murine Ly–6 cDNA reveals a new multigene family." *Embo J 5*(12): 3227–3234.

Leong et al. (1992). "Structure and functional expression of the acid–labile subunit of the insulin–like growth factor–binding protein complex." *Mol Endocrinol 6*(6): 870–876.

Lesage and Lazdunski (2000). "Molecular and functional properties of two–pore–domain potassium channels." *Am J Physiol Renal Physiol 279*(5): F793–F801.

Lesage et al. (1996). "TWIK–1, a ubiquitous human weakly inward rectifying K+ channel with a novel structure." *Embo J 15*(5): 1004–1011.

Li and Snyder (1995). "Molecular cloning of Ebnerin, a von Ebner's gland protein associated with taste buds." *J Biol Chem 270*(30): 176741–17679.

Lopez and Dong (1997). "Structure and function of the glycoprotein Ib–IX–V complex." *Curr Opin Hematol 4*(5): 323–329.

Madisen et al. (1988). "Transforming growth factor–beta 2: cDNA cloning and sequence analysis." *DNA 7*(1): 1–8.

Mages et al. (1989). "Increased methylation of chloroform extractable products and CTP: cholinephosphate cytidylyltransferase in brain membrane preparations from triethyltin–intoxicated rats." *Pharmacol Toxicol 65*(4): 302–305.

Matsumoto et al. (2001). "Early complications of high–dose methylprednisolone sodium succinate treatment in the follow–up of acute cervical spinal cord injury." *Spine 26*(4): 426–430.

Matsushita et al. (2000). "Vomeroglandin/CRP–Ductin is strongly expressed in the glands associated with the mouse vomeronasal organ: identification and characterization of mouse vomeroglandin." *Biochem Biophys Res Commun 268*(2): 275–281.

McNally and Vale (1993). "Identification of katanin, an ATPase that severs and disassembles stable microtubules." *Cell 75*(3): 419–429.

McNally et al. (1996). "Katanin, the microtubule–severing ATPase, is concentrated at centrosomes." *J Cell Sci 109*(Pt 3): 561–567.

Medhurst et al. (2001). "Distribution analysis of human two pore domain potassium channels in tissues of the central nervous system and periphery." *Mol Brain Res 86*(1–2): 101–114.

Milatovich et al. (1994). "Gene for a tissue–specific transcriptional activator (EBF or Olf–1), expressed in early B lymphocytes, adipocytes, and olfactory neurons, is located on human chromosome 5, band q34, and proximal mouse chromosome 11." *Mamm Genome 5*(4): 211–215.

Miyamoto et al. (1995). "Mutations of the basic amino acid transporter gene associated with cystinuria." *Biochem J 310*(Pt 3): 951–955.

Moll et al. (1982). "Different keratin polypeptides in epidermis and other epithelia of human skin: a specific cytokeratin of molecular weight 46,000 in epithelia of the pilosebaceous tract and basal cell epitheliomas." *J Cell Biol 95*(1): 285–295.

Mollenhauer et al. (1997). "DMBT1, a new member of the SRCR superfamily, on chromosome 10q25.3–26.1 is deleted in malignant brain tumours." *Nat Genet 17*(1): 32–39.

Nishimura et al. (1993). "Linkage localization of TGFB2 and the human homeobox gene HLX1 to chromosome 1q." *Genomics 15*(2): 357–364.

Ollendorff et al. (1994). "The GARP gene encodes a new member of the family of leucine–rich repeat–containing proteins." *Cell Growth Differ 5*(2): 213–219.

Oshima et al. (1996). "Oncogenic regulation and function of keratins 8 and 18." *Cancer Metastasis Rev 15*(4): 445–471.

Penning et al. (2000). "Human 3alpha–hydroxysteroid dehydrogenase isoforms (AKR1C1–AKR1C4) of the aldo–keto reductase superfamily: functional plasticity and tissue distribution reveals roles in the inactivation and formation of male and female sex hormones." *Biochem J 351*(Pt 1): 67–77.

Pittenger et al. (1999). "Multilineage potential of adult human mesenchymal stem cells." *Science 284*(5411): 143–147.

Potter et al. (1999). "The cadherin–catenin system: implications for growth and differentiation of endocrine tissues." *Endocr Rev 20*(2): 207–239.

Pountney et al. (1999). "Identification and cloning of TWIK–originated similarity sequence (TOSS): a novel human 2–pre K+ channel principal subunit." *FEBS Lett 450*(3): 191–196.

Rajan et al. (2000). "TASK–3, a novel tandem pore domain acid–sensitive K+ channel. An extracellular histiding as pH sensor." *J Biol Chem 275*(22): 16650–16657.

Ranscht (2000). "Cadherins: molecular codes for axon guidance and synapse formation." *Int J Dev Neurosci 18*(7): 643–651.

Ross et al. (2001). "Elevated activity of phospholipid biosynthetic enzymes in *substantia nigra* of patients with Parkinson's disease." *Neuroscience 102*(4): 899–904.

Roth (1991). "Developing relationships: arterial platelet adhesion, glycoprotein Ib, and leucine–rich glycoproteins." *Blood 77*(1): 5–19.

Sagne et al. (2001). "Identification and characterization of a lysosomal transporter for small neutral amino acids." *Proc Natl Acad Sci U S A 98*(13): 7206–7211.

Saita and Hatase (1988). "[Problems associated with reassignment of nursing supervisors and their management]." *Kango Tenbo 13*(6): 655–660. No English Abstract Available.

Sasaki et al. (2000). "Excilatory amino acid transporter 1 and 2 immunoreactivity in the spinal cord in amyotrophic lateral sclerosis." *Acta Neuropathol (Berl) 100*(2): 138–144.

Shapiro and Colman (1999). "The diversity of cadherins and implications for a synaptic adhesive code in the CNS." *Neuron 23*(3): 427–430.

Simons et al. (1993). "Relation between activated smooth-–muscle cells in coronary–artery lesions and restenosis after atherectomy." *N Engl J Med 328*(9): 608–613.

Singh et al. (1996). "Tumor cell invasion of basement membrane in vitro is regulated by amino acids." *Cancer Invest 14*(1): 6–18.

Suyama et al. (1998). "Regulated tRNA import in *Leishmania mitochondria.*" *Biochim Biophys Acta 1396*(2): 138–142.

Takito et al. (1999). "Hensin, the polarity reversal protein, is encoded by DMBT1, a gene frequently deleted in malignant gliomas." *Am J Physiol 277*(2 Pt 2): F277–F289.

Travis et al. (1993). "Purification of early–B–cell factor and characterization of its DNA– binding specificity." *Mol Cell Biol 13*(6): 3392–3400.

Wandji et al. (2000). "Messenger ribonucleic acids for MAC25 and connective tissue growth factor (CTGF) are inversely regulated during folliculogenesis and early luteogenesis." *Endocrinology 141*(7): 2648–2657.

Wang and Reed (1993). "Molecular cloning of the olfactory neuronal transcription factor Olf–1 by genetic selection in yeast." *Nature 364*(6433): 121–126.

Waseem et al. (1990). "Localization of the gene for human simple epithelial keratin 18 to chromosome 12 using polymerase chain reaction." *Genomics* 7(2): 188–194.

Wayne et al. (1996). "Localization of the Usher syndrome type ID gene (Ush1D) to chromosome 10." *Hum Mol Genet* 5(10): 1689–1692.

Williamson et al. (1999). "Platelet adhesion receptors: novel targets for anti-thombotic therapy." *Aust N Z J Med* 29(3): 452–461.

Wootton and Federhen (1996). "Analysis of compositionally biased regions in sequence databases." *Methods Enzymol* 266: 554–571.

Worby et al. (2001). "The sorting nexin, DSH3PX1, connects the axonal guidance receptor, Dscam, to the actin cytoskeleton." *J Biol Chem* 276(45): 41782–41789.

Wrann et al. (1987). "T cell suppressor factor from human glioblastoma cells is a 12.5-kd protein closely related to transforming growth factor-beta." *Embo J* 6(6): 1633–1636.

Wu and Maniatis (1999). "A striking organization of a large family of human neural cadherin-like cell adhesion genes." *Cell* 97(6): 779–790.

Yamamoto et al. (1990). "Cloning and sequence of cDNA for human placental cytokeratin 8. Regulation of the mRNA in trophoblastic cells by cAMP." *Mol Endocrinol* 4(3): 370–374.

Yuan et al. (1992). "Genetic mapping of the gene coding for the integrin beta 7 subunit to the distal part of mouse chromosome 15." *Immunogenetics* 35(6): 403–407.

Zhou and Gitschier (1997). "hCTR1: a human gene for copper uptake identified by complementation in yeast." *Proc Natl Acad Sci U S A* 94(14): 7481–7486.

* cited by examiner

PROTEINS, POLYNUCLEOTIDES ENCODING THEM AND METHODS OF USING THE SAME

RELATED APPLICATIONS

This application claims priority to U.S. Ser. No. 60/270,523, filed Feb. 21 2001; U.S. Ser. No. 60/322,712, filed Sep. 17, 2001; U.S. Ser. No. 60/311,980, filed Aug. 13, 2001; U.S. Ser. No. 60/330,307, filed Oct. 18, 2001; U.S. Ser. No. 60/278,796, filed Mar. 26, 2001; U.S. Ser. No. 60/281,521, filed Apr. 4, 2001; U.S. Ser. No. 60/276,677, filed Mar. 16, 2001; U.S. Ser. No. 60/311,595, filed Aug. 10, 2001, U.S. Ser. No. 60/270,220, filed Feb. 21, 2001; U.S. Ser. No. 60/274,295, filed Mar. 8, 2001; U.S. Ser. No. 60/318,526, filed Sep. 10, 2001; U.S. Ser. No. 60/286,548, filed Apr. 25, 2001; U.S. Ser. No. 60/291,765, filed May 17, 2001; U.S. Ser. No. 60/270,797, filed Feb. 23, 2001; U.S. Ser. No. 60/276,400, filed Mar. 16, 2001; and U.S. Ser. No. 60/270,810, filed Feb. 23, 2001 each of which is incorporated by reference in its entirety.

FIELD OF THE INVENTION

The invention relates to polynucleotides and the polypeptides encoded by such polynucleotides, as well as vectors, host cells, antibodies and recombinant methods for producing the polypeptides and polynucleotides, as well as methods for using the same.

BACKGROUND OF THE INVENTION

The present invention is based in part on nucleic acids encoding proteins that are new members of the following protein families: Androgen-Regulated Short-Chain Dehydrogenase/Reductase-like, Aryl-Acylamidase-like, Insulysin-like, Integrin Beta-7 Precursor-like, Membrane protein-like, BCSC-1-like, Amino Acid Transporter-like, Lymphocyte Antigen Precursor-like, Lymphocyte Antigen LY-6F-like, Early B-Cell Factor-like, High-Affinity Camp-Specific and IBMX-Insensitive-like, KIAA0216-like, TWIK 3-like, TASK 4-like, Copper Transporter-like, Cytokeratin-like, Protocadherin-like, Protocadherin Beta-like, Cadherin 23-like, Transforming Growth Factor Beta 2-like, Ebnerin-like, Fatty Acid Binding-like, Platelet glycoprotein V-like, GARPIN-like, Centaurin Beta 2-like, Sorting Nexin 9-like, Katanin-like, Calpain-like, Keratin 18-like, Polycystic Kidney Disease Associated, Cholinephosphate Cytidylyltransferase-like and mac25/IGFBP7-like. More particularly, the invention relates to nucleic acids encoding novel polypeptides, as well as vectors, host cells, antibodies, and recombinant methods for producing these nucleic acids and polypeptides.

SUMMARY OF THE INVENTION

The invention is based in part upon the discovery of nucleic acid sequences encoding novel polypeptides. The novel nucleic acids and polypeptides are referred to herein as NOVX, or NOV1, NOV2, NOV3, NOV4, NOV5, NOV6, NOV7, NOV8, NOV9, NOV10, NOV11, NOV12, NOV13, NOV14, NOV15, NOV16, NOV17, NOV18, NOV19, NOV20, NOV21, NOV22, NOV23, NOV24, NOV25, NOV26, NOV27, NOV28, NOV29 and NOV30 nucleic acids and polypeptides. These nucleic acids and polypeptides, as well as derivatives, homologs, analogs and fragments thereof, will hereinafter be collectively designated as "NOVX" nucleic acid or polypeptide sequences.

In one aspect, the invention provides an isolated NOVX nucleic acid molecule encoding a NOVX polypeptide that includes a nucleic acid sequence that has identity to the nucleic acids disclosed in SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93. In some embodiments, the NOVX nucleic acid molecule will hybridize under stringent conditions to a nucleic acid sequence complementary to a nucleic acid molecule that includes a protein-coding sequence of a NOVX nucleic acid sequence. The invention also includes an isolated nucleic acid that encodes a NOVX polypeptide, or a fragment, homolog, analog or derivative thereof. For example, the nucleic acid can encode a polypeptide at least 80% identical to a polypeptide comprising the amino acid sequences of SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94. The nucleic acid can be, for example, a genomic DNA fragment or a cDNA molecule that includes the nucleic acid sequence of any of SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93.

Also included in the invention is an oligonucleotide, e.g., an oligonucleotide which includes at least 6 contiguous nucleotides of a NOVX nucleic acid (e.g. SEQ ID NOS:1, 3, 5, 7, 9, 11, 13, 15, 17, 19, 21, 23, 25, 27, 29, 31, 33, 35, 37, 39, 41,43, 45, 47, 49, 51, 53, 55, 57, 59, 61, 63, 65, 67, 69, 71, 73, 75, 77, 79, 81, 83, 85, 87, 89, 91 and 93) or a complement of said oligonucleotide. Also included in the invention are substantially purified NOVX polypeptides (SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94). In certain embodiments, the NOVX polypeptides include an amino acid sequence that is substantially identical to the amino acid sequence of a human NOVX polypeptide.

The invention also features antibodies that immunoselectively bind to NOVX polypeptides, or fragments, homologs, analogs or derivatives thereof.

In another aspect, the invention includes pharmaceutical compositions that include therapeutically- or prophylactically-effective amounts of a therapeutic and a pharmaceutically-acceptable carrier. The therapeutic can be, e.g., a NOVX nucleic acid, a NOVX polypeptide, or an antibody specific for a NOVX polypeptide. In a further aspect, the invention includes, in one or more containers, a therapeutically- or prophylactically-effective amount of this pharmaceutical composition.

In a further aspect, the invention includes a method of producing a polypeptide by culturing a cell that includes a NOVX nucleic acid, under conditions allowing for expression of the NOVX polypeptide encoded by the DNA. If desired, the NOVX polypeptide can then be recovered.

In another aspect, the invention includes a method of detecting the presence of a NOVX polypeptide in a sample. In the method, a sample is contacted with a compound that selectively binds to the polypeptide under conditions allowing for formation of a complex between the polypeptide and the compound. The complex is detected, if present, thereby identifying the NOVX polypeptide within the sample.

The invention also includes methods to identify specific cell or tissue types based on their expression of a NOVX.

Also included in the invention is a method of detecting the presence of a NOVX nucleic acid molecule in a sample by contacting the sample with a NOVX nucleic acid probe or primer, and detecting whether the nucleic acid probe or primer bound to a NOVX nucleic acid molecule in the sample.

In a further aspect, the invention provides a method for modulating the activity of a NOVX polypeptide by contacting a cell sample that includes the NOVX polypeptide with a compound that binds to the NOVX polypeptide in an amount sufficient to modulate the activity of said polypeptide. The compound can be, e.g., a small molecule, such as a nucleic acid, peptide, polypeptide, peptidomimetic, carbohydrate, lipid or other organic (carbon containing) or inorganic molecule, as further described herein.

Also within the scope of the invention is the use of a therapeutic in the manufacture of a medicament for treating or preventing disorders or syndromes including, e.g., trauma, regeneration (in vitro and in vivo), viral/bacterial/parasitic infections, Von Hippel-Lindau (VHL) syndrome, Alzheimer's disease, stroke, Tuberous sclerosis, hypercalceimia, Parkinson's disease, Huntington's disease, Cerebral palsy, Epilepsy, Lesch-Nyhan syndrome, Multiple sclerosis, Ataxia-telangiectasia, Leukodystrophies, behavioral disorders, addiction, anxiety, pain, actinic keratosis, acne, hair growth diseases, allopecia, pigmentation disorders, endocrine disorders, connective tissue disorders, such as severe neonatal Marfan syndrome, dominant ectopia lentis, familial ascending aortic aneurysm, isolated skeletal features of Marfan syndrome, Shprintzen-Goldberg syndrome, genodermatoses, contractural arachnodactyly, inflammatory disorders such as osteo- and rheumatoid-arthritis, inflammatory bowel disease, Crohn's disease; immunological disorders, AIDS; cancers including but not limited to lung cancer, colon cancer, Neoplasm; adenocarcinoma; lymphoma; prostate cancer; uterus cancer, leukemia or pancreatic cancer; blood disorders; asthma; psoriasis; vascular disorders, hypertension, skin disorders, renal disorders including Alport syndrome, immunological disorders, tissue injury, fibrosis disorders, bone diseases, Ehlers-Danlos syndrome type VI, VII, type IV, S-linked cutis laxa and Ehlers-Danlos syndrome type V, osteogenesis imperfecta, Neurologic diseases, Brain and/or autoimmune disorders like encephalomyelitis, neurodegenerative disorders, immune disorders, hematopoietic disorders, muscle disorders, inflammation and wound repair, bacterial, fungal, protozoal and viral infections (particularly infections caused by HIV-1 or HIV-2), pain, acute heart failure, hypotension, hypertension, urinary retention, osteoporosis, Treatment of Albright Hereditary Ostoeodystrophy, angina pectoris, myocardial infarction, ulcers, benign prostatic hypertrophy, arthrogryposis multiplex congenita, osteogenesis imperfecta, keratoconus, scoliosis, duodenal atresia, esophageal atresia, intestinal malrotation, Pancreatitis, Obesity Systemic lupus erythematosus, Autoimmune disease, Emphysema, Scleroderma, allergy, ARDS, Neuroprotection, Fertility Myasthenia gravis, Diabetes, obesity, Growth and reproductive disorders Hemophilia, Hypercoagulation, Idiopathic thrombocytopenic purpura, Immunodeficiencies, Graft vesus host, Adrenoleukodystrophy, Congenital Adrenal Hyperplasia, Endometriosis, Xerostomia, Ulcers, Cirrhosis, Transplantation, Diverticular disease, Hirschsprung's disease, Appendicitis, Arthritis, Ankylosing spondylitis, Tendinitis, Renal artery stenosis, Interstitial nephritis, Glomerulonephritis, Polycystic kidney disease, erythematosus, Renal tubular acidosis, IgA nephropathy, anorexia, bulimia, psychotic disorders, including anxiety, schizophrenia, manic depression, delirium, dementia, severe mental retardation and dyskinesias, such as Huntington's disease and/or other pathologies and disorders of the like.

The therapeutic can be, e.g., a NOVX nucleic acid, a NOVX polypeptide, or a NOVX-specific antibody, or biologically-active derivatives or fragments thereof.

For example, the compositions of the present invention will have efficacy for treatment of patients suffering from the diseases and disorders disclosed above and/or other pathologies and disorders of the like. The polypeptides can be used as immunogens to produce antibodies specific for the invention, and as vaccines. They can also be used to screen for potential agonist and antagonist compounds. For example, a cDNA encoding NOVX may be useful in gene therapy, and NOVX may be useful when administered to a subject in need thereof. By way of non-limiting example, the compositions of the present invention will have efficacy for treatment of patients suffering from the diseases and disorders disclosed above and/or other pathologies and disorders of the like.

The invention further includes a method for screening for a modulator of disorders or syndromes including, e.g., the diseases and disorders disclosed herein and/or other pathologies and disorders of the like. The method includes contacting a test compound with a NOVX polypeptide and determining if the test compound binds to said NOVX polypeptide. Binding of the test compound to the NOVX polypeptide indicates the test compound is a modulator of activity, or of latency or predisposition to the aforementioned disorders or syndromes.

Also within the scope of the invention is a method for screening for a modulator of activity, or of latency or predisposition to disorders or syndromes including, e.g., the diseases and disorders disclosed above and/or other pathologies and disorders of the like by administering a test compound to a test animal at increased risk for the aforementioned disorders or syndromes. The test animal expresses a recombinant polypeptide encoded by a NOVX nucleic acid. Expression or activity of NOVX polypeptide is then measured in the test animal, as is expression or activity of the protein in a control animal which recombinantly-expresses NOVX polypeptide and is not at increased risk for the disorder or syndrome. Next, the expression of NOVX polypeptide in both the test animal and the control animal is compared. A change in the activity of NOVX polypeptide in the test animal relative to the control animal indicates the test compound is a modulator of latency of the disorder or syndrome.

In yet another aspect, the invention includes a method for determining the presence of or predisposition to a disease associated with altered levels of a NOVX polypeptide, a NOVX nucleic acid, or both, in a subject (e.g., a human subject). The method includes measuring the amount of the NOVX polypeptide in a test sample from the subject and comparing the amount of the polypeptide in the test sample to the amount of the NOVX polypeptide present in a control sample. An alteration in the level of the NOVX polypeptide in the test sample as compared to the control sample indicates the presence of or predisposition to a disease in the subject. Preferably, the predisposition includes, e.g., the diseases and disorders disclosed above and/or other pathologies and disorders of the like. Also, the expression levels of the new polypeptides of the invention can be used in a method to screen for various cancers as well as to determine the stage of cancers.

In a further aspect, the invention includes a method of treating or preventing a pathological condition associated with a disorder in a mammal by administering to the subject a NOVX polypeptide, a NOVX nucleic acid, or a NOVX-specific antibody to a subject (e.g., a human subject), in an amount sufficient to alleviate or prevent the pathological condition. In preferred embodiments, the disorder, includes, e.g., the diseases and disorders disclosed above and/or other pathologies and disorders of the like.

In yet another aspect, the invention can be used in a method to identity the cellular receptors and downstream effectors of the invention by any one of a number of techniques commonly employed in the art. These include but are not limited to the two-hybrid system, affinity purification, co-precipitation with antibodies or other specific-interacting molecules.

NOVX nucleic acids and polypeptides are further useful in the generation of antibodies that bind immunospecifically to the novel NOVX substances for use in therapeutic or diagnostic methods. These NOVX antibodies may be generated according to methods known in the art, using prediction from hydrophobicity charts, as described in the "Anti-NOVX Antibodies" section below. The disclosed NOVX proteins have multiple hydrophilic regions, each of which can be used as an immunogen. These NOVX proteins can be used in assay systems for functional analysis of various human disorders, which will help in understanding of pathology of the disease and development of new drug targets for various disorders.

The NOVX nucleic acids and proteins identified here may be useful in potential therapeutic applications implicated in (but not limited to) various pathologies and disorders as indicated below. The potential therapeutic applications for this invention include, but are not limited to: protein therapeutic, small molecule drug target, antibody target (therapeutic, diagnostic, drug targeting/cytotoxic antibody), diagnostic and/or prognostic marker, gene therapy (gene delivery/gene ablation), research tools, tissue regeneration in vivo and in vitro of all tissues and cell types composing (but not limited to) those defined here.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

The present invention provides novel nucleotides and polypeptides encoded thereby. Included in the invention are the novel nucleic acid sequences and their encoded polypeptides. The sequences are collectively referred to herein as "NOVX nucleic acids" or "NOVX polynucleotides" and the corresponding encoded polypeptides are referred to as "NOVX polypeptides" or "NOVX proteins." Unless indicated otherwise, "NOVX" is meant to refer to any of the novel sequences disclosed herein. Table A provides a summary of the NOVX nucleic acids and their encoded polypeptides.

TABLE A

Sequences and Corresponding SEQ ID Numbers

| NOVX Assignment | Internal Identification | SEQ ID NO (nucleic acid) | SEQ ID NO (polypeptide) | Homology |
|---|---|---|---|---|
| 1 | CG57413-01 | 1 | 2 | Androgen-Regulated Short-Chain Dehydrogenase/Reductase-like |
| 2a | CG57391-01 | 3 | 4 | Aryl-Acylamidase-like |
| 2b | CG57391-02 | 5 | 6 | Aryl-Acylamidase-like |
| 3a | CG57433-01 | 7 | 8 | Insulysin-like |
| 3b | CG57433-02 | 9 | 10 | Insulysin-like |
| 4a | CG57185-01 | 11 | 12 | Integrin Beta-7 Precursor-like |
| 4b | CG57185-02 | 13 | 14 | Integrin Beta-7 Precursor-like |
| 5 | CG57360-01 | 15 | 16 | Membrane protein-like |
| 6 | CG57362-01 | 17 | 18 | BCSC-1 like |
| 7a | CG57387-01 | 19 | 20 | Amino Acid Transporter-like |
| 7b | CG57387-02 | 21 | 22 | Amino Acid Transporter-like |
| 7c | CG57387-03 | 23 | 24 | Amino Acid Transporter-like |
| 8a | CG56417-01 | 25 | 26 | Lymphocyte Antigen Precursor-like |
| 8b | CG56417-02 | 27 | 28 | Lymphocyte Antigen Precursor-like |
| 8c | CG56417-03 | 29 | 30 | Lymphocyte Antigen Precursor-like |
| 8d | CG56417-04 | 31 | 32 | Lymphocyte Antigen LY-6F-like |
| 8e | 172885384 | 33 | 34 | Lymphocyte Antigen LY-6F-like |
| 9a | CG57480-01 | 35 | 36 | Early B-Cell Factor-like |
| 9b | CG57480-02 | 37 | 38 | Early B-Cell Factor-like |
| 10 | CG57389-01 | 39 | 40 | High-Affinity Camp-Specific and IBMX-Insensitive-like |
| 11 | CG57337-01 | 41 | 42 | KIAA0216-like |
| 12a | CG57220-01 | 43 | 44 | TWIK 3-like |
| 12b | CG57220-02 | 45 | 46 | TWIK 3-like |
| 12c | CG57220-03 | 47 | 48 | TWIK 3-like |
| 13 | CG57220-04 | 49 | 50 | TASK 4-like |
| 14 | CG57458-01 | 51 | 52 | Copper Transporter-like |
| 15 | CG57454-01 | 53 | 54 | Cytokeratin-like |
| 16a | CG57448-01 | 55 | 56 | Protocadherin-like |

TABLE A-continued

Sequences and Corresponding SEQ ID Numbers

| NOVX Assignment | Internal Identification | SEQ ID NO (nucleic acid) | SEQ ID NO (polypeptide) | Homology |
| --- | --- | --- | --- | --- |
| 16b | CG57446-01 | 57 | 58 | Protocadherin-like |
| 16c | CG57444-01 | 59 | 60 | Protocadherin-like |
| 16d | CG57442-01 | 61 | 62 | Protocadherin Beta-like |
| 17a | CG57429-01 | 63 | 64 | Cadherin 23-like |
| 17b | CG57429-02 | 65 | 66 | Cadherin 23-like |
| 18 | CG55887-02 | 67 | 68 | Transforming Growth Factor Beta 2-like |
| 19 | CG57333-01 | 69 | 70 | Ebnerin-like |
| 20a | CG57556-01 | 71 | 72 | Fatty Acid Binding-like |
| 20b | CG57556-02 | 73 | 74 | Fatty Acid Binding-like |
| 21 | CG57436-01 | 75 | 76 | Platelet glycoprotein V-like |
| 22 | CG57529-01 | 77 | 78 | GARPIN-like |
| 23 | CG57351-01 | 79 | 80 | Centaurin Beta 2-like |
| 24 | CG57515-01 | 81 | 82 | Sorting Nexin 9-like |
| 25 | CG57568-01 | 83 | 84 | Katanin-like |
| 26 | CG57509-01 | 85 | 86 | Calpain-like |
| 27 | CG57484-01 | 87 | 88 | Keratin 18-like |
| 28 | CG57236-01 | 89 | 90 | Polycystic Kidney Disease Associated-like |
| 29 | CG57589-01 | 91 | 92 | Cholinephosphate Cytidylyltransferase-like |
| 30 | CG57558-01 | 93 | 94 | mac25/IGFBP7-like |

NOVX nucleic acids and their encoded polypeptides are useful in a variety of applications and contexts. The various NOVX nucleic acids and polypeptides according to the invention are useful as novel members of the protein families according to the presence of domains and sequence relatedness to previously described proteins. Additionally, NOVX nucleic acids and polypeptides can also be used to identify proteins that are members of the family to which the NOVX polypeptides belong.

The NOVX nucleic acids and polypeptides can also be used to screen for molecules, which inhibit or enhance NOVX activity or function. Specifically, the nucleic acids and polypeptides according to the invention may be used as targets for the identification of small molecules that modulate or inhibit, e.g., neurogenesis, cell differentiation, cell proliferation, hematopoiesis, wound healing and angiogenesis.

Additional utilities for the NOVX nucleic acids and polypeptides according to the invention are disclosed herein.

NOV1

A disclosed NOV1 nucleic acid of 872 nucleotides (also referred to as CG57413-01) encoding a novel Androgen-Regulated Short-Chain Dehydrogenase/Reductase-like protein is shown in Table 1A. An open reading frame was identified beginning with an ATG initiation codon at nucleotides 11–13 and ending with a TAA codon at nucleotides 845–847. Putative untranslated regions, if any, upstream from the initiation codon and downstream from the termination codon are underlined in Table 1A, and the start and stop codons are in bold letters.

TABLE 1A

NOV1 Nucleotide Sequence.

(SEQ ID NO:1)
CTCGTGAAGGATGGTACGTGATGCTCTTGTTTCCCTTGCCGATAGGAAGTTCTTTGCTGGTGGAGTGTGTAG

AACAAATGTGCAGCTTCCTGGCAAGGTAGTGGTGATCACTGGCGCCAACACGGGCATTGGCAAGGAGACGGC

CAGAGAGCTCGCTAGCCGAGGAGCCCGAGTCTATATTGCCTGCAGAGATGTACTGAAGGGGAGTCTGCTGC

CAGTGAAATCCGAGTGGATACAAAGAACTCCCAGGTGCTGGTGCGGAAATTGGACCTATCCGACACCAAATC

TATCCGAGCCTTTGCTGAGGGCTTTCTGGCAGAGGAAAAGCAGCTCCATATTCTGATCAACAATGCGGGAGT

AATGATGTGTCCATATTCCAAGACAGCTGATGGCTTTGAAACCCACCTGGGAGTCAACCACCTGGGCCACTT

CCTCCTCACCTACCTGCTCCTGGAGCGGCTAAAGGTGTCTGCCCCTGCACGGGTGGTTAATGTGTCCTCGGT

GGCTCACCACATTGGCAAGATTCCCTTCCACGACCTCCAGAGCGAGAAGCGCTACAGCAGGGGTTTTGCCTA

TTGCCACAGCAAGCTGGCCAATGTGCTTTTTACTCGTGAGCTGGCCAAGAGGCTCCAAGGCACCGGGGTCAC

CACCTACGCAGTGCACCCAGGCGTCGTCCGCTCTGAGCTGGTCCGGCACTCCTCCCTGCTCTGCCTGCTCTG

GCGGCTCTTCTCCCCCTTTGTCAAGACGGCACGGGAGGGGGCGCAGACCAGCCTGCACTGCGCCCTGGCTGA

TABLE 1A-continued

NOV1 Nucleotide Sequence.

GGGCCTGGAGCCCCTGAGTGGCAAGTACTTCGGTGTCTCCAAGGGCCCGAAATAACAAAACAGCTGAGCGCC

TATGGAAT

The NOV1 nucleic acid sequence maps to chromosome 14 and has 584 of 797 bases (73%) identical to a gb:GENBANK-ID:AX041971|acc:AX041971.1 mRNA from *Homo sapiens* (Sequence 1 from Patent WO0065067) (E=2.1 e$^{-84}$). Similiarity information was assessed using public nucleotide databases including all GenBank databases and the GeneSeq patent database. Chromosome information was assigned using OMIM and the electronic northern tool from Curatools to derive the the chromosomal mapping of the SeqCalling assemblies, Genomic clones, and/or EST sequences that were included in the invention.

In all BLAST alignments herein, the "E-value" or "Expect" value is a numeric indication of the probability that the aligned sequences could have achieved their similarity to the BLAST query sequence by chance alone, within the database that was searched. For example, the probability that the subject ("Sbjct") retrieved from the NOV1 BLAST analysis, e.g., mRNA from *Homo sapiens* (Sequence 1 from Patent WO0065067), matched the Query NOV1 sequence purely by chance is 2.1e$^{-84}$. The Expect value (E) is a parameter that describes the number of hits one can "expect" to see just by chance when searching a database of a particular size. It decreases exponentially with the Score (S) that is assigned to a match between two sequences. Essentially, the E value describes the random background noise that exists for matches between sequences.

The Expect value is used as a convenient way to create a significance threshold for reporting results. The default value used for blasting is typically set to 0.0001. In BLAST 2.0, the Expect value is also used instead of the P value (probability) to report the significance of matches. For example, an E value of one assigned to a hit can be interpreted as meaning that in a database of the current size one might expect to see one match with a similar score simply by chance. An E value of zero means that one would not expect to see any matches with a similar score simply by chance. See, e.g., http://www.ncbi.nlm.nih.gov/Education/BLASTinfo/. Occasionally, a string of X's or N's will result from a BLAST search. This is a result of automatic filtering of the query for low-complexity sequence that is performed to prevent artifactual hits. The filter substitutes any low-complexity sequence that it finds with the letter "N" in nucleotide sequence (e.g., "NNNNNNNN") or the letter "X" in protein sequences (e.g., "XXX"). Low-complexity regions can result in high scores that reflect compositional bias rather than significant position-by-position alignment. Wootton and Federhen, Methods Enzymol 266:554–571, 1996.

The disclosed NOV1 polypeptide (SEQ ID NO:2) encoded by SEQ ID NO:1 has 278 amino acid residues and is presented in Table 1B using the one-letter amino acid code. Signal P, Psort and/or Hydropathy results predict that NOV1 does not contain a signal peptide and is likely to be localized to the mitochondrial matrix space with a certainty of 0.4843 and to the microbody (peroxisome) with a certainty of 0.3713.

TABLE 1B

Encoded NOV1 protein sequence.

(SEQ ID NO:2)
MVRDALVSLADRKFFAGGVCRTNVQLPGKVVVITGANTGIGKETARELASRGARVYIACRDVLKGESAASEI

RVDTKNSQVLVRKLDLSDTKSIRAFAEGFLAEEKQLHILINNAGVMMCPYSKTADGFETHLGVNHLGHFLLT

YLLLERLKVSAPARVVNVSSVAHHIGKIPFHDLQSEKRYSRGFAYCHSKLANVLFTRELAKRLQGTGVTTYA

VHPGVVRSELVRHSSLLCLLWRLFSPFVKTAREGAQTSLHCALAEGLEPLSGKYFGVSKGPK

The NOV1 amino acid sequence has 197 of 260 amino acid residues (75%) identical to, and 228 of 260 amino acid residues (87%) similar to, the 318 amino acid residue ptnr:SPTREMBL-ACC:Q9NRW0 protein from *Homo sapiens* (Androgen-Regulated Short-Chain Dehydrogenase/Reductase 1) (E=4.6e$^{-105}$).

NOV1 is expressed in at least the following tissues: kidney, pancreas, retina and vulva. This information was derived by determining the tissue sources of the sequences that were included in the invention including but not limited to SeqCalling sources, public EST sources, and/or RACE sources.

Possible small nucleotide polymorphisms (SNPs) found for NOV1 are listed in Table 1C. Depth, when shown, represents the number of clones covering the region of the SNP. The putative allele frequency (PAF), when shown, is the fraction of these clones containing the SNP. A dash, when shown, means that a base is not present. The sign ">" means "is changed to." Silent, when indicated, means that the SNP did not result in an amino acid change.

TABLE 1C

SNPs

| Variant | Nucleotide Position | Base Change | Amino Acid Position | Base Change |
|---|---|---|---|---|
| 13375950 | 327 | A > G | 106 | Lys > Arg |

NOV1 has homology to the amino acid sequences shown in the BLASTP data listed in Table 1D.

The homology between these and other sequences is shown graphically in the ClustalW analysis shown in Table 1E. In the ClustalW alignment of the NOV1 protein, as well as all other ClustalW analyses herein, the black outlined amino acid residues indicate regions of conserved sequence (i.e., regions that may be required to preserve structural or functional properties), whereas non-highlighted amino acid residues are less conserved and can potentially be altered to a much broader extent without altering protein structure or function.

TABLE 1D

BLAST results for NOV1

| Gene Index/ Identifier | Protein/Organism | Length (aa) | Identity (%) | Positives (%) | Expect |
|---|---|---|---|---|---|
| gi\|12861668\|dbj\|BAB32258.1\| (AK020927) | data source: SPTR, source key: Q9NRW0, evidence: ISS~homolog to ANDROGEN-REGULATED SHORT-CHAIN DEHYDROGENASE/REDUCTASE 1~putative [*Mus musculus*] | 316 | 217/264 (82%) | 227/264 (85%) | e-117 |
| gi\|16740649\|gb\|AAH16204.1\| AAH16204 (BC016204) | Similar to RIKEN cDNA A930033N07 gene [*Mus musculus*] | 304 | 207/264 (78%) | 216/264 (81%) | e-109 |
| gi\|9622124\|gb\|AAF89632.1\| AF167438_1 (AF167438) | androgen-regulated short-chain dehydrogenase/reductase 1 [*Homo sapiens*] | 318 | 187/260 (71%) | 217/260 (82%) | e-105 |
| gi\|7705791\|ref\|NP_057110.1\| (NM_016026) | CGI-82 protein; likely ortholog of mouse cell line MC/9.IL4 derived transcript 1 [*Homo sapiens*] | 318 | 187/260 (71%) | 217/260 (82%) | e-105 |
| gi\|12835589\|dbj\|BAB23296.1\| (AK004413) | cell line MC/9.IL4 derived transcript 1~data source: MGD, source key: MGI: 102581, evidence: ISS~putative [*Mus musculus*] | 316 | 184/266 (69%) | 218/266 (81%) | e-103 |

TABLE 1E

Clustal Analysis of NOV1

1) NOV1 (SEQ ID NO:2)
2) gi 12861668|dbj|BAB32258.1| (AK020927) data source:SPTR, source key:Q9NRW0, evidence:ISS~homolog to ANDROGEN-REGULATED SHORT-CHAIN DEHYDROGENASE 1~putative [*Mus musculus*] (SEQ ID NO:95)
3) gi'16740649|gb|AAH16204.1|AAH16204 (BC016204) Similar to RIKEN cDNA A930033N07 gene [*Mus musculus*] (SEQ ID NO:96)
4) gi|9622124|gb|AAF89632.1|AF167438_1 (AF167438) androgen-regulated short-chain dehydrogenase/reductase 1 [*Homo sapiens*]] (SEQ ID NO:97)
5) gi.7705791|refNP_057110.1| (NM_016026) CGI-82 protein; likely ortholog of mouse cell line MC/9.1L4 derived transcript 1 [*Homo sapiens*] (SEQ ID NO:98)
6) gi.12835589|dbj|BAB23296.1| (AK004413) cell line MC/9.IL4 derived transcript 1~data source:MGD, source key: MGI: 102581,evidence: ISS~putative [*Mus musculus*] (SEQ ID NO:99)

TABLE 1E-continued

Clustal Analysis of NOV1

```
                10        20        30        40        50        60        70
              ....|....|....|....|....|....|....|....|....|....|....|....|....|....|
NOV1          ---------------MVRDALVSLADRKFFAGGVCRINVQLPGKVVVITGANTGIGKETARELASRGARVY
gi|12861668|  ---MLFILVLLTSFLSILYLTAPSIRKFFAGGVCTINVQIPGKVVVITGANTGIGKETARELARRGARVY
gi|16740649|  ---MLFILVLLTSFLSILYLTAPSIRKFFAGGVCTINVQIPGKVVVITGANTGIGKETARELARRGARVY
gi|9622124|   MVEIMFPLLLL-LPFLLYMAAPQIRMMLSSGVCTSTVQLPGKVVVVTGANTGIGKETAKELADRGARVY
gi|7705791|   MVEIMFPLLLL-LPFLLYMAAPQIRMMLSSGVCTSTVQLPGKVVVVTGANTGIGKETAKELADRGARVY
gi|12835589|  ----MFGFLLLLSLPFILYLVTPKIRKMLSSGVCTSNVQLPGKVAIVTGANTGIGKETAKDLARGARVY 80        90       100       110       120       130       140
              ....|....|....|....|....|....|....|....|....|....|....|....|....|....|
NOV1          IACRDVLKGESAASEIFVDIKNSQVLVRKLDLSDTKSIRAFAEGFLAEEKQLELLINNAGVMMCPYSKTA
gi|12861668|  IACRDVLKGESAASEIFADIKNSQVLVRKLDLSDTKSIRAFAERFLAEEKKLDLLINNAGVMMCPYSKTT
gi|16740649|  IACRDVLKGESAASEIFADIKNSQVLVRKLDLSDTKSIRAFAERFLA------------GVMMCPYSKTT
gi|9622124|   LACRDVEKGELVAKEIQTTIGNQQVLVRKLDLSDTKSIRAFAKGFLAEEKHLEVLINNAGVMMCPYSKTA
gi|7705791|   LACRDVEKGELVAKEIQTTIGNQQVLVRKLDLSDTKSIRAFAKGFLAEEKHLEVLINNAGVMMCPYSKTA
gi|12835589|  LACRDVDKGELAAREIIAVIGNSQVFVRKLDIADTKSIRAFAKDFLAEEKHLEVLINNAGVMMCPYSKTA 150       160       170       180       190       200       210
              ....|....|....|....|....|....|....|....|....|....|....|....|....|....|
NOV1          DGFFTHLGVNHLGHFLLTYLLLERLKVSAPARVVNVSSVAHHICKIPFHDLQSEKRYSRGFAYCHSKLAN
gi|12861668|  DGFETHFGVNHLGHFLLTYLLLERLKESAPARVVNLSSIAHLICKIRFHDLQGQKRYCSAFAYCHSKLAN
gi|16740649|  DGFETHFGVNHLGHFLLTYLLLERLKESAPARVVNLSSIAHLICKIRFHDLQGQKRYCSAFAYCHSKLAN
gi|9622124|   DGFEMHIGVNHLGHFLLTILLLERLKESAPSRIVNVSSEAHHICRIHFHNLQGEKFYNACLAYCHSKLAN
gi|7705791|   DGFEMHIGVNHLGHFLLTILLLERLKESAPSRIVNVSSEAHHICRIHFHNLQGEKFYNACLAYCHSKLAN
gi|12835589|  DGFEMHIGVNHLGHFLLTILLLERLKESAPSRIVNISSEGHHICRIHFHNLQGEKFYSNCLAYCHSKLAN 220       230       240       250       260       270       280
              ....|....|....|....|....|....|....|....|....|....|....|....|....|....|
NOV1          VLFTRELAKRLCGTGVTTYAVHPGVVRSELVRHSSLLCLLWRLFSPEVKTAREGAQTSLHCALAEGLEPI
gi|12861668|  ILFTRELAKRLCGTGVTAMAVHPGVVLSEITRNSYLLCLLWRLFSPFFKSTSQGAQTSLHCALAEDLEPI
gi|16740649|  ILFTRELAKRLCGTGVTAMAVHPGVVLSEITRNSYLLCLLWRLFSPFFKSTSQGAQTSLHCALAEDLEPI
gi|9622124|   ILFTQELARRLKGSGVTTYSVHPGTVQSELVRHSSFMRWMWLFSFFIKTPQQGAQTSLHCALTEGLEII
gi|7705791|   ILFTQELARRLKGSGVTTYSVHPGTVQSELVRHSSFMRWMWLFSFFIKTPQQGAQTSLHCALTEGLEII
gi|12835589|  ILFTKELAKRLKGSGVTTYSVHPGTVHSEITRSSLMRWLWQLFPVFIKTPQEGAQTSLYCALTEGLESI 290       300       310       320
              ....|....|....|....|....|....|....|....|
NOV1          SGKYFG------VSKGPK---------------------
gi|12861668|  SGKYFSDCKRMWVSSRARNKKTAERLWNVSCELLGIQWE-
gi|16740649|  SGKYFSDCKRMWVSSRARNKKTAERLWNVSCELLGIQWE-
gi|9622124|   SGNHFSDCHVAWVSVQARNRTIARRLWDVSCDLLGLPID-
gi|7705791|   SGNHFSDCHVAWVSAQARNRTIARRLWDVSCDLLGLPID-
gi|12835589|  SGSHFSDCQLAWVSYQGRNRIIARRLWDVSCDLLGLPVDW
```

The presence of identifiable domains in NOV1, as well as all other NOVX proteins, was determined by searches using software algorithms such as PROSITE, DOMAIN, Blocks, Pfam, ProDomain, and Prints, and then determining the Interpro number by crossing the domain match (or numbers) using the Interpro website (http:www.ebi.ac.uk/interpro). DOMAIN results for NOV1, as disclosed in Table 1F, were collected from the Conserved Domain Database (CDD) with Reverse Position Specific BLAST analyses. This BLAST analysis software samples domains found in the Smart and Pfam collections. For Table 1F and all successive DOMAIN sequence alignments, fully conserved single residues are indicated by black shading or by the sign (|) and "strong" semi-conserved residues are indicated by grey shading or by the sign (+). The "strong" group of conserved amino acid residues may be any one of the following groups of amino acids: STA, NEQK, NHQK, NDEQ, QHRK, MILV, MILF, HY, FYW.

Table 1F lists the domain description from DOMAIN analysis results against NOV1. This indicates that the NOV1 sequence has properties similar to those of other proteins known to contain these domains.

TABLE 1F

Domain Analysis of NOV1 gnl|Pfam|pfam00106, adh_short, short chain dehydrogenase. This family
contains a wide variety of dehydrogenases. (SEQ ID NO:100)
CD-Length = 249 residues, 99.6% aligned
Score = 124 bits (310), Expect = 9e-30

```
Query:  27  PGKVVVITGANTGIGKETARELASRGARVYIACRDVLKGESAASEIRVDTKNSQVLVRKL  86
                |||  ++||| ++|||   |+ ||   ||+| +   |  |+||         +  |  +|
Sbjct:   1  TGKVALVTGASSGIGLAIAKRLAEEGAKVVVVDRREEKAEAAAELKA--ELGDRALFIQL  58

Query:  87  DLSDTKSIRAFAEGFLAEEKQLHILINNAGVM--MCPYSKTADGFETHLGVNHLGHFLLT  144
                |++| +||+|        + |  +| +|+|||||++      |+  +  +| + ||   | ||||
```

TABLE 1F-continued

Domain Analysis of NOV1

```
Sbjct:   59 DVTDEESIKAAVAQAVEELGRLDVLVNNAGILGPGEPFELSEDDWERVIDVNLTGVFLLT 118

Query:  145 YLLLERLKVSAPARVVNVSSVAHHIGKIPFHDLQSEKRYSRGFAYCHSKLANVLFTRELA 204
              +|   +    +  |+||+||||    +                    |  |  ||| ||
Sbjct:  119 QAVLPHMLKRSGGRIVNISSVAGLVP------------SPGLSAYSASKAAVVGFTRSLA 166

Query:  205 KRLQGTGVTTYAVHPGVVRSELV-RHSSLLCLLWRLFSPFVK---------TAREGAQTS 254
              |   |+   |+ ||  |  +++     |+       |             |  |  |
Sbjct:  167 LELAPHGIRVANAIAPGGVDTDMTKALRSIAPADPELVERITSALVPLGRYGTPEEVANAV 226

Query:  255 LHCALAEGLEPLSGKYFGVSKG                                       276
              | |        ++|+    |  |
Sbjct:  227 LFLASDGASYSVTGQTLNVDGG                                       248
```

Most mammalian hydroxysteroid dehydrogenases known thus far belong to the protein superfamilies of short-chain dehydrogenases/reductases (SDR) and aldo-keto reductases (AKR). Whereas members of the AKR family are soluble, cytoplasmic enzymes, SDR-type hydroxysteroid dehydrogenases are also located to other subcellular compartments, i.e. endoplasmic reticulum, mitochondria or peroxisomes. Differential localization might play an important role in influencing the reaction direction of hydroxy dehydrogenase/oxo reductase pathways by determining the available nucleotide cofactor pool. Targeting signals for different subcellular organelles in human hydroxysteroid dehydrogenases have been identified, however, in several enzymes localization signals remain to be determined. The short-chain dehydrogenases/reductases family (SDR) is a very large family of enzymes, most of which are known to be NAD- or NADP-dependent oxidoreductases. As the first member of this family to be characterized was *Drosophila* alcohol dehydrogenase, this family used to be called 'insect-type', or 'short-chain' alcohol dehydrogenases. Most members of this family are proteins of about 250 to 300 amino acid residues. Most dehydrogenases possess at least 2 domains, the first binding the coenzyme, often NAD, and the second binding the substrate. This latter domain determines the substrate specificity and contains amino acids involved in catalysis. Little sequence similarity has been found in the coenzyme binding domain although there is a large degree of structural similarity, and it has therefore been suggested that the structure of dehydrogenases has arisen through gene fusion of a common ancestral coenzyme nucleotide sequence with various substrate specific domains.

The NOV1 nucleic acid of the invention encoding a Androgen-Regulated Short-Chain Dehydrogenase/Reductase-like protein includes the nucleic acid whose sequence is provided in Table 1A, or a fragment thereof. The invention also includes a mutant or variant nucleic acid any of whose bases may be changed from the corresponding base shown in Table 1A while still encoding a protein that maintains its Androgen-Regulated Short-Chain Dehydrogenase/Reductase-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 27% of the residues may be so changed.

The NOV1 protein of the invention includes the Androgen-Regulated Short-Chain Dehydrogenase/Reductase-like protein whose sequence is provided in Table 1B. The invention also includes a mutant or variant protein any of whose residues may be changed from the corresponding residue shown in Table 1B while still encoding a protein that maintains its Androgen-Regulated Short-Chain Dehydrogenase/Reductase-like activities and physiological functions, or a functional fragment thereof. In the mutant or variant protein, up to about 25% of the bases may be so changed.

The NOV1 nucleic acids and proteins of the invention are useful in potential diagnostic and therapeutic applications implicated in various diseases and disorders described below and/or other pathologies. For example, the compositions of the present invention will have efficacy for treatment of patients suffering from: diabetes, autoimmune disease, renal artery stenosis, interstitial nephritis, glomerulonephritis, polycystic kidney disease, systemic lupus erythematosus, renal tubular acidosis, IgA nephropathy, hypercalceimia, Lesch-Nyhan syndrome, Von Hippel-Lindau (VHL) syndrome, pancreatitis, obesity, tuberous sclerosis, fertility and other diseases, disorders and conditions of the like.

NOV1 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV1 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV2

NOV2 includes two novel Aryl-acylamidase-like proteins disclosed below. The disclosed proteins have been named NOV2a and NOV2b.

NOV2a

A disclosed NOV2a nucleic acid of 1527 nucleotides (also referred to as CG57391-01) encoding a novel Aryl-acylamidase-like protein is shown in Table 2A. An open reading frame was identified beginning with an ATG initiation codon at nucleotides 37–39 and ending with a TAA codon at nucleotides 1240–1242. Putative untranslated regions, if any, upstream from the initiation codon and downstream from the termination codon are underlined in Table 2A, and the start and stop codons are in bold letters.

TABLE 2A

NOV2a nucleotide sequence.

(SEQ ID NO:3)

TCTCAGTACTGTGAAGAAGCTGGAAAAAGGGATATTATGGGGCTAAAAGCTCTCTGTTTGGGGCTGCTTTGT

GTTCTTTTTGTCTCTCATTTTTACACACCCATGCCAGACAACATTGAAGAAAGCTGGAAAATAATGGCCTTG

GATGCCATCGCTAAAACTTTGTTCTTACAGGCTATGTGTTTTGAAAATATGCGTATTATGAGATATGAAGAG

TTTATATCCATGATATTCAGGCTGGATTATACCCAACCACTTTCAGATGAATACATCACAGTGACTGATACA

ACATTTGTTGACATTCCAGTACGATTGTACTTGCCAAAAAGAAAGTCAGAAACCCGAAGGCGAGCTGTGATA

TATTTTCATGGTGGTGGTTTTTGTTTTGGAAGTTCCAAACAGAGGGCTTTTGACTTCCTGAATAGATGGACG

GCAAACACGCTTGATGCTGTTGTTGTAGGCGTGGACTATAGGCTGGCTCCTCAACACCACTTTCCTGCTCAG

TTTGAAGATGGCCTTGCTGCAGTCAAATTTTTTCTTTTGGAAAAAATTCTTACAAAATATGGAGTGGATCCC

ACCCGAATCTGCATTGCGGGAGACAGTTCTGGGGGCAATTTAGCAACAGCGGTCACTCAACAGGTGCAGAAT

GATGCTGAAATAAAACATAAAATCAAGATGCAAGTCTTACTTTACCCTGGCTTACAGATAACAGATTCTTAT

TTGCCATCTCACCGAGAAAATGAGCATGGTATAGTTTTGACCAGGGATGTAGCCATAAAACTCGTGAGCTTA

TATTTCACCAAGGATGAAGCACTTCCCTGGGCAATGAGAAGAAACCAACACATGCCTCTGGAGTCAAGACAT

CTGTTTAAGTTTGTTAACTGGAGTATTCTTCTTCCTGAGAAGTATAGAAAAGACTATGTATATACTGAACCA

ATTCTTGGAGGACTTAGTTATTCATTGCCAGGACTTACAGACAGCAGAGCATTACCCTTGTTGGCCAATGAT

TCTCAGTTACAGAATTTGCCACTAACCTATATTCTTACTTGTCAACATGATCTCTTAAGAGATGATGGACTT

ATGTATGTTACAAGACTTCGAAATGTTGGAGTCCAAGTTGTTCATGAACATATTGAGGATGGAATTCATGGA

GCTTTATCATTCATGACTTCACCATTTTATTTACGTCTAGGTCTTAGGATAAGAGATATGTATGTAAGTTGG

CTGGATAAGAATTTATAAATATGTGATGTGTATGTATAGCCCTTACATAGTGGATTGTAATTTGTGATATTT

TGTGGTTTTGGAGCAAAGAACAATGTCATTTGAGTTATCTAAATCTACATTTGCAACATTTGTAGCAGTTAA

TGTGTGTCCTTGAAGAGTTATTAAATTTTCTGACTTGCAGACCCTGAATATGTAAAATGTATGTAATCCTGC

CTATTTTCTCCTTACTTATAATTTATTATAATTATGTTGGTTCTAATAAGAACCAATGCTTATTAAAGTTGA

GAAATAAGAGTGGTT

The disclosed NOV2a nucleic acid sequence, localized to chromsome 3, has 770 of 1205 bases (63%) identical to a gb:GENBANK-ID:HUMARDE|acc:L32179.1 mRNA from *Homo sapiens* (Human arylacetamide deacetylase mRNA, complete cds) (E=1.3e$^{-75}$).

A NOV2a polypeptide (SEQ ID NO:4) encoded by SEQ ID NO:3 has 401 amino acid residues and is presented using the one-letter code in Table 2B. Signal P, Psort and/or Hydropathy results predict that NOV2a contains a signal peptide and is likely to be localized to the cytoplasm with a certainty of 0.8524 or extracellularly with a certainty of 0.7714. The most likely cleavage site for a NOV2a peptide is between amino acids 18 and 19: VSH-FY.

TABLE 2B

Encoded NOV2a protein sequence.

(SEQ ID NO:4)

MGLKALCLGLLCVLFVSHFYTPMPDNIEESWKIMALDAIAKTLFLQAMCFENMRIMRYEEFISMIFRLDYTQ

PLSDEYITVTDTFFVDIPVRLYLPKRKSETRRRAVIYFHGGGFCFGSSKQRAFDFLNRWTANTLDAVVVGVD

YRLAPQHHFPAQFEDGLAAVKFFLLEKILTKYGVDPTRICIAGDSSGGNLATAVTQQVQNDAEIKHKIKMQV

LLYPGLQITDSYLPSHRENEHGIVLTRDVAIKLVSLYFTKDEALPWAMRRNQHMPLESRHLFKFVNWSILLP

EKYRKDYVYTEPILGGLSYSLPGLTDSRALPLLANDSQLQNLPLTYILTCQHDLLRDDGLMYVTRLRNVGVQ

VVHEHIEDGIHGALSFMTSPFYLRLGLRIRDMYVSWLDKNL

The NOV2a amino acid sequence has 205 of 401 amino acid residues (51%) identical to, and 282 of 401 amino acid residues (70%) similar to, the 399 amino acid residue ptnr:pir-id:A53856 protein from human (aryl-acylamidase (EC 3.5.1.13)) (E=2.7e$^{-107}$).

The disclosed NOV2a is expressed in at least the following tissues: heart, uterus and colon. This information was derived by determining the tissue sources of the sequences that were included in the invention including but not limited to SeqCalling sources, Public EST sources, Literature sources, and/or RACE sources.

NOV2b

A disclosed NOV2b nucleic acid of 1324 nucleotides (also referred to as CG57391-02) encoding a novel Aryl-acylamidase-like protein is shown in Table 2C. An open reading frame was identified beginning with an ATG initiation codon at nucleotides 34–36 and ending with a TAA codon at nucleotides 1237–1239. Putative untranslated regions, if any, upstream from the initiation codon and downstream from the termination codon are underlined in Table 2C, and the start and stop codons are in bold letters.

gb:GENBANK-ID:HUMARDE|acc:L32179.1 mRNA from *Homo sapiens* (Human arylacetamide deacetylase mRNA, complete cds) (E=1.4e$^{-76}$).

A NOV2b polypeptide (SEQ ID NO:6) encoded by SEQ ID NO:5 has 401 amino acid residues and is presented using the one-letter code in Table 2D. Signal P, Psort and/or Hydropathy results predict that NOV2b contains a signal peptide and is likely to be localized to the cytoplasm with a certainty of 0.8524 or extracellularly with a certainty of 0.7714. The most likely cleavage site for a NOV2b peptide is between amino acids 18 and 19: VSH-FY.

TABLE 2C

NOV2b nucleotide sequence.

(SEQ ID NO:5)
CAGTACTGTGAAGAAGCTGGAAAAAGGGATATTATGGGGCTAAAAGCTCTCTGTTTGGGGCTGCTTTGTGTT

CTTTTTGTCTCTCATTTTTACACACCCATGCCAGACAACATTGAAGAAAGCTGGAAAATAATGGCCTTGGAT

GCCATCGCTAAAACTTGTACATTTACGGCTATGTGTTTTGAAAATATGCGTATTATGAGATATGAAGAGTTT

ATATCCATGATATTCAGGCTGGATTATACCCAACCACTTTCAGATGAATACATCACAGTGACTGATACAACA

TTTGTTGACATTCCAGTACGATTGTACTTGCCAAAAAGAAAGTCAGAAACCCGAAGGCGAGCTGTGATATAT

TTTCATGGTGGTGGTTTTTGTTTTGGAAGTTCCAAACAGAGGGCTTTTGACTTCCTGAATAGATGGACGGCA

AACACGCTTGATGCTGTTGTTGTAGGCGTGGACTATAGGCTGGCTCCTCAACACCACTTTCCTGCTCAGTTT

GAAGATGGCCTTGCTGCAGTCAAATTTTTTCTTTTGGAAAAAATTCTTACAAAATATGGAGTGGATCCCACC

CGAATCTGCATTTCGGGAGACAGTTCTGGGGGCAATTTAGCAACAGCGGTCACTCAACAGGTGCAGAATGAT

GCTGAAATAAAACATAAAATCAAGATGCAAGTCTTACTTTACCCTGGCTTACAGATAACAGATTCTTATTTG

CCATCTCACCGAGAAAATGAGCATGGTATAGTTTTGACCAGGGATGTAGCCATAAAACTCGTGAGCTTATAT

TTCACCAAGGATGAAGCACTTCCCTGGGCAATGAGAAGAAACCAACACATGCCTCTGGAGTCAAGACATCTG

TTTAAGTTTGTTAACTGGAGTATTCTTCTTCCTGAGAAGCATAGAAAAGACTATGTATATACTGAACCAATT

CTTGGAGGACTTAGTTATTCATTGCCAGGACTTACAGACAGCAGAGCATTACCCTTGTTGGCCAATGATTCT

CAGTTACAGAATTTGCCACTAACCTATATTCTTACTTGTCAACATGATCTCTTAAGAGATGATGGACTTATG

TATGTTACAAGACTTCGAAATGTTGGAGTCCAAGTTGTTCATGAACATATTGAGGATGGAATTCATGGAGCT

TTATCATTCATGACTTCACCATTTTATTTACGTCTAGGTCTTAGGATAAGAGATATGTATGTAAGTTGGCTG

GATAAGAATTTATAAATATGTGATGTGTATGTATAGCCTTTACATAGTGGATTGTAATTTGTGATATTTTGT

GGTTTTGGAGCAAAGAACAATGTCATTT

The disclosed NOV2b nucleic acid sequence, localized to chromsome 3, 805 of 1261 bases (63%) identical to a

TABLE 2D

Encoded NOV2b protein sequence.

(SEQ ID NO:6)
MGLKALCLGLLCVLFVSHFYTPMPDNIEESWKIMALDAIAKTCTFTAMCFENMRIMRYEEFISMIFRLDYTQ

TABLE 2D-continued

Encoded NOV2b protein sequence.

PLSDEYITVTDTTFBDIPVRLYLPKRKSETRRRAVIYFHGGGFCFGSSKQRAFDFLNRWTANTLDAVVVGVD

YRLAPQHHFPAQFEDGLAAVKFFLLEKILTKYGVDPTRICISGDSSGGNLATAVTQQVQNDAEIKHKIKMQV

LLYPGLQITDSYLPSHRENEHGIVLTRDVAIKLVSLYFTKDEALPWAMRRNQHMPLESRHLFKFVNWSILLP

EKHRKDYVYTEPILGGLSYSLPGLTDSRALPLLANDSQLQNLPLTYILTCQHDLLRDDGLMYVTRLRNVGVQ

VVHEHIEDGIHGALSFMTSPFYLRLGLRIRDMYVSWLDKNL

The NOV2b amino acid sequence has 206 of 401 amino acid residues (51%) identical to, and 280 of 401 amino acid residues (69%) similar to, the 399 amino acid residue ptnr:pir-id:A53856 protein from human (aryl-acylamidase (EC 3.5.1.13)) (E=$3.9e^{-107}$).

The disclosed NOV2b is expressed in at least the following tissues: heart, uterus and colon. This information was derived by determining the tissue sources of the sequences that were included in the invention including but not limited to SeqCalling sources, Public EST sources, Literature sources, and/or RACE sources.

Possible small nucleotide polymorphisms (SNPs) found for NOV2a are listed in Table 2E.

TABLE 2E

SNPs

| Variant | Nucleotide Position | Base Change | Amino Acid Position | Base Change |
|---|---|---|---|---|
| 13377048 | 179 | T > A | 48 | Met > Lys |
| 13377047 | 839 | A > T | 268 | Gln > Leu |
| 13377046 | 853 | G > A | 273 | Glu > Lys |
| 13377045 | 907 | T > C | 291 | Tyr > His |
| 13377044 | 1044 | T > C | Silent | N/A |
| 13377043 | 1140 | T > C | Silent | N/A |
| 13377042 | 1210 | A > G | 392 | Met > Val |
| 13377041 | 1266 | C > T | Silent | N/A |

NOV2a and NOV2b are very closely homologous as is shown in the amino acid alignment in Table 2F.

TABLE 2F

Amino Acid Alignment of NOV2a and NOV2b

```
            10        20        30        40        50        60        70
             |         |         |         |         |         |         |
NOV2a  MGLKALCLGLLCVLFVSEFYTPMPDNIEESWKIMALDAIAKTLFLQAMCFENMRIMRYEEFISMIFRLDY
NOV2b  MGLKALCLGLLCVLFVSEFYTPMPDNIEESWKIMALDAIAKTCTFTAMCFENMRIMRYEEFISMIFRLDY 80        90       100       110       120       130       140
             |         |         |         |         |         |         |
NOV2a  TQPLSDEYITVTDTTFVDIPVRLYLPKRKSETRRRAVIYFHGGGFCFGSSKQRAFDFLNRWTANTLDAVV
NOV2b  TQPLSDEYITVTDTTFVDIPVRLYLPKRKSETRRRAVIYFHGGGFCFGSSKQRAFDFLNRWTANTLDAVV 150       160       170       180       190       200       210
             |         |         |         |         |         |         |
NOV2a  VGVDYRLAPQHHFPAQFEDGLAAVKFFLLEKILTKYGVDPTRICIAGDSSGGNLATAVTQQVQNDAEIKK
NOV2b  VGVDYRLAPQHHFPAQFEDGLAAVKFFLLEKILTKYGVDPTRICISGDSSGGNLATAVTQQVQNDAEIKK 220       230       240       250       260       270       280
             |         |         |         |         |         |         |
NOV2a  KIKMQVLLYPGLQITDSYLPSHRENEHGIVLTRDVAIKLVSLYFTKDEALPWAMRENQHMPLESRHLFKP
NOV2b  KIKMQVLLYPGLQITDSYLPSHRENEHGIVLTRDVAIKLVSLYFTKDEALPWAMRENQHMPLESRHLFKP 290       300       310       320       330       340       350
             |         |         |         |         |         |         |
NOV2a  VNWSILLPEKYRKDYVYTEPILGGLSYSLPGLTDSRALPLLANDSQLQNLPLTYILTCQHDLLRDDGLMY
NOV2b  VNWSILLPEKHRKDYVYTEPILGGLSYSLPGLTDSRALPLLANDSQLQNLPLTYILTCQHDLLRDDGLMY 360       370       380       390       400
             |         |         |         |         |.
NOV2a  VTRLRNVGVQVVHEHIEDGIHGALSEMTSPFYLRLGLRIRDMYVSWLDKNL
NOV2b  VTRLRNVGVQVVHEHIEDGIHGALSEMTSPFYLRLGLRIRDMYVSWLDKNL
```

Homologies to any of the above NOV2 proteins will be shared by the other NOV2 proteins insofar as they are homologous to each other as shown above. Any reference to NOV2 is assumed to refer to both of the NOV2 proteins in general, unless otherwise noted.

NOV2a has homology to the amino acid sequences shown in the BLASTP data listed in Table 2G.

TABLE 2G

BLAST results for NOV2a

| Gene Index/ Identifier | Protein/ Organism | Length (aa) | Identity (%) | Positives (%) | Expect |
|---|---|---|---|---|---|
| gi\|11433103\|ref\|XP_003002.1\| (XM_003002) | arylacetamide deacetylase [Homo sapiens] | 399 | 201/386 (52%) | 272/386 (70%) | e−113 |
| gi\|4557227\|ref\|NP_001077.1\| (NM_001086) | arylacetamide deacetylase [Homo sapiens] | 399 | 200/386 (51%) | 270/386 (69%) | e−112 |
| gi\|75135571\|pir\|\|A58922 | esterase/N-deacetylase (EC 3.5.1.-), 50K hepatic [Oryctolagus cuniculus] | 398 | 199/386 (51%) | 264/386 (67%) | e−111 |
| gi\|18043412\|gb\|AAH19999.1\| AAH19999 (BC019999) | arylacetamide deacetylase (esterase) [Mus musculus] | 398 | 200/386 (51%) | 262/386 (67%) | e−105 |
| gi\|13184050\|ref\|NP_075872.1\| (NM_023383) | arylacetamide deacetylase (esterase) [Mus musculus] | 398 | 199/386 (51%) | 261/386 (67%) | e−105 |

The homology of these sequences is shown graphically in the ClustalW analysis shown in Table 2H.

TABLE 2H

ClustalW Analysis of NOV2a

1) NOV2a (SEQ ID NO:4)
2) gi 11433103|ref|XP_003002.1| (XM_003002) arylacetamide deacetylase [Homo sapiens] (SEQ ID NO:101)
2) gi|4557227|refNP_001077.1| (NM_001086) arylacetamide deacetylase [Homo sapiens] (SEQ ID NO:102)
3) gi|7513557|pir..A58922 esterase/N-deacetylase (EC 3.5.1.-), 50K hepatic [Orycotagus cuniculus] (SEQ ID NO:103)
4) gi 18043412|gb AAH19999.1 AAH19999 (BC019999) arylacetamide deacetylase (esterase) [Mus musculus] (SEQ ID NO:104)
5) gi 13184050|ref|NP_075872.1| (NM_023383) arylacetamide deacctylase (esterase) [Mus musculus] (SEQ ID NO:105)

```
                         10         20         30         40         50         60         70
                 ....|....|....|....|....|....|....|....|....|....|....|....|....|....|
NOV2a            MGLKALCLGLICVLFVSHPYTEMPDNIEDSWRIMALDAIAKTLFLQAMCFENMRIMRVEEFISMIFRLDY
gi|11433103|     MGRKSIYLLIVGILHAYYEYTPLPDNVEEPWRMWINAHLKTIQNLATEVELLGIHHFMDSFKVVGSFDE
gi|4557227|      MGRKSIYLLIVGILHAYYEYTPLPDNVEEPWRMWINAHLKTIQNLATEVELHGSSIFMDSFKVVGSFDE
gi|7513557|      -GVKTVLLLIVGVLGAYYWYTPLPDNIEEPWRLWVNAHMKTLTNLALEAEYLGSSIFMNTVKFLTSFQE
gi|18043412|     MG-KTISLLISVVLVAYYEMIPLPDAIEEPWKVWETAFVKIGTDLASEGELLGISHFMEFIDLLMSFQE
gi|13184050|     MG-KTISLLISVVLVAYYEYIPLPDAIEEPWKVWETAFVKIGTDLASEGELLGISHFMEFIDLLMSFQE 80         90        100        110        120        130        140
                 ....|....|....|....|....|....|....|....|....|....|....|....|....|....|
NOV2a            TQELSDEYITVTETFVDIPVRLMLPKRKSETRRRAVIMFHGGGECFGSSKQRAFDFLNRWTANTLDAVV
gi|11433103|     VPPTSDENVTVTETKENNILVRVYVPKRKSEALRRGLFYIHGGGWCVGSAALSGYDLLSRWTADRLDAVV
gi|4557227|      VPPTSDENVTVTETKFNNILVRVYVPKRKSEALRRGLFYIHGGGWCVGSAALSGYDLLSRWTADRLDAVV
gi|7513557|      VPPTSDENVTVTETTFNNVPVRVYVPKRKSNTLRRGLFYIHGGGWCVGSAALSGYDLLSRRTADRLDVVV
gi|18043412|     VPPTSDEHVTVMETAFDSVPVRRYIPKRKSMTLRRGLFYIHGGGWCLGSAAHFSYDTLSRWTAHKLDAVV
gi|13184050|     VPPTSDEHVTVMETAFDSVPVREYIPKRKSMALRRGLFYIHGGGWCLGSAAHFSYDTLSRWTAHKLDAVV
```

TABLE 2H-continued

ClustalW Analysis of NOV2a

```
               150       160       170       180       190       200       210
           ....|....|....|....|....|....|....|....|....|....|....|....|....|
NOV2a      VGVDYRLAPQHHFPAQFEDGLAAVKFFLLEKILTKYGVDPTRICTAGDSSGGNLATAVTQQVQNDAEIKH
gi|11433103| VSTNYRLAPKYHFPIQFEDVYNALRWFLRKKVLAKYGVNPERICISGDSAGGNLAAAVTQQLEDDPDVKI
gi|4557227|  VSTNYRLAPKYHFPIQFEDVYNALRWFLRKKVLAKYGVNPERICISGDSAGGNLAAAVTQQLEDDPDVKI
gi|7513557|  VSTNYRLAPKYHFPIQFEDVYDALKWFLRQDVLEKYGVDPERVCVSGDSAGGNLAAAVAQQLIKDPDVKI
gi|18043412| VSTDYGLAPKHHFPRQFEDVYRSLRWFLQRDVLEKYGVDPRRVCVSGDSAGGNLAAAVTQQLIQDPDVKI
gi|13184050| VSTDYGLAPKHHFPRQFEDVYRSLRWFLQRDVLEKYGVDPRRVCVSGDSAGGNLAAAVTQQLIQDPDVKI 220       230       240       250       260       270       280
           ....|....|....|....|....|....|....|....|....|....|....|....|....|
NOV2a      KIKMQVLLYPGLQITDSYLPSHRENEHGIVLTRDVAIKLVSLYFTKDEALPWAMRRNQHMPLESRHLFKF
gi|11433103| KLKIQSLIYPALQPLDVDLPSYQENSNFLFLSKSLMVRFWSEYFTTDRSLEKAMLSRQHVPVESSHLFKF
gi|4557227|  KLKIQSLIYPALQPLDVDLPSYQENSNFLFLSKSLMVRFWSEYFTTDRSLEKAMLSRQHVPVESSHLFKF
gi|7513557|  KLKTQSLIYPALQTLDMDLPSYRENAQFPTLSKSEMVRLWSEYFTSDRSLEKAMLLNQHVPVESSHLFKF
gi|18043412| KLKVQALIYPALQALDTNVPSQQEGSHFPVLTRSLMVRFWSEYFTTDRGLEKAMLLNQHVPMESSHLLQF
gi|13184050| KLKVQALIYPALQALDTNVPSQQEGSHFPVLTRSLMVRFWSEYFTTDRGLEKAMLLNQHVPMESSHLLQF 290       300       310       320       330       340       350
           ....|....|....|....|....|....|....|....|....|....|....|....|....|
NOV2a      VNWSILLPEKYRKDYVYTEPILGG--LSYSLPGLTDSRALPLLANDSQLQNLPLTYIFTCQHDLLRDDGL
gi|11433103| VNWSSLLPERFIKGHVYNNPNYGSSELAKKYPGFIDVRAAPLLADDNKLRGLPLTYVITCQYDLLRDDGL
gi|4557227|  INWSSLLPERFIKGHVYNNPNYGSSELAKKYPGFIDVRAAPLLADDNKLRGLPLTYVITCQYDLLRDDGL
gi|7513557|  TNWSSLLPERIKKGHVYNTPTYGSSELARKYPGFIDVRAAPLLADDAQLRGFPLTYVITCQYDVLRDDGV
gi|18043412| VNWSSLLPERYKKSPVYKNPTPGSSELAQKYPGFIDVKACPLLANDNILHHLPKTYIITCQYDVLRDDGL
gi|13184050| VNWSSLLPERYKKSPVYKNPTPGSSELAQKYPGFIDVKACPLLANDNILHHLPKTYIITCQYDVLRDDGL 360       370       380       390       400
           ....|....|....|....|....|....|....|....|....|...
NOV2a      MYVTRLRNVGVQVVHEHREDGIHGALSEMTSPFYLKLGLRIRDMYISWLDKNL
gi|11433103| MYVTRLRNTGVQVTHNHVEDGFHGAFSELG----LKISHRLINQYIEWLKENL
gi|4557227|  MYVTRLRNTGVQVTHNHVEDGFHGAFSELG----LKISHRLINQYIEWLKENL
gi|7513557|  MYVTRLRNAGVQVTHNHREDGFHGALSYNG----FKTGYRVEKQYFEWLRENM
gi|18043412| MYVKRLQNVGVHVTHHHVEDGFHGTFSFPG----LKLSERMKNQYLSWLIKNL
gi|13184050| MYVKRLQNVGVHVTHHHVEDGFHGTFSFPG----LKLSERMKNQYLSWLIKNL
```

The NOV2 nucleic acid of the invention encoding a Aryl-acylamidase-like protein includes the nucleic acid whose sequence is provided in Tables 2A and 2C, or a fragment thereof. The invention also includes a mutant or variant nucleic acid any of whose bases may be changed from the corresponding base shown in Tables 2A and 2C while still encoding a protein that maintains its Aryl-acylamidase-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 37% of the residues may be so changed.

The NOV2 protein of the invention includes the Aryl-acylamidase-like protein whose sequence is provided in Tables 2B and 2D. The invention also includes a mutant or variant protein any of whose residues may be changed from the corresponding residue shown in Tables 2B and 2D while still encoding a protein that maintains its Aryl-acylamidase-like activities and physiological functions, or a functional fragment thereof. In the mutant or variant protein, up to about 49% of the bases may be so changed.

The NOV2 nucleic acids and proteins of the invention are useful in potential diagnostic and therapeutic applications implicated in various diseases and disorders described below and/or other pathologies. For example, the compositions of the present invention will have efficacy for treatment of patients suffering from: Cardiomyopathy, Atherosclerosis, Hypertension, Congenital heart defects, Aortic stenosis, Atrial septal defect (ASD), Atrioventricular (A-V) canal defect, Ductus arteriosus, Pulmonary stenosis, Subaortic stenosis, Ventricular septal defect (VSD), valve diseases, Tuberous sclerosis, Scleroderma, Obesity, Transplantation, Endometriosis, Fertility and other diseases, disorders and conditions of the like.

NOV2 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV2 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV3

NOV3 includes two novel Insulysin-like proteins disclosed below. The disclosed proteins have been named NOV3a and NOV3b.

NOV3a

A disclosed NOV3a nucleic acid of 4321 nucleotides (also referred to as CG57433-01) encoding a novel Insulysin-like protein is shown in Table 3A. An open reading frame was identified beginning with an ATG initiation codon at nucleotides 58–60 and ending with a TGA codon at nucleotides 3115–3117. Putative untranslated regions, if any, upstream from the initiation codon and downstream from the termination codon are underlined in Table 3A, and the start and stop codons are in bold letters.

TABLE 3A

NOV3a nucleotide sequence.

(SEQ ID NO:7)
CCGGCTCGAAGCGCAACGAGGAAGCGTTTGCGGTGATCCCGGCGACTGCGCTGGCTAATGCGGTACCGGCTA
GCGTGGCTTCTGCACCCCGCACTGCCCAGCACCTTCCGCTCAGTCCTCGGCGCCCGCCTGCCGCCTCCGGAG
CGCCTGTGTGGTTTCCAAAAAAAGACTTACAGCAAAATGAATAATCCAGCCATCAAGAGAATAGGAAATCAC
ATTACCAAGTCTCCTGAAGACAAGCGAGAATATCGAGGGCTAGAGCTGGCCAATGGTATCAAAGTACTTCTT
ATCAGTGATCCCACCACGGATAAGTCATCAGCAGCACTTGATGTGCACATAGGTTCATTGTCGGATCCTCCA
AATATTGCTGGCTTAAGTCATTTTTGTGAACATATGCTTTTTTTGGGAACAAAGAAATACCCTAAAGAAAAT
GAATACAGCCAGTTTCTCAGTGAGCATGCAGGAAGTTCAAATGCCTTTACTAGTGGAGAGCATACCAATTAC
TATTTTGATGTTTCTCATGAACACCTAGAAGGTGCCCTAGACAGGTTTGCACAGTTTTTTCTGTGCCCCTTG
TTCGATGAAAGTTGCAAAGACAGAGAGGTGAATGCAGTTGATTCAGAACATGAGAAGAATGTGATGAATGAT
GCCTGGAGACTCTTTCAATTGGAAAAAGCTACAGGGAATCCTAAACACCCCTTCAGTAAATTTGGGACAGGT
AACAAATATACTCTGGAGACTAGACCAAACCAAGAAGGCATTGATGTAAGACAAGAGCTACTGAAATTCCAT
TCTGCTTACTATTCATCCAACTTAATGGCTGTTTGTGTTTTAGGTCGAGAATCTTTAGATGACTTGACTAAT
CTGGTGGTAAAGTTATTTTCTGAAGTAGAGAACAAAAATGTTCCATTGCCAGAATTTCCTGAACACCCTTTC
CAAGAAGAACATCTTAAACAACTTTACAAAATAGTACCCATTAAAGATATTAGGAATCTCTATGTGACATTT
CCCATACCTGACCTTCAGAAATACTACAAATCAAATCCTGGTCATTATCTTGGTCATCTCATTGGGCATGAA
GGTCCTGGAAGTCTGTTATCAGAACTTAAGTCAAAGGGCTGGGTTAATACTCTTGTTGGTGGGCAGAAGGAA
GGAGCCCGAGGTTTTATGTTTTTTATCATTAATGTGGACTTGACCGAGGAAGGATTATTACATGTTGAAGAT
ATAATTTTGCACATGTTTCAATACATTCAGAAGTTACGTGCAGAAGGACCTCAAGAATGGGTTTTCCAAGAG
TGCAAGGACTTGAATGCTGTTGCTTTTAGGTTTAAAGACAAAGAGAGGCCACGGGGCTATACATCTAAGATT
GCAGGAATATTGCATTATTATCCCCTAGAAGAGGTGCTCACAGCGGAATATTTACTGGAAGAATTTAGACCT
GACTTAATAGAGATGGTTCTCGATAAACTCAGACCAGAAAATGTCCGGGTTGCCATAGTTTCTAAATCTTTT
GAAGGAAAAACTGATCGCACAGAAGAGTGGTATGGAACCCAGTACAAACAAGAAGCTATACCGGATGAAGTC
ATCAAGAAATGGCAAAATGCTGACCTGAATGGGAAATTTAAACTTCCTACAAAGAATGAATTTATTCCTACG
AATTTTGAGATTTTACCGTTAGAAAAAGAGGCGACACCATACCCTGCTCTTATTAAGGATACAGCTATGAGC
AAACTTTGGTTCAAACAAGATGATAAGTTTTTTTTGCCGAAGGCTTGTCTCAACTTTGAATTTTTCAGTCGC
TACATTTATGCTGATCCTCTCCATTGCAACATGACATACCTGTTTATCAGGTTATTGAAGGATGATTTAAAA
GAGTATACATATGCAGCACGCCTCTCAGGTTTGAGCTATGGCATTGCATCAGGAATGAATGCAATACTTCTT
TCAGTGAAAGGTTACAATGACAAGCACCCAATTTTACTAAAGAAGATTATTGAGAAAATGGCTACCTTTGAG
ATTGATGAAAAAGATTTGAAATTATCAAAGAAGCATATATGCGATCTCTTAACAATTTCCGGGCTGAACAG
CCTCACCAGCATGCCATGTACTACCTCCGCTTGCTGATGACTGAAGTGGCCTGGACTAAAGATGAGTTAAAA
GAAGCTCTGGATGATGTAACCCTTCCTCGCCTTAAGGCCTTCATACCTCAGCTCCTGTCACGGCTGCACATT
GAAGCCCTTCTCCATGGAAACATAACAAAGCAGGCTGCATTAGGAATTATGCAGATGGTTGAAGACACCCTC
ATTGAACATGCTCATACCAAACCTCTCCTTCCAAGTCAGCTGGTTCGGTATAGAAGTTCAGCTCCCTGAC
AGAGGATCGTTTGTTTATCAGCAGAGAGATGAAGTTCACAATAACTGTGGCATCGAGATATACTACCAAACA
GACATGCAAAGCACCTCAGAGAATATGTTTCTGGAGCTCTTCTGTCAGATTATCTCGGAACCTTGCTTCAAC
ACCCTGCGCACCAAGGAGCAGTTGGGCTATATCGTCTTCAGCGGGCCACGTCGAGCTAATGGCATACAGGGC
TTGAGATTCATCATCCAGTCAGAAAAGCCACCTCACTACCTAGAAAGCAGAGTGGAAGCTTTCTTAATTACC
ATGGAAAAGTCCATAGAGGACATGACAGAAGAGGCCTTCCAAAAACACATTCAGGCATTAGCAATTCGTCGA

TABLE 3A-continued

NOV3a nucleotide sequence.

CTAGACAAACCAAAGAAGCTATCTGCTGAGTGTGCTAAATACTGGGGAGAAATCATCTCCCAGCAATATAAT

TTTGACAGAGATAACACTGAGGTTGCATATTTAAAGACACTTACCAAGGAAGATATCATCAAATTCTACAAG

GAAATGTTGGCAGTAGATGCTCCAAGGAGACATAAGGTATCCGTCCATGTTCTTGCCAGGGAAATGGATTCT

TGTCCTGTTGTTGGAGAGTTCCCATGTCAAAATGACATAAATTTGTCACAAGCACCAGCCTTGCCACAACCT

GAAGTGATTCAGAACATGACCGAATTCAAGCGTGGTCTGCCACTGTTTCCCCTTGTGAAACCACATATTAAC

TTCATGGCTGCAAAACTCTGAAGATTCCCCATGCATGGGAAAGTGCAAGTGGATGCATTCCTGAGTCTTCCA

GAGCCTAAGAAAATCATCTTGGCCACTTTAATAGTTTCTGATTCACTATTAGAGAAACAAACAAAAAATTGT

CAAATGTCATTATGTAGAAATATTATAAATCCAAAGTAAATTACAAAATCTTATAGATGTAGAATATTTTTT

AAATACATGCCTCTTAAATATTTTAAAATTTTTCTTTTGATTACTGAGAGAAATTTCCCCAATATAACAATG

CTTAAAATGAATGATATTCCTATAGAATCTTCCTTCCCTATTCTGTAAAATAGTCACTTGTCCGAAGAAAGT

TAAAAGTTAGCTCTTTTCTAAAAGCCTCCTAGCTTGACATAGAAGGCTTCACAACATTTAGAAAGGTAATAA

CTTTTTAAAAATTGATCCTCAAATTTGCTTTCTACTTGATGGTTTCATGTAAATCAGTGGAAAACATTACAT

TTGGCAGATGATAAAGCAATGTCATCTTTTATTAGTGAAATGCTGGTTATATAAGGCATGGTTTTAATCTTT

TTATAAAATTTGAACATGTTTTTTATGCCAACTCGTAAAATGCTAGAAAACCCTACTTATTTACAATGCTAG

AAATACAGACTTACCTTACATCAATTTTGTCCTAAACCGAATTTCTCAGGATTACTGTGGTTTCTTTCATTC

TGATTGAATTATATTGACCTACTTCTTCATAGTTGGTTTGCAGTGTTCCATGAGTTTTACTTTTCCTCATCA

ACATATTGCTTTAACACAACATATTTATTTAACACGTACAAATAGGGTCAACTTCAGATCCTACTGAGTGTG

TGACATGCTTTTCCAACATCAGCTTTTTGTAACCACCTGTATAACTTTTTATTACAGTGAAATTGCAGTCAG

TATGTGAACCAAAATATCTTGCCCCTTTATGAATTTAAAAGGCAGCCAATACAAAGCCACCTTTTTGGAAAT

ATAAAAAGTAAAGCCTTGCATTCTTATATAGCAGGTCTTCATAAAACTCTAAAATCCCTTGTTGCTACCAGT

CTAATCTTGCCTTAAATGTTAAGTTATTTTTTGAATATATAAATATAAACATATAAACACAGATGATGACTG

GAGTAGACTTTTAAAAAAATATTTTTTTCATGAGATACTATTTTAGGTGAAATTGTACTGTAGATTTACAGC

T

The disclosed NOV3a nucleic acid sequence, localized to chromsome 10, has 3265 of 3336 bases (97%) identical to a gb:GENBANK-ID:HUMIDE|acc:M21188.1 mRNA from Homo sapiens (Human insulin-degrading enzyme (IDE) mRNA, complete cds) (E=0.0).

A NOV3a polypeptide (SEQ ID NO:8) encoded by SEQ ID NO:7 has 1019 amino acid residues and is presented using the one-letter code in Table 3B. Signal P, Psort and/or Hydropathy results predict that NOV3a contains a signal peptide and is likely to be localized to the peroxisome (microbody) with a certainty of 0.8347 or the mitochondrial matrix space with a certainty of 0.6517. The most likely cleavage site for a NOV3a peptide is between amino acids 22 and 23: VLG-AR.

TABLE 3B

Encoded NOV3a protein sequence.

(SEQ ID NO:8)

MRYRLAWLLHPALPSTFRSVLGARLPPPERLCGFQKKTYSKMNNPAIKRIGNHITKSPEDKREYRGLELANG

IKVLLISDPTTDKSSAALDVHIGSLSDPPNIAGLSHFCEHMLFLGTKKYPKENEYSQFLSEHAGSSNAFTSG

EHTNYYFDVSHEHLEGALDRFAQFFLCPLFDESCKDREVNAVDSEHEKNVMNDAWRLFQLEKATGNPKHPFS

KFGTGNKYTLETRPNQEGIDVRQELLKFHSAYYSSNLMAVCVLGRESLDDLTNLVVKLFSEVENKNVPLPEF

PEHPFQEEHLKQLYKIVPIKDIRNLYVTFPIPDLQKYYKSNPGHYLGHLIGHEGPGSLLSELKSKGWVNTLV

GGGQKEGARGFMFFIINVDLTEEGLLHVEDIILHMFQYIQKLRAEGPQEWVFQECKDLNAVAFRFKDKERPRG

YTSKIAGILHYYPLEEVLTAEYLLEEFRPDLIEMVLDKLRPENVRVAIVSKSFEGKTDRTEEWYGTQYKQEA

TABLE 3B-continued

Encoded NOV3a protein sequence.

IPDEVIKKWQNADLNGKFKLPTKNEFIPTNFEILPLEKEATPYPALIKDTAMSKLWFKQDDKFFLPKACLNF

EFFSRYIYADPLHCNMTYLFIRLLKDDLKEYTYAARLSGLSYGIASGMNAILLSVKGYNDKQPILLKKIIEK

MATFEIDEKRFEIIKEAYMRSLNNFRAEQPHQHAMYYLRLLMTEVAWTKDELKEALDDVTLPRLKAFIPQLL

SRLHIEALLHGNITKQAALGIMQMVEDTLIEHAHTKPLLPSQLVRYREVQLPDRGWFVYQQRDEVHNNCGIE

IYYQTDMQSTSENMFLELFCQIISEPCFNTLRTKEQLGYIVFSGPRRANGIQGLRFIIQSEKPPHYLESRVE

AFLITMEKSIEDMTEEAFQKHIQALAIRRLDKPKKLSAECAKYWGEIISQQYNFDRDNTEVAYLKTLTKEDI

IKFYKEMLAVDAPRRHKVSVHVLAREMDSCPVVGEFPCQNDINLSQAPALPQPEVIQNMTEFKRGLPLFPLV

KPHINFMAAKL

The NOV3a amino acid sequence has 989 of 1019 amino acid residues (97%) identical to, and 999 of 1019 amino acid residues (98%) similar to, the 1019 amino acid residue ptnr:pir-id:SNHUIN protein from human (insulysin (EC 3.4.24.56)) (E=0.0).

The disclosed NOV3a is expressed in at least the following tissues: Cervix, Liver, Spleen, Testis, Melanocyte, Heart and Uterus. This information was derived by determining the tissue sources of the sequences that were included in the invention including but not limited to SeqCalling sources, Public EST sources, Literature sources, and/or RACE sources.

NOV3b

A disclosed NOV3b nucleic acid of 3153 nucleotides (also referred to as CG57433-02) encoding a novel Insulysin-like protein is shown in Table 3C. An open reading frame was identified beginning with an ATG initiation codon at nucleotides 37–39 and ending with a TGA codon at nucleotides 3094–3096. Putative untranslated regions, if any, upstream from the initiation codon and downstream from the termination codon are underlined in Table 3C, and the start and stop codons are in bold letters.

TABLE 3C

NOV3b nucleotide sequence.

(SEQ ID NO:9)

<u>AAGCGTTTGCGGTGATCCCGGCGACTGCGCTGGCTA</u>ATGCGGTACCGGCTAGCGTGGCTTCTGCACCCCGCA

CTGCCCAGCACCTTCCGCTCAGTCCTCGGCGCCCGCCTGCCGCCTCCGGAGCGCCTGTGTGGTTTCCAAAAA

AAGACTTACAGCAAAATGAATAATCCAGCCATCAAGAGAATAGGAAATCACATTACCAAGCCTCCTGAAGAC

AAGCGAGAATATCGAGGGCTAGAGCTGGCCAATGGTATCAAAGTACTTCTTATCAGTGATCCCACCACGGAT

AAGTCATCAGCAGCACTTGATGTGCACATAGGTTCATTGTCGGATCCTCCAAATATTGCTGGCTTAAGTCAT

TTTTGTGAACATATGCTTTTTTTGGGAACAAAGAAATACCCTAAAGAAAATGAATACAGCCAGTTTCTCAGT

GAGCATGCAGGAAGTTCAAATGCCTTTACTAGTGGAGAGCATACCAATTACTATTTTGATGTTTCTCATGAA

CACCTACAAGGTGCCCTACACAGGTTTGCACAGTTTTTTCTGTGCCCCTTGTTCGATGAAAGTTGCAAAGAC

AGAGAGGTGAATGCAGTTGATTCAGAACATGAGAAGAATGTGATGAATGATGCCTCGAGACTCCTTCAATTG

GAAAAAGCTACAGGGAATCCTAAACACCCCTTCAGTAAATTTGGGACAGGTAACAAATATACTCTGGAGACT

AGACCAAACCAAGAAGGCATTGATGTAAGACAAGAGCTACTGAAATTCCATTCTGCTTACTATTCATCCAAC

TTAATGGCTGTTTGTGTTTTAGGTCGAGAATCTTTAGATGACTTGACTAATCTGGTGGTAAAGTTATTTTCT

GAAGTAGAGAACAAAAATGTTCCATTGCCAGAATTTCCTGAACACCCTTTCCAAGAAGAACATCTTAAACAA

CTTTACAAAATAGTACCCATTAAAGATATTAGGAATCTCTATGTGACATTTCCCATACCTGACCTTCAGAAA

TACTACAAATCAAATCCTGGTCATTATCTTGGTCATCTCATTGGGCATGAAGGTCCTGGAAGTCTGTTATCA

GAACTTAAGTCAAAGGGCTGGGTTAATACTCTTGTTGGTGGGCAGAAGGAAGGAGCCCGAGGTTTTATGTTT

TTTATCATTAATGTGGACTTGACCGAGGAAGGATTATTACATGTTGAAGATATAATTTTGCACATGTTTCAA

TACATTCAGAGGTTACGTGCAGAAGGACCTCAAGAATGGGTTTTCCAAGAGTGCAAGGACTTGAATGCTGTT

TABLE 3C-continued

NOV3b nucleotide sequence.

ACTTTTAGGTTTAAAGACAAAGAGAGGCCACGGGGCTATACATCTAAGATTGCAGGAATATTGCATTATTAT

CCCCTAGAAGAGGTGCTCACAGCGGAATATTTACTGGAAGAATTTAGACCTGACTTAATAGAGATGGTTCTC

GATAAACTCAGACCAGAAAATGTCCGGGTTGCCATAGTTTCTAAATCTTTTGAAGGAAAAACTGATCGCACA

GAAGAGTGGTATGGAACCCAGTACAAACAAGAAGCTATACCGGATGAAGTCATCAAGAAATGGCAAAATGCT

GACCTGAATGGGAAATTTAAACTTCCTACAAAGAATGAATTTATTCCTACGAATTTTGAGATTTTACCGTTA

GAAAAAGAGGCGACACCATACCCTGCTCTTATTAAGGATACAGCTATGAGCAAACTTTGGTTCAAACAAGAT

GATAAGTTTTTTTTGCCGAAGGCTTGTCTCAACTTTGAATTTTTCAGTCGCTACATTTATGCTGATCCTCTC

CATTGCAACATGACATACCTGTTTATCAGGTTATTGAAGGATGATTTAAAAGAGTATACATATGCAGCACGC

CTCTCAGGTTTGAGCTATGGCATTGCATCAGGAATGAATGCAATACTTCTTTCAGTGAAAGGTTACAATGAC

AAGCAGCCAATTTTACTAAAGAAGATTATTGAGAAAATGGCTACCTTTGAGATTGATGAAAAAGATTTGAA

ATTATCAAAGAAGCATATATGCGATCTCTTAACAATTTCCGGGCTGAACAGCCTCACCAGCATGCCATGTAC

TACCTCCGCTTGCTGATGACTGAAGTGGCCTGGACTAAAGATGAGTTAAAAGAGGCTCTGGATGATGTAACC

CTTCCTCGCCTTAAGGCCTTCATACCTCAGCTCCTGTCACGGCTGCACATTGAAGCCCTTCTCCATGGAAAC

ATAACAAAGCAGGCTGCATTAGGAATTATGCAGATGGTTGAAGACACCCTCATTGAACATGCTCATACCAAA

CCTCTCCTTCCAAGTCAGCTGGTTCGGTATAGAGAAGTTCAGCTCCCTGACAGAGGATGGTTTGTTTATCAG

CAGAGAAATGAAGTTCACAATAACTGTGGCATCGAGATATACTACCAAACAGACATGCAAAGCACCTCAGAG

AATATGTTTCTGGAGCTCTTCTGTCAGATTATCTCGGAACCTTGCTTCAACACCCTGCGCACCAAGGAGCAG

TTGGGCTATATCGTCTTCAGCGGGCCACGTCGAGCTAATGGCATACAGGGCTTGAGATTCATCATCCAGTCA

GAAAAGCCACCTCACTACCTAGAAAGCAGAGTGGAAGCTTTCTTAATTACCATGGAAAAGTCCATAGAGGAC

ATGACAGAAGAGGCCTTCCAAAAACACATTCAGGCATTAGCAATTCGTCGACTAGACAAACCAAAGAAGCTA

TCTGCTGAGTGTGCTAAATACTGGGGAGAAATCATCTCCCAGCAATATAATTTTGACAGAGATAACACTGAG

GTAGCATATTTAAAGACACTTACCAAGGAAGATATCATCAAATTCTACAAGGAAATGTTGGCAGTAGATGCT

CCAAGGAGACATAAGGTATCCGTCCATGTTCTTGCCAGGGAAATGGATTCTTGTCCTGTTGTTGGAGAGTTC

CCATGTCAAAATGACATAAATTTGTCACAAGCACCAGCCTTGCCACAACCTGAAGTGATTCAGAACATGACC

GAATTCAAGCGTGGTCTGCCACTGTTTCCCCTTGTGAAACCACATATTAACTTCATCGCTGCAAAACTCTGA

AGATTCCCCATGCATGGGAAAGTGCAAGTGGATGCATTCCTGAGTCTTCCAGAGCCT

The disclosed NOV3b nucleic acid sequence, localized to chromsome 10q23-q25, 3078 of 3153 bases (97%) identical to a gb:GENBANK-ID:HUMIDE|acc:M21188.1 mRNA from *Homo sapiens* (Human insulin-degrading enzyme (IDE) mRNA, complete cds) (E=0.0).

A NOV3b polypeptide (SEQ ID NO:10) encoded by SEQ ID NO:9 has 1019 amino acid residues and is presented using the one-letter code in Table 3D. Signal P, Psort and/or Hydropathy results predict that NOV3b contains a signal peptide and is likely to be localized to the peroxisome (microbody) with a certainty of 0.8347 or the mitochondrial matrix space with a certainty of 0.6517. The most likely cleavage site for a NOV3b peptide is between amino acids 22 and 23: VLG-AR.

TABLE 3D

Encoded NOV3b protein sequence.

(SEQ ID NO:10)
MRYRLAWLLHPALPSTFRSVLGARLPPPERLCGFQKKTYSKMNNPAIKRIGNHITKPPEDKREYRGLELANG

IKVLLISDPTTDKSSAALDVHIGSLSDPPNIAGLSHFCEHMLFLGTKKYPKENEYSQFLSEHAGSSNAFTSG

EHTNYYFDVSHEHLEGALDRFAQFFLCPLFDESCKDREVNAVDSEHEKNVMNDAWRLLQLEKATGNPKHPFS

KFGTGNKYTLETRPNQEGIDVRQELLKFHSAYYSSNLMAVCVLGRESLDDLTNLVVKLFSEVENKNVPLPEF

TABLE 3D-continued

Encoded NOV3b protein sequence.

PEHPFQEEHLKQLYKIVPIKDIRNLYVTFPIPDLQKYYKSNPGHYLGHLIGHEGPGSLLSELKSKGWVNTLV

GGQKEGARGFMFFIINVDLTEEGLLHVEDIILHMFQYIQRLRAEGPQEWVFQECKDLNAVTFRFKDKERPRG

YTSKIAGILHYYPLEEVLTAEYLLEEFRPDLIEMVLDKLRPENVRVAIVSKSFEGKTDRTEEWYGTQYKQEA

IPDEVIKKWQNADLNGKFKLPTKNEFIPTNFEILPLEKEATPYPALIKDTAMSKLWFKQDDKFFLPKACLNF

EFFSRYIYADPLHCNMTYLFIRLLKDDLKEYTYAARLSGLSYGIASGMNAILLSVKGYNDKQPILLKKIIEK

MATFEIDEKRFEIIKEAYMRSLNNFRAEQPHQHAMYYLRLLMTEVAWTKDELKEALDDVTLPRLKAFIPQLL

SRLHIEALLHGNITKQAALGIMQMVEDTLIEHAHTKPLLPSQLVRYREVQLPDRGWFVYQQRNEVHNNCGIE

IYYQTDMQSTSENMFLELFCQIISEPCFNTLRTKEQLGYIVFSGPRRANGIQGLRFIIQSEKPPHYLESRVE

AFLITMEKSIEDMTEEAFQKHIQALAIRRLDKPKKLSAECAKYWGEIISQQYNFDRDNTEVAYLKTLTKEDI

IKFYKEMLAVDAPRRHKVSVHVLAREMDSCPVVGEFPCQNDINLSQAPALPQPEVIQNMTEFKRGLPLFPLV

KPHINFMAAKL

The NOV3b amino acid sequence has 986 of 1019 amino acid residues (96%) identical to, and 996 of 1019 amino acid residues (97%) similar to, the 1019 amino acid residue ptnr:pir-id:SNHUIN protein from human (insulysin (EC 3.4.24.56)) (E=0.0).

The disclosed NOV3b is expressed in at least the following tissues: Lung, skin, uterus, colon, breast, liver, spleen, testis, and pediatric pre-B cell acute lymphoblastic leukemia. This information was derived by determining the tissue sources of the sequences that were included in the invention including but not limited to SeqCalling sources, Public EST sources, Literature sources, and/or RACE sources.

Possible SNPs found for NOV3a are listed in Table 3E and possible SNPs found for NOV3b are listed in Table 3F.

TABLE 3E

SNPs

| Variant | Nucleotide Position | Base Change | Amino Acid Position | Base Change |
|---------|---------------------|-------------|---------------------|-------------|
| 13375689 | 177 | C > T | Silent | N/A |
| 13375688 | 184 | A > G | 43 | Asn > Asp |
| 13375672 | 223 | A > T | 56 | Lys > End |
| 13375687 | 226 | T > C | 57 | Ser > Pro |
| 13375686 | 270 | T > C | Silent | N/A |
| 13375685 | 322 | G > T | 89 | Ala > Ser |
| 13375684 | 330 | T > C | Silent | N/A |
| 13375683 | 355 | C > T | 100 | Pro > Ser |
| 13375682 | 435 | A > G | Silent | N/A |
| 13375681 | 450 | C > T | Silent | N/A |

TABLE 3E-continued

SNPs

| Variant | Nucleotide Position | Base Change | Amino Acid Position | Base Change |
|---------|---------------------|-------------|---------------------|-------------|
| 13375326 | 661 | T > C | 202 | Phe > Leu |
| 13375680 | 685 | A > G | 210 | Asn > Asp |
| 13375679 | 905 | T > C | 283 | Val > Ala |
| 13375327 | 1256 | A > G | 400 | Lys > Arg |
| 13375328 | 1318 | G > A | 421 | Ala > Thr |
| 13375329 | 1412 | C > T | 452 | Ala > Val |
| 13375678 | 2686 | A > G | 877 | Met > Val |
| 13375677 | 2751 | G > A | Silent | N/A |
| 13375676 | 2815 | A > G | 920 | Arg > Gly |
| 13375675 | 2895 | A > G | Silent | N/A |
| 13375674 | 2910 | A > G | Silent | N/A |
| 13375673 | 2984 | A > G | 976 | Asn > Ser |
| 13377049 | 3077 | T > A | 1007 | Leu > His |

TABLE 3F

SNPs

| Consensus Position | Depth | Base Change | PAF |
|--------------------|-------|-------------|-----|
| 656 | 7 | C > T | 0.429 |

NOV3a and NOV3b are very closely homologous as is shown in the amino acid alignment in Table 3G.

TABLE 3G

Amino Acid Alignment of NOV3a and NOV3b

```
              10        20        30        40        50        60        70
     ....|....|....|....|....|....|....|....|....|....|....|....|....|....|
NOV3a MRYRLAWLLHPALPSTFRSVLGARLPPPERLCGFQKKTYSKMNNPAIKRIGNHITKSPEDKREYRGLELA
NOV3b MRYRLAWLLHPALPSTFRSVLGARLPPPERLCGFQKKTYSKMNNPAIKRIGNHITKPPEDKREYRGLELA
```

TABLE 3G-continued

Amino Acid Alignment of NOV3a and NOV3b

```
              80        90       100       110       120       130       140
         ....|....|....|....|....|....|....|....|....|....|....|....|....|
NOV3a    NGIKVLLISDPTTDKSSAALDVHIGSLSDPPNIAGLSHFCEHMLFLGTKKYPKENEYSQFLSEHAGSSNA
NOV3b    NGIKVLLISDPTTDKSSAALDVHIGSLSDPPNIAGLSHFCEHMLFLGTKKYPKENEYSQFLSEHAGSSNA 150       160       170       180       190       200       210
         ....|....|....|....|....|....|....|....|....|....|....|....|....|
NOV3a    TSGEHTNYYFDVSHEHLEGALDRFAQFFLCPLFDESCKDREVNAVDSEHEKNVMNDAWRLFQLEKATGN
NOV3b    TSGEHTNYYFDVSHEHLEGALDRFAQFFLCPLFDESCKDREVNAVDSEHEKNVMNDAWRLLQLEKATGN 220       230       240       250       260       270       280
         ....|....|....|....|....|....|....|....|....|....|....|....|....|
NOV3a    PKHPFSKFGTGNKYTLETRPNQEGIDVRQELLKFHSAYYSSNLMAVCVLGRESLDDLTNLVVKLFSEVEN
NOV3b    PKHPFSKFGTGNKYTLETRPNQEGIDVRQELLKFHSAYYSSNLMAVCVLGRESLDDLTNLVVKLFSEVEN 290       300       310       320       330       340       350
         ....|....|....|....|....|....|....|....|....|....|....|....|....|
NOV3a    KNVPLPEFPEHPFQEEHLKQLYKIVPIKDIRNLYVTFPIPDLQKYYKSNPGHYLGHLIGHEGPGSLLSEL
NOV3b    KNVPLPEFPEHPFQEEHLKQLYKIVPIKDIRNLYVTFPIPDLQKYYKSNPGHYLGHLIGHEGPGSLLSEL 360       370       380       390       400       410       420
         ....|....|....|....|....|....|....|....|....|....|....|....|....|
NOV3a    KSKGWVNTLVGGQKEGARGFMFFIINVDLTEEGLLHVEDIILHMFQYIQKLRAEGPQEWVFQECKDINAV
NOV3b    KSKGWVNTLVGGQKEGARGFMFFIINVDLTEEGLLHVEDIILHMFQYIQRLRAEGPQEWVFQECKDINAV 430       440       450       460       470       480       490
         ....|....|....|....|....|....|....|....|....|....|....|....|....|
NOV3a    AFRFKDKERPRGYTSKIAGILHYYPLEEVLTAEYLLEEFRPDLIEMVLDKLRPENVRVAICSKSFEGKTD
NOV3b    TFRFKDKERPRGYTSKIAGILHYYPLEEVLTAEYLLEEFRPDLIEMVLDKLRPENVRVAICSKSFEGKTD 500       510       520       530       540       550       560
         ....|....|....|....|....|....|....|....|....|....|....|....|....|
NOV3a    RTEEWYGTQYKQEAIPDEVIKKWQNADLNGKFKLPTKNEFIPTNFEILPLEKEATPYPALIKDTAMSKLW
NOV3b    RTEEWYGTQYKQEAIPDEVIKKWQNADLNGKFKLPTKNEFIPTNFEILPLEKEATPYPALIKDTAMSKLW 570       580       590       600       610       620       630
         ....|....|....|....|....|....|....|....|....|....|....|....|....|
NOV3a    FKQDDKFFLPKACLNFEFFSRYIYADPLHCNMTYLFIRLLKDDLKEYTYAARLSGLSYGIASGMNAILLS
NOV3b    FKQDDKFFLPKACLNFEFFSRYIYADPLHCNMTYLFIRLLKDDLKEYTYAARLSGLSYGIASGMNAILLS 640       650       660       670       680       690       700
         ....|....|....|....|....|....|....|....|....|....|....|....|....|
NOV3a    VKGYNDKQPILLKKIIEKMATFEIDEKRFEIIKEAYMRSLNNFRAEQPHQHAMYYLRLLMTEVAWTKDEL
NOV3b    VKGYNDKQPILLKKIIEKMATFEIDEKRFEIIKEAYMRSLNNFRAEQPHQHAMYYLRLLMTEVAWTKDEL 710       720       730       740       750       760       770
         ....|....|....|....|....|....|....|....|....|....|....|....|....|
NOV3a    KEALDDVTLPRLKAFIPQLLSRLHIEALLHGNITKQAALGIMQMVEDTLIEHAHTKPLLPSQLVRYREVQ
NOV3b    KEALDDVTLPRLKAFIPQLLSRLHIEALLHGNITKQAALGIMQMVEDTLIEHAHTKPLLPSQLVRYREVQ 780       790       800       810       820       830       840
         ....|....|....|....|....|....|....|....|....|....|....|....|....|
NOV3a    LPDRGWFVYQQRDEVHNNCGIEIYYQTDMQSTSENMFLELFCQIISEPCFNTLRTKEQLGYIVFSGPRRA
NOV3b    LPDRGWFVYQQRDEVHNNCGIEIYYQTDMQSTSENMFLELFCQIISEPCFNTLRTKEQLGYIVFSGPRRA 850       860       870       880       890       900       910
         ....|....|....|....|....|....|....|....|....|....|....|....|....|
NOV3a    NGIQGLRFIIQSEKPPHYLESRVEAFLITMEKSIEDMTEEAFQKHIQALAIRRLDKPKKLSAECAKYWCE
NOV3b    NGIQGLRFIIQSEKPPHYLESRVEAFLITMEKSIEDMTEEAFQKHIQALAIRRLDKPKKLSAECAKYWCE 920       930       940       950       960       970       980
         ....|....|....|....|....|....|....|....|....|....|....|....|....|
NOV3a    IISQQYNFDRDNTEVAYLKTLTKEDIIKFYKEMLAVDAPRRHKVSVHVLAREMDSCPVVGEFPCQNDINL
NOV3b    IISQQYNFDRDNTEVAYLKTLTKEDIIKFYKEMLAVDAPRRHKVSVHVLAREMDSCPVVGEFPCQNDINL 990       1000      1010
         ....|....|....|....|....|....|
NOV3a    SQAPALPQPEVIQNMTEFKRGLPLFPLVKPHINFMAAKL
NOV3b    SQAPALPQPEVIQNMTEFKRGLPLFPLVKPHINFMAAKL
```

Homologies to any of the above NOV3 proteins will be shared by the other NOV3 proteins insofar as they are homologous to each other as shown above. Any reference to NOV3 is assumed to refer to both of the NOV3 proteins in general, unless otherwise noted.

NOV3a has homology to the amino acid sequences shown in the BLASTP data listed in Table 3H.

TABLE 3H

BLAST results for NOV3a

| Gene Index/ Identifier | Protein/ Organism | Length (aa) | Identity (%) | Positives (%) | Expect |
|---|---|---|---|---|---|
| gi\|4826770\|ref\|NP_004960.1\| (NM_004969) | insulysin; insulinase [Homo sapiens] | 1019 | 974/1019 (95%) | 984/1019 (95%) | 0.0 |
| gi\|6981076\|ref\|NP_037291.1\| (NM_013159) | insulin degrading enzyme [Rattus norvegicus] | 1019 | 934/1019 (91%) | 965/1019 (94%) | 0.0 |
| gi\|13621162\|ref\|NP_112419.1\| (NM_031156) | insulin degrading enzyme [Mus musculus] | 1019 | 929/1019 (91%) | 963/1019 (94%) | 0.0 |
| gi\|18576366\|ref\|XP_051153.2\| (XM_051153) | insulysin [Homo sapiens] | 554 | 530/554 (95%) | 539/554 (96%) | 0.0 |
| gi\|7296294\|gb\|AAF51584.1\| (AE003591) | Ide gene product [Drosophila melanogaster] | 990 | 439/966 (45%) | 634/966 (65%) | 0.0 |

The homology of these sequences is shown graphically in the ClustalW analysis shown in Table 3I.

TABLE 3I

ClustalW Analysis of NOV3a

1) NOV3a (SEQ ID NO:8)
2) gi|4826770|ref|NP_004960.1| (NM_004969) insulysin; insulinase [Homo sapiens] (SEQ ID NO:106)
2) gi|6981076|ref|NP_013159.1| (NM_013159) insulin degrading enzyme [Rattus norvegicus] (SEQ ID NO:107)
3) gi|13621162|ref|NP_112419.1| (NM_031156) insulin degrading enzyme [Mus musculus] (SEQ ID NO:108)
4) gi|18576366|ref|XP_051153.2| (XM_051153) insulysin [Homo sapiens] (SEQ ID NO:109)
5) gi|7296294|gb AAF51584.1| (AE003591) Ide gene product [Drosophila melanogaster] (SEQ ID NO:110)

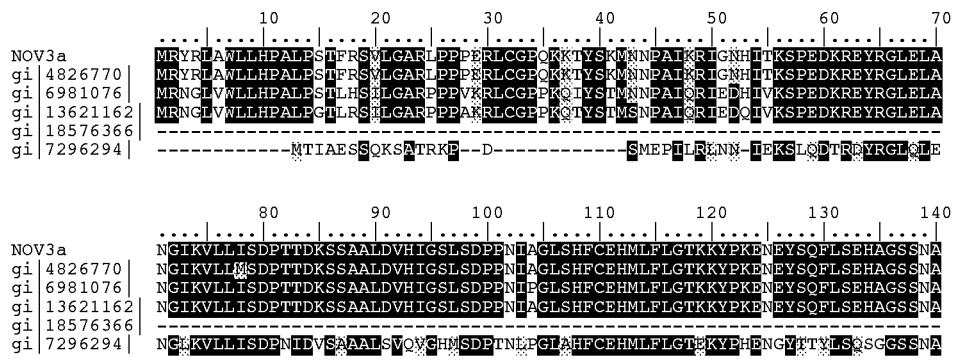

TABLE 3I-continued

ClustalW Analysis of NOV3a

```
                    150       160       170       180       190       200       210
                ....|....|....|....|....|....|....|....|....|....|....|....|....|....|
NOV3a           FTSGEHTNYYFDVSHEHLEGALDRFAQFFLCPLFDESCKDREVNAVDSEHEKNVMNDAWRLFQLEKATCN
gi|4826770|     FTSGEHTNYYFDVSHEHLEGALDRFAQFFLCPLFDESCKDREVNAVDSEHEKNVMNDAWRLFQLEKATCN
gi|6981076|     FTSGEHTNYYFDVSHEHLEGALDRFAQFFLCPLFDASCKDREVNAVDSEHEKNVMNDAWRLFQLEKATCN
gi|13621162|    FTSGEHTNYYFDVSHEHLEGALDRFAQFFLCPLLDASCKDREVNAVDSEHEKNVMNDAWRLFQLEKATCN
gi|18576366|    ----------------------------------------------------------------------
gi|7296294|     ALYPLMTKYHFHVLPDKLEGALDRFAQFFIAPLETPSATEREINAVNSEHEKNLPSDLWRIKQVNKHLAK 220       230       240       250       260       270       280
                ....|....|....|....|....|....|....|....|....|....|....|....|....|....|
NOV3a           PKHPFSKFGTGNKYTLETRFNQEGIDVRQELLKFHSAYYSSNLMAVCVLGRESLDDLINLVVKLFSEVEN
gi|4826770|     PKHPFSKFGTGNKYTLETRFNQEGIDVRQELLKFHSAYYSSNLMAYCVLGRESLDDLTNLVVKLFSEVEN
gi|6981076|     PKHPFSKFGTGNKYTLETRFNQEGIDVREELLKFHSTYYSSNLMAICVLGRESLDDLINLVVKLFSEVEN
gi|13621162|    PKHPFSKFGTGNKYTLETRFNQEGIDVREELLKFHSTYYSSNLMAICVLGRESLDDLINLVVKLFSEVEN
gi|18576366|    ----------------------------------------------------------------------
gi|7296294|     EDHAYSKFGSGNKTILSEIEKSKNIDVRDELLKFHKQWYSANIKCLAVIGKESLDELEGMVLEKESEEN 290       300       310       320       330       340       350
                ....|....|....|....|....|....|....|....|....|....|....|....|....|....|
NOV3a           KNVPLPEFPEHPFQEEHLKQLYKIVPIKDIRNLYVTFPIPDLQKYYKSNPGHYLGHLIGHEGPGSLLSEL
gi|4826770|     KNVPLPEFPEHPFQEEHLKQLYKIVPIKDIRNLYVTFPIPDLQKYYKSNPGHYLGHLIGHEGPGSLLSEL
gi|6981076|     KNVPLPEFPEHPFQEEHLKQLYKIVPIKDIRNLYVTFPIPDLQKYYKSNPGHYLGHLIGHEGPGSLLSEL
gi|13621162|    KNVPLPEFPEHPFQEEHLKQLYKIVPIKDIRNLYVTFPIPDLQKYYKSNPGYYLGHLIGHEGPGSLLSEL
gi|18576366|    ----------------------------------------------------------------------
gi|7296294|     KNVKVEGWPRHPVAEERYGQKVKIVPIKDIRSLTLSFTTDDITQRYKSGEDNYITHLIGHEGKGSILSEL 360       370       380       390       400       410       420
                ....|....|....|....|....|....|....|....|....|....|....|....|....|....|
NOV3a           KSKGWVNTLVGGQKEGARGFMFFIINVDLTEEGLLHVEDIILHMFQYIQKLRAEGPQEWVFQECKDLNAV
gi|4826770|     KSKGWVNTLVGGQKEGARGFMFFIINVDLTEEGLLHVEDIILHMFQYIQKLRAEGPQEWVFQECKDLNAV
gi|6981076|     KSKGWVNTLVGGQKEGARGFMFFIINVDLTEEGLLHVEDIILHMFQYIQKLRAEGPQEWVFQECKDLNAV
gi|13621162|    KSKGWVNTLVGGQKEGARGFMFFIINVDLTEEGLLHVEDIILHMFQYIQKLRAEGPQEWVFQECKDLNAV
gi|18576366|    ----------------------------------------------------------------------
gi|7296294|     ERLGWCNDLMAGHDNTQNGFGFFDIVVDLTQEGLEHVDDIVKIVFQYLEMLRKEGPKKWIFDECVKLNEM 430       440       450       460       470       480       490
                ....|....|....|....|....|....|....|....|....|....|....|....|....|....|
NOV3a           AFRFKDKERPRGYTSKIAGILHYYPLEEVLTAEYLLEEFRPDLIEMVLDKLRPENVRVAIVSKSFEGKTD
gi|4826770|     AFRFKDKERPRGYTSKIAGILHYYPLEEVLTAEYLLEEFRPDLIEMVLDKLRPENVRVAIVSKSFEGKTD
gi|6981076|     AFRFKDKERPRGYTSKIAGKLHYYPLNGVLTAEYLLEEFRPDLIDMVLDKLRPENVRVAIVSKSFEGKTD
gi|13621162|    AFRFKDKERPRGYTSKIAGKLHYYPLNGVLTAEYLLEEFRPDLIDMVLDKLRPENVRVAIVSKSFEGKTD
gi|18576366|    ---------------------------------------------MVLDKLRPENVRVAIVSKSFEGKTD
gi|7296294|     RFRFKEKEQPENLVIHAVSSMQIFPLEEVIIAPYLSNEWRPDLIKGLLDELVPSKSRIVSQSPEPDCD 500       510       520       530       540       550       560
                ....|....|....|....|....|....|....|....|....|....|....|....|....|....|
NOV3a           RTEEWYGTQYKQEAIPDEVIKKWQNADLNGKFKLPTKNEFIPINFEILPLEKEATPYPALIKDTAMSKLW
gi|4826770|     RTEEWYGTQYKQEAIPEDVIQKWQNADLNGKFKLPTKNEFIPINFEILALEKDATPYPALIKDTVMSKLW
gi|6981076|     RTEQWYGTQYKQEAIPEDVIQKWQNADLNGKFKLPTKNEFIPINFEILALEKDATPYPALIKDTAMSKLW
gi|13621162|    RTEEWYGTQYKQEAIPDEVIKKWQNADLNGKFKLPTKNEFIPINFEILPLEKSATPYPALIKDTAMSKLW
gi|18576366|    RTEEWYGTQYKQEAIPDEVIKKWQNADLNGKFKLPTKNEFIPINFEILPLEKSATPYPALIKDTAMSKLW
gi|7296294|     LAEPYYKIKYGITRVAKDTVQSWENCELNENLKIALPNSFIPTNFDISDVPADAPKEPTIILDTPILRVW 570       580       590       600       610       620       630
                ....|....|....|....|....|....|....|....|....|....|....|....|....|....|
NOV3a           FKQDDKFFLPKACINFEFFSRYIYADPLHCNMTYLFIRLLKDDLKEYTYAARLSGLSYGIASGMNAILLS
gi|4826770|     FKQDDKFFLPKACINFEFFSPFAYVDPLHCNMAYLYLELLKDSINEYAYAAELAGLSYDLQNTIYGMYLS
gi|6981076|     FKQDDKFFLPKACINFEFFSPFAYVDPLHCNMAYLYLELLKDSINEYAYAAELAGLSYDLQNTIYGMYLS
gi|13621162|    FKQDDKFFLPKACINFEFFSPFAYVDPLHCNMAYLYLELLKDSINEYAYAAELAGLSYDLQNTIYGMYLS
gi|18576366|    FKQDDKFFLPKACINFEFFSPFAYVDPLHCNMAYLYLELLKDSINEYAYAAELAGLSYDLQNTIYGMYLS
gi|7296294|     HKQDNQFNKPKACNTFIMSNPIAYEDPLNCNLNHMMVMLLKDQLNEYLYDAELASLKLSVMGKSCGIDFT 640       650       660       670       680       690       700
                ....|....|....|....|....|....|....|....|....|....|....|....|....|....|
NOV3a           VKGYNDKQPILLKKIIEKMATFEICEKRFEIIKEAYMRSINNFRAEQPHQHAMYYLRLLMTEVAWTKDEL
gi|4826770|     VKGYNDKQPILLKKIIEKMATFEICEKRFEIIKEAYMRSINNFRAEQPHQHAMYYLRLLMTEVAWTKDEL
gi|6981076|     VKGYNDKQPILLKKITEKMATFEICKKRFEIIKEAYMRSINNFRAEQPHQHAMYYLRLLMTEVAWTKDEL
gi|13621162|    VKRYNDKQPILLKKITEKMATFEICKKRFEIIKEAYMRSINNFRAEQPHQHAMYYLRLLMTEVAWTKDEL
gi|18576366|    VKGYNDKQPILLKKIIEKMATFEICEKRFEIIKEAYMRSINNFRAEQPHQHAMYYLRLLMTEVAWTKDEL
gi|7296294|     IRGESDKQVVLLEKELLHLFDFSIDEKRFCIELKEEYVRSLKNEKAEQEYQHSIYYLALLITENAWANMEL 710       720       730       740       750       760       770
                ....|....|....|....|....|....|....|....|....|....|....|....|....|....|
NOV3a           KEALDDVTLPRLKAFIPQLLSRLHIEALLHGNITKQAALGIMQMVEDTLIEH-AHTKPLLPSQLVRYREV
gi|4826770|     KEALDDVTLPRLKAFIPQLLSRLHIEALLHGNITKQAALGIMQMVEDTLIEH-AHTKPLLPSQLVRYREV
gi|6981076|     KEALDDVTLPRLKAFIPQLLSRLHIEALLHGNITKQAALGVMQMVEDTLIEH-AHTKPLLPSQLVRYREV
gi|13621162|    KEALDDVTLPRLKAFIPQLLSRLHIEALLHGNITKQAALGIMQMVEDTLIEH-AHTKPLLPSQLVRYREV
gi|18576366|    KEALDDVTLPRLKAFIPQLLSRLHIEALLHGNITKQAALGIMQMVEDTLIEH-AHTKPLLPSQLVRYREV
gi|7296294|     LDAMELVTYDRVLNEAKEFFQRLHTECFIFGNVIKQQATDIAGRVNTRLEATNASKLPELAROMLKKREY
```

TABLE 3I-continued

ClustalW Analysis of NOV3a

```
                      780        790        800        810        820        830        840
                 ....|....|....|....|....|....|....|....|....|....|....|....|....|....|
NOV3a            QLPDRGWFVYQQRDEVHNNCGIEIYYQTDMQSTSENMFLELFCQIISEPCFNTLRTKEQLGYIVFSGPRR
gi|4826770|      QLPDRGWFVYQQRNEVHNNCGIEIYYQTDMQSTSENMFLELFCQIISEPCFNTLRTKEQLGYIVFSGPRR
gi|6981076|      QLPDRGWFVYQRNEVHNNCGIEIYYQTDMQSTSENMFLELFCQIISEPCFNTLRTKEQLGYIVFSGPRR
gi|13621162|     QLPDRGWFVYQQRNEVHNNCGIEIYYQTDMQSTSENMFLELFCQIISEPCFNTLRTKEQLGYIVFSGPRR
gi|18576366|     QLPDRGWFVYQQRNEVHNNCGIEIYYQTDMQSTSENMFLELFCQIISEPCFNTLRTKEQLGYIVFSGPRR
gi|7296294|      KLLAGDSYLFEKENEFHKSSCAQLVLQCGAQIDHTNIMVNLVSQVLSEPCYDCLRTKEQLGYIVFSCVRK 850        860        870        880        890        900        910
                 ....|....|....|....|....|....|....|....|....|....|....|....|....|....|
NOV3a            ANGIQGLRFIIQSEKPPHYLESRVEAFLITMEKSIEDMTEEAFQKHIQALAIRRLDKPKKLSAECAKYWG
gi|4826770|      ANGIQSLRFIIQSEKPPHYLESRVEAFLITMEKSIEDMTEEAFQKHIQALAIRRLDKPKKLSAECAKYWG
gi|6981076|      ANGIQGLRFIIQSEKPPHYLESRVEAFLITMEKAIEDMTEEAFQKHIQALAIRRLDKPKKLSAECAKYWG
gi|13621162|     ANGIQGLRFIIQSEKPPHYLESRVEAFLITMEKAIEDMTEEAFQKHIQALAIRRLDKPKKLSAECAKYWG
gi|18576366|     ANGIQGLRFIIQSEKPPHYLESRVEAFLITMEKSIEDMTEEAFQKHIQALAIRRLDKPKKLSAECAKYWG
gi|7296294|      VNGANGIRIIVQSAKHPSYMEDRIENFLQTYLQVIEDMPLDEFRRHKEALAVKKLEKPKTIFQQFSQFVG 920        930        940        950        960        970        980
                 ....|....|....|....|....|....|....|....|....|....|....|....|....|....|
NOV3a            EIISQQYNFDRDNTEVAYLKTLTKEDIIKFYKEMLAVDAPRRHKVSVHVLAREMDSCPVVGEFPCQNDIN
gi|4826770|      EIISQQYNFDRDNTEVAYLKTLTKEDIIKFYKEMLAVDAPRRHKVSVHVLAREMDSCPVVGEFPCQNDIN
gi|6981076|      EIISQQYNYDRDNIEVAYLKTLSKEDIIKFYKEMLAVDAPRRHKVSVHVLAREMDSCPVVGEFPSQNDIN
gi|13621162|     EIISQQYNNDRDNIEVAYLKTLTKEDIIRFYQEMLAVDAPRRHKVSVHVLAREMDSCPVVGEFSQNDIN
gi|18576366|     EIISQQYNFDRDNTEVAYLKTLTKEDIIKFYKEMLAVDAPRRHKVSVHVLAREMDSCPVVGEFPCQNDIN
gi|7296294|      EIAMQTYHFERSEAEVAILRKLSKADFVDYFKKFIAKDGEERRVLSVHLVSQQTDEN-------ATSEAE 990       1000       1010       1020
                 ....|....|....|....|....|....|....|....|....
NOV3a            LSQAPALPQPEVIQNMTEFKRGLPLFPLVKPHINFMAAKL----
gi|4826770|      LSQAPALPQPEVIQNMTEFKRGLPLFPLVKPHINFMAAKL----
gi|6981076|      LSEAPPLPQPEVIHNMTEFKRGLPLFPLVKPHINFMAAKL----
gi|13621162|     LSEAPPLPQPEVIHNMTEFKRGLPLFPLVKPHINFMAAKL----
gi|18576366|     LSQAPALPQPEVIQNMTEFKRGLPLFPLVKPHINFMAAKL----
gi|7296294|      PVLITNMERHRPLSDIVTFKSCKELYEIALPFLDIKAKGARSKL
```

Table 3J lists the domain description from DOMAIN analysis results against NOV3a. This indicates that the NOV3a sequence has properties similar to those of other proteins known to contain these domains.

TABLE 3J

Domain Analysis of NOV3a gnl|Pfam|pfam00675, Peptidase_M16, Insulinase (Peptidase family M16).
(SEQ ID NO:111)
CD-Length = 149 residues, 99.3% aligned
Score = 157 bits (396), Expect = 4e-39

```
Query:    74 KVLLISDPTTDKSSAALDVHIGSLSDPPNIAGLSHFCEHMLFLGTKKYPKENEYSQFLSE  133
             +|   ||   |+   |   ||   +| +   ||+||  |||  |  ||||||   ||  + | +
Sbjct:     1 RVALEHDPPADTSAVGLWVDAGSRYEPDDNNGLAHFLEHMAFKGTKKYP-SNELEEELEK   59

Query:   134 HAGSSNAFTSGEHTNYYFDVSHEHLEGALDRFAQFFLCPLFDESCKDR-------EVNAV  186
             ||  ||+||  |||  ||  +|  ++    |+||   |||  |||   |   +|    || ||
Sbjct:    60 LGGSLNAYTSREHTAYYVEVLNDDLPKAVDRLADFFLNPLFSPSEVERERLVVLYEVEAV  119

Query:   187 DSEHEKNVMN----DAWRLFQLEKATGNP                                211
             |+|  +   +++      |+|    |  ++    |
Sbjct:   120 DAEPQAVLLDNLHAAAYRGTPLGRSLLGP                                148
```

After binding to its receptor on the cell surface, insulin is internalized by receptor-mediated endocytosis and degraded within components of the endosomal apparatus. Degradation of insulin is important in the termination of signaling and clearance of the circulating hormone. It has been proposed that insulin-degrading enzyme (IDE), an evolutionarily conserved, neutral thiol-metalloendopeptidase, plays a crucial role in the degradation of internalized insulin in many types of cells. Despite the substantial evidence supporting the importance of IDE in cellular insulin degradation, there is controversy over its mode and site of action, mainly because of its cytosolic location. Its physiological location in cells has recently been elucidated through subcellular fractionation of liver parenchyma and through immunofluorescence microscopy of stably transfected Chinese hamster ovary cells that overexpress IDE. These experiments have excluded the presence of the enzyme in endosomes and have defined a peroxisomal location, consistent with the presence of a peroxisomal targeting sequence at the carboxyl terminus of the protein. Recently, researchers have demonstrated the functional significance of peroxisome-associated IDE (type I peroxisomal enzyme) in degrading cleaved leader peptides of peroxisomal proteins targeted by the type II motif. IDE is the first cloned and characterized proteinase to be localized to peroxisomes. Moreover, IDE appears to be a member of a newly identified superfamily of metalloendopeptidases that has an HXXEH active-site motif. Although fundamental questions concerning the biological role of IDE remain, its high degree of evolutionary conservation suggests that it must have important functions and multifaceted biological significance (Authier et al., Clin Invest Med 19(3):149–60, 1996)

Insulin degradation is a regulated process that plays a role in controlling insulin action by removing and inactivating the hormone. Abnormalities in insulin clearance and degradation are present in various pathological conditions including type 2 diabetes and obesity and may be important in producing clinical problems. The uptake, processing, and degradation of insulin by cells is a complex process with multiple intracellular pathways. Most evidence supports IDE as the primary degradative mechanism, but other systems (PDI, lysosomes, and other enzymes) undoubtedly contribute to insulin metabolism. Recent studies support a multifunctional role for IDE, as an intracellular binding, regulatory, and degradative protein. IDE increases proteasome and steroid hormone receptor activity, and this activation is reversed by insulin. This raises the possibility of a direct intracellular interaction of insulin with IDE that could modulate protein and fat metabolism. The recent findings would place intracellular insulin-IDE interaction into the insulin signal transduction pathway for mediating the intermediate effects of insulin on fat and protein turnover (Duckworth et al., Endocr Rev 19(5):608–24, 1998).

A number of proteases dependent on divalent cations for their activity have been shown to belong to one family, on the basis of sequence similarity. These enzymes include those listed below.

Insulinase (EC 3.4.24.56) (also known as insulysin or insulin-degrading enzyme or IDE), a cytoplasmic enzyme which seems to be involved in the cellular processing of insulin, glucagon and other small polypeptides.

*Escherichia coli* protease III (EC 3.4.24.55) (pitrilysin) (gene ptr), a periplasmic enzyme that degrades small peptides.

Mitochondrial processing peptidase (EC 3.4.24.64) (MPP). This enzyme removes the transit peptide from the precursor form of proteins imported from the cytoplasm across the mitochondrial inner membrane. It is composed of two nonidentical homologous subunits termed alpha and beta. The beta subunit seems to be catalytically active while the alpha subunit has probably lost its activity.

Nardilysin (EC 3.4.24.61) (N-arginine dibasic convertase or NRD convertase) this mammalian enzyme cleaves peptide substrates on the N-terminus of Arg residues in dibasic stretches.

*Klebsiella pneumoniae* protein pqqF. This protein is required for the biosynthesis of the coenzyme pyrroloquinoline-quinone (PQQ). It is thought to be protease that cleaves peptide bonds in a small peptide (gene pqqA) thus providing the glutamate and tyrosine residues necessary for the synthesis of PQQ.

Yeast protein AXL1, which is involved in axial budding.

*Eimeria bovis* sporozoite developmental protein.

*Escherichia coli* hypothetical protein yddC and HI1368, the corresponding *Haemophilus influenzae* protein.

*Bacillus subtilis* hypothetical protein ymxG.— *Caenorhabditis elegans* hypothetical proteins C28F5.4 and F56D2.1.

It should be noted that in addition to the above enzymes, this family also includes the core proteins I and II of the mitochondrial bc1 complex (also called cytochrome c reductase or complex III), but the situation as to the activity or lack of activity of these subunits is quite complex. In mammals and yeast, core proteins I and II lack enzymatic activity. In *Neurospora crassa* and in potato core protein I is equivalent to the beta subunit of MPP. In *Euglena gracilis*, core protein I seems to be active, while subunit II is inactive.

These proteins do not share many regions of sequence similarity; the most noticeable is in the N-terminal section. This region includes a conserved histidine followed, two residues later by a glutamate and another histidine. In pitrilysin, it has been shown that this H-x-x-E-H motif is involved in enzyme activity; the two histidines bind zinc and the glutamate is necessary for catalytic activity. Non active members of this family have lost from one to three of these active site residues. A signature pattern has been developed that detect active members of this family as well as some inactive members.

The NOV3 nucleic acid of the invention encoding a Insulysin-like protein includes the nucleic acid whose sequence is provided in Tables 3A and 3C, or a fragment thereof. The invention also includes a mutant or variant nucleic acid any of whose bases may be changed from the corresponding base shown in Tables 3A and 3C while still encoding a protein that maintains its Insulysin-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 3% of the residues may be so changed.

The NOV3 protein of the invention includes the Insulysin-like protein whose sequence is provided in Tables 3B and 3D. The invention also includes a mutant or variant protein any of whose residues may be changed from the corresponding residue shown in Tables 3B and 3D while still encoding a protein that maintains its Insulysin-like activities and physiological functions, or a functional fragment thereof. In the mutant or variant protein, up to about 4% of the bases may be so changed.

The NOV3 nucleic acids and proteins of the invention are useful in potential diagnostic and therapeutic applications implicated in various diseases and disorders described below and/or other pathologies. For example, the compositions of the present invention will have efficacy for treatment of patients suffering from: Cardiomyopathy, Atherosclerosis, Hypertension, Congenital heart defects, Aortic stenosis, Atrial septal defect (ASD), Atrioventricular (A-V) canal defect, Ductus arteriosus, Pulmonary stenosis, Subaortic stenosis, Ventricular septal defect (VSD), valve diseases, Tuberous sclerosis, Scleroderma, Obesity, Transplantation, Endometriosis, Fertility, Von Hippel-Lindau (VHL)

syndrome, Cirrhosis, Transplantation, Hemophilia, Hypercoagulation, Idiopathic thrombocytopenic purpura, Immunodeficiencies, Retinitis pigmentosa, autosomal dominant; Retinitis pigmentosa, autosomal recessive; SEMD, Pakistani type; Urofacial syndrome; Alzheimer disease 6; Cholesteryl ester storage disease; Corneal dystrophy, Thiel-Behnke type; Dubin-Johnson syndrome; Leukemia, T-cell acute lymphocytic; Leukemia, T-cell acute lymphocytic; Spinocerebellar ataxia, infantile-onset, with sensory neuropathy; Split hand/foot malformation, type 3; Tolbutamide poor metabolizer; Warfarin sensitivity; Wolman disease; Anterior segment mesenchymal dysgenesis and cataract; Cataract, congenital; Neurofibrosarcoma; Diabetes mellitus, insulin-dependent, 17; Diabetes mellitus, insulin-dependent, 17; obesity, insulin resistance, Graft vesus host and other diseases, disorders and conditions of the like.

NOV3 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV3 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV4

NOV4 includes two novel Integrin Beta-7 Precursor-like proteins disclosed below. The disclosed proteins have been named NOV4a and NOV4b.

NOV4a

A disclosed NOV4a nucleic acid of 2798 nucleotides (designated CuraGen Acc. No. CG57185-01) encoding a novel Integrin Beta-7 Precursor-like protein is shown in Table 4A. An open reading frame was identified beginning with an ATG initiation codon at nucleotides 152–154 and ending with a TAA codon at nucleotides 2545–2547. Putative untranslated regions upstream from the initiation codon and downstream from the termination codon are underlined in Table 4A, and the start and stop codons are in bold letters.

TABLE 4A

NOV4a Nucleotide Sequence (SEQ ID NO:11)
CGTTGCTGTCGCTCTGCACGCACCTATGTGGAAACTAAAGCCCAGAGAGAAAGTCTGACTTGCCCCACAG

CCAGTGAGTGACTGCAGCAGCACCAGAATCTGGTCTGTTTCCTGTTTGGCTCTTCTACCACTACGGCTTG

GGATCTCGGGCATGGTGGCTTTGCCAATGGTCCTTGTTTTGCTGCTGGTCCTGAGCAGAGGTGAGAGTGA

ATTGGACGCCAAGATCCCATCCACAGGGGATGCCACAGAATGGCGGAATCCTCACCTGTCCATGCTGGGG

TCCTGCCAGCCAGCCCCCTCCTGCCAGAAGTGCATCCTCTCACACCCCAGCTGTGCATGGTGCAAGCAAC

TGAACTTCACCGCGTCGGGAGAGGCGGAGGCGCGGCGCTGCGCCCGACGAGAGGAGCTGCTGGCTCGAGG

CTGCCCGCTGGAGGAGCTGGAGGAGCCCCGCGGCCAGCAGGAGGTGCTGCAGGACCAGCCGCTCAGCCAG

GGCGCCCGCGGAGAGGGTGCCACCCAGCTGGCGCCGCAGCGGGTCCGGGTCACGCTGCGGCCTGGGGAGC

CCCAGCAGCTCCAGGTCCGCTTCCTTCGTGCTGAGGGATACCCGGTGGACCTGTACTACCTTATGGACCT

GAGCTACTCCATGAAGGACGACCTGGAACGCGTGCGCCAGCTCGGGCACGCTCTGCTGGTCCGGCTGCAG

GAAGTCACCCATTCTGTGCGCATTGGTTTTGGTTCCTTTGTGGACAAAACGGTGCTGCCCTTTGTGAGCA

CAGTACCCTCCAAACTGCGCCACCCCTGCCCCACCCGGCTGGAGCGCTGCCAGTCACCATTCAGCTTTCA

CCATGTGCTGTCCCTGACGGGGACGCACAAGCCTTCGAGCGGGAGGTGGGGCGCCAGAGTGTGTCCGGC

AATCTGGACTCGCCTGAAGGTGGCTTCGATGCCATTCTGCAGGCTGCACTCTGCCAGGAGCAGATTGGCT

GGAGAAATGTGTCCCGGCTGCTGGTGTTCACTTCAGACGACACATTCCATACAGCTGGGGACGGGAAGTT

GGGCGGCATTTTCATGCCCAGTGATGGGCACTGCCACTTGGACAGCAATGGCCTCTACAGTCGCACCACA

GAGTTTGACTACCCTTCTGTGGGTCAGGTAGCCCAGGCCCTCTCTGCAGCAAATATCCAGCCCATCTTTG

CTGTCACCAGTGCCGCACTGCCTGTCTACCAGGAGCTGAGTAAACTGATTCCTAAGTCTGCAGTTGGGGA

GCTGAGTGAGGACTCCAGCAACGTGGTACAGCTCATCATGGATGCTTATAATAGCCTGTCTTCCACCGTG

ACCCTTGAACACTCTTCACTCCCTCCTGGGGTCCACATTTCTTACGAATCCCAGTGTGAGGGTCCTGAGA

AGAGGGAGGGTAAGGCTGAGGATCGAGGACAGTGCAACCACGTCCGAATCAACCAGACGGTGACTTTCTG

GGTTTCTCTCCAAGCCACCCACTGCCTCCCAGAGCCCCATCTCCTGAGGCTCCGGGCCCTTGGCTTCTCA

GAGGAGCTGATTGTGGAGTTGCACACGCTGTGTGACTGTAATTGCAGTGACACCCAGCCCCAGGCTCCCC

ACTGCAGTGATGGCCAGGGACACCTACAATGTGGTGTATGCAGCTGTGCCCCTGGCCGCCTAGGTCGGCT

TABLE 4A-continued

NOV4a Nucleotide Sequence

CTGTGAGTGCTCTGTGGCAGAGCTGTCCTCCCCAGACCTGGAATCTGGGTGCCGGGCTCCCAATGGCACA

GGGCCCCTGTGCAGTGGAAAGGGTCACTGTCAATGTGGACGCTGCAGCTGCAGTGGACAGAGCTCTGGGC

ATCTGTGCGAGTGTGACGATGCCAGCTGTGAGCGACATGAGGGCATCCTCTGCGGAGGCTTTGGTCGCTG

CCAATGTGGAGTATGTCACTGTCATGCCAACCGCACGGGCAGAGCATGCGAATGCAGTGGGGACATGGAC

AGTTGCATCAGTCCCGAGGGAGGGCTCTGCAGTGGGCATGGACGCTGCAAATGCAACCGCTGCCAGTGCT

TGGACGGCTACTATGGTGCTCTATGCGACCAATGCCCAGGCTGCAAGACACCATGCGAGAGACACCGGGA

CTGTGCAGAGTGTGGGGCCTTCAGGACTGGCCCACTGGCCACCAACTGCAGTACAGCTTGTGCCCATACC

AATGTGACCCTGGCCTTGGCCCCTATCTTGGATGATGGCTGGTGCAAAGAGCGGACCCTGGACAACCAGC

TGTTCTTCTTCTTGGTGGAGGATGACGCCAGAGGCACGGTCGTGCTCAGAGTGAGACCCCAAGAAAAGGG

AGCAGACCACACGCAGGCCATTGTGCTGGGCTGCGTAGGGGGCATCGTGGCAGTGGGGCTGGGGCTGGTC

CTGGCTTACCGGCTCTCGGTGGAAATCTATGACCGCCGGGAATACAGTCGCTTTGAGAAGGAGCAGCAAC

AACTCAACTGGAAGCAGGACAGTAATCCTCTCTACAAAAGTGCCATCACGACCACCATCAATCCTCGCTT

TCAAGAGGCAGACAGTCCCACTCTCTGAAGGAGGGAGGGACACTTACCCAAGGCTCTTCTCCTTGGAGGA

CAGTGGGAACTGGAGGGTGAGAGGAAGGGTGGGTCTGTAAGACCTTGGTAGGGGACTAATTCACTGGCGA

GGTGCGGCCACCACCCTACTTCATTTTCAGAGTGACACCCAAGAGGGCTGCTTCCCATGCCTGCAACCTT

GCATCCATCTGGGCTACCCCACCCAAGTATACAATAAAGTCTTACCTCAGAAAAAAAAAAAAAAAAAA

A NOV4a polypeptide (SEQ ID NO:12) encoded by SEQ ID NO:11 is 798 amino acid residues and is presented using the one letter code in Table 4B.

TABLE 4B

NOV4a protein sequence (SEQ ID NO:12)
MVALPMVLVLLLVLSRGESELDAKIPSTGDATEWRNPHLSMLGSCQPAPSCQKCILSHPSCAWCKQLNFTASGE

AEARRCARREELLARGCPLEELEEPRGQQEVLQDQPLSQGARGEGATQLAPQRVRVTLRPGEPQQLQVRFLRAE

GYPVDLYYLMDLSYSMKDDLERVRQLGHALLVRLQEVTHSVRIGFGSFVDKTVLPFVSTVPSKLRHPCPTRLER

CQSPFSFHHVLSLTGDAQAFEREVGRQSVSGNLDSPEGGFDAILQAALCQEQIGWRNVSRLLVFTSDDTFHTAG

DGKLGGIFMPSDGHCHLDSNGLYSRSTEFDYPSVGQVAQALSAANIQPIFAVTSAALPVYQELSKLIPKSAVGE

LSEDSSNVVQLIMDAYNSLSSTVTLEHSSLPPGVHISYESQCEGPEKREGKAEDRGQCNHVRINQTVTFWVSLQ

ATHCLPEPHLLRLRALGFSEELIVELHTLCDCNCSDTQPQAPHCSDGQGHLQCGVCSCAPGRLGRLCECSVAEL

SSPDLESGCRAPNGTGPLCSGKGHCQCGRCSCSGQSSGHLCECDDASCERHEGILCGGFGRCQCGVCHCHANRT

GRACECSGDMDSCISPEGGLCSGHGRCKCNRCQCLDGYYGALCDQCPGCKTPCERHRDCAECGAFRTGPLATNC

STACAHTNVTLALAPILDDGWCKERTLDNQLFFFLVEDDARGTVVLRVRPQEKGADHTQAIVLGCVGGIVAVGL

GLVLAYRLSVEIYDRREYSRFEKEQQQLNWKQDSNPLYKSAITTTINPRFQEADSPTL

NOV4b

A disclosed NOV4b nucleic acid of 2211 nucleotides (designated CuraGen Acc. No. CG57185-02) encoding a novel Integrin Beta-7 Precursor-like protein is shown in Table 4C. An open reading frame was identified beginning with an ATG initiation codon at nucleotides 13–15 and ending with a TAA codon at nucleotides 1801–1803. Putative untranslated regions upstream from the initiation codon and downstream from the termination codon are underlined in Table 4C, and the start and stop codons are in bold letters.

TABLE 4C

NOV4b Nucleotide Sequence (SEQ ID NO:13)

GTGGCTTTGCCAATGGTCCTTGTTTTGCTGCTGGTCCTGAGCAGAGGTGAGAGTGAATTGGACGCCAAGA

TCCCATCCACAGGGGATGCCACAGAATGGCGGAATCCTCACCTGTCCATGCTGGGGTCCTGCCAGCCAGC

CCCCTCCTGCCAGAAGTGCATCCTCTCACACCCCAGCTCTGCATGGTGCAAGCAACTGAACTTCACCGCG

TCGGGAGAGGCGGAGGCGCGGCGCTGCGCCCGACGAGAGGAGCTGCTGGCTCGAGGCTGCCCGCTGGAGG

AGCTGGAGGAGCCCCGCGGCCAGCAGGAGGTGCTGCAGGACCAGCCGCTCAGCCAGGGCGCCCGCGGAGA

GGGTGCCACCCAGCTGGCGCCGCAGCGGGTCCGGGTCACGCTGCGGCCTGGGGAGCCCCAGCAGCTCCAG

GTCCGCTTCCTTCGTGCTGAGGGATACCCGGTGGACCTGTACTACCTTATGGACCTGAGCTACTCCATGA

AGGACGACCTGGAACGCGTGCGCCAGCTCGGGCACGCTCTGCTGGTCCGGCTGCAGGAAGTCACCCATTC

TGTGCGCATTGGTTTTGGTTCCTTTGTGGACAAAACGGTGCTGCCCTTTGTGAGCACAGTACCCTCCAAA

CTGCGCCACCCCTGCCCCACCCGGCTGGAGCGCTGCCAGTCACCATTCAGCTTTCACCATGTGCTGTCCC

TGACGGGGACGCACAAGCCTTCGAGCGGGAGGTGGGGCGCCAGAGTGTGTCCGGCAATCTGGACTCGCC

TGAAGGTGGCTTCGATGCCATTCTGCAGGCTGCACTCTGCCAGGAGCAGATTGGCTGGAGAAATGTGTCC

CGGCTGCTGGTGTTCACTTCAGACGACACATTCCATACAGCTGGGGACGGGAAGTTGGGCGGCATTTTCA

TGCCCAGTGATGGGCACTGCCACTTGGACAGCAATGGCCTCTACAGTCGCAGCACAGAGTTTGACTACCC

TTCTGTGGGTCAGGTAGCCCAGGCCCTCTCTGCAGCAAATATCCAGCCCATCTTTGCTGTCACCAGTGCC

GCACTGCCTGTCTACCAGGAGCTGAGTAAACTGATTCCTAAGTCTGCAGTTGGGGAGCTGAGTGAGGACT

CCAGCAACGTGGTACAGCTCATCATGGATGCTTATAATAGCCTGTCTTCCACCGTGACCCTTGAACACTC

TTCACTCCCTCCTGGGGTCCACATTTCTTACGAATCCCAGTGTGAGGGTCCTGAGAAGAGGGAGGGTAAG

GCTGAGGATCGAGGACAGTGCAACCACGTCCGAATCAACCAGACGGTGACTTTCTGGGTTTCTCTCCAAG

CCACCCACTGCCTCCCAGAGCCCCATCTCCTGAGGCTCCGGGCCCTTGGCTTCTCAGAGGAGCTGATTGT

GGAGTTGCACACGCTGTGTGACTGTAATTGCAGTGACACCCAGCCCCAGGCTCCCCACTGCAGTGATGGC

CAGGGACACCTACAATGTGGTGTATGCAGCTGTGCCCCTGGCCGCCTAGGTCGGCTCTGTGAGTGCTCTG

TGGCAGAGCTGTCCTCCCCAGACCTGGAATCTGGGTGCCGGGCTCCCAATGGCACAGGGCCCCTGTGCAG

TGGAAAGGGTCACTGTCAATGTGGACGCTGCAGCTGCAGTGGACAGAGCTCTGGGCATCTGTGCGAGTGT

GACGATGCCAGCTGTGAGCGACATGAGGGCATCCTCTGCGGAGGGACTGTGCAGAGTGTGGGGCCTTCAG

GACTGGCCCACTGGCCACCAACTGCAGTACAGCTTGTGCCCATACCAATGTGACCCTGGCCTTGGCCCCT

ATCTTGGATGATGGCTGGTGCAAAGAGCGGACCCTGGACAACCAGCTGTTCTTCTTCTTGGTGGAGGATG

ACGCCAGAGGCACGGTCGTGCTCAGAGTGAGACCCCAAGAAAAGGGAGCAGACCACACGCAGGCCATTGT

GCTGGGCTGCGTAGGGGGCATCGTGGCAGTGGGGCTGGGGCTGGTCCTGGCTTACCGGCTCTCGGTGGAA

ATCTATGACCGCCGGGAATACAGTCGCTTTGAGAAGGAGCAGCAACAACTCAACTGGAAGCAGGTGAGGA

GACTTCCTGGTTAGGCCCCTTTTTAGCTGTTCCCCCACCACAAGACCAGCCCTGATTCCTCCCACTGGGT

TCCCCCAGCCCCTAGCACATGTAACCAACCCCTCTGCTAAC

---

The nucleic acid sequence of NOV4b maps to chromosome 12 and has 1813 of 1881 bases (96%) identical to a gb:GENBANK-ID:HUMINTB7|acc:M68892.1 mRNA from *Homo sapiens* (Human integrin beta-7 subunit mRNA, complete cds) (E=0.0).

A NOV4b polypeptide (SEQ ID NO:14) encoded by SEQ ID NO:13 is 596 amino acid residues and is presented using the one letter code in Table 4D. Signal P, Psort and/or Hydropathy results predict that NOV4b contains a signal peptide and is likely to be localized to the mitochondrial matrix space with a certainty of 0.4542 and the mitochondrial intermembrane space with a certainty of 0.4030. The most likely cleavage site for a NOV4b polypeptide is between amino acids 14 and 15: GES-EL.

TABLE 4D

NOV4b protein sequence (SEQ ID NO:14)
MVLVLLLVLSRGESELDAKIPSTGDATEWRNPHLSMLGSCQPAPSCQKCILSHPSCAWCKQLNFTASGEAEARR

CARREELLARGCPLEELEEPRGQQEVLQDQPLSQGARGEGATQLAPQRVRVTLRPGEPQQLQVRFLRAEGYPVD

LYYLMDLSYSMKDDLERVRQLGHALLVRLQEVTHSVRIGFGSFVDKTVLPFVSTVPSKLRHPCPTRLERCQSPF

SFHHVLSLTGDAQAFEREVGRQSVSGNLDSPEGGFDAILQAALCQEQIGWRNVSRLLVFTSDDTFHTAGDGKLG

GIFMPSDGHCHLDSNGLYSRSTEFDYPSVGQVAQALSAANIQPIFAVTSAALPVYQELSKLIPKSAVGELSEDS

SNVVQLIMDAYNSLSSTVTLEHSSLPPGVHISYESQCEGPEKREGKAEDRGQCNHVRINQTVTFWVSLQATHCL

PEPHLLRLRALGFSEELIVELHTLCDCNCSDTQPQAPHCSDGQGHLQCGVCSCAPGRLGRLCECSVAELSSPDL

ESGCRAPNGTGPLCSGKGHCQCGRCSCSGQSSGHLCECDDASCERHEGILCGGTVQSVGPSGLAHWPPTAVQLV

PIPM

The NOV4b amino acid sequence has 571 of 571 amino acid residues (100%) identical to, and 571 of 571 amino acid residues (100%) similar to, the 798 amino acid residue ptnr:SWISSNEW-ACC:P26010 protein from *Homo sapiens* (Human) (Integrin Beta-7 Precursor) (E=5.9e$^{-318}$).

NOV4b is expressed in at least the following tissues: Colon, Lung, Lymph node, Lymphoid tissue, Peripheral Blood, Placenta, Salivary Glands, Spleen, Thyroid and Tonsils. Expression information was derived from the tissue sources of the sequences that were included in the derivation of NOV4b.

Possible small nucleotide polymorphisms (SNPs) found for NOV4a are listed in Table 4E.

TABLE 4E

SNPs

| Variant | Nucleotide Position | Base Change | Amino Acid Position | Base Change |
|---|---|---|---|---|
| 13377057 | 423 | G > A | 91 | Cys > Tyr |
| 13377058 | 1133 | C > T | 328 | Pro > Ser |
| 13377059 | 1261 | G > A | Silent | N/A |
| 13377056 | 2126 | A > G | 659 | Thr > Ala |
| 13377055 | 2241 | T > C | 697 | Leu > Pro |
| 13377054 | 2285 | C > T | 712 | Leu > Phe |
| 13377053 | 2303 | G > A | 718 | Glu > Lys |
| 13377052 | 2414 | C > T | 755 | Arg > Cys |
| 13377051 | 2443 | G > A | Silent | N/A |
| 13377050 | 2447 | C > T | 766 | Gln > End |

NOV4a and NOV4b are very closely homologous as is shown in the amino acid alignment in Table 4F.

TABLE 4F

Amino Acid Alignment of NOV4a and NOV 4b

```
              10        20        30        40        50        60        70
           ....|....|....|....|....|....|....|....|....|....|....|....|....|....|
NOV4a  MVALPMVLVLLLVLSRGESELDAKIPSTGDATEWRNPHLSMLGSCQPAPSCQKCILSHPSCAWCKQLNFT
NOV4b  -----MVLVLLLVLSRGESELDAKIPSTGDATEWRNPHLSMLGSCQPAPSCQKCILSHPSCAWCKQLNFT 80        90       100       110       120       130       140
           ....|....|....|....|....|....|....|....|....|....|....|....|....|....|
NOV4a  ASGEAEARRCARREELLARGCPLEELEEPRGQQEVLQDQPLSQGARGEGATQLAPQRVRVTLRPGEPQQL
NOV4b  ASGEAEARRCARREELLARGCPLEELEEPRGQQEVLQDQPLSQGARGEGATQLAPQRVRVTLRPGEPQQL 150       160       170       180       190       200       210
           ....|....|....|....|....|....|....|....|....|....|....|....|....|....|
NOV4a  QVRFLRAEGYPVDLYYLMDLSYSMKDDLERVRQLGHALLVRLQEVTHSVRIGFGSFVDKTVLPFVSTVPS
NOV4b  QVRFLRAEGYPVDLYYLMDLSYSMKDDLERVRQLGHALLVRLQEVTHSVRIGFGSFVDKTVLPFVSTVPS 220       230       240       250       260       270       280
           ....|....|....|....|....|....|....|....|....|....|....|....|....|....|
NOV4a  KLRHPCPTRLERCQSPFSFHHVLSLTGDAQAFEREVGRQSVSGNLDSPEGGFDAILQAALCQEQIGQRNV
NOV4b  KLRHPCPTRLERCQSPFSFHHVLSLTGDAQAFEREVGRQSVSGNLDSPEGGFDAILQAALCQEQIGQRNV 290       300       310       320       330       340       350
           ....|....|....|....|....|....|....|....|....|....|....|....|....|....|
NOV4a  SRLLVFTSDDTFHTAGDGKLGGIFMPSDGHCHLDSNGLYSRSTEFDYPSVGQVAQALSAANIQPIFAVTS
NOV4b  SRLLVFTSDDTFHTAGDGKLGGIFMPSDGHCHLDSNGLYSRSTEFDYPSVGQVAQALSAANIQPIFAVTS
```

TABLE 4F-continued

Amino Acid Alignment of NOV4a and NOV 4b

```
              360       370       380       390       400       410       420
         ....|....|....|....|....|....|....|....|....|....|....|....|....|
NOV4a    AALPVYQELSKLIPKSAVGELSEDSSNVVQLIMDAYNSLSSTVTLEHSSLPPGVHISYESQCEGPEKREG
NOV4b    AALPVYQELSKLIPKSAVGELSEDSSNVVQLIMDAYNSLSSTVTLEHSSLPPGVHISYESQCEGPEKREG 430       440       450       460       470       480       490
         ....|....|....|....|....|....|....|....|....|....|....|....|....|
NOV4a    KAEDRGQCNHVRINQTVTFWVSLQATHCLPEPHLLRLRALGFSEELIVELHTLCDCNCSDTQPQAPHCSD
NOV4b    KAEDRGQCNHVRINQTVTFWVSLQATHCLPEPHLLRLRALGFSEELIVELHTLCDCNCSDTQPQAPHCSD 500       510       520       530       540       550       560
         ....|....|....|....|....|....|....|....|....|....|....|....|....|
NOV4a    GQGHLQCGVCSCAPGRLGRLCECSVAELSSPDLESGCRAINGTGPLCSGKGHCQCGRCSCSGQSSGHLCE
NOV4b    GQGHLQCGVCSCAPGRLGRLCECSVAELSSPDLESGCRAINGTGPLCSGKGHCQCGRCSCSGQSSGHLCE 570       580       590       600       610       620       630
         ....|....|....|....|....|....|....|....|....|....|....|....|....|
NOV4a    CDDASCERHEGILCCGFGRCQCGVCHCHANRTGRACECSGDMDSCISPEGGLCSGHGRCKCNRCQCLDGY
NOV4b    CDDASCERHEGILCC----------------GTVQS--------VGPSG---------------------

640       650       660       670       680       690       700
         ....|....|....|....|....|....|....|....|....|....|....|....|....|
NOV4a    YGALCDQCPGCKTPCERHRDCAECGAFRTGPLATNCSTACAHINVILALAPELDDGWCKERTLDNQLFFF
NOV4b    ---LAHWPP---------------------------------IAVQLVPIEY-----------------

710       720       730       740       750       760       770
         ....|....|....|....|....|....|....|....|....|....|....|....|....|
NOV4a    LVEDDARGTVVLRVRPQEKGADHTQAIVLGCVGGIVAVGLGLVLAYRLSVEIYDRREYSRFEKEQQQLNW
NOV4b    ---------------------------------------------------------------------

780       790
         ....|....|....|....|....|....|...
NOV4a    KQDSNPLYKSAITTTINPRFQEADSPTL
NOV4b    ----------------------------
```

Homologies to any of the above NOV4 proteins will be shared by the other NOV4 proteins insofar as they are homologous to each other as shown above. Any reference to NOV4 is assumed to refer to both of the NOV4 proteins in general, unless otherwise noted.

NOV4a also has homology to the amino acid sequences shown in the BLASTP data listed in Table 4G.

TABLE 4G

BLAST results for NOV4a

| Gene Index/ Identifier | Protein/Organism | Length (aa) | Identity (%) | Positives (%) | Expect |
|---|---|---|---|---|---|
| gi|4504777|ref|NP_000880.1| (NM_000889) | integrin, beta 7 [Homo sapiens] | 798 | 737/798 (92%) | 737/798 (92%) | 0.0 |
| gi|400075 sp|P26011| ITB7|MOUSE | INTEGRIN BETA-7 PRECURSOR (INTEGRIN BETA-P) (M290 IEL ANTIGEN) [Mus musculus] | 806 | 632/784 (80%) | 673/784 (85%) | 0.0 |
| gi|255139|gb|AAB23193.1| (S44607) | beta 7 integrin [Mus musculus] | 806 | 631/784 (80%) | 672/784 (85%) | 0.0 |
| gi|7305193|ref|NP_038594.1| (NM_013566) | integrin beta 7 [Mus musculus] | 805 | 631/784 (80%) | 672/784 (85%) | 0.0 |
| gi|2196784|gb|AAB61241.1| (AF003598) | integrin beta-7 subunit [Rattus norvegicus] | 640 | 513/632 (81%) | 551/632 (87%) | 0.0 |

The homology of these sequences is shown graphically in the ClustalW analysis shown in Table 4H.

TABLE 4H

ClustalW Analysis of NOV4

1) NOV4a (SEQ ID NO:12)
2) gi|4504777|refNP_000880.1| (NM_000889) integrin, beta 7 [*Homo sapiens*]
(SEQ ID NO:112)
3) gi|400075|sp|P26011|ITB7_MOUSE INTEGRIN BETA-7 PRECURSOR (INTEGRIN BETA-P)
(M290 IEL ANTIGEN) [*Mus musculus*] (SEQ ID NO:113)
4) gi 255139|gb|AAB23193.1| (S44607) beta 7 integrin [*Mus musculus*] (SEQ ID NO:114)
5) gi 7305193|ref|NP_038594.1| (NM_013566) integrin beta 7 [*Mus musculus*]
(SEQ ID NO:115)
6) gi 2196784|gb|AAB61241.1| (AF003598) integrin beta-7 subunit [*Rattus norvegicus*]
(SEQ ID NO:116)

```
                  10        20        30        40        50        60        70
                  ....|....|....|....|....|....|....|....|....|....|....|....|....|....|
NOV4a             MVALPMVLVLLLVLSRGESELDAKIPSTGDATEWRNPHLSMLGSCQPAPSCQKCILSHPSCAWCKQLNFT
gi|4504777|       MVALPMVLVLLLVLSRGESELDAKIPSTGDATEWRNPHLSMLGSCQPAPSCQKCILSHPSCAWCKQLNFT
gi|400075|        MVDSSTVLIFLLVLGGGQSELDTKITSSGDAAEWEDPDLSLQGSCQPVPSCQKCILSHPSCAWCKQLNFT
gi|255139|        MVDSSTVLIFLLVLGGGQSELDTKITSSGDAAEWEDPDLSLQGSCQPVPSCQKCILSHPSCAWCKQLNFT
gi|7305193|       MVDSSTVLIFLLVLGGGQSELDTKITSSGSAAEWEDPDLSLQGSCQPVPSCQKCILSHPSCAWCKQLNFT
gi|2196784|       ----------------------------------------------------------------------

80        90       100       110       120       130       140
                  ....|....|....|....|....|....|....|....|....|....|....|....|....|....|
NOV4a             ASGEAEARRCARREELLARGCPLEELEEPRGQQEVLQDQPLSQGARGEGATQLAPQRVRVTLRPGEPQQL
gi|4504777|       ASGEAEARRCARREELLARGCPLEELEEPRGQQEVLQDQPLSQGARGEGATQLAPQRVRVTLRPGEPQQL
gi|400075|        ASGEAEARRCARREELLARGCPAQELEEPRGRQEVLQDKPLSQGDRGEGATQLAPQRIRVTLRPGEPQKF
gi|255139|        ASGEAEARRCGRREELLARGCPAQELEEPRGRQEVLQDKPLSQGDRGEGATQLAPQRIRVTLRPGEPQKF
gi|7305193|       ASGEAEARRCARREELLARGCPAQELEEPRGRQEVLQDKPLSQGDRGEGATQLP-QRIRVTLRPGEPQKF
gi|2196784|       ----------------------------------------------------------------------

150       160       170       180       190       200       210
                  ....|....|....|....|....|....|....|....|....|....|....|....|....|....|
NOV4a             QVRFLRAEGYPVDLYYLMDLSYSMKDDLERVRQLGHALLVRLQEVTHSVRIGFGSFVDKTVLPFVSTVPS
gi|4504777|       QVRFLRAEGYPVDLYYLMDLSYSMKDDLERVRQLGHALLVRLQEVTHSVRIGFGSFVDKTVLPFVSTVPS
gi|400075|        RVRFLRAAGYPVDLYYLMDLSYSMKDDLERVRQLGHALLVRLQEVTHSVRIGFGSFVDKTVLPFVSTVPS
gi|255139|        RVRFLRAAGYPVDLYYLMDLSYSMKDDLERVRQLGHALLVRLQEVTHSVRIGFGSFVDKTVLPFVSTVPS
gi|7305193|       RVRFLRAAGYPVDLYYLMDLSYSMKDDLERVRQLGHALLVRLQEVTHSVRIGFGSFVDKTVLPFVSTVPS
gi|2196784|       --------------------------LERVRQLGQALLERLREVTHSVRIGFGSFVDKTVLPFVSTVPS 220       230       240       250       260       270       280
                  ....|....|....|....|....|....|....|....|....|....|....|....|....|....|
NOV4a             KLRHPCPTRLERCQSPFSFHHVLSLTGDAQAFEREVGRQSVSGNLDSPEGGFDAILQAALCQEQIGWRNV
gi|4504777|       KLRHPCPTRLERCQSPFSFHHVLSLTGDAQAFEREVGRQSVSGNLDSPEGGFDAILQAALCQEQIGWRNV
gi|400075|        KLHHPCPSRLERCQPPFSFHHVLSLTGDAQAFEREVGRQNVSGNLDSPEGGFDAILQAALCQEQIGWRNV
gi|255139|        KLHHPCPSRLERCQPPFSFHHVLSLTGDAQAFEREVGRQNVSGNLDSPEGGFDAILQAALCQEQIGWRNV
gi|7305193|       KLHHPCPSRLERCQPPFSFHHVLSLTGDAQAFEREVGRQNVSGNLDSPEGGFDAILQAALCQEQIGWRNV
gi|2196784|       KLNHPCPSRLERCQAPFSMHHVLPLTRDAQAFEREVGRQNVSGNLDSPEGGFDAILQAALCQEQIGWRNV 290       300       310       320       330       340       350
                  ....|....|....|....|....|....|....|....|....|....|....|....|....|....|
NOV4a             SRLLVFTSDDTFHTAGDGKLGGIFMPSDGHCHLDSNGLYSRSTEFDYPSVGQVAQALSAANIQPIFAVTS
gi|4504777|       SRLLVFTSDDTFHTAGDGKLGGIFMPSDGHCHLDSNGLYSRSTEFDYPSVGQVAQALSAANIQPIFAVTS
gi|400075|        SRLLVFTSDDTFHTAGDGKLGGIFMPSDGRCHLDSNGVYTNSAEFDYPSVGQVAQALTAANIQPIFAVTG
gi|255139|        SRLLVFTSDDTFHTAGDGKLGGIFMPSDGRCHLDSNGVYTNSAEFDYPSVGQVAQALTAANIQPIFAVTG
gi|7305193|       SRLLVFTSDDTFHTAGDGKLGGIFMPSDGRCHLDSNGVYTNSAEFDYPSVGQVAQALTAANIQPIFAVTG
gi|2196784|       SRLLVFTSDDTFHTAGDGKLGGIFMPSDGRCHLDSNGVYTNSAEFDYPSVGQVAQALTAANIQPIFAVTG 360       370       380       390       400       410       420
                  ....|....|....|....|....|....|....|....|....|....|....|....|....|....|
NOV4a             AALPVYQELSKLIPKSAVGELSEDSSNVVQLIMDAYNSLSSTVTLEHSSLPPGVHISVESQCEGPEKREG
gi|4504777|       AALPVYQELSKLIPKSAVGELSEDSSNVVQLIMDAYNSLSSTVTLEHSSLPPGVHISVESQCEGPEKREG
gi|400075|        ATLPVYQELRQLIPKSAVGELSEDSSNVVQLIMDAYDSLSSTVTLEHSPLPPGVSISFESHCKGPEKTEG
gi|255139|        ATLPVYQELRQLIPKSAVGELSEDSSNVVQLIMDAYDSLSSTVTLEHSPLPPGVSISFESHCKGPEKTEG
gi|7305193|       ATLPVYQELRQLIPKSAVGELSEDSSNVVQLIMDAYDSLSSTVTLEHSPLPPGVSISFESHCKGPEKTEG
gi|2196784|       ATLPVYQELSQLIPKSAVGELSEDSSNVVQLIMDAYDNLSSTVTLEHSSLPPGVSISFESHCESPEKSEG 430       440       450       460       470       480       490
                  ....|....|....|....|....|....|....|....|....|....|....|....|....|....|
NOV4a             KAEDR-GQCNHVRINQTVTFWVSLQATHCLPEPHLRIRALGFSEELIVELHTKCDCNCSDIQPQAPHCS
gi|4504777|       KAEDR-GQCNHVRINQTVTFWVSLQATHCLPEPHLRIRALGFSEELIVELHTKCDCNCSDIQPQAPHCS
gi|400075|        EAGDR-GQCNDVRVNQTVDFWVTLQATHCLPEAHVLRIWALGFSEELTVELHTVCDCNCGDAQPHAPYCS
gi|255139|        EAGDR-GQCNDVRVNQTVDFWVTLQATHCLPEAHVLRIWALGFSEELTVELHTVCDCNCGDAQPHAPYCS
gi|7305193|       EAGDR-GQCNHVRVNRMVDFWVTLQATHCLPEAHVLRIWALGFSEELTVELHTVCDCNCGDAQPHAPYCS
gi|2196784|       EAGDRRGQCNHVRVNRMVDFWVTLQASHCLPEAHVLRIWALGFSEELTVELHTVCDCNCSDAQPRAPYCS
```

TABLE 4H-continued

ClustalW Analysis of NOV4

```
                   500       510       520       530       540       550       560
             ....|....|....|....|....|....|....|....|....|....|....|....|....|....|
NOV4a        CGQGHLQCCVCSCAPGRLGRLCECSVAELSSPDLESGCRAPNGTGPLCSGKGHCQCGRCSCSGQSSGHLC
gi|4504777|  CGQGHLQCCVCSCAPGRLGRLCECSVAELSSPDLESGCRAPNGTGPLCSGKGHCQCGRCSCSGQSSGHLC
gi|400075|   CGQGDLQCGICSCAPGRLGQLCECSEADLSSPDLESGCRAPNGTGPLCSGKGRCQCGRCSCSGQSSGRLC
gi|255139|   CGQGDLQCGICSCAPGRLGQLCECSEADLSSPDLESGCRAPNGTGPLCGKGRCQCGRCSCSGQSSGRLC
gi|7305193|  CGQGDLQCGICSCAPGRLGQLCECSEADLSSPDLESGCRAPNGTGPLCSGKGRCQCGRCSCSGQSSGHLC
gi|2196784|  CGQGDLQCGICSCAPGRLGQLCECSEADLSSPDLESGCRAPNGTGPLCSGKGRCQCGHCSCSGQSSGRLC 570       580       590       600       610       620       630
             ....|....|....|....|....|....|....|....|....|....|....|....|....|....|
NOV4a        ECDDASCERHEGILCGGFGRCQCGVCHCHANRTGRACECSGDMDSCTSPEGGLCSGHGRCKCNRCQCLDG
gi|4504777|  ECDDASCERHEGILCGGFGRCQCGVCHCHANRTGRACECSGDMDSCESPEGGLCSGHGRCKCNRCQCLDG
gi|400075|   ECDDASCERHEGILCGGFGHCQCGVCHCHANHTGRACECSKSVDSCVSPEGGLCSGHGYCKCNRCQCLDG
gi|255139|   ECDDASCERHEGILCGGFGHCQCGVCHCHANHTGRACECSKSVDSCVSPEGGLCSGHGYCKCNRCQCLDG
gi|7305193|  ECDDASCERHEGILCGGFGHCQCGVCHCHANHTGRACECSKSVDSCVSPEGGLCSGHGYCKCNRCQCLDG
gi|2196784|  ECDDASCERHGGIFCGGFGHCQCGVCHCHANRTGRACECSESVDSCVSPEGGLCSGHGDCKCNRCQCLDG 640       650       660       670       680       690       700
             ....|....|....|....|....|....|....|....|....|....|....|....|....|....|
NOV4a        YYGALCDQCPGCKTPCERHRDCAECGAFRTGPLATNCSTACAHTNVTLALAPILDDGWCKERTEDNQLFF
gi|4504777|  YYGALCDQCPGCKTPCERHRDCAECGAFRTGPLATNCSTACAHTNVTLALAPILDDGWCKERTEDNQLFF
gi|400075|   YYGALCDQCLGCKSPCEQYRDCAECGAFGTGPLAANCSVVCADVNVTLTLAPNLDDGWCKERTIDNQLFF
gi|255139|   YYGALCDQCLGCKSPCEQYRDCAECGAFGTGPLAANCSVVCADVNVTLTLAPNLDDGWCKERTEDNQLFF
gi|7305193|  YYGALCDQCLGCKSPCEQYRDCAECGAFGTGPLAANCSVVCADVNVTLTLAPNLDDGWCKERTEDNQLFF
gi|2196784|  YYGALCDQCLGCKSPCEQYRDCAECGAFGTGPLAANCSAACADVNVTLALAPNLDDGWCKERTEDNQLFF 710       720       730       740       750       760       770
             ....|....|....|....|....|....|....|....|....|....|....|....|....|....|
NOV4a        FLVEDDARGTVVLRVRPQDKGADHTQAIVLGCVGGIVAVGLGLVLAYRLSVEIYDRREYSRFEKEQQQLN
gi|4504777|  FLVEDDARGTVVLRVRPQDKGADHTQAIVLGCVGGIVAVGLGLVLAYRLSVEIYDRREYSRFEKEQQQLN
gi|400075|   FLVEHAASG-IVLRVRPQDKGVDHTRAIILGCTGGIVAVGLGLVLAYRLSVEIYDRREYRRFEKEQQQLN
gi|255139|   FLVEHAASG-IVLRVRPQDKGVDHTRAIILGCTGGIVAVGLGLVLAYRLSVEIYDRREYRRFEKEQQQLN
gi|7305193|  FLVEHAASG-IVLRVRPQDKGVDHTRAIILGCTGGIVAVGLGLVLAYRLSVEIYDRREYRRFEKEQQQLN
gi|2196784|  FLVENSARG-VILRVRPQDKGADHTRAIILGCVGGIVAVGLGLVLAYRLSVEVYDRLEYSRFEKERQQLN 780       790       800
             ....|....|....|....|....|....|...
NOV4a        WKQDSNPLYKSAITTTINFRFQEAD--SPTL-------
gi|4504777|  WKQDSNPLYKSAITTTINFRFQEAD--SPTL-------
gi|400075|   WKQDNNPLYKSAITTTVNFRFQGTNGRSPSLSLTREAD
gi|255139|   WKQDNNPLYKSAITTTVNFRFQGTNGRSPSLSLTREAD
gi|7305193|  WKQDNNPLYKSAITTTVNFRFQGTNGRSPSLSLTREAD
gi|2196784|  WKQDSNPLYKSAVTTTVNFRFQGGNKQSLSLPLTQEAD
```

Tables 4I and 4J lists the domain description from DOMAIN analysis results against NOV4a. This indicates that the NOV4a sequence has properties similar to those of other proteins known to contain these domains.

TABLE 4I

Domain Analysis of NOV4a

```
gnl|Pfam|pfam00362, integrin_B, Integrins, beta chain.
Sequences cut off at repeats due to overlap with EGF. (SEQ ID NO: 117)
CD-Length = 428 residues. 100.0% aligned
Score = 633 bits (1632), Expect = 0.0
Query:   50 SCQKCILSHPSCAWCKQLNFTASGEAEARRCARREELLARGCPLEELEEPRGQQEVLQDQ 109
             ||++|+||  |  ||||  + + +||+  || ++ ||   | ||++||||+ +|  ||    |+|+|
Sbjct:    1 SCEECLLSGPGCAWCTKEDFTSPGEPDSERCDTRANLLSKGCPLDSIENPRSSAEILEDQ  60

Query:  110 PLSQGARGEGATQLAPQRVRVTLRPGEPQQLQVRFLRAEGYPVDLYYLMDLSYSMKDDLE 169
             |||   + +|||+|| ||+ |||||  | |+   ||| ||||||||||||||||||||
Sbjct:   61 PLSNKGSRDSSTQLSPQEVRLRLRPGEEQTFQLTVRRAEDYPVDLYYLMDLSYSMKDDLE 120

Query:  170 RVRQLGHALLVRLQEVTHSVRIGFGSFVDKTVLPFVSTVPSKLRHPCPTRLERCQSPFSF 229
             |+ ||   | +  + ++|  ||||||||||||| ||||| | |||+||| + + || || |
Sbjct:  121 NVKSLGTDLAREMSKLTSDFRIGFGSFVDKTVSPFVSTHPEKLRNPCPNKEKNCQPPFGF 180

Query:  230 HHVLSLTGDAQAFEREVGRQSVSGNLDSPEGGFDAILQAALCQEQIGWRN-VSRLLVFTS 288
             ||||||  |     |||+ +|||||+|||||||||+|+|+|+||||||| |+||||++
Sbjct:  181 KHVLSLTDDVDEFNEEVGKQRISGNLDAPEGGFDAIMQAAVCKEKIGWRNDVTRLLVFST 240

Query:  289 DDTFHTAGDGKLGGIFMPSDGHCHLDSNGLYSRSTEFDYPSVGQVAQALSAANIQPIFAV 348
             |  ||  ||||||||  |+|| ||||||  +|+  ||||||||||+ + ||  ||||||||
Sbjct:  241 DAGFHFAGDGKLGGIVQPNDGRCHLDSNNMYTMSTTMDYPSVGQLVEKLSENNIQPIFAV 300
```

TABLE 4I-continued

Domain Analysis of NOV4a

```
Query:  349 TSAALPVYQELSKLIPKSAVGELSEDSSNVVQLIMDAYNSLSSTVTLEHSSLPPGVHISY  408
            |  + +|++|++|||  ||||||||||||||||+||||  |  |  ||  |  ||  |+++|
Sbjct:  301 TEKQVHLYEKLTELIPGSAVGELSEDSSNVVQLIIDAYNKLRSEVELEVSDLPEGLNLSY  360

Query:  409 ESQCEGPEKREGKAEDRGQCNHVRINQTVTFWVSLQATHCLPEP--HLLRLRALGFSEEL  466
            |  |+        |   +  ||+|+  |+|    ||+|  ||+  |  ||       | + ++ ||||+ |
Sbjct:  361 TSFCKNGVSSPG--QRRGKCSGVQIGDTVSFEVSVTARECPPEGQKHSIIIKPLGFSDTL  418

Query:  467 IVELHTLCDC  476
            | +|  |||
Sbjct:  419 EVHVHPNCDC  428
```

TABLE 4J

Domain Analysis of NOV4a gnl|Smart|smart00187, INB, Integrin beta subunits (N-terminal portion
of extracellular region); Portion of beta integrins that lies N-terminal
to their EGF-like repeats. Integrins are cell adhesion
molecules that mediate cell-extracellular matrix and cell-cell
interactions. They contain both alpha and beta subunits. Beta
integrins are proposed to have a von Willebrand factor type-A "insert"
or "I"-like domain (SEQ ID NO:118)
CD-Length = 423 residues, 100.0% aligned
Score = 614 bits (1584), Expect = 5e-177

```
Query:   50 SCQKCILSHPSCAWCKQLNFTASGEAEARRCARREELLARGCPLEELEEPRGQQEVLQDQ  109
            || +||  |||+||||   |||+ | +             ||  | +|+|+ + |||+||
Sbjct:    1 SCGECIQSHPNCAWCTDENFTSGGSSARCDSRANLLAK--GCSPESIEDPKSEIEVLEDQ   58

Query:  110 PLSQGARGEGATQLAPQRVRVTLRPGEPQQLQVRFLRAEGYPVDLYYLMDLSYSMKDDLE  169
            |||          |  |++|||||+  |||||||    +  ++ ||||||||||||||||||+
Sbjct:   59 PLSDSESSGQAVQVSPQRVRLKLRPGEPQNFTLTVRQAEDYPVDLYYLMDLSYSMKDDLD  118

Query:  170 RVRQLGHALLVRLQEVTHSVRIGFSFVDKTVLPFVSTVPSKLRHPCPTRLERCQSPFSF  229
            ++ ||    | ++ +| + |+|||||||||| |||| |  | ||| |+ | | + |
Sbjct:  119 NLKSLGDDLAREMKGLTSNFRLGFSFVDKTVSPFVSTRPEKLENPCPNYNLTCEPPYGF  178

Query:  230 HHVLSLTGDAQAFEREVGRQSVSGNLDSPEGGFDAILQAALCQEQIGWRN-VSRLLVFTS  288
            ||||||  |    ||  +|  +||||+|||||||||+|||  ||||| ||||||  ||||++
Sbjct:  179 KHVLSLTDDTDEFNEEVKKQRISGNLDAPEGGFDAIMQAAVCTEQIGWREDARRLLVFST  238

Query:  289 DDTFHTAGDGKLGGIFMPSDGHCHLDSNGLYSRSTEFDYPSVGQVAQALSAANIQPIFAV  348
            | ||  ||||||  ||  |+| ||||+|  |+ ||   ||||+|+  | +| ||  |||||
Sbjct:  239 DAGFHFAGDGKLAGIVQPNDGQCHLDNNGEYTMSTTQDYPSIGQLNQKLAENNINPIFAV  298

Query:  349 TSAALPVYQELSKLIPKSAVGELSEDSSNVVQLIMDAYNSLSSTVTLEHSSLPPGVHISY  408
            |  + +|+|||  |||  |+|| ||||||||||+|| |||| +|| | ||  +|||   ||  ++|
Sbjct:  299 TKKQVSLYKELSALIPGSSVGVLSEDSSNVVELIKDAYNKISSRVELEDNSLPEGVSVTY  358

Query:  409 ESQCEGPEKREGKAEDRGQCNHVRINQTVTFWVSLQATHCLPE-PHLLRLRALGFSEELI  467
            |||         |        +|  |+|   ||+|  |++  ||  |  ||  | +|+ +||||  |
Sbjct:  359 TSSCPGGVVGPGTR----KCEGVKIGDTVSFEVTVTATKCPPEKEHSIRIRPVGFSETLE  414

Query:  468 VELHTLCDC  476
            |||  ||||
Sbjct:  415 VELTFLCDC  423
```

The integrins are a large family of heterodimeric cell-surface glycoproteins that play key roles in the adherence of cells to other cells and to extracellular matrix proteins. Leukocytes express a variety of integrins that are crucial participants in the inflammatory and immune responses. All integrins are composed of 1 alpha subunit and 1 beta subunit that are translated separately and are noncovalently associated. The cDNA sequences of 6 mammalian beta subunits, numbered beta-1 through beta-6, had previously been reported. Erle et al. (J. Biol. Chem. 266: 11009–11016, 1991) determined the complete sequence of a novel integrin beta subunit from leukocytes, designated beta-7. The cDNA contained a single large open reading frame predicted to encode a 798-amino acid protein precursor (signal peptide plus mature protein). Like other beta-subunit proteins, it was predicted to contain a large extracellular domain, a transmembrane domain, and a cytoplasmic tail. The deduced beta-7 amino acid sequence was 32 to 46% identical to the 6 previously sequenced subunits. It was most similar to the leukocyte integrin common beta subunit (ITGB2; CD18; 116920). Erle et al. (1991) predicted that integrin beta-7 plays a role in adhesive interactions of leukocytes. Krissansen et al. (Immunogenetics 35: 58–61, 1992) assigned the ITGB7 gene to human chromosome 12 by analysis of somatic cell hybrids. Krissansen et al. (1992) commented on the fact that the gene encoding the alpha subunit of the fibronectin receptor (FNRA; 135620) resides on chromosome 12 also. They stated that the 'extent and evolutionary significance of linkages between integrin genes . . . remains to be determined.' Baker et al. (Mammalian Genome 2:272–273, 1992) assigned the ITGB7 gene to 12q13.13 by nonisotopic in situ hybridization. Yuan et al. (Immunogenetics 35: 403–407, 1992) mapped the mouse homolog Itgb-7 to chromosome 15 by study of mouse-hamster somatic cell hybrids and by interspecific backcrosses.

The NOV4 nucleic acid of the invention encoding a Integrin Beta-7 Precursor-like protein includes the nucleic acid whose sequence is provided in Tables 4A and 4C, or a fragment thereof. The invention also includes a mutant or variant nucleic acid any of whose bases may be changed from the corresponding base shown in Tables 4A and 4C while still encoding a protein that maintains its Integrin Beta-7 Precursor-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 4% of the residues may be so changed.

The NOV4 protein of the invention includes the Integrin Beta-7 Precursor-like protein whose sequence is provided in Tables 4B and 4D. The invention also includes a mutant or variant protein any of whose residues may be changed from the corresponding residue shown in Tables 4B and 4D while still encoding a protein that maintains its Integrin Beta-7 Precursor-like activities and physiological functions, or a functional fragment thereof.

The NOV4 nucleic acids and proteins of the invention are useful in potential diagnostic and therapeutic applications implicated in various diseases and disorders described below and/or other pathologies. For example, the compositions of the present invention will have efficacy for treatment of patients suffering from: systemic lupus erythematosus, autoimmune disease, asthma, emphysema, scleroderma, allergy, ARDS; atherosclerosis, thrombosis, cancer, asthma, lymphedema; fertility, xerostomia, hyperthyroidism, hypothyroidism and other diseases, disorders and conditions of the like.

NOV4 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV4 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV5

A disclosed NOV5 nucleic acid of 1360 nucleotides (also referred to as CG57360-01) encoding a novel membrane protein-like protein is shown in Table 5A. An open reading frame was identified beginning with an ATG initiation codon at nucleotides 244–246 and ending with a TGA codon at nucleotides 1282–1284. Putative untranslated regions upstream from the intitation codon and downstream from the termination codon are underlined in Table 5A, and the start and stop codons are in bold letters.

TABLE 5A

NOV5 Nucleotide Sequence (SEQ ID NO:15)
<u>GTCGAATATCCATGCAGAGTACCTGGAATACATCAGGGATCCTTGCTCTCATGAGGTCAGAGATGAGGAATTC</u>

<u>CATAGGATGAGTCTTCTGTTCTTAAACCGAGTGTAAGGATAAGGCTGTCGGAGAGGAGGGAGTAGGATTTGGG</u>

<u>CATCAGAGCCCCCCAGCTGCTGCTCGTGGGGGTGAGGACACCAGGCCCCTGACTTTGCTCTGGTCTCTCTCCC</u>

<u>AGCTCCCTGCCCAGGCCCACAGCC</u>ATGGCCATGGCCCAGAAACTCAGCCACCTCCTGCCGAGTCTGCGGCAGG

TCATCCAGGAGCCTCAGCTATCTCTGCAGCCAGAGCCTGTCTTCACGGTGGATCGAGCTGAGGTGCCGCCGCT

CTTCTGGAAGCCGTACATCTATGCGGGCTACCGGCCGCTGCATCAGACCTGGCGCTTCTATTTCCGCACGCTG

TTCCAGCAGCACAACGAGGCCGTGAATGTCTGGACCCACCTGCTGGCGGCCCTGGCACTGCTGCTGCGGCTGG

CCCTCTTTGTGGAGACCGTGGACTTCTGGGGAGACCCACACGCCCTGCCCCTCTTCATCATTGTCCTTGCCTC

TTTCACCTACCTCTCCTTCAGTGCCTTGGCTCACCTCCTGCAGGCCAAGTCTGAGTTCTGGCATTACAGCTTC

TTCTTCCTGGACTATGTGGGGGTGGCCGTGTACCAGTTTGGCAGTGCCTTGGCACACTTCTACTATGCTATCG

AGCCCGCCTGGCATGCCCAGGTGCAGGCTGTTTTTCTGCCCATGGCTGCCTTTCTCGCCTGGCTTTCCTGCAT

TGGCTCCTGCTATAACAAGTACATCCAGAAACCAGGCCTGCTGGGCCGCACATGCCAGGAGGTGCCCTCCGTC

CTGGCCTACGCACTGGACATTAGTCCTGTGGTGCATCGTATCTTCGTGTCCTCCGACCCCACCACGGATGATC

CAGCTCTTCTCTACCACAAGTGCCAGGTGGTCTTCTTTCTGCTGGCTGCTGCCTTCTTCTCTACCTTCATGCC

TABLE 5A-continued

NOV5 Nucleotide Sequence

CGAGCGCTGGTTCCCTGGCAGCTGCCATGTCTTCGGGCAGCGCCACCAACTTTTCCACATCTTCTTGGTGCTG

TGCACGCTGGCTCAGCTGGAGGCTGTGGCACTGGACTATGAGGCCCGACGGCCCATCTATGAGCCTCTGCACA

CGCACTGGCCTCACAACTTTTCTGGCCTCTTCCTGCTCACGGTGGGCAGCAGCATCCTCACTGCATTCCTCCT

GAGCCAGCTGGTACAGCGCAAACTTGATCAGAAGACCAAGTGAAGGGGGATGGCATCTGGTAGGGAGGGAGGT

ATAGTTGGGGGACAGGGGTCTGGGTTTGGCTCCAGGTGGGAACAAG

The NOV5 nucleic acid was identified on chromosome 1 and has 308 of 508 bases (60%) identical to a gb:GENBANK-ID:RNU87960|acc:U87960.1 mRNA from *Rattus norvegicus* (*Rattus norvegicus* leukocyte common antigen receptor (LAR) gene, trans-spliced alternative untranslated exon) (E=1.5e$^{-06}$).

A disclosed NOV5 polypeptide (SEQ ID NO:16) encoded by SEQ ID NO:15 is 346 amino acid residues and is presented using the one-letter code in Table 5B. Signal P, Psort and/or Hydropathy results predict that NOV5 does not contain a signal peptide and is likely to be localized at the plasma membrane with a certainty of 0.6000 and the Golgi body with a certainty of 0.4000.

sources, literature sources, and/or RACE sources. The NOV5 sequence is also predicted to be expressed in the following tissues because of the expression pattern of (GENBANK-ID: gb:GENBANK-ID:RNU87960|acc:U87960.1) a closely related *Rattus norvegicus* leukocyte common antigen receptor (LAR) gene, trans-spliced alternative untranslated exon homolog in species *Rattus norvegicus*: leukocyte.

Possible small nucleotide polymorphisms (SNPs) found for NOV5 are listed in Table 5C.

TABLE 5B

Encoded NOV5 protein sequence (SEQ ID NO:16)
MAMAQKLSHLLPSLRQVIQEPQLSLQPEPVFTVDRAEVPPLFWKPYIYAGYRPLHQTWRFYFRTLFQQHNEA

VNVWTHLLAALALLLRLALFVETVDFWGDPHALPLFIIVLASFTYLSFSALAHLLQAKSEFWHYSFFFLDYV

GVAVYQFGSALAHFYYAIEPAWHAQVQAVFLPMAAFLAWLSCIGSCYNKYIQKPGLLGRTCQEVPSVLAYAL

DISPVVHRIFVSSDPTTDDPALLYHKCQVVFFLLAAAFFSTFMPERWFPGSCHVFGQGHQLFHIFLVLCTLA

QLEAVALDYEARRPIYEPLHTHWPHNFSGLFLLTVGSSILTAFLLSQLVQRKLDQKTK

The NOV5 amino acid sequence has 171 of 349 amino acid residues (48%) identical to, and 230 of 349 amino acid residues (65%) similar to, the 359 amino acid residue ptnr:TREMBLNEW-ACC:CAC05478 protein from Homo sapiens (Human) (DJ304B14.1 (NOVEL PROTEIN) (E=3.4e$^{-84}$).

NOV5 is expressed in at least the following tissues: Adrenal Gland/Suprarenal gland, Bone Marrow, Kidney, Liver, Prostate and Testis. This information was derived by determining the tissue sources of the sequences that were included in the invention including but not limited to Seq-Calling sources, Public EST sources, genomic clone

TABLE 5C

| | SNPs | | | |
|---|---|---|---|---|
| Variant | Nucleotide Position | Base Change | Amino Acid Position | Base Change |
| 13377060 | 967 | A > G | 242 | Lys > Glu |
| 13377061 | 1233 | A > G | Silent | N/A |

NOV5 has homology to the amino acid sequences shown in the BLASTP data listed in Table 5D.

TABLE 5D

BLAST results for NOV5

| Gene Index/ Identifier | Protein/Organism | Length (aa) | Identity (%) | Positives (%) | Expect |
|---|---|---|---|---|---|
| gi|18549110|ref|XP_089356.1| (XM_089356) | hypothetical protein XP_089356 [Homo sapiens] | 346 | 324/346 (93%) | 324/346 (93%) | e−168 |
| gi|12844255|dbj|BAB26296.1| | data source: SPTR, | 345 | 266/346 | 283/346 | e−130 |

TABLE 5D-continued

BLAST results for NOV5

| Gene Index/ Identifier | Protein/Organism | Length (aa) | Identity (%) | Positives (%) | Expect |
|---|---|---|---|---|---|
| (AK009450) | source key: Q9HD02, evidence: ISS~homolog to DJ304B14.1 (NOVEL PROTEIN) (FRAGMENT) ~putative [Mus musculus] | | (76%) | (80%) | |
| gi\|12839033\|dbj\|BAB24412.1\| (AK006107) | data source: SPTR, source key: Q9HD02, evidence: ISS~homolog to DJ304B14.1 (NOVEL PROTEIN) (FRAGMENT) ~putative [Mus musculus] | 354 | 158/351 (45%) | 215/351 (61%) | 4e−69 |
| gi\|9955433\|emb\|CAC05478.1\| (AL136125) | dJ304B14.1 (novel protein) [Homo sapiens] | 359 | 146/316 (46%) | 199/316 (62%) | 2e−66 |
| gi\|18564176\|ref\|XP_094815.1\| (XM_094815) | hypothetical protein XP_094815 [Homo sapiens] | 354 | 146/316 (46%) | 199/316 (62%) | 2e−66 |

The homology of these sequences is shown graphically in the ClustalW analysis shown in Table 5E.

TABLE 5E

Clustal W Sequence Alignment

1) NOV5 (SEQ ID NO:16)
2) gi|18549110|ref|XP_089356.1| (XM_089356) hypothetical protein XP_089356 [Homo sapiens] (SEQ ID NO:119)
3) gi|12844255|dbj|BAB26296.1| (AK009450) data source:SPTR, source key:Q9HD02, evidence:ISS~to DJ304B14.1 (NOVEL PROTEIN) (FRAGMENT)~putative [Mus musculus] (SEQ ID NO:120)
4) gi|12839033|dbj|BAB24412.1| (AK006107) data source:SPTR, source key:Q9HD02, evidence:ISS~to DJ304B14.1 (NOVEL PROTEIN) (FRAGMENT)~putative [Mus musculus] (SEQ ID NO:121)
5) gi|9955433|emb|CAC05478.1| (AL136125) dJ304B14.1 (novel protein) [Homo sapiens] (SEQ ID NO:122)
6) gi|18564176|ref|XP_094815.1| (XM_094815) hypothetical protein XP_094815 [Homo sapiens] (SEQ ID NO:123)

```
                    10        20        30        40        50        60        70
              ....|....|....|....|....|....|....|....|....|....|....|....|....|....|
NOV5          -------MAMAQKLSHLLPSLRQVIQEEQLSLQ--PEPVFTVDRAEVPPLFWKPYIYAGYRPLHQTWRRY
gi|18549110|  -------MAMAQKLSHLLPSLRQVIQEEQLSLQ--PEPVFTVDRAEVPPLFWKPYIYAGYRPLHQTWRRY
gi|12844255|  -----MAMAVAQKFNHLLSSLWHVGGQKP---PQ--PEPVFTVDRAQVPPLFWKPYIYAGYRPLHQNWCRY
gi|12839033|  -------MTTAILERLSTLSMSGQQLRRLPKILEEGLPKMPCTVPETDVPQLFREPYIRAGYTPTGHEWRRY
gi|9955433|   MRAAAMTTAILERLSTLSVSGQQLRRLPKILEDGLPKMPCTVPETDVPQLFREPYIRTGYTPTGHEWRRY
gi|18564176|  -----MTTAILERLSTLSVSGQQLRRLPKILEDGLPKMPCTVPETDVPQLFREPYIRTGYTPTGHEWRRY 80        90       100       110       120       130       140
              ....|....|....|....|....|....|....|....|....|....|....|....|....|....|
NOV5          FRTLFQQHNEAVNVWTHLLAALALLLRLALFVETVDF-WGDPHALPLFIIVLASFTYLSFSALAHLLQAK
gi|18549110|  FRTLFQQHNEAVNVWTHLLAALVLLLRLALFVETVDF-WGDPHALPLFIIVLASFTYLSFSALAHLLQAK
gi|12844255|  FRTLFQRHNEAVNVWTHLLAALALLLRLIGLAASVDF-REDPHALPLFFIVLASFTYLSFSAVAHLLQAK
gi|12839033|  FFSLFQKHNEVVNVWTHLLAALAVLLRFWAFVEAGALQMASPHTLPLLIFILSSITYLTCSLLAHLLQSK
gi|9955433|   FFSLFQKHNEVVNVWTHLLAALAVLLRFWAFAEAEALPWASTHSLPLLIFILSSITYLTCSLLAHLLQSK
gi|18564176|  FFSLFQKHNEVVNVWTHLLAALAVLLRFWAFAEAEALPWASTHSLPLLIFILSSITYLTCSLLAHLLQSK 150       160       170       180       190       200       210
              ....|....|....|....|....|....|....|....|....|....|....|....|....|....|
NOV5          SEFWHYSFEFLDYVGVAVYQFGSALAHFYYAIEPAWEAQVQAVFLEMAAFLAWLSCIGSCYNKYIQKP--
gi|18549110|  SEFWHYSFEFLDYVGVAVYQFGSALAHFYYAIEPAWEAQVQAVFLEMAAFLAWLSCIGSCYNKYIQKP--
gi|12844255|  SEFWHYSFEFLDYVGVAVYQFGSALAHFYYAIEPSWHDEVQAVFLPTAAFLAWLSCAGSCYNKYSQKP--
gi|12839033|  SELSHYTFEYDYVGVSVYQYGSALAHFYSSDQAWYELFWIFFLPAAAFCGWLSCAGCCYAKYRYRPY
gi|9955433|   SELSHYTFEYDYVGVSVYQYGSALAHFYSSDQAWYDRFWLFFLPAAAFCGWLSCAGCCYAKYRYRRPY
gi|18564176|  SELSHYTFEYDYVGVSVYQYGSALAHFYSSDQAWYDRFWLFFLPAAAFCGWLSCAGCCYAKYRYRRPY
```

TABLE 5E-continued

Clustal W Sequence Alignment

```
                220       230       240       250       260       270       280
            ....|....|....|....|....|....|....|....|....|....|....|....|....|....|
NOV5        GLLGRTCQEVPSVLAYALDISPVVHRIFVSSDPTTDDPALLYHKCQVVFFLLAAAFFSTFMPERWFPGSC
gi|18549110|GLLGRTCQEVPSVLAYALDISPVVHRIFVSSDPTTDDPALLYHKCQVVFFLAAAFFSTFMPERWFPGSC
gi|12844255|GLLGRIFQEAPSALAYVLDISPVLHRIIVSPLPAEKDPALLYHKCQVVFFLLAAAFFSTVMPESWFPGSC
gi|12839033|PVMRKICQVVPAGLAFVLDISPVAHRVALCHLAGCQEQAAWYHTLQIFFLVSAYFFSCPVPEKYFPGSC
gi|9955433| PVMRKICQVVPAGLAFILDISPVAHRVALCHLAGCQEQAAWYHTLQIFFLVSAYFFSCPVPEKYFPGSC
gi|18564176|PVMRKICQVVPAGLAFILDISPVAHRVALCHLAGCQEQAAWYHTLQILFFLVSAYFFSCPVPEKYFPGSC 290       300       310       320       330       340       350
            ....|....|....|....|....|....|....|....|....|....|....|....|....|....|
NOV5        HVFGQGHQLFHIFIVLCTLAQLEAVALDYEARRPIYEPLHTHWPHNFLGL-ELLTVGSSILTAFLLSQLV
gi|18549110|HVFGQGHQLFHIFIVLCTLAQLEAVALDYEARRPIYEPLHTHWPHNFLGL-ELLTVGSSILTAFLLSQLV
gi|12844255|HIFGQGHQVFHVFIVLCTLAQLEAVTLDYQARRPIYEPLHARWPHNFLGL-ELLTVASSSLTALLLSQLV
gi|12839033|DLVGHGHQLFHAFISVCTLSQLEAILLDYCGRHEIFLQRHGPLSVYSACLSFFVLAACSAATATLRHKV
gi|9955433| DLVGHGHQLFHAFISICTLSQLEAILLDYCGRQEIFLQRHGPLSVHMACLSFFLAACSAATAALLRHKV
gi|18564176|DLVGHGHQLFHAFISICTLSQLEAILLDYCGRQEIFLQRHGPLSVHMACLSFFLAACSAATAALLRHKV

....|....|
NOV5        QRKLDQKTK
gi|18549110|QRKLDQKTK
gi|12844255|RRKLHQKTK
gi|12839033|KDRLIKKDS
gi|9955433| KARLTKKDS
gi|18564176|KARLTKKDS
```

Table 5F list the domain description from DOMAIN analysis results against NOV5. This indicates that the NOV5 sequence has properties similar to those of other proteins known to contain these domains.

TABLE 5F

Domain Analysis of NOV5 gnl Pfam pfam03006, UPF0073, Uncharacterised protein family (Hly-III/
UPF0073). Members of this family are integral membrane proteins. This
family includes a protein with hemolytic activity from Bacillus
cereus. It is not clear if all the members of this family are
hemolysins. (SEQ ID NO:124)
CD-Length = 238 residues, 99.2% aligned
Score = 81.6 bits (200), Expect = 7e-17

```
Query:   57 TWRFYFRTLFQQHNEAVNVWTHLLAALALLLRLALFVETVDFWGDPHALPLFIIVL---A  113
            +++  |+++|    |||  |+|||||   +     | ||    +            +
Sbjct:    2 SFKKCFKSIFSWHNETSNIWTHLLGFILFFFLLILFFLFLLPPILATWQDRVVFGFFLAG   61

Query:  114 SFTYLSFSALAHLLQAKSEFWHYSFFFLDYVGVAVYQFGSALAHFYYAIEPAWHAQVQAV  173
            +|   |  |++ |     ||      |   |||+ |+++     |  +  |||    | + +
Sbjct:   62 AFLCLLLSSIYHTFSCHSEKHSEFFLKLDYLGISLLIVASFIPIIYYAFYC--HPFFRTL  119

Query:  174 FLPMAAFLAWLSCIGSCYNKYIQKPGLLGRTCQEVPSVLAYALDISPVVHRIFVSSD-PT  232
            ++ +   |    ++    |    | +|++       |     +         ||    + |++| + +
Sbjct:  120 YISIILVLGLIAIYVSLSDKFVSPKF---RPLRAGFFVLLGCSGVIPLLHALILFGGHEN  176

Query:  233 TDDPALLYHKCQVVFFLLAAAFFSTFMPERWFPGSCHVFGQGHQLFHIFLVLCTLAQLEA  292
                ||  +      |  +++  |   |+  |  +|||+|||     ++|    |||||+  +||            |
Sbjct:  177 LVRIALPWVLLMAVLYIVGAVFYGTRIPERFFPGKFDIWGHSHQLFHLLVVLAAFYHYRA  236

Query:  293 V                                                             293

Sbjct:  237 G                                                             237
```

The NOV5 nucleic acid of the invention encoding a membrane protein-like protein includes the nucleic acid whose sequence is provided in Table 5A, or a fragment thereof. The 10 invention also includes a mutant or variant nucleic acid any of whose bases may be changed from the corresponding base shown in Table 5A while still encoding a protein that maintains its membrane protein-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 40% of the residues may be so changed.

The NOV5 protein of the invention includes the membrane protein-like protein whose sequence is provided in Table 5B. The invention also includes a mutant or variant protein any of whose residues may be changed from the corresponding residue shown in Table 5B while still encoding a protein that maintains its membrane protein-like activities and physiological functions, or a functional fragment thereof. In the mutant or variant protein, up to about 52% of the bases may be so changed.

The NOV5 nucleic acids and proteins of the invention are useful in potential diagnostic and therapeutic applications implicated in various diseases and disorders described below and/or other pathologies. For example, the compositions of the present invention will have efficacy for treatment of patients suffering from: cancer, trauma, regeneration (in vitro and in vivo), viral/bacterial/parasitic infections, adrenoleukodystrophy, congenital adrenal hyperplasia, Von Hippel-Lindau (VHL) syndrome, cirrhosis, transplantation, hemophilia, hypercoagulation, idiopathic thrombocytopenic purpura, autoimmune disease, allergies, immunodeficiencies, fertility, hypogonadism, diabetes, autoimmune disease, renal artery stenosis, interstitial nephritis, glomerulonephritis, polycystic kidney disease, systemic lupus erythematosus, renal tubular acidosis, IgA nephropathy, hypercalceimia, Lesch-Nyhan syndrome and other diseases, disorders and conditions of the like.

NOV5 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV5 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV6

A disclosed NOV6 nucleic acid of 3509 nucleotides (also referred to as CG57362-01) encoding a novel BCSC-1-like protein is shown in Table 6A. An open reading frame was identified beginning with an ATG initiation codon at nucleotides 155–157 and ending with a TGA codon at nucleotides 3206–3208. Putative untranslated regions upstream from the intitation codon and downstream from the termination codon are underlined in Table 6A, and the start and stop codons are in bold letters.

TABLE 6A

NOV6 Nucleotide Sequence (SEQ ID NO:17)

GGTCCGAGCGGGGCTCTGTGACGACAGCCCCACCAGCTGCTTCGGGGTGGGCAGCCTTCAGGAGGAAGGGCTG

GCCTGGGAGGAGCTGGCTGCCCCTCGGGACGTGTTCTCAGGCCCTGCCCGCTGCCCTGCCCCATATACCTTCT

CCTTCGAGATGCTGGTGACTGGGCCATGCCTGCTTGCAGGCCTGGAGAGCCCCTCTCATGCTCTGCGGGCAGA

TGCCCCCCCTCATGCCAGCTCTGCAGCCACCATCTGTGTCACACTGGCAGAGGGCCACCACTGTGACCGGGCC

TTGGAGATCCTGCTGCACCCCAGTGAGCCCCATCAGCCACACCTGATGCTGGAGGGCGGCAGCCTGAGCTCAG

CAGAATATGAGGCCCGGGTGAGGGCCCGCCGAGATTTTCAGAGGCTACAGCGAGGGGACAGTGATGGGGACCG

GCAGGTGTGGTTCCTGCAGCGACGCTTCCACAAGGACATCCTGCTGAACCCCGTGCTGGCGCTGAGCTTCTGC

CCAGACCTGAGCTCCAAGCCCGGACACCTGGGGACAGCTACTCGGGAGCTACTCTTCCTTTTGGATAGCAGCA

GCGTGGCACACAAGGATGCCATTGTTTTGGCTGTGAAGTCCCTCCCACCCCAGAGCGCTTATCAACCTGGCCGT

GTTTGGGACGTTGGTGCAGCCACTCTTCCCAGAGAGCCGGCCTTGCAGTGATGATGCTGTGCAGCTGATCTGC

GAGAGCATTGAGACCCTGCAGGTTCCGAGTGGGCCCCCAGACGTGCTGGCTGCTCTGGACTGGGCCGTGGGGC

AGCCCCAGCACAGGGCCTACCCTCGGCAGCTGTTCCTGCTCACTGCTGCCTCACCCATGGCCGCCACTACCCA

CCGAACCCTGGAGCTCATGAGGTGGCACAGGGGGACAGCCAGGTGCTTCTCCTTTGGGCTGGGGCCCACCTGC

CACCAGCTGCTCCAGGGTTTATCTGCCCTCAGCAGCCGAGGTCGCGCCACTGCACTCCAGCCTGGCCGACAGA

GCAAGCCACAGCTGGTACAGGCTCTGCGGAAGGCACTGGAGCCTGCTTTGAGTGACATCTCTGTGGACTGGTT

TGTGCCCGACACTGTGGAGGCACTGCTGACCCCTCGGGAGATCCCAGCACTCTACCCTGGGGACCAGCTGCTC

GGTTACTGCTCACTCTTCAGGGTGGATGGCTTCCGGTCCCGCCCACCAGGGGGCAAGAGCCTGGCTGGCAGA

GCTCGGGTGGGTCCGTGTTTCCATCCCCAGAAGAGGCCCCGTCTGCTGCCAGCCCTGGCACTGAGCCCACTGG

CACCTCAGAGCCACTGGGAACAGGCACTGTCTCAGCAGAACTGTCCAGCCCATGGGCTGCCAGGGACTCGGAG

CAGAGTGGTACTGATGCTCTGACAGACCCAGTCACGGATCCTGGACCCAACCCCTCTGACACAGCCATATGGC

GCCGCATCTTTCAGTCCTCGTACATTCGGGAGCAGTATGTGCTCACCCACTGCTCTGCCAGCCCCGAGCCAGG

CCCAGGCTCCACAGGCAGCAGTGAGTCCCCAGGCTCACAGGGCCCTGGCTCCCCCGAAGGTAGTGCTCCCTTG

CAGCCCCCTTCTCAGCAGGGCTGCCGCAGTCTGGCCTGGGGAGAACCTGCAGGCTCCCGCTCCTGTCCCCTGC

TABLE 6A-continued

NOV6 Nucleotide Sequence

CTGCACCCACACCAGCTCCATTCAAGGTGGGGGCCTTGAGTACTGAGGTGCTGGGCCGTCAGCACAGAGCGGC

TCTGGCTGGCCGAAGCCTCTCATCCCCTCCAGGCCGGGCAAACCAAGTCCCCGGCCGACCCCGGAAACCCTCT

TTGGGTGCAATACTAGATGGCCCAAGTCCTGAGCCAGGCCAACAGTTGGGACAAGGCCTGGATGACTCAGGTA

ACCTGCTCTCCCCAGCCCCTATGGACTGGGACATGCTGATGGAACCACCCTTCTTATTCACGGCTGTGCCTCC

TAGTGGGGAGTTGGCCCCTCCAGCAGTGCCTCCCCAGGCTCCACGCTGCCATGTGGTGATCCGGGGCCTGTGT

GGGGAGCAGCCCATGTGCTGGGAGGTGGGTGTTGGGCTGGAGACACTGTGGGGACCTGGAGATGGCTCACAGC

CTCCCTCACCTCCTGTAAGAGAAGCTGCTTGGGACCAAGCACTCCATCGGCTGACAGCAGCCTCTGTGGTCCG

GGACAATGAGCAGCTGGCCCTCCGAGGAGGGGCAGAGACCACAGCTGACCGGGGCCATGCCCGGAGGTGCTGG

CTTCGAGCCCTTCAAACAAGTAAGGTCAGCTCTGCCCCCTCCTGCTTCACTTGCCCTGTAGCTGTGGATGCTA

CTACTAGGGAGGTCCTGCCTGGGGCCCTGCAGGTGTGCAGCTCAGAGCCCGCTGAGCCCCCAGGAACCCCTCC

TGCCTCTCACAGCCATCTAGATGCAGCTCCTCTGCCCACTGTTGTCTACTCTAAAGGTGCCTGGGACTCGGAC

CAAAATGGCAACTCCAAGCGTGCTTTGGGGGACCCTGCCACTCCCACGGAAGGTCCTCGCCGCCCACCTCCCC

GTCCTCCCTGTCGGCTCAGCATGGGCCGCCGTCACAAACTCTGTAGCCCTGACCCGGGCCAGGCCAACAACAG

TGAAGGCAGCGACCATGACTACCTGCCCTTGGTGCGGCTGCAGGAGGCACCAGGCTCCTTCCGCCTGGACGCG

CCCTTCTGCGCCGCTGTGCGCATCTCGCAGGAGCGCCTCTGCCGTGCCTCGCCCTTTGCCGTGCACCGCGCCA

GCCTCAGCCCCACCTCGGCCTCATTGCCCTGGGCACTTCTGGGCCCTGGTGTTGGCCAGGGTGACAGTGCCAC

GGCCTCCTGCAGCCCGTCCCCCAGCTCGGGCTCTGAGGGGCCAGGCCAGGTGGACAGTGGGCGGGGCTCAGAC

ACCGAGGCCTCCGAGGGGGCGGAAGGGCTGGGCGGCACCGACCTGCGGGGCCGGACCTGGGCCACTGCCGTAG

CACTCGCCTGGCTGGAGCACCGATGCGCCGCTGCCTTCGACGAGTGGGAACTGACAGCGGCCAAGGCTGATTG

CTGGCTGCGGGCCCAGCACTTGCCTGACGGCCTTGACCTGGCCGCCCTCAAGGCCGCAGCCCGAGGGCTCTTC

CTGCTACTGCGCCACTGGGACCAAAACCTGCAGCTACACCTGCTGTGCTACAGCCCAGCGAACGTGTGAAGGC

TGCCCCCTGCTGCTTGGGCTGGCGCCCCACCCAACACACTCAAGTCACTGCCGCCCAGGGCTGGCCTCTTGGT

GCTGGGAAAGTGTAGGCTGGTTCCAGCCTGTCCCCCACTGCTTCTTACTCCCTCCCTAGAGCCCTCTTGCCCC

CACAAAAAGTGCCTGCCTGTGCTCTCTCCCTCTCCTCCCACCCCACTCACACTCCCCTCCATCCTTTGAGCTC

CCTGCAACACAGTGGAAGGGTAGAGAGCCACAGTCCCCAAATCCTATGCAATAAAGTGCCTCTTAGGGAAAAA

AAAAA

The NOV6 nucleic acid was identified on chromosome 3 and has 2669 of 2799 bases (95%) identical to a gb:GENBANK-ID:AB047829|acc:AB047829.1 mRNA from *Macaca fascicularis* (*Macaca fascicularis* brain cDNA, clone:QccE-10361) (E=0.0).

A disclosed NOV6 polypeptide (SEQ ID NO:18) encoded by SEQ ID NO:17 is 1017 amino acid residues and is presented using the one-letter code in Table 6B. Signal P, Psort and/or Hydropathy results predict that NOV6 contains a signal peptide and is likely to be localized to the nucleus with a certainty of 0.6000. The most likely cleavage site is between amino acids 18 and 19: SHA-LR.

TABLE 6B

Encoded NOV6 protein sequence (SEQ ID NO:18)
MLVTGPCLLAGLESPSHALRADAPPHASSAATICVTLAEGHHCDRALEILLHPSEPHQPHLMLEGGSLSSAE

YEARVRARRDFQRLQRGDSDGDRQVWFLQRRFHKDILLNPVLALSFCPDLSSKPGHLGTATRELLFLLDSSS

VAHKDAIVLAVKSLPPQTLINLAVFGTLVQPLFPESRPCSDDAVQLICESIETLQVPSGPPDVLAALDWAVG

TABLE 6B-continued

Encoded NOV6 protein sequence

QPQHRAYPRQLFLLTAASPMAATTHRTLELMRWHRGTARCFSFGLGPTCHQLLQGLSALSSRGRATALQPGR

QSKPQLVQALRKALEPALSDISVDWFVPDTVEALLTPREIPALYPGDQLLGYCSLFRVDGFRSRPPGGQEPG

WQSSGGSVFPSPEEAPSAASPGTEPTGTSEPLGTGTVSAELSSPWAARDSEQSGTDALTDPVTDPGPNPSDT

AIWRRIFQSSYIREQYVLTHCSASPEPGPGSTGSSESPGSQGPGSPEGSAPLEPPSQQGCRSLAWGEPAGSR

SCPLPAPTPAPFKVGALSTEVLGRQHRAALAGRSLSSPPGRANQVPGRPRKPSLGAILDGPSPEPGQQLGQG

LDDSGNLLSPAPMDWDMLMEPPFLFTAVPPSGELAPPAVPPQAPRCHVVIRGLCGEQPMCWEVGVGLETLWG

PGDGSQPPSPPVREAAWDQALHRLTAASVVRDNEQLALRGGAETTADRGHARRCWLRALQTSKVSSAPSCFT

CPVAVDATTREVLPGALQVCSSEPAEPPGTPPASHSHLDAAPLPTVVYSKGAWDSDQNGNSKRALGDPATPT

EGPRRPPPRPPCRLSMGRRHKLCSPDPGQANNSEGSDHDYLPLVRLQEAPGSFRLDAPFCAAVRISQERLCR

ASPFAVHRASLSPTSASLPWALLGPGVGQGDSATASCSPSPSSGSEGPGQVDSGRGSDTEASEGAEGLGGTD

LRGRTWATAVALAWLEHRCAAAFDEWELTAAKADCWLRAQHLPDGLDLAALKAAARGLFLLLRHWDQNLQLH

LLCYSPANV

The NOV6 amino acid sequence has 767 of 803 amino acid residues (95%) identical to, and 779 of 803 amino acid residues (97%) similar to, the 803 amino acid residue ptnr:TREMBLNEW-ACC:BAB12255 protein from *Macaca fascicularis* (Crab eating macaque) (Cynomolgus monkey) (Hypothetical 84.7 Kda Protein) (E=0.0).

NOV6 is expressed in at least the following tissues: lung. This information was derived by determining the tissue sources of the sequences that were included in the invention including but not limited to SeqCalling sources, Public EST sources, genomic clone sources, literature sources, and/or RACE sources. The NOV6 sequence is also predicted to be expressed in the following tissues because of the expression pattern of (GENBANK-ID: gb:GENBANK-ID:AB047829|acc:AB047829.1) a closely related *Macaca fascicularis* brain cDNA, clone:QccE-10361 homolog in species *Macaca fascicularis*: brain.

Possible small nucleotide polymorphisms (SNPs) found for NOV6 are listed in Table 6C.

TABLE 6C

| | SNPs | | | |
|---|---|---|---|---|
| Variant | Nucleotide Position | Base Change | Amino Acid Position | Base Change |
| 13377063 | 3196 | A > G | Silent | N/A |

NOV6 has homology to the amino acid sequences shown in the BLASTP data listed in Table 6D.

TABLE 6D

BLAST results for NOV6

| Gene Index/ Identifier | Protein/Organism | Length (aa) | Identity (%) | Positives (%) | Expect |
|---|---|---|---|---|---|
| gi|12654717|gb|AAH01200.1| (AAH01200) (BC001200) | Unknown (protein for IMAGE: 3356192) [*Homo sapiens*] | 1001 | 826/972 (84%) | 831/972 (84%) | 0.0 |
| gi|9967105|dbj|BAB12255.1| (AB047829) | hypothetical protein [*Macaca fascicularis*] | 803 | 646/804 (80%) | 657/804 (81%) | 0.0 |
| gi|15295425|ref|XP_029078.2| (XM_029078) | similar to Unknown (protein for IMAGE: 3356192) [*Homo sapiens*] | 620 | 494/611 (80%) | 494/611 (80%) | 0.0 |
| gi|11231113|dbj|BAB18151.1| (AB051125) | hypothetical protein [*Macaca fascicularis*] | 260 | 192/247 (77%) | 194/247 (77%) | 5e-97 |
| gi|12855146|dbj|BAB30227.1| (AK016425) | data source: SPTR, source key: O75668, evidence: ISS~homolog to DJ745E8.1 (BREAST CANCER SUPPRESSOR CANDIDATE 1 | 1209 | 142/346 (41%) | 229/346 (66%) | 2e-72 |

TABLE 6D-continued

BLAST results for NOV6

| Gene Index/<br>Identifier | Protein/Organism | Length<br>(aa) | Identity<br>(%) | Positives<br>(%) | Expect |
|---|---|---|---|---|---|
| | (BCSC-1) LIKE)<br>(FRAGMENT) ~putative<br>[Mus musculus | | | | |

The homology of these sequences is shown graphically in the ClustalW analysis shown in Table 6E.

TABLE 6E

Clustal W Sequence Sequence Alignment

1) NOV6 (SEQ ID NO:18)
2) gi|12654717|gb|AAH01200.1|AAH01200 (BC001200) Unknown (protein for IMAGE:3356192)
[Homo sapiens] (SEQ ID NO:125)
3) gi|9967105|dbj|BAB12255.1| (AB047829) hypothetical protein [Macaca fascicularis]
(SEQ ID NO:126)
4) gi|15295425|refXP_029078.2| (XM_029078) similar to Unknown (protein for
IMAGE:3356192) [Homo sapiens](SEQ ID NO:127)
5) gi|1231113|dbj|BAB18151.1| (AB051125) hypothetical protein [Macaca fascicularis]
(SEQ ID NO:128)
6) gi|12855146|dbj|BAB30227.1| (AK016425) data source:SPTR, source key:O75668,
evidence:ISS~homolog to DJ745E8.1 (BREAST CANCER SUPRESSOR CANDIDATE 1 (BCSC-1) LIKE)
(FRAGMENT)~putative [Mus musculus] (SEQ ID NO:129)

```
                         10        20        30        40        50        60        70
                ....|....|....|....|....|....|....|....|....|....|....|....|....|....|
NOV6            ----------------------------------------------------------------------
gi|12654717|    ----------------------------------------------------------------------
gi|9967105|     ----------------------------------------------------------------------
gi|15295425|    ----------------------------------------------------------------------
gi|11231113|    ----------------------------------------------------------------------
gi|12855146|    MPGLLNCLTGAALPLMESDVTSYVSGYALGLTASLTYGNLEAQPFQGLFVYPIDEYSTVVGFEAVIADRV 80        90       100       110       120       130       140
                ....|....|....|....|....|....|....|....|....|....|....|....|....|....|
NOV6            ----------------------------------------------------------------------
gi|12654717|    ----------------------------------------------------------------------
gi|9967105|     ----------------------------------------------------------------------
gi|15295425|    ----------------------------------------------------------------------
gi|11231113|    ----------------------------------------------------------------------
gi|12855146|    VTIQLRDKAKLDRSHLDIQPATVTGNFPEEESPIAPGKVTLDEDLERVLFVVNLGTIAPMANVTVFISTS 150       160       170       180       190       200       210
                ....|....|....|....|....|....|....|....|....|....|....|....|....|....|
NOV6            ----------------------------------------------------------------------
gi|12654717|    ----------------------------------------------------------------------
gi|9967105|     ----------------------------------------------------------------------
gi|15295425|    ----------------------------------------------------------------------
gi|11231113|    ----------------------------------------------------------------------
gi|12855146|    SELPTLPSGAVRVLLPAICAPTVPPSCTHRFGSSSPQPQGKDPHCFGTQTKDSYNRLCLATLLDTKVTNP 220       230       240       250       260       270       280
                ....|....|....|....|....|....|....|....|....|....|....|....|....|....|
NOV6            ---------MLVTGPCLLAGLESPSHALRADAPPHASSAATICVTLAEGHHCDRALEILLHPSEPHQPHLM
gi|12654717|    --------------------------KAGPAGSSWTVKLGTWGP-EAGPSLTELCPLLSEPHQPHLM
gi|9967105|     ----------------------------------------------------------------------
gi|15295425|    ----------------------------------------------------------------------
gi|11231113|    ----------------------------------------------------------------------
gi|12855146|    MEYEFKFQLEIRGPCLLAGVESPTHEIRADAAPSAHSAKSIIITLAKKHTFDRPVEILLHPSEPHMPHVL 290       300       310       320       330       340       350
                ....|....|....|....|....|....|....|....|....|....|....|....|....|....|
NOV6            LEGGSLSSAEYEARVRARRDFQRLQRGDSDGDRQVWFLQRRFHKDILLNPVLALSFCPDLSSKPGHLGTA
gi|12654717|    LEGGSLSSAEYEARVRARRDFQRLQRGDSDGDRQVWFLQRRFHKDILLNPVLALSFCPDLSSKPGHLGTA
gi|9967105|     ----------------------------------------------------------------------
gi|15295425|    ----------------------------------------------------------------------
gi|11231113|    ----------------------------------------------------------------------
gi|12855146|    VEKGDMTLGEYDQHLKGKADFIRGTKKDNSAERKTEVIRKRLHKDIPHHSVIMLNFCPDLQSVQPNPRKA
```

TABLE 6E-continued

Clustal W Sequence Sequence Alignment

```
                 360        370        380        390        400        410        420
            ....|....|....|....|....|....|....|....|....|....|....|....|....|....|
NOV6        TRELLFLLDSSSVAHKD-------AIVLAVKSLPPQTLINLAVFGTLVQPLFPESRPCSDDAVQLICESI
gi|12654717|TRELLFLLDSSSVAHKD-------AIVLAVKSLPPQTLINLAVFGTLVQPLFPESRPCSDDAVQLICESI
gi|9967105| ----------------------------------------------------------------------
gi|15295425|----------------------------------------------------------------------
gi|11231113|----------------------------------------------------------------------
gi|12855146|HGEFIFLIDRSNSMSKTNIQCIKEAMLVALKSLMPACFFNIIGFGSTFKAVFASSRIYNEENLTMACDCI 430        440        450        460        470        480        490
            ....|....|....|....|....|....|....|....|....|....|....|....|....|....|
NOV6        ETLQVPSGPPDVLAALDWAVGQPQHRAYPRQLFLLTAASPMAATTHRTLELMRWHRGTARCFSFGLGE-T
gi|12654717|ETLQVPSGPPDVLAALDWAVGQPQHRAYPRQLFLLTAASPMAATTHPTLELMRWHRGTARCFSFGLGE-T
gi|9967105| ------------------MGQPQHRAYPRQLFLLTAASPMAATTHRTLELMRWHRGTARCFSFGLGE-T
gi|15295425|----------------------------------------------------------------------
gi|11231113|----------------------------------------------------------------------
gi|12855146|QRMQADMGGTNMLSPLKWVLRQPLRRGHPRLLFLITDGS--VNNTGKVLELVRNHASSTRCYSFGIGETV 500        510        520        530        540        550        560
            ....|....|....|....|....|....|....|....|....|....|....|....|....|....|
NOV6        CHGLLQGLSALSSRGRATALQPGRQSKPQLVQALRKALEPALSDISVDNFVPDIVEALTPREIPALYPC
gi|12654717|CHQLLQGLSALS-RGQAYFLRPGQRLQPMLVQALRKALEPALSDISVDNFVPDIVEALTPREIPALYPC
gi|9967105| CHQLLQGLSALS-RGQAYFLRPGQRLQPMLVQALRKALEPALSDISVDNFVPDIVEALTPREIPALYPC
gi|15295425|----------------------------------------------------------------------
gi|11231113|----------------------------------------------------------------------
gi|12855146|CYRLVEGLASVS-KGSAEFLMEGERLQPKMVKSLKKAMAEVLSDVTVENVLPETTEALISPVSTSSLPPC 570        580        590        600        610        620        630
            ....|....|....|....|....|....|....|....|....|....|....|....|....|....|
NOV6        DQLEGYCSLFRVDGERSRPPGGQEPGWQSSGGSVFPSPEEAPSAASPGTEPTGTSEPLGTGTVSAELSSP
gi|12654717|DQLEGYCSLFRVDGERSRPPGGQEPGWQSSGGSVFPSPEEAPSAASPGTEPTGTSEPLGTGTVSAELSSP
gi|9967105| DQLEGYCSLFRVDGERSRPPGGQEPGWQSSGGSVFPSPEEAPSAVSPGTEPTGTSEPLGTGTVSAELSSP
gi|15295425|------------------------MGCQGLG---------------------------------------
gi|11231113|----------------------------------------------------------------------
gi|12855146|ERLMGYGIVCDASLYISNSRSDKRRKYGMLHTQ---------------------------------------

640        650        660        670        680        690        700
            ....|....|....|....|....|....|....|....|....|....|....|....|....|....|
NOV6        WAARDSEQSGTDALTDPVTDPGPNPS-DTAIWRRIFQSSYIREQYVLTHCSASPEPGPGSTGSSESPGSQ
gi|12654717|WAARDSEQS-TDALTDPVTDPGPNPS-DTAIWRRIFQSSYIREQYVLTHCSASPEPGPGSTGSSESPGSQ
gi|9967105| WAAGDLERTGTDALTDPVTDPGPNPSDDTAIWRRIFQSSYIREQYVLTHCSASPEPGPGSTGSSESPGSQ
gi|15295425|-------ADTDALTDPVTDPGPNPS-DTAIWRRIFQSSYIREQYVLTHCSASPEPGPGSTGSSESPGSQ
gi|11231113|----------------------------------------------------------------------
gi|12855146|----ESSSVFYPSQDEGLSPGSGNCAKNVNQGGTKDAHPCNGDSPTHHGLDVSTTTTAYSTNQISSHKT 710        720        730        740        750        760        770
            ....|....|....|....|....|....|....|....|....|....|....|....|....|....|
NOV6        GPGSPEGSAPLEPPSQQGCRSLAQGEPAGSRSCE-LPAPTPAPFKVGALSTEVLGRQHRAALAGRSLSSP
gi|12654717|GPGSPEGSAPLEPPSQQGCRSLAQGEPAGSRSCE-LPAPTPAPFKVGALSTEVLGRQHRAALAGRSLSSP
gi|9967105| GPGSPEGSAPLEPPSQQGCRSLAQGEPAGSRSCE-LPAPTPAPFKVGALSTEVLGRQHRAALAGRSLSSP
gi|15295425|GPGSPEGSAPLEPPSQQGCRSLAQGEPAGSRSCE-LPAPTPAPFKVGALSTEVLGRQHRAALAGRSLSSP
gi|11231113|----------------------------------------------------------------------
gi|12855146|CPRATTASDETGTAREYPLRKAKVQLLASESDWESQKWQTDLQTLINEGHNLSQCPKLHGPGARRPSLLP 780        790        800        810        820        830        840
            ....|....|....|....|....|....|....|....|....|....|....|....|....|....|
NOV6        PGRANQVPGRPRKPSLGAILDGPSPEPGQQLGQGLDDSGNLLSPAPMDWDMLMEPPFLFTAVPPSGELAP
gi|12654717|PGRANQVPGRPRKPSLGAILDGPSPEPGQQLGQGLDDSGNLLSPAPMDWDMLMEPPFLFTAVPPSGELAP
gi|9967105| PGRANQVPGRPRKPSLGAILDGPSPEPGQQLGQGLDDSGSLLSPAPMDWDMLMEPPFLFTAVPPSGEPAP
gi|15295425|PGRANQVPGRPRKPSLGAILDGPSPEPGQQLGQGLDDSGNLLSPAPMDWDMLMEPPFLFTAVPPSGELAP
gi|11231113|----------------------------------------------------------------------
gi|12855146|QGCQLMRFFDQKPQAWGPVRELDCGASRTSAPNSQSSEDLAIEPAHCPSTFERETSLDLEPMAESEEQAN 850        860        870        880        890        900        910
            ....|....|....|....|....|....|....|....|....|....|....|....|....|....|
NOV6        PA--VPPQAPRCHVVIRGLCGEQPMCWEVGVGLETLWGPGDGSQPPSPPVREAAWDQALHRLTAASVVRD
gi|12654717|PA--VPPQAPRCHVVIRGLCGEQPMCWEVGVGLETLWGPGDGSQPPSPPVREAAWDQALHRLTAASVVRD
gi|9967105| PA--VPPQAPRCHVVIRGLCGEQPMCWEVGVGLETLWGPGDGSQPPSPPVREAAWDQALHRLTAASVVRD
gi|15295425|PA--VPPQAPRCHVVIRGLCGEQPMCWEVGVGLETLWGPGDGSQPPSPPVREAAWDQALHRLTAASVVRD
gi|11231113|----------------------------------------------------------------------
gi|12855146|PCRTATPSPVVGKALVKGLCANQRMQWEVSFELEPPALKRGDICN------ADMMSETFHHLAARAIRE 920        930        940        950        960        970        980
            ....|....|....|....|....|....|....|....|....|....|....|....|....|....|
NOV6        NEQLALRGGAETTADRGHARRCWLRALQTSKVSSAPSCFTCPVAVDATTREVLPGALQVCSS--------
gi|12654717|NEQLALRGGAETTADRGHARRCWLRALQTSKVSSAPSCFTCPVAVDATTREVLPGALQVCSS--------
gi|9967105| NEQLALRGGAETTADRGHARRCWLRALQTSKVSSAPSCFTCPVAVDATTREVLPGVLQVCSS--------
gi|15295425|NEQLALRGGAETTADRGHARRCWLRALQTSKVSSAPSCFTCPVAVDATTREVLPGALQVCSS--------
gi|11231113|---------------------------------------------------------MIP----------
gi|12855146|FEHLAER--EDE-IELGSNRRYQVNAVHTSKACSVISKYIAFVPVDINKRQYLPTVVKYPNSGAMLSFRN
```

TABLE 6E-continued

Clustal W Sequence Sequence Alignment

```
                 990       1000      1010      1020      1030      1040      1050
              ....|....|....|....|....|....|....|....|....|....|....|....|....|
NOV6          ------EPAEPPGTEPASHSHLDAAPLPTVVYSK--------CAWDSDQNGNSKRALGDPATPTEGPRR
gi|12654717|  ------EPAEPPGTEPASHSHLDAAPLPTVVYSKGLQRGSPACAWDSDQNGNSKRALGDPATPTEGPRR
gi|9967105|   ------EPAEPPGTEPASHSHLDAAPLPTVVYSK--------CAWDSDENGNSKCALGDAATPMEGPRC
gi|15295425|  ------EPAEPPGTEPASHSHLDAAPLPTVVYSKGLQRGSPACAWDSDQNGNSKRALGDPATPTEGPRR
gi|11231113|  -------TAGLQGGSPA---------------G---------AWDSDENGNSKCALGDAATPMEGPRC
gi|12855146|  LTRQWGGSSAGLGRPQSMLREHSSAAGDSKFQILALQDSPTSTFNKTPSPGHEKQTTASGPPQNLSASA 1060      1070      1080      1090      1100      1110      1120
              ....|....|....|....|....|....|....|....|....|....|....|....|....|
NOV6          P------CRLSMGRRHKLCSPDPGQANNSE---------CSDHDYLPLVRLQEAPGSFRLDAPFCA
gi|12654717|  P------CRLSMGRRHKLCSPDPGQANNSE---------CSDHDYLPLVRLQEAPGSFRLDAPFCA
gi|9967105|   S------SRLSLGRRHKLCRPDLGQANNSE---------CIDHDYLPLVRLQEAPGSFRLDAPFCA
gi|15295425|  P------CRLSMGRRHKLCSPDPGQANNSE---------CSDHDYLPLVRLQEAPGSFRLDAPFCA
gi|11231113|  S------SRLSLGRRHKLCRPDLGQANNSE---------CIDHDYLPLVRLQEAPGSFRLDAPFCA
gi|12855146|  SSMKATETLFGSXLNLNKSRLLTRATKGFLSKSLPKASEATPGSQSSDYRPLVSLQLASGAFLLNEAFCT 1130      1140      1150      1160      1170      1180      1190
              ....|....|....|....|....|....|....|....|....|....|....|....|....|
NOV6          AVRISQERLCRASPFAVHRASLSPTSASLPWALLGPGVGQGDSATASCSPSPSSGSEGPGQVDSGRGSDT
gi|12654717|  AVRISQERLCRASPFAVHRASLSPTSASLPWALLGPGVGQGDSATASCSPSPSSGSEGPGQVDSGRGSDT
gi|9967105|   AVRISQERLCRASPFAVHRASLSPTSASLPWALLGPGVGQGDSATASCSPSPSSGSEGPGQVDSGRGSDT
gi|15295425|  AVRISQERLCRASPFAVHRASLSPTSASLPWALLGPGVGQGDSATASCSPSPSSGSEGPGQVDSGRGSDT
gi|11231113|  AVRISQERLCRASPFAVHRASLSPTSASLPWALLGPGVGQGDSATAFCSPSPSSGSEGPGQVDSGRGSDT
gi|12855146|  TIQIPMEKLKWTSPFSCLRMSLVTRRQDLKTQSP------QDCTSLSSSPPSCDGIS----LKSEESSDQ 1200      1210      1220      1230      1240      1250      1260
              ....|....|....|....|....|....|....|....|....|....|....|....|....|
NOV6          EASEGAEGLGGTDLRGRTWATAVALAWLEHRCAAAFDEWELTAAKADCQLRAQHLPDGLDLAALKAAARG
gi|12654717|  EASEGAEGLGGTDLRGRTWATAVALAWLEHRCAAAFDEWELTAAKADCQLRAQHLPDGLDLAALKAAARG
gi|9967105|   EASEGAEGLGGTDLRGRTWATAVALAWLEHRCAAAFGEWELTAAKADCQLRAQHLPDGLDLAALKAAARG
gi|15295425|  EASEGAEGLGGTDLRGRTWATAVALAWLEHRCAAAFDEWELTAAKADCQLRAQHLPDGLDLAALKAAARG
gi|11231113|  EASEGAEGLGGTDLRGRTWATAVALAWLEHRCAAAFGEWELTAAKADCQLRAQHLPDGLDLAALKAAARG
gi|12855146|  ESNAMLEHMG------KLWATVVALAWLEHSSANYIIEWELVAAKASSWYEKQKVPEGRTLSTLKNTARQ 1270      1280
              ....|....|....|....
NOV6          LFLLLRHWDQNLQLHLLCYSPANV
gi|12654717|  LFLLLRHWDQNLQLHLLCYSPANV
gi|9967105|   LFLLLRHWDQNLQLHLLCYSPANV
gi|15295425|  LFLLLRHWDQNLQLHLLCYSPANV
gi|11231113|  LFLLLRHWDQNLQLHLLCYSPANV
gi|12855146|  LFVLLRHWDEKLFFNMLC------
```

Table 6F list the domain description from DOMAIN analysis results against NOV6. This indicates that the NOV6 sequence has properties similar to those of other proteins known to contain these domains.

TABLE 6F

Domain Analysis of NOV6 gnl|Smart|smart00327, VWA, von Willebrand factor (vWF) type A domain;
VWA domains in extracellular eukaryotic proteins mediate adhesion via
metal ion-dependent adhesion sites (MIDAS). Intracellular VWA domains
and homologues in prokaryotes have recently been identified. The
proposed VWA domains in integrin beta subunits have recently been
substantiated using sequence-based methods (Ponting et al. Adv Prot
Chem (2000) in press). (SEQ ID NO:130)
CD-Length = 180 residues, 97.2% aligned
Score = 42.0 bits (97), Expect = 2e-04

```
Query:  134  RELLFLLDSS-SVAH------KDAIVLAVKSL---PPQTLINLAVFGTLVQPLFPESRPC  183
             +++||||  |  |+        |+ ++  |+  |      +  |    | +  +|||  +
Sbjct:    2  LDVVFLLDGSGSMGGNRFELAKEFVLKLVEQLDIGPDGDRVGLVTFSSDARVLFPLNDSQ   61

Query:  184  SDDAVQLICESIETLQV-PSGPPDVLAALDWAVGQPQH------RAYPRQLFLLTAASPM  236
              |  ||+    |++ +|      |  ++ ||||++|+              |  |+ |  |+|
Sbjct:   62  SKDALL---EALASLSYSLGGGTNLGAALEYALENLFSESAGSRRGAPKVLILITDGESN  118

Query:  237  AATTHRTLELMRWHRGTARCFSFGLGPTCHQLLQGLSALSSRGRATALQPGRQSKPQLVQ  296
                  +  |   |+|          +  |   |+|          +       |    |+
Sbjct:  119  DGGEDILKAAKELKRSGVKVFVVGVGN--DVDEEELKKLASAPGGVFVVEDLPSLLDLLI  176
```

NOV6 described herein bears resemblance to BCSC-1 a molecule that is a candidate for suppression of breast cancer and this molecule may play a similar role in the lung and brain.

The NOV6 nucleic acid of the invention encoding a BCSC-1-like protein includes the nucleic acid whose sequence is provided in Table 6A, or a fragment thereof. The invention also includes a mutant or variant nucleic acid any of whose bases may be changed from the corresponding base shown in Table 6A while still encoding a protein that maintains its BCSC-1-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 5% of the residues may be so changed.

The NOV6 protein of the invention includes the BCSC-1-like protein whose sequence is provided in Table 6B. The invention also includes a mutant or variant protein any of whose residues may be changed from the corresponding residue shown in Table 6B while still encoding a protein that maintains its BCSC-1-like activities and physiological functions, or a functional fragment thereof. In the mutant or variant protein, up to about 5% of the bases may be so changed.

The NOV6 nucleic acids and proteins of the invention are useful in potential diagnostic and therapeutic applications implicated in various diseases and disorders described below and/or other pathologies. For example, the compositions of the present invention will have efficacy for treatment of patients suffering from: cancer, trauma, regeneration (in vitro and in vivo), viral/bacterial/parasitic infections, systemic lupus erythematosus, autoimmune disease, asthma, emphysema, scleroderma, allergy, ARDS and other diseases, disorders and conditions of the like.

NOV6 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV6 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV7

NOV7 includes three novel Amino Acid Transporter-like proteins disclosed below. The disclosed proteins have been named NOV7a, NOV7b and NOV7c.

NOV7a

A disclosed NOV7a nucleic acid of 1513 nucleotides (also referred to as CG57387-01) encoding a novel Amino Acid Transporter-like protein is shown in Table 7A. An open reading frame was identified beginning with an ATG initiation codon at nucleotides 2–4 and ending with a TAG codon at nucleotides 1502–1504. Putative untranslated regions, if any, upstream from the initiation codon and downstream from the termination codon are underlined in Table 7A, and the start and stop codons are in bold letters.

TABLE 7A

NOV7a nucleotide sequence.

(SEQ ID NO:19)
<u>T</u>ATGGAGCTAAAGGCTCCAGCTGCAGGAGGTCTTAATGCTGGCCCTGTCCCCCCAGCTGCCATGTCCACGCA

GAGACTTCGGAATGAAGACTACCACGACTACAGCTCCACGGACGTGAGCCCTGAGGAGAGCCCGTCGGAAGG

CCTCAACAACCTCTCCTCCCCGGGCTCCTACCAGCGCTTTGGTCAAAGCAATAGCACAACGTGGTTCCAGAC

CTTGATCCACCTGTTAAAAGGCAACATTGGCACAGGACTCCTGGGACTCCCTCTGGCGGTGAAAAATGCAGG

CATCGTGATGGGTCCCATCAGCCTGCTGATCATAGGCATCGTGGCCGTGCACTGCATGGGTATCCTGGTGAA

ATGTGCTCACCACTTCTGCCGCAGGCTGAATAAATCCTTTGTGGATTATGGTGATACTGTGATGTATGGACT

AGAATCCAGCCCCTGCTCCTGGCTCCGGAACCACGCACACTGGGGAAGACGTGTTGTGGACTTCTTCCTGAT

TGTCACCCAGCTGGGATTCTGCTGTGTCTATTTTGTGTTTCTGGCTGACAACTTTAAACAGGTGATAGAAGC

GGCCAATGGGACCACCAATAACTGCCACAACAATGAGACGGTGATTCTGACGCCTACCATGGACTCGCGACT

CTACATGCTCTCCTTCCTGCCCTTCCTGGTGCTGCTGGTTTTCATCAGGAACCTCCGAGCCCTGTCCATCTT

CTCCCTGTTGGCCAACATCACCATGCTGGTCAGCTTGGTCATGATCTACCAGTTCATTGTTTTCAGGTACAT

GCTTTCTGTCTTTCAGAGGATCCCAGACCCCAGCCACCTCCCCTTGGTGGCCCCTTGGAAGACCTACCCTCT

CTTCTTTGGCACAGCGATTTTTTCATTTGAAGGCATTGGAATGGTACTGCCCCTGGAAAACAAAATGAAGGA

TCCTCGGAAGTTCCCACTCATCCTGTACCTGGGCATGGTCATCGTCACCATCCTCTACATCAGCCTGGGGTG

TCTGGGGTACCTGCAATTTGGAGCTAATATCCAAGGCAGCATAACCCTCAACCTGCCCTTGTACCAGTCAGT

TABLE 7A-continued

NOV7a nucleotide sequence.

TAAGCTGCTGTACTCCATCGGGATCTTTTTCACCTACGCACTCCAGTTCTACGTCCCGGCTGAGATCATCAT

CCCCTTCTTTGTGTCCCGAGCGCCCGAGCACTGTGAGTTAGTGGTGGACCTGTTTGTGCGCACAGTGCTGGT

CTGCCTGACAATCTTGGCCATCCTCATCCCCCGCCTGGACCTGGTCATCTCCCTGGTGGGCTCCGTGAGCAG

CAGCGCCCTGGCCCTCATCATCCCACCGCTCCTGGAGGTCACCACCTTCTACTCAGAGGGCATGAGCCCCCT

CACCATCTTTAAGGACGCCCTGATCAGCATCCTGGGCTTCGTGGGCTTTGTGGTGGGGACCTATGAGGCTCT

CTATGAGCTGATCCAGCCAAGCAATGCTCCCATCTTCATCAATTCCACCTGTGCCTTCATATAGGGATCTGG

G

The disclosed NOV7a nucleic acid sequence, localized to chromsome 5, has 94 of 104 bases (90%) identical to a gb:GENBANK-ID:HSU42412|acc:U42412.1 mRNA from *Homo sapiens* (Human 5'-AMP-activated protein kinase, gamma-1 subunit mRNA, complete cds) (E=2.4e$^{-08}$).

A NOV7a polypeptide (SEQ ID NO:20) encoded by SEQ ID NO:19 has 500 amino acid residues and is presented using the one-letter code in Table 7B. Signal P, Psort and/or Hydropathy results predict that NOV7a does not contain a signal peptide and is likely to be localized to the plasma membrane with a certainty of 0.6000.

The disclosed NOV7a is expressed in at least the following tissues: Adrenal Gland/Suprarenal gland, Cerebral Medulla/Cerebral white matter, Ovary and Synovium. This information was derived by determining the tissue sources of the sequences that were included in the invention including but not limited to SeqCalling sources, Public EST sources, Literature sources, and/or RACE sources.

NOV7b

A disclosed NOV7b nucleic acid of 1501 nucleotides (also referred to as CG57387-02) encoding a novel Amino Acid Transporter-like protein is shown in Table 7C. An open

TABLE 7B

Encoded NOV7a protein sequence.

(SEQ ID NO:20)

MELKAPAAGGLNAGPVPPAAMSTQRLRNEDYHDYSSTDVSPEESPSEGLNNLSSPGSYQRFGQSNSTTWFQT

LIHLLKGNIGTGLLGLPLAVKNAGIVMGPISLLIIGIVAVHCMGILVKCAHHFCRRLNKSFVDYGDTVMYGL

ESSPCSWLRNHAHWGRRVVDFFLIVTQLGFCCVYFVFLADNFKQVIEAANGTTNNCHNNETVILTPTMDSRL

YMLSFLPFLVLLVFIRNLRALSIFSLLANITMLVSLVMIYQFIVFRYMLSVFQRIPDPSHLPLVAPWKTYPL

FFGTAIFSFEGIGMVLPLENKMKDPRKFPLILYLGMVIVTILYISLGCLGYLQFGANIQGSITLNLPLYQSV

KLLYSIGIFFTYALQFYVPAEIIIPFFVSRAPEHCELVVDLFVRTVLVCLTILAILIPRLDLVISLVGSVSS

SALALIIPPLLEVTTFYSEGMSPLTIFKDALISILGFVGFVVGTYEALYELIQPSNAPIFINSTCAFI

The NOV7a amino acid sequence has 127 of 276 amino acid residues (46%) identical to, and 175 of 276 amino acid residues (63%) similar to, the 486 amino acid residue ptnr:SPTREMBL-ACC:Q9VLM4 protein from *Drosophila melanogaster* (Fruit fly) (CG13384 PROTEIN)) (E=9.3e$^{-84}$).

reading frame was identified beginning with an ATG initiation codon at nucleotides 2–4 and ending with a TAG codon at nucleotides 1490–1492. Putative untranslated regions, if any, upstream from the initiation codon and downstream from the termination codon are underlined in Table 7C, and the start and stop codons are in bold letters.

TABLE 7C

NOV7b nucleotide sequence.

(SEQ ID NO:21)

TATGGAGCTAAAGGCTCCAGCTGCAGGAGGTCTTAATGCTGGCCCTGTCCCCCCAGCTGCCATGTCCACGCA

GAGACTTCGGAATGAAGACTACCACGACTACAGCTCCACGGACGTGAGCCCTGAGGAGAGCCCGTCGGAAGG

CCTCAACAACCTCTCCTCCCCGGGCTCCTACCAGCGCTTTGGTCAAAGCAATAGCACAACATGGTTCCAGAC

CTTGATCCACCTGTTAAAAGGCAACATTGGCACAGGACTGCTGGGACTCCCTCTGGCGGTGAAAAATGCAGG

CATCGTGATGGGTCCCATCAGCCTGCTGATCATAGGCATCGTGGCCGTGCACTGCATGGGTATCCTGGTGAA

TABLE 7C-continued

NOV7b nucleotide sequence.

```
ATGTGCTCACCACTTCTGCCGCAGGCTGAATAAATCCTTTGTGGATTATGGTGATACTGTGATGTATGGACT
AGAATCCAGCCCCTGCTCCTGGCTCCGGAACCACGCACACTGGGGAAGACGTGTTGTGGACTTCTTCCTGAT
TGTCACCCAGCTGGTATTCTGCTGTGTCTATTTTGTGTTTCTGGCTGACAACTTTAAACAGGTGATAGAAGC
GGCCAATGGGACCACCAATAACTGCCACAACAATGAGACGGTGATTCTGACGCCTACCATGGACTCGCGACT
CTACATGCTCTCCTTCCTGCCCTTCCTGGTGCTGCTGGTTTTCATCAGGAACCTCCGAGCCCTGTCCATCTT
CTCCCTGTTGGCCAACATCACCATGCTGGTCAGCTTGGTCATGATCTACCAGTTCATTGTTCAGAGGATCCC
AGACCCCAGCCACCTCCCCTTGGTGGCCCCTTGGAAGACCTACCCTCTCTTCTTTGGCACAGCGATTTTTC
ATTTGAAGGCATTGGAATGGTTCTGCCCCTGGAAAACAAAATGAAGGATCCTCGGAAGTTCCCACTCATCCT
GTACCTGGGCATGGTCATCGTCACCATCCTCTACATCAGCCTGGGGTGTCTGGGGTACCTGCAATTTGGAGC
TAATATCCAAGGCAGCATAACCCTCAACCTGCCCAACTGCTGGTTGTACCAGTCAGTTAAGCTGCTGTACTC
CATCGGGATCTTTTTCACCTACGCACTCCAGTTCTACGTCCCCGCTGAGATCATCATCCCCTTCTTTGTGTC
CCGAGCGCCCGAGCACTGTGAGTTAGTGGTGGACCTGTTTGTGCGCACAGTGCTGGTCTGCCTGACATGCAT
CTTGGCCATCCTCATCCCCCGCCTGGACCTGGTCATCTCCCTGGTGGGCTCCGTGAGCAGCAGCGCCCTGGC
CCTCATCATCCCACCGCTCCTGGAGGTCACCACCTTCTACTCAGAGGGCATGAGCCCCCTCACCATCTTTAA
GGACGCCCTGATCAGCATCCTGGGCTTCGTGGGCTTTGTGGTGGGGACCTATGAGGCTCTCTATGAGCTGAT
CCAGCCAAGCAATGCTCCCATCTTCATCAATTCCACCTGTGCCTTCATATAGGGATCTGGG
```

The disclosed NOV7b nucleic acid sequence, localized to chromsome 5, has 1364 of 1428 bases (95%) identical to a gb:GENBANK-ID:AX049362|acc:AX049362.1 mRNA from *Homo sapiens* (Sequence 32 from Patent WO0071709) (E=1.4e$^{-290}$).

A NOV7b polypeptide (SEQ ID NO:22) encoded by SEQ ID NO:21 has 496 amino acid residues and is presented using the one-letter code in Table 7D. Signal P, Psort and/or Hydropathy results predict that NOV7b does not contain a signal peptide and is likely to be localized to the plasma membrane with a certainty of 0.6000.

ptnr:TREMBLNEW-ACC:AAK67316 protein from *Rattus norvegicus* (Rat) (Lysosomal Amino Acid Transporter 1) (E=3.1e$^{-221}$).

The disclosed NOV7b is expressed in at least the following tissues: Adrenal Gland/Suprarenal gland, Cerebral Medulla/Cerebral white matter, Ovary and Synovium. This information was derived by determining the tissue sources of the sequences that were included in the invention including but not limited to SeqCalling sources, Public EST sources, Literature sources, and/or RACE sources.

NOV7c

A disclosed NOV7c nucleic acid of 953 nucleotides (also referred to as CG57387-03) encoding a novel Amino Acid

TABLE 7D

Encoded NOV7b protein sequence.

(SEQ ID NO:22)

```
MELKAPAAGGLNAGPVPPAAMSTQRLRNEDYHDYSSTDVSPEESPSEGLNNLSSPGSYQRFGQSNSTTWFQT
LIHLLKGNIGTGLLGLPLAVKNAGIVMGPISLLIIGIVAVHCMGILVKCAHHFCRRLNKSFVDYGDTVMYGL
ESSPCSWLRNHAHWGRRVVDFFLIVTQLVFCCVYFVFLADNFKQVIEAANGTTNNCHNNETVILTPTMDSRL
YMLSFLPFLVLLVFIRNLRALSIFSLLANITMLVSLVMIYQFIVQRIPDPSHLPLVAPWKTYPLFFGTAIFS
FEGIGMVLPLENKMKDPRKFPLILYLGMVIVTILYISLGCLGYLQFGANIQGSITLNLPNCWLYQSVKLLYS
IGIFFTYALQFYVPAEIIIPFFVSRAPEHCELVVDLFVRTVLVCLTCILAILIPRLDLVISLVGSVSSSALA
LIIPPLLEVTTFYSEGMSPLTIFKDALISILGFVGFVVGTYEALYELIQPSNAPIFINSTCAFI
```

The NOV7b amino acid sequence has 407 of 476 amino acid residues (85%) identical to, and 443 of 476 amino acid residues (93%) similar to, the 475 amino acid residue Transporter-like protein is shown in Table 7E. An open reading frame was identified beginning with an ATG initiation codon at nucleotides 2–4 and ending with a TGA codon at nucleotides 791–793. Putative untranslated regions, if any, upstream from the initiation codon and downstream from the termination codon are underlined in Table 7E, and the start and stop codons are in bold letters.

The NOV7c amino acid sequence has 209 of 241 amino acid residues (86%) identical to, and 228 of 241 amino acid residues (94%) similar to, the 475 amino acid residue ptnr:TREMBLNEW-ACC:AAK67316 protein from *Rattus*

TABLE 7E

NOV7c nucleotide sequence.

(SEQ ID NO:23)
TATGGAGCTAAAGGCTCCAGCTGCAGGAGGTCTTAATGCTGGCCCTGTCCCCCAGCTGCCATGTCCACGCA

GAGACTTCGGAATGAAGACTACCACGACTACAGCTCCACGGACGTGAGCCCTGAGGAGAGCCCGTCGGAAGG

CCTCAACAACCTCTCCTCCCCGGGCTCCTACCAGCGCTTTGGTCAAAGCAATAGCACAACATGGTTCCAGAC

CTTGATCCACCTGTTAAAAGGCAACATTGGCCACAGGACTGCTGGGACTCCCTCTGGCGGTGAAAATGCAGG

CATCGTGATGGGTCCCATCAGCCTGCTGATCATAGGCATCGTGGCCGTGCACTGCATGGGTATCCTGGTGAA

ATGTGCTCACCACTTCTGCCGCAGGCTGAATAAATCCTTTGTGGATTATGGTGATACTGTGATGTATGGACT

AGAATCCAGCCCCTGCTCCTGGCTCCGGAACCACGCACACTGGGGAAGACGTGTTGTGGACTTCTTCCTGAT

TGTCACCCAGCTGGGATTCTGCTGTGTCTATTTTGTGTTTCTGGCTGACAACTTTAAACAGGTGATAGAAGC

GGCCAATGGGACCACCAATAACTGCCACAACAATGAGACGGTGATTCTGACGCCTACCATGGACTCGCGACT

CTACATGCTCTCCTTCCTGCCCTTCCTGGTGCTGCTGGTTTTCATCAGGAACCTCCGAGCCCTGTCCATCTT

CTCCCTGTTGGCCAACATCACCATGCTCGTCAGCTTGGTCATGATCTACCAGTTCATTGTTCAGATCCTGTG

AATGGATTTACAGCCCATGTAGCAGACCAAGGTCTTCCACAGAGAGCAGGTTCCTCTCTGTCTTCAGCATGT

GGAGTCTCAAATGGAACAGTTCTGGGCAGAGTGCTTTGCACAGAGGGTGCTCCCAATAAATGTTTTATCACT

GCAAAAAAAAAAAAAAA

The disclosed NOV7c nucleic acid sequence, localized to chromsome 5, has 723 of 724 bases (99%) identical to a gb:GENBANK-ID:AX049362|acc:AX049362.1 mRNA from *Homo sapiens* (Sequence 32 from Patent WO0071709) (E=3.5e$^{-157}$).

A NOV7c polypeptide (SEQ ID NO:24) encoded by SEQ ID NO:23 has 263 amino acid residues and is presented using the one-letter code in Table 7F. Signal P, Psort and/or Hydropathy results predict that NOV7c does not contain a signal peptide and is likely to be localized to the plasma membrane with a certainty of 0.6000.

*norvegicus* (Rat) (Lysosomal Amino Acid Transporter 1) (E=6.8e$^{-114}$).

The disclosed NOV7c is expressed in at least the following tissues: Adrenal Gland/Suprarenal gland, Cerebral Medulla/Cerebral white matter, Ovary and Synovium. This information was derived by determining the tissue sources of the sequences that were included in the invention including but not limited to SeqCalling sources, Public EST sources, Literature sources, and/or RACE sources.

TABLE 7F

Encoded NOV7c protein sequence.

(SEQ ID NO:24)
MELKAPAAGGLNAGPVPPAAMSTQRLRNEDYHDYSSTDVSPEESPSEGLNNLSSPGSYQRFGQSNSTTWFQT

LIHLLKGNIGTGLLGLPLAVKNAGIVMGPISLLIIGIVAVHCMGILVKCAHHFCRRLNKSFVDYGDTVMYGL

ESSPCSWLRNHAHWGRRVVDFFLIVTQLGFCCVYFVFLADNFKQVIEAANGTTNNCHNNETVILTPTMDSRL

YMLSFLPFLVLLVFIRNLRALSIFSLLANITMLVSLVMIYQFIVQIL

Possible SNPs found for NOV7a are listed in Table 7G.

TABLE 7G

| | | SNPs | | |
|---|---|---|---|---|
| Variant | Nucleotide Position | Base Change | Amino Acid Position | Base Change |
| 13377064 | 256 | C > G | Silent | N/A |
| 13377065 | 519 | G > T | 173 | Gly > Val |
| 13377066 | 1153 | C > T | Silent | N/A |

NOV7a, NOV7b and NOV7c are very closely homologous as is shown in the amino acid alignment in Table 7H.

TABLE 7H

Amino Acid Alignment of NOV7a, NOV7b and NOV7c

```
                 10        20        30        40        50        60        70
          ....|....|....|....|....|....|....|....|....|....|....|....|....|....|
NOV7a    MELKAPAAGGLNAGPVPPAAMSTQRLRNEDYHDYSSTDVSPEESPSEGLNNLSSPGSYQRFGQSNSTIWP
NOV7b    MELKAPAAGGLNAGPVPPAAMSTQRLRNEDYHDYSSTDVSPEESPSEGLNNLSSPGSYQRFGQSNSTIWP
NOV7c    MELKAPAAGGLNAGPVPPAAMSTQRLRNEDYHDYSSTDVSPEESPSEGLNNLSSPGSYQRFGQSNSTIWP 80        90       100       110       120       130       140
          ....|....|....|....|....|....|....|....|....|....|....|....|....|....|
NOV7a    QTLIHLLKGNIGTGLLGLPLAVKNAGIVMGPISLLIIGIVAVHCMGILVKCAHHFCRRLNKSFVDYGDTV
NOV7b    QTLIHLLKGNIGTGLLGLPLAVKNAGIVMGPISLLIIGIVAVHCMGILVKCAHHFCRRLNKSFVDYGDTV
NOV7c    QTLIHLLKGNIGTGLLGLPLAVKNAGIVMGPISLLIIGIVAVHCMGILVKCAHHFCRRLNKSFVDYGDTV 150       160       170       180       190       200       210
          ....|....|....|....|....|....|....|....|....|....|....|....|....|....|
NOV7a    MYGLESSPCSWLRNHAHWGRRVVDFFLIVTQLGFCCVYFVFLADNFKQVIEAANGTTNNCHNNETVILTP
NOV7b    MYGLESSPCSWLRNHAHWGRRVVDFFLIVTQLVFCCVYFVFLADNFKQVIEAANGTTNNCHNNETVILTP
NOV7c    MYGLESSPCSWLRNHAHWGRRVVDFFLIVTQLGFCCVYFVFLADNFKQVIEAANGTTNNCHNNETVILTP 220       230       240       250       260       270       280
          ....|....|....|....|....|....|....|....|....|....|....|....|....|....|
NOV7a    TMDSRLYMLSFLPFLVLLVFIRNLRALSIFSLLANITMLVSLVMIYQFIVFRYMLSVFQRIPDPSHLPLV
NOV7b    TMDSRLYMLSFLPFLVLLVFIRNLRALSIFSLLANITMLVSLVMIYQFIV-------QRIPDPSHLPLV
NOV7c    TMDSRLYMLSFLPFLVLLVFIRNLRALSIFSLLANITMLVSLVMIYQFIV-------QIN---------

290       300       310       320       330       340       350
          ....|....|....|....|....|....|....|....|....|....|....|....|....|....|
NOV7a    APWKTYPLFFGTAIFSFEGIGMVLFLENKMKDPRKFPLILYLGMVIVTILYISLGCLGYLQFGANIQGSI
NOV7b    APWKTYPLFFGTAIFSFEGIGMVLFLENKMKDPRKFPLILYLGMVIVTILYISLGCLGYLQFGANIQGSI
NOV7c    ----------------------------------------------------------------------

360       370       380       390       400       410       420
          ....|....|....|....|....|....|....|....|....|....|....|....|....|....|
NOV7a    TLNLP---LYQSVKLLYSIGIFFTYALQFYVPAEIIIPFFVSRAPEHCELVVDLFVRTVLVCLT-ILAIL
NOV7b    TLNLPNCWLYQSVKLLYSIGIFFTYALQFYVPAEIIIPFFVSRAPEHCELVVDLFVRTVLVCLTCILAIL
NOV7c    ----------------------------------------------------------------------

430       440       450       460       470       480       490
          ....|....|....|....|....|....|....|....|....|....|....|....|....|....|
NOV7a    IPRLDLVISLVGSVSSSALALIIPPLLEVITFYSEGMSPLTIFKDALISILGFVGFVVGTYEALYELIQP
NOV7b    IPRLDLVISLVGSVSSSALALIIPPLLEVITFYSEGMSPLTIFKDALISILGFVGFVVGTYEALYELIQP
NOV7c    ----------------------------------------------------------------------

500
          ....|....|....
NOV7a    SNAPIFINSTCAFI
NOV7b    SNAPIFINSTCAFI
NOV7c    --------------
```

Homologies to any of the above NOV7 proteins will be shared by the other NOV7 proteins insofar as they are homologous to each other as shown above. Any reference to NOV7 is assumed to refer to the NOV7 proteins in general, unless otherwise noted.

NOV7a has homology to the amino acid sequences shown in the BLASTP data listed in Table 7I.

TABLE 7I

BLAST results for NOV7a

| Gene Index/ Identifier | Protein/ Organism | Length (aa) | Identity (%) | Positives (%) | Expect |
|---|---|---|---|---|---|
| gi\|4826770\|ref\|NP_004960.1\| (NM_004969) | Amino Acid Transporter; insulinase [Homo sapiens] | 1019 | 974/1019 (95%) | 984/1019 (95%) | 0.0 |
| gi\|6981076\|ref\|NP_037291.1\| (NM_013159) | insulin degrading enzyme [Rattus norvegicus] | 1019 | 934/1019 (91%) | 965/1019 (94%) | 0.0 |
| gi\|13621162\|ref\|NP_112419.1\| (NM_031156) | insulin degrading enzyme [Mus musculus] | 1019 | 929/1019 (91%) | 963/1019 (94%) | 0.0 |
| gi\|18576366\|ref\|XP_051153.2\| (XM_051153) | Amino Acid Transporter [Homo sapiens] | 554 | 530/554 (95%) | 539/554 (96%) | 0.0 |
| gi\|7296294\|gb\|AAF51584.1\| (AE003591) | Ide gene product [Drosophila melanogaster] | 990 | 439/966 (45%) | 634/966 (65%) | 0.0 |

The homology of these sequences is shown graphically in the ClustalW analysis shown in Table 7J.

TABLE 7J

ClustalW Analysis of NOV7a

1) NOV7a (SEQ ID NO:20)
2) gi|4826770|ref|NP_004960.1| (NM_004969) Amino Acid Transporter; insulinase
[Homo sapiens] (SEQ ID NO:131)
2) gi|6981076|ref|NP_037291.1| (NM_013159) insulin degrading enzyme
[Rattus norvegicus] (SEQ ID NO:132)
3) gi|13621162|ref|NP_112419.1| (NM_031156) insulin degrading enzyme [Mus musculus]
(SEQ ID NO:133)
4) gi|18576366|ref|XP_051153.2| (XM_051153) Amino Acid Transporter [Homo sapiens]
(SEQ ID NO:134)
5) gi|7296294|gb|AAF51584.1| (AE003591) Ide gene product [Drosophila melanogaster]
(SEQ ID NO:135)

```
                    10        20        30        40        50        60        70
                ....|....|....|....|....|....|....|....|....|....|....|....|....|....|
NOV7a           -----------------------------MELKAPAAGGLNAGPVPPAAMSTQRLRNEDYHDYSSTDVSPE
gi|17505223     --------------------------------------------------MSTQRLRNEDYHDYSSTDVSPE
gi|18426842     --------------------------------------------------MSTQRLRNEDYHDYSSTDVSPE
gi|17473038     -------------------------------MEAAATPAAAGAARRLEIDMLVMRPLINEQNFDG
gi|17449820     ----------------------------------------------------------------------
gi|18467570     MEDLTPLTNLQQIPEGAPRKKKMTERQPLLLQSDASDYEGSRGSAARPYRSSPPDNTLVNVESEDSLAAS 80        90       100       110       120       130       140
                ....|....|....|....|....|....|....|....|....|....|....|....|....|....|
NOV7a           ESPSEGLNNLSS-PGSYQRFGQSNSTTWFQTLTHLLKGNIGTGLLGLPLAVKNAGIVMGPISLLIGIVA
gi|17505223     ESPSEGLNNLSS-PGSYQRFGQSNSTTWFQTLTHLLKGNIGTGLLGLPLAAKNAGIVMGPISLLIGIVA
gi|18426842     ESPSEGLGSFS--PGSYQRLGENSSMTWFQTLIHLLKGNIGTGLLGLPLAVKNAGLLLGPLSLLVIGIVA
gi|17473038     TSDEEHEQELLP-VQKLYQLDDQEGISFVQTLMHLLKGNIGTGLLGLPLAIKNAGIVLGPISLVFIGIIS
gi|17449820     ----------------------------------------------------MGPISLLIGIVA
gi|18467570     GSGDLEIGSTDKSYNPTHHRDLEHPTSNEDTLVHLLKGNIGTGLIAMEDAFKNAGIYVGLFGTMIMGAIC 150       160       170       180       190       200       210
                ....|....|....|....|....|....|....|....|....|....|....|....|....|....|
NOV7a           VHCMGILVKCAHHFCRRINKSFVDYGDTVMYGLESSPCSWLRNHAHWGRRVVDFFLIVTQLGFCCVYFVP
gi|17505223     VHCMGILVKCAHHFCRRINKSFVDYGDTVMYGLESSPCSWLRNHAHWGRRVVDFFLIVTQLGFCCVYFVP
gi|18426842     VHCMGILVKCAHHLCRRINKPFLDYGDTVMYGLECSPSTWIRNHSHWGRRIVDFFLVVTQLGFCCVYFVP
gi|17473038     VHCMHILVRCSHFLCLRFKKSTLGYSDTVSHAMEVSPWSCLQRQAAWGRSVVDFFLVITQLGFCSVYIVP
gi|17449820     VHCMGILVKCAHHFCRRINKSFVDYGDTVMYGLESSPCSWLRNHAHWGRRVVDFFLIVTQLGFCCVYFVP
gi|18467570     THCMHMLVNCSHELCRRFQQPSLDESRVAYCSFESGPLG-LRAYSMLARRIVTTFLFITQIGFCCVYFIF
```

TABLE 7J-continued

ClustalW Analysis of NOV7a

```
                220        230        240        250        260        270        280
             ....|....|....|....|....|....|....|....|....|....|....|....|....|....|
NOV7a        LADNFKQVIE---AANGTTNNCHNNETVILTPTMDSRLYMLSFLPFLVLLVFIRNLRALSIFSLLANIMM
gi|17505223  LADNFKQVIE---AANGTTNNCHNNETVILTPTMDSRLYMLSFLPFLVLLVFIRNLRALSIFSLLANIMM
gi|18426842  LADNFKQVIE---AANGTTTNCNNNETVILTPTMDSRLYMLTFLPFLVLLSFIRNLRILSIFSLLANISM
gi|17473038  LAENVKQVHEGFLESKVFISNSTNSSNPCERRSVDLRIYMLCFLPFLILLVFIRELKNLFNLSFLANMSM
gi|17449820  LADNFKQVIE---AANGTTNNCHNNETVILTPTMDSRLYMLSFLPFLVLLVFIRNLRALSIFSLLANIMM
gi|18467570  VALNIKDVMD-----------HYYK-------MPVQIYLIIMLGPMILLNLVRNLKYLPPVSLMAALLT 290        300        310        320        330        340        350
             ....|....|....|....|....|....|....|....|....|....|....|....|....|....|
NOV7a        LVSLVMIYQFIVFRYMLSVFQRIPDPSHLPLVAPWKTYPLFFGTAIFSFEGICMVLPLENKMKDPRKFP-
gi|17505223  LVSLVMIYQFIVQ-------RIPDPSHLPLVAPWKTYPLFFGTAIFSFEGICMVLPLENKMKDPRKFP-
gi|18426842  FVSLIMIYQFIVQ-------RIPDPSHLPLVAPWKTYPLFFGTAIFAFEGICVVLPLENKMKLSQKFP-
gi|17473038  AVSLVIIYQXVVR-------NMPDPHNLPIVACWKKYPLFFGTAVFAFEGICMVLPLENQMKESKRFP-
gi|17449820  LVSLVMIYQFIVQ--IL----------------------------------------------------
gi|18467570  VAGLAITFSYMLV-------DLPDVHTVKPVATWATLPLYFGTAIYAFEGICVVLPLENNMRTPEDEGG 360        370        380        390        400        410        420
             ....|....|....|....|....|....|....|....|....|....|....|....|....|....|
NOV7a        --LILYEGMVIVTILYISLGCLGYLQFGANIQGSITLNLP----LYQSVKLLYSIGIFFTYALQFYVPAE
gi|17505223  --LILYEGMVIVTILYISLGCLGYLQFGANIQGSITLNLPN-CWLYQSVKLLYSIGIFFTYALQFYVPAE
gi|18426842  --LILYEGMAIIIVLYISLGSLGYLQFGADILGSITLNLPN-CWLYQSVKILYSIGIFFTYALQFYVAAE
gi|17473038  --QALNIGMGIVTILYVTLATLGYYCFHDEIKGSITLNLPQDVWLYQSVKILYSFGIFVTYSTQFYVPAE
gi|17449820  --------------------------------------------------------------------
gi|18467570  TTGVINTGMVIVACLYTAVCFFGYLKYGEHVEGSITLNLPQGDTISQLVRISMAVAIFLSYTLQFYVPVN 430        440        450        460        470        480        490
             ....|....|....|....|....|....|....|....|....|....|....|....|....|....|
NOV7a        IILEFFVSRAPE-HCELVVDLFVRTVIVCL-TILAILIPRLDLVISLVGSVSSSALALIPPPLEVTTFY
gi|17505223  IIS---------------------------------LVGSVSSSALALIPPLEVTTFY
gi|18426842  IILEAIVSRVPE-RFELVVDLSARTAMVCVTCVLAVLIPRIDLVISLVGSVSSSALALIPPLEVTIIY
gi|17473038  IILEGITSKFHT-KWKQICEFGIRSFLVSITCAGAILIPRLDIVISFVGAVSSSTLALIPPLVEILTFS
gi|17449820  --------------------------------------------------------------------
gi|18467570  IVEEFVRSHFDTTRAKDLSATVLFVVLVTFTFLLATCIENLGSRISLVGAVSSSALALIAPPIIEVITFY 500        510        520        530        540        550
             ....|....|....|....|....|....|....|....|....|....|....|....|....|
NOV7a        SEGM -- LTIFKDALISILGFVGFVVGTYEALYPLIQPSNAPIFINSTCAFI------------
gi|17505223  SEGM -- LTIFKDALISILGFVGFVVGTYEALYDLIRPSNAPIFINSTCAFI------------
gi|18426842  GECI -- LTITKDALISILGFVGFVVGTYEALWDLIQPSHSDSSTNSTSAFI------------
gi|17473038  KEHYN--IWMVLKNISLAFTGVVGFLLGTYITVPEIIYPIPKVVAGTPQSPELNLSTCLTSGLK
gi|17449820  --------------------------------------------------------------------
gi|18467570  NVGYGRFNWMLWKDVLILIFGLCGFVFGIWASLAQILNDRTH-----------------------
```

Table 7K lists the domain description from DOMAIN analysis results against NOV7a. This indicates that the NOV7a sequence has properties similar to those of other proteins known to contain these domains.

TABLE 7K

Domain Analysis of NOV7a gnl|Pfam|pfam01490, Aa_trans, Transmembrane amino acid transporter
protein. This transmembrane region is found in many amino acid
transporters including UNC-47 and MTR. UNC-47 encodes a vesicular
amino butyric acid (GABA) transporter, (VGAT). UNC-47 is predicted to
have 10 transmembrane domains. MTR is a N system amino acid
transporter system protein involved in methyltryptophan resistance.
Other members of this family include proline transporters and amino
acid permeases. (SEQ ID NO:136)
CD-Length = 370 residues, 85.1% aligned
Score = 119 bits (299), Expect = 3e-28

```
Query:   91 AVKNAGIVMGPISLLIIGIVAVHCMGILVKCAHHFCRRLNKSFVDYGDTVMYGLESSPCS  150
               | |  | + | +  | | + ++    +| +|   +    + | |++|  | +    |         |
Sbjct:    1 AFKQLGWIPGLVLLLLAGFITLYTGLLLSECYEYVPGKRNDSYLDLGRSAYGGKGLLLTS   60

Query:  151 WLRNHAHWGRRVVDFFLIVTQLGFCCVYFVFLADNFKQVIEAANGTTNNCHNNETVILTP  210
               ++             |    |   | +   |   ++|         ++ |  +|
```

TABLE 7K-continued

Domain Analysis of NOV7a

```
Sbjct:   61 FVG------------QYVNLFGVNIGYLILAGDLLPKII------SSFCGDNCD-----    96

Query:  211 TMDSRLYMLSFLPFLVLLVFIRNLRALSI--FSLLANITMLVSLVMIYQFIVFRYMLSVF  268
              +|   +++ |    ++ | | |     | | |    | +++ |    + +      | + +
Sbjct:   97 HLDGNSWIIIFAAIIITLSFIPNFNLLSISSLSAFSSLAYLSIISFLIIVAVIAGIFVLL 156

Query:  269 QRIPDPSHLPLVAPWKTYPLFFGTAIFSFEGIGMVLPLENKNKDPR--KFPLILYLGMVI 326
                +        |       |   |  +|+|||   ++|  |++|  | |      || +| + ++|
Sbjct:  157 GAVYGILWSPSFTKLTGLFLAIGIIVFAFEGHAVLLPIQNTMKSPSAKKFKKVLNVAIII 216

Query:  327 VTILYISLGCLGYLQFGANIQGSITLNLP---LYQSVKLLYSIGIFFTYALQFYVPAEII 383
             | |+| | |  +|    ||| ||  |++|+|  ||||      +   | |    +   |+  ||  +       ||
Sbjct:  217 VTVLYILVGFFGYLTFGNNVKGNILLNLPNNPFWLIVNLNLVVAILLTFPLQAFPIVRII 276

Query:  384 IPFFV---SRAPEHCELVVDLFVRTVLVCLTILAILIPR                      419
               + ||    +|  +  +      ++|     ++| | |+|
Sbjct:  277 ENLLTKKNNFAPNKSKLLRVVIRSGLVVFTLLIAILVPF                      315
```

NOV7 has significant homology in the transmembrane region found in many amino acid transporters including UNC-47 and MTR. UNC-47 encodes a vesicular amino butyric acid(GABA) transporter, (VGAT). UNC-47 is predicted to have 10 transmembrane domains. MTR is a N system amino acid transporter system protein involved in methyltryptophan resistance. Other members of this family include proline transporters and amino acid permeases. Amino acid transporters may play an important role in a number of diseases as exemplified below.

Because most cancer deaths result from disseminated disease, understanding the regulation of tumor invasion and metastasis is a central theme in tumor cell biology. Interactions between extracellular matrices (ECM) and cellular microenvironment play a crucial role in this process. Selected amino acids and polyamines have been tested for their ability to regulate RL95-2 cell invasion through both intact human amniotic basement membrane and a novel human ECM (Amgel). Three major systems for neutral amino acid transport, systems L, A, and ASC, are operational in these neoplastic cells. Amino acids entering the cell via transport system A or N, i.e., (methyl amino)-isobutyrate (MeAIB) or Asn, markedly enhanced invasiveness of these human adenocarcinoma cells as measured by a standard 72-hr amnion or Amgel invasion assay. Addition of 2-amino-2-norborane carboxylic acid (BCH; 1 mM), a model substrate of the L transport system, caused a significant decrease in invasive activity when tested in the Amgel assay. Interestingly, Val lowers steady-state levels of MeAIB uptake and blocks the increase in cell invasion elicited by MeAIB. At the same time, these amino acids do not influence cell proliferation activity. Neither the charged amino acid Lys or Asp (not transported by A/N/L systems) nor the polyamines putrescine, spermidine, or spermine modulate invasiveness under similar experimental conditions. Moreover, the observed time-dependent stimulation of system A activity (cellular influx of MeAIB) by substrate depletion is prevented by the addition of actinomycin D (5 microM) or cycloheximide (100 microM), suggesting the involvement of de novo RNA and protein synthesis events in these processes. MeAIB treatment of tumor cells selectively increased the activities of key invasion-associated type IV collagenases/gelatinases. These results indicate that in the absence of defined regulators (growth factors or hormones), certain amino acids may contribute to the epigenetic control of human tumor cell invasion and, by extension, metastasis. This study suggests that amino acids, acting via specific signaling pathways, modulate phenotypic cell behavior by modulating the levels of key regulatory enzymatic proteins (Singh et al., Cancer Invest 14(1):6–18, 1996).

To investigate the function of a basic and neutral amino acid transporter-like protein (rBAT) which is a candidate gene for cystinuria, the rBAT gene was analysed in cystinuric patients. Patient 1 is a compound heterozygote with mutations in the rBAT gene causing a glutamine-to-lysine transition at amino acid 268, and a threonine-to-alanine transition at amino acid 341, who inherited these alleles from his mother (E268K) and father (T341A), respectively. Injection of T341A and E268K mutant cRNAs into oocytes decreased transport activity to 53.9% and 62.5% of control (L-cystine transport activity in oocytes injected with wild-type rBAT cRNA), respectively. Co-injection of E268K and T341A into oocytes strongly decreased amino acid transport activity to 28% of control. On the other hand, co-injection of wild-type and mutant rBAT did not decrease transport activity. Furthermore, immunological studies have demonstrated that the reduction of amino acid transport is not due to a decrease in the amount of rBAT protein expressed in oocyte membranes. These results indicate that mutations in the rBAT gene are crucial disease-causing lesions in cystinuria. In addition, co-injection experiments suggest that rBAT may function as a transport activator orregulatory subunit by homo- or hetero-multimer complex formation (Miyamoto et al., Biochem J 310 (Pt 3):951–5, 1995).

The spinal cord of 20 patients with amyotrophic lateral sclerosis (ALS) and 5 patients with lower motor neuron disease (LMND) were investigated immunohistochemically using anti-human excitatory amino acid transporter 1 (EAAT1) and EAAT2 antibodies which are the astrocytic transporters. The purpose of the study was to examine relationships between EAAT1 and EAAT2 immunoreactivity and degeneration of anterior horn neurons. Specimens from 20 patients without any neurological disease served as controls. In controls, spinal cord gray matter was densely immunostained by antibodies, whereas the white matter was generally not immunostained. In motor neuron disease (MND) patients, EAAT1 immunoreactivity was relatively well preserved in the gray matter despite neuronal loss of anterior horn cells. On the other hand, EAAT2 immunoreactivity in anterior horns correlated with the degree of neuronal loss of anterior horn cells: in the patients with mild neuronal depletion, anterior horns were densely immunostained by the antibody, whereas in the patients with severe neuronal loss, EAAT2 expression was markedly reduced. Degenerated anterior horn cells frequently showed a much denser EAAT1 and EAAT2 immunoreactivity around the surface of the neurons and their neuronal processes than that observed in normal-appearing neurons. There was no difference in the expression of EAAT1 and EAAT2 immunoreactivity between LMND and ALS patients. These findings suggest that in the early stage of degeneration of anterior horn cells, EAAT1 and EAAT2 immunoreactivity is preserved in the astrocytic foot directly attached to normal-appearing neurons, whereas levels of EAAT1 and EAAT2 protein rather increase in the astrocytic foot directly attached to degenerated anterior horn neurons; the latter effect most probably reduces the elevated glutamate level, compensates for the reduced function of astroglial glutamate transporters, or represents a condensation of EAAT1 and EAAT2 immunoreactivity secondary to loss of neurites and greater condensation of astrocytic processes. Thus, the study demonstrates a difference in EAAT1 and EAAT2 immunoreactivity in different stages of progression in ALS, as a feature of the pathomechanism of this disease (Sasaki et al., Acta Neuropathol (Berl) 100(2):138–44, 2000).

The NOV7 nucleic acid of the invention encoding a Amino Acid Transporter-like protein includes the nucleic acid whose sequence is provided in Tables 7A, 7C and 7E, or a fragment thereof. The invention also includes a mutant or variant nucleic acid any of whose bases may be changed from the corresponding base shown in Tables 7A, 7C and 7E while still encoding a protein that maintains its Amino Acid Transporter-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 10% of the NOV7a residues, about 5% of the NOV7b residues and about 1% of the NOV7c residues may be so changed.

The NOV7 protein of the invention includes the Amino Acid Transporter-like protein whose sequence is provided in Tables 7B, 7D and 7F. The invention also includes a mutant or variant protein any of whose residues may be changed from the corresponding residue shown in Tables 7B, 7D and 7F while still encoding a protein that maintains its Amino Acid Transporter-like activities and physiological functions, or a functional fragment thereof. In the mutant or variant protein, up to about 54% of the NOV7a bases, about 15% of the NOV7b bases and about 14% of the NOV7c bases may be so changed.

The NOV7 nucleic acids and proteins of the invention are useful in potential diagnostic and therapeutic applications implicated in various diseases and disorders described below and/or other pathologies. For example, the compositions of the present invention will have efficacy for treatment of patients suffering from: cancer, trauma, regeneration (in vitro and in vivo), viral/bacterial/parasitic infections, Von Hippel-Lindau (VHL) syndrome, Alzheimer's disease, stroke, tuberous sclerosis, hypercalceimia, Parkinson's disease, Huntington's disease, cerebral palsy, epilepsy, Lesch-Nyhan syndrome, multiple sclerosis, ataxia-telangiectasia, leukodystrophies, behavioral disorders, addiction, anxiety, pain, neurodegeneration, fertility, adrenoleukodystrophy, congenital adrenal hyperplasia and other diseases, disorders and conditions of the like.

NOV7 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV7 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV8

NOV8 includes five novel Lymphocyte antigen precursor-like or Lymphocyte antigen LY-6F-like proteins disclosed below. The disclosed proteins have been named NOV8a–NOV8e.

NOV8a

A disclosed NOV8a nucleic acid of 468 nucleotides (also referred to as CG56417-01) encoding a novel Lymphocyte antigen precursor-like protein is shown in Table 8A. An open reading frame was identified beginning with an ATG initiation codon at nucleotides 31–33 and ending with a TGA codon at nucleotides 439–441. Putative untranslated regions, if any, upstream from the initiation codon and downstream from the termination codon are underlined in Table 8A, and the start and stop codons are in bold letters.

TABLE 8A

NOV8a nucleotide sequence.

(SEQ ID NO:25)
TGAAGTTTGTCTGTGCACTAGCACCCTGGAATGAGCAGTCTCCAGGCCATGAAGACCTTGTCCCTGGTCCTG

CTGGTGGCCCTGCTGAGCATGGAGAGAGCTCAGGGTCTGCGCTGCTACAGATGCTTGGCGGTCTTGGAAGGG

GCCTCCTGCAGCGTGGTCTCGTGCCCCTTCCTGGATGGGGTCTGTGTCTCCCAGAAAGTGAGCTTAAGTCTG

AGCAAGAAAAGAAGAAAAGAAAAAAACAAGCTCTCCCTCCTCTCCTGCCAGAAGGACGTCGGATTCCCCCTG

CTGAAACTTACAAGTGCCGTTGTGGACTCCCAGATCTCTTGCTGCAAGGGAGACCTCTGCAATGCGGTGGTC

CTGGCAGCCAGCAGCCCCTGGGCCCTGTGCGTACAGCTCCTGCTCAGCCTGGGGTCAGTCTTCCTCTGGGCC

CTGCTGTGAGGGCCCTTTCCCGCCCTCTCCCCCGCA

A NOV8a polypeptide (SEQ ID NO:26) encoded by SEQ ID NO:25 has 136 amino acid residues and is presented using the one-letter code in Table 8B.

TABLE 8B

Encoded NOV8a protein sequence.

(SEQ ID NO:26)
MSSLQAMKTLSLVLLVALLSMERAQGLRCYRCLAVLEGASCSVVSCPFLDGVCVSQKVSLSLSKKRRKEKNK

LSLLSCQKDVGFPLLKLTSAVVDSQISCCKGDLCNAVVLAASSPWALCVQLLLSLGSVFLWALL

NOV8b

A disclosed NOV8b nucleic acid of 610 nucleotides (also referred to as CG56417-02) encoding a novel Lymphocyte antigen precursor-like protein is shown in Table 8C. An open reading frame was identified beginning with an ATG initiation codon at nucleotides 47–49 and ending with a TAG codon at nucleotides 515–517. Putative untranslated regions, if any, upstream from the initiation codon and downstream from the termination codon are underlined in Table 8C, and the start and stop codons are in bold letters.

ptnr:SWISSNEW-ACC:P35460 protein from *Mus musculus* (Mouse) (Lymphocyte Antigen LY-6F.1 Precursor) (E=2.3e$^{-16}$).

The disclosed NOV8b is expressed in at least the following tissues: Adrenal Gland/Suprarenal gland, Brain, Kidney, Lung, Pituitary Gland, Placenta, Trachea and Whole Organism. This information was derived by determining the tissue sources of the sequences that were included in the invention including but not limited to SeqCalling sources, Public EST sources, Literature sources, and/or RACE sources.

TABLE 8C

NOV8b nucleotide sequence.

(SEQ ID NO:27)
CTTGTAAGGGCGAGACAGCAGAGACTGGCACCAGGGAGGCTCCTCCATGGGAGTCTTCCATGATTACTCACA

GCGGGTGGGCAGAGGTGTTGCTAGGAAGCATGTTCTGGGGGGGTCCTCTGGGTGCACACGTGCAGTAGCTGC

ACCTGCTTGCTCATACGTCGCATGTGTCATTAGCATCTTAAATCTCCACCAGGGGTGTGTTTTCTTGCCCTC

TCTCCCAGCTCAGGGTCTGCGCTGCTACAGATGCTTGGCGGTCTTGGAAGGGGCCTCCTGCAGCGTGGTCTC

GTGCCCCTTCCTGGATGGGGTCTGTGTCTCCCAGAAAGTGAGCGTTTTGGCAGTGAGTCCCTGGGGTGCCAG

GGCAGAGGGCAGGTTAAGTGCCGTTGTGGACTCCCAGATCTCTTGCTGCAAGGGAGACCTCTGCAATGCGGT

GGTCCTGGCAGCCGGCAGCCCCTGGGCCCTGTGCGTACAGCTCCTGCTCAGCCTGGGGTCAGTCTTCCTCTG

GGCCCTGCTGTGAGGGCCTTTCCCGCCCTCTCCCCCGCAGGCCTACCCTCTGTCCCTGTGCGTCACCAGCTG

CTTGGTTTTGAAGAGCTGCCTCACTGAATTGCAG

The disclosed NOV8b nucleic acid sequence, localized to chrmsome 8, has 192 of 249 bases (77%) identical to a gb:GENBANK-ID:HSU85047|acc:U85047.1 mRNA from *Homo sapiens* (Human FRA3B region corresponding to the breakpoint junction in lung tumor cell line NCIH211) (E=1.1e$^{-22}$).

A NOV8b polypeptide (SEQ ID NO:28) encoded by SEQ ID NO:27 has 156 amino acid residues and is presented using the one-letter code in Table 8D. Signal P, Psort and/or Hydropathy results predict that NOV8b does not contain a signal peptide and is likely to be localized to the plasma membrane with a certainty of 0.6000.

The NOV8b amino acid sequence has 53 of 126 amino acid residues (42%) identical to, and 69 of 126 amino acid residues (54%) similar to, the 134 amino acid residue

NOV8c

A disclosed NOV8c nucleic acid of 406 nucleotides (also referred to as CG56417-03) encoding a novel Lymphocyte antigen precursor-like protein is shown in Table 8E. An open reading frame was identified beginning with an ATG initiation codon at nucleotides 2–4 and ending with a TGA codon at nucleotides 404–406. Putative untranslated regions, if any, upstream from the initiation codon and downstream from the termination codon are underlined in Table 8E, and the start and stop codons are in bold letters.

TABLE 8D

Encoded NOV8b protein sequence.

(SEQ ID NO:28)
MGVFHDYSQRVGRGVARKHVLGGSSGCTRAVAAPACSYVACVISILNLHQGCVFLPSLPAQGLRCYRCLAVL

EGASCSVVSCPFLDGVCVSQKVSVLAVSPWGARAEGRLSAVVDSQISCCKGDLCNAVVLAAGSPWALCVQLL

LSLGSVFLWALL

TABLE 8E

NOV8c nucleotide sequence.

(SEQ ID NO:29)

AATGAGCAGTCTCCAGGCCATGAAGACCTTGTCCCTGGTCCTGCTGGTGGCCCTGCTGAGCATGGAGAGAGC

TCAGGGTCTGCGCTGCTACAGATGCTTGGCGGTCTTGGAAGGGGCCTCCTGCAGCGTGGTCTCGTGCCCCTT

CCTGGATGGGGTCTGTCTCTCCCAGAAAGTGAGCGTCTTTGGCAGTAAAGTGAGAGGGGAGAACAAGCTCTC

CCTCCTCTCCTGCCAGAAGGACGTCGGATTCCCCCTGCTGAAACTTACAAGTGCCGTTGTGGACTCCCAGAT

CTCTTGCTGCAAGGGAGACCTCTGCAATGCGGTGGTCCTGGCAGCCGGCAGCCCCGGGCCCTGTGCGTACA

GCTCCTGCTCAGCCTGGGGTCAGTCTTCCTCTGGGCCCTGCTGTGA

The disclosed NOV8c nucleic acid sequence, localized to chromsome 8, has 260 of 403 bases (64%) identical to a gb:GENBANK-ID:RATLY6CA|acc:M30691.1 mRNA from *Rattus norvegicus* (Rat Ly6-C antigen mRNA, exon 2) (E=1.2e$^{-16}$).

A NOV8c polypeptide (SEQ ID NO:30) encoded by SEQ ID NO:29 has 134 amino acid residues and is presented using the one-letter code in Table 8F. Signal P, Psort and/or Hydropathy results predict that NOV8c contains a signal peptide and is likely to be localized to the plasma membrane with a certainty of 0.9190. The most likely cleavage site for a NOV8c polypeptide is between amino acids 26 and 27: AQG-LR

TABLE 8F

Encoded NOV8c protein sequence.

(SEQ ID NO:30)

MSSLQAMKTLSLVLLVALLSMERAQGLRCYRCLAVLEGASCSVVSCPFLDGVCVSQKVSVFGSKVRGENKLS

LLSCQKDVGFPLLKLTSAVVDSQISCCKGDLCNAVVLAAGSPRALCVQLLLSLGSVFLWALL

The NOV8c amino acid sequence has 61 of 134 amino acid residues (45%) identical to, and 79 of 134 amino acid residues (58%) similar to, the 134 amino acid residue ptnr:SPTREMBL-ACC:Q63318 protein from *Rattus norvegicus* (Rat) (RAT LY6-C ANTIGEN) (E=4.4e$^{-22}$).

NOV8d

A disclosed NOV8d nucleic acid of 611 nucleotides (also referred to as CG56417-04) encoding a novel Lymphocyte antigen LY-6F-like protein is shown in Table 8G. An open reading frame was identified beginning with an ATG initiation codon at nucleotides 47–49 and ending with a TGA codon at nucleotides 602–604. Putative untranslated regions, if any, upstream from the initiation codon and downstream from the termination codon are underlined in Table 8G, and the start and stop codons are in bold letters.

TABLE 8G

NOV8d nucleotide sequence.

(SEQ ID NO:31)

<u>CTTGTAAGGGCGAGACAGCAGAGACTGGCACCAGGGAGGCTCCTCC</u>ATGGGAGTCTTCCATGATTACTCACA

GCGGGTGGGCAGAGGTGTTGCTAGGAAGCATGTTCTGGGGGGGTCCTCTGGGTGCACACGTGCAGTAGCTGC

ACCTGCTTGCTCATACGTCGCATGTGTCATTAGCATCTTAAATCTCCACCAGGGGTGTGTTTTCTTGCCCTC

TCTCCCAGCTCAGGGTCTGCGCTGCTACAGATGCTTGGCGGTCTTGGAAGGGGCCTCCTGCAGCGGGGTCTC

GTGCCCCTTCCTGGATGGGGTCTGTGTCTCCCAGAAAGTGAGCGTCTTTGGCAGTGAGTCCCTGGGGTGCCA

GGGCAGAGGGCAGGTTAAGTGCCGTTGTGGACTCCCAGATCTCTTGCTGCAAGGGAGACCTCTGCAATGCGG

TGGTCCTGGCAGCCGGCAGCCCCTGGGCCCTGTGCGTACAGCTCCTGCTCAGCCTGGGGTCAGTCTTCCTCT

GGGCCCTGCTGTGAGGGCCTTTCCCGCCCTCTCCCCGCAGGCCTACCCTCTGTCCCTGTGCGTCACCAGCT

GCTTGGTTTTGAAGAGCTGCCTCACTGA<u>ATTGCAG</u>

The disclosed NOV8d nucleic acid sequence, localized to chromsome 8, has 198 of 256 bases (77%) identical to a gb:GENBANK-ID:AP000509|acc:AP000509.1 mRNA from Homo sapiens (Homo sapiens genomic DNA, chromosome 6p21.3, HLA Class I region, section 8/20) (E=5.4e−23).

A NOV8d polypeptide (SEQ ID NO:32) encoded by SEQ ID NO:31 has 185 amino acid residues and is presented using the one-letter code in Table 8H. Signal P, Psort and/or Hydropathy results predict that NOV8d does not contain a signal peptide and is likely to be localized to the plasma membrane with a certainty of 0.7900.

TABLE 8H

Encoded NOV8d protein sequence.

(SEQ ID NO:32)
MGVFHDYSQRVGRGVARKHVLGGSSGCTRAVAAPACSYVACVISILNLHQGCVFLPSLPAQGLRCYRCLAVL

EGASCSVVSCPFLDGVCVSQKVSVFGSESLGCQGRGQVKCRCGLPDLLLQGRPLQCGGPGSRQPLGPVRTAP

AQPGVSLPLGPAVRAFPALSPAGLPSVPVRHQLLGFEELPH

The NOV8d amino acid sequence has 24 of 57 amino acid residues (42%) identical to, and 35 of 57 amino acid residues (61%) similar to, the 134 amino acid residue ptnr:SWISSNEW-ACC:P35460 protein from *Mus musculus* (Mouse) (Lymphocyte Antigen LY-6F. 1 Precursor) (E=2.4e$^{-07}$).

The disclosed NOV8d is expressed in at least the following tissues: Brain, Pituitary Gland, Placenta, Lung, Trachea, Kidney, Colon and Whole Organism. This information was derived by determining the tissue sources of the sequences that were included in the invention including but not limited to SeqCalling sources, Public EST sources, Literature sources, and/or RACE sources.

NOV8e

A disclosed NOV8e nucleic acid assembly (also referred to as 172885384) of NOV8d (CG56417-04) encoding a novel Lymphocyte antigen LY-6F-like protein is shown in Table 8I. The cDNA coding for the mature form of the full length NOV8d from residue 49 to 183 was targeted for "in-frame" cloning by PCR. The insert 172885384 was found to encode an open reading frame between residues 49 and 183 of the target sequence of NOV8d.

TABLE 8I

NOV8e nucleotide sequence.

(SEQ ID NO:33)
GGATCCCACCAGGGGTGTGTTTTCTTGCCCTCTCTCCCAGCTCAGGGTCTGCGCTGCTACAGATGCTTGGCG

GTCTTGGAAGGGGCCTCCTGCAGCGTGGTCTCGTGCCCCTTCCTGGATGGGGTCTGTGTCTCCCAGAAAGTG

AGCGTCTTTGGCAGTGAGTCCCTGGGGTGCCAGGGCAGAGGGCAGGTTAAGTGCCGTTGTGGACTCCCAGAT

CTCTTGCTGCAAGGGAGACCTCTGCAATGCGGTCGTCCTGGCACCCGGCAGCCCTGGGCCCTGTGCGTACA

GCTCCTGCTCAGCCTGGGGTCAGTCTTCCTCTGGGCCCTGCTGTGAGGGCCTTTCCCGCCCTCTCCCCCGCA

GGCCTACCCTCTGTCCCTGTGCGTCACCAGCTGCTTGGTTTTGAAGAGCTGCCTCACCTCGAG

A NOV8e polypeptide (SEQ ID NO:34) encoded by SEQ ID NO:33 has 136 amino acid residues and is presented using the one-letter code in Table 8J.

TABLE 8J

Encoded NOV8e protein sequence.

(SEQ ID NO:34)
GSHQGCVFLPSLPAQGLRCYRCLAVLEGASCSVVSCPFLDGVCVSQKVSVFGSESLGCQGRGQVKCRCGLPD

LLLQGRPLQCGGPGSRQPLGPVRTAPAQPGVSLPLGPAVRAFPALSPAGLPSVPVRHQLLGFEELPHLE

Possible SNPs found for NOV8a are listed in Table 8K and possible SNPs for NOV8d are listed in Table 8L.

TABLE 8K

SNPs

| Variant | Nucleotide Position | Base Change | Amino Acid Position | Base Change |
|---|---|---|---|---|
| 13377070 | 53 | A > G | 8 | Lys > Arg |
| 13377074 | 161 | T > C | 44 | Val > Ala |
| 13377075 | 166 | T > C | 46 | Cys > Arg |
| 13377076 | 194 | C > A | 55 | Ser > Tyr |
| 13377077 | 196 | C > T | 56 | Gln > End |
| 13377078 | 300 | A > G | Silent | N/A |
| 13377068 | 362 | T > C | 111 | Leu > Pro |
| 13377079 | 370 | A > G | 114 | Ser > Gly |
| 13377067 | 371 | G > A | 114 | Ser > Asn |
| 13377080 | 431 | C > T | 134 | Ala > Val |
| 13377081 | 468 | A > G | Silent | N/A |

TABLE 8L

SNPs

| Consensus Position | Depth | Base Change | PAF |
|---|---|---|---|
| 61 | 31 | G > — | 0.065 |
| 79 | 32 | A > G | 0.062 |
| 89 | 33 | A > G | 0.061 |
| 105 | 48 | G > A | 0.042 |
| 166 | 51 | C > T | 0.157 |
| 174 | 51 | A > G | 0.039 |
| 192 | 51 | A > C | 0.039 |
| 207 | 51 | C > T | 0.039 |
| 236 | 51 | T > C | 0.059 |
| 237 | 51 | A > G | 0.039 |
| 265 | 52 | T > A | 0.038 |
| 294 | 49 | G > T | 0.327 |
| 322 | 49 | A > G | 0.041 |
| 327 | 49 | A > G | 0.061 |
| 360 | 48 | A > C | 0.042 |
| 373 | 48 | A > G | 0.042 |
| 419 | 47 | G > A | 0.043 |
| 448 | 47 | G > A | 0.064 |

NOV8a–NOV8e are very closely homologous as is shown in the amino acid alignment in Table 8M.

TABLE 8M

Amino Acid Alignment of NOV8a–NOV8e

```
                    10        20        30        40        50        60        70
               ....|....|....|....|....|....|....|....|....|....|....|....|....|....|
NOV8a          ---------------------MSSLQAMKTLSLVLLVALLSMER---------AQGLRCYRCLA
NOV8b          MGVFHDYSQRVGRGVARKHVLGGSSGCTRAVAAPACSYVACVISLLNLHQGCVFLPSLPAQGLRCYRCLA
NOV8c          ---------------------MSSLQAMKTLSLVLLVALLSMER---------AQGLRCYRCLA
NOV8d          MGVFHDYSQRVGRGVARKHVLGGSSGCTRAVAAPACSYVACVISLLNLHQGCVFLPSLPAQGLRCYRCLA
NOV8e          -----------------------GS---------------------HQGCVFLPSLPAQGLRCYRCLA 80        90       100       110       120       130       140
               ....|....|....|....|....|....|....|....|....|....|....|....|....|....|
NOV8a          VLEGASCSVVSCPFLDGVCVSQKVSLSLSKKRRKEKNKLSLLSCQKDVGFPLLKLTSAVVDSQISCCKGD
NOV8b          VLEGASCSVVSCPFLDGVCVSQKVSVLAVSPWG----------ARAEG---R--LSAVVDSQISCCKGD
NOV8c          VLEGASCSVVSCPFLDGVCVSQKVSVFGSKVRGE--NKLSLLSCQKDVGFPLLKLTSAVVDSQISCCKGD
NOV8d          VLEGASCSVVSCPFLDGVCVSQKVSVFGSESLG----CQGRGQVMCRCGLPDLLLQGRPLQCGGPGSRQP
NOV8e          VLEGASCSVVSCPFLDGVCVSQKVSVFGSESLG----CQGRGQVMCRCGLPDLLLQGRPLQCGGPGSRQP 150       160       170       180       190
               ....|....|....|....|....|....|....|....|....|....|.
NOV8a          LCNAVVLAASS----PWALCVQLLLSLG-----SVFLWALL----------
NOV8b          LCNAVVLAAGS----PWALCVQLLLSLG-----SVFLWALL----------
NOV8c          LCNAVVLAAGS----PRALCVQLLLSLG-----SVFLWALL----------
NOV8d          LGPVRTAPAQPGVSLPLGPAVRAFPALSPAGLPSVPVRHQLLGFEELPH--
NOV8e          LGPVRTAPAQPGVSLPLGPAVRAFPALSPAGLPSVPVRHQLLGFEELPHLE
```

Homologies to any of the above NOV8 proteins will be shared by the other NOV8 proteins insofar as they are homologous to each other as shown above. Any reference to NOV8 is assumed to refer to the NOV8 proteins in general, unless otherwise noted.

NOV8a has homology to the amino acid sequences shown in the BLASTP data listed in Table 8N.

TABLE 8N

BLAST results for NOV8a

| Gene Index/ Identifier | Protein/ Organism | Length (aa) | Identity (%) | Positives (%) | Expect |
|---|---|---|---|---|---|
| gi\|17505223\|ref\|NP_510968.1\| (NM_078483) | lysosomal amino acid transporter 1 [Homo sapiens] | 434 | 405/483 (83%) | 409/483 (83%) | 0.0 |
| gi\|18426842\|ref\|NP_569099.1\| (NM_130415) | lysosomal amino acid transporter 1 [Rattus norvegicus] | 475 | 371/484 (76%) | 406/484 (83%) | 0.0 |
| gi\|17473038\|ref\|XP_058449.1\| (XM_058449) | similar to lysosomal amino acid transporter 1 [Homo sapiens] | 504 | 231/514 (44%) | 307/514 (58%) | e-101 |
| gi\|17449820\|ref\|XP_059717.1\| (XM_059717) | similar to lysosomal amino acid transporter 1 (H. sapiens) [Homo sapiens] | 165 | 147/162 (90%) | 147/162 (90%) | 6e-76 |
| gi\|18467570\|ref\|XP_079250.1\| (XM_079250) | CG13384 gene product [Drosophila melanogaster] | 504 | 169/433 (39%) | 234/433 (54%) | 9e-69 |

The homology of these sequences is shown graphically in the ClustalW analysis shown in Table 8O.

TABLE 8O

ClustalW Analysis of NOV8a

1) NOV8a (SEQ ID NO:26)
2) gi|17505223|refNP_510968.1| (NM_078483) lysosomal amino acid transporter 1 [Homo sapiens] (SEQ ID NO:137)
2) gi|18426842|refNP_569099.1| (NM_130415) lysosomal amino acid transporter 1 [Rattus norvegicus] (SEQ ID NO:138)
3) gi|17473038|refXP_058449.1| (XM_058449) similar to lysosomal amino acid transporter 1 [Homo sapiens] (SEQ ID NO:139)
4) gi|17449820|refXP_059717.1| (XM_059717) similar to lysosomal amino acid transporter 1 (H. sapiens) [Homo sapiens] (SEQ ID NO:140)
5) gi|18467570|refXP_079250.1| (XM_079250) CG13384 gene product [Drosophila melanogaster] (SEQ ID NO:141)

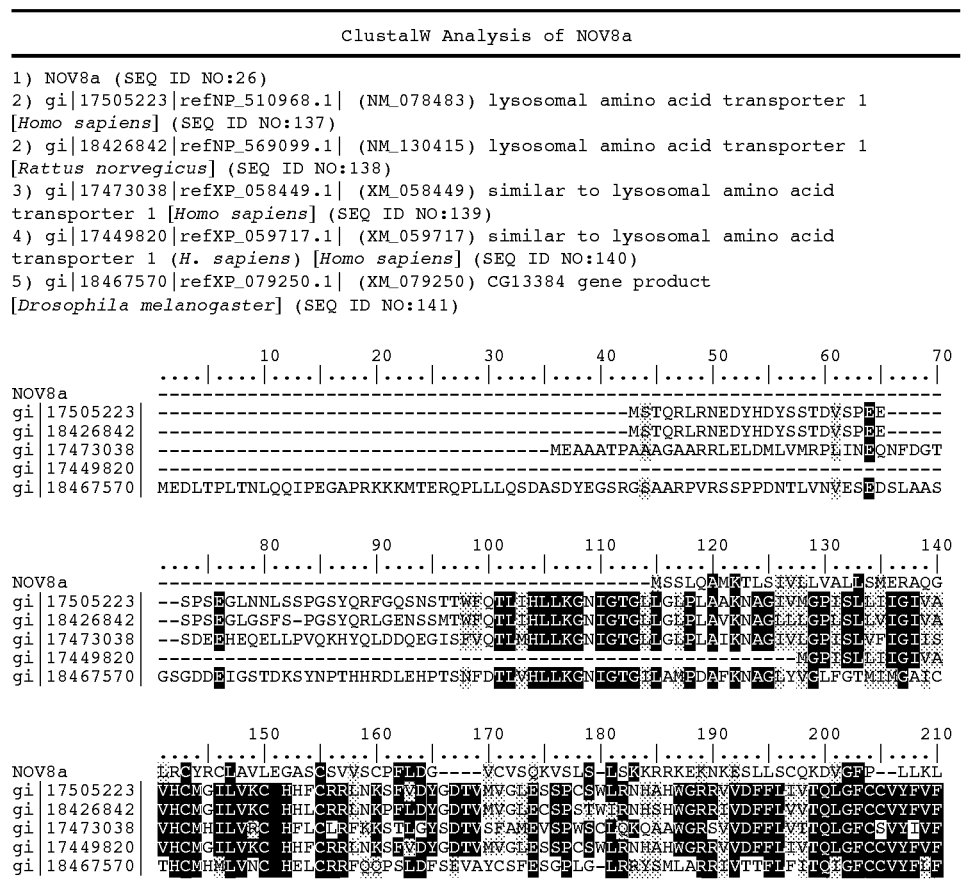

TABLE 80-continued

ClustalW Analysis of NOV8a

```
                220       230       240       250       260       270       280
              ....|....|....|....|....|....|....|....|....|....|....|....|....|
NOV8a         TSAVVDSQIS-------CCKG-----------DLCNAVVLAASSFWALCVQLLLSLGSVFLWALL-----
gi|17505223|  LAONFKQVIE---AANGTTNNCHNNETVILTPTMDSRLYMLSFLPFLVLLVFIRNLRALSIFSLLANITM
gi|18426842|  LAONFKQVIE---AANGTTNNCHNNETVILTPTMDSRLYMLTFLPFLVLLSFIRNLRILSIFSLLANISM
gi|17473038|  LAENFKQVHEGFLESKVFISNSTNSSNPCERRSVDLRIYMLCFLPFILLLVFIRELKNLFVLSFLANVSM
gi|17449820|  LAONFKQVIE---AANGTTNNCHNNETVILTPTMDSRLYMLSFLPFLVLLVFIRNLRALSIFSLLANITM
gi|18467570|  VALNIKDVMF-------HYY-----------KMPVQIYLIMLGPMILLNLVRNLKYLIPVSLVAALLT 290       300       310       320       330       340       350
              ....|....|....|....|....|....|....|....|....|....|....|....|....|
NOV8a         ------------------------------------------------------------------
gi|17505223|  LVSIVMIYQFIVQRIPDPSHLPLVAPWKTYPLFFGTAIISFEGIGMVLPLENKMKDPRKFP---LILYLG
gi|18426842|  FVSIIMIYQFIVQRIPDPSHLPLVAPWKTYPLFFGTAIFAFEGIGVVLPLENKMKDPRKFP---LILYLG
gi|17473038|  AVSIVIIYQYVVKNYPDPHNLPIVAGWKKYPLFFGTAVFAFEGIGVVLPLENQMKESKRFP---QALNIG
gi|17449820|  LVSIVMIYQFIVQIL-----------------------------------------------------
gi|18467570|  VAGLAITFSYMLVDLPDVHTVKPVATWATLPLFFGTALYAFEGIGVVLPLENNMRTPEDFGGTTGVLNTG 360       370       380       390       400       410       420
              ....|....|....|....|....|....|....|....|....|....|....|....|....|
NOV8a         ------------------------------------------------------------------
gi|17505223|  MVIVTILYISLGCLGYLQFGANIQGSITIINLPN-CWLYQSVKLLYSIGIFFTYALQFYVPAEIIS-----
gi|18426842|  MAITVLYISLGSLGYLQFGADIKGSITIINLPN-CWLYQSVKLLYSIGIFFTYALQFYVAAEIIIPAIVS
gi|17473038|  MGIVTTLYVTLATLGYMCFHDELKGSITIINLPQDVWLYQSVKLLYSFGIFVTYSIQFYVPAEIIIPGITS
gi|17449820|  ------------------------------------------------------------------
gi|18467570|  MMIVACLYTAVGFFGYLKYGEHVEGSITIINLPQGDTLSQLVRISMAVAIFLSYTIQFYVPVNIVEPFVRS 430       440       450       460       470       480       490
              ....|....|....|....|....|....|....|....|....|....|....|....|....|
NOV8a         --------------------------------LVGSVSSSALALIIPELLEVTIFYSEGMS--P
gi|17505223|  --------------------------------LVGSVSSSALALIIPELLEVTIFYSEGMS--P
gi|18426842|  RVPE-RFELVVDLSARTAMVCVTCVLAVLIPRLDLVISLVGSVSSSALALIIPELLEVTIYYGEGIS--P
gi|17473038|  KFHT-KWKQICEFGIRSFLVSITCAGAILIPRLDIVISFVCAVSSSTLALILPELVEILIFSKEHYN--I
gi|17449820|  ------------------------------------------------------------------
gi|18467570|  HFDTTRAKDLSATVLRVVLVTFTFLLATCIPNLGSIISLVCAVSSSALALIAPEIIEVIIKYNVGYGRFN 500       510       520       530       540
              ....|....|....|....|....|....|....|....|....|....|..
NOV8a         ------------------------------------------------
gi|17505223|  LTIFKDALISILGFVGFVVGTYEALYEIIRPSNAPIFINSTCAFI------------
gi|18426842|  LTITKDALISILGFVGFVVGTYESLWELIQPSHSDSSTNSTSAFI------------
gi|17473038|  WMVLKNISLAFTGVGFILGTYITVEELIYPTPKVVAGTPQSPFLNLNSTCLTSGLK
gi|17449820|  ------------------------------------------------
gi|18467570|  WMLWKDVLILIFGLCGFVFGTWASLADIENDRTH----------------------
```

Table 8P lists the domain description from DOMAIN analysis results against NOV8a. This indicates that the NOV8a sequence has properties similar to those of other proteins known to contain these domains.

TABLE 8P

Domain Analysis of NOV8a gnl|Pfam|pfam01490, Aa_trans, Transmembrane Lymphocyte antigen
precursor protein. This transmembrane region is found in many
Lymphocyte antigen precursors including UNC-47 and MTR. UNC-47 encodes
a vesicular amino butyric acid (GABA) transporter, (VGAT). UNC-47 is
predicted to have 10 transmembrane domains. MTR is a N system
Lymphocyte antigen precursor system protein involved in
methyltryptophan resistance. Other members of this family include
proline transporters and amino acid permeases. (SEQ ID NO:142)
CD-Length = 370 residues, 85.1% aligned
Score = 119 bits (299), Expect = 3e-28

```
Query:    91  AVKNAGIVMGPISLLIIGIVAVHCMGILVKCAHHFCRRLNKSFVDYGDTVMYGLESSPCS  150
              |  |  + | + || + | + ++   +| +|    +  + | |++| | +   |    |
Sbjct:     1  AFKQLGWIPGLVLLLLAGFITLYTGLLLSECYEVVPGKRNDSYLDLGRSAYGGKGLLLTS   60

Query:   151  WLRNHAHWGRRVVDFFLIVTQLGFCCVYFVFLADNFKQVIEAANGTTNNCHNNETVILTP  210
              ++           |   |   | +   |   ++|     ++|       ++ +|
Sbjct:    61  FVG-----------QYVNLFGVNIGYLILAGDLLPKII------SSFCGDNCD-----   96

Query:   211  TMDSRLYMLSFLPFLVLLVFIRNLRALSI--FSLLANITMLVSLVMIYQFIVFRYMLSVF  268
              +|  +++ |   ++ | |||    |  +++     +  +  + +
Sbjct:    97  HLDGNSWIIIFAAIIITLSFIPNFNLLSISSLSAFSSLAYLSIISFLIIVAVIAGIFVLL  156
```

TABLE 8P-continued

Domain Analysis of NOV8a

```
Query:  269 QRIPDPSHLPLVAPWKTYPLFFGTAIFSFEGIGMVLPLENKMKDPR--KFPLILYLGMVI  326
              +         |   | +|+|||   ++||++| || |   || +|  + ++|
Sbjct:  157 GAVYGILWSPSFTKLTGLFLAIGIIVFAFEGHAVLLPIQNTMKSPSAKKFKKVLNVAIII  216

Query:  327 VTILYISLGCLGYLQFGANIQGSITLNLP---LYQSVKLLYSIGIFFTYALQFYVPAEII  383
            ||+||| +|    ||| || |++|+| ||||    + | |  + |  |+ || +    ||
Sbjct:  217 VTVLYILVGFFGYLTFGNNVKGNILLNLPNNPFWLIVNLNLVVAILLTFPLQAFPIVRII  276

Query:  384 IPFFV---SRAPEHCELVVDLFVRTVLVCLTILAILIPR                      419
              + ||   +|+ +    ++|    ++|||+|
Sbjct:  277 ENLLTKKNNFAPNKSKLLRVVIRSGLVVFTLLIAILVPF                      315
```

Murine Ly-6 molecules are a family of cell surface glycoproteins which have interesting patterns of tissue expression during haematopoiesis from multipotential stem cells to lineage committed precursor cells, and on specific leucocyte subpopulations in the peripheral lymphoid tissues. These interesting patterns of tissue expression suggest an intimate association between the regulation of Ly-6 expression and the development and homeostasis of the immune system. Ly-6 molecules are low molecular weight phosphatidyl inositol anchored glycoproteins with remarkable amino acid homology throughout a distinctive cysteine rich protein domain that is associated predominantly with O-linked carbohydrate. The in vivo functions of Ly-6 molecules are not known although in vitro studies suggest a role in cellular activation (Gumley et al., Immunol Cell Biol.;73 (4):277–96, 1995).

The Ly-6 alloantigens have been shown to play a critical role in T lymphocyte activation. LeClair et al. (LeClair et al., EMBO J. 5(12):3227–34, 1986) isolated a Ly-6 cDNA, synthetic oligonucleotides, based on the partial amino acid sequence of purified Ly-6E.1 protein, were used to probe a cDNA library. The synthetic oligonucleotides or the isolated cDNA detected a 1.1-kb RNA species. Sequence analysis of the cDNA clone revealed that the Ly-6E.1 protein consists of a 26-amino acid leader followed by a 108-residue, cysteine-rich, core protein with no N-linked glycosylation sites. Southern blot analysis of genomic DNAs revealed multiple bands indicating a family of related genes. Using recombinant inbred and Ly-6 congenic strains of mice, restriction fragment length polymorphisms were demonstrable, and correlated with the Ly-6 allotype of the DNA donors. This probe will enable further molecular genetic analysis of the role of Ly-6-linked proteins in the process of T lymphocyte activation. Isolation of Ly-6 genomic clones may promote a further understanding of the complex tissue-specific expression patterns characteristic of Ly-6-linked genes (LeClair et al., 1986).

NOV8 will have similar properties as other lymphocyte antigen precursor and Ly-6 proteins and may be involved in the regulation of T lymphocyte activation.

The NOV8 nucleic acid of the invention encoding a Lymphocyte antigen precursor-like protein includes the nucleic acid whose sequence is provided in Tables 8A, 8C, 8E, 8G and 8I or a fragment thereof. The invention also includes a mutant or variant nucleic acid any of whose bases may be changed from the corresponding base shown in Tables 8A, 8C, 8E, 8G and 8I while still encoding a protein that maintains its Lymphocyte antigen precursor-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 23% of the NOV8b residues, about 36% of the NOV8c residues and about 23% of the NOV8d residues may be so changed.

The NOV8 protein of the invention includes the Lymphocyte antigen precursor-like protein whose sequence is provided in Tables 8B, 8D, 8F, 8H and 8J. The invention also includes a mutant or variant protein any of whose residues may be changed from the corresponding residue shown in Tables 8B, 8D, 8F, 8H and 8J while still encoding a protein that maintains its Lymphocyte antigen precursor-like activities and physiological functions, or a functional fragment thereof. In the mutant or variant protein, up to about 58% of the NOV8b bases, about 55% of the NOV8c bases and about 58% of the NOV8d bases may be so changed.

The NOV8 nucleic acids and proteins of the invention are useful in potential diagnostic and therapeutic applications implicated in various diseases and disorders described below and/or other pathologies. For example, the compositions of the present invention will have efficacy for treatment of patients suffering from: adrenoleukodystrophy, congenital adrenal hyperplasia, Von Hippel-Lindau (VHL) syndrome, Alzheimer's disease, stroke, tuberous sclerosis, hypercalceimia, Parkinson's disease, Huntington's disease, cerebral palsy, epilepsy, Lesch-Nyhan syndrome, multiple sclerosis, ataxia-telangiectasia, leukodystrophies, behavioral disorders, addiction, anxiety, pain, neurodegeneration, diabetes, autoimmune disease, renal artery stenosis, interstitial nephritis, glomerulonephritis, polycystic kidney disease, systemic lupus erythematosus, renal tubular acidosis, IgA nephropathy, hypercalceimia, Lesch-Nyhan syndrome, growth and reproductive disorders, systemic lupus erythematosus, autoimmune disease, asthma, emphysema, scleroderma, allergy, ARDS and other diseases, disorders and conditions of the like.

NOV8 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV8 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV9

NOV9 includes two novel Early B-Cell Factor-like proteins disclosed below. The disclosed proteins have been named NOV9a and NOV9b.

NOV9a

A disclosed NOV9a nucleic acid of 1873 nucleotides (also referred to as CG57480-01) encoding a novel Early B-Cell Factor-like protein is shown in Table 9A. An open reading frame was identified beginning with an ATG initiation codon at nucleotides 25–27 and ending with a TGA codon at nucleotides 1813–1815. Putative untranslated regions, if any, upstream from the initiation codon and downstream from the termination codon are underlined in Table 9A, and the start and stop codons are in bold letters.

TABLE 9A

NOV9a nucleotide sequence.

(SEQ ID NO:35)
CTGCGGCCGCCGCCAGCAGTTTTCATGTTTGGGATTCAGGAGAATATTCCGCGCGGGGGACGACCATGAAG

GAGGAGCCGCTGGGCAGCCGCATGAACCCGGTGCGCTCGTGGATGCACACGGCGGGCGTGGTGGACGCCAAC

ACGGCCGCCCAGAGCGGCGTGGGGCTGGCGCGGGCGCACTTCGAGAAGCAGCCGCCTTCCAACCTCCGGAAA

TCCAATTTCTTCCACTTCGTGCTGGCGCTCTACGATAGGCAGGGGCAGCCGGTGGAGATTGAAAGGACCGCT

TTTGTGGACTTTGTGGAGAAAGAGAAAGAGCCAAACAACGAGAAAACCAACAACGGCATCCACTATAAACTC

CAGTTATTGTACAGCAACGGTGTCAGAACAGAGCAAGATCTGTATGTTCGCCTCATAGATTCAATGACCAAA

CAGGCCATCGTCTACGAGGGCCAGGACAAGAACCCGGAGATGTGCCGTGTGCTGCTGACCCACGAGATCATG

TGCAGCCGGTGCTGTGACAAGAAAAGTTGTGGCAATAGAAACGAAACGCCCTCAGACCCTGTAATCATTGAC

AGGTTCTTTCTAAAGTTTTTCCTCAAGTGCAATCAGAACTGTTTGAAGAATGCAGGCAACCCTCGAGATATG

CGGAGATTCCAGGTAGTTGTATCGACAACAGTCAACGTGGACGGCCACGTGCTGGCCGTGTCAGACAACATG

TTTGTGCACAACAATTCCAAACACGGGAGGCGGGCCCGCCGCCTAGACCCGTCAGAAGGTACGGCCCCTTCT

TATCTGGAAAATGCCACTCCGTGCATCAAGGCCATCAGTCCCAGTGAAGGCTGGACCACGGGGGGTGCCACC

GTCATCATAATTGGCGACAACTTCTTTGACGGGCTGCAAGTTGTATTCGGAACTATGTTGGTGTGGAGCGAG

CTGATAACTCCCCATGCCATCCGAGTCCAGACCCCGCCGAGGCACATTCCTGGCGTCGTCCAAGTGACCCTC

TCCTACAAATCCAAGCAGTTCTGCAAAGGTGCTCCTGGGCGCTTTGTCTACACCGCCCTTAATGAACCAACC

ATAGATTACGGCTTTCAGAGGTTGCAGAAAGTGATCCCAAGACATCCGGGTGATCCCGAAAGGTTACCCAAG

GAGGTGTTACTGAAGCGGGCGGCGGACCTGGTGGAAGCCTTATACGGAATGCCTCACAACAACCAGGAGATC

ATCTTGAAGCGAGCGGCGGACATCGCCCAGGCGCTGTACAGCGTTCCCCGCAATCACAACCAGATCCCCACC

CTGGGCAACAACCCTGCACACACGGGCATGATGGGCGTCAACTCCTTCAGCAGCCAGCTAGCCGTCAACGTG

TCAGAGACGTCACAAGCCAACGACCAAGTCGGCTACAGTCGCAATACAAGCAGCGTGTCCCCGCGAGGCTAC

GTCCCCAGCAGTACTCCCCAGCAGTCCAATTACAACACAGTCAGCACTAGCATGAATGGATATGGAAGTGGC

GCCATGGCCAGTCTAGGGGTCCCTGGCTCGCCTGGATTTCTTAATGGCTCCTCCGCTAACTCTCCCTACGGC

GTAGTGCCGTCCAGCCCCACCATGGCAGCCTCTTCGGTCACCCTCCCTTCAAACTGTAGCAGCACACACGGC

ATTTTCTCATTCTCACCTGCCAATGTCATCTCCGCAGTGAAACAGAAGAGCCCCTTCGCGCCCGTGGTCCGG

CCCCAAGCCTCTCCTCCTCCTTCCTGCACCAGCGCCAACGGGAATGGACTGCAAGCTATGTCTGGGCTGGTA

GTCCCGCCAATGTGAGGGACTTCTGTTTACCTTCCGCAGCACCCAGCATCAAAGGACGGACTTCAGGGGACA

C

The disclosed NOV9a nucleic acid sequence, localized to chromsome 10, has 1769 of 1871 bases (94%) identical to a gb:GENBANK-ID:MMU92702|acc:U92702.1 mRNA from *Mus musculus* (*Mus musculus* Olf-1/EBF-like-2(9L) transcription factor (O/E-2(9L)) mRNA, complete cds) (E=0.0).

A NOV9a polypeptide (SEQ ID NO:36) encoded by SEQ ID NO:35 has 596 amino acid residues and is presented using the one-letter code in Table 9B. Signal P, Psort and/or Hydropathy results predict that NOV9a does not contain a signal peptide and is likely to be localized to the cytoplasm with a certainty of 0.6500.

ID:MMU92702|acc:U92702.1) a closely related *Mus musculus* Olf-1/EBF-like-2(9L) transcription factor (O/E-2(9L)) mRNA, complete cds homolog in species Mus musculus: adult olfactory epithelium; in embryo, expressed in epithalamus, hypothalamus, throughout the brainstem and near the ventricular zones of mesencephalon, in rostral rhombencephalon, in vomeronasal organ, at high level in developing retina, developing spinal cord, at low level in dorsal root ganglia, trigeminal ganglia, glossopharyngeal nerve ganglia.

TABLE 9B

Encoded NOV9a protein sequence.

(SEQ ID NO:36)
MFGIQENIPRGGTTMKEEPLGSGMNPVRSWMHTAGVVDANTAAQSGVGLARAHFEKQPPSNLRKSNFFHFVL

ALYDRQGQPVEIERTAFVDFVEKEKEPNNEKTNNGIHYKLQLLYSNGVRTEQDLYVRLIDSMTKQAIVYEGQ

DKNPEMCRVLLTHEIMCSRCCDKKSCGNRNETPSDPVIIDRFFLKFFLKCNQNCLKNAGNPRDMRRFQVVVS

TTVNVDGHVLAVSDNMFVHNNSKHGRRARRLDPSEGTAPSYLENATPCIKAISPSEGWTTGGATVIIIGDNF

FDGLQVVFGTMLVWSELITPHAIRVQTPPRHIPGVVEVTLSYKSKQFCKGAPGRFVYTALNEPTIDYGFQRL

QKVIPRHPGDPERLPKEVLLKRAADLVEALYGMPHNNQEIILKRAADIAEALYSVPRNHNQIPTLGNNPAHT

GMMGVNSFSSQLAVNVSETSQANDQVGYSRNTSSVSPRGYVPSSTPQQSNYNTVSTSMNGYGSGAMASLGVP

GSPGFLNGSSANSPYGVVPSSPTMAASSVTLPSNCSSTHGIFSFSPANVISAVKQKSAFAPVVRPQASPPPS

CTSANGNGLQAMSGLVVPPM

The NOV9a amino acid sequence has 593 of 596 amino acid residues (99%) identical to, and 595 of 596 amino acid residues (99%) similar to, the 596 amino acid residue ptnr:SWISSPROT-ACC:O08791 protein from *Mus musculus* (Mouse) (Early B-Cell Factor-3 (Early B-Cell Factor 3) (EBF-3) (OLF-1/EBF- Like 2) (OE-2) (O/E-2)) (E=0.0).

The disclosed NOV9a is expressed in at least the following tissue: because of the expression pattern of (GENBANK-ID: gb:GENBANK- NOV9b A disclosed NOV9b nucleic acid of 1667 nucleotides (also referred to as CG57480-02) encoding a novel Early B-Cell Factor-like protein is shown in Table 9C. An open reading frame was identified beginning with an ATG initiation codon at nucleotides 5–7 and ending with a TAA codon at nucleotides 1625–1627. Putative untranslated regions, if any, upstream from the initiation codon and downstream from the termination codon are underlined in Table 9C, and the start and stop codons are in bold letters.

TABLE 9C

NOV9b nucleotide sequence.

(SEQ ID NO:37)
TTTCATGTTTCCGATTCAGGAGAATATTCCGCGCGGGGGACGACCATGAAGGAGGAGCCGCTGGGCAGCGG

CATGAACCCGGTGCGCTCGTGGATGCACACGGCGGGCGTGGTGGATGCCAACACGGCCGCCCAGAGCGGCGT

GGGGCTGGCGCGGGCGCACTTCGAGAAGCAGCCGCCTTCCAACCTCCGGAAATCCAATTTCTTCCACTTCGT

GCTGGCGCTCTACGATAGGCAGGGGCAGCCGGTGGAGATTGAAAGGACCGCTTTTGTGGACTTTGTGGAGAA

AGAGAAAGAGCCAAACAACGAGAAAACCAACAACGGCATCCACTATAAACTCCAGTTATTGTACAGCAACGG

AGTCAGAACAGAGCAAGATCTGTATGTTCGCCTCATAGATTCAATGACCAAACAGGCCATCGTCTACGAGGG

CCAGGACAAGAACCCGGAGATGTGCCGTGTGCTGCTGACCCACGAGATCATGTGCAGCCGGTGCTGTGACAA

GAAAAGTTGTGGCAATAGAAACGAAACGCCCTCAGACCCTGTAATCATTGACAGATTCTTTCTAAAGTTTTT

CCTCAAGTGCAATCAGAACTGTTTGAAGAATGCAGGCAACCCTCGAGATATGCGGAGATTCCAGGTTGTTGT

TABLE 9C-continued

NOV9b nucleotide sequence.

ATCGACAACAGTCAACGTGGACGGCCACGTGCTGGCCGTGTCAGACAACATGTTTGTGCACAACAATTCCAA
ACACGGGAGGCGGGCCCGCCGCCTAGACCCGTCAGAAGCCACTCCGTGCATCAAGGCCATCAGTCCCAGTGA
AGGCTGGACCACGGGGGGTGCCACCGTCATCATAATTGGCGACAACTTCTTTGACGGGCTGCAAGTTGTATT
CGGAACTATGTTGGTGTGGAGCGAGCTGATAACTCCCCATGCCATCCGAGTCCAGACCCCGCCGAGGCACAT
TCCTGGCGTCGTCGAAGTGACCCTCTCCTACAAATCCAAGCAGTTCTGCAAAGGTGCTCCTGGGCGCTTTGT
CTACACCGCCCTTAATGAACCAACCATAGATTACGGCTTTCAGAGGTTGCAGAAAGTGATCCCAAGACATCC
GGGTGATCCCGAAAGGTTACCCAAGGAGGTGTTACTGAAGCGGGCGGCGGACCTGGTGGAAGCCTTATACGG
AATGCCTCACAACAACCAGGAGATCATCTTGAAGCGAGCGGCGGACATCGCCGAGGCGCTGTACAGCGTTCC
CCGCAATCACAACCAGATCCCCACCCTGGGCAACAACCCTGCACACACGGGCATGATGGGCGTCAACTCCTT
CAGCAGCCAGCTAGCCGTCAACGTGTCAGAGACGTCACAAGCCAACGACCAAGTCCGCTACAGTCGCAATAC
AAGCAGCGTGTCCCCGCGAGGCTACGTCCCCAGCAGTACTCCCCAGCAGTCCAATTACAACACAGTCAGCAC
TAGCATGAATGGATATGGAAGTGGCGCCATGGCCAGTCTAGGGGTCCCTGGCTCGCCTGGATTTCTTAATGG
CTCCTCCGCTAACTCTCCCTACGGCATGAAACAGAAGAGCGCCTTCGCGCCCGTGGTCCGGCCCCAAGCCTC
TCCTCCTCCTTCCTGCACCAGCGCCAACGGGAATGGACTGTAAGCTATGTCTGGGCTGGTAGTCCCGCCAAT
GTGAGGGACTT

The disclosed NOV9b nucleic acid sequence, localized to chromsome 10, has 1568 of 1665 bases (94%) identical to a gb:GENBANK-ID:MMU92704|acc:U92704.1 mRNA from *Mus musculus* (*Mus musculus* Olf-1/EBF-like-2(0S) transcription factor (O/E-2(0S)) mRNA, alternative splice variant, complete cds) (E=0.0).

A NOV9b polypeptide (SEQ ID NO:38) encoded by SEQ ID NO:37 has 540 amino acid residues and is presented using the one-letter code in Table 9D. Signal P, Psort and/or Hydropathy results predict that NOV9b does not contain a signal peptide and is likely to be localized to the plasma membrane with a certainty of 0.6500.

The NOV9b amino acid sequence has 526 of 526 amino acid residues (100%) identical to, and 526 and 526 amino acid residues (100%) similar to, the 537 amino acid residue ptnr:TREMBLNEW-ACC:CAC16113 protein from *Homo sapiens* (Human) (BA234G16.1.1 (Novel Protein Similar Early B-Cell Factor (EBF)) (E=6.5e$^{-289}$).

The disclosed NOV9b is expressed in at least the following tissues: olfactory tissue. This information was derived by determining the tissue sources of the sequences that were included in the invention including but not limited to Seq-Calling sources, Public EST sources, Literature sources, and/or Race sources.

Possible SNPs found for NOV9a are listed in Table 9E and possible SNPs for NOV9b are listed in Table 9F.

TABLE 9D

Encoded NOV9b protein sequence.

(SEQ ID NO:38)
MFGIQENIPRGGTTMKEEPLGSGMNPVRSWMHTAGVVDANTAAQSGVGLARAHFEKQPPSNLRKSNFFHFVL
ALYDRQGQPVEIERTAFVDFVEKEKEPNNEKTNNGIHYKLQLLYSNGVRTEQDLYVRLIDSMTKQAIVYEGQ
DKNPEMCRVLLTHEIMCSRCCDKKSCGNRNETPSDPVIIDRFFLKFFLKCNQNCLKNAGNPRDMRRFQVVVS
TTVNVDGHVLAVSDNMFVHNNSKHGRRARRLDPSEATPCIKAISPSEGWTTGGATVIIIGDNFFDGLQVVFG
TMLVWSELITPHAIRVQTPPRHIPGVVEVTLSYKSKQFCKGAPGRFVYTALNEPTIDYGFQRLQKVIPRHPG
DPERLPKEVLLKRAADLVEALYGMPHNNQEIILKRAADIAEALYSVPRNHNQIPTLGNNPAHTGMMGVNSFS
SQLAVNVSETSQANDQVGYSRNTSSVSPRGYVPSSTPQQSNYNTVSTSMNGYGSGAMASLGVPGSPGFLNGS
SANSPYGMKQKSAFAPVVRPQASPPPSCTSANGNGL

TABLE 9E

| Variant | SNPs Nucleotide Position | Base Change | Amino Acid Position | Base Change |
|---|---|---|---|---|
| 13377086 | 138 | C > T | Silent | N/A |
| 13377087 | 172 | G > A | 50 | Ala > Thr |
| 13377088 | 506 | G > A | 161 | Cys > Tyr |
| 13377089 | 1088 | A > C | 355 | Tyr > Ser |
| 13377084 | 1394 | A > T | 457 | Gln > Leu |
| 13377083 | 1671 | A > G | Silent | N/A |
| 13377085 | 1780 | C > T | 586 | Gln > End |

TABLE 9F

| Consensus Position | SNPs Depth | Base Change | PAF |
|---|---|---|---|
| 133 | 41 | A > G | 0.049 |
| 268 | 41 | A > G | 0.049 |
| 324 | 41 | A > G | 0.049 |
| 372 | 41 | A > G | 0.049 |
| 376 | 41 | A > — | 0.049 |
| 456 | 40 | T > C | 0.050 |
| 488 | 32 | A > G | 0.344 |

NOV9a and NOV9b are very closely homologous as is shown in the amino acid alignment in Table 9G.

TABLE 9G

Amino Acid Alignment of NOV9a and NOV9b

```
              10        20        30        40        50        60        70
              |         |         |         |         |         |         |
NOV9a  MFGIQENIPRGGTTMKEEPLGSGMNPVRSWMHTAGVVDANTAAQSGVGLARAHFEKQPPSNLRKSNFFHF
NOV9b  MFGIQENIPRGGTTMKEEPLGSGMNPVRSWMHTAGVVDANTAAQSGVGLARAHFEKQPPSNLRKSNFFHF 80        90       100       110       120       130       140
              |         |         |         |         |         |         |
NOV9a  VLALYDRQGQPVEIERTAFVDFVEKEKEPNNEKTNNGIHYKLQLLYSNGVRTEQDLYVRLIDSMTKQAIV
NOV9b  VLALYDRQGQPVEIERTAFVDFVEKEKEPNNEKTNNGIHYKLQLLYSNGVRTEQDLYVRLIDSMTKQAIV 150       160       170       180       190       200       210
              |         |         |         |         |         |         |
NOV9a  YEGQDKNPEMCRVLLTHEIMCSRCCDKKSCCGNRNETPSDPVIIDRFFLKFFLKCNQNDLKNAGNPRDMRR
NOV9b  YEGQDKNPEMCRVLLTHEIMCSRCCDKKSCCGNRNETPSDPVIIDRFFLKFFLKCNQNDLKNAGNPRDMRR 220       230       240       250       260       270       280
              |         |         |         |         |         |         |
NOV9a  FQVVVSTIVNVDGHVLAVSDNMFVHNNSKHGRRARRLDPSEGTAPSYLENATPCIKAISPSEGWTTGGAT
NOV9b  FQVVVSTIVNVDGHVLAVSDNMFVHNNSKHGRRARRLDPSE---------ATPCIKAISPSEGWTTGGAT 290       300       310       320       330       340       350
              |         |         |         |         |         |         |
NOV9a  VIIIGDNFFDGLQVVFGTMLVWSELITPHAIRVQTPPRHIPGVVEVTLSYKSKQFCKGAPGRFVYTALNF
NOV9b  VIIIGDNFFDGLQVVFGTMLVWSELITPHAIRVQTPPRHIPGVVEVTLSYKSKQFCKGAPGRFVYTALNF 360       370       380       390       400       410       420
              |         |         |         |         |         |         |
NOV9a  PTIDYGFQRLQFVIPRHPGDPERLPKEVLLKRAADLVEALYGMPHNNQEIILKRAADIAEALYSVPRNHN
NOV9b  PTIDYGFQRLQFVIPRHPGDPERLPKEVLLKRAADLVEALYGMPHNNQEIILKRAADIAEALYSVPRNHN 430       440       450       460       470       480       490
              |         |         |         |         |         |         |
NOV9a  QIPTLCNNPAHTGMMGVNSFSSQLAVNVSETSQANDQVGYSRNTSSVSPRGYVPSSTPQQSNYNTVSTSM
NOV9b  QIPTLCNNPAHTGMMGVNSFSSQLAVNVSETSQANDQVGYSRNTSSVSPRGYVPSSTPQQSNYNTVSTSM 500       510       520       530       540       550       560
              |         |         |         |         |         |         |
NOV9a  NGYGSGAMASLGVPGSPGFLNGSSANSPYCVVPSSPTMAASSVTLPSNCSSTHGIFSGSPANVISAVKQK
NOV9b  NGYGSGAMASLGVPGSPGFLNGSSANSPYC---------------------------------MKQK 570       580       590
              |         |         |
NOV9a  AFAPVVRPQASPPPSCTSANCNGLQAMSGLVVPPM
NOV9b  AFAPVVRPQASPPPSCTSANCNGL-----------
```

Homologies to any of the above NOV9 proteins will be shared by the other NOV9 proteins insofar as they are homologous to each other as shown above. Any reference to NOV9 is assumed to refer to both of the NOV9 proteins in general, unless otherwise noted.

NOV9a has homology to the amino acid sequences shown in the BLASTP data listed in Table 9H.

TABLE 9H

BLAST results for NOV9a

| Gene Index/ Identifier | Protein/ Organism | Length (aa) | Identity (%) | Positives (%) | Expect |
|---|---|---|---|---|---|
| gi|13959320|sp|Q9H4 W6|COE3_HUMAN | TRANSCRIPTION FACTOR COE3 (EARLY B-CELL FACTOR 3) (EBF-3) (OLF-1/EBF-LIKE 2) (OE-2) (O/E-2) | 596 | 582/596 (97%) | 583/596 (97%) | 0.0 |
| gi|6226802|sp|O08791| COE3_MOUSE | TRANSCRIPTION FACTOR COE3 (EARLY B-CELL FACTOR 3) (EBF-3) (OLF-1/EBF-LIKE 2) (OE-2) (O/E-2) | 596 | 580/596 (97%) | 582/596 (97%) | 0.0 |
| gi|12314255|emb|CAC16112.1| (AL354950) | bA234G16.1.2 (novel protein similar to early B-cell factor (EBF)) [Homo sapiens] | 582 | 568/582 (97%) | 569/582 (97%) | 0.0 |
| gi|13959679|sp|O73742| COE3_XENLA | Transcription factor COE3 (XCOE3) (OLF-1/EBF-like 2) (OE-2) (XOE-2) (XEBF-3) | 598 | 558/589 (94%) | 566/589 (95%) | 0.0 |
| gi|6753706|ref|NP_034226.1| (NM_010096) | early B-cell factor 3; Olf-1/EBF-like 2 [Mus musculus] | 551 | 535/596 (89%) | 537/596 (89%) | 0.0 |

The homology of these sequences is shown graphically in the ClustalW analysis shown in Table 9I.

TABLE 9I

ClustalW Analysis of NOV9a

1) NOV9a (SEQ ID NO:36)
2) gi|13959320|sp|Q9H4W6 COE3_HUMAN TRANSCRIPTION FACTOR COE3 (EARLY B-CELL FACTOR 3) (EBF-3) (OLF-1/EBF-LIKE 2) (OE-2) (O/E-2) [Homo sapiens] (SEQ ID NO:143)
2) gi|6226802|sp.O08791 COE3_MOUSE TRANSCRIPTION FACTOR COE3 (EARLY B-CELL FACTOR 3) (EBF-3) (OLF-1/EBF-LIKE 2) (OE-2) (O/E-2) [Mus musculus] (SEQ ID NO:144)
3) gi 12314255|emb|CAC16112.1 (AL354950) bA234G16.1.2 (novel protein similar to early B-cell factor (EBF)) [Homo sapiens] (SEQ ID NO:145)
4) gi|13959679|sp|O73742 COE3_XENLA Transcription factor COE3 (XCOE3) (OLF-1/EBF-like 2) (OE-2) (XOE-2) (XEBF-3) [Xenopus laevis] (SEQ ID NO:146)
5) gi 6753706|refNP_034226.1| (NM_010096) early B-cell factor 3; Olf-1/EBF-like 2 [Mus musculus] (SEQ ID NO:147)

TABLE 9I-continued

ClustalW Analysis of NOV9a

```
                  80        90       100       110       120       130       140
              ....|....|....|....|....|....|....|....|....|....|....|....|....|
NOV9a         VLALYDRQGQPVEIERTAFVDFVEKEKEPNNEKTNNGIHYKLQLLYSNGVRTEQDLYVRLIDSMTKQAIV
gi|13959320|  VLALYDRQGQPVEIERTAFVDFVEKEKEPNNEKTNNGIHYKLQLLYSNGVRTEQDLYVRLIDSMTKQAIV
gi|6226802|   VLALYDRQGQPVEIERTAFVDFVEKEKEPNNEKTNNGIHYKLQLLYSNGVRTEQDLYVRLIDSMTKQAIV
gi|12314255|  VLALYDRQGQPVEIERTAFVDFVEKEKEPNNEKTNNGIHYKLQLLYSNGVRTEQDLYVRLIDSMTKQAIV
gi|13959679|  VLAMYDRQGQPVEIERTTFVDFVEKEKEPNSEKTNNGIHYKLQLLYSNGVRTEQDLYVRLIDSMTKQAIT
gi|6753706|   VLALYDRQGQPVEIERTAFVDFVEKEKEPNNEKTNNGIHYKLQLLYSNGVRTEQDLYVRLIDSMTKQAIV 150       160       170       180       190       200       210
              ....|....|....|....|....|....|....|....|....|....|....|....|....|
NOV9a         YEGQDKNPEMCRVLLTHEIMCSRCCDKKSCCNRNETPSDPVIIDRFFLKFFLKCNQNCLKNAGNPRDMRR
gi|13959320|  YEGQDKNPEMCRVLLTHEIMCSRCCDKKSCCNRNETPSDPVIIDRFFLKFFLKCNQNCLKNAGNPRDMRR
gi|6226802|   YEGQDKNPEMCRVLLTHEIMCSRCCDKKSCCNRNETPSDPVIIDRFFLKFFLKCNQNCLKNAGNPRDMRR
gi|12314255|  YEGQDKNPEMCRVLLTHEIMCSRCCDKKSCCNRNETPSDPVIIDRFFLKFFLKCNQNCLKNAGNPRDMRR
gi|13959679|  YEGQDKNPEMCRVLLTHEIMCSRCCDKKSCCNRNETPSDPVIIDRFFLKFFLKCNQNCLKNAGNPRDMRR
gi|6753706|   YEGQDKNPEMCRVLLTHEIMCSRCCDKKSCCNRNETPSDPVIIDRFFLKFFLKCNQNCLKNAGNPRDMRR 220       230       240       250       260       270       280
              ....|....|....|....|....|....|....|....|....|....|....|....|....|
NOV9a         FCVVVSTTVNVDGHVLAVSDNMFVHNNSKHGRRARRLDPSEGTAPSYLP-NATPCIKAISPSEGQTTGGA
gi|13959320|  FCVVVSTTVNVDGHVLAVSDNMFVHNNSKHGRRARRLDPSEGTAPSYLP-NATPCIKAISPSEGQTTGGA
gi|6226802|   FCVVVSTTVNVDGHVLAVSDNMFVHNNSKHGRRARRLDPSEGTAPSYLP-NATPCIKAISPSEGQTTGGA
gi|12314255|  FCVVVSTTVNVDGHVLAVSDNMFVHNNSKHGRRARRLDPSEGTAPSYLP-NATPCIKAISPSEGQTTGGA
gi|13959679|  FCVVVSTTVNVDGHVLAVSDNMFVHNNSKHGRRARRLDPSEGTAPSYLPNVATPCIKAISPSEGQTTGGA
gi|6753706|   FCVVVSTTVNVDGHVLAVSDNMFVHNNSKHGRRARRLDPSE---------ATPCIKAISPSEGQTTGGA 290       300       310       320       330       340       350
              ....|....|....|....|....|....|....|....|....|....|....|....|....|
NOV9a         TVIIIGDNFFDGLQVVFGTMLVWSELITPHAIRVQTPPRHIPGVVEVTLSYKSKQFCKGAPGRFVYTAIN
gi|13959320|  TVIIIGDNFFDGLQVVFGTMLVWSELITPHAIRVQTPPRHIPGVVEVTLSYKSKQFCKGAPGRFVYTAIN
gi|6226802|   TVIIIGDNFFDGLQVVFGTMLVWSELITPHAIRVQTPPRHIPGVVEVTLSYKSKQFCKGAPGRFVYTAIN
gi|12314255|  TVIIIGDNFFDGLQVVFGTMLVWSELITPHAIRVQTPPRHIPGVVEVTLSYKSKQFCKGAPGRFVYTAIN
gi|13959679|  TVIIIGDNFFDGLQVVFGTMLVWSELITPHAIRVQTPPRHIPGVVEVTLSYKSKQFCKGAPGRFVYTAIN
gi|6753706|   TVIIIGDNFFDGLQVVFGTMLVWSELITPHAIRVQTPPRHIPGVVEVTLSYKSKQFCKGAPGRFVYTAIN 360       370       380       390       400       410       420
              ....|....|....|....|....|....|....|....|....|....|....|....|....|
NOV9a         EPTIDYGFQRLQKVIPRHPGDPERLPKEVLLKRAADLVEALYGMPHNNQEIILKRAADIAEALYSVPRNR
gi|13959320|  EPTIDYGFQRLQKVIPRHPGDPERLPKEVLLKRAADLVEALYGMPHNNQEIILKRAADIAEALYSVPRNR
gi|6226802|   EPTIDYGFQRLQKVIPRHPGDPERLPKEVLLKRAADLVEALYGMPHNNQEIILKRAADIAEALYSVPRNR
gi|12314255|  EPTIDYGFQRLQKVIPRHPGDPERLPKEVLLKRAADLVEALYGMPHNNQEIILKRAADIAEALYSVPRNR
gi|13959679|  EPTIDYGFQRLQKVIPRHPGDPERLPKEVLLKRAADLVEALYGMPHNNQEIILKRAADIAEALYSVPRNR
gi|6753706|   EPTIDYGFQRLQKVIPRHPGDPERLPKEVLLKRAADLVEALYGMPHNNQEIILKRAADIAEALYSVPRNR 430       440       450       460       470       480       490
              ....|....|....|....|....|....|....|....|....|....|....|....|....|
NOV9a         NQIPTLGNNPAHTGMMGVNSFSSQLAVNVSETSQANDQVGYSRNTSSVSPRGYVPSSTPQQSNYNTVSTS
gi|13959320|  NQIPTLGNNPAHTGMMGVNSFSSQLAVNVSETSQANDQVGYSRNTSSVSPRGYVPSSTPQQSNYNTVSTS
gi|6226802|   NQIPTLGNTPAHTGMMGVNSFSSQLAVNVSETSQANDQVGYSRNTSSVSPRGYVPSSTPQQSNYNTVSTS
gi|12314255|  NQIPTLGNNPAHTGMMGVNSFSSQLAVNVSETSQANDQVGYSRNTSSVSPRGYVPSSTPQQSNYNTVSTS
gi|13959679|  NQIPSLANTPSHSGMMGVNSFSSQLAVNVSETSQANDQVGYSRNTSSVSPRGYVPSSTPQQSNYNTVSNS
gi|6753706|   NQIPTLGNNPAHTGMMGVNSFSSQLAVNVSETSQANDQVGYSRNTSSVSPRGYVPSSTPQQSNYNTVSTS 500       510       520       530       540       550       560
              ....|....|....|....|....|....|....|....|....|....|....|....|....|
NOV9a         MNGYGSGAMASLGVPGSPGFLNGSSANSPYGVVPSSPTMAASSVTLPSNCSSTHGIFSFSPANVISAVKQ
gi|13959320|  MNGYGSGAMASLGVPGSPGFLNGSSANSPYGIVPSSPTMAASSVTLPSNCSSTHGIFSFSPANVISAVKQ
gi|6226802|   MNGYGSGAMANLGVPGSPGFLNGSSANSPYGIVPSSPTMAASSVTLPSNCSSTHGIFSFSPANVISAVKQ
gi|12314255|  MNGYGSGAMASLGVPGSPGFLNGSSANSPYGIVPSSPTMAASSVTLPSNCSSTHGIFSFSPANVISAVKQ
gi|13959679|  MNGYCNAGMPNLGVPGSPGFLNGSSANSPYGIVPSSPTMAASSVTLPSNCSSTHGIFSFSPANVISAVKQ
gi|6753706|   MNGYGSGAMANLGVPGSPGFLNGSSANSPYG---------------------------------MKQ 570       580       590
              ....|....|....|....|....|...
NOV9a         KSAFAPVVRPQASPPPSCTSANGNGLQAMSGLVVPPM-
gi|13959320|  KSAFAPVVRPQASPPPSCTSANGNGLQAMSGLVVPPM-
gi|6226802|   KSAFAPVVRPQASPPPSCTSANGNGLQAMSGLVVPPM-
gi|12314255|  KSAFAPVVRPQASPPPSCTSANGNGLQAMSGLVVPPM-
gi|13959679|  KSAFAPVVRPQASPPPSCTSANGNGLQDMYFSPTFSKS
gi|6753706|   KSAFAPVVRPQASPPPSCTSANGNGLQAMSGLVVPPM-
```

Tables 9J, 9K and 9L lists the domain description from DOMAIN analysis results against NOV9a. This indicates that the NOV9a sequence has properties similar to those of other proteins known to contain these domains.

TABLE 9J

Domain Analysis of NOV9a gnl|Pfam|pfam01833, TIG, IPT/TIG domain. This family consists of a
domain that has an immunoglobulin like fold. These domains are found
in cell surface receptors such as Met and Ron as well as in
intracellular transcription factors where it is involved in DNA
binding. CAUTION: This family does not currently recognise a
significant number of members. (SEQ ID NO:148)
CD-Length = 85 residues, 100.0% aligned
Score = 51.2 bits (121), Expect = 2e-07

```
Query:  263 PCIKAISPSEGWTTGGATVIIIGDNFF--DGLQVVFGTMLVWSELITPHAIRVQTPPRHI  320
                | +||||  | +||  +  | | |     + ++| ||            |  +|||
Sbjct:    1 PVITSISPSSGPLSGGTEITITGSNLGSGEDIKVTFGGTECDVVSQEASQIVCKTPPYAN   60

Query:  321 PGVVEVTLSYKSKQFCKGAPGRFVYT                                    346
                |  ||+|        +|  | |
Sbjct:   61 GGPQPVTVSLDGGGLS-SSPVTFTYV                                     85
```

TABLE 9K

Domain Analysis of NOV9a gnl|Smart|smart00429, IPT, ig-like, plexins, transcription factors
(SEQ ID NO:149)
CD-Length = 93 residues, 98.9% aligned
Score = 39.3 bits (90), Expect = 6e-04

```
Query:  263 PCIKAISPSEGWTTGGATVIIIGDNFFDGLQVVFGTMLVWS-------ELITPHAIRVQT  315
                |  | |||+ |   +|| | | +     | +  ||| + |         ++ ||  +|
Sbjct:    2 PVITRISPNSGPLSGG-TRITLCGKNLDSISVVFVEVGVGEVPCTFLPSDVSQTAIVCKT   60

Query:  316 PPRH---IPGVVEVTLSYKSKQFCKGAPGRFVYT                            346
            || |       | | + ++     | | | |
Sbjct:   61 PPYHNIPGSVPVRVEVGLRNGGV-PGEPSPFTYV                             93
```

TABLE 9L

Domain Analysis of NOV9a gnl|Smart smart00353, HLH, helix loop helix domain. (SEQ ID
NO:150)
CD-Length = 53 residues, 75.5% aligned
Score = 37.0 bits (84), Expect = 0.003

```
Query:  353 IDYGFQRLQKVIPRHPGDPERLPKEVLLKRAADLVEALYGM  393
              +  |  |+ ++|   | + ++|    +|+ |  |  +++|
Sbjct:   11 INEAFDELRSLLPPLPNN-KKLSKASILRLAIDYIKSLQEQ   50
```

Murine B lymphocytes, adipocytes, and olfactory neurons contain a DNA-binding protein that participates in the regulation of genes encoding tissue-specific components of signal transduction. Purification and cloning of this protein, termed early B-cell factor (EBF), from murine B lymphocytes and independent cloning of a protein, termed Olf-1, from olfactory neuronal cells revealed virtual complete amino acid sequence identity between these proteins.

Early B-cell factor (EBF) is a tissue-specific and differentiation stage-specific DNA-binding protein that participates in the regulation of the pre-B and B lymphocyte-specific MB1 gene. Travis et al. (Molec. Cell. Biol. 13: 3392–3400, 1993) purified the mouse Ebf protein from pre-B cells and found that it is composed of two 62- to 65-kD subunits. Hagman et al. (Genes Dev. 7: 760–773, 1993) determined partial amino acid sequences of Ebf and used them to isolate mouse pre-B-cell cDNAs encoding Ebf. The predicted 591-amino acid protein has 2 functional domains: an N-terminal cysteine-rich region essential for DNA binding, and a C-terminal dimerization region containing two 15-amino acid repeats with similarity to the dimerization domains of basic helix-loop-helix (bHLH) proteins. The calculated molecular mass of the encoded Ebf protein is 64.4 kD. The authors found that recombinant Ebf binds to DNA as a homodimer, forms complexes with the Mb1 promoter, and is a strong activator of transcription. Northern blot analysis detected multiple Ebf transcripts in pre-B- and early B-cell lines but not in other hematopoietic cells. S1 nuclease protection analysis of adult mouse RNAs showed high levels of Ebf expression in lymph node, spleen, and adipose tissues and low levels in several nonlymphoid tissues. By Southern blot analysis of somatic cell hybrid DNAs using a murine Ebf cDNA as a probe, and by fluorescence in situ hybridization using human genomic cosmids, Milatovich et al. (Genome 5: 211–215, 1994) mapped the human EBF gene to 5q34. The study mapped the mouse Ebf gene to proximal chromosome 11 by Southern blot analysis of somatic cell hybrid DNAs and by analysis of recombinant inbred strains.

The mammalian olfactory system has the remarkable ability to detect odorants with high sensitivity and specificity. The initial events in the olfactory signal transduction pathway occur in the specialized cilia of the sensory neurons. Unlike other neurons, the olfactory sensory cells are continually replaced throughout adult life. Cells within the olfactory epithelium follow an orderly developmental program resulting in the high level of expression of gene products essential for odorant signal transduction. The mature neurons express several olfactory-specific genes, some of which appear to mediate the odorant signal transduction cascade. Evidence supporting the involvement of a G protein-coupled receptor pathway in odorant signal transduction was provided by the isolation of olfactory-specific components that correspond to each step in the pathway, e.g., G-alpha-olf. Additional olfactory neuron-specific genes have been identified. The establishment of the mature olfactory neuronal phenotype probably results from the coordinated expression of olfactory-specific genes. In the investigation of these genes, Wang and Reed (Nature 364: 121–126, 1993) found that each contains at least 1 binding site for the DNA-binding protein Olf1. The binding of an olfactory-specific factor, Olf1, was first described in the olfactory marker protein gene (OMP). Olf1 activity was detectable in nuclear extracts from nasal epithelium and absent from nuclear extracts of a variety of other tissues. Using a novel genetic selection in yeast, Wang and Reed (1993) isolated a cDNA for the rat transcriptional activator Olf1, which binds to the regulatory sequences of several olfactory-specific genes. Expressed exclusively in the olfactory receptor neurons and their precursors, the Olf1 protein contains a new helix-loop-helix motif and functions as an apparent homodimer. They suggested that Olf1 may be the first member of a family of related proteins that may direct cellular differentiation in a variety of neuronal tissues.

Using homology screening methods, two additional Olf-1/EBF-like cDNAs were identified from a mouse embryonic cDNA library. The Olf-1/EBF-like (O/E) proteins O/E-1, O/E-2, and O/E-3 define a family of transcription factors that share structural similarities and biochemical activities. Although these O/E genes are expressed within olfactory epithelium in an identical pattern, they exhibit different patterns of expression in the developing nervous system. Although O/E-1 mRNA is present in several tissues in addition to olfactory neurons and developing B-cells, O/E-2 and O/E-3 are expressed at high levels only in olfactory tissue. In O/E-1 knock-out animals, the presence of two additional O/E family members in olfactory neurons may provide redundancy and allow normal olfactory neurodevelopment. Further, the identification of the O/E family of HLH transcription factors and their embryonic expression patterns suggest that the O/E proteins may have a more general function in neuronal development.

The independent cloning of rodent EBF/Olf-1 and *Drosophila* Collier has defined a family of transcription factors, the Collier or COE family. COE proteins have various functions in different organisms. Proteins currently known to belong to this family include: mammalian COE1 (OLF-1; EBF-1; OE-1), COE2 (EBF-2; OE-3) and COE3 (EBF-3; OE-2); *Xenopus* XCOE2 and XCOE3; zebrafish ZCOE2; *Drosophila* Collier; and *Caenorhabditis elegans* UNC-3. In mouse, COE1 has a role in B-cell differentiation, and could also perform a role in neuronal differentiation. All three COE are expressed in immature olfactory neuronal precursors and mature olfactory neurons as well as in developping nervous system during embryogenesis. In *Drosophila*, Collier is involved in the formation of the embryonic somatic muscle DA3, in the patterning of the wing by mediating Hedgehog activity. It could also act as a second-level regulator in the patterning of embryonic head. In *Xenopus*, XCOE2 is expressed in precursors of primary neurons, and may play a pivotal role in the transcriptional cascade specifying primary neurons in embryo. It promotes neuronal differentiation by activating XNeuroD expression. In Zebrafish, ZCOE2 is expressed in a subset of primary neuroblasts in the spinal cord and at later stages is a marker of the olfactory placodes. *Caenorhabditis elegans* mutants for UNC-3 move abnormally, suggesting that UNC-3 might regulate expression of genes involved in growth cone pioneering long the ventral cord or in fasciculation.

The NOV9 nucleic acid of the invention encoding a Early B-Cell Factor-like protein includes the nucleic acid whose sequence is provided in Tables 9A and 9C, or a fragment thereof. The invention also includes a mutant or variant nucleic acid any of whose bases may be changed from the corresponding base shown in Tables 9A and 9C while still encoding a protein that maintains its Early B-Cell Factor-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 6% of the NOV9 residues may be so changed.

The NOV9 protein of the invention includes the Early B-Cell Factor-like protein whose sequence is provided in Tables 9B and 9D. The invention also includes a mutant or variant protein any of whose residues may be changed from the corresponding residue shown in Tables 9B and 9D while still encoding a protein that maintains its Early B-Cell Factor-like activities and physiological functions, or a functional fragment thereof. In the mutant or variant protein, up to about 1% of the NOV9 bases may be so changed.

The NOV9 nucleic acids and proteins of the invention are useful in potential diagnostic and therapeutic applications implicated in various diseases and disorders described below and/or other pathologies. For example, the compositions of the present invention will have efficacy for treatment of patients suffering from: Von Hippel-Lindau (VHL) syndrome, Alzheimer's disease, stroke, tuberous sclerosis, hypercalceimia, Parkinson's disease, Huntington's disease, cerebral palsy, epilepsy, Lesch-Nyhan syndrome, multiple sclerosis, ataxia-telangiectasia, leukodystrophies, behavioral disorders, addiction, anxiety, pain, neuroprotection, multiple sclerosis, myasthenia gravis, diabetes, obesity, neuronal development and other diseases, disorders and conditions of the like.

NOV9 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV9 protein have multiple hydrophilic regions, each of which can be used as an immunogen. This novel protein also has value in development of powerful assay system for functional analysis of various human disorders, which will help in understanding of pathology of the disease and development of new drug targets for various disorders. NOV10

A disclosed NOV10 nucleic acid of 3892 nucleotides (also referred to as CG57389-01) encoding a novel High-Affinity CAMP Specific and IBMX-Insensitive-like protein is shown in Table 10A. An open reading frame was identified beginning with an ATG initiation codon at nucleotides 137–139 and ending with a TAG codon at nucleotides 2624–2626. Putative untranslated regions upstream from the intitation codon and downstream from the termination codon are underlined in Table 10A, and the start and stop codons are in bold letters.

TABLE 10A

NOV10 Nucleotide Sequence (SEQ ID NO:39)

<u>ACGCGAGATCCGCGCTCGCCGCCGCCCGCCCAGGCGGCGATGACACGGCGCCCGCGGCGGCCCGGAGGCGCCG</u>

<u>GGTGGGCCGTTTGCTGACCGGATCGCGGCTACCCGCCAGCGTGTCCGCGGCGCCGCCGCCAGC</u>ATGGGCTGTG

CCCCGAGCATCCACATTTCCGAGCGCCTGGTGGCCGAGGACGCGCCTAGCCCCGCGGCACCGCCGCTGTCGTC

CGGCGGGCCGCGCCTCCCGCAGGGCCAGAAGACGGCCGCCTTGCCCCGGACCCGCGGCGCCGGCCTCTTGGAG

TCGGAGGTTCGCGACGGCAGCGGCAAGAAGGTAGCAGTAGCTGATGTGCAGTTTGGCCCCATGAGATTTCATC

AAGATCAACTTCAGGTACTTTTAGTGTTTACCAAAGAAGATAACCAATGTAATGGATTCTGCAGGGCATGTGA

AAAAGCAGGGTTTAAGTGTACAGTTACCAAGGAGGCTCAGGCTGTCCTTGCCTGTTTCCTGGACAAACATCAT

GACATTATCATCATAGACCACAGAAATCCTCGACAGCTGGATGCAGAGGCACTGTGCAGGTCTATCAGATCAT

CAAAACTCTCAGAAAACACAGTTATTGTTGGTGTAGTACGCAGGGTGGATAGAGAAGAGTTGTCCGTAATGCC

TTTCATTTCTGCTGGATTTACAAGGAGGTATGTAGAAAACCCCAACATCATGGCCTGCTACAATGAACTGCTC

CAGCTGGAGTTTGGAGAGGTGCGATCACAACTGAAACTCAGGGCTTGTAACTCAGTATTCACTGCATTAGAAA

ACAGTGAAGATGCAATTGAAATTACAAGCGAAGACCGTTTTATACAGTATGCAAATCCTGCATTTGAAACAAC

AATGGGCTATCAGTCAGGTGGAATTAATAGGGAAGGAGTTAGGAGAAGTGCCTATAAATGAAAAAAGGCTGAC

TTGCTCGATACTATAAATTCATGCATCAGGATAGGCAAGGAGTGGCAAGGAATTTACTATGCCAAAAAGAAAA

ACGGAGATAATATACAACAAAATGTGAAGATAATACCTGTCATTGGACAGGGAGGAAAAATTAGACACTATGT

GTCCATTATCAGAGTGTGCAATGGCAACAATAAGGCTGAGAAAATATCCGAATGTGTTCAGTCTGACACTCGT

ACAGATAATCAGACAGGCAAACATAAAGACAGGAGAAAAGGCTCACTAGACGTCAAAGCTGTTGCCTCCCGTG

CAACTGAAGTTTCCAGCCAGAGACGACACTCTTCCATGGCCCGGATACATTCCATGACAATTGAGGCGCCCAT

CACCAAGGTAATCAATATTATCAATGCTGCCCAGGAAAGTAGTCCCATGCCTGTGACAGAAGCCCTAGACCGT

GTGCTGGAAATTCTAAGAACCACTGAGTTATATTCACCACAGTTTGGTGCTAAAGATGATGATCCCCATGCCA

ATGACCTTGTTGGGGGCTTAATGTCTGATGGTTTGCGAAGACTATCAGGGAATGAATATGTTCTTTCAACAAA

AAACACTCAAATGGTTTCAAGCAATATAATCACTCCCATCTCCCTTGATGATGTCCCACCACGGATAGCTCGG

GCCATGGAAAATGAGGAATACTGGGACTTTGATATTTTTGAACTGGAGGCTGCCACCCACAATAGGCCTTTGA

TTTATCTTGGTCTCAAAATGTTTGCTCGCTTTGGAATCTGTGAATTCTTACACTGCTCCGAGTCAACGCTAAG

ATCATGGTTACAAATTATCGAAGCCAATTATCATTCCTCCAATCCCTACCACAATTCTACACATTCTGCTGAT

GTGCTTCATGCCACTGCCTATTTTCTCTCCAAGGAGAGGATAAAGGAAACTTTAGATCCAATTGATGAGGTCG

CTGCACTCATCGCAGCCACCATTCATGATGTGGATCACCCTGGGAGAACCAACTCCTTCCTGTGTAATGCTGG

AAGTGAGCTGGCCATTTTGTACAATGACACTGCTGTGCTGGAGAGCCACCATGCGGCCTTGGCCTTCCAGCTG

ACCACTGGAGATGATAAATGCAATATATTTAAAAACATGGAGAGGAATGATTATCGGACACTGCGCCAGGGGA

TTATCGACATGGTCTTAGCCACAGAAATGACAAAGCACTTTGAGCATGTCAACAAATTTGTCAACAGCATCAA

CAAACCCTTGGCAACACTAGAAGAAATGGGGAAACTGATAAAAACCAGGAAGTGATAAACACTATGCTTAGG

ACTCCAGAGAACCGGACCCTAATCAAACGAATGCTGATTAAATGTGCTGATGTGTCCAATCCCTGCCGACCCC

TGCAGTACTGCATCGAGTGGGCTGCACGCATTTCGGAAGAATATTTTTCTCAGACTGATGAAGAGAAGCAGCA

GGGCTTACCTGTGGTGATGCCAGTGTTTGACAGAAATACCTGCAGCATCCCCAAATCCCAAATCTCTTTCATT

GATTACTTCATCACAGACATGTTTGATGCTTGGGATGCCTTTGTAGACCTGCCTGATTTAATGCAGCATCTTG

TABLE 10A-continued

NOV10 Nucleotide Sequence

ACAACAACTTTAAATACTGGAAAGGACTGGACGAAATGAAGCTGCGGAACCTCCGACCACCTCCTGAATAGTG

GGAGACACCACCCAGAGCCCTGAAGCTTTGTTCCTTCGGTCATTTGGAATTCCTGAGGGCAGCCAGAGCTCCT

TGGTCCTTTCAGTACTAGGCAGAACAGCCCCCGATCTGCATAGCCTGTGAAAGCCCACGGGGACATCAGTAAC

CTTCTGCAGCCACCATCCAATGCCATTACTGTCAAGTGAGACTTGGCCACTGTAGCCTGGGCCTCCTGCAGGA

GCTCTTCAGAAAGGCACATGAGGACCACGGTTTGCCTCAGTTTCTGGTAAAACACAAGGTCTGGAGTGCCCCT

GCAAAGGGTATTGATGGACTTCCTGCCAGTGACAGAGCATGTCTATTGCAAACAATTCTCTCAGTTACGTTCA

GCACTTAAGAACGGCTAATGGCAATAGGATCTTTAGCAACTTTTTCACATCATAGAAGGTGCAATCGCTCACT

TGGGAACACTACTGAGAGTGACTTCTCTTTTAAAATTGAGTAGCAGATGAAAAATTAAAATTTGAACTTGATT

ATTAATATCAATTAAAATGTTTTATTTATTTTATTAAAAGCTCAATATTTTCTATGAATTCAAAAATACTTCA

GAGCCAAAGCCAACTTCAAATACCGTGACCAAATTTACATGATTCATATTCATTATGCATTACTTGGTATACA

GACTTATTTTCATAATGCAAATTAATAAAATGACACTTTTACTGCACTATAGAAATATTCATGTATGTTAAAC

TTTTCTGATTGAGGCTAACTGGAAAAAGCTGGGGTCGTATTCTAAGTGCTAAAGAAGGCTGCTTCTACTGTAT

AGAACCCAGGGCTCTGAAACAGCTCTAGCCGCCTAATGCACTTCACAGGTAACTCCCCAAGGTAAAACTAGAC

TCTCTTGTTGGTTCGCAAAGAAAAGTTAGGACTTAACACTTTTTTCTAAAATTTTATAATTCAATTTCCAAAA

GTCTACTCTATTTTATACTGTTTCTACAAAATATTCCTTATAAAAACAAAGAACAAAAATTGAATATTTAATG

AATTGACATTTTATAACCAACCTGTTTTTATCTACGGTGGGAATCTTTGATGCCAGAAATTTATAAAGAGGTT

CTGTATCTTCACACCTTGAATAAGCATAATACCATAAAAAATGACACTTGACATGTCAATGTATTTGTCATTT

CATTTTAAACTCGTATTTGTGGTTTTTTTCCCAGATAAAAATGAAATTAAACCATTTCTTTTTAAGAAATCAA

AAAAAAAAAAAAAAAAAAAAAAA

The NOV10 nucleic acid was identified on chromosome 15 and has 3393 of 3396 bases (99%) identical to a gb:GENBANK-ID:AF056490|acc:AF056490.1 mRNA from Homo sapiens (Homo sapiens cAMP-specific phosphodiesterase 8A (PDE8A) mRNA, partial cds) (E=0.0).

A disclosed NOV10 polypeptide (SEQ ID NO:40) encoded by SEQ ID NO:39 is 829 amino acid residues and is presented using the one-letter code in Table 10B. Signal P, Psort and/or Hydropathy results predict that NOV10 contains a signal peptide and is likely to be localized to the cytoplasm with a certainty of 0.4500.

TABLE 10B

Encoded NOV10 protein sequence (SEQ ID NO:40)
MGCAPSIHISERLVAEDAPSPAAPPLSSGGPRLPQGQKTAALPRTRGAGLLESEVRDGSGKKVAVADVQFGP

MRFHQDQLQVLLVFTKEDNQCNGFCRACEKAGFKCTVTKEAQAVLACFLDKHHDIIIDHRNPRQLDAEALC

RSIRSSKLSENTVIVGVVRRVDREELSVMPFISAGFTRRYVENPNIMACYNELLQLEFGEVRSQLKLRACNS

VFTALENSEDAIEITSEDRFIQYANPAFETTMGYQSGELIGKELGEVPINEKKADLLDTINSCIRIGKEWQG

IYYAKKKNGDNIQQNVKIIPVIGQGGKIRHYVSIIRVCNGNNKAEKISECVQSDTRTDNQTQKHKDRRKGSL

DVKAVASRATEVSSQRRHSSMARIHSMTIEAPITKVINIINAAQESSPMPVTEALDRVLEILRTTELYSPQF

GAKDDDPHANDLVGGLMSDGLRRLSGNEYVLSTKNTQMVSSNIITPISLDDVPPRIARAMENEEYWDFDIFE

LEAATHNRPLIYLGLKMFARFGICEFLHCSESTLRSWLQIIEANYHSSNPYHNSTHSADVLHATAYFLSKER

IKETLDPIDEVAALIAATIHDVDHPGRTNSFLCNAGSELAILYNDTAVLESHHAALAFQLTTGDDKCNIFKN

MERNDYRTLRQGIIDMVLATEMTKHFEHVNKFVNSINKPLATLEENGETDKNQEVINTMLRTPENRTLIKRM

TABLE 10B-continued

Encoded NOV10 protein sequence

LIKCADVSNPCRPLQYCIEWAARISEEYFSQTDEEKQQGLPVVMPVFDRNTCSIPKSQISFIDYFITDMFDA

WDAFVDLPDLMQHLDNNFKYWKGLDEMKLRNLRPPPE

The NOV10 amino acid sequence has 712 of 713 amino acid residues (99%) identical to, and 713 of 713 amino acid residues (100%) similar to, the 713 amino acid residue ptnr:SWISSNEW-ACC:060658 protein from *Homo sapiens* (Human) (High-Affinity CAMP-Specific And IBMX-Insensitive 3',5'-Cyclic Phosphodiesterase 8A (EC 3.1.4.17) (E=0.0).

NOV10 is expressed in at least the following tissues: kidney, lung, uterus, ovary and heart. This information was derived by determining the tissue sources of the sequences that were included in the invention including but not limited to SeqCalling sources, Public EST sources, genomic clone sources, literature sources, and/or RACE sources.

NOV10 has homology to the amino acid sequences shown in the BLASTP data listed in Table 10C.

TABLE 10C

BLAST results for NOV10

| Gene Index/ Identifier | Protein/Organism | Length (aa) | Identity (%) | Positives (%) | Expect |
|---|---|---|---|---|---|
| gi\|14248761\|gb\|AAK57641.1\| AF332653_1 (AF332653) | cAMP-specific cyclic nucleotide phosphodiesterase PDE8A1 [*Homo sapiens*] | 829 | 803/829 (96%) | 804/829 (96%) | 0.0 |
| gi\|16417190\|gb\|AAL18610.1\| AF388183_1 (AF388183) | cAMP phosphodiesterase PDE8A1 [*Homo sapiens*] | 829 | 802/829 (96%) | 803/829 (96%) | 0.0 |
| gi\|17477753\|ref\|XP_ 031443.2\| (XM_031443) | phosphodiesterase 8A [*Homo sapiens*] | 757 | 745/757 (98%) | 745/757 (98%) | 0.0 |
| gi\|16417192\|gb\|AAL18611.1\| AF388184_1 (AF388184) | cAMP phosphodiesterase PDE8A2 [*Homo sapiens*] | 783 | 756/829 (91%) | 757/829 (91%) | 5e-97 |
| gi\|5921805\|sp\|O60658\| CN8A_HUMAN | High-affinity cAMP-specific and IBMX-insensitive 3',5'-cyclic phosphodiesterase 8A [*Homo sapiens*] | 713 | 701/713 (98%) | 702/713 (98%) | 2e-72 |

The homology of these sequences is shown graphically in the ClustalW analysis shown in Table 10D.

TABLE 10D

Clustal W Sequence Alignment

1) NOV10 (SEQ ID NO:40)

2) gi 14248761|gb AAK57641.1 AF332653_1 (AF332653) cAMP-specific cyclic nucleotide phosphodiesterase PDE8A1 [*Homo sapiens*] (SEQ ID NO:151)

3) gi 16417190|gb|AAL18610.1|AF388183_1 (AF388183) cAMP phosphodiesterase PDE8A1 [*Homo sapiens*] (SEQ ID NO:152)

4) gi|17477753|refXP_031443.2| (XM_031443) phosphodiesterase 8A [*Homo sapiens*] (SEQ ID NO:153)

5) gi|16417192|gb|AAL18611.1|AF388184_1 (AF388184) cAMP phosphodiesterase PDE8A2 [*Homo sapiens*] (SEQ ID NO:154)

6) gi|5921805|sp|O60658|CN8A_HUMAN High-affinity cAMP-specific and IBMX-insensitive 3',5'-cyclic phosphodiesterase 8A [*Homo sapiens*] (SEQ ID NO:155)

TABLE 10D-continued

Clustal W Sequence Alignment

```
                   10        20        30        40        50        60        70
             ....|....|....|....|....|....|....|....|....|....|....|....|....|....|
NOV10        MGCAPSIHISERLVAEDAPSPAAPPLSSGGPRLPQGQKTAALPRTRGAGLLESEVRDGSGKKVAVADVQP
gi|14248761| MGCAPSIHISERLVAEDAPSPAAPPLSSGGPRLPQGQKTAALPRTRGAGLLESEVRDGSGKKVAVADVQP
gi|16417190| MGCAPSIHISERLVAEDAPSPAAPPLSSGGPRLPQGQKTAALPRTRGAGLLESEGRDGSGKKVAVADVQP
gi|17477753| ----------------------------------------------------------------------
gi|16417192| MGCAPSIHISERLVAEDAPSPAAPPLSSGGPRLPQGQKTAALPRTRGAGLLESEGRDGSGKKVAVADVQP
gi|5921805|  ----------------------------------------------------------------------

80        90       100       110       120       130       140
             ....|....|....|....|....|....|....|....|....|....|....|....|....|....|
NOV10        GPMRFHQDQLQVLLVFTKEDNQCNGFCRACEKAGFKCTVTKEAQAVLACFLDKHHDIIIIDHRNPRQLDA
gi|14248761| GPMRFHQDQLQVLLVFTKEDNQCNGFCRACEKAGFKCTVTKEAQAVLACFLDKHHDIIIIDHRNPRQLDA
gi|16417190| GPMRFHQDQLQVLLVFTKEDNQCNGFCRACEKAGFKCTVTKEAQAVLACFLDKHHDIIIIDHRNPRQLDA
gi|17477753| --MRFHQDQLQVLLVFTKEDNQCNGFCRACEKAGFKCTVTKEAQAVLACFLDKHHDIIIIDHRNPRQLDA
gi|16417192| GPMRFHQDQLQVLLVFTKEDNQCNGFCRACEKAGFKCTVTKEAQAVLACFLDKHHDIIIIDHRNPRQLDA
gi|5921805|  -------------------------------------------LACFLDKHHDIIIIDHRNPRQLDA 150       160       170       180       190       200       210
             ....|....|....|....|....|....|....|....|....|....|....|....|....|....|
NOV10        EALCRSIRSSKLSENTVIVGVVRRVDREELSVMPFISAGFTRRYVENPNIMACYNELLQLEFGEVRSQLK
gi|14248761| EALCRSIRSSKLSENTVIVGVVRRVDREELSVMPFISAGFTRRYVENPNIMACYNELLQLEFGEVRSQLK
gi|16417190| EALCRSIRSSKLSENTVIVGVVRRVDREELSVMPFISAGFTRRYVENPNIMACYNELLQLEFGEVRSQLK
gi|17477753| EALCRSIRSSKLSENTVIVGVVRRVDREELSVMPFISAGFTRRYVENPNIMACYNELLQLEFGEVRSQLK
gi|16417192| EALCRSIRSSKLSENTVIVGVVRRVDREELSVMPFISAGFTRRYVENPNIMACYNELLQLEFGEVRSQLK
gi|5921805|  EALCRSIRSSKLSENTVIVGVVRRVDREELSVMPFISAGFTRRYVENPNIMACYNELLQLEFGEVRSQLK 220       230       240       250       260       270       280
             ....|....|....|....|....|....|....|....|....|....|....|....|....|....|
NOV10        LRACNSVFTALENSEDAIEITSEDRFIQYANPAFETTMGYQSGELIGKELGEVPINEKKADLLDTINSCI
gi|14248761| LRACNSVFTALENSEDAIEITSEDRFIQYANPAFETTMGYQSGELIGKELGEVPINEKKADLLDTINSCI
gi|16417190| LRACNSVFTALENSEDAIEITSEDRFIQYANPAFETTMGYQSGELIGKELGEVPINEKKADLLDTINSCI
gi|17477753| LRACNSVFTALENSEDAIEITSEDRFIQYANPAFETTMGYQSGELIGKELGEVPINEKKADLLDTINSCI
gi|16417192| LRACNSVFTALENSEDAIEITSEDRFIQ------------------------------------------
gi|5921805|  LRACNSVFTALENSEDAIEITSEDRFIQYANPAFETTMGYQSGELIGKELGEVPINEKKADLLDTINSCI 290       300       310       320       330       340       350
             ....|....|....|....|....|....|....|....|....|....|....|....|....|....|
NOV10        RIGKEWQGIYYAKKKNGDNIQQNVKIIPVIGQGGKIRHYVSIIRVCNGNNKAEKISECVQSDIRTDNQTG
gi|14248761| RIGKEWQGIYYAKKKNGDNIQQNVKIIPVIGQGGKIRHYVSIIRVCNGNNKAEKISECVQSDIRTDNQTG
gi|16417190| RIGKEWQGIYYAKKKNGDNIQQNVKIIPVIGQGGKIRHYVSIIRVCNGNNKAEKISECVQSDIHTDNQTG
gi|17477753| RIGKEWQGIYYAKKKNGDNIQQNVKIIPVIGQGGKIRHYVSIIRVCNGNNKAEKISECVQSDIHTDNQTG
gi|16417192| ----EWQGIYYAKKKNGDNIQQNVKIIPVIGQGGKIRHYVSIIRVCNGNNKAEKISECVQSDIHTDNQTG
gi|5921805|  RIGKEWQGIYYAKKKNGDNIQQNVKIIPVIGQGGKIRHYVSIIRVCNGNNKAEKISECVQSDIRTDNQTG 360       370       380       390       400       410       420
             ....|....|....|....|....|....|....|....|....|....|....|....|....|....|
NOV10        KHKDRRKGSLDVKAVASRATEVSSQRRHSSMARIHSMTIEAPITKVINIINAAQESSPMPVTEALDRVLE
gi|14248761| KHKDRRKGSLDVKAVASRATEVSSQRRHSSMARIHSMTIEAPITKVINVINAAQESSPMPVTEALDRVLE
gi|16417190| KHKDRRKGSLDVKAVASRATEVSSQRRHSSMARIHSMTIEAPITKVINIINAAQESSPMPVTEALDRVLE
gi|17477753| KHKDRRKGSLDVKAVASRATEVSSQRRHSSMARIHSMTIEAPITKVINIINAAQESSPMPVTEALDRVLE
gi|16417192| KHKDRRKGSLDVKAVASRATEVSSQRRHSSMARIHSMTIEAPITKVINIINAAQESSPMPVTEALDRVLE
gi|5921805|  KHKDRRKGSLDVKAVASRATEVSSQRRHSSMARIHSMTIEAPITKVINVTNAAQESSPMPVTEALDRVLE 430       440       450       460       470       480       490
             ....|....|....|....|....|....|....|....|....|....|....|....|....|....|
NOV10        ILRITELYSPQFGAKDDDPHANDLVGGLMSDGLRRLSGNEYVLSTKNTQMVSSNIITPISLDDVPPRIAR
gi|14248761| ILRITELYSPQFGAKDDDPHANDLVGGLMSDGLRRLSGNEYVLSTKNTQMVSSNIITPISLDDVPPRIAR
gi|16417190| ILRITELYSPQFGAKDDDPHANDLVGGLMSDGLRRLSGNEYVLSTKNTQMVSSNIITPISLDDVPPRIAR
gi|17477753| ILRITELYSPQFGAKDDDPHANDLVGGLMSDGLRRLSGNEYVLSTKNTQMVSSNIITPISLDDVPPRIAR
gi|16417192| ILRITELYSPQFGAKDDDPHANDLVGGLMSDGLRRLSGNEYVLSTKNTQMVSSNIITPISLDDVPPRIAR
gi|5921805|  ILRITELYSPQFGAKDDDPHANDLVGGLMSDGLRRLSGNEYVLSTKNTQMVSSNIITPISLDDVPPRIAR 500       510       520       530       540       550       560
             ....|....|....|....|....|....|....|....|....|....|....|....|....|....|
NOV10        AMENEEYWDFDIFELEAATHNRPLIYLGLKMFARFGICEFLHCSESTLRSWLQIIEANYHSSNPYHNSTR
gi|14248761| AMENEEYWDFDIFELEAATHNRPLIYLGLKMFARFGICEFLHCSESTLRSWLQIIEANYHSSNPYHNSTR
gi|16417190| AMENEEYWDFDIFELEAATHNRPLIYLGLKMFARFGICEFLHCSESTLRSWLQIIEANYHSSNPYHNSTR
gi|17477753| AMENEEYWDFDIFELEAATHNRPLIYLGLKMFARFGICEFLHCSESTLRSWLQIIEANYHSSNPYHNSTR
gi|16417192| AMENEEYWDFDIFELEAATHNRPLIYLGLKMFARFGICEFLHCSESTLRSWLQIIEANYHSSNPYHNSTR
gi|5921805|  AMENEEYWDFDIFELEAATHNRPLIYLGLKMFARFGICEFLHCSESTLRSWLQIIEANYHSSNPYHNSTR 570       580       590       600       610       620       630
             ....|....|....|....|....|....|....|....|....|....|....|....|....|....|
NOV10        SADVLHATAYFLSKERIKETLDPIDEVAALIAATIHDVDHPGRTNSFLCNAGSELAILYNDTAVLESHHA
gi|14248761| SADVLHATAYFLSKERIKETLDPIDEVAALIAATIHDVDHPGRTNSFLCNAGSELAILYNDTAVLESHHA
gi|16417190| SADVLHATAYFLSKERIKETLDPIDEVAALIAATIHDVDHPGRTNSFLCNAGSELAILYNDTAVLESHHA
gi|17477753| SADVLHATAYFLSKERIKETLDPIDEVAALIAATIHDVDHPGRTNSFLCNAGSELAILYNDTAVLESHHA
gi|16417192| SADVLHATAYFLSKERIKETLDPIDEVAALIAATIHDVDHPGRTNSFLCNAGSELAILYNDTAVLESHHA
gi|5921805|  SADVLHATAYFLSKERIKETLDPIDEVAALIAATIHDVDHPGRTNSFLCNAGSELAILYNDTAVLESHHA
```

TABLE 10D-continued

Clustal W Sequence Alignment

```
                640        650        660        670        680        690        700
             ....|....|....|....|....|....|....|....|....|....|....|....|....|....|
NOV10        ALAFQLTTGDDKCNIFKNMERNDYRTLRQGIIDMVLATEMTKHFEHVNKFVNSINKPLATLEENGETDKN
gi|14248761  ALAFQLTTGDDKCNIFKNMERNDYRTLRQGIIDMVLATEMTKHFEHVNKFVNSINKPLATLEENGETDKN
gi|16417190  ALAFQLTTGDDKCNIFKNMERNDYRTLRQGIIDMVLATEMTKHFEHVNKFVNSINKPLATLEENGETDKN
gi|17477753  ALAFQLTTGDDKCNIFKNMERNDYRTLRQGIIDMVLATEMTKHFEHVNKFVNSINKPLATLEENGETDKN
gi|16417192  ALAFQLTTGDDKCNIFKNMERNDYRTLRQGIIDMVLATEMTKHFEHVNKFVNSINKPLATLEENGETDKN
gi|5921805|  ALAFQLTTGDDKCNIFKNMERNDYRTLRQGIIDMVLATEMTKHFEHVNKFVNSINKPLATLEENGETDKN 710        720        730        740        750        760        770
             ....|....|....|....|....|....|....|....|....|....|....|....|....|....|
NOV10        QEVINTMLRTPENRTLIKRMLIKCADVSNPCRPLQYCIEWAARISEEYFSQTDEEKQQGLPVVMPVFDRN
gi|14248761  QEVINTMLRTPENRTLIKRMLIKCADVSNPCRPLQYCIEWAARISEEYFSQTDEEKQQGLPVVMPVFDRN
gi|16417190  QEVINTMLRTPENRTLIKRMLIKCADVSNPCRPLQYCIEWAARISEEYFSQTDEEKQQGLPVVMPVFDRN
gi|17477753  QEVINTMLRTPENRTLIKRMLIKCADVSNPCRPLQYCIEWAARISEEYFSQTDEEKQQGLPVVMPVFDRN
gi|16417192  QEVINTMLRTPENRTLIKRMLIKCADVSNPCRPLQYCIEWAARISEEYFSQTDEEKQQGLPVVMPVFDRN
gi|5921805|  QEVINTMLRTPENRTLIKRMLIKCADVSNPCRPLQYCIEWAARISEEYFSQTDEEKQQGLPVVMPVFDRN 780        790        800        810        820
             ....|....|....|....|....|....|....|....|....|....
NOV10        TCSIPKSQISFIDYFITDMFDAWDAFVDLPDLMQHLDNNFKYWKGLDIMKLRNLRPPPE
gi|14248761  TCSIPKSQISFIDYFITDMFDAWDAFVDLPDLMQHLDNNFKYWKGLDIMKLRNLRPPPE
gi|16417190  TCSIPKSQISFIDYFITDMFDAWDAFVDLPDLMQHLDNNFKYWKGLDIMKLRNLRPPPE
gi|17477753  TCSIPKSQISFIDYFITDMFDAWDAFVDLPDLMQHLDNNFKYWKGLDIMKLRNLRPPPE
gi|16417192  TCSIPKSQISFIDYFITDMFDAWDAFVDLPDLMQHLDNNFKYWKGLDIMKLRNLRPPPE
gi|5921805|  TCSIPKSQISFIDYFITDMFDAWDAFVDLPDLMQHLDNNFKYWKGLDIMKLRNLRPPPE
```

Tables 10E, 10F and 10G list the domain description from DOMAIN analysis results against NOV10. This indicates that the NOV10 sequence has properties similar to those of other proteins known to contain these domains.

TABLE 10E

Domain Analysis of NOV10 gnl|Pfam|pfam00233, PDEase, 3'5'-cyclic nucleotide phosphodiesterase.
(SEQ ID NO:156)
CD-Length = 240 residues, 99.6% aligned
Score = 202 bits (514), Expect = 6e-53

```
Query:  555 YHNSTHSADVLHATAYFLSKERIKETLDPIDEVAALIAATIHDVDHPGRTNSFLCNAGSE  614
            |||  |+ ||      |      +   |  ++ +| + ||  |||||  |   |||  + ||
Sbjct:    1 YHNWRHAFDVTQTTHLLLLTLALDRYLTDLEILALVFAAACHDVDHRGTNNSFQIQSKSE   60

Query:  615 LAILYNDTAVLESHHAALAFQLTTGDDKCNIFKNMERNDYRTLRQGIIDMVLATEMTKHF  674
            |||||||  +|||+||   +|   |++|||| |+ + |++|||  +|+|+|||+|+ ||
Sbjct:   61 LAILYNDESVLENHHLAQGIKLLQ-DEECNIFINLSKKDFQTLRDLVIEMILATDMSLHF  119

Query:  675 EHVNKFVNSINKPLATLEENGETDKNQEVINTMLRTPENRTLIKRMLIKCADVSNPCRPL  734
              +  +                     ++  ||  ++ |+ +++ ||+|||  +
Sbjct:  120 QKEKRLKTM---------------VEQKKTYMLDNQTHKILLMSLIMTAADLSNPTKSW  163

Query:  735 QYCIEWAARISEEYFSQTDEEKQQGLPVVMPVFDRNTCSIPKSQISFIDYFITDMFDAWD  794
            ||   |  ||+|   |  |++  |||    |+ || +  +|||||  ||||+ +   +|
Sbjct:  164 SVHRRWAELIMEEFFDQGDLERELGLP-PSPMCDRTSAYVPKSQIGFIDRIVEPIFKLLA  222

Query:  795 AFV--DLPDLMQHLDNN                                            809
             |+   |+   +++|
Sbjct:  223 DVTEKDIIPLLDRIEDN                                            239
```

TABLE 10F

Domain Analysis of NOV10 gnl|Pfam|pfam00989, PAS, PAS domain. CAUTION. This family does not currently match all known examples of PAS domains. PAS motifs appear in archaea, eubacteria and eukarya. Probably the most surprising identification of a PAS domain was that in EAG-like K+-channels. (SEQ ID NO:157)
CD-Length = 65 residues, 87.7% aligned
Score = 40.8 bits (94), Expect = 3e-04

```
Query:  221 LENSEDAIEITSEDRFIQYANPAFETTMGYQSGELIGKELGEVPINEKKADLLDTIN  277
            ||+  | |  + ||  |||  |  |   |+||| ++     | | + +
Sbjct:    7 LESLPDPIFVVDEDGRILYWNAAAEELTGLSREEVIGKSLLDLVHEEDLARVREILQ   63
```

TABLE 10G

Domain Analysis of NOV10

```
gnl Smart|smart00091, PAS, PAS domain; PAS motifs appear in archaea,
eubacteria and eukarya. Probably the most surprising identification of
a PAS domain was that in EAG-like K+-channels. (SEQ ID NO:158)
CD-Length = 67 residues, 92.5% aligned
Score = 37.4 bits (85), Expect = 0.003
Query:  220 ALENSEDAIEITSEDRFIQYANPAFETTMGYQSGELIGKELGEVPINEKKADLLDTINSC  279
            ||+   | + +    |   | ||||| |   +||    ||||| | |+    | + +| + +
Sbjct:    6 ILESLPDGVFVLDLDGRILYANPAAEELLGYSPEELIGKSLLELIHPEDREELQERLQRL   65

Query:  280 IR  281
            +
Sbjct:   66 LS  67
```

The NOV10 nucleic acid of the invention encoding a High-Affinity CAMP Specific and IBMX-Insensitive-like protein includes the nucleic acid whose sequence is provided in Table 10A, or a fragment thereof. The invention also includes a mutant or variant nucleic acid any of whose bases may be changed from the corresponding base shown in Table 10A while still encoding a protein that maintains its High-Affinity CAMP Specific and IBMX-Insensitive-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 1% of the residues may be so changed.

The NOV10 protein of the invention includes the High-Affinity CAMP Specific and IBMX-Insensitive-like protein whose sequence is provided in Table 10B. The invention also includes a mutant or variant protein any of whose residues may be changed from the corresponding residue shown in Table 10B while still encoding a protein that maintains its High-Affinity CAMP Specific and IBMX-Insensitive-like activities and physiological functions, or a functional fragment thereof. In the mutant or variant protein, up to about 1% of the bases may be so changed.

The NOV10 nucleic acids and proteins of the invention are useful in potential diagnostic and therapeutic applications implicated in various diseases and disorders described below and/or other pathologies. For example, the compositions of the present invention will have efficacy for treatment of patients suffering from: Cardiomyopathy, Atherosclerosis, Hypertension, Congenital heart defects, Aortic stenosis, Atrial septal defect (ASD), Atrioventricular (A-V) canal defect, Ductus arteriosus, Pulmonary stenosis, Subaortic stenosis, Ventricular septal defect (VSD), valve diseases, Tuberous sclerosis, Scleroderma, Obesity, Transplantation, Endometriosis, Fertility, Systemic lupus erythematosus, Autoimmune disease, Asthma, Emphysema, Scleroderma, allergy, Diabetes, Autoimmune disease, Renal artery stenosis, Interstitial nephritis, Glomerulonephritis, Polycystic kidney disease, Systemic lupus erythematosus, Renal tubular acidosis, IgA nephropathy, Hypercalceimia, Lesch-Nyhan syndrome and other diseases, disorders and conditions of the like.

NOV10 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV10 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV11

A disclosed NOV11 nucleic acid of 6524 nucleotides (also referred to as CG57337-01) encoding a novel KIAA0216-like protein is shown in Table 11A. An open reading frame was identified beginning with an ATG initiation codon at nucleotides 485–487 and ending with a TAG codon at nucleotides 5273–5275. Putative untranslated regions upstream from the intitation codon and downstream from the termination codon are underlined in Table 11A, and the start and stop codons are in bold letters.

TABLE 11A

NOV11 Nucleotide Sequence (SEQ ID NO:41)

<u>AGTCTCCTTGCTCTGGGCTGCTCCAGGCCAGGCCATGCGGAAAGTGTGTTGTTATGAGGATTCAATGAGGAGA</u>

<u>CCTGTATGAAGTGCCTTCCCCTGTGCCTGGCTCATAGCGAAAACAGAAGAACAGATTGCAGCAGAAGAGGCCT</u>

<u>GGAATGAGACGGAGAAGGTGTGGCTGGTCCATAGGGACGGCTTCTCACTGGCCAGTCAACTCAAATCTGAGGA</u>

TABLE 11A-continued

NOV11 Nucleotide Sequence

<u>GCTCAACTTGCCTGAGGGGAAGGTGCGTGTGAAGCTGGACCACGATGGGGCCATCCTGGATGTGGATGAGGAT</u>

<u>GACGTTGAGAAGGCTAATGCTCCCTCCTGCGACCGTCTGGAGGATCTGGCCTCACTGGTGTACCTCAATGAGT</u>

<u>CCAGCGTCCTGCACACCTTGCGCCAGCGCTATGGCGCTAGCCTGCTGCACACGTATGCTGGCCCCAGCCTGCT</u>

<u>GGTTCTTGGCCCCGTGGGGCCCCTGCTGTGTACTCTGAGAAGGTG</u>ATGCACATGTTCAAGGGTTGTCGGCGG

GAGGACATGGCACCCCACATCTATGCAGTGGCCCAGACCGCATACAGGGCGATGCTGATGAGCCGTCAGGATC

AGTCAATCATCCTCCTGGGCAGTAGTGGCAGTGGCAAGACCACCAGCTGCCAGCATCTGGTGCAGTACCTGGC

CACCATCGCGGGCATCAGCGGGAACAAGGTGTTTTCTGTGGAGAAGTGGCAGGCTCTGTACACCCTCCTGGAA

GCCTTTGGGAACAGCCCCACCATCATTAATGGCAATGCCACCCGCTTCTCCCAGATCCTCTCCCTGGACTTTG

ACCAAGCTGGCCAGGTGGCCTCAGCCTCCATTCAGACAATGCTTCTGGAGAAGCTGCGTGTGGCTCGGCGCCC

AGCCAGTGAAGCCACATTCAACGTCTTCTACTACCTGCTGGCCTGTGGGGATGGCACCCTCAGGACAGAGCTC

CACCTCAACCACTTGGCAGAGAACAATGTGTTTGGGATTGTGCCACTGGCCAAGCCTGAGGAAAAGCAGAAGG

CAGCTCAGCAGTTTAGTAAGCTGCAGGCGGCCATGAAGGTGCTGGGCATCTCCCCCGATGAACAGAAGGCCTG

CTGGTTCATTCTGGCTGCCATCTACCACCTGGGGGCTGCGGGAGCCACCAAAGAAGCTGCTGAAGCTGGGCGC

AAGCAGTTTGCCCGCCATGAGTGGGCCCAGAAGGCTGCGTACCTACTGGGCTGCAGCCTGGAGGAGCTGTCCT

CAGCCATCTTCAAGCACCAGCACAAGGGTGGCACCCTGCAGCGCTCCACCTCCTTCCGCCAGGGCCCCGAGGA

GAGTGGCCTGGGAGATGGGACAGGCCCGAAACTGAGTGCACTGGAGTGCCTTGAGGGCATGGCGGCCGGCCTC

TACAGCGAGCTCTTCACCCTTCTCGTCTCCCTGGTGAATAGGGCTCTCAAGTCCAGCCAGCACTCACTCTGCT

CCATGATGATTGTCGACACCCCGGGCTTCCAGAACCCTGAGCAGGGTGGGTCAGCCCGCGGAGCCTCCTTTGA

GGAGCTGTGCCACAACTACACCCAAGACCGGCTGCAGAGGCTCTTCCACGAGCGCACCTTCGTGCAGGAGTTG

GAAAGATACAAGGAGGAGAACATCGAGCTGGCGTTTGACGACTTGGAACCCCCCACGGATGACTCTGTGGCTG

CTGTGGACCAGGCCTCCCATCAGTCCCTGGTCCGCTCGCTGGCCCGCACAGACGAGGCGAGGGCCTGCTCTG

GCTATTGGAAGAGGAGGCTCTGGTGCCAGGGGCCAGTGAGGACACCCTCCTGGAGCGCCTTTTCTCCTATTAT

GGCCCCCAGGAAGGTGACAAAAAAGGCCAAAGCCCCCTTCTGCACAGCAGCAAACCACACCACTTTCTCCTGG

GCCACAGCCATGGCACCAACTGGGTAGAGTACAATGTGACTGGCTGGCTGAACTACACCAAGCAGAACCCAGC

CACCCAGAATGTCCCCCGGCTCCTGCAGGACTCCCAGAAAAAAATCATCAGCAACCTGTTTCTGGGCCGCGCA

GGCAGTGCCACGGTGCTCTCTGGCTCCATCGCGGGCCTGGAGGGCGGCTCGCAGCTGGCACTGCGCCGGGCCA

CCAGCATGCGGAAAACCTTTACCACAGGCATGGTGGCTGTCAAAAAGAAGTCACTGTGCATCCAGATGAAGCT

ACAGGTGGACGCCCTCATCGACACCATCAAGAAGTCAAAGCTGCATTTTGTGCACTGCTTCCTGCCTGTAGCT

GAGGGCTGGGCTGGGGAGCCCCGTTCCGCCTCCTCCCGCCGAGTCAGCAGCAGCAGTGAGCTGGACCTGCCCT

CGGGAGACCACTGCGAGGCTGGGCTCCTGCAGCTCGACGTGCCCCTGCTCCGCACCCAGCTCCGCGGCTCCCG

CCTGCTCGATGCCATGCGCATGTACCGCCAAGGTTACCCTGACCACATGGTGTTTTCCGAGTTCCGCCGCCGC

TTTGATGTCCTGGCCCCGCACCTGACCAAGAAACACGGGCGTAACTACATCGTGGTGGATGAAAGGCGGGCAG

TGGAGGAGCTGCTGGAGTGCTTGGATCTGGAGAAGAGCAGCTGCTGCATGGGCCTGAGCCGGGTGTTCTTCCG

GGCGGGCACCTTGGCACGGCTGGAGGAGCAGCGGGATGAACAAACCAGCAGGAACCTAACCCTGTTCCAAGCA

GCCTGCAGGGGCTACCTGGCCCGCCAGCACTTCAAGAAGAGAAAGATCCAGGACCTGGCCATTCGCTGTGTAC

AGAAGAACATCAAGAAGAACAAAGGGGTGAAGGACTGGCCCTGGTGGAAGCTTTTTACCACAGTGAGGCCCCT

CATCGAAGTACAGCTGTCAGAGGAGCAGATCCGGAACAAAGACGAGGAGATCCAGCAGCTGCGGAGCAAGCTC

GAGAAGGCGGAGAAGGAGAGGAACGAGCTGCGGCTCAACAGTGACCGGCTGGAGAGCCGGATCTCAGAGCTGA

CATCGGAGCTGACAGATGAGCGTAACACAGGAGAGTCCGCCTCCCAGCTGCTGGACGCGGAGACAGCAGAGAG

TABLE 11A-continued

NOV11 Nucleotide Sequence

GCTCCGGGCTGAGAAGGAGATGAAGGAACTGCAGACCCAGTACGATGCACTGAAGAAGCAGATGGAGGTTATG

GAAATGGAGGTGATGGAGGCCCGTCTCATCCGGGCAGCGGAGATCAACGGGGAAGTGGATGATGATGATGCAG

GTGGCGAGTGGCGGCTGAAGTATGAGCGGGCTGTGCGGGAGGTGGACTTCACCAAGAAACGGCTCCAGCAGGA

GTTTGAGGACAAGCTGGAGGTGGAGCAGCAGAACAAGAGGCAGCTGGAACGGCGGCTCGGGGACCTGCAGGCA

GATAGTGAGGAGAGTCAGCGGGCTCTGCAGCAGCTCAAGAAGAAGTGCCAGCGACTGACGGCTGAGCTGCAAG

ACACCAAGCTGCACCTGGAGGGCCAGCAGGTCCGCAACCACGAACTGGAGAAGAAGCAGAGGAGGTTTGACAG

TGAGCTCTCGCAGGCACATGAGGAGGCCCAGCGGGAGAAGCTGCAGCGGGAGAAGCTGCAGCGGGAGAAGGAC

ATGCTCCTCGCTGAGGCTTTCAGCCTGAAGCAGCAACTAGAGGAAAAAGACATGGACATTGCAGGGTTCACCC

AGAAGGTTGTGTCTCTAGAGGCAGAGCTCCAGGACATTTCTTCCCAAGAGTCCAAGGATGAGGCTTCTCTGGC

CAAGGTCAAGAAACAGCTCCGGGACCTGGAGGCCAAAGTCAAGGATCAGGAAGAAGAGCTGGATGAGCAGGCA

GGGACCATCCAGATGCTGGAACAGGCCAAGCTGCGTCTGGAGATGGAGATGGAGCGGATGAGACAGACCCATT

CTAAGGAGATGGAGAGTCGGGATGAGGAGGTGGAGGAGGCCCGGCAGTCGTGTCAGAAGAAGTTAAAACAGAT

GGAGGTGCAGCTAGAGGAAGAGTATGAGGACAAGCAGAAGGTTCTGCGAGAGAAGCGGGAGCTGGAGGGCAAG

CTCGCCACCCTCAGCGACCAGGTGAACCGGCGGGACTTTGAGTCAGAGAAGCGGCTGCGGAAGGACCTGAAGC

GCACCAAGGCCCTGCTGGCAGATGCCCAGCTCATGCTGGACCACCTGAAGAACAGTGCTCCCAGCAAGCGAGA

GATTGCCCAGCTCAAGAACCAGCTGGAGGAGTCAGAGTTCACCTGTGCGGCAGCCGTGAAAGCACGGAAAGCA

ATGGAGGTGGAGATCGAAGACCTGCACCTGCAGATTGATGACATCGCCAAAGCCAAGACAGCGCTGGAGGAGC

AGCTGAGCCGCCTTCAGCGTGAGAAGAATGAGATCCAGAACCGGCTGGAGGAAGATCAGGAAGACATGAACGA

ATTGATGAAGAAGCACAAGGCTGCCGTGGCTCAGGCTTCCCGGGACCTGGCTCAGATAAATGATCTCCAAGCT

CAGCTAGAAGAAGCCAACAAAGAGAAGCAGGAGCTGCAGGAGAAGCTACAAGCCCTCCAGAGCCAGGTGGAGT

TCCTGGAGCAGTCCATGGTGGACAAGTCCCTGGTGAGCAGGCAGGAAGCTAGGATACGGGAGATGGAGCACG

CCTGGAGTTTGAAAGGACGCAAGTGAAACGGCTGGAGAGCCTGGCTAGCCGTCTCAAGGAAAACATGGAGAAG

CTGACTGAGGAGCGGGATCAGCGCATTGCAGCCGAGAACCGGGAGAAGGAACAGAACAAGCGGCTACAGAGGC

AGCTCCGGGACACCAAGGAGGAGATGGGCGAGCTTGCCAGGAAGGAGGCCGAGGCGAGCCGCAAGAAGCACGA

ACTGGAGATGGATCTAGAAAGCCTGGAGGCTGCTAACCAGAGCCTGCAGGCTGACCTAAAGTTGGCATTCAAG

CGCATCGGGGACCTGCAGGCTGCCATTGAGGATGAGATGGAGAGTGATGAGAATGAGGACCTCATCAACAGTT

TGCAGGACATGGTGACAAAGTATCAGAAAAGAAAGAATAAACTTGAGGGAGACTCTGATGTGGACTCGGAGCT

GGAGGACCGTGTTGACGGGGTCAAGTCCTGGTTGTCAAAAAACAAGGGACCTTCCAAGGCAGCTTCTGATGAT

GGCAGCTTAAAGAGTTCCAGCCCCACCAGCTACTGGAAGTCCCTTGCCCCTGATCGGTCAGATGATGAGCACG

ACCCTCTCGACAACACCTCCAGACCGCGATACTCCCACAGTTATCTGAGTGACAGCGACACAGAGGCCAAGCT

GACGGAGACTAACGCATAGCCCAGGGGAGTGGTTGGCAGCCCTCTCACCCCAGGGCCTGTGGCTGCCTGGGCA

CCTCTCCCAGGAAGTGGTGGGGCACCGGTCTCCCCCACCCGACTGCTGATCTGCATGGGAAACACCCTGACCT

TCTTCTGTCAGGGGCACTTTCCAGGCTATGGGTGTCTGATGTCTCCACGTGGAAGAGGTGGGGGAAAGAGGAG

TTTCTGAAGAGAACTTTTTGCTCCTCTGTCTCAAAATGCCAGACTCTTGGCTTCTACCCTGTGTCACCGTGGG

CAGTGGCAGGTGGCCTGGCACTGCATGGAGCCAGCACGTTGACCTCCCTCTCAGCTCCCTGCTCAGGGACGGT

GGACAGGTTGCCTACTGGGACACTCTAGGTTGCTGGGTCCATGGGGAGGATTGGGGAGGAGAAGCAGTGCCT

TCCCTCTCGTGTGGGTGGGGCTCTCTCTTCTTGGTGCCTGCTGTCTTTCTACTTTTTAATTTAAATACCCA

ACCTCTCCATCACAGCTGCATCCCTGAGAGTGGGAGGGGGCTGTAGTGGTAGCTGGGGCTCCCAAGAACGACT

TABLE 11A-continued

NOV11 Nucleotide Sequence

CGGGAATGTCATCTCCATCTTCACCCTTCAGAGAGCAGTCCTTTCTCTGTGCAGCTGGAGACGCTGGTGAGGA

GAGCCGGGTCCAGGTTCTTAAGAATGAGGTGCGGAGGGGCTCTCCGGTGCTGCTGGGCTGGGTTGAGCAAGCC

TACGCAGACAAGTGTGTGTGTGGACCATCCGCACCTCCAGCCCCCACCCCACCCTCTTTGTCTCAGCGTGTTA

TGTGCAATGACCTATTTAAGGTAAACCCATTCCAACTACAGCAGTTCAGGGCTGATCCAAGCACTGCCTCCCT

CCTGCTCTGTCCAGGTGGTCTGGACCATAAACTCAACTTGAGAGGGAAGGCTTGGGGTTGAGGACTTGTGATC

AGAAAAACTGAAGATGGAAGTTTTGGCCGGTGCTCATTAGACATGAGTCCTCACTCTGTGTCCTGAGCCCGTG

TCATTCTTCCAACCTCCCTGCCCCCACACACTTATCCCAGACACAACACCATGTGGTCTGGAGGTCCCAGCCC

CCACCCTAAAAAGGTTATCCCTGAGAACTCCACCAGACTTGGGAGCCCAAGTGCAGTGCCTGGTGCTGCTCCC

ATCTGCCGCCCCCCTTCTCTCCTGCAATTGGTTTGTACTCACTGGGCTGTGCTCTCCCCTGTTTACCCGATGT

ATGGAAATAAAGGCCCTTTTCCTCCTG

The NOV11 nucleic acid was identified on chromosome 17 and has 4969 of 4979 bases (99%) identical to a gb:GENBANK-ID:D86970|acc:D86970.1 mRNA from *Homo sapiens* (Human mRNA for KIAA0216 gene, complete cds) (E=0.0).

A disclosed NOV11 polypeptide (SEQ ID NO:42) encoded by SEQ ID NO:41 is 1596 amino acid residues and is presented using the one-letter code in Table 11B. Signal P, Psort and/or Hydropathy results predict that NOV11 contains a signal peptide and is likely to be localized to the nucleus with a certainty of 0.9800. Although SignalP, Psort and/or hydropathy suggest that the NOV11 protein may be localized in the nucleus, the NOV11 protein is similar to the myosin family, some members of which are expected to have intracellular sub-cellular localization (Trends Cell Biol April 1998; 8(4):138–41). Therefore it is likely that NOV11 is available at the same sub-cellular localization and hence accessible to a diagnostic probe and for various therapeutic applications.

TABLE 11B

Encoded NOV11 protein sequence (SEQ ID NO:42)

MHMFKGCRREDMAPHIYAVAQTAYRAMLMSRQDQSIILLGSSGSGKTTSCQHLVQYLATIAGISGNKVFSVE

KWQALYTLLEAFGNSPTIINGNATRFSQILSLDFDQAGQVASASIQTMLLEKLRVARRPASEATFNVFYYLL

ACGDGTLRTELHLNHLAENNVFGIVPLAKPEEKQKAAQQFSKLQAAMKVLGISPDEQKACWFILAAIYHLGA

AGATKEAAEAGRKQFARHEWAQKAAYLLGCSLEELSSAIFKMQHKGGTLQRSTSFRQGPEESGLGDGTGPKL

SALECLEGMAAGLYSELFTLLVSLVNRALKSSQHSLCSMMIVDTPGFQNPEQGGSARGASFEELCHNYTQDR

LQRLFHERTFVQELERYKEENIELAFDDLEPPTDDSVAAVDQASHQSLVRSLARTDEARGLLWLLEEEALVP

GASEDTLLERLFSYYGPQEGDKKGQSPLLHSSKPHHFLLGHSHGTNWVEYNVTGWLNYTKQNPATQNVPRLL

QDSQKKIISNLFLGRAGSATVLSGSIAGLEGGSQLALRRATSMRKTFTTGMVAVKKKSLCIQMKLQVDALID

TIKKSKLHFVHCFLPVAEGWAGEPRSASSRRVSSSSELDLPSGDHCEAGLLQLDVPLLRTQLRGSRLLDAMR

MYRQGYPDHMVFSEFRRRFDVLAPHLTKKHGRNYIVVDERRAVEELLECLDLEKSSCCMGLSRVFFRAGTLA

RLEEQRDEQTSRNLTLFQAACRGYLARQHFKKRKIQDLAIRCVQKNIKKNKGVKDWPWWKLFTTVRPLIEVQ

LSEEQIRNKDEEIQQLRSKLEKAEKERNELRLNSDRLESRISELTSELTDERNTGESASQLLDAETAERLRA

EKEMKELQTQYDALKKQMEVMEMEVMEARLIRAAEINGEVDDDDAGGEWRLKYERAVREVDFTKKRLQQEFE

DKLEVEQQNKRQLERRLGDLQADSEESQRALQQLKKKCQRLTAELQDTKLHLEGQQVRNHELEKKQRRFDSE

LSQAHEEAQREKLQREKLQREKDMLLAEAFSLKQQLEEKDMDIAGFTQKVVSLEAELQDISSQESKDEASLA

KVKKQLRDLEAKVKDQEEELDEQAGTIQMLEQAKLRLEMEMERMRQTHSKEMESRDEEVEEARQSCQKKLKQ

MEVQLEEEYEDKQKVLREKRELEGKLATLSDQVNRRDFESEKRLRKDLKRTKALLADAQLMLDHLKNSAPSK

REIAQLKNQLEESEFTCAAAVKARKAMEVEIEDLHLQIDDIAKAKTALEEQLSRLQREKNEIQNRLEEDQED

TABLE 11B-continued

Encoded NOV11 protein sequence

MNELMKKHKAAVAQASRDLAQINDLQAQLEEANKEKQELQEKLQALQSQVEFLEQSMVDKSLVSRQEARIRE

METRLEFERTQVKRLESLASRLKENMEKLTEERDQRIAAENREKEQNKRLQRQLRDTKEEMGELARKEAEAS

RKKHELEMDLESLEAANQSLQADLKLAFKRIGDLQAAIEDEMESDENEDLINSLQDMVTKYQKRKNKLEGDS

DVDSELEDRVDGVKSWLSKNKGPSKAASDDGSLKSSSPTSYWKSLAPDRSDDEHDPLDNTSRPRYSHSYLSD

SDTEAKLTETNA

The NOV11 amino acid sequence has 1579 of 1596 amino acid residues (98%) identical to, and 1581 of 1596 amino acid residues (99%) similar to, the 1581 amino acid residue ptnr:SPTREMBL-ACC:Q92614 protein from *Homo sapiens* (Human) (MYELOBLAST KIAA0216) (E=0.0). The NOV11 amino acid sequence has additional 15 internal amino acids, when compared to ptnr:SPTREMBL-ACC:Q92614 protein from *Homo sapiens* (Human) (MYELOBLAST KIAA0216).

NOV11 is expressed in at least the following tissues: adrenal gland, bone marrow, brain—amygdala, brain—cerebellum, brain—hippocampus, brain—substantia nigra, brain—thalamus, brain—whole, fetal brain, fetal kidney, fetal liver, fetal lung, heart, kidney, lymphoma—Raji, mammary gland, pancreas, pituitary gland, placenta, prostate, salivary gland, skeletal muscle, small intestine, spinal cord, spleen, stomach, testis, thyroid, trachea and uterus, aorta, ascending colon, bronchus, cervix, colon, coronary artery, epidermis, gall bladder, hypothalamus, lung, lymph node, lymphoid tissue, muscle, ovary, peripheral blood, pharynx, pineal gland, retina, right cerebellum, tonsils and whole organism. This information was derived by determining the tissue sources of the sequences that were included in the invention including but not limited to SeqCalling sources, Public EST sources, genomic clone sources, literature sources, and/or RACE sources.

Possible SNPs found for NOV11 are listed in Tables 11C and 11D.

TABLE 11C

SNPs

| Variant | Nucleotide Position | Base Change | Amino Acid Position | Base Change |
|---|---|---|---|---|
| 13377093 | 491 | A > G | 3 | Met > Val |
| 13377092 | 570 | T > C | 29 | Met > Thr |
| 13377091 | 1783 | G > A | Silent | N/A |
| 13377090 | 3657 | T > C | 1058 | Val > Ala |
| 13374495 | 4848 | C > T | 1455 | Ala > Val |
| 13374496 | 4939 | T > C | Silent | N/A |
| 13374497 | 4998 | A > T | 1505 | Lys > Met |
| 13374498 | 5114 | A > G | 1544 | Ser > Gly |

TABLE 11D

SNPs

| Consensus Position | Depth | Base Change | PAF |
|---|---|---|---|
| 455 | 24 | C > T | 0.083 |
| 546 | 27 | T > C | 0.074 |
| 605 | 27 | A > T | 0.074 |
| 721 | 27 | A > G | 0.074 |
| 753 | 26 | C > T | 0.077 |
| 891 | 13 | C > T | 0.154 |

NOV11 has homology to the amino acid sequences shown in the BLASTP data listed in Table 11E.

TABLE 11E

BLAST results for NOV11

| Gene Index/ Identifier | Protein/Organism | Length (aa) | Identity (%) | Positives (%) | Expect |
|---|---|---|---|---|---|
| gi|17978507|ref|NP_510880.1| (NM_078471) | TGFB1-induced anti-apoptotic factor 1, isoform 1; TGF-beta-1-induced antiapoptotic factor 1; molecule associated with Jak-3 N-terminal [*Homo sapiens*] | 1581 | 1511/1596 (94%) | 1513/1596 (94%) | 0.0 |
| gi|7416032|dbj|BAA93660.1| (AB026497) | myosin containing PDZ domain [*Mus musculus*] | 2035 | 1425/1596 (89%) | 1469/1596 (91%) | 0.0 |
| gi|18587640|ref|XP_031413.3| (XM_031413) | similar to TGFB1-induced anti-apoptotic factor 1, isoform 1; | 1355 | 1257/1318 (95%) | 1259/1318 (95%) | 0.0 |

TABLE 11E-continued

BLAST results for NOV11

| Gene Index/<br>Identifier | Protein/Organism | Length<br>(aa) | Identity<br>(%) | Positives<br>(%) | Expect |
|---|---|---|---|---|---|
| | TGF-beta-1-<br>induced<br>antiapoptotic<br>factor 1;<br>molecule<br>associated with<br>Jak-3 N-terminal<br>[Homo sapiens] | | | | |
| gi|15718364|emb|CAC<br>70712.1| (AJ310931) | myosin heavy<br>chain [Homo<br>sapiens] | 2566 | 651/1530<br>(42%) | 996/1530<br>(64%) | 5e-97 |
| gi|18250662|emb|CAC<br>70714.2| (AJ310932) | myosin heavy<br>chain [Homo<br>sapiens] | 2566 | 651/1530<br>(42%) | 996/1530<br>(64%) | 2e-72 |

The homology of these sequences is shown graphically in the ClustalW analysis shown in Table 11F.

TABLE 11F

```
                        Clustal W Sequence Alignment

1) NOV11 (SEQ ID NO:42)
2) gi|7978507|refNP_510880.1| (NM_078471) TGFB1-induced anti-apoptotic 1, isoform 1;
TGF-beta-1-induced antiapoptotic factor 1; molecule associated with Jak-3
N-terminal [Homo sapiens] (SEQ ID NO:159)
3) gi 7416032|dbj|BAA93660.1| (AB026497) myosin containing PDZ domain [Mus musculus]
(SEQ ID NO:160)
4) gi|18587640|refXP_031413.3| (XM_031413) similar to TGFB1-induced anti-apoptotic
factor 1, isoform 1; TGF-beta-1-induced antipoptotic factor 1; molecular associated
with Jak-3 N-terminal [Homo sapiens] (SEQ ID NO:161)
5) gi 15718364|emb CAC70712.1| (AJ310931) myosin heavy chain [Homo sapiens]
(SEQ ID NO:162)
6) gi|18250662|emb|CAC70714.2| (AJ310932) myosin heavy chain [Homo sapiens]
(SEQ ID NO:163)

10        20        30        40        50        60        70
                ....|....|....|....|....|....|....|....|....|....|....|....|....|....|
NOV11           ----------------------------------------------------------------------
gi|17978507|    ----------------------------------------------------------------------
gi|7416032|     --------MFNLMKKDKDKD---------------------GGRKEKKEKKEKKERMSAAELRSLEEM
gi|18587640|    ----------------------------------------------------------------------
gi|15718364     MAISSRLALWEQKIREEDKSPPPSSPPPLFSVIPGGFIKQLVRGTEKEAKEARQRKQLAVASPEREIPEI
gi|18250662     MAXSSRLALWEQKIREEDKSPPPSSPPPLFSVIPGGFIKQLVRGTEKEAKEARQRKQLAVASPEREIPEI 80        90       100       110       120       130       140
                ....|....|....|....|....|....|....|....|....|....|....|....|....|....|
NOV11           ----------------------------------------------------------------------
gi|17978507|    ----------------------------------------------------------------------
gi|7416032|     SMRRGFFN--------------------------------LNRSSKRESKTRLEISNPIPIKVASGSDLH
gi|18587640|    ----------------------------------------------------------------------
gi|15718364     SISQPNSKSSSGTRSGSQQISQDDQSSSPGSSDILGKESEGSRSPDPEQMTSINGEKAQELGSSATPTKK
gi|18250662     SISQPNSKSSSGTRSGSQQISQDDQSSSPGSSDILGKESEGSRSPDPEQMTSINGEKAQELGSSATPTKK 150       160       170       180       190       200       210
                ....|....|....|....|....|....|....|....|....|....|....|....|....|....|
NOV11           ----------------------------------------------------------------------
gi|17978507|    ----------------------------------------------------------------------
gi|7416032|     LTDIDSDSNRGSIILDSGHLSTASSSDDLKGEEGSFRGSVLQRAAKFGSLAKQNSQMIVKRFSFSQRSRD
gi|18587640|    ----------------------------------------------------------------------
gi|15718364     TVPFKRGVRRGDVLLMVAKLDPDSAKPEKTHPHDAPPCKTSPPATDTGKEKKGETSRTPCGSQASTEILA
gi|18250662     TVPFKRGVRRGDVLLMVAKLDPDSAKPEKTHPHDAPPCKTSPPATDTGKEKKGETSRTPCGSQASTEILA 220       230       240       250       260       270       280
                ....|....|....|....|....|....|....|....|....|....|....|....|....|....|
NOV11           ----------------------------------------------------------------------
gi|17978507|    ----------------------------------------------------------------------
gi|7416032|     ESASETSTPSEHSAAPSPQVEVRTLEGQLMQHPGLGIPRPGPRSRVPELVTKRFPADLRLPALVPPPPPA
gi|18587640|    ----------------------------------------------------------------------
gi|15718364     PKAEKTRTGGLGDPGQGTVALKKGEEGQSIVGKGLGTPKTTELKEAEPQGKDRQGTRPQAQGPGEGVRPG
gi|18250662     PKAEKTRTGGLGDPGQGTVALKKGEEGQSIVGKGLGTPKTTELKEAEPQGKDRQGTRPQAQGPGEGVRPG
```

TABLE 11F-continued

Clustal W Sequence Alignment

```
                290       300       310       320       330       340       350
              ....|....|....|....|....|....|....|....|....|....|....|....|....|
NOV11         ------------------------------------------------------------------
gi|17978507|  ------------------------------------------------------------------
gi|7416032|   LRELE------------------------LQRRPTGDFGFSLRRTTMLD-----RAPEGQAYRRVVHFAE
gi|18587640|  ------------------------------------------------------------------
gi|15718364|  KAEKEGAEPTNTVEKGNVSKDVGSEGKHVRPQIPGRKWGGFLGRRSKWDGPQNKKDKEGVLLSKAEKTGE
gi|18250662|  KAEKEGAEPTNTVEKGNVSKDVGSEGKHVRPQIPGRKWGGFLGRRSKWDGPQNKKDKEGVLLSKAEKTGE 360       370       380       390       400       410       420
              ....|....|....|....|....|....|....|....|....|....|....|....|....|
NOV11         ------------------------------------------------------------------
gi|17978507|  ------------------------------------------------------------------
gi|7416032|   P----------GAGTKDLALGLVPGDRLVEINGQNVENKSRDEIVEMIRQSGDSVRLKVQPIP------
gi|18587640|  ------------------------------------------------------------------
gi|15718364|  PQTQMEKTSQVQGELGDDLRMGEKAGELRSTTGKAGESWDKKEKMGQPQGKSGNAGEARSQTEKGCEAPK
gi|18250662|  PQTQMEKTSQVQGELGDDLRMGEKAGELRSTTGKAGESWDKKEKMGQPQGKSGNAGEARSQTEKGCEAPK 430       440       450       460       470       480       490
              ....|....|....|....|....|....|....|....|....|....|....|....|....|
NOV11         ------------------------------------------------------------------
gi|17978507|  ------------------------------------------------------------------
gi|7416032|   ELSELSRSWLRTGEG--------------------------------------HRREPADAKT-
gi|18587640|  ------------------------------------------------------------------
gi|15718364|  EVSTMVESPAAPGKGGWPGSRGQEAEEPCSRAGDGAGALETELEGPSQPALEKDAERPRIRKENQDGPAP
gi|18250662|  EVSTMVESPAAPGKGGWPGSRGQEAEEPCSRAGDGAGALETELEGPSQPALEKDAERPRIRKENQDGPAP 500       510       520       530       540       550       560
              ....|....|....|....|....|....|....|....|....|....|....|....|....|
NOV11         ------------------------------------------------------------------
gi|17978507|  ------------------------------------------------------------------
gi|7416032|   ----------EEQIAAEEAWYETEKVWLVHRDGFSLASQLKSEE--LSLPEGKARVKLDHDGAELDVDED
gi|18587640|  ------------------------------------------------------------------
gi|15718364|  QEEGKGGQSRDSDQAPEDRWYEAEKVWLAQKDGFTLATVLKPDEGTADLPAGRVRLWIDADKTITEVDEE
gi|18250662|  QEEGKGGQSRDSDQAPEDRWYEAEKVWLAQKDGFTLATVLKPDEGTADLPAGRVRLWIDADKTITEVDEE 570       580       590       600       610       620       630
              ....|....|....|....|....|....|....|....|....|....|....|....|....|
NOV11         ------------------------------------------------------------MHMFKG
gi|17978507|  ------------------------------------------------------------MHMFKG
gi|7416032|   DIEKANAPSCDRLEDLASLVYLNESSVLHTLRQRYGASLLHTYAGPSLLVLSTRGAPAVYSEKVMHMFKG
gi|18587640|  ------------------------------------------------------------------
gi|15718364|  HVHRANPPELDQVEDLASLISVNESSVLNTLLQRYKAQLLHTCTGPDLIVLQPRG-P---SVPSAGKVPK
gi|18250662|  HVHRANPPELDQVEDLASLISVNESSVLNTLLQRYKAQLLHTCTGPDLIVLQPRG-P---SVPSAGKVPK 640       650       660       670       680       690       700
              ....|....|....|....|....|....|....|....|....|....|....|....|....|
NOV11         CRREDMAPHIYAVAQTAYRAMLMSRQDQSIILLGSSGSGKTTSCQHLVQYLATIAGISGNKVFSVEKWQA
gi|17978507|  CRREDMAPHIYAVAQTAYRAMLMSRQDQSIILLGSSGSGKTTSCQHLVQYLATIAGISGNKVFSVEKWQA
gi|7416032|   CRREDMAPHIYAVAQTAYRAMLMSRQDQSIILLGSSGSGKTISFQHLVQYLATIAGTSGTKVFSVEKWQA
gi|18587640|  ------------------------------------------------------------------
gi|15718364|  GRRDGLPAHIGSMAQRAYWALLNQRRDQSIVALCWSGAGKTICCEQVLEHLVGMAGSVDGRVS-VEKIRA
gi|18250662|  GRRDGLPAHIGSMAQRAYWALLNQRRDQSIVALCWSGAGKTICCEQVLEHLVGMAGSVDGRVS-VEKIRA 710       720       730       740       750       760       770
              ....|....|....|....|....|....|....|....|....|....|....|....|....|
NOV11         LYTLLEAFGNSPTIINGNATRFSQILSLDFDQAGCVASASIQTMLLEKLRVARRPASEATFNVEYYLLAC
gi|17978507|  LYTLLEAFGNSPTIINGNATRFSQILSLDFDQAGCVASASIQTMLLEKLRVARRPASEATFNVEYYLLAC
gi|7416032|   LSTLLEAFGNSPTIMNGSATRFSQILSLDFDQAGCVASASIQTMLLEKLRVARRPASEATFNVEYYLLAC
gi|18587640|  ------------------------------------------------------------------
gi|15718364|  TFTVLRAFGSVSMAHSRSATRFSMVMSLDFNATGRITAAQLQTMLLEKSRVARQPEGESNFLVFSQMLAG
gi|18250662|  TFTVLRAFGSVSMAHSRSATRFSMVMSLDFNATGRITAAQLQTMLLEKSRVARQPEGESNFLVFSQMLAG 780       790       800       810       820       830       840
              ....|....|....|....|....|....|....|....|....|....|....|....|....|
NOV11         GDGTLRTELHLNHIAENNVEGIVPLAKPEEKQKAAQQFSKLQAAMKVLGISPDEQKACWFILAAIYHLGA
gi|17978507|  GDGTLRTELHLNHIAENNVEGIVPLAKPEEKQKAAQQFSKLQAAMKVLGISPDEQKACWFILAAIYHLGA
gi|7416032|   GDGTLRTELHLNHIAENNVEGIVPLAKPEEKQKAAQQFSKLQAAMKVLAISPDEQKTCWLILASIYHLGA
gi|18587640|  ------------------------MKVLGISPDEQKACWFILAAIYHLGA
gi|15718364|  LDLDLRTENHLHQMADSSSFGMGVQSKPEEKQKAAAAFAQLQGAMEMLGISESEQRAVWRVLAAIYHLGA
gi|18250662|  LDLDLRTENHLHQMADSSSFGMGVQSKPEEKQKAAAAFAQLQGAMEMLGISESEQRAVWRVLAAIYHLGA 850       860       870       880       890       900       910
              ....|....|....|....|....|....|....|....|....|....|....|....|....|
NOV11         AGATKEAAEAGRKQFARHEWAQKAAYLLGCSLEELSSAIFKHQHKGGTLQRSTSFRQGPEESGLGDG---
gi|17978507|  AGATKEAAEAGRKQFARHEWAQKAAYLLGCSLEELSSAIFKHQHKGGTLQRSTSFRQGPEESGLGDG---
gi|7416032|   AGATKEAAEAGRKQFARHEWAQKAAYLLGCSLEELSSAIFKHQLKGGTLQRSTSFRQGPEESGLGEG---
gi|18587640|  AGATKEAAEAGRKQFARHEWAQKAAYLLGCSLEELSSAIFKHQHKGGTLQRSTSFRQGPEESGLGDG---
gi|15718364|  AG----ACKVGRKQFMRFEWANYAAEALGQEYEELNTATFKHHLN----QIIQQMTFGPSRWGLEDEETS
gi|18250662|  AG----ACKVGRKQFMRFEWANYAAEALGQEYEELNTATFKHHLN----QIIQQMTFGPSRWGLEDEETS
```

TABLE 11F-continued

Clustal W Sequence Alignment

```
              920       930       940       950       960       970       980
              |         |         |         |         |         |         |
NOV11         TGPKLSALECLEGMAAGLYSELFTLLVSLVNRALKSSQHSLCSMMIVDTPGFQNFSQGGSARGASFEELC
gi|17978507|  TGPKLSALECLEGMAAGLYSELFTLLVSLVNRALKSSQHSLCSMMIVDTPGFQNFSQGGSARGASFEELC
gi|7416032|   T--KLSALECLEGMAAGLYSELFTLLISLVNRALKSSQHSLCSMMIVDTPGFQNFSWGGSARGASFEELC
gi|18587640|  TGPKLSALECLEGMAAGLYSELFTLLVSLVNRALKSSQHSLCSMMIVDTPGFQNFSQGGSARGASFEELC
gi|15718364|  SCLKMIGVDCVEGMASGLYQELFAAVVLLINRSFSSHHLSMASIMVVDSPGFQNPRHQCKDRAATFEELC
gi|18250662|  SCLKMIGVDCVEGMASGLYQELFAAVVLLINRSFSSHHLSMASIMVVDSPGFQNPRHQCKDRAATFEELC 990       1000      1010      1020      1030      1040      1050
              |         |         |         |         |         |         |
NOV11         HNYTQDRLQRLFHERTFVQELERYKEENIELAFDDLEPPTDDSVAAVDQASHQSLVRSLARTDEARGLLW
gi|17978507|  HNYTQDRLQRLFHERTFVQELERYKEENIELAFDDLEPPTDDSVAAVDQASHQSLVRSLARTDEARGLLW
gi|7416032|   HNYAQDRLQRLFHERTFEQELERYKEDNIELAFDDLEPVDDSVAAVDQASH--LVRSLAHADEARGLLW
gi|18587640|  HNYTQDRLQRLFHERTFVQELERYKEENIELAFDDLEPPTDDSVAAVDQASHQSLVRSLARTDEARGLLW
gi|15718364|  HNYAHERLQLLFYQRTFVSTLQRYQEEGYPVQFDLPDPSPGTTVAVVDQNPSQVRLPAGGGAQDARGLFW
gi|18250662|  HNYAHERLQLLFYQRTFVSTLQRYQEEGYPVQFDLPDPSPGTTVAVVDQNPSQVRLPAGGGAQDARGLFW 1060      1070      1080      1090      1100      1110      1120
              |         |         |         |         |         |         |
NOV11         LLEEEALVPGASEDTLLERLFSYYGPQEGDKKGQSPLLHSSKPHHFLLGHSHGTNWVEYNVTGWLNYTKQ
gi|17978507|  LLEEEALVPGASEDTLLERLFSYYGPQEGDKKGQSPLLHSSKPHHFLLGHSHGTNWVEYNVTGWLNYTKQ
gi|7416032|   LLEEEALVPGATEDALLDRLFSYYGPQEGDKKGQSPLLHSSKPRHFLLGHSHGTNWVEYNVAGWLNYTKQ
gi|18587640|  LLEEEALVPGASEDTLLERLFSYYGPQEGDKKGQSPLLHSSKPHHFLLGHSHGTNWVEYNVTGWLNYTKQ
gi|15718364|  VLQEEVHVEGSSDSVVLERICAAEEKKGAGTEGSSALRTCEQPLQCEIHQLGWDPVRYDITGWLHRAKP
gi|18250662|  VLQEEVHVEGSSDSVVLERICAAEEKKGAGTEGSSALRTCEQPLQCEIHQLGWDPVRYDITGWLHRAKP 1130      1140      1150      1160      1170      1180      1190
              |         |         |         |         |         |         |
NOV11         NPATQNVPRLLQDSQKKIISNLFLGRAGSATVLSGSIAGLEGGSQLALRRATSMRKTFTTGMVAVKKKSL
gi|17978507|  NPATQNVPRLLQDSQKKIISNLFLGRAGSATVLSGSIAGLEGGSQLALRRATSMRKTFTTGMVAVKKKSL
gi|7416032|   NPATQNAPRLLQDSQKKIISNLFLGRAGSATVLSGSIAGLEGGSQLALRRATSMRKTFTTGMAAVKKKSL
gi|18587640|  NPATQNAPRLLQDSQKKIISNLFLGRAGSATVLSGSIAGLEGGSQLALRRATSMRKTFTTGMAAVKKKSL
gi|15718364|  NLSALDAPQVLHQSKREELRSLFQARAKLPPVCR-AVAGLEGTSQQALCRSRMVRRTFASSIAAVRRKAP
gi|18250662|  NLSALDAPQVLHQSKREELRSLFQARAKLPPVCR-AVAGLEGTSQQALCRSRMVRRTFASSIAAVRRKAP 1200      1210      1220      1230      1240      1250      1260
              |         |         |         |         |         |         |
NOV11         CIQMKLQVDALIDTIKKSKLHFVHCFLPVAEGWAGEPRSASSRRVSSSSELDLPSGDHCEAGLLQLDVPL
gi|17978507|  CIQMKLQVDALIDTIKKSKLHFVHCFLPVAEGWAGEPRSASSRRVSSSSELDLPSGDHCEAGLLQLDVPL
gi|7416032|   CIQRKLQVDALIDTIKKSKMHFVHCFLPVAEGWPGEPRSASSRRVSSSSELDLPPGDPCEAGLLQLDVSL
gi|18587640|  CIQMKLQVDALIDTIKKSKLHFVHCFLPVAEGWAGEPRSASSRRVSSSSELDLPSGDHCEAGLLQLDVPL
gi|15718364|  CSQTKLQMDALTSMIKRSRLHFIHCLVPNPV---VESRSGQESPPPPQPGRDKPGAG----GPLALDIPA
gi|18250662|  CSQTKLQMDALTSMIKRSRLHFIHCLVPNPV---VESRSGQESPPPPQPGRDKPGAG----GPLALDIPA 1270      1280      1290      1300      1310      1320      1330
              |         |         |         |         |         |         |
NOV11         LRTQLRGSRLLDAMRMYRQGYPDHMVFSEFRRRFDVLAPHLTKKHGRNYIVVDERRAVEELLECLDLEKS
gi|17978507|  LRTQLRGSRLLDAMRMYRQGYPDHMVFSEFRRRFDVLAPHLTKKHGRNYIVVDERRAVEELLESLDLEKS
gi|7416032|   LRAQLRGSRLLDAMRMYRQGYPDHMVFSEFRRRFDVLAPHLTKKHGRNYIVVDEKRAVEELLESLDLEKS
gi|18587640|  LRTQLRGSRLLDAMRMYRQGYPDHMVFSEFRRRFDVLAPHLTKKHGRNYIVVDERRAVEELLESLDLEKS
gi|15718364|  LFVQLAGFHILEAERLHRTGYADHMGLIRFRRQFQVLDAPLLKKLMSTSEGIDERKAVEELLETLDLEKK
gi|18250662|  LFVQLAGFHILEAERLHRTGYADHMGLIRFRRQFQVLDAPLLKKLMSTSEGIDERKAVEELLETLDLEKK 1340      1350      1360      1370      1380      1390      1400
              |         |         |         |         |         |         |
NOV11         SCCMGLSRVFFRAGTLARLEEQRDEQTSRNLTLFQAACRGYLARQHFKKRKIQDLAIRCVQKNIKKNGV
gi|17978507|  SCCMGLSRVFFRAGTLARLEEQRDEQTSRKLTLFQAACRGYLARQHFKKRKIQDLAIRCVQKNIKKNGV
gi|7416032|   SCCIGLSRVFFRAGTLARLEEQRDEQTSRHLTLFQAACRGYLARQHFKKRKIQDLAIRCVQKNIKKNGV
gi|18587640|  SCCMGLSRVFFRAGTLARLEEQRDEQTSRNLTLFQAACRGYLARQHFKKRKIQDLAIRCVQKNIKKNGV
gi|15718364|  AVAVGHSQVFLKAGVLSRLEKQREKLVSQSIVLFQAACKGFLSRQEFKKLKIRRLAAQCEQKNVAVFLAV
gi|18250662|  AVAVGHSQVFLKAGVLSRLEKQREKLVSQSIVLFQAACKGFLSRQEFKKLKIRRLAAQCEQKNVAVFLAV 1410      1420      1430      1440      1450      1460      1470
              |         |         |         |         |         |         |
NOV11         KDWPWWKLFTTVRPLIEVQLSEEQIRNKDEEIQQLRSKLEKAEKERNELRLNSDRLESRISELTSELTDE
gi|17978507|  KDWPWWKLFTTVRPLIEVQLSEEQIRNKDEEIQQLRSKLEKAEKERNELRLNSDRLESRISELTSELTDE
gi|7416032|   KDWPWWKLFTTVRPLIQVQLSEEQIRNKDEEIQQLRSKLEKAEKERNELRLSSDRTRISELTSELTDE
gi|18587640|  KDWPWWKLFTTVRPLIEVQLSEEQIRNKDEEIQQLRSKLEKAEKERNELRLNSDRLESRISELTSELTDE
gi|15718364|  KDWPWWQLLGSLQPLLSATIGTEQFRAKEEETTLPRKLEKSEKLRNELRQNTDLLESKIADLTSDLADE
gi|18250662|  KDWPWWQLLGSLQPLLSATIGTEQFRAKEEETTLPRKLEKSEKLRNELRQNTDLLESKIADLTSDLADE 1480      1490      1500      1510      1520      1530      1540
              |         |         |         |         |         |         |
NOV11         RNTGESASQLLDAETAEKLRAEKEMKELQTQYDALKKQMEVMEMEVMEARLIRAAEINGEVDDDAGGEW
gi|17978507|  RNTGESASQLLDAETAEKLRAEKEMKELQTQYDALKKQMEVMEMEVMEARLIRAAEINGEVDDDAGGEW
gi|7416032|   RNTGESASQLLDAETAEKLRTEKEMKELQTQYDALKKQMEVMEMEVMEARLIRAAEINGEVDDDAGGEW
gi|18587640|  RNTGESASQLLDAETAEKLRAEKEMKELQTQYDALKKQMEVMEMEVMEARLIRAAEINGEVDDDAGGEW
gi|15718364|  RFKCLVACQVLESERAERLCAFREVQELRSKHEQVQKRIGDVNKQLEEAQQK--IQLNDLERNPTGGDEW
gi|18250662|  RFKCLVACQVLESERAERLCAFREVQELRSKHEQVQKRIGDVNKQLEEAQQK--IQLNDLERNPTGGDEW
```

TABLE 11F-continued

Clustal W Sequence Alignment

```
                1550       1560       1570       1580       1590       1600       1610
                  .    |    .    |    .    |    .    |    .    |    .    |    .    |
NOV11         RLKYERAVREVDFTKKRLQQEFEDKLEVEQQNKRQLERRLGDLQADSEESQRALQQLKKKCQRLTAELQD
gi|17978507|  RLKYERAVREVDFTKKRLQQEFEDKLEVEQQNKRQLERRLGDLQADSEESQRALQQLKKKCQRLTAELQD
gi|7416032|   RLKYERAVREVDFTKKRLQQELEDKMEVEQQSRRQLERRLGDLQADSDESQRALQQLKKKCQRLTAELQD
gi|18587640|  RLKYERAVREVDFTKKRLQQEFEDKLEVEQQNKRQLERRLGDLQADSEESQRALQQLKKKCQRLTAELQD
gi|15718364|  QMRRDCAQMENRFLRKRLQQ-CEERLDSELTARKELEQRLGELQSAYDGAKKMAHQLKRKCHHLTCDLED
gi|18250662|  QMRRDCAQMENRFLRKRLQQ-CEERLDSELTARKELEQRLGELQSAYDGAKKMAHQLKRKCHHLTCDLED 1620       1630       1640       1650       1660       1670       1680
                  .    |    .    |    .    |    .    |    .    |    .    |    .    |
NOV11         TKLHLEGQQVRNHELEKKQRRFDSELSQAHEEAQREKLQREKLQREKDMLLAEAFSLKQQLEEKDMDIAG
gi|17978507|  TKLHLEGQQVRNHELEKKQRRFDSELSQAHEEAQREKLQREKLQREKDMLLAEAFSLKQQLEEKDMDIAG
gi|7416032|   TKLHLEGQQVRNHELEKKQRRFDSELSQAHEETQREKLQREKLQREKDMLLAEAFSLKQQMEEKDLDIAG
gi|18587640|  TKLHLEGQQVRNHELEKKQRRFDSELSQAHEEAQREKLQREKLQREKDMLLAEAFSLKQQLEEKDMDIAG
gi|15718364|  TCVLLENQQSRNHELEKKQEKFDLQLAQALGESVFEKGLREKVTQENTSVRWELGQLQQQLKQKEQEASQ
gi|18250662|  TCVLLENQQSRNHELEKKQEKFDLQLAQALGESVFEKGLREKVTQENTSVRWELGQLQQQLKQKEQEASQ 1690       1700       1710       1720       1730       1740       1750
                  .    |    .    |    .    |    .    |    .    |    .    |    .    |
NOV11         FTQKVVSLEAELQDISSQESKDEASLAKVKKQLRDLEAKVKDQEEELDEQAGTIQMLEQAKLRLEMEMER
gi|17978507|  FTQKVVSLEAELQDISSQESKDEASLAKVKKQLRDLEAKVKDQEEELDEQAGTIQMLEQAKLRLEMEMER
gi|7416032|   FTQKVVSLEAELQDISSQESKDEASLAKVKKQLRDLEAKVKDQEEELDEQAGSIQMLEQAKLRLEMEMER
gi|18587640|  FTQKVVSLEAELQDISSQESKDEASLAKVKKQLRDLEAKVKDQEEELDEQAGTIQMLEQAKLRLEMEMER
gi|15718364|  LKQQVEMLQDHKRELLGSPSLGENCVAGLKKRLWKLESSALEQQKIQSQQENTIKQLEQLRQRFELEIER
gi|18250662|  LKQQVEMLQDHKRELLGSPSLGENCVAGLKKRLWKLESSALEQQKIQSQQENTIKQLEQLRQRFELEIER 1760       1770       1780       1790       1800       1810       1820
                  .    |    .    |    .    |    .    |    .    |    .    |    .    |
NOV11         MRQTHSKEMESRDEEVEEARQSCQKKLKQMEVQLEEEYEDKQKVLREKRELEGKIATLSDQVNRRDFESE
gi|17978507|  MRQTHSKEMESRDEEVEEARQSCQKKLKQMEVQLEEEYEDKQKVLREKRELEGKIATLSDQVNRRDFESE
gi|7416032|   MRQTHSKEMESRDEEVEEARQSCQKKLKQMEVQLEEEYEDKQALREKRELESKISTLSDQVNQRDFESE
gi|18587640|  MRQTHSKEMESRDEEVEEARQSCQKKLKQMEVQLEEEYEDKQKVLREKRELEGKIATLSDQVNRRDFESE
gi|15718364|  MKQMHQKDREDQREELEDVRQSCQKRLHQLEMQLEQEYEEKQMVLHEKQDLEGLIGTLCDQICHRDFDVE
gi|18250662|  MKQMHQKDREDQREELEDVRQSCQKRLHQLEMQLEQEYEEKQMVLHEKQDLEGLIGTLCDQICHRDFDVE 1830       1840       1850       1860       1870       1880       1890
                  .    |    .    |    .    |    .    |    .    |    .    |    .    |
NOV11         KRLRKDLKRTKALLADAQLMLDHLKN--SAPSKREIAQLKNQLEESEFTCAAAVKARKAMEVEIEDLHLQ
gi|17978507|  KRLRKDLKRTKALLADAQLMLDHLKN--SAPSKREIAQLKNQLEESEFTCAAAVKARKAMEVEIEDLHLQ
gi|7416032|   KRLRKDLKRTKALLADAQIMLDHLKN--NAPSKREIAQLKNQLEESEFTCAAAVKARKAMEVEIEDLHLQ
gi|18587640|  KRLRKDLKRTKALLADAQLMLDHLKN--SAPSKREIAQLKNQLEESEFTCAAAVKARKAMEVEIEDLHLQ
gi|15718364|  KRLRRDLKRTHALLSDVQLELGTMEDGKTSVSKEEIEKVHSQLEQSEAKCEEAIKTQKVLTADIESMHSR
gi|18250662|  KRLRRDLKRTHALLSDVQLELGTMEDGKTSVSKEEIEKVHSQLEQSEAKCEEAIKTQKVLTADIESMHSR 1900       1910       1920       1930       1940       1950       1960
                  .    |    .    |    .    |    .    |    .    |    .    |    .    |
NOV11         IDDIAKAKTALEEQLSRLQREKNEIQNRLEEDQEDMNELMKKHKAAVAQASRDIAQINDLQAQLEEANKE
gi|17978507|  IDDIAKAKTALEEQLSRLQREKNEIQNRLEEDQEDMNELMKKHKAAVAQASRDIAQINDLQAQLEEANKE
gi|7416032|   IDDIAKAKTALEEQLSRLQREKNEIQNRLEEDQEDMNELMKKHKAAVAQASRDMAQMNDLQAQIEESNKE
gi|18587640|  IDDIAKAKTALEEQLSRLQREKNEIQNRLEEDQEDMNELMKKHKAAVAQASRDIAQINDLQAQLEEANKE
gi|15718364|  LENMTRNKSLVDEQLYRLQFEKADELKRIEDQDDENELMQKHDLIAQSAADIGQIQELQLQLEEAKKE
gi|18250662|  LENMTRNKSLVDEQLYRLQFEKABLLKRIEDQDDLNELMQKHDLIAQSAADIGQIQELQLQLEEAKKE 1970       1980       1990       2000       2010       2020       2030
                  .    |    .    |    .    |    .    |    .    |    .    |    .    |
NOV11         KQELQEKLQALQSQVEFLEQSMVDKSLVSRQEARIREMETRLEFERTQVKRLESLASRLKENMEKLTEER
gi|17978507|  KQELQEKLQALQSQVEFLEQSMVDKSLVSRQEARIRELETRLEFERTQVKRLESLASRLKENMEKLTEER
gi|7416032|   KQELQEKLQALQSQVEFLEQSMVDKSLVSRQEAKIRELETRLEFEKTQVKRLENLASRLKEIMEKLTEER
gi|18587640|  KQELQEKLQALQSQVEFLEQSMVDKSLVSRQEAKIRELETRLEFEKTQVKRLESLASRLKENMEKLTEER
gi|15718364|  KHKLQEEQLQVAQMRIEYLEQSTVDRAIVSRQEAVICDLENMTEEQKVQEIKRFEVLVIRLRDSLIKMGEEL
gi|18250662|  KHKLQEEQLQVAQMRIEYLEQSTVDRAIVSRQEAVICDLENMTEEQKVQEIKRFEVLVIRLRDSLIKMGEEL 2040       2050       2060       2070       2080       2090       2100
                  .    |    .    |    .    |    .    |    .    |    .    |    .    |
NOV11         DQRIAAENREKEQNKRLQRQLRDTKEEMGELARKEAEASRKKHELEMDLESLEAANQSLQADLKLAFKRI
gi|17978507|  DQRIAAENREKEQNKRLQRQLRDTKEEMGELARKEAEASRKKHELEMDLESLEAANQSLQADLKLAFKRI
gi|7416032|   DQRAAAENREKEQNKRLQRQLRDTKEEMSELARKEAEASRKKHELEMDLESLEAANQSLQADLKLAFKRI
gi|18587640|  DQRIAAENREKEQNKRLQRQLRDTKEEMGELARKEAEASRKKHELEMDLESLEAANQSLQADLKLAFKRI
gi|15718364|  SCAATSESQQRESSQYYQRRLEFLKADMEELVQREAEASRRCMELEKYVEELAAVRQRLQTDLFTSIRRI
gi|18250662|  SCAATSESQQRESSQYYQRRLEFLKADMEELVQREAEASRRCMELEKYVEELAAVRQRLQTDLFTSIRRI
```

TABLE 11F-continued

Clustal W Sequence Alignment

```
                 2110      2120      2130      2140      2150      2160      2170
            ....|....|....|....|....|....|....|....|....|....|....|....|....|....|
NOV11       GDLQAAIEDEMESDENEDLINSLQDMVTKYQKRKN----------------------------------
gi|17978507|GDLQAAIEDEMESDENEDLINS-------------------------------------------------
gi|7416032| GDLQAAIEDEMESDENEDLINS-------------------------------------------------
gi|18587640|GDLQAAIEDEMESDENEDLINS-------------------------------------------------
gi|15718364|ADLQAAEEVASSDSDTESVQTAVDCGSSGRKEMDNVSILSSQPEGSLQSWLSCTLSLATDTMRTPSRQS
gi|18250662|ADLQAAEEVASSDSDTESVQTAVDCGSSGRKEMDNVSILSSQPEGSLQSWLSCTLSLATDTMRTPSRQS 2180      2190      2200      2210      2220      2230      2240
            ....|....|....|....|....|....|....|....|....|....|....|....|....|....|
NOV11       -------------KLEGDSD--------------------------------------------------
gi|17978507|-------------EGDSD----------------------------------------------------
gi|7416032| -------------EGDSD----------------------------------------------------
gi|18587640|----------------------------------------------------------------------
gi|15718364|ATSSRILSPRINEEAGDRERTQSALALSRARSTNVHSKTSGDKPVSPHFVRRQKYCHFGDGEVLAVQRKS
gi|18250662|ATSSRILSPRINEEAGDRERTQSALALSRARSTNVHSKTSGDKPVSPHFVRRQKYCHFGDGEVLAVQRKS 2250      2260      2270      2280      2290      2300      2310
            ....|....|....|....|....|....|....|....|....|....|....|....|....|....|
NOV11       ------VDSELEDRVDGVKSWLSKNKGPSK----------------------------------------
gi|17978507|------VDSELEDRVDGVKSWLSKNKGPSK----------------------------------------
gi|7416032| ------VDSELEDRVDGVKSWLSKNKGPSK----------------------------------------
gi|18587640|---------LQDMVT--KYQKRKNKLVR------------------------------------------
gi|15718364|TERLEPASSPLASRSTN-TSPLSREKLPSPSAALSEFVEGLRRKRAQRGQGSTLGLEDWPTLPIYQTTGA
gi|18250662|TERLEPASSPLASRSTN-TSPLSREKLPSPSAALSEFVEGLRRKRAQRGQGSTLGLEDWPTLPIYQTTGA 2320      2330      2340      2350      2360      2370      2380
            ....|....|....|....|....|....|....|....|....|....|....|....|....|....|
NOV11       -------AASDDGSL-------------------------------------------------------
gi|17978507|-------AASDDGSL-------------------------------------------------------
gi|7416032| -------APSDDGSL-------------------------------------------------------
gi|18587640|----------------------------------------------------------------------
gi|15718364|STLRRGRAGSDEGNLSLRVGAKSPLEIEGAAGGLLRSTSLKCISSDGVGGTTLLPEKSKTQFSSCESLLE
gi|18250662|STLRRGRAGSDEGNLSLRVGAKSPLEIEGAAGGLLRSTSLKCISSDGVGGTTLLPEKSKTQFSSCESLLE 2390      2400      2410      2420      2430      2440      2450
            ....|....|....|....|....|....|....|....|....|....|....|....|....|....|
NOV11       -------KSSSPTSYWKSLAP----------DRSDDEH--------------------------------
gi|17978507|-------KSSSPTSYWKSLAP----------DRSDDEH--------------------------------
gi|7416032| -------KSSSPTSYWKSLAP----------DRSDDEH--------------------------------
gi|18587640|-------ETLMWTRSWRTVLT----------GSS------------------------------------
gi|15718364|SRPSMGRKLSSPTTPRDMLLSPTLRPRRRCLESSVDLAGCPDLGKEPLVFQNRQFAHLMEEPLGSDPFSW
gi|18250662|SRPSMGRKLSSPTTPRDMLLSPTLRPRRRCLESSVDLAGCPDLGKEPLVFQNRQFAHLMEEPLGSDPFSW 2460      2470      2480      2490      2500      2510      2520
            ....|....|....|....|....|....|....|....|....|....|....|....|....|....|
NOV11       ----------------------DPLDNTSRP--------------------RYSHSYLS----------
gi|17978507|----------------------DPLDNTSRP--------------------RYSHSYLS----------
gi|7416032| ----------------------DPVDSISRP--------------------RFSHSYLS----------
gi|18587640|----------------------PGCQKTR-----------------------------------------
gi|15718364|KLPSLDYERKTKVDFDDFLPAIRKPQTPTSLAGSAKGGQDGSQRSSIHFETEEANRSFLSGIKTILKKSP
gi|18250662|KLPSLDYERKTKVDFDDFLPAIRKPQTPTSLAGSAKGGQDGSQRSSIHFETEEANRSFLSGIKTILKKSP 2530      2540      2550      2560      2570      2580      2590
            ....|....|....|....|....|....|....|....|....|....|....|....|....|....|
NOV11       -DSDTEAKLTETNA--------------------------------------------------------
gi|17978507|-DSDTEAKLTETNA--------------------------------------------------------
gi|7416032| -DSDTEAKLTETSA--------------------------------------------------------
gi|18587640|---DLPRQLLMMAA--------------------------------------------------------
gi|15718364|EPKRDPAHLSDSSSSSGSIVSFKSADSIKSRPGIPRLAGDGGERTSPERREPGTGRKDDDVASIMKKYLQ
gi|18250662|EPKRDPAHLSDSSSSSGSIVSFKSADSIKSRPGIPRLAGDGGERTSPERREPGTGRKDDDVASIMKKYLQ

NOV11       -
gi|17978507|-
gi|7416032| -
gi|18587640|-
gi|15718364|K
gi|18250662|K
```

Tables 11G, 11H, 11I and 11J list the domain description from DOMAIN analysis results against NOV11. This indicates that the NOV11 sequence has properties similar to those of other proteins known to contain these domains.

TABLE 11G

Domain Analysis of NOV11 gnl|Smart|smart00242, MYSc, Myosin. Large ATPases.; ATPase; molecular motor. Muscle contraction consists of a cyclical interaction between myosin and actin. The core of the myosin structure is similar in fold to that of kinesin. (SEQ ID NO:164)
CD-Length = 688 residues, 91.4% aligned
Score = 326 bits (836), Expect = 5e-90

```
Query:     1 MHMFKGCRREDMAPHIYAVAQTAYRAMLMSRQDQSIILLGSSGSGKTTSCQHLVQYLATI   60
             + ++|  | ++ ||++|+|   ||| ||  +++||||+ | ||+|| + + ++|||| +
Sbjct:    60 IKKYRGKSRGELPPHVFAIADNAYRNMLNDKENQSIIISGESGAGKTENTKKIMQYLAAV  119

Query:    61 AGISGNKVFSVEKWQALYT--LLEAFGNSPTIINGNATRFSQILSLDFDQAGQVASASIQ  118
             +|  ||+   |||   |  + +||||||+ |+  | |++| + + +  ||  |++   |+
Sbjct:   120 SGSSGSVG-SVED-QILESNPILEAFGNAKTLRNNNSSRFGKFIEIHFDAKGKIVGAKIE  177

Query:   119 TMLLEKLRVARRPASEATFNVFYYLLACGDGTLRTELHLNHLAENNVFGIVPLAKPEEKQ  178
             |  |||| ||  +   |  +++|| |||    |+ +|    |+ +           +
Sbjct:   178 TYLLEKSRVVSQAKGERNYHIFYQLLAGASEELKKKLGLKKSPEDYRLNQGGCLTVDGI   237

Query:   179 KAAQQFSKLQAAMKVLGISPDEQKACWFILAAIYHLGAAGATKEAAEAGRKQFARHEWAQ  238
             |++|  +   ||+|||  | +||++ + |||||  |||   +    +     +    |
Sbjct:   238 DDAEEFKETLNAMRVLGFSEEEQESIFKILAAILHLGNIEFEEGRNDNAAETVKDKEELD  297

Query:   239 KAAYLLGCSLEELSSAIFKHQHKGGTLQRSTSFRQGPEESGLGDTGPKLSALECLEGMA   298
             || |||   |||  |+       +|         |           ||+  + +|
Sbjct:   298 NAAELLGVDPEELEKAL---------TKRKIKTGGEVITVPLT-----VEQALDARDALA  343

Query:   299 AGLYSELFTLLVSLVNRALK-SSQHSLCSMMIVDTPGFQNPEQGGSARGASFEELCHNYT  357
             +|| ||  || +|++|       |   + ++|| |+ |+          |||+|| ||
Sbjct:   344 KAIYSRLFDWLVKRINQSLSFKRDGSTNFIGVLDIYGFEIFEKN------SFEQLCINYA  397

Query:   358 QDRLQRLFHERTFVQELERYKEENIELAFDDLEPPTDDSVAAVDQASHQSLVRSLARTDE  417
             ++||+ |++  |   | || + ||            +|  +| + +    +
Sbjct:   398 NEKLQQFFNQHVFKLEQEEYEREGIE-------------WTFIDFFDNQDCIDLI--EKK  442

Query:   418 ARGLLWLLEEEALVPGASEDTLLERLFSYYGPQEGDKKGQSPLLHSSK---PHHFLLGHS  474
             |+|  ||+||     |  ++  ||+|    +          |        |++ |
Sbjct:   443 PLGILSLLDEECRFPKGTDQTFLEKLNKQ-------HLKKHPHFSKPKKNGRTEFIIKHY  495

Query:   475 HGTNWVEYNVTGWLNYTKQNPATQNVPRLLQDSQKKIISNLFLGRAGSATVLGSIAGLE   534
             |   | +|||+|  | + + ++ |||+  +|+ ||   ||
Sbjct:   496 AGD--VTYDVTGFLEKNK-DTLSDDLIELLQSSKNPLIALLFPEEAGQT----------  541

Query:   535 GGSQLALRRATSMRKTFTTGMVAVKKKSLCIQMKLQVDALIDTIKKSKLHFVHCFLPVAE  594
             |    ++ +           ++ || |  ++ |+|+  + ||+ |  |
Sbjct:   542 --SSAPKEKSAKKKFQ---------TVGSQFKESLNELMDTLNSTNPHFIRCIKPNEE   588

Query:   595 GWAGEPRSASSRRVSSSSELDLPSGDHCEAGLLQLDVPLLRTQLRGSRLLDAMRMYRQGY  654
             |                             | |+ |||   +| +|+ + +|+  | |+
Sbjct:   589 KKPG-------------------------DFDSSLVLHQLRYLGVLETIRIRRAGF   619

Query:   655 PDHMVFSEFRRRFDVLAPHLTKKHGRNYIVVDDERRAVEELLECLDLEKSSCCMGLSRVFF  714
             |  + |  ||+| ||   |    | +| ||+ |   ++ +|+||
Sbjct:   620 PYRLPFDEFLQRYRVLLPDTWPPWG-----GDAKEACELLLQSLGLDEDEYQIGKTKVFL  674

Query:   715 RAGTLARLEEQRDE                                                728
             | | ||| ||| |+|
Sbjct:   675 RPGQLAELEELREE                                                688
```

TABLE 11H

Domain Analysis of NOV11 gnl|Pfam|pfam00063, myosin_head, Myosin head (motor domain). (SEQ ID NO:165)
CD-Length = 670 residues, 92.2% aligned
Score = 283 bits (723), Expect = 7e-77

```
Query:     1 MHMFKGCRREDMAPHIYAVAQTAYRAMLMSRQDQSIILLGSSGSGKTTSCQHLVQYLATI   60
             + ++|  || ++ |||+|+|   |||+|| +++||||++ | ||+||| + + ++|||| +
Sbjct:    53 IKKYRGKRRYELPPHIFAIADEAYRSMLSDKENQSILISGESGAGKTENTKKVMQYLAAV  112

Query:    61 AGISGNKVFSVEKWQALYT--LLEAFGNSPTIINGNATRFSQILSLDFDQAGQVASASIQ  118
             +| +|  ||  ||    |  + +|||||+ |      |++|     | + ++ ||+  | |+
Sbjct:   113 SGGNGGKVGRVED-QILQSNPILEAFGNAKTTRNNNSSRFGKYIEIQFDKTGKIVGAKIE  171

Query:   119 TMLLEKLRVARRPASEATFNVFYYLLACGDGTLRTELHLNHLAENNVFGIVPLAKPEEKQ  178
```

TABLE 11H-continued

Domain Analysis of NOV11

```
              |||| || +   |  |++|| |||     |+ ||+|   ++  +       +
Sbjct:  172  NYLLEKSRVVYQTPGERNFHIFYQLLAGASQQLKKELNLTD-PDDYHYLNQGGCYTVDGI  230

Query:  179  KAAQQFSKLQAAMKVLGISPDEQKACWFILAAIYHLGAAGATKEAAEAGRKQFARHEWAQ  238
              +++| +   || +|| |  | +|| + + |+||| ||    |+  +    +   +   |
Sbjct:  231  DDSEEFKETDKAMDILGFSDEEQLSIFRIVAAILHL-GNIKFKQRRKEEAAEPDDTKALQ  289

Query:  239  KAAYLLGCSLEELSSAIFKHQHKGGTLQRSTSFRQGPEESGLGDGTGPKLSALECLEGMA  298
              || |||  +|| |+  + |    +      |  |+             |    + +|
Sbjct:  290  IAAELLGVDAKELEKALLSRRIKTGGEGVTVP--QNVEQ-----------ANYARDALA  335

Query:  299  AGLYSELFTLLVSLVNRALKSSQHSLCSMMIV-DTPGFQNPEQGGSARGASFEELCHNYT  357
              ||| ||  +|+ +|++|      + + |    ||+ |+       |||+|| |||
Sbjct:  336  KALYSRLFDWIVNRINKSLDFKAKEGANFIGVLDIYGFEIFEKN------SFEQLCINYT  389

Query:  358  QDRLQRLFNERTFVQELERYKEENIELAFDDLEPPTDDSVAAVDQASHQSLVRSLARTDE  417
              ++||+ |+   |   | || ||  |    |+  +|   +
Sbjct:  390  NEKLQQFFNHHMFKLEQEEYKREGIEWTFIDF----GDNQPCIDLEKKPP---------  436

Query:  418  ARGLLWLLEEEALVPGASEDTLLERLPSYYGPQEGDKKCQSPLLHSSKPHHFLLGHSHGT  477
              |+| ||+||    |  |++  |++|+  +      + |    +   |++  |
Sbjct:  437  --GILSLLDEECRFPKATDQTFLDKLYSEF---SNHPHFKKP--RFRQKKSFIIKHYAGD  489

Query:  478  NWVEYNVTGWLNYTKQNPATQNVPRLLQDSQKKIISNLFLGRAGSATVLSGSIAGLEGGS  537
              ||||| |+|   | +|   ++  ||+ |    +++ ||              |
Sbjct:  490  --VEYNVEGFLEKNK-DPLFDDLIELLKSSSNPLLAELF------------PDYEEADPS  534

Query:  538  QLALRRATSMRKTFTTGMVAVKKKSLCIQMKLQVDALIDTIKKSKLHFVHCFLPVAEGWA  597
              |+ +|  + +  ||          +  |   ++ |+ |+  + |||   |
Sbjct:  535  SLSKKRKITKKSNFIT---------VGAQFKESLNTLMKTLSSTNPHFVRCIKPNEEKKP  585

Query:  598  GEPRSASSRRVSSSSELDLPSGDHCEAGLLQLDVPLLRTQLRGSRLLDAMRMYRQGYPDH  657
              |                              |+ |||   +|+ +|+  |  |+|
Sbjct:  586  G---------------------------VFDASLVLHQLRCLQVLEGIRIRRAGFPSR  616

Query:  658  MVFSEFRRRFDVLAPHLTKKHGRNYIVVDERRAVEELLECLDLEKSSCCMGLSRVFFR  715
              +  |  ||+ +|||    |   +  ++ |  | | ||+ |+|+|     |+++|||
Sbjct:  617  ITFDEFLQRYRILAPKTWPK----WSGDAKKGACELLLQALNLDKEEYQFGKTKIFFR  670
```

TABLE 11I

Domain Analysis of NOV11 gnl|Pfam|pfam01576, Myosin tail, Myosin tail. The myosin molecule is a multi-subunit complex made up of two heavy chains and four light chains it is a fundamental contractile protein found in all eukaryote cell types. This family consists of the coiled-coil myosin heavy chain tail region. The coiled-coil is composed of the tail from two molecules of myosin. These can then assemble into the macromolecular thick filament. The coiled-coil region provides the structural backbone the thick filament. (SEQ ID NO:166)
CD-Length = 860 residues, 77.1% aligned
Score = 87.4 bits (215), Expect = 6e-18

```
Query:  791  VQLSEEQIRNKDEEIQQLRSKLEKAEKERNELRLNSDRLESRISELTSELTDERNTGESA  850
              |  +++|+ +  |++| +||     |  +    | ||+  | +   +
Sbjct:   34  VAQLQKKIKELEARIRELEEELEAERAARAKAEKARADLSRELEELSERLEEAGGATAAQ  93

Query:  851  SQLLDAETAERLRAEKEMKELQTQYD----ALKKQMEVMEMEVMEARLIRAAEINGEVDD  906
              |+    ||   + |+++|    |++    |++  +|++ +              |++ +++
Sbjct:   94  IELNKKREAELAKLRKDLEEANLQHEEALATLRKKHQD-----------AINELSEQIEQ  142

Query:  907  -DDAGGEWRLKYERAVREVDFTKKRLQQEFEDKLEVEQQNKRQLERRLGDLQADSEESQR  965
                +  +   |||  +|     +|   +  + ||  |++ |  ||+ | +||   +| ||
Sbjct:  143  LQKQKAKAEKEKSQLQAEVDDLLAQLDSITKAKLNAEKKAK-QLESQLSELQVKLDELQR  201

Query:  966  ALQQLKKKCQRLTAELQDTKLHLEGQQVRNHELEKKQRRFDSELSQAHEEAQREKLQREK  1025
              |  |  + || +|    ||   ++    | + + +|+| +|  + | +|
Sbjct:  202  QLNDLTSQKSRLQSENSDLTRQLEEAEAQVSNLSKLKSQLESQLEEAKRSLEEESRERAN  261

Query:  1026 LQREKDMLLAEAFSLKQQLEEKDMDIAGFTQKVVSLEAELQDISSQ-ESKDEASLAKVKK  1084
              || + |   + |+|||+|   | |+||+|+   |++|   |+ |++
Sbjct:  262  LQAQLRQLEHDLDSLREQLEEESSEAKAELERQLSKANAEIQQWRSKFESEGALRAEELEE  321

Query:  1085 QLRDLEAKVKDQEEELDEQAGTIQMLEQAKLRLEMEMERMR------QTHSKEMESRDEE  1138
```

TABLE 11I-continued

Domain Analysis of NOV11

```
                     + |   |+ + ||  +         ||+ |  ||+ |+| ++           + |+| + +
Sbjct:    322  LKKKLNQKISELEEAAEAANAKCDSLEKTKSRLQSELEDLQIELERANAAASELEKKQKN   381

Query:   1139  VEEARQSCQKKLKQMEVQLEEEYEDKQKVLREKRELEGKLATLSDQVNRRDFESEKRLRK  1198
                ++      ++|+ +++ +|+      + + +   |   |+ +|   | |||     |   | |+
Sbjct:    382  FDKILAEWKRKVDELQAELDTAQREARNLSTELFRLKNELEELKDQVEALRRE-NKNKQD   440

Query:   1199  DLKRTKALLADAQLMLDHL-KNSAPSKREIAQLKNQLEESEFTCAAAVKARKAMEVEIED  1257
                ++        | +    + | |         + |    +|+   ||+|             +||+
Sbjct:    441  EIHDLTDQLGEGGRNVHELEKARRRLEAEKDELQAALEEAEAALELEESKVLFAQVELSQ   500

Query:   1258  LHLQIDDIAKAKTALEEQLSR-LQREKNEIQNRLEEDQEDMNELMKKHKAAVAQASRDLA  1316
                +  +|+         |      |    +  ||     +|   || + +       | +   |            +
Sbjct:    501  IRSEIERRLAEKEEEFENTRKNHQRAIESLQATLEAETKGKAEASRLK--------KLEG   553

Query:   1317  QINDLQAQLEEANKEKQELQEKLQALQSQVEFLEQSMVDKS-LVSRQEARIREMETRLEF  1375
                |  |+|                              +  ++   ++ +       |  + +  +++|++|++|
Sbjct:    554  DINEL--------------------EIALDHANKANAEAQKNVKKYQQQVKELQTQVEE   592

Query:   1376  ERTQVKRLESLASRLKENMEKLTEERDQRIAAENREKEQNKRLQRQLRDTKEEMGELARK  1435
                |+      +      + +         |     | ++   +|   + +    |+ + +|  +    |  + ||   +
Sbjct:    593  EQRAREDAREQLAVAERRATALEAELEELRSALEQAERARKQAETELAEASERVNELTAQ   652

Query:   1436  EAEASRKKHELEMDLESLEAANQSLQADLKLAFKRIGDLQAAIE                 1479
                |         +|  +||  +|  +|++          +||   |+     ||
Sbjct:    653  NSSLIAQKRKLEGELAALQSDLDEAVNELKAAEERAEKAQADAA                 696
```

TABLE 11J

Domain Analysis of NOV11

```
gnl Pfam pfam00038, filament, Intermediate filament protein. (SEQ ID NO:167)
CD-Length = 312 residues, 89.7% aligned
Score = 43.9 bits (102), Expect = 7e-05
Query:   1041  KQQLEEKDMDIAGFTQKVVSLEAELQDISSQESKDEASLAKVKKQLRDLEAKVKDQEEEL  1100
                |+|++   +   +|  +  ||    ||  + +++     |||         |        +  |  +           | |+
Sbjct:      3  KEQMQNLNDRLASYIDKVEFLEQQNKEL---EVKIEELRQKQAPSVSRLYSLY---ETEI    56

Query:   1101  DEQAGTIQMLEQAKLRLEMEMERMRQTHSKEMESRDEEVEEARQSCQKKLKQMEVQLEEE  1160
                  +|       |     |    + ||++|++ +|+        + ++|+   ||    +    |    +|+|
Sbjct:     57  EELRRQIDQLTNERARLQLEIDNLREAAEDFRKKYEDEINL-RQEAENDLVGLRKDLEA    115

Query:   1161  YEDKQKVLREKRELEGKLATLSDQVN--RRDFESE-KRLRKDLKRTKALLADAQLMLD--  1215
                        +            +||   |+ +|   +++      +++    | | |  |+  ++ |   +    ||     ||
Sbjct:    116  TLARV-------DLENKVESLQEELEFLKKNHEEEVKELQAQIQDTVNVEMDAARKLDT    168

Query:   1216  ---------HLKNSAPSKREI-AQLKNQLEESEFTCAAAVKARKAMEVEIEDLHLQIDDI  1265
                              + + +  +++|       |++|||| +       |   +| ++ ++ ||  +|   ||   +
Sbjct:    169  KALREIRAQYEEIAKKNRQEAEEWYKSKLEELQTAAARNGEALRSAKEEITELRRQIQSL    228

Query:   1266  AKAKTALEEQLSRLQREKNEIQNRLEEDQEDMNELMKKHKAAVAQASRDLAQIN        1319
                      +|+  |  + |+|+  |++  | |      |+ + +  +      |+ + + +  |       ++|+
Sbjct:    229  EIELQSLKAQNASLERQLAELEERYELELRQYQALISQLEEELQQLREEMARQL        282
```

In an effort to sequence human cDNA clones which correspond to relatively long and nearly full-length transcripts, the sequence of KIAA0216 has been determined. It has been obtained from human immature myeloid cell line KG-1. KIAA0216 contains a myosin head (motor domain). Myosins are molecular motors that upon interaction with actin filaments convert energy from ATP hydrolysis into mechanical force. Evidence has emerged for the existence of a large, widely expressed and evolutionarily ancient superfamily of myosin genes.

In addition to the well-catheterized conventional, filament-forming, two-headed myosin-II of muscle and non-muscle cells, at least ten additional classes of myosins have been identified. In vertebrates, at least seven classes are expressed, and many myosins can be expressed in a single cell type. Distance matrix and maximum parsimony methods have been used to study the evolutionary relationships between members of the myosin superfamily of molecular motors. Amino acid sequences of the conserved core of the motor region have been used in the analysis.

Myosins can be divided into at least three main classes, with two types of unconventional myosin being no more related to each other than they are to conventional myosin. Myosins have traditionally been classified as conventional or unconventional, with many of the unconventional myosin proteins thought to be distributed in a narrow range of organisms. It has been found that members of all three of these main classes are likely to be present in most (or all) eukaryotes. The structure of the trees suggests that these ungrouped proteins and some of the subclasses of the main classes are also likely to be widely distributed, implying that most eukaryotic cells contain many different myosin proteins. The groupings derived from phylogenetic analysis of myosin head sequences agree strongly with those based on tail structure, developmental expression, and (where available) enzymology, suggesting that specific head sequences have been tightly coupled to specific tail sequences throughout evolution.

Analysis of the relationships within each class has interesting implications. For example, smooth muscle myosin and striated muscle myosin seem to have independently evolved from nonmuscle myosin. Furthermore, brush border myosin I, a type of protein initially thought to be specific to specialized metazoan tissues, probably has relatives that are much more broadly distributed. Myosin II, the conventional two-headed myosin that forms bipolar filaments, is directly involved in regulating cytokinesis, cell motility and cell morphology in nomnuscle cells. To understand the mechanisms by which nonmuscle myosin-II regulates these processes, investigators are looking at the regulation of this molecule in vertebrate nomnuscle cells. The identification of multiple isoforms of nonmuscle myosin-II, whose activities and regulation differ from that of smooth muscle myosin-II, suggests that, in addition to regulatory light chain phosphorylation, other regulatory mechanisms control vertebrate nonmuscle myosin-II activity. It has been shown that nonmuscle myosin II, along with other myosins and cytoskeletal proteins, assembles on Golgi membranes. Nonmuscle myosin II associates transiently with membranes of the trans-Golgi network during the budding of a subpopulation of transport vesicles. The exact role of myosin II in vesicular trafficking is not yet understood, but its participation heralds a novel role for actin-based motors in vesicle budding.

In the aortic wall of mammalian species, the maturation phase of smooth muscle cell (SMC) lineage is characterized by two temporally correlated but opposite regulatory processes of gene expression: upregulation of SM type SM2 myosin isoform and downregulation of brain (myosin heavy chain B)- and platelet (myosin heavy chain A(pla))-type nonmuscle myosins. There is propensity of the immature type SMC population to be activated in experimental models and human vascular diseases that are characterized by proliferation and migration of medial SMCs into the subendothelial space. Neointimal proliferation leading to restenosis frequently develops after coronary angioplasty. This process is associated with a change in vascular smooth-muscle cells from a contractile (quiescent) phenotype to a synthetic or proliferating (activated) one. The expression of the B isoform of nonmuscle myosin heavy chain is increased in some coronary atherosclerotic plaques and that this increase in expression identifies a group of lesions at high risk for restenosis after atherectomy. The human homologue of the mouse dilute gene combines elements from both nonmuscle myosin type I and nonmuscle myosin type II. Mutations in the mouse dilute gene result not only in the lightening of coat color, but also in the onset of severe neurological defects shortly after birth, indicating that this gene is important in maintaining the normal neuronal function.

The NOV11 nucleic acid of the invention encoding a KIAA0216-like protein includes the nucleic acid whose sequence is provided in Table 11A, or a fragment thereof. The invention also includes a mutant or variant nucleic acid any of whose bases may be changed from the corresponding base shown in Table 11A while still encoding a protein that maintains its KIAA0216-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 1% of the residues may be so changed.

The NOV11 protein of the invention includes the KIAA0216-like protein whose sequence is provided in Table 11B. The invention also includes a mutant or variant protein any of whose residues may be changed from the corresponding residue shown in Table 11B while still encoding a protein that maintains its KIAA0216-like activities and physiological functions, or a functional fragment thereof. In the mutant or variant protein, up to about 2% of the bases may be so changed.

The NOV11 nucleic acids and proteins of the invention are useful in potential diagnostic and therapeutic applications implicated in various diseases and disorders described below and/or other pathologies. For example, the compositions of the present invention will have efficacy for treatment of patients suffering from: restenosis, neurological, glomerular diseases and other diseases, disorders and conditions of the like. Enhanced embryonic nonmuscle myosin heavy chain isoform and matrix metalloproteinase expression in aortic abdominal aneurysm with rapid progression has been found (Cardiovasc Pathol 1999 September–October; 8(5) :291–5). In addition, the expression of a nonmuscle myosin heavy chain in glomerular cells differentiates various types of glomerular disease in rats. The nonmuscle type myosin heavy chain, Smemb, is especially useful to detect both mesangial and glomerular epithelial cell activation in these glomerular disease models. Understanding the functional difference and regulatory mechanisms of these cytoskeletal proteins will provide insight into the pathogenesis and progression of glomerular diseases (Kidney Int 1996 May;49(5): 1231–41). The expression of the B isoform of nomnuscle myosin heavy chain is increased in some coronary atherosclerotic plaques and this increase in expression identifies a group of lesions at high risk for restenosis after atherectomy (N Engl J Med 1993 March 4;328(9):608–13). The human homologue of the mouse dilute gene, which may be important in maintaining the normal neuronal function in the mouse, combines elements from both nonmuscle myosin type I and nonmuscle myosin type II (Genomics 1994 February;19(3):407–16).

NOV11 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV11 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV12

NOV12 includes three novel TWIK 3-like proteins disclosed below. The disclosed proteins have been named NOV12a, NOV12b and NOV12c.

NOV12a

A disclosed NOV12a nucleic acid of 1011 nucleotides (also referred to as CG57220-01) encoding a novel TWIK 3-like protein is shown in Table 12A. An open reading frame was identified beginning with an ATG initiation codon at nucleotides 17–19 and ending with a TAG codon at nucleotides 953–955. Putative untranslated regions, if any, upstream from the initiation codon and downstream from the termination codon are underlined in Table 12A, and the start and stop codons are in bold letters.

TABLE 12A

NOV12a nucleotide sequence.

(SEQ ID NO:43)
CCCCGCCTCTCCCGCTATGTACCGACCGCGAGCCCGGGCGGCTCCCGAGGGCAGGGTCCGGGGCTGCGCGGT

GCCCGGCACCGTGCTCCTGCTGCTCGCCTACCTGGCTTACCTGGCGCTGGGCACCGGCGTGTTCTGGACGCT

GGAGGGCCGCGCGGCGCAGGACTCCAGCCGCAGCTTCCAGCGCGACAAGTGGGAGCTGTTGCAGAACTTCAC

GTGTCTGGACCGCCCGGCGCTGGACTCGCTGATCCGGGATGTCGTCCAAGCATACAAAAACGGAGCCAGCCT

CCTCAGCAACACCACCAGCATGGGGCGCTGGGAGCTCGTGGGCTCCTTCTTCTTTTCTGTGTCCACCATCTT

CTTTGCCCTTGTGGGGATCCCACTCAACCTCGTGGTGCTCAACCGACTGGGGCATCTCATGCAGCAGGGAGT

AAACCACTGGGCCAGCAGGCTGGGGGGCACCTGGCAGGATCCTGACAAGGCGCGGTGGCTGGCGGGCTCTGG

CGCCCTCCTCTCGGGCCTCCTGCTCTTCCTGCTGCTGCCACCGCTGCTCTTCTCCCACATGGAGGGCTGGAG

CTACACAGAGGGCTTCTACTTCGCCTTCATCACCCTCAGCACCGTGGGCTTCGGCGACTACGTGATTGGAAT

GAACCCCTCCCAGAGGTACCCACTGTGGTACAAGAACATGGTGTCCCTGTGGATCCTCTTTGGGATGGCATG

GCTGGCCTTGATCATCAAACTCATCCTCTCCCAGCTGGAGACGCCAGGGAGGGTATGTTCCTGCTGCCACCA

CAGCTCTAAGGAAGACTTCAAGTCCCAAAGCTGGAGACAGGGACCTGACCGGGAGCCAGAGTCCCACTCCCC

ACAGCAAGGATGCTATCCAGAGGGACCCATGGGAATCATACAGCATCTGGAACCTTCTGCTCACGCTGCAGG

CTGTGGCAAGGACAGCTAGTTATACTCCATTCTTTGGTCGTCGTCCTCGGTAGCAAGACCCCTGATTTTAAG

CTT

The disclosed NOV12a nucleic acid sequence, localized to chromsome 6p21.1-21.2, has 384 of 641 bases (59%) identical to a gb:GENBANK-ID:AF006823|acc:AF006823.1 mRNA from *Homo sapiens* (*Homo sapiens* TWIK-related acid-sensitive K+ channel (TASK) mRNA, complete cds) (E=3.1e$^{-15}$).

A NOV12a polypeptide (SEQ ID NO:44) encoded by SEQ ID NO:43 has 312 amino acid residues and is presented using the one-letter code in Table 12B. Signal P, Psort and/or Hydropathy results predict that NOV12a contains a signal peptide and is likely to be localized to the plasma membrane with a certainty of 0.6400. The most likely cleavage site for a NOV12a polypeptide is between amino acids 48 and 49: RAA-QD.

sapiens (Human) (DJ137F1.1 (Novel Member Of The Potassium Channel Subfamily K)) (E=2.4e$^{-108}$).

The disclosed NOV12a is expressed in at least the following tissues: amygdala, brain—cerebellum, brain—hippocampus, brain—substantia nigra, brain—thalamus, brain—whole, fetal brain, fetal kidney, fetal liver, fetal lung, heart, kidney, lymphoma—Raji, mammary gland, pancreas, pituitary gland, placenta, prostate, salivary gland, skeletal muscle, small intestine, spinal cord, spleen, stomach, testis, thyroid, trachea and uterus. This information was derived by determining the tissue sources of the sequences that were included in the invention including but not limited to Seq-Calling sources, Public EST sources, Literature sources, and/or RACE sources.

NOV12b

A disclosed NOV12b nucleic acid of 1083 nucleotides (also referred to as CG57220-02) encoding a novel TWIK

TABLE 12B

Encoded NOV12a protein sequence.

(SEQ ID NO:44)
MYRPRARAAPEGRVRGCAVPGTVLLLLAYLAYLALGTGVFWTLEGRAAQDSSRSFQRDKWELLQNFTCLDRP

ALDSLIRDVVQAYKNGASLLSNTTSMGRWELVGSFFFSVSTIFFALVGIPLNLVVLNRLGHLMQQGVNHWAS

RLGGTWQDPDKARWLAGSGALLSGLLLFLLLPPLLFSHMEGWSYTEGFYFAFITLSTVGFGDYVIGMNPSQR

YPLWYKNMVSLWILFGMAWLALIIKLILSQLETPGRVCSCCHHSSKEDFKSQSWRQGPDREPESHSPQQGCY

PEGPMGIIQHLEPSAHAAGCGKDS

The NOV12a amino acid sequence has 113 of 114 amino acid residues (99%) identical to, and 113 of 114 amino acid residues (99%) similar to, the 229 amino acid residue ptnr:TREMBLNEW-ACC:CAC07335 protein from *Homo*

3-like protein is shown in Table 12C. An open reading frame was identified beginning with an ATG initiation codon at nucleotides 17–19 and ending with a TAG codon at nucleotides 1025–1027. Putative untranslated regions, if any, upstream from the initiation codon and downstream from the termination codon are underlined in Table 12C, and the start and stop codons are in bold letters.

The NOV12b amino acid sequence has 228 of 233 amino acid residues (97%) identical to, and 228 of 233 amino acid residues (97%) similar to, the 229 amino acid residue

TABLE 12C

NOV12b nucleotide sequence.

(SEQ ID NO:45)
<u>CCCCGCCTCTCCCGCT</u>ATGTACCGACCGCGAGCCCGGGCGGCTCCCGAGGGCAGGGTCCGGGGCTGCGCGGT

GCCCGGCACCGTGCTCCTGCTGCTCGCCTACCTGGCTTACCTGGCGCTGGGCACCGGCGTGTTCTGGACGCT

GGAGGGCCGCGCGGCGCAGGACTCCAGCCGCAGCTTCCAGCGCGACAAGTGGGAGCTGTTGCAGAACTTCAC

GTGTCTGGACCGCCCGGCGCTGGACTCGCTGATCCGGCCTCTTCCCCAGGATGTCGTCCAAGCATACAAAAA

CGGAGCCAGCCTCCTCAGCAACACCACCAGCATGGGGCGCTGGGAGCTCGTGGGCTCCTTCTTCTTTTCTGT

GTCCACCATCACCACCATTGGCTATGGCAACCTGAGCCCCAACACGATGGCTGCCCGCCTCTTCTGCATCTT

CTTTGCCCTTGTGGGGATCCCACTCAACCTCGTGGTGCTCAACCGACTGGGGCATCTCATGCAGCAGGGAGT

AAACCACTGGGCCAGCAGGCTGGGGGGCACCTGGCAGGATCCTGACAAGGCGCGGTGGCTGGCGGGCTCTGG

CGCCCTCCTCTCGGGCCTCCTGCTCTTCCTGCTGCTGCCACCGCTGCTCTTCTCCCACATGGAGGGCTGGAG

CTACACAGAGGGCTTCTACTTCGCCTTCATCACCCTCAGCACCGTGGGCTTCGGCGACTACGTGATTGGAAT

GAACCCCTCCCAGAGGTACCCACTGTGGTACAAGAACATGGTGTCCCTGTGGATCCTCTTTGGGATGGCATG

GCTGGCCTTGATCATCAAACTCATCCTCTCCCAGCTGGAGACGCCAGGGAGGGTATGTTCCTGCTGCCACCA

CAGCTCTAAGGAAGACTTCAAGTCCCAAAGCTGGAGACAGGGACCTGACCGGGAGCCAGAGTCCCACTCCCC

ACAGCAAGGATGCTATCCAGAGGGACCCATGGGAATCATACAGCATCTGGAACCTTCTGCTCACGCTGCAGG

CTGTGGCAAGGACAGCTAG<u>TTATACTCCATTCTTTGGTCGTCGTCCTCGGTAGCAAGACCCCTGATTTTAAG

CTT</u>

The disclosed NOV12b nucleic acid sequence, localized to chromsome 6p21.1–21.2, has 496 of 795 bases (62%) identical to a gb:GENBANK-ID:AF006823|acc:AF006823.1 mRNA from *Homo sapiens* (*Homo sapiens* TWIK-related acid-sensitive K+ channel (TASK) mRNA, complete cds) (E=1.2e$^{-27}$).

A NOV12b polypeptide (SEQ ID NO:46) encoded by SEQ ID NO:45 has 336 amino acid residues and is presented using the one-letter code in Table 12D. Signal P, Psort and/or Hydropathy results predict that NOV12b contains a signal peptide and is likely to be localized to the plasma membrane with a certainty of 0.6400. The most likely cleavage site for a NOV12a polypeptide is between amino acids 48 and 49: RAA-QD.

ptnr:TREMBLNEW-ACC:CAC07335 protein from *Homo sapiens* (Human) (DJ137F1.1 (Novel Member Of The Potassium Channel Subfamily K)) (E=1.1e$^{-119}$).

The disclosed NOV12b is expressed in at least the following tissues: adrenal gland, bone marrow, brain—amygdala, brain—cerebellum, brain—hippocampus, brain—substantia nigra, brain—thalamus, brain—whole, fetal brain, fetal kidney, fetal liver, fetal lung, heart, kidney, lymphoma—Raji, mammary gland, pancreas, pituitary gland, placenta, prostate, salivary gland, skeletal muscle, small intestine, spinal cord, spleen, stomach, testis, thyroid, trachea and uterus. This information was derived by determining the tissue sources of the sequences that were included in the invention including but not limited to Seq-Calling sources, Public EST sources, Literature sources, and/or RACE sources.

TABLE 12D

Encoded NOV12b protein sequence.

(SEQ ID NO:46)
MYRPRARAAPEGRVRGCAVPGTVLLLLAYLAYLALGTGVFWTLEGRAAQDSSRSFQRDKWELLQNFTCLDRP

ALDSLIRPLPQDVVQAYKNGASLLSNTTSMGRWELVGSFFFSVSTITTIGYGNLSPNTMAARLFCIFFALVG

IPLNLVVLNRLGHLMQQGVNHWASRLGGTWQDPDKARWLAGSGALLSGLLLFLLLPPLLFSHMEGWSYTEGF

YFAFITLSTVGFGDYVIGMNPSQRYPLWYKNMVSLWILFGMAWLALIIKLILSQLETPGRVCSCCHHSSKED

FKSQSWRQGPDREPESHSPQQGCYPEGPMGIIQHLEPSAHAAGCGKDS

NOV12c

A disclosed NOV12c nucleic acid of 1256 nucleotides (also referred to as CG57220-03) encoding a novel TWIK 3-like protein is shown in Table 12E. An open reading frame was identified beginning with an ATG initiation codon at nucleotides 17–19 and ending with a TAG codon at nucleotides 953–955. Putative untranslated regions, if any, upstream from the initiation codon and downstream from the termination codon are underlined in Table 12E, and the start and stop codons are in bold letters.

A NOV12c polypeptide (SEQ ID NO:48) encoded by SEQ ID NO:47 has 312 amino acid residues and is presented using the one-letter code in Table 12F. Signal P, Psort and/or Hydropathy results predict that NOV12c contains a signal peptide and is likely to be localized to the plasma membrane with a certainty of 0.6400. The most likely cleavage site for a NOV12a polypeptide is between amino acids 48 and 49: RAA-QD.

TABLE 12E

NOV12c nucleotide sequence.

(SEQ ID NO:47)

CCCCGCCTCTCCCGCTATGTACCGACCGCGAGCCCGGGCGGCTCCCGAGGGCAGGGTCCGGGGCTGCGCGGT

GCCCGGCACCGTGCTCCTGCTGCTCGCCTACCTGGCTTACCTGGCGCTGGGCACCGGCGTGTTCTGGACGCT

GGAGGGCCGCGCGGCGCAGGACTCCAGCCGCAGCTTCCAGCGCGACAAGTGGGAGCTGTTGCAGAACTTCAC

GTGTCTGGACCGCCCGGCGCTGGACTCGCTGATCCGGGATGTCGTCCAAGCATACAAAAACGGAGCCAGCCT

CCTCAGCAACACCACCAGCATGGGCGCTGGGAGCTCGTGGGCTCCTTCTTCTTTTCTGTGTCCACCATCTT

CTTTGCCCTTGTGGGGATCCCACTCAACCTCGTGGTGCTCAACCGACTGGGGCATCTCATGCAGCAGGGAGT

AAACCACTGGGCCAGCAGGCTGGGGGGCACCTGGCAGGATCCTGACAAGGCGCGGTGGCTGGCGGGCTCTGG

CGCCCTCCTCTCGGGCCTCCTGCTCTTCCTGCTGCTGCCACCGCTGCTCTTCTCCCACATGGAGGGCTGGAG

CTACACAGAGGGCTTCTACTTCGCCTTCATCACCCTCAGCACCGTGGGCTTCGGCGACTACGTGATTGGAAT

GAACCCCTCCCAGAGGTACCCACTGTGGTACAAGAACATGGTGTCCCTGTGGATCCTCTTTGGGATGGCATG

GCTGGCCTTGATCATCAAACTCATCCTCTCCCAGCTGGAGACGCCAGGGAGGGTATGTTCCTGCTGCCACCA

CAGCTCTAAGGAAGACTTCAAGTCCCAAAGCTGGAGACAGGGACCTGACCGGGAGCCAGAGTCCCACTCCCC

ACAGCAAGGATGCTATCCAGAGGGACCCATGGGAATCATACAGCATCTGGAACCTTCTGCTCACGCTGCAGG

CTGTGGCAAGGACAGCTAGTTATACTCCATTCTTTGGTCGTCGTCCTCGGTAGCAAGACCCCTGATTTTAAG

CTTTGCACATGTCCACCCAAACTAAAGACTACATTTTCCATCCACCCTAGAGGCTGGGTGCAGCTATATGAT

TAATTCTGCCCAATAGGGTATACAGAGACATGTCCTGGGTGACATGGGATGTGACTTTCGGGTGTCGGGGCA

GCATGCCCTTCTCCCCCACTTCCTTACTTTAGCGGGCTGCAATGCCGCCGATATGATGGCTGGGAGCTCTGG

CAGCCATACGGCACCATGAAGTAGCGGCAATG

The disclosed NOV12c nucleic acid sequence, localized to chromsome 6p21.1–21.2, has 384 of 641 bases (59%) identical to a gb:GENBANK-ID:AF006823|acc:AF006823.1 mRNA from *Homo sapiens* (*Homo sapiens* TWIK-related acid-sensitive K+ channel (TASK) mRNA, complete cds) (E=1.3e$^{-14}$).

TABLE 12F

Encoded NOV12c protein sequence.

(SEQ ID NO:48)

MYRPRARAAPEGRVRGCAVPGTVLLLLAYLAYLALGTGVFWTLEGRAAQDSSRSFQRDKWELLQNFTCLDRP

ALDSLIRDVVQAYKNGASLLSNTTSMGRWELVGSFFFSVSTIFFALVGIPLNLVVLNRLGHLMQQGVNHWAS

RLGGTWQDPDKARWLAGSGALLSGLLLFLLLPPLLFSHMEGWSYTEGFYFAFITLSTVGFGDYVIGMNPSQR

YPLWYKNMVSLWILFGMAWLALIIKLILSQLETPGRVCSCCHHSSKEDFKSQSWRQGPDREPESHSPQQGCY

PEGPMGIIQHLEPSAHAAGCGKDS

The NOV12c amino acid sequence has 67 of 132 amino acid residues (50%) identical to, and 97 of 132 amino acid residues (73%) similar to, the 294 amino acid residue ptnr:SPTREMBL-ACC:Q9H591 protein from Homo sapiens (Human) (DJ137F1.2 (Novel Member Of The Potassium Channel Subfamily K)) (E=2.1e$^{-47}$).

The disclosed NOV12c is expressed in at least the following tissues: amygdala, brain—cerebellum, brain—hippocampus, brain—substantia nigra, brain—thalamus, brain—whole, fetal brain, fetal kidney, fetal liver, fetal lung, heart, kidney, lymphoma—Raji, mammary gland, pancreas, pituitary gland, placenta, prostate, salivary gland, skeletal muscle, small intestine, spinal cord, spleen, stomach, testis, thyroid, trachea and uterus. This information was derived by determining the tissue sources of the sequences that were included in the invention including but not limited to Seq-Calling sources, Public EST sources, Literature sources, and/or RACE sources.

Possible SNPs found for NOV12a are listed in Table 12G.

TABLE 12G

| | SNPs | | | |
|---|---|---|---|---|
| Variant | Nucleotide Position | Base Change | Amino Acid Position | Base Change |
| 13377098 | 77 | G > A | 21 | Gly > Ser |
| 13377097 | 593 | T > C | 193 | Tyr > His |
| 13377096 | 718 | A > G | Silent | N/A |
| 13377095 | 856 | C > T | Silent | N/A |

NOV12a, NOV12b and NOV12c are very closely homologous as is shown in the amino acid alignment in Table 12H.

TABLE 12H

Amino Acid Alignment of NOV12a, NOV12b and NOV12c

```
                10        20        30        40        50        60        70
         ....|....|....|....|....|....|....|....|....|....|....|....|....|....|
NOV12a   MYRPRARAAPEGRVRGCAVPGTVLLLLAYLAYLALGTGVFWTLEGRAAQDSSRSFQRDKWELLQNFTCLD
NOV12b   MYRPRARAAPEGRVRGCAVPGTVLLLLAYLAYLALGTGVFWTLEGRAAQDSSRSFQRDKWELLQNFTCLD
NOV12c   MYRPRARAAPEGRVRGCAVPGTVLLLLAYLAYLALGTGVFWTLEGRAAQDSSRSFQRDKWELLQNFTCLD 80        90       100       110       120       130       140
         ....|....|....|....|....|....|....|....|....|....|....|....|....|....|
NOV12a   RPALDSLIR----DVVQAYKNGASLLSNTTSMGRWELVGSFFFSVSTI-------------------FF
NOV12b   RPALDSLIRPLPQDVVQAYKNGASLLSNTTSMGRWELVGSFFFSVSTITTIGYGNLSPNTMAARLFCIFF
NOV12c   RPALDSLIR----DVVQAYKNGASLLSNTTSMGRWELVGSFFFSVSTI-------------------FF 150       160       170       180       190       200       210
         ....|....|....|....|....|....|....|....|....|....|....|....|....|....|
NOV12a   ALVGIPLNLVVLNRLGHLMQQGVNHWASRLGGTWQDPDKARWLAGSGALLSGLLLFLLLPPLLFSHMEGW
NOV12b   ALVGIPLNLVVLNRLGHLMQQGVNHWASRLGGTWQDPDKARWLAGSGALLSGLLLFLLLPPLLFSHMEGW
NOV12c   ALVGIPLNLVVLNRLGHLMQQGVNHWASRLGGTWQDPDKARWLAGSGALLSGLLLFLLLPPLLFSHMEGW 220       230       240       250       260       270       280
         ....|....|....|....|....|....|....|....|....|....|....|....|....|....|
NOV12a   SYTEGFYFAFITLSTVGFGDYVIGMNPSQRYPLWYKNMVSLWILFGMAQLALIIKLILSQLETPGRVCSC
NOV12b   SYTEGFYFAFITLSTVGFGDYVIGMNPSQRYPLWYKNMVSLWILFGMAQLALIIKLILSQLETPGRVCSC
NOV12c   SYTEGFYFAFITLSTVGFGDYVIGMNPSQRYPLWYKNMVSLWILFGMAQLALIIKLILSQLETPGRVCSC 290       300       310       320       330
         ....|....|....|....|....|....|....|....|....|....|.
NOV12a   CHHSSKEDFKSQSWRQGPDREPESHSPQQGCYPEGPMGIIQHLEPSAHAAGCGKDS
NOV12b   CHHSSKEDFKSQSWRQGPDREPESHSPQQGCYPEGPMGIIQHLEPSAHAAGCGKDS
NOV12c   CHHSSKEDFKSQSWRQGPDREPESHSPQQGCYPEGPMGIIQHLEPSAHAAGCGKDS
```

Homologies to any of the above NOV12 proteins will be shared by the other NOV12 proteins insofar as they are homologous to each other as shown above. Any reference to NOV12 is assumed to refer to the NOV12 proteins in general, unless otherwise noted.

NOV12a has homology to the amino acid sequences shown in the BLASTP data listed in Table 12I.

TABLE 12I

| BLAST results for NOV12a | | | | | |
|---|---|---|---|---|---|
| Gene Index/ Identifier | Protein/ Organism | Length (aa) | Identity (%) | Positives (%) | Expect |
| gi\|17025230\|ref\|NP_113648.2\| (NM_031460) | potassium channel, subfamily K, member 17; 2P | 332 | 276/332 (83%) | 276/332 (83%) | e-155 |

TABLE 12I-continued

BLAST results for NOV12a

| Gene Index/ Identifier | Protein/ Organism | Length (aa) | Identity (%) | Positives (%) | Expect |
|---|---|---|---|---|---|
| | domain potassium channel Talk-2; potassium channel TASK-4; potassium channel TALK-2 [Homo sapiens] | | | | |
| gi|13507377|gb|AAK28551.1| AF339912_1 (AF339912) | potassium channel TASK-4 [Homo sapiens] | 343 | 204/259 (78%) | 204/259 (78%) | e-108 |
| gi|9988111|emb|CAC07335.1| (AL136087) | dJ137F1.1 (novel member of the potassium channel subfamily K) [Homo sapiens] | 229 | 173/229 (75%) | 173/229 (75%) | 5e-90 |
| gi|9988112|emb|CAC07336.1| (AL136087) | dJ137F1.2 (novel member of the potassium channel subfamily K) [Homo sapiens] | 294 | 75/226 (33%) | 118/226 (52%) | 3e-30 |
| gi|14149764|ref|NP_ 115491.1| (NM_032115) | pancreatic 2P domain potassium channel TALK-1; potassium family, subfamily K, member 16 [Homo sapiens] | 309 | 75/226 (33%) | 118/226 (52%) | 4e-30 |

The homology of these sequences is shown graphically in the ClustalW analysis shown in Table 12J.

TABLE 12J

ClustalW Analysis of NOV12a

1) NOV12a (SEQ ID NO:44)
2) gi|17025230|refNP_113648.2| (NM_031460) potassium channel, subfamily K, member 17; 2P domain potassium channel Talk-2; potassium channel TASK-4; potassium channel TALK-2 [Homo sapiens] (SEQ ID NO:168)
2) gi 13507377|gb AAK28551.1 AF339912_1 (AF339912) potassium channel TASK-4 [Homo sapiens] (SEQ ID NO:169)
3) gi|9988111|emb CAC07335.1| (AL136087) dJ137F1.1 (novel member of the potassium channel subfamily K) [Homo sapiens] (SEQ ID NO:170)
4) gi|9988112|emb CAC07336.1| (AL136087) dJ137F1.2 (novel member of the potassium channel subfamily K) [Homo sapiens] (SEQ ID NO:171)
5) gi 14149764|refNP_115491.1| (NM_032115) pancreatic 2P domain potassium channel TALK-1; potassium family, subfamily K, member 16 [Homo sapiens] (SEQ ID NO:172)

```
                        10        20        30        40        50        60        70
                ....|....|....|....|....|....|....|....|....|....|....|....|....|....|
NOV12a          MYRPRARAAPEGRVRGCAVPGTVLLLLAYLAYLALGTGVFWTLEGRAAQDSSRSFQRDKWELLQNFTCLD
gi|17025230     MYRPRARAAPEGRVRGCAVPGTVLLLLAYLAYLALGTGVFWTLEGRAAQDSSRSFQRDKWELLQNFTCLD
gi|13507377|    MYRPRARAAPEGRVRGCAVPGTVLLLLAYLAYLALGTGVFWTLEGRAAQDSSRSFQRDKWELLQNFTCLD
gi|9988111|     MYRPRARAAPEGRVRGCAVPSTVLLLLAYLAYLALGTGVFWTLEGRAAQDSSRSFQRDKWELLQNFTCLD
gi|9988112|     MYRPRARAAPEGRVRGCAVPSTVLLLLAYLAYLALGTGVFWTLEGRAAQDSSRSFQRDKWELLQNFTCLD
gi|14149764|    --------MPSAGLCSCWGGRVLPLLLAYVCYLLLCATTFQLLERQAEAQSRDQFQLEKLRFLFNYTCLD
```

TABLE 12J-continued

ClustalW Analysis of NOV12a

```
                   80         90        100        110        120        130        140
              ....|....|....|....|....|....|....|....|....|....|....|....|....|....|
NOV12a        RPALDSLIRDVVQAYKNGASLLSNTTSMGRWELVGSFFFSVSTI--------------------FFALVG
gi|17025230|  RPALDSLIRDVVQAYKNGASLLSNTTSMGRWELVGSFFFSVSTITTIGYGNLSPNTMAARLFCIFFALVG
gi|13507377|  RPALDSLIRDVVQAYKNGASLLSNTTSMGRWELVGSFFFSVSTITTIGYGNLSPNTMAARLFCIFFALVG
gi|9988111|   RPALDSLIRDVVQAYKNGASLLSNTTSMGRWELVGSFFFSVSTITTIGYGNLSPNTMAARLFCIFFALVG
gi|9988112|   RPALDSLIRDVVQAYKNGASLLSNTTSMGRWELVGSFFFSVSTITTIGYGNLSPNTMAARLFCIFFALVG
gi|14149764|  QWAMLQFVQVIMEAWVKGVNPKGNSTLPSNWDFGSSFFEAGIVVTTIGYGNLAESTEAGVFCVPYALKG 150        160        170        180        190        200        210
              ....|....|....|....|....|....|....|....|....|....|....|....|....|....|
NOV12a        IPLNLVVINRLG---HLMQQGVNHWASRLGGTWQDPDKARWLAGSGALLSGLLLFLLLPPLLFSHMEGWS
gi|17025230|  IPLNLVVINRLG---HLMQQGVNHWASRLGGTWQDPDKARWLAGSGALLSGLLLFLLLPPLLFSHMEGWS
gi|13507377|  IPLNLVVINRLG---HLMQQGVNHWASRLGGTWQDPDKARWLAGSGALLSGLLLFLLLPPLLFSHMEGWS
gi|9988111|   IPLNLVVINRLG---HLMQQGVNHWASRLGGTWQDPDKARWLAGSGALLSGLLLFLLLPPLLFSHMEGWS
gi|9988112|   IPLNLVVINRLG---HLMQQGVNHWASRLGGTWQDPDKARWLAGSGALLSGLLLFLLLPPLLFSHMEGWS
gi|14149764|  IPLNVIFLNHLGRGLRAHLAAIERWEDRP----RRSQVLQVLGLALFLTLGTLVILIFPPMVFSHVEGWS 220        230        240        250        260        270        280
              ....|....|....|....|....|....|....|....|....|....|....|....|....|....|
NOV12a        YTEGFYFAFITLSTVGFGDYVIGMNPSQRYPLWYKNYVSLWIIFGMAWLALIKLILSQLETPGRVCSCC
gi|17025230|  YTEGFYFAFITLSTVGFGDYVIGMNPSQRYPLWYKNYVSLWIIFGMAWLALIKLILSQLETPGRVCSCC
gi|13507377|  YTEGFYFAFITLSTVGFGDYVIGMNPSQRYPLWYKNYVSLWIIFGMAWLALISNSSSPSWRRQGGYVPAA
gi|9988111|   YTEGFYFAFITLSTVGFGDYVI-----------------------------------------------
gi|9988112|   YTEGFYFAFITLSTVGFGDYVI-----------------------------------------------
gi|14149764|  FSEGFYFAFITLSTIGFGDYVVGTDPSRHYISVYPSLAAIWILLGLAWLALILPLGPLLLHR---CCQLW 290        300        310        320        330        340
              ....|....|....|....|....|....|....|....|....|....|....|....|.
NOV12a        HHSSKE--DFKSQSWRQGPDREPESHSP---QQGCYPEGPMG-IIQHLEPSAHAAG----CGKDS-
gi|17025230|  HHSSKE--DFKSQSWRQGPDREPESHSP---QQGCYPEGPMG-IIQHLEPSAHAAG----CGKDS-
gi|13507377|  TTAKRKTSSPKAGDRDLTGSSSPTPHSKDAIQPDPWESYSIWNLLLTLQAVARTASYTPFFGRRPR
gi|9988111|   -----------------------------------------------------------------
gi|9988112|   -----------------------------------------------------------------
gi|14149764|  LLSLRQ-----GCGAKAAPGRRP--------RRGSTAARGVQVTPQDFPISKKGLG--------S-
```

Potassium channels are amongst the most heterogeneous class of ion channels known and are responsible for mediating a diverse range of biological functions. The most recently described family of K(+) channels, the 'two pore-domain family', contain four membrane spanning domains and two pore-forming domains, suggesting that two channel subunits associate to form a functional K(+) pore. Several sub-families of the two pore domain potassium channel family have been described, including the weakly inward rectifying K(+) channel (TWIK), the acid-sensitive K(+) channel (TASK), the TWIK-related K(+) channel (TREK) and the TWIK-related arachidonic acid stimulated K(+) channel (TRAAK). TWIK-1 and the TWIK-1-like channel KCNK7 were predominantly expressed in the CNS, in contrast to TWIK-2 which was preferentially expressed in peripheral tissues such as pancreas, stomach, spleen and uterus. TASK-1 was expressed in the CNS and some peripheral tissues, whereas TASK-2 was exclusively expressed in the periphery except for mRNA expression observed in dorsal root ganglion and spinal cord. In addition, mRNA expression of the recently identified TASK-3, was almost completely exclusive to cerebellum with little or no mRNA detected in any other tissues. TREK-1 and TRAAK mRNA expression was predominantly CNS specific in contrast to the closely related TREK-2, which was expressed in both CNS and peripheral tissues. (Medhurst et al., Brain Res Mol Brain Res 86:101–114).

The two-pore-domain K(+) channels, or K(2P) channels produce currents with unusual characteristics. They are quasi-instantaneous and noninactivating, and they are active at all membrane potentials and insensitive to the classic K(+) channel blockers. These properties designate them as background K(+) channels. They are expected to play a major role in setting the resting membrane potential in many cell types. Another salient feature of K(2P) channels is the diversity of their regulatory mechanisms. The weak inward rectifiers TWIK-1 and TWIK-2 are stimulated by activators of protein kinase C and decreased by internal acidification, the baseline TWIK-related acid-sensitive K(+) (TASK)-1 and TASK-2 channels are sensitive to external pH changes in a narrow range near physiological pH, and the TWIK-related (TREK)-1 and TWIK-related arachidonic acid-stimulated K(+) (TRAAK) channels are the first cloned polyunsaturated fatty acids-activated and mechanogated K(+) channels. The recent demonstration that TASK-1 and TREK-1 channels are activated by inhalational general anesthetics, and that TRAAK is activated by the neuroprotective agent riluzole, indicates that this novel class of K(+) channels is an interesting target for new therapeutic developments (Lesage and Lazdunski, Am J Physiol Renal Physiol 2000, 279(5):F793–801).

TWIK-1, the founding member of the 2P domain mammalian family, is widely expressed in human tissues and is particularly abundant in brain and heart. hTWIK-1 currents expressed in Xenopus oocytes are K+-selective, are time-independent, and present a nearly linear I-V relationship that rectifies for depolarizations positive to 0 mV. TWIK-1 is blocked by Ba2+, quinine, and quinidine (Lesage et al., 1996 EMBO J. 15: 1004–1011). Recently, hTWIK-2 (also called hTOSS), a TWIK-1-related gene, was cloned by two independent groups. Although both hTWIK-2 and hTOSS sequences are identical, conflicting results were published concerning functional expression in heterologous systems (Chavez, et al., 1999 J. Biol. Chem. 274: 7887–7892; Pountney, et al., 1999 FEBS Lett. 450: 191–196). hTWIK-2 expressed in Xenopus oocytes was shown to be a noninactivating, time-independent, weak inward rectifier with biophysical properties identical to TWIK-1.

Pharmacologically, hTWIK-2 was reported to be different from TWIK-1 with a lack of sensitivity to quinine, quinidine, and Ba2+. On the contrary, no significant current was observed in hTOSS cRNA-injected *Xenopus laevis* oocytes or in hTOSS cDNA-transfected HEK293T cells. Co-injection of equimolar concentrations of hTWIK-1 and hTOSS cRNA also failed to generate currents in *Xenopus* oocytes. These negative findings have led these authors and others to propose that hTOSS may be targeted to locations other than the plasma membrane or that it may possess a regulatory function, modulating the properties of other principal channel-forming subunits with tissue-specific implications (Chavez, et al., 1999, J. Biol. Chem. 274: 7887–7892; Pountney, et al., 1999 FEBS Lett. 450: 191–196; Rajan, et al., 2000 J. Biol. Chem. 275: 16650–16657).

The NOV12 nucleic acid of the invention encoding a TWIK 3-like protein includes the nucleic acid whose sequence is provided in Tables 12A, 12C and 12E, or a fragment thereof. The invention also includes a mutant or variant nucleic acid any of whose bases may be changed from the corresponding base shown in Tables 12A, 12C and 12E while still encoding a protein that maintains its TWIK 3-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 41% of the NOV12a residues, about 38% of the NOV12b residues and about 41% of the NOV12c residues may be so changed.

The NOV12 protein of the invention includes the TWIK 3-like protein whose sequence is provided in Tables 12B, 12D and 12F. The invention also includes a mutant or variant protein any of whose residues may be changed from the corresponding residue shown in Tables 12B, 12D and 12F while still encoding a protein that maintains its TWIK 3-like activities and physiological functions, or a functional fragment thereof. In the mutant or variant protein, up to about 1% of the NOV12a, about 3% of the NOV12b and about 50% of the NOV12c bases may be so changed.

The NOV12 nucleic acids and proteins of the invention are useful in potential diagnostic and therapeutic applications implicated in various diseases and disorders described below and/or other pathologies. For example, the compositions of the present invention will have efficacy for treatment of patients suffering from: central nervous system disorder; dementia; epilepsy; Alzheimer's disease; Parkinson's disease; multiple sclerosis; depression; amyotrophic lateral sclerosis; progressive supranuclear palsy; mania; Creutzfeldt-Jacob disease; psychiatric disorder; schizophrenic disorder; Korsakoff's psychosis; anxiety disorder; phobic disorder; amnesia; learning disorder; memory disorder; age-related memory loss; obesity; neurological disorder; cardiac disorder and other diseases, disorders and conditions of the like.

NOV12 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV12 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV13

A disclosed NOV13 nucleic acid of 1260 nucleotides (also referred to as CG57220-04) encoding a novel TASK 4-like protein is shown in Table 13A. An open reading frame was identified beginning with an ATG initiation codon at nucleotides 107–109 and ending with a TAG codon at nucleotides 1163–1165. Putative untranslated regions upstream from the intitation codon and downstream from the termination codon are underlined in Table 13A, and the start and stop codons are in bold letters.

TABLE 13A

NOV13 Nucleotide Sequence (SEQ ID NO:49)
<u>CTCAAGCAGGCGTTTGCGAGAGGAGATACGAGCTGGACGCCTGGCCCTTCCCTCCCACCGGGTCCTAGTCCAC</u>

<u>CGCTCCCGGCGCCGGCTCCCCGCCTCTCCCGCT</u>ATGTACCGACCGCGAGCCCGGGCGGCTCCCGAGGGCAGGG

TCCGGGGCTGCGCGGTGCCCGGCACCGTGCTCCTGCTGCTCGCCTACCTGGCTTACCTGGCGCTGGGCACCGG

CGTGTTCTGGACGCTGGAGGGCCGCGCGGCGCAGGACTCCAGCCGCAGCTTCCAGCGCGACAAGTGGGAGCTG

TTGCAGAACTTCACGTGTCTGGACCGCCCGGCGCTGGACTCGCTGATCCGGGATGTCGTCCAAGCATACAAAA

ACGGAGCCAGCCTCCTCAGCAACACCACCAGCATGGGGCGCTGGGAGCTCGTGGGCTCCTTCTTCTTTTCTGT

GTCCACCATCACCACCATTGGCTATGGCAACCTGAGCCCCAACACGATGGCTGCCCGCCTCTTCTGCATCTTC

TTTGCCCTTGTGGGGATCCCACTCAACCTCGTGGTGCTCAACCGACTGGGGCATCTCATGCAGCAGGGAGTAA

ACCACTGGGCCAGCAGGCTGGGGGGCACCTGGCAGGATCCTGACAAGGCGCGGTGGCTGGCGGGCTCTGGCGC

CCTCCTCTCGGGCCTCCTGCTCTTCCTGCTGCTGCCACCGCTGCTCTTCTCCCACATGGAGGGCTGGAGCTAC

TABLE 13A-continued

NOV13 Nucleotide Sequence

ACAGAGGGCTTCTACTTCGCCTTCATCACCCTCAGCACCGTGGGCTTCGGCGACTACGTGATTGGAATGAACC

CCTCCCAGAGGTACCCACTGTGGTACAAGAACATGGTGTCCCTGTGGATCCTCTTTGGGATGGCATGGCTGGC

CTTGATCATCAAACTCATCCTCTCCCAGCTGGAGACAAACCCATCCTCTCCCAGCTGGAGACAACAGGGAGGG

TATGTTCCTGCTGCCACCACAGCTCTAAGGAAGACTTCAAGTCCCAAAGCTGGAGACAGGGACCTGACCGGGA

GCCAGAGTCCCACTCCCCACAGCAAGGATGCTATCCAGAGGGACCCATGGGAATCATACAGCATCTGGAACCT

TCTGCTCACGCTGCAGGCTGTGGCAAGGACAGCTAGTTATACTCCATTCTTTGGTCGTCGTCCTCGGTAGCAA

GACCCCTGATTTTAAGCTTTGCACATGTCCACCCAAACTAAAGACTACATTTTCCATCCACCCTAGAGGCTGG

GTGCAGCTATATGATTAAT

The NOV13 nucleic acid was identified on chromosome 6 and has 508 of 827 bases (61%) identical to a gb:GENBANK-ID:AF006823|acc:AF006823.1 mRNA from Homo sapiens (Homo sapiens TWIK-related acid-sensitive K+ channel (TASK) mRNA, complete cds) (E=1.2e$^{-29}$).

A disclosed NOV13 polypeptide (SEQ ID NO:50) encoded by SEQ ID NO:49 is 352 amino acid residues and is presented using the one-letter code in Table 13B. Signal P, Psort and/or Hydropathy results predict that NOV13 contains a signal peptide and is likely to be localized to the extracellularly with a certainty of 0.6400. The most likely cleavage site for a NOV13 polypeptide is between amino acids 48 and 49: RAA-QD.

NOV13 is expressed in at least the following tissues: liver, lung, pancreas, placenta, aorta and heart. This information was derived by determining the tissue sources of the sequences that were included in the invention including but not limited to SeqCalling sources, Public EST sources, genomic clone sources, literature sources, and/or RACE sources. The sequence is predicted to be expressed in the following tissues because of the expression pattern of (GENBANK-ID: gb:GENBANK-ID:AF006823|acc:AF006823.1) a closely related Homo sapiens TWIK-related acid-sensitive K+ channel (TASK) mRNA, complete cds homolog in species Homo sapiens:

TABLE 13B

Encoded NOV13 protein sequence (SEQ ID NO:50)

MYRPRARAAPEGRVRGCAVPGTVLLLLAYLAYLALGTGVFWTLEGRAAQDSSRSFQRDKWELLQNFTCLDRP

ALDSLIRDVVQAYKNGASLLSNTTSMGRWELVGSFFFSVSTITTIGYGNLSPNTMAARLFCIFFALVGIPLN

LVVLNRLGHLMQQGVNHWASRLGGTWQDPDKARWLAGSGALLSGLLLFLLLPPLLFSHMEGWSYTEGFYFAF

ITLSTVGRGDYVIGMNPSQRYPLWYKNMVSLWILFGMAWLALIIKLILSQLETNPSSPSWRQQGGYVPAATT

ALRKTSSPKAGDRDLTGSQSPTPHSKDAIQRDPWESYSIWNLLLTLQAVARTASYTPFFGRRPR

The NOV13 amino acid sequence has 340 of 352 amino acid residues (96%) identical to, and 342 of 352 amino acid residues (97%) similar to, the 343 amino acid residue ptnr:TREMBLNEW-ACC:AAK28551 protein from Homo sapiens (Human) (Potassium Channel TASK-4) (E=5.0e$^{-183}$).

pancreas, placenta, brain, lung, prostate, heart, kidney, uterus, small intestine and colon.

NOV13 has homology to the amino acid sequences shown in the BLASTP data listed in Table 13C.

TABLE 13C

BLAST results for NOV13

| Gene Index/Identifier | Protein/Organism | Length (aa) | Identity (%) | Positives (%) | Expect |
|---|---|---|---|---|---|
| gi|13507377|gb|AAK28551.1| AF339912_1 (AF339912) | potassium channel TASK-4 [Homo sapiens] | 343 | 305/352 (86%) | 307/352 (86%) | e-164 |
| gi|17025230|ref|NP_113648.2| (NM_031460) | potassium channel, subfamily K, | 332 | 233/269 (86%) | 233/269 (86%) | e-128 |

TABLE 13C-continued

BLAST results for NOV13

| Gene Index/ Identifier | Protein/Organism | Length (aa) | Identity (%) | Positives (%) | Expect |
|---|---|---|---|---|---|
| gi\|9988111\|emb\|CAC07335.1\| (AL136087) | dJ137F1.1 (novel member of the potassium channel subfamily K) [Homo sapiens] | 229 | 193/229 (84%) | 193/229 (84%) | e−103 |
| gi\|9988112\|emb\|CAC07336.1\| (AL136087) | dJ137F1.2 (novel member of the potassium channel subfamily K) [Homo sapiens] | 294 | 87/226 (38%) | 136/226 (59%) | 1e−41 |
| gi\|14149764\|ref\|NP_115491.1\| (NM_032115) | pancreatic 2P domain potassium channel TALK-1; potassium family, subfamily K, member 16 [Homo sapiens] | 309 | 87/226 (38%) | 136/226 (59%) | 1e−41 |

The homology of these sequences is shown graphically in the ClustalW analysis shown in Table 13D.

TABLE 13D

Clustal W Sequence Alignment

1) NOV13 (SEQ ID NO:50)
2) gi|13507377|gb|AAK28551.1 AF339912_1 (AF339912) potassium channel TASK-4 [Homo sapiens] (SEQ ID NO:173)
3) gi|17025230|ref|NP_113648.2|(NM_031460) potassium channel, subfamily K, member 17; 2P domain potassium channel Talk-2; potassium channel TASK-4; potassium channel TALK-2 [Homo sapiens] (SEQ ID NO:174)
4) gi|9988111|cmb|CAC07335.1|(AL136087) dJ137F1.1 (novel member of the potassium channel subfamily K) [Homo sapiens] (SEQ ID NO: 175)
5) gi|9988112|emb|CAC07336.1|(AL136087) dJ137F1.2 (novel member of the potassium channel subfamily K) [Homo sapiens] (SEQ ID NO: 176)
6) gi|14149764|ref|NP_115491.1|(NM_032115) pancreatic 2P domain potassium channel TALK-1; potassium family, subfamily K, member 16 [Homo sapiens] (SEQ ID NO: 177)

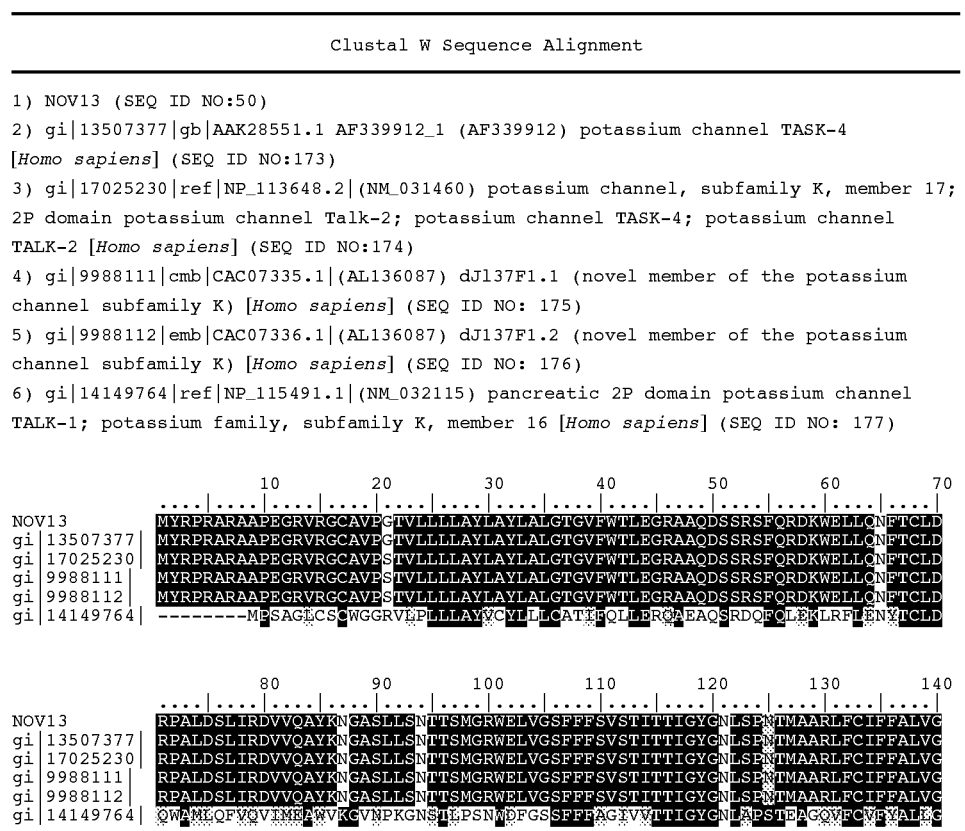

TABLE 13D-continued

Clustal W Sequence Alignment

```
                     150       160       170       180       190       200       210
               ....|....|....|....|....|....|....|....|....|....|....|....|....|....|
NOV13          IPLNLVVLNRLG---HLMQQGVNHWASRLGGTWQDPDKARWLAGSGALLSGLLLFLLLPPLLFSHMEGWS
gi|13507377|   IPLNLVVLNRLG---HLMQQGVNHWASRLGGTWQDPDKARWLAGSGALLSGLLLFLLLPPLLFSHMEGWS
gi|17025230|   IPLNLVVLNRLG---HLMQQGVNHWASRLGGTWQDPDKARWLAGSGALLSGLLLFLLLPPLLFSHMEGWS
gi|9988111|    IPLNLVVLNRLG---HLMQQGVNHWASRLGGTWQDPDKARWLAGSGALLSGLLLFLLLPPLLFSHMEGWS
gi|9988112|    IPLNLVVLNRLG---HLMQQGVNHWASRLGGTWQDPDKARWLAGSGALLSGLLLFLLLPPLLFSHMEGWS
gi|14149764|   IPLNVIFLNHLGTGLRAHLAALERWEDRP----RRSQVLQVLGLALFLTLGTLYILIFPPMVFSHVEGWS 220       230       240       250       260       270       280
               ....|....|....|....|....|....|....|....|....|....|....|....|....|....|
NOV13          YTEGFYFAFITLSTVGFGDYVIGMNPSQRYPLWYKNMVSLWILFGMAWLALIIKLILSQLETNPSSPSWR
gi|13507377|   YTEGFYFAFITLSTVGFGDYVIGMNPSQRYPLWYKNMVSLWILFGMAWLALIS---------NSSSPSWR
gi|17025230|   YTEGFYFAFITLSTVGFGDYVIGMNPSQRYPLWYKNMVSLWILFGMAWLALIIKLILS----QLETPG-R
gi|9988111|    YTEGFYFAFITLSTVGFGDYVI------------------------------------------------
gi|9988112|    YTEGFYFAFITLSTVGFGDYVI------------------------------------------------
gi|14149764|   FSEGFYFAFITLSTLGFGDYVVGTDPSKHYISVYRSLAAIWILLGLAWLALILPLG--------PLLLHR 290       300       310       320       330       340       350
               ....|....|....|....|....|....|....|....|....|....|....|....|....|....|
NOV13          QQGGYVPAATTALRKTSSPKAGDRDLTGSQSPTPHSKDAIQRDEWESYSIWNLLLTLQAVARTASYTPFF
gi|13507377|   RQGGYVPAATTALRKTSSPKAGDRDLTGSQSPTPHSKDAIQRDEWESYSIWNLLLTLQAVARTASYTPFF
gi|17025230|   VCSCCHHSSKEDFKSQSWRQGPDREPE-SHSPQ---QGCYPEGPMG------IIQHIEPSAHAAG----C
gi|9988111|    ----------------------------------------------------------------------
gi|9988112|    ----------------------------------------------------------------------
gi|14149764|   CCQLWLLSLRQGCGAKAAP--GRRPRRGSTAAR----G-VQVTEQD--------FPIS---KKG-----L

....|
NOV13          GRRPR
gi|13507377|   GRRPR
gi|17025230|   GKDS-
gi|9988111|    -----
gi|9988112|    -----
gi|14149764|   GS---
```

The NOV13 nucleic acid of the invention encoding a TASK 4-like protein includes the nucleic acid whose sequence is provided in Table 13A, or a fragment thereof. The invention also includes a mutant or variant nucleic acid any of whose bases may be changed from the corresponding base shown in Table 13A while still encoding a protein that maintains its TASK 4-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 39% of the residues may be so changed.

The NOV13 protein of the invention includes the TASK 4-like protein whose sequence is provided in Table 13B. The invention also includes a mutant or variant protein any of whose residues may be changed from the corresponding residue shown in Table 13B while still encoding a protein that maintains its TASK 4-like activities and physiological functions, or a functional fragment thereof. In the mutant or variant protein, up to about 4% of the bases may be so changed.

The NOV13 nucleic acids and proteins of the invention are useful in potential diagnostic and therapeutic applications implicated in various diseases and disorders described below and/or other pathologies. For example, the compositions of the present invention will have efficacy for treatment of patients suffering from: cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, tuberous sclerosis, sclerodermia, obesity, transplantation, aneurysm, fibromuscular dysplasia, stroke, systemic lupus erythematosus, autoimmune disease, asthma, emphysema, allergy, ARDS, Von Hippel-Lindau (VHL) syndrome, cirrhosis, diabetes, pancreatitis, fertility, cancer, tissue degeneration, bacterial/viral/parasitic infections and other diseases, disorders and conditions of the like.

NOV13 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV13 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV14

A disclosed NOV14 nucleic acid of 627 nucleotides (also referred to as CG57458-01) encoding a novel Copper transporter-like protein is shown in Table 14A. An open reading frame was identified beginning with an ATG initiation codon at nucleotides 31–33 and ending with a TGA codon at nucleotides 598–600. Putative untranslated regions upstream from the intitation codon and downstream from the termination codon are underlined in Table 14A, and the start and stop codons are in bold letters.

TABLE 14A

NOV14 Nucleotide Sequence

(SEQ ID NO:51)

TCTGCTGACTCTCAACTTTTCTTGGAAAAAATGGATCATTCCCATCATACGGGGATGAGCTGTATGGACTCCA

ACAGTACCATGCAACGTCCTCACCATCACCCAACCACTTCAGCCTCACACTCCCGTGGTGGAGGAGACAGCAA

CATGATGATGATGATGCCTATGACCTTCTACTTTGGCTTTAAGAATGTGGAACTACTGTTTTCCAGTTTGGTG

ATCAATACAGCTGGAGAAATGGCTGGAGCTTTTGTGGCAGTGCTTTTGCTACAATTCCATGCCTGTCCCATAG

CCCAAGAGAGCCTGCTGTGTAAGTCACAAGTCAGCTTTTGCTACAATTCCATGCCTGTCCCAGGACCAAATGG

AACCATCCTTATGGAGACACACAAAACTGTTGGGCAGCAGATGCTGAGCTTTCCTCACCTCCTGCAAACAGTG

CTGCACATCATCCAGGTGGTCATAAGCTACCTCCTCATGCTCATCTTCATGACCTACAATGGGTACCTCTGCA

TTGCAGTAACAGCAGGGGCCGGTACAAGATACTTCCTCTTCAGCTGGAAGAAGGCAGTGGTAGTGGACATCAC

AGAGTATTGCCATTGACGTCAAACTCTATGGCATGGCCTTATC

---

The NOV14 nucleic acid was identified on chromosome 3.

A disclosed NOV14 polypeptide (SEQ ID NO:52) encoded by SEQ ID NO:51 is 189 amino acid residues and is presented using the one-letter code in Table 14B. Signal P, Psort and/or Hydropathy results predict that NOV14 contains a signal peptide and is likely to be localized to the plasma membrane with a certainty of 0.6000. The most likely cleavage site for a NOV14 polypeptide is between amino acids 68 and 69: TAG-EM.

residues (89%) similar to, the 190 amino acid residue ptnr:SWISSNEW-ACC:015431 protein from Homo sapiens (Human) (High-Affinity Copper Uptake Protein 1 (HCTR1) (E=1.9e$^{-83}$).

NOV14 is expressed in at least the following tissues: brain. This information was derived by determining the tissue sources of the sequences that were included in the invention including but not limited to SeqCalling sources, Public EST sources, genomic clone sources, literature sources, and/or RACE sources.

TABLE 14B

Encoded NOV14 protein sequence

(SEQ ID NO:52)

MDHSHHTGMSCMDSNSTMQRPHHHPTTSASHSRGGGDSNMMMMMPMTFYFGFKNVELLFSSLVINTAGEMAG

AFVAVLLLQFHACPIAQESLLCKSQVSFCYNSMPVPGPNGTILMETHKTVGQQMLSFPHLLQTVLHIIQVVI

SYLLMLIFMTYNGYLCIAVTAGAGTRYFLFSWKKAVVVDITEYCH

---

The NOV14 amino acid sequence has 166 of 190 amino acid residues (87%) identical to, and 170 of 190 amino acid NOV14 has homology to the amino acid sequences shown in the BLASTP data listed in Table 14C.

TABLE 14C

BLAST results for NOV14

| Gene Index/ Identifier | Protein/Organism | Length (aa) | Identity (%) | Positives (%) | Expect |
|---|---|---|---|---|---|
| gi|4507015|ref|NP_001850.1| (NM_001859) | solute carrier family 31 (copper transporters), member 1; hCTR1; copper transporter 1 [Homo sapiens] | 190 | 149/191 (78%) | 153/191 (80%) | 2e-67 |
| gi|17940111|gb|AAL49494.1| AF320815_1 (AF320815) | high-affinity copper uptake protein [Sus scrofa] | 189 | 135/191 (70%) | 141/191 (73%) | 6e-59 |
| gi|12229733|sp|Q9JK41| COP1_RAT | High-affinity copper uptake | 187 | 133/187 (71%) | 139/187 (74%) | 1e-58 |

TABLE 14C-continued

BLAST results for NOV14

| Gene Index/ Identifier | Protein/Organism | Length (aa) | Identity (%) | Positives (%) | Expect |
|---|---|---|---|---|---|
| gi\|18652812\|gb\|AAL76092.1\| (AY077715) | protein 1 (rCTR1) (Copper transporter 1) high affinity copper uptake protein [Danio rerio] | 188 | 113/189 (59%) | 130/189 (67%) | 3e-50 |
| gi\|17462341\|ref\|XP_067707.1\| (XM_067707) | similar to solute carrier family 31 (copper transporters), member 1; hCTR1; copper transporter 1 [Homo sapiens] | 175 | 118/189 (62%) | 126/189 (66%) | 6e-50 |

The homology of these sequences is shown graphically in the ClustalW analysis shown in Table 14D.

TABLE 14D

Clustal W Sequence Alignment

1) NOV14 (SEQ ID NO:52)
2) gi|4507015|ref|NP_001850.1|(NM_001859) solute carrier family 31 (copper transporters), member 1; hCTR1; copper transporter 1 [Homo sapiens] (SEQ ID NO:178)
3) gi|17940111|gb|AAL49494.1|AF320815_1 (AF320815) high-affinity copper uptake protein [Sus scrofa] (SEQ ID NO:179)
4) gi|12229733|sp|Q9JK41|COP1_RAT High-affinity copper uptake protein 1 (rCTR1) (Copper transporter 1) (SEQ ID NO:180)
5) gi|18652812|gb AAL76092.1|(AY077715) high affinity copper uptake protein [Danio rerio] (SEQ ID NO:181)
6) gi|17462341|ref|XP_067707.1|(XM_067707) similar to solute carrier family 31 (copper transporters), member 1; hCTR; copper transporter 1 [Homo sapiens] (SEQ ID NO:182)

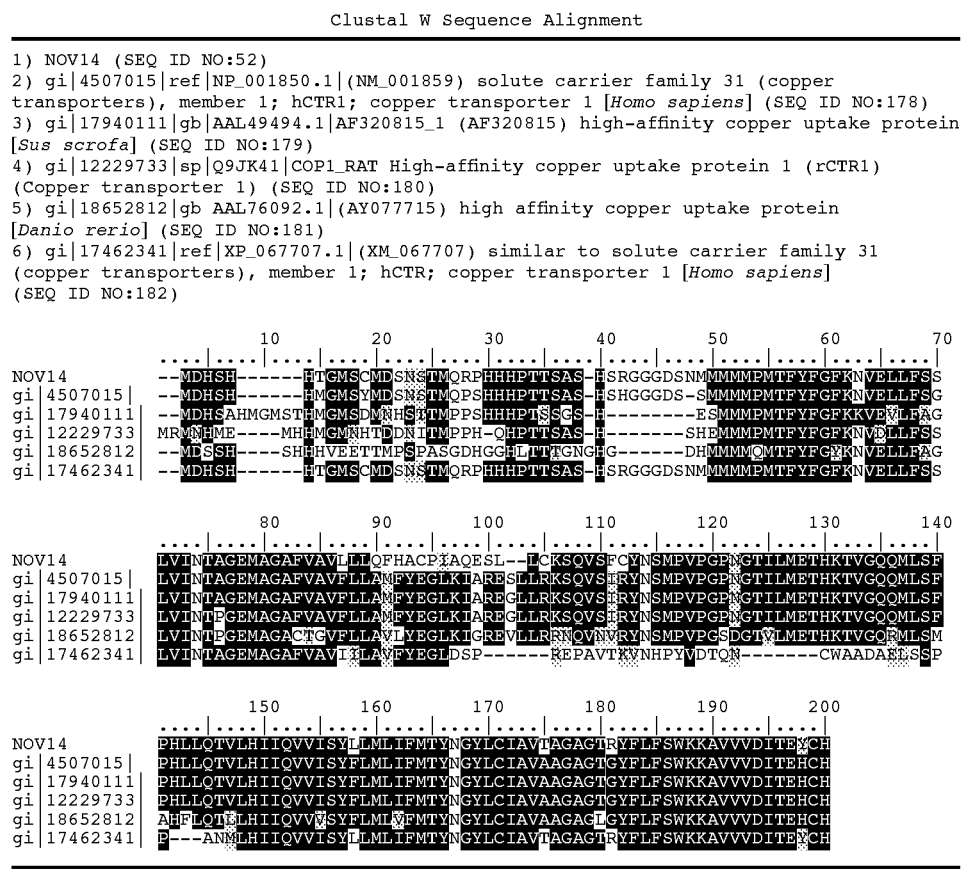

Copper is an element essential for life, but excessive copper can be toxic or even lethal to the cell. Therefore, cells have developed sophisticated ways to maintain a critical copper balance, with the intake, export, and intracellular compartmentalization or buffering of copper strictly regulated. The two related genes ATP7A and ATP7B, responsible for the human diseases Menkes syndrome and Wilson disease (WND), respectively, are involved in copper export. In S. cerevisiae, three copper uptake genes CTR1, CTR2, and CTR3 have been identified.

In mammals, however, the molecular basis for copper uptake is unknown. Zhou and Gitschier (Proc Natl Acad Sci U S A. 94(14):7481–6, 1997) isolated a human cDNA encoding COPT1, which they called CTR1, by functional complementation of the yeast high-affinity copper uptake mutant ctr1. The deduced 190-amino acid human CTR1 protein is similar to yeast CTR1 and Arabidopsis COPT1, a copper transporter also isolated by functional complementation of yeast ctr1. All 3 predicted proteins have 3 transmembrane domains and an N terminus that is rich in methionine and serine residues; the N terminus of human CTR1 is also abundant in histidines. The authors proposed that human CTR1 is a high-affinity copper uptake gene because it can complement the yeast ctr1 mutation, it can rescue multiple defects in ctr1 yeast, its expression in ctr1 yeast increases the concentration of cellular copper, and its overexpression in yeast leads to a vulnerability to the toxicity of copper overload. Northern blot analysis detected 2 major CTR1 transcripts of approximately 2 kb and 5.5 kb and a less abundant transcript of about 8.5 kb in all human organs and tissues examined. Zhou and Gitschier (1997) found that the 3-prime untranslated region of the human CTR1 gene contains a CA repeat marker (D9S262) that had been previously mapped to 9q31-q32. By analysis of YAC clones, they showed that CTR1 and CTR2 (COPT2) which is also located in 9q31-q32, are not adjacent genes. The molecular mechanisms responsible for the cellular uptake of copper in mammalian cells are unknown. The isolation of a human gene involved in this process by complementation of the yeast high-affinity copper uptake mutant, ctr1 is described. Besides complementing ctr1 growth defect on nonfermentable media, the human gene also rescues iron transport and SOD1 defects in ctr1 yeast. Overexpression of the gene in yeast leads to vulnerability to the toxicity of copper overload. In addition, its expression in ctr1 yeast significantly increases the level of cellular copper, as demonstrated by atomic absorption. It is proposed that this gene is a candidate for high-affinity copper uptake in humans and by analogy have named it hCTR1. The hCTR1 and yeast CTR1 predicted transmembrane proteins are 29% identical, but the human protein is substantially smaller in both the extracellular metal-binding and intracellular domains. An additional human gene similar to hCTR1, here named hCTR2, was identified in a database search. Both hCTR1 and hCTR2 are expressed in all human tissues examined, and both genes are located in 9q31/32. These studies, together with the previously recognized functional and sequence similarity between the Menkes/Wilson copper export proteins and CCC2 in yeast, demonstrate that similar copper homeostatic mechanisms are used in these evolutionarily divergent organisms.

The NOV14 nucleic acid of the invention encoding a Copper transporter-like protein includes the nucleic acid whose sequence is provided in Table 14A, or a fragment thereof. The invention also includes a mutant or variant nucleic acid any of whose bases may be changed from the corresponding base shown in Table 14A while still encoding a protein that maintains its Copper transporter-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 13% of the residues may be so changed.

The NOV14 protein of the invention includes the Copper transporter-like protein whose sequence is provided in Table 14B. The invention also includes a mutant or variant protein any of whose residues may be changed from the corresponding residue shown in Table 14B while still encoding a protein that maintains its Copper transporter-like activities and physiological functions, or a functional fragment thereof. In the mutant or variant protein, up to about 13% of the bases may be so changed.

The NOV14 nucleic acids and proteins of the invention are useful in potential diagnostic and therapeutic applications implicated in various diseases and disorders described below and/or other pathologies. For example, the compositions of the present invention will have efficacy for treatment of patients suffering from: Von Hippel-Lindau (VHL) syndrome, Alzheimer's disease, Stroke, Tuberous sclerosis, hypercalceimia, Parkinson's disease, Huntington's disease, Cerebral palsy, Epilepsy, Lesch-Nyhan syndrome, Multiple sclerosis, Ataxia-telangiectasia, Leukodystrophies, Behavioral disorders, Addiction, Anxiety, Pain, Neuroprotection and other diseases, disorders and conditions of the like.

NOV14 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV14 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV15

A disclosed NOV15 nucleic acid of 1478 nucleotides (also referred to as CG57454-01) encoding a novel Cytokeratin-like protein is shown in Table 15A. An open reading frame was identified beginning with an ATG initiation codon at nucleotides 21–23 and ending with a TGA codon at nucleotides 1464–1466. Putative untranslated regions upstream from the intitation codon and downstream from the termination codon are underlined in Table 15A, and the start and stop codons are in bold letters.

TABLE 15A

NOV15 Nucleotide Sequence (SEQ ID NO:53)
<u>ACTCCACTCCTGCCTCCACC</u>ATGTCCATCAGGGTGACCCAGAAGTCCTACAAGGTGTCCACCTCTGGCCCCCA TABLE 15A-continued NOV15 Nucleotide Sequence

GGCCTTTAGCAGCCGCTTTTACACGAATGGGCCTGGTGCCCACATCAGCTCTTCAAGCCTCTCCCGAGTGAGC

AGCAGCAGCTTCCGGGGTGGCCTGGGCAGAGGCTATGGTGGGGCCAGCGGCATAGGAGGCATCACCACTGTCA

CGTTCAACCAGAGCCTGCTGAGCCCTGTTAACCTGGAGGTAGATCCCAATATCCAGGCCATGCACACCCAGGA

GAAGGAGCAGATCAAGACCCTCAACAACAAGTTTGCCTCCTTCATCGACAAGGTACGGTTCCTGCAGCAGAAG

AACAAGATGCTGGAGACCAAGTGGAGCCTCCTGCAGCAGCAGAAGATGGCTCGGATCAACGTATTTGAGAGCT

ACATGAACAACCTTAGGCGGCAGCTGGAGGCTCTGGGCCAGGAGAAGCTGAAGCTGGAGGCGGAGCTTGGCAA

TATGCAGGGGCTGGTGGAGGACTTCAAGAACAAGTATGAGGATGAGATCAATAAGCGTACAGAAACGGAGAAT

GAATTTGTCCTCATCAAGAAGGACATGGATGAAGCTTACATGAACAAGGCAGAGCTGGAGTCTCGCCTGGAAG

GGCTGACTGACGAGATCAACTTCCTCAGGCAACTGCATGAAGAGGAGATCCAGGAGCTGCAGTCCCAGATCTC

GGGCACGTCTGCGGTGCTGTCCATGGACAACAGCCTCTCCCTGGACATGGACAGCATCATCGCTGAGGTCAAG

GCACAGGAGGAGGAGATCGCCAACCGCAGCTGGGCTGAGGCTGAGAGCATGTACCAGATCAAGTATGCAGAGC

TGCAGACGCTGGCTGGCAAGCACGGGGATGACCTGCGGTGTACAAAGACTAAGATCTCCGAGATGAACCGGAA

CATCAGCCGGCTCCAGGCTGAGATTGAGGGCCTCAAAGGCCAGAGGGCTTCCCTGGAGGCCCCCATCGCAGAT

ACCGAGCAGCGTGGGGAGCTGGCCGTTAAGGATGCCAGCGCCAAGCGGTCGGAGCTGGAGGCCGCCCTGCAGC

GGGCCAAGCAGGACATGGCGCAGCAGCTGCGTGAGTACCAGGAGCTGATGAACGTCAAACTGGCCCTGGACAT

GGAGATCGCCACCTACAGGAAGCTGCTGGAGGGCGAGGAGAGCGCCCGGCTGGAGTCTGGGATGCAGAACACG

AGTATCCATAGGAAGACCACCAGCGGCTATGCAGGTGGTCTGAGTTCCGCCTATGGGGCCTCACAAGCCCTG

GCCTCAGCTATGGCCTAAGCTCCAGCTTTGGCTCTGTCGCGGGCTCCAGCTCATTCAGCCGCACCGGCTCCGC

CAGGGCCATGGTTGTGCAGAAGATTGAGACCCGCGATGGGAAGCTGGTATCCGAGTCCTCTGACGTCCTGCCC

AAGTGAAGAGCTGCGGCA

The NOV15 nucleic acid was identified on chromosome 3 and has 1187 of 1344 bases (88%) identical to a gb:GENBANK-ID:AF213884S2|acc:AF224669.1 mRNA from *Homo sapiens* (*Homo sapiens* mannosidase, beta A, lysosomal (MANBA) gene, and ubiquitin-conjugating enzyme E2D 3 (UBE2D3) genes, complete cds) (E=7.3e$^{-228}$).

A disclosed NOV15 polypeptide (SEQ ID NO:54) encoded by SEQ ID NO:53 is 481 amino acid residues and is presented using the one-letter code in Table 15B. Signal P, Psort and/or Hydropathy results predict that NOV15 contains a signal peptide and is likely to be localized to the plasma membrane with a certainty of 0.3600.

TABLE 15B

Encoded NOV15 protein sequence (SEQ ID NO:54)
MSIRVTQKSYKVSTSGPQAFSSRFYTNGPGAHISSSSLSRVSSSSFRGGLGRGYGGASGIGGITTVTFNQSL

LSPVNLEVDPNIQAMHTQEKEQIKTLNNKFASFIDKVRFLQQKNKMLETKWSLLQQQKMARINVFESYMNNL

RRQLEALGQEKLKLEAELGNMQGLVEDFKNKYEDEINKRTETENEFVLIKKDMDEAYMNKAELESRLEGLTD

EINFLRQLHEEEIQELQSQISGTSAVLSMDNSLSLDMDSIIAEVKAQEEEIANRSWAEAESMYQIKYAELQT

LAGKHGDDLRCTKTKISEMNRNISRLQAEIEGLKGQRASLEAPIADTEQRGELAVKDASAKRSELEAALQRA

KQDMAQQLREYQELMNVKLALDMEIATYRKLLEGEESARLESGMQNTSIHRKTTSGYAGGLSSAYGGLTSPG

LSYGLSSSFGSVAGSSSFSRTGSARAMVVQKIETRDGKLVSESSDVLPK

The NOV15 amino acid sequence has 424 of 482 amino acid residues (87%) identical to, and 448 of 482 amino acid residues (92%) similar to, the 482 amino acid residue ptnr:SWISSPROT-ACC:P05787 protein from *Homo sapiens* (Human) (Keratin, Type II Cytoskeletal 8 (Cytokeratin 8) (K8) (CK 8)) (E=4.9e$^{-213}$).

NOV15 is expressed in at least the following tissues: Heart, Kidney, Liver, Lung, Muscle, Nose, Ovary, Pancreas, Parathyroid, Placenta, Pooled, Prostate, Stomach, Synovial membrane, Testis, Thyroid, Tonsil and Uterus. This information was derived by determining the tissue sources of the sequences that were included in the invention including but not limited to SeqCalling sources, Public EST sources, genomic clone sources, literature sources, and/or RACE sources.

NOV15 has homology to the amino acid sequences shown in the BLASTP data listed in Table 15C.

TABLE 15C

BLAST results for NOV15

| Gene Index/ Identifier | Protein/Organism | Length (aa) | Identity (%) | Positives (%) | Expect |
|---|---|---|---|---|---|
| gi\|105815\|pir\|\|A34720 | keratin 8, type II cytoskeletal [Homo sapiens] | 483 | 335/484 (69%) | 355/484 (73%) | e-145 |
| gi\|2506774\|sp\|P05787\| K2C8_HUMAN | KERATIN, TYPE II CYTOSKELETAL 8 (CYTOKERATIN 8) (K8) (CK 8) [Homo sapiens] | 483 | 335/484 (69%) | 354/484 (72%) | e-145 |
| gi\|4504919\|ref\|NP_002264.1\| (NM_002273) | keratin 8; Keratin-8 [Homo sapiens] | 483 | 335/484 (69%) | 354/484 (72%) | e-145 |
| gi\|181400\|gb\|AAA35748.1\| (M34225) | cytokeratin 8 [Homo sapiens] | 483 | 333/484 (68%) | 354/484 (72%) | 1e-144 |
| gi\|87303\|pir\|\|JS0487 | cytokeratin 8 (version 1) [Homo sapiens] | 482 | 335/484 (69%) | 354/484 (72%) | 1e-143 |

The homology of these sequences is shown graphically in the ClustalW analysis shown in Table 15D.

TABLE 15D

Clustal W Sequence Alignment

1) NOV15 (SEQ ID NO:54)
2) gi|105815|pir||A34720 keratin 8, type II cytoskeletal [Homo sapiens] (SEQ ID NO:183)
3) gi|2506774|sp|P05787|K2C8_HUMAN KERATIN, TYPE II CYTOSKELETAL 8 (CYTOKERATIN 8) (K8) (CK 8) [Homo sapiens] (SEQ ID NO:184)
4) gi|4504919|refNP_002264.1|(NM_002273) keratin 8; Keratin-8 [Homo sapiens] (SEQ ID NO:185)
5) gi|181400|gb AAA35748.1|(M34225) cytokeratin 8 [Homo sapiens] (SEQ ID NO:186)
6) gi|87303 pir||JS0487 cytokeratin 8 (version 1) [Homo sapiens] (SEQ ID NO:187)

TABLE 15D-continued

Clustal W Sequence Alignment

```
               150       160       170       180       190       200       210
           ....|....|....|....|....|....|....|....|....|....|....|....|....|
NOV15      ESYVNNLRRQLEALGQEKLKLEAELGNMQGLVEDFKNKYEDEINKRTETENEFVLIKKDMDEAYMNKAEL
gi|105815| ESYINNLRRQLETLGQEKLKLEAELGNMQGLVEDFKNKYEDEINKRTEMENEFVLIKKDVDEAYMNKVEL
gi|2506774|ESYINNLRRQLETLGQEKLKLEAELGNMQGLVEDFKNKYEDEINKRTEMENEFVLIKKDVDEAYMNKVEL
gi|4504919|ESYINNLRRQLETLGQEKLKLEAELGNMQGLVEDFKNKYEDEINKRTEMENEFVLIKKDVDEAYMNKVEL
gi|181400| ESYINNLRRQLETLGQEKLKLEAELGNMQGLVEDFKNKYEDEINKRTEMENEFVLIKKDVDEAYMNKVEL
gi|87303|  ESYINNLRRQLETLGQEKLKLEAELGNMQGLVEDFKNKYEDEINKRTEMENEFVLIKKDVDEAYMNKVEL 220       230       240       250       260       270       280
           ....|....|....|....|....|....|....|....|....|....|....|....|....|
NOV15      ESRLEGLTDEINFLRQLHEEEIQELQSQISGTSAVLSMDNSLSLDMDSIIAEVKAQEEEIANRSWAEAES
gi|105815| ESRLEGLTDEINFLRQLYEEEIRELQSQISDTSVVLSMDNSRSLDMDSIIAEVKAQYEDIANRSRAEAES
gi|2506774|ESRLEGLTDEINFLRQLYEEEIRELQSQISDTSVVLSMDNSRSLDMDSIIAEVKAQYEDIANRSRAEAES
gi|4504919|ESRLEGLTDEINFLRQLYEEEIRELQSQISDTSVVLSMDNSRSLDMDSIIAEVKAQYEDIANRSRAEAES
gi|181400| ESRLEGLTDEINFLRQLYEEEIRELQSQISDTSVVLSMDNSRSLDMSIIAEVKAQYEDIANRSRAEAES
gi|87303|  ESRLEGLTDEINFLRQLYEEEIRELQSQISDTSVVLSMDNSRSLDMDSIIAEVKAQYEDIANRSRAEAES 290       300       310       320       330       340       350
           ....|....|....|....|....|....|....|....|....|....|....|....|....|
NOV15      MYQIKYAELQTLAGKHGDDLRCTKTKISEMNRNISRLQAEIEGLKGQRASLEAPIADTEQRGELAVKDAS
gi|105815| MYQIKYEELQSLAGKHGDDLRRTKTEISEMNRNISRLQAEIEGLKGQRASLEAAIADAEQRGELAIKDAN
gi|2506774|MYQIKYEELQSLAGKHGDDLRRTKTEISEMNRNISRLQAEIEGLKGQRASLEAAIADAEQRGELAIKDAN
gi|4504919|MYQIKYEELQSLAGKHGDDLRRTKTEISEMNRNISRLQAEIEGLKGQRASLEAAIADAEQRGELAIKDAN
gi|181400| MYQIKYEELQSLAGKHGDDLRRTKTEISEMNRNISRLQAEIEGLKGQRASLEAAIADAEQRGELAIKDAN
gi|87303|  MYQIKYEELQSLAGKHGDDLRRTKTEISEMNRNISRLQAEIEGLKGQRASLEAAIADAEQRGELAIKDAN 360       370       380       390       400       410       420
           ....|....|....|....|....|....|....|....|....|....|....|....|....|
NOV15      AKRSELEAALQRAKQDMAQQLREYQELMNVKLALDMEIATYRKLLEGEESARLESGMQNTSIHRKTTSGY
gi|105815| AKLSELEAALQRAKQDMARQLREYQELMNVKLALDIEIATYRKLLEGE-SRLESGMQNMSIHTKTTGGY
gi|2506774|AKLSELEAALQRAKQDMARQLREYQELMNVKLALDIEIATYRKLLEGE-SRLESGMQNMSIHTKTTGGY
gi|4504919|AKLSELEAALQRAKQDMARQLREYQELMNVKLALDIEIATYRKLLEGE-SRLESGMQNMSIHTKTTSGY
gi|181400| AKLSELEAALQRAKQDMARQLREYQELMNVKLALDIEIATYRKLLEGE-SPLESGMQNMSIHTKTTGGY
gi|87303|  AKLSELEAALQRAKQDMARQLREYQELMNVKLALDIEIATYRKLLEGE-SRLESGMQNMSIHTKTTGGY 430       440       450       460       470       480
           ....|....|....|....|....|....|....|....|....|....|....|
NOV15      AGGLSSAYGGLTSPGLSYGLSSSFGSVAGSSSFSRTSSARAMVVQKIETRDGKLVSESSDVLPK
gi|105815| AGGLSSAYGDLTSPGLSYSLGSSFGSGAGSSSFSRTSSSRAVVVKKIETRDGKLVSESSDVLPK
gi|2506774|AGGLSSAYGGLTSPGLSYSLGSSFGSGAGSSSFSRTSSSRAVVVKKIETRDGKLVSESSDVLPK
gi|4504919|AGGLSSAYGGLTSPGLSYSLGSSFGSGAGSSSFSRTSSSRAVVVKKIETRDGKLVSESSDVLPK
gi|181400| AGGLSSAYGDLTSPGLSYSLGSSFGSGAGSSSFSRTSSSRAVVVKKIETRDGKLVSESSDVLPK
gi|87303|  AGGLSSAYGG-SQAGLSYSLGSSFGSGAGSSSFSRTSSSRAVVVKKIETRDGKLVSESSDVLPK
```

Table 15E lists the domain description from DOMAIN analysis results against NOV15. This indicates that the NOV15 sequence has properties similar to those of other proteins known to contain these domains.

TABLE 15E

Domain analysis of NOV15 gnl|Pfam|pfam00038, filament, Intermediate filament protein. (SEQ ID NO:188)
CD-Length = 312 residues, 99.7% aligned
Score = 261 bits (668), Expect = 5e-71

```
Query:    90 QEKEQIKTLNNKFASFIDKVRFLQQKNKMLETKWSLLQQQKMARI----NVFESYMNNLR 145
             ||||++ ||++ ||+|||||||+|+||  || |    |+|++    +    +++|+ +  ||
Sbjct:     1 NEKEQMQNLNDRLASYIDKVRFLEQQNKELEVKIEELRQKQAPSVSRLYSLYETEIEELR  60

Query:   146 RQLEALGQEKLKLEAELGNMQGLVEDFKNKYEDEINKRTETENEFVLIKKDMDEAYMNKA 205
             ||++ |   |+ +|+ |+ |++   |||+ ||||||||  |  ||+  ++||+||| + +
Sbjct:    61 RQIDQLTNERARLQLEIDNLREAAEDFRKKYEDEINLRQEAENDLVGLRKDLDEATLARV 120

Query:   206 ELESRLEGLTDEINFLRQLHEEEIQELQSQISGTSAVLSMDNSLSLDMDSIIAEVKAQEE 265
             +||+++|  | +|+ ||++  ||||++|||+||  |  |                  +  |++|| |
Sbjct:   121 DLENKVESLQEELEFLKKNHEEEVKELQAQIQDTVNVEMDAARKLDLTK-ALREIRAQYE 179

Query:   266 EIANRSWAEAESMYQIKYAELQTLAGKHGDDLRCTKTKISEMNRNISRLQAEIEGLKGQR 325
             ||| ++   |||   |+  |    |||| |  ++|+ ||   +|+|+  |   |+ |++ || |
Sbjct:   180 EIAKKNRQEAEEWYKSKLEELQTAAARNGEALRSAKEEITELRRQIQSLEIELQSLKAQN 239

Query:   326 ASLEAPIADTEQRGELAVKDASAKRSELEAALQRAKQDMAQQLREYQELMNVKLALDMEI 385
```

TABLE 15E-continued

Domain analysis of NOV15

```
               ||||  +|+ |+|  || ++    |  |+||  ||+ +++||+||||||||++||||||+||
Sbjct:   240   ASLERQLAELEERYELELRQYQALISQLEEELQQLREEMARQLREYQELLDVKLALDIEI   299

Query:   386   ATYRKLLEGEES                                                   397
               ||||||||||||
Sbjct:   300   ATYRKLLEGEES                                                   311
```

Keratin 8 is a type II keratin (Moll et al., 1982). Endo A is the mouse equivalent. Endo B, which is the equivalent of human keratin 18, a type I keratin, is coexpressed with Endo A; the 2 appear to be the first intermediate filament (IF) proteins expressed during murine development (Jackson et al., Differentiation. 17(3):161–79, 1980). Yamamoto et al. (Mol Endocrinol. 4(3):370–4, 1990) studied a full-length cDNA for cytokeratin 8 from placenta. They determined the distribution of cytokeratin 8 mRNA in various fetal tissues and in placentae of different gestational ages. Keratins 8 and 18 of simple epithelia differ from the keratins of stratified epithelium in tissue expression and regulation.

Using PCR to study DNAs from somatic cell hybrids, Waseem et al. (Genomics. 7(2):188–94, 1990) located a single active gene for keratin 8 on chromosome 12. This chromosome contains several genes for type II keratins and also the gene for keratin 18, the type I keratin that is coexpressed with keratin 8. This location of both members of a keratin pair on a single chromosome is unique among keratin genes; it is consistent with the hypothesis that keratins 8 and 18 may be closer to an ancestral gene than the keratins of more highly differentiated epithelia. Casanova et al. (J Clin Invest. 103(11):1587–95, 1999) generated mice expressing the human KRT8 gene, leading to a moderate increase in the content of keratin in simple epithelia. These mice displayed progressive exocrine pancreas alterations, including dysplasia and loss of acinar architecture, redifferentiation of acinar to ductal cells, inflammation, fibrosis, and substitution of exocrine by adipose tissue, as well as increased cell proliferation and apoptosis. The phenotype was very similar to that reported for transgenic mice expressing a dominant-negative mutant TGF-beta type II receptor. Casanova et al. (1999) showed that these Tgfbr2 mutant mice also had elevated KRT8/KRT18 levels. The results indicated that simple epithelial keratins play a relevant role in the regulation of exocrine pancreas homeostasis and supported the idea that disruption of mechanisms that normally regulate keratin expression in vivo could be related to inflammatory and neoplastic pancreatic disorders.

The NOV15 nucleic acid of the invention encoding a Cytokeratin-like protein includes the nucleic acid whose sequence is provided in Table 15A, or a fragment thereof. The invention also includes a mutant or variant nucleic acid any of whose bases may be changed from the corresponding base shown in Table 15A while still encoding a protein that maintains its Cytokeratin-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 12% of the residues may be so changed.

The NOV15 protein of the invention includes the Cytokeratin-like protein whose sequence is provided in Table 15B. The invention also includes a mutant or variant protein any of whose residues may be changed from the corresponding residue shown in Table 15B while still encoding a protein that maintains its Cytokeratin-like activities and physiological functions, or a functional fragment thereof. In the mutant or variant protein, up to about 13% of the bases may be so changed.

The NOV15 nucleic acids and proteins of the invention are useful in potential diagnostic and therapeutic applications implicated in various diseases and disorders described below and/or other pathologies. For example, the compositions of the present invention will have efficacy for treatment of patients suffering from: Cardiomyopathy, Atherosclerosis, Hypertension, Congenital heart defects, Aortic stenosis, Atrial septal defect (ASD), Atrioventricular (A-V) canal defect, Ductus arteriosus, Pulmonary stenosis, Subaortic stenosis, Ventricular septal defect (VSD), valve diseases, Tuberous sclerosis, Scleroderma, Obesity, Transplantation, Von Hippel-Lindau (VHL) syndrome, Alzheimer's disease, Stroke, Tuberous sclerosis, hypercalceimia, Parkinson's disease, Huntington's disease, Cerebral palsy, Epilepsy, Lesch-Nyhan syndrome, Multiple sclerosis, Ataxia-telangiectasia, Leukodystrophies, Behavioral disorders, Addiction, Anxiety, Pain, Neuroprotection and other diseases, disorders and conditions of the like.

NOV15 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV15 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV16

NOV16 includes four novel Protocadherin-like proteins disclosed below. The disclosed proteins have been named NOV16a, NOV16b, NOV16c and NOV16d.

NOV16a

A disclosed NOV16a nucleic acid of 2907 nucleotides (also referred to as CG57448-01) encoding a novel Protocadherin-like protein is shown in Table 16A. An open reading frame was identified beginning with an ATG initiation codon at nucleotides 10–12 and ending with a TGA codon at nucleotides 2896–2898. Putative untranslated regions, if any, upstream from the initiation codon and downstream from the termination codon are underlined in Table 16A, and the start and stop codons are in bold letters.

TABLE 16A

NOV16a nucleotide sequence.

(SEQ ID NO:55)
GGCCGCTGAATGCTAGCTAGAATTCAGCGGCCGCTGAATTCTAGGCGCTGCCGAGGGAATGCGCGCAGCTCA
CAGGCCCTGGGAGTGAGCTGGTGCCCGGCGACCTGGCACCCGCGCCTGGATATGGGGCGTCTACATCGTCCC
AGGAGCAGCACCAGCTACAGGAACCTGCCGCATCTGTTTCTGTTTTTCCTCTTCGTGGGACCCTTCAGCTGC
CTCGGGAGTTACAGCCGGGCCACCGAGCTTCTGTACAGCCTAAACGAGGGACTACCCGCGGGGTGCTCATC
GGCAGCCTGGCCGAGGACCTGCGGCTGCTGCCCAGGTCTGCAGGGAGGCCGGACCCGCAGTCGCAGCTGCCA
GAGCGCACCGGTGCTGAGTGGAACCCCCCTCTCTCCTTCAGCCTGGCCTCCCGGGGACTGAGTGGCCAGTAC
GTGACCCTAGACAACCGCTCTGGGGAGCTGCACACTTCAGCTCAGGAGATCGACAGGGAGGCCCTGTGTGTT
GAAGGGGTGGAGGGACTGCGTGGAGCGGCAGCGTTTCCATCTCCTCCTCTCCTTCTGACTCTTGTCTTTTG
CTGCTGGATGTGCTTGTCCTGCCTCAGGAATACTTCAGGTTTGTGAAGGTGAAGATCGCCATCAGAGACATC
AATGACAACGCCCCGCAGTTCCCTGTTTCCCAGATCTCGGTGTGGGTCCCGGAAAATGCACCTGTAAACACC
CGACTGGCCATAGAGCATCCTGCTGTGGACCCAGATGTAGGCATTAATGGGGTACAGACCTATCGCTTACTG
GACTACCATGGTATGTTCACCCTGGACGTGGAGGAGAATGAGAATGGGGAGCGCACCCCCTACCTAATTGTC
ATGGGTGCTTTGGACAGGGAAACCCAGGACCAGTATGTGAGCATCATCATAGCTGAGGATGGTGGGTCTCCA
CCACTTTTGGGCAGTGCCACTCTCACCATTGGCATCAGTGACATTAATGACAATTGCCCTCTCTTCACAGAC
TCACAAATCAATGTCACTGTGTATGGGAATGCTACAGTGGGCACCCCAATTGCAGCTGTCCAGGCTGTGGAT
AAAGACTTGGGGACCAATGCTCAAATTACTTATTCTTACAGTCAGAAAGTTCCACAAGCATCTAAGGATTTA
TTTCACCTGGATGAAAACACTGGAGTCATTAAACTTTTCAGTAAGATTGGAGGAAGTGTTCTGGAGTCCCAC
AAGCTCACCATCCTTGCTAATGGACCAGGCTGCATCCCTGCTGTAATCACTGCTCTTGTGTCCATTATTAAA
GTTATTTTCAGACCCCCTGAAATTGTCCCTCGTTACATAGCAAACGAGATAGATGGTGTTGTTTATCTGAAA
GAACTGGAACCCGTTAACACTCCCATTGCGTTTTTCACCATAAGAGATCCAGAAGGTAAATACAAGGTTAAC
TGCTACCTGGATGGTGAAGGGCCGTTTAGGTTATCACCTTACAAACCATACAATAATGAATATTTACTAGAG
ACCACAAAACCTATGGACTATGAGCTACAGCAGTTCTATGAAGTAGCTGTGGTGGCTTGGAACTCTGAGGGA
TTTCATGTCAAAAGGGTCATTAAAGTGCAACTTTTAGATGACAATGATAATGCTCCAATTTTCCTTCAACCC
TTAATAGAACTAACCATCGAAGAGAACAACTCACCCAATGCCTTTTTGACTAAGCTGTATGCTACAGATGCC
GACAGCGAGGAGAGAGGCCAAGTTTCATATTTTCTGGGACCTGATGCTCCATCATATTTTTCCTTAGACAGT
GTCACAGGAATTCTGACAGTTTCTACTCAGCTGGACCGAGAAGAGAAAGAAAAGTACAGATACACTGTCAGA
GCTGTTGACTGTGGGAAGCCACCCAGAGAATCAGTAGCCACTGTGGCCCTCACAGTGTTGGATAAAAATGAC
AACAGTCCTCGGTTTATCAACAAGGACTTCAGCTTTTTTGTGCCTGAAAACTTTCCAGGCTATGGTGAGATT
GGAGTAATTAGTGTAACAGATGCTGACGCTGGACGAAATGGATGGGTCGCCCTCTCTGTGGTGAACCAGAGT
GATATTTTGTCATAGATACAGGAAAGGGTATGCTGAGGGCTAAAGTCTCTTTGGACAGAGAGCAGCAAAGC
TCCTATACTTTGTGGGTTGAAGCTGTTGATGGGGTGAGCCTGCCCTCTCCTCTACAGCAAAAATCACAATT
CTCCTTCTAGATATCAATGACAACCCTCCTCTTGTTTTGTTTCCTCAGTCTAATATGTCTTATCTGTTAGTA
CTGCCTTCTACTCTGCCAGGCTCCCCGGTTACAGAAGTCTATGCTGTCGACAAAGACACAGGCATGAATGCT
GTCATAGCTTACAGCATCATAGGGAGAAGAGGTCCTAGGCCTGAGTCCTTCAGGATTGACCCTAAAACTGGC
AACATTACTTTGGAAGAGGCATTGCTGCAGACAGATTATGGGCTCCATCGCTTACTGGTGAAAGTGAGTGAT
CATGGTTATCCCGAGCCTCTCCACTCCACAGTCATGGTGAACCTATTTGTCAATGACACTGTCAGTAATGAG

TABLE 16A-continued

NOV16a nucleotide sequence.

AGTTACATTGAGAGTCTTTTAAGAAAAGAACCAGAGATTAATATAGAGGAGAAAGAACCACAAATCTCAATA

GAACCGACTCATAGGAAGGTAGAATCTGTGTCTTGTATGCCCACCTTAGTAGCTCTGTCTGTAATAAGCTTG

GGTTCCATCACACTGGTCACAGGGATGGGCATATACATCTGTTTAAGGAAAGGGGAAAAGCATCCCAGGGAA

GATGAAAATTTGGAAGTACAGATTCCACTGAAAGGAAAAATTGACTTGCATATGCGAGAGAGAAAGCCAATG

GATATTTCTAATATTTGATATTTCATG

The disclosed NOV16a nucleic acid sequence was localized to chromsome 5.

A NOV16a polypeptide (SEQ ID NO:56) encoded by SEQ ID NO:55 has 962 amino acid residues and is presented using the one-letter code in Table 16B. Signal P, Psort and/or Hydropathy results predict that NOV16a contains a signal peptide and is likely to be localized to the mitochondrial inner membrane with a certainty of 0.6916, to the mitochondrial intermembrane space with a certainty of 0.6185, to the plasma membrane with a certainty of 0.6000 and to the mitochondrial matrix space with a certainty of 0.5077. The most likely cleavage site for a NOV16a polypeptide is between amino acids 13 and 14: SRR-CR

TABLE 16B

Encoded NOV16a protein sequence.

(SEQ ID NO:56)
MLARIQRPLNSRRCRGNARSSQALGVSWCPATWHPRLDMGRLHRPRSSTSYRNLPHLFLFFLFVGPFSCLGS

YSRATELLYSLNEGLPAGVLIGSLAEDLRLLPRSAGRPDPQSQLPERTGAEWNPPLSFSLASRGLSGQYVTL

DNRSGELHTSAQEIDREALCVEGGGGTAWSGSVSISSSPSDSCLLLLDVLVLPQEYFRFVKVKIAIRDINDN

APQFPVSQISVWVPENAPVNTRLAIEHPAVDPDVGINGVQTYRLLDYHGMFTLDVEENENGERTPYLIVMGA

LDRETQDQYVSIIIAEDGGSPPLLGSATLTIGISDINDNCPLFTDSQINVTVYGNATVGTPIAAVQAVDKDL

GTNAQITYSYSQKVPQASKDLFHLDENTGVIKLFSKIGGSVLESHKLTILANGPGCIPAVITALVSIIKVIF

RPPEIVPRYIANEIDGVVYLKELEPVNTPIAFFTIRDPEGKYKVNCYLDGEGPFRLSPYKPYNNEYLLETTK

PMDYELQQFYEVAVVAWNSEGFHVKRVIKVQLLDDNDNAPIFLQPLIELTIEENNSPNAFLTKLYATDADSE

ERGQVSYFLGPDAPSYFSLDSVTGILTVSTQLDREEKEKYRYTVRAVDCGKPPRESVATVALTVLDKNDNSP

RFINKDFSFFVPENFPGYGEIGVISVTDADAGRNGWVALSVVNQSDIFVIDTGKGMLRAKVSLDREQQSSYT

LWVEAVDGGEPALSSTAKITILLLDINDNPPLVLFPQSNMNYLLVLPSTLPGSPVTEVYAVDKDTGMNAVIA

YSIIGRRGPRPESFRIDPKTGNITLEEALLQTDYGLHRLLVKVSDHGYPEPLHSTVMVNLFVNDTVSNESYI

ESLLRKEPEINIEEKEPQISIEPTHRKVESVSCMPTLVALSVISLGSITLVTGMGIYICLRKGEKHPREDEN

LEVQIPLKGKIDLHMRERKPMDISNI

The NOV16a amino acid sequence has 946 of 947 amino acid residues (99%) identical to, and 946 of 947 amino acid residues (99%) similar to, the 947 amino acid residue ptnr:SPTREMBL-ACC:Q9NRT9 protein from *Homo sapiens* (Human) (Protocadherin 10) (E=0.0).

The disclosed NOV16a is expressed in at least the following tissues: Uterus, colon, eye and retina. This information was derived by determining the tissue sources of the sequences that were included in the invention including but not limited to SeqCalling sources, Public EST sources, Literature sources, and/or RACE sources.

NOV16b

A disclosed NOV16b nucleic acid of 2801 nucleotides (also referred to as CG57446-01) encoding a novel Protocadherin-like protein is shown in Table 16C. An open reading frame was identified beginning with an ATG initiation codon at nucleotides 6–8 and ending with a TAA codon at nucleotides 2724–2726. Putative untranslated regions, if any, upstream from the initiation codon and downstream from the termination codon are underlined in Table 16C, and the start and stop codons are in bold letters.

TABLE 16C

NOV16b nucleotide sequence.

(SEQ ID NO:57)

ACCGGATGCACCCGGAGATCTCCTACTCAATTCCTGAGGAAAGAGAGAAAGGCTCTTTCGTGGGCAACATCT

CCAAGGACTTGGGTCTGGCGCCCCGGGAGCTGGCGGAGCGCGGAGTCCGCATAGTCTCCAGAGGTAGGACGC

AGCTTTTCTCTCTGAACCCGCGCAGCGGCAGCTTGGTCACCGCGGGCAGGATAGACCGGGAGGAGCTCTGCG

CTCAGAGCGCGCGGTGCGTGGTGAGTTTTAATATCCTTGTGGAAGACAGGGTGAAACTTTTTGGGATAGAAA

TAGAAGTAACTGATATCAATGACAATGCTCCAAAATTCCAAGCAGAAAATCTAGACGTAAAAATTAATGAAA

ATGTCGCTGCGGGAATGCGTTTTCCTCTCCCGGAAGCTATTGATCCGGATATAGGTGTAAACTCCCTGCAGG

GTTACCAGCTCAACTCAAACGGTTACTTTTCCCTGGACGTGCAAAGTGGGGCCGATGGGATTAAGTACCCAG

AGCTGGTGCTGGAACGCGCTCTAGATCGCGAGGAAGAGGCGGTTCACCACCTGGTCCTTACTGCCATGGATG

GCGGCGACCCTCTCCGCTCAAGCGTCGCCCAAATTCTGGTAACAGTTCTAGATGTGAATGACAACACTCCAA

TGTTTACTCAGCCTGTCTACCGTGTAAGTGTTCCTGAAAACCTGCCAGCTCCCGGAACTCGGGTGCTGATGG

TTAATGCAACGGATCCAGATGAAGGAGTCAATGCGGAAGTAATGTATTCATTTCGGAAAGTCAGAGACGAAA

GAGCACAGCTATTACAGTTGTTTTATCTGAGTGCGGAGATAACGATAATGAGGGTCTGGAGGATGTGGACT

ATGGATACTATGACATAGATGACATAGACGATGAAGGCCATGGTGTCCGTGCTAGAAGAGCGGTACGCAAGG

TAGTGGTGGAAGTTTTGGATGAAAATGACAACGCCCCAGAAATCACAGTCACCTCCGTCACCACCGCAGTCC

CCGAAGCTGCTTCTGGAACTGCCATTATTTTCCTCAATGATAGTGACCGAGAGGACGGGGGGAACAGTCCAT

TTATCAGTTCTGTCAATCCGGGTCTTTCATTCAAAAAATTAGATAAAAAAGATGATTATTTCATTTTTAAAA

CGACTCAAGACATAGACCGAAAAACTGTGTCCGAATACAACATCACCGCAATAGCCCCAGAAACCCGAGCTC

CTTCCCCTTCAACTCATATTACACTCCTTGTGCTAGTGATCGACATCAATGAAAACCCTCCCCCTTATTCTC

AATCCTCCTACTACGTTTACGTAAACGAAACAACGGCGCCGGCACTTCAATTATGACCGTTAATGACTCTG

ACCCCGATGACAATTCTAGTGTTATTTACTCCTTGGCAGAGGCTACCCAAGGAGCTCCTCCCTCCTCCACCT

ATGCCTCTATCACATCAAACACTGGTGTGCTTGATGTGTTGTCCTTCTTCTACTATGAGTATTTTGATTTTC

TGCAAATGCAGATGACGGCTAATGACAGTGGCAGCCCACCACTTAGCAGTAATGCGTCAATGAGATTGTTTG

TGTTGGACAAGGATGACAATGCCCAAGACCTCCAGTACCCTGCCCCCCCCACTGGTGGTACTGCTGTTGAGG

TGCTGCCCCGCTCTGCAGCGCCTGGCTACCTGGTGACCAAGGTGGTGGCAGTGGACGGAGACTCAGGCCAGA

ATGCTTGGCTCTCCTACCGCCTATTCGAGGCCAGTGAGCCGGGGCTCTTCTCGGTGGGGCTGCACACAGGTG

GAAAAGTGCGCACCGCTCGGGCCCTGCTAGATAGAGATGCGCTCAAACAGAGCCTTGTGGTGGCTGTACAGG

ACCATGGCCAGCCCCCTCTCTCCGCCGCCACCCTCACTGTGGCGGTTGCCGACGACTCCCTCCAAGACCTCG

CGGATTTCTTCGGCAGCCTCACGCCTTCAGAACACCAAGACGACTCCGGCCTCACACTCCTTCTTGTGGTAG

TAGTGGCTGCAGTCTGCTTCGTCTTCCCGGTCTTCGTCGTCGTGCTGCTAGTACTCAAGCTGAGGCGCTGGC

ACAAGTCCCGCCTGCTTCACGCTGAAGGCAGCAGGTTGGCAGGGGTGGCTGCCTCCCACTTTGGGGCGTGG

AGGGGGTTGGGGTTTTCCTGCCGAACTATTCCCACGAGGTCTCCCTCACCGCGGACTCGCGGAAGAGCCCCC

TGATCCCCACCCAACCCCGCGCTGAAATTCCCCTCAGCAACCGGGAGAGTGGAGAGAGAAGCCGCCGTCTGG

TGATACTTAAGGATGTGCTTGAAACAGAGGGCGACCCTAGTGGACAGCAAGCCCCGCCCAACACGGACTGGC

GTTTCTCTCAGGCCCAGAGACCCGGCACCAGCGGCTCCCAAAATGGCGATGACACCGGCACCTGGCCCAACA

ACCAGTTTGACACAGAGATGCTGCAAGCCATGATCTTGGCGTCCGCCAGTGAAGCTGCTGATGGGAGCTCCA

CCCTGGGAGGGGTGCCGGCACCATGGGATTGAGCGCCCGCTACGGACCCCAGTTCACCCTGCAGCACGTGC

CCGACTACCGCCAGAATGTCTACATCCCAGGCAGCAATGCCACACTGACCAACGCAGCTGGCAAGCGGGATG

TABLE 16C-continued

NOV16b nucleotide sequence.

GCAAGGCCCCAGCAGGTGGCAATGGCAACAAGAAGAAGTCGGGCAAGAAGGAGAAGAAGTAA<u>CATGGAGGCC</u>

<u>AGGCCAAGAGCCACAGGGCGGCCTCTCCCCAACCAGCCCAGCTTCTCCTTACCTGCACCCAGGCC</u>

The disclosed NOV16b nucleic acid sequence, localized to chromsome 5, has 2214 of 2786 bases (79%) identical to a gb:GENBANK-ID:AF152324|acc:AF152324.1 mRNA from Homo sapiens (protocadherin gamma A4 (PCDH-gamma-A4) mRNA, complete cds) (E=0.0).

A NOV16b polypeptide (SEQ ID NO:58) encoded by SEQ ID NO:57 has 906 amino acid residues and is presented using the one-letter code in Table 16D. Signal P, Psort and/or Hydropathy results predict that NOV16b does not contain a signal peptide and is likely to be localized to the plasma membrane with a certainty of 0.7000 and to the nucleus with a certainty of 0.6000.

TABLE 16D

Encoded NOV16b protein sequence.

(SEQ ID NO:58)
MHPEISYSIPEEREKGSFVGNISKDLGLAPRELAERGVRIVSRGRTQLFSLNPRSGSLVTAGRIDREELCAQ

SARCVVSFNILVEDRVKLFGIEIEVTDINDNAPKFQAENLDVKINENVAAGMRFPLPEAIDPDIGVNSLQGY

QLNSNGYFSLDVQSGADGIKYPELVLERALDREEEAVHHLVLTAMDGGDPLRSSVAQILVTVLDVNDNTPMF

TQPVYRVSVPENLPAPGTRVLMVNATDPDEGVNAEVMYSFRKVRDERAQLLQLFYLSAEITIMRGLEDVDYG

YYDIDDIDDEGHGVRARRAVRKVVVEVLDENDNAPEITVTSVTTAVPEAASGTAIIFLNDSDREDGGNSPFI

SSVNPGLSFKKLDKKDDYFIFKTTQDIDRKTVSEYNITAIAPETRAPSPSTHITLLVLVIDINENPPPYSQS

SYYVYVNENNGAGTSIMTVNDSDPDDNSSVIYSLAEATQGAPPSSTYASITSNTGVLDVLSFFYYEYFDFLQ

MQMTANDSGSPPLSSNASMRLFVLDKDDNAQDLQYPAPPTGGTAVEVLPRSAAPGYLVTKVVAVDGDSGQNA

WLSYRLFEASEPGLFSVGLHTGGKVRTARALLDRDALKQSLVVAVQDHGQPPLSAATLTVAVADDSLQDLAD

FFGSLTPSEHQDDSGLTLLLVVVVAAVCFVFPVFVVVLLVLKLRRWHKSRLLHAEGSRLAGVAASHFGGVEG

VGVFLPNYSHEVSLTADSRKSPLIPTQPRAEIPLSNRESGERSRRLVILKDVLETEGDPSGQQAPPNTDWRF

SQAQRPGTSGSQNGDDTGTWPNNQFDTEMLQAMILASASEAADGSSTLGGGAGTMGLSARYGPQFTLQHVPD

YRQNVYIPGSNATLTNAAGKRDGKAPAGGNGNKKKSGKKEKK

The NOV16b amino acid sequence has 635 of 903 amino acid residues (70%) identical to, and 721 of 903 amino acid residues (79%) similar to, the 931 amino acid residue ptnr:SPTREMBL-ACC:Q9Y5G9 protein from Homo sapiens (Human) (Protocadherin Gamma A4) (E=0.0).

The disclosed NOV16b is expressed in at least the following tissues: Uterus, colon, eye and retina. This information was derived by determining the tissue sources of the sequences that were included in the invention including but not limited to SeqCalling sources, Public EST sources, Literature sources, and/or RACE sources.

NOV16c

A disclosed NOV16c nucleic acid of 2836 nucleotides (also referred to as CG57444-01) encoding a novel Protocadherin-like protein is shown in Table 16E. An open reading frame was identified beginning with an ATG initiation codon at nucleotides 15–17 and ending with a TAA codon at nucleotides 2802–2804. Putative untranslated regions, if any, upstream from the initiation codon and downstream from the termination codon are underlined in Table 16E, and the start and stop codons are in bold letters.

TABLE 16E

NOV16c nucleotide sequence.

(SEQ ID NO:59)

AACCCGAGCGAACGATGGGAGGGAGCTGCGCGCAGAGGCGCCGGGCCGGCCCGCGGCAGGTACTATTTCCTT
TGCTGCTGCCTTTGTTCTACCCCACGCTGTGTGAGCCGATCCGCTACTCGATTCCGGAGGAGCTGGCCAAGG
GCTCGGTGGTGGGGAACCTCGCTAAGGATCTAGGGCTTAGTGTCCTGGATGTGTCGGCTCGCGAGCTGCGAG
TGAGCGCGGAGAAGCTGCACTTCAGCGTAGACGCGCAGAGCGGGGACTTACTTGTGAAGGACCGAATAGACC
GTGAGCAAATATGCAAAGAGAAGAAGATGTGAGTTGCAATTGGAAGCTGTGGTGGAAAATCCTTTAAATA
TTTTTCATGTCATTGTGGTGATTGAGGATGTTAATGACCACGCCCCTCAATTCCGGAAAGATGAAATAAACT
TAGAAATCAGTGAATCCGTCAGCCTGGGGATGGGAACAATTCTTGAGTCTGCAGAAGATCCTGATATTAGTA
TGAATTCGCTGAGCAAATACCAACTAAGTCCTAACGAGTATTTCTCATTGGTGGAGAAAGACAATCCTGATG
GTGGCAAATATCCAGAATTAGTATTGCAGAAGACTCTGGACCGAGAAACGCAGAGCGCTCACCACTTGATAT
TGACCGCCTTGGACGGAGGGGACCCACCAAGAAGTGCCACCGCTCACATAGAAATTTCTGTCAAGGATACCA
ATGATAACCCCCGGTTTTCAGCAGAGACGAATATAGAATTAGTCTTAGTGAAAATCTGCCCCCTGGGTCCC
CTGTGTTGCAAGTGACAGCCACTGACCAGGATGAGGGGGTCAATGCTGAGATAAACTACTACTTCCGAAGCA
CTGCCCAGAGCACAAAACATATGTTCTCATTGGATGAGAAAACAGGTATGATTAAGAATAACCAGTCATTTG
ATTTTGAAGATGTAGAAAGGTACACCATGGAAGTGGAAGCGAAGGACGGAGGTGGTCTCTCTACCCAGTGTA
AAGTAATCATAGAAATCCTTGATGAAAACGACAACAGCCCAGAAATAATCATCACTTCTCTCTCTGATCAGA
TTTTGGAGAATTCACCTCCAGGAATGGTTGTTGCCCTCTTCAAAACACGGGATCTGGATTTCGGAGGAAATG
GAGAAGTCAGGTGTAATATAGAAACAGACATTCCATTCAAGATTTATTCTTCTTCCAATAACTACTACAAAC
TGGTGACAGATGGAGCCCTGGACCGAGAGCAGACACCAGAATACAATGTCACCATCGTAGCCACTGACAGGG
GCAAGCCGCCTCTTTCTTCCAGTAGAAGCATCACCTTGTATGTCGCTGACATCAACGACAACGCCCCAGTTT
TCGACCAGACGTCCTACGTGGTCCACGTGGCCGAGAACAACCCGCCAGGAGCCTCCATTGCGCAAGTGAGCG
CCTCTGACCCGGATTTGGGGCTCAATGGCCACATCTCCTACTCTCTCATTGCCAGCGACCTGGAGTCACGAA
CGCTGTCGTCCTACGTGTCCGTGAGCGCGCAGAGCGGGGTGGTGTTCGCGCAGCGCGCCTTCGACCACGAGC
AGCTGCGCGCCTTCGCGCTCACGCTGCAGGCCCGCGACCAGGGCTCGCCCGCGCTCAGCGCGAACGTGAGCC
TGCGCGTGTTAGTGGACGACCGCAACGACAATGCGCCACGGGTGCTGTACCCAGCTCTGGGTCCTGACGGCT
CCGCGTTCTTCGATATGGTACCTCGCTCTGCAGAGCCCGGCTACCTAGTGACTAAGGTGGTAGCGGTGGACG
CCGACTCGGGACACAACGCCTGGCTGTCCTACCACGTGCTGCAGGCCAGTGAGCCCGGGCTCTTCAGCCTGG
GGCTGCGAACAGGCGAGGTGCGCATGGTGCGTGCTTTGGGTGACAAGGACTCGGTCCGCCAGCGCCTGCTAG
TCGCTATAAGAGATGGAGGACAGCCACCCCTTTCAGCCACTGCCACGCTGCACCTGGTGTTCGCAGATAGCT
TGCAAGAGGTACTGCCGGATTTCAGCGACCATCCCACACCCTCTGACTCCCAGGCTGAGATGCAGTTTTACC
TGGTGGTGGCCTTGGCCTTGATTTCTGTGCTCTTTCTCCTCGCGGTGATTCTAGCTATTGCTCTACGCCTGC
GACAGTCTTTCAGCCCTACTGCAGGAGACTGCTTTGAGTCAGTTCTCTGCTCCAAGTCCGGACCTGTGGGTC
CCCCCAACTACAGTGAGGGAACGTTGCCCTATGCCTATAATTTTTGTGTGCCTGGGGATCAAATGAATCCAG
AATTTAATTTTTTCACATCTGTTGATCATTGTCCAGCCACACAAGATAACCTCAACAAAGATAGCATGCTAC
TGGCTAGCATTTTAACTCCCAGCGTTGAAGCAGATAAGAAGATTCTTAAACAGCAAGCCCCGCCCAACACGG
ACTGGCGTTTCTCTCAGGCCCAGAGACCCGGCACCAGCGGCTCCCAAAATGGCGATGACACCGGCACCTGGC
CCAACAACCAGTTTGACACAGAGATGCTGCAAGCCATGATCTTGGCGTCCGCCAGTGAAGCTGCTGATGGGA
GCTCCACCCTGGGAGGGGGTGCCGGCACCATGGGATTGAGCGCCCGCTACGACCCCAGTTCACCCTGCAGC
ACGTGCCCGACTACCGCCAGAATGTCTACATCCCAGGCAGCAATGCCACACTGACCAACGCAGCTGGCAAGC

TABLE 16E-continued

NOV16c nucleotide sequence.

GGGATGGCAAGGCCCCAGCAGGTGGCAATGGCAACAAGAAGAAGTCGGGCAAGAAGGAGAAGAAGTAACATG

GAGGCCAGGCCAAGAGCCACAGGGCGGC

The disclosed NOV16c nucleic acid sequence, localized to chromsome 5, has 2584 of 2822 bases (91%) identical to a gb:GENBANK-ID:AF152336|acc:AF152336.1 mRNA from *Homo sapiens* (protocadherin gamma B7 (PCDH-gamma-B7) mRNA, complete cds) (E=0.0).

A NOV16c polypeptide (SEQ ID NO:60) encoded by SEQ ID NO:59 has 929 amino acid residues and is presented using the one-letter code in Table 16F. Signal P, Psort and/or Hydropathy results predict that NOV16c does not contain a signal peptide and is likely to be localized to the plasma membrane with a certainty of 0.5140. The most likely cleavage site for a NOV16c polypeptide is between amino acids 30 and 31: TLC-EP tocadherin Beta-like protein is shown in Table 16G. An open reading frame was identified beginning with an ATG initiation codon at nucleotides 1–3 and ending with a TGA codon at nucleotides 2398–2400. Putative untranslated regions, if any, upstream from the initiation codon and downstream from the termination codon are underlined in Table 16G, and the start and stop codons are in bold letters.

TABLE 16F

Encoded NOV16c protein sequence.

(SEQ ID NO:60)
MGGSCAQRRRAGPRQVLFPLLLPLFYPTLCEPIRYSIPEELAKGSVVGNLAKDLGLSVLDVSARELRVSAEK

LHFSVDAQSGDLLVKDRIDREQICKERRRCELQLEAVVENPLNIFHVIVVIEDVNDHAPQFRKDEINLEISE

SVSLGMGTILESAEDPDISMNSLSKYQLSPNEYFSLVEKDNPDGGKYPELVLQKTLDRETQSAHHLILTALD

GGDPPRSATAHIEISVKDTNDNPPVFSRDEYRISLSENLPPGSPVLQVTATDQDEGVNAEINYYFRSTAQST

KHMFSLDEKTGMIKNNQSFDFEDVERYTMEVEAKDGGGLSTQCKVIIEILDENDNSPEIIITSLSDQILENS

PPGMVVALFKTRDLDFGGNGEVRCNIETDIPFKIYSSSNNYYKLVTDGALDREQTPEYNVTIVATDRGKPPL

SSSRSITLYVADINDNAPVFDQTSYVVHVAENNPPGASIAQVSASDPDLGLNGHISYSLIASDLESRTLSSY

VSVSAQSGVVFAQRAFDHEQLRAFALTLQARDQGSPALSANVSLRVLVDDRNDNAPRVLYPALGPDGSAFFD

MVPRSAEPGYLVTKVVAVDADSGHNAWLSYHVLQASEPGLFSLGLRTGEVRMVRALGDKDSVRQRLLVAIRD

GGQPPLSATATLHLVFADSLQEVLPDFSDHPTPSDSQAEMQFYLVVALALISVLFLLAVILAIALRLRQSFS

PTAGDCFESVLCSKSGPVGPPNYSEGTLPYAYNFCVPGDQMNPEFNFFTSVDHCPATQDNLNKDSMLLASIL

TPSVEADKKILKQQAPPNTDWRFSQAQRPGTSGSQNGDDTGTWPNNQRDTEMLQAMILASASEAADGSSTLG

GGAGTMGLSARYGPQFTLQHVPDYRQNVYIPGSNATLTNAAGKRDGKAPAGGNGNKKKSGKKEKK

The NOV16c amino acid sequence has 842 of 929 amino acid residues (90%) identical to, and 881 of 929 amino acid residues (94%) similar to, the 929 amino acid residue ptnr:SPTREMBL-ACC:Q9Y5F8 protein from *Homo sapiens* (Human) (Protocadherin Gamma B7) (E=0.0).

The disclosed NOV16c is expressed in at least the following tissues: Uterus, colon, eye and retina. This information was derived by determining the tissue sources of the sequences that were included in the invention including but not limited to SeqCalling sources, Public EST sources, Literature sources, and/or RACE sources.

NOV16d

A disclosed NOV16d nucleic acid of 2436 nucleotides (also referred to as CG57442-01) encoding a novel Pro-

TABLE 16G

NOV16d nucleotide sequence.

(SEQ ID NO:61)

ATGGCTGTCAGAGAGTTGTGCTTCCCAAGACAAAGGCAAGTCCTGTTTCTTTTTCTTTTTTGGGGAGTGTCC

TTGGCAGGTTCTGGGTTTGGACGTTATTCGGTGACTGAGGAAACAGAGAAAGGATCCTTTGTGGTCAATCTG

GCAAAGGATCTGGGACTAGCAGAGGGGGAGCTGGCTGCAAGGGGAACCAGGGTGGTTTCCGATGATAACAAA

CAATACCTGCTCCTGGATTCACATACCGGGAATTTGCTCACAAATGAGAAACTGGACCGAGAGAAGCTGTGT

GGCCCTAAAGAGCCCTGTATGCTGTATTTCCAAATTTTAATGGATGATCCCTTTCAGATTTACCGGGCTGAG

CTGAGAGTCAGGGATATAAATGATCACGCGCCAGTATTTCAGGACAAAGAAACAGTCTTAAAAATATCAGAA

AATACAGCTGAAGGACAGCATTTAGACTAGAAAGAGCACAGGATCCAGATGGAGGACTTAACGGTATCCAA

AACTACACGATCAGCCCCAACTCTTTTTTCCATATTAACATTAGTGGCGGTGATGAAGGCATGATATATCCA

GAGCTAGTGTTGGACAAAGCACTGGATCGGGAGGAGCAGGGAGAGCTCAGCTTAACCCTCACAGCGCTGGAT

GGTGGGTCTCCATCCAGGTCTGGGACCTCTACTGTACGCATCGTTGTCTTGGACGTCAATGACAATGCCCCA

CAGTTTGCCCAGGCTCTGTATGAGACCCAGGCTCCAGAAAACAGCCCCATTGGGTTCCTTATTGTTAAGGTA

TGGGCAGAAGATGTAGACTCTGGAGTCAACGCGGAAGTATCCTATTCATTTTTTGATGCCTCAGAAAATATT

CGAACAACCTTTCAAATCAATCCTTTTTCTGGGGAAATCTTTCTCAGAGAATTGCTTGATTATGAGTTAGTA

AATTCTTACAAAATAAATATACAGGCAATGGACGGTGGAGGCCTTTCTGCAAGATGTAGGGTTTTAGTGGAA

GTATTGGACACCAATGACAATCCCCCTGAACTGATCGTATCATCATTTTCCAACTCTGTTGCTGAGAATTCT

CCTGAGACGCCGCTGGCTGTTTTTAAGATTAATGACAGAGACTCTGGAGAAAATGGAAGGATGGTGTGCTAC

ATTCAAGATGATCTGCCATTCCTACTAAAACCTTCTGTTGAGAATTTTTACATCCTAATGACTGAAGGCGCG

CTGGACAGAGAAGCAAGAGCTGAATATAATATCACCCTCACCGTCACAGATATGGGGACTCCAAGGCTGAAA

ACGGAGCACAACATAACAGTGCAGATATCAGATGTCAATGATAACGCCCCCACTTTCACCCAAACCTCCTAC

GCCCTGTTCGTCCGCGAGAACAACAGCCCCGCCCTGCACATCGGCAGCGTCAGCGCCACAGACAGAGACTCA

GGCACCAACGCCCAGGTCACCTACTCGCTGCTGCCGCCCCAGGACCCGCACCTGCCCCTCGCCTCCCTGGTC

TCCATCAACGCAGACAACGGCCACCTGTTCGCCCTCAGGTCGCTGGACTACGAGGCCCTGCAGGCTTTCGAG

TTCCGCGTGGGCGCCACAGACCGCGGCTCCCCCGCGCTGAGCAGAGAGGCGCTGGTGCGCGTGCTGGTGCTG

GACGCCAACGACAACTCGCCCTTCGTGCTGTACCCGCTGCAGAACGGCTCCGCGCCCTGCACTGAGCTGGTG

CCCCGGGCGGCCGAGCCGGGCTACCTGGTGACCAAGGTGGTGGCGGTGGACGGCGACTCGGGCCAGAACGCC

TGGCTGTCGTACCAGCTGCTCAAGGCCACGGAGCCCGGGCTGTTCGGTGTGTGGGCGCACAATGGGGAGGTG

CGCACCGCCAGGCTGCTGAGCGAGCGCGACGCAGCCAAGCACAGGCTCGTGGTGCTTGTCAAGGACAATGGC

GAGCCTCCTCGCTCGGCCACCGCCACGCTGCACTTGCTCCTGGTGGACGGCTTCTCCCAGCCCTACCTGCCT

CTCCCGGAGGCGGCCCCGGCCCAGGCCCAGGCCGAGGCCGACTTGCTCACCGTCTACCTGGTGGTGGCGTTG

GCCTCGGTGTCTTCGCTCTTCCTCCTCTCGGTGCTCCTGTTCGTGGCGGTGCGGCTGTGCAGGAGGAGCAGG

GCGGCCTCGGTGGGTCGCTGCTCGGTGCCCGAGGGTCCTTTTCCAGGGCATCTGGTGGACGTGAGCGGCACC

GGGACCCTGTTCCAGAGCTACCAGTACGAGGTGTGTCTGACTGGAGGTTCAGAGACCGGCGAGTTCAAGTTC

TTGAAGCCGATTACCCCCCACCTCCCGCCCCATAGGGGTGGGAAAGAAATAGAGGAAAATTCTACTCTCCCC

AATAGCTTTGGATTTAATTATTGAAAGGAACCCACTTAATAAAGACATTTACTTCTTTAA

The disclosed NOV16d nucleic acid sequence, localized to chromsome 5, has 2319 of 2400 bases (96%) identical to a gb:GENBANK-ID:AF152489|acc:AF152489.1 mRNA from Homo sapiens (Homo sapiens protocadherin beta 10 (PCDH-beta10) mRNA, complete cds) (E=0.0).

A NOV16d polypeptide (SEQ ID NO:62) encoded by SEQ ID NO:61 has 799 amino acid residues and is presented using the one-letter code in Table 16H. Signal P, Psort and/or Hydropathy results predict that NOV16d does not contain a signal peptide and is likely to be localized to the plasma membrane with a certainty of 0.4600. The most likely cleavage site for a NOV16d polypeptide is between amino acids 26 and 27: SLA-GS.

TABLE 16H

Encoded NOV16d protein sequence.

(SEQ ID NO:62)
MAVRELCFPRQRQVLFLFLFWGVSLAGSGFGRYSVTEETEKGSFVVNLAKDLGLAEGELAARGTRVVSDDNK

QYLLLDSHTGNLLTNEKLDREKLCGPKEPCMLYFQILMDDPFQIYRAELRVRDINDHAPVFQDKETVLKISE

NTAEGTAFRLERAQDPDGGLNGIQNYTISPNSFFHINISGGDEGMIYPELVLDKALDREEQGELSLTLTALD

GGSPSRSGTSTVRIVVLDVNDNAPQFAQALYETQAPENSPIGFLIVKVWAEDVDSGVNAEVSYSFFDASENI

RTTFQINPFSGEIFLRELLDYELVNSYKINIQAMDGGGLSARCRVLVEVLDTNDNPPELIVSSFSNSVAENS

PETPLAVFKINDRDSGENGRMVCYIQDDLPFLLKPSVENFYILMTEGALDREARAEYNITLTVTDMGTPRLK

TEHNITVQISDVNDNAPTFTQTSYALFVRENNSPALHIGSVSATDRDSGTNAQVTYSLLPPQDPHLPLASLV

SINADNGHLFALRSLDYEALQAFEFRVGATDRGSPALSREALVRVLVLDANDNSPFVLYPLQNGSAPCTELV

PRAAEPGYLVTKVVAVDGDSGQNAWLSYQLLKATEPGLFGVWAHNGEVRTARLLSERDAAKHRLVVLVKDNG

EPPRSATATLHLLLVDGFSQPYLPLPEAAPAQAQAEADLLTVYLVVALASVSSLFLLSVLLFVAVRLCRRSR

AASVGRCSVPEGPFPGHLVDVSGTGTLFQSYQYEVCLTGGSETGEFKFLKPITPHLPPHRGGKEIEENSTLP

NSFGFNY

The NOV16d amino acid sequence has 765 of 798 amino acid residues (95%) identical to, and 776 of 798 amino acid residues (97%) similar to, the 800 amino acid residue ptnr:SPTREMBL-ACC:Q9UN67 protein from Homo sapiens (Human) (Protocadherin Beta 10) (E=0.0).

The disclosed NOV16d is expressed in at least the following tissues: Uterus, colon, eye and retina. This information was derived by determining the tissue sources of the sequences that were included in the invention including but not limited to SeqCalling sources, Public EST sources, Literature sources, and/or RACE sources.

Possible SNPs found for NOV16c are listed in Table 16I.

TABLE 16I

| | SNPs | | | |
|---|---|---|---|---|
| Variant | Nucleotide Position | Base Change | Amino Acid Position | Base Change |
| 13377099 | 218 | G > T | Silent | N/A |

NOV16a–NOV16d are very closely homologous as is shown in the amino acid alignment in Table 16J.

TABLE 16J

Amino Acid Alignment of NOV16a–NOV16d

```
                 10        20        30        40        50        60        70
           ....|....|....|....|....|....|....|....|....|....|....|....|....|....|
    NOV16a MLARIQRPLNSRRCRGNARSSQALGVSWCPATWHPRLDMGRLHRPRSSTSYRNLPHLFLFFLFVGPFSCL
    NOV16b ---------------------------------------------------------------------
    NOV16c ---------------------------------------MGGSCAQRRRAGPRQVLFPLLLPLFY------
    NOV16d ----------------------------------------MAVRELCFPRQRQVLFLFLFWGVS------

80        90        100       110       120       130       140
           ....|....|....|....|....|....|....|....|....|....|....|....|....|....|
    NOV16a GSYSRATELLYSLNEGLPAGVLIGSLAEDIRLLPRSAGRPDPQSQLPERTGAEWNPPLSFSLASRGLSGQ
    NOV16b ----MHPEISYSIPEEREKGSFVGNISKDLGIAPRELAERGVRIVSRGRT-------------------Q
    NOV16c --PTLCEPIRYSIPEELAKGSVVGNLAKDLGISVLDVSARELRVS--AEK-------------------L
    NOV16d --LAGSGFGRYSVTEETEKGSFVVLAKDLGIAEGELAARGTRVVSDDNK-------------------Q 150       160       170       180       190       200       210
           ....|....|....|....|....|....|....|....|....|....|....|....|....|....|
    NOV16a YVTIDNRSGEIHISAQEIDREALCVEGGGGTAWSGSVSISSSPSDSCLLLDVLVLPQKYFRFVKVKIAI
    NOV16b LFSINPRSGSIVI-AGRIDREELCA----------------QSARCVVSFNILVF--DRVKLEGIEIEV
    NOV16c HFSVDAQSGDLLV-KDRIDREQICK----------------ERRRCELQLEAVVK--NPLNIFHVIVVI
    NOV16d YLLLDSHTGNLLI-NEKIDREKLCG----------------PKEPCYLYFQILME--DPFQIYRAELRV
```

TABLE 16J-continued

Amino Acid Alignment of NOV16a–NOV16d

```
              220        230        240        250        260        270        280
              ....|....|....|....|....|....|....|....|....|....|....|....|....|....|
NOV16a   RDINDNAPQPPVSQISVWVPENAPVNTRLAIEHPAVDPDVGINGVQTYRLLDYHGMETLDVLENENGEPT
NOV16b   TDINDNAPKFQAENLDVKIMENVAAGMRFPLPE-AIDPDIGVNSLQGYQLNSNG-YFSLDVQSCADGIKY
NOV16c   EDVNDHAPQEKKDEINLFISESVSLGMGTILES-AIDPDISMNSISKVQLSPNE-VFSLVEKDNPDCGKY
NOV16d   RDINDHAPVEQDKETVLKISENTAECTAFRLER-AQDPDGGLNGLQNYTISPNS-FFHINISGCDECMIY 290        300        310        320        330        340        350
              ....|....|....|....|....|....|....|....|....|....|....|....|....|....|
NOV16a   PYLIVMGALDRETQDQIVSIIIAEDGGSEPLLGSATLTTGISDINDNCELFIDSQINVIYYGNAT-VGIP
NOV16b   PELVLERALDREELAVHHLVLTAMDGGDELRSSVAQILVTVLDVNDNTEMPTQPVYRVSVPENLEAPGIR
NOV16c   PELVLQKTLDRETQSAHHLILTALDGGDPRSATAHIEISVKDTNDNPPVESRDEYRISLSENLP-PCSP
NOV16d   PELVLDKALDREEQGELSITLTALDGGSESRSGTSTVRIVVLDVNDNAPQPAQALYETQAPENSP-IGFL 360        370        380        390        400        410        420
              ....|....|....|....|....|....|....|....|....|....|....|....|....|....|
NOV16a   IAAVQAVDKDLGTNAQITYSYSQKVPQASKDLFHLDENTGVIKLFSKIGGSVLESHKLTILANGPGCIPA
NOV16b   VLMVNATDPDEGVNAEVMYSFRKVR-DERAQLLQLFYLSAEITTMRGLEDVDYGYYDIDDIDDECHGVRA
NOV16c   VLQVFTATDQDEGVNAEINMYFRSTA-QSTKHMFSLDEKTGMIKNNQSFQFEDVERYTMEVEAKDGGGLST
NOV16d   IVKVWAEDVDSGVNAEVSYSFFDAS-ENIPTTFQIKPFSGEIFLRELLDYELVNSYKINIQAMIGGCLSA 430        440        450        460        470        480        490
              ....|....|....|....|....|....|....|....|....|....|....|....|....|....|
NOV16a   V---ITALVSIIKVIFRPPEIVPRYIANEIDGVVYLKELEPVNTPIAFFTIRDPE--GKYKVNCYLDGEG
NOV16b   RRAVRKVVVEVLDENDNAPEITVTSVTTAVP------EAAS-GTAIIFLNDSDREDGGNSPFISSVNPGL
NOV16c   Q---CKVIEILDENDNSPEIIITSLSDQIL------ENSPPGMVVALFKTRDLNFGGNGEVRCNIETDI
NOV16d   R---CRVLVEVLDTNDNPPELIVSSFSNSVA------ENSP-ETPLAVFKINDRDSGENGRMVCYIQDDL 500        510        520        530        540        550        560
              ....|....|....|....|....|....|....|....|....|....|....|....|....|....|
NOV16a   PERTSPYKPYNNEYLLETTKPMDYELQQFYERAVVAWN--SEGFHVKRVLKVQILDDNDNAPIPLQPLIE
NOV16b   SEKKLDKK--DDYPIFKITQDTDRKTVSEYNILAIAPETRAPSPSTHITTLVLVLIDINENPPVSQSSYY
NOV16c   PEKDYSSS--NKYYKLVLDGALDREQTPEYNVTIVATDRGKPPLSSSRSITLYVADINDNAEVPDQTSYV
NOV16d   PELLKPSV--ENFYILMIEGALDREARAEYNILTLVTDMGTPRLKIEHNITVQISDVNDNAPTPTQTSYA 570        580        590        600        610        620        630
              ....|....|....|....|....|....|....|....|....|....|....|....|....|....|
NOV16a   LTIEPNNSPNAFLTKLYATDADSEE GQVSYFLG------PDAPSYFSLDSVTGHTVSTQLDRPEKEKY
NOV16b   VYVNENNGACTSIMTVNDSDPDD--NSSVIYSLAEATQGAPPSSTVASITSNTGVLDVLSFFYYEYFDFL
NOV16c   VHVAENNPPGASIAQVSASDPDLGLNGHISYSLIASDLESTRLSSYVSVSAQSGVVFAQRAFDHEQLRAF
NOV16d   LFVRENNSPALHIGSVSATDRDSGTNAQVIYSLLPPQDPHLPLASLVSINADNGHLFALRSLDYEALQAN 640        650        660        670        680        690        700
              ....|....|....|....|....|....|....|....|....|....|....|....|....|....|
NOV16a   RYTVRAVDCGKEPRESVATVALTVLDKNDNSERFIN-------KDFSFFVPENFPGYGETGVISVTDADA
NOV16b   QMQMTANDSGSPPLSSNASMRLFVLKDDNAQDLQYPAP-PTGGTAVEVLPRSAPAPGYLVTKVVAVDGDS
NOV16c   ALTLQARDQGSPALSANVSLRVLVDDRNDNAERVLYPALGPDGSAFFDMVLPRSAEPGYLVTKVVAVDADS
NOV16d   EFRVGATDRGSPALSREALVRVLVLDANDNSPFVLYPLQ-NGSAPCTELVPRAAEPGYLVTKVVAVDGDS 710        720        730        740        750        760        770
              ....|....|....|....|....|....|....|....|....|....|....|....|....|....|
NOV16a   GRNGWVALSVVNQSD--IFVIDTGKG-MLFAKVSLDREQQSSYTLWVEAVDGGEEALSSTAKITILLLDI
NOV16b   GQNAWLSYRIFEASEPGLFSVGLHIGGKVRTARALLDRDALKQSLVVAVQDHGQPPLSA-ATLTVAVADD
NOV16c   GHNAWLSYHVLQASEPGLFSLGLRIC-EVRMVRALGDKDSVRQRLIVAIRDGGQPPLSATATLHLVFADS
NOV16d   GQNAWLSYQLLKATEPGLFGVWAHNG-EVRTARLLSERDAAKHRLVVLVKDNGEPPRSATATLHLLLVDG 780        790        800        810        820        830        840
              ....|....|....|....|....|....|....|....|....|....|....|....|....|....|
NOV16a   NDNPPLVLFPQSNMSYLLVLPSTLPGSPVTEVYAVDKDTGMNAVIAYSIIGRRGPRPESFRIDPKTGNIT
NOV16b   -SLQDLADFFGSLTPSEHQDDSGLTLLLVVVAAVCFVFPVFVVVLLVLKLRRWHKSRLL---HAEGSRL
NOV16c   -LQEVLPDFSDHPTPSDSQ--AEMQFYLVVALALISVLFLLAVILAIALRLRQSFSP-------TAGDCF
NOV16d   -FSQPULPLPEAAPAQAQAEEADLLTVYLVVALASVSSIFLLSVLLFVAVRICRRSRAA------SVGRCS 850        860        870        880        890        900        910
              ....|....|....|....|....|....|....|....|....|....|....|....|....|....|
NOV16a   LEEALLQTD-YGLHRLLVKVSDHGYPEPLHSTVMVN------------LFVNDTVSNESYIESLLRKEPE
NOV16b   AGVAASHFG--GVEGVGVFLPNYSREVSLTADSRKSPLIPTQPRAEIPLSNRESGERSRRLV-SILKDVLE
NOV16c   ESVLCSKSGPVGPPNYSEGTLPYAYNFCVPGDQMNPEFNFFTSVDHCPARQDNLNKDSMLLASILTPSVE
NOV16d   VPEGPFPGHLVDVSCTGTLFQSYQYEVCLTGGSE-----------------TG-------------

920        930        940        950        960        970        980
              ....|....|....|....|....|....|....|....|....|....|....|....|....|....|
NOV16a   INIEEKEPQISIEPTHRKVESVSCMP------------------------TLVALSVISLGSITLVTGM
NOV16b   TEGDPSGQQAPPNTDWRFSQAQRPGTSGSQNGDDTGTWPNNQFDTEMLQAMILAEASEAADGSSTLGGA
NOV16c   ALKKILKQQAPPNTDWRFSQAQRPGTSGSQNGDDTGTWPNNQFDTEMLQAMILASASEAADGSSTLGGA
NOV16d   --------------EEKFLKPITP-------------------------------------------
```

TABLE 16J-continued

Amino Acid Alignment of NOV16a–NOV16d

```
              990       1000      1010      1020      1030      1040
         ....|....|....|....|....|....|....|....|....|....|....|....|..
NOV16a   G---------------IYICLRRGEKHPREDENLEVQIPLKGKIDLHMRERKPMDISNI---
NOV16b   GTNGKSARYGPQFTLQHVPDYRQNVYIPGSNATLTNAAGKRDGKAPAGGNGNKKKSGKKEKK
NOV16c   GTMGLSARYGPQFTLQHVPDYRQNVYIPGSNATLTNAAGKRDGKAPAGGNGNKKKSGKKEKK
NOV16d   ---------------HLPPNRGGKEIE-ENSTLPNIFGFNY--------------------
```

Homologies to any of the above NOV16 proteins will be shared by the other NOV16 proteins insofar as they are homologous to each other as shown above. Any reference to NOV16 is assumed to refer to the NOV16 proteins in general, unless otherwise noted.

NOV16a has homology to the amino acid sequences shown in the BLASTP data listed in Table 16K.

TABLE 16K

BLAST results for NOV16a

| Gene Index/ Identifier | Protein/ Organism | Length (aa) | Identity (%) | Positives (%) | Expect |
|---|---|---|---|---|---|
| gi\|9622242\|gb\|AAF89690.1\| AF169693_1 (AF169693) | protocadherin 13 [Homo sapiens] | 947 | 911/947 (96%) | 911/947 (96%) | 0.0 |
| gi\|15302224\|ref\|XP_054521.1\| (XM_054521) | protocadherin 20 [Homo sapiens] | 924 | 889/924 (96%) | 889/924 (96%) | 0.0 |
| gi\|14589939\|ref\|NP_073754.1\| (NM_022843) | protocadherin 20 precursor; protocadherin 13 [Homo sapiens] | 924 | 888/924 (96%) | 888/924 (96%) | 0.0 |
| gi\|9966883\|ref\|NP_065136.1\| (NM_020403) | protocadherin 9 precursor; cadherin superfamily protein VR4-11 [Homo sapiens] | 1203 | 359/815 (44%) | 495/815 (60%) | e–178 |
| gi\|14388339\|dbj\|BAB60731.1\| (AB062939) | hypothetical protein [Macaca fascicularis] | 1032 | 358/815 (43%) | 495/815 (59%) | e–178 |

The homology of these sequences is shown graphically in the ClustalW analysis shown in Table 16L.

TABLE 16L

ClustalW Analysis of NOV16a

1) NOV16a (SEQ ID NO:56)
2) gi 9622242|gb|AAF89690.1|AF169693_1 (AF169693) protocadherin 13 [Homo sapiens] (SEQ ID NO:189)
2) gi 15302224|refXP_054521.1|(XM_054521) protocadherin 20 [Homo sapiens] (SEQ ID NO:190)
3) gi 14589939|refNP_073754.1|(NM_022843) protocadherin 20 precursor; protocadherin 13 [Homo sapiens] (SEQ ID NO:191)
4) gi|9966883|ref|NP_065136.1|(NM_020403) protocadherin 9 precursor; cadherin superfamily protein VR4-11 [Homo sapiens] (SEQ ID NO:192)
5) gi|14388339|dbj|BAB60731.1|(AB062939) hypothetical protein [Macaca fascicularis] (SEQ ID NO:193)

TABLE 16L-continued

ClustalW Analysis of NOV16a

```
                 10         20         30         40         50         60         70
            ....|....|....|....|....|....|....|....|....|....|....|....|....|....|
NOV16a      MLARIQRPLNSRRCRGNARSSQALGVSWCPATWHPRLDMGRLHRDRSSTSYRNLPHLFLFFLFVGPFGCL
gi|9622242|  ---------------GNARSSQALGVSWCPATWHPRLDMGRLHRDRSSTSYRNLPHLFLFFLFVGPFGCL
gi|15302224  -------------------------------------MGRLHRDRSSTSYRNLPHLFLFFLFVGPFGCL
gi|14589939  -------------------------------------MGRLHRDRSSTSYRNLPHLFLFFLFVGPFGCL
gi|9966883|  ------------------------------------------------MDLRDEYLLAALIACL
gi|14388339  ------------------------------------------------MDLRDEYLLAALIACL 80         90         100        110        120        130        140
            ....|....|....|....|....|....|....|....|....|....|....|....|....|....|
NOV16a      G-SYSRATELLYSINEGLPAGVLIGSLAEDLRLLPRSAGRPDPQSQLPERTGAEWNPPLSFSLASRGLSG
gi|9622242|  G-SYSRATELLYSINEGLPAGVLIGSLAEDLRLLPRSAGRPDPQSQLPERTGAEWNPPLSFSLASRGLSG
gi|15302224  G-SYSRATELLYSINEGLPAGVLIGSLAEDLRLLPRSAGRPDPQSQLPERTGAEWNPPLSFSLASRGLSG
gi|14589939  G-SYSRATELLYSINEGLPAGVLIGSLAEDLRLLPRSAGRPDPQSQLPERTGAEWNPPLSFSLASRGLSG
gi|9966883|  RLDSAIAQELIYTIREELPENVPIGNIPKDLNISHINAATGTSAS-------------LVYRLVSKAGDA
gi|14388339  RLDSAIAQELIYTIREELPENVPIGNIPKDLNISHINAATGTSAS-------------LVYRLVSKAGDA 150        160        170        180        190        200        210
            ....|....|....|....|....|....|....|....|....|....|....|....|....|....|
NOV16a      QYVTLDNRSGELHTSAQEIDREALCVEGGGGTAWSGSVSISSSPSDSCLLLLDVLVLPQEYFRFVKVKIA
gi|9622242|  QYVTLDNRSGELHTSAQEIDREALCVEGGGGTAWSGSVSISSSPSDSCLLLLDVLVLPQEYFRFVKVKIA
gi|15302224  QYVTLDNRSGELHTSAQEIDREALCVEGGGGTAWSGSVSISSSPSDSCLLLLDVLVLPQEYFRFVKVKIA
gi|14589939  QYVTLDNRSGELHTSAQEIDREALCVEGGGGTAWSGSVSISSSPSDSCLLLLDVLVLPQEYFRFVKVKIA
gi|9966883|  PLVKVSSTGEIFTTSNRIDREKLCA--G----------ASYAEENECFFELVVILPNDFFRLIKIKII
gi|14388339  PLVKVSSTGEIFTTSNRIDREKLCA--G----------ASYAEENECFFELVVILPNDFFRLIKIKII 220        230        240        250        260        270        280
            ....|....|....|....|....|....|....|....|....|....|....|....|....|....|
NOV16a      IRDINDNAPQFPVSQISVWVPENAPVNTRLAIEHPAVDPDVGINGVQTYRLLDYHGMFTLDVEBNENGER
gi|9622242|  IRDINDNAPQFPVSQISVWVPENAPVNTRLAIEHPAVDPDVGINGVQTYRLLDYHGMFTLDVEBNENGER
gi|15302224  IRDINDNAPQFPVSQISVWVPENAPVNTRLAIEHPAVDPDVGINGVQTYRLLDYHGMFTLDVEBNENGER
gi|14589939  IRDINDNAPQFPVSQISVWVPENAPVNTRLAIEHPAVDPDVGINGVQTYRLLDYHGMFTLDVEBNENGER
gi|9966883|  VKDTNDNAPMFFSPVINISIPENTLINSRFPIPS-ATDPDTGFNGVQHYELLNGQSVFGLDIVETPEGEK
gi|14388339  VKDTNDNAPMFFSPVINISIPENTLINSRFPIPS-ATDPDTGFNGVQHYELLNGQSVFGLDIVETPEGEK 290        300        310        320        330        340        350
            ....|....|....|....|....|....|....|....|....|....|....|....|....|....|
NOV16a      TPYLIVMGALDRETQDQYVSIIIAEDGGSPPLLGSATLTIGISDININCPLFTDSQINVTVYGNATVGTP
gi|9622242|  TPYLIVMGALDRETQDQYVSIIIAEDGGSPPLLGSATLTIGISDININCPLFTDSQINVTVYGNATVGTP
gi|15302224  TPYLIVMGALDRETQDQYVSIIIAEDGGSPPLLGSATLTIGISDININCPLFTDSQINVTVYGNATVGTP
gi|14589939  TPYLIVMGALDRETQDQYVSIIIAEDGGSPPLLGSATLTIGISDININCPLFTDSQINVTVYGNATVGTP
gi|9966883|  WPQLIVQQNLDREQKDTYVMKIKVEDGCTEQKSSTAILQVTVSDVNINREVEKEGQVEVHIPENAPVGTS
gi|14388339  WPQLIVQQNLDREQKDTYVMKIKVEDGCTEQKSSTAILQVTVSDVNINREVEKEGQVEVHIPENAPVGTS 360        370        380        390        400        410        420
            ....|....|....|....|....|....|....|....|....|....|....|....|....|....|
NOV16a      IAAVQAVDKDLGTNAQITYSYSQKVPQASKDLFHLDFNTGVIKLFSKIGGSVLESHKLTILANGPCIPA
gi|9622242|  IAAVQAVDKDLGTNAQITYSYSQKVPQASKDLFHLDFNTGVIKLFSKIGGSVLESHKLTILANGPCIPA
gi|15302224  IAAVQAVDKDLGTNAQITYSYSQKVPQASKDLFHLDFNTGVIKLFSKIGGSVLESHKLTILANGPCIPA
gi|14589939  IAAVQAVDKDLGTNAQITYSYSQKVPQASKDLFHLDFNTGVIKLFSKIGGSVLESHKLTILANGPCIPA
gi|9966883|  VIQIHATDADIGSNAEIRYIPGAQVAPATKRLEALNNTTSLITVQRSLDREETAIHKVIVLASDGSSTPA
gi|14388339  VIQIHATDADIGSNAEIRYIPGAQVAPATKRLEALNNTTSLITVQRSLDREETAIHKVIVLASDGSSTPA 430        440        450        460        470        480        490
            ....|....|....|....|....|....|....|....|....|....|....|....|....|....|
NOV16a      VITALVSIIKVIFRPPEIVPRYIANEIDGVVYLKELEPVNTPIAFFTIRDPEGKY--KVNCYLDGEGPFR
gi|9622242|  VITALVSIIKVIFRPPEIVPRYIANEIDGVVYLKELEPVNTPIAFFTIRDPEGKY--KVNCYLDGEGPFR
gi|15302224  VITALVSIIKVIFRPPEIVPRYIANEIDGVVYLKELEPVNTPIAFFTIRDPEGKY--KVNCYLDGEGPFR
gi|14589939  VITALVSIIKVIFRPPEIVPRYIANEIDGVVYLKELEPVNTPIAFFTIRDPEGKY--KVNCYLDGEGPFR
gi|9966883|  RALVTINVTDVNDPPNIDLRYISPINGTVYLSEKDPVNIKIALITVSDKDTDVNGKVICFIRREVPFH
gi|14388339  RALVTINVTDVNDPPNIDLRYISPINGTVYLSEKDPVNIKIALITVSDKDTDVNGKVICFIRREVPFH 500        510        520        530        540        550        560
            ....|....|....|....|....|....|....|....|....|....|....|....|....|....|
NOV16a      LSPYKPYNNEYLLETTKPMDYELQQFYEVAVVAWNS--EGFHVKRVIKVQLLDDNDNAPIFLQPLIELTI
gi|9622242|  LSPYKPYNNEYLLETTKPMDYELQQFYEVAVVAWNS--EGFHVKRVIKVQLLDDNDNAPIFLQPLIELTI
gi|15302224  LSPYKPYNNEYLLETTKPMDYELQQFYEVAVVAWNS--EGFHVKRVIKVQLLDDNDNAPIFLQPLIELTI
gi|14589939  LSPYKPYNNEYLLETTKPMDYELQQFYEVAVVAWNS--EGFHVKRVIKVQLLDDNDNAPIFLQPLIELTI
gi|9966883|  LK--AVYDNQYLLETSSLIDYEGTKEESFKIVASDSGKPSLNQTALVRVKLEDENDNPPIFNQEVIELSV
gi|14388339  LK--AVYDNQYLLETSSLIDYEGTKEESFKIVASDSGKPSLNQTALVRVKLEDENDNPEVNQEVIELSV 570        580        590        600        610        620        630
            ....|....|....|....|....|....|....|....|....|....|....|....|....|....|
NOV16a      EENNSPNAFLTKLYATDADSEERGQVSYFLGPDAPSYFSLDSVTGILTVSTQLDREEKEKYRYTVRAVDC
gi|9622242|  EENNSPNAFLTKLYATDADSEERGQVSYFLGPDAPSYFSLDSVTGILTVSTQLDREEKEKYRYTVRAVDC
gi|15302224  EENNSPNAFLTKLYATDADSEERGQVSYFLGPDAPSYFSLDSVTGILTVSTQLDREEKEKYRYTVRAVDC
gi|14589939  EENNSPNAFLTKLYATDADSEERGQVSYFLGPDAPSYFSLDSVTGILTVSTQLDREEKEKYRYTVRAVDC
gi|9966883|  SENNRRCLYLTTISATDEDSGKNADIVYQLGENA-SFEDLDRKTGVLTASRVFDREEQERFIPTVTARDN
gi|14388339  SENNRRCLYLTTISATDEDSGKNADIVYQLGENA-SFEDLDRKTGVLTASRVFDREEQERFIPTVTARDN
```

TABLE 16L-continued

ClustalW Analysis of NOV16a

```
                    640        650        660        670        680        690        700
                ....|....|....|....|....|....|....|....|....|....|....|....|....|....|
NOV16a          GKPPRESVATVALTVLDKNDNSPRFINKDFSFFVPFNFPGYGRIGVISVTDADAGRNGWVALSVVNQSDI
gi|9622242|     GKPPRESVATVALTVLDKNDNSPRFINKDFSFFVPFNFPGYGRIGVISVTDADAGRNGWVALSVVNQSDI
gi|15302224|    GKPPRESVATVALTVLDKNDNSPRFINKDFSFFVPFNFPGYGRIGVISVTDADAGRNGWVALSVVNQSDI
gi|14589939|    GKPPRESVATVALTVLDKNDNSPRFINKDFSFFVPFNFPGYGRIGVISVTDADAGRNGWVALSVVNQSDI
gi|9966883|     GTPPLQSQAAIVTVLDENDNSPKFTHNHFQFFVSENLEKYSTVGVITVTDADAGENKAVTLSIINDMDN
gi|14388339|    GTPPLQSQAAIVTVLDENDNSPKFTHNHFQFFVSENLEKYSTVGVITVTDADAGENKAVTLSIINDMDN 710        720        730        740        750        760        770
                ....|....|....|....|....|....|....|....|....|....|....|....|....|....|
NOV16a          FVIDTGKGMLRAKVSLDREQQSSYTLWVEAVDGGEPALSSTAKITILLLDINDNPPLVLFPQSNMSYLLV
gi|9622242|     FVIDTGKGMLRAKVSLDREQQSSYTLWVEAVDGGEPALSSTAKITILLLDINDNPPLVLFPQSNMSYLLV
gi|15302224|    FVIDTGKGMLRAKVSLDREQQSSYTLWVEAVDGGEPALSSTAKITILLLDINDNPPLVLFPQSNMSYLLV
gi|14589939|    FVIDTGKGMLRAKVSLDREQQSSYTLWVEAVDGGEPALSSTAKITILLLDINDNPPLVLFPQSNMSYLLV
gi|9966883|     FVLEPYSGVIKSNVSFDREQQSSYTFDVKATDGGQPPRSSTAKYTINVMDVNDSPVVISEPSNTSPKLV
gi|14388339|    FVLEPYSCVIKSNVSFDREQQSSYTFDVKATDGGQPPRSSTAKYTINVMDVNDSPVVISEPSNTSPKLV 780        790        800        810        820        830        840
                ....|....|....|....|....|....|....|....|....|....|....|....|....|....|
NOV16a          LESTLPGSPVTEVYAVDKDTGMNAVIAYSIIGRRGPRPESFRIDPKTGNITLEEALLQTDYGLHRLLVKV
gi|9622242|     LESTLPGSPVTEVYAVDKDTGMNAVIAYSIIGRRGPRPESFRIDPKTGNITLEEALLQTDYGLHRLLVKV
gi|15302224|    LESTLPGSPVTEVYAVDKDTGMNAVIAYSIIGRRGPRPESFRIDPKTGNITLEEALLQTDYGLHRLLVKV
gi|14589939|    LESTLPGSPVTEVYAVDKDTGMNAVIAYSIIGRRGPRPESFRIDPKTGNITLEEALLQTDYGLHRLLVKV
gi|9966883|     PLSAIPGSVVAEVAVDVDTGMNAELKYTIVS--GNNKGLFRIDPVTGNITLEEKPAPTDVGLHRLVVNI
gi|14388339|    PLSAIPGSVVAEVAVDVDTGMNAELKYTIVS--GNNKGLFRIDPVTGNITLEEKPAPTDVGLHRLVVNI 850        860        870        880        890        900        910
                ....|....|....|....|....|....|....|....|....|....|....|....|....|....|
NOV16a          SCHGYPEPLHSTVMVNLFVNDTVSNESYIESLLRKEPEINIEP---KEPQISIEPTHRKVESVSCMPTLV
gi|9622242|     SCHGYPEPLHSTVMVNLFVNDTVSNESYIESLLRKEPEINIEP---KEPQISIEPTHRKVESVSCMPTLV
gi|15302224|    SCHGYPEPLHSTVMVNLFVNDTVSNESYIESLLRKEPEINIEP---KEPQISIEPTHRKVESVSCMPTLV
gi|14589939|    SCHGYPEPLHSTVMVNLFVNDTVSNESYIESLLRKEPEINIEP---KEPQISIEPTHRKVESVSCMPTLV
gi|9966883|     SDLGYPKSLHILVEVFLXVNDTAGNASYIYDLIRRTMETPLDRNIGDSSQPYQNEDYLTIMIAIIAGAMV
gi|14388339|    SDLGYPKSLHILVEVFLXVNDTAGNASYIYDLIRRTMETPLDRNIGDSSQPYQNEDYLTIMIAIIAGAMV 920        930        940        950        960        970        980
                ....|....|....|....|....|....|....|....|....|....|....|....|....|....|
NOV16a          ALSVISLGSITLVTGMGIYICLRKGE-------------------KHPRE----------DENLE
gi|9622242|     ALSVISLGSITLVTGMGIYICLRKGE-------------------KHPRE----------DENLE
gi|15302224|    ALSVISLGSITLVTGMGIYICLRKGE-------------------KHPRE----------DENLE
gi|14589939|    ALSVISLGSITLVTGMGIYICLRKGE-------------------KHPRE----------DENLE
gi|9966883|     VIVVIFYTVLVTCRHASRFKAAQESKQGAEWMSPNQENKQNKKKKRKKRKSEKSSLLNFVTIEESKPDDA
gi|14388339|    VIVVIFYTVLVTCRHASRFKAAQESKQGAEWMSPNQENKQNKKKKRKKRKSEKSSLLNFVTIEESKPDDA 990       1000       1010       1020       1030       1040       1050
                ....|....|....|....|....|....|....|....|....|....|....|....|....|....|
NOV16a          VQIPLKGKIDL-----------------------------------HMRERKPMDISNI----
gi|9622242|     VQIPLKGKIDL-----------------------------------HMRERKPMDISNI----
gi|15302224|    VQIPLKGKIDL-----------------------------------HMRERKPMDISNI----
gi|14589939|    VQIPLKGKIDL-----------------------------------HMRERKPMDISNI----
gi|9966883|     VHEEINGTISLPAELEEQSIGRFDWGPAPPTTFKPNSPDLAKHYKSASPQPAFELKPDTEVSVKKHHVIQ
gi|14388339|    VHEEINGTISLPAELEEQSIGRFDWGPAPPTTFKPNSPDLAKHYKSASPQPAFELKPDTEVSVKKHHVIQ 1060       1070       1080       1090       1100       1110       1120
                ....|....|....|....|....|....|....|....|....|....|....|....|....|....|
NOV16a          ----------------------------------------------------------------------
gi|9622242|     ----------------------------------------------------------------------
gi|15302224|    ----------------------------------------------------------------------
gi|14589939|    ----------------------------------------------------------------------
gi|9966883|     ELPLDNTFVGGCDTLSKRSSTSSDHFSASECSSQGGFKTKFPLHTRQSQRRVTFHLPDGSQESCSDSGLG
gi|14388339|    ELPLDNTFVGGCDTLSKRSSTSSDHFSASECSSQGGFKTKFPLHTRQVN---------------------

1130       1140       1150       1160       1170       1180       1190
                ....|....|....|....|....|....|....|....|....|....|....|....|....|....|
NOV16a          ----------------------------------------------------------------------
gi|9622242|     ----------------------------------------------------------------------
gi|15302224|    ----------------------------------------------------------------------
gi|14589939|    ----------------------------------------------------------------------
gi|9966883|     DHEPVGSGTLISHPLPLVQPQDEFYDQASPDKRTEADGNSDPNSDGPLGPTGLAEATEMCTQECLVLGHS
gi|14388339|    ----------------EHFYWSIS---------------------T----------------------

1200       1210       1220       1230       1240       1250       1260
                ....|....|....|....|....|....|....|....|....|....|....|....|....|....|
NOV16a          ----------------------------------------------------------------------
gi|9622242|     ----------------------------------------------------------------------
gi|15302224|    ----------------------------------------------------------------------
gi|14589939|    ----------------------------------------------------------------------
gi|9966883|     DNCWMPPGLGPYQHPKSPLSTFAPQKEWVKKDKLVNGHTLTRAWKEDSNRNQFNDRKQYGSNEGHFNNGS
gi|14388339|    ----------AYKCP---------VNQY------------------------------------------
```

TABLE 16L-continued

ClustalW Analysis of NOV16a

```
                    1270      1280
             ....|....|....|....|....|...
NOV16a       ---------------------------
gi|9622242|  ---------------------------
gi|15302224| ---------------------------
gi|14589939| ---------------------------
gi|9966883|  HMTDIPLANLKSYKQAGGATESPKEHQL
gi|14388339| ---------------------------
```

Tables 16M and 16N list the domain description from DOMAIN analysis results against NOV16a. This indicates that the NOV16a sequence has properties similar to those of other proteins known to contain these domains.

TABLE 16M

Domain Analysis of NOV16a gnl|Smartsmart00112, CA, Cadherin repeats.; Cadherins are
glycoproteins involved in Ca2+-mediated cell-cell adhesion. Cadherin
domains occur as repeats in the extracellular regions which are
thought to mediate cell-cell contact when bound to calcium. (SEQ ID NO:194)
CD-Length = 82 residues, 100.0% aligned
Score = 89.4 bits (220), Expect = 9e-19

```
Query:  672 ISVTDADAGRNGWVALSVV--NQSDIFVIDTGKGMLRAKVSLDREQQSSYTLWVEAVDGG  729
                +| ||||+| || |  |++ |   +| ||   |++       ||||+
                || ||| ||| |||
Sbjct:    1 VSATDADSGENGKVTYSILSGNDGGLFSIDPETGIITTTKPLDREEQSEYTLTVEATDGG   60

Query:  730 EPALSSTAKITILLLDINDNPP                                        751
                |  ||||| +|+ +||+||| |
Sbjct:   61 GPPLSSTATVTVTVLDVNDNAP                                         82
```

TABLE 16N

Domain Analysis of NOV16a gnl|Pfam|pfam00028, cadherin, Cadherin domain. (SEQ ID NO:195)
CD-Length = 92 residues, 100.0% aligned
Score = 75.5 bits (184), Expect = 1e-14

```
Query:  655 FSFFVPENFPGYGEIGVISVTDADAGRNGWVALSVVNQ--SDIFVIDTGKGMLRAKVSLD  712
                +| |||| |  |+ ++ |||| | || + |++       | ||   | |       ||
Sbjct:    1 YSASVPENAPVGTEVLTVTATDADLGPNGRIFYSILGGGPGGWFRIDPDTGDLSTTKPLD   60

Query:  713 REQQSSYTLWVEAVDGGEPALSSTAKITILLL                              744
                ||   | | | | | | ||  |  +|| +|
Sbjct:   61 RESIGEYELTVLATDSGGPPLSGTTTVTITVL                               92
```

Cadherins, a family of calcium-dependent cell-cell adhesion molecules, mediate neural cell-cell interactions. Sperry (1963) proposed that neurons recognize their synaptic partners through lock-and-key interactions mediated by millions of specifier molecules. Cadherins were likely candidates for components of the lock-and-key mechanism based on their neural location, their adhesive diversity, and the structural biology of their adhesive interactions maintaining a synapse gap size of approximately 200 angstroms (Shapiro and Colman, Neuron. 23(3):427–30, 1999). Neural cadherins (CDH2, 114020), as well as epithelial (CDH1, 192090), placental (CDH3, 114021), and retinal (CDH4, 603006) cadherins, have homophilic binding specificities in that they preferentially adhere to cells expressing the same cadherin type. Cadherins of the 'classic' type have a highly conserved extracellular sequence motif of approximately 110 amino acids that is repeated 5 times as well as a highly conserved cytoplasmic domain of approximately 200 amino acids that associates with intracellular actin microfilaments via catenins (see CTNNA1). 'Nonclassic' cadherins differ in that they may have 6 or 7 repeated extracellular domains or have cytoplasmic domains that connect to intermediate filaments instead of actin.

Protocadherins constitute a subfamily of the nonclassic cadherins. Kohmura et al. (Neuron. 20(6):1137–51, 1998) described cadherin-related neuronal receptors (CNR) in the mouse. By EST database searching for cadherin-like sequences, Wu and Maniatis (Cell 97(6):779–90, 1999) identified 52 novel genes organized into 3 closely linked tandem clusters on human chromosome 5q31. A distinct large exon of approximately 2,400 nucleotides encodes the 6 N-terminal extracellular domains and the transmembrane domain of each cadherin. In contrast, the C terminus of each of these proteins is identical within each cluster and is encoded by 3 small exons located downstream from the array of N-terminal exons. Wu and Maniatis (1999) designated the clusters alpha, beta and gamma. Each large exon is independently spliced to the first exon encoding the intracellular domain. The authors also denoted the extracellular portion as the variable region and the cytoplasmic portion as the constant region. The alpha cluster contains at least 15 proteins encoded by large, uninterrupted exons whose sequences most closely resemble those of the mouse CNR proteins. Wu and Maniatis (1999) proposed 4 models to explain protocadherin gene regulation and noted that several neurologic disorders map to chromosome 5q31.

The NOV16 nucleic acid of the invention encoding a Protocadherin-like protein includes the nucleic acid whose sequence is provided in Tables 16A, 16C, 16E and 16G, or a fragment thereof. The invention also includes a mutant or variant nucleic acid any of whose bases may be changed from the corresponding base shown in Tables 16A, 16C, 16E and 16G while still encoding a protein that maintains its Protocadherin-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 21% of the NOV16b residues, about 9% of the NOV16c residues and about 4% of the NOV16d residues may be so changed.

The NOV16 protein of the invention includes the Protocadherin-like protein whose sequence is provided in Tables 16B, 16D, 16F and 16H. The invention also includes a mutant or variant protein any of whose residues may be changed from the corresponding residue shown in Tables 16B, 16D, 16F and 16H while still encoding a protein that maintains its Protocadherin-like activities and physiological functions, or a functional fragment thereof. In the mutant or variant protein, up to about 1% of the NOV16a bases, about 30% of the NOV16b bases, about 10% of the NOV16c bases and about 5% of the NOV16d bases may be so changed.

The NOV16 nucleic acids and proteins of the invention are useful in potential diagnostic and therapeutic applications implicated in various diseases and disorders described below and/or other pathologies. For example, the compositions of the present invention will have efficacy for treatment of patients suffering from: Hirschsprung's disease, Crohn's Disease, Appendicitis, Von Hippel-Lindau (VHL) syndrome, Diabetes, Tuberous sclerosis, Endometriosis, Fertility and other diseases, disorders and conditions of the like.

NOV16 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV16 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV17

NOV17 includes two novel Cadherin 23-like proteins disclosed below. The disclosed proteins have been named NOV17a and NOV17b.

NOV17a

A disclosed NOV17a nucleic acid of 1303 nucleotides (also referred to as CG57429-01) encoding a novel Cadherin 23-like protein is shown in Table 17A. An open reading frame was identified beginning with an ATG initiation codon at nucleotides 31–33 and ending with a TAG codon at nucleotides 1291–1293. Putative untranslated regions, if any, upstream from the initiation codon and downstream from the termination codon are underlined in Table 17A, and the start and stop codons are in bold letters.

TABLE 17A

NOV17a nucleotide sequence.

(SEQ ID NO:63)

[001b]
ATATCCAATGGGCTGATTTATCTGACGGTCATGGCCATGGATGCTGGCAACCCCCCTCTCAACAGCACCGTC

CCTGTCACCATCGAGGTGTTTGATGAGAATGACAACCCTCCCACCTTCAGCAAGCCCGCCTACTTCGTCTCC

GTGGTGGAGAACATCATGGCAGGAGCCACGGTGCTGTTCCTGAATGCCACAGACCTGGACCGCTCCCGGGAG

TACGGCCAGGAGTCCATCATCTACTCCTTGGAAGGCTCCACCCAGTTTCGGATCAATGCCCGCTCAGGGGAA

ATCACCACCACGTCTCTGCTTGACCGAGAGACCAAGTCTGAATACATCCTCATCGTTCGCGCAGTGGACGGG

GGTGTGGGCCACAACCAGAAAACTGGCATCGCCACCGTAAACATCACCCTCCTGGACATCAACGACAACCAC

CCCACGTGGAAGGACGCACCCTACTACATCAACCTGGTGGAGATGACCCCTCCAGACTCTGACGTGACCACG

GTGGTGGCTGTTGACCCAGACCTGGGGGAGAATGGCACCCTGGTGTACAGCATCCAGCCACCCAACAAGTTC

TACAGCCTCAACAGCACCACGGGCAAGATCCGCACCACCCACGCCATGCTGGACCGGGAGAACCCCGACCCC

CATGAGGCCGAGCTGATGCGCAAAATCGTCGTCTCTGTTACTGACTGTGGCAGGCCCCTCTGAAAGCCACC

AGCAGTGCCACAGTGTTTGTGAACCTCTTGGATCTCAATGACAATGACCCCACCTTTCAGAACCTGCCTTTT

TABLE 17A-continued

NOV17a nucleotide sequence.

```
GTGGCCGAGGTGCTTGAAGGCATCCCGGCGGGGGTCTCCATCTACCAAGTGGTGGCCATCGACCTCGATGAG

GGCCTGAACGGCCTGGTGTCCTACCGCATGCCGGTGGGCATGCCCCGCATGGACTTCCTCATCAACAGCAGC

AGCGGCGTGGTGGTCACCACCACCGAGCTGGACCGCGAGCGCATCGCGGAGTACCAGCTGCGGGTGGTGGCC

AGTGATGCAGGCACGCCCACCAAGAGCTCCACCAGCACGCTCACCATCCATGTGCTGGATGTGAACGACGAG

ACGCCCACCTTCTTCCCGGCCGTGTACAATGTGTCTGTGTCCGAGGACGTGCCACGCGAGTTCCGGGTGGTC

TGGCTGAACTGCACGGACAACGACGTGGGCCTCAATGCAGAGCTCAGCTACTTCATCACAGGTGCTGCCCCG

GCCTCCGCCCACCTGTGCAGGCCTCCTGGGGCCCTGCCTCCACCCCTCCCAGATGGACAGCCAGACTAGGTG

GGGGCAG
```

The disclosed NOV17a nucleic acid sequence, localized to chromsome 10, has 702 of 703 bases (99%) identical to a gb:GENBANK-ID:AY010111|acc:AY010111.1 mRNA from *Homo sapiens* (*Homo sapiens* cadherin-23 (CDH23) mRNA, partial cds) (E=$6.9e^{-152}$).

A NOV17a polypeptide (SEQ ID NO:64) encoded by SEQ ID NO:63 has 420 amino acid residues and is presented using the one-letter code in Table 17B. Signal P, Psort and/or Hydropathy results predict that NOV17a does not contain a signal peptide and is likely to be localized to the plasma membrane with a certainty of 0.7900.

TABLE 17B

Encoded NOV17a protein sequence.

(SEQ ID NO:64)
```
MAMDAGNPPLNSTVPVTIEVFDENDNPPTFSKPAYFVSVVENIMAGATVLFLNATDLDRSREYGQESIIYSL

EGSTQFRINARSGEITTTSLLDRETKSEYILIVRAVDGGVGHNQKTGIATVNITLLDINDNHPTWKDAPYYI

NLVEMTPPDSDVTTVVAVDPDLGENGTLVYSIQPPNKFYSLNSTTGKIRTTHAMLDRENPDPHEAELMRKIV

VSVTDCGRPPLKATSSATVFVNLLDLNDNDPTFQNLPFVAEVLEGIPAGVSIYQVVAIDLDEGLNGLVSYRM

PVGMPRMDFLINSSSGVVVTTTELDRERIAEYQLRVVASDAGTPTKSSTSTLTIHVLDVNDETPTFFPAVYN

VSVSEDVPREFRVVWLNCTDNDVGLNAELSYFITGAAPASAHLCRPPGALPPPLPDGQPD
```

The NOV17a amino acid sequence has 233 of 234 amino acid residues (99%) identical to, and 234 of 234 amino acid residues (100%) similar to, the 2552 amino acid residue ptnr:TREMBLNEW-ACC:AAG27034 protein from *Homo sapiens* (Human) (CADHERIN-23) (E=$1.8e^{-120}$).

The disclosed NOV17a is expressed in at least the following tissues: lung, pancreas, spinal chord and testis. This information was derived by determining the tissue sources of the sequences that were included in the invention including but not limited to SeqCalling sources, Public EST sources, Literature sources, and/or RACE sources.

NOV17b

A disclosed NOV17b nucleic acid of 1278 nucleotides (also referred to as CG57429-02) encoding a novel Cadherin 23-like protein is shown in Table 17C. An open reading frame was identified beginning with an ATG initiation codon at nucleotides 6–8 and ending with a TAG codon at nucleotides 1266–1268. Putative untranslated regions, if any, upstream from the initiation codon and downstream from the termination codon are underlined in Table 17C, and the start and stop codons are in bold letters.

TABLE 17C

NOV17b nucleotide sequence.

(SEQ ID NO:65)
```
TGGTCATGGCCATGGATGCTGGCAACCCCCCTCTCAACAGCACCGTCCCTGTCACCATCGAGGTGTTTGATG

AGAATGACAACCCTCCCACCTTCAGCAAGCCCGCCTACTTCGTCTCCGTGGTGGAGAACATCATGGCAGGAG

CCACGGTGCTGTTCCTGAATGCCACAGACCTGGACCGCTCCCGGGAGTACGGCCAGGAGTCCATCATCTACT

CCTTGGAAGGCTCCACCCAGTTTCGGATCAATGCCCGCTCAGGGGAAATCACCACCACGTCTCTGCTTGACC

GAGAGACCAAGTCTGAATACATCCTCATCGTTCGCGCAGTGGACGGGGGTGTGGGCCACAACCAGAAAACTG

GCATCGCCACCGTAAACATCACCCTCCTGGACATCAATGACAACCACCCCACGTGGAAGGACGCACCCTACT
```

TABLE 17C-continued

NOV17b nucleotide sequence.

ACATCAACCTGGTGGAGATGACCCCTCCAGACTCTGATGTGACCACGGTGGTGGCTGTTGACCCAGACCTGG

GGGAGAATGGCACCCTGGTGTACAGCATCCAGCCACCCAACAAGTTCTACAGCCTCAACAGCACCACGGGCA

AGATCCGCACCACCCACGCCATGCTGGACCGGGAGAACCCCGACCCCCATGAGGCCGAGCTGATGCGCAAAA

TCGTCGTCTCTGTTACTGACTGTGGCAGGCCCCCTCTGAAAGCCACCAGCAGTGCCACAGTGTTTGTGAACC

TCTTGGATCTCAATGACAATGACCCCACCTTTCAGAACCTGCCTTTTGTGGCCGAGGTGCTTGAAGGCATCC

CGACGGGGGTCTCCATCTACCAAGTGGTGGCCATCGACCTCGATGAGGGCCTGAACGGCCTGGTGTCCTACC

GCATGCCGGTGGGCATGCCCCGCATGGACTTCCTCATCAACAGCAGCAGCGGCGTGGTGGTCACCACCACCG

AGCTGGACCGCGAGCGCATCGCGGAGTACCAGCTGCGGGTGGTGGCCAGTGATGCAGGCACGCCCACCAAGA

GCTCCACCAGCACGCTCACCATCCATGTGCTGGATGTGAACGACGAGACGCCCACCTTCTTCCCGGCCGTGT

ACAATGTGTCTGTGTCCGAGGACGTGCCACGCGAGTTCCGGGTGGTCTGGCTGAACTGCACGGACAACGACG

TGGGCCTCAATGCAGAGCTCAGCTACTTCATCACAGGTGCTGCCCCGGCCTCCGCCCACCTGTGCAGGCCTC

CTGGGGCCCTGCCTCCACCCCTCCCAGATGGACAGCCAGACTAGGTGGGGCAG

---

The disclosed NOV17b nucleic acid sequence, localized to chromsome 10, has 1188 of 1190 bases (99%) identical to a gb:GENBANK-ID:AF312024|acc:AF312024.1 mRNA from *Homo sapiens* (cadherin related 23 (CDH23) mRNA, complete cds) (E=6.6e$^{-263}$).

A NOV17b polypeptide (SEQ ID NO:66) encoded by SEQ ID NO:65 has 420 amino acid residues and is presented using the one-letter code in Table 17D. Signal P, Psort and/or Hydropathy results predict that NOV17b does not contain a signal peptide and is likely to be localized to the plasma membrane with a certainty of 0.7900.

TABLE 17D

Encoded NOV17b protein sequence.

(SEQ ID NO:66)
MAMDAGNPPLNSTVPVTIEVFDENDNPPTFSKPAYFVSVVENIMAGATVLFLNATDLDRSREYGQESIIYSL

EGSTQFRINARSGEITTTSLLDRETKSEYILIVRAVDGGVGHNQKTGIATVNITLLDINDNHPTWKDAPYYI

NLVEMTPPDSDVTTVVAVDPDLGENGTLVYSIQPPNKFYSLNSTTGKIRTTHAMLDRENPDPHEAELMRKIV

VSVTDCGRPPLKATSSATVFVNLLDLNDNDPTFQNLPFVAEVLEGIPTGVSIYQVVAIDLDEGLNGLVSYRM

PVGMPRMDFLINSSSGVVVTTTELDRERIAEYQLRVVASDAGTPTKSSTSTLTIHVLDVNDETPTFFPAVYN

VSVSEDVPREFRVVWLNCTDNDVGLNAELSYFITGAAPASAHLCRPPGALPPPLPDGQPD

---

The NOV17b amino acid sequence has 394 of 395 amino acid residues (99%) identical to, and 394 of 395 amino acid residues (99%) similar to, the 3354 amino acid residue ptnr:SPTREMBL-ACC:Q9H251 protein from *Homo sapiens* (Human) (Cadherin Related 23) (E=3.9e$^{-208}$).

The disclosed NOV17b is expressed in at least the following tissues: lung, pancreas, spinal chord and testis. This information was derived by determining the tissue sources of the sequences that were included in the invention including but not limited to SeqCalling sources, Public EST sources, Literature sources, and/or RACE sources.

Possible SNPs found for NOV17a are listed in Table 17E.

TABLE 17E

| | SNPs | | | |
|---|---|---|---|---|
| Variant | Nucleotide Position | Base Change | Amino Acid Position | Base Change |
| 13377100 | 495 | C > T | Silent | N/A |
| 13377100 | 820 | G > Z | 264 | Ala > Thr |

NOV17a and NOV17b are very closely homologous as is shown in the nucleic acid alignment in Table 17F.

TABLE 17F

Nucleic Acid Alignment of NOV17a and NOV17b

```
                10        20        30        40        50        60        70
        ....|....|....|....|....|....|....|....|....|....|....|....|....|....|
NOV17a  ATATCCAATGGGCTGATTTATCTGACGGTCATGGCCATGGATGCTGGCAACCCCCCTCTCAACAGCACCG
NOV17b  -------------------------TGGTCATGGCCATGGATGCTGGCAACCCCCCTCTCAACAGCACCG 80        90       100       110       120       130       140
        ....|....|....|....|....|....|....|....|....|....|....|....|....|....|
NOV17a  TCCCTGTCACCATCGAGGTGTTTGATGAGAATGACAACCCTCCCACCTTCAGCAAGCCCGCCTACTTCGT
NOV17b  TCCCTGTCACCATCGAGGTGTTTGATGAGAATGACAACCCTCCCACCTTCAGCAAGCCCGCCTACTTCGT 150       160       170       180       190       200       210
        ....|....|....|....|....|....|....|....|....|....|....|....|....|....|
NOV17a  CTCCGTGGTGGAGAACATCATGGCAGGAGCCACGGTGCTGTTCCTGAATGCCACAGACCTGGACCGCTCC
NOV17b  CTCCGTGGTGGAGAACATCATGGCAGGAGCCACGGTGCTGTTCCTGAATGCCACAGACCTGGACCGCTCC 220       230       240       250       260       270       280
        ....|....|....|....|....|....|....|....|....|....|....|....|....|....|
NOV17a  CGGGAGTACGGCCAGGAGTCCATCATCTACTCCTTGGAAGGCTCCACCCAGTTTCGGATCAATGCCCGCT
NOV17b  CGGGAGTACGGCCAGGAGTCCATCATCTACTCCTTGGAAGGCTCCACCCAGTTTCGGATCAATGCCCGCT 290       300       310       320       330       340       350
        ....|....|....|....|....|....|....|....|....|....|....|....|....|....|
NOV17a  CAGGGGAAATCACCACCACGTCTCTGCTTGACCGAGAGACCAAGTCTGAATACATCCTCATCGTTCGCGC
NOV17b  CAGGGGAAATCACCACCACGTCTCTGCTTGACCGAGAGACCAAGTCTGAATACATCCTCATCGTTCGCGC 360       370       380       390       400       410       420
        ....|....|....|....|....|....|....|....|....|....|....|....|....|....|
NOV17a  AGTGGACGGGGGTGTGGGCCACAACCAGAAAACTGGCATCGCCACCGTAAACATCACCCTCCTGGACATC
NOV17b  AGTGGACGGGGGTGTGGGCCACAACCAGAAAACTGGCATCGCCACCGTAAACATCACCCTCCTGGACATC 430       440       450       460       470       480       490
        ....|....|....|....|....|....|....|....|....|....|....|....|....|....|
NOV17a  AACGACAACCACCCCACGTGGAAGGACGCACCCTACTACATCAACCTGGTGGAGATGACCCCTCCAGACT
NOV17b  AATGACAACCACCCCACGTGGAAGGACGCACCCTACTACATCAACCTGGTGGAGATGACCCCTCCAGACT 500       510       520       530       540       550       560
        ....|....|....|....|....|....|....|....|....|....|....|....|....|....|
NOV17a  CTGACGTGACCACGGTGGTGGCTGTTGACCCAGACCTGGGGGAGAATGGCACCCTGGTGTACAGCATCCA
NOV17b  CTGATGTGACCACGGTGGTGGCTGTTGACCCAGACCTGGGGGAGAATGGCACCCTGGTGTACAGCATCCA 570       580       590       600       610       620       630
        ....|....|....|....|....|....|....|....|....|....|....|....|....|....|
NOV17a  GCCACCCAACAAGTTCTACAGCCTCAACAGCACCACGGGCAAGATCCGCACCACCCACGCCATGCTGGAC
NOV17b  GCCACCCAACAAGTTCTACAGCCTCAACAGCACCACGGGCAAGATCCGCACCACCCACGCCATGCTGGAC 640       650       660       670       680       690       700
        ....|....|....|....|....|....|....|....|....|....|....|....|....|....|
NOV17a  CGGGAGAACCCCGACCCCCATGAGGCCGAGCTGATGCGCAAAATCGTCGTCTCTGTTACTGACTGTGGCA
NOV17b  CGGGAGAACCCCGACCCCCATGAGGCCGAGCTGATGCGCAAAATCGTCGTCTCTGTTACTGACTGTGGCA 710       720       730       740       750       760       770
        ....|....|....|....|....|....|....|....|....|....|....|....|....|....|
NOV17a  GGCCCCCTCTGAAAGCCACCAGCAGTGCCACAGTGTTTGTGAACCTCTTGCATCTCAATGACAATGACCC
NOV17b  GGCCCCCTCTGAAAGCCACCAGCAGTGCCACAGTGTTTGTGAACCTCTTGCATCTCAATGACAATGACCC 780       790       800       810       820       830       840
        ....|....|....|....|....|....|....|....|....|....|....|....|....|....|
NOV17a  CACCTTTCAGAACCTGCCTTTTGTGGCCGAGGTGCTTGAAGGCATCCCGGCGGGGGTCTCCATCTACCAA
NOV17b  CACCTTTCAGAACCTGCCTTTTGTGGCCGAGGTGCTTGAAGGCATCCCGACGGGGGTCTCCATCTACCAA 850       860       870       880       890       900       910
        ....|....|....|....|....|....|....|....|....|....|....|....|....|....|
NOV17a  GTGGTGGCCATCGACCTCGATGAGGGCCTGAACGGCCTGGTGTCCTACCGCATGCCGGTGGGCATGCCCG
NOV17b  GTGGTGGCCATCGACCTCGATGAGGGCCTGAACGGCCTGGTGTCCTACCGCATGCCGGTGGGCATGCCCG 920       930       940       950       960       970       980
        ....|....|....|....|....|....|....|....|....|....|....|....|....|....|
NOV17a  GCATGGACTTCCTCATCAACAGCAGCAGCGGCGTGGTGGTCACCACCACCGAGCTGGACCGCGAGCGCAT
NOV17b  GCATGGACTTCCTCATCAACAGCAGCAGCGGCGTGGTGGTCACCACCACCGAGCTGGACCGCGAGCGCAT 990      1000      1010      1020      1030      1040      1050
        ....|....|....|....|....|....|....|....|....|....|....|....|....|....|
NOV17a  CGCGGAGTACCAGCTGCGGGTGGTGGCCAGTGATGCAGGCACGCCCACCAAGAGCTCCACCAGCACGCTC
NOV17b  CGCGGAGTACCAGCTGCGGGTGGTGGCCAGTGATGCAGGCACGCCCACCAAGAGCTCCACCAGCACGCTC
```

TABLE 17F-continued

Nucleic Acid Alignment of NOV17a and NOV17b

```
              1060       1070       1080       1090       1100       1110       1120
         ....|....|....|....|....|....|....|....|....|....|....|....|....|....|
NOV17a   ACCATCCATCTGCTGGATGTGAACGACCAGACGCCCACCTTCTTCCCGGCCGTGTACAATGTGTCTGTGT
NOV17b   ACCATCCATCTGCTGGATGTGAACGACCAGACGCCCACCTTCTTCCCGGCCGTGTACAATGTGTCTGTGT 1130       1140       1150       1160       1170       1180       1190
         ....|....|....|....|....|....|....|....|....|....|....|....|....|....|
NOV17a   CCGAGGACGTGCCACGCGAGTTCCGGGTGGTCTGGCTGAACTGCACGGACAACGACGTGGGCCTCAATGC
NOV17b   CCGAGGACGTGCCACGCGAGTTCCGGGTGGTCTGGCTGAACTGCACGGACAACGACGTGGGCCTCAATGC 1200       1210       1220       1230       1240       1250       1260
         ....|....|....|....|....|....|....|....|....|....|....|....|....|....|
NOV17a   AGAGCTCAGCTACTTCATCACAGGTGCTGCCCCGGCCTCCGCCCACCTGTGCAGGCCTCCTGGGGCCCTG
NOV17b   AGAGCTCAGCTACTTCATCACAGGTGCTGCCCCGGCCTCCGCCCACCTGTGCAGGCCTCCTGGGGCCCTG 1270       1280       1290       1300
         ....|....|....|....|....|....|....|....|...
NOV17a   CCTCCACCCCTCCCAGATGGACAGCCAGACTAGGTGGGGCAG
NOV17b   CCTCCACCCCTCCCAGATGGACAGCCAGACTAGGTGGGGCAG
```

Homologies to any of the above NOV17 nucleic acids and encoded proteins will be shared by the other NOV17 nucleic acids and encoded proteins insofar as they are homologous to each other as shown above. Any reference to NOV17 is assumed to refer to both of the NOV17 nucleic acids and encoded proteins in general, unless otherwise noted.

NOV17a has homology to the amino acid sequences shown in the BLASTP data listed in Table 17G.

TABLE 17G

BLAST results for NOV17a

| Gene Index/ Identifier | Protein/ Organism | Length (aa) | Identity (%) | Positives (%) | Expect |
|---|---|---|---|---|---|
| gi|18576726|ref|XP_057519.3| (XM_057519) | similar to cadherin related 23 (*H. sapiens*) [*Homo sapiens*] | 3399 | 395/395 (100%) | 395/395 (100%) | 0.0 |
| gi|16507962|ref|NP_071407.2| (NM_022124) | cadherin related 23, isoform 1 precursor; cadherin-23; otocadherin [*Homo sapiens*] | 3354 | 395/395 (100%) | 395/395 (100%) | 0.0 |
| gi|17366834|sp|Q9H251| CADN_HUMAN | Cadherin 23 precursor (Otocadherin) [*Homo sapiens*] | 3354 | 395/395 (100%) | 395/395 (100%) | 0.0 |
| gi|14017841|dbj|BAB47441.1| (AB058715) | Cadherin 23 [*Homo sapiens*] | 803 | 395/395 (100%) | 395/395 (100%) | 0.0 |
| gi|17865345|ref|NP_446096.1| (NM_053644) | cadherin related 23 [*Rattus norvegicus*] | 3317 | 377/394 (95%) | 385/394 (97%) | 0.0 |

The homology of these sequences is shown graphically in the ClustalW analysis shown in Table 17H.

TABLE 17H

ClustalW Analysis of NOV17a

1) NOV17a (SEQ ID NO:64)
2) gi 18576726|refXP_057519.3|(XM_057519) similar to cadherin related 23 (*H. sapiens*) [*Homo sapiens*] (SEQ ID NO:196)
2) gi 16507962|refNP_071407.2|(NM_022124) cadherin related 23, isoform 1 precurso; cadherin-23; otocadherin [*Homo sapiens*] (SEQ ID NO:197)
3) gi 17366834|sp|Q9H251.CADN_HUMAN Cadherin 23 precursor (Otocadherin)[*Homo sapiens*] (SEQ ID NO:198)
4) gi 14017841|dbj|BAB47441.1|(AB058715) KIAA1812 protein [*Homo sapiens*] (SEQ ID NO:199)
5) gi 17865345|refNP_446096.1|(NM_053644) cadherin related 23 [*Rattus norvegicus*] (SEQ ID NO:200)

```
                       10        20        30        40        50        60        70
                ....|....|....|....|....|....|....|....|....|....|....|....|....|....|
NOV17a          ------------------------------------------------------------------------
gi|18576726|    MSLRAGGKTRRWPGPEQAARGGRSGGEQSPRRGEARRRCTHAHGAMGRHVATSCHVAWLLIVLISGCWGQV
gi|16507962|    ----------------------------------------------MGRHVATSCHVAWLLIVLISGCWGQV
gi|17366834|    ----------------------------------------------MGRHVATSCHVAWLLIVLISGCWGQV
gi|14017841|    ------------------------------------------------------------------------
gi|17865345|    ----------------------------------------------MRHPPVTWCAMLWLLIMLVSGSWGQV 80        90       100       110       120       130       140
                ....|....|....|....|....|....|....|....|....|....|....|....|....|....|
NOV17a          ------------------------------------------------------------------------
gi|18576726|    NRLPFFTNHFFDTYLLISEDTPVGSSVTQLLAQDMDNDPLVFGVSGEEASRFFAVEPDTGVVWLRQPLDP
gi|16507962|    NRLPFFTNHFFDTYLLISEDTPVGSSVTQLLAQDMDNDPLVFGVSGEEASRFFAVEPDTGVVWLRQPLDP
gi|17366834|    NRLPFFTNHFFDTYLLISEDTPVGSSVTQLLAQDMDNDPLVFGVSGEEASRFFAVEPDTGVVWLRQPLDP
gi|14017841|    ------------------------------------------------------------------------
gi|17865345|    NRLPFFTNHFFDTYLLISEDTPVGSSVTQLLASDMDNDPLVFGVSGEEASRFFAVEPDTGVVWLRQPLDP 150       160       170       180       190       200       210
                ....|....|....|....|....|....|....|....|....|....|....|....|....|....|
NOV17a          ------------------------------------------------------------------------
gi|18576726|    ETKSEFTVEFSVSDEQGVITRKVNIQVGDVNDNAPTFHNQPYSVRIPENTPVGTPIFIVNATDPDLGAGG
gi|16507962|    ETKSEFTVEFSVSDEQGVITRKVNIQVGDVNDNAPTFHNQPYSVRIPENTPVGTPIFIVNATDPDLGAGG
gi|17366834|    ETKSEFTVEFSVSDEQGVITRKVNIQVGDVNDNAPTFHNQPYSVRIPENTPVGTPIFIVNATDPDLGAGG
gi|14017841|    ------------------------------------------------------------------------
gi|17865345|    ETKSEFTVEFSVSDEQGVITRKVNIQVGDVNDNAPTFHNQPYSVRIPENTPVGTPIFIVNATDPDLGAGG 220       230       240       250       260       270       280
                ....|....|....|....|....|....|....|....|....|....|....|....|....|....|
NOV17a          ------------------------------------------------------------------------
gi|18576726|    SVLYSFQPPSQFFAIDSARGIVTVIRELDYRTTQAYQLTVNATDQDKTRPLSTLANLAIIITDVQDMDPI
gi|16507962|    SVLYSFQPPSQFFAIDSARGIVTVIRELDYRTTQAYQLTVNATDQDKTRPLSTLANLAIIITDVQDMDPI
gi|17366834|    SVLYSFQPPSQFFAIDSARGIVTVIRELDYRTTQAYQLTVNATDQDKTRPLSTLANLAIIITDVQDMDPI
gi|14017841|    ------------------------------------------------------------------------
gi|17865345|    SVLYSFQPPSQFFAIDSARGIVTVIRELDYRVTQAYQLTVNATDQDKTRPLSTLANLAIIITDVQDMDPI 290       300       310       320       330       340       350
                ....|....|....|....|....|....|....|....|....|....|....|....|....|....|
NOV17a          ------------------------------------------------------------------------
gi|18576726|    FINLPYSTNIYEHSPPGTTVRIITAIDQDKGRPRGIGYTIVSGNTNSIFALDYISGVLTLNGLLDRENPL
gi|16507962|    FINLPYSTNIYEHSPPGTTVRIITAIDQDKGRPRGIGYTIVSGNTNSIFALDYISGVLTLNGLLDRENPL
gi|17366834|    FINLPYSTNIYEHSPPGTTVRIITAIDQDKGRPRGIGYTIVSGNTNSIFALDYISGVLTLNGLLDRENPL
gi|14017841|    ------------------------------------------------------------------------
gi|17865345|    FINLPYSTNIYEHSPPGTTVRVITAVDQDKGRPRGIGYTIVSGNTNSIFALDYISGALTLNGLLDRENPL 360       370       380       390       400       410       420
                ....|....|....|....|....|....|....|....|....|....|....|....|....|....|
NOV17a          ------------------------------------------------------------------------
gi|18576726|    YSHGFILTVKGTEINDDRTPSDATVTTTFNILVIDINDNAPERNSSEYSVAITELAQVGFALPLFIQVVD
gi|16507962|    YSHGFILTVKGTEINDDRTPSDATVTTTFNILVIDINDNAPERNSSEYSVAITELAQVGFALPLFIQVVD
gi|17366834|    YSHGFILTVKGTEINDDRTPSDATVTTTFNILVIDINDNAPERNSSEYSVAITELAQVGFALPLFIQVVD
gi|14017841|    ------------------------------------------------------------------------
gi|17865345|    YSHGFILTVKGTEINDDRSPSDATVTTTFNILVIDINDNAPERNSSEYSVAITELAQVGFALPLFIQVVD 430       440       450       460       470       480       490
                ....|....|....|....|....|....|....|....|....|....|....|....|....|....|
NOV17a          ------------------------------------------------------------------------
gi|18576726|    KDETQGLNSMFEVYLVGNNSHHFIISPTSVQGKADIRIRVAIPLDYETVDRYDFDLFANESVPDHVGYAK
gi|16507962|    KDENLGLNSMFEVYLVGNNSHHFIISPTSVQGKADIRIRVAIPLDYETVDRYDFDLFANESVPDHVGYAK
gi|17366834|    KDENLGLNSMFEVYLVGNNSHHFIISPTSVQGKADIRIRVAIPLDYETVDRYDFDLFANESVPDHVGYAK
gi|14017841|    ---------------------------------DIRIRVAIPLDYETVDRYDFDLFANESVPDHVGYAK
gi|17865345|    KDE--GLNSMFEVYLVGNNSHHFIISPTSVQGKADIRIRVAIPLDYETVDRYDFDLFANESVPDHVGYAK
```

TABLE 17H-continued

ClustalW Analysis of NOV17a

```
                        500         510         520         530         540         550         560
                   ....|....|....|....|....|....|....|....|....|....|....|....|....|....|
NOV17a             ------------------------------------------------------------
gi|18576726|       VKITLINENDNRPIFSQPLYNISLYENVTVGTSVLTVLATDNDAATFGEVSYFFSDDPDRFSLDKDTGLI
gi|16507962|       VKITLINENDNRPIFSQPLYNISLYENVTVGTSVLTVLATDNDAGTFGEVSYFFSDDPDRFSLDKDTGLI
gi|17366834|       VKITLINENDNRPIFSQPLYNISLYENVTVGTSVLTVLATDNDAGTFGEVSYFFSDDPDRFSLDKDTGLI
gi|14017841|       VKITLINENDNRPIFSQPLYNISLYENVTVGTSVLTVLATDNDAGTFGEVNYFFSDDPDRFSLDKDTGLI
gi|17865345|       VKITLINENDNRPIFSQPLYNVSLYENITVGTSVLTVLATDNDVGTFGEVNYFFSDDPDRFSLDKDTGLI 570         580         590         600         610         620         630
                   ....|....|....|....|....|....|....|....|....|....|....|....|....|....|
NOV17a             ------------------------------------------------------------
gi|18576726|       MLIARLDYELIQRFTLTIIARDGGGEETTGRVRINVLDVNDNVPTFQKDAYVGALRENEPSVTQLVRLRA
gi|16507962|       MLIARLDYELIQRFTLTIIARDGGGEETTGRVRINVLDVNDNVPTFQKDAYVGALRENEPSVTQLVRLRA
gi|17366834|       MLIARLDYELIQRFTLTIIARDGGGEETTGRVRINVLDVNDNVPTFQKDAYVGALRENEPSVTQLVRLRA
gi|14017841|       MLIARLDYELIQRFTLTIIARDGGGEETTGRVRINVLDVNDNVPTFQKDAYVGALRENEPSVTQLVRLRA
gi|17865345|       MLIARLDYELIQRFTLTVIARDGGGEETTGRVRINVLDVNDNVPTFQKDAYVGALRENEPSVTQLVRLRA 640         650         660         670         680         690         700
                   ....|....|....|....|....|....|....|....|....|....|....|....|....|....|
NOV17a             ------------------------------------------------------MAMDAGNPPLNSTV
gi|18576726|       TDEDSPPNNQITUSIVSASAFGSYFDISLYEGYGVISVSRPLDYEQISNGLIYLTVMAMDAGNPPLNSTV
gi|16507962|       TDEDSPPNNQITUSIVSASAFGSYFDISLYEGYGVISVSRPLDYEQISNGLIYLTVMAMDAGNPPLNSTV
gi|17366834|       TDEDSPPNNQITUSIVSASAFGSYFDISLYEGYGVISVSRPLDYEQISNGLIYLTVMAMDAGNPPLNSTV
gi|14017841|       TDEDSPPNNQITUSIVSASAFGSYFDISLYEGYGVISVSRPLDYEQISNGLIYLTVMAMDAGNPPLNSTV
gi|17865345|       TDEDSPPNNLITUSIVMASAFGSYFDISVYEGYGVISVSRPLDYEQIPNGLIYLTVMAKDAGNPPLYSTV 710         720         730         740         750         760         770
                   ....|....|....|....|....|....|....|....|....|....|....|....|....|....|
NOV17a             PVTIEVFDENDNPPTFSKPAYFVSVVENIMAGATVLFLNATDLDRSREYGQESIITSLEGSTQFRINARS
gi|18576726|       PVTIEVFDENDNPPTFSKPAYFVSVVENIMAGATVLFLNATDLDRSREYGQESIITSLEGSTQFRINARS
gi|16507962|       PVTIEVFDENDNPPTFSKPAYFVSVVENIMAGATVLFLNATDLDRSREYGQESIITSLEGSTQFRINARS
gi|17366834|       PVTIEVFDENDNPPTFSKPAYFVSVVENIMAGATVLFLNATDLDRSREYGQESIITSLEGSTQFRINARS
gi|14017841|       PVTIEVFDENDNPPTFSKPAYFVSVVENIMAGATVLFLNATDLDRSREYGQESIITSLEGSTQFRINARS
gi|17865345|       PVTIEVFDENDNPPTFSKPAYFVSVVENIMAGATVLFLNATDLDRSREYGQESIITSLEGSRQFRINARS 780         790         800         810         820         830         840
                   ....|....|....|....|....|....|....|....|....|....|....|....|....|....|
NOV17a             GEITTTSLLDRETKSEYILIVRAVDGGVGENQKTGIATVNITLLDINDNHPTWKDAPYYINLVEMTPFDS
gi|18576726|       GEITTTSLLDRETKSEYILIVRAVDGGVGENQKTGIATVNITLLDINDNHPTWKDAPYYINLVEMTPFDS
gi|16507962|       GEITTTSLLDRETKSEYILIVRAVDGGVGENQKTGIATVNITLLDINDNHPTWKDAPYYINLVEMTPFDS
gi|17366834|       GEITTTSLLDRETKSEYILIVRAVDGGVGENQKTGIATVNITLLDINDNHPTWKDAPYYINLVEMTPFDS
gi|14017841|       GEITTTSLLDRETKSEYILIVRAVDGGVGENQKTGIATVNITLLDINDNHPTWKDAPYYINLVEMTPFDS
gi|17865345|       GEITTTSLLDRETKAEYILIVRAVDGGVGENQKTGIATVNVTLLDINDNHPTWKDAPYYINLVEMTPFDS 850         860         870         880         890         900         910
                   ....|....|....|....|....|....|....|....|....|....|....|....|....|....|
NOV17a             DVTTVVAVDPDLGENGTLVYSIQPPNKFYSLNSTTGKIRTTHAMLDRENPDPHEAELMRKIVVSVTDCGR
gi|18576726|       DVTTVVAVDPDLGENGTLVYSIQPPNKFYSLNSTTGKIRTTHAMLDRENPDPHEAELMRKIVVSVTDCGR
gi|16507962|       DVTTVVAVDPDLGENGTLVYSIQPPNKFYSLNSTTGKIRTTHAMLDRENPDPHEAELMRKIVVSVTDCGR
gi|17366834|       DVTTVVAVDPDLGENGTLVYSIQPPNKFYSLNSTTGKIRTTHAMLDRENPDPHEAELMRKIVVSVTDCGR
gi|14017841|       DVTTVVAVDPDLGENGTLVYSIQPPNKFYSLNSTTGKIRTTHAMLDRENPDPHEAELMRKIVVSVTDCGR
gi|17865345|       DVTTVVAVDPDLGKNGTLVYSIQPPNKFYSLNSTTGKIRTTHVMLDRENPDPVEAELMRKIIVSVTDCGR 920         930         940         950         960         970         980
                   ....|....|....|....|....|....|....|....|....|....|....|....|....|....|
NOV17a             PPLKATSSATVFVNLLDINDNDPTFQNLPFVAEVLEGIPAGVSIYQVVAIDLDEGLNGLVSYRMPVGMPR
gi|18576726|       PPLKATSSATVFVNLLDINDNDPTFQNLPFVAEVLEGIPAGVSIYQVVAIDLDEGLNGLVSYRMPVGMPR
gi|16507962|       PPLKATSSATVFVNLLDINDNDPTFQNLPFVAEVLEGIPAGVSIYQVVAIDLDEGLNGLVSYRMPVGMPR
gi|17366834|       PPLKATSSATVFVNLLDINDNDPTFQNLPFVAEVLEGIPAGVSIYQVVAIDLDEGLNGLVSYRMPVGMPR
gi|14017841|       PPLKATSSATVFVNLLDINDNDPTFQNLPFVAEVLEGIPAGVSIYQVVAIDLDEGLNGLVSYRMPVGMPR
gi|17865345|       PPLKATSSATVFVNLLDINDNDPTFQNLPFVAEVLEGTPAGVSVYQVVAIDLDEGLNGLVSYRMQVGMPR 990        1000        1010        1020        1030        1040        1050
                   ....|....|....|....|....|....|....|....|....|....|....|....|....|....|
NOV17a             MDFLINSSSGVVVTTTELDRERIAEYQLRVVASDAGTPTKSSTSTLTIHVLDVNDETPTFFPAVYNVSVS
gi|18576726|       MDFLINSSSGVVVTTTELDRERIAEYQLRVVASDAGTPTKSSTSTLTIHVLDVNDETPTFFPAVYNVSVS
gi|16507962|       MDFLINSSSGVVVTTTELDRERIAEYQLRVVASDAGTPTKSSTSTLTIHVLDVNDETPTFFPAVYNVSVS
gi|17366834|       MDFLINSSSGVVVTTTELDRERIAEYQLRVVASDAGTPTKSSTSTLTIHVLDVNDETPTFFPAVYNVSVS
gi|14017841|       MDFLINSSSGVVVTTTELDRERIAEYQLRVVASDAGTPTKSSTSTLTIHVLDVNDETPTFFPAVYNVSVS
gi|17865345|       MDFVINSSSGVVTTTAELDRERIAEYQLRVVASDAGTPTKSSTSTLTIRVLDVNDETPTFFPAVYNVSVS 1060        1070        1080        1090        1100        1110        1120
                   ....|....|....|....|....|....|....|....|....|....|....|....|....|....|
NOV17a             EDVPREFRVVWLNCTDNDVGLNAELSYFITG---------------------------------------
gi|18576726|       EDVPREFRVVWLNCTDNDVGLNAELSYFITGGNVDGKFSVGYRDAVVRTVVGLDRETTAAYMLILEAIDN
gi|16507962|       EDVPREFRVVWLNCTDNDVGLNAELSYFITGGNVDGKFSVGYRDAVVRTVVGLDRETTAAYMLILEAIDN
gi|17366834|       EDVPREFRVVWLNCTDNDVGLNAELSYFITGGNVDGKFSVGYRDAVVRTVVGLDRETTAAYMLILEAIDN
gi|14017841|       EDVPREFRVVWLNCTDNDVGLNAELSYFITGGNVDGKFSVGYRDAVVRTVVGLDRETTAAYMLILEAIDN
gi|17865345|       EDVPREFRVVWLNCTDNDVGLNAELSYFITAGNVDGKFSVGYRDAVVRTVVGLDRETTAAYTLVLEAIDN
```

TABLE 17H-continued

ClustalW Analysis of NOV17a

```
                1130      1140      1150      1160      1170      1180      1190
                ....|....|....|....|....|....|....|....|....|....|....|....|....|
NOV17a          ----------------------------------------------------------------
gi|18576726     GPVGKRHTGTATVFVTVLDVNDNRPIFLQSSYEASVPEDIPEGHSILQLKATDADEGEFGRVWYRILHCN
gi|16507962     GPVGKRHTGTATVFVTVLDVNDNRPIFLQSSYEASVPEDIPEGHSILQLKATDADEGEFGRVWYRILHCN
gi|17366834     GPVGKRHTGTATVFVTVLDVNDNRPIFLQSSYEASVPEDIPEGHSILQLKATDADEGEFGRVWYRILHCN
gi|14017841     GPVGKRHTGTATVFVTVLDVNDNRPIFLQSSYEASVPEDIPEGHSILQ------EEQL-----------A
gi|17865345     VPVGKRRTGTATVFVTVLDVNDNRPIFLQSSYEASVPEDIPEGHSIVQLKATDADEGEFGRVWYRILHCN 1200      1210      1220      1230      1240      1250      1260
                ....|....|....|....|....|....|....|....|....|....|....|....|....|
NOV17a          ------------AAPASAH---------------------------------------------------
gi|18576726     HCNNFRIHVSNGLLMRGPRPLDRERNSSHVLIVEAYNHDLGPMRSSVRVIVYVEDINDEAPVFTQQQYSR
gi|16507962     HCNNFRIHVSNGLLMRGPRPLDRERNSSHVLIVEAYNHDLGPMRSSVRVIVYVEDINDEAPVFTQQQYSR
gi|17366834     HCNNFRIHVSNGLLMRGPRPLDRERNSSHVLIVEAYNHDLGPMRSSVRVIVYVEDINDEAPVFTQQQYSR
gi|14017841     SP--C---IS-----PAEPRRAFQSS--------------------------------------------
gi|17865345     HCNNFRLHVSSGLLVRGPRPLDRERNSSHVLMAEAYNHDLGPMRSSVRVIVYVEDVNDEAPVFTQQQYNR 1270      1280      1290      1300      1310      1320      1330
                ....|....|....|....|....|....|....|....|....|....|....|....|....|
NOV17a          ----------------------------------------------------------------
gi|18576726     LGLRETAGIGTSVIVVQATDRDSGDGGLVNYRILSGAEGKFEIDESTGLIITVNYLDYETKTSYMMNVSA
gi|16507962     LGLRETAGIGTSVIVVQATDRDSGDGGLVNYRILSGAEGKFEIDESTGLIITVNYLDYETKTSYMMNVSA
gi|17366834     LGLRETAGIGTSVIVVQATDRDSGDGGLVNYRILSGAEGKFEIDESTGLIITVNYLDYETKTSYMMNVSA
gi|14017841     -GEKETS---------------------------------------------------------------
gi|17865345     LGLRETAGIGTSVIVVAATDRDSGDGGLVNYRILSGAEGKFEIDESTGLIVTVDYLDYETKTSYMMNVSA 1340      1350      1360      1370      1380      1390      1400
                ....|....|....|....|....|....|....|....|....|....|....|....|....|
NOV17a          --------------------------------------LCRPPG--------------ALPP
gi|18576726     TDQAPPFNQGFCSVYITLLNELDEAVQFSNASYEAAILENLALGTEIVRVQAYSIDNINQITYRFNAYTS
gi|16507962     TDQAPPFNQGFCSVYITLLNELDEAVQFSNASYEAAILENLALGTEIVRVQAYSIDNINQITYRFNAYTS
gi|17366834     TDQAPPFNQGFCSVYITLLNELDEAVQFSNASYEAAILENLALGTEIVRVQAYSIDNINQITYRFDAYTS
gi|14017841     ----------------------QFP---------G----KELRREPGPSKA--QNRA----AETE
gi|17865345     TDGAPPFNQGFCSVYITLLNELDEAVQFSNASYEAVIMENLALGTEIVRVQAYSIDNINQITYRFDAYTS 1410      1420      1430      1440      1450      1460      1470
                ....|....|....|....|....|....|....|....|....|....|....|....|....|
NOV17a          PLPDG-----------------------------------------------------------------
gi|18576726     TQAKALFKIDAITGVITVQGLVDREKGDFYTLTVVADDGGPKVDSTVQVYITVLDENDNSPRFDFTSDSA
gi|16507962     TQAKALFKIDAITGVITVQGLVDREKGDFYTLTVVADDGGPKVDSTVQVYITVLDENDNSPRFDFTSDSA
gi|17366834     TQAKALFKIDAITGVITVQGLVDREKGDFYTLTVVADDGGPKVDSTVQVYITVLDENDNSPRFDFTSDSA
gi|14017841     PLAEAP----------------------L-----------------------------------------
gi|17865345     AQAKALFKIDAITGVITVRGLVDREKGDFYTLTVVADDGGPKVDSTVKVYVTVLDENDNSPRFDFTSDSA 1480      1490      1500      1510      1520      1530      1540
                ....|....|....|....|....|....|....|....|....|....|....|....|....|
NOV17a          ----------------------------------------------------------------
gi|18576726     VSIPEDCPVGQRVATVKAWDPDAGSNGQVVFSLASGNIAGAFEIVTTNDSIGEVFVARPLDREELDHYIL
gi|16507962     VSIPEDCPVGQRVATVKAWDPDAGSNGQVVFSLASGNIAGAFEIVTTNDSIGEVFVARPLDREELDHYIL
gi|17366834     VSIPEDCPVGQRVATVKAWDPDAGSNGQVVFSLASGNIAGAFEIVTTNDSIGEVFVARPLDREELDHYIL
gi|14017841     ------------------------------LGS-------------------------------------
gi|17865345     LSVPEDCPVGQRVATVKARDPDAGSNGQVVFSLASGNIAGAFEIITSNDSIGEVFVAKPLDREELDHYIL 1550      1560      1570      1580      1590      1600      1610
                ....|....|....|....|....|....|....|....|....|....|....|....|....|
NOV17a          ---QPD----------------------------------------------------------------
gi|18576726     QVVASDRGTPPRKKDHILQVTILDINDNPPVIESPFGYNVSVNDNVGGGIAVVQVRATDRDIGINSVLSY
gi|16507962     QVVASDRGTPPRKKDHILQVTILDINDNPPVIESPFGYNVSVNDNVGGGIAVVQVRATDRDIGINSVLSY
gi|17366834     QVVASDRGTPPRKKDHILQVTILDINDNPPVIESPFGYNVSVNDNVGGGIAVVQVRATDRDIGINSVLSY
gi|14017841     KQAQEERAPLPRE-----QAQQLQG---------------S-EGEKGGP--------------------
gi|17865345     KIVASDRGTPPRKKDHILQVTILDVNDNPPVIESPFGYNVSVNDNVGGGIAVVQVRATDRDIGINSVLSY 1620      1630      1640      1650      1660      1670      1680
                ....|....|....|....|....|....|....|....|....|....|....|....|....|
NOV17a          ----------------------------------------------------------------
gi|18576726     YITEGNKDMAFRMDRISGEIATRPAPPDRERQSFYHLVAIVEDEGTPTLSATTHVYVTIVDENDNAEMFQ
gi|16507962     YITEGNKDMAFRMDRISGEIATRPAPPDRERQSFYHLVAIVEDEGTPTLSATTHVYVTIVDENDNAEMFQ
gi|17366834     YITEGNKDMTFRMDRISGEIATRPAPPDRERQSFYHLVAIVEDEGTPTLSATTHVYVTIVDENDNAEMFQ
gi|14017841     ----------------------------------------------------------------
gi|17865345     YITEGNKDMTFRMDRISGEIATRPAPPDREROFYHLVVTVEDEGTPTLSATTHVYVTIVDENDNAEMFQ
```

TABLE 17H-continued

ClustalW Analysis of NOV17a

```
                  1690       1700       1710       1720       1730       1740       1750
              ....|....|....|....|....|....|....|....|....|....|....|....|....|....|
NOV17a        ----------------------------------------------------------------------
gi|18576726|  QPHYEVLDEGPDTLNTSLITIQALDLDEGPNGTVTYAIVAGNIVNTFRIDRHMGVITAAKELDYEISHG
gi|16507962|  QPHYEVLDEGPDTLNTSLITIQALDLDEGPNGTVTYAIVAGNIVNTFRIDRHMGVITAAKELDYEISHG
gi|17366834|  QPHYEVLDEGPDTLNTSLITIQALDLDEGPNGTVTYAIVAGNIVNTFRIDRHMGVITAAKELDYEISHG
gi|14017841|  ----------------------------------------------------------------------
gi|17865345|  QPHYEVVLDEGPDTVNTSLITVQALDLDEGPNGTVTYAIVAGNIVNTFRINRRTGVITAAKELDYEISHG 1760       1770       1780       1790       1800       1810       1820
              ....|....|....|....|....|....|....|....|....|....|....|....|....|....|
NOV17a        ----------------------------------------------------------------------
gi|18576726|  RYTLIVTATDQCPILSHRLTSTTTVLVNVNDINDNVPTFPRDYEGPFEVTEGQPGPRVWTFLAHDRDSGP
gi|16507962|  RYTLIVTATDQCPILSHRLTSTTTVLVNVNDINDNVPTFPRDYEGPFEVTEGQPGPRVWTFLAHDRDSGP
gi|17366834|  RYTLIVTATDQCPILSHRLTSTTTVLVNVNDINDNVPTFPRDYEGPFEVTEGQPGPRVWTFLAHDRDSGP
gi|14017841|  ----------------------------------------------------------------------
gi|17865345|  RYTLIVTATDQCPILSHRLTSTTTVLVNVNDINDNVPTFPRDYEGPFEVTEGQPGPRVWTFLAHDRDSGP 1830       1840       1850       1860       1870       1880       1890
              ....|....|....|....|....|....|....|....|....|....|....|....|....|....|
NOV17a        ----------------------------------------------------------------------
gi|18576726|  NGQVEYSIMDGDPLGEFVISPVEGVLRVRKDVELDRETIAFYNLTICARDRGMPPLSSTMLVGIRVLDIN
gi|16507962|  NGQVEYSIMDGDPLGEFVISPVEGVLRVRKDVELDRETIAFYNLTICARDRGMPPLSSTMLVGIRVLDIN
gi|17366834|  NGQVEYSIMDGDPLGEFVISPVEGVLRVRKDVELDRETIAFYNLTICARDRGMPPLSSTMLVGIRVLDIN
gi|14017841|  ----------------------------------------------------------------------
gi|17865345|  NGQVEYSVVDGDPLGEFVISPVEGVLRVRKDVELDRETIAFYNLTICARDRGVPPLSSTMLVGIRVLDIN 1900       1910       1920       1930       1940       1950       1960
              ....|....|....|....|....|....|....|....|....|....|....|....|....|....|
NOV17a        ----------------------------------------------------------------------
gi|18576726|  DNDPVLLNLPMNITISENSPVSSFVAHVLASDADSGCNARLTFNITAGNRERAFFINATTGIVTVNRPLD
gi|16507962|  DNDPVLLNLPMNITISENSPVSSFVAHVLASDADSGCNARLTFNITAGNRERAFFINATTGIVTVNRPLD
gi|17366834|  DNDPVLLNLPMNITISENSPVSSFVAHVLASDADSGCNARLTFNITAGNRERAFFINATTGIVTVNRPLD
gi|14017841|  ----------------------------------------------------------------------
gi|17865345|  DNDPVLLNLPMNITISENSPVSSFVAHVLASDADSGCNALLTFNITAGNRERAFFINATTGIVTVNRPLD 1970       1980       1990       2000       2010       2020       2030
              ....|....|....|....|....|....|....|....|....|....|....|....|....|....|
NOV17a        ----------------------------------------------------------------------
gi|18576726|  RERIPEYKLTISVKDNPPNPRIARRDYDLLLIFLSDENDNHPLFTKSTYQAEVMENSPAGTPLTVLNGPI
gi|16507962|  RERIPEYKLTISVKDNPPNPRIARRDYDLLLIFLSDENDNHPLFTKSTYQAEVMENSPAGTPLTVLNGPI
gi|17366834|  RERIPEYKLTISVKDNPPNPRIARRDYDLLLIFLSDENDNHPLFTKSTYQAEVMENSPAGTPLTVLNGPI
gi|14017841|  ----------------------------------------------------------------------
gi|17865345|  RERIPEYRLTVSVKDNPPNPRIARRDPDLLLVSLADENDNHPLFTEGTYQAEVMENSPAGTPLTVLNGPI 2040       2050       2060       2070       2080       2090       2100
              ....|....|....|....|....|....|....|....|....|....|....|....|....|....|
NOV17a        ----------------------------------------------------------------------
gi|18576726|  LALDALQDIYAVVTYQLLGAQSGLFDINSSTGVVTVRSGVIIDREAFSPPILELLLLAEDIGLINSTARL
gi|16507962|  LALDALQDIYAVVTYQLLGAQSGLFDINSSTGVVTVRSGVIIDREAFSPPILELLLLAEDIGLINSTARL
gi|17366834|  LALDALQDIYAVVTYQLLGAQSGLFDINSSTGVVTVRSGVIIDREAFSPPILELLLLAEDIGLINSTARL
gi|14017841|  ----------------------------------------------------------------------
gi|17865345|  LALDALQDIYAVVTYQLLGAQSGLFDINSSTGVVTVRSGVIIDREAFSPPILELLLLAEDIGLINSTARL 2110       2120       2130       2140       2150       2160       2170
              ....|....|....|....|....|....|....|....|....|....|....|....|....|....|
NOV17a        ----------------------------------------------------------------------
gi|18576726|  LITILDDNDNRPTFSPATLIVHLLENCPPGFSVLQVTATDEDSGLNGELVYRIEAGAQDRFLIHLVTGVI
gi|16507962|  LITILDDNDNRPTFSPATLIVHLLENCPPGFSVLQVTATDEDSGLNGELVYRIEAGAQDRFLIHLVTGVI
gi|17366834|  LITILDDNDNRPTFSPATLIVHLLENCPPGFSVLQVTATDEDSGLNGELVYRIEAGAQDRFLIHLVTGVI
gi|14017841|  ----------------------------------------------------------------------
gi|17865345|  FITILDDNDNWPTFSPPAYTVHLLENCPPGFSVLQITATDEDSGLNGELVYRIEAGAQDRFLIHPVTGVI 2180       2190       2200       2210       2220       2230       2240
              ....|....|....|....|....|....|....|....|....|....|....|....|....|....|
NOV17a        ----------------------------------------------------------------------
gi|18576726|  RVCNATIDREEQESYRLTVVATDRGTVPLSGTAIVTILIDDINDSRPEFINPIQTVSVLESAEPGTVIAN
gi|16507962|  RVCNATIDREEQESYRLTVVATDRGTVPLSGTAIVTILIDDINDSRPEFINPIQTVSVLESAEPGTVIAN
gi|17366834|  RVCNATIDREEQESYRLTVVATDRGTVPLSGTAIVTILIDDINDSRPEFINPIQTVSVLESAEPGTVIAN
gi|14017841|  ----------------------------------------------------------------------
gi|17865345|  RVCNATIDREEQESYRLTVVATDRGTVPLSGTAIVTILIDDINDSRPEFINPIQTVSVLESTEPGTVIAN 2250       2260       2270       2280       2290       2300       2310
              ....|....|....|....|....|....|....|....|....|....|....|....|....|....|
NOV17a        ----------------------------------------------------------------------
gi|18576726|  ITAIDHDINPKLEYHIVGIVAKDDTDRLVPNQEDAFAVNINTGSVMVKSPMNRELVATYEVTLSVIDNAS
gi|16507962|  ITAIDHDINPKLEYHIVGIVAKDDTDRLVPNQEDAFAVNINTGSVMVKSPMNRELVATYEVTLSVIDNAS
gi|17366834|  ITAIDHDINPKLEYHIVGIVAKDDTDRLVPNQEDAFAVNINTGSVMVKSPMNRELVATYEVTLSVIDNAS
gi|14017841|  ----------------------------------------------------------------------
gi|17865345|  VTAIDLDINPKLEYHIISIVAKDDTDRLVPDQEDAFAVNINTGSVIVKSPLNRELVATYEVTLSVIDNAS
```

TABLE 17H-continued

ClustalW Analysis of NOV17a

```
                2320      2330      2340      2350      2360      2370      2380
             ....|....|....|....|....|....|....|....|....|....|....|....|....|
NOV17a       ------------------------------------------------------------------
gi|18576726  DLPERSVSVPNAKLTVNVLDVNDNTPQFKPFGITYYMERILEGATPGTTLIAVAAVDPDKGLNGLVTYTL
gi|16507962  DLPERSVSVPNAKLTVNVLDVNDNTPQFKPFGITYYMERILEGATPGTTLIAVAAVDPDKGLNGLVTYTL
gi|17366834  DLPERSVSVPNAKLTVNVLDVNDNTPQFKPFGITYYMERILEGATPGTTLIAVAAVDPDKGLNGLVTYTL
gi|14017841  ------------------------------------------------------------------
gi|17865345  DLPERSVSVPNAKLTVNILDVNDNTPQFKPFGITYYTERVLEGATPGTTLIAVAAVDPDKGLNGLITYTL 2390      2400      2410      2420      2430      2440      2450
             ....|....|....|....|....|....|....|....|....|....|....|....|....|
NOV17a       ------------------------------------------------------------------
gi|18576726  LDLYPPGYVQLEDSSAGKVIANRTVDYEEVHWLNFTVRASDNGSPPRAAEIPVYLEIVDINDNNPIFDQP
gi|16507962  LDLYPPGYVQLEDSSAGKVIANRTVDYEEVHWLNFTVRASDNGSPPRAAEIPVYLEIVDINDNNPIFDQP
gi|17366834  LDLYPPGYVQLEDSSAGKVIANRTVDYEEVHWLNFTVRASDNGSPPRAAEIPVYLEIVDINDNNPIFDQP
gi|14017841  ------------------------------------------------------------------
gi|17865345  LDLFPPGYVQLEDSSAGKVIANRTVDYEEVHWLNFTVRASDNGSPPRAAEIPVYLEIVDINDNNPIFDQL 2460      2470      2480      2490      2500      2510      2520
             ....|....|....|....|....|....|....|....|....|....|....|....|....|
NOV17a       ------------------------------------------------------------------
gi|18576726  SYQEAVFEDVPVGTIILTVTATDADSGNFALIEYSLGDGESKFAINPITGDIYVLSSLDREKKDHYILTA
gi|16507962  SYQEAVFEDVPVGTIILTVTATDADSGNFALIEYSLGDGESKFAINPITGDIYVLSSLDREKKDHYILTA
gi|17366834  SYQEAVFEDVPVGTIILTVTATDADSGNFALIEYSLGDGESKFAINPITGDIYVLSSLDREKKDHYILTA
gi|14017841  ------------------------------------------------------------------
gi|17865345  SYQEAVFEDVAVGTVILRVTATDADSGNFALIEYSLVDGEGKFAINPNTGDIYVLSSLDREKKDHYILTA 2530      2540      2550      2560      2570      2580      2590
             ....|....|....|....|....|....|....|....|....|....|....|....|....|
NOV17a       ------------------------------------------------------------------
gi|18576726  LAKDNPGDVASNRRENSVQVVIQVLDVNDCRPQFSKPQFSTSVYENEPAGTSVITMMATDQDEGPNGELT
gi|16507962  LAKDNPGDVASNRRENSVQVVIQVLDVNDCRPQFSKPQFSTSVYENEPAGTSVITMMATDQDEGPNGELT
gi|17366834  LAKDNPGDVASNRRENSVQVVIQVLDVNDCRPQFSKPQFSTSVYENEPAGTSVITMMATDQDEGPNGELT
gi|14017841  ------------------------------------------------------------------
gi|17865345  LAKDNPGDVASNRRENSVQVVIRVLDVNDCRPQFSKPQFSTSVYENEPAGTSVITMEATDQDEGSNGQLT 2600      2610      2620      2630      2640      2650      2660
             ....|....|....|....|....|....|....|....|....|....|....|....|....|
NOV17a       ------------------------------------------------------------------
gi|18576726  YSLEGPGYEAFHVDMDSGLVTIQRPLQSYEKFSLTVVATDGGEPPLWGTTMLLVEVIDVNDNRPVFVRPP
gi|16507962  YSLEGPGYEAFHVDMDSGLVTIQRPLQSYEKFSLTVVATDGGEPPLWGTTMLLVEVIDVNDNRPVFVRPP
gi|17366834  YSLEGPGYEAFHVDMDSGLVTIQRPLQSYEKFSLTVVATDGGEPPLWGTTMLLVEVIDVNDNRPVFVRPP
gi|14017841  ------------------------------------------------------------------
gi|17865345  YSLEGPGMEAFSVDMDSGLVTIQRPLQSYERFNLTVVATDGGEPPLWGTTMLLVEVIDVNDNRPVFVRPP 2670      2680      2690      2700      2710      2720      2730
             ....|....|....|....|....|....|....|....|....|....|....|....|....|
NOV17a       ------------------------------------------------------------------
gi|18576726  NGTILHIREEIPLRSNVYEVYATDKDEGLNCAVRYSFLKIAGNRDWEFFIDPISGLIQTAQRLDRESQA
gi|16507962  NGTILHIREEIPLRSNVYEVYATDKDEGLNCAVRYSFLKIAGNRDWEFFIDPISGLIQTAQRLDRESQA
gi|17366834  NGTILHIREEIPLRSNVYEVYATDKDEGLNCAVRYSFLKIAGNRDWEFFIDPISGLIQTAQRLDRESQA
gi|14017841  ------------------------------------------------------------------
gi|17865345  NGTILHIKEEIPLRSNVYEVYATDKDEGLNCAVRYSFLKSTGNRDWEYFIDPISGLIQTAQRLDREKQA 2740      2750      2760      2770      2780      2790      2800
             ....|....|....|....|....|....|....|....|....|....|....|....|....|
NOV17a       ------------------------------------------------------------------
gi|18576726  VYSLILVASDLGQPVPYETMQPLQVALEDIDDNEPLFVRPPKGSPQYQLLTVPEHSPRGTLVGNVTGAVD
gi|16507962  VYSLILVASDLGQPVPYETMQPLQVALEDIDDNEPLFVRPPKGSPQYQLLTVPEHSPRGTLVGNVTGAVD
gi|17366834  VYSLILVASDLGQPVPYETMQPLQVALEDIDDNEPLFVRPPKGSPQYQLLTVPEHSPRGTLVGNVTGAVD
gi|14017841  ------------------------------------------------------------------
gi|17865345  VYSLILVASDLGQPVPYETMQPLQVALEDIDDNEPLFVRPPKGSPQYQLLTVPEHSPRGTLVGNVTGAVD 2810      2820      2830      2840      2850      2860      2870
             ....|....|....|....|....|....|....|....|....|....|....|....|....|
NOV17a       ------------------------------------------------------------------
gi|18576726  ADEGPNAIVYYFIAAGNEEKNFHLQPDGCLLVLRDLDREREAIFSFIVKASSNRSWTPPRGPSETLDLVA
gi|16507962  ADEGPNAIVYYFIAAGNEEKNFHLQPDGCLLVLRDLDREREAIFSFIVKASSNRSWTPPRGPSETLDLVA
gi|17366834  ADEGPNAIVYYFIAAGNEEKNFHLQPDGCLLVLRDLDREREAIFSFIVKASSNRSWTPPRGPSETLDLVA
gi|14017841  ------------------------------------------------------------------
gi|17865345  ADEGPNAIVYYFIAAGNEEKNFHLQPDGRLLVLRDLDRETEAIFSFIVKASSNRSWTPPRGPSEALDLVA
```

TABLE 17H-continued

ClustalW Analysis of NOV17a

```
                2880       2890       2900       2910       2920       2930       2940
            ....|....|....|....|....|....|....|....|....|....|....|....|....|....|
NOV17a      ----------------------------------------------------------------------
gi|18576726 DLTLQEVRVVLEDINDQPPRFTKAEYTAGVATDAKVGSELIQVLALDADIGNNSLVFYSILAIHYFRALA
gi|16507962 DLTLQEVRVVLEDINDQPPRFTKAEYTAGVATDAKVGSELIQVLALDADIGNNSLVFYSILAIHYFRALA
gi|17366834 DLTLQEVRVVLEDINDQPPRFTKAEYTAGVATDAKVGSELIQVLALDADIGNNSLVFYSILAIHYFRALA
gi|14017841 ---------------------------------------------------------------------
gi|17865345 DLTLQEVRVVLEDINDQPPRFTKAEYTAGVATDAKVGSELIQVLALDADIGNNSLVFYGILAIHYFRALA 2950       2960       2970       2980       2990       3000       3010
            ....|....|....|....|....|....|....|....|....|....|....|....|....|....|
NOV17a      ----------------------------------------------------------------------
gi|18576726 NDSEDVGQVFTMGSMDGILRTFDLFMAYSPGYFVVDIVARDLAGHNDTAIIGIYILRDDQRVKIVINEIP
gi|16507962 NDSEDVGQVFTMGSMDGILRTFDLFMAYSPGYFVVDIVARDLAGHNDTAIIGIYILRDDQRVKIVINEIP
gi|17366834 NDSEDVGQVFTMGSMDGILRTFDLFMAYSPGYFVVDIVARDLAGHNDTAIIGIYILRDDQRVKIVINEIP
gi|14017841 ----------------------------------------------------------------------
gi|17865345 NDSEDVGQVFTMGSYDGILRTFDLFMAYSPGYFVVDIVARDLAGHNDTAIIGIYILRDDQRVKIVINEIP 3020       3030       3040       3050       3060       3070       3080
            ....|....|....|....|....|....|....|....|....|....|....|....|....|....|
NOV17a      ----------------------------------------------------------------------
gi|18576726 DRVRGFEEEFIHLLSNITGAIVNTDNVQFHVDKKGRVNFAQTELLIHVVNRDTNRILDVDRVIQMIDENK
gi|16507962 DRVRGFEEEFIHLLSNITGAIVNTDNVQFHVDKKGRVNFAQTELLIHVVNRDTNRILDVDRVIQMIDENK
gi|17366834 DRVRGFEEEFIHLLSNITGAIVNTDNVQFHVDKKGRVNFAQTELLIHVVNRDTNRILDVDRVIQMIDENK
gi|14017841 ----------------------------------------------------------------------
gi|17865345 DRVRGFEEEFIRLLSNITGAIVNTDNVQFHVDMKGRVNFAQTELLIHVVNRDTNRILDVDRVIQMIDENK 3090       3100       3110       3120       3130       3140       3150
            ....|....|....|....|....|....|....|....|....|....|....|....|....|....|
NOV17a      ----------------------------------------------------------------------
gi|18576726 EQLRNLFRNYNVLDVQPAISVRLPDDMSALQMAIIVLAILLFLAAMLFVLMNWYYRTVHKRKLKAIVAGS
gi|16507962 EQLRNLFRNYNVLDVQPAISVRLPDDMSALQMAIIVLAILLFLAAMLFVLMNWYYRTVHKRKLKAIVAGS
gi|17366834 EQLRNLFRNYNVLDVQPAISVRLPDDMSALQMAIIVLAILLFLAAMLFVLMNWYYRTVHKRKLKAIVAGS
gi|14017841 ----------------------------------------------------------------------
gi|17865345 EQLRNLFRNYNVLDVQPAISVQLPDDMSALQMAIIVLAILLFLAAMLFVLMNWYYRTIHKRKLKAIVAGS 3160       3170       3180       3190       3200       3210       3220
            ....|....|....|....|....|....|....|....|....|....|....|....|....|....|
NOV17a      ----------------------------------------------------------------------
gi|18576726 AGNRGFIDIMDMPNINKYSFDGANPVWLDPFCHNLELAAQAEHEDDLPENLSEIADLWNSPTRTHGTFGR
gi|16507962 AGNRGFIDIMDMPNINKYSFDGANPVWLDPFCHNLELAAQAEHEDDLPENLSEIADLWNSPTRTQGTFGR
gi|17366834 AGNRGFIDIMDMPNINKYSFDGANPVWLDPFCHNLELAAQAEHEDDLPENLSEIADLWNSPTRTHGTFGR
gi|14017841 ----------------------------------------------------------------------
gi|17865345 AGNRGFIDIMDMPNINKYSFDGANPVWLDPFCHNLELAAQAEHEDDLPENLSEIADLWNSPTRTHGTFGR 3230       3240       3250       3260       3270       3280       3290
            ....|....|....|....|....|....|....|....|....|....|....|....|....|....|
NOV17a      ----------------------------------------------------------------------
gi|18576726 EPAAVKPEDDRYLRAAIQEYDNIAKLGQIIREGPIKGSLLKVVLEDYLRLKKLFAQRMVQKASSCHSSIS
gi|16507962 EPAAVKPEDDRYLRAAIQEYDNIAKLGQIIREGPIKGSLLKVVLEDYLRLKKLFAQRMVQKASSCHSSIS
gi|17366834 EPAAVKPEDDRYLRAAIQEYDNIAKLGQIIREGPIKGSLLKVVLEDYLRLKKLFAQRMVQKASSCHSSIS
gi|14017841 ----------------------------------------------------------------------
gi|17865345 EPAAVKPEDDRYLRAAIQEYDNIAKLGQIIREGPIK----------------------------------

3300       3310       3320       3330       3340       3350       3360
            ....|....|....|....|....|....|....|....|....|....|....|....|....|....|
NOV17a      ----------------------------------------------------------------------
gi|18576726 ELIQTELEEEPGDHSPGQGSLRFRHKPEVELKGPDGIHVVHGSTGTLLATDLNSLPEEDQKGLCRSLETI
gi|16507962 ELIQTELEEEPGDHSPGQGSLRFRHKPEVELKGPDGIHVVHGSTGTLLATDLNSLPEEDQKGLCRSLETI
gi|17366834 ELIQTELEEEPGDHSPGQGSLRFRHKPEVELKGPDGIHVVHGSTGTLLATDLNSLPEEDQKGLCRSLETI
gi|14017841 ----------------------------------------------------------------------
gi|17865345 -LIHTDLEEEPGDHSPGQGSLRFRHKPETELKGPDGIHIVHGSTGTLLATDLNSLPEEDQKGLDRSLETI 3370       3380       3390
            ....|....|....|....|....|....
NOV17a      ------------------------------
gi|18576726 TAAEATAFERNARTESAKSTPLHKLRDVIMETPLEITEL
gi|16507962 TAAEATAFERNARTESAKSTPLHKLRDVIMETPLEITEL
gi|17366834 TAAEATAFERNARTESAKSTPLHKLRDVIMETPLEITEL
gi|14017841 ---------------------------------------
gi|17865345 TASEATAFERNARTESAKSTPLHKLRDVIMESPLEITEL
```

Tables 17I and 17J list the domain description from DOMAIN analysis results against NOV17a. This indicates that the NOV17a sequence has properties similar to those of other proteins known to contain these domains.

TABLE 17I

Domain Analysis of NOV17a gnl|Smart|smart00112, CA, Cadherin repeats.; Cadherins are
glycoproteins involved in Ca2+-mediated cell-cell adhesion. Cadherin
domains occur as repeats in the extracellular regions which are
thought to mediate cell-cell contact when bound to calcium. (SEQ ID NO:201)
CD-Length = 82 residues, 100.0% aligned
Score = 85.1 bits (209), Expect = 7e-18

```
Query:  271 VVAIDLDEGLNGLVSYRMPVGMPRMDFLINSSSGVVVTTTELDRERIAEYQLRVVASDAG  330
            | | | | || |+| +  |    | |+ +|++ ||  |||| +|| | | |+| |
Sbjct:    1 VSATDADSGENGKVTYSILSGNDGGLFSIDPETGIITTTKPLDREEQSEYTLTVEATDGG   60

Query:  331 TPTKSSTSTLTIHVLDVNDETP                                       352
            |  |||+|+|+ ||||||  |
Sbjct:   61 GPPLSSTATVTVTVLDVNDNAP                                        82
```

TABLE 17J

Domain Analysis of NOV17a gnl|Pfam|pfam00028, cadherin, Cadherin domain. (SEQ ID NO:202)
CD-Length = 92 residues, 100.0% aligned
Score = 80.9 bits (198), Expect = 1e-16

```
Query:  254 FVAEVLEGIPAGVSIYQVVAIDLDEGLNGLVSYRMPVGMPRMDFLINSSSGVVVTTTELD  313
            + | | | | | + | | | | || + |  | |  | |+ +| +|| ||
Sbjct:    1 YSASVPENAPVGTEVLTVTATDADLGPNGRIFYSILGGGPGGWFRIDPDTGDLSTTKPLD   60

Query:  314 RERIAEYQLRVVASDAGTPTKSSTSTLTIHVL                             345
            || | ||+| |+|+|+| |  | |+|+|| ||
Sbjct:   61 RESIGEYELTVLATDSGGPPLSGTTTVTITVL                              92
```

Cadherins are a family of animal glycoproteins responsible for calcium-dependent cell-cell adhesion. Cadherins preferentially interact with themselves in a homophilic manner in connecting cells; thus acting as both receptor and ligand. A wide number of tissue-specific forms of cadherins are known, including epithelial (E-cadherin, also known as uvomorulin or L-CAM; CDH1), neural (N-cadherin; CDH2), placental (P-cadherin; CDH3), retinal (R-cadherin; CDH4), vascular endothelial (VE-cadherin; CDH5), kidney (K-cadherin; CDH6), cadherin-8 (CDH8), osteoblast (OB-cadherin; CDH11), brain (BR-cadherin; CDH12), T-cadherin (truncated cadherin; CDH13), muscle (M-cadherin; CDH14), liver-intestine (LI-cadherin), and EP-cadherin.

Structurally, cadherins are built of the following domains: a signal sequence, followed by a propeptide of about 130 residues, then an extracellular domain of around 600 residues, then a transmembrane region, and finally a C-terminal cytoplasmic domain of about 150 residues. The extracellular domain can be sub-divided into five parts: there are four repeats of about 110 residues followed by a region that contains four conserved cysteines. It is suggested that the calcium-binding region of cadherins is located in the extracellular repeats. Cadherins are evolutionary related to the desmogleins which are component of intercellular desmosome junctions involved in the interaction of plaque proteins.

A form of nonsyndromic autosomal recessive deafness is caused by mutation in the cadherin-23 gene (CDH23), which is also the site of mutation in a form of Usher syndrome, USH1D. Chaib et al. (Hum Mol Genet. 5(7):1061–4, 1996) reviewed the frequency and inheritance of congenital isolated deafness and causes for difficulties associated with mapping of deafness genes. They noted that in the U.S., deafness affects 1 in 1000 children at birth or during infancy. About 75% of the inherited forms of congenital isolated deafness have an autosomal recessive mode of transmission. Chaib et al. (1996) noted that difficulties in localization of deafness genes are due to several factors, including extreme genetic heterogeneity of the defect (there are an estimated 40 deafness genes segregating in the population); the absence of clinical criteria to allow differentiation between inner ear defects; and the high proportion of marriages between deaf persons in Western countries leading to coexistence of several defective genes responsible for clinically indistinguishable phenotypes in one family. In an effort to simplify mapping of deafness genes, Chaib et al. (1996) carried out studies in consanguineous families living in isolated regions. Marker data from these families was initially analyzed using a lod-score approach. Subsequently they performed homozygosity mapping. They localized a 'new' gene for nonsyndromal recessive deafness (symbolized DFNB12) to chromosome 10q21-q22 in a consanguineous Sunni family who lived in an isolated village in Syria. Affected members in this family have profound prelingual sensorineural hearing impairment. A significant lod score (6.40 at theta=0.00) was obtained with the marker D10S535. Analysis of adjacent markers placed the gene distal to D10S529 and proximal to D10S532 in a 11- to 15-cM region. All affected individuals were homozygous for polymorphic markers located in this region. Chaib et al. (1996) stated that the gene encoding the mitochondrial transcription factor 6-like 2 is a possible candidate gene for DFNB12. They also noted that the homologous murine region for DFNB12 contains 3 deaf mouse mutants, including Jackson circler (jc), Waltzer (v), and Ames Waltzer (av). Bork et al. (Am J Hum Genet. 68(1):26–37, 2001) demonstrated that DFNB12 and a form of Usher syndrome characterized by deafness associated with retinitis pigmentosa and vestibular dysfunction (USH1D) are allelic disorders due to different mutations in the cadherin-23 gene.

Usher syndrome type I is an autosomal recessive disorder characterized by profound congenital hearing impairment with unintelligible speech, early retinitis pigmentosa, and constant vestibular dysfunction. Three different loci had been found by linkage analysis: USH1A on 14q34, USH1B on 11q13, and USH1C on 11p15. Gerber et al. (J Med Genet. 33(1):77–9, 1996) suggested the existence of yet a fourth form of Usher syndrome type I from the fact that the 3 previously reported loci were excluded by linkage studies in 2 families of Moroccan and Pakistani ancestry. Wayne et al. (Hum Mol Genet. 5(10): 1689–92, 1996) reported that a first-cousin union in a family of Pakistani origin produced 4 children with clinical signs of Usher syndrome, including profound prelingual auditory impairment of sensorineural type, congenital vestibular dysfunction, and progressive pigmentary retinopathy. Wayne et al. (1996) prepared 2 genomic DNA pools, one from the affected children and the other from the parents, and screened 161 polymorphic markers evenly spaced across the autosomal genome. The only region showing homozygosity by descent in the affected sibs was a 15-cM interval on chromosome 10 bounded by D10S529 and D10S573. Wayne et al. (1996) concluded that this was the location of the gene responsible for Usher syndrome in this family. They symbolized the locus USH1D. Bolz et al. (Nat Genet. 27(1): 108–12, 2001) identified mutations in the CDH23 gene in a Cuban family and a German patient with USH1D. Di Palma et al. (Nat Genet. 27(1):103–7, 2001; Gene. 281(1–2):31–41, 2001) demonstrated that mutations in the mouse Cdh23 gene are responsible for the 'waltzer' mutation, thus establishing it as a model for USH1D. Bork et al. (2001) showed that USH1D and DFNB12 are allelic disorders due to different mutations in the cadherin-23 gene.

Truncated or alternatively-spliced cadherins have been identified, and some may play roles in disease. Berx et al. (Hum Mutat. 12(4):226–37, 1998) found reports of 69 somatic mutations of the CDH1 gene. These comprised, in addition to a few missense mutations, mainly splice site mutations and truncation mutations caused by insertions, deletions, and nonsense mutations. There was a major difference in mutation type between diffuse gastric and infiltrative lobular breast cancers. In diffuse gastric tumors, the predominant defects were exon skippings, which caused in-frame deletions. By contrast, most mutations found in infiltrating lobular breast cancers were out-of-frame mutations, which were predicted to yield secreted truncated E-cadherin fragments. Two different forms of human OB-cadherin cDNA were cloned; one was a counterpart of the mouse gene and the other encoded a protein with a truncated cytoplasmic domain. Sequence analysis demonstrated that Ksp-cadherin, like LI-cadherin (CDH17), lacks the prosequence and tripeptide HAV adhesion recognition sequence typical of most classical cadherins, and possesses a truncated cytoplasmic domain.

The NOV17 nucleic acid of the invention encoding a Cadherin 23-like protein includes the nucleic acid whose sequence is provided in Tables 17A and 17C, or a fragment thereof. The invention also includes a mutant or variant nucleic acid any of whose bases may be changed from the corresponding base shown in Tables 17A and 17C while still encoding a protein that maintains its Cadherin 23-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 1% of the NOV17 residues may be so changed.

The NOV17 protein of the invention includes the Cadherin 23-like protein whose sequence is provided in Tables 17B and 17D. The invention also includes a mutant or variant protein any of whose residues may be changed from the corresponding residue shown in Tables 17B and 17D while still encoding a protein that maintains its Cadherin 23-like activities and physiological functions, or a functional fragment thereof. In the mutant or variant protein, up to about 1% of the NOV17 bases may be so changed.

The NOV17 nucleic acids and proteins of the invention are useful in potential diagnostic and therapeutic applications implicated in various diseases and disorders described below and/or other pathologies. For example, the compositions of the present invention will have efficacy for treatment of patients suffering from: nonsyndromic autosomal recessive deafness, Usher syndrome type I, systemic lupus erythematosus, autoimmune disease, asthma, emphysema, scleroderma, allergy, ARDS, diabetes, Von Hippel-Lindau (VHL) syndrome, pancreatitis, obesity, multiple sclerosis, leukodystrophies, pain, neuroprotection, fertility and other diseases, disorders and conditions of the like.

NOV17 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV17 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV18

A disclosed NOV18 nucleic acid of 1614 nucleotides (also referred to as CG55887-02) encoding a novel Transforming Growth Factor Beta 2 (TGF Beta 2)-like protein is shown in Table 18A. An open reading frame was identified beginning with an ATG initiation codon at nucleotides 182–184 and ending with a TAA codon at nucleotides 1343–1345. Putative untranslated regions upstream from the intitation codon and downstream from the termination codon are underlined in Table 18A, and the start and stop codons are in bold letters.

TABLE 18A

NOV18 Nucleotide Sequence (SEQ ID NO:67)
CAAGCAGGATACGTTTTTCTGTTGGGCATTGACTAGATTGTTTGCAAAAGTTTCGCATCAAAAACAAACAACA
ACAACAAAAAACCAAACAACTCTCCTTGATCTATACTTTGAGAATTGTTGATTTCTTTTTTTTTATTCTGACT
TTTAAAAACAACTTTTTTTTCCACTTTTTAAAAAATGCACTACTGTGTGCTGAGCGCTTTTCTGATCCTGCA
TCTGGTCACGGTCGCGCTCAGCCTGTCTACCTGCAGCACACTCGATATGGACCAGTTCATGCGCAAGAGGATC
GAGGCGATCCGCGGGCAGATCCTGAGCAAGCTGAAGCTCACCAGTCCCCCAGAAGACTATCCTGAGCCCGAGG
AAGTCCCCCCGGAGGTGATTTCCATCTACAACAGCACCAGGGACTTGCTCCAGGAGAAGGCGAGCCGGAGGGC
GGCCGCCTGCGAGCGCGAGAGGAGCGACGAAGAGTACTACTTCAGAATTGTTCGATTTGACGTCTCAGCAATG
GAGAAGAATGCTTCCAATTTGGTGAAAGCAGAGTTCAGAGTCTTTCGTTTGCAGAACCCAAAAGCCAGAGTGC
CTGAACAACGGATTGAGCTATATCAGATTCTCAAGTCCAAAGATTTAACATCTCCAACCCAGCGCTACATCGA
CAGCAAAGTTGTGAAAACAAGAGCAGAAGGCGAATGGCTCTCCTTCGATGTAACTGATGCTGTTCATGAATGG
CTTCACCATAAAGACAGGAACCTGGGATTTAAAATAAGCTTACACTGTCCCTGCTGCACTTTTGTACCATCTA
ATAATTACATCATCCCAAATAAAAGTGAAGAACTAGAAGCAAGATTTGCAGGTATTGATGGCACCTCCACATA
TACCAGTGGTGATCAGAAAACTATAAAGTCCACTAGGAAAAAAAACAGTGGGAAGACCCCACATCTCCTGCTA
ATGTTATTGCCCTCCTACAGACTTGAGTCACAACAGACCAACCGGCGGAAGAAGCGTGCTTTGGATGCGGCCT
ATTGCTTTAGAAATGTGCAGGATAATTGCTGCCTACGTCCACTTTACATTGATTTCAAGAGGGATCTAGGGTG
GAAATGGATACACGAACCCAAAGGGTACAATGCCAACTTCTGTGCTGGAGCATGCCCGTATTTATGGAGTTCA
GACACTCAGCACAGCAGGGTCCTGAGCTTATATAATACCATAAATCCAGAAGCATCTGCTTCTCCTTGCTGCG
TGTCCCAAGATTTAGAACCTCTAACCATTCTCTACTACATTGGCAAAACACCCAAGATTGAACAGCTTTCTAA
TATGATTGTAAAGTCTTGCAAATGCAGCTAAAATTCTTGGAAAAGTGGCAAGACCAAAATGACAATGATGATG
ATAATGATGATGACGACGACAACGATGATGCTTGTAACAAGAAAACATAAGAGAGCCTTGGTTCATCAGTGTT
AAAAAATTTTTGAAAAGGCGGTACTAGTTCAGACACTTTGGAAGTTTGTGTTCTGTTTGTTAAAACTGGCATC
TGACACAAAAAAAGTTGAAGGCCTTATTCTACATTTCACCTACTTTGTAAGTGAGAGAGACAAGAAGCAAATT
TTTTTAAA The NOV18 nucleic acid was identified on chromosome 1 and has 1140 of 1140 bases (100%) identical to a gb:GENBANK-ID:HSGTSF|acc:Y00083.1 mRNA from *Homo sapiens* (Human mRNA for glioblastoma-derived T-cell suppressor factor G-TsF (transforming growth factor-beta2, TGF-beta2)) (E=0.0).

A disclosed NOV18 polypeptide (SEQ ID NO:68) encoded by SEQ ID NO:67 is 387 amino acid residues and is presented using the one-letter code in Table 18B. Signal P, Psort and/or Hydropathy results predict that NOV18 contains a signal peptide and is likely to be localized to the extracellularly with a certainty of 0.8200. The most likely cleavage site for a NOV18 polypeptide is between amino acids 20 and 21: ALS-LS.

TABLE 18B

Encoded NOV18 protein sequence (SEQ ID NO:68)
MHYCVLSAFLILHLVTVALSLSTCSTLDMDQFMRKRIEAIRGQILSKLKLTSPPEDYPEPEEVPPEVISIYN
STRDLLQEKASRRAAACERERSDEEYYFRIVRFDVSAMEKNASNLVKAEFRVFRLQNPKARVPEQRIELYQI
LKSKDLTSPTQRYIDSKVVKTRAEGEWLSFDVTDAVHEWLHHKDRNLGFKISLHCPCCTFVPSNNYIIPNKS
EELEARFAGIDGTSTYTSGDQKTIKSTRKKNSGKTPHLLLMLLPSYRLESQQTNRRKKRALDAAYCFRNVQD
NCCLRPLYIDFKRDLGWKWIHEPKGYNANFCAGACPYLWSSDTQHSRVLSLYNTINPEASASPCCVSQDLEP
LTILYYIGKTPKIEQLSNMIVKSCKCS The NOV18 amino acid sequence 289 of 289 amino acid residues (100%) identical to, and 289 of 289 amino acid residues (100%) similar to, the 414 amino acid residue ptnr:SWISSPROT-ACC:P08112 protein from *Homo sapiens* (Human), and (Transforming Growth Factor Beta 2 Precursor (TGF-BETA 2) (Glioblastoma-Derived T-Cell Suppressor Factor) (G-TSF) (BSC-1 Cell Growth Inhibitor) (Polyergin) (Cetermin)) ($E=1.2e^{-210}$).

NOV18 is expressed in at least the following tissues: Lung, Mammary gland/Breast, Placenta, Thymus, Uterus, Whole OrganismAorta, Brain, Cervix, Foreskin, Heart, Kidney, Prostate, Retina, Right Cerebellum and Spinal Chord. This information was derived by determining the tissue sources of the sequences that were included in the invention including but not limited to SeqCalling sources, Public EST sources, genomic clone sources, literature sources, and/or RACE sources.

Possible SNPs found for NOV18 are listed in Table 18C.

TABLE 18C

| | SNPs | | | |
|---|---|---|---|---|
| Variant | Nucleotide Position | Base Change | Amino Acid Position | Base Change |
| 13377104 | 785 | T > C | 202 | Cys > Arg |

NOV18 has homology to the amino acid sequences shown in the BLASTP data listed in Table 18D.

TABLE 18D

BLAST results for NOV18

| Gene Index/ Identifier | Protein/Organism | Length (aa) | Identity (%) | Positives (%) | Expect |
|---|---|---|---|---|---|
| gi|557563|gb|AAA50405.1| (M19154) | transforming growth factor beta 2 [*Homo sapiens*] | 413 | 357/413 (86%) | 357/413 (86%) | 0.0 |
| gi|4507463|ref|NP_003229.1| (NM_003238) | transforming growth factor, beta 2 [*Homo sapiens*] | 414 | 357/414 (86%) | 357/414 (86%) | 0.0 |
| gi|1729919|sp|P09858| TGF2_PIG | Transforming growth factor beta 2 precursor (TGF-beta 2) [*Sus scrofa*] | 435 | 353/414 (85%) | 355/414 (85%) | 0.0 |
| gi|164689|gb|AAB03850.1| (L08375) | transforming growth factor beta 2 [*Sus scrofa*] | 434 | 352/413 (85%) | 354/413 (85%) | 0.0 |
| gi|15029892|gb|AAH11170.1| AAH11170 (BC011170) | Similar to transforming growth factor, beta 2 [*Mus musculus*] | 414 | 344/414 (83%) | 349/414 (84%) | 0.0 |

The homology of these sequences is shown graphically in the ClustalW analysis shown in Table 18E.

TABLE 18E

Clustal W Sequence Alignment

```
1) NOV 18 (SEQ ID NO:68)
2) gi 557563|gbAAA50405.1|(M19154) transforming growwth factor beta 2 [Homo sapiens]
(SEQ ID NO:203)
3) gi 4507463|refNP_003229.1|(NM_003238) transforming growth factor, beta 2
[Homo sapiens] (SEQ ID NO:204)
4) gi 1729919|sp|P09858|TGF2_PIG Transforming growth factor beta 2 precursor
(TGF-beta 2) [Sus scrofa] (SEQ ID NO:205)
5) gi|15029892|gb|AAH11170.1|AAH11170 (BC011170) Similar to transforming growth
factor, beta 2 [Mus musculus] (SEQ ID NO:206)
6) gi|18250662|emb|CAC70714.2| (AJ310932) myosin heavy chain [Homo sapiens]
(SEQ ID NO:207)

10        20        30        40        50        60        70
                ....|....|....|....|....|....|....|....|....|....|....|....|....|....|
NOV18           MHYCVLSAFLILHLVTVALSLSTCSTLDMDQFMRKRIEAIRGQILSKLKLTSPPEDYPEPEEVPPEVISI
gi|557563|      MHYCVLSAFLILHLVTVALSLSTCSTLDMDQFMRKRIEAIRGQILSKLKLTSPPEDYPEPEEVPPEVISI
gi|4507463|     MHYCVLSAFLILHLVTVALSLSTCSTLDMDQFMRKRIEAIRGQILSKLKLTSPPEDYPEPEEVPPEVISI
gi|1729919|     MHYCVLSAFLILHLVTVALSLSTCSTLDMDQFMRKRIEAIRGQILSKLKLTSPPEDYPEPEEVPPEVISI
gi|164689|      -HYCVLSAFLILHLVTVALSLSTCSTLDMDQFMRKRIEAIRGQILSKLKLTSPPEDYPEPEEVPPEVISI
gi|15029892|    MHYCVLSTFLILHLVPVALSLSTCSTLDMDQFMRKRIEAIRGQILSKLKLTSPPEDYPEPDEVPPEVISI
```

TABLE 18E-continued

Clustal W Sequence Alignment

```
                    80         90        100        110        120        130        140
               ....|....|....|....|....|....|....|....|....|....|....|....|....|....|
NOV18          YNSTRDLLQEKASRRAAACERERSDEEY---------------------------------------------
gi|557563|     YNSTRDLLQEKASRRAAACERERSDEEYYAKEVYKIDMPPFFPSETVCPVVTTPSGSVGSLCSRQSQVLC
gi|4507463|    YNSTRDLLQEKASRRAAACERERSDEEYYAKEVYKIDMPPFFPSE-------------------------
gi|1729919|    YNSTRDLLQEKASRRAAACERERSDEEYYAKEVYKIDMPPFFPSE-------------------------
gi|164689|     YNSTRDLLQEKASRRAAACERERSDEEYYAKEVYKIDMPPFFPSE-------------------------
gi|15029892|   YNSTRDLLQEKASRRAAACERERSDEEYYAKEVYKIDMPSHLPSE-------------------------

150        160        170        180        190        200        210
               ....|....|....|....|....|....|....|....|....|....|....|....|....|....|
NOV18          -------------YFRIVRFDVSAMEKNASNLVKAEFRVFRLQNPKARVPFQRIELYQILKSKDLTSPTQ
gi|557563|     GYLDAIPPTFYRPYFRIVRFDVSAMEKNASNLVKAEFRVFRLQNPKARVPEQRIELYQILKSKDLTSPTQ
gi|4507463|    ---NAIPPTFYRPYFRIVRFDVSAMEKNASNLVKAEFRVFRLQNPKARVPEQRIELYQILKSKDLTSPTQ
gi|1729919|    ---NAIPPTFYRPYFRIVRFDVSAMEKNASNLVKAEFRVFRLQNPKARVPEQRIELYQILKSKDLTSPTQ
gi|164689|     ---NAIPPTFYRPYFRIVRFDVSAMEKNASNLVKAEFRVFRLQNPKARVPEQRIELYQILKSKDLTSPTQ
gi|15029892|   ---NAIPPTFYRPYFRIVRFDVSTMEKNASNLVKAEFRVFRLQNPKARVPEQRIELYQILKSKDLTSPTQ 220        230        240        250        260        270        280
               ....|....|....|....|....|....|....|....|....|....|....|....|....|....|
NOV18          RYIDSKVVKTRAEGEWLSFDVTDAVHEWLHHKDRNLGFKISLHCPCCTFVPSNNYIIPNKSEELEARFAG
gi|557563|     RYIDSKVVKTRAEGEWLSFDVTDAVHEWLHHKDRNLGFKISLHCPCCTFVPSNNYIIPNKSEELEARFAG
gi|4507463|    RYIDSKVVKTRAEGEWLSFDVTDAVHEWLHHKDRNLGFKISLHCPCCTFVPSNNYIIPNKSEELEARFAG
gi|1729919|    RYIDSKVVKTRAEGEWLSFDVTDAVHEWLHHKDRNLGFKISLHCPCCTFVPSNNYIIPNKSEELEARFAG
gi|164689|     RYIDSKVVKTRAEGEWLSFDVTDAVHEWLHHKDRNLGFKISLHCPCCTFVPSNNYIIPNKSEELEARFAG
gi|15029892|   RYIDSKVVKTRAEGEWLSFDVTDAVQEWLHHKDRNLGFKISLHCPCCTFVPSNNYIIPNKSEELEARFAG 290        300        310        320        330        340        350
               ....|....|....|....|....|....|....|....|....|....|....|....|....|....|
NOV18          IDGTSTYTSGDQKTIKSTRKKNSGKTPHLLLMLLPSYRLESQQTNRRKKRALDAAYCFRNVQDNCCLRPL
gi|557563|     IDGTSTYTSGDQKTIKSTRKKNSGKTPHLLLMLLPSYRLESQQTNRRKKRALDAAYCFRNVQDNCCLRPL
gi|4507463|    IDGTSTYTSGDQKTIKSTRKKNSGKTPHLLLMLLPSYRLESQQTNRRKKRALDAAYCFRNVQDNCCLRPL
gi|1729919|    IDGTSTYTSGDQKTIKSTRKKNSGKTPHLLLMLLPSYGLESQQSNRRKKRALDAAYCFRNVQDNCCLRPL
gi|164689|     IDGTSTYTSGDQKTIKSTRKKNSGKTPHLLLMLLPSYGLESQQSNRRKKRALDAAYCFRNVQDNCCLRPL
gi|15029892|   IDGTSTYASGDQKTIKSTRKKTSGKTPHLLLMLLPSYRLESQQSSRKKKRALDAAYCFRNVQDNCCLRPL 360        370        380        390        400        410        420
               ....|....|....|....|....|....|....|....|....|....|....|....|....|....|
NOV18          YIDFKRDLGWKWIHEPKGYNANFCAGACPYLWSSDTQHSRVLSLYNTINPEASASPCCVSQDLEPLTILY
gi|557563|     YIDFKRDLGWKWIHEPKGYNANFCAGACPYLWSSDTQHSRVLSLYNTINPEASASPCCVSQDLEPLTILY
gi|4507463|    YIDFKRDLGWKWIHEPKGYNANFCAGACPYLWSSDTQHSRVLSLYNTINPEASASPCCVSQDLEPLTILY
gi|1729919|    YIDFKRDLGWKWIHEPKGYNANFCAGACPYLWSSDTQHSRVLSLYNTINPEASASPCCVSQDLEPLTILY
gi|164689|     YIDFKRDLGWKWIHEPKGYNANFCAGACPYLWSSDTQHSRVLSLYNTINPEASASPCCVSQDLEPLTILY
gi|15029892|   YIDFKRDLGWKWIHEPKGYNANFCAGACPYLWSSDTQHTKVLSLYNTINPEASASPCCVSQDLEPLTILY 430        440        450        460
               ....|....|....|....|....|....|....|....|...
NOV18          YIGKTPKIEQLSNMIVKSCKCS---------------------
gi|557563|     YIGKTPKIEQLSNMIVKSCKCS---------------------
gi|4507463|    YIGKTPKIEQLSNMIVKSCKCS---------------------
gi|1729919|    YIGKTPKIEQLSNMIVKSCKCSKTKLAAFARLYHSHSNLGSET
gi|164689|     YIGKTPKIEQLSNMIVKSCKCSKTKLAAFARLYHSHSNLGSET
gi|15029892|   YIGNTPKIEQLSNMIVKSCKCS---------------------
```

Tables 18F, 18G and 18H list the domain description from DOMAIN analysis results against NOV18. This indicates that the NOV18 sequence has properties similar to those of other proteins known to contain these domains.

TABLE 18F

Domain Analysis of NOV18 gnl Pfam pfam00688, TGFb_propeptide, TGF-beta propeptide. This
propeptide is known as latency associated peptide (LAP) in TGF-beta.
LAP is a homodimer which is disulfide linked to TGF-beta binding
protein. (SEQ ID NO:208)
CD-Length = 227 residues, 100.0% aligned
Score = 152 bits (383), Expect = 4e-38

```
Query:   24  CSTLDMDQFMR-KRIEAIRGQILSKLKLTSPPEDYPEPEEVPPEVISIYNSTRDLLQEKA   82
             |  ||+ +  +  |+|||  ||||||| |    ||  ||  ++ +||+  +| +  |
Sbjct:    1  CRPLDLRRSQKQDRLEAIEGQILSKLGLRRRPRPSKEPMVVPEYMLDLYNALSELEEGKV   60

Query:   83  SRRAAACERERSDEE---------------------YYFRIVRFDVSAMEKNASNLVKA  120
             |       + + +                        + + ||++|++ +  +      |
Sbjct:   61  GRVPEISDYDGREAGRANTIRSFSHLESDDFEESTPESHRKRFRFNLSSIPEGETLTA-A  119
```

TABLE 18F-continued

Domain Analysis of NOV18

```
Query:  121 EFRVFRLQNPKARVPEQRIELYQILKSKDLTSPTQRYIDSKVVKTRAEGEWLSFDVTDAV 180
            |  |++|              |+|+||+||      ||  | +||++|  |  | ||||||| ||
Sbjct:  120 ELRLYRDPLALRSRATVRVEIYQLLKPGSDGSPDTRLLDSRLVDARDSGGWLSFDVTSAV 179

Query:  181 HEWLHHKDRNLGFKISLHCPCCTFVPSNNYIIPNKSEELEARFAGIDG             228
            + || + + ||| ++ + | |    ||   +|      |
Sbjct:  180 NRWLSNPESNLGLQLEVECLCGHVRPSRAGLIGEPGPEQLQPLLVTFF             227
```

TABLE 18G

Domain Analysis of NOV18 gnl|Pfam|pfam00019, TGF-beta, Transforming growth factor beta like domain. (SEQ ID NO:209)
CD-Length = 105 residues, 100.0% aligned
Score = 124 bits (310), Expect = 1e-29

```
Query:  287 QDNCCLRPLYIDFKRDLGWK-WIHEPKGYNANFCAGACPYLWSSDTQ---HSRVLSLYNT 342
            | || ||+|| ||||| ||  |+|| ||+|+|+||+      |+ + +|
Sbjct:    1 ARPCRLRSLYVDG-RDLGWGDWIIAPEGYIANYCSGSCPFPLRDDLNLSNHAILQTLVRL  59

Query:  343 INPEASASPCCVSQDLEPLTILYYI-GKTPKIEQLSNMIVKSCKCS              387
            ||| ||||  | ||++||       +    || || | |
Sbjct:   60 RNPRAVPQPCCVPTKLSPLSMLYLDDNSNVVLRLYPNMSVKECGCR              105
```

TABLE 18H

Domain Analysis of NOV18 gnl|Smart|smart00204, TGFB, Transforming growth factor-beta (TGF-beta) family; Family members are active as disulphide-linked homo- or heterodimers. TGFB is a multifunctional peptide that controls proliferation, differentiation, and other functions in many cell types. (SEQ ID NO:210)
CD-Length = 102 residues, 100.0% aligned
Score = 109 bits (273), Expect = 3e-25

```
Query:  290 CCLRPLYIDFKRDLGWK-WIHEPKGYNANFCAGACPYLWSSD---TQHSRVLSLYNTINP 345
            |    ||+||| ||||  ||  ||||||| +|  ||+  |    |+  ||  + ++|
Sbjct:    1 CRRHDLYVDFK-DLGWDDWIIAPKGYNAYYCEGECPFPLSERLNATNHAIVQSLVHALDP  59

Query:  346 EASASPCCVSQDLEPLTILYYI-GKTPKIEQLSNMIVKSCKCS                387
            |   ||||   | ||++|||       +    ||+|+ | |
Sbjct:   60 GAVPKPCCVPTKLSPLSMLYYDDDGNVVLRNYPNMVVEECGCR                102
```

The human (de Martin et al., EMBO J. 6(6):1633–6, 1987; de Martin et al., EMBO J. 6(12):3673–7, 1987; Madisen et al., DNA. 7(1):1–8, 1988) and simian (Hanks et al., Proc Natl Acad Sci U S A. 85(1):79–82, 1988) forms of TGF-beta-2 have identical C-terminal 112 amino acid residues. The beta-2 form was derived from human glioblastoma cells. It has suppressive effects on interleukin-2-dependent T-cell growth. For these reasons it is also called glioblastoma-derived T-cell suppressor factor (G-TSF). It may have an autocrine function in enhancing tumor growth and/or reducing immunosurveillance of tumor development. By Southern blot analysis of somatic cell hybrid lines and, for the human locus, also by in situ chromosomal hybridization, Barton et al. (Oncogene Res. 3(4):323–31, 1988) mapped TGFB2 to 1q41 in the human and to chromosome 1 in the mouse, most likely in the known conserved syntenic region. Dickinson et al. (Genomics. 6(3):505–20, 1990) also assigned the mouse Tgfb-2 gene to chromosome 1. Nishimura et al. (Genomics. 15(2):357–64, 1993) identified 4 RFLPs and SSCPs (single strand conformation polymorphisms) for TGFB2 in humans and gorillas. Using these, they localized the gene within a framework map of distal 1q and showed close linkage to homeo box gene HLX1 (142995); maximum lod score of 14.49 at theta=0.031.

The NOV18 nucleic acid of the invention encoding a Transforming Growth Factor Beta 2-like protein includes the nucleic acid whose sequence is provided in Table 18A, or a fragment thereof. The invention also includes a mutant or variant nucleic acid any of whose bases may be changed from the corresponding base shown in Table 18A while still encoding a protein that maintains its Transforming Growth Factor Beta 2-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

The NOV18 protein of the invention includes the Transforming Growth Factor Beta 2-like protein whose sequence is provided in Table 1 8B. The invention also includes a mutant or variant protein any of whose residues may be changed from the corresponding residue shown in Table 18B while still encoding a protein that maintains its Transforming Growth Factor Beta 2-like activities and physiological functions, or a functional fragment thereof.

The NOV18 nucleic acids and proteins of the invention are useful in potential diagnostic and therapeutic applications implicated in various diseases and disorders described below and/or other pathologies. For example, the compositions of the present invention will have efficacy for treatment of patients suffering from: cancer and other diseases, disorders and conditions of the like.

NOV18 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV18 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV19

A disclosed NOV19 nucleic acid of 2939 nucleotides (also referred to as CG57333-01) encoding a novel Ebnerin-like protein is shown in Table 19A. An open reading frame was identified beginning with an ATG initiation codon at nucleotides 20–22 and ending with a TAG codon at nucleotides 2912–2914. Putative untranslated regions upstream from the intitation codon and downstream from the termination codon are underlined in Table 19A, and the start and stop codons are in bold letters.

TABLE 19A

NOV19 Nucleotide Sequence (SEQ ID NO:69)

GAATGGAGGGAAGGCCTAGATGGATGAGTGGAAAGGAAGATGGGGGGAGGGAAAGGTGGATGAAGAGTCAGGA

GGCTGGGCGGCTTCCCCGACTCTAATTCTTTGGGTCTCTTCTACCCCAGGGTCCCCCAGCTGCGCCTGGTGG

CTGGGCCCAGCAAGTGCTCAGGTCGACTGGAGGTGTGGCATGACCAGCGCTGGGGGACCGTGTGTGACGATAG

CTGGGACATGCGGGATTCAGCTGTGGTCTGCCGGGAGCTGGGCTGTGGTGGACCTCAGCAGCCAGACCCTGCT

GCCGGCCGCCTGGAGGTCTGGCACGGGGGTCGCTGGGGGTCGGTGTGTGACGACGCCTGGGACCTGCGAGACG

CCGCTGTGGCCTGCCGAGAGCTGGGCTGCGGAGGGGCGCTGGCCGCCCCCGGGGCGCCTTCTTTGGGGAGGG

GTCTGGACCCATCATCCTGGACGACCTTCGGTGTCGGGGAAACGAGACGGCCTTACGATTCTGCCCAGCTCGG

CCCTGGGGCCAGCATGACTGTCACCACCGCGAGGACGCCGGGGCCGTGTGTGACGGCATGCCCCTGGGCTACG

TCCCTCCCACGGCCCCCACGGACAGCAACAACTCCACGCCCAGGGAGGCTGCCTCCAGGCCCCGTCCACCAT

GACGAGCCAGGCTCCAGGGACGGCAGGCGTTTCACCTCCTCCAGCCTCCCCTACTGTCCTTTGGGAGCCTGGA

CCGGAAGCCGGGTCCCCCCAGCTGCGCCTGGTGGCTGGGCCCAGCAAGTGCTCAGGTCGACTGGAGGTGTGGC

ATGACCAGCGCTGGGGGACCGTGTGTGACGATAGCTGGGACATGCGGGATTCAGCTGTGGTCTGCCGGGAGCT

GGGCTGTGGTGGACCTCAGCAGCCAGACCCTGCTGCTGGCCGCTTTGGCTGGGGTGCGGGCCCCATCTGGCTA

GATGATGTGAGCTGTGTGGGGACCGAGGCTTCACTGTCCGACTGCCCTGCTGCTCCCTGGGGAAAGCACAACT

GCGCTCACAATGAGGATGTTGGGGTCACCTGCACTGGGCCCCAGGCCTGGACTCCATCTCAGACCCCTTCAG

CTGGAGCTGGATTCCTGGACTGGGGAGAGATCGGGATGCCTGGCTCCCGGGAGAGCTGGCCACCAAGCCCTCT

GCAAGTGTGACTGCCAGTGTTCTGGAGAAAACAACCACGAAGGCCCCAGGGAAAATGCCTAAGAGTACTAAGA

AGTGGGTGACAAAAAATGCAAAGAGACCAACCACTCAACCCCCAGTGATGCCAACCACGAAACACTCCAGGGC

CCAAAGCCCCCCAGACCTAACTTCACAGACCACTGCAGCACTGACCACTGAGGCCTCCCGAAGACCTACCTCT

GAGTTTACCAGAAGGCCGACCACGGAGGCCCCCCAGAGATGGACCTCTCACACCACTGCCACGCTGACCCCTC

AGGCCCCCCGAGAACGGACCACTAAGACCATGGCAATGCTGACCACTCAAGGCCCCCAAGAAATGACCTCTGA

GTCCACTATCAAGAGTATCCCTCAGGCCTCCCTGGAGCCATCTGCTGAGATCCCAGAAGGGTCTCCAGAGTCA

CCCAAAGACCCGGCCCCCTCTCCCAGTGTTAGCACCACTGGGGAATCAGGCCTGTTCCGGGTTCGTCTGGCCG

ATGGGCCCAACCGCTGTGCTGGCCGGCTGGAAGTGTGGCATGCCGGACGCTGGGGAACAGTGTGTGATGACAA

TABLE 19A-continued

NOV19 Nucleotide Sequence

CTGGGACCTGCGGGACGCCACTGTGGCCTGCTGGGAACTGGGCTGTGGAAAGGTCCGGCCTCGAGTAGGCAAA

ACCCATTACGGTCCTGGGACTGGGCCCATCTGGCTGGATGACATGGGCTGTAAGGGAAGCGAGGCCTCACTGA

GCGACTGCCCCTCGGGGGCTTGGGGGAAGCACAACTGTGACCACGAGGAAGACGTGGGGCTCACCTGCACTGG

CTACACAGACTATGACGATTATCCCCCCTGGACCTGGGACCCCACCTCAAGAGAGGACCTGGCCAAGGGGACT

ACCACAGCGGGGGTACCTGGACACACTCTCCCCTGGAGGACCACCCGGCGCCCGGGTAGCTCCTCCCCAGCAA

TAAGGCGCCTGCCGGACACAGGCAGCAAAGATGGTTACAAGCTTCCCTGGACGTGGGACACACCATCAGGAAG

GGGCCTGGCTGAGGGGACCCCTACCGCAGGCAAACTAGGACCAACTCTTGGGGCTGGCACCACCAGGAGCCCA

GGCAGTCCTCCAACTCCGAGAGTCCATGGAGACACAGGTTCCCCGAGGAAACCGTGGCCCGAGCGCCGGCCAC

CGCGGCCCGCTGCGACCAGGACAGCGCCCCAACCCCGTCCCAGGTCCCTCCGCCTCTCCGGGACCCCAGG

CCCAGCGCTGACCTCTGACTCCAGTCGAGAGCTCACTCCCCACTCAGCCTTGACGTCCGAGGCGACCTCTGAC

GCTCCGGACACTTCACCACCCACCCCAGACCCGGCCTCCCGGACGAACCCCGACCTCATCTTGACAAGCCCTG

ACTTTGCTTTGTCCACCCCTGACTCCAGTGTGGTTCCCGCGTTGACCCCGGAGCCCTCACCCACGCCCTTACC

CACCTTGCCCAAAGAGCTGACCTCTGACCCTTCTACACCGTCGGAGGTGACCAGCCTTTCCCCTACCTCAGAG

CAGGTCCCAGAATCTGACACAACCCCAGATTTGGACACAACTCCATACTCCAGTACANGACTCCTGACCCCAC

CACGACCCCTTACCCCACCACTACTCCTGATCCCACCACGACCCCTCACCCCACAACTCCTGACCCTTCCTCA

ACCCCTGTCATCACTACTGTGTCCCTTCCAACCTCCTTGGGGACAGAACTCTCCTCTCCCACTCTAGCACCAA

CAGTCAAGCCCAGTCTGCA

The NOV19 nucleic acid and has 313 of 490 bases (63%) identical to a gb:GENBANK-ID:HSA243224|acc:AJ243224.1 mRNA from *Homo sapiens* (*Homo sapiens* mRNA for DMBT1 protein 8 kb transcript variant 1 (DMBT1/8kb.1)) (E=7.0e$^{-46}$).

A disclosed NOV19 polypeptide (SEQ ID NO:70) encoded by SEQ ID NO:69 is 964 amino acid residues and is presented using the one-letter code in Table 19B. Signal P, Psort and/or Hydropathy results predict that NOV19 does not contain a signal peptide and is likely to be localized to the cytoplasm with a certainty of 0.4500.

TABLE 19B

Encoded NOV19 protein sequence (SEQ ID NO:70)
MDEWKGRWGEGKVDEESGGWAASPTLILWVSSTPGSPQLRLVAGPSKCSGRLEVWHDQRWGTVCDDSWDMRD

SAVVCRELGCGGPQQPDPAAGRLEVWHGGRWGSVCDDAWDLRDAAVACRELGCGGALAAPGGAFFGEGSGPI

ILDDLRCRGNETALRFCPARPWGQHDCHHREDAGAVCDGMPLGYVPPTAPTDSNNSTPREAASRPPSTMTSQ

APGTAGVSPPPASPTVLWEPGPEAGSPQLRLVAGPSKCSGRLEVWHDQRWGTVCDDSWDMRDSAVVCRELGC

GGPQQPDPAAGRFGWGAGPIWLDDVSCVGTEASLSDCPAAPWGKHNCAHNEDVGVTCTGPPGLDSISDPFSW

SWIPGLGRDRDAWLPGELATKPSASVTASVLEKTTTKAPGKMPKSTKKWVTKNAKRPTTQPPVMPTTKHSRA

QSPPDLTSQTTAALTTEASRRPTSEFTRRPTTEAPQRWTSHTTATLTPQAPRERTTKTMAMLTTQGPQEMTS

ESTIKSIPQASLEPSAEIPEGSPESPKDPAPSPSVSTTGESGLFRVRLADGPNRCAGRLEVWHAGRWGTVCD

DNWDLRDATVACWELGCGKVRPRVGKTHYGPGTGPIWLDDMGCKGSEASLSDCPSGAWGKHNCDHEEDVGLT

CTGYTDYDDYPPWTWDPTSREDLAKGTTTAGVPGHTLPWRTTRRPGSSSPAIRRLPDTGSKDGYKLPWTWDT

PSGRGLAEGTPTAGKLGPTLGAGTTRSPGSPPTPRVHGDTGSPRKPWPERRPPRPAATRTAPPTPSPGPSAS

PGPPGPALTSDSSRELTPHSALTSEATSDAPDTSPPTPDPASRTNPDLILTSPDFALSTPDSSVVPALTPEP

TABLE 19B-continued

Encoded NOV19 protein sequence

SPTPLPTLPKELTSDPSTPSEVTSLSPTSEQVPESDTTPDLDTTPYSSTXLLTPPRPLTPPLLLIPPRPLTP

QLLTLPQPLSSLLCPFQPPWGQNSPLPL

The NOV19 amino acid sequence has 57 of 109 amino acid residues (52%) identical to, and 75 of 109 amino acid residues (68%) similar to, the 1594 amino acid residue ptnr:SPTREMBL-ACC:Q95218 protein from *Oryctolagus cuniculus* (Rabbit) (HENSIN) (E=2.2e$^{-40}$).

NOV19 is expressed in at least the following tissues: adrenal gland, bone marrow, brain—amygdala, brain—cerebellum, brain—hippocampus, brain—substantia nigra, brain—thalamus, brain—whole, fetal brain, fetal kidney, fetal liver, fetal lung, heart, kidney, lymphoma—Raji, mammary gland, pancreas, pituitary gland, placenta, prostate, salivary gland, skeletal muscle, small intestine, spinal cord, spleen, stomach, testis, thyroid, trachea and uterus. This information was derived by determining the tissue sources of the sequences that were included in the invention including but not limited to SeqCalling sources, Public EST sources, genomic clone sources, literature sources, and/or RACE sources.

NOV19 has homology to the amino acid sequences shown in the BLASTP data listed in Table 19C.

TABLE 19C

BLAST results for NOV19

| Gene Index/ Identifier | Protein/Organism | Length (aa) | Identity (%) | Positives (%) | Expect |
|---|---|---|---|---|---|
| gi|13434994|dbj|BAB39761.1| (AB051832) | PIT 54 [*Gallus gallus*] | 470 | 115/331 (34%) | 160/331 (47%) | 2e-49 |
| gi|7513558|pir||T30549 | hensin - rabbit | 1594 | 119/328 (36%) | 153/328 (46%) | 4e-47 |
| gi|18152779|ref|NP_542782.1| (NM_080744) | scavenger receptor cysteine-rich protein SRCRB-S4D [*Homo sapiens*] | 575 | 114/262 (43%) | 138/262 (52%) | 4e-47 |
| gi|14765505|ref|XP_051448.1| (XM_051448) | similar to deleted in malignant brain tumors 1 (*H. sapiens*) [*Homo sapiens*] | 1051 | 123/349 (35%) | 157/349 (44%) | 6e-47 |
| gi|2135587|pir||I38005 | M130 antigen precursor, splice form 4 [*Homo sapiens*] | 1156 | 124/361 (34%) | 168/361 (46%) | 8e-47 |

The homology of these sequences is shown graphically in the ClustalW analysis shown in Table 19D.

TABLE 19D

Clustal W Sequence Alignment

```
1) NOV19 (SEQ ID NO:70)
2) gi 13434994|dbj|BAB39761.1|(AB051832) PIT 54 [Gallus gallus] (SEQ ID NO:211)
3) gi 7513558|pir T30549 hensin - rabbit (SEQ ID NO:212)
4) gi 18152779|refNP_542782.1|(NM_080744) scavenger receptor cysteine-rich protein
SRCRB-S4D [Homo sapiens] (SEQ ID NO:213)
5) gi 14765505|refXP_051448.1|(XM_051448) similar to deleted in malignant brain tumors
1 (H. sapiens) [Homo sapiens] (SEQ ID NO:214)
6) gi|2135587|pirp51 I38005 M130 antigen precursor, splice form 4 [Homo sapiens]
(SEQ ID NO:215)

710       720       730       740       750       760       770
              ....|....|....|....|....|....|....|....|....|....|....|....|....|....|
NOV19         ----------------------------------------------------------------------
gi|13434994|  ----------------------------------------------------------------------
gi|7513558|   VIYESTPVHISGLQLRLVNGSDRCEGRVEVLYQGSWGTVCDDSWDLNDASVVCRQLGCGTALSAPASAQF
gi|18152779|  DWAWQTDPSATGVG------PQPSR--------------E-TALLT---T--------------------
gi|14765505|  --------NLP---------A-------------------L-T---------------------------
gi|2135587|   G---TVEVEIQRLLG---------------------KVCDRGWGLKEADVVCRQLGCGSALKTSYQVYS
```

TABLE 19D-continued

Clustal W Sequence Alignment

```
                   780       790       800       810       820       830       840
                  ....|....|....|....|....|....|....|....|....|....|....|....|....|
NOV19             ------------------------------------------WIPGLGRDRDAWLPGELATRPSASVTA
gi|13434994|      ------------------------------------------GISISTSVRLVGGPNRCSGRVEVLH
gi|7513558|       GQSSGSIVLDDVSCSGSEPNLWSCSHRGWLSHNCGHHEDAGVVCSGPDSRLAVRLVNGSTRCQGRVEVLY
gi|18152779|      ------------------------------------AAWAAGKKSGRLRLVGGPGPCRGRVEVLH
gi|14765505|      -------------------------------------V-GSESSLAERLVNGDRCRGRVEVLY
gi|2135587|       KIQATNTWLFLSSCNGNETSLWDCKNWQWGG---LTCDHYEEAKITCSAHREPRLVGGDIPCSGRVEVKH 850       860       870       880       890       900       910
                  ....|....|....|....|....|....|....|....|....|....|....|....|....|
NOV19             SVLEKTTTKAPGKMPKSVKKWVTKNAKRPTTQPPVMPTTKHSRAQSPPDETSQTTAALTVEASRRPTSEF
gi|13434994|      NNVWGTVCDDNWDLREAKVVCLQLGCGTALSALPESKVGEGKGQTWLSDLNCTGTFGSLTECEAKPWGEN
gi|7513558|       RGSWGTVCDDSWDTNDASVVCRQLGCGWAVSAPGSARFGQGSGSIFLDEVSCSGQEPYLWNCSHRGWLSE
gi|18152779|      AGGWGTVCDDDWDFADARVACRDAGCGPALGATCLGHFGYGRGPVLLDNYGCAGTEARLSDCFHLGWGQH
gi|14765505|      RGSWGTVCDDSWDTNDANVVCRQLGCGWAMSAPGCNARFGQGSGPTVLDVRCSGNESYLWSCPHKGWLTH
gi|2135587|       GDTWGSICDSDFSLEAASVLCRELQCCGTVVSILGGAHFGENGQIWAEEFQCEGHESHISLCPVAPRPEG 920       930       940       950       960       970       980
                  ....|....|....|....|....|....|....|....|....|....|....|....|....|
NOV19             TRRPTTKAPQRWTS------------------------------------HTTATL
gi|13434994|      VCNHVEDASVECS---------------------------------------
gi|7513558|       NCGHYEDAGVICSDGWTTVTPPAPTTDWWEPTVTTTVGPSSNCGGFLYNATGSFSSPSYPGYYPNNALCV
gi|18152779|      NCGHHEDAGALCAG---------------------------------PE---
gi|14765505|      NCGHHEDAGVICSA--TQIN--STTTDWWHPTTTTTARPSSNCGGFLFYASGTFSSPSYPAYYPNNAKCV
gi|2135587|       TCSHSRDVGVVCSRYTEIRLVNGKTPCEGRVELKTLGAWGSLCNSHWDIEDAHVLCQQLKCGVALSTPGG 990       1000      1010      1020      1030      1040      1050
                  ....|....|....|....|....|....|....|....|....|....|....|....|....|
NOV19             TPQAPRERTTKTMAMLTTQGPQEMTSESTIKSIPQASLEPSAEIPEGSPESPKDPAPSP----S--VSTT
gi|13434994|      -------------------EQ--------D---TS-----------
gi|7513558|       WEIAVPSGYLINLGFSQLRLEQHSYCNFDYVEIFDGSTDSS-LLGKICNDSGQIFTTSSNRMTVLFRSDI
gi|18152779|      ----------------ELGLQVQQ----------DGS-----------ETTRVPTP------
gi|14765505|      WEIEVNSGYTINLGFSNLKLEAHHNCSFDYVEIFDGSLNSSLLGKICNDIRQIFTSSYNRMTIHFRSDI
gi|2135587|       ARFGKGNGQIWRHMFHCTGREQHMG--DCPVTALGASLCPSEQVASVICSGNQSQTLSCNSSSLGPIRP 1060      1070      1080      1090      1100      1110      1120
                  ....|....|....|....|....|....|....|....|....|....|....|....|....|
NOV19             GE-----------SGLFRVRLADGPNR---CAGRLEVMHAGRWGTVCDDNWDLRDATVACWELGCGKVR
gi|13434994|      ----------------EIGPVRLVDGPNQ---CAGRVEVRHENRWGSVCDDNWDMKDAKVVCKQVGCCSPL
gi|7513558|       SVQNTGFLAWYNSFPRDASLRLVSGNSSYGACAGRVEIYHGGRWGTVCDDSWDTDAQVVCRQLCCGDAV
gi|18152779|      --R-----------PRDGHLRLVNGAHR---CAGRVEYLGGRWGTVCDDSWDLAWDLRAACVECRQLGCGQAL
gi|14765505|      SFQNTGFLAWYNSFPSDATLRLVNLNSSYGLCAGRVEIYHGGTWGTVCDDSWTIQEAEVVCRQLGCGRAV
gi|2135587|       TIPEES----AVACIESGQLRLVNGGGR---CAGRVEIYHEGSWGTICDDSWDLSDAHVVCRQLGCGEAT 1130      1140      1150      1160      1170      1180      1190
                  ....|....|....|....|....|....|....|....|....|....|....|....|....|
NOV19             PRVCKTHYCPGCIGPIWLDDMGCKSEASLSDCPSGAWGKHNQDHEEDVGLTCTCGVTDYDDYPPWTWDPTS
gi|13434994|      SALGSARYCRGPDVIWLDDVNCEEESIFDCKARPWGEHNCGHHEDASVFCTVNKN--------LEETE
gi|7513558|       SAPCGAYFCSGSGPITLDDVNCSCEATIWQCRSQSWFSHNCGHHEDASVICTGNYGTTTASVPNISTSN
gi|18152779|      AAPCEAHFCPCRGPILLDDNVKCREEESALLLCSHIRWDAHNCDHSEDASVLCQPS----------
gi|14765505|      SALCNAYFCSGSGPITLDDVECSCIESSPIWQCRNRGWFSHNCNHREDACVICSGNHLSTPAPFLNITRPN
gi|2135587|       NATCSAHFCEGTGPIWLDEMKCNCKESRIWQCHSHGWGQQNCREHKEDAGVICSEKMS------LRLTSEA 1200      1210      1220      1230      1240      1250      1260
                  ....|....|....|....|....|....|....|....|....|....|....|....|....|
NOV19             REDLAKGTTTAGVPGHTLPWRTTRRPGSSSPAIRRLPD--------------------
gi|13434994|      TS-----------------------------------
gi|7513558|       ASYSCGGFLSQHSGRFSSPFYPGNYPNNARCVWDIEVQNNYQVTVTFTDVQLEGGCQYDYIEVFDGPYHS
gi|18152779|      -------------------------------------
gi|14765505|      TDYSCGGFLSQPSGDFSSPFYPGNYPNNAKCVWDIEVQNNYRVTVIFRDVQLEGGCNYDYIEVFDGPYRS
gi|2135587|       SREACAGRLEVFYNGAWGTVGKSSMSETTVGVVCRQLG--------------------

1270      1280      1290      1300      1310      1320      1330
                  ....|....|....|....|....|....|....|....|....|....|....|....|....|
NOV19             ------------------------T--GSKDGYKLPWIWDTPSGRGLAEGTPTAGKLGPTLG
gi|13434994|      -------------------------------------
gi|7513558|       SPLIARVCDGARGSFTSSSNFLSVRFVSDGSITRRGFQAEETSLPSNDSTNLLCLMNHMQASVSRAYLQS
gi|18152779|      -------------------------------------
gi|14765505|      SPLIARVCDGARGSFTSSSNFMSIRFISDHSITRRGFRAEYYSSPENDSTNLLCLPNHMQASVSRSYLQS
gi|2135587|       ------CADKGKINPASLDKAMSIPMQVDNVQCPKGPDTLWQCPSSPWEKRLASPSEETWITCDNKIRLQ 1340      1350      1360      1370      1380      1390      1400
                  ....|....|....|....|....|....|....|....|....|....|....|....|....|
NOV19             AGTTRSPGSPPTPR----------------------VHGDTGSPRKPWPERRPPRPAATRTAPP
gi|13434994|      -------------------------------------
gi|7513558|       LGFSAWELVVSGWNGNYQCQRQITPSQVIFTIPYSGCGTIKQVDNLIITYSNFLKAAVSSGVIKRKKDLH
gi|18152779|      -------------------------------------
gi|14765505|      LGFSASDLVISTWNGYYECRPQITPNLVIFTIPYSGCGTFKQADNDTIDYSNFLTAAVSGGIIKRRTDLR
gi|2135587|       EGPISCSGRVEIWHG--------GSWGTVCDDSWDLDDAQVVCQQLGCGPALKAFK
```

TABLE 19D-continued

Clustal W Sequence Alignment

```
                  1410       1420       1430       1440       1450       1460       1470
             ....|....|....|....|....|....|....|....|....|....|....|....|....|....|
NOV19        TPSPGPSASPGPPGPALTS----------------DSSRELTPHSALTSEATSDAPDTSPPTPDPASRTN
gi|13434994| ----------------------------------------------------------------------
gi|7513558|  IHVSCRMLQDSWVHTMYIANDTIEVS-------EVQYSNFNVNVSFYTSSSFSYPVTSSPYYVDLDQNLY
gi|18152779| ----------------------------------------------------------------------
gi|14765505| IHVSCRMLQNTWVDTMYIANDTIHVANNTIQVEEVQYGNFDVNISFYTSSSFLYPVTSRPYYVDLNQDLY
gi|2135587|  EAEFGQGTGPIQLNEVKCK------GN--------ESSLWDCPARRWGHSECGHKEDAAVNCTDISVQKT 1480       1490       1500       1510       1520       1530       1540
             ....|....|....|....|....|....|....|....|....|....|....|....|....|....|
NOV19        PDLILTSPDFALSTPDSSVVPALTPEPSPTPLPTLPKELTSDPSTPSEVTSLSPTSEQVPE-----SDTT
gi|13434994| ----------------------------------------------------------------------
gi|7513558|  LQAEILHSDASLALFVDTCVASPNPNDFTSVTYDLIRSGCVRDETYRSYAQPSPRVVRFRFNSFHFLNRF
gi|18152779| ----------------------------------------------------------------------
gi|14765505| VQAEILHSDAVLTLFVDTCVASPYSNDFTSLTYDLIRSGCVRDDTYGPYSSPSLRIARFRFRAFHFLNRF
gi|2135587|  PQKATTGRSSRQSSFIAVGILGVVLLAIFVALFFLTKK-RRQRQRLAVSSRGENLVHQIQYREMNSCLNA 1550       1560       1570       1580       1590       1600
             ....|....|....|....|....|....|....|....|....|....|....|....|....
NOV19        PDLDTTPYSSTCLLTPPRPLTPPLLLIPPRPLTPQLLTLPQPLSSLLCPFQPPWGQNSPLPL--
gi|13434994| ----------------------------------------------------------------
gi|7513558|  PAVYLRCKMVVCRAYDYSSRCYRGCVVRSKRDVGSYQERVDVVLGPIQLLDPPAGKKSPGKGSP
gi|18152779| ----------------------------------------------------------------
gi|14765505| PSVYLRCKMVVCRAYDPSSRCYRGCVLRSKRDVGSYQEKVDVVLGPIQLQTPPRREEEPR----
gi|2135587|  DDLDLMNSSGLWVLGGSIAQGFR-SVAAVEAQTFYFDKQLKKSKNVIGSLDAYNGQE-------
```

Tables 19E and 19F list the domain description from DOMAIN analysis results against NOV19. This indicates that the NOV19 sequence has properties similar to those of other proteins known to contain these domains.

TABLE 19E

Domain Analysis of NOV19 gnl|Smart|smart00202, SR, Scavenger receptor Cys-rich; The sea ucrhin egg peptide speract contains 4 repeats of SR domains that contain 6 conserved cysteines. May bind bacterial antigens in the protein MARCO. (SEQ ID NO:216)
CD-Length = 101 residues, 100.0% aligned
Score = 142 bits (359), Expect = 7e-35

```
Query:  550  VRLADGPNRCAGRLEVWHAGRWGTVCDDNWDLRDATVACWELGCGKVRPRVGKTHYGPGT  609
             |||   | +  |  ||+||+| |+||||||| ||||||  |  +||  |      |  ++|||+
Sbjct:    1  VRLVGGGSPCEGRVEVYHNGQWGTVCDDGWDLRDANVVCRQLGFGGAVSASGSAYFGPGS   60

Query:  610  GPIWLDDMGCKGSEASLSDCPSGAWGKHNCDHEEDVGLTCT                    650
             ||||||++ |  |+||||||||    ||  ||| |  ||  |+  |+
Sbjct:   61  GPIWLDNVRCTGTEASLSDCPHSGWGSHNCSHSEDAGVVCS                   101
```

TABLE 19F

Domain Analysis of NOV19 gnl Pfam|pfam00530, SRCR, Scavenger receptor cysteine-rich domain. These domains are disulphide rich extracellular domains. These domains are found in several extracellular receptors and may be involved in protein-protein interactions. (SEQ ID NO:217)
CD-Length = 95 residues, 96.8% aligned
Score = 95.9 bits (237), Expect = 9e-21

```
Query:  250  GPSKCSGRLEVWHDQRWGTVCDDSWDMRDSAVVCRELGCGGPQQPDPAAGRFGWGAGPIW  309
             |  |+|  ||+||       +||||||| ||  +||+  ||||+|||||         |   |||
Sbjct:    3  GSSRCEGRVEVRDGSKWGTVCDSSWTLRDANVVCRQLGCGGALSS-LGGPYFSEGGGPIP   61

Query:  310  LDDVSCVGTEASLSDCPAAPWGHKNCAHNEDVGVTC                         345
             ||  |+|   |+|||  |         |+|  ||  || |
Sbjct:   62  LDGVNCSGNESSLSQC---PHRSRQCSHGEDAGVVC                          94
```

Saliva is the first digestive fluid secreted by the gastrointestinal pathway and performs a variety of functions. It is essential in the formation of small boluses of food, provides lubrication for swallowing and speech, dissolves a number of chemicals in food substances, and provides digestive enzymes such as amylase and lipase (Hamosh & Scow, 1973, J. Clin. Invest.52:88–95; Field & Hand, 1987, Am. J. Physiol.253:G217–G225). About 90% of saliva is produced by three major glands, the parotid, the submaxillary, and the sublingual glands, whose secretions drain into the oral cavity.

von Ebner's glands are unique salivary glands contained within the tongue that drain directly into the clefts of the circumnvallate and foliate papillae, which contain the major taste buds. Secretions of von Ebner's gland directly modulate taste perception (Gurkan & Bradley, 1988, Chem. Senses 13: 655–661). Xiao-Jiang Li and Solomon H. Snyder (1995, J Biol Chem 270:17674–9) have identified a novel von Ebner's gland (VEG) protein, designated Ebnerin, which is formed in the ducts of von Ebner's gland and released into fluid bathing the taste buds contained in the taste papillae. Ebnerin possesses a putative single transmembrane domain at the C terminus with 17 amino acids in the cytoplasmic area. The extracellular region of Ebnerin contains a number of repeated domains with homology to the scavenger receptor cysteine-rich domain and to a repeated domain of bone morphogenetic protein-I and other related proteins. Western blot analysis reveals that Ebnerin exists in particulate and soluble forms in VEG and is present in secretions from VEG. The unique structure and localization of Ebnerin suggest that it may function as a binding protein in saliva for the regulation of taste sensation.

Ebnerin is a modular protein containing a signal peptide, SRCR ("scavenger receptor, cysteine rich") domains. Other proteins known to have this domain include CRP-ductin, a cDNA expressed at high levels in mouse intestine (8 SRCR), hensin, the polarity reversal protein cloned from a rabbit kidney (8SRCR), and DMBT1, a sequence in human chromosome 10q25-26 frequently deleted in malignant gliomas (9 SRCR) (Cheng, et al., 1996, Anat. Rec. 244: 327–343; Mollenhauer, 1997, Nat. Genet. 17: 32–39; Takito et al., 1999, Am J Physiol 277:F277–89). Hensin, DMBT1, CRP-ductin, and ebnerin are alternately spliced products from a single gene located on human chromosome 10q25-26, a region often deleted in several cancers, especially malignant gliomas. Hensin is expressed in many epithelial cell types, and it plays a critical role in terminal differentiation of the intercalated cell and perhaps other epithelia (Al-Awqati et al., 2000, Exp Nephrol 8:66–71).

Vomeroglandin, a subform of mouse CRP-ductin, is a protein strongly expressed in the glands of mouse vomeronasal system. Both the proteins contain several of scavenger receptor cysteine-rich and CUB domains and one ZP domain. This domain arrangement is similar to those of rat Ebnerin, human DMBT1, and rabbit hensin. In situ hybridization analysis shows strong expression of vomeroglandin mRNA in the glands of vomeronasal system. Immunological analyses detect both membrane-bound and secreted forms of vomeroglandin. The secreted protein seems to be localized in the lumen of the vomeronasal organ, playing a certain role in the pheromone perception (Matsushita et al., 2000, Biochem Biophys Res Commun 268:275–81).

The NOV19 nucleic acid of the invention encoding a Ebnerin-like protein includes the nucleic acid whose sequence is provided in Table 19A, or a fragment thereof.

The invention also includes a mutant or variant nucleic acid any of whose bases may be changed from the corresponding base shown in Table 19A while still encoding a protein that maintains its Ebnerin-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 37% of the residues may be so changed.

The NOV19 protein of the invention includes the Ebnerin-like protein whose sequence is provided in Table 19B. The invention also includes a mutant or variant protein any of whose residues may be changed from the corresponding residue shown in Table 19B while still encoding a protein that maintains its Ebnerin-like activities and physiological functions, or a functional fragment thereof. In the mutant or variant protein, up to about 48% of the bases may be so changed.

The NOV19 nucleic acids and proteins of the invention are useful in potential diagnostic and therapeutic applications implicated in various diseases and disorders described below and/or other pathologies. For example, the compositions of the present invention will have efficacy for treatment of patients suffering from: several cancers, especially malignant gliomas, glioblastoma multiforme, medulloblastoma and other diseases, disorders and conditions of the like.

NOV19 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV19 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV20

NOV20 includes two novel Fatty Acid Binding-like proteins disclosed below. The disclosed proteins have been named NOV20a and NOV20b.

NOV20a

A disclosed NOV20a nucleic acid of 400 nucleotides (also referred to as CG57556-01) encoding a novel Fatty Acid Binding-like protein is shown in Table 20A. An open reading frame was identified beginning with an ATG initiation codon at nucleotides 2–4 and ending with a TAG codon at nucleotides 398–400. Putative untranslated regions, if any, upstream from the initiation codon and downstream from the termination codon are underlined in Table 20A, and the start and stop codons are in bold letters.

TABLE 20A

NOV20a nucleotide sequence.

(SEQ ID NO:71)

TATGGTAAGGGTGGAGGAGGCTTTCTGTGCTACCTGGAAGCTGACCAACAGTCAGAACTTTGATGAGTACAT

GAAGGCTCTAGGCGTGGGCTTTGCCACTAGGCAGGTGGGAAATGTGACCAAACCAACGGTAATTATCAGTCA

AGAAGGAGACAAAGTGGTCATCAGGACTCTCAGCACATTCAAGAACACGGAGATTAGTTTCCAGCTGGGAGA

AGAGTTTGATGAAACCACTGCAGATGATAGAAACTGTAAGTCTGTTGTTAGCCTGGATGGAGACAAACTTGT

TCACATACAGAAATGGGATGGCAAAGAAACAAATTTTGTAAGAGAAATTAAGGATGGCAAAATGGTTATGAC

CCTTACTTTTGGTGATGATGTGGTTGCCGTTCACCACTAG

The disclosed NOV20a nucleic acid sequence, localized to chromsome 6q22-23, has 389 of 398 bases (97%) identical to a gb:GENBANK-ID:HSAJ2962|acc:AJ002962.1 mRNA from Homo sapiens (Homo sapiens mRNA for hB-FABP) (E=$2.5e^{-79}$).

A NOV20a polypeptide (SEQ ID NO:72) encoded by SEQ ID NO:71 has 132 amino acid residues and is presented using the one-letter code in Table 20B. Signal P, Psort and/or Hydropathy results predict that NOV20a does not contain a signal peptide and is likely to be localized to the microbody (peroxisome) with a certainty of 0.4849 and to the mitochondrial matrix space with a certainty of 0.4750. Although PSORT suggests that the NOV20a protein may be localized in the intracellularly, the NOV20a protein is similar to the Fatty Acid Binding Protein family, some members of which are localized at the plasma membrane. Therefore it is likely that this novel Fatty Acid Binding Protein-like protein is localized to the same sub-cellular compartment.

(Brain Lipid-Binding Protein) (BLBP) (Mammary Derived Growth Inhibitor Related)) (E=$1.9e^{-62}$).

The disclosed NOV20a is expressed in at least the following tissues: Bone, Brain, Heart, Kidney, Lung, Retina, Temporal Lobe and Uterus. This information was derived by determining the tissue sources of the sequences that were included in the invention including but not limited to Seq-Calling sources, Public EST sources, Literature sources, and/or RACE sources. The disclosed NOV20a is also predicted to be expressed in the following tissues because of the expression pattern of (gb:GENBANK-ID:HSAJ2962|acc:AJ002962.1) a closely related Homo sapiens mRNA for hB-FABP homolog in species Homo sapiens: brain.

NOV20b

A disclosed NOV20b nucleic acid of 417 nucleotides (also referred to as CG57556-02) encoding a novel Fatty Acid Binding-like protein is shown in Table 20C. An open

TABLE 20B

Encoded NOV20a protein sequence.

(SEQ ID NO:72)

MVRVEEAFCATWKLTNSQNFDEYMKALGVGFATRQVGNVTKPTVIISQEGDKVVIRTLSTFKNTEISFQLGE

EFDETTADDRNCKSVVSLDGDKLVHIQKWDGKETNFVREIKDGKMVMTLTFGDDVVAVHH

The NOV20a amino acid sequence has 125 of 127 amino acid residues (98%) identical to, and 125 of 127 amino acid residues (98%) similar to, the 131 amino acid residue ptnr:SWISSNEW-ACC:O15540 protein from Homo sapiens (Human) (Fatty Acid-Binding Protein, Brain (B-FABP)

reading frame was identified beginning with an ATG initiation codon at nucleotides 5–7 and ending with a TAA codon at nucleotides 410–412. Putative untranslated regions, if any, upstream from the initiation codon and downstream from the termination codon are underlined in Table 20C, and the start and stop codons are in bold letters.

TABLE 20C

NOV20b nucleotide sequence.

(SEQ ID NO:73)

TATAATGGTAAGGGTGGAGGAGGCTTTCTGTGCTACCTGGAGGCTGACCAACAGTCAGAACTTTGATGAGTA

CATGAAGGCTCTAGGCGTGGGCTTTGCCACTAGGCAGGTGGGAAATGTGACCAAACCAACGGTAATTATCAG

TCAAGAAGGAGACAAAGTGGTCATCAGGACTCTCAGCACATTCAAGAACACGGAGATTAGTTTCCAGCTGGG

AGAAGAGTTTGATGAAACCACTGCAGATGATAGAAACTGTAAGTCTGTTGTTAGCCTGGATGGAGACAAACT

TGTTCACATACAGAAATGGGATGGCAAAGAAACAAATTTTGTAAGAGAAATTAAGGATGGCAAAATGGTTAT

GACCCTTACTTTTGGTGATGTGGTTGCCGTTCACCACTATAAGAAGGCATAAAAATA

The disclosed NOV20b nucleic acid sequence, localized to chromsome 6q22-23, has 405 of 413 bases (98%) identical to a gb:GENBANK-ID:HSAJ2962|acc:AJ002962.1 mRNA from *Homo sapiens* (*Homo sapiens* mRNA for hB-FABP) (E=6.6e$^{-84}$).

A NOV20b polypeptide (SEQ ID NO:74) encoded by SEQ ID NO:73 has 135 amino acid residues and is presented using the one-letter code in Table 20D. Signal P, Psort and/or Hydropathy results predict that NOV20b does not contain a signal peptide and is likely to be localized to the mitochondrial matrix space with a certainty of 0.5834 and to the peroxisome (microbody) with a certainty of 0.4915.

TABLE 20D

Encoded NOV20b protein sequence.

(SEQ ID NO:74)
MVRVEEAFCATWRLTNSQNFDEYMKALGVGFATRQVGNVTKPTVIISQEG

DKVVIRTLSTFKNTEISFQLGEEFDETTADDRNCKSVVSLDGDKLVHIQK

WDGKETNFVREIKDGKMVMTLTFGDVVAVHHYKKA

The NOV20b amino acid sequence has 127 of 130 amino acid residues (97%) identical to, and 129 of 130 amino acid residues (99%) similar to, the 131 amino acid residue ptnr:SWISSNEW-ACC:O15540 protein from *Homo sapiens* (Human) (Fatty Acid-Binding Protein, Brain (B-FABP) (Brain Lipid-Binding Protein) (BLBP) (Mammary Derived Growth Inhibitor Related)) (E=6.8e$^{-65}$).

The disclosed NOV20b is expressed in at least the following tissues: Bone, Brain, Heart, Kidney, Lung, Retina, Temporal Lobe and Uterus. This information was derived by determining the tissue sources of the sequences that were included in the invention including but not limited to Seq-Calling sources, Public EST sources, Literature sources, and/or RACE sources. The disclosed NOV20b is also predicted to be expressed in the following tissues because of the expression pattern of (gb:GENBANK-ID:HSAJ2962|acc:AJ002962.1) a closely related *Homo sapiens* mRNA for hB-FABP homolog in species *Homo sapiens*: brain.

Possible SNPs found for NOV20a are listed in Table 20E.

TABLE 20E

| | SNPs | | |
|---|---|---|---|
| Consensus Position | Depth | Base Change | PAF |
| 42 | 6 | A > G | 0.333 |
| 170 | 6 | A > G | 0.333 |
| 388 | 6 | C > T | 0.333 |

NOV20a and NOV20b are very closely homologous as is shown in the amino acid alignment in Table 20F.

TABLE 20F

Amino Acid Alignment of NOV20a and NOV20b

```
              10        20        30        40        50        60        70
         ....|....|....|....|....|....|....|....|....|....|....|....|....|....|
NOV20a   MVRVEEAFCATWKLTNSQNFDEYMKALGVGFATRQVGNVTKPTVIISQEGDKVVIRTLSTFKNTEISFQL
NOV20b   MVRVEEAFCATWRLTNSQNFDEYMKALGVGFATRQVGNVTKPTVIISQEGDKVVIRTLSTFKNTEISFQL 80        90       100       110       120       130
         ....|....|....|....|....|....|....|....|....|....|....|....|.
NOV20a   GEEFDETTADDRNCKSVVSLDGDKLVHIQKWDGKETNFVREIKDGKMVMTLTFGDDVVAVHH----
NOV20b   GEEFDETTADDRNCKSVVSLDGDKLVHIQKWDGKETNFVREIKDGKMVMTLTFG-DVVAVHHYKKA
```

Homologies to any of the above NOV20 proteins will be shared by the other NOV20 proteins insofar as they are homologous to each other as shown above. Any reference to NOV20 is assumed to refer to the NOV20 proteins in general, unless otherwise noted.

NOV20a has homology to the amino acid sequences shown in the BLASTP data listed in Table 20G.

TABLE 20G

BLAST results for NOV20a

| Gene Index/ Identifier | Protein/ Organism | Length (aa) | Identity (%) | Positives (%) | Expect |
|---|---|---|---|---|---|
| gi|4557585|ref|NP_001437.1| (NM_001446) | fatty acid binding protein 7, brain; B-FABP [*Homo sapiens*] | 132 | 125/127 (98%) | 125/127 (98%) | 2e−61 |
| gi|15826067|pdb|1FDQ|A | Chain A, Crystal Structure Of Human Brain Fatty Acid Binding | 131 | 125/127 (98%) | 125/127 (98%) | 3e−61 |

TABLE 20G-continued

BLAST results for NOV20a

| Gene Index/ Identifier | Protein/ Organism | Length (aa) | Identity (%) | Positives (%) | Expect |
|---|---|---|---|---|---|
| gi|2605596|dbj|BAA23324.1| (D50373) | Protein [*Homo sapiens*] fatty acid binding protein [*Homo sapiens*] | 132 | 124/127 (97%) | 125/127 (97%) | 1e−60 |
| gi|12224842|emb|CAC21646.1| (AL512688) | hypothetical protein [*Homo sapiens*] | 166 | 114/114 (100%) | 114/114 (100%) | 2e−58 |
| gi|462065|sp|Q05423| FABB_CHICK | FATTY ACID-BINDING PROTEIN, RETINA (R-FABP) [*Gallus gallus*] | 132 | 114/127 (89%) | 119/127 (92%) | 9e−57 |

The homology of these sequences is shown graphically in the ClustalW analysis shown in Table 20H.

TABLE 20H

ClustalW Analysis of NOV20a

1) NOV20a (SEQ ID NO:72)
2) gi 4557585|refNP_0014371.1|(NM_001446) fatty acid binding protein 7, brain; B-FABP [*Homo sapiens*] (SEQ ID NO:218)
2) gi 15826062|pdb|1FDQ|A Chain A, Crystal Structure Of Human Brain Fatty Acid Binding Protein [*Homo sapiens*] (SEQ ID NO:219)
3) gi 2605596|dbj|BAA23324.1| (D50373) fatty acid binding protein [*Homo sapiens*] (SEQ ID NO:220)
4) gi 12224842|emb|CAC21646.1 (AL512688) hypothetical protein [*Homo sapiens*] (SEQ ID NO:221)
5) gi 462065|sp Q05423|FABB_CHICK FATTY ACID-BINDING PROTEIN, RETINA (R-FABP) [*Gallus gallus*] (SEQ ID NO:222)

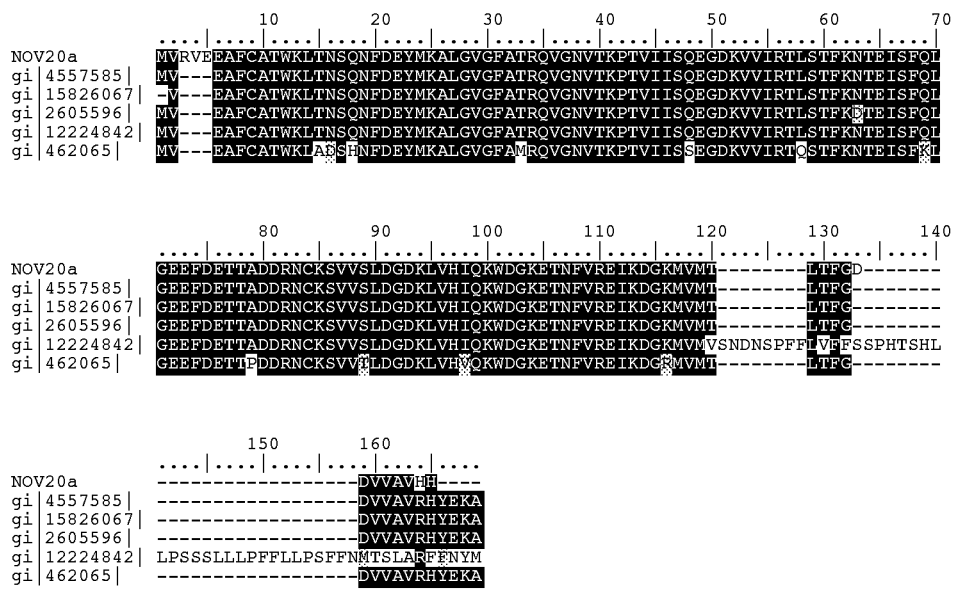

Table 20I lists the domain description from DOMAIN analysis results against NOV20a. This indicates that the NOV20a sequence has properties similar to those of other proteins known to contain these domains.

TABLE 20I

Domain Analysis of NOV20a gnl|Pfam|pfam00061, lipocalin, Lipocalin/cytosolic fatty-acid binding protein family. Lipocalins are transporters for small hydrophobic molecules, such as lipids, steroid hormones, bilins, and retinoids. Alignment subsumes both the lipocalin and fatty acid binding protein signatures from PROSITE. This is supported on structural and functional grounds. Structure is an eight-stranded beta barrel. (SEQ ID NO:223)
CD-Length = 145 residues, 86.2% aligned
Score = 63.2 bits (152), Expect = 9e-12

```
Query:     7 AFCATWKLTNSQNFDEYMK-ALGVGFATRQVGNVTK-PTVIISQEGDKVVIRTLSTFKNT    64
               |  | | |  |||  +|   |||   |||+      |   + | +|||   |   + |
Sbjct:     1 KFAGKWYLVASANFDPELKEELGVLEATRKEITPLKEGNLEIVFDGDKNGICEETFGKLE    60

Query:    65 EISFQLGEEFDETTADDRNCKSVVSLDGDKLVHIQKWDGKETNFVREIKDGKMVMTLTFG   124
               +   +||  |||   | |+|         |   || +|| || | |+    |+       ++
Sbjct:    61 KTK-KLGVEFDYYTGDNRFVVLDTDYDNYLLVCVQKGDGNETSRTAELYGRTPELSPEAL   119

Query:   125 DDVVAV                                                        130
               +
Sbjct:   120 ELFETA                                                        125
```

The murine brain fatty acid binding protein (B-FABP) is encoded by a developmentally regulated gene that is expressed in radial glial cells and immature astrocytes. The human B-FABP gene has been cloned and mapped to chromosome 6q22-23. B-FABP mRNA is expressed in human malignant glioma tumor biopsies and in a subset of malignant glioma cell lines, as well as in human fetal retina and brain. Malignant glioma tumors are characterized by cytoplasmic bundles of glial fibrillary acidic protein (GFAP), a protein normally expressed in mature astrocytes. Establishment of malignant glioma cell lines often results in loss of GFAP. The subset of malignant glioma cell lines that express GFAP mRNA also express B-FABP mRNA. Co-localization experiments in cell lines indicate that the same cells produce both GFAP and B-FABP. These data suggest that some malignant gliomas may be derived from astrocytic precursor cells which can express proteins that are normally produced at different developmental stages in the astrocytic differentiation pathway (Godbout et al., Oncogene. 16(15):1955–62, 1998).

The NOV20 nucleic acid of the invention encoding a Fatty Acid Binding-like protein includes the nucleic acid whose sequence is provided in Tables 20A and 20C, or a fragment thereof. The invention also includes a mutant or variant nucleic acid any of whose bases may be changed from the corresponding base shown in Tables 20A and 20C while still encoding a protein that maintains its Fatty Acid Binding-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 3% of the NOV20a residues and up to about 2% of the NOV20b residues may be so changed.

The NOV20 protein of the invention includes the Fatty Acid Binding-like protein whose sequence is provided in Tables 20B and 20D. The invention also includes a mutant or variant protein any of whose residues may be changed from the corresponding residue shown in Tables 20B and 20D while still encoding a protein that maintains its Fatty Acid Binding-like activities and physiological functions, or a functional fragment thereof. In the mutant or variant protein, up to about 2% of the NOV20a bases and up to about 3% of the NOV20b bases may be so changed.

The NOV20 nucleic acids and proteins of the invention are useful in potential diagnostic and therapeutic applications implicated in various diseases and disorders described below and/or other pathologies. For example, the compositions of the present invention will have efficacy for treatment of patients suffering from: malignant glioma tumors, Arthropathy, progressive pseudorheumatoid, of childhood; Muscular dystrophy, congenital merosin-deficient; Nephropathy, IgA type; Oculodentodigital dysplasia; Ossification of posterior longitudinal ligament of spine; Syndactyly, type III; Hepatic fibrosis susceptibility due to Schistosoma mansoni infection; Hepatic fibrosis susceptibility due to Schistosoma mansoni infection; endometriosis, fertility; Von Hippel-Lindau (VHL) syndrome, Alzheimer's disease, stroke, tuberous sclerosis, hypercalceimia, Parkinson's disease, Huntington's disease, cerebral palsy, epilepsy, Lesch-Nyhan syndrome, multiple sclerosis, ataxia-telangiectasia, leukodystrophies, behavioral disorders, addiction, anxiety, pain, neurodegeneration; cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, tuberous sclerosis, scleroderma, obesity, transplantation; diabetes, autoimmune disease, renal artery stenosis, interstitial nephritis, glomerulonephritis, polycystic kidney disease, systemic lupus erythematosus, renal tubular acidosis, IgA nephropathy, hypercalceimia, systemic lupus erythematosus, autoimmune disease, asthma, emphysema, scleroderma, allergy, ARDS and other diseases, disorders and conditions of the like.

NOV20 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV20 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV21

A disclosed NOV21 nucleic acid of 1931 nucleotides (also referred to as CG57436-01) encoding a novel Platelet Glycoprotein V-like protein is shown in Table 21 A. An open reading frame was identified beginning with an ATG initiation codon at nucleotides 135–137 and ending with a TAA codon at nucleotides 1878–1880. Putative untranslated regions upstream from the intitation codon and downstream from the termination codon are underlined in Table 21A, and the start and stop codons are in bold letters.

TABLE 21A

NOV21 Nucleotide Sequence (SEQ ID NO:75)

AGCATGCGTTCAGTATGTGATGATGGGGTTCAAAGCCAAGCCAGCATTGGCACTGGAGTTGATGTTGGCTTAA

AACTTGCCAGTGTCAGGTAGAGGACCCTGACTAACGTGTGCTCTCTCCCCTTGCACAGGCTATGCCACTGAAG

CATTATCTCCTTTTGCTGGTGGGCTGCCAAGCCTGGGGTGCAGGGTTGGCCTACCATGGCTGCCCTAGCGAGT

GTACCTGCTCCAGGGCCTCCCAGGTGGAGTGCACCGGGGCACGCATTGTGGCGGTGCCCACCCCTCTGCCCTG

GAACGCCATGAGCCTGCAGATCCTCAACACGCACATCACTGAACTCAATGAGTCCCCGTTCCTCAATATTTCA

GCCCTCATCGCCCTGAGGATTGAGAAGAATGAGCTGTCGCGCATCACGCCTGGGGCCTTCCGAAACCTGGGCT

CGCTGCGCTATCTCAGCCTCGCCAACAACAAGCTGCAGGTTCTGCCCATCGGCCTCTTCCAGGGCCTGGACAG

CCTTGAGTCTCTCCTTCTGTCCAGTAACCAGCTGTTGCAGATCCAGCCGGCCCACTTCTCCCAGTGCAGCAAC

CTCAAGGAGCTGCAGTTGCACGGCAACCACCTGGAATACATCCCTGACGGAGCCTTCGACCACCTGGTAGGAC

TCACGAAGCTCAATCTGGGCAAGAATAGCCTCACCCACATCTCACCCAGGGTCTTCCAGCACCTGGGCAATCT

CCAGGTCCTCCGGCTGTATGAGAACAGGCTCACGGATATCCCCATGGGCACTTTTGATGGGCTTGTTAACCTG

CAGGAACTGGCTCTACAGCAGAACCAGATTGGACTGCTCTCCCCTGGTCTCTTCCACAACAACCACAACCTCC

AGAGACTCTACCTGTCCAACAACCACATCTCCCAGCTGCCACCCAGCATCTTCATGCAGCTGCCCCAGCTCAA

CCGTCTTACTCTCTTTGGGAATTCCCTGAAGGAGCTCTCTCTGGGGATCTTCGGGCCCATGCCCAACCTGCGG

GAGCTTTGGCTCTATGACAACCACATCTCTTCTCTACCCGACAATGTCTTCAGCAACCTCCGCCAGTTGCAGG

TCCTGATTCTTAGCCGCAATCAGATCAGCTTCATCTCCCCGGGTGCCTTCAACGGGCTAACGGAGCTTCGGGA

GCTGTCCCTCCACACCAACGCACTGCAGGACCTGGACGGGAATGTCTTCCGCATGTTGGCCAACCTGCAGAAC

ATCTCCCTGCAGAACAATCGCCTCAGACAGCTCCCAGGGAATATCTTCGCCAACGTCAATGGCCTCATGGCCA

TCCAGCTGCAGAACAACCAGCTGGAGAACTTGCCCCTCGGCATCTTCGATCACCTGGGGAAACTGTGTGAGCT

GCGGCTGTATGACAATCCCTGGAGGTGTGACTCAGACATCCTTCCGCTCCGCAACTGGCTCCTGCTCAACCAG

CCTAGGTTAGGGACGGACACTGTACCTGTGTGTTTCAGCCCAGCCAATGTCCGAGGCCAGTCCCTCATTATCA

TCAATGTCAACGTTGCTGTTCCAAGCGTCCATGTACCTGAGGTGCCTAGTTACCCAGAAACACCATGGTACCC

AGACACACCCAGTTACCCTGACACCACATCCGTCTCTTCTACCACTGAGCTAACCAGCCCTGTGGAAGACTAC

ACTGATCTGACTACCATTCAGGTCACTGATGACCGCAGCGTTTGGGGCATGACCCATGCCCATAGCGGGCTGG

CCATTGCCGCCATTGTAATTGGCATTGTCGCCCTGGCCTGCTCCCTGGCTGCCTGCGTCGGCTGTTGCTGCTG

CAAGAAGAGGAGCCAAGCTGTCCTGATGCAGATGAAGGCACCCAATGAGTGTTAAAGAGGCAGGCTGGAGCAG

GGCTGGGGAATGATGGGACTGGAGGACCTGGGA

The NOV21 nucleic acid was identified on chromosome 1 and has 779 of 1317 bases (59%) identical to gb:GENBANK-ID:AF163101|acc:AF163101.1 mRNA from Mus musculus (Mus musculus platelet glycoprotein V gene, partial cds) (E=4.4e$^{-43}$).

A disclosed NOV21 polypeptide (SEQ ID NO:76) encoded by SEQ ID NO:75 is 581 amino acid residues and is presented using the one-letter code in Table 21B. Signal P, Psort and/or Hydropathy results predict that NOV21 contains a signal peptide and is likely to be localized to the plasma membrane with a certainty of 0.4600. The most likely cleavage site for a NOV21 polypeptide is between amino acids 21 and 22: GLA-YH.

TABLE 21B

Encoded NOV21 protein sequence (SEQ ID NO:76)

MPLKHYLLLLVGCQAWGAGLAYHGCPSECTCSRASQVECTGARIVAVPTPLPWNAMSLQILNTHITELNESP

FLNISALIALRIEKNELSRITPGAFRNLGSLRYLSLANNKLQVLPIGLFQGLDSLESLLLSSNQLLQIQPAH

FSQCSNLKELQLHGNHLEYIPDGAFDHLVGLTKLNLGKNSLTHISPRVFQHLGNLQVLRLYENRLTDIPMGT

FDGLVNLQELALQQNQIGLLSPGLFHNNHNLQRLYLSNNHISQLPPSIFMQLPQLNRLTLFGNSLKELSLGI

FGPMPNLRELWLYDNHISSLPDNVFSNLRQLQVLILSRNQISFISPGAFNGLTELRELSLHTNALQDLDGNV

FRMLANLQNISLQNNRLRQLPGNIFANVNGLMAIQLQNNQLENLPLGIFDHLGKLCELRLYDNPWRCDSDIL

PLRNWLLLNQPRLGTDTVPVCFSPANVRGQSLIIINVNVAVPSVHVPEVPSYPETPWYPDTPSYPDTTSVSS

TTELTSPVEDYTDLTTIQVTDDRSVWGMTHAHSGLAIAAIVIGIVALACSLAACVGCCCCKKRSQAVLMQMK

APNEC

The NOV21 amino acid sequence 165 of 434 amino acid residues (38%) identical to, and 235 and 434 amino acid residues (54%) similar to, the 567 amino acid residue ptnr:SPTREMBL-ACC:Q9QZU3 protein from *Mus musculus* (Mouse) (Platelet Glycoprotein V) (E=7.5e$^{-73}$).

NOV21 is expressed in at least the following tissues: Mammary Gland/Breast. This information was derived by determining the tissue sources of the sequences that were included in the invention including but not limited to Seq-Calling sources, Public EST sources, genomic clone sources, literature sources, and/or RACE sources.

Possible SNPs found for NOV21 are listed in Table 21C.

TABLE 21C

SNPs

| Variant | Nucleotide Position | Base Change | Amino Acid Position | Base Change |
|---|---|---|---|---|
| 13377106 | 166 | T > C | 11 | Val > Ala |
| 13377107 | 287 | G > A | Silent | N/A |
| 13377108 | 399 | C > T | Silent | N/A |
| 13377109 | 576 | T > C | 148 | Cys > Arg |
| 13377110 | 1423 | A > G | 430 | Asp > Gly |
| 13377111 | 1517 | C > T | Silent | N/A |
| 13377112 | 1595 | A > G | Silent | N/A |
| 13377113 | 1618 | G > A | 495 | Ser > Asn |
| 13377114 | 1749 | C > T | Silent | N/A |

NOV21 has homology to the amino acid sequences shown in the BLASTP data listed in Table 21D.

TABLE 21D

BLAST results for NOV21

| Gene Index/ Identifier | Protein/ Organism | Length (aa) | Identity (%) | Positives (%) | Expect |
|---|---|---|---|---|---|
| gi\|18554959\|ref\|XP_067453.2\| (XM_067453) | similar to putative (*H. sapiens*) [*Homo sapiens*] | 787 | 510/581 (87%) | 510/581 (87%) | 0.0 |
| gi\|18677767\|ref\|NP_570843.1\| (NM_130830) | leucine-rich repeat protein induced by beta amyloid [*Homo sapiens*] | 581 | 508/581 (87%) | 508/581 (87%) | 0.0 |
| gi\|18565266\|dbj\| BAB 84586.1\| (AB071036) | Lib [*Rattus norvegicus*] | 578 | 426/581 (73%) | 462/581 (79%) | 0.0 |
| gi\|12856544\|dbj\| BAB 30702.1\| (AK017350) | Leucine Rich Repeat containing protein-data source: Pfam, source key: PF00560, evidence: ISS-putative [*Mus musculus*] | 391 | 294/367 (80%) | 317/367 (86%) | e-156 |
| gi\|6980974\|ref\|NP_036927.1\| (NM_012795) | platelete glyco- protein 5 [*Rattus norvegicus*] | 567 | 157/452 (34%) | 224/452 (48%) | 6e-61 |

The homology of these sequences is shown graphically in the ClustalW analysis shown in Table 21E.

TABLE 21E

Clustal W Sequence Alignment

1) NOV21 (SEQ ID NO:76)
2) gi 18554959|refXP_067453.2|(XM_067453) similar to putative (H. sapiens) [Homo sapiens] (SEQ ID NO:224)
3) gi 18677767|refNP_570843.1|(NM_130830) leucine-rich repeat protein induced by beta amyloid [Homo sapiens] (SEQ ID NO:225)
4) gi 18565266|dbj|BAB84586.1|(AM071036) Lib [Rattus norvegicus](SEQ ID NO:226)
5) gi 12856544|dbj|BAB30702.1|(AK017350) Leucine Rich Repeat containing protein~data source: Pfam, source key:PF00560, evidence:ISS~putative [Mus musculus] (SEQ ID NO:227)
6) gi 6980974|refNP_036927.1|(NM_012795) platelete glycoprotein 5 [Rattus norvegicus] (SEQ ID NO:228)

```
                    10        20        30        40        50        60        70
                ....|....|....|....|....|....|....|....|....|....|....|....|....|....|
NOV21           ------------------------------------------------------------------------
gi|18554959|    MSRMSRHPDKDLAQGPFNTCCGCTLMASPANLPPNTQAAAERALSQSRWKRVQVPAPASLSPFPLAMASV
gi|18677767|    ------------------------------------------------------------------------
gi|18565266|    ------------------------------------------------------------------------
gi|12856544|    ------------------------------------------------------------------------
gi|6980974|     ------------------------------------------------------------------------

80        90       100       110       120       130       140
                ....|....|....|....|....|....|....|....|....|....|....|....|....|....|
NOV21           ------------------------------------------------------------------------
gi|18554959|    AFWISILIGCEEQTLCRGWRSPVGDGCAHVPPQERATAEADPPGRCSTSTASSTICGLWHLSPRLQLLPP
gi|18677767|    ------------------------------------------------------------------------
gi|18565266|    ------------------------------------------------------------------------
gi|12856544|    ------------------------------------------------------------------------
gi|6980974|     ------------------------------------------------------------------------

150       160       170       180       190       200       210
                ....|....|....|....|....|....|....|....|....|....|....|....|....|....|
NOV21           ---------------------------------------------------------------MPLK
gi|18554959|    LHSRQGEESGKTEKVLLWGREGLHVWKPGVLQPDVHGTSNLGNCSFLHGLVTAPSCPRRAGAELLAMPLK
gi|18677767|    ---------------------------------------------------------------MPLK
gi|18565266|    ---------------------------------------------------------------MPLK
gi|12856544|    ---------------------------------------------------------------MPLK
gi|6980974|     ------------------------------------------------------------------------

220       230       240       250       260       270       280
                ....|....|....|....|....|....|....|....|....|....|....|....|....|....|
NOV21           HYLLLLVGCQAWGAGLAYHGCPSECTCSRASQVECTGARIVAVPTP-LPWNAMSLQILNTHITELNESPP
gi|18554959|    HYLLLLVGCQAWGAGLAYHGCPSECTCSRASQVECTGARIVAVPTP-LPWNAMSLQILNTHITELNESPP
gi|18677767|    HYLLLLVGCQAWGAGLAYHGCPSECTCSRASQVECTGARIVAVPTP-LPWNAMSLQILNTHITELNESPP
gi|18565266|    HYLLLLVGCQAWALGLAYHGCPSECTCSRASQVECTGARIVAMPTP-LPWNAMSLQVVNTHITELPENLP
gi|12856544|    HYLLLLVSCQAWAAGLAYHGCPSECTCSRASQVECTGAQIVAMPSP-LPWNAMSLQILNTHITELNEDKP
gi|6980974|     MLRSVLESAVLSLVGAQPFPCPKTQKCVVRDAVQCSGGSVAHIAELGLPTNLTHILLFRMDRGVLQSHSP 290       300       310       320       330       340       350
                ....|....|....|....|....|....|....|....|....|....|....|....|....|....|
NOV21           LNISALIALRIEKNELSRITPGAFRNLGSLRYLSLANNKLQVLPIGLFQGLDSLESLLLSSNQLQIQPA
gi|18554959|    LNISALIALRIEKNELSRITPGAFRNLGSLRYLSLANNKLQVLPIGLFQGLDSLESLLLSSNQLQIQPA
gi|18677767|    LNISALIALRIEKNELSRITPGAFRNLGSLRYLSLANNKLQVLPIGLFQGLDSLESLLLSSNQLQIQPA
gi|18565266|    LNISALIALKMEKNELSTIMPGAFRNLGSLRYLSLANNKLRMLPIRVFQDVNNLESLLLSNNQLVQIQPA
gi|12856544|    LNISALIALKMEKNELANIMPGAFRNLGSLRHLSLANNKLKNLEVRLFQDVNNLETLLLSNNQLVQIQPA
gi|6980974|     SGMTVLQRLMLSDSHISAIDPGTENDLVKIKTLRITRNKISHLERAILDKMVLEQLFIDHNALRDLDQN 360       370       380       390       400       410       420
                ....|....|....|....|....|....|....|....|....|....|....|....|....|....|
NOV21           HFSQCSNLKELQLHGNHLEYIPDGAFDHKVGLTKLNLGKNSLTHRSPRVFQHLGNLQVLRLYENRLIDIP
gi|18554959|    HFSQCSNLKELQLHGNHLEYIPDGAFDHKVGLTKLNLGKNSLTHRSPRVFQHLGNLQVLRLYENRLIDIP
gi|18677767|    HFSQCSNLKELQLHGNHLEYIPDGAFDHKVGLTKLNLGKNSLTHRSPRVFQHLGNLQVLRLYENRLIDIP
gi|18565266|    QFSQFSNLEELQLHGNKLESIPEEAFDHKVGLTKLNLGRNSFTHRSPRIFQHLGNLQVLRLHENRLSDIP
gi|12856544|    QFSQFSNLKELQLYGNNLEYIPEGVFDHKVGLTKLNLGNGFTHRSPRVFQHLGNLQVLRLYENRLSDIP
gi|6980974|     LFQNLLNIRDLCLNQNQLSELPANLFSSLGKLKVLDLSRNKLTHIPQGELGAQIKLEKLLYSNRLMSLD 430       440       450       460       470       480       490
                ....|....|....|....|....|....|....|....|....|....|....|....|....|....|
NOV21           MGTELGLVNLQELALQLNQIGLLSPGLFHNNHNLQRLYLSNNHISQLPPSIFMQLPQLNRLTLFGNSLKE
gi|18554959|    MGTELGLVNLQELALQLNQIGLLSPGLFHNNHNLQRLYLSNNHISQLPPSIFMQLPQLNRLTLFGNSLKE
gi|18677767|    MGTELGLVNLQELALQLNQIGLLSPGLFHNNHNLQRLYLSNNHISQLPPSIFMQLPQLNRLTLFGNSLKE
gi|18565266|    MGTELAIGNLQELALQENQIGTLSPGLFHNNRNLQRLYLSNNHISQLPPGIFMQLPQLNKLTLFGNSLRE
gi|12856544|    MGTELAIGNLQELALQENQIGTLSPGLFHNNRNLQRLYLSNNHISHLPPGIFMQPHLNKLTLFGNSLKE
gi|6980974|     SGLLANLGALTELRLHRNHIRSIAPGAFDSLGNLSTLTLSGNLLESLPPNLFLHMSWLTRLTLFENPLEE
```

TABLE 21E-continued

Clustal W Sequence Alignment

```
              500        510        520        530        540        550        560
          ....|....|....|....|....|....|....|....|....|....|....|....|....|....|
NOV21     LSLCNFGPMPNLRELWLYDNHISSLPDNVFSNLRQLQVLILSRN-QISRISPGAFNGLTELRELSLHTNA
gi|18554959| LSLCIFGPMPNLRELWLYENHISSLPDNVFSNLRQLQVLILSRN-QISKISPGAFNGLTELRELSLHTNA
gi|18677767| LSLCVFGPMPNLRELWLYDNHISSLPDNVFSNLRQLQVLILSRN-QKSPISPGAFNGLTELRELSLHTNA
gi|18565266| LSLCVFGPMPNLRELWLYNNHITSLADNIFSELNQLQVLILSHN-QLTYISPGAFNGLTNLRELSLHTNA
gi|12856544| LSLCVFGPMPNLRELWLYNNHITSLPDNTFSELNQLQVLILSHN-QISVISPGAFNGLTNLRELSLHTNA
gi|6980974|  LPEVLFGEMAGLRELWLNGTHLRTLPAAAERNLSGLQTLGLTRNPLESALPPGMPHGLTELRVLAVHTNA 570        580        590        600        610        620        630
          ....|....|....|....|....|....|....|....|....|....|....|....|....|....|
NOV21     LQDLDGNVFRMLANLQNISLQNNRLRQLPGMIFANVNGIMAIQLQNNQLENLPLGIFDHLGKLCELRLYD
gi|18554959| LQDLDGNVFRMLANLQNISLQNNRLRQLPGNIFANVNGIMAIQLQNNQLENLPLGIFDHLGKLCELRLYD
gi|18677767| LQDLDGNVFRMLANLQNISLQNNRLRQLPGNIFANVNGIMAIQLQNNQLENLPLGIFDHLGKLCELRLYD
gi|18565266| LQDLDSNVFRSLANLSLQSNRLRQLPGSIFANVNGITTIQLQNNNLENLPLGIFDHLVNLCELRLYD
gi|12856544| LQDLDGNVFRSLANLG------------------------------------------------------
gi|6980974|  LEELPELALRGLGRLRQVSIRHNRLKALERTLFRNLSSLVTVQLEHNQLKTLPGDVEAALPQLTRVLLGH 640        650        660        670        680        690        700
          ....|....|....|....|....|....|....|....|....|....|....|....|....|....|
NOV21     NPWRCDSDILPLRNWLLLNQPRLGTDTVPVCFSPANVRGQSLIIINVNVAVPSVHVPEVESYPETPWYPD
gi|18554959| NPWRCDSDILPLRNWLLLNQPRLGTDTVPVCFSPANVRGQSLIIINVNVAVPSVHVPEVESYPETPWYPD
gi|18677767| NPWRCDSDILPLRNWLLLNQPRLGTDTVPVCFSPANVRGQSLIIINVNVAVPSVHVPEVESYPETPWYPD
gi|18565266| NPWRCDSDILPLHNWLLLNRARLGTDTLPVCSSPANVRGQSLVIININFPGPSVQGPETE---EVESYPD
gi|12856544| ---------------------------------------------------------------TSHSR
gi|6980974|  NPWLCDCGLWPFLQWLRHHLELLGRDEPEQCNGPESRASLTFWELLQG----------DQWCPSSRGLPP 710        720        730        740        750        760        770
          ....|....|....|....|....|....|....|....|....|....|....|....|....|....|
NOV21     TPSYPDTTSVSSTTELTSPVEDYTDLTTIQVTDDRSVWGMTHAHSGLAIAAIVIGIVALACSLAACVGCC
gi|18554959| TPSYPDTTSVSSTTELTSPVEDYTDLTTIQVTDDRSVWGMTHAHSGLAIAAIVIGIVALACSLAACVGCC
gi|18677767| TPSYPDTTSVSSTTELTSPVEDYTDLTTIQVTDDRSVWGMTQAQSGLAIAAIVIGIVALACSLAACVGCC
gi|18565266| TPSYPDTTSVSSTTEITSAVDDYTDLTTIEATDDRNTWGMTEAQSGLAIAAIVIGILALACSLAACICCC
gi|12856544| ITAEDSSLAASSPLSMVS---------------------------------------------------
gi|6980974|  DPPTENALKAPDPLSRPNSSQSWAWVQLVARGLSPDNRFYWNLYILLLIAQATIAGFIVFAMIKIGQLFR
```

Table 21F lists the domain description from DOMAIN analysis results against NOV21. This indicates that the NOV21 sequence has properties similar to those of other proteins known to contain these domains.

TABLE 21F

Domain Analysis of NOV21 gnlSmart|smart00082, LRRCT, Leucine rich repeat C-terminal
domain (SEQ ID NO:229)
CD-Length = 51 residues, 76.5% aligned
Score = 36.6 bits (83), Expect = 0.004

Query:   423  NPWRCDSDILPLRNWLLLNQPRLGTDTVPVCFSPANVRGQ  462
              ||+ || ++  |  || |+  |       ||  ++||
Sbjct:     1  NPFICDCELRWLLRWLQANR-HLQDPVDLRCASPESLRGP   39

Following injury to a blood vessel, platelets rapidly adhere to the site of exposed subendothelial matrix in the vessel wall, become activated, and secrete granule contents that will recruit and activate other platelets, which then aggregate at the site (thrombus) and seal the defect in the vessel wall. The clot that forms prevents further blood loss (Lopez and Dong, Curr Opin Hematol 4(5):323–9, 1997). Cell-cell and cell-extracellular matrix adhesion are critical aspects of platelet function, regulating interactions between circulating platelets in the bloodstream with the blood vessel wall. The platelet glycoprotein Ib-IX-V complex plays crucial roles in both of these processes by mediating platelet adhesion to sites of blood vessel injury and by participating in the thrombin induced aggregation of platelets in both haemostasis and thrombosis under conditions of high shear blood flow (Lopez and Dong, 1997; Andrews and Berndt, Histol Histopathol 13(3):837–44, 1998). Emerging evidence suggests GP Ib-IX-V-dependent signalling may involve receptor cross-linking and the cytoplasmic signalling protein, 14-3-3 zeta. (Andrews and Berndt, 1998; Williamson et al., Aust N Z J Med 29(3):452–61, 1999).

In addition to this normal physiological response, platelet adhesion is critical in the pathological process of thrombosis, where circulating platelets adhere to sclerotic lesions or undergo shear-induced aggregation within vessels occluded by atherosclerotic plaque (Andrews and Berndt, 1998). Under these circumstances, the resulting thrombus may result in acute myocardial infarction or stroke. The critical role of platelets in the development of the acute coronary syndromes is now well recognised, and a great deal of effort has therefore focused on elucidating the key adhesion receptors mediating platelet-vessel wall and platelet-platelet interactions. The vascular adhesion protein von Willebrand factor (vWf) plays a key role in supporting platelet adhesion to the damaged vessel wall and binds to two adhesion receptors on the platelet surface, the glycoprotein (GP) Ib-V-IX complex and glycoprotein IIb-IIa (Lopez and Dong, 1997; Andrews et al., Thromb Haemost 82(2):357–64, 1999). The GP Ib-V-IX complex is a unique adhesion receptor which enables platelets to roll on a vWf matrix under conditions of rapid blood flow as well as transducing signals leading to the activation of GP IIb-IIIa (Andrews and Berndt, 1998).

Genetic defects of the blood platelet membrane glycoproteins, GPIIb-IIIa (alpha IIb/beta 3; CD41/CD61) and GPIb-V-IX (CD42) are the origin of several rare bleeding disorders, the best known of which are Glanzmann's thrombasthenia, Bernard-Soulier syndrome, and platelet-type von Willebrand's disease (Hayashi and Suzuki, Semin Thromb Hemost 26(1):53–9, 2000; Clemetson and Clemetson, Curr Opin Hematol 1(5):388–93, 1994). In Glanzmann's thrombasthenia, GPIIb-IIa are missing or defective and platelet aggregation is lacking or reduced. Either gene can be affected and mutations leading to lack of expression or to expression of poorly functional form have been described. In Bernard-Soulier syndrome, GPIb-V-IX are missing or defective, leading to poor platelet adhesion at high-shear stress to damaged vessel wall and reduced platelet response to thrombin. Mutations in both GPIb alpha (CD42b) and GPIX (CD42a) have been described. Mutations in GPIb alpha can also lead to platelet-type von Willebrand's disease in which GPIb-V-IX are expressed normally but bind von Willebrand's factor spontaneously, which leads to platelet aggregation and thrombocytopenia. (Clemetson and Clemetson, 1994). Given the homology of the novel protein in this invention to platelet glycoprotein V, which has a critical role in thrombosis, the novel protein in this invention is an excellent antibody target in thrombosis, arterial thrombotic disorders, bleeding disorders, stroke and atherosclerosis.

The NOV21 nucleic acid of the invention encoding a Platelet Glycoprotein V-like protein includes the nucleic acid whose sequence is provided in Table 21A, or a fragment thereof. The invention also includes a mutant or variant nucleic acid any of whose bases may be changed from the corresponding base shown in Table 21A while still encoding a protein that maintains its Platelet Glycoprotein V-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 41% of the NOV21 residues may be so changed.

The NOV21 protein of the invention includes the Platelet Glycoprotein V-like protein whose sequence is provided in Table 21B. The invention also includes a mutant or variant protein any of whose residues may be changed from the corresponding residue shown in Table 21B while still encoding a protein that maintains its Platelet Glycoprotein V-like activities and physiological functions, or a functional fragment thereof. In the mutant or variant protein, up to about 62% of the NOV21 bases may be so changed.

The NOV21 nucleic acids and proteins of the invention are useful in potential diagnostic and therapeutic applications implicated in various diseases and disorders described below and/or other pathologies. For example, the compositions of the present invention will have efficacy for treatment of patients suffering from: cancer, fertility and other diseases, disorders and conditions of the like.

NOV21 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV21 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV22

A disclosed NOV22 nucleic acid of 2189 nucleotides (also referred to as CG57529-01) encoding a novel GARPIN-like protein is shown in Table 22A. An open reading frame was identified beginning with an ATG initiation codon at nucleotides 10–12 and ending with a TGA codon at nucleotides 2056–2058. Putative untranslated regions upstream from the intitation codon and downstream from the termination codon are underlined in Table 22A, and the start and stop codons are in bold letters.

TABLE 22A

NOV22 Nucleotide Sequence (SEQ ID NO:77)
<u>CCGGAGACG</u>ATGCGCCCCCCTTCAAGCCTTCTCATTATTGCTGTTCTCTGTGCACTGGCCAGGCAAGCGGGCT

GGCAACCACGTTTCGTTAACCACCTTTATTCTTGCCGAGGGCAGAGCCTCGCTTCGGTGCCCAGCAGCCTCCC

GCCCCACGCCCGGATGCTCACCCTGGATGCCAACCCTCTCAAGACCCTGTGGAATCACTCCCTCCAGCCTTAC

CCTCTCCTGGAGAGCCTCAGCCTGCACAGCTGCCACCTGGAGCGCATCAGCCGCGGCGCCTTCCAGGAGCAAG

GTCACCTGCGCAGCCTGGTCCTGGGGGACAACTGCCTCTCAGAGAACTACGAAGAGACGGCAGCCGCCCTCCA

CGCCCTGCCGGGCCTGCGGAGGCTGGACTTGTCAGGAAACGCCCTGACGGAGGACATGGCAGCCCTCATGCTC

CAGAACCTCTCCTCGCTGCGGTCCGTGTCCCTGGCGGGGAACACCATCATGCGGCTGGACGACTCCGTCTTCG

TABLE 22A-continued

NOV22 Nucleotide Sequence

AGGGCCTGGAGCGTCTCCGGGAGCTGGATCTGCAGAGGAACTACATCTTCGAGATCGAGGGCGGCGCTTTCGA

CGGCCTGGCTGAGCTGAGGCACCTCAACCTGGCCTTCAACAACCTCCCCTGCATCGTGGACTTCGGGCTCACG

CGGCTGCGGGTCCTCAACGTCAGCTACAACGTCCTGGAGTGGTTCCTCGCGACCGGGGGAGAGGCTGCCTTCG

AGCTGGAGACGCTGGACCTGTCTCACAACCAGCTGCTGTTCTTCCCGCTGCTGCCCCAGTACAGCAAGTTGCG

GACCCTCCTGCTGCGCGACAACAACATGGGCTTCTACCGGGACCTGTACAACACCTCGTCGCCGAGGGAGATG

GTGGCCCAGTTCCTCCTCGTGGACGGCAACGTGACCAACATCACCACCGTCAGCCTCTGGGAAGAATTCTCCT

CCAGCGACCTCGCAGATCTCCGCTTCCTGGACATGAGCCAGAACCAGTTCCAGTACCTGCCAGACGGCTTCCT

GAGGAAAATGCCTTCCCTCTCCCACCTGAACCTCCACCAGAATTGCCTGATGACGCTTCACATTCGGGAGCAC

GAGCCCCCCGGAGCGCTCACCGAGCTGGACCTGAGCCACAACCAGCTGTCGGAGCTGCACCTGGCTCCGGGGC

TGGCCAGCTGCCTGGGCAGCCTGCGCTTGTTCAACCTGAGCTCCAACCAGCTCCTGGGCGTCCCCCCTGGCCT

CTTCGCCAATGCTAGGAACATCACTACACTTGACATGAGCCACAATCAGATCTCACTTTGTCCCCTGCCAGCT

GCCTCGGACCGGGTGGGCCCCCCTAGCTGTGTGGATTTCAGGAATATGGCATCTTTAAGGAGCCTGTCTCTGG

AGGGCTGTGGCCTGGGGGCATTGCCAGACTGCCCATTCCAAGGGACCTCCCTGACCTACTTAGACCTCTCAAG

CAACTGGGGGGTTCTGAATGGGAGCCTCGCCCCACTCCAGGATGTTGCCCCATGTTACAGGTCCTGTCTCTC

AGGAACATGGGCCTCCACTCCAGCTTTATGGCGTTGGACTTCTCTGGGTTTGGGAATCTCAGGGACTTAGATC

TGTCGGGGAATTGCTTGACCACCTTCCCAAGGTTTGGGGGCAGCCTGGCCCTGGAGACCCTGGATCTCCGTAG

AAAACTCGCTCACAGCCCTTCCCCAGAAGGCTGTGTCTGAGCAGCTCTCGAGAGGTCTGCGGACCATCTACCTC

AGTCAGAATCCATATGACTGCTGTGGGGTGGATGGCTGGGGGCCCTGCAGCATGGGCAGACGGTGGCCGACT

GGGCCATGGTCACCTGCAACCTCTCCTCCAAGATCATCCGCGTGACGGAGCTGCCCGGAGGTGTGCCTCGGGA

CTGCAAGTGGGAGCGGCTGGACCTGGGCCTGCTCTACCTCGTGCTCATCCTCCCCAGCTGCCTCACCCTGCTG

GTGGCCTGCACTGTCATCGTCCTCACTTTTAAGAAGCCTCTGCTTCAGGTCATCAAGAGCCGCTGCCACTGGT

CCTCCGTTTACTGACCTGGCTGTGTGCCAAGACTCGAAATTCGGTCCGCACACAACAGGACACTTTCTCTGCC

AGCTTTCAAGATGTGATGCAGAGGCCAAGTCTGACGAATTGAAGTTTCAATTAAAATTTAATATGTTTCCAT

The NOV22 nucleic acid was identified on chromosome 3 and has 671 of 1132 bases (59%) identical to a gb:GENBANK-ID:HUMIGFACID|acc:M86826.1 mRNA from Homo sapiens (Human IGF binding protein complex acid-labile subunit a mRNA, complete cds) (E=2.5e$^{-08}$).

A disclosed NOV22 polypeptide (SEQ ID NO:78) encoded by SEQ ID NO:77 is 682 amino acid residues and is presented using the one-letter code in Table 22B. Signal P, Psort and/or Hydropathy results predict that NOV22 contains a signal peptide and is likely to be localized to the plasma membrane with a certainty of 0.4600. The most likely cleavage site for a NOV22 polypeptide is between amino acids 22 and 23: AGW-QP.

TABLE 22B

Encoded NOV22 protein sequence (SEQ ID NO:78)

MRPPSSLLIIAVLCALARQAGWQPRFVNHLYSCRGQSLASVPSSLPPHARMLTLDANPLKTLWNHSLQPYPL

LESLSLHSCHLERISRGAFQEQGHLRSLVLGDNCLSENYEETAAALHALPGLRRLDLSGNALTEDMAALMLQ

NLSSLRSVSLAGNTIMRLDDSVFEGLERLRELDLQRNYIFEIEGGAFDGLAELRHLNLAFNNLPCIVDFGLT

RLRVLNVSYNVLEWFLATGGEAAFELETLDLSHNQLLFFPLLPQYSKLRTLLLRDNNMGFYRDLYNTSSPRE

MVAQFLLVDGNVTNITTVSLWEEFSSSDLADLRFLDMSQNQFQYLPDGFLRKMPSLSHLNLHQNCLMTLHIR

EHEPPGALTELDLSHNQLSELHLAPGLASCLGSLRLFNLSSNQLLGVPPGLFANARNITTLDMSHNQISLCP

LPAASDRVGPPSCVDFRNMASLRSLSLEGCGLGALPDCPFQGTSLTYLDLSSNWGVLNGSLAPLQDVAPMLQ

TABLE 22B-continued

Encoded NOV22 protein sequence

VLSLRNMGLHSSFMALDFSGFGNLRDLDLSGNCLTTFPRFGGSLALETLDLRRNSLTALPQKAVSEQLSRGL

RTIYLSQNPYDCCGVDGWGALQHGQTVADWAMVTCNLSSKIIRVTELPGGVPRDCKWERLDLGLLYLVLILP

SCLTLLVACTVIVLTFKKPLLQVIKSRCHWSSVY

The NOV22 amino acid sequence 253 of 660 amino acid residues (38%) identical to, and 341 of 660 amino acid residues (51%) similar to, the 662 amino acid residue ptnr:SWISSNEW-ACC:Q14392 protein from *Homo sapiens* (Human) (GARP Protein Precursor (GARPIN) (Glycoprotein A Repetitions Predominant) (E=1.7e$^{-82}$).

NOV22 is expressed in at least the following tissues: ovary, colon, breast and testis. This information was derived by determining the tissue sources of the sequences that were included in the invention including but not limited to Seq-Calling sources, Public EST sources, genomic clone sources, literature sources, and/or RACE sources and because of the expression pattern of (gb:GENBANK-ID:HUMIGFACID|acc:M86826.1) a closely related Human IGF binding protein complex acid-labile subunit a mRNA, complete cds homolog in species *Homo sapiens*.

Possible SNPs found for NOV22 are listed in Table 22C.

TABLE 22C

| | | | SNPs | |
|---|---|---|---|---|
| Variant | Nucleotide Position | Base Change | Amino Acid Position | Base Change |
| 13377115 | 1038 | C > T | Silent | N/A |

TABLE 22D

BLAST results for NOV22

| Gene Index/ Identifier | Protein/ Organism | Length (aa) | Identity (%) | Positives (%) | Expect |
|---|---|---|---|---|---|
| gi/18599627|ref|XP_093473.1| (XM_093473) | hypothetical protein XP_093473 [*Homo sapiens*] | 1558 | 617/658 (93%) | 621/658 (93%) | 0.0 |
| gi|5031707|ref|NP_005503.1| (NM_005512) | glycoprotein A repetitions predominant precursor; garpin [*Homo sapiens*] | 662 | 229/616 (37%) | 305/616 (49%) | 2e-70 |
| gi|7287886|gb| AAF44 924.1| AE003406_129 (AE003416) | hypothetical protein [*Drosophila melanogaster*] | 1471 | 146/505 (28%) | 217/505 (42%) | 3e-22 |
| gi|10728795|gb| AAF5 3442.2| (AE003646) | BG: DS03192.2 gene product [*Drosophila melanogaster*] | 1216 | 146/505 (28%) | 217/505 (42%) | 7e-22 |
| gi|7301872|gb| AAF56 980.1| (AE003772) | CG7896 gene product [*Drosophila melanogaster*] | 1348 | 145/555 (26%) | 230/555 (41%) | 3e-20 |

NOV22 has homology to the amino acid sequences shown in the BLASTP data listed in Table 22D.

The homology of these sequences is shown graphically in the ClustalW analysis shown in Table 22E.

TABLE 22E

Clustal W Sequence Alignment

1) NOV22 (SEQ ID NO:78)
2) gi 18599627|refXP_093473.1|(XM_093473) hypothetical protein XP_093473 [*Homo sapiens*] (SEQ ID NO:230)
3) gi 5031707|refNP_005503.1|(NM_005512) glycoprotein A repetitions predominant precursor; garpin [*Homo sapiens*] (SEQ ID NO:231)
4) gi 7287886|gb AAF44924.1 AE003406_129 (AE003416) hypothetical protein [*Drosophila melanogaster*] (SEQ ID NO:232)
5) gi 10728795|gb AAF53442.2|(AE003646) BG:DS03192.2 gene product [*Drosophila melanogaster*] (SEQ ID NO:233)
6) gi 7301872|gb AAF56980.1|(AE003772) CG7896 gene product [*Drosophila melanogaster*] (SEQ ID NO:234)

TABLE 22E-continued

Clustal W Sequence Alignment

```
                    10        20        30        40        50        60        70
                ....|....|....|....|....|....|....|....|....|....|....|....|....|....|
NOV22           ----------------------------------------------------------------------
gi|18599627|    MVLTHEVGARSRLVLDRLNVATKPGLGTLGGVPRPLNVKSEHSLTSTKPFHTHCPIQSRHNPVRPSRQVL
gi|5031707|     ----------------------------------------------------------------------
gi|7287886|     ----------------------------------------------------------------------
gi|10728795|    ----------------------------------------------------------------------
gi|7301872|     ----------------------------------------------------------------------

80        90        100       110       120       130       140
                ....|....|....|....|....|....|....|....|....|....|....|....|....|....|
NOV22           ----------------------------------------------------------------------
gi|18599627|    SSVVTTRRVKEPGLGPGLLPQPRVPSSTQVPPAPSYREGRWQVATPSEVTRGNKLVILKGNQMLMRYAVER
gi|5031707|     ----------------------------------------------------------------------
gi|7287886|     ----------------------------------------------------------------------
gi|10728795|    ----------------------------------------------------------------------
gi|7301872|     ------------------------MGGKPVSPTERLQRRELAQKRSPRQKQKTAKLPSSQATKSLKCNL 150       160       170       180       190       200       210
                ....|....|....|....|....|....|....|....|....|....|....|....|....|....|
NOV22           ----------------------------------------------------------------------
gi|18599627|    LSAEIMWVSPIEREASWLIRGPKEVRAEQGGAQSGLLTLAVWSRCGKGPGEEGLLGPLNPPPMEAEPHPF
gi|5031707|     ----------------------------------------------------------------------
gi|7287886|     ----------------------------------------------------------------------
gi|10728795|    ----------------------------------------------------------------------
gi|7301872|     QAAPKTETENTFGQLKLTIEELDLSYNLIRRIPEKAFDGLKDSLNELRLANNLLGDNLNPIFSTAELHVL 220       230       240       250       260       270       280
                ....|....|....|....|....|....|....|....|....|....|....|....|....|....|
NOV22           ----------------------------------------------------------------------
gi|18599627|    PESLSPRAPVQRRLTREPENRVYKNVILQVPVGLTVHTSLQTCHKLLELPCATSQPLSFYTLSAGSTGLY
gi|5031707|     ----------------------------------------------------------------------
gi|7287886|     ----------------------------------------------------------------------
gi|10728795|    ----------------------------------------------------------------------
gi|7301872|     KN-------------------LRLLDLSGNKIKLIEEGLLKGCMDLKEFYIDRNSLTSVPTNSLNGPSAL 290       300       310       320       330       340       350
                ....|....|....|....|....|....|....|....|....|....|....|....|....|....|
NOV22           ----------------------------------------------------------------------
gi|18599627|    PALDSKLHCFALPLPASRPSSVPDACSVHCISLFPEEFTTFLPLFGYLLLFGARAGSKEELPEGARLFAEE
gi|5031707|     ----------------------------------------------------------------------
gi|7287886|     ----------------------------------------------------------------------
gi|10728795|    ----------------------------------------------------------------------
gi|7301872|     RHLSLRQNQIG---------SLLADSFNAQRQLEIIDLRHNVIRSIDSLAFKGLQKIREIKLAGNRISHLN 360       370       380       390       400       410       420
                ....|....|....|....|....|....|....|....|....|....|....|....|....|....|
NOV22           ----------------------------------------------------------------------
gi|18599627|    VRSRVIGREVRGSREGAESSGARIMQGPEPVVPPQEGPVHTSRKFGLHCPSGCALRALPLPGLSQHRVPI
gi|5031707|     ----------------------------------------------------------------------
gi|7287886|     ----------------------------------------------------------------------
gi|10728795|    ----------------------------------------------------------------------
gi|7301872|     SDVFEKLQSLQKLDLSENFFGQFPTVALAAVPGLKHLNLSSNMLQQLDYTHMQVVRSLESLDISRNTITT 430       440       450       460       470       480       490
                ....|....|....|....|....|....|....|....|....|....|....|....|....|....|
NOV22           ----------------------------------------------------------------------
gi|18599627|    FPKVLSALDQTMDRKRQCPHRGQSPESVAAGGHGQQGARGADLRIGDRHLLQEEKHAGKSPQPHPTPALP
gi|5031707|     ----------------------------------------------------------------------
gi|7287886|     ----------------------------------------------------------------------
gi|10728795|    ----------------------------------------------------------------------
gi|7301872|     ITPGTFREMGALKYLDLSLNSLRTIEDDALEG----------LDS-----LQTLIIKDNNILLVPGSALG 500       510       520       530       540       550       560
                ....|....|....|....|....|....|....|....|....|....|....|....|....|....|
NOV22           ----------------------------------------------------------------------
gi|18599627|    SASALTPPLFQDGHHEALSGTNVGGLGR--LGGVPRPLNVKSEHSLTSTKPFHTHCPIQSRHNPVRPSRQ
gi|5031707|     ----------------------------------------------------------------------
gi|7287886|     ----------------------------------------------------------------------
gi|10728795|    ----------------------------------------------------------------------
gi|7301872|     RLPQLTSLQLDYNRVAALSAEILGSLQAGDITTLSLSRNVIRELPPGSFQMFSSLHTLDLSGNSLAVINA 570       580       590       600       610       620       630
                ....|....|....|....|....|....|....|....|....|....|....|....|....|....|
NOV22           ----------------------------------------------------------------------
gi|18599627|    VLSSVVTTRRVKEPGLGPGLLPQPRVPSSTQVPPAPSYTEGRWQVATPSAVTRGNKLVILKGNQMLMRYAV
gi|5031707|     ----------------------------------------------------------------------
gi|7287886|     ----------------------------------------------------------------------
gi|10728795|    ----------------------------------------------------------------------
gi|7301872|     DTFAGLESTLMALKLSQNRLTGLGGAPWVLPELRSLDLSGNTLTELPSTIFEELENVQSLNLSGNHLTPL
```

TABLE 22E-continued

Clustal W Sequence Alignment

```
                   640        650        660        670        680        690        700
               ....|....|....|....|....|....|....|....|....|....|....|....|....|....|
NOV22          --------------------MRPP----------SSLLITAVLCALAR--------------------
gi|18599627|   ERLSAEIMWVSPIEREASWLIRGPKEVRAEQGGAQSGILTLAVWSRCGKGPGEEGLLGPLNPPPMEAEPH
gi|5031707|    --------------------MRPQ-------------ILLLLALLTLG--------------------
gi|7287886|    ----------------------------------------------------------------------
gi|10728795|   ----------------------------------------------------------------------
gi|7301872|    TGALFKPLDRLQVIDLSGCNIRQISG----------DLIAGLQDLKHIYLNDN-----------------

710        720        730        740        750        760        770
               ....|....|....|....|....|....|....|....|....|....|....|....|....|....|
NOV22          ----------------------------------------------------------QAGWQPR-
gi|18599627|   PFPESLSPRAPVQRRLTREPENRIQFFDTQGQLFQRDWSHSSRAALEMELLPLWLCLGFHFLTVGWRNRS
gi|5031707|    -----------------------------------------------------------LAAQHQDKV
gi|7287886|    ---------------------------------------------------------------------
gi|10728795|   ---------------------------------------------------------------------
gi|7301872|    ----------------------------------------------------------QLQELQDGS 780        790        800        810        820        830        840
               ....|....|....|....|....|....|....|....|....|....|....|....|....|....|
NOV22          -------------FVNHLYSCRGQSLALVPSSLPEHARMLTLDANPLKTLWNHSLQPYPLLRSLSLHSVHL
gi|18599627|   GTATAASQGVCKLVGGAADCRGQSLALVPSSLPEHARMLTLDANPLKTLWNHSLQPYPLLRSLSLHSVHL
gi|5031707|    P---------CKMVDKKVSCQVLGLLQVPSVLPEDTETLDLSGNQLRSILASPLGFYTALRHLDLSINEI
gi|7287886|    -----------MQRTNIELERQRHLANWLMNSREHMPGGPAAATTTS---AAAATTPTASAIKGATITTA
gi|10728795|   -----------METPDTYYSKDEYVEIASGNKVSRHTVLCGSQN-------ILLNGKVIVQSGAIIRGDL
gi|7301872|    FVN-----LWNISSIDLSNNRIGSIRSGAFVNVMKLQKLDLHGNQLSAFKGEYFNTGTGIKELDISDNQL 850        860        870        880        890        900        910
               ....|....|....|....|....|....|....|....|....|....|....|....|....|....|
NOV22          ERISRGAFQEQGHLRSIVLGDNCLSENYEETAAALHALPGLRRIDLSGNALTEDMAALMLQNLSSLRSVS
gi|18599627|   ERISRGAFQEQGHLRSIVLGDNCLSENYEETAAALHALPGLRRIDLSGNALTEDMAALMLQNLSSLRSVS
gi|5031707|    SFLQPGAFQALTHLEHLSLAHNRLAMATALSAGGLGPLPRVTSIDLSGNSLYSGLERLLGEAPSLHTLS
gi|7287886|    TTTNPGSTVGGAGAGPVGGNGVATAAAAGAPSNSVAAAAAAACNGGAAVGAHHGHHSAAGARKPKLRRFN
gi|10728795|   ANVRTGRYCVIGKNSVIRPPYKQFSKG-----IAFFPMHVGEHVFVGEGAVVS---AATIGSYVYIGKNA
gi|7301872|    SYLFPSEFEIHPRLREIRAANNKFSF---FPAELISTLQYLEHIDLSHNQLKT-IEELDFARLPRLRVLL 920        930        940        950        960        970        980
               ....|....|....|....|....|....|....|....|....|....|....|....|....|....|
NOV22          LAGNTIMRLDDSVFEGLERLRELDLQRNYIFEIEGGAFDGIAELRHLNLAFNNLPCIVD-----FGLTRL
gi|18599627|   LAGNTIMRLDDSVFEGLERLRELDLQRNYIFEIEGGAFDGIAELRHLNLAFNNLPCIVD-----FGLTRL
gi|5031707|    LAFNSLTRLTRHTPRLMPALEQLDLHSNVLMDIEDCAFSGLPRITHLNLSRNSITCISD-----FSLQQL
gi|7287886|    SHDTSSNMFSVADFENARLARRNLIELN---QRRARRVRGSANNSTYGLGSGS-GLLGG-----AHSGYC
gi|10728795|   IIGRRCVLKDCCVIEDGAVTPPETTVSSYMRYTARGTIEGGQGNPFVP-----AAMQD-----------
gi|7301872|    VANNQLDMYSEMAPHNSTQLQILDLAHNNLDRIGERTFRGLVRLEQLNIEGNRISELSDGVFERTKLQML 990        1000       1010       1020       1030       1040       1050
               ....|....|....|....|....|....|....|....|....|....|....|....|....|....|
NOV22          RVLNVSYNVLEWFLATGG-EAAFDLETFDLSHNQLFFP-LLPQYSKLRTLLLRDNNMGFYRDLYNTSSE
gi|18599627|   RVLNVSYNVLEWFLATGG-EAAFDLETFDLSHNQLFFP-LLPQYSKLRTLLLRDNNMGFYRDLYNTSSE
gi|5031707|    RVLDLSCNSIEAFQTASQPQAEFQLTWFDLRENKTLHFP-DIAALPRLIYINLSNNLIRLP-----IGPF
gi|7287886|    DALNGSGDYSTGDSKASKGSSEGALTAIEFLE-RN--S---LPRVVKILHASKSSNETLQSS----ESHG
gi|10728795|   EMINYTKSFYEHFVRAPAPAS-------------------------------------------------
gi|7301872|    ENLAHNRFEYAPLNALQRQFFFVSSVDLSHNKIKELPGDDSIMVNIKRIDLSFNPDSSKAVHNVLNEE 1060       1070       1080       1090       1100       1110       1120
               ....|....|....|....|....|....|....|....|....|....|....|....|....|....|
NOV22          EEMVAQFLLVDGNVTNITTVSLWEEFSSSDLADLRFLLMSQNPFQYLPDGFLRKMPSLSHLMLHQNCLMI
gi|18599627|   EEMVAQFLLVDGNVTNITTVSLWEEFSSSDLADLRFLLMSQNPFQYLPDGFLRKMPSLSHLMLHQNCLMI
gi|5031707|    QDSKGIHAPSEG-WSALPLSAPSGNASGRPLSQLLNLDLSYNEISLLPDSFLEHLTSLCFLNLSRNCLRI
gi|7287886|    SSTAASSSSSTG-------------ANPFGSGGSGGGNISSGNIDTGTHSSSSGGSATGNGTGSGPGLSS
gi|10728795|   ---------------------------------------------------------------------
gi|7301872|    KTVRELSLAGTG----------IENLELLETPFLQFLNLSHNKLKNVKPEVFQRVTLLETLDLSSNQLES 1130       1140       1150       1160       1170       1180       1190
               ....|....|....|....|....|....|....|....|....|....|....|....|....|....|
NOV22          LHIR--EHEPPGALTELDLSHNQLSELHLAPG-LASCLGSLRLFNLS------SNQLLGVPPGLFANARN
gi|18599627|   LHIR--EHEPPGALTELDLSHNQLSELHLAPG-LASCLGSLRLFNLS------SNQLLGVPPGLFANARN
gi|5031707|    FEAR--RLGSLPCLMLLDLSHNALETELG----ARALGSLRTLLLQ-------GNALRDLPPYTFANLAS
gi|7287886|    GSGS----GSGSGHQNNNGRHSSNGGTPPG---HDELFLLYRLVRQR--------NIYHGHNAKTQASQRK
gi|10728795|   ---------------------------------------------------------------------
gi|7301872|    LEDLSMAWPQLQVLQSLDVSNNSFEIVSQSNFGKLEMLRSLRLSHLPQCTRIEKNAFKQLPNLVSLEAYD 1200       1210       1220       1230       1240       1250       1260
               ....|....|....|....|....|....|....|....|....|....|....|....|....|....|
NOV22          ITTLDMSHNQ--ISLCPLPAASDRVGPPSCVDFRNMASLR-----SLSLEGCGLGALPDCPFQGTSLTYL
gi|18599627|   ITTLDMSHNQ--ISLCPLPAASDRVGPPSCVDFRNMASLR-----SLSLEGCGLGALPDCPFQGTSLTYL
gi|5031707|    LQRLNLQGNR--VSPVGGP---DEPGPSGCVAFSGITSLR-----SLSLVDNEIELIRAGAFLHTPLTEL
gi|7287886|    KTLLIPQEFP-------GY--------FSMLSEKGLP--------TALQYGSLIQLVRERVYKFVSVDNM
gi|10728795|   ---------------------------------------------------------------------
gi|7301872|    LPLLGYLDLQGIIELLPGLEVLDIEVKDSSIGSEQIQPLKHPRLKSLGIRCDRLKSISSGTLAGLKSNDL
```

TABLE 22E-continued

Clustal W Sequence Alignment

```
                1270      1280      1290      1300      1310      1320      1330
             ....|....|....|....|....|....|....|....|....|....|....|....|....|....|
NOV22        DLSSNWGVLNGSLAPLQDVAPMLQVLSLRNMGLHSSFMALDFSGFGNLEDLDLSGNCLTTFPRLGGS---
gi|18599627| DLSSNWGVLNGSLAPLQDVAPMLQVLSLRNMGLHSSFMALDFSGFGNLEDLDLSGNCLTTFPRLGGS---
gi|5031707|  DLSENPG-LEVATGALGGLEASLEVLSLQGNGLM--VLQVDLPCFICLKRLNLAENRLSHLPANRQA---
gi|7287886|  PAFTESS------PNSTSSPTHEGCLPINKGRPQ------------YVKTTARGGQVFRLLAVEEDG---
gi|10728795| ----------------------------------------------------------------------
gi|7301872|  SVQLRNTSLNALPPALLFPVPRSSHLSLNVEGSKITVLVPQFLNALEDKRASLQLQGLASNPIVCDCNAR 1340      1350      1360      1370      1380      1390      1400
                     ....|....|....|....|....|....|....|....|....|....|....|....|....|
NOV22        ----------------------LALLTLDLRRNSLIALPQKAVSEQLSRGLRTIYLSQNPYDCCGVDGWG
gi|18599627| ----------------------LALLTLDLRRNSLIALPQKAVSEQLSRGLRTIYLSQNPYDCCGVDGWG
gi|5031707|  ----------------------VSLLVLDIRNNSFSLLPGSAMGG-LETSLRRLYLQGNPLSCCGNGWLA
gi|7287886|  ----------------------K-QDQVNMSQHGNGNATRSHGSGYMGREKEKNRYAQLLNENRQVLYVP
gi|10728795| ----------------------------------------------------------------------
gi|7301872|  ALRRWLPSSGMPDVTCASPAYLLNRVLIEVGDDELTCDARRMTSSTSRPTASVPULLKTSSQLVTRSSST 1410      1420      1430      1440      1450      1460      1470
             ....|....|....|....|....|....|....|....|....|....|....|....|....|....|
NOV22        ALQHGQTVADWAMVTCNLSSKIIRVTELPGGVPRDCKWERLDLGLLYLVLILPSCLTLLVACTVIVLTFK
gi|18599627| ALQHGQTVADWAMVTCNLSSKIIRVTELPGGVPRDCKWERLDLGLLYLVLILPSCLTLLVACTVIVLTFK
gi|5031707|  AQLHQGRVDVDATQDLICRFSSQEEVSLSHVRPEDCEKGGLKNINLIIILTFILVSAILITTLAACCCVR
gi|7287886|  LSTKGKFYEIEPGI--------------------------------------------------------
gi|10728795| ----------------------------------------------------------------------
gi|7301872|  TEEPLIIWSLEPTQPPSLKKMKTKAPLMKAQSPIISNDDTLIIGIVGGVVAFIAILIIIICIIRLRMSNA 1480      1490      1500      1510      1520      1530      1540
             ....|....|....|....|....|....|....|....|....|....|....|....|....|....|
NOV22        KPLLQV--IKSR----------------CHWSSVY-----------------------------------
gi|18599627| KPLLQVPWLHTRSLWQTDMTLPWRNQENNNWPRVYPVSKPTARDSPRSEGNKFCPLSLLLPLRPGPIGEP
gi|5031707|  RQKFNQQYKA------------------------------------------------------------
gi|7287886|  ----------------------------------------------------------------------
gi|10728795| ----------------------------------------------------------------------
gi|7301872|  EYQQNATMIGIPAGMQMGAHNAAYNYKNGAGAALYAVPPYHATLPHKAASIHQSSQNLSQRQQQQQQQQQ 1550      1560      1570      1580      1590      1600
             ....|....|....|....|....|....|....|....|....|....|....|....|...
NOV22        ------------------------------------------------------------------
gi|18599627| TGEGRTHKACYQSSSCGKQIPSAECPGEEAQCFLLSYQRCKMQVRNKAKRGKGEKNGKLSWLDRNASL
gi|5031707|  ------------------------------------------------------------------
gi|7287886|  ------------------------------------------------------------------
gi|10728795| ------------------------------------------------------------------
gi|7301872|  VAAAAAAYSTMSRMSYFSGAGGGNGDGAESLTHQHPHQHQPYIIYSDDKAYR--------------
```

The NOV22 protein described herein belongs to the leucine-rich repeat protein family. It is homologous to GARPIN, insulin-like growth factor-binding protein, and platelet glycoprotein V. The leucine-rich repeat (INTERPRO IPR001611) is a recently characterized structural motif used in molecular recognition processes as diverse as signal transduction, cell adhesion, cell development, DNA repair and RNA processing. All proteins containing these repeats are thought to be involved in protein-protein interactions (Deisenhofer and Kobe, Trends Biochem. Sci. 19: 415–421, 1994).

Ollendorff et al. reported a new human gene, named GARP, encodes a putative transmembrane protein of 662 amino acids, the extracellular portion of which is almost entirely made of leucine-rich repeats. The molecular weight of the protein immunoprecipitated from transfected cells is 80,000. The GARP protein has structural similarities with the human GP Ib alpha and GP V platelet proteins, and with the Chaoptin, Toll, and Connectin adhesion molecules of Drosophila (Ollendorff et al., Cell Growth Differ 5(2):213–9, 1994).

Human platelet glycoprotein (GP) V, is a part of the Ib-V-IX system of surface glycoproteins (GPs Ib alpha, Ib beta, V, IX) that constitute the receptor for von Willebrand factor (vWf) and mediate the adhesion of platelets to injured vascular surfaces in the arterial circulation, a critical initiating event in hemostasis. System members share physical associations, leucine-rich glycoprotein (LRG) structures, and a congenital deficiency state, Bernard-Soulier syndrome (Hickey et al., Proc Natl Acad Sci U S A 90(18):8327–31, 1993). A 16-amino acid signal peptide is present. Mature GP V is a 544-amino acid transmembrane protein with a 504-amino acid extracellular domain that encompasses a set of 15 tandem LRG repeats in a "flank-LRG center-flank" array (Roth, Blood 77, 5–19, 1991) along with eight putative N-linked glycosylation sites and cleavage sites for thrombin and calpain. GP V is a transmembrane, adhesive LRG protein that plays an undefined, but potentially critical, role in the expression and/or function of the Ib-V-IX receptor for vWf/shear-dependent platelet adhesion in arteries (Hickey et al., Proc Natl Acad Sci U S A 90(18):8327–31, 1993).

Nearly all of the insulin-like growth factor (IGF) in the circulation is bound in a heterotrimeric complex composed of IGF, IGF-binding protein-3, and the acid-labile subunit (ALS). Full-length clones encoding ALS have been isolated from human liver cDNA libraries by using probes based on amino acid sequence data from the purified protein. These clones encode a mature protein of 578 amino acids preceded by a 27-amino acid hydrophobic sequence indicative of a secretion signal. Expression of the cDNA clones in mammalian tissue culture cells results in the secretion into the culture medium of ALS activity that can form the expected complex with IGF-I and IGF-binding protein-3. The amino acid sequence of ALS is largely composed of 18–20 leucine-rich repeats of 24 amino acids. These repeats are found in a number of diverse proteins that, like ALS, participate in protein-protein interactions (Leong et al., Mol Endocrinol 6(6):870–6, 1992).

Because of the presence of the Leucine rich repeat domains and the homology to the GARPIN, platelet glycoprotein (GP) V, and IGFBP, it is anticipated that NOV22 described here will have useful properties and functions similar to these genes.

The NOV22 nucleic acid of the invention encoding a GARPIN-like protein includes the nucleic acid whose sequence is provided in Table 22A, or a fragment thereof. The invention also includes a mutant or variant nucleic acid any of whose bases may be changed from the corresponding base shown in Table 22A while still encoding a protein that maintains its GARPIN-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 41% of the NOV22 residues may be so changed.

The NOV22 protein of the invention includes the GARPIN-like protein whose sequence is provided in Table 22B. The invention also includes a mutant or variant protein any of whose residues may be changed from the corresponding residue shown in Table 22B while still encoding a protein that maintains its GARPIN-like activities and physiological functions, or a functional fragment thereof. In the mutant or variant protein, up to about 62% of the NOV22 bases may be so changed.

The NOV22 nucleic acids and proteins of the invention are useful in potential diagnostic and therapeutic applications implicated in various diseases and disorders described below and/or other pathologies. For example, the compositions of the present invention will have efficacy for treatment of patients suffering from: fertility, hypogonadism, endometriosis and other diseases, disorders and conditions of the like.

NOV22 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV22 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV23

A disclosed NOV23 nucleic acid of 2484 nucleotides (also referred to as CG57351-01) encoding a novel Centaurin Beta 2-like protein is shown in Table 23A. An open reading frame was identified beginning with an ATG initiation codon at nucleotides 15–17 and ending with a TAG codon at nucleotides 2307–2309. Putative untranslated regions upstream from the intitation codon and downstream from the termination codon are underlined in Table 23A, and the start and stop codons are in bold letters.

TABLE 23A

NOV23 Nucleotide Sequence (SEQ ID NO:79)
<u>CGGCCGCCGCAGCC</u>ATGACCGTGGAGTTCGAGAAGTGCGTCAAGAACTCCCCGCGCTTCAGGGCGACCATTGA

CGAGGTGGAGACGGACGTGGTGGAGATTGAGGCCAAACTGGACAAGCTGGTGAAGCTGTGCAGTGGCATGGTG

GAAGCCGGTAAGGCCTACGTCAGCACCAGCAGGCTTTTCGTGAGCGGCGTCCGCGACCTGTCCCAGCAGTGCC

AGGGCGACACCGTCATCTCGGAATGTCTGCAGAGGTTCGCTGACAGCCTACAGGAGGTGGTGAACTACCACAT

GATCCTGTTTGACCAGGCCCAGAGGTCCGTGCGGCAGCAGCTCCAGAGCTTTGTCAAAGAGGATGTGCGGAAG

TTCAAGGAGACAAAGAAGCAGTTTGACAAGGTGCGGGAGGACCTGGAGCTGTCCCTGGTGAGGAACGCCCAGG

CCCCGAGGCACCGGCCCCACGAGGTGGAGGAAGCCACCGGGGCCCTCACCCTCACCAGGAAGTGCTTCCGCCA

CCTGGCACTGGACTATGTGCTCCAGATCAATGTTCTGCAGGCCAAGAAGAAGTTTGAGATCCTGGACTCTATG

CTGTCCTTCATGCACGCCCAGTCCAGCTTCTTCCAGCAGGGCTACAGCCTCCTGCACCAGCTGGACCCCTACA

TGAAGAAGCTGGCAGCCGAGCTGGACCAGCTGGTGATCGACTCTGCGGTGGAAAAGCGTGAGATGGAGCGAAA

GCACGCCGCCATCCAGCAGCGGACCCTTAGGGACTTCTCCTACGATGAGTCCAAAGTGGAGTTTGACGTGGAC

GCGCCCAGTGGGGTGGTGATGGAGGGCTACCTCTTCAAGAGGGCCAGCAACGCTTTCAAGACATGGAACCGGC

GCTGGTTCTCCATTCAGAACAGCCAGCTGGTCTACCAGAAGAAGCTCAAGGATGCCCTCACCGTGGTGGTGGA

TGACCTCCGCCTGTGCTCTGTGAAGCCGTGTGAGGACATCGAGCGGAGGTTCTGCTTCGAGGTGCTGTCACCC

ACCAAGAGCTGCATGCTGCAGGCTGACTCCGAGAAGCTGCGGCAAGCCTGGGTCCAGGCTGTGCAGGCCAGCA

TCGCCTCCGCCTACCGCGAGAGCCCTGACAGTTGCTATAGCGAGAGGCTGGACCGCACAGCATCCCCGTCCAC

TABLE 23A-continued

NOV23 Nucleotide Sequence

GAGCAGCATCGACTCCGCCACCGACACTCGGGAGCGTGGCGTGAAGGGCGAGAGTGTGCTGCAGCGTGTGCAG

AGTGTGGCCGGCAACAGCCAGTGCGGCGACTGCGGCCAGCCGGACCCCCGCTGGGCCAGCATCAACCTGGGCG

TGCTGCTCTGCATTGAGTGCTCCGGCATCCACAGGAGCCTGGGTGTCCACTGCTCCAAGGTGCGGTCCCTGAC

GCTGGACTCGTGGGAGCCTGAGCTGCTAAAGCTGATGTGTGAGCTTGGAAACAGCGCTGTGAATCAGATCTAT

GAGGCCCAGTGTGAGGGTGCAGGCAGCAGGAAACCCACAGCCAGCAGCTCCCGGCAGGACAAGGAGGCCTGGA

TCAAGGACAAATACGTGGAAAAGAAGTTTCTGCGGAAGGCGCCCATGGCACCAGCCCTGGAGGCCCCAAGACG

CTGGAGGGTGCAGAAGTGCCTGCGGCCCCACAGCTCTCCCCGCGCTCCCACTGCCCGCCGCAAGGTCCGGCTT

GAGCCCGTTCTGCCCTGTGTGGCCGCTCTGTCCTCAGAGGGTGCAGAGTCGGAGGAGTCCAGCGGTGAGGCAG

ACGGGGACACTGAGGCCGAGGCCTGGGGCCTGGCGGACGTGCGCGAGCTGCACCCGGGGCTCTTGGCGCACCG

CGCAGCGCGTGCCCGCGACCTTCCTGCGCTGGCGGCGGCGCTGGCCCACGGGGCCGAGGTCAACTGGGCGGAC

GCGGAGGATGAGGGCAAGACGCCGCTGGTGCAGGCCGTGCTAGGGGGCTCCTTGATCGTCTGTGAGTTCCTGC

TGCAAAACGGAGCGGACGTGAACCAAAGAGACAGCCGGGGCCGGGCGCCCCTGCACCACGCCACGCTGCTGGG

CCGCACCGGCCAGGTTTGCCTGTTCCTGAAGCGGGGCGCGGACCAGCACGCCCTGGACCAAGAGCAGCGGGAC

CCGTTGGCCATCGCAGTGCAGGCGGCCAACGCTGACATCGTGACACTGCTCCGTCTGGCGCGCATGGCGGAGG

AAATGCGCGAGGCCGAGGCTGCCCCTGGTCCCCGGGCGCCCTGGCGGGCAGCCCCACGGAGCTCCAGTTCCG

CAGGTGTATCCAGGAGTTCATCAGCCTCCACCTGGAAGAGAGCTAGGGCCGGGCAGGCCGGGCAGCTGCCACC

CCGCCCGGCCCGACGCCCCGCATGCCCCGAAGTCCCTGGCGCCCACCCGGCCGCGGCCCTGCGTGTGACCCGC

GGGTCGATACCTGGCAGCCCCAGTGCTGGGGCGCCGCGGCCCTGCTCGCCCAGGAGGAGAGCGAGGGCCCCAC

AC

The NOV23 nucleic acid was identified on chromosome 1p36.33 and has 608 of 891 bases (68%) identical to a gb:GENBANK-ID:HSA238248|acc:AJ238248.1 mRNA from *Homo sapiens* (*Homo sapiens* mRNA for centaurin beta2) (E=5.9e$^{-149}$).

A disclosed NOV23 polypeptide (SEQ ID NO:80) encoded by SEQ ID NO:79 is 764 amino acid residues and is presented using the one-letter code in Table 23B. Signal P, Psort and/or Hydropathy results predict that NOV23 contains a signal peptide and is likely to be localized to the plasma membrane with a certainty of 0.7000 and to the nucleus with a certainty of 0.6000.

TABLE 23B

Encoded NOV23 protein sequence (SEQ ID NO:80)
MTVEFEKCVKNSPRFRATIDEVETDVVEIEAKLDKLVKLCSGMVEAGKAYVSTSRLFVSGVRDLSQQCQGDT

VISECLQRFADSLQEVVNYHMILFDQAQRSVRQQLQSFVKEDVRKFKETKKQFDKVREDLELSLVRNAQAPR

HRPHEVEEATGALTLTRKCFRHLALDYVLQINVLQAKKKFEILDSMLSFMHAQSSFFQQGYSLLHQLDPYMK

KLAAELDQLVIDSAVEKREMERKHAAIQQRTLRDFSYDESKVEFDVDAPSGVVMEGYLFKRASNAFKTWNRR

WFSIQNSQLVYQKKLKDALTVVVDDLRLCSVKPCEDIERRFCFEVLSPTKSCMLQADSEKLRQAWVQAVQAS

IASAYRESPDSCYSERLDRTASPSTSSIDSATDTRERGVKGESVLQRVQSVAGNSQCGDCGQPDPRWASINL

GVLLCIECSGIHRSLGVHCSKVRSLTLDSWEPELLKLMCELGNSAVNQIYEAQCEGAGSRKPTASSSRQDKE

AWIKDKYVEKKFLRKAPMAPALEAPRRWRVQKCLRPHSSPRAPTARRKVRLEPVLPCVAALSSEGAESEESS

GEADGDTEAEAWGLADVRELHPGLLAHRAARARDLPALAAALAHGAEVNWADAEDEGKTPLVQAVLGGSLIV

CEFLLQNGADVNQRDSRGRAPLHHATLLGRTGQVCLFLKRGADQHALDQEQRDPLAIAVQAANADIVTLLRL

ARMAEEMREAEAAPGPPGALAGSPTELQFRRCIQEFISLHLEES

The NOV23 amino acid sequence 456 of 744 amino acid residues (61%) identical to, and 576 of 744 amino acid residues (77%) similar to, the 778 amino acid residue ptnr:SPTREMBL-ACC:Q9UQR3 protein from *Homo sapiens* (Human) (CENTAURIN BETA2) (E=3.4e$^{-237}$).

NOV23 is expressed in at least the following tissues: Brain, mammary gland/breast, pituitary gland, germ cell, ovary, testis and muscle. This information was derived by determining the tissue sources of the sequences that were included in the invention including but not limited to Seq-Calling sources, Public EST sources, genomic clone sources, literature sources, and/or RACE sources.

Possible SNPs found for NOV23 are listed in Table 23C.

TABLE 23C

SNPs

| Variant | Nucleotide Position | Base Change | Amino Acid Position | Base Change |
|---|---|---|---|---|
| 13377116 | 1390 | T > C | 459 | Leu > Pro |
| 13376624 | 1464 | G > A | 484 | Ala > Thr |
| 13376623 | 1480 | C > T | 489 | Ala > Val |
| 13376622 | 1576 | C > T | 521 | Pro > Leu |

NOV23 has homology to the amino acid sequences shown in the BLASTP data listed in Table 23D.

TABLE 23D

BLAST results for NOV23

| Gene Index/ Identifier | Protein/ Organism | Length (aa) | Identity (%) | Positives (%) | Expect |
|---|---|---|---|---|---|
| gi\|12697977\|dbj\| BAB21807.1\| | KIAA1716 protein | 804 | 665/770 (86%) | 666/ 770 | 0.0 |
| (AB051503) | [*Homo sapiens*] | | | (86%) | |
| gi\|16945966\|ref\|NP_ 085152.1\| (NM_030649) | centaurin, beta 5 [*Homo sapiens*] | 759 | 654/759 (86%) | 655/ 759 (86%) | 0.0 |
| gi\|174348171\|ref\|XP_ 027698.2\| (XM_027698) | KIAA1716 protein [*Homo sapiens*] | 834 | 547/566 (96%) | 550/ 566 (96%) | 0.0 |
| gi\|17977656\|ref\|NP_ 036419.1\| (NM_012287) | centaurin, beta 2; centaurin beta2; Arf GAP with coiled coil, ANK repeat and PH domains 2 [*Homo sapiens*] | 778 | 328/519 (63%) | 410/ 519 (78%) | 0.0 |
| gi\|7661880\|ref\|NP_0 55531.1\| (NM_014716) | centaurin beta1; KIAA0050 gene product; Arf GAP with coiled coil, ANK repeat and PH domains 1 [*Homo sapiens*] | 740 | 350/728 (48%) | 454/ 728 (62%) | e-168 |

The homology of these sequences is shown graphically in the ClustalW analysis shown in Table 23E.

TABLE 23E

Clustal W Sequence Alignment

1) NOV23 (SEQ ID NO:80)
2) gi 12697977|dbj|BAB21807.1|(AB051503) KIAA1716 protein [*Homo sapiens*]
(SEQ ID NO:235)
3) gi 16945966|ref|NP_085152.1|(NM_030649) centaurin, beta 5 [*Homo sapiens*]
(SEQ ID NO:236)
4) gi 17434817|ref|XP_027698.2|(XM_027698) KIAA1716 protein [*Homo sapiens*]
(SEQ ID NO:237)
5) gi 17977656|ref|NP_036419.1|(NM_012287) centaurin, beta 2; centaurin beta2; Arf GAP with coiled coil, ANK repeat and PH domains 2 [*Homo sapiens*]
(SEQ ID NO:238)
6) gi 7661880|refNP_055531.1|(NM_014716) centaurin beta1; KIAA0050 gene product; Arf GAP with coiled coil, ANK repeat and PH domains 1 [*Homo sapiens*]
(SEQ ID NO:239)

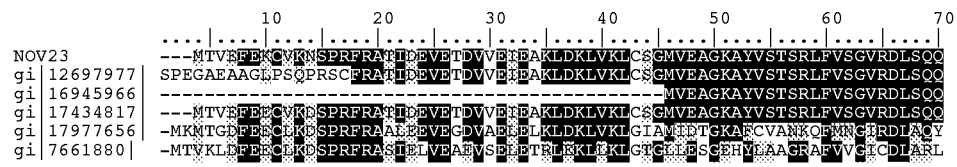

TABLE 23E-continued

Clustal W Sequence Alignment

```
               80         90        100        110        120        130        140
               ....|....|....|....|....|....|....|....|....|....|....|....|....|....|
NOV23          CQGDTVISECLQRFADSLQEVVNYHMILFDQAQRSVRQQLQSFVKEDVRKFKETKKQFDKVREDLELSLV
gi|12697977|   CQGDTVISECLQRFADSLQEVVNYHMILFDQAQRSVRQQLQSFVKEDVRKFKETKKQFDKVREDLELSLV
gi|16945966|   CQGDTVISECLQRFADSLQEVVNYHMILFDQAQRSVRQQLQSFVKEDVRKFKETKKQFDKVREDLELSLV
gi|17434817|   CQGDTVISECLQRFADSLQEVVNYHMILFDQAQRSVRQQLQSFVKEDVRKFKETKKQFDKVREDLELSLV
gi|17977656|   SSNDAVVETSLTKFSDSLQEMINFHTILLPNSLINLRHSFSNFVKEDFRKFKDAKKQFEKVSEEKENALV
gi|7661880|    GPPLPMMAECLEKFTVSLNHKLDSHAELLDATQHTLQQQIQILVKEGLRGFREARRDFWEGAESLFAALT 150        160        170        180        190        200        210
              ....|....|....|....|....|....|....|....|....|....|....|....|....|....|
NOV23         RNAQAPRHRPHEVEEATGALTLTRKCFRHLALDYVLQINVLQAKKKFEILDSMLSFMHAQSSFFQQGYSL
gi|12697977|  RNAQAPRHRPHEVEEATGALTLTRKCFRHLALDYVLQINVLQAKKKFEILDSMLSFMHAQSSFFQQGYSL
gi|16945966|  RNAQAPRHRPHEVEEATGALTLTRKCFRHLALDYVLQINVLQAKKKFEILDSMLSFMHAQSSFFQQGYSL
gi|17434817|  RNAQAPRHRPHEVEEATGALTLTRKCFRHLALDYVLQINVLQAKKKFEILDSMLSFMHAQSSFFQQGYSL
gi|17977656|  YNAQVQRNKQHEVEEATNILTATRKCFRHLALDYVLQINVLQSKRRSEILKSMLSFMYAHLAFFHQGYDL
gi|7661880|   HNAEVPRRRAQEAEEEAGAALRTARAGVRGRALDYALQINVLEEDKRKFDIMPFVLRLVEAQASHFQQGHEE 220        230        240        250        260        270        280
              ....|....|....|....|....|....|....|....|....|....|....|....|....|....|
NOV23         LHQLDPYMKKLAAELDQLVIDSAVEKREMERKHAAIQQRT-LRDFSYDESKVEFDVDAPSGVVMEGYLFK
gi|12697977|  LHQLDPYMKKLAAELDQLVIDSAVEKREMERKHAAIQQRTLLQDFSYDESKVEFDVDAPSGVVMEGYLFK
gi|16945966|  LHQLDPYMKKLAAELDQLVIDSAVEKREMERKHAAIQQRTLLQDFSYDESKVEFDVDAPSGVVMEGYLFK
gi|17434817|  LHQLDPYMKKLAAELDQLVIDSAVEKREMERKHAAIQQRTLLQDFSYDESKVEFDVDAPSGVVMEGYLFK
gi|17977656|  FSELGPYMKDLGAQLDRLVGDAAKEKREMEQKHSTIQQ----KDFSRDESKLKYNVDAANGIVMEGYLFK
gi|7661880|   LSRLSQYRKELGAQLHQLVENSAREKRDMEQEHVLLKQ----KELGGEFPEPSLR-EGFGGLVMEGHLFK 290        300        310        320        330        340        350
              ....|....|....|....|....|....|....|....|....|....|....|....|....|....|
NOV23         RASNAFKTWNRRWFSIQNSQLVYQKKLKDALTVVVDDLRLCSVKPCEDIERRFCFEVLSPTKSCMLQADS
gi|12697977|  RASNAFKTWNRRWFSIQNSQLVYQKKLKDALTVVVDDLRLCSVKPCEDIERRFCFEVLSPTKSCMLQADS
gi|16945966|  RASNAFKTWNRRWFSIQNSQLVYQKKLKDALTVVVDDLRLCSVKPCEDIERRFCFEVLSPTKSCMLQADS
gi|17434817|  RASNAFKTWNRRWFSIQNSQLVYQKKLKDALTVVVDDLRLCSVKPCEDIERRFCFEVLSPTKSCMLQADS
gi|17977656|  RASNAFKTWNRRWFSIQNNQVVYQKKFKDNPTVVVSDLRLCTVKHCEDIERRFCFEVVSPTKSCMLQADS
gi|7661880|   RASNAFKTWSRRWFTIQSNQLVYQKKYKDPVTVVVDDLRLCNVKLCPDSERRFCFEVVSTSKSCILQADS 360        370        380        390        400        410        420
              ....|....|....|....|....|....|....|....|....|....|....|....|....|....|
NOV23         EKLRQAWVQAVQASIASAYRES--PDS--CYSERLDRTASPSTSSIDSATDTRERGVKGE-SVLQRVQSV
gi|12697977|  EKLRQAWVQAVQASIASAYRES--PDS--CYSERLDRTASPSTSSIDSATDTRERGVKGE-SVLQRVQSV
gi|16945966|  EKLRQAWVQAVQASIASAYRES--PDS--CYSERLDRTASPSTSSIDSATDTRERGVKGE-SVLQRVQSV
gi|17434817|  EKLRQAWVQAVQASIASAYRES--PDS--CYSERLDRTASPSTSSIDSATDTRERGVKGE-SVLQRVQSV
gi|17977656|  EKLRQAWIKAVQTSIATAYREK--GD----ESEKLDKKSSPSTGSLDSGNESREKLLKGE-SALQRVQCI
gi|7661880|   ERLLQLWVSAVQSSIASARSQARLDDSPRGPGQGSGHLAIGSAATLGSGGMARGREPGCVGHVVAQVQSV 430        440        450        460        470        480        490
              ....|....|....|....|....|....|....|....|....|....|....|....|....|....|
NOV23         AGNSQCGDCGQPDPRWASINLGVLLCIECSGIHRSLGVHCSKVRSLTLDSWEPELLKLMCELGNSAVNQI
gi|12697977|  AGNSQCGDCGQPDPRWASINLGVLLCIECSGIHRSLGVHCSKVRSLTLDSWEPELLKLMCELGNSAVNQI
gi|16945966|  AGNSQCGDCGQPDPRWASINLGVLLCIECSGIHRSLGVHCSKVRSLTLDSWEPELLKLMCELGNSAVNQI
gi|17434817|  AGNSQCGDCGQPDPRWASINLGVLLCIECSGIHRSLGVHCSKVRSLTLDSWEPELLKLMCELGNSAVNQI
gi|17977656|  PGNASCCDCGLADPRWASINLGETLCIECSGIHRSLGVHFSKVRSLTLDIWEPELLKLMCELGNDVINKV
gi|7661880|   DGNAQCCDCREPAPEWASINLGVTLCIQCSGIHRSLGVHFSKVRSLTLDSWEPELVKLMCELGNVIINQI 500        510        520        530        540        550        560
              ....|....|....|....|....|....|....|....|....|....|....|....|....|....|
NOV23         YEAQCEGAGSRKPTASSSRQDKEAWIKDKYVEKKFLRKAPMAPALEAPRRWRVQKCLRPHSSPRAPTARR
gi|12697977|  YEAQCEGAGSRKPTASSSRQDKEAWIKDKYVEKKFLRKAPMAPALEAPRRWRVQKCLRPHSSPRAPTARR
gi|16945966|  YEAQCEGAGSRKPTASSSRQDKEAWIKDKYVEKKFLRKAPMAPALEAPRRWRVQKCLRPHSSPRAPTARR
gi|17434817|  YEAQCEGAGSRKPTASSSRQDKEAWIKDKYVEKKFLRKAPMAPALEAPRRWRVQKCLRPHSSPRAPTARR
gi|17977656|  YEANVEKMGIKKPQPGQ-RQEKEAWIEAKYVERKFVDKYSIS--LSPPE--QQKKFVSKSSEEKRLSISK
gi|7661880|   YEARVEAMAVKKPGPSCSRQEKEAWIHAKYVEKKFLTKLPEIRGRRGGR----GRPRGQPPVPKPESIR- 570        580        590        600        610        620        630
              ....|....|....|....|....|....|....|....|....|....|....|....|....|....|
NOV23         KVRLEPVLPCVAALSSE-----------------------------------------------------
gi|12697977|  KVRLEPVLPCVAALSSVGTLDRKFRRDSLFCPDELDSLFSYFDAGAAGAGPR------------------
gi|16945966|  KVRLEPVLPCVAALSSVGTLDRKFRRDSLFCPDELDSLFSYFDAGAAGAGPR------------------
gi|17434817|  KVRLEPVLPCVAALSSVGTLDRKFRRDSLFCPDELDSLFSYFDAGAAGAGPRSLSSDSGLGGSSDGSSDV
gi|17977656|  FGPGQQVR--ASAQSSVRSNDSGIQQSS---DDGRESLPS------------------------------
gi|7661880|   ------PR--------------------------------------------------------------

640        650        660        670        680        690        700
              ....|....|....|....|....|....|....|....|....|....|....|....|....|....|
NOV23         -----------------GAESEESSGEADGDTEAEAWGLADVRELHPGLLAHRAA-RARDLPALAAALAHG
gi|12697977|  ----------------KGAESEESSGEADGDTEAEAWGLADVRELHPGLLAHRAA-RARDLPALAAALAHG
gi|16945966|  ----------------KGAESEESSGEADGDTEAEAWGLADVRELHPGLLAHRAA-RARDLPALAAALAHG
gi|17434817|  LAFGSGSVVDSVTEEEGAESEESSGEADGDTEAEAWGLADVRELHPGLLAHRAA-RARDLPALAAALAHG
gi|17977656|  -------------------TVSANSLYEPEGFRQDSSM-FLDSKHLNPGLQLYRAS-YEINLPKMAEALAHG
gi|7661880|   -------------------PGSLRSKPEPPSE---------DLGSLHPGALLFRASGHPPSLPTMADALAHG
```

TABLE 23E-continued

Clustal W Sequence Alignment

```
                      710        720        730        740        750        760        770
              ....|....|....|....|....|....|....|....|....|....|....|....|....|....|
NOV23         AEVNWADAEDEGKTPLVQAVLGGSLIVCEFLLQNGADVNQRDSRGRAPLHHATLLGRTGQVCLFLKRGAD
gi|12697977|  AEVNWADAEDEGKTPLVQAVLGGSLIVCEFLLQNGADVNQRDSRGRAPLHHATLLGRTGQVCLFLKRGAD
gi|16945966|  AEVNWADAEDEGKTPLVQAVLGGSLIVCEFLLQNGADVNQRDSRGRAPLHHATLLGRTGQVCLFLKRGAD
gi|17434817|  AEVNWADAEDEGKTPLVQAVLGGSLIVCEFLLQNGADVNQRDSRGRAPLHHATLLGRTGQVCLFLKRGAD
gi|17977656|  ADVNWANSEENKATPLIQAVLGGSLVTCEFLLQNGANVNQRDVDGRGPLHHATVLGHTGQVCLFLKRGAN
gi|7661880|   ADVNWVNGGQDNATPLIQATAANSLIACEFLLQNGANVNQADSAGRGPLHHATRLGHTGLACLFLKRCAD 780        790        800        810        820        830        840
              ....|....|....|....|....|....|....|....|....|....|....|....|....|....|
NOV23         QHALDQEQRDPLAIAVQAANADIVTLLRLARMAEEMREAEAAPGPPGALAGSPTELQFRRCIQ---EFIS
gi|12697977|  QHALDQEQRDPLAIAVQAANADIVTLLRLARMAEEMREAEAAPGPPGALAGSPTELQFRRCIQ---EFIS
gi|16945966|  QHALDQEQRDPLAIAVQAANADIVTLLRLARMAEEMREAEAAPGPPGALAGSPTELQFRRCIQ---EFIS
gi|17434817|  QHALDQEQRDPLAIAVQAANADIVTLLRLARMAEEMREAEAAPGPPGALAGSPTELQFRRCIQ---EFIS
gi|17977656|  QHATDEEGKDPLSIAVEAANADIVTLLRLARMNEEMRESEGLYGQPGDETYQDIFRDFSLMASNNPEKEN
gi|7661880|   LGARDSEGRDPLTIANETANADIVTLLRLA---K-MREAEAAQGQAGDETYLDIFRDFSLMASDDPEKES

....|....
NOV23         LHLEES---
gi|12697977|  LHLEES---
gi|16945966|  LHLEES---
gi|17434817|  LHLEES---
gi|17977656|  RFQQDSQKF
gi|7661880|   RRSHDLHTL
```

Tables 23F, 23G and 23H list the domain description from DOMAIN analysis results against NOV23. This indicates that the NOV23 sequence has properties similar to those of other proteins known to contain these domains.

TABLE 23F

Domain Analysis of NOV23 gnl Pfam:pfam01412, ArfGap, Putative GTP-ase activating protein for Arf. Putative zinc fingers with GTPase activating proteins (GAPs) towards the small GTPase, Arf. The GAP of ARD1 stimulates GTPase hydrolysis for ARD1 but not ARFs. (SEQ ID NO:240)
CD-Length = 122 residues, 97.5% aligned
Score = 153 bits (387), Expect = 3e-38

```
Query:  402 ESVLQRVQSVAGNSQCGDCGQPDPRWASINLGVLLCIECSGIHRSLGVHCSKRVSLTLDS  461
            ||+ ++|+ || +| ||| |+| |||+|||| +|||||||||||| ||||||||||+
Sbjct:    1 RRVLKLLRSLDGNKKCFDCGAPNPTWASVNLGVFICIECSGIHRSLGVHISKVRSLTLDT   60

Query:  462 WEPELLKLMCELGNSAVNQIYEAQCEGAGSRKPTASSSRQDKEAWIKLKYVEKKFLRKAP  521
            | ||  |+ | + ||    |  +|+        ||| | ||  |++|  || ||  |+ |
Sbjct:   61 WTPEELRKMEKGGNENANSFWESN-LDDFSLKPKDSDDRQKYESFIAAKYEEKLFVLKEG  119
```

TABLE 23G

Domain Analysis of NOV23 gnl Smart|smart00233, PH, Pleckstrin homology domain.; Domain commonly found in eukaryotic signalling proteins. The domain family possesses multiple functions including the abilities to bind inositol phosphates, and various proteins. PH domains have been found to possess inserted domains (such as in PLC gamma, syntrophins) and to be inserted within other domains. Mutations in Brutons tyrosine kinase (Btk) within its PH domain cause X-linked agammaglobulinaemia (XLA) in patients. Point mutations cluster into the positively charged end of the molecule around the predicted binding site for phosphatidylinositol lipids. (SEQ ID NO:241)
CD-Length = 104 residues, 100.0% aligned
Score = 66.6 bits (161), Expect = 5e-12

```
Query:  268 VVMEGYLFKRASNAFKTWNRRWFSIQNSQLVYQKKLKDAL------TVVVDDLRLCSVKP  321
            |+ ||+| |++|   |+| +|+| + |  |+| | |           ++ +    +
Sbjct:    1 VIKEGWLLKKSSGGKKSWKKRYFVLFNGVLLYYKSKKKKSSSKPKGSIPLSGCTVREAPD   60

Query:  322 CEDIERRFCFEVLSPTKSCM-LQADSEKLRQAWVQAVQASIASA                 364
            +  +++ |||+++| +  + |||+||+ |+ ||+|++ +||
Sbjct:   61 SDSDKKKNCFEIVTPDRKTLLLQAESEEERKEWVEALRKAIAKL                104
```

TABLE 23H

Domain Analysis of NOV23

```
gnl|Pfam pfam00023, ank, Ank repeat. Ankyrin
repeats generally consist of a beta, alpha, alpha,
  beta order of secondary structures. The repeats
     associate to form a higher order structure.
                    (SEQ ID NO:242)
       CD-Length = 33 residues, 97.0% aligned
       Score = 45.1 bits (105), Expect = 2e-05
Query:   632  EGKTPLVQAVLGGSLIVCEFLLQNGADVNQRD  663
              +| |||  |   | | | + ||+ ||||| ||
Sbjct:     1  DGNTPLHLAARNGHLEVVKILLEAGADVNARD   32
```

Phosphoinositide (PI) 3-kinases play a role in the regulation of cell growth and survival, metabolism, transcription, vesicular trafficking and cytoskeletal organization. Receptor-regulated (class I) PI 3-kinases phosphorylate phosphatidylinositol 4,5-bisphosphate [PtdIns(4,5)P2] to phosphatidylinositol 3,4,5-trisphosphate [PtdIns(3,4,5)P3]. Proteins in the centaurin family are regulated by phosphoinositide and are regulatory proteins for Arfs (ADP ribosylation factors) (Jackson et al., Trends Biochem. Sci. 25: 489–95, 2000). Arfs are small GTP-binding proteins that function in vesicular trafficking and cytoskeletal regulation. Centaurin family members are GTPase-activating proteins (GAPs) for Arf or have homology to Arf GAPs and Arf effectors. ARFs are essential and ubiquitous in eukaryotes, being involved in vesicular transport and functioning as activators of phospholipase D. The functions of ARF proteins in membrane traffic and organelle integrity are intimately tied to their reversible association with membranes and specific interactions with membrane phospholipids.

The NOV23 protein described herein is predicted to share the attributes of the other centaurin family members and is thus implicated in signal transduction pathways that regulate cell growth and survival, metabolism and transcription. Its potential role in the regulation of ARF activity suggests that the centaurin beta 2-like protein may play an important role in vesicular trafficking and cytoskeletal regulation. Therefore, the NOV23 protein is an attractive target for drug intervention in the treatment of human metabolic diseases, central nervous system disorders, and cancer, among others.

The NOV23 nucleic acid of the invention encoding a Centaurin Beta 2-like protein includes the nucleic acid whose sequence is provided in Table 23A, or a fragment thereof. The invention also includes a mutant or variant nucleic acid any of whose bases may be changed from the corresponding base shown in Table 23A while still encoding a protein that maintains its Centaurin Beta 2-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 32% of the NOV23 residues may be so changed.

The NOV23 protein of the invention includes the Centaurin Beta 2-like protein whose sequence is provided in Table 23B. The invention also includes a mutant or variant protein any of whose residues may be changed from the corresponding residue shown in Table 23B while still encoding a protein that maintains its Centaurin Beta 2-like activities and physiological functions, or a functional fragment thereof. In the mutant or variant protein, up to about 39% of the NOV23 bases may be so changed.

The NOV23 nucleic acids and proteins of the invention are useful in potential diagnostic and therapeutic applications implicated in various diseases and disorders described below and/or other pathologies. For example, the compositions of the present invention will have efficacy for treatment of patients suffering from: cancer, trauma, bacterial and viral infections, in vitro and in vivo regeneration, Von Hippel-Lindau (VHL) syndrome, Alzheimer's disease, stroke, tuberous sclerosis, hypercalceimia, Parkinson's disease, Huntington's disease, cerebral palsy, epilepsy, Lesch-Nyhan syndrome, multiple sclerosis, ataxia-telangiectasia, leukodystrophies, behavioral disorders, addiction, anxiety, pain, neurodegeneration endocrine dysfunctions, diabetes, obesity, growth and reproductive disorders, endometriosis, fertility, hypogonadism, muscular dystrophy, Lesch-Nyhan syndrome, and myasthenia gravis and other diseases, disorders and conditions of the like.

NOV23 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV23 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV24

A disclosed NOV24 nucleic acid of 1930 nucleotides (also referred to as CG57515-01) encoding a novel Sorting Nexin 9-like protein is shown in Table 24A. An open reading frame was identified beginning with an ATG initiation codon at nucleotides 32–34 and ending with a TAA codon at nucleotides 1904–1906. Putative untranslated regions upstream from the intitation codon and downstream from the termination codon are underlined in Table 24A, and the start and stop codons are in bold letters.

TABLE 24A

NOV24 Nucleotide Sequence (SEQ ID NO:81)

AGTCGGGACCGCCAGTCGGGGCGCCGGGACCATGGCGCTGCGCGCCCGGGCGCTGTACGACTTCAGGTCGGAG

AACCCAGGAGAGATCTCGCTGCGAGAGCACGAGGTGCTGAGCCTGTGCAGCGAGCAGGACATCGAGGGCTGGC

TABLE 24A-continued

NOV24 Nucleotide Sequence

TCGAGGGGGTCAACAGCCGCGGCGACCGCGGCCTCTTCCCGGCCTCCTATGTGCAGGTGATCCGCGCCCCGA
GCCTGGCCCGGCGGGAGACGGCGGCCCGGGCGCCCCGGCCCGCTACGCCAATGTGCCCCCCGGGGGCTTCGAG
CCCCTGCCCGTCGCGCCCCCCGCCTCCTTCAAGCCGCCGCCTGACGCCTTCCAGGCGCTGCTGCAGCCACAGC
AGGCGCCGCCTCCGAGCACCTTCCAGCCGCCCGGCGCGGGCTTCCCGTACGGCGGGGCGCCCTGCAGCCGTC
GCCTCAGCAGCTCTACGGCGGCTACCAGGCCAGCCAAGGCAGCGATGATGACTGGGACGACGAGTGGGACGAC
AGCTCCACGGTGGCGGACGAGCCGGGCGCTCTGGGCAGCGGAGCATACCCGGACCTCGACGGCTCGTCTTCGG
CGGGTGTGGGCGCAGCCGGCCGCTACCGCCTGTCCACGCGCTCCGACCTGTCCCTGGGCTCCCGCGGCGGCTC
GGTCCCCCCGCAGCACCACCCGTCGGGGCCCAAGAGCTCGGCCACCGTGAGCCGCAACCTCAATCGCTTCTCC
ACCTTCGTCAAGTCCGGCGGGGAGGCCTTCGTGCTGGGGGAGGCGTCAGGCTTCGTGAAGGACGGGACAAGC
TGTGCGTGGTGCTGGGGCCCTATGGCCCCGAGTGGCAGGAGAACCCCTACCCGTTCCAGTGCACCATCGACGA
CCCCACCAAGCAGACCAAGTTCAAGGGCATGAAGAGCTACATCTCCTACAAGCTGGTGCCCACGCACACGCAG
GTGCCGGTGCATCGGCGCTACAAGCACTTCGACTGGCTGTACGCGCGCCTGGCGGAGAAGTTCCCGGTCATCT
CCGTGCCCCACCTGCCCGAGAAGCAGGCCACCGGCCGCTTCGAGGAGGACTTCATCTCTAAGCGCAGGAAGGG
CCTGATCTGGTGGATGAACCACATGGCCAGCCACCCAGTGCTGGCGCAGTGCGACGTCTTCCAGCACTTCCTG
ACGTGCCCCAGCAGCACCGACGAGAAAGCCTGGAAGCAGGGCAAGAGGAAGGCCGAGAAGGACGAGATGGTGG
GCGCCAACTTCTTCCTGACCCTTAGCACGCCCCCCGCCGCTGCCCTTGACCTGCAGGAGGTGGAGAGCAAGAT
AGACGGCTTCAAGTGCTTCACCAAGAAGATGGACGACAGCGCGCTGCAGCTCAACCACACGGCCAACGAGTTC
GCGCGCAAGCAGGTGACCGGCTTCAAAAAGGAGTATCAGAAGGTGGGCCAGTCCTTCCGCGGCCTCAGCCAGG
CCTTTGAGCTGGACCAGCAGGCCTTCTCGGTGGGCCTGAACCAGGCTATCGCCTTCACCGGAGATGCCTATGA
CGCCATTGGCGAGCTCTTCGCGGAGCAGCCCAGGCAGGACCTGGATCCCGTCATGGACCTATTAGCGCTGTAT
CAGGGGCATCTGGCTAACTTCCCGGACATCATCCACGTTCAGAAAGGAGCTCTTACCAAAGTCAAGGAGAGTA
GGCGACACGTGGAGGAAGGGAAGATGGAGGTGCAGAAGGCTGACGGCATTCAGGATCGCTGTAACACTATTTC
TTTTGCCACTTTGGCTGAAATTCACCACTTCCATCAAATTCGAGTGAGAGACTTTAAATCACAGATGCAGCAT
TTCTTACAACAACAAATAATATTTTTCCAAAAAGTTACCCAGAAGTTGGAAGAAGCTCTTCACAAATATGATA
GTGTTTAATGACTGGACGTTGGATTATGGACT

The NOV24 nucleic acid was identified on chromosome 5 and has 275 of 435 bases (63%) identical to a gb:GENBANK-ID:AF121859|acc:AF121859.1 mRNA from *Homo sapiens* (*Homo sapiens* sorting nexin 9 (SNX9) mRNA, complete cds) (E=1.7e$^{-14}$).

A disclosed NOV24 polypeptide (SEQ ID NO:82) encoded by SEQ ID NO:81 is 624 amino acid residues and is presented using the one-letter code in Table 24B. Signal P, Psort and/or Hydropathy results predict that NOV24 contains a signal peptide and is likely to be localized to the cytoplasm with a certainty of 0.7284.

TABLE 24B

Encoded NOV24 protein sequence (SEQ ID NO:82)
MALRARALYDFRSENPGEISLREHEVLSLCSEQDIEGWLEGVNSRGDRGLFPASYVQVIRAPEPGPAGDGGP

GAPARYANVPPGGFEPLPVAPPASFKPPPDAFQALLQPQQAPPPSTFQPPGAGFPYGGGALQPSPQQLYGGY

QASQGSDDDWDDEWDDSSTVADEPGALGSGAYPDLDGSSSAGVGAAGRYRLSTRSDLSLGSRGGSVPPQHHP

SGPKSSATVSRNLNRFSTFVKSGGEAFVLGEASGFVKDGDKLCVVLGPYGPEWQENPYPFQCTIDDPTKQTK

TABLE 24B-continued

Encoded NOV24 protein sequence

FKGMKSYISYKLVPTHTQVPVHRRYKHFDWLYARLAEKFPVISVPHLPEKQATGRFEEDFISKRRKGLIWWM

NHMASHPVLAQCDVFQHFLTCPSSTDEKAWKQGKRKAEKDEMVGANFFLTLSTPPAAALDLQEVESKIDGFK

CFTKKMDDSALQLNHTANEFARKQVTGFKKEYQKVGQSFRGLSQAFELDQQAFSVGLNQAIAFTGDAYDAIG

ELFAEQPRQDLDPVMDLLALYQGHLANFPDIIHVQKGALTKVKESRRHVEEGKMEVQKADGIQDRCNTISFA

TLAEIHHFHQIRVRDFKSQMQHFLQQQIIFFQKVTQKLEEALHKYDSV

The NOV24 amino acid sequence 171 of 401 amino acid residues (42%) identical to, and 239 of 401 amino acid residues (59%) similar to, the 595 amino acid residue ptnr:SWISSNEW-ACC:Q9Y5X1 protein from *Homo sapiens* (Human) (Sorting Nexin 9 (SH3 and PX Domain-Containing Protein 1) (SDP1 Protein)) (E=1.0e$^{-99}$).

NOV24 is expressed in at least the following tissues: lung, colon, mammary gland/breast, peripheral blood, pituitary gland, thyroid gland, and vulva. This information was derived by determining the tissue sources of the sequences that were included in the invention including but not limited to SeqCalling sources, Public EST sources, genomic clone sources, literature sources, and/or RACE sources.

NOV24 has homology to the amino acid sequences shown in the BLASTP data listed in Table 24C.

TABLE 24C

BLAST results for NOV24

| Gene Index/ Identifier | Protein/ Organism | Length (aa) | Identity (%) | Positives (%) | Expect |
|---|---|---|---|---|---|
| gi\|16418371\|ref\|NP_443102.1\| (NM_052870) | sorting nexin 18 [*Homo sapiens*] | 628 | 441/541 (81%) | 441/541 (81%) | 0.0 |
| gi\|18644890\|ref\|NP_570614.1\| (NM_130796) | sorting nexin associated golgi protein 1 [*Mus musculus*] | 614 | 462/633 (72%) | 468/633 (72%) | 0.0 |
| gi\|17511850\|gb\|AAH18775.1\| AAH18775 (BC018775) | Unknown (protein for MGC:32065) [*Homo sapiens*] | 574 | 243/464 (52%) | 310/464 (66%) | e-134 |
| gi\|13385132\|ref\|NP_079940.1\| (NM_025664) | sorting nexin 9 [*Mus musculus*] | 395 | 166/394 (42%) | 221/394 (55%) | 3e-80 |
| gi\|15928697\|gb\|AAH14814.1\| AAH14814 (BC014814) | Similar to sorting nexin 9 [*Mus musculus*] | 595 | 166/394 (42%) | 221/394 (55%) | 6e-80 |

The homology of these sequences is shown graphically in the ClustalW analysis shown in Table 24D.

TABLE 24E

Clustal W Sequence Alignment

1) NOV24 (SEQ ID NO:82)
2) gi 16418371|ref|NP_443102.1|(NM_052870) sorting nexin 18 [Homo sapiens] (SEQ ID NO:243)
3) gi 18644890|ref|NP_570614.1|(NM_130796) sorting nexin associated golgi protein 1 [Mus musculus] (SEQ ID NO:244)
4) gi 17511850|gb|AAH18775.1 AAH18775 (BC018775) Unknown (protein for MGC:32065) [Homo sapiens] (SEQ ID NO:245)
5) gi 13385132|refNP_079940.1|(NM_025664) sorting nexin 9 [Mus musculus] (SEQ ID NO:246)
6) gi 15928697|gb|AAH14814.1 AAH14814 (BC014814) Similar to sorting nexin 9 [Mus musculus] (SEQ ID NO:247)

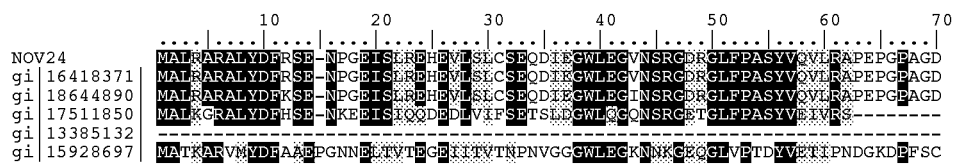

TABLE 24E-continued

Clustal W Sequence Alignment

```
                    80         90        100        110        120        130        140
             ....|....|....|....|....|....|....|....|....|....|....|....|....|....|
NOV24        GGPGAPARVANVPPGGFEPLPVAPPASFKPPPDAFQALLQPQQAPPPSTFQPPGAGFPYGGGALQPSPQQ
gi|16418371| GGPGAPARVANVPPGGFEPLPVAPPASFKPPPDAFQALLQPQQAPPPSTFQPPGAGFPYGGGALQPSPQQ
gi|18644890| GGPGAPARVANVPPGGFEPLPVAPPAAFPP-------LLQPQAP--GSFQPPGAGFPYGGGALQPSPQQ
gi|17511850| GISTNHADVSSSPAG----SPGAQVSLYNS---------PSVAS----PARS------GGGSGFLSNQ-
gi|13385132| ------------------------------------------------------------------
gi|15928697| GNSVADQAFLISLTAS---TAQTNSSSANS---------NNQVGGNDPWTAWNAPKPGNWDSSDAWGSR 150        160        170        180        190        200        210
             ....|....|....|....|....|....|....|....|....|....|....|....|....|....|
NOV24        LYGGYLASQGSDDDWDDEWDDSSTVADEP--GALGSGAYPDLDGSSSAGVGAAGRYRLSTRSDLSLGSRG
gi|16418371| LYGGYQASQGSDDDWDDEWDDSSTVADEP--GALGSGAYPDLDGSSSAGVGAAGRYRLSTRSDLSLGSRG
gi|18644890| LYGGYQASLGSDDDWDDEWDDSSTVADEP--GALGSGAYPDLDGSSSAGVGAAGRYRLSTRSDLSLGSRG
gi|17511850| --GSFEED--DDDDWDD-WDDGCTVVEEPRAGGLGINGHPPLNLSYPG---AYPSQHMAFRPKPPLER--
gi|13385132| ------------------------------------------------------------------
gi|15928697| TDGTSAQRNSSANMWDTGVGHP-QAYQGE---ATGDDDEWDEDWDDPK----SSSPYFKDSEPAEAGG--

220        230        240        250        260        270        280
             ....|....|....|....|....|....|....|....|....|....|....|....|....|....|
NOV24        GSVPPQHHPSGPMSSATVSRNLNRFSTFVKSGGEAFVLGEASGFVKDGDKLCVVLGPYGPEWQENPYPEQ
gi|16418371| GSVPPQHHPSGPMSSATVSRNLNRFSTFVKSGGEAFVLGEASGFVKDGDKLCVVLGPYGPEWQENPYPEQ
gi|18644890| VSAPPAPSVWSQKLGHGEPQ-PQSLLHLRQVGRGGLRACRGVRLREGWGQAVRGAGSYGPEWQENPYPEQ
gi|17511850| -----QDSLASAERGSVVGRNLNRFSCEVRSGVEAFILGDVPMMAKIAKTYSIEMGPRGPQWEANPHPEA
gi|13385132| ------------------MKLPLNKPPGEAKPGMEQYLL--AKQLAKPKEKLAIIVGDYGPMWVYPTSTED
gi|15928697| -----IQRGNSRAGASSMKLPLNKPPGEAKPGMEQYLL--AKQLAKPKEKLAIIVGDYGPMWVYPTSTED 290        300        310        320        330        340        350
             ....|....|....|....|....|....|....|....|....|....|....|....|....|....|
NOV24        CTIDDPTKQTKFKGMKSYISYKLVPTHTQVPVHRRYKHFDWLYARLAEKP-PVISVPHLPEKQATGRFEE
gi|16418371| CTIDDPTKQTKFKGMKSYISYKLVPTHTQVPVHRRYKHFDWLYARLAEKP-PVISVPHLPEKQATGRFEE
gi|18644890| CTIDDPTKQTKFKGMKSYISYKLVPTHTQVPVHRRYKHFDWLYARLAEKP-PVISVPHLPEKQATGRFEE
gi|17511850| CSVEDPTKQTKFKGIKSYISYKLTPTHAASPVYRRYKHFDWLYNRLLHKP-TVISVPHLPEKQATGRFEE
gi|13385132| CVVADPRKGSKMYCLKSYIEYQLTPTNINRSVNHRYKHFDWLYBRLLVKFGSALPIPSLPDKQVTGRFEE
gi|15928697| CVVADPRKGSKMYCLKSYIEYQLTPTNINRSVNHRYKHFDWLYBRLLVKFGSALPIPSLPDKQVTGRFEE 360        370        380        390        400        410        420
             ....|....|....|....|....|....|....|....|....|....|....|....|....|....|
NOV24        DFISKRRKGLIWWMNHMASHPVLAQCDVFQHFLTCPSSTDEKAWKQGRKAEKDEMVGANFFLTLSTPPA
gi|16418371| DFISKRRKGLIWWMNHMASHPVLAQCDVFQHFLTCPSSTDEKAWKQGRKAEKDEMVGANFFLTLSTPPA
gi|18644890| DFISKRRKGLIWWMNHMASHPVLAQCDVFQHFLTCPSSTDEKAWKQGRKAEKDEMVGANFFLTLSTPPA
gi|17511850| DFIEKRKRRLILWMDHMTSHPVLSQYPGFQHFLSC---LDDKQWKMGKRAEKDEMVGASFLLTFQIP-T
gi|13385132| EFIKMRMERLQAWMTRMCRHPVVSESEVFQQFLNFR---DEKEWKTGKRKAEKDEDVGVMIFSTMEPE-A
gi|15928697| EFIKMRMERLQAWMTRMCRHPVVSESEVFQQFLNFR---DEKEWKTGKRKAEKDEDVGVMIFSTMEPE-A 430        440        450        460        470        480        490
             ....|....|....|....|....|....|....|....|....|....|....|....|....|....|
NOV24        AALDLQEVESKIDGFKCFTKKMDDSALQLNHTANEFARKQVTGEKKEYQKVGQSERGLSQAFEIDQQAFS
gi|16418371| AALDLQEVESKIDGFKCFTKKMDDSALQLNHTANEFARKQVTGEKKEYQKVGQSERGLSQAFEIDQQAFS
gi|18644890| AALDLQEVESKIDGFKCFTKKMDDSALQLNHTANEFARKQVTGEKKEYQKVGQSERGLSQAFEIDQQAFS
gi|17511850| EHQDLQDVEDRVDTFKAFSKKMDDSVLQLSTVASELVRKHQVGERKEFQKLCSAEQAISHEFQMDPPFCS
gi|13385132| PDLDLIERERQKCDAVGKFTKAMDLDGVKELLTVGQEHWKEPCTGTLPKEYWKIGKALQSLAAVESSSGYQGE
gi|15928697| PDLDLIERERQKCDAVGKFTKAMDLDGVKELLTVGQEHWKEPCTGTLPKEYWKIGKALQSLAAVESSSGYQGE 500        510        520        530        540        550        560
             ....|....|....|....|....|....|....|....|....|....|....|....|....|....|
NOV24        VGLNQAIAFTGDAVDAIGELFAEQPRQDLDPVMDLLALYQGHLANFPDIIHVQKG---ALTKVKESRRHV
gi|16418371| VGLNQAIAFTGDAVDAIGELFAEQPRQDLDPVMDLLALYQGHLANFPDIIHVQKGKAWPLEQVIQSVLCR
gi|18644890| VGLNQAIAFTGDAVDAIGELFAEQPRQDLDPVMDLLALYQGHLANFPDIIHVQKG---ALTKVKESRRHV
gi|17511850| EALNSAISHTGRTVKAIGEMFAEQPKNDLFQMLDTLSLYQGLLSNFPDIIHLQKG---AFAKVKESQRMS
gi|13385132| TDLNDAITEAGKTYEEIASLVAEQPKKDLHFLMECNHEYKGFLGCFPDIIGAHKG---AIEKVKESDELV
gi|15928697| TDLNDAITEAGKTYEEIASLVAEQPKKDLHFLMECNHEYKGFLGCFPDIIGAHKG---AIEKVKESDELV 570        580        590        600        610        620        630
             ....|....|....|....|....|....|....|....|....|....|....|....|....|....|
NOV24        EEGKMEVQKADGIQDRCNTISEATLAEIHHFHQIRVRDFKSQMQHFLQQQIIEFQKVTQKLEEALHKYDS
gi|16418371| LKGATLTAVPLQVSDSYSIGEEASRDVDAWVFSLECK-LDCSTGGSFLLEYLALGNEYSFSKVQRVPLMTV
gi|18644890| EEGKMEVQKADGIQDRCNTISEATLAEIHHFHQIRVRDFKSQMQHFLQQQIIEFQKVTQKLEEALHKYDS
gi|17511850| DEGRMVQDEADGIRRRCRVVGEALQAEMNHFHQRRELDFKHMMQNYLRQQILFYQRVGQQLEKTLRMYDN
gi|13385132| ATSKITPQDKQTMVKRVGTMSYALQAEMNHFHSNRIYDYNSVIPLYLEQQVQFYETIAEKIRQALSRFPV
gi|15928697| ATSKITPQDKQTMVKRVGTMSYALQAEMNHFHSNRIYDYNSVIPLYLEQQVQFYETIAEKIRQALSRFPV

...
NOV24        V--
gi|16418371| LSF
gi|18644890| V--
gi|17511850| L--
gi|13385132| M--
gi|15928697| M--
```

Tables 24E and 24F list the domain description from DOMAIN analysis results against NOV24. This indicates that the NOV24 sequence has properties similar to those of other proteins known to contain these domains.

intervention in the treatment of human metabolic diseases, immune disorders, and cancer, among others.

The NOV24 nucleic acid of the invention encoding a Sorting Nexin 9-like protein includes the nucleic acid whose sequence is provided in Table 24A, or a fragment thereof. The invention also includes a mutant or variant nucleic acid any of whose bases may be changed from the corresponding base shown in Table 24A while still encoding a protein that maintains its Sorting Nexin 9-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 37% of the NOV24 residues may be so changed.

The NOV24 protein of the invention includes the Sorting Nexin 9-like protein whose sequence is provided in Table 24B. The invention also includes a mutant or variant protein any of whose residues may be changed from the corresponding residue shown in Table 24B while still encoding a protein that maintains its Sorting Nexin 9-like activities and physiological functions, or a functional fragment thereof. In the mutant or variant protein, up to about 58% of the NOV24 bases may be so changed.

TABLE 24E

Domain Analysis of NOV24

```
gnl Smart|smart00312, PX, PhoX homologous domain, present in p47phox
and p40phox.; Eukaryotic domain of unknown function present in phox
proteins.; PLD isoforms, a PI3K isoform. (SEQ ID NO:248)
CD-Length = 112 residues, 100.0% aligned
Score = 77.8 bits (190), Expect = 2e-15
Query:  273 PYPFQCTIDDPTKQTKFKGMKSYISYKLVPTHTQVP--VHRRYKHFDWLYARLAEKFPVI  330
                |+ +    +|    |    |    +   +       |  |||   |  |+++|   |||
Sbjct:    1 DNILIVTVVEF--ETYGDGKHYYYVIEIETSTGLKEWTVKRRYSDFLELHSKLKRKFPRR   58

Query:  331 SVPHLPEKQATGR-FEEDFISKRRKGLIWWMNHMASHPVLAQ-CDVFQHFLTCP        382
               +|  ||  |+    |     |+||   |||+||   ++  + +||   |    +|    ||
Sbjct:   59 ILPPLPGKKLFVRYLSEEFIEKRRRGLEKYLQKLLNHPELINHSEVVLEFLESS       112
```

TABLE 24F

Domain Analysis of NOV24

```
gnl|Pfam pfam00018, SH3, SH3 domain. SH3 (Src homology 3) domains are
often indicative of a protein involved in signal transduction related
to cytoskeletal organization. First described in the Src cytoplasmic
tyrosine kinase. The structure is a partly opened beta barrel. (SEQ ID
NO :249)
CD-Length = 57 residues, 98.2% aligned
Score = 60.1 bits (144), Expect = 4e-10
Query:   4 RARALYDFRSENPGEISLREHEVLSLCSEQDIEGWLEGVNSRGDRGLFPASYVQVI    59
              +   ||||+++      |+|  ++ +++ +   +  |    ||  +|           ||  |++||+ +
Sbjct:   2 KVVALYDYQARESDELSFKKGDIIIVLEKSDDGGWWKGRLKGTKEGLIPSNYVEPV    57
```

Sorting nexins are a family of phox homology (PX) domain containing proteins that are homologous to yeast proteins involved in protein trafficking. Sorting nexin-1 (SNX1) was identified based on its ability to bind to a region of the epidermal growth factor receptor (EGFR) containing the lysosomal targeting code (Kurten et al., Science 272:1008–10, 1996). The SNX1 protein contains a region of homology to a yeast vacuolar sorting protein, and overexpression of SNX1 decreased the amount of EGFR on the cell surface as a result of enhanced rates of constitutive and ligand-induced degradation. Human SNX1, SNX1A, SNX2, SNX3, and SNX4 are part of a larger family of hydrophilic molecules including proteins identified in *Caenorhabditis elegans* and *Saccharomyces cerevisiae* (Haft et al., Mol. Cell. Biol. 18:7278–87, 1998). Despite their hydrophilic nature, these sorting nexins are found partially associated with cellular membranes. They are widely expressed, although the tissue distribution of each sorting nexin mRNA varies. The sorting nexins have been demonstrated to interact with a variety of receptor types (including EGFR, platelet derived growth factor receptor, and leptin) suggesting that these proteins may be involved in several stages of intracellular trafficking in mammalian cells.

The NOV24 protein described in this invention is predicted to share the attributes of the other sorting nexin family members and is thus implicated in protein trafficking. Its potential role in the regulation of growth factor receptor localization and levels suggests that the NOV24 protein may play an important role in cell growth and differentiation. Therefore, the NOV24 protein is an attractive target for drug The NOV24 nucleic acids and proteins of the invention are useful in potential diagnostic and therapeutic applications implicated in various diseases and disorders described below and/or other pathologies. For example, the compositions of the present invention will have efficacy for treatment of patients suffering from: cancer, trauma, bacterial and viral infections, in vitro and in vivo regeneration, systemic lupus erythematosus, autoimmune disease, asthma, emphysema, scleroderma, allergy, ARDS, Hirschsprung's disease, Crohn's Disease, appendicitis, hyperthyroidism, hypothyroidism, fertility, anemia, ataxia-telangiectasia, immunodeficiencies, endocrine dysfunctions, diabetes, obesity, growth and reproductive disorders and other diseases, disorders and conditions of the like.

NOV24 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV24 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV25

A disclosed NOV25 nucleic acid of 1514 nucleotides (also referred to as CG57568-01) encoding a novel Katanin-like protein is shown in Table 25A. An open reading frame was identified beginning with an ATG initiation codon at nucleotides 102–104 and ending with a TGA codon at nucleotides 1191–1193. Putative untranslated regions upstream from the intitation codon and downstream from the termination codon are underlined in Table 25A, and the start and stop codons are in bold letters.

TABLE 25A

NOV25 Nucleotide Sequence (SEQ ID NO:83)
AGTAGTTTTAAACATATTTTAAAGAATAATAAATGTTTTAAAGTCAGTGCTGAAAATTTTTAAAAAGTCATTA

TATTTTATGTTTAGGTCTCTGAAAGAAGATGAATTTGGCTGAGATTTGTGATAATGCAAAGAAAGGAAGAGAA

TATGCCCTTCTTGGAAATTACGACTCATCAATGGTATATTACCAGGGGGTGATGCAGCAGATTCAGAGACATT

GCCAGTCAGTCAGAGATCCAGCTATCAAAGGCAAATGGCAACAGGTAAGATGGGGTTATGATAAGGATCTGGT

GGAAGCCCTTGAAAGAGACATTGTATCCAGGAATCCTAGCATTCATTGGGATGACATAGCAGATCTGGAAGAA

GCTAAGAAGTTGCTAAGGGAAGCTGTTGTTCTTCCAATGTGGATGCCTGACTTTTTCAAAGGGATTAGAAGGC

CATGGAAGGGTGTACTGATGGTTGGACCCCCAGGCACTGGTAAAACTATGCTAGCTAAAGCTGTTGCCACTGA

ATGTGGTACAACATTCTTCAACGTTTCGTCTTCTACACTGACATCTAAATACAGAGGTGAATCTGAGAAGTTA

GTTCGTCTGTTGTTTGAGATGGCTAGATTTTATGCCCCTACCACGATCTTCATTGATGAGATAGATTCTATCT

GCAGTCGAAGAGGAACCTCTGATGAACATGAGGCAAGTCGCAGGGTCAAGTCTGAACTGCTCATTCAGATGGA

TGGTGTTGGAGGAGCTTTAGAAAATGATGATCCTTCCAAAATGGTTATGGTATTGGCTGCTACTAATTTCCCG

TGGGACATTGATGAAGCTTTGCGAAGAAGGTTAGAAAAAAGGATATATATACCTCTCCCAACAGCAAAAGGAA

GAGCTGAGCTTCTGAAGATCAACCTTCGTGAGGTCGAATTAGATCCTGATATTCAACTGGAAGATATAGCCGA

GAAGATTGAGGGCTATTCTGGTGCTGACATCACTAATGTTTGCAGGGATGCCTCTTTAATGGCAATGAGACGG

CGTATCAATGGCTTAAGTCCAGAAGAAATCCGTGCACTTTCTAAAGAGGAACTTCAGATGCCTGTTACCAAAG

GAGACTTTGAATTGGCCCTAAAAAAAATTGCTAAGTCTGTCTCTGCTGCAGACTTGGAGAAGTATGAAAAATG

GATGGTTGAATTTGGATCTGCTTGAATTTCTGTCAGCTCTTTAATTTCTGGTATTTTTGTTGATAAAATACGA

AGAAATTCCTGCAATTTTTAAAAAACAAGTTTGGAACTTTTTTCAGTGGAGTGGTTTTCGCAAAAAAAAAAAA

AAAATCTAAAACTGCGAAGAATACTAAATGTAGTTGAGAAATAATTGATGGCGAGAGTTTGCTAGTCTCCCTC

CCCGGCTTTGTGCTGGTATTCCACGTATTCCTGCATTAATATTGCACACCCAAACCAGTCTATCAGGGAGGCT

GAAGCAGGGCGCAGTGTGATATTTAGGAATCAGAAGATTAGAAATCCCCTATTC

The NOV25 nucleic acid was identified on chromosome 13 and has 720 of 953 bases (75%) identical to a gb:GENBANK-ID:AF056022|acc:AF056022.1 mRNA from *Homo sapiens* (*Homo sapiens* p60 katanin mRNA, complete cds) (E=1.6e$^{-123}$).

A disclosed NOV25 polypeptide (SEQ ID NO:84) encoded by SEQ ID NO:83 is 363 amino acid residues and is presented using the one-letter code in Table 25B. Signal P, Psort and/or Hydropathy results predict that NOV25 does not contain a signal peptide and is likely to be localized to cytoplasm with a certainty of 0.6500.

TABLE 25B

Encoded NOV25 protein sequence (SEQ ID NO:84)

MNLAEICDNAKKGREYALLGNYDSSMVYYQGVMQQIQRHCQSVRDPAIKGKWQQVRWGYDKDLVEALERDIV

SRNPSIHWDDIADLEEAKKLLREAVVLPMWMPDFFKGIRRPWKGVLMVGPPGTGKTMLAKAVATECGTTFFN

VSSSTLTSKYRGESEKLVRLLFEMARFYAPTTIFIDEIDSICSRRGTSDEHEASRRVKSELLIQMDGVGGAL

ENDDPSKMVMVLAATNFPWDIDEALRRRLEKRIYIPLPTAKGRAELLKINLREVELDPDIQLEDIAEKIEGY

SGADITNVCRDASLMAMRRRINGLSPEEIRALSKEELQMPVTKGDFELALKKIAKSVSAADLEKYEKWMVEF

GSA

The NOV25 amino acid sequence 260 of 305 amino acid residues (85%) identical to, and 285 of 305 amino acid residues (93%) similar to, the 491 amino acid residue ptnr:SPTREMBL-ACC:O75449 protein from *Homo sapiens* (Human) (P60 Katanin) (E=$1.2e^{-155}$).

NOV25 is expressed in at least the following tissues: lung, testis and b-cell. This information was derived by determining the tissue sources of the sequences that were included in the invention including but not limited to SeqCalling sources, Public EST sources, genomic clone sources, literature sources, and/or RACE sources.

Possible SNPs found for NOV25 are listed in Table 25C.

TABLE 25C

SNPs

| Variant | Nucleotide Position | Base Change | Amino Acid Position | Base Change |
|---|---|---|---|---|
| 13377117 | 1050 | A > G | 317 | Ile > Val |
| 13377118 | 1061 | T > C | Silent | N/A |
| 13377119 | 1073 | A > G | Silent | N/A |
| 13377120 | 1074 | C > T | 325 | Leu > Phe |
| 13377121 | 1085 | T > C | Silent | N/A |
| 13377122 | 1111 | C > T | 337 | Ala > Val |
| 13377123 | 1127 | T > C | Silent | N/A |
| 13377124 | 1178 | A > G | Silent | N/A |
| 13377125 | 1190 | T > C | Silent | N/A |
| 13377126 | 1297 | T > C | Silent | N/A |

TABLE 25D

BLAST results for NOV25

| Gene Index/ Identifier | Protein/ Organism | Length (aa) | Identity (%) | Positives (%) | Expect |
|---|---|---|---|---|---|
| gi|14149767|ref|NP_115492.1| (NM_032116) | hypothetical protein MGC2599 similar to katanin p60 subunit A 1 [*Homo sapiens*] | 490 | 306/306 (100%) | 306/306 (100%) | e-170 |
| gi|5825592|gb| AAD53310.1| AF177942 1 (AF177942) | katanin p60 [*Xenopus laevis*] | 486 | 257/304 (84%) | 288/304 (94%) | e-149 |
| gi|5901990|ref|NP_008975.1| (NM_007044) | katanin p60 subunit A 1 [*Homo sapiens*] | 491 | 260/305 (85%) | 285/305 (93%) | e-148 |
| gi|7594619|emb| CAB88114.1| (AL078581) | dJ12G14.4 (katanin p60) (ATPase-containing) subunit A 1) [*Homo sapiens*] | 384 | 260/305 (85%) | 285/305 (93%) | e-148 |
| gi|6754410|ref|NP_035965.1| (NM_011835) | katanin p60 (ATPase-containing) subunit A1 [*Mus musculus*] | 491 | 259/305 (84%) | 285/305 (92%) | e-147 |

NOV25 has homology to the amino acid sequences shown in the BLASTP data listed in Table 25D.

The homology of these sequences is shown graphically in the ClustalW analysis shown in Table 25E.

TABLE 25E

Clustal W Sequence Alignment

1) NOV25 (SEQ ID NO:84)
2) gi|14149767|ref|NP_115492.1|(NM_032116) hypothetical protein MGC2599 similar to katanin p60 subunit A 1 [*Homo sapiens*] (SEQ ID NO:250)
3) gi 5825592|gb AAD53310.1|AF177942_1 (AF177942) katanin p60 [*Xenopus laevis*] (SEQ ID NO:251)
4) gi 5901990|refNP_008975.1|(NM_007044) katanin p60 subunit A 1 [*Homo sapiens*] (SEQ ID NO:252)

TABLE 25E-continued

Clustal W Sequence Alignment 5) gi 7594619|emb|CAB88114.1|(AL078581) dJ12G14.4 (katanin p60 (ATPase-containing) subunit A 1) [Homo sapiens] (SEQ ID NO:253)
6) gi 6754410|refNP_035965.1|(NM_011835) katanin p60 (ATPase-containing) subunit A1 [Mus musculus] (SEQ ID NO:254)

```
                        10        20        30        40        50        60        70
                 ....|....|....|....|....|....|....|....|....|....|....|....|....|....|
NOV25            MNLAEICDNAKKGREYALLGNYDSMVYYQGVMQQIQRLCQSVRLPAIRGKWQQVR--------------
gi 14149767|     MNLAEICDNAKKGREYALLGNYDSMVYYQGVMQQIQRLCQSVRLPAIRGKWQQVRQELLEEYEQVKSIY
gi 5825592|      MSLLMISENVKLAREYALLGNYDSAMVYYQGVLDQMNKYLYSVKLTFLQQKWQQVWQEINMECKHVKDIM
gi 5901990|      MSLLMISENVKLAREYALLGNYDSAMVYYQGVLDQMNKYLYSVKLTYLQQKWQQVWQEINVEAKHVKDIM
gi 7594619|      ------------------------MAVLLETTLGDVVIDLYIEERPRACLNKLKECK-------------
gi 6754410|      MSLQMIVENVKLAREYALLGNYDSAMVYYQGVLDQMNKYLYSVKDTHLRQKWQQVWQEINVEAKQVKDIM 80        90       100       110       120       130       140
                 ....|....|....|....|....|....|....|....|....|....|....|....|....|....|
NOV25            ------------------------W---------------------------------------------
gi 14149767|     STLESFKLDKPPDFPVSCQDEPFRDPAVWPPPVEAEHRAPPQIRRPNREVRPLRKEMAGVGARGPVGR-A
gi 5825592|      STLEGFKLDSSP-VKTTQHEFPSHDGEVWSLPVEVERRPSPGPRK--RQSVQCNDNKSHNNRFSAAAKGP
gi 5901990|      KTLESFKLDSTP-LKAAQHDLPASEGEVWSMPVEVERRPSPGPRK--RQSSQYSDPKSHGNRPSTTVR-V
gi 7594619|      ----------------------------------------IKY---------------------------
gi 6754410|      KTLESFKLDITS-LQAAQHELPAAEGEVWSLPVEVERRPLPGPRK--RQSSQHSDPKPHSNRPSTVVR-A 150       160       170       180       190       200       210
                 ....|....|....|....|....|....|....|....|....|....|....|....|....|....|
NOV25            -----------------------------------------GYDKDLVEALERDIVSRNPS
gi 14149767|     HPISKSEKPSTSRDKDYRARGRDD----KGRKN-MQDGASQGEMPKFDGAGYDKDLVEALERDIVSRNPS
gi 5825592|      NLPS-ARNANNVKMKPVRAREKKD----ALIKNKSSADVSRTEVKRFDGSGYDKDLIEALERDIISQNPN
gi 5901990|      HRSS-AQNVHNDRGKAVRCREKKEQNKGREEKNKSPAAVTEPETNKFDSTGYDKDLVEALERDIISQNPN
gi 7594619|      -----------------------------------------YNYCLIHNVQRDEIIQTGD
gi 6754410|      HRPS-PQNLHNDRGKAVRSREKKEQSKGREEKNKLPAAVTEPEANKFDGTGYDKDLVEALERDIISQNPN 220       230       240       250       260       270       280
                 ....|....|....|....|....|....|....|....|....|....|....|....|....|....|
NOV25            IHWDDIADLEEAKKLLREAVVLPMWMPDFFKGIRRPWKGVLMVGPPGTGKTMLAKAVATECGTTFFNVSS
gi 14149767|     IHWDDIADLEEAKKLLREAVVLPMWMPDFFKGIRRPWKGVLMVGPPGTGKTMLAKAVATECGTTFFNVSS
gi 5825592|      IRWDDIADIEEAKKLLKEAVVLPMWMPEFFKGIRRPWKGVLMVGPPGTGKTLLAKAVATECKTTFFNISS
gi 5901990|      VRWDDIADLVEAKKLLKEAVVLPMWMPEFFKGIRRPWKGVLMVGPPGTGKTLLAKAVATECKTTFFNVSS
gi 7594619|      PTGTGRGGESIFGQLYGDQASF--PEAEKVPRIKHKKGTVSMVNNGSDQHGSQFLITLGENLDTLDGVH
gi 6754410|      VRWYDIADIVEAKKLLKEAVVLPMWMPEFFKGIRRPWKGVLMVGPPGTGKTLLAKAVATECKTTFFNVSS 290       300       310       320       330       340       350
                 ....|....|....|....|....|....|....|....|....|....|....|....|....|....|
NOV25            STLTSKYRGESEKLVRLLFEMARFYAPTTIFIDEIDSICSRRGTSDEHEASRRVKSELLIQMDGVGGALE
gi 14149767|     STLTSKYRGESEKLVRLLFEMARFYAPTTIFIDEIDSICSRRGTSDEHEASRRVKSELLIQMDGVGGALE
gi 5825592|      STLTSKYRGESEKLVRLLFEMARFYAPTTIFIDEIDSICSRRGTSEEHEASRRVKAELLVQMDGVGGASE
gi 5901990|      STLTSKYRGESEKLVRLLFEMARFYSPATIFIDEIDSICSRRGTSEEHEASRRVKAELLVQMDGVGGTSE
gi 7594619|      TVFGEVTEC---------MDIIKKINEIFVDKDFVPYQDIRINHIVILDDPFDDPPDLLIP-DR------
gi 6754410|      STLTSKYRGESEKLVRLLFEMARFYSPATIFIDEIDSICSRRGTSEEHEASRRVKAELLVQMDGVGGASE 360       370       380       390       400       410       420
                 ....|....|....|....|....|....|....|....|....|....|....|....|....|....|
NOV25            NDDPSKMVMVLAATNFPWDIDEALRRRLEKRIYIPLPTAKGRAELLKINLREVELDPDIQLEDIAEKIEQ
gi 14149767|     NDDPSKMVMVLAATNFPWDIDEALRRRLEKRIYIPLPTAKGRAELLKINLREVELDPDIQLEDIAEKIEQ
gi 5825592|      NEDPSKMVMVLAATNFPWDIDEALRRRLEKRIYIPLPSAKGRAELLKILLKELELADDVNLECIAENMEQ
gi 5901990|      NDDPSKMVMVLAATNFPWDIDEALRRRLEKRIYIPLPSAKGREELLRISLRELELADDVDLASIAENMEQ
gi 7594619|      SPEETEEQLDSGRIGADEEIDDFKGRSAESVEEIKAEKEAKTQARL------LEMVGDIPDADIKPPENV
gi 6754410|      NDDPSKMVMVLAATNFPWDIDEALRRRLEKRIYIPLPSAKGREELLRISLRELELADDVNLASIAENMEQ 430       440       450       460       470       480       490
                 ....|....|....|....|....|....|....|....|....|....|....|....|....|....|
NOV25            YSGADITNVCRDASLMAMRRRINGLSPEEIRALSKEEIQMPVTKGDFEALKKIAKSVSAADLEKYEKWM
gi 14149767|     YSGADITNVCRDASLMAMRRRINGLSPEEIRALSKEEIQMPVTKGDFEALKKIAKSVSAADLEKYEKWM
gi 5825592|      YSGADITNVCRDASLMAMRRRIEGLTPEEIRNLSRDDMHMPTIMEDFEMALKKVSKSVSASDLEKYEKWI
gi 5901990|      YSGADITNVCRDASLMAMRRRIEGLTPEEIRNLSKEEMHMPTIMEDFEMALKKVSKSVSAADIERYEKWI
gi 7594619|      LFVCKINPVTTDEDLEIIFSRFGPIRSCEVIRDWKTGESLCYAFIEFEK---------------------
gi 6754410|      YSGADITNVCRDASLMAMRRRIEGLTPEEIRNLSREAMHMPTIMEDFEMALKKVSKSVSAADIERYEKWI

....|.
NOV25            VEFGSA
gi 14149767|     VEFGSA
gi 5825592|      FEFG--
gi 5901990|      FEFGSC
gi 7594619|      ------
gi 6754410|      VEFGSC
```

Table 25F lists the domain description from DOMAIN analysis results against NOV25. This indicates that the NOV25 sequence has properties similar to those of other proteins known to contain these domains.

TABLE 25F

Domain Analysis of NOV25

```
gnl|Pfam pfam00004, AAA, ATPase family associated with various
cellular activities (AAA). AAA family proteins often perform
chaperone-like functions that assist in the assembly, operation, or
disassembly of protein complexes. (SEQ ID NO:255)
CD-Length = 186 residues, 100.0% aligned
Score = 199 bits (505), Expect = 3e-52
Query:  116 GVLMVGPPGTGKTMLAKAVATECGTTFFNVSSSTLTSKYRGESEKLVRLLFEMARFYAPT  175
            |+|+ |||||||+||||| | | +| | | ||| |||||||| || +|| ||
Sbjct:    1 GILLYGPPGTGKTLLAKAVAKELGVPFIEISGSELLSKYVGESEKLVRALFSLARKSAPC   60

Query:  176 TIFIDEIDSICSRRGTSDEHEASRRVKSELLIQMDGVGGALENDDPSKMVMVLAATNFPW  235
            ||||||++ +||   + | || ++|| +|||       +   |+|+ ||| |
Sbjct:   61 IIFIDEIDALAPKRGDVGTGDVSSRVVNQLLTEMDGF-------EKLSNVIVIGATNRPD  113

Query:  236 DIDEALRR--RLEKRIYIPLPTAKGRAELLKINLREVELDPDIQLEDIAEKIEGYSGADI  293
            +| || |  | ++|| +||| +  | |+|||+|++ |+ |+ |++|| + |+||||+
Sbjct:  114 LLDPALLRPGRFDRRIEVPLPDEEERLEILKIHLKKKPLEKDVDLDEIARRTPGFSGADL  173

Query:  294 TNVCRDASLMAMR                                                306
            +||+|+| |+|
Sbjct:  174 AALCREAALRAIR                                                186
```

Microtubule disassembly at centrosomes is involved in mitotic spindle function. The microtubule-severing protein katanin, a heterodimer of 60- and 80-kD subunits, was purified and shown to localize to centrosomes in vivo (McNally and Vale, Cell 75: 419–429, 1993; McNally et al., J. Cell Sci. 109: 561–567, 1996). By homology to the sequence of S. purpuratus, Hartman et al. (Cell 93: 277–287, 1998) cloned the cDNA for the human p80 subunit. This protein contains WD40 repeats, which are frequently involved in protein-protein interactions. The p80 WD40 domain does not participate in p60 dimerization, but localizes to centrosomes in transfected mammalian cells. The results of the studies of Hartman et al. (1998) in yeast indicated that the activities of katanin are segregated into a subunit (p60) that possesses enzymatic activity and a subunit (p80) that targets the enzyme to the centrosome.

Microtubule disassembly at centrosomes is involved in mitotic spindle function. The microtubule-severing protein katanin, a heterodimer of 60 and 80 kDa subunits, was previously purified and shown to localize to centrosomes in vivo. The sequences and activities of the katanin subunits were reported. p60 is a new member of the AAA family of ATPases, and expressed p60 has microtubule-stimulated ATPase and microtubule-severing activities in the absence of p80. p80 is a novel protein containing WD40 repeats, which are frequently involved in protein-protein interactions. The p80 WD40 domain does not participate in p60 dimerization, but localizes to centrosomes in transfected mammalian cells. These results indicate katanin's activities are segregated into a subunit p60) that possesses enzymatic activity and a subunit (p80) that targets the enzyme to the centrosome (Hartman et al., Cell 93: 277–287, 1998).

The assembly and function of the mitotic spindle involve specific changes in the dynamic properties of microtubules. One such change results in the poleward flux of tubulin in which spindle microtubules polymerize at their kinetochore-attached plus ends while they shorten at their centrosome-attached minus ends. Since free microtubule minus ends do not depolymerize in vivo, the poleward flux of tubulin suggests that spindle microtubules are actively disassembled at or near their centrosomal attachment points. The microtubule-severing ATPase, katanin, has the ability actively to sever and disassemble microtubules and is thus a candidate for the role of a protein mediating the poleward flux of tubulin. The subcellular localization of katanin by immunofluorescence was identified as a preliminary step in determining whether katanin mediates the poleward flux of tubulin. Katanin is highly concentrated at centrosomes throughout the cell cycle. Katanin's localization is different from that of gamma-tubulin in that microtubules are required to maintain the centrosomal localization of katanin. Direct comparison of the localization of katanin and gamma-tubulin reveals that katanin is localized in a region surrounding the gamma-tubulin-containing pericentriolar region in detergent-extracted mitotic spindles. The centrosomal localization of katanin is consistent with the hypothesis that katanin mediates the disassembly of microtubule minus ends during poleward flux (McNally and Vale, Cell 75: 419–429, 1993).

The NOV25 nucleic acid of the invention encoding a Katanin-like protein includes the nucleic acid whose sequence is provided in Table 25A, or a fragment thereof. The invention also includes a mutant or variant nucleic acid any of whose bases may be changed from the corresponding base shown in Table 25A while still encoding a protein that maintains its Katanin-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 25% of the NOV25 residues may be so changed.

The NOV25 protein of the invention includes the Katanin-like protein whose sequence is provided in Table 25B. The invention also includes a mutant or variant protein any of whose residues may be changed from the corresponding residue shown in Table 25B while still encoding a protein that maintains its Katanin-like activities and physiological functions, or a functional fragment thereof. In the mutant or variant protein, up to about 15% of the NOV25 bases may be so changed.

The NOV25 nucleic acids and proteins of the invention are useful in potential diagnostic and therapeutic applications implicated in various diseases and disorders described below and/or other pathologies. For example, the compositions of the present invention will have efficacy for treatment of patients suffering from: developmental disorders, fertility, hypogonadism, systemic lupus erythematosus, autoimmune disease, asthma, emphysema, scleroderma, allergy, ARDS, immunological diseases and other diseases, disorders and conditions of the like.

NOV25 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV25 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV26

A disclosed NOV26 nucleic acid of 2442 nucleotides (also referred to as CG57509-01) encoding a novel Calpain-like protein is shown in Table 26A. An open reading frame was identified beginning with an ATG initiation codon at nucleotides 77–79 and ending with a TGA codon at nucleotides 2396–2398. Putative untranslated regions upstream from the intitation codon and downstream from the termination codon are underlined in Table 26A, and the start and stop codons are in bold letters.

TABLE 26A

NOV26 Nucleotide Sequence (SEQ ID NO:85)

TGCAGTTGCTTCCTTTCCTTGAAGGTAGCTGTATCTTATTTTCTTTAAAAAGCTTTTTCTTCCAAAGCCACTT

GCCATGCCGACCGTCATTAGCGCATCTGTGGCTCCAAGGACAGCGGCTGAGCCCCGGTCCCCAGGGCCAGTTC

CTCACCCGGCCCAGAGCAAGGCCACTGAGGCTGGGGGTGGAAACCCAAGTGGCATCTATTCAGCCATCATCAG

CCGCAATTTTCCTATTATCGGAGTGAAAGAGAAGACATTCGAGCAACTTCACAAGAAATGTCTAGAAAAGAAA

GTTCTTTATGTGGACCCTGAGTTCCCACCGGATGAGACCTCTCTCTTTTATAGCCAGAAGTTCCCCATCCAGT

TCGTCTGGAAGAGACCTCCGGAAATTTGCGAGAATCCCCGATTTATCATTGATGGAGCCAACAGAACTGACAT

CTGTCAAGGAGAGCTAGGGGACTGCTGGTTTCTCGCAGCCATTGCCTGCCTGACCCTGAACCAGCACCTTCTT

TTCCGAGTCATACCCCATGATCAAAGTTTCATCGAAAACTACGCAGGGATCTTCCACTTCCAGTTCTGGCGCT

ATGGAGAGTGGGTGGACGTGGTTATAGATGACTGCCTGCCAACGTACAACAATCAACTGGTTTTCACCAAGTC

CAACCACCGCAATGAGTTCTGGAGTGCTCTGCTGGAGAAGGCTTATGCTAAGCTCCATGGTTCCTACGAAGCT

CTGAAAGGTGGGAACACCACAGAGGCCATGGAGGACTTCACAGGAGGGGTGGCAGAGTTTTTTGAGATCAGGG

ATGCTCCTAGTGACATGTACAAGATCATGAAGAAAGCCATCGAGAGAGGCTCCCTCATGGGCTGCTCCATTGA

TACAATCATTCCGGTTCAGTATGAGACAAGAATGGCCTGCGGGCTGGTCAGAGGTCACGCCTACTCTGTCACG

GGGCTGGATGAGGTCCCGTTCAAAGGTGAGAAAGTGAAGCTGGTGCGGCTGCGGAATCCGTGGGGCCAGGTGG

AGTGGAACGGTTCTTGGAGTGATAGATGGAAGGACTGGAGCTTTGTGGACAAAGATGAGAAGGCCCGTCTGCA

GCACCAGGTCACTGAGGATGGAGAGTTCTGGATGTCCTATGAGGATTTCATCTACCATTTCACAAAGTTGGAG

ATCTGCAACCTCACGGCCGATGCTCTGCAGTCTGACAAGCTTCAGACCTGGACAGTGTCTGTGAACGAGGGCC

GCTGGGTACGGGGTTGCTCTGCCGGAGGCTGCCGCAACTTCCCAGATACTTTCTGGACCAACCCTCAGTACCG

TCTGAAGCTCCTGGAGGAGGACGATGACCCTGATGACTCGGAGGTGATTTGCAGCTTCCTGGTGGCCCTGATG

CAGAAGAACCGGCGAAGGACCGGAAGCTAGGGGCCAGTCTCTTCACCATTGGCTTCGCCATCTACGAGGTTC

CCAAAGAGATGCACGGGAACAAGCAGCACCTGCAGAAGGACTTCTTCCTGTACAACGCCTCCAAGGCCAGGAG

CAAAACCTACATCAACATGCGGGAGGTGTCCCAGCGCTTCCGCCTGCCTCCCAGCGAGTACGTCATCGTGCCC

TCCACCTACGAGCCCCACCAGGAGGGGAATTCATCCTCCGGGTCTTCTCTGAAAAGAGGAACCTCTCTGAGG

AAGTTGAAAATACCATCTCCGTGGATCGGCCAGTGAAAAAGAAAAAAACCAAGCCCATCATCTTCGTTTCGGA

CAGAGCAAACAGCAACAAGGAGCTGGGTGTGGACCAGGAGTCAGAGGAGGGCAAAGGCAAAACAAGCCCTGAT

AAGCAAAAGCAGTCCCCACAGCCACAGCCTGGCAGCTCTGATCAGGAAAGTGAGGAACAGCAACAATTCCGGA

TABLE 26A-continued

NOV26 Nucleotide Sequence

ACATTTTCAAGCAGATAGCAGGAGATGACATGGAGATCTGTGCAGATGAGCTCAAGAAGGTCCTTAACACAGT

CGTGAACAAACACAAGGACCTGAAGACACACGGGTTCACACTGGAGTCCTGCCGTAGCATGATTGCGCTCATG

GATACAGATGGCTCTGGAAAGCTCAACCTGCAGGAGTTCCACCACCTCTGGAACAAGATTAAGGCCTGGCAGA

AAATTTTCAAACACTATGACACAGACCAGTCCGGCACCATCAACAGCTACGAGATGCGAAATGCAGTCAACGA

CGCAGGATTCCACCTCAACAACCAGCTCTATGACATCATTACCATGCGGTACGCAGACAAACACATGAACATC

GACTTTGACAGTTTCATCTGCTGCTTCGTTAGGCTGGAGGGCATGTTCAGAGCTTTTCATGCATTTGACAAGG

ATGGAGATGGTATCATCAAGCTCAACGTTCTGGAGTGGCTGCAGCTCACCATGTATGCCTGAACCAGGCTGGC

CTCATCCAAAGCCATGCAGGATCACTCAGGATT

The NOV26 nucleic acid was identified on chromosome 15 and has 1717 of 1720 bases (99%) identical to a gb:GENBANK-ID:AF127765|acc:AF127765.3 mRNA from Homo sapiens (Homo sapiens calpain 3 (CAPN3) mRNA, complete cds, alternatively spliced) (E=0.0).

A disclosed NOV26 polypeptide (SEQ ID NO:86) encoded by SEQ ID NO:85 is 773 amino acid residues and is presented using the one-letter code in Table 26B. Signal P, Psort and/or Hydropathy results predict that NOV26 does not contain a signal peptide and is likely to be localized to the cytoplasm with a certainty of 0.6526. The most likely cleavage site for a NOV26 polypeptide is between amino acids 15 and 16: TAA-EP

TABLE 26B

Encoded NOV26 protein sequence (SEQ ID NO:86)
MPTVISASVAPRTAAEPRSPGPVPHPAQSKATEAGGGNPSGIYSAIISRNFPIIGVKEKTFEQLHKKCLEKK

VLYVDPEFPPDETSLFYSQKFPIQFVWKRPPEICENPRFIIDGANRTDICQGELGDCWFLAAIACLTLNQHL

LFRVIPHDQSFIENYAGIFHFQFWRYGEWVDVVIDDCLPTYNNQLVFTKSNHRNEFWSALLEKAYAKLHGSY

EALKGGNTTEAMEDFTGGVAEFFEIRDAPSDMYKIMKKAIERGSLMGCSIDTIIPVQYETRMACGLVRGHAY

SVTGLDEVPFKGEKVKLVRLRNPWGQVEWNGSWSDRWKDWSFVDKDEKARLQHQVTEDGEFWMSYEDFIYHF

TKLEICNLTADALQSDKLQTWTVSVNEGRWVRGCSAGGCRNFPDTFWTNPQYRLKLLEEDDDPDDSEVICSF

LVALMQKNRRKDRKLGASLFTIGFAIYEVPKEMHGNKQHLQKDFFLYNASKARSKTYINMREVSQRFRLPPS

EYVIVPSTYEPHQEGEFILRVFSEKRNLSEEVENTISVDRPVKKKKTKPIIFVSDRANSNKELGVDQESEEG

KGKTSPDKQKQSPQPQPGSSDQESEEQQQFRNIFKQIAGDDMEICADELKKVLNTVVNKHKDLKTHGFTLES

CRSMIALMDTDGSGKLNLQEFHHLWNKIKAWQKIFKHYDTDQSGTINSYEMRNAVNDAGFHLNNQLYDIITM

RYADKHMNIDFDSFICCFVRLEGMFRAFHAFDKDGDGIIKLNVLEWLQLTMYA

Subunit (EC 3.4.22.17) (Calpain L3) (Calpain P94, Large [Catalytic] Subunit) (Calcium-Activated Neutral Proteinase 3) (CANP 3) (Muscle-Specific Calcium-Activated Neutral Protease 3 Large Subunit)).

NOV26 is expressed in at least the following tissues: adrenal gland, bone marrow, brain—amygdala, brain—cerebellum, brain—hippocampus, brain—substantia nigra, brain—thalamus, brain—whole, fetal brain, fetal kidney, fetal liver, fetal lung, heart, kidney, lymphoma—Raji, mammary gland, pancreas, pituitary gland, placenta, prostate, salivary gland, skeletal muscle, small intestine, spinal cord, spleen, stomach, testis, thyroid, trachea, uterus, aorta, epidermis, foreskin, heart, hypothalamus, liver, lung, lymph The NOV26 amino acid sequence 506 of 506 amino acid residues (100%) identical to, and 506 of 506 amino acid residues (100%) similar to, the 821 amino acid residue ptnr:SWISSNEW-ACC:P20807 protein from Homo sapiens (Human) (Calpain 3 Large Subunit (EC 3.4.22.17) (Calpain L3) (Calpain P94, Large [Catalytic] Subunit) (Calcium-Activated Neutral Proteinase 3) (CANP 3) (Muscle-Specific Calcium-Activated Neutral Protease 3 Large Subunit)) (E=0.0). The NOV26 amino acid lacks 48 internal amino acids when compared to ptnr:SWISSNEW-ACC:P20807 protein from Homo sapiens (Human) (Calpain 3 Large node, lymphoid tissue, muscle, peripheral blood, skin and whole organism. This information was derived by determining the tissue sources of the sequences that were included in the invention including but not limited to SeqCalling sources, Public EST sources, genomic clone sources, literature sources, and/or RACE sources. NOV26 is predicted to be expressed in leukocytes because of the expression pattern of (gb:GENBANK-ID:AF127765|acc:AF127765.3) a closely related Homo sapiens calpain 3 (CAPN3) mRNA, complete cds, alternatively spliced homolog in species Homo sapiens.

Possible SNPs found for NOV26 are listed in Table 26C and Table 26D.

TABLE 26C

SNPs

| Variant | Nucleotide Position | Base Change | Amino Acid Position | Base Change |
|---|---|---|---|---|
| 13377127 | 72 | T > C | Silent | N/A |
| 13377128 | 78 | T > C | 1 | Met > Thr |
| 13377129 | 201 | T > C | 42 | Ile > Thr |
| 13377130 | 412 | C > T | Silent | N/A |
| 13377131 | 2253 | A > G | 726 | His > Arg |

TABLE 26D

SNPs

| Consensus Position | Depth | Base Change | PAF |
|---|---|---|---|
| 2258 | 29 | A > G | 0.379 |

NOV26 has homology to the amino acid sequences shown in the BLASTP data listed in Table 26E.

TABLE 26E

BLAST results for NOV26

| Gene Index/ Identifier | Protein/ Organism | Length (aa) | Identity (%) | Positives (%) | Expect |
|---|---|---|---|---|---|
| gi/4557405/ref/NP_000061.1/ (NM_000070) | calpain, large polypeptide L3; p94 [Homo sapiens] | 821 | 738/821 (89%) | 738/821 (89%) | 0.0 |
| gi/4704752/gb/ AAD28 253.1/ AF127764_1 (AF127764) | calpain 3; calcium activated neutral protease; CAPN3; CL1 [Homo sapiens] | 815 | 732/821 (89%) | 732/821 (89%) | 0.0 |
| gi/11037484/gb/ AAG2 7599.1/ AF277376_1 (AF277376) | calpain 3 [Macaca fascicularis] | 815 | 720/821 (87%) | 727/821 (87%) | 0.0 |
| gi/7684607/gb/ AAD28 254.3/ AF127765_1 (AF127765) | calpain 3; calcium activated neutral protease; CAPN3; CL1 [Homo sapiens] | 729 | 710/773 (91%) | 713/773 (91%) | 0.0 |
| gi/8393041/ref/NP_058813.1/ (NM_017117) | calpain 3 [Rattus norvegicus] | 821 | 699/821 (85%) | 718/821 (87%) | 0.0 |

The homology of these sequences is shown graphically in the ClustalW analysis shown in Table 26F.

TABLE 26E

Clustal W Sequence Alignment

1) NOV26 (SEQ ID NO:86)
2) gi 4557405|refNP_000061.1|(NM_000070) calpain, large polypeptide L3; p94 [Homo sapiens] (SEQ ID NO:256)
3) gi 4704752|gb AAD28253.1|AF127764_1 (AF127764) calpain 3; calcium activated neutral protease; CAPN3; CL1 [Homo sapiens] (SEQ ID NO:257)
4) gi 11037484|gb AAG27599.1 AF277376_1 (AF277376) calpain 3 [Macaca fascicularis] (SEQ ID NO:258)
5) gi 7684607|gb AAD28254.3|AF127765_1 (AF127765) calpain 3; calcium activated neutral protease; CAPN3; CL1 [Homo sapiens] (SEQ ID NO:259)
6) gi 8393041|refNP_058813.1|(NM_017117) calpain 3 [Rattus norvegicus] (SEQ ID NO:260)

```
                   10        20        30        40        50        60        70
                ....|....|....|....|....|....|....|....|....|....|....|....|....|....|
NOV26           MPTVISASVAPRTAAEPRSPGPVPHPAQSKATEAGGGNPSGIYSAIISRNFPIIGVKEKTFEQLHKKCLL
gi|4557405|     MPTVISASVAPRTAAEPRSPGPVPHPAQSKATEAGGGNPSGIYSAIISRNFPIIGVKEKTFEQLHKKCLL
gi|4704752|     MPTVISASVAPRTAAEPRSPGPVPHPAQSKATEAGGGNPSGIYSAIISRNFPIIGVKEKTFEQLHKKCLL
gi|11037484|    MPTVISASVAPRTAAEPRSPGPVPHPAQSKATEAGGGNASGIYSAIISRNFPIIGVKEKTFEQLHKKCLL
gi|7684607|     MPTVISASVAPRTAAEPRSPGPVPHPAQSKATEAGGGNPSGIYSAIISRNFPIIGVKEKTFEQLHKKCLL
gi|8393041|     MPTVISPTVAPRTGAEPRSPGPVPHPAQGKTTEAGGGRPGGIYSAIISRNFPIIGVKEKTFEQLHKKCLL 80        90       100       110       120       130       140
                ....|....|....|....|....|....|....|....|....|....|....|....|....|....|
NOV26           KKVLYVDPEFPPDETSLFYSQKFPIQFVWKRPPEICENPRFIIDGANRTDICQGELGDCWFLAAIACLTL
gi|4557405|     KKVLYVDPEFPPDETSLFYSQKFPIQFVWKRPPEICENPRFIIDGANRTDICQGELGDCWFLAAIACLTL
gi|4704752|     KKVLYVDPEFPPDETSLFYSQKFPIQFVWKRPPEICENPRFIIDGANRTDICQGELGDCWFLAAIACLTL
gi|11037484|    KKVLYVDPEFPPDETSLFYSQKFPIQFIWKRPPEICENPRFIIDGANRTDICQGDLGDCWFLAAIACLTL
gi|7684607|     KKVLYVDPEFPPDETSLFYSQKFPIQFVWKRPPEICENPRFIIDGANRTDICQGELGDCWFLAAIACLTL
gi|8393041|     KKVLYEDPEFPPDETSLFYSQKFPIQFVWKRPPEICENPRFIIGGANRTDICQGDLGDCWLAAIACLTL
```

TABLE 26E-continued

Clustal W Sequence Alignment

```
              150        160        170        180        190        200        210
              ....|....|....|....|....|....|....|....|....|....|....|....|....|
NOV26         NQHLLFRVIPHDQSFIENYAGIFHFQFWRYGEWVDVVIDDCLPTYNNQLVFTKSNHRNEFWSALLEKAYA
gi|4557405|   NQHLLFRVIPHDQSFIENYAGIFHFQFWRYGEWVDVVIDDCLPTYNNQLVFTKSNHRNEFWSALLEKAYA
gi|4704752|   NQHLLFRVIPHDQSFIENYAGIFHFQFWRYGEWVDVVIDDCLPTYNNQLVFTKSNHRNEFWSALLEKAYA
gi|11037484|  NQRLLFRVIPHDQSFIENYAGIFHFQFWRYGEWVDVVIDDCLPTYNNQLVFTKSNHRNEFWSALLEKAYA
gi|7684607|   NQHLLFRVIPHDQSFIENYAGIFHFQFWRYGEWVDVVIDDCLPTYNNQLVFTKSNHRNEFWSALLEKAYA
gi|8393041|   NERLLFRVIPHDQSFTENYAGIFHFQFWRYGEWVDVVIDDCLPTYNNQLVFTKSNHRNEFWSALLEKAYA 220        230        240        250        260        270        280
              ....|....|....|....|....|....|....|....|....|....|....|....|....|
NOV26         KLHGSYEALKGGNTTEAMEDFTGGVAEFFEIRDAPSDMYKIMKKAIERGSLMGCSID-------------
gi|4557405|   KLHGSYEALKGGNTTEAMEDFTGGVAEFFEIRDAPSDMYKIMKKAIERGSLMGCSIDDGTNMTYGTSPSG
gi|4704752|   KLHGSYEALKGGNTTEAMEDFTGGVAEFFEIRDAPSDMYKIMKKAIERGSLMGCSIDDGTNMTYGTSPSG
gi|11037484|  KLHGSYEALKGGNTTEAMEDFTGGVTEFFEIRDAPSDMKIMKKAIERGSLMGCSIDDGTNMTYGTSPSG
gi|7684607|   KLHGSYEALKGGNTTEAMEDFTGGVAEFFEIRDAPSDMYKIMKKAIERGSLMGCSID-------------
gi|8393041|   KLHGSYEALKGGNTTEAMEDFTGGVTEFFEIKDAPSDMYKIMRKAIERGSLMGCSIDDGTNMTYGTSPSG 290        300        310        320        330        340        350
              ....|....|....|....|....|....|....|....|....|....|....|....|....|
NOV26         -------------------------------TIIPVQYETRMACGLVRGHAYSVTGLDEVPFKGEK
gi|4557405|   LNMGELIARMVRNMDNSLLQDSDLDPPGSDERPTRTIIPVQYETRMACGLVRGHAYSVTGLDEVPFKGEK
gi|4704752|   LNMGELIARMVRNMDNSLLQDSDLDPPGSDERPTRTIIPVQYETRMACGLVRGHAYSVTGLDEVPFKGEK
gi|11037484|  LNMGELIARMVRNMDNSLFRDSDLDPPASVERPKRTIVPVQYETRMACGLVRGHAYSVTGLDEVLFKGEK
gi|7684607|   -------------------------------TIIPVQYETRMACGLVRGHAYSVTGLDEVPFKGEK
gi|8393041|   LNMGELIARMVRNMDNSLLRDSDLDPPASDRPSRTIVPVQYETRMACGLVKGHAYSVTGLEEALFKGEK 360        370        380        390        400        410        420
              ....|....|....|....|....|....|....|....|....|....|....|....|....|
NOV26         VKLVRLRNPWGQVEWNGSWSDRWKDWSFVDKDEKARLQHQVTEDGEFWMSYEDFIYHFTKLEICNLTADA
gi|4557405|   VKLVRLRNPWGQVEWNGSWSDRWKDWSFVDKDEKARLQHQVTEDGEFWMSYEDFIYHFTKLEICNLTADA
gi|4704752|   VKLVRLRNPWGQVEWNGSWSDRWKDWSFVDKDEKARLQHQVTEDGEFWMSYEDFIYHFTKLEICNLTADA
gi|11037484|  VKLVRLRNPWGQVEWNGSWSDGWKDWSFVDKDEKARLQHQVTEDGEFWMSYEDFIYHFTKLEICNLTADA
gi|7684607|   VKLVRLRNPWGQVEWNGSWSDRWKDWSFVDKDEKARLQHQVTEDGEFWMSYEDFIYHFTKLEICNLTADA
gi|8393041|   VKLVRLRNPWGQVEWNGSWSDGWKDWSFVDKDEKARLQHQVTEDGEFWMSYDDFVYHFTKLEICNLTADA 430        440        450        460        470        480        490
              ....|....|....|....|....|....|....|....|....|....|....|....|....|
NOV26         LQSDKLQTWTVSVNEGRWVRGCSAGGCRNFPDTFWTNPQYRLKLLEEDDDPDDSEVICSFLVALMQKNRR
gi|4557405|   LQSDKLQTWTVSVNEGRWVRGCSAGGCRNFPDTFWTNPQYRLKLLEEDDDPDDSEVICSFLVALMQKNRR
gi|4704752|   LQSDKLQTWTVSVNEGRWVRGCSAGGCRNFPDTFWTNPQYRLKLLEEDDDPDDSEVICSFLVALMQKNRR
gi|11037484|  LQSDKLQTWTVSVNEGRWVRGCSAGGCRNFPDTFWTNPQYRLKLLEEDDDPDDSEVICSFLVALMQKNRR
gi|7684607|   LQSDKLQTWTVSVNEGRWVRGCSAGGCRNFPDTFWTNPQYRLKLLEEDDDPDDSEVICSFLVALMQKNRR
gi|8393041|   LESDKLQTWTVSVNEGRWVRGCSAGGCRNFPDTFWTNPQYRLKLLEEDDDPDDSEVICSFLVALMQKNRR 500        510        520        530        540        550        560
              ....|....|....|....|....|....|....|....|....|....|....|....|....|
NOV26         KDRKLGASLFTIGFAIYEVPKEMHGNKQHLQKDFFLYNASKARSKTYINMREVSQRFRLPPSEYVIVPST
gi|4557405|   KDRKLGASLFTIGFAIYEVPKEMHGNKQHLQKDFFLYNASKARSKTYINMREVSQRFRLPPSEYVIVPST
gi|4704752|   KDRKLGASLFTIGFAIYEVPKEMHGNKQHLQKDFFLYNASKARSKTYINMREVSQRFRLPPSEYVIVPST
gi|11037484|  KDRKLGANLFTIGFAIYEVPKEMHGNRQHLQKDFFLYNASRARSKTYINMREVSQRFRLPPSEYVIVPST
gi|7684607|   KDRKLGASLFTIGFAIYEVPKEMHGNKQHLQKDFFLYNASKARSKTYINMREVSQRFRLPPSEYVIVPST
gi|8393041|   KDRKLGANLFTIGFAIYEVPKEMHGNKQHLQKDFFLYNASKARSKTYINMREVSQRFRLPPSEYVIVPST 570        580        590        600        610        620        630
              ....|....|....|....|....|....|....|....|....|....|....|....|....|
NOV26         YEPHQEGEFILRVFSEKRNLSEEVENTISVDRPVKKKKKKPIIFVSDRANSNKELGVDQESEEGKGKTSP
gi|4557405|   YEPHQEGEFILRVFSEKRNLSEEVENTISVDRPVKKKKKKPIIFVSDRANSNKELGVDQESEEGKGKTSP
gi|4704752|   YEPHQEGEFILRVFSEKRNLSEEVENTISVDRPVP------IIFVSDRANSNKELGVDQESEEGKGKTSP
gi|11037484|  YEPHQEGEFILRVFSEKRNLSEEVENTISVDRPVP------IIFVSDRANSNKELGVDQESEEGKGKTSP
gi|7684607|   YEPHQEGEFILRVFSEKRNLSEEVENTISVDRPV-------------------P-------------
gi|8393041|   YEPHQEGEFILRVFSEKRNLSEEAENTISVDRPVKKKKKKPIIFVSDRANSNKELGVDQEAEEGKDKTGP 640        650        660        670        680        690        700
              ....|....|....|....|....|....|....|....|....|....|....|....|....|
NOV26         DKQKQSPQPQPGSSDQESEEQQQFRNIFKQIAGDDMEICADELKKVLNTVVNKHKDLKTHGFTLESCRSN
gi|4557405|   DKQRQSPQPQPGSSDQESEEQQQFRNIFKQIAGDDMEICADELKKVLNTVVNKHKDLKTHGFTLESCRSN
gi|4704752|   DKQLQSPQPQPGSSDQESEEQQQFRNIFKQIAGDDMEICADELKKVLNTVVNKHKDLKTHGFTLESCRSN
gi|11037484|  DKQRQSPQPQPGSSDQESEEQQQFRNIFKQIAGDDMEICADELKKVLNTVVNKHKDLKTHGFTLESCRSN
gi|7684607|   ---------QPGSSDQESEEQQQFRNIFKQIAGDDMEICADELKKVLNTVVNKHKDLKTHGFTLESCRSN
gi|8393041|   DKQGESPQERPGHTDQESEEQQQFRNIFRQIAGDDMEICADELKNVLNTVVNKHKDLKTQGFTLESCRSN 710        720        730        740        750        760        770
              ....|....|....|....|....|....|....|....|....|....|....|....|....|
NOV26         IALMDTDGSGKLNLQEFHHLWNKIKAWQKIFKHYDTDQSGTINSYEMRNAVNDAGFHLNNQLYDIITMRY
gi|4557405|   IALMDTDGSGKLNLQEFHHLWNKIKAWQKIFKHYDTDQSGTINSYEMRNAVNDAGFHLNNQLYDIITMRY
gi|4704752|   IALMDTDGSGKLNLQEFHHLWNKIKAWQKIFKHYDTDQSGTINSYEMRNAVNDAGFHLNNQLYDIITMRY
gi|11037484|  IALMDTDGSGKLNLQEFHHLWNKIKAWQKIFKHYDTDQSGTINSYEMRNAVNDAGFHLNNQLYDIITMRY
gi|7684607|   IALMDTDGSGKLNLQEFHHLWNKIKAWQKIFKHYDTDQSGTINSYEMRNAVNDAGFHLNNQLYDIITMRY
gi|8393041|   IALMDTDGSGRLNLQEFHHLWKKIKAWQKIFKHYDTDHSGTINSYEMRNAVNDAGFHLNSQLYDIITMRY
```

TABLE 26E-continued

Clustal W Sequence Alignment

```
                 780        790        800        810        820
               ....|....|....|....|....|....|....|....|....|....|.
NOV26          ADKHMNIDFDSFICCFVRLEGMFRAFHAFDKDGDGIIKLNVLEWLQLTMYA
gi|4557405|    ADKHMNIDFDSFICCFVRLEGMFRAFHAFDKDGDGIIKLNVLEWLQLTMYA
gi|4704752|    ADKHMNIDFDSFICCFVRLEGMFRAFHAFDKDGDGIIKLNVLEWLQLTMYA
gi|11037484|   ADKHMNIDFDSFICCFVRLEGMFRAFHAFDKDGDGIIKLNVLEWLQLTMYA
gi|7684607|    ADKHMNIDFDSFICCFVRLEGMFRAFHAFDKDGDGIIKLNVLEWLQLTMYA
gi|8393041|    ADKHMNIDFDSFICCFVRLEGMFRAFHAFDKDGDGIIKLNVLEWLQLTMYA
```

Tables 26G, 26H, 26I and 26J list the domain description from DOMAIN analysis results against NOV26. This indicates that the NOV26 sequence has properties similar to those of other proteins known to contain these domains.

TABLE 26G

Domain Analysis of NOV26

```
gnl|Pfam_pfam00648, Peptidase_C2, Calpain family cysteine protease.
(SEQ ID NO:261)
CD-Length = 298 residues, 100.0% aligned
Score = 518 bits (1335), Expect = 4e-148
Query:   74 LYVDPEFPPDETSLFYSQKFPIQFVWKRPPEICENPRFIIDGANRTDICQGELGDCWFLA  133
            |+||| ||    || |    |    |||| || |||+||+ || |||||||| ||||| ||
Sbjct:    1 LFVDPSFPAAPKSLGYKPLGPRGIEWKRPHEINENPQFIVGGATRTDICQGALGDCWLLA   60

Query:  134 AIACLTLNQHLLFRVIPHDQSFIENYAGIFHFQFWRYGEWVDVVIDDCLPTYNNQLVFTK  193
            |+| ||||+ || ||+|||||||||| ||||||||||+|++|||||||+| ||| + +|+|
Sbjct:   61 ALASLTLNEPLLLRVVPHDQSFQENYAGIFHFRFWQFGEWVDVVVDDLLPTKDGKLLFVH  120

Query:  194 SNHRNEFWSALLEKAYAKLHGSYEALKGGNTTEAMEDFTGGVAEFFEIRDAPS---DMYK  250
            |  |||||||||||||||||+| ||||  ||+||||+|| |||| | +|++ |||   ++
Sbjct:  121 SAERNEFWSALLEKAYAKLNGCYEALSGGSTTEALEDLTGGVCESYELKLAPSSMLNLGN  180

Query:  251 IMKKAIERGSLMGCSIDTIIPVQYETRMACGLVRGHAYSVTGLDEVPFKGEKVKLVRLRN  310
            |+|| +|||||+||||   ||  | |||| |||+||||||||+ ||  ++|| |||+||||
Sbjct:  181 IIKKMLERGSLLGCSIDITSPVDMEARMAKGLVKGHAYSVTGVKEVNYRGEGVKLIRLRN  240

Query:  311 PWGQVEWNGSWSDRWKDWSFVDKDEKARLQHQVTEDGEFWMSYEDFIYHFTKLEICNLT  369
            ||||||| | |||   ||+ || ||||||||| +  ||||||||+|||+ ||++||||||||
Sbjct:  241 PWGQVEWTGDWSDSSPDWNIVDPDEKARLQLKF-EDGEFWMSFEDFLRHFSRLEICNLT  298
```

TABLE 26H

Domain Analysis of NOV26

```
gnl|Smart|smart00230, Cyspc, Calpain-like thiol protease family.;
Calpain-like thiol protease family (peptidase family C2). Calcium
activated neutral protease (large subunit). (SEQ ID NO:262)
CD-Length = 323 residues, 100.0% aligned
Score = 491 bits (1263), Expect = 8e-140
Query:   56 VKEKTFEQLHKKCLEKKVLYVDPEFPPDETSLFYSQKFPIQFVWKRPPEICENPRFIIDG  115
            + + +|+| ++|||+  |+||| ||   +||+||      |||| || |+|   |+ |
Sbjct:    1 FENQDYEELRQECLEEGGLFVDPLFPAKPSSLFFSQLQRKFVVWKRPHEIFEDPPLIVGG   60

Query:  116 ANRTDICQGELGDCWFLAAIACLTLNQHLLFRVIPHDQSFIENYAGIFHFQFWRYGEWVD  175
            |+|||||||  ||||| |||+|   |+ || + || |||| ||  |||||+|+||||+|||
Sbjct:   61 ASRTDICQGVLGDCWLLAALAALTLREELLARVIPKDQEFSENYAGIYHFRFWRYGKWVD  120

Query:  176 VVIDDCLPTYNNQLVFTKSNHRNEFWSALLEKAYAKLHGSYEALKGGNTTEAMEDFTGGV  235
            |||| ||||| +|   ||  || ||||||||||||||  |||||| ||+||||+|| ||||
Sbjct:  121 VVIDDRLPTYNGDLLFMHSNSRNEFWSALLEKAYAKLRGCYEALKGGSTTEALEDLTGGV  180

Query:  236 AEFFEIRDA---PSDMYKIMKKAIERGSLMGCSIDTIIPVQYETRMACGLVRGHAYSVTG  292
            ||  |++    |+++|+||| ||||||||||  |+ |  ||| ||| |||||+| ||||
Sbjct:  181 AESIELKKISKDPDELFKDLKKAFERGSLNGCSIGAGTAVEEEEQKRNGLVKGHAYSVTD  240

Query:  293 LDEVPFKGEKVKLVRLRNPWGQVEWNGSWSDRWKDWSFVDKDEKARLQHQVTEDGEFWMS  352
            + || +    ||+|||||||+ |||| |||    +| | ||| |   + +|||||||||
Sbjct:  241 VREVDGRRR-QKLLRLRNPWGESEWNGPWSDDSPEWRSVSAEEKKNLGLTMDDDGEFWMS  299
Query:  353 YEDFIYHFTKLEICNLTADALQSD                                     376
            +|||+ ||||+||||||   +
Sbjct:  300 FEDFLRHFTKVEICNLRPDWFEYR                                     323
```

TABLE 26I

Domain Analysis of NOV26

```
gnl Pfam pfam01067, Calpain_III, Calpain large subunit, domain III.
The function of the domain III and I are currently unknown. Domain II
is a cysteine protease and domain IV is a calcium binding domain.
Calpains are believed to participate in intracellular signaling
pathways mediated by calcium ions. (SEQ ID NO:263)
CD-Length = 148 residues, 100.0% aligned
Score =  223 bits (567), Expect = 4e-59
Query:   380  TWTVSVNEGRWVRGCSAGGCRNFPDTFWTNPQYRLKLLEEDDDPDDSEVICSFLVALMQK  439
              | ++ || | || +||||||+|||||||||| + | | ||| +||  || |||||||
Sbjct:     1  KWEEAIVEGEWTRGSTAGGCRNYPDTFWTNPQYIITLPEPDDDDEDS---CSVLVALMQK   57

Query:   440  NRRKDRKLGASLFTIGFAIYEVPKEMHGNKQHLQKDFFLYNASKARSKTYINMREVSQRF  499
              +||++|++|| + ||||||+|+|| |++     || +||||||| |+||| ||||+|||| ||
Sbjct:    58  DRRRERRMGADMLTIGFAVYKVPDELN----HLSRDFFLYNQSRARSSTYINLREVSLRF  113

Query:   500  RLPPSEYVIVPSTYEPHQEGEFILRVFSEKRNLSE                          534
              |||| |||+||||+||++|||||||||||||   +
Sbjct:   114  RLPPGEYVLVPSTFEPNEEGEFILRVFSEKPINTR                          148
```

TABLE 26J

Domain Analysis of NOV26

```
gnl|Pfam pfam00036, efhand, EF hand. The EF-hands
can be divided into two classes: signaling
proteins and buffering/transport proteins. The
first group is the largest and includes the most
well-known members of the family such as
calmodulin, troponin C and S100B. These proteins
typically undergo a calcium-dependent conforma-
tional change which opens a target binding site.
The latter group is represented by calbindin D9k
and do not undergo calcium dependent conforma-
tional changes. (SEQ ID NO:264)
CD-Length = 29 residues, 96.6% aligned
Score = 36.2 bits (82), Expect = 0.007
Query:  649   CRSMIALMDTDGSGKLNLQEFHHLWNKI   676
              + +       | || ||++ +||   | |+
Sbjct:    2   LKEIFKEFDKDGDGKISFEEFKELLKKL    29
```

Calpains are intracellular cysteine proteases that are regulated by calcium. Cysteine protease activity is dependent on an active dyad of cysteine and histidine, the order and spacing of these residues varying in the 20 or so known families. Families C1, C2 and C10 are loosely termed papain-like, and nearly half of all cysteine proteases are found exclusively in viruses. Calpain is an intracellular protease involved in many important cellular functions that are regulated by calcium.

The protein is a complex of 2 polypeptide chains (light and heavy), with three known forms in mammals: a highly calcium-sensitive (i.e., micro-molar range) form known as mu-calpain, mu-CANP or calpain I; a form sensitive to calcium in the milli-molar range, known as m-calpain, m-CANP or calpain II; and a third form, known as p94, which is found in skeletal muscle only. All three forms have identical light but different heavy chains. The heavy chain comprises four domains: domain 2 contains the catalytic region; domain 4 binds calcium and regulates activity. Domain 2 shows low levels of sequence similarity to papain; although the catalytic His has not been located by biochemical means, it is likely that calpain and papain are related. Domain 4 has four EF hand calcium-binding regions and is simmilar to sorcin and the $Ca^{2+}$-binding region of calpain light chain. Calpain shows preferential cleavage for Tyr- with leucine or valine as the P2 residue.

The product of the *Drosophila* gene sol has also been shown to be similar to calpain. Many calcium-binding proteins belong to the same evolutionary family and share a type of calcium-binding domain known as the EF-hand. This type of domain consists of a twelve residue loop flanked on both side by a twelve residue alpha-helical domain. In an EF-hand loop the calcium ion is coordinated in a pentagonal bipyramidal configuration. The six residues involved in the binding are in positions 1, 3, 5, 7, 9 and 12; these residues are denoted by X, Y, Z, -Y, -X and -Z. The invariant Glu or Asp at position 12 provides two oxygens for liganding Ca (bidentate ligand).

Calpains are known to be involved in a number of cellular processes, such as apoptosis, protein processing, cell differentiation, metabolism etc. As such, their role in patho-physiologies extends to—but is not restricted to—tissue remodeling and regeneration (in response to a variety of injury models in the eye, brain, spinal cord, kidney etc.), fertility, tumorigenesis and myopathies. One of the genes identified in susceptibility to type II diabetes is a calpain (calpain-10). Polymorphisms within this gene are correlated with insulin resistance. Therapies targeting calpain are relevant to disease areas such as cataract, spinal cord injury, Alzheimer's disease, muscular dystrophy, acoustic trauma, diabetes, cancer, learning and memory defects and infertility. Knockout and transgenic models of various calpains also point to a potential role for this family of proteases in a number of cellular and disease processes.

The NOV26 nucleic acid of the invention encoding a Calpain-like protein includes the nucleic acid whose sequence is provided in Table 26A, or a fragment thereof. The invention also includes a mutant or variant nucleic acid any of whose bases may be changed from the corresponding base shown in Table 26A while still encoding a protein that maintains its Calpain-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 1% of the NOV26 residues may be so changed.

The NOV26 protein of the invention includes the Calpain-like protein whose sequence is provided in Table 26B. The invention also includes a mutant or variant protein any of whose residues may be changed from the corresponding residue shown in Table 26B while still encoding a protein that maintains its Calpain-like activities and physiological functions, or a functional fragment thereof. In the mutant or variant protein, up to about 1% of the NOV26 bases may be so changed.

The NOV26 nucleic acids and proteins of the invention are useful in potential diagnostic and therapeutic applications implicated in various diseases and disorders described below and/or other pathologies. For example, the compositions of the present invention will have efficacy for treatment of patients suffering from: obesity, diabetes, autoimmune disease, Von Hippel-Lindau (VHL) syndrome, cirrhosis, transplantation disorders, pancreatitis, renal artery stenosis, interstitial nephritis, glomerulonephritis, polycystic kidney disease, systemic lupus erythematosus, renal tubular acidosis, IgA nephropathy, hypercalcemia, Lesch-Nyhan syndrome, developmental defects, cataract, spinal cord injury, Alzheimer's disease, muscular dystrophy, acoustic trauma, cancer, learning and memory defects, infertility and other diseases, disorders and conditions of the like.

NOV26 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV26 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV27

A disclosed NOV27 nucleic acid of 1327 nucleotides (also referred to as CG57484-01) encoding a novel Keratin 18-like protein is shown in Table 27A. An open reading frame was identified beginning with an ATG initiation codon at nucleotides 67–69 and ending with a TAA codon at nucleotides 1273–1275. Putative untranslated regions upstream from the intitation codon and downstream from the termination codon are underlined in Table 27A, and the start and stop codons are in bold letters.

TABLE 27A

NOV27 Nucleotide Sequence (SEQ ID NO:87)
GCTTCACCACTCCCTCCACCTTCTCCACCAACTACCAGTCCCTGGGCTCTGTCCAGCCGCCCAGCTATGGCAC

CTGGCCGGTCAGCAGCGCAGCCAGCATCTATGCAGGCACTGGGGGGCTTGGGATCCCAGATCTCCATGTCCTG

TTCTACCAGTTTCTGGGGCGGCTTGGGGTCTGGGGGCCTGGCCACAGAGATGGCTGGGGGTCTGGCAGAAATG

GGGGGCATCCAGAATGAGAAGGAGACCATGCAAAGCCTGAACGACCACCTGGACTACCTGGACAGAGTGAGGA

ACCTGGAGACCGAGAACTGGAGGCTGGAGAGCAAAATCCAGGAGTATCTGGAGAAGAGACCCCATGTCAGAGA

CTGGGGCCATTACTTCAAGACCATCAAGGAACTGAGGGCTCAGATCTTCGCAAATACTGTGGACAATGTCCAC

ATCATTCTGCAGATCGACAATGCCCGTCTTGCTGCTGATGACTTCAGAGTCAAGTATGAGACAAGAGCTGGCC

ATGCGCCAGTCTGTGGAGAGAACATCCATGGGCTCTCCAAGGTCATTGATGACACCAATGTCACTCTGCTGCA

GCTGGAGACAGAGATGGGCGCTCTCAAGGAGGAGCTGCTCCTCATGAAGAAGAACCATGAAGAGGAAGTAAAA

GGCTTGCAAGTCCAGATTGCCAACTCTGGGTTGGCCGTGGAGGTAGATGCCCCCAAATCTCAAGTCCTCGCCA

AGGTCATGGCAGACATCAGGGCCCAAGATGAGCTGTCTCAGAAGAACTCAGAGAAGCTAGGCAAGTACTGGTC

TCAGCAGACTGAGGAGAGCACCACAGTGGTCACCACACACTCTGCCAAGGTCAGAGCTGCTGAGATGACAACG

GAGCTGAGACGTACAGTCCAGTGCTTGGAGATTGACCTGGACTCAATGAGAAATCTGAAGACCAGCTTGAACA

GCCTGAGGGAGGTGGAGGCCCGCTACGCCCTGCAGATGGAGCAGCTCAACAGAATCCTGCTGTACTTGGAGTC

AAAGCTGGCACAGAACTGGGCAGAGGGCCAGCGCAAGGTCCAGGAGTACAAGGACTTGCTGAACATCAGGGTC

AAGCTGGAGGCTGAGATCGCCACCTACCGCCGCCTGCTGGAAGACAGCGAGGGCCTCAATCTTGGTGATGCCC

TGGACAGCAGCAACTCCATGCAAACCATCCAAAAGACCACCACCCGCCAGATAGTGGATAGCAAAGTGGTGTC

TGAGATCAGTGACACCAAAGTTCTGAGACATTAAGCCAGCAGAAGCAGGGTACCCTGTGGGGAGTAAGAGGCC

AATAAAAAGTTCA

The NOV27 nucleic acid was identified on chromosome 12 and has 367 of 415 bases (88%) identical to a gb:GENBANK-ID:AF179904|acc:AF179904.1 mRNA from *Homo sapiens* (*Homo sapiens* keratin 18 (KRT18) gene, complete cds) (E=5.1e$^{-180}$).

A disclosed NOV27 polypeptide (SEQ ID NO:88) encoded by SEQ ID NO:87 is 402 amino acid residues and is presented using the one-letter code in Table 27B. Signal P, Psort and/or Hydropathy results predict that NOV27 contains a signal peptide and is likely to be localized to the cytoplasm with a certainty of 0.4500.

TABLE 27B

Encoded NOV27 protein sequence (SEQ ID NO:88)
MAPGRSAAQPASMQALGGLGSQISMSCSTSFWGGLGSGGLATEMAGGLAEMGGIQNEKETMQSLNDHLDYLD

RVRNLETENWRLESKIQEYLEKPRHVRDWGHYFKTIKELRAQIFANTVDNVHIILQIDNARLAADDFRVKYE

TRAGHAPVCGENIHGLCKVIDDTNVTLLQLETEMGALKEELLLMKKNHEEEVKGLQVQIANSGLAVEVDAPK

SQVLAKVMADIRAQDELSQKNSEKLGKYWSQQTEESTTVVTTHSAKVRAAEMTTELRRTVQCLEIDLDSMRN

LKTSLNSLREVEARYALQMEQLNRILLYLESKLAQNWAEGQRKVQEYKDLLNIRVKLEAEIATYRRLLEDSE

GLNLGDALDSSNSMQTIQKTTTRQIVDSKVVSEISDTKVLRH

The NOV27 amino acid sequence 315 of 404 amino acid residues (77%) identical to, and 344 of 404 amino acid residues (85%) similar to, the 429 amino acid residue ptnr:SWISSNEW-ACC:P05783 protein from *Homo sapiens* (Human) (Keratin, Type I Cytoskeletal 18 (Cytokeratin 18) (K18) (CK 18)) (E=2.9e$^{-151}$).

NOV27 is expressed in at least the following tissues: adrenal gland, bone marrow, brain—amygdala, brain—cerebellum, brain—hippocampus, brain—substantia nigra, brain—thalamus, brain—whole, fetal brain, fetal kidney, fetal liver, fetal lung, heart, kidney, lymphoma—Raji, mammary gland, pancreas, pituitary gland, placenta, prostate, salivary gland, skeletal muscle, small intestine, spinal cord, spleen, stomach, testis, thyroid, trachea and uterus. This information was derived by determining the tissue sources of the sequences that were included in the invention including but not limited to SeqCalling sources, Public EST sources, genomic clone sources, literature sources, and/or RACE sources.

NOV27 has homology to the amino acid sequences shown in the BLASTP data listed in Table 27C.

TABLE 27C

BLAST results for NOV27

| Gene Index/ Identifier | Protein/ Organism | Length (aa) | Identity (%) | Positives (%) | Expect |
|---|---|---|---|---|---|
| gi|4557888|ref|NP_000215.1| (NM_000224) | keratin 18 [*Homo sapiens*] | 430 | 303/404 (75%) | 332/404 (82%) | e-142 |
| gi|106851|pir||S06889 | keratin 18, cytoskeletal [*Homo sapiens*] | 424 | 303/404 (75%) | 332/404 (82%) | e-142 |
| gi|12653819|gb| AAH00698.1| AAH00698 (BC000698) | keratin 18 [*Homo sapiens*] | 430 | 302/404 (74%) | 332/404 (81%) | e-141 |
| gi|14602495|gb| AAH09754.1| AAH09754 (BC009754) | Similar to keratin 18 [*Homo sapiens*] | 375 | 286/372 (76%) | 310/372 (82%) | e-132 |
| gi|532610|gb| AAA37552.1| (M22832) | cytokeratin [*Mus musculus*] | 423 | 268/405 (66%) | 313/405 (77%) | e-121 |

The homology of these sequences is shown graphically in the ClustalW analysis shown in Table 27D.

TABLE 27E

Clustal W Sequence Alignment

1) NOV27 (SEQ ID NO:88)
2) gi 4557888|refNP_000215.1|(NM_000224) keratin 18 [*Homo sapiens*] (SEQ ID NO:265)
3) gi 106851|pir||S06889 keratin 18, cytoskeletal [*Homo sapiens*] (SEQ ID NO:266)
4) gi 12653819|gb AAH00698.1 AAH00698 (BC000698) keratin 18 [*Homo sapiens*] (SEQ ID NO:267)

TABLE 27E-continued

Clustal W Sequence Alignment 5) gi 14602495|gb|AAH09754.1|AAH09754 (BC009754) Similar to keratin 18 [Homo sapiens] (SEQ ID NO:268)
6) gi 532610|gb AAA37552.1|(M22832) cytokeratin [Mus musculus] (SEQ ID NO:269)

```
                       10        20        30        40        50        60        70
                  ....|....|....|....|....|....|....|....|....|....|....|....|....|....|
NOV27             --------------------MAPG---RSAAQPASMQA-LGGLGSQISMSCSTSFWGGLGSGGLATEMAG
gi|4557888|       MSFTTR-STFSTNYRSLGSVQAPSYGARPVSSAASVYAGAGGSGSRISVSRSTSFRGGMGSGGLATGIAG
gi|106851|        -------STFSTNYRSLGSVQAPSYGARPVSSAASVYAGAGGSGSRISVSRSTSFRGGMGSGGLATGIAG
gi|12653819|      MSFTTR-STFSTNYRSLGSVQAPSYGARPVSSAASVYAGAGGSGSRISVSRSTSFRGGMGSGGLATGIAG
gi|14602495|      ------------------------------------------------------ARC--GSGGLATGIAG
gi|532610|        MSFTTRSITFSTNYRSLGSVRTPSQRVREASSAASVYAGAGGSGSRISVSR--SVWGQ------SVGSAG 80        90       100       110       120       130       140
                  ....|....|....|....|....|....|....|....|....|....|....|....|....|....|
NOV27             GLAPMGGIQNEKETMQSLNDHLD-YLDRVRNLETENWRLESKIQEVLEKR-PH-VTDWGHYFKTIKELRA
gi|4557888|       GLAGMGGIQNEKETMQSLNDRLASYLDRVRSLETENRRLESKIREHLEKKGPQ-VRDWSHYFKIIEDLRA
gi|106851|        GLAGMGGIQNEKETMQSLNDRLASYLDRVRSLETENRRLESKIREHLEKKGPQ-VRDWSHYFKIIEDLRA
gi|12653819|      GLAGMGGIQNEKETMQSLNDRLASYLDRVRSLETENRRLESKIREHLEKKGPQ-VRDWSHYFKIIEDLRA
gi|14602495|      GLAGMGGIQNEKETMQSLNDRLASYLDRVRSLETENRRLESKIREHLEKKGPQ-VRDWSHYFKIIEDLRA
gi|532610|        -LAGMGGIQTEKETMQDLNDRLASYLDRVKSLETENRRLESKIREHLEKKGPQCVRDWGHYFKIIEDLRA 150       160       170       180       190       200       210
                  ....|....|....|....|....|....|....|....|....|....|....|....|....|....|
NOV27             QIFANTVDNVHIELQIDNARLAADDFRVKYETRAGHAPVCGENIHGLCKVIDDTNVTLLQLETEMGALKE
gi|4557888|       QIFANTVDNARIVLQIDNARLAADDFRVKYETELAMRQSVENDIHGLRKVIDDTNITRLQLETEIEALKE
gi|106851|        QIFANTVDNARIVLQIDNARLAADDFRVKYETELAMRQSVENDIHGLRKVIDDTNITRLQLETEIEALKE
gi|12653819|      QIFANTVDNARIVLQIDNARLAADDFRVKEETELAMRQSVENDIHGLRKVIDDTNITRLQLETEIEALKE
gi|14602495|      QIFANTVDNARIVLQIDNARLAADDFRVKYETELAMRQSVENDIHGLRKVIDDTNITRLQLETEIEALKE
gi|532610|        QIFANSVDNARIVLQIDNARLAADDFRVKYETELAMRQSVESDIHGLRKVWDDTNITRLQLETEIEALKE 220       230       240       250       260       270       280
                  ....|....|....|....|....|....|....|....|....|....|....|....|....|....|
NOV27             ELLLMKKNHEEEVKGLQVQIANSGLAVEVDAPKSQVLAKVMADIRAQ-DELSQKNSEKLGKYWSQQTEES
gi|4557888|       ELLFMKKNHEEEVKGLQAQIASSGLTVEVDAPKSQDLAKIMADIRAQYDELARKNREELDKYWSQQIEES
gi|106851|        ELLFMKKNHEEEVKGLQAQIASSGLTVEVDAPKSQDLAKIMADIRAQYDELARKNREELDKYWSQQIEES
gi|12653819|      ELLFMKKNHEEEVKGLQAQIASSGLTVEVDAPKSQDLAKIMADIRAQYDELARKNREELDKYWSQQIEES
gi|14602495|      ELLFMKKNHEEEVKGLQAQIASSGLTVEVDAPKSQDLAKIMADIRAQYDELARKNREELDKYWSQQIEES
gi|532610|        ELLFMKKNHEEEVQGLSAQIASSGLTVEVDAPKSQDLSKIMADIRAQYEALAQKNREELDKYWSQQIEES 290       300       310       320       330       340       350
                  ....|....|....|....|....|....|....|....|....|....|....|....|....|....|
NOV27             TTVVTIHSAKVRAAEMT-TELRRTVQCLEIDLDSMRNLKTSLN-SLREVEARYALQMEQLNRILLYLESK
gi|4557888|       TTVVTTQSAEVGAAETTLTELRRTVQSLEIDLDSMRNLKASLENSLREVEARYALQMEQLNGILLHLESE
gi|106851|        TTVVTTQSAEVGAAETTLTELRRTVQSLEIDLDSMRNLKASLENSLREVEARYALQMEQLNGILLHLESE
gi|12653819|      TTVVTTQSAEVGAAETTLTELRRTVQSLEIDLDSMRNLKASLENSLREVEARYALQMEQLNGILLHLESE
gi|14602495|      TTVVTTQSAEVGAAETTLTELRRTVQSLEIDLDSMRNLKASLENSLREVEARYALQMEQLNGILLHLESE
gi|532610|        TTVVTTKSAEIRDAETTLTELRRTIQTLEIDLDSMKNQNINLENSLGDVEARYKAQMEQLNGVLLHLESE 360       370       380       390       400       410       420
                  ....|....|....|....|....|....|....|....|....|....|....|....|....|....|
NOV27             LAQNWAEGQRKVQEYRDLLNIRVKLEAEIATYRRLLEDSEGLNLGDALDSSNSMQTIQKTTTRQIVDSKV
gi|4557888|       LAQTRAEGQRQAQEYEALLNIKVKLEAEIATYRRLLEDGEDFNLGDALDSSNSMQTIQKTTTRRIVDGKV
gi|106851|        LAQTRAEGQRQAQEYEALLNIKVKLEAEIATYRRLLEDGEDFNLGDALDSSNSMQTIQKTTTRRIVDGKV
gi|12653819|      LAQTRAEGQRQAQEYEALLNIKVKLEAEIATYRRLLEDGEDFNLGDALDSSNSMQTIQKTTTRRIVDGKV
gi|14602495|      LAQTRAEGQRQAQEYEALLNIKVKLEAEIATYRRLLEDGEDFNLGDALDSSNSMQTIQKTTTRRIVDGKV
gi|532610|        LAQTRAEGQRQAQEYEALLNIKVKLEAEIATYRRLLEDGEDFSLNDALDSSNSMQTVQKTTTRKIVDGRV

430
                  ....|....|
NOV27             VSEISDTKVLRH
gi|4557888|       VSETNDTKVLRH
gi|106851|        VSETNDTKVLRH
gi|12653819|      VSETNDTKVLRH
gi|14602495|      VSETNDTKVLRH
gi|532610|        VSETNDTRVLRH
```

Table 27E lists the domain description from DOMAIN analysis results against NOV27. This indicates that the NOV27 sequence has properties similar to those of other proteins known to contain these domains.

TABLE 27E

Domain Analysis of NOV27

```
gnl Pfam.pfam00038, filament, Intermediate filament protein. (SEQ ID
NO:270)
CD-Length = 312 residues, 99.4% aligned
Score = 204 bits (520), Expect = 6e-54
Query:   56 NEKETMQSLNDEL-DYLDRVRNLETENWRLESKIQEYLEKRPHV--RDWGHYFKTIKELR  112
            ||||  ||+|||  |   |+|+||  || +|   || ||+|  +|+      | +   | |+|||
Sbjct:    1 NEKEQMQNLNDRLASYIDKVRFLEQQNKELEVKIEELRQKQAPSVSRLYSLYETEIEELR   60

Query:  113 AQIFANTVDNVHIILQIDNARLAADDFRVKYETRAGHAPVCGENIHGLCKVIDDTNVTLL  172
            ||    |  +  +|+|||   |  ||+|||   |||         ++ ||  | +|+  +  +
Sbjct:   61 RQIDQLTNERARLQLEIDNLREAAEDFRKKYEDEINLRQEAENDLVGLRKDLDEATLARV  120

Query:  173 QLETEMGALKEELLLMKKNHEEEVKGLQVQIANSGLAVEVDAPKSQVLAKVMADIRAQ-D  231
            ||  ++ +|+|||   +|||||||||| ||  || ++     ||+||  +    |  + +||||  +
Sbjct:  121 DLENKVESLQEELEFLKKNHEEEVKELQAQIQDTVN-VEMDAARKLDLTKALREIRAQYE  179

Query:  232 ELSQKNSEKLGKYWSQQTEESTTVVTTHSAKVRAA-EMTTELRRTVQCLEIDLDSMRNLK  290
            |+++||  ++  +++  +  ||    |      +     +|+|  |  |||||  +|   |||+|  |++
Sbjct:  180 EIAKKNRQEAEEWYKSKLEELQTAAARNGEALRSAKEEITELRRQIQSLEIELQSLKAQN  239

Query:  291 TSL-NSLREVEARYALQMEQLNRILLYLESKLAQNWAEGQRKVQEYKDLLNIRVKLEAEI  349
            ||    |   |+|  ||  |++   ++   ||  +|  |    |+++||++||++++ |+ ||
Sbjct:  240 ASLERQLAELEERYELELRQYQALISQLEEELQQLREEMARQLREYQELLDVKLALDIEI  299

Query:  350 ATYRRLLEDSE                                                   360
            ||||+|||  |
Sbjct:  300 ATYRKLLEGEE                                                   310
```

Keratin 8 (K8) and keratin 18 (K18) are the most common and characteristic members of the large intermediate filament gene family expressed in 'simple' or single layer epithelial tissues of the body. Their persistent expression in tumor cells derived from these epithelia has led to the wide spread use of keratin monoclonal antibodies as aids in the detection and identification of carcinomas. Oncogenes which activate ras signal transduction pathways stimulate expression of the K18 gene through transcription factors including members of the AP-1 (jun and fos) and ETS families. The persistent expression of K8 and K18 may reflect the integrated transcriptional activation of such transcription factors and, in the cases of ectopic expression, an escape from the suppressive epigenetic mechanisms of DNA methylation and chromatin condensation. Comparison of the mechanisms of transcriptional control of K18 expression with expression patterns documented in both normal and pathological conditions leads to the proposal that persistent K8 and K18 expression is a reflection of the action of multiple different oncogenes converging on the nucleus through a limited number of transcription factors to then influence the expression of a large number of genes including these keratins. Furthermore, correlation of various tumor cell characteristics including invasive behavior and drug sensitivity with K8 and K18 expression has stimulated consideration of the possible functions of these proteins in both normal development and in tumorigenesis. Recent developments in the analysis of the functions of these intermediate filament proteins provide new insights into diverse functions influenced by K8 and K18 (Oshima et al., Cancer Metastasis Rev 15:445–71, 1996).

Keratin 8 (K8) and keratin 18 (K18) form intermediate filaments characteristic of liver and other single cell layered, internal epithelia and their derivative cancers. K8-deficient (K8(−)) mice, which escape embryonic lethality, develop inflammatory colorectal hyperplasia, mild liver abnormalities, and tolerate hepatectomy poorly. Normal and malignant epithelial cells deficient in K8 and K18 have been shown to be approximately 100 times more sensitive to TNF-induced death. K8 and K18 both bind the cytoplasmic domain of TNFR2 and moderate TNF-induced, Jun NH(2)-terminal kinase (JNK) intracellular signaling and NFkappaB activation. Furthermore, K8(−) and K18(−) mice are much more sensitive to TNF dependent, apoptotic liver damage induced by the injection of concanavalin A. This moderation of the effects of TNF may be the fundamental function of K8 and K18 common to liver regeneration, inflammatory bowel disease, hepatotoxin sensitivity, and the diagnostic, persistent expression of these keratins in many carcinomas (Caulin et al., J Cell Biol 149:17–22, 2000).

The NOV27 nucleic acid of the invention encoding a Keratin 18-like protein includes the nucleic acid whose sequence is provided in Table 27A, or a fragment thereof. The invention also includes a mutant or variant nucleic acid any of whose bases may be changed from the corresponding base shown in Table 27A while still encoding a protein that maintains its Keratin 18-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 12% of the NOV27 residues may be so changed.

The NOV27 protein of the invention includes the Keratin 18-like protein whose sequence is provided in Table 27B. The invention also includes a mutant or variant protein any of whose residues may be changed from the corresponding residue shown in Table 27B while still encoding a protein that maintains its Keratin 18-like activities and physiological functions, or a functional fragment thereof. In the mutant or variant protein, up to about 23% of the NOV27 bases may be so changed.

The NOV27 nucleic acids and proteins of the invention are useful in potential diagnostic and therapeutic applications implicated in various diseases and disorders described below and/or other pathologies. For example, the compositions of the present invention will have efficacy for treatment of patients suffering from: inflammatory colorectal hyperplasia, mild liver abnormalities, skin abnormalities, inflammatory bowel disease, hepatotoxin sensitivity, chronic hepatitis, breast cancer, pancreatic cancer, mammary gland tumours, benign prostatic hyperplasia, prostate cancer, cryptogenic cirrhosis and other diseases, disorders and conditions of the like.

NOV27 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV27 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV28

A disclosed NOV28 nucleic acid of 12992 nucleotides (also referred to as CG57236-01) encoding a novel Polycystic Kidney Disease Associated-like protein is shown in Table 28A. An open reading frame was identified beginning with an ATG initiation codon at nucleotides 53–55 and ending with a TAG codon at nucleotides 12950–12952. Putative untranslated regions upstream from the intitation codon and downstream from the termination codon are underlined in Table 28A, and the start and stop codons are in bold letters.

TABLE 28A

NOV28 Nucleotide Sequence (SEQ ID NO:89)

CGCGCGCGGGCGGGCCTGGGGACGGCGGGGCCATGCGCGCGCTGCCCTAACGATGCCGCCCGCCGCGCCCGCC

CGCCTGGCGCTGGCCCTGGGCCTGGGCCTGTGGCTCGGGGCGCTGGCGGGGGCCCCGGGCGCGGCTGCGGGC

CCTGCGAGCCCCCCTGCCTCTGCGGCCCAGCGCCCGGCGCCGCCTGCCGCGTCAACTGCTCGGGCCGCGGGCT

GCGGACGCTCGGTCCCGCGCTGCGCATCCCCGCGGACGCCACAGCGCTAGACGTCTCCCACAACCTGCTCCGG

GCGCTGGACGTTGGGCTCCTGGCGAACCTCTCGGCGCTGGCAGAGCTGGATATAAGCAACAACAAGATTTCTA

CGTTAGAAGAAGGAATATTTGCTAATTTATTTAATTTAAGTGAAATAAACCTGAGTGGGAACCCGTTTGAGTG

TGACTGTGGCCTGGCGTGGCTGCCGCGATGGGCGGAGGAGCAGCAGGTGCGGGTGGTGCAGCCCGAGGCAGCC

ACGTGTGCTGGGCCTGGCTCCCTGGCTGGCCAGCCTCTGCTTGGCATCCCCTTGCTGGACAGTGGCTGTGGTG

AGGAGTATGTCGCCTGCCTCCCTGACAACAGCTCAGGCACCGTGGCAGCAGTGTCCTTTTCAGCTGCCCACGA

AGGCCTGCTTCAGCCAGAGGCCTGCAGCGCCTTCTGCTTCTCCACCGGCCAGGGCCTCGCAGCCCTCTCGGAG

CAGGGCTGGTGCCTGTGTGGGGCGGCCCAGCCCTCCAGTGCCTCCTTTGCCTGCCTGTCCCTCTGCTCCGGCC

CCCCGCCACCTCCTGCCCCCACCTGTAGGGGCCCCACCCTCCTCCAGCACGTCTTCCCTGCCTCCCCAGGGGC

CACCCTGGTGGGGCCCCACGGACCTCTGGCCTCTGGCCAGCTAGCAGCCTTCCACATCGCTGCCCCGCTCCCT

GTCACTGCCACACGCTGGGACTTCGGAGACGGCTCCGCCGAGGTGGATGCCGCTGGGCCGGCTGCCTCGCATC

GCTATGTGCTGCCTGGGCGCTATCACGTGACGGCCGTGCTGGCCCTGGGGGCCGGCTCAGCCCTGCTGGGGAC

AGACGTGCAGGTGGAAGCGGCACCTGCCGCCCTGGAGCTCGTGTGCCCGTCCTCGGTGCAGAGTGACGAGAGC

CTTGACCTCAGCATCCAGAACCGCGGTGGTTCAGGCCTGGAGGCCGCCTACAGCATCGTGGCCCTGGGCGAGG

AGCCCGGCCCGAGCGGTGCACCCGCTCTGCCCCTCGGACACGGAGATCTTCCCTGGCAACGGGCACTGCTACCG

CCTGGTGGTGGAGAAGGCGGCCTGGCTGCAGGCGCAGGAGCAGTGTCAGGCCTGGGCCGGGGCCGCCCTGGCA

ATGGTGGACAGTCCCGCCGTGCAGCGCTTCCTGGTCTCCCGGGTCACCAGGAGCCTAGACGTGTGGATCGGCT

TCTCGACTGTGCAGGGGGTGGAGGTGGGCCCAGCGCCGCAGGGCGAGGCCTTCAGCCTGGAGAGCTGCCAGAA

CTGGCTGCCCGGGGAGCCACACCCAGCCACAGCCGAGCACTGCGTCCGGCTCGGGCCCACCGGGTGGTGTAAC

ACCGACCTGTGCTCAGCGCCGCACAGCTACGTCTGCGAGCTGCAGCCCGGAGGCCCAGTGCAGGATGCCGAGA

ACCTCCTCGTGGGAGCGCCCAGTGGGGACCTGCAGGGACCCCTGACGCCTCTGGCACAGCAGGACGGCCTCTC

AGCCCCGCACGAGCCCGTGGAGGTCATGGTATTCCCGGGCCTGCGTCTGAGCCGTGAAGCCTTCCTCACCACG

TABLE 28A-continued

NOV28 Nucleotide Sequence

```
GCCGAATTTGGGACCCAGGAGCTCCGGCGGCCCGCCCAGCTGCGGCTGCAGGTGTACCGGCTCCTCAGCACAG

CAGGGACCCCGGAGAACGGCGAGCGAGCCTGAGAGCAGGTCCCCGGACAACAGGACCCGCTGGCCCCCGCGTG

CATGCCAGGGGACGCTGGTGCCCTGGAGCCAACATCTGCTTGCCGCTGGACGCCTCTTGCCACCCCCAGGCC

TGCGCCAATGGCTGCACGTCAGGGCCAGGGCTACCCGGGGCCCCCTATGCGCTATGGAGAGAGTTCCTCTTCT

CCGTTGCCGCGGGGCCCCCCGCGCAGTACTCGGTCACCCTCCACGGCCAGGATGTCCTCATGCTCCCTGGTGA

CCTCGTTGGCTTGCAGCACGACGCTGGCCCTGGCGCCCTCCTGCACTGCTCGCCGGCTCCCGGCCACCCTGGT

CCCCAGGCCCCGTACCTCTCCGCCAACGCCTCGTCATGGCTGCCCCACTTGCCAGCCCAGCTGGAGGGCACTT

GGGCCTGCCCTGCCTGTGCCCTGCGGCTGCTTGCAGCCACGGAACAGCTCACCGTGCTGCTGGGCTTGAGGCC

CAACCCTGGACTGCGGATGCCTGGGCGCTATGAGGTCCGGGCAGAGGTGGGCAATGGCGTGTCCAGGCACAAC

CTCTCCTGCAGCTTTGACGTGGTCTCCCCAGTGGCTGGGCTGCGGGTCATCTACCCTGCCCCCCGCGACGGCC

GCCTCTACGTGCCCACCAACGGCTCAGCCTTGGTGCTCCAGGTGGACTCTGGTGCCAACGCCACGGCCACGGC

TCGCTGGCCTGGGGGCAGTGTCAGCGCCCGCTTTGAGAATGTCTGCCCTGCCCTGGTGGCCACCTTCGTGCCC

GGCTGCCCCTGGGAGACCAACGATACCCTGTTCTCAGTGGTAGCACTGCCGTGGCTCAGTGAGGGGGAGCACG

TGGTGGACGTGGTGGTGGAAAACAGCGCCAGCCGGGCCAACCTCAGCCTGCGGGTGACGGCGGAGGAGCCCAT

CTGTGGCCTCCGCGCCACGCCCAGCCCCGAGGCCCGTGTACTGCAGGGAGTCCTAGTGAGGTACAGCCCCGTG

GTGGAGGCCGGCTCGGACATGGTCTTCCGGTGGACCATCAACGACAAGCAGTCCCTGACCTTCCAGAACGTGG

TCTTCAATGTCATTTATCAGAGCGCGCGGTCTTCAAGCTCTCACTGACGGCCTCCAACCACGTGAGCAACGT

CACCGTGAACTACAACGTAACCGTGGAGCGGATGAACAGGATGCAGGGTCTGCAGGTCTCCACAGTGCCGGCC

GTGCTGTCCCCCAATGCCACGCTAGCACTGACGGCGGGCGTGCTGGTGGACTCGGCCGTGGAGGTGGCCTTCC

TGTGGAACTTTGGGGATGGGGAGCAGGCCCTCCACCAGTTCCAGCCTCCGTACAACGAGTCCTTCCCGGTTCC

AGACCCCTCGGTGGCCCAGGTGCTGGTGGAGCACAATGTCATGCACACCTACGCTGCCCCAGGTGAGTACCTC

CTGACCGTGCTGGCATCTAATGCCTTCGAGAACCTGACGCAGCAGGTGCCTGTGAGCGTGCGCGCCTCCCTGC

CCTCCGTGGCTGTGGGTGTGAGTGACGGCGTCCTGGTGGCCGGCCGGCCCGTCACCTTCTACCCGCACCCGCT

GCCCTCGCCTGGGGGTGTTCTTTACACGTGGGACTTCGGGGACGGCTCCCCTGTCCTGACCCAGAGCCAGCCG

GCTGCCAACCACACCTATGCCTCGAGGGGCACCTACCACGTGCGCCTGGAGGTCAACAACACGGTGAGCGGTG

CGGCGGCCCAGGCGGATGTGCGCGTCTTTGAGGAGCTCCGCGGACTCAGCGTGGACATGAGCCTGGCCGTGGA

GCAGGGCGCCCCCGTGGTGGTCAGCGCCGCGGTGCAGACGGGCGACAACATCACGTGGACCTTCGACATGGGG

GACGGCACCGTGCTGTCGGGCCCGGAGGCAACAGTGGAGCATGTGTACCTGCGGGCACAGAACTGCACAGTGA

CCGTGGGTGCGGCCAGCCCCGCCGGCCACCTGGCCCGGAGCCTGCACGTGCTGGTCTTCGTCCTGGAGGTGCT

GCGCGTTGAACCCGCCGCCTGCATCCCCACGCAGCCTGACGCGCGGCTCACGGCCTACGTCACCGGGAACCCG

GCCCACTACCTCTTCGACTGGACCTTCGGGGATGGCTCCTCCAACACGACCGTGCGGGGGTGCCCGACGGTGA

CACACAACTTCACGCGGAGCGGCACGTTCCCCCTGGCGCTGGTGCTGTCCAGCCGCGTGAACAGGGCGCATTA

CTTCACCAGCATCTGCGTGGAGCCAGAGGTGGGCAACGTCACCCTGCAGCCAGAGAGGCAGTTTGTGCAGCTC

GGGGACGAGGCCTGGCTGGTGGCATGTGCCTGGCCCCCGTTCCCCTACCGCTACACCTGGGACTTTGGCACCG

AGGAAGCCGCCCCCACCCGTGCCAGGGGCCCTGAGGTGACGTTCATCTACCGAGACCCAGGCTCCTATCTTGT

GACAGTCACCGCGTCCAACAACATCTCTGCTGCCAATGACTCAGCCCTGGTGGAGGTGCAGGAGCCCGTGCTG

GTCACCAGCATCAAGGTCAATGGCTCCCTTGGGCTGGAGCTGCAGCAGCCGTACCTGTTCTCTGCTGTGGGCC

GTGGGCGCCCCGCCAGCTACCTGTGGGATCTGGGGGACGGTGGGTGGCTCGAGGGTCCGGAGGTCACCCACGC

TTACAACAGCACAGGTGACTTCACCGTTAGGGTGGCCGGCTGGAATGAGGTGAGCCGCAGCGAGGCCTGGCTC
```

TABLE 28A-continued

NOV28 Nucleotide Sequence

AATGTGACGGTGAAGCGGCGCGTGCGGGGGCTCGTCGTCAATGCAAGCCGCACGGTGGTGCCCCTGAATGGGA

GCGTGAGCTTCAGCACGTCGCTGGAGGCCGGCAGTGATGTGCGCTATTCCTGGGTGCTCTGTGACCGCTGCAC

GCCCATCCCTGGGGGTCCTACCATCTCTTACACCTTCCGCTCCGTGGGCACCTTCAATATCATCGTCACGGCT

GAGAACGAGGTGGGCTCCGCCCAGGACAGCATCTTCGTCTATGTCCTGCAGCTCATAGAGGGGCTGCAGGTGG

TGGGCGGTGGCCGCTACTTCCCCACCAACCACACGGTACAGCTGCAGGCCGTGGTTAGGGATGGCACCAACGT

CTCCTACAGCTGGACTGCCTGGAGGGACAGGGGCCCGGCCCTGGCCGGCAGCGGCAAAGGCTTCTCGCTCACC

GTGCTCGAGGCCGGCACCTACCATGTGCAGCTGCGGGCCACCAACATGCTGGGCAGCGCCTGGGCCGACTGCA

CCATGGACTTCGTGGAGCCTGTGGGGTGGCTGATGGTGACCGCCTCCCCGAACCCAGCTGCCGTCAACACAAG

CGTCACCCTCAGTGCCGAGCTGGCTGGTGGCAGTGGTGTCGTATACACTTGGTCCTTGGAGGAGGGGCTGAGC

TGGGAGACCTCCGAGCCATTTACCACCCATAGCTTCCCCACACCCGGCCTGCACTTGGTCACCATGACGGCAG

GGAACCCGCTGGGCTCAGCCAACGCCACCGTGGAAGTGGATGTGCAGGTGCCTGTGAGTGGCCTCAGCATCAG

GGCCAGCGAGCCCGGAGGCAGCTTCGTGGCGGCCGGGTCCTCTGTGCCCTTTTGGGGGCAGCTGGCCACGGGC

ACCAATGTGAGCTGGTGCTGGGCTGTGCCCGGCGGCAGCAGCAAGCGTGGCCCTCATGTCACCATGGTCTTCC

CGGATGCTGGCACCTTCTCCATCCGGCTCAATGCCTCCAACGCAGTCAGCTGGGTCTCAGCCACGTACAACCT

CACGGCGGAGGAGCCCATCGTGGGCCTGGTGCTGTGGGCCAGCAGCAAGGTGGTGGCGCCCGGGCAGCTGGTC

CATTTTCAGATCCTGCTGGCTGCCGGCTCAGCTGTCACCTTCCGCCTGCAGGTCGGCGGGGCCAACCCCGAGG

TGCTCCCCGGGCCCCGTTTCTCCCACAGCTTCCCCCGCGTCGGAGACCACGTGGTGAGCGTGCGGGGCAAAAA

CCACGTGAGCTGGGCCCAGGCGCAGGTGCGCATCGTGGTGCTGGAGGCCGTGAGTGGGCTGCAGATGCCCAAC

TGCTGCGAGCCTGGCATCGCCACGGGCACTGAGAGGAACTTCACAGCCCGCGTGCAGCGCGGCTCTCGGGTCG

CCTACGCCTGGTACTTCTCGCTGCAGAAGGTCCAGGGCGACTCGCTGGTCATCCTGTCGGGCCGCGACGTCAC

CTACACGCCCGTGGCCGCGGGGCTGTTGGAGATCCAGGTGCGCGCCTTCAACGCCCTGGGCAGTGAGAACCGC

ACGCTGGTGCTGGAGGTTCAGGACGCCGTCCAGTATGTGGCCCTGCAGAGCGGCCCCTGCTTCACCAACCGCT

CGGCGCAGTTTGAGGCCGCCACCAGCCCCAGCCCCCGGCGTGTGGCCTACCACTGGGACTTTGGGGATGGGTC

GCCAGGGCAGGACACAGATGAGCCCAGGGCCGAGCACTCCTACCTGAGGCCTGGGGACTACCGCGTGCAGGTG

AACGCCTCCAACCTGGTGAGCTTCTTCGTGGCGCAGGCCACGGTGACCGTCCAGGTGCTGGCCTGCCGGGAGC

CGGAGGTGGACGTGGTCCTGCCCCTGCAGGTGCTGATGCGGCGATCACAGCGCAACTACTTGGAGGCCCACGT

TGACCTGCGCGACTGCGTCACCTACCAGACTGAGTACCGCTGGGAGGTGTATCGCACCGCCAGCTGCCAGCGG

CCGGGGCGCCCAGCGCGTGTGGCCCTGCCCGGCGTGGACGTGAGCCGGCCTCGGCTGGTGCTGCCGCGGCTGG

CGCTGCCTGTGGGGCACTACTGCTTTGTGTTTGTCGTGTCATTTGGGACACGCCACTGACACAGAGCATCCA

GGCCAATGTGACGGTGGCCCCCGAGCGCCTGGTGCCCATCATTGAGGGTGGCTCATACCGCGTGTGGTCAGAC

ACACGGGACCTGGTGCTGGATGGGAGCGAGTCCTACGACCCCAACCTGGAGGACGGCGACCAGACGCCGCTCA

GTTTCCACTGGGCCTGTGTGGCTTCGACACAGAGGGAGGCTGGCGGGTGTGCGCTGAACTTTGGGGCCCGCGG

GAGCAGCACGGTCACCATTCCACGGGAGCGGCTGGCGGCTGGCGTGGAGTACACCTTCAGCCTGACCGTGTGG

AAGGCCGGCCGCAAGGAGGAGGCCACCAACCAGACGGTGCTGATCCGGAGTGGCCGGGTGCCCATTGTGTCCT

TGGAGTGTGTGTCCTGCAAGGCACAGGCCGTGTACGAAGTGAGCCGCAGCTCCTACGTGTACTTGGAGGGCCG

CTGCCTCAATTGCAGCAGCGGCTCCAAGCGAGGGCGGTGGGCTGCACGTACGTTCAGCAACAAGACGCTGGTG

CTGGATGAGACCACCACATCCACGGGCAGTGCAGGCATGCGACTGGTGCTGCGGCGGGCGTGCTGCGGGACG

GCGAGGGATACACCTTCACGCTCACGGTGCTGGGCCGCTCTGGCGAGGAGGAGGGCTGCGCCTCCATCCGCCT

TABLE 28A-continued

NOV28 Nucleotide Sequence

GTCCCCCAACCGCCCGCCGCTGGGGGGCTCTTGCCGCCTCTTCCCACTGGGCGCTGTGCACGCCCTCACCACC
AAGGTGCACTTCGAATGCACGGGCTGGCATGACGCGGAGGATGCTGGCGCCCCGCTGGTGTACGCCCTGCTGC
TGCGGCGCTGTCGCCAGGGCCACTGCGAGGAGTTCTGTGTCTACAAGGGCAGCCTCTCCAGCTACGGAGCCGT
GCTGCCCCCGGGTTTCAGGCCACACTTCGAGGTGGGCCTGGCCGTGGTGGTGCAGGACCAGCTGGGAGCCGCT
GTGGTCGCCCTCAACAGGTCTTTGGCCATCACCCTCCCAGAGCCCAACGGCAGCGCAACGGGGCTCACAGTCT
GGCTGCACGGGCTCACCGCTAGTGTGCTCCCAGGGCTGCTGCGGCAGGCCGATCCCCAGCACGTCATCGAGTA
CTCGTTGGCCCTGGTCACCGTGCTGAACGAGTACGAGCGGGCCCTGGACGTGGCGGCAGAGCCCAAGCACGAG
CGGCAGCACCGAGCCCAGATACGCAAGAACATCACGGAGACTCTGGTGTCCCTGAGGGTCCACACTGTGGATG
ACATCCAGCAGATCGCTGCTGCGCTGGCCCAGTGCATGGGGCCCAGCAGGGAGCTCGTATGCCGCTCGTGCCT
GAAGCAGACGCTGCACAAGCTGGAGGCCATGATGCTCATCCTGCAGGCAGAGACCACCGCGGGCACCGTGACG
CCCACCGCCATCGGAGACAGCATCCTCAACATCACAGGAGACCTCATCCACCTGGCCAGCTCGGACGTGCGGG
CACCACAGCCCTCAGAGCTGGGAGCCGAGTCACCATCTCGGATGGTGGCGTCCCAGGCCTACAACCTGACCTC
TGCCCTCATGCGCATCCTCATGCGCTCCCGCGTGCTCAACGAGGAGCCCCTGACGCTGGCGGGCGAGGAGATC
GTGGCCCAGGGCAAGCGCTCGGACCCGCGGAGCCTGCTGTGCTATGGCGGCGCCCCAGGGCCTGGCTGCCACT
TCTCCATCCCCGAGGCTTTCAGCGGGGCCCTGGCCAACCTCAGTGACGTGGTGCAGCTCATCTTTCTGGTGGA
CTCCAATCCCTTTCCCTTTGGCTATATCAGCAACTACACCGTCTCCACCAAGGTGGCCTCGATGGCATTCCAG
ACACAGGCCGGCGCCCAGATCCCCATCGAGCGGCTGGCCTCAGAGCGCGCCATCACCGTGAAGGTGCCCAACA
ACTCGGACTGGGCTGCCCGGGGCCACCGCAGCTCCGCCAACTCCGTTGTGGTCCAGCCCCAGGCCTCCGTCGG
TGCTGTGGTCACCCTGGACAGCAGCAACCCTGCGGCCGTGCTGCATCTGCAGCTCAACTATACGCTGCTGGAC
GGCCACTACCTGTCTGAGGAACCTGAGCCCTACCTGGCAGTCTACCTACACTCGGAGCCCCGGCCCAATGAGC
ACAACTGCTCGGCTAGCAGGAGGATCCGCCCAGAGTCACTCCAGGGTGCTGACCACCGGCCCTACACCTTCTT
CATTTCCCCGGGGAGCAGAGACCCAGCGGGGAGTTACCATCTGAACCTCTCCAGCCACTTCCGCTGGTCGGCG
CTGCAGGTGTCCGTGGGCCTGTACACGTCCCTGTGCCAGTACTTCAGCGAGGAGGACATGGTGTGGCGGACAG
AGGGGCTGCTGCCCCTGGAGGAGACCTCGCCCCGCCAGGCCGTCTGCCTCACCCGCCACCTCACCGCCTTCGG
CGCCAGCCTCTTCGTGCCCCCAAGCCATGTCCGCTTTGTGTTTCCTGAGCCGACAGCGGATGTAAACTACATC
GTCATGCTGACATGTGCTGTGTGCCTGGTGACCTACATGGTCATGGCCGCCATCCTGCACAAGCTGGACCAGT
TGGATGCCAGCCGGGGCCGCGCCATCCCTTTCTGTGGGCAGCGGGGCCGCTTCAAGTACGAGATCCTCGTCAA
GACAGGCTGGGGCCGGGGCTCAGGTACCACGGCCCACGTGGGCATCATGCTGTATGGGGTGGACAGCCGGAGC
GGCCACCGGCACCTGGACGGCGACAGAGCCTTCCACCGCAACAGCCTGGACATCTTCCGGATCGCCACCCCGC
ACAGCCTGGGTAGCGTGTGGAAGATCCGAGTGTGGCACGACAACAAAGGGCTCAGCCCTGCCTGGTTCCTGCA
GCACGTCATCGTCAGGGACCTGCAGACGGCACGCAGCGCCTTCTTCCTGGTCAATGACTGGCTTTCGGTGGAG
ACGGAGGCCAACGGGGGCCTGGTGGAGAAGGAGGTGCTGGCCGCGAGCGACGCAGCCCTTTTGCGCTTCCGGC
GCCTGCTGGTGGCTGAGCTGCAGCGTGGCTTCTTTGACAAGCACATCTGGCTCTCCATATGGGACCGGCCGCC
TCGTAGCCGTTTCACTCGCATCCAGAGGGCCACCTGCTGCGTTCTCCTCATCTGCCTCTTCCTGGGCGCCAAC
GCCGTGTGGTACGGGCTGTTGGCGACTCTGCCTACAGCACGGGCATGTGTCCAGGCTGAGCCCGCTGAGCG
TCGACACAGTCGCTGTTGGCCTGGTGTCCAGCGTGGTTGTCTATCCCGTCTACCTGGCCATCCTTTTTCTCTT
CCGGATGTCCCGGAGCAAGGTGGCTGGGAGCCCGAGCCCCACACCTGCCGGGCAGCAGGTGCTGGACATCGAC
AGCTGCCTGGACTCGTCCGTGCTGGACAGCTCCTTCCTCACGTTCTCAGGCCTCCACGCTGAGGCCTTTGTTG
GACACATGAAGAGTGACTTGTTTCTGGATGATTCTAAGAGTCTGGTGTGCTGGCCCTCCGGCGAGGGAACGCT

TABLE 28A-continued

NOV28 Nucleotide Sequence

CAGTTGGCCGGACCTGCTCAGTGACCCGTCCATTGTGGGTAGCAATCTGCGGCAGCTGGCACGGGGCCAGGCG

GGCCATGGGCTGGGCCCAGAGGAGGACGGCTTCTCCCTGGCCAGCCCCTACTCGCCTGCCAAATCCTTCTCAG

CATCAGATGAAGACCTGATCCAGCAGGTCCTTGCCGAGGGGGTCAGCAGCCCAGCCCCTACCCAAGACACCCA

CATGGAAACGGACCTGCTCAGCAGCCTGTCCAGCACTCCTGGGGAGAAGACAGAGACGCTGGCGCTGCAGAGG

CTGGGGGAGCTGGGGCCACCCAGCCCAGGCCTGAACTGGGAACAGCCCCAGGCAGCGAGGCTGTCCAGGACAG

GACTGGTGGAGGGTCTGCGGAAGCGCCTGCTGCCGGCCTGGTGTGCCTCCCTGGCCCACGGGCTCAGCCTGCT

CCTGGTGGCTGTGGCTGTGGCTGTCTCAGGGTGGGTGGGTGCGAGCTTCCCCCCGGGCGTGAGTGTTGCGTGG

CTCCTGTCCAGCAGCGCCAGCTTCCTGGCCTCATTCCTCGGCTGGGAGCCACTGAAGGTCTTGCTGGAAGCCC

TGTACTTCTCACTGGTGGCCAAGCGGCTGCACCCGGATGAAGATGACACCCTGGTAGAGAGCCCGGCTGTGAC

GCCTGTGAGCGCACGTGTGCCCCGCGTACGGCCACCCCACGGCTTTGCACTCTTCCTGGCCAAGGAAGAAGCC

CGCAAGGTCAAGAGGCTACATGGCATGCTGCGGAGCCTCCTGGTGTACATGCTTTTTCTGCTGGTGACCCTGC

TGGCCAGCTATGGGGATGCCTCATGCCATGGGCACGCCTACCGTCTGCAAAGCGCCATCAAGCAGGAGCTGCA

CAGCCGGGCCTTCCTGGCCATCACGCGGTCTGAGGAGCTCTGGCCATGGATGGCCCACGTGCTGCTGCCCTAC

GTCCACGGGAACCAGTCCAGCCCAGAGCTGGGGCCCCACGGCTGCGGCAGGTGCGGCTGCAGGAAGCACTCT

ACCCAGACCCTCCCGGCCCCAGGGTCCACACGTGCTCGGCCGCAGGAGGCTTCAGCACCAGCGATTACGACGT

TGGCTGGGAGAGTCCTCACAATGGCTCGGGGACGTGGGCCTATTCAGCGCCGGATCTGCTGGGGGCATGGTCC

TGGGGCTCCTGTGCCGTGTATGACAGCGGGGGCTACGTGCAGGAGCTGGGCCTGAGCCTGGAGGAGAGCCGCG

ACCGGCTGCGCTTCCTGCAGCTGCACAACTGGCTGGACAACAGGAGCCGCGCTGTGTTCCTGGAGCTCACGCG

CTACAGCCCGCCCGTGGGGCTGCACGCCGCCGTCACGCTGCGCCTCGAGTTCCCGGCGGCCGGCCGCGCCCTG

GCCGCCCTCAGCGTCCGCCCCTTTGCGCTGCGCCGCCTCAGCGCGGGCCTCTCGCTGCCTCTGCTCACCTCGG

TGTGCCTGCTGCTGTTCGCCGTGCACTTCGCCGTGGCCGAGGCCCGTACTTGGCACAGGGAAGGGCGCTGGCG

CGTGCTGCGGCTCGGAGCCTGGGCGCGGTGGCTGCTGGTGGCGCTGACGGCGGCCACGGCACTGGTACGCCTC

GCCCAGCTGGGTGCCGCTGACCGCCAGTGGACCCGTTTCGTGCGCGGCCGCCCGCGCCGCTTCACTAGCTTCG

ACCAGGTGGCGCAGCTGAGCTCCGCAGCCCGTGGCCTGGCGGCCTCGCTGCTCTTCCTGCTTTTGGTCAAGGC

TGCCCAGCAGCTACGCTTCGTGCGCCAGTGGTCCGTCTTTGGCAAGACATTATGCCGAGCTCTGCCAGAGCTC

CTGGGGGTCACCTTGGGCCTGGTGGTGCTCGGGGTAGCCTACGCCCAGCTGGCCATCCTGCTCGTGTCTTCCT

GTGTGGACTCCCTCTGGAGCGTGGCCCAGGCCCTGTTGGTGCTGTGCCCTGGGACTGGGCTCTCTACCCTGTG

TCCTGCCGAGTCCTGGCACCTGTCACCCCTGCTGTGTGTGGGGCTCTGGGCACTGCGGCTGTGGGGCGCCCTA

CGGCTGGGGGCTGTTATTCTCCGCTGGCGCTACCACGCCTTGCGTGGAGAGCTGTACCGGCCGGCCTGGGAGC

CCCAGGACTACGAGATGGTGGAGTTGTTCCTGCGCAGGCTGCGCCTCTGGATGGGCCTCAGCAAGGTCAAGGA

GTTCCGCCACAAAGTCCGCTTTGAAGGGATGGAGCCGCTGCCCTCTCGCTCCTCAGGGGCTCCAAGGTATCC

CCGGATGTGCCCCCACCCAGCGCTGGCTCCGATGCCTCGCACCCCTCCACCTCCTCCAGCCAGCTGGATGGGC

TGAGCGTGAGCCTGGGCCGGCTGGGGACAAGGTGTGAGCCTGAGCCCTCCCGCCTCCAAGCCGTGTTCGAGGC

CCTGCTCACCCAGTTTGACCGACTCAACCAGGCCACAGAGGACGTCTACCAGCTGGAGCAGCAGCTGCACAGC

CTGCAAGGCCGCAGGAGCAGCCGGGCGCCCGCCGGATCTTCCCGTGGCCCATCCCCGGGCCTGCGGCCAGCAC

TGCCCAGCCGCCTTGCCCGGGCCAGTCGGGGTGTGGACCTGGCCACTGGCCCAGCAGGACACCCCTTCGGGC

CAAGAACAAGGTCCACCCCAGCAGCACTTAGTCCTCCTTCCTGGCGGGGTGGGCCGTGGAGTCGGAGTGG

The NOV28 nucleic acid was identified on chromosome 16p13.3 and has 8732 of 8732 bases (100%) identical to a gb:GENBANK-ID:HUMPKD1A|acc:L33243.1 mRNA from *Homo sapiens* (*Homo sapiens* polycystic kidney disease 1 protein (PKD1) mRNA, complete cds) (E=0.0).

A disclosed NOV28 polypeptide (SEQ ID NO:90) encoded by SEQ ID NO:89 is 4299 amino acid residues and is presented using the one-letter code in Table 28B. Signal P, Psort and/or Hydropathy results predict that NOV28 contains a signal peptide and is likely to be localized to the plasma membrane with a certainty of 0.8200. The most likely cleaveage site for a NOV28 polypeptide is between amino acids 23 and 24: ALA-GG.

TABLE 28B

Encoded NOV28 protein sequence (SEQ ID NO:90)
MPPAAPARLALALGLGLWLGALAGGPGRGCGPCEPPCLCGPAPGAACRVNCSGRGLRTLGPALRIPADATAL

DVSHNLLRALDVGLLANLSALAELDISNNKISTLEEGIFNALFNLSEINLSGNPFECDCGLAWLPRWEEQQ

VRVVQPEAATCAGPGSLAGQPLLGIPLLDSGCGEEYVACLPDNSSGTVAAVSFSAAHEGLLQPEACSAFCFS

TGQGLAALSEQGWCLCGAAQPSSASFACLSLCSGPPPPPAPTCRGPTLLQHVFPASPGATLVGPHGPLASGQ

LAAFHIAAPLPVTATRWDFGDGSAEVDAAGPAASHRYVLPGRYHVTAVLAIGAGSALLGTDVQVEAAPAALE

LVCPSSVQSDESLDLSIQNRGGSGLEAAYSIVALGEEPARAVHPLCPSDTEIFPGNGHCYRLVVEKAAWLQA

QEQCQAWAGAALAMVDSPAVQRFLVSRVTRSLDVWIGFSTVQGVEVGPAPQGEAFSLESCQNWLPGEPHPAT

AEHCVRLGPTGWCNTDLCSAPHSYVCELQPGGPVQDAENLLVGAPSGDLQGPLTPLAQQDGLSAPHEPVEVM

VFPGLRLSREAFLTTAEFGTQELRRPAQLRLQVRLLSTAGTPENGSEPESRSPDDNRTQLAPACMPGGRWCP

GANICLPLDASCHPQACANGCTSGPGLPGAPYALWREFLFSVAAGPPAQYSVTLHGQDVLMLPGDLVGLQHD

AGPGALLHCSPAPGHPGPQAPYLSANASSWLPHLPAQLEGTWACPACALRLLAATEQLTVLLGLRPNPGLRM

PGRYEVRAEVGNGVSRHNLSCSFDVVSPVAGLRVIYPAPRDGRLYVPTNGSALVLQVDSGANATATARWPGG

SVSARFENVCPALVATFVPGCPWETNDTLFSVVALPWLSEGEHVVDVVVENSASRANLSLRVTAEEPICGLR

ATPSPEARVLQGVLVRYSPVVEAGSDMVFRWTINDKQSLTFQNVVFNVIYQSAAVFKLSLTASNHVSNVTVN

YNVTVERNNRMQGLQVSTVPAVLSPNATLALTAGVLVDSAVEVAFLWNFGDGEQALHQFQPPYNESFPVPDP

SVAQVLVEHNVMHTYAAPGEYLLTVLASNAFENLTQQVPVSVRASLPSVAVGVSDGVLVAGRPVTFYPHPLP

SPGGVLYTWDFGDGSPVLTQSQPAANHTYASRGTYHVRLEVNNTVSGAAAQADVRVFEELRGLSVDMSLAVE

QGAPVVVSAAVQTGDNITWTFDMGDGTVLSGPEATVEHVYLRAQNCTVTVGAASPAGHLARSLHVLVFVLEV

LRVEPAACIPTQPDARLTAYVTGNPAHYLFDWTFGDSSNTTVRGCPTVTHNFTRSGTFPLALVLSSRVNRA

HYFTSICVEPEVNVTLQPERQFVQLGDEAWLVACAWPPFPYRYTWDFGTEEAAPTRARGPEVTFIYRDPGS

YLVTVTASNNISAANDSALVEVQEPVLVTSIKVNGSLGLELQQPYLFSAVGRGRPASYLWDLGDGGWLEGPE

VTHAYNSTGDFTVRVAGWNEVSRSEAWLNVTVKRRVRGLVVNASRTVVPLNGSVSFSTSLEAGSDVRYSWVL

CDRCTPIPGGPTISYTFRSVGTFNIIVTAENEVGSAQDSIFVYVLQLIEGLQVVGGGRYFPTNHTVQLQAVV

RDGTNVSYSWTAWRDRGPALAGSGKGFSLTVLEAGTYHVQLRATNMLGSAWADCTMDFVEPVGWLMVTASPN

PAAVNTSVTLSAELAGGSGVVYTWSLEEGLSWETSEPFTTHSFPTPGLHLVTMTAGNPLGSANATVEVDVQV

PVSGLSIRASEPGGSFVAACSSVPFWGQLATGTNVSWCWAVPGGSSKRGPHVTMVFPDAGTFSIRLNASNAV

SWVSATYNLTAEEPIVGLVLWASSKVVAPGQLVHFQILLAAGSAVTFRLQVGGANPEVLPGPRFSHSFPRVG

DHVVSVRGKNHVSWAQAQVRIVVLEAVSGLQMPNCCEPGIATGTERNFTARVQRGSRVAYAWYFSLQKVQGD

SLVILSGRDVTYTPVAAGLLEIQVRAFNALGSENRTLVLEVQDAVQYVALQSGPCFTNRSAQFEAATSPSPR

RVAYHWDFGDGSPGQDTDEPRAEHSYLRPGDYRVQVNASNLVSFFVAQATVTVQVLACREPEVDVVLPLQVL

MRRSQRNYLEAHVDLRDCVTYQTEYRWEVYRTASCQRPGRPARVALPGVDVSRPRLVLPRLALPVGHYCFVF

VVSFGDTPLTQSIQANVTVAPERLVPIIEGGSYRVWSDTRDLVLDGSESYDPNLEDGDQTPLSFHWACVAST

QREAGGCALNFGPRGSSTVTIPRERLAAGVEYTFSLTVWKAGRKEEATNQTVLIRSGRVPIVSLECVSCKAQ

TABLE 28B-continued

Encoded NOV28 protein sequence

AVYEVSRSSYVYLEGRCLNCSSGSKRGRWAARTFSNKTLVLDETTTSTGSAGMRLVLRRGVLRDGEGYTFTL

TVLGRSGEEEGCASIRLSPNRPPLGGSCRLFPLGAVHALTTKVHFECTGWHDAEDAGAPLVYALLLRRCRQG

HCEEFCVYKGSLSSYGAVLPPGFRPHFEVGLAVVVQDQLGAAVVALNRSLAITLPEPNGSATGLTVWLHGLT

ASVLPGLLRQADPQHVIEYSLALVTVLNEYERALDVAAEPKHERQHRAQIRKNITETLVSLRVHTVDDIQQI

AAALAQCMGPSRELVCRSCLKQTLHKLEAMMLILQAETTAGTVTPTAIGDSILNITGDLIHLASSDVRAPQP

SELGAESPSRMVASQAYNLTSALMRILMRSRVLNEEPLTLAGEEIVAQGKRSDPRSLLCYGGAPGPGCHFSI

PEAFSGALJANLSDVVQLIFLVDSNPFPFGYISNYTVSTKASMAFQTQACAQIPIERLASEPAITVKVPNNS

DWAARGHRSSANSVVVQPQASVGAVVTLDSSNPAAVLHLQLNYTLLDGHYLSEEPEPYLAVYLHSEPRPNEH

NCSASRRIRPESLQGADHRPYTFFISPGSRDPAGSYHLNLSSHFRWSALQVSVGLYTSLCQYFSEEDMVWRT

EGLLPLEETSPRQAVCLTRHLTAFGASLFVPPSHVRFVFPEPTADVNYIVMLTCAVCLVTYMVMAAILHKLD

QLDASRGRAIPFCGQRGRFKYEILVKTGWGRGSGTTAHVGIMLYGVDSRSGHRHLDGDRAFHRNSLDIFRIA

TPHSLGSVWKIRVWHDNKGLSPAWFLQHVIVRDLQTARSAFFLVNDWLSVETEANGGLVEKEVLAASDAALL

RFRRLLVAELQRGFFDKHIWLSIWDRPPRSRFTRIQRATCCVLLICLFLGANANWYGAVGDSAYSTGHVSRL

SPLSVDTVAVGLVSSVVVYPVYLAILFLFRMSRSKVAGSFSPTPAGQQVLDIDSCLDSSVLDSSFLTFSGLH

AFAFVGQMKSDLFLDDSKSLVCWPSGEGTLSWPDLLSDPSIVGSNLRQLARGQAGHGLGPEBDGFSLASPYS

PAKSFSASDEDLIQQVLAEGVSSPAPTQDTHMETDLLSSLSSTPGEKTETLALQRLCELGPPSPGLNWEQPQ

AARLSRTGLVEGLRKRLLPAWCASLAHGLSLLLVAVAVAVSGWVGASFPPGVSVAWLLSSSASFLASFLGWE

PLKVLLEALYFSLVAKRLHPDEDDTLVESPAVTPVSARVPRVRPPHGFALFLAKEEARKVKRLHGMLRSLLV

YMLFLLVTLLASYGDASCHGHAYRLQSAIKQELHSRAFLAITRSEELWPWMAHVLLPYVHGNQSSPELGPPR

LRQVRLQEALYPDPPGPRVHTCSAAGGFSTSDYDVGWESPHNGSGTWAYSAPDLLGAWSWGSCAVYDSGGYV

QELGLSLEESRDRLRFLQLHNWLDNRSRAVFLELTRYSPAVGLHAAVTLRLEFPAAGRALAALSVRPFALRR

LSAGLSLPLLTSVCLLLFAVHFAVAEARTWHREGRWRVLRLGAWARWLLVALTAATALVRLAQLGAADRQWT

RFVRGRPRRFTSFDQVAQLSSAARGLAASLLFLLLVKAAQQLRFLRQWSVFGKTLCRALPELLGVTLGLVVL

GVAYAQLAILLVSSCVDSLWSVAQALLVLCPGTGLSTLCPAESWHLSPLLCVGLWALRLWGALRLGAVILRW

RYHALRGELYRPAWEPQDYEMVELFLRRLRLWMGLSKVKEFRHKVRFEGMEPLPSRSSRGSKVSPDVPPPSA

GSDASHPSTSSSQLDGLSVSLGRLGTRCEPEPSRLQAVFEALLTQFDRLNQATEDVYQLEQQLHSLQGRRSS

RAPAQSSRGPSPGLRPALPSRLAPASRGVDLATGPSRTPLRAKNKVHPSST

The NOV28 amino acid sequence 4298 of 4302 amino acid residues (99%) identical to, and 4298 of 4302 amino acid residues (99%) similar to, the 4302 amino acid residue ptnr:SPTREMBL-ACC:Q15140 protein from *Homo sapiens* (Human) (Polycystic Kidney Disease 1 Protein) (E=0.0).

NOV28 is expressed in at least the following tissues: adrenal gland, bone marrow, brain—amygdala, brain—cerebellum, brain—hippocampus, brain—substantia nigra, brain—thalamus, brain—whole, fetal brain, fetal kidney, fetal liver, fetal lung, heart, kidney, lymphoma—Raji, mammary gland, pancreas, pituitary gland, placenta, prostate, salivary gland, skeletal muscle, small intestine, spinal cord, spleen, stomach, testis, thyroid, trachea and uterus. This information was derived by determining the tissue sources of the sequences that were included in the invention including but not limited to SeqCalling sources, Public EST sources, genomic clone sources, literature sources, and/or RACE sources. NOV28 is also predicted to be expressed in the following tissues because of the expression pattern of (gb:GENBANK-ID:HUMPKD1A|acc:L33243.1) a closely related *Homo sapiens* polycystic kidney disease 1 protein (PKD 1) mRNA, complete cds homolog in species *Homo sapiens*: kidney.

NOV28 has homology to the amino acid sequences shown in the BLASTP data listed in Table 28C.

TABLE 28C

BLAST results for NOV28

| Gene Index/ Identifier | Protein/ Organism | Length (aa) | Identity (%) | Positives (%) | Expect |
|---|---|---|---|---|---|
| gi|4505833|ref|NP_0 00287.1| | polycystic kidney | 4302 | 3847/ 4254 | 3847/ 4254 | 0.0 |

TABLE 28C-continued

BLAST results for NOV28

| Gene Index/ Identifier | Protein/ Organism | Length (aa) | Identity (%) | Positives (%) | Expect |
|---|---|---|---|---|---|
| (NM_000296) | disease 1 (autosomal dominant); Polycystin-1 [Homo sapiens] | | (90%) | (90%) | |
| gi|1586345|prf||2203412A | polycystin [Homo sapiens] | 4302 | 3844/4254 (90%) | 3844/4254 (90%) | 0.0 |
| gi|903758|gb|AAC41765.1| (L43619) | polycystic kidney disease 1 protein [Homo sapiens] | 4292 | 3836/4254 (90%) | 3836/4254 (90%) | 0.0 |
| gi|1730587|sp|P98161|PKD1_HUMAN | Polycystin precursor (Autosomal dominant polycystic kidney disease protein 1) [Homo sapiens] | 4303 | 3833/4255 (90%) | 3838/4255 (90%) | 0.0 |
| gi|11320978|gb|AAG33986.1| (AF277452) | Pkd1 [Rattus norvegicus] | 4283 | 3009/4254 (70%) | 3292/4254 | 0.0 4254 |

The homology of these sequences is shown graphically in the ClustalW analysis shown in Table 28D.

TABLE 28E

Clustal W Sequence Alignment

1) NOV28 (SEQ ID NO:90)
2) gi 4505833|refNP_000287.1|(NM_000296) polycystic kidney disease 1 (autosomal dominant); Polycystin-1 [Homo sapiens] (SEQ ID NO:271)
3) gi 1586345|prf|2203412A polycystin [Homo sapiens] (SEQ ID NO:272)
4) gi 903758|gb AAC41765.1|(L43619) polycystic kidney disease 1 protein [Homo sapiens] (SEQ ID NO:273)
5) gi 1730587|sp P98161 PKD1_HUMAN Polycystin precursor (Autosomal dominant polycystic kidney disease protein 1) [Homo sapiens] (SEQ ID NO:274)
6) gi 11320978|gb AAG33986.1 (AF277452) Pkd1 [Rattus norvegicus] (SEQ ID NO:275)

```
                       10        20        30        40        50        60        70
                 ....|....|....|....|....|....|....|....|....|....|....|....|....|....|
NOV28            MPPAAPARLALALGLGLWLGALAGGPGRGCGPCEPPCLCGPAPGAACRVNCSGRGLRTLGPALRIPADAT
gi|4505833|      MPPAAPARLALALGLGLWLGALAGGPGRGCGPCEPPCLCGPAPGAACRVNCSGRGLRTLGPALRIPADAT
gi|1586345|      MPPAAPARLALALGLGLWLGALAGGPGRGCGPCEPPCLCGPAPGAACRVNCSGRGLRTLGPALRIPADAT
gi|903758|       MPPAAPARLALALGLGLWLGALAGGPGRGCGPCEPPCLCGPAPGAACRVNCSGRGLRTLGPALRIPADAT
gi|1730587|      MPPAAPARLALALGLGLWLGALAGGPGRGCGPCEPPCLCGPAPGAACRVNCSGRGLRTLGPALRIPADAT
gi|11320978|     ---------ALALGLGLWLGALAGDPGRGCGPCPLPCFCSPAPDAACRVNCSGRWLQTLGPSLRIPADAT 80        90       100       110       120       130       140
                 ....|....|....|....|....|....|....|....|....|....|....|....|....|....|
NOV28            ALDVSHNLLRALDVGLLANLSALAELDISNNKISTLEEGIFANLFNLSEINLSGNPFECDCGLAWLPRWA
gi|4505833|      ALDVSHNLLRALDVGLLANLSALAELDISNNKISTLEEGIFANLFNLSEINLSGNPFECDCGLAWLPRWA
gi|1586345|      ALDVSHNLLRALDVGLLANLSALAELDISNNKISTLEEGIFANLFNLSEINLSGNPFECDCGLAWLPRWA
gi|903758|       ALDVSHNLLRALDVGLLANLSALAELDISNNKISTLEEGIFANLFNLSEINLSGNPFECDCGLAWLPRWA
gi|1730587|      ELDVSHNLLRALDVGLLANLSALAELDISNNKISTLEEGIFANLFNLSEINLSGNPFECDCGLAWLPQWA
gi|11320978|     ALDESHNLLQTLDIRLLVNLSGLVELDESNNRISTLEEGVFANLFNLSEINLSGNPFECNCGLAWLPRWA 150       160       170       180       190       200       210
                 ....|....|....|....|....|....|....|....|....|....|....|....|....|....|
NOV28            EEQQVRVVQPEAATCAGPGSLAGQPLLGIPLLDSGCGEEYVACLPDNSSGTVAAVSFSAAHEGLLQPEAC
gi|4505833|      EEQQVRVVQPEAATCAGPGSLAGQPLLGIPLLDSGCGEEYVACLPDNSSGTVAAVSFSAAHEGLLQPEAC
gi|1586345|      EEQQVRVVQPEAATCAGPGSLAGQPLLGIPLLDSGCGEEYVACLPDNSSGTVAAVSFSAAHEGLLQPEAC
gi|903758|       EEQQVRVVQPEAATCAGPGSLAGQPLLGIPLLDSGCGEEYVACLPDNSSGTVAAVSFSAAHEGLLQPEAC
gi|1730587|      EEQQVRVVQPEAATCAGPGSLAGQPLLGIPLLDSGCGEEYVACLPDNSSGTVAAVSFSAAHEGLLQPEAC
gi|11320978|     KEQQVHVVQSEATTCRGPVPLAGRPLLSTPLLDNACGEEYVACLPDNSSGAVAAVPFFAHQCPLFTAAC 220       230       240       250       260       270       280
                 ....|....|....|....|....|....|....|....|....|....|....|....|....|....|
NOV28            SAFCFSTGQGLAALSEQGWCLCGAAQPSSASFACLSLCSGPPPPPAPTCRGPTLLQHVFPASPGARLVGP
gi|4505833|      SAFCFSTGQGLAALSEQGWCLCGAAQPSSASFACLSLCSGPPPPPAPTCRGPTLLQHVFPASPGARLVGP
gi|1586345|      SAFCFSTGQGLAALSEQGWCLCGAAQPSSASFACLSLCSGPPPPPAPTCRGPTLLQHVFPASPGARLVGP
gi|903758|       SAFCFSTGQGLAALSEQGWCLCGAAQPSSASFACLSLCSGPPPPPAPTCRGPTLLQHVFPASPGARLVGP
gi|1730587|      SAFCFSTGQGLAALSEQGWCLCGAAQPSSASFACLSLCSGPPAPPAPTCRGPTLLQHVFPASPGARLVGP
gi|11320978|     SAFCFSAGHGLAALSEQNQCLCGAGQPSNTSAACSSWCSSILLSFNSACGGPTLLQHTFPASPGAALVGH
```

TABLE 28E-continued

Clustal W Sequence Alignment

```
                290        300        310        320        330        340        350
             ....|....|....|....|....|....|....|....|....|....|....|....|....|....|
NOV28        HGPLASGQLAAFHIAAPLPVTATRWDFGDGSAEVDAAGPAASHRYVLPGRYHVTAVLALGAGSALLGTDV
gi|4505833|  HGPLASGQLAAFHIAAPLPVTATRWDFGDGSAEVDAAGPAASHRYVLPGRYHVTAVLALGAGSALLGTDV
gi|1586345|  HGPLASGQLAAFHIAAPLPVTATRWDFGDGSAEVDAAGPAASHRYVLPGRYHVTAVLALGAGSALLGTDV
gi|903758|   HGPLASGQLAAFHIAAPLPVTATRWDFGDGSAEVDAAGPAASHRYVLPGRYHVTAVLALGAGSALLGTDV
gi|1730587|  HGPLASGQLAAFHIAAPLPVTDTRWDFGDGSAEVDAAGPAASHRYVLPGRYHVTAVLALGAGSALLGTDV
gi|11320978| HGPLASGQPADFHINSPLPISSTCWNFGDGSPEVDMAGPAATHSYVLPGGYHVTVVLTLGAGSALLETDV 360        370        380        390        400        410        420
             ....|....|....|....|....|....|....|....|....|....|....|....|....|....|
NOV28        QVEAAPAALELVCPSSVQSDESLDLSIQNRGGSGLEAAYSIVALGEEPARAVHPLCPSDTEIFPGNGHCY
gi|4505833|  QVEAAPAALELVCPSSVQSDESLDLSIQNRGGSGLEAAYSIVALGEEPARAVHPLCPSDTEIFPGNGHCY
gi|1586345|  QVEAAPAALELVCPSSVQSDESLDLSIQNRGGSGLEAAYSIVALGEEPARAVHPLCPSDTEIFPGNGHCY
gi|903758|   QVEAAPAALELVCPSSVQSDESLDLSIQNRGGSGLEAAYSIVALGEEPARAVHPLCPSDTEIFPGNGHCY
gi|1730587|  QVEAAPAALELVCPSSVQSDESLDLSIQNRGGSGLEAAYSIVALGEEPARAVHPLCPSDTEIFPGNGHCY
gi|11320978| QVEVAPTVLELVCPSFVHSDESLDLGIPHRGGSALEVTYSIEAIDKEPAQVVHPLCPSDTEIFPGNGHCY 430        440        450        460        470        480        490
             ....|....|....|....|....|....|....|....|....|....|....|....|....|....|
NOV28        RLVVEKAAWLQAQEQCQAEAGAALAMVDSPAVQRFLVSRVIRSLDVWIGFSTVQGVEVGPAPQGEAFSLE
gi|4505833|  RLVVEKAAWLQAQEQCQAEAGAALAMVDSPAVQRFLVSRVIRSLDVWIGFSTVQGVEVGPAPQGEAFSLE
gi|1586345|  RLVVEKAAWLQAQEQCQAEAGAALAMVDSPAVQRFLVSRVIRSLDVWIGFSTVQGVEVGPAPQGEAFSLE
gi|903758|   RLVVEKAAWLQAQEQCQAEAGAALAMVDSPAVQRFLVSRVIRSLDVWIGFSTVQGVEVGPAPQGEAFSLE
gi|1730587|  RLVVEKAAWLQAQEQCQAEAGAALAMVDSPAVQRFLVSRVIRSLDVWIGFSTVQGVEVGPAPQGEAFSLE
gi|11320978| RLVAEKAPWLQAQEQCRTWAGAALAMVDSPAIQHFLVSKVTRSLDVWIGFSEVECKE-GLDPQGEAFSLE 500        510        520        530        540        550        560
             ....|....|....|....|....|....|....|....|....|....|....|....|....|....|
NOV28        SCQNWLPGEPHPATAEHCVRLGPTGWCNTDLCSAPHSYVCELQPGGPVQDAENLLVGAPSGDLQGPLTPL
gi|4505833|  SCQNWLPGEPHPATAEHCVRLGPTGWCNTDLCSAPHSYVCELQPGGPVQDAENLLVGAPSGDLQGPLTPL
gi|1586345|  SCQNWLPGEPHPATAEHCVRLGPTGWCNTDLCSAPHSYVCELQPGGPVQDAENLLVGAPSGDLQGPLTPL
gi|903758|   SCQNWLPGEPHPATAEHCVRLGPTGWCNTDLCSAPHSYVCELQPGGPVQDAENLLVGAPSGDLQGPLTPL
gi|1730587|  SCQNWLPGEPHPATAEHCVRLGPTGWCNTDLCSAPHSYVCELQPGGPVQDAENLLVGAPSGDLQGPLTPL
gi|11320978| SCQNWLPGEPHPATEEHCVRLGPAGQCNTDLCSAPHSYVCELRPGGPVGDADNFLEGVSGGGRSGPLQPL 570        580        590        600        610        620        630
             ....|....|....|....|....|....|....|....|....|....|....|....|....|....|
NOV28        AQQDGLSAPHEPVEVMVFPGLRLSREAFLTTAEFGTQELRRPAQLRLQVYRLLSTAGTPENGSEPESRSP
gi|4505833|  AQQDGLSAPHEPVEVMVFPGLRLSREAFLTTAEFGTQELRRPAQLRLQVYRLLSTAGTPENGSEPESRSP
gi|1586345|  AQQDGLSAPHEPVEVMVFPGLRLSREAFLTTAEFGTQELRRPAQLRLQVYRLLSTAGTPENGSEPESRSP
gi|903758|   AQQDGLSAPHEPVEVMVFPGLRLSREAFLTTAEFGTQELRRPAQLRLQVYRLLSTAGTPENGSEPESRSP
gi|1730587|  AQQDGLSAPHEPVEVMVFPGLRLSREAFLTTAEFGTQELRRPAQLRLQVYRLLSTAGTPENGSEPESRSP
gi|11320978| AQQGTLQGFLQPVEVMVFPGLSPSREAFLTAAEFETQELEDPVQLRLQVYRHSREAVAPEGSSE-----L 640        650        660        670        680        690        700
             ....|....|....|....|....|....|....|....|....|....|....|....|....|....|
NOV28        DNRTQLAPACMPGGRWCPGANICLPLDASCHPQACANGCTSGPGLPGAPYALWREFLFSVAAGPPAQYSV
gi|4505833|  DNRTQLAPACMPGGRWCPGANICLPLDASCHPQACANGCTSGPGLPGAPYALWREFLFSVAAGPPAQYSV
gi|1586345|  DNRTQLAPACMPGGRWCPGANICLPLDASCHPQACANGCTSGPGLPGAPYALWREFLFSVAAGPPAQYSV
gi|903758|   DNRTQLAPACMPGGRWCPGANICLPLDASCHPQACANGCTSGPGLPGAPYALWREFLFSVAAGPPAQYSV
gi|1730587|  DNRTQLAPACMPGGRWCPGANICLPLDASCHPQACANGCTSGPGLPGAPYALWREFLFSVPAGPPAQYSV
gi|11320978| DNSTEPAPKCVPEELWCPGANVCVPFDALCNSHVCINGSASRLGLPRASYTLWKEFFSVPAGPFTQYLV 710        720        730        740        750        760        770
             ....|....|....|....|....|....|....|....|....|....|....|....|....|....|
NOV28        TLHGQDVLMLPGDLVGLQHDAGPGALLHCSPAPGHPGPQAPYLSANASSWLPHLPAQLEGTWACPACALR
gi|4505833|  TLHGQDVLMLPGDLVGLQHDAGPGALLHCSPAPGHPGPQAPYLSANASSWLPHLPAQLEGTWACPACALR
gi|1586345|  TLHGQDVLMLPGDLVGLQHDAGPGALLHCSPAPGHPGPQAPYLSANASSWLPHLPAQLEGTWACPACALR
gi|903758|   TLHGQDVLMLPGDLVGLQHDAGPGALLHCSPAPGHPGPQAPYLSANASSWLPHLPAQLEGTWACPACALR
gi|1730587|  TLHGQDVLMLPGDLVGLQHDAGPGALLHCSPAPGHPGPRAPYLSANASSWLPHLPAQLEGTWGCPACALR
gi|11320978| TLHGQDVPMLPGDLVALQHDAGPGTFLHCPLASSCPG-QALYLSTNASDWMTNLPVHLEEAWAGPVCSLQ 780        790        800        810        820        830        840
             ....|....|....|....|....|....|....|....|....|....|....|....|....|....|
NOV28        LLAATEQLTVLLGLRPNPGLRMPGRYEVRAEVGNGVSRHNLSCSFDVVSPVAGLRVIYPAPRDGRLYVPT
gi|4505833|  LLAATEQLTVLLGLRPNPGLRMPGRYEVRAEVGNGVSRHNLSCSFDVVSPVAGLRVIYPAPRDGRLYVPT
gi|1586345|  LLAATEQLTVLLGLRPNPGLRMPGRYEVRAEVGNGVSRHNLSCSFDVVSPVAGLRVIYPAPRDGRLYVPT
gi|903758|   LLAATEQLTVLLGLRPNPGLRMPGRYEVRAEVGNGVSRHNLSCSFDVVSPVAGLRVIYPAPRDGRLYVPT
gi|1730587|  LLAQREQLTVLLGLRPNPGLREPGRYEVRAEVGNGVSRHNLSCSFDVVSPVAGLRVIYPAPRDGRLYVPT
gi|11320978| LLVTEQLTPLLGLGSNPGLCHPGHYEVRATVGNSIDRQNLSCSFSVVSPVAGLRVIHPTPLDGHEYVPT 850        860        870        880        890        900        910
             ....|....|....|....|....|....|....|....|....|....|....|....|....|....|
NOV28        NGSALVLQVDSGANATATARWPGGSVSARFENVCPALVATFVPGCPWETNDTLFSVVALPWLSEGEHVVD
gi|4505833|  NGSALVLQVDSGANATATARWPGGSVSARFENVCPALVATFVPGCPWETNDTLFSVVALPWLSEGEHVVD
gi|1586345|  NGSALVLQVDSGANATATARWPGGSVSARFENVCPALVATFVPGCPWETNDTLFSVVALPWLSEGEHVVD
gi|903758|   NGSALVLQVDSGANATATARWPGGSVSARFENVCPALVATFVPGCPWETNDTLFSVVALPWLSEGEHVVD
gi|1730587|  NGSALVLQVDSGANATATARWPGGSVSARFENVCPALVATFVEACPWETNDTLFSVVALPWLSEGEHVVD
gi|11320978| NGSTLVLQVDSGANATAIAHWFGGMVSAPFEDACPPEVDFLKQDCTEEANATLFSVEVLPRLKEGEHTVR
```

TABLE 28E-continued

Clustal W Sequence Alignment

```
                 920       930       940       950       960       970       980
              ....|....|....|....|....|....|....|....|....|....|....|....|....|
NOV28         VVVENSASRANLSLRVTAEEPICGLRATPSPEARVLQGVLVRYSPVVEAGSDMVFRWTINDKQSLTFQNV
gi|4505833|   VVVENSASRANLSLRVTAEEPICGLRATPSPEARVLQGVLVRYSPVVEAGSDMVFRWTINDKQSLTFQNV
gi|1586345|   VVVENSASRANLSLRVTAEEPICGLRATPSPEARVLQGVLVRYSPVVEAGSDMVFRWTINDKQSLTFQNV
gi|903758|    VVVENSASRANLSLRVTAEEPICGLRATPSPEARVLQGVLVRYSPVVEAGSDMVFRWTINDKQSLTFQNV
gi|1730587|   VVVENSASRANLSLRVTAEEPICGLRATPSPEARVLQGVLVRYSPVVEAGSDMVFRWTINDKQSLTFQNV
gi|11320978|  IVAGNGASCANLSLRVTAEEPICGLRAVPSPEARVLQGELVTYSPMVEAGSDVAERWTIDDKQSLTFHNT 990      1000      1010      1020      1030      1040      1050
              ....|....|....|....|....|....|....|....|....|....|....|....|....|
NOV28         VFNVIYQSAAVFKLSLTASNHVSNVTVNYNVTVERMNRMQGLQVSTVPAVLSPNATLALTAGVLVDSAVE
gi|4505833|   VFNVIYQSAAVFKLSLTASNHVSNVTVNYNVTVERMNRMQGLQVSTVPAVLSPNATLALTAGVLVDSAVE
gi|1586345|   VFNVIYQSAAVFKLSLTASNHVSNVTVNYNVTVERMNRMQGLQVSTVPAVLSPNATLVLTGGVLVDSAVE
gi|903758|    VFNVIYQSAAVFKLSLTASNHVSNVTVNYNVTVERMNRMQGLQVSTVPAVLSPNATLALTAGVLVDSAVE
gi|1730587|   VFNVIYQSAAVFKLSLTASNHVSNVTVNYNVTVERMNRMQGLQVSTVPAVLSPNATLALTAGVLVDSAVE
gi|11320978|  VFNVIYQAAAVFKLSLTASNHVSNITVNYNVTVERMNKMHGLWVSAVPAVLPPNATLALTGGVLVDSAVE 1060      1070      1080      1090      1100      1110      1120
              ....|....|....|....|....|....|....|....|....|....|....|....|....|
NOV28         VAFLWNFGDGEQALHQFQPPYNESFPVPDPSVAQVLVEHNVMHTYAAPGEYLLTVLASNAFENLTQQVPV
gi|4505833|   VAFLWNFGDGEQALHQFQPPYNESFPVPDPSVAQVLVEHNVMHTYAAPGEYLLTVLASNAFENLTQQVPV
gi|1586345|   VAFLWNFGDGEQALHQFQPPYNESFPVPDPSVAQVLVEHNVMHTYAAPGEYLLTVLASNAFENLTQQVPV
gi|903758|    VAFLWNFGDGEQALHQFQPPYNESFPVPDPSVAQVLVEHNVMHTYAAPGEYLLTVLASNAFENLTQQVPV
gi|1730587|   VAFLWTFGDGEQALHQFQPPYNESFPVPDPSVAQVLVEHNVTHTYAAPGEYLLTVLASNAFENLTQQVPV
gi|11320978|  VAFLWNFGDGEQVLRQFKPPYEESFQVPDPRVAQVLVEHNTTHIYNTPGEYNLTVTVSNTYENLTQQVPV 1130      1140      1150      1160      1170      1180      1190
              ....|....|....|....|....|....|....|....|....|....|....|....|....|
NOV28         SVRASLPSVAVGVSDGVLVAGRPVTFYPHPLPSPGGVLYTWDFGDGSPVLTQSQPAANHTYASRGTYHVR
gi|4505833|   SVRASLPSVAVGVSDGVLVAGRPVTFYPHPLPSPGGVLYTWDFGDGSPVLTQSQPAANHTYASRGTYHVR
gi|1586345|   SVRASLPSVAVGVSDGVLVAGRPVTFYPHPLPSPGGVLYTWDFGDGSPVLTQSQPAANHTYASRGTYHVR
gi|903758|    SVRASLPSVAVGVSDGVLVAGRPVTFYPHPLPSPGGVLYTWDFGDGSPVLTQSQPAANHTYASRGTYHVR
gi|1730587|   SVRASLPSVAVGVSDGVLVAGRPVTFYPHPLPSPGGVLYTWDFGDGSPVLTQSQPAANHTYASRGTYHVR
gi|11320978|  SVRTVLPNVTIGMSSNVLEAGQPEIFFEXPLPSADGVLYTWDFGDGSPVLIQSQPVLNHTYSMTGTYRIS 1200      1210      1220      1230      1240      1250      1260
              ....|....|....|....|....|....|....|....|....|....|....|....|....|
NOV28         LEVNNTVSGAAAQADVRVFEELRGLSVDMSLAVEQGAPVVVSAAVQTGDNITWTFDMGDGTVLSGPEATV
gi|4505833|   LEVNNTVSGAAAQADVRVFEELRGLSVDMSLAVEQGAPVVVSAAVQTGDNITWTFDMGDGTVLSGPEATV
gi|1586345|   LEVNNTVSGAAAQADVRVFEELRGLSVDMSLAVEQGAPVVVSAAVQTGDNITWTFDMGDGTVLSGPEATV
gi|903758|    LEVNNTVSGAAAQADVRVFEELRGLSVDMSLAVEQGAPVVVSAAVQTGDNITWTFDMGDGTVLSGPEATV
gi|1730587|   LEVNNTVSGAAAQADVRVFEELRGLSVDMSLAVEQGAPVVVSAAVQTGDNITWTFDMGDGTVLSGPEATV
gi|11320978|  LEVNNTVSSVAAHVDICVFQELHGLTVYLNQSVEQGABMVVNASVSSGDNITWTFDMGDGTVFTGPEATV 1270      1280      1290      1300      1310      1320      1330
              ....|....|....|....|....|....|....|....|....|....|....|....|....|
NOV28         EHVYLRAQNCTVTVGAASPAGHLARSLHVLVFVLEVLRVEPAACIPTQPDARLTAYVTGNPAHYLFDWTP
gi|4505833|   EHVYLRAQNCTVTVGAASPAGHLARSLHVLVFVLEVLRVEPAACIPTQPDARLTAYVTGNPAHYLFDWTP
gi|1586345|   EHVYLRAQNCTVTVGAASPAGHLARSLHVLVFVLEVLRVEPAACIPTQPDARLTAYVTGNPAHYLFDWTP
gi|903758|    EHVYLRAQNCTVTVGASPAGHLARSLHVLVFVLEVLRVEPAACIPTQPDARLTAYVTGNPAHYLFDWTP
gi|1730587|   EHVYLRAQNCTVTVGAASPAGHLARSLHVLVFVLEVLRVEPAACIPTQPDARLTAYVTGNPAHYLFDWTP
gi|11320978|  EHVYLRAQNFTVTVGATSPAGHLSGSLHVQVFVLEVLRIEPSTCIPTQPSAQIMAHVTGDPAHYLFDWTP 1340      1350      1360      1370      1380      1390      1400
              ....|....|....|....|....|....|....|....|....|....|....|....|....|
NOV28         CDGSSNTTVRGCPTVTHNFTRSGTFPLALVLSSRVNRAHYFTSICVEPEVGNVTLQPERQFVQLGDEAWL
gi|4505833|   CDGSSNTTVRGCPTVTHNFTRSGTFPLALVLSSRVNRAHYFTSICVEPEVGNVTLQPERQFVQLGDEAWL
gi|1586345|   CDGSSNTTVRGCPTVTHNFTRSGTFPLALVLSSRVNRAHYFTSICVEPEVGNVTLQPERQFVQLGDEAWL
gi|903758|    CDGSSNTTVRGCPTVTHNFTRSGTFPLALVLSSRVNRAHYFTSICVEPEVGNVTLQPERQFVQLGDEAWL
gi|1730587|   CDGSSNTTVRGCPTVTHNFTRSGTFPLALVLSSRVNRAHYFTSICVEPEVGNVTLQPERQFVQLGDEAWL
gi|11320978|  GDGSSNVTVHGHPSVTHNFTRSGIFPLALVLSSHVNKAHYFTSICVEPEKCNVTLQPERQVVRLGDEAWL 1410      1420      1430      1440      1450      1460      1470
              ....|....|....|....|....|....|....|....|....|....|....|....|....|
NOV28         VACAWPPFPYRYTWDFGTEEAAPTRARGPEVTFIYRDPGSYLVIVTASNNISAANDSALVEVQEPVLVTS
gi|4505833|   VACAWPPFPYRYTWDFGTEEAAPTRARGPEVTFIYRDPGSYLVIVTASNNISAANDSALVEVQEPVLVTS
gi|1586345|   VACAWPPFPYRYTWDFGTEEAAPTRARGPEVTFIYRDPGSYLVIVTASNNISAANDSALVEVQEPVLVTS
gi|903758|    VACAWPPFPYRYTWDFGTEEAAPTRARGPEVTFIYRDPGSYLVIVTASNNISAANDSALVEVQEPVLVTS
gi|1730587|   VACAWPPFPYRYTWDFGTEEAAPTRARGPEVTFIYRDPGSYLVIVTASNNISAANDSALVEVQEPVLVTS
gi|11320978|  VAYPWPPFPYRYTWDFGTEDEIHTGTGGSDVTFIYREPGSYLVIVTVSNNISSTNDSAFVQVQEPVSVTG
```

TABLE 28E-continued

Clustal W Sequence Alignment

```
                 1480      1490      1500      1510      1520      1530      1540
                 ....|....|....|....|....|....|....|....|....|....|....|....|....|....|
NOV28            IKVNGSLGLELQQPYLFSAVGRGRPASYLWDLGDGGWLEGPEVTHAYNSTGDFTVRVAGWNEVSRSEAWD
gi|4505833|      IKVNGSLGLELQQPYLFSAVGRGRPASYLWDLGDGGWLEGPEVTHAYNSTGDFTVRVAGWNEVSRSEAWD
gi|1586345|      IKVNGSLGLELQQPYLFSAVGRGRPASYLWDLGDGGWLEGPEVTHAYNSTGDFTVRVAGWNEVSRSEAWD
gi|903758|       IKVNGSLGLELQQPYLFSAVGRGRPASYLWDLGDGGWLEGPEVTHAYNSTGDFTVRVAGWNEVSRSEAWD
gi|1730587|      IKVNGSLGLELQQPYLFSAVGRGRPASYLWDLGDGGWLEGPEVTHAYNSTGDFTVRVAGWNEVSRSEAWD
gi|11320978|     IRINGSHVLELQQPYLFSAMGNGSPAAYLWKLGDGSQHEGPEVTHIYSSTGDFTVRVSGWNEVSRSEAQL 1550      1560      1570      1580      1590      1600      1610
                 ....|....|....|....|....|....|....|....|....|....|....|....|....|....|
NOV28            NVTVKRRVRGLVVNASRTVVPLNGSVSFSTSLEAGSDVRYSWVLCDRCTPIPGGPTISYTFRSVGTFNII
gi|4505833|      NVTVKRRVRGLVVNASRTVVPLNGSVSFSTSLEAGSDVRYSWVLCDRCTPIPGGPTISYTFRSVGTFNII
gi|1586345|      NVTVKRRVRGLVVNASRTVVPLNGSVSFSTSLEAGSDVRYSWVLCDRCTPIPGGPTISYTFRSVGTFNII
gi|903758|       NVTVKRRVRGLVVNASRTVVPLNGSVSFSTSLEAGSDVRYSWVLCDRCTPIPGGPTISYTFRSVGTFNII
gi|1730587|      NVTVKRRVRGLVVNASRTVVPLNGSVSFSTSLEAGSDVRYSWVLCDRCTPIPGGPTISYTFRSVGTFNII
gi|11320978|     NITVKQRVRGLTENASPTVVPLNGSVSFSTLLEVGSDVHYSWVLCDRCTPIPGGPTISYTFRSVGTFNII 1620      1630      1640      1650      1660      1670      1680
                 ....|....|....|....|....|....|....|....|....|....|....|....|....|....|
NOV28            VTAENEVGSAQDSIFVYVLQLIEGLQVVGG--GRYFPTNHTVQLQAVVRDGTNVSYSWTAWRDRGPALAG
gi|4505833|      VTAENEVGSAQDSIFVYVLQLIEGLQVVGG--GRYFPTNHTVQLQAVVRDGTNVSYSWTAWRDRGPALAG
gi|1586345|      VTAENEVGSAQDSIFVYVLQLIEGLQVVGG--GRYFPTNHTVQLQAVVRDGTNVSYSWTAWRDRGPALAG
gi|903758|       VTAENEVGSAQDSIFVYVLQLIEGLQVVGG--GRYFPTNHTVQLQAVVRDGTNVSYSWTAWRDRGPALAG
gi|1730587|      VTAENEVGSAQDSIFVYVLQLIEGLQVVGG--GRYFPTNHTVQLQAVVRDGTNVSYSWTAWRDRGPALAG
gi|11320978|     VTAENEVGSAQDSIFIYVLQLIEGLQVVGGDGGCCFPTNMTEQLQAAVRDGTNISYSWTAQQDGGPTLIS 1690      1700      1710      1720      1730      1740      1750
                 ....|....|....|....|....|....|....|....|....|....|....|....|....|....|
NOV28            SGKGFSLTVLEAGTYHVQLRATNMLGSQEQDCTMDFVEPVGWLMVTASPNPAAVNTSVTLSAELAGGSGV
gi|4505833|      SGKGFSLTVLEAGTYHVQLRATNMLGSQEQDCTMDFVEPVGWLMVTASPNPAAVNTSVTLSAELAGGSGV
gi|1586345|      SGKGFSLTVLEAGTYHVQLRATNMLGSQEQDCTMDFVEPVGWLMVTASPNPAAVNTSVTLSAELAGGSGV
gi|903758|       SGKGFSLTVLEAGTYHVQLRATNMLGSQEQDCTMDFVEPVGWLMVTASPNPAAVNTSVTLSAELAGGSGV
gi|1730587|      SGKGFSLTVLEAGTYHVQLRATNMLGSQEQDCTMDFVEPVGWLMVAASPNPAAVNTSVTLSAELAGGSGV
gi|11320978|     SGKSFSLTALKASTYYVHLRATNMLGSASANRTEDFVEPVESLKKSASPNPAAVNTSETLGAELAGGSGV 1760      1770      1780      1790      1800      1810      1820
                 ....|....|....|....|....|....|....|....|....|....|....|....|....|....|
NOV28            VYTWSLEEGLSWETSEPFTTHSFPTPGLHLVTMTAGNPLGSANATVEVDVQVPVSGLSIRASEPGGSFVA
gi|4505833|      VYTWSLEEGLSWETSEPFTTHSFPTPGLHLVTMTAGNPLGSANATVEVDVQVPVSGLSIRASEPGGSFVA
gi|1586345|      VYTWSLEEGLSWETSEPFTTHSFPTPGLHLVTMTAGNPLGSANATVEVDVQVPVSGLSIRASEPGGSFVA
gi|903758|       VYTWSLEEGLSWETSEPFTTHSFPTPGLHLVTMTAGNPLGSANATVEVDVQVPVSGLSIRASEPGGSFVA
gi|1730587|      VYTWSLEEGLSWETSEPFTTHSFPTPGLHLVTMTAGNPLGSANATVEVDVQVPVSGLSIRASEPGGSFVA
gi|11320978|     VYTWYLEEGLSRETSMPSTTHTFAAPGLHLVRVTAENQLGSVNATTEVAVHGPVGGLSIRTSEPDSIFVA 1830      1840      1850      1860      1870      1880      1890
                 ....|....|....|....|....|....|....|....|....|....|....|....|....|....|
NOV28            AGSSVPFWGQLATGINVSWCWAVPGGSSKRGPHVTMVFPDAGTFSIRLNASNAVSWVSATYNLTAEEPIV
gi|4505833|      AGSSVPFWGQLATGINVSWCWAVPGGSSKRGPHVTMVFPDAGTFSIRLNASNAVSWVSATYNLTAEEPIV
gi|1586345|      AGSSVPFWGQLATGINVSWCWAVPGGSSKRGPHVTMVFPDAGTFSIRLNASNAVSWVSATYNLTAEEPIV
gi|903758|       AGSSVPFWGQLATGINVSWCWAVPGGSSKRGPHVTMVFPDAGTFSIRLNASNAVSWVSATYNLTAEEPIV
gi|1730587|      AGSSVPFWGQLATGINVSWCWAVPGGSSKRGPHVTMVFPDAGTFSIRLNASNAVSWVSATYNLTAEEPIV
gi|11320978|     AGSTVPFWGQLAEGTNVIWCWTEPGGS-KYSQYIDVRFPAAGHFSLWLNASNAVSWVSAVYNLTVEEPIN 1900      1910      1920      1930      1940      1950      1960
                 ....|....|....|....|....|....|....|....|....|....|....|....|....|....|
NOV28            GLVLWASSKVVAPGQLVHFQILLAAGSAVTFRLQVGGANPEVLPGPRFSHSFPRVGDHVVSVRGKNHVSW
gi|4505833|      GLVLWASSKVVAPGQLVHFQILLAAGSAVTFRLQVGGANPEVLPGPRFSHSFPRVGDHVVSVRGKNHVSW
gi|1586345|      GLVLWASSKVVAPGQLVHFQILLAAGSAVTFRLQVGGANPEVLPGPRFSHSFPRVGDHVVSVRGKNHVSW
gi|903758|       GLVLWASSKVVAPGQLVHFQILLAAGSAVTFRLQVGGANPEVLPGPRFSHSFPRVGDHVVSVRGKNHVSW
gi|1730587|      GLVLWASSKVVAPGQLVHFQILLAAGSAVTFRLQVGGANPEVLPGPRFSHSFPRVGDHVVSVRGKNHVSW
gi|11320978|     NLVLWASSKVVAPGQPVHFQILLAAGSAVTFRLQVGGSIPEVLPSLHFSHSFFRVGDHMVSVQAENHVSR 1970      1980      1990      2000      2010      2020      2030
                 ....|....|....|....|....|....|....|....|....|....|....|....|....|....|
NOV28            AQAQVRIVVLEAVSGLQMPNCCEPGIATGTERNFTARVQRGSRVAYAWYFSLQKVQGDSLVILSCRDVTY
gi|4505833|      AQAQVRIVVLEAVSGLQMPNCCEPGIATGTERNFTARVQRGSRVAYAWYFSLQKVQGDSLVILSCRDVTY
gi|1586345|      AQAQVRIVVLEAVSGLQMPNCCEPGIATGTERNFTARVQRGSRVAYAWYFSLQKVQGDSLVILSCRDVTY
gi|903758|       AQAQVRIVVLEAVSGLQMPNCCEPGIATGTERNFTARVQRGSRVAYAWYFSLQKVQGDSLVILSCRDVTY
gi|1730587|      AQAQVRIVVLEAVSGLQVPNCCEPGIATGTERNFTARVQRGSRVAYAWYFSLQKVQGDSLVILSCRDVTY
gi|11320978|     AQAQVRIEVLEAEVGLQVPNCCEPGMATGTEKNFTARVQRGSRVAYAWYFSLQKVQGDSLVILSGRDVTY 2040      2050      2060      2070      2080      2090      2100
                 ....|....|....|....|....|....|....|....|....|....|....|....|....|....|
NOV28            TPVAAGLLEIQVRAFNALGSENRTLVLEVQDAVQYVALQSGPCFTNRSAQFEAATSPSPRRVAYHWDFGD
gi|4505833|      TPVAAGLLEIQVRAFNALGSENRTLVLEVQDAVQYVALQSGPCFTNRSAQFEAATSPSPRRVAYHWDFGD
gi|1586345|      TPVAAGLLEIQVRAFNALGSENRTLVLEVQDAVQYVALQSGPCFTNRSAQFEAATSPSPRRVAYHWDFGD
gi|903758|       TPVAAGLLEIQVRAFNALGSENRTLVLEVQDAVQYVALQSGPCFTNRSAQFEAATSPSPRRVAYHWDFGD
gi|1730587|      TPVAAGLLEIQVRAFNALGSENRTLVLEVQDAVQYVALQSGPCFTNRSAQFEAATSPSPRRVAYHWDFGD
gi|11320978|     TPVAAGILEIHVRAFNELGGVNLTLVVEVQDIEQYVTLQSGRCFTNRSAMFEAATSPSPRRVTYHWDFGD
```

TABLE 28E-continued

Clustal W Sequence Alignment

```
                  2110       2120       2130       2140       2150       2160       2170
                  ....|....|....|....|....|....|....|....|....|....|....|....|....|....|
NOV28             GSPGQDTDEPRAEHSYLRPGDYRVQVNASNLVSFFVAQATVTVQVLACREPEVDVVLPLQVLMRRSQRNY
gi|4505833|       GSPGQDTDEPRAEHSYLRPGDYRVQVNASNLVSFFVAQATVTVQVLACREPEVDVVLPLQVLMRRSQRNY
gi|1586345|       GSPGQDTDEPRAEHSYLRPGDYRVQVNASNLVSFFVAQATVTVQVLACREPEVDVVLPLQVLMRRSQRNY
gi|903758|        GSPGQDTDEPRAEHSYLRPGDYRVQVNASNLVSFFVAQATVTVQVLACREPEVDVVLPLQVLMRRSQRNY
gi|1730587|       GSPGQDTDEPRAEHSYLRPGDYRVQVNASNLVSFFVAQATVTVQVLACREPEVDVVLPLQVLMRRSQRNY
gi|11320978|      GSPVQETEFSWTDHYYLHPGDYRVEVNAINLVSFFVAQAQVTVQVLACREPEVRVALPLQVLMRRSQRNY 2180       2190       2200       2210       2220       2230       2240
                  ....|....|....|....|....|....|....|....|....|....|....|....|....|....|
NOV28             LEAHVDLRDCVTYQTEYRWEVYRTASCQRPGRPARVALPGVDVSRPRLVLPRLALPVGHYCFVFVVSFGD
gi|4505833|       LEAHVDLRDCVTYQTEYRWEVYRTASCQRPGRPARVALPGVDVSRPRLVLPRLALPVGHYCFVFVVSFGD
gi|1586345|       LEAHVDLRDCVTYQTEYRWEVYRTASCQRPGRPARVALPGVDVSRPRLVLPRLALPVGHYCFVFVVSFGD
gi|903758|        LEAHVDLRDCVTYQTEYRWEVYRTASCQRPGRPARVALPGVDVSRPRLVLPRLALPVGHYCFVFVVSFGD
gi|1730587|       LEAHVDLRDCVTYQTEYRWEVYRTASCQRPGRPARVALPGVDVSRPRLVLPRLALPVGHYCFVFVVSFGD
gi|11320978|      LEAHVDLRNCVSYQTEYRWEVYRTTSCQRAGRMTQMVLPGVDVSRPQLVVPRLALPVGHYCFVFVVSFGD 2250       2260       2270       2280       2290       2300       2310
                  ....|....|....|....|....|....|....|....|....|....|....|....|....|....|
NOV28             TPLTQSIQANVTVAPERLVPIIEGGSYRVWSDTRDLVLDGSESYDPNLEDGDQTPLSFHWACVASTQREA
gi|4505833|       TPLTQSIQANVTVAPERLVPIIEGGSYRVWSDTRDLVLDGSESYDPNLEDGDQTPLSFHWACVASTQREA
gi|1586345|       TPLTQSIQANVTVAPERLVPIIEGGSYRVWSDTRDLVLDGSESYDPNLEDGDQTPLSFHWACVASTQREA
gi|903758|        TPLTQSIQANVTVAPERLVPIIEGGSYRVWSDTRDLVLDGSESYDPNLEDGDQTPLSFHWACVASTQREA
gi|1730587|       TPLTQSIQANVTVAPERLVPIIEGGSYRVWSDTRDLVLDGSESYDPNLEDGDQTPLSFHWACVASTQREA
gi|11320978|      TPLARSIQANVTVAAERLVPIIEGGSYRVWSDTQDLVLDGSKSYDPNLEDGDQTPLNFHWACVASTQSET 2320       2330       2340       2350       2360       2370       2380
                  ....|....|....|....|....|....|....|....|....|....|....|....|....|....|
NOV28             GGCALNFGPRGSSTVTIPRERLAAGVEYTPSLTVWKAGRKEEATNQTVLIRSGRVPIVSLECVSCKAQAV
gi|4505833|       GGCALNFGPRGSSTVTIPRERLAAGVEYTPSLTVWKAGRKEEATNQTVLIRSGRVPIVSLECVSCKAQAV
gi|1586345|       GGCALNFGPRGSSTVTIPRERLAAGVEYTPSLTVWKAGRKEEATNQTVLIRSGRVPIVSLECVSCKAQAV
gi|903758|        GGCALNFGPRGSSTVTIPRERLAAGVEYTPSLTVWKAGRKEEATNQTVLIRSGRVPIVSLECVSCKAQAV
gi|1730587|       GGCALNFGPRGSSTVTIPRERLAAGVEYTPSLTVWKAGRKEEATNQTVLIRSGRVPIVSLECVSCKAQAV
gi|11320978|      GGCVLKLWARGSSVVTIPLERLEAGVEYTPMLIVWKAGRKEEATNQTVLIRSGRVPIVSLECVSCKAQAV 2390       2400       2410       2420       2430       2440       2450
                  ....|....|....|....|....|....|....|....|....|....|....|....|....|....|
NOV28             YEVSRSSYVYLEGRCLNCSSGSKRGRWAARTFSNKTLVLDETTTSTGSAGMRLVLRRGVLRDGEGYTFTL
gi|4505833|       YEVSRSSYVYLEGRCLNCSSGSKRGRWAARTFSNKTLVLDETTTSTGSAGMRLVLRRGVLRDGEGYTFTL
gi|1586345|       YEVSRSSYVYLEGRCLNCSSGSKRGRWAARTFSNKTLVLDETTTSTGSAGMRLVLRRGVLRDGEGYTFTL
gi|903758|        YEVSRSSYVYLEGRCLNCSSGSKRGRWAARTFSNKTLVLDETTTSTGSAGMRLVLRRGVLRDGEGYTFTL
gi|1730587|       YEVSRSSYVYLEGRCLNCSSGSKRGRWAARTFSNKTLVLDETTTSTGSAGMRLVLRRGVLRDGEGYTFTL
gi|11320978|      YEVSRSSYVYLEGHCHNCSSGSKQGRWAARTFSNKTLMLNENTTSTGSTGMHLVVRPGALHDGEGYIFTL 2460       2470       2480       2490       2500       2510       2520
                  ....|....|....|....|....|....|....|....|....|....|....|....|....|....|
NOV28             TVLGRSGEEEGCASIRLSPNRPPLGGSCRLFPLGAVHALTTKVHFECTGWHDAEDAGAPLVYALLLRRCH
gi|4505833|       TVLGRSGEEEGCASIRLSPNRPPLGGSCRLFPLGAVHALTTKVHFECTGWHDAEDAGAPLVYALLLRRCH
gi|1586345|       TVLGRSGEEEGCASIRLSPNRPPLGGSCRLFPLGAVHALTTKVHFECTGWHDAEDAGAPLVYALLLRRCH
gi|903758|        TVLGRSGEEEGCASIRLSPNRPPLGGSCRLFPLGAVHALTTKVHFECT-------A---LVYALLLRRCH
gi|1730587|       TVLGRSGEEEGCASIRLSPNRPPLGGSCRLFPLGAVHALTTKVHFECTGWHDAEDAGAPLVYALLLRRCH
gi|11320978|      TVLCHSGEEEGCRSIRLLPNRPPLGGSCRLFPLESVRGLTTKVHFECTGWRDAEDGGAPLVYALRLKRCH 2530       2540       2550       2560       2570       2580       2590
                  ....|....|....|....|....|....|....|....|....|....|....|....|....|....|
NOV28             QGHCEEFCVYKGSLSSYGAVLPPGFRPHFEVGLAVVVQDQLGAAVVALNRSLAITLPEPNGSATGLTVWL
gi|4505833|       QGHCEEFCVYKGSLSSYGAVLPPGFRPHFEVGLAVVVQDQLGAAVVALNRSLAITLPEPNGSATGLTVWL
gi|1586345|       QGHCEEFCVYKGSLSSYGAVLPPGFRPHFEVGLAVVVQDQLGAAVVALNRSLAITLPEPNGSATGLTVWL
gi|903758|        QGHCEEFCVYKGSLSSYGAVLPPGFRPHFEVGLAVVVQDQLGAAVVALNRSLAITLPEPNGSATGLTVWL
gi|1730587|       QGHCEEFCVYKGSLSSYGAVLPPGFRPHFEVGLAVVVQDQLGAAVVALNRSLAITLPEPNGSATGLTVWL
gi|11320978|      QNYCEDFCIYKGSLSTYGAVLPPGFQPLFVVSLTVVVEDQLGASVVALNRSLTIVLPEPSGNPADLIPWL 2600       2610       2620       2630       2640       2650       2660
                  ....|....|....|....|....|....|....|....|....|....|....|....|....|....|
NOV28             HGLTASVLPGLLRQADPQHVIEYSLALVTVLNEYERALDVAAEPKHERQHRAQIRKNITETLVSLRVHTV
gi|4505833|       HGLTASVLPGLLRQADPQHVIEYSLALVTVLNEYERALDVAAEPKHERQHRAQIRKNITETLVSLRVHTV
gi|1586345|       HGLTASVLPGLLRQADPQHVIEYSLALVTVLNEYERALDVAAEPKHERQHRAQIRKNITETLVSLRVHTV
gi|903758|        HGLTASVLPGLLRQADPQHVIEYSLALVTVLNEYERALDVAAEPKHERQHRAQIRKNITETLVSLRVHTV
gi|1730587|       HGLTASVLPGLLRQADPQHVIEYSLALVTVLNEYERALDVAAEPKHERQHRAQIRKNITETLVSLRVHTV
gi|11320978|      HSLTASVLPGLLRQADPQHVIEYSLALFTVLNEYECAEDMVSEPNLEQQLRAQMRKNITETLISLRVMTV
```

TABLE 28E-continued

Clustal W Sequence Alignment

```
                      2670       2680       2690       2700       2710       2720       2730
                 ....|....|....|....|....|....|....|....|....|....|....|....|....|....|
NOV28            DDIQQIAAALAQCMGPSRELVCRSCLKQTLHKLEAMMLILQAETTAGTVTPTAIGDSILNITGDLIHLAS
gi|4505833|      DDIQQIAAALAQCMGPSRELVCRSCLKQTLHKLEAMMLILQAETTAGTVTPTAIGDSILNITGDLIHLAS
gi|1586345|      DDIQQIAAALAQCMGPSRELVCRSCLKQTLHKLEAMMLILQAETTAGTVTPTAIGDSILNITGDLIHLAS
gi|903758|       DDIQQIAAALAQCMGPSRELVCRSCLKQTLHKLEAMMLILQAETTAGTVTPTAIGDSILNITGDLIHLAS
gi|1730587|      DDIQQIAAALAQCMGPSRELVCRSCLKQTLHKLEAMMLILQAETTAGTVTPTAIGDSILNITGDLIHLAS
gi|11320978|     DDIQQITAALAQCMVSSRELMCRSCLKKMLQKLEGMMRILQAETTEGTETPTTIADSILNITGDLIHLAS 2740       2750       2760       2770       2780       2790       2800
                 ....|....|....|....|....|....|....|....|....|....|....|....|....|....|
NOV28            SDVRAPQPSELGAESPSRMVASQAYNLTSALMRILMRSRVLNEEPLTLAGEEIVAQGKRSDPRGLLCYGC
gi|4505833|      SDVRAPQPSELGAESPSRMVASQAYNLTSALMRILMRSRVLNEEPLTLAGEEIVAQGKRSDPRGLLCYGC
gi|1586345|      SDVRAPQPSELGAESPSRMVASQAYNLTSALMRILMRSRVLNEEPLTLAGEEIVAQGKRSDPRGLLCYGC
gi|903758|       SDVRAPQPSELGAESPSRMVASQAYNLTSALMRILMRSRVLNEEPLTLAGEEIVAQGKRSDPRGLLCYGC
gi|1730587|      SDVRAPQPSELGAESPSRMVASQAYNLTSALMRILMRSRVLNEEPLTLAGEEIVAQGKRSDPRGLLCYGC
gi|11320978|     LDMQGPQPLELGAEPPSLMVASKAYNLSSALMCTLMRSRVLNEEPLTLAGEEIVALGKRADPLSLLCYGK 2810       2820       2830       2840       2850       2860       2870
                 ....|....|....|....|....|....|....|....|....|....|....|....|....|....|
NOV28            APGPGCHFSIPEAFSGALANLSDVVQLIFLVDSNPFPFGYISNYTVSTKVASMAFQTQAGAQIPIERLAS
gi|4505833|      APGPGCHFSIPEAFSGALANLSDVVQLIFLVDSNPFPFGYISNYTVSTKVASMAFQTQAGAQIPIERLAS
gi|1586345|      APGPGCHFSIPEAFSGALANLSDVVQLIFLVDSNPFPFGYISNYTVSTKVASMAFQTQAGAQIPIERLAS
gi|903758|       APGPGCHFSIPEAFSGALANLSDVVQLIFLVDSNPFPFGYISNYTVSTKVASMAFQTQAGAQIPIERLAS
gi|1730587|      APGPGCHFSIPEAFSGALANLSDVVQLIFLVDSNPFPFGYISNYTVSTKVASMAFQTQAGAQIPIERLAS
gi|11320978|     AWGPSCHFSIPEAFSGALSDLSDVVQLILLVDSNPFPFGYISNYTVSTKVASMAFQTQTGTQIPIEQLAA 2880       2890       2900       2910       2920       2930       2940
                 ....|....|....|....|....|....|....|....|....|....|....|....|....|....|
NOV28            BRAITVKVPNNSDWAARGHRSSAN---SVVVQPQASVGAVVTLDSSNPAAVLHLQLNYTLLDGHYLSEEP
gi|4505833|      BRAITVKVPNNSDWAARGHRSSANSANSVVVQPQASVGAVVTLDSSNPAAGLHLQLNYTLLDGHYLSEEP
gi|1586345|      BRAITVKVPNNSDWAARGHRSSANSANSVVVQPQASVGAVVTLDSSNPAAGLHLQLNYTLLDGHYLSEEP
gi|903758|       BRAITVKVPNNSDWAARGHRSSANSANSVVVQPQASVGAVVTLDSSNPAAGLHLQLNYTLLDGHYLSEEP
gi|1730587|      BRAITVKVPNNSDWAARGHRSSANSANSVVVQPQASVGAVVTLDSSNPAAGLHLQLNYTLLDGHYLSEEP
gi|11320978|     DGSITVKVPNNSDQAAGSSHSPVG---STIVQPRASVSAVVTADNSNPQAGLHLRITYTVLNARYLSEER 2950       2960       2970       2980       2990       3000       3010
                 ....|....|....|....|....|....|....|....|....|....|....|....|....|....|
NOV28            EPYLAVYLHSEPRPNEHNCSASRRIRPESLQGADHRPYTFFISPGSRDPAGSYHLNLSSHFRWSALQVSV
gi|4505833|      EPYLAVYLHSEPRPNEHNCSASRRIRPESLQGADHRPYTFFISPGSRDPAGSYHLNLSSHFRWSALQVSV
gi|1586345|      EPYLAVYLHSEPRPNEHNCSASRRIRPESLQGADHRPYTFFISPGSRDPAGSYHLNLSSHFRWSALQVSV
gi|903758|       EPYLAVYLHSEPRPNEHNCSASRRIRPESLQGADHRPYTFFISPGSRDPAGSYHLNLSSHFRWSALQVSV
gi|1730587|      EPYLAVYLHSEPRPNEHNCSASRRIRPESLQGADHRPYTFFISPGSRDPAGSYHLNLSSHFRWSALQVSV
gi|11320978|     EPYLAVYLHSVSQPNEYNCSASRRISLEVLEGADHRPYTFFIAPGTGTLGRSYELNLRSHFHWSALEVSV 3020       3030       3040       3050       3060       3070       3080
                 ....|....|....|....|....|....|....|....|....|....|....|....|....|....|
NOV28            GLYTSLCQYFSEEDMVWRTEGLLPLEETSPRQAVCLTRHLTAFGASLFVPPSHVRFVFPEPTADVNYIVM
gi|4505833|      GLYTSLCQYFSEEDMVWRTEGLLPLEETSPRQAVCLTRHLTAFGASLFVPPSHVRFVFPEPTADVNYIVM
gi|1586345|      GLYTSLCQYFSEEDMVWRTEGLLPLEETSPRQAVCLTRHLTAFGASLFVPPSHVRFVFPEPTADVNYIVM
gi|903758|       GLYTSLCQYFSEEDMVWRTEGLLPLEETSPRQAVCLTRHLTAFGASLFVPPSHVRFVFPEPTADVNYIVM
gi|1730587|      GLYTSLCQYFSEEDMVWRTEGLLPLEETSPRQAVCLTRHLTAFGASLFVPPSHVRFVFPEPTADVNYIVM
gi|11320978|     GLYTSLCQYFSEEAMMWRTEGIVPLEETSPSQAVCLTRHLTAFGASLFVPPSHVQFTFPEPSVSINYIVE 3090       3100       3110       3120       3130       3140       3150
                 ....|....|....|....|....|....|....|....|....|....|....|....|....|....|
NOV28            LTCAVCLVTYMVMAAILHKLDQLDASRGRAIPFCGQRGRFKYEILVKTGWGRGSGTTAHVGIMLYGVDSR
gi|4505833|      LTCAVCLVTYMVMAAILHKLDQLDASRGRAIPFCGQRGRFKYEILVKTGWGRGSGTTAHVGIMLYGVDSR
gi|1586345|      LTCAVCLVTYMVMAAILHKLDQLDASRGRAIPFCGQRGRFKYEILVKTGWGRGSGTTAHVGIMLYGVDSR
gi|903758|       LTCAVCLVTYMVMAAILHKLDQLDASRGRAIPFCGQRGRFKYEILVKTGWGRGSGTTAHVGIMLYGVDSR
gi|1730587|      LTCAVCLVTYMVMAAILHKLDQLDASRGRAIPFCGQRGRFKYEILVKTGWGRGSGTTAHVGIMLYGVDSR
gi|11320978|     LTCVICLVTYVIMAMILRKLDQLDVSRVRVIPFCGKGGRFKYEILVKTGWSRGSGTTAHVGIMLYGEDNR 3160       3170       3180       3190       3200       3210       3220
                 ....|....|....|....|....|....|....|....|....|....|....|....|....|....|
NOV28            SGHRHLDGDRAFHRNSLDIFRIATPHSLGSVWKIRVWHDNKGLSPAWFLQHVIVRDLQTARSAFFLVNDW
gi|4505833|      SGHRHLDGDRAFHRNSLDIFRIATPHSLGSVWKIRVWHDNKGLSPAWFLQHVIVRDLQTARSAFFLVNDW
gi|1586345|      SGHRHLDGDRAFHRNSLDIFRIATPHSLGSVWKIRVWHDNKGLSPAWFLQHVIVRDLQTARSAFFLVNDW
gi|903758|       SGHRHLDGDRAFHRNSLDIFRIATPHSLGSVWKIRVWHDNKGLSPAWFLQHVIVRDLQTARSAFFLVNDW
gi|1730587|      SGHRHLDGDRAFHRNSLDIFRIATPHSLGSVWKIRVWHDNKGLSPAWFLQHVIVRDLQTARSAFFLVNDW
gi|11320978|     SGHRHLDGDRAFHRNSLDIFQIATPQSLGSVWKIRVWHDNKGLSPAWFLQHTIVRDLQSARSTFFLVNDW 3230       3240       3250       3260       3270       3280       3290
                 ....|....|....|....|....|....|....|....|....|....|....|....|....|....|
NOV28            LSVETEANGGLVEKEVLAASDAALLRFRRLLVAELQRGFFDKHIWLSIWDRPPRSRFTRIQRATCCVLLI
gi|4505833|      LSVETEANGGLVEKEVLAASDAALLRFRRLLVAELQRGFFDKHIWLSIWDRPPRSRFTRIQRATCCVLLI
gi|1586345|      LSVETEANGGLVEKEVLAASDAALLRFRRLLVAELQRGFFDKHIWLSIWDRPPRSRFTRIQRATCCVLLI
gi|903758|       LSVETEANGGLVEKEVLAASDAALLRFRRLLVAELQRGFFDKHIWLSIWDRPPRSRFTRIQRATCCVLLI
gi|1730587|      LSVETEANGGLVEKEVLAASDAALLRFRRLLVAELQRGFFDKHIWLSIWDRPPRSRFTRIQRATCCVLLI
gi|11320978|     LSVETEANGGLVEKEVLAANEAAILWQFQRLLVAELQRGFFDKHIWLSIWDRPPRSRFTRVQRVTCCVLLE
```

TABLE 28E-continued

Clustal W Sequence Alignment

```
              3300      3310      3320      3330      3340      3350      3360
              ....|....|....|....|....|....|....|....|....|....|....|....|....|
NOV28         CLFLCANAVWYGAVGDSAYSTGHVSRLSPLSVDTVAVGLVSSVVVYPVYLAILFLFRMSRSKVACSPSPT
gi|4505833|   CLFLCANAVWYGAVGDSAYSTGHVSRLSPLSVDTVAVGLVSSVVVYPVYLAILFLFRMSRSKVACSPSPT
gi|1586345|   CLFLCANAVWYGAVGDSAYSTGHVSRLSPLSVDTVAVGLVSSVVVYPVYLAILFLFRMSRSKVACSPSPT
gi|903758|    CLFLCANAVWYGAVGDSAYSTGHVSRLSPLSVDTVAVGLVSSVVVYPVYLAILFLFRMSRSKVACSPSPT
gi|1730587|   CLFLCANAVWYGAVGDSAYSTGHVSRLSPLSVDTVAVGLVSSVVVYPVYLAILFLFRMSRSKVACSPSPT
gi|11320978|  CLFLAANAVWYGVVGDTTYSMGPVSSLMSPSVDTVARGLVSSVVVYPVYLAVLFLFRMSRSKVSGDQNPT 3370      3380      3390      3400      3410      3420      3430
              ....|....|....|....|....|....|....|....|....|....|....|....|....|
NOV28         PAGQQVLDIDSCLDSSVLDSSFLTFSGLHAE-AFVGQMKSDLFLDDSKSLVCWPSGEGTLSWPDLLSDPS
gi|4505833|   PAGQQVLDIDSCLDSSVLDSSFLTFSGLHAE-AFVGQMKSDLFLDDSKSLVCWPSGEGTLSWPDLLSDPS
gi|1586345|   PAGQQVLDIDSCLDSSVLDSSFLTFSGLHAE-AFVGQMKSDLFLDDSKSLVCWPSGEGTLSWPDLLSDPS
gi|903758|    PAGQQVLDIDSCLDSSVLDSSFLTFSGLHAE-AFVGQMKSDLFLDDSKSLVCWPSGEGTLSWPDLLSDPS
gi|1730587|   PAGQQVLDIDSCLDSSVLDSSFLTFSGLHAE-AFVGQMKSDLFLDDSKSLVCWPSGEGTLSWPDLLSDPS
gi|11320978|  PTGQQALDVDSYLDPSVLDSSLLTLSGLTEA--FSGQVKNDLFLEDAKSLVCWPSSEGTLSWPDLLSDPS 3440      3450      3460      3470      3480      3490      3500
              ....|....|....|....|....|....|....|....|....|....|....|....|....|
NOV28         IVGSNLRQLARGQAGHGLGPEEDGFSLASPYSPAKSFSASDEDLIQQVLAEGVSSPAPTQDTHMETDLLS
gi|4505833|   IVGSNLRQLARGQAGHGLGPEEDGFSLASPYSPAKSFSASDEDLIQQVLAEGVSSPAPTQDTHMETDLLS
gi|1586345|   IVGSNLRQLARGQAGHGLGPEEDGFSLASPYSPAKSFSASDEDLIQQVLAEGVSSPAPTQDTHMETDLLS
gi|903758|    IVGSNLRQLARGQAGHGLGPEEDGFSLASPYSPAKSFSASDEDLIQQVLAEGVSSPAPTQDTHMETDLLS
gi|1730587|   IVGSNLRQLARGQAGHGLGPEEDGFSLASPYSPAKSFSASDEDLIQQVLAEGVSSPAPTQDTHMETDLLS
gi|11320978|  VMSSTLQRLAQGRPGCMLGSEEDGASLVSPSLPAKYLSASDEDLIHQVLADGAMNPDPTQDALIERDLLT 3510      3520      3530      3540      3550      3560      3570
              ....|....|....|....|....|....|....|....|....|....|....|....|....|
NOV28         SLSSTPGEKTETLALQRLGELGPPSPGLNWEQPQAARLSRTGLVEGLRKRLLPAWCASLAHGLSLLLVAV
gi|4505833|   SLSSTPGEKTETLALQRLGELGPPSPGLNWEQPQAARLSRTGLVEGLRKRLLPAWCASLAHGLSLLLVAV
gi|1586345|   SLSSTPGEKTETLALQRLGELGPPSPGLNWEQPQAARLSRTGLVEGLRKRLLPAWCASLAHGLSLLLVAV
gi|903758|    SLSSTPGEKTETLALQRLGELGPPSPGLNWEQPQAARLSRTGLVEGLRKRLLPAWCASLAHGLSLLLVAV
gi|1730587|   SLSSTPGEKTETLALQRLGELGPPSPGLNWEQPQAARLSRTGLVEGLRKRLLPAWCASLAHGLSLLLVAV
gi|11320978|  SLSSAPGEKTETLILQTMGEKRPPSMGLTWEQSPVTRLSRTGLVEGLRKRLLPTWCAPLAHGLSLLLVAV 3580      3590      3600      3610      3620      3630      3640
              ....|....|....|....|....|....|....|....|....|....|....|....|....|
NOV28         AVAVSGWVGASFPPGVSVAELLSSSASFLASFLGWEPLKVLLEALYFSLVAKRLHPDEDDTLVESPAVTP
gi|4505833|   AVAVSGWVGASFPPGVSVAELLSSSASFLASFLGWEPLKVLLEALYFSLVAKRLHPDEDDTLVESPAVTP
gi|1586345|   AVAVSGWVGASFPPGVSVAELLSSSASFLASFLGWEPLKVLLEALYFSLVAKRLHPDEDDTLVESPAVTP
gi|903758|    AVAVSGWVGASFPPGVSVAELLSSSASFLASFLGWEPLKVLLEALYFSLVAKRLHPDEDDTLVESPAVTP
gi|1730587|   AVAVSGWVGASFPPGVSVAELLSSSASFLASFLGWEPLKVLLEALYFSLVAKRLHPDEDDTLVESPAVTP
gi|11320978|  AVAVSGWIGASFPPSVSVMELLSSSSSFLASFLGWEPLKVLLEALYFSLVAKRLHPDEDDTLVESPAVTP 3650      3660      3670      3680      3690      3700      3710
              ....|....|....|....|....|....|....|....|....|....|....|....|....|
NOV28         VSARVPRVRPPHGFALFLAKEEARKVKRLHGMLRSLLVYMLFLLVTLLASYGDASCHGHAYRLQSAIKQE
gi|4505833|   VSARVPRVRPPHGFALFLAKEEARKVKRLHGMLRSLLVYMLFLLVTLLASYGDASCHGHAYRLQSAIKQE
gi|1586345|   VSARVPRVRPPHGFALFLAKEEARKVKRLHGMLRSLLVYMLFLLVTLLASYGDASCHGHAYRLQSAIKQE
gi|903758|    VSARVPRVRPPHGFALFLAKEEARKVKRLHGMLRSLLVYMLFLLVTLLASYGDASCHGHAYRLQSAIKQE
gi|1730587|   VSARVPRVRPPHGFALFLAKEEARKVKRLHGMLRSLLVYMLFLLVTLLASYGDASCHGHAYRLQSAIKQE
gi|11320978|  VSERVPRVRPPHGFALFLAKEEARKVKRLHDMLKSLLVYMLFLLVTLLANYGDASCHGHAYRLQSAIKQE 3720      3730      3740      3750      3760      3770      3780
              ....|....|....|....|....|....|....|....|....|....|....|....|....|
NOV28         LHSRAFLAITRSEELWPWMAHVLLPYVHGNQSSPELGPPRLRQVRLQEALYPDPPGPRVHTCSAAGGFST
gi|4505833|   LHSRAFLAITRSEELWPWMAHVLLPYVHGNQSSPELGPPRLRQVRLQEALYPDPPGPRVHTCSAAGGFST
gi|1586345|   LHSRAFLAITRSEELWPWMAHVLLPYVHGNQSSPELGPPRLRQVRLQEALYPDPPGPRVHTCSAAGGFST
gi|903758|    LHSRAFLAITRSEELWPWMAHVLLPYVHGNQSSPELGPPRLRQVRLQEALYPDPPGPRVHTCSAAGGFST
gi|1730587|   LHSRAFLAITRSEELWPWMAHVLLPYVHGNQSSPELGPPRLRQVRLQEALYPDPPGPRVHTCSAAGGFST
gi|11320978|  LDSGAFLAITRSDEFWPWMSHVLLPYVHGNQSSPELGPPRLRQVRLQEAFCPDPSSS-EHMCSATGSLST 3790      3800      3810      3820      3830      3840      3850
              ....|....|....|....|....|....|....|....|....|....|....|....|....|
NOV28         SDYDVGWESP-HNGSGTWAYSAPDLLGAWSWGSCAVYDSGGYVQELGLSLEESRDLRFLQLHNWLDNRS
gi|4505833|   SDYDVGWESP-HNGSGTWAYSAPDLLGAWSWGSCAVYDSGGYVQELGLSLEESRDLRFLQLHNWLDNRS
gi|1586345|   SDYDVGWESP-HNGSGTWAYSAPDLLGAWSWGSCAVYDSGGYVQELGLSLEESRDLRFLQLHNWLDNRS
gi|903758|    SDYDVGWESP-HNGSGTWAYSAPDLLGAWSWGSCAVYDSGGYVQELGLSLEESRDLRFLQLHNWLDNRS
gi|1730587|   SDYDVGWESP-HNGSGTWAYSAPDLLGAWSWGSCAVYDSGGYVQELGLSLEESRDLRFLQLHNWLDNRS
gi|11320978|  SDYGVGWQSVVQNGSETWAYSAPDLLGAWYWGYCAVYDSGGYIQELGLSLEESRARLGFLQLHNWLDSRS
```

TABLE 28E-continued

Clustal W Sequence Alignment

```
                    3860       3870       3880       3890       3900       3910       3920
              ....|....|....|....|....|....|....|....|....|....|....|....|....|....|
NOV28         RAVFLELTRYSPAVGLHAAVTLRLEFPAAGRALAALSVRPFALRRLSAGLSLPLLTSVCLLLGAVHGAVA
gi|4505833|   RAVFLELTRYSPAVGLHAAVTLRLEFPAAGRALAALSVRPFALRRLSAGLSLPLLTSVCLLLGAVHGAVA
gi|1586345|   RAVFLELTRYSPAVGLHAAVTLRLEFPAAGRALAALSVRPFALRRLSAGLSLPLLTSVCLLLGAVHGAVA
gi|903758|    RAVFLELTRYSPAVGLHAAVTLRLEFPAAGRALAALSVRPFALRRLSAGLSLPLLTSVCLLLGAVHGAVA
gi|1730587|   RAVFLELTRYSPAVGLHAAVTLRLEFPAAGRALAALSVRPFALRRLSAGLSLPLLTSVCLLLGAVHGAVA
gi|11320978|  RAVFVELTRYSPAVGLHAAVTLRLEFPVAGHALAAFSVRPFALRRLSTGLSLPLLTSVCLLLGAIYGSVA 3930       3940       3950       3960       3970       3980       3990
              ....|....|....|....|....|....|....|....|....|....|....|....|....|....|
NOV28         EARTWHREGRWRVLRLGAWARWLLVALTAATALVRLAQLGAADRQWTRFVRGRPRRFTSFDQVAQLSSAA
gi|4505833|   EARTWHREGRWRVLRLGAWARWLLVALTAATALVRLAQLGAADRQWTRFVRGRPRRFTSFDQVAQLSSAA
gi|1586345|   EARTWHREGRWRVLRLGAWARWLLVALTAATALVRLAQLGAADRQWTRFVRGRPRRFTSFDQVAQLSSAA
gi|903758|    EARTWHREGRWRVLRLGAWARWLLVALTAATALVRLAQLGAADRQWTRFVRGRPRRFTSFDQVAQLSSAA
gi|1730587|   EARTWHREGRWRVLRLGAWARWLLVALTAATALVRLAQLGAADRQWTRFVRGRPRRFTSFDQVAHVSSAA
gi|11320978|  EVHTWRREGCARTARPDVGARWLLVMLTAATGLVRLAQLRIADRQWTRFVHDHPHHFTSFDQVAQLGSVA 4000       4010       4020       4030       4040       4050       4060
              ....|....|....|....|....|....|....|....|....|....|....|....|....|....|
NOV28         RGLAAGLLFLLLVKAAQQLRFVRQWSVFGKTLCRALPELLGVTLGLVVLGVAYAQLAILLVSSCVDSLWS
gi|4505833|   RGLAAGLLFLLLVKAAQQLRFVRQWSVFGKTLCRALPELLGVTLGLVVLGVAYAQLAILLVSSCVDSLWS
gi|1586345|   RGLAAGLLFLLLVKAAQQLRFVRQWSVFGKTLCRALPELLGVTLGLVVLGVAYAQLAILLVSSCVDSLWS
gi|903758|    RGLAAGLLFLLLVKAAQQLRFVRQWSVFGKTLCRALPELLGVTLGLVVLGVAYAQLAILLVSSCVDSLWS
gi|1730587|   RGLAAGLLFLLLVKAAQHVRFVRQWSVFGKTLCRALPELLGVTLGLVVLGVAYAQLAILLVSSCVDSLWS
gi|11320978|  RGLAAGLLFLLLVKAAQHVRFVRQWSVFGKTLCRALPELMGATLGLVELGVAYAQMAILLISSGADTLYS 4070       4080       4090       4100       4110       4120       4130
              ....|....|....|....|....|....|....|....|....|....|....|....|....|....|
NOV28         VAQALLVLCPGTGLSTLCPAESWHLSPLLCVGLWALRLWGALRLGAVILRWRYHALRGALYRPAWEPQDY
gi|4505833|   VAQALLVLCPGTGLSTLCPAESWHLSPLLCVGLWALRLWGALRLGAVILRWRYHALRGALYRPAWEPQDY
gi|1586345|   VAQALLVLCPGTGLSTLCPAESWHLSPLLCVGLWALRLWGALRLGAVILRWRYHALRGALYRPAWEPQDY
gi|903758|    VAQALLVLCPGTGLSTLCPAESWHLSPLLCVGLWALRLWGALRLGAVILRWRYHALRGALYRPAWEPQDY
gi|1730587|   VAQALLVLCPGTGLSTLCPAESWHLSPLLCVGLWALRLWGALRLGAVILRWRYHALRGALYRPAWEPQDY
gi|11320978|  MARAFLVLCPGARVPTLCPSESWSLSPLLCVGLWALRWWGALRLGAVELRWRYHALRGALYRPAWEPQDY 4140       4150       4160       4170       4180       4190       4200
              ....|....|....|....|....|....|....|....|....|....|....|....|....|....|
NOV28         EMVELFLRRLRLWMGLSKVKEFRHKVRFEGMEPLPSRSSRGSKVSPDVPPPSAGSDASHPSTSSSQLDGL
gi|4505833|   EMVELFLRRLRLWMGLSKVKEFRHKVRFEGMEPLPSRSSRGSKVSPDVPPPSAGSDASHPSTSSSQLDGL
gi|1586345|   EMVELFLRRLRLWMGLSKVKEFRHKVRFEGMEPLPSRSSRGSKVSPDVPPPSAGSDASHPSTSSSQLDGL
gi|903758|    EMVELFLRRLRLWMGLSKVKEFRHKVRFEGMEPLPSRSSRGSKVSPDVPPPSAGSDASHPSTSSSQLDGL
gi|1730587|   EMVELFLRRLRLWMGLSKVKEFRHKVRFEGMEPLPSRSSRGSKVSPDVPPPSAGSDASHPSTSSSQLDGL
gi|11320978|  EMVELFLRRLRLWMGFTKVKEFRHKVRFEGMDPLPSRSSRGSKSSPVVPPPSAGSEASHPSTSSSQPDGL 4210       4220       4230       4240       4250       4260       4270
              ....|....|....|....|....|....|....|....|....|....|....|....|....|....|
NOV28         SVSLCRLGTRCEPEPSRLQAVFEALLTQFDRLNQATEDVYQLEQQLHSLQGRRSSRAPAGSSRGPSPGLR
gi|4505833|   SVSLCRLGTRCEPEPSRLQAVFEALLTQFDRLNQATEDVYQLEQQLHSLQGRRSSRAPAGSSRGPSPGLR
gi|1586345|   SVSLCRLGTRCEPEPSRLQAVFEALLTQFDRLNQATEDVYQLEQQLHSLQGRRSSRAPAGSSRGPSPGLR
gi|903758|    SVSLCRLGTRCEPEPSRLQAVFEALLTQFDRLNQATEDVYQLEQQLHSLQGRRSSRAPAGSSRGPSPGLR
gi|1730587|   SVSLCRLGTRCEPEPSRLQAVFEALLTQFDRLNQATEDVYQLEQQLHSLQGRRSSRAPAGSSRGPSPGLR
gi|11320978|  SAGLRRSALRLEPEPSRLHAVFESLLVQFDRLNQATEDVYQLEQQLQSLRGHGHSGPESSPSPGGFPASQ 4280       4290       4300
              ....|....|....|....|....|....|....|.
NOV28         PALPSRLARASRGVDLATGPSRTPLRAKNKVHPSST
gi|4505833|   PALPSRLARASRGVDLATGPSRTPLRAKNKVHPSST
gi|1586345|   PALPSRLARASRGVDLATGPSRTPLRAKNKVHPSST
gi|903758|    PALPSRLARASRGVDLATGPSRTPLRAKNKVHPSST
gi|1730587|   PALPSRLARASRGVDLATGPSRTPLRAKNKVHPSST
gi|11320978|  PALPSRLARASQGPDQTTGPSRVSLWPNNKVHPSST
```

Tables 28E, 28F, 28G and 28H list the domain description from DOMAIN analysis results against NOV28. This indicates that the NOV28 sequence has properties similar to those of other proteins known to contain these domains.

TABLE 28E

Domain Analysis of NOV28 gnl|Pfam.pfamC2010, REJ, REJ domain. The REJ (Receptor for Egg Jelly) domain is found in PKD1, and the sperm receptor for egg jelly. The function of this domain is unknown. The domain is 600 amino acids long so is probably composed of multiple structural domains. There are six completely conserved cysteine residues that may form disulphide bridges. (SEQ ID NO:276)

TABLE 28E-continued

Domain Analysis of NOV28

```
CD-Length = 547 residues, 100.0% aligned
Score = 557 bits (1435), Expect = 5e-159
Query:  2168  YLEAHVDLRDCVTYQTEYRWEVYRTASCQR-PGRPARVALPGVDVSRPRLVLPRLALPV-  2225
              ||| |||+ |  |  +|+|+++  ||   |||   + || ||||| | +
Sbjct:     1  TLEASVDLKCCDAYTIDYKWQIFSVPSCDDDPGRTTPIPLPAVDVSRTRQLHIPRGALPY    60

Query:  2226  GEYCFVPVVSFG----DTP-LTQSIQANVTVAPERLVPIIEGGSYRVWSDTRDLVLDGSE  2280
              |  |  | +|        |  +||  + +   ||  +|||+||||   |+|+||||
Sbjct:    61  GVYVFNFTLSIRLKTSGEPTLKKSIISYLWVQAPPLVAVIEGGAyRVWSFTQDLILDGSN   120

Query:  2281  SYDPNLEDGDQTPLSFHWACVAS------------TQREAGGCALNFGPRGSST--VTIP  2326
              ||||+ +  |+ |  ||| ||                 +|   |+|| |||   +|||
Sbjct:   121  SYDPDADPGSQSNLQFHWYCVTVPRDYMGSSLDEASQNVCHPCQLSFGWPSSGSVLTIP   180

Query:  2327  RERLAAGVEYTFSLTVWKAGRKEEATNQTVLIRSGRVPIVSLECVSCKAQAVYEVSRSSY  2386
              |   |   |||||| + ||    |+|| + || +||| + |+ || +||||| |
Sbjct:   181  PETLEANVEYTFRLVISKEGRITEFTDQTVHVLSGLLPIVHISCISNCAQYLYEVSRFSL   240

Query:  2387  VYLEGRCLNCSSGSKRGRWAARTFSNKTLVLDET-TTSTGSAGMRLVLRRGVLRDGEGYT  2445
              |||     | ||  |   |||+  + ||  |+||| +  +|||  |   |||  |+
Sbjct:   241  VYL---CTNC-DGDDSGRWSALSLSNTTVVLDWSGQTTTGSNGPYLVLKPGAFRSGEEYS   296

Query:  2446  FTLTVLGRSGEEEGCASIRLSP--NRPPLCGSCRLFPLGAVHALTTKVHFECTGWHDAED  2503
              |||+| | + || ||| |   |  ||||+| |   || ||   ||+ +  |
Sbjct:   297  FTLSVTGSSWDSEGYASISLHPPINRPPAGGSCKLNPAE-GIALQTKFTVECSNF---RD   352

Query:  2504  AGAPLVYALLLRRCR-----QGHCEEFCVYKGSLSSY-GAVLPPGF-RPHFEVGLAVVVQ  2556
              || | +++ |||      +|| |+|+||  || || ||  +| |||
Sbjct:   353  VDEPLTYKIIVSRCRSVGMISSYCENFLLYEGSAPIKPGAFLPVGFGTDQHDVSLYVQVY   412

Query:  2557  DQLGAAVVALNRSLAITLPEPNGSATGLTVWLRGLT--ASVLPGLLRQADPQHVIEYSLA  2614
              | ||||  || +    +|  |   |   |+| ||+ ||| | |||
Sbjct:   413  DSLGAASQVLNSATVHVPTDPASSKNVLQQLLSMLLLPESLLSTLLQQGDPQQAGELSLA   472

Query:  2615  LVTVLNEYERALDVAAEPKHERQHRAQIRKNITETLVSLRVHTVDDIQQIAAALAQCMGP  2674
              |++|||| |+ |  + || ||++|||+ + | +| |+|||||||| +||||||
Sbjct:   473  LISVLNEIEQEDDS----EVERDDRARLRKNLVDQLAALPVNTVDDIQQSSAALAQCTQK   528

Query:  2675  SRELVCRSCLKQTLHKLEA                                          2693
              |||   |  + || |||
Sbjct:   529  SREFSCHVQMIATLRLLEA                                           547
```

TABLE 28F

Domain Analysis of NOV28 gnl|Pfam'fam01477, PLAT, PLAT/LH2 domain. This domain is found in a variety of membrane or lipid associated proteins. It is called the PLAT (Polycystin-1, Lipoxygenase, Alpha-Toxin) domain or LH2 (Lipoxygenase homology) domain. The known structure of pancreatic lipase shows this domain binds to procolipase pfam01114, which mediates membrane association. So it appears possible that this domain mediates membrane attachment via other protein binding partners. The structure of this domain is known for many members of the family and is composed of a beta sandwich. (SEQ ID NO:277)

```
CD-Length = 113 residues, 92.0% aligned
Score = 100 bits (248), Expect = 2e-21
Query:  3115  FKYEILVKTGWGRGSGTTAHVGINLYGVDSRSGHRHLDGDRAFHRNSLDIFRIATPHSLG  3174
              +|+++| ||   |+|||  | | ||| +  ||        |      |       ||
Sbjct:     1  VRYQLVVATGGDEGAGTTGKVSISLYGEEGESGKIPLLKGEGAGPGSTFSFTFDVDEDLG   60

Query:  3175  SVWKIRVWHDNKGL-SPAWFLQHVIVRDLQTARSAFFLVNDWLS                  3217
              +  +|+ +++ || || ||||+ + | |    |  |   |+
Sbjct:    61  ELGAVRIPMEHSGLFSPEWFLKSITVEDGGTQGKVHFPCNSWVY                  104
```

TABLE 28G

Domain Analysis of NOV28 gnl|Smart|smartc00308, LH2, Lipoxygenase homology 2 (beta barrel) domain (SEQ ID NO:278)
CD-Length = 120 residues, 87.5% aligned TABLE 28G-continued Domain Analysis of NOV28

```
Score = 87.4 bits (215), Expect = 1e-17
Query:  3115  FKYEILVKTGWGRGSGTTAHVGIMLYGVDSRSGHRHLDG---DRAFHRNSLDIFRIATPH  3171
              | |++ |  ||    +||||  | + | | + |      ||     | | |    |
Sbjct:     1  AKYKVTVTTGVLDFAGTTASVSLSLIGAEGRGKESKLDYLERPLLFARGSTYSFTFDVDV    60

Query:  3172  SLGSVWKIRVIDNKGLSPAWFLQHVIVRDLQTARSAFFLVNDWL                  3216
              | +  +++ +++ || |  |||+ + |+|   |    | | |+
Sbjct:    61  DFGELGAVKIKNEHAGLHPEWFLKSITVKDGPTGGKVHFPCNSWV                  105
```

TABLE 28H

Domain Analysis of NOV28

```
gnl|Pfampfam00801, PKD, PKD domain. This domain was first identified
in the Polycystic kidney disease protein PKD1. This domain has been
predicted to Contain an Ig-like fold. (SEQ ID NO:279)
CD-Length = 84 residues, 100.0% aligned
Score = 79.0 bits (193), Expect = 5e-15
Query:  1716  EPVGWLMVTASPNPAAVNTSVTLSAELAGGSGVVYTWSLEEGLSWETSEPFTTHSFPTPG  1775
              |||   | |+|||+  |+ +|| +|     ||||  |   +   ++ |  ||++ ||
Sbjct:     1  EPVPGLSVSASPSVVALGLTVTFTATSPDGSIVSYLWDFGDSPGLTSTGPNVTHTYLKPG    60

Query:  1776  LHLVTMTAGNPLGSANATVEVDVQ                                      1799
              + ||+||  | +|||+||+ | |
Sbjct:    61  TYTVTLTATNDVGSASATLTVTVV                                        84
```

Polycystic Kidney Disease Associated 8 (K8) and keratin 18 (K18) are the most common and characteristic members of the large intermediate filament gene family expressed in 'simple' or single layer epithelial tissues of the body. Their persistent expression in tumor cells derived from these epithelia has led to the wide spread use of keratin monoclonal antibodies as aids in the detection and identification of carcinomas. Oncogenes which activate ras signal transduction pathways stimulate expression of the K18 gene through transcription factors including members of the AP-1 (jun and fos) and ETS families. The persistent expression of K8 and K18 may reflect the integrated transcriptional activation of such transcription factors and, in the cases of ectopic expression, an escape from the suppressive epigenetic mechanisms of DNA methylation and chromatin condensation. Comparison of the mechanisms of transcriptional control of K18 expression with expression patterns documented in both normal and pathological conditions leads to the proposal that persistent K8 and K18 expression is a reflection of the action of multiple different oncogenes converging on the nucleus through a limited number of transcription factors to then influence the expression of a large number of genes including these keratins. Furthermore, correlation of various tumor cell characteristics including invasive behavior and drug sensitivity with K8 and K18 expression has stimulated consideration of the possible functions of these proteins in both normal development and in tumorigenesis. Recent developments in the analysis of the functions of these intermediate filament proteins provide new insights into diverse functions influenced by K8 and K18 (Oshima et al., Cancer Metastasis Rev 15:445–71, 1996).

Polycystic Kidney Disease Associated 8 (K8) and keratin 18 (K18) form intermediate filaments characteristic of liver and other single cell layered, internal epithelia and their derivative cancers. K8-deficient (K8(−)) mice, which escape embryonic lethality, develop inflammatory colorectal hyperplasia, mild liver abnormalities, and tolerate hepatectomy poorly. Normal and malignant epithelial cells deficient in K8 and K18 have been shown to be approximately 100 times more sensitive to TNF-induced death. K8 and K18 both bind the cytoplasmic domain of TNFR2 and moderate TNF-induced, Jun NH(2)-terminal kinase (JNK) intracellular signaling and NFkappaB activation. Furthermore, K8(−) and K18(−) mice are much more sensitive to TNF dependent, apoptotic liver damage induced by the injection of concanavalin A. This moderation of the effects of TNF may be the fundamental function of K8 and K18 common to liver regeneration, inflammatory bowel disease, hepatotoxin sensitivity, and the diagnostic, persistent expression of these keratins in many carcinomas (Caulin et al., J Cell Biol 149:17–22, 2000).

The NOV28 nucleic acid of the invention encoding a Polycystic Kidney Disease Associated-like protein includes the nucleic acid whose sequence is provided in Table 28A, or a fragment thereof. The invention also includes a mutant or variant nucleic acid any of whose bases may be changed from the corresponding base shown in Table 28A while still encoding a protein that maintains its Polycystic Kidney Disease Associated-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 1% of the NOV28 residues may be so changed.

The NOV28 protein of the invention includes the Polycystic Kidney Disease Associated-like protein whose sequence is provided in Table 28B. The invention also includes a mutant or variant protein any of whose residues may be changed from the corresponding residue shown in Table 28B while still encoding a protein that maintains its Polycystic Kidney Disease Associated-like activities and physiological functions, or a functional fragment thereof. In the mutant or variant protein, up to about 1% of the NOV28 bases may be so changed.

The NOV28 nucleic acids and proteins of the invention are useful in potential diagnostic and therapeutic applications implicated in various diseases and disorders described below and/or other pathologies. For example, the compositions of the present invention will have efficacy for treatment of patients suffering from: polycystic kidney disease and renal carcinoma and other diseases, disorders and conditions of the like.

NOV28 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV28 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV29

A disclosed NOV29 nucleic acid of 1222 nucleotides (also referred to as CG57589-01) encoding a novel Cholinephosphate Cytidylyltransferase-like protein is shown in Table 29A. An open reading frame was identified beginning with an ATG initiation codon at nucleotides 67–69 and ending with a TAA codon at nucleotides 1156–1158. Putative untranslated regions upstream from the intitation codon and downstream from the termination codon are underlined in Table 29A, and the start and stop codons are in bold letters.

TABLE 29A

NOV29 Nucleotide Sequence (SEQ ID NO:91)
<u>ATTGCGGGCGGCGGCGTTCCGAGTCGCCGGGAGCTGCCAGGCTGTCCGCGCCGCCGCTGCGCGGCC</u>ATGATCC

CGAACGGGCGCGGGGCTGCAGGCGGCGCAGAGCAGCCGGGCCCGGGGGGCAGGCGCGCCGTGAGGGTGTGGTG

CGATGGCTGCTATGACATGGTGCATTACGGCCACTCCAACCAGCTGCGCCAGGCACGGGCCATGGGTGACTAC

CTCATCGTAGGCGTGCACACCGATGAGAGATCGCCAAGCACAAGGGGCCCCCGGTGTTCACTCAGGAGGGAGA

GATACAAGATGGTGCAGGCCATCAAATGGGTGGACGAGGTGGTGCCAGCGGCTCCCTACGTCACTCACTAGA

GACCCTGGACAAATACAACTGTGACTTCTGTGTTCACGGCAATGACATCACCCTGACTGTAGATGGCCGGGAC

ACCTATGAGGAAGTAAAGCAGGCTGGGAGGTACAGAGAATGCAAGCGCACGCAAGGGGTGTCCACCACAGACC

TCGTGGGCCGCATGCTGCTGGTAACCAAAGCCCATCACAGCAGCCAGGAGATGTCCTCTGAGTACCGGGAGTA

TGCAGACAGTTTTGGCAAGTGCCCTGGTGGGCGCACCCCTGGACCGGGTATCCCAGTTCCTGCAGACATCT

CAGAAGATCATCCAGTTTGCTTCTGGGAAGGAGCCCCAGCCAGGGGAGACAGTCATCTATGTGGCTGGTGCCT

TCGACCTGTTCCACATCGGGCATGTGGACTTCCTGGAGAAGGTGCACAGGCTGGCAGAGAGGCCCTACATCAT

CGCGGGCTTACACTTTGACCAGTACGTGTCAGAAGTGGTGATTGGAGCCCCGTACGCGGTCACAGCAGAGCTC

CTAAGTCACTTCAAGGTGGACCTGGTGTGTCACGGCAAGACAGGAATTATCCCTGACAGGGATGGCTCCGACC

CATACCAGGAGCCCAAGAGAAGGGGCATCTTCCGTCAGATTGACAGTGGCAGCAACCTCACCACAGACCTCAT

CGTCCAGCGGATCATCACCACAGGTTGGAGTATGAGGCGCGAAACCAGAAGAAGGAAGCCAAGGACCTGGCC

TTCCTGGACGGTGCCAGGCAGCAGGCGGCACAGCCCCTGGGGGAGCGCGATGGTGACTTCTAA<u>CCTGGCAGAG</u>

<u>GCCCTGGCCGGCCCTCCCCCTGCTCTGCTTCTGCGCCTTCTGCGTTTGGACATA</u>

The NOV29 nucleic acid was identified on chromosome 17 and has 828 of 830 bases (99%) identical to a gb:GENBANK-ID:D84307|acc:D84307.1 mRNA from *Homo sapiens* (mRNA for phosphoethanolamine cytidylyltransferase, complete cds) (E=6.4e$^{-181}$).

A disclosed NOV29 polypeptide (SEQ ID NO:92) encoded by SEQ ID NO:91 is 363 amino acid residues and is presented using the one-letter code in Table 29B. Signal P, Psort and/or Hydropathy results predict that NOV29 contains a signal peptide and is likely to be localized to the nucleus with a certainty of 0.3000.

TABLE 29B

Encoded NOV29 protein sequence (SEQ ID NO:92)
MIRNGRGAAGGAEQPGPGGRRAVRVWCDGCYDMVHYGHSNQLRQARAMGDYLIVGVHTDEEIAKHKGPPVFT

QEERYKMVQAIKWVDEVVPAAPYVTTLETLDKYNCDFCVHGNDITLTVDGRDTYEEVKQAGRYRECKRTQGV

STTDLVGMLLVTKAHHSSQEMSSEYREYADSFGKCPGGRNPWTGVSQFLQTSQKIIQFASGKEPQPGETVI

YVAGAFDLFHIGHVDFLEKVHRLAERPYIIAGLHFDQYVSEVVIGAPYAVTAELLSHFKVDLVCHGKTGIIP

DRDGSDPYQEPKRRGIFRQIDSGSNLTTDLIVQRIITNRLEYEARNQKKEAKRLAFLEAARQQAAQPLGERD

GDF

The NOV29 amino acid sequence 254 of 256 amino acid residues (99%) identical to, and 255 of 256 amino acid residues (99%) similar to, the 389 amino acid residue ptnr:SWISSNEW-ACC:Q99447 protein from *Homo sapiens* (Human) (Ethanolamine-Phosphate Cytidylyltransferase (EC 2.7.7.14) (Phosphorylethanolamine Transferase) (CTP:Phosphoethanolamine Cytidylyltransferase)) (E=2.3e$^{-196}$).

NOV29 is expressed in at least the following tissues: adrenal gland/suprarenal gland, bone marrow, brain, bronchus, coronary artery, dermis, epidermis, heart, hypothalamus, kidney, left cerebellum, liver, lung pleura, lymphoid tissue, mammary gland/breast, ovary, pancreas, peripheral blood, pituitary gland, placenta, prostate, skeletal muscle, spinal chord, spleen, stomach, substantia nigra, testis, thalamus, thymus, thyroid, uterus and whole organism. This information was derived by determining the tissue sources of the sequences that were included in the invention including but not limited to SeqCalling sources, Public EST sources, genomic clone sources, literature sources, and/or RACE sources.

NOV29 has homology to the amino acid sequences shown in the BLASTP data listed in Table 29C.

TABLE 29C

BLAST results for NOV29

| Gene Index/ Identifier | Protein/ Organism | Length (aa) | Identity (%) | Positives (%) | Expect |
|---|---|---|---|---|---|
| gi\|4505651\|ref\|NP_002852.1\| (NM_002861) | phosphate cytidylyl-transferase 2, ethanolamine [*Homo sapiens*] | 389 | 331/389 (85%) | 331/389 (85%) | 0.0 |
| gi\|14603223\|gb\| AAH10075.1\| AAH10075 (BC010075) | phosphate cytidylyl-transferase 2, ethanolamine [*Homo sapiens*] | 389 | 330/389 (84%) | 331/389 (84%) | 0.0 |
| gi\|6758340\|ref\|NP_446020.1\| (NM_053568) | phosphate cytidylyl-transferase 2, ethanolamine [*Rattus norvegicus*] | 404 | 310/404 (76%) | 323/404 (79%) | e-174 |
| gi\|14198445\|gb\| AAH08276.1\| AAH08276 (BC008276) | RIKEN cDNA 1110033E03 gene [*Mus musculus*] | 404 | 309/404 (76%) | 322/404 (79%) | e-174 |
| gi\|13195654\|ref\|NP_077191.1\| (NM_024229) | RIKEN cDNA 1110033E03 [*Mus musculus*] | 404 | 308/404 (76%) | 321/404 (79%) | e-172 |

The homology of these sequences is shown graphically in the ClustalW analysis shown in Table 29D.

TABLE 29D

Clustal W Sequence Alignment

1) NOV29 (SEQ ID NO:92)
2) gi 4505651|refNP_002852.1|(NM_002861) phosphate cytidylyltransferase 2, ethanolamine [*Homo sapiens*] (SEQ ID NO:280)
3) gi 14603223|gb AAH10075.1 AAH10075 (BC010075) phosphate cytidylyltransferase 2, ethanolamine [*Homo sapiens*] (SEQ ID NO:281)
4) gi 16758340|refNP_446020.1|(NM_053568) phosphate cytidylyltransferase 2, ethanolamine [*Rattus norvegicus*] (SEQ ID NO:282)
5) gi 14198445|gbAAH08276.1 AAH08276 (BC008276) RIKEN cDNA 1110033E03 gene [*Mus musculus*] (SEQ ID NO:283)
6) gi 13195654|refNP_077191.1|(NM_024229) RIKEN cDNA 1110033E03 [*Mus musculus*] (SEQ ID NO:284)

TABLE 29D-continued

Clustal W Sequence Alignment

```
                   10         20         30         40         50         60         70
              ....|....|....|....|....|....|....|....|....|....|....|....|....|....|
NOV29         MIRNGRGAAGGAEQPGPGGRRAVRVWCDGCYDMVHYGHSNQLRQARAMGDYLIVGVHTDEEIAKHKGPPV
gi|4505651|   MIRNGRGAAGGAEQPGPGGRRAVRVWCDGCYDMVHYGHSNQLRQARAMGDYLIVGVHTDEEIAKHKGPPV
gi|14603223|  MIRNGRGAAGGAEQPGPGGRRAVRVWCDGCYDMVHYGHSNQLRQARAMGDYLIVGVHTDEEIAKHKGPPV
gi|16758340|  MIRNGHGAGGAAGLKGPGGQRTVRVWCDGCYDMVHYGHSNQLRQARAMGDYLIVGVHTDEEIAKHKGPPV
gi|14198445|  MIRNGHGAASAAGLKGPGDQRIVRVWCDGCYDMVHYGHSNQLRQARAMGDYLIVGVHTDEEIAKHKGPPV
gi|13195654|  MIRNGHGAASAAGLKGPGDQRIVRVWCDGCYDMVHYGHSNQLRQARAMGDYLIVGVHTDEEIAKHKGPPV 80         90        100        110        120        130        140
              ....|....|....|....|....|....|....|....|....|....|....|....|....|....|
NOV29         FTQEERYKMVQAIKWVDEVVPAAPYVTTLETLDKYNCDFCVHGNDITLTVEGRDTYEEVKQAGRYRECKP
gi|4505651|   FTQEERYKMVQAIKWVDEVVPAAPYVTTLETLDKYNCDFCVHGNDITLTVEGRDTYEEVKQAGRYRECKP
gi|14603223|  FTQEERYKMVQAIKWVDEVVPAAPYVTTLETLDKYNCDFCVHGNDITLTVEGRDTYEEVKQAGRYRECKP
gi|16758340|  FTQEERYKMVQAIKWVDEVVPAAPYVTTLETLDKYNCDFCVHGNDITLTVEGRDTYEEVKQAGRYRECKP
gi|14198445|  FTQEERYKMVQAIKWVDEVVPAAPYVTTLETLDKHNCDFCVHGNDITLTVEGRDTYEEVKQAGRYRECKP
gi|13195654|  FTQEERYKMVQAIKWVDEVVPAAPYVTTLETLDKHNCDFSVHGNDITLTVEGRDTYEEVKQAGRYRECKP 150        160        170        180        190        200        210
              ....|....|....|....|....|....|....|....|....|....|....|....|....|....|
NOV29         TQGVSTTDLVGRMLLVTKAHHSSQEMSSEYREYADSFGK------------------CPGGRNPWTGVSQ
gi|4505651|   TQGVSTTDLVGRMLLVTKAHHSSQEMSSEYREYADSFGK------------------CPGGRNPWTGVSQ
gi|14603223|  TQGVSTTDLVGRMLLVTKAHHSSQEMSSEYREYADSFGK------------------CPGGRNPWTGVSQ
gi|16758340|  TQGVSTTDLVGRMLLVTKAHHSSQEMSSEYREYADSFGKPPHPTPAGDTLSSEVSSQCPGGQSPWTGVSQ
gi|14198445|  TQGVSTTDLVGRMLLVTKAHHSSQEMSSEYREYADSFGKPPHPTPAGDTLSSEVSSQCPGGQSPWTGVSQ
gi|13195654|  TQGVSTTDLVGRMLLVTKAHHSSQEMSSEYREYADSFGKPPHPTPAGDTLSSEVSSQCPGGQSPWTGVSQ 220        230        240        250        260        270        280
              ....|....|....|....|....|....|....|....|....|....|....|....|....|....|
NOV29         FLQTSQKIIQFASGKEPQPGETVIYVAGAFDLFHIGHVDFLPKVHRLAERPYIIAGLHFDQ---------
gi|4505651|   FLQTSQKIIQFASGKEPQPGETVIYVAGAFDLFHIGHVDFLPKVHRLAERPYIIAGLHFDQEVNHYKGKN
gi|14603223|  FLQTSQKIIQFASGKEPQPGETVIYVAGAFDLFHIGHVDFLPKVHRLAERPYIIAGLHFDQEVNHYKGKN
gi|16758340|  FLQTSQKIIQFASGKEPQPGETVIYVAGAFDLFHIGHVDFLQEVHKLAKRPYVIAGLHFDQEVNRYKGKN
gi|14198445|  FLQTSQKIIQFASGKEPQPGETVIYVAGAFDLFHIGHVDFLQEVHKLAKRPYVIAGLHFDQEVNRYKGKN
gi|13195654|  FLQTSQKIIQFASGKEPQPGETVIYVAGAFDLFHIGHVDFLQEVHKLAKRPYVIAGLHFDQEVNRYKGKN 290        300        310        320        330        340        350
              ....|....|....|....|....|....|....|....|....|....|....|....|....|....|
NOV29         -----------------YVSEVVIGAPYAVTAELLSHFKVDLVCHGKTGILPDRDGSDPYQEPKRRGIFR
gi|4505651|   YPIMNLHERTLSVLACRYVSEVVIGAPYAVTAELLSHFKVDLVCHGKTEILPDRDGSDPYQEPKRRGIFR
gi|14603223|  YPIMNLHERTLSVLACRYVSEVVIGAPYAVTAELLSHFKVDLVCHGKTEILPDRDGSDPYQEPKRRGIFR
gi|16758340|  YPIMNLHERTLSVLACRYVSEVVIGAPYAVTAELLNHFKVDLVCHGKTEIVPDRDGSDPYEEPKRRGIFC
gi|14198445|  YPIMNLHERTLSVLACRYVSEVVIGAPYSVTAELLNHFKVDLVCHGKTEIVPDRDGSDPYQEPKRRGIFY
gi|13195654|  YPIMNLHERTLSVLACRYVSEVVIGAPYSVTAELLNHFKVDLVCHGKTEIVPDRDGSDPYQEPKRRGIFY 360        370        380        390        400
              ....|....|....|....|....|....|....|....|....|....|..
NOV29         QIDSGSNLTTDLIVQRIITNRLEYEARNQKKEAKELAFLEAARQQAAQPLGERDGDF
gi|4505651|   QIDSGSNLTTDLIVQRIITNRLEYEARNQKKEAKELAFLEAARQQAAQPLGERDGDF
gi|14603223|  QIDSGSNLTTDLIVQRIITNRLEYEARNQKKEAKELAFLEAARQQAAQPLGERDGDF
gi|16758340|  QIDSGSDLTTDLIVQRIIKNRLEYEARNQKKEAKELAFLEALRQQEAQPRGETD---
gi|14198445|  QIDSGSDLTTDLIVQRIIKNRLEYEARNQKKEAKELAFLEATKQQEAPPGGEID---
gi|13195654|  QIDSGSDLTTDLIVQRIIKNRLEYEARNQKKEAKELAFLEATKQQEAPPGGEID---
```

Table 29E lists the domain description from DOMAIN analysis results against NOV29. This indicates that the NOV29 sequence has properties similar to those of other proteins known to contain these domains.

TABLE 29E

Domain Analysis of NOV29 gnl.Pfam:pfam01467, Cytidylyltransf, Cytidylyltransferase. This family includes: Cholinephosphate cytidylyltransferase and Glycerol-3-phosphate cytidylyltransferase. (SEQ ID NO:285)
CD-Length = 129 residues, 99.2% aligned
Score = 128 bits (321), Expect = 6e-31

```
Query:   23 VRVWCDGCYDMVHYGHSNQLRQARAMGDYLIVGVHTDEEIAKHKGPPVFTQEERYKMVQA   82
            ||    | +|  | || + | +|+ +||  |||| +||    |    +|  |   +++|
Sbjct:    2 KRVIYGGTFDPFHLGHLDLLERAKELGDELIVGVASDESKKKLK--PFTAEERRKMLLEA   59

Query:   83 IKWVDEVVPAAPYVTTLETLDKYNCDFCVRGNDITLTVDGRDTYEEVKQAG-RYRECKRT  141
            +| ||||   ||  |+|  |+|  +    |  |  |+  +  |   ||+||        ||
Sbjct:   60 LKDVDEVYVFAPDDLTVEFIKEIKPDVIVRGLDVV-SFEYELLYALVKRAGLEVVFLPRT  118

Query:  142 QGVSTTDLVGR                                                  152
```

TABLE 29E-continued

Domain Analysis of NOV29

```
            +|  ||+|+|  |
Sbjct:  119 EGFSTSDIVKR                                              129
```

Ross et al. (*Neuroscience* 2001; 102:899–904) reported that the activities of phospholipase A(2), phosphocholine cytidylyltransferase and phosphoethanolamine cytidylyltransferase, key phospholipid metabolic enzymes, are low in substantia nigra of normal human brain and that this might reduce the ability of nigral neurons to repair damage to cell membranes. To determine whether adaptive changes in nigral phospholipid metabolism can occur in idiopathic Parkinson's disease they compared activities of 11 catabolic and anabolic enzymes in autopsied brain of 10 patients with Parkinson's disease to those in control subjects. Nigral activity of the catabolic enzyme phospholipase A(2) was normal in the Parkinson's disease group, whereas that of the biosynthetic enzymes phosphoethanolamine cytidylyltransferase, phosphocholine cytidylyltransferase, and phosphatidylserine synthase were elevated 193, 48 and 38%, respectively, possibly representing a compensatory response to repair membrane phospholipids. Enzyme activities were normal in all other brain areas with the exception of increased (+26%) activity of calcium-stimulated phospholipase A(2) in putamen, a change which could be consequent to either decreased dopaminergic striatal input or to a dopamine nerve terminal degenerative process. Their data indicate that the normally low rate of membrane phospholipid synthesis in the substantia nigra, the primary area of neurodegeneration in Parkinson's disease, is increased during the course of the disorder. It was suggested that pharmacotherapies which augment this compensatory response might have utility as a treatment for Parkinson's disease.

The NOV29 nucleic acid of the invention encoding a Cholinephosphate Cytidylyltransferase-like protein includes the nucleic acid whose sequence is provided in Table 29A, or a fragment thereof. The invention also includes a mutant or variant nucleic acid any of whose bases may be changed from the corresponding base shown in Table 29A while still encoding a protein that maintains its Cholinephosphate Cytidylyltransferase-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 1% of the NOV29 residues may be so changed.

The NOV29 protein of the invention includes the Cholinephosphate Cytidylyltransferase-like protein whose sequence is provided in Table 29B. The invention also includes a mutant or variant protein any of whose residues may be changed from the corresponding residue shown in Table 29B while still encoding a protein that maintains its Cholinephosphate Cytidylyltransferase-like activities and physiological functions, or a functional fragment thereof. In the mutant or variant protein, up to about 1% of the NOV29 bases may be so changed.

The NOV29 nucleic acids and proteins of the invention are useful in potential diagnostic and therapeutic applications implicated in various diseases and disorders described below and/or other pathologies. For example, the compositions of the present invention will have efficacy for treatment of patients suffering from: Parkinson's disease and other diseases, disorders and conditions of the like.

NOV29 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV29 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOV30

A disclosed NOV30 nucleic acid of 893 nucleotides (also referred to as CG57558-01) encoding a novel mac25/IGFBP7-like protein is shown in Table 30A. An open reading frame was identified beginning with an ATG initiation codon at nucleotides 49–51 and ending with a TAA codon at nucleotides 871–873. Putative untranslated regions upstream from the intitation codon and downstream from the termination codon are underlined in Table 30A, and the start and stop codons are in bold letters.

TABLE 30A

NOV30 Nucleotide Sequence (SEQ ID NO:93)

GTACCTTAAAGACAACAAACAAGCAAACACAACTTATAATTAAAAAACATGCAAAGGGCTCACCTTCCACTTC

CTTCTGGTCCTGCTCCTCTTCTTCCTCCTCTCCTGCCTCCTCTTCTCCCTGTTCCATCAGACCTTCTGGGCC

CCTTTCAATAAGCAGCTGCTGGCCGGCCAGCCCTTGGGGGCAGGGCTGGAACCGGGGCAGGGGAGGCTGCGGG

TABLE 30A-continued

NOV30 Nucleotide Sequence

GCCACTCGCTGGAGAGGCAAACAAGGAAGGACTGCCCCCTGAGCGCCAGGCTTCGGGCCCGGGAATCGCCGCCG

CCGCCGCCGCAGAGCTGCAGCTCGGGGCCGAGGGTAAGGAGGCGAGCCGGGAGCGGGAGGCCCGGGAGAGCTC

CGCGGGTCCCCGCGCCCAGTCCCCAGCCGCGCCCCGACCCCGCCGCCCCGGGCCTAACGCGGCGGCGAGGCC

TACGCGGCGGCCGCCGTCACCGTGCTGGAGCCGCCGGCCTCCGACCCCGAGCTGCAGCCCGCCGAGCGCCCGC

TGCCATCGCCGCCGGGGTCCGGGAGGGCGCCCCGGTCTTCCTCACGGGGCCTCGATCCCAGTGGGTGCTGCGGGG

GGCGGAGGTGGTGCTGACGTGCCGGGCGGGGGGCCTCCCCGAGCCCACACTGTACTGGGAGAAGGACGGGATG

GCCCTGGACGAAGTGTGGGACAGCAGCCACTTCGCGCTCCAGCCGGGCCGCGCCGAGGACGGCCCCGGCGCGA

GCCTGGCACTGCGCATCCTGGCGGCTCGGCTGCCGGATTCCGGCGTCTACGTGTGCCACGCCCGCAACGCGCA

CGGCCACGCGCAGGCGGGGCGCTGCTCCAGGTGCTGACCCCACCTTCCTGCCGCCAAGACAGCCCTAACCA

AGGCCCAGAAAGGGTAG

The NOV30 nucleic acid was identified on chromosome 2 and has 564 of 779 bases (72%) identical to a gb:GENBANK-ID:S56581|acc:S56581.1 mRNA from *Rattus* sp. (alpha inhibin gene {5' region} [rats, Genomic, 2141 nt]) (E=1.3e$^{-68}$).

A disclosed NOV30 polypeptide (SEQ ID NO:94) encoded by SEQ ID NO:93 is 274 amino acid residues and is presented using the one-letter code in Table 30B. Signal P, Psort and/or Hydropathy results predict that NOV30 contains a signal peptide and is likely to be localized to the extracellularly with a certainty of 0.3700. The most likely cleavage site for a NOV30 polypeptide is between amino acids 32–33: LLG-PL.

TABLE 30B

Encoded NOV30 protein sequence (SEQ ID NO:94)
MQRAHLFLPSGPAPLLPPLLFPLLPVPSDLLGPLSISSCWPASPWGQGWNRGRGGCGATRWRGKQEGLPPER

QASGPGIAAAAAAELQLGAEGKEASREREARESSAGPRAQSPAAPRPRRPGPNAAGEAYAAAAVTVLEPPAS

DPELQPAERPLPSPGSGEGAPVFLTGPRSQWVLRGAEVVLTCRAGGLPEPTLYWEKDGMALDEVWDSSHFAL

QPGRAEDGPGASLALRILAARLPDSGVYVCHAHNAHGHAQAGALLQVLTPTFLPPRQP

The NOV30 amino acid sequence 80 of 266 amino acid residues (30%) identical to, and 112 of 266 amino acid residues (42%) similar to, the 277 amino acid residue ptnr:SPTREMBL-ACC:Q07822 protein from *Homo sapiens* (Human) (mac25 protein) (E=2.0e$^{-17}$).

NOV30 is expressed in at least the following tissues: brain, ovary, breast and testis. This information was derived by determining the tissue sources of the sequences that were included in the invention including but not limited to Seq-Calling sources, Public EST sources, genomic clone sources, literature sources, and/or RACE sources and the expression pattern of (gb:GENBANK-ID:S56581|acc:S56581.1) a closely related alpha inhibin gene {5' region} [rats, Genomic, 2141 nt] homolog in species *Rattus* sp.

NOV30 has homology to the amino acid sequences shown in the BLASTP data listed in Table 30C.

TABLE 30C

BLAST results for NOV30

| Gene Index/ Identifier | Protein/ Organism | Length (aa) | Identity (%) | Positives (%) | Expect |
|---|---|---|---|---|---|
| gi\|14734071\|ref\|XP_051017.1\| (XM_051017) | K1AA0657 protein [*Homo sapiens*] | 1025 | 120/139 (86%) | 120/139 (86%) | 1e−60 |
| gi\|13938170\|gb\| | Unknown | 1044 | 120/139 | 120/ | 3e−60 |

TABLE 30C-continued

BLAST results for NOV30

| Gene Index/ Identifier | Protein/ Organism | Length (aa) | Identity (%) | Positives (%) | Expect |
|---|---|---|---|---|---|
| AAH07201.1\| AAH07201 (BC007201) | (protein for IMAGE: 2961284) [*Homo sapiens*] | | (86%) | 139 (86%) | |
| gi\|18552587\|ref\|XP_087161.1\| (XM_087161) | similar to Unknown (protein for IMAGE: 2961284) [*Homo sapiens*] | 180 | 38/58 (65%) | 39/58 (66%) | 1e−11 |

TABLE 30C-continued

BLAST results for NOV30

| Gene Index/ Identifier | Protein/ Organism | Length (aa) | Identity (%) | Positives (%) | Expect |
|---|---|---|---|---|---|
| gi\|14043550\|gb\| AAH07758.1\| AAH07758 (BC007758) | hypothetical protein FKSG28 [Homo sapiens] | 304 | 37/126 (29%) | 49/ 126 (38%) | 9e−06 |
| gi\|15026974\|emb\| CAC44768.1\| (AJ002535) | obscurin [Homo sapiens] | 6620 | 40/101 (39%) | 48/ 101 (46%) | 1e−05 |

The homology of these sequences is shown graphically in the ClustalW analysis shown in Table 30D.

TABLE 30D

Clustal W Sequence Alignment

1) NOV30 (SEQ ID NO:94)
2) gi 14734071|refXP_051017.1|(XM_051017) KIAA0657 protein [Homo sapiens] (SEQ ID NO:286)
3) gi 13938170|gb AAH07201.1 AAH07201 (BC007201) Unknown (protein for IMAGE:2961284) [Homo sapiens] (SEQ ID NO:287)
4) gi 18552587|refXP_087161.1|(XM_087161) similar to Unknown (protein for IMAGE:2961284) [Homo sapiens] (SEQ ID NO:288)
5) gi 14043550|gbAAH07758.1 AAH07758 (BC007758) hypothetical protein FKSG28 [Homo sapiens] (SEQ ID NO:289)
6) gi 15026974|emb CAC44768.1 (AJ002535) obscurin [Homo sapiens] (SEQ ID NO:290)

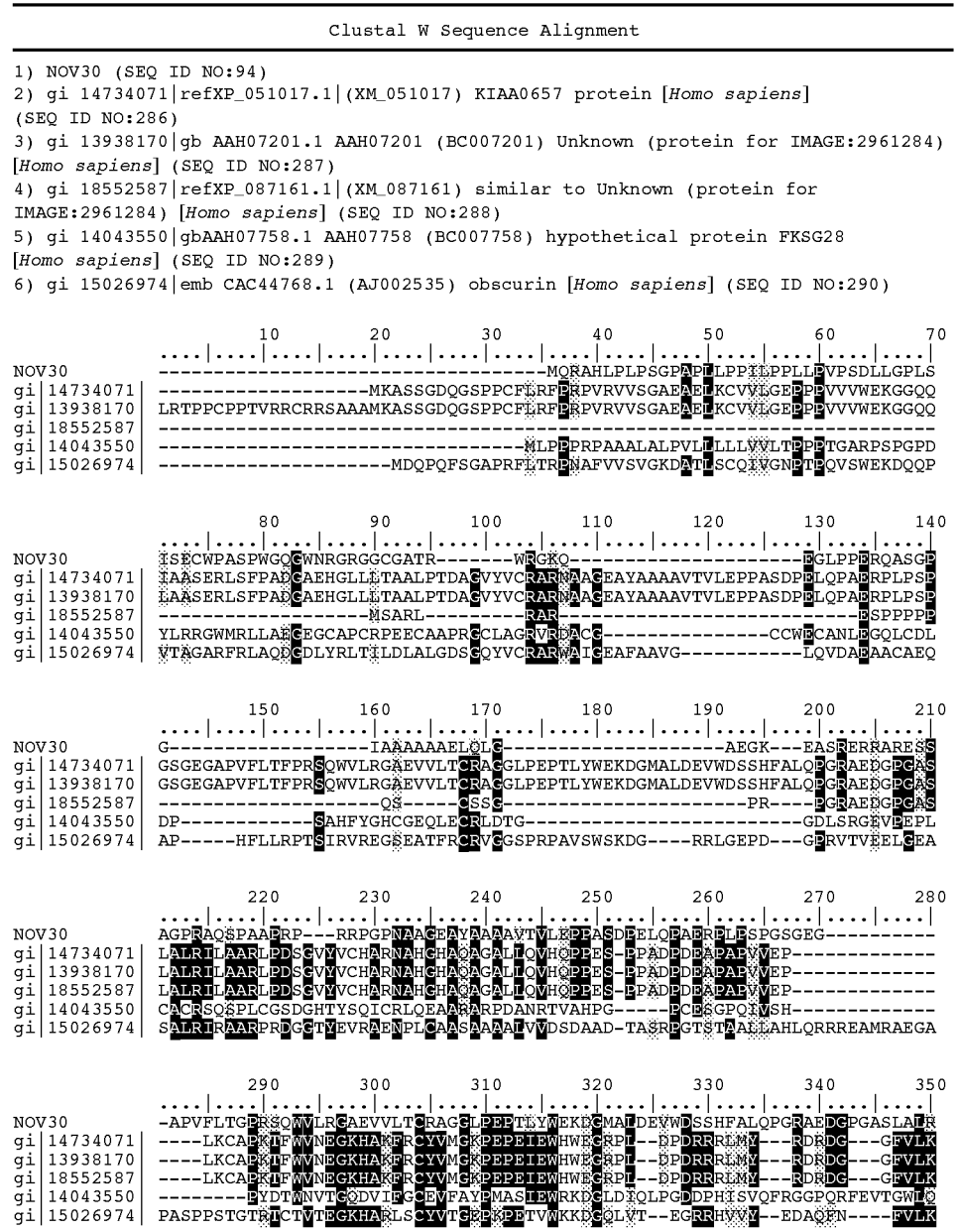

TABLE 30D-continued

Clustal W Sequence Alignment

```
                    360         370         380         390         400         410         420
                 ....|....|....|....|....|....|....|....|....|....|....|....|....|....|
NOV30            ILAARLPDSGVYVCHARNAHGHAQAGALQVLTETFLPPRQP--------------------------------
gi|14734071|     VLYCQAKDRGLYVCAARNQAGQTLSAVQLHVKEERLRFTRPLQDVEGREHGIAVLECKVPNSRIPTAWFR
gi|13938170|     VLYCQAKDRGLYVCAARNQAGQTLSAVQLHVKEERLRFTRPLQDVEGREHGIAVLECKVPNSRIPTAWFR
gi|18552587|     VLYCQAKDRGLYVCAARNQAGQTLSAVQLHVK---------------------------------------
gi|14043550|     IQAVRPSDEGTYRCLGRNALGQVEAPASLTVLTEDQLNSTGIPQLRSLN---------LVPEEEAE--SE
gi|15026974|     LLRCEQSDRGLYTCTASNLVGQTYSSVLVVVREEAVPFKKRLQDLEVREKESATFLCEVPQPSTEAAWFK 430         440         450         460         470         480         490
                 ....|....|....|....|....|....|....|....|....|....|....|....|....|....|
NOV30            -----------------------------------------------------------------------
gi|14734071|     EDQRLLPCRKYEQIEEGTVRRLIIHRLKADDDGIYLCEMRGRVRTVANVTVKGPILKRLPRKLDVLEGEN
gi|13938170|     EDQRLLPCRKYEQIEEGTVRRLIIHRLKADDDGIYLCEMRGRVRTVANVTVKGPILKRLPRKLDVLEGEN
gi|18552587|     -----------------------------------------------------------------------
gi|14043550|     ENDDYY-----------------------------------------------------------------
gi|15026974|     ETRLWASAKYGIEEEGTERRLTVRNVSADDDAVYICETPEGSRTVAELAVQGNLLRKLPRKTAVRVGDT 500         510         520         530         540         550         560
                 ....|....|....|....|....|....|....|....|....|....|....|....|....|....|
NOV30            -----------------------------------------------------------------------
gi|14734071|     AVLLVETLEAGVEGRWSRDGEELPV---ICQSSSGHMHALVLPGVTREDAGEVTFSLGNSRTTTLLRVKC
gi|13938170|     AVLLVETLEAGVEGRWSRDGEELPV---ICQSSSGHMHALVLPGVTREDAGEVTFSLGNSRTTTLLRVKC
gi|18552587|     -----------------------------------------------------------------------
gi|14043550|     -----------------------------------------------------------------------
gi|15026974|     AMFCVELAVPVGPVHWLRNQEEVVAGGRVAISAEGTRHTLTISQCCLEDVGQVAFMAGDCQTSTRFCVSA 570         580         590         600         610         620         630
                 ....|....|....|....|....|....|....|....|....|....|....|....|....|....|
NOV30            -----------------------------------------------------------------------
gi|14734071|     VKHSPPGPPILAEMFKGHKNTVLLTWKPPEPAP--ETPFIYRLERQEVGSEDWIQCFSIEKAGAVEVPGD
gi|13938170|     VKHSPPGPPILAEMFKGHKNTVLLTWKPPEPAP--ETPFIYRLERQEVGSEDWIQCFSIEKAGAVEVPGD
gi|18552587|     -----------------------------------------------------------------------
gi|14043550|     -----------------------------------------------------------------------
gi|15026974|     PRKPPLQPPVDPVVKARMESSVILSWSPPPHGERPVTIDGYLVEKKKLGTYTWIRCHEAEWVATPELTVA 640         650         660         670         680         690         700
                 ....|....|....|....|....|....|....|....|....|....|....|....|....|....|
NOV30            -----------------------------------------------------------------------
gi|14734071|     CVPSEGDYRFRICTVSGHGRSPHVVFHGSAHLVPTARLVAGLEDVQVYDGEDAVFSLDLSTIIQGTWFLN
gi|13938170|     CVPSEGDYRFRICTVSGHGRSPHVVFHGSAHLVPTARLVAGLEDVQVYDGEDAVFSLDLSTIIQGTWFLN
gi|18552587|     -----------------------------------------------------------------------
gi|14043550|     -----------------------------------------------------------------------
gi|15026974|     DVAEEGNFQFRVSALNSFGQSPYLEFPGTVHLAPKLAVRTPLKAVQAVEGGEVTFSVDLTVASAGEWFLD 710         720         730         740         750         760         770
                 ....|....|....|....|....|....|....|....|....|....|....|....|....|....|
NOV30            -----------------------------------------------------------------------
gi|14734071|     GEELKSNEPEGQVEP--------------------------------------------------------
gi|13938170|     GEELKSNEPEGQVEP--------------------------------------------------------
gi|18552587|     -----------------------------------------------------------------------
gi|14043550|     -----------------------------------------------------------------------
gi|15026974|     GQALKASSVYEIHCDRTRHTLTIREVPASLHGAQLKFVANGIESSIRMEVRAAPGLTANKPPAAAAREVL 780         790         800         810         820         830         840
                 ....|....|....|....|....|....|....|....|....|....|....|....|....|....|
NOV30            -----------------------------------------------------------------------
gi|14734071|     -----------------------------------------------------------------------
gi|13938170|     -----------------------------------------------------------------------
gi|18552587|     -----------------------------------------------------------------------
gi|14043550|     -----------------------------------------------------------------------
gi|15026974|     ARLHEEAQLLAELSDQAAAVTWLKDGRTLSPGPKYEVQASAGRRVLLVRDVARDDAGLYECVSRGGRIAY 850         860         870         880         890         900         910
                 ....|....|....|....|....|....|....|....|....|....|....|....|....|....|
NOV30            -----------------------------------------------------------------------
gi|14734071|     ------------------------------------------------------GALRYRIEQKGLQHRLIL
gi|13938170|     ------------------------------------------------------GALRYRIEQKGLQHRLIL
gi|18552587|     -----------------------------------------------------------------------
gi|14043550|     -----------------------------------------------------------------------
gi|15026974|     QLSVQGLARFLHKDMAGSCVDAVAGGPAQFECETSEAHVHVHWYKDGMELGHSGERFLQEDVGTRHRLVA 920         930         940         950         960         970         980
                 ....|....|....|....|....|....|....|....|....|....|....|....|....|....|
NOV30            -----------------------------------------------------------------------
gi|14734071|     HAVKHQDSGALVGFSCPGVQDSAALTIQESPVHILSPQDRVSLTFTTSERVVLTCELSRVDFPATWYKDG
gi|13938170|     HAVKHQDSGALVGFSCPGVQDSAALTIQESPVHILSPQDRVSLTFTTSERVVLTCELSRVDFPATWYKDG
gi|18552587|     -----------------------------------------------------------------------
gi|14043550|     -----------------------------------------------------------------------
gi|15026974|     ATVTRQDEGTYSCRVGEDSVDFRLRVSEPKVVFAKEQLARRKLQAEAGASATLSCEVAQAQTEVTWYKDG
```

TABLE 30D-continued

Clustal W Sequence Alignment

```
                 990       1000      1010      1020      1030      1040      1050
            ....|....|....|....|....|....|....|....|....|....|....|....|....|
NOV30       ----------------------------------------------------------------
gi|14734071 QKVEESELLVVKMDGRKHRLILPEAKVQDSGEFECRTEGVSAFFGVTVQDP-PVHIVDPREHVFVHAITS
gi|13938170 QKVEESELLVVKMDGRKHRLILPEAKVQDSGEFECRTEGVSAFFGVTVQDP-PVHIVDPREHVFVHAITS
gi|18552587 ----------------------------------------------------------------
gi|14043550 ----------------------------------------------------------------
gi|15026974 KKLSSSSKVCMEATGCTRRLVVQQAGQADAGEYSCEAGGQRLSFHLDVKEPKVVFAKDQVAHSEVQAEAG 1060      1070      1080      1090      1100      1110      1120
            ....|....|....|....|....|....|....|....|....|....|....|....|....|
NOV30       ----------------------------------------------------------------
gi|14734071 ECVMLACEVDREDAPVRWYKDGQEVEESDFVVLENEGPHRRLVLPATQPSDGGEFQCVAGDECAYFTVTI
gi|13938170 ECVMLACEVDREDAPVRWYKDGQEVEESDFVVLENEGPHRRLVLPATQPSDGGEFQCVAGDECAYFTVTI
gi|18552587 ----------------------------------------------------------------
gi|14043550 ----------------------------------------------------------------
gi|15026974 ANATLSCEVAQAQAEVMWYKDGKKLSSSLKVHVEAKGCRRRLVVQQAGKTDAGDYSCEARGQRVSFRLHI 1130      1140      1150      1160      1170      1180      1190
            ....|....|....|....|....|....|....|....|....|....|....|....|....|
NOV30       ----------------------------------------------------------------
gi|14734071 TDVSSWIVY-PSGKVYVAAVRLERVVLTCELCRPWAEVRWTKDGEEVVESPALLLQKEDTVRRLVLPAVQ
gi|13938170 TDVSSWIVY-PSGKVYVAAVRLERVVLTCELCRPWAEVRWTKDGEEVVESPALLLQKEDTVRRLVLPAVQ
gi|18552587 ----------------------------------------------------------------
gi|14043550 ----------------------------------------------------------------
gi|15026974 TEPKMMFAKEQSVHNEVQAEAGASAMLSCEVAQAQTEVTWYKDGKKLSSSSKVGMEVKGCTRRLVLPQAG 1200      1210      1220      1230      1240      1250      1260
            ....|....|....|....|....|....|....|....|....|....|....|....|....|
NOV30       ----------------------------------------------------------------
gi|14734071 LEDSGEYLCEIDDESASFTVTVTES-----------YQSQDSSNNNPELCVLLKKPKTRRLWSRFPPWRR
gi|13938170 LEDSGEYLCEIDDESASFTVTVTES-----------YQSQDSSNNNPELCVLLKKPKTRRLWSRFPPWRR
gi|18552587 ----------------------------------------------------------------
gi|14043550 ----------------------------------------------------------------
gi|15026974 KADAGEYSCEAGGQRVSFHLHITEPKGVFAKEQSVHNEVQAEAGTTAMLSCEVAQPQTEVTWYKDGKKLS 1270      1280      1290      1300      1310      1320      1330
            ....|....|....|....|....|....|....|....|....|....|....|....|....|
NOV30       ----------------------------------------------------------------
gi|14734071 TAGTE-----------------------------------------------------------
gi|13938170 TAGTE-----------------------------------------------------------
gi|18552587 ----------------------------------------------------------------
gi|14043550 ----------------------------------------------------------------
gi|15026974 SSSKVRMEVKGCTRRLVVQQVGKADAGEYSCEAGGQRVSFQLHITEPKAVFAKEQLVHNEVRTEAGASAT 1340      1350      1360      1370      1380      1390      1400
            ....|....|....|....|....|....|....|....|....|....|....|....|....|
NOV30       ----------------------------------------------------------------
gi|14734071 ----------------------------------------------------------------
gi|13938170 ----------------------------------------------------------------
gi|18552587 ----------------------------------------------------------------
gi|14043550 ----------------------------------------------------------------
gi|15026974 LSCEVAQAQTEVTWYKDGKKLSSSSKVRIEAAGCMRQLVVQQAGQADAGEYTCEAGGQRLSFHLDVSEPK 1410      1420      1430      1440      1450      1460      1470
            ....|....|....|....|....|....|....|....|....|....|....|....|....|
NOV30       ----------------------------------------------------------------
gi|14734071 ----------------------------------------------------------------
gi|13938170 ----------------------------------------------------------------
gi|18552587 ----------------------------------------------------------------
gi|14043550 ----------------------------------------------------------------
gi|15026974 AVFAKEQLAHRKVQAEAGAIATLSCEVAQAQTEVTWYKDGKKLSSSSKVRMEAVGCTRRLVVQQACQADT 1480      1490      1500      1510      1520      1530      1540
            ....|....|....|....|....|....|....|....|....|....|....|....|....|
NOV30       ----------------------------------------------------------------
gi|14734071 ----------------------------------------------------------------
gi|13938170 ----------------------------------------------------------------
gi|18552587 ----------------------------------------------------------------
gi|14043550 ----------------------------------------------------------------
gi|15026974 GEYSCEAGGQRLSFSLDVAEPKVVFAKEQPVHREVQAQAGASTTLSCEVAQAQTEVMWYKDGKKLSFSSK 1550      1560      1570      1580      1590      1600      1610
            ....|....|....|....|....|....|....|....|....|....|....|....|....|
NOV30       ----------------------------------------------------------------
gi|14734071 ----------------------------------------------------------------
gi|13938170 ----------------------------------------------------------------
gi|18552587 ----------------------------------------------------------------
gi|14043550 ----------------------------------------------------------------
gi|15026974 VRMEAVGCTRRLVVQQAGQADAGEYSCEAGSQRLSFHLHVAEPKAVFAKEQPASREVQAEAGTSATLSCE
```

TABLE 30D-continued

Clustal W Sequence Alignment

```
                     1620      1630      1640      1650      1660      1670      1680
                ....|....|....|....|....|....|....|....|....|....|....|....|....|
NOV30         | ----------------------------------------------------------------
gi|14734071   | ----------------------------------------------------------------
gi|13938170   | ----------------------------------------------------------------
gi|18552587   | ----------------------------------------------------------------
gi|14043550   | ----------------------------------------------------------------
gi|15026974   | VAQAQTEVTWYKDGKKLSSSSKVRMEAVGCTRRLVVQEAGQADAGEYSCKAGDQRLSFHLHVAEPKVVFA 1690      1700      1710      1720      1730      1740      1750
                ....|....|....|....|....|....|....|....|....|....|....|....|....|
NOV30         | ----------------------------------------------------------------
gi|14734071   | ----------------------------------------------------------------
gi|13938170   | ----------------------------------------------------------------
gi|18552587   | ----------------------------------------------------------------
gi|14043550   | ----------------------------------------------------------------
gi|15026974   | KEQPAHREVQAEAGASATLSCEVAQAQTEVTWYKDGKKLSSSSKVRVEAVGCTRRLVVQQAGQADAGEYS 1760      1770      1780      1790      1800      1810      1820
                ....|....|....|....|....|....|....|....|....|....|....|....|....|
NOV30         | ----------------------------------------------------------------
gi|14734071   | ----------------------------------------------------------------
gi|13938170   | ----------------------------------------------------------------
gi|18552587   | ----------------------------------------------------------------
gi|14043550   | ----------------------------------------------------------------
gi|15026974   | CEAGGQRLSFRLHVAELEPQISERPCRREPLVVKEHEDIILTATLATPSAATVTWLKDGVEIRRSKRHET 1830      1840      1850      1860      1870      1880      1890
                ....|....|....|....|....|....|....|....|....|....|....|....|....|
NOV30         | ----------------------------------------------------------------
gi|14734071   | ----------------------------------------------------------------
gi|13938170   | ----------------------------------------------------------------
gi|18552587   | ----------------------------------------------------------------
gi|14043550   | ----------------------------------------------------------------
gi|15026974   | ASQGDTHTLTVHGAQVLDSAIYSCRVGAEGQDFPVQVEEVAAKFCRLLEPVCGELGGTVTLACELSPACA 1900      1910      1920      1930      1940      1950      1960
                ....|....|....|....|....|....|....|....|....|....|....|....|....|
NOV30         | ----------------------------------------------------------------
gi|14734071   | ----------------------------------------------------------------
gi|13938170   | ----------------------------------------------------------------
gi|18552587   | ----------------------------------------------------------------
gi|14043550   | ----------------------------------------------------------------
gi|15026974   | EVVWRCGNTQPRVGKRFQMVAEGPVRSLTVLGLRAEDAGEYVCESRDDHTSAQLTVSVPRVVKFMSGLST 1970      1980      1990      2000      2010      2020      2030
                ....|....|....|....|....|....|....|....|....|....|....|....|....|
NOV30         | ----------------------------------------------------------------
gi|14734071   | ----------------------------------------------------------------
gi|13938170   | ----------------------------------------------------------------
gi|18552587   | ----------------------------------------------------------------
gi|14043550   | ----------------------------------------------------------------
gi|15026974   | VVAEEGGEATFQCVVSPSDVAVVWFRDGALLQPSEKFAISQSGASHSLTISDLVLEDAGQITVEAEGASS 2040      2050      2060      2070      2080      2090      2100
                ....|....|....|....|....|....|....|....|....|....|....|....|....|
NOV30         | ----------------------------------------------------------------
gi|14734071   | ----------------------------------------------------------------
gi|13938170   | ----------------------------------------------------------------
gi|18552587   | ----------------------------------------------------------------
gi|14043550   | ----------------------------------------------------------------
gi|15026974   | SAALRVREAPVLFKKKLEPQTVEERSSVTLEVELTRPWPELRWTRNATALAPGKNVEIHAEGARHRLVLH 2110      2120      2130      2140      2150      2160      2170
                ....|....|....|....|....|....|....|....|....|....|....|....|....|
NOV30         | ----------------------------------------------------------------
gi|14734071   | ----------------------------------------------------------------
gi|13938170   | ----------------------------------------------------------------
gi|18552587   | ----------------------------------------------------------------
gi|14043550   | ----------------------------------------------------------------
gi|15026974   | NVGFADRGFFGCETPDDKTQAKLTVEMRQVRLVRGLQAVEAREQGTATMEVQLSHADVDGSWTRDGLRFQ 2180      2190      2200      2210      2220      2230      2240
                ....|....|....|....|....|....|....|....|....|....|....|....|....|
NOV30         | ----------------------------------------------------------------
gi|14734071   | ----------------------------------------------------------------
gi|13938170   | ----------------------------------------------------------------
gi|18552587   | ----------------------------------------------------------------
gi|14043550   | ----------------------------------------------------------------
gi|15026974   | QGPTCHLAVRGPMHTLTLSGLRPEDSGLMVFKAEGVHTSARLVVTELPVSFSRPLQDVVTTEKEKVTLEC
```

TABLE 30D-continued

Clustal W Sequence Alignment

```
                     2250      2260      2270      2280      2290      2300      2310
                ....|....|....|....|....|....|....|....|....|....|....|....|....|
NOV30           ------------------------------------------------------------------
gi|14734071|    ------------------------------------------------------------------
gi|13938170|    ------------------------------------------------------------------
gi|18552587|    ------------------------------------------------------------------
gi|14043550|    ------------------------------------------------------------------
gi|15026974|    ELSRPNVDVRWLKDGVELRAGKEMAIAAQGACRSLTIYRCEFADQGVYVCDAHDAQSSASVKVQGRTYTL 2320      2330      2340      2350      2360      2370      2380
                ....|....|....|....|....|....|....|....|....|....|....|....|....|
NOV30           ------------------------------------------------------------------
gi|14734071|    ------------------------------------------------------------------
gi|13938170|    ------------------------------------------------------------------
gi|18552587|    ------------------------------------------------------------------
gi|14043550|    ------------------------------------------------------------------
gi|15026974|    IYRRVLAEDAGEIQFVAENAESRAQLRVKELPVTLVRPLRDKIAMEKHRGVLECQVSRASAQVRWFKGSQ 2390      2400      2410      2420      2430      2440      2450
                ....|....|....|....|....|....|....|....|....|....|....|....|....|
NOV30           ------------------------------------------------------------------
gi|14734071|    ------------------------------------------------------------------
gi|13938170|    ------------------------------------------------------------------
gi|18552587|    ------------------------------------------------------------------
gi|14043550|    ------------------------------------------------------------------
gi|15026974|    ELZPGPKYELVSDGLYRKLIISDVHAEDEDTYTCDAGDVKTSAQFFVEEQSITIVRGLQDVTVMEPAPAW 2460      2470      2480      2490      2500      2510      2520
                ....|....|....|....|....|....|....|....|....|....|....|....|....|
NOV30           ------------------------------------------------------------------
gi|14734071|    ------------------------------------------------------------------
gi|13938170|    ------------------------------------------------------------------
gi|18552587|    ------------------------------------------------------------------
gi|14043550|    ------------------------------------------------------------------
gi|15026974|    FECETSIPSVRPPKWLLGKTVLQAGGNVGLEQEGTVHRLMLRRTCSTMTGPVHFTVGKSRSSARLVVSDI 2530      2540      2550      2560      2570      2580      2590
                ....|....|....|....|....|....|....|....|....|....|....|....|....|
NOV30           ------------------------------------------------------------------
gi|14734071|    ------------------------------------------------------------------
gi|13938170|    ------------------------------------------------------------------
gi|18552587|    ------------------------------------------------------------------
gi|14043550|    ------------------------------------------------------------------
gi|15026974|    PVVLTRPLEPKTGRELQSVVLSCDFRPAPKAVQWYKDDTPLSPSEKFKMSLEGQMAELRILRLMPADAGV 2600      2610      2620      2630      2640      2650      2660
                ....|....|....|....|....|....|....|....|....|....|....|....|....|
NOV30           ------------------------------------------------------------------
gi|14734071|    ------------------------------------------------------------------
gi|13938170|    ------------------------------------------------------------------
gi|18552587|    ------------------------------------------------------------------
gi|14043550|    ------------------------------------------------------------------
gi|15026974|    YRCQAGSAHSSTEVTVEAREVTVTGPLQDAEATEEGWASFSCELSHEDEEVEWSLNGMPLYNDSFHEISH 2670      2680      2690      2700      2710      2720      2730
                ....|....|....|....|....|....|....|....|....|....|....|....|....|
NOV30           ------------------------------------------------------------------
gi|14734071|    ------------------------------------------------------------------
gi|13938170|    ------------------------------------------------------------------
gi|18552587|    ------------------------------------------------------------------
gi|14043550|    ------------------------------------------------------------------
gi|15026974|    KGRRHTLVLKSIQRADAGIVRASSLKVSTSARLEVRVKPVVFLKALDDLSAEERGTLALQCEVSDPEAHV 2740      2750      2760      2770      2780      2790      2800
                ....|....|....|....|....|....|....|....|....|....|....|....|....|
NOV30           ------------------------------------------------------------------
gi|14734071|    ------------------------------------------------------------------
gi|13938170|    ------------------------------------------------------------------
gi|18552587|    ------------------------------------------------------------------
gi|14043550|    ------------------------------------------------------------------
gi|15026974|    VWRKDGVQLGPSDKYDFLHTAGTRGLVVHDVSPEDAGLYTCHVGSEETRARVRVHDLHVGITKRLKTMEV 2810      2820      2830      2840      2850      2860      2870
                ....|....|....|....|....|....|....|....|....|....|....|....|....|
NOV30           ------------------------------------------------------------------
gi|14734071|    ------------------------------------------------------------------
gi|13938170|    ------------------------------------------------------------------
gi|18552587|    ------------------------------------------------------------------
gi|14043550|    ------------------------------------------------------------------
gi|15026974|    LEGESCSFECVLSHESASDPAMWTVGGKTVGSSSRFQATRQGRKYILVVREAAPSDAGEVVFSVRGLTSK
```

TABLE 30D-continued

Clustal W Sequence Alignment

```
                    2880      2890      2900      2910      2920      2930      2940
                 ....|....|....|....|....|....|....|....|....|....|....|....|....|
NOV30            ------------------------------------------------------------------
gi|14734071|     ------------------------------------------------------------------
gi|13938170|     ------------------------------------------------------------------
gi|18552587|     ------------------------------------------------------------------
gi|14043550|     ------------------------------------------------------------------
gi|15026974|     ASLIVRERPAAIIKPLEDQWVAPGEDVELRCELSRAGTPVHWLKDRKAIRKSQKYDVVCEGTMAMLVIRG 2950      2960      2970      2980      2990      3000      3010
                 ....|....|....|....|....|....|....|....|....|....|....|....|....|
NOV30            ------------------------------------------------------------------
gi|14734071|     ------------------------------------------------------------------
gi|13938170|     ------------------------------------------------------------------
gi|18552587|     ------------------------------------------------------------------
gi|14043550|     ------------------------------------------------------------------
gi|15026974|     ASLKDAGEYTCEBEASKSTASLHVEEKANCFTEELTNLQVEEKGTAVFTCKTEHPAATVTWRKGLLELRA 3020      3030      3040      3050      3060      3070      3080
                 ....|....|....|....|....|....|....|....|....|....|....|....|....|
NOV30            ------------------------------------------------------------------
gi|14734071|     ------------------------------------------------------------------
gi|13938170|     ------------------------------------------------------------------
gi|18552587|     ------------------------------------------------------------------
gi|14043550|     ------------------------------------------------------------------
gi|15026974|     SGKHQPSQEGLTLRLTISALEKADSDTYTCDIGQAQSRAQLLVQGRRVHIIEDLEDVDVQEGSSATFRCR 3090      3100      3110      3120      3130      3140      3150
                 ....|....|....|....|....|....|....|....|....|....|....|....|....|
NOV30            ------------------------------------------------------------------
gi|14734071|     ------------------------------------------------------------------
gi|13938170|     ------------------------------------------------------------------
gi|18552587|     ------------------------------------------------------------------
gi|14043550|     ------------------------------------------------------------------
gi|15026974|     ISPANYEPVHWFLDKTPLHANELNEIDAQPGGYHVLTLRQLALKDSGTIYFEAGDQRASAALRVTEKPSV 3160      3170      3180      3190      3200      3210      3220
                 ....|....|....|....|....|....|....|....|....|....|....|....|....|
NOV30            ------------------------------------------------------------------
gi|14734071|     ------------------------------------------------------------------
gi|13938170|     ------------------------------------------------------------------
gi|18552587|     ------------------------------------------------------------------
gi|14043550|     ------------------------------------------------------------------
gi|15026974|     FSRELTDATITEGEDLTLVCETSTCDIPMCWTKDGKTLRGSARCQLSHEGHRAQLLITGATLQDSGRYKC 3230      3240      3250      3260      3270      3280      3290
                 ....|....|....|....|....|....|....|....|....|....|....|....|....|
NOV30            ------------------------------------------------------------------
gi|14734071|     ------------------------------------------------------------------
gi|13938170|     ------------------------------------------------------------------
gi|18552587|     ------------------------------------------------------------------
gi|14043550|     ------------------------------------------------------------------
gi|15026974|     EAGGACSSSIVRVHARPVRFQEALKDLEVLEGGAATLRCVLSSVAAPVKWCYGNNVLRPGDKYSLRQEGA 3300      3310      3320      3330      3340      3350      3360
                 ....|....|....|....|....|....|....|....|....|....|....|....|....|
NOV30            ------------------------------------------------------------------
gi|14734071|     ------------------------------------------------------------------
gi|13938170|     ------------------------------------------------------------------
gi|18552587|     ------------------------------------------------------------------
gi|14043550|     ------------------------------------------------------------------
gi|15026974|     MLELVVRNLRPQDSGRYSCSFGDQTISATLTVTALPAQFIGKLRNKEATEGATATLRCELSKTAPVEWRK 3370      3380      3390      3400      3410      3420      3430
                 ....|....|....|....|....|....|....|....|....|....|....|....|....|
NOV30            ------------------------------------------------------------------
gi|14734071|     ------------------------------------------------------------------
gi|13938170|     ------------------------------------------------------------------
gi|18552587|     ------------------------------------------------------------------
gi|14043550|     ------------------------------------------------------------------
gi|15026974|     GSETLRDGDRYCLRQDGAMCELQIRGLAMVDAAEYSCVCGEERTSASLTIRPMPAHFIGRLRHQESIEGA 3440      3450      3460      3470      3480      3490      3500
                 ....|....|....|....|....|....|....|....|....|....|....|....|....|
NOV30            ------------------------------------------------------------------
gi|14734071|     ------------------------------------------------------------------
gi|13938170|     ------------------------------------------------------------------
gi|18552587|     ------------------------------------------------------------------
gi|14043550|     ------------------------------------------------------------------
gi|15026974|     TATLRCELSKAAPVEWRKGRESLRDGDRHSLRQDGAVCELQICGLAVADAGEYSCVCGEERTSATLTVKA
```

TABLE 30D-continued

Clustal W Sequence Alignment

```
                  3510       3520       3530       3540       3550       3560       3570
             ....|....|....|....|....|....|....|....|....|....|....|....|....|....|
NOV30        ----------------------------------------------------------------------
gi|14734071| ----------------------------------------------------------------------
gi|13938170| ----------------------------------------------------------------------
gi|18552587| ----------------------------------------------------------------------
gi|14043550| ----------------------------------------------------------------------
gi|15026974| LPAKFTEGLRNEEAVEGATAMLWCELSKVAPVEWRKGPENLRDGDRYILRQEGTRCELQICGLAMADAGE 3580       3590       3600       3610       3620       3630       3640
             ....|....|....|....|....|....|....|....|....|....|....|....|....|....|
NOV30        ----------------------------------------------------------------------
gi|14734071| ----------------------------------------------------------------------
gi|13938170| ----------------------------------------------------------------------
gi|18552587| ----------------------------------------------------------------------
gi|14043550| ----------------------------------------------------------------------
gi|15026974| YLCVCGQERTSATLTIRALPARFIEDVKNQEAREGATAVLQCELNSAAPVEWRKGSETLRDGDRYSLRQD 3650       3660       3670       3680       3690       3700       3710
             ....|....|....|....|....|....|....|....|....|....|....|....|....|....|
NOV30        ----------------------------------------------------------------------
gi|14734071| ----------------------------------------------------------------------
gi|13938170| ----------------------------------------------------------------------
gi|18552587| ----------------------------------------------------------------------
gi|14043550| ----------------------------------------------------------------------
gi|15026974| GTKCELQIRGLAMADTGEYSCVCGQERTSAMLTVRALPIKFTEGLRNEEATEGATAVLRCELSKMAPVEW 3720       3730       3740       3750       3760       3770       3780
             ....|....|....|....|....|....|....|....|....|....|....|....|....|....|
NOV30        ----------------------------------------------------------------------
gi|14734071| ----------------------------------------------------------------------
gi|13938170| ----------------------------------------------------------------------
gi|18552587| ----------------------------------------------------------------------
gi|14043550| ----------------------------------------------------------------------
gi|15026974| WKGHETLRDGDRHSLRQDGARCELQIRGLVAEDAGEYLCMCGKERTSAMLTVRAMPSKFIEGLRNEEATE 3790       3800       3810       3820       3830       3840       3850
             ....|....|....|....|....|....|....|....|....|....|....|....|....|....|
NOV30        ----------------------------------------------------------------------
gi|14734071| ----------------------------------------------------------------------
gi|13938170| ----------------------------------------------------------------------
gi|18552587| ----------------------------------------------------------------------
gi|14043550| ----------------------------------------------------------------------
gi|15026974| GDTATLWCELSKAAPVEWRKGHETLRDGDRHSLRQDGSRCELQIRGLAVVDAGEYSCVCGQERTSATLTV 3860       3870       3880       3890       3900       3910       3920
             ....|....|....|....|....|....|....|....|....|....|....|....|....|....|
NOV30        ----------------------------------------------------------------------
gi|14734071| ----------------------------------------------------------------------
gi|13938170| ----------------------------------------------------------------------
gi|18552587| ----------------------------------------------------------------------
gi|14043550| ----------------------------------------------------------------------
gi|15026974| RALPARFIEDVKNQEAREGATAVLQCELSKAAPVEWRKGSETLRGGDRYSLRQDGTRCELQIHGLSVADT 3930       3940       3950       3960       3970       3980       3990
             ....|....|....|....|....|....|....|....|....|....|....|....|....|....|
NOV30        ----------------------------------------------------------------------
gi|14734071| ----------------------------------------------------------------------
gi|13938170| ----------------------------------------------------------------------
gi|18552587| ----------------------------------------------------------------------
gi|14043550| ----------------------------------------------------------------------
gi|15026974| GEYSCVCGQERTSATLTVRAPQPVFREPLQSLQAEEGSTATLQCELSEPTATVVWSKGGLQLQANGRREP 4000       4010       4020       4030       4040       4050       4060
             ....|....|....|....|....|....|....|....|....|....|....|....|....|....|
NOV30        ----------------------------------------------------------------------
gi|14734071| ----------------------------------------------------------------------
gi|13938170| ----------------------------------------------------------------------
gi|18552587| ----------------------------------------------------------------------
gi|14043550| ----------------------------------------------------------------------
gi|15026974| RLQGCTAELVLQDLQREDTGEYTCTCGSQATSATLTVTAAPVRFLRELQHQEVDEGGTAHLCCELSRAGA 4070       4080       4090       4100       4110       4120       4130
             ....|....|....|....|....|....|....|....|....|....|....|....|....|....|
NOV30        ----------------------------------------------------------------------
gi|14734071| ----------------------------------------------------------------------
gi|13938170| ----------------------------------------------------------------------
gi|18552587| ----------------------------------------------------------------------
gi|14043550| ----------------------------------------------------------------------
gi|15026974| SVEWRKGSLQLFPCAKYQMVQDGAAAELLVRGVEQEDAGDYTCDTGHTQSMASLSVRVPRPKFKTRLQSL
```

TABLE 30D-continued

Clustal W Sequence Alignment

```
                         4140       4150       4160       4170       4180       4190       4200
                    ....|....|....|....|....|....|....|....|....|....|....|....|....|....|
NOV30               ----------------------------------------------------------------------
gi|14734071|        ----------------------------------------------------------------------
gi|13938170|        ----------------------------------------------------------------------
gi|18552587|        ----------------------------------------------------------------------
gi|14043550|        ----------------------------------------------------------------------
gi|15026974|        EQETGDIARLCCQLSDAESGAVVQWLKEGVELHAGPKYEMRSQGATRELLIHQLEAKDTGEYACVTGGQK 4210       4220       4230       4240       4250       4260       4270
                    ....|....|....|....|....|....|....|....|....|....|....|....|....|....|
NOV30               ----------------------------------------------------------------------
gi|14734071|        ----------------------------------------------------------------------
gi|13938170|        ----------------------------------------------------------------------
gi|18552587|        ----------------------------------------------------------------------
gi|14043550|        ----------------------------------------------------------------------
gi|15026974|        TAASLRVTEPEVTIVRGLVDAEVTADEDVEFSCEVSRAGATGVQWCLQGLPLQSNEVTEVAVRDGRIHTL 4280       4290       4300       4310       4320       4330       4340
                    ....|....|....|....|....|....|....|....|....|....|....|....|....|....|
NOV30               ----------------------------------------------------------------------
gi|14734071|        ----------------------------------------------------------------------
gi|13938170|        ----------------------------------------------------------------------
gi|18552587|        ----------------------------------------------------------------------
gi|14043550|        ----------------------------------------------------------------------
gi|15026974|        RLKGVTPEDAGTVSFHLGNHASSAQLTVRAPEVTILEPLQDVQLSEGQDASFQCRLSRASGQEARWALGG 4350       4360       4370       4380       4390       4400       4410
                    ....|....|....|....|....|....|....|....|....|....|....|....|....|....|
NOV30               ----------------------------------------------------------------------
gi|14734071|        ----------------------------------------------------------------------
gi|13938170|        ----------------------------------------------------------------------
gi|18552587|        ----------------------------------------------------------------------
gi|14043550|        ----------------------------------------------------------------------
gi|15026974|        VPLQANEMNDITVEQGTLHLLTLHKVTLEDAGTVSFHVGTCSSEAQLKVTAKNTVVRGLENVEALEGGEA 4420       4430       4440       4450       4460       4470       4480
                    ....|....|....|....|....|....|....|....|....|....|....|....|....|....|
NOV30               ----------------------------------------------------------------------
gi|14734071|        ----------------------------------------------------------------------
gi|13938170|        ----------------------------------------------------------------------
gi|18552587|        ----------------------------------------------------------------------
gi|14043550|        ----------------------------------------------------------------------
gi|15026974|        LFECQLSQPEVAAHTWLLDDEPVRTSENAEVVFFENGLRHLLLLKNLRPQDSCRVTFLAGDMVTSAFLTV 4490       4500       4510       4520       4530       4540       4550
                    ....|....|....|....|....|....|....|....|....|....|....|....|....|....|
NOV30               ----------------------------------------------------------------------
gi|14734071|        ----------------------------------------------------------------------
gi|13938170|        ----------------------------------------------------------------------
gi|18552587|        ----------------------------------------------------------------------
gi|14043550|        ----------------------------------------------------------------------
gi|15026974|        RGWRLEILEPLKNAAVRAGAQARFTCTLSEAVPVGEASWYINGAAVQPDDSDWTVTADGSHQALLLRSAQ 4560       4570       4580       4590       4600       4610       4620
                    ....|....|....|....|....|....|....|....|....|....|....|....|....|....|
NOV30               ----------------------------------------------------------------------
gi|14734071|        ----------------------------------------------------------------------
gi|13938170|        ----------------------------------------------------------------------
gi|18552587|        ----------------------------------------------------------------------
gi|14043550|        ----------------------------------------------------------------------
gi|15026974|        PHHAGEVTFACRDAVASARLTVLGLPDPPEDAEVVAHSSHTVTLSWAAPMSDGGGGLCGYRVEVKEGATG 4630       4640       4650       4660       4670       4680       4690
                    ....|....|....|....|....|....|....|....|....|....|....|....|....|....|
NOV30               ----------------------------------------------------------------------
gi|14734071|        ----------------------------------------------------------------------
gi|13938170|        ----------------------------------------------------------------------
gi|18552587|        ----------------------------------------------------------------------
gi|14043550|        ----------------------------------------------------------------------
gi|15026974|        QWRLCHELVPGPECVVDGLAPGETYRFRVAAVGPVGAGEPVHLPQTVRLAEPPKPVPPQPSAPESRQVAA 4700       4710       4720       4730       4740       4750       4760
                    ....|....|....|....|....|....|....|....|....|....|....|....|....|....|
NOV30               ----------------------------------------------------------------------
gi|14734071|        ----------------------------------------------------------------------
gi|13938170|        ----------------------------------------------------------------------
gi|18552587|        ----------------------------------------------------------------------
gi|14043550|        ----------------------------------------------------------------------
gi|15026974|        GEDVSLELEVVAEAGEVIWHKGMERIQPGGRFEVVSQGRQQMLVIKGFTAEDQGEYHCGLAQGSICPAAA
```

TABLE 30D-continued

Clustal W Sequence Alignment

```
                  4770       4780       4790       4800       4810       4820       4830
              ....|....|....|....|....|....|....|....|....|....|....|....|....|....|
NOV30         ----------------------------------------------------------------------
gi|14734071|  ----------------------------------------------------------------------
gi|13938170|  ----------------------------------------------------------------------
gi|18552587|  ----------------------------------------------------------------------
gi|14043550|  ----------------------------------------------------------------------
gi|15026974|  TFQVALSPASVDEAPQPSLPPEAAQEGDLHLLWEALARKRRMSREPTLDSISELPEEDGRSQRLPQEAEE 4840       4850       4860       4870       4880       4890       4900
              ....|....|....|....|....|....|....|....|....|....|....|....|....|....|
NOV30         ----------------------------------------------------------------------
gi|14734071|  ----------------------------------------------------------------------
gi|13938170|  ----------------------------------------------------------------------
gi|18552587|  ----------------------------------------------------------------------
gi|14043550|  ----------------------------------------------------------------------
gi|15026974|  VAPDLSEGYSTADELARTGDADLSHTSSDDESRAGTPSLVTYLKKAGRPGTSPLASKVGAPAAPSVKPQQ 4910       4920       4930       4940       4950       4960       4970
              ....|....|....|....|....|....|....|....|....|....|....|....|....|....|
NOV30         ----------------------------------------------------------------------
gi|14734071|  ----------------------------------------------------------------------
gi|13938170|  ----------------------------------------------------------------------
gi|18552587|  ----------------------------------------------------------------------
gi|14043550|  ----------------------------------------------------------------------
gi|15026974|  QQEPLAAVRPPLGDLSTKDLGDPSMDKAAVKIQAAFKGYKVRKEMKQQEGPMFSHTFGDTEAQVGDALRL 4980       4990       5000       5010       5020       5030       5040
              ....|....|....|....|....|....|....|....|....|....|....|....|....|....|
NOV30         ----------------------------------------------------------------------
gi|14734071|  ----------------------------------------------------------------------
gi|13938170|  ----------------------------------------------------------------------
gi|18552587|  ----------------------------------------------------------------------
gi|14043550|  ----------------------------------------------------------------------
gi|15026974|  ECVVASKADVRARWLKDGVELTDGRHHHIDQLGDGTCSLLIAGLDRADAGCYTCQVSNKFGQVTHSACVV 5050       5060       5070       5080       5090       5100       5110
              ....|....|....|....|....|....|....|....|....|....|....|....|....|....|
NOV30         ----------------------------------------------------------------------
gi|14734071|  ----------------------------------------------------------------------
gi|13938170|  ----------------------------------------------------------------------
gi|18552587|  ----------------------------------------------------------------------
gi|14043550|  ----------------------------------------------------------------------
gi|15026974|  VSGSESEAESSSGGELDDAFRRAARRLHRLFRTKSPAEVSDEELFLSADEGPAEPEEPADWQTYREDEHF 5120       5130       5140       5150       5160       5170       5180
              ....|....|....|....|....|....|....|....|....|....|....|....|....|....|
NOV30         ----------------------------------------------------------------------
gi|14734071|  ----------------------------------------------------------------------
gi|13938170|  ----------------------------------------------------------------------
gi|18552587|  ----------------------------------------------------------------------
gi|14043550|  ----------------------------------------------------------------------
gi|15026974|  ICIRFEALTEARQAVTRFQEMFATLGIGVEIKLVEQGPRRVEMCISKETPAPVVPPEPLPSLLTSDAAPY 5190       5200       5210       5220       5230       5240       5250
              ....|....|....|....|....|....|....|....|....|....|....|....|....|....|
NOV30         ----------------------------------------------------------------------
gi|14734071|  ----------------------------------------------------------------------
gi|13938170|  ----------------------------------------------------------------------
gi|18552587|  ----------------------------------------------------------------------
gi|14043550|  ----------------------------------------------------------------------
gi|15026974|  FLTELQNQEVQDGYPVSFDCVVTGQPMPSVRWFKDGKLLEEDDHYMINEDQQGGHQLIITAVVPADMGVY 5260       5270       5280       5290       5300       5310       5320
              ....|....|....|....|....|....|....|....|....|....|....|....|....|....|
NOV30         ----------------------------------------------------------------------
gi|14734071|  ----------------------------------------------------------------------
gi|13938170|  ----------------------------------------------------------------------
gi|18552587|  ----------------------------------------------------------------------
gi|14043550|  ----------------------------------------------------------------------
gi|15026974|  RCLAENSMGVSSTKAELRVDLTSTDYDTAADATESSSYFSAQGYLSSREQEGTESTTDEGQLPQVVEELR 5330       5340       5350       5360       5370       5380       5390
              ....|....|....|....|....|....|....|....|....|....|....|....|....|....|
NOV30         ----------------------------------------------------------------------
gi|14734071|  ----------------------------------------------------------------------
gi|13938170|  ----------------------------------------------------------------------
gi|18552587|  ----------------------------------------------------------------------
gi|14043550|  ----------------------------------------------------------------------
gi|15026974|  DLQVAPGTRLAKFQLKVKGYPAPRLYWFKDGQPLTASAHIRMTDKKILHTLEIISVTREDSGQYAAYISN
```

TABLE 30D-continued

Clustal W Sequence Alignment

```
                 5400      5410      5420      5430      5440      5450      5460
            ....|....|....|....|....|....|....|....|....|....|....|....|....|
NOV30       ------------------------------------------------------------------
gi|14734071 ------------------------------------------------------------------
gi|13938170 ------------------------------------------------------------------
gi|18552587 ------------------------------------------------------------------
gi|14043550 ------------------------------------------------------------------
gi|15026974 AMGAAYSSARLLVRGPDEPEEKPASDVHEQLVPPRMLERFTPKKVKKGSSITFCVKVEGRPVPTVHWLRE 5470      5480      5490      5500      5510      5520      5530
            ....|....|....|....|....|....|....|....|....|....|....|....|....|
NOV30       ------------------------------------------------------------------
gi|14734071 ------------------------------------------------------------------
gi|13938170 ------------------------------------------------------------------
gi|18552587 ------------------------------------------------------------------
gi|14043550 ------------------------------------------------------------------
gi|15026974 EAERGVLWIGPDTPGYTVASSAQQHSLVLLDVGRQHQGTYTCIASNAAGQALCSASLHVSGLPKVEEQEK 5540      5550      5560      5570      5580      5590      5600
            ....|....|....|....|....|....|....|....|....|....|....|....|....|
NOV30       ------------------------------------------------------------------
gi|14734071 ------------------------------------------------------------------
gi|13938170 ------------------------------------------------------------------
gi|18552587 ------------------------------------------------------------------
gi|14043550 ------------------------------------------------------------------
gi|15026974 VKEALISTFLQGTTQAISAQGFQTASFADLGGQRKEEPLAAKEALGHLSLAEVGTEEFLQKLTSQITEMV 5610      5620      5630      5640      5650      5660      5670
            ....|....|....|....|....|....|....|....|....|....|....|....|....|
NOV30       ------------------------------------------------------------------
gi|14734071 ------------------------------------------------------------------
gi|13938170 ------------------------------------------------------------------
gi|18552587 ------------------------------------------------------------------
gi|14043550 ------------------------------------------------------------------
gi|15026974 SAKITQAKLQVPGGDSDEDSKTPSASPRHGRSRPSSSIQESSSESEDGDARGEIFDIYVVTADYLPLGAE 5680      5690      5700      5710      5720      5730      5740
            ....|....|....|....|....|....|....|....|....|....|....|....|....|
NOV30       ------------------------------------------------------------------
gi|14734071 ------------------------------------------------------------------
gi|13938170 ------------------------------------------------------------------
gi|18552587 ------------------------------------------------------------------
gi|14043550 ------------------------------------------------------------------
gi|15026974 QDAITLREGQYVEVLDAAHPLRWLVRTKPTKSSPSRQGWVSPAYLDRRLKLSPEWGAAEAPEFPGEAVSE 5750      5760      5770      5780      5790      5800      5810
            ....|....|....|....|....|....|....|....|....|....|....|....|....|
NOV30       ------------------------------------------------------------------
gi|14734071 ------------------------------------------------------------------
gi|13938170 ------------------------------------------------------------------
gi|18552587 ------------------------------------------------------------------
gi|14043550 ------------------------------------------------------------------
gi|15026974 DEYKARLSSVIQELLSSEQAFVEELQFLQSHHLQHLERCPHVPIAVAGQKAVIFRNVRDIGRFHSSFLQE 5820      5830      5840      5850      5860      5870      5880
            ....|....|....|....|....|....|....|....|....|....|....|....|....|
NOV30       ------------------------------------------------------------------
gi|14734071 ------------------------------------------------------------------
gi|13938170 ------------------------------------------------------------------
gi|18552587 ------------------------------------------------------------------
gi|14043550 ------------------------------------------------------------------
gi|15026974 LQQCDTDDDVAMCFIKNQAAFEQYLEFLVGRVQAESVVVSTAIQEFYKKYAEEALLAGDPSQPPPPPLQH 5890      5900      5910      5920      5930      5940      5950
            ....|....|....|....|....|....|....|....|....|....|....|....|....|
NOV30       ------------------------------------------------------------------
gi|14734071 ------------------------------------------------------------------
gi|13938170 ------------------------------------------------------------------
gi|18552587 ------------------------------------------------------------------
gi|14043550 ------------------------------------------------------------------
gi|15026974 YLEQPVERVQRYQALLKELIRNKARNRQNCALLEQAYAVVSALPQRAENKLHVSLMENYPGTLQALGEPI 5960      5970      5980      5990      6000      6010      6020
            ....|....|....|....|....|....|....|....|....|....|....|....|....|
NOV30       ------------------------------------------------------------------
gi|14734071 ------------------------------------------------------------------
gi|13938170 ------------------------------------------------------------------
gi|18552587 ------------------------------------------------------------------
gi|14043550 ------------------------------------------------------------------
gi|15026974 RQGHFIVWEGAPGARMPWKGHNRHVFLFRNHLVICKPRRDSRTDTVSYVFRNMMKLSSIDLNDQVEGDDR
```

TABLE 30D-continued

Clustal W Sequence Alignment

```
                  6030      6040      6050      6060      6070      6080      6090
              ....|....|....|....|....|....|....|....|....|....|....|....|....|
NOV30         ------------------------------------------------------------------
gi|14734071|  ------------------------------------------------------------------
gi|13938170|  ------------------------------------------------------------------
gi|18552587|  ------------------------------------------------------------------
gi|14043550|  ------------------------------------------------------------------
gi|15026974|  AFEVWQEREDSVRKYLLQARTAIIKSSWVKEICGIQQRLALPVWRPPDFEEELADCTAELGETVKLACRV 6100      6110      6120      6130      6140      6150      6160
              ....|....|....|....|....|....|....|....|....|....|....|....|....|
NOV30         ------------------------------------------------------------------
gi|14734071|  ------------------------------------------------------------------
gi|13938170|  ------------------------------------------------------------------
gi|18552587|  ------------------------------------------------------------------
gi|14043550|  ------------------------------------------------------------------
gi|15026974|  TGTPKPVISWYKDGKAVQVDPHHILIEDPDGSCALILDSLTGVDSGQYMCFAASAAGNCSTLGKILVQVP 6170      6180      6190      6200      6210      6220      6230
              ....|....|....|....|....|....|....|....|....|....|....|....|....|
NOV30         ------------------------------------------------------------------
gi|14734071|  ------------------------------------------------------------------
gi|13938170|  ------------------------------------------------------------------
gi|18552587|  ------------------------------------------------------------------
gi|14043550|  ------------------------------------------------------------------
gi|15026974|  PRFVNKVLASPFVEGEDAQFTCTIEGAPYPQIRWYKDGALLTTGNKFQTLSEPRSGLLVLVIRAASKEDL 6240      6250      6260      6270      6280      6290      6300
              ....|....|....|....|....|....|....|....|....|....|....|....|....|
NOV30         ------------------------------------------------------------------
gi|14734071|  ------------------------------------------------------------------
gi|13938170|  ------------------------------------------------------------------
gi|18552587|  ------------------------------------------------------------------
gi|14043550|  ------------------------------------------------------------------
gi|15026974|  GLYECELVNRLGSARASAELRIQSPMLQAQEQCHREQLVAAVEVTEQETKVPKKTVIIEETITTVVKSPR 6310      6320      6330      6340      6350      6360      6370
              ....|....|....|....|....|....|....|....|....|....|....|....|....|
NOV30         ------------------------------------------------------------------
gi|14734071|  ------------------------------------------------------------------
gi|13938170|  ------------------------------------------------------------------
gi|18552587|  ------------------------------------------------------------------
gi|14043550|  ------------------------------------------------------------------
gi|15026974|  GQRRSPSKSPSRSPSRCSASPLRPGLLAPDDLYLPGAGQPRRPEAEPGQKPVVPTLYVTEAEAHSPALPG 6380      6390      6400      6410      6420      6430      6440
              ....|....|....|....|....|....|....|....|....|....|....|....|....|
NOV30         ------------------------------------------------------------------
gi|14734071|  ------------------------------------------------------------------
gi|13938170|  ------------------------------------------------------------------
gi|18552587|  ------------------------------------------------------------------
gi|14043550|  ------------------------------------------------------------------
gi|15026974|  LSGPQPKWVEVEETIEVRVKKMGPQGVSPTTEVPRSSSGHLFTLPGATPGGDPNSNNSNNKLLAQEAWAQ 6450      6460      6470      6480      6490      6500      6510
              ....|....|....|....|....|....|....|....|....|....|....|....|....|
NOV30         ------------------------------------------------------------------
gi|14734071|  ------------------------------------------------------------------
gi|13938170|  ------------------------------------------------------------------
gi|18552587|  ------------------------------------------------------------------
gi|14043550|  ------------------------------------------------------------------
gi|15026974|  GTAMVGVREPLVFRVDARGSVDWAASGMGSLEEEGTMEEAGEEEGEDGDAFVTEESQDTHSLGDRDPKIL 6520      6530      6540      6550      6560      6570      6580
              ....|....|....|....|....|....|....|....|....|....|....|....|....|
NOV30         ------------------------------------------------------------------
gi|14734071|  ------------------------------------------------------------------
gi|13938170|  ------------------------------------------------------------------
gi|18552587|  ------------------------------------------------------------------
gi|14043550|  ------------------------------------------------------------------
gi|15026974|  THNGRMLTLADLEDYVPGEGETFHCGGPGPGAPDDPPCEVSVIQREIGEPTVGQPVLLSVGHALGPRGPL 6590      6600      6610      6620      6630      6640      6650
              ....|....|....|....|....|....|....|....|....|....|....|....|....|
NOV30         ------------------------------------------------------------------
gi|14734071|  ------------------------------------------------------------------
gi|13938170|  ------------------------------------------------------------------
gi|18552587|  ------------------------------------------------------------------
gi|14043550|  ------------------------------------------------------------------
gi|15026974|  GLFRPEPRGASPPGPQVRSLEGTSFLLREAPARPVGSAPWTQSFCTRIRRSADSGQSSFTTELSTQTVNF
```

TABLE 30D-continued

Clustal W Sequence Alignment

```
                       6660       6670
                ....|....|....|....|...
NOV30           ----------------------
gi|14734071     ----------------------
gi|13938170     ----------------------
gi|18552587     ----------------------
gi|14043550     ----------------------
gi|15026974     GTVGETVTLHICPDRDGDEAAQP
```

Tables 30E and 30F list the domain description from DOMAIN analysis results against NOV30. This indicates that the NOV30 sequence has properties similar to those of other proteins known to contain these domains.

TABLE 30E

Domain Analysis of NOV30

```
gnl Smart|smart00409, IG, Immunoglobulin (SEQ ID NO:291)
CD-Length = 86 residues, 100.0% aligned
Score = 57.4 bits (137), Expect = 1e-09
Query:   171 PRSQWVLRGAEVVLTCRAGGLPEPTLYWEKLGMALDEVWDSSHFALQPGRAE-DGPGASL  229
              |  |  |  |  | |+|  |  |  ||+ |                 + ||     | +
Sbjct:     1 PPSVTVKEGESVTLSCEASGNPPPTVTW---------YKQGGKLLAESGRFSVSRSGGNS   51

Query:   230 ALRILAARLPDSGVYVCHARNAHGHAQAGALLQVL                           264
              | |      ||| | | | |+ | | +|   | ||
Sbjct:    52 TLTISNVTPEDSGTYTCAATNSSGSASSGTTLTVL                            86
```

TABLE 30F

Domain Analysis of NOV30

```
gnl Smart|smart00408, IGc2, Immunoglobulin C-2 Type (SEQ ID NO:292)
CD-Length = 63 residues, 96.8% aligned
Score = 48.1 bits (113), Expect = 6e-07
Query:   179 GAEVVLTCRAGGLPEPTLYWEKDGMALDE-VWDSSEFALQPGRAEDGPGASLALRILAAR  237
              |    |||| |  |  | +  |  |||   |     +|    |
Sbjct:     3 GESVTLTCPASGDPVPNITWLKDGKPLPESRVVASGSTLTIKNVSLE-------------   49

Query:   238 LPDSGVYVCHARNAHG                                              253
              | | |+|    ||  | +  |
Sbjct:    50 --DSGLYTCVAPNSVG                                               63
```

NOV30 described here has homology to mac25, a potent tumor inhibitor. Mac25 is a follistatin (FS)-like protein that has a growth-suppressing effect on a p53-deficient osteosarcoma cell line (Saos-2). The protein exhibits a strong homology to FS, an activin-binding protein, and part of its sequence includes the consensus sequence of the member of the Kazal serine protease inhibitor family. The mac25 protein was localized in the cytoplasm and secreted into culture medium (Kato, Mol Med 6(2):126–35, 2000). Addition of recombinant mac25 protein (10-7 M) into the culture medium induced significant suppression of the growth of human cervical carcinoma cells (HeLa) and murine embryonic carcinoma cells (P19), as well as osteosarcoma cells (Saos-2). The mac25 protein was co-immunoprecipitated with activin A, a result that suggests that mac25 may be a secreted tumor-suppressor that binds activin A. The mac25 exhibits homology to insulin-like growth factor-binding proteins (IGF-BPs) and to fibroblast growth factor receptor. The multi-functional nature of mac25 protein may be important for growth-suppression and/or cellular senescence (Kato, 2000).

The mac25 is strongly induced in senescent epithelial cells, whereas CTGF stimulates angiogenesis and wound healing. Using in situ hybridization and immunohistochemistry, Wandji et al. examined the possibilities that mac25 is inhibited, whereas CTGF is induced during active periods of follicular development and luteogenesis (Wandji et al., Endocrinology 141(7):2648–57, 2000). Ovaries were collected during the follicular and early luteal phases from prostaglandin F2alpha-treated mature pigs and from slaughterhouse sows. CTGF transcripts were induced during the late preantral stage in granulosa and theca cells concomitantly with the appearance of endothelial cells in the theca. CTGF mRNA expression increased in granulosa cells to a maximum (P<0.01) in mid-antral follicles but was down regulated (P<0.01) in preovulatory follicles. In contrast, granulosa cell mac25 mRNA expression was undetectable between the preantral and mid-antral stage but was strongly induced in terminally differentiated granulosa cells of preovulatory follicles. CTGF mRNA and peptide were also detected in the theca externa/interstitium and in vascular endothelial cells of ovarian blood vessels, whereas mac25 transcripts, which were also abundant in ovarian blood vessels increased in the theca interna with follicular development. Transcripts of cyclin D 1, a marker of cell proliferation, appeared during the early antral stage and were moderate in granulosa cells but abundant in capillary endothelial cells in the theca interna, underneath the basement membrane. Following ovulation, CTGF and cyclin D1 mRNAs were associated with the migration of endothelial cells into the CL. Subsequently, there was a marked up-regulation of CTGF mRNA expression in granulosa luteins concomitantly with an increase in endothelial cell proliferation within the CL. Those data suggested that CTGF may promote ovarian cell growth and blood vessel formation during follicular and luteal development whereas mac25, a tumor inhibitor, may promote terminal differentiation of granulosa cells in preovulatory follicles (Wandji et al., 2000).

It is important to know the regulation of the expression of the mac25 gene because of its reduced expression in several cancer cells and of its induction by some hormonal factors. Kanemitsu et al. cloned the promoter region of the murine mac25 gene and found five repeats of CCAAT sequences, four Sp1 sites, a TATA-like sequence, and an initiator (INR) sequence. Analysis using luciferase reporter plasmids indicated that CCAAT repeats have a strong enhancer activity and the second to fourth Sp1 sites are essential for basal activity of the expression of the mac25 gene. The 1 kb region that contains the promoter and exon 1 of the mac25 gene was in a typical CpG island. As hypermethylation and reduced expression of the mac25 gene were reported in murine liver tumors, methylation of this CpG island may be directly associated with the expression of the mac25 gene and tumorigenesis (Kanemitsu et al., Biochem Biophys Res Commun 279(1):251–7, 2000).

Komatsu et al., used restriction landmark genomic scanning for methylation (RLGS-M) to detect alterations in DNA methylation associated with murine SV40 T/t antigen-induced hepatocarcinogenesis (Komatsu et al., Biochem Biophys Res Commun 267(1):109–17, 2000). An altered locus/spot (S130) was cloned and found to correspond to sequences in the 5' flanking region and 5' portion of the cDNA for the murine mac25/insulin-like growth factor binding protein-7 (Igfbp-7) gene. IGFBPs are believed to be capable of binding insulin, Igf1, and Igf2 and modulating mitogenic effects. Previous studies have shown that Igf2 has an important role in promoting liver tumorigenesis. Quantitative PCR was used to access the methylation status of the NotI site just 5' to the coding region and the expression level of the mac25/igfbp-7 gene. The results indicated that the degree of methylation was inversely related to the expression level and is consistent with a role for DNA methylation in silencing mac25/Igfbp-7 gene expression and function for mac25/Igfbp-7 as a tumor suppressor gene (Komatsu et al., 2000).

Because of the homology to mac25/IGFBP7, the NOV30 described here will have useful properties and functions similar to these genes.

The NOV30 nucleic acid of the invention encoding a mac25/IGFBP7-like protein includes the nucleic acid whose sequence is provided in Table 30A, or a fragment thereof. The invention also includes a mutant or variant nucleic acid any of whose bases may be changed from the corresponding base shown in Table 30A while still encoding a protein that maintains its mac25/IGFBP7-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject. In the mutant or variant nucleic acids, and their complements, up to about 28% of the NOV30 residues may be so changed.

The NOV30 protein of the invention includes the mac25/IGFBP7-like protein whose sequence is provided in Table 30B. The invention also includes a mutant or variant protein any of whose residues may be changed from the corresponding residue shown in Table 30B while still encoding a protein that maintains its mac25/IGFBP7-like activities and physiological functions, or a functional fragment thereof. In the mutant or variant protein, up to about 70% of the NOV30 bases may be so changed.

The NOV30 nucleic acids and proteins of the invention are useful in potential diagnostic and therapeutic applications implicated in various diseases and disorders described below and/or other pathologies. For example, the compositions of the present invention will have efficacy for treatment of patients suffering from: Von Hippel-Lindau (VHL) syndrome, Alzheimer's disease, stroke, tuberous sclerosis, hypercalceimia, Parkinson's disease, Huntington's disease, cerebral palsy, epilepsy, Lesch-Nyhan syndrome, multiple sclerosis, ataxia-telangiectasia, leukodystrophies, behavioral disorders, addiction, anxiety, pain, neurodegeneration, fertility, hypogonadism, endometriosis, hemophilia, hypercoagulation, idiopathic thrombocytopenic purpura, immunodeficiencies, graft versus host disease and other diseases, disorders and conditions of the like.

NOV30 nucleic acids and polypeptides are further useful in the generation of antibodies that bind immunospecifically to the novel substances of the invention for use in therapeutic or diagnostic methods. These antibodies may be generated according to methods known in the art, using prediction from hydrophobicity charts, as described in the "Anti-NOVX Antibodies" section below. For example the disclosed NOV30 protein have multiple hydrophilic regions, each of which can be used as an immunogen. This novel protein also has value in development of powerful assay system for functional analysis of various human disorders, which will help in understanding of pathology of the disease and development of new drug targets for various disorders.

NOVX Nucleic Acids and Polypeptides

One aspect of the invention pertains to isolated nucleic acid molecules that encode NOVX polypeptides or biologically active portions thereof. Also included in the invention are nucleic acid fragments sufficient for use as hybridization probes to identify NOVX-encoding nucleic acids (e.g., NOVX mRNAs) and fragments for use as PCR primers for the amplification and/or mutation of NOVX nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule may be single-stranded or double-stranded, but preferably is comprised double-stranded DNA.

An NOVX nucleic acid can encode a mature NOVX polypeptide. As used herein, a "mature" form of a polypeptide or protein disclosed in the present invention is the product of a naturally occurring polypeptide or precursor form or proprotein. The naturally occurring polypeptide, precursor or proprotein includes, by way of nonlimiting example, the full-length gene product, encoded by the corresponding gene. Alternatively, it may be defined as the polypeptide, precursor or proprotein encoded by an ORF described herein. The product "mature" form arises, again by way of nonlimiting example, as a result of one or more naturally occurring processing steps as they may take place within the cell, or host cell, in which the gene product arises. Examples of such processing steps leading to a "mature" form of a polypeptide or protein include the cleavage of the N-terminal methionine residue encoded by the initiation codon of an ORF, or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

The term "probes", as utilized herein, refers to nucleic acid sequences of variable length, preferably between at least about 10 nucleotides (nt), 100 nt, or as many as approximately, e.g., 6,000 nt, depending upon the specific use. Probes are used in the detection of identical, similar, or complementary nucleic acid sequences. Longer length probes are generally obtained from a natural or recombinant source, are highly specific, and much slower to hybridize than shorter-length oligomer probes. Probes may be single- or double-stranded and designed to have specificity in PCR, membrane-based hybridization technologies, or ELISA-like technologies.

The term "isolated" nucleic acid molecule, as utilized herein, is one, which is separated from other nucleic acid molecules which are present in the natural source of the nucleic acid. Preferably, an "isolated" nucleic acid is free of sequences which naturally flank the nucleic acid (i.e., sequences located at the 5'- and 3'-termini of the nucleic acid) in the genomic DNA of the organism from which the nucleic acid is derived. For example, in various embodiments, the isolated NOVX nucleic acid molecules can contain less than about 5 kb, 4 kb, 3 kb, 2 kb, 1 kb, 0.5 kb or 0.1 kb of nucleotide sequences which naturally flank the nucleic acid molecule in genomic DNA of the cell/tissue from which the nucleic acid is derived (e.g., brain, heart, liver, spleen, etc.). Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the invention, e.g., a nucleic acid molecule having the nucleotide sequence SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93, or a complement of this aforementioned nucleotide sequence, can be isolated using standard molecular biology techniques and the sequence information provided herein. Using all or a portion of the nucleic acid sequence of SEQ ID NOS:1, 3, 5, 7, 9, 11, 13, 15, 17, 19, 21, 23, 25, 27, 29, 31, 33, 35, 37,3 9, 41, 43, 45, 47, 49, 51, 53, 55, 57, 59, 61, 63, 65, 67, 69, 71, 73, 75, 77, 79, 81, 83, 85, 87, 89, 91 and 93 as a hybridization probe, NOVX molecules can be isolated using standard hybridization and cloning techniques (e.g. as described in Sambrook, et al., (eds.), MOLECULAR CLONING: A LABORATORY MANUAL $2^{nd}$ Ed., Cold Spring Harbor Laboratory Press, Cold Spring Harbor, N.Y., 1989; and Ausubel, et al., (eds.), CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to NOVX nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment of the invention, an oligonucleotide comprising a nucleic acid molecule less than 100 nt in length would further comprise at least 6 contiguous nucleotides SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93, or a complement thereof. Oligonucleotides may be chemically synthesized and may also be used as probes.

In another embodiment, an isolated nucleic acid molecule of the invention comprises a nucleic acid molecule that is a complement of the nucleotide sequence shown in SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93, or a portion of this nucleotide sequence (e.g., a fragment that can be used as a probe or primer or a fragment encoding a biologically-active portion of an NOVX polypeptide). A nucleic acid molecule that is complementary to the nucleotide sequence shown NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93 is one that is sufficiently complementary to the nucleotide sequence shown NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93 that it can hydrogen bond with little or no mismatches to the nucleotide sequence shown SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type. Homologs are nucleic acid sequences or amino acid sequences of a particular gene that are derived from different species.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, or 95% identity (with a preferred identity of 80–95%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below.

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of NOVX polypeptides. Isoforms can be expressed in different tissues of the same organism as a result of, for example, alternative splicing of RNA. Alternatively, isoforms can be encoded by different genes. In the invention, homologous nucleotide sequences include nucleotide sequences encoding for an NOVX polypeptide of species other than humans, including, but not limited to: vertebrates, and thus can include, e.g., frog, mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the exact nucleotide sequence encoding human NOVX protein. Homologous nucleic acid sequences include those nucleic acid sequences that encode conservative amino acid substitutions (see below) in SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93, as well as a polypeptide possessing NOVX biological activity. Various biological activities of the NOVX proteins are described below.

An NOVX polypeptide is encoded by the open reading frame ("ORF") of an NOVX nucleic acid. An ORF corresponds to a nucleotide sequence that could potentially be translated into a polypeptide. A stretch of nucleic acids comprising an ORF is uninterrupted by a stop codon. An ORF that represents the coding sequence for a full protein begins with an ATG "start" codon and terminates with one of the three "stop" codons, namely, TAA, TAG, or TGA. For the purposes of this invention, an ORF may be any part of a coding sequence, with or without a start codon, a stop codon, or both. For an ORF to be considered as a good candidate for coding for a bona fide cellular protein, a minimum size requirement is often set, e.g., a stretch of DNA that would encode a protein of 50 amino acids or more.

The nucleotide sequences determined from the cloning of the human NOVX genes allows for the generation of probes and primers designed for use in identifying and/or cloning NOVX homologues in other cell types, e.g. from other tissues, as well as NOVX homologues from other vertebrates. The probe/primer typically comprises substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93; or an anti-sense strand nucleotide sequence of SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93; or of a naturally occurring mutant of SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93.

Probes based on the human NOVX nucleotide sequences can be used to detect transcripts or genomic sequences encoding the same or homologous proteins. In various embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissues which mis-express an NOVX protein, such as by measuring a level of an NOVX-encoding nucleic acid in a sample of cells from a subject e.g., detecting NOVX mRNA levels or determining whether a genomic NOVX gene has been mutated or deleted.

"A polypeptide having a biologically-active portion of an NOVX polypeptide" refers to polypeptides exhibiting activity similar, but not necessarily identical to, an activity of a polypeptide of the invention, including mature forms, as measured in a particular biological assay, with or without dose dependency. A nucleic acid fragment encoding a "biologically-active portion of NOVX" can be prepared by isolating a portion SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93, that encodes a polypeptide having an NOVX biological activity (the biological activities of the NOVX proteins are described below), expressing the encoded portion of NOVX protein (e.g., by recombinant expression in vitro) and assessing the activity of the encoded portion of NOVX.

NOVX Nucleic Acid and Polypeptide Variants

The invention further encompasses nucleic acid molecules that differ from the nucleotide sequences shown in SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93 due to degeneracy of the genetic code and thus encode the same NOVX proteins as that encoded by the nucleotide sequences shown in SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93. In another embodiment, an isolated nucleic acid molecule of the invention has a nucleotide sequence encoding a protein having an amino acid sequence shown in SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94.

In addition to the human NOVX nucleotide sequences shown in SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93, it will be appreciated by those skilled in the art that DNA sequence polymorphisms that lead to changes in the amino acid sequences of the NOVX polypeptides may exist within a population (e.g., the human population). Such genetic polymorphism in the NOVX genes may exist among individuals within a population due to natural allelic variation. As used herein, the terms "gene" and "recombinant gene" refer to nucleic acid molecules comprising an open reading frame (ORF) encoding an NOVX protein, preferably a vertebrate NOVX protein. Such natural allelic variations can typically result in 1–5% variance in the nucleotide sequence of the NOVX genes. Any and all such nucleotide variations and resulting amino acid polymorphisms in the NOVX polypeptides, which are the result of natural allelic variation and that do not alter the functional activity of the NOVX polypeptides, are intended to be within the scope of the invention.

Moreover, nucleic acid molecules encoding NOVX proteins from other species, and thus that have a nucleotide sequence that differs from the human SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93 are intended to be within the scope of the invention. Nucleic acid molecules corresponding to natural allelic variants and homologues of the NOVX cDNAs of the invention can be isolated based on their homology to the human NOVX nucleic acids disclosed herein using the human cDNAs, or a portion thereof, as a hybridization probe according to standard hybridization techniques under stringent hybridization conditions.

Accordingly, in another embodiment, an isolated nucleic acid molecule of the invention is at least 6 nucleotides in length and hybridizes under stringent conditions to the nucleic acid molecule comprising the nucleotide sequence of SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93. In another embodiment, the nucleic acid is at least 10, 25, 50, 100, 250, 500, 750, 1000, 1500, or 2000 or more nucleotides in length. In yet another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding NOVX proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in Ausubel, et al., (eds.), CURRENT PROTOCOLS IN MOLECULAR BIOLOGY, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2×SSC, 0.01% BSA at 50° C. An isolated nucleic acid molecule of the invention that hybridizes under stringent conditions to the sequences SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93, or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known within the art. See, e.g., Ausubel, et al. (eds.), 1993, CURRENT PROTOCOLS IN MOLECULAR BIOLOGY, John Wiley & Sons, NY, and Kriegler, 1990; GENE TRANSFER AND EXPRESSION, A LABORATORY MANUAL, Stockton Press, NY.

In a third embodiment, a nucleic acid that is hybridizable to the nucleic acid molecule comprising the nucleotide sequences SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel, et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981. *Proc Natl Acad Sci USA* 78: 6789–6792.

Conservative Mutations

In addition to naturally-occurring allelic variants of NOVX sequences that may exist in the population, the skilled artisan will further appreciate that changes can be introduced by mutation into the nucleotide sequences SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93, thereby leading to changes in the amino acid sequences of the encoded NOVX proteins, without altering the functional ability of said NOVX proteins. For example, nucleotide substitutions leading to amino acid substitutions at "non-essential" amino acid residues can be made in the sequence SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94. A "non-essential" amino acid residue is a residue that can be altered from the wild-type sequences of the NOVX proteins without altering their biological activity, whereas an "essential" amino acid residue is required for such biological activity. For example, amino acid residues that are conserved among the NOVX proteins of the invention are predicted to be particularly non-amenable to alteration. Amino acids for which conservative substitutions can be made are well-known within the art.

Another aspect of the invention pertains to nucleic acid molecules encoding NOVX proteins that contain changes in amino acid residues that are not essential for activity. Such NOVX proteins differ in amino acid sequence from SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93 yet retain biological activity. In one embodiment, the isolated nucleic acid molecule comprises a nucleotide sequence encoding a protein, wherein the protein comprises an amino acid sequence at least about 45% homologous to the amino acid sequences SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94. Preferably, the protein encoded by the nucleic acid molecule is at least about 60% homologous to SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94; more preferably at least about 70% homologous SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94; still more preferably at least about 80% homologous to SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94; even more preferably at least about 90% homologous to SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94; and most preferably at least about 95% homologous to SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94.

An isolated nucleic acid molecule encoding an NOVX protein homologous to the protein of SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94 can be created by introducing one or more nucleotide substitutions, additions or deletions into the nucleotide sequence of SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93, such that one or more amino acid substitutions, additions or deletions are introduced into the encoded protein.

Mutations can be introduced into SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93 by standard techniques, such as site-directed mutagenesis and PCR-mediated mutagenesis. Preferably, conservative amino acid substitutions are made at one or more predicted, non-essential amino acid residues. A "conservative amino acid substitution" is one in which the amino acid residue is replaced with an amino acid residue having a similar side chain. Families of amino acid residues having similar side chains have been defined within the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g. threonine, valine, isoleucine) and aromatic side chains (e.g., tyrosine, phenylalanine, tryptophan, histidine). Thus, a predicted non-essential amino acid residue in the NOVX protein is replaced with another amino acid residue from the same side chain family. Alternatively, in another embodiment, mutations can be introduced randomly along all or part of an NOVX coding sequence, such as by saturation mutagenesis, and the resultant mutants can be screened for NOVX biological activity to identify mutants that retain activity. Following mutagenesis SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93, the encoded protein can be expressed by any recombinant technology known in the art and the activity of the protein can be determined.

The relatedness of amino acid families may also be determined based on side chain interactions. Substituted amino acids may be fully conserved "strong" residues or fully conserved "weak" residues. The "strong" group of conserved amino acid residues may be any one of the following groups: STA, NEQK, NHQK, NDEQ, QHRK, MILV, MILF, HY, FYW, wherein the single letter amino acid codes are grouped by those amino acids that may be substituted for each other. Likewise, the "weak" group of conserved residues may be any one of the following: CSA, ATV, SAG, STNK, STPA, SGND, SNDEQK, NDEQHK, NEQHRK, HFY, wherein the letters within each group represent the single letter amino acid code.

In one embodiment, a mutant NOVX protein can be assayed for (i) the ability to form protein:protein interactions with other NOVX proteins, other cell-surface proteins, or biologically-active portions thereof, (ii) complex formation between a mutant NOVX protein and an NOVX ligand; or (iii) the ability of a mutant NOVX protein to bind to an intracellular target protein or biologically-active portion thereof; (e.g. avidin proteins).

In yet another embodiment, a mutant NOVX protein can be assayed for the ability to regulate a specific biological function (e.g., regulation of insulin release).

Antisense Nucleic Acids

Another aspect of the invention pertains to isolated antisense nucleic acid molecules that are hybridizable to or complementary to the nucleic acid molecule comprising the nucleotide sequence of SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93, or fragments, analogs or derivatives thereof. An "antisense" nucleic acid comprises a nucleotide sequence that is complementary to a "sense" nucleic acid encoding a protein (e.g., complementary to the coding strand of a double-stranded cDNA molecule or complementary to an mRNA sequence). In specific aspects, antisense nucleic acid molecules are provided that comprise a sequence complementary to at least about 10, 25, 50, 100, 250 or 500 nucleotides or an entire NOVX coding strand, or to only a portion thereof. Nucleic acid molecules encoding fragments, homologs, derivatives and analogs of an NOVX protein of SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94, or antisense nucleic acids complementary to an NOVX nucleic acid sequence of SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93, are additionally provided.

In one embodiment, an antisense nucleic acid molecule is antisense to a "coding region" of the coding strand of a nucleotide sequence encoding an NOVX protein. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding the NOVX protein. The term "noncoding region" refers to 5' and 3' sequences which flank the coding region that are not translated into amino acids (i.e., also referred to as 5' and 3' untranslated regions).

Given the coding strand sequences encoding the NOVX protein disclosed herein, antisense nucleic acids of the invention can be designed according to the rules of Watson and Crick or Hoogsteen base pairing. The antisense nucleic acid molecule can be complementary to the entire coding region of NOVX mRNA, but more preferably is an oligonucleotide that is antisense to only a portion of the coding or noncoding region of NOVX mRNA. For example, the antisense oligonucleotide can be complementary to the region surrounding the translation start site of NOVX mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally-occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used).

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an NOVX protein to thereby inhibit expression of the protein (e.g., by inhibiting transcription and/or translation). The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface (e.g., by linking the antisense nucleic acid molecules to peptides or antibodies that bind to cell surface receptors or antigens). The antisense nucleic acid molecules can also be delivered to cells using the vectors described herein. To achieve sufficient nucleic acid molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other. See, e.g., Gaultier, et al., 1987. *Nucl. Acids*

Res. 15: 6625–6641. The antisense nucleic acid molecule can also comprise a 2'-o-methylribonucleotide (See, e.g., Inoue, et al. 1987. *Nucl. Acids Res.* 15: 6131–6148) or a chimeric RNA-DNA analogue (See, e.g., Inoue, et al., 1987. *FEBS Lett.* 215: 327–330.

Ribozymes and PNA Moieties

Nucleic acid modifications include, by way of non-limiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

In one embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes as described in Haselhoff and Gerlach 1988. *Nature* 334: 585–591) can be used to catalytically cleave NOVX mRNA transcripts to thereby inhibit translation of NOVX mRNA. A ribozyme having specificity for an NOVX-encoding nucleic acid can be designed based upon the nucleotide sequence of an NOVX cDNA disclosed herein (i.e., SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93). For example, a derivative of a *Tetrahymena* L-19 IVS RNA can be constructed in which the nucleotide sequence of the active site is complementary to the nucleotide sequence to be cleaved in an NOVX-encoding mRNA. See, e.g., U.S. Pat. No. 4,987,071 to Cech, et al. and U.S. Pat. No. 5,116,742 to Cech, et al. NOVX mRNA can also be used to select a catalytic RNA having a specific ribonuclease activity from a pool of RNA molecules. See, e.g., Bartel et al., (1993) *Science* 261:1411–1418.

Alternatively, NOVX gene expression can be inhibited by targeting nucleotide sequences complementary to the regulatory region of the NOVX nucleic acid (e.g., the NOVX promoter and/or enhancers) to form triple helical structures that prevent transcription of the NOVX gene in target cells. See, e.g., Helene, 1991. *Anticancer Drug Des.* 6: 569–84; Helene, et al. 1992. *Ann. N.Y. Acad. Sci.* 660: 27–36; Maher, 1992. *Bioassays* 14: 807–15.

In various embodiments, the NOVX nucleic acids can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids. See, e.g., Hyrup, et al., 1996. *Bioorg Med Chem* 4: 5–23. As used herein, the terms "peptide nucleic acids" or "PNAs" refer to nucleic acid mimics (e.g., DNA mimics) in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup, et al., 1996. supra; Perry-O'Keefe, et al., 1996. *Proc. Natl. Acad. Sci. USA* 93: 14670–14675.

PNAs of NOVX can be used in therapeutic and diagnostic applications. For example, PNAs can be used as antisense or antigene agents for sequence-specific modulation of gene expression by, e.g., inducing transcription or translation arrest or inhibiting replication. PNAs of NOVX can also be used, for example, in the analysis of single base pair mutations in a gene (e.g., PNA directed PCR clamping; as artificial restriction enzymes when used in combination with other enzymes, e.g., $S_1$ nucleases (See, Hyrup, et al., 1996. supra); or as probes or primers for DNA sequence and hybridization (See, Hyrup, et al., 1996, supra; Perry-O'Keefe, et al., 1996. supra).

In another embodiment, PNAs of NOVX can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of NOVX can be generated that may combine the advantageous properties of PNA and DNA. Such chimeras allow DNA recognition enzymes (e.g., RNase H and DNA polymerases) to interact with the DNA portion while the PNA portion would provide high binding affinity and specificity. PNA-DNA chimeras can be linked using linkers of appropriate lengths selected in terms of base stacking, number of bonds between the nucleobases, and orientation (see, Hyrup, et al., 1996. supra). The synthesis of PNA-DNA chimeras can be performed as described in Hyrup, et al., 1996. supra and Finn, et al., 1996. *Nucl Acids Res* 24: 3357–3363. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA. See, e.g., Mag, et al., 1989. *Nucl Acid Res* 17: 5973–5988. PNA monomers are then coupled in a stepwise manner to produce a chimeric molecule with a 5' PNA segment and a 3' DNA segment. See, e.g., Finn, et al., 1996. supra. Alternatively, chimeric molecules can be synthesized with a 5' DNA segment and a 3' PNA segment. See, e.g., Petersen, et al., 1975. *Bioorg. Med. Chem. Lett.* 5: 1119–11124.

In other embodiments, the oligonucleotide may include other appended groups such as peptides (e.g., for targeting host cell receptors in vivo), or agents facilitating transport across the cell membrane (see, e.g., Letsinger, et al., 1989. *Proc. Natl. Acad. Sci. U.S.A.* 86: 6553–6556; Lemaitre, et al., 1987. *Proc. Natl. Acad. Sci.* 84: 648–652; PCT Publication No. WO88/09810) or the blood-brain barrier (see, e.g., PCT Publication No. WO 89/10134). In addition, oligonucleotides can be modified with hybridization triggered cleavage agents (see, e.g., Krol, et al., 1988. *BioTechniques* 6:958–976) or intercalating agents (see, e.g., Zon, 1988. *Pharm. Res.* 5: 539–549). To this end, the oligonucleotide may be conjugated to another molecule, e.g., a peptide, a hybridization triggered cross-linking agent, a transport agent, a hybridization-triggered cleavage agent, and the like.

NOVX Polypeptides

A polypeptide according to the invention includes a polypeptide including the amino acid sequence of NOVX polypeptides whose sequences are provided in SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94. The invention also includes a mutant or variant protein any of whose residues may be changed from the corresponding residues shown in SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94 while still encoding a protein that maintains its NOVX activities and physiological functions, or a functional fragment thereof.

In general, an NOVX variant that preserves NOVX-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated NOVX proteins, and biologically-active portions thereof, or derivatives, fragments, analogs or homologs thereof. Also provided are polypeptide fragments suitable for use as immunogens to raise anti-NOVX antibodies. In one embodiment, native NOVX proteins can be isolated from cells or tissue sources by an appropriate purification scheme using standard protein purification techniques. In another embodiment, NOVX proteins are produced by recombinant DNA techniques. Alternative to recombinant expression, an NOVX protein or polypeptide can be synthesized chemically using standard peptide synthesis techniques.

An "isolated" or "purified" polypeptide or protein or biologically-active portion thereof is substantially free of cellular material or other contaminating proteins from the cell or tissue source from which the NOVX protein is derived, or substantially free from chemical precursors or other chemicals when chemically synthesized. The language "substantially free of cellular material" includes preparations of NOVX proteins in which the protein is separated from cellular components of the cells from which it is isolated or recombinantly-produced. In one embodiment, the language "substantially free of cellular material" includes preparations of NOVX proteins having less than about 30% (by dry weight) of non-NOVX proteins (also referred to herein as a "contaminating protein"), more preferably less than about 20% of non-NOVX proteins, still more preferably less than about 10% of non-NOVX proteins, and most preferably less than about 5% of non-NOVX proteins. When the NOVX protein or biologically-active portion thereof is recombinantly-produced, it is also preferably substantially free of culture medium, i.e., culture medium represents less than about 20%, more preferably less than about 10%, and most preferably less than about 5% of the volume of the NOVX protein preparation.

The language "substantially free of chemical precursors or other chemicals" includes preparations of NOVX proteins in which the protein is separated from chemical precursors or other chemicals that are involved in the synthesis of the protein. In one embodiment, the language "substantially free of chemical precursors or other chemicals" includes preparations of NOVX proteins having less than about 30% (by dry weight) of chemical precursors or non-NOVX chemicals, more preferably less than about 20% chemical precursors or non-NOVX chemicals, still more preferably less than about 10% chemical precursors or non-NOVX chemicals, and most preferably less than about 5% chemical precursors or non-NOVX chemicals.

Biologically-active portions of NOVX proteins include peptides comprising amino acid sequences sufficiently homologous to or derived from the amino acid sequences of the NOVX proteins (e.g., the amino acid sequence shown in SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94) that include fewer amino acids than the full-length NOVX proteins, and exhibit at least one activity of an NOVX protein. Typically, biologically-active portions comprise a domain or motif with at least one activity of the NOVX protein. A biologically-active portion of an NOVX protein can be a polypeptide which is, for example, 10, 25, 50, 100 or more amino acid residues in length.

Moreover, other biologically-active portions, in which other regions of the protein are deleted, can be prepared by recombinant techniques and evaluated for one or more of the functional activities of a native NOVX protein.

In an embodiment, the NOVX protein has an amino acid sequence shown SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94. In other embodiments, the NOVX protein is substantially homologous to SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94, and retains the functional activity of the protein of SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94, yet differs in amino acid sequence due to natural allelic variation or mutagenesis, as described in detail, below. Accordingly, in another embodiment, the NOVX protein is a protein that comprises an amino acid sequence at least about 45% homologous to the amino acid sequence SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94, and retains the functional activity of the NOVX proteins of SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94.

Determining Homology Between Two or More Sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch, 1970. *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides NOVX chimeric or fusion proteins. As used herein, an NOVX "chimeric protein" or "fusion protein" comprises an NOVX polypeptide operatively-linked to a non-NOVX polypeptide. An "NOVX polypeptide" refers to a polypeptide having an amino acid sequence corresponding to an NOVX protein SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94, whereas a "non-NOVX polypeptide" refers to a polypeptide having an amino acid sequence corresponding to a protein that is not substantially homologous to the NOVX protein, e.g., a protein that is different from the NOVX protein and that is derived from the same or a different organism. Within an NOVX fusion protein the NOVX polypeptide can correspond to all or a portion of an NOVX protein. In one embodiment, an NOVX fusion protein comprises at least one biologically-active portion of an NOVX protein. In another embodiment, an NOVX fusion protein comprises at least two biologically-active portions of an NOVX protein. In yet another embodiment, an NOVX fusion protein comprises at least three biologically-active portions of an NOVX protein. Within the fusion protein, the term "operatively-linked" is intended to indicate that the NOVX polypeptide and the non-NOVX polypeptide are fused in-frame with one another. The non-NOVX polypeptide can be fused to the N-terminus or C-terminus of the NOVX polypeptide.

In one embodiment, the fusion protein is a GST-NOVX fusion protein in which the NOVX sequences are fused to the C-terminus of the GST (glutathione S-transferase) sequences. Such fusion proteins can facilitate the purification of recombinant NOVX polypeptides.

In another embodiment, the fusion protein is an NOVX protein containing a heterologous signal sequence at its N-terminus. In certain host cells (e.g., mammalian host cells), expression and/or secretion of NOVX can be increased through use of a heterologous signal sequence.

In yet another embodiment, the fusion protein is an NOVX-immunoglobulin fusion protein in which the NOVX sequences are fused to sequences derived from a member of the immunoglobulin protein family. The NOVX-immunoglobulin fusion proteins of the invention can be incorporated into pharmaceutical compositions and administered to a subject to inhibit an interaction between an NOVX ligand and an NOVX protein on the surface of a cell, to thereby suppress NOVX-mediated signal transduction in vivo. The NOVX-immunoglobulin fusion proteins can be used to affect the bioavailability of an NOVX cognate ligand. Inhibition of the NOVX ligand/NOVX interaction may be useful therapeutically for both the treatment of proliferative and differentiative disorders, as well as modulating (e.g. promoting or inhibiting) cell survival. Moreover, the NOVX-immunoglobulin fusion proteins of the invention can be used as immunogens to produce anti-NOVX antibodies in a subject, to purify NOVX ligands, and in screening assays to identify molecules that inhibit the interaction of NOVX with an NOVX ligand.

An NOVX chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel, et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). An NOVX-encoding nucleic acid can be cloned into such an expression vector such that the fusion moiety is linked in-frame to the NOVX protein.

NOVX Agonists and Antagonists

The invention also pertains to variants of the NOVX proteins that function as either NOVX agonists (i.e., mimetics) or as NOVX antagonists. Variants of the NOVX protein can be generated by mutagenesis (e.g., discrete point mutation or truncation of the NOVX protein). An agonist of the NOVX protein can retain substantially the same, or a subset of, the biological activities of the naturally occurring form of the NOVX protein. An antagonist of the NOVX protein can inhibit one or more of the activities of the naturally occurring form of the NOVX protein by, for example, competitively binding to a downstream or upstream member of a cellular signaling cascade which includes the NOVX protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the NOVX proteins.

Variants of the NOVX proteins that function as either NOVX agonists (i.e., mimetics) or as NOVX antagonists can be identified by screening combinatorial libraries of mutants (e.g., truncation mutants) of the NOVX proteins for NOVX protein agonist or antagonist activity. In one embodiment, a variegated library of NOVX variants is generated by combinatorial mutagenesis at the nucleic acid level and is encoded by a variegated gene library. A variegated library of NOVX variants can be produced by, for example, enzymatically ligating a mixture of synthetic oligonucleotides into gene sequences such that a degenerate set of potential NOVX sequences is expressible as individual polypeptides, or alternatively, as a set of larger fusion proteins (e.g., for phage display) containing the set of NOVX sequences therein. There are a variety of methods which can be used to produce libraries of potential NOVX variants from a degenerate oligonucleotide sequence.

Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential NOVX sequences. Methods for synthesizing degenerate oligonucleotides are well-known within the art. See, e.g., Narang, 1983. *Tetrahedron* 39: 3; Itakura, et al., 1984. *Annu. Rev. Biochem.* 53: 323; Itakura, et al., 1984. *Science* 198: 1056; Ike, et al., 1983. *Nucl. Acids Res.* 11: 477.

Polypeptide Libraries

In addition, libraries of fragments of the NOVX protein coding sequences can be used to generate a variegated population of NOVX fragments for screening and subsequent selection of variants of an NOVX protein. In one embodiment, a library of coding sequence fragments can be generated by treating a double stranded PCR fragment of an NOVX coding sequence with a nuclease under conditions wherein nicking occurs only about once per molecule, denaturing the double stranded DNA, renaturing the DNA to form double-stranded DNA that can include sense/antisense pairs from different nicked products, removing single stranded portions from reformed duplexes by treatment with $S_1$ nuclease, and ligating the resulting fragment library into an expression vector. By this method, expression libraries can be derived which encodes N-terminal and internal fragments of various sizes of the NOVX proteins.

Various techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of NOVX proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify NOVX variants. See, e.g., Arkin and Yourvan, 1992. *Proc. Natl. Acad. Sci. USA* 89: 7811–7815; Delgrave, et al., 1993. *Protein Engineering* 6:327–331.

Antibodies

The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. In general, antibody molecules obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

An isolated protein of the invention intended to serve as an antigen, or a portion or fragment thereof, can be used as an immunogen to generate antibodies that immunospecifically bind the antigen, using standard techniques for polyclonal and monoclonal antibody preparation. The full-length protein can be used or, alternatively, the invention provides antigenic peptide fragments of the antigen for use as immunogens. An antigenic peptide fragment comprises at least 6 amino acid residues of the amino acid sequence of the full length protein, such as an amino acid sequence shown in SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92 and 94, and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the invention, at least one epitope encompassed by the antigenic peptide is a region of SECX that is located on the surface of the protein, e.g., a hydrophilic region. A hydrophobicity analysis of the human SECX protein sequence will indicate which regions of a SECX polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, Proc. Nat. Acad. Sci. USA 78: 3824–3828; Kyte and Doolittle 1982, J. Mol. Biol. 157: 105–142, each incorporated herein by reference in their entirety. Antibodies that are specific for one or more domains within an antigenic protein, or derivatives, fragments, analogs or homologs thereof, are also provided herein.

A protein of the invention, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the invention, or against derivatives, fragments, analogs homologs or orthologs thereof (see, for example, Antibodies: A Laboratory Manual, Harlow E, and Lane D, 1988, Cold Spring Harbor Laboratory Press, Cold Spring Harbor, N.Y., incorporated herein by reference). Some of these antibodies are discussed below.

Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25–28).

Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980). It is an objective, especially important in therapeutic applications of monoclonal antibodies, to identify antibodies having a high degree of specificity and a high binding affinity for the target antigen.

After the desired hybridoma cells are identified, the clones can be subdloned by limiting dilution procedures and grown by standard methods (Goding, 1986). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subdlones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, *Nature* 368, 812–13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Humanized Antibodies

The antibodies directed against the protein antigens of the invention can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, *Curr. Op. Struct. Biol.*, 2:593–596 (1992)).

Human Antibodies

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77–96). Human monoclonal antibodies may be utilized in the practice of the present invention and may be produced by using human hybridomas (see Cote, et al., 1983. Proc Natl Acad Sci USA 80: 2026–2030) or by transforming human B-cells with Epstein Barr Virus in vitro (see Cole, et al., 1985 In: MONOCLONAL ANTIBODIES AND CANCER THERAPY, Alan R. Liss, Inc., pp. 77–96).

In addition, human antibodies can also be produced using additional techniques, including phage display libraries (Hoogenboom and Winter, *J. Mol. Biol.*, 227:381 (1991); Marks et al., *J. Mol. Biol.* 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (*Bio/Technology* 10, 779–783 (1992)); Lonberg et al. (*Nature* 368 856–859 (1994)); Morrison (*Nature* 368, 812–13 (1994)); Fishwild et al, (*Nature Biotechnology* 14, 845–51 (1996)); Neuberger (*Nature Biotechnology* 14, 826 (1996)); and Lonberg and Huszar (*Intern. Rev. Immunol.* 13 65–93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

$F_{ab}$ Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275–1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537–539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217–225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5): 1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., *J. Exp Med.*, 176: 1191–1195 (1992) and Shopes, *J. Immunol.*, 148: 2918–2922 (1992). Homodimeric antibodies with enhanced anti-tumor activity can also be prepared using heterobifunctional cross-linkers as described in Wolff et al. *Cancer Research*, 53: 2560–2565 (1993). Alternatively, an antibody can be engineered that has dual Fc regions and can thereby have enhanced complement lysis and ADCC capabilities. See Stevenson et al., *Anti-Cancer Drug Design*, 3: 219–230 (1989).

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

Immunoliposomes

The antibodies disclosed herein can also be formulated as immunoliposomes. Liposomes containing the antibody are prepared by methods known in the art, such as described in Epstein et al., *Proc. Natl. Acad. Sci. USA*, 82: 3688 (1985); Hwang et al., *Proc. Natl Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.*, 257: 286–288 (1982) via a disulfide-interchange reaction. A chemotherapeutic agent (such as Doxorubicin) is optionally contained within the liposome. See Gabizon et al., *J. National Cancer Inst.*, 81(19): 1484 (1989).

Diagnostic Applications of Antibodies Directed Against the Proteins of the Invention Antibodies directed against a protein of the invention may be used in methods known within the art relating to the localization and/or quantitation of the protein (e.g., for use in measuring levels of the protein within appropriate physiological samples, for use in diagnostic methods, for use in imaging the protein, and the like). In a given embodiment, antibodies against the proteins, or derivatives, fragments, analogs or homologs thereof, that contain the antigen binding domain, are utilized as pharmacologically-active compounds (see below).

An antibody specific for a protein of the invention can be used to isolate the protein by standard techniques, such as immunoaffinity chromatography or immunoprecipitation. Such an antibody can facilitate the purification of the natural protein antigen from cells and of recombinantly produced antigen expressed in host cells. Moreover, such an antibody can be used to detect the antigenic protein (e.g., in a cellular lysate or cell supernatant) in order to evaluate the abundance and pattern of expression of the antigenic protein. Antibodies directed against the protein can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Therapeutics

Antibodies of the invention, including polyclonal, monoclonal, humanized and fully human antibodies, may used as therapeutic agents. Such agents will generally be employed to treat or prevent a disease or pathology in a subject. An antibody preparation, preferably one having high specificity and high affinity for its target antigen, is administered to the subject and will generally have an effect due to its binding with the target. Such an effect may be one of two kinds, depending on the specific nature of the interaction between the given antibody molecule and the target antigen in question. In the first instance, administration of the antibody may abrogate or inhibit the binding of the target with an endogenous ligand to which it naturally binds. In this case, the antibody binds to the target and masks a binding site of the naturally occurring ligand, wherein the ligand serves as an effector molecule. Thus the receptor mediates a signal transduction pathway for which ligand is responsible.

Alternatively, the effect may be one in which the antibody elicits a physiological result by virtue of binding to an effector binding site on the target molecule. In this case the target, a receptor having an endogenous ligand which may be absent or defective in the disease or pathology, binds the antibody as a surrogate effector ligand, initiating a receptor-based signal transduction event by the receptor.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Pharmaceutical Compositions of Antibodies

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

If the antigenic protein is intracellular and whole antibodies are used as inhibitors, internalizing antibodies are preferred. However, liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889–7893 (1993). The formulation herein can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

ELISA Assay

An agent for detecting an analyte protein is an antibody capable of binding to an analyte protein, preferably an antibody with a detectable label. Antibodies can be polyclonal, or more preferably, monoclonal. An intact antibody, or a fragment thereof (e.g., $F_{ab}$ or $F_{(ab)2}$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Thory of Enzyme Immunoassays", P. Tijssen, Elsevier Science Publishers, Amsterdam, 1985. Furthermore, in vivo techniques for detection of an analyte protein include introducing into a subject a labeled anti-an analyte protein antibody. For example, the antibody can be labeled with a radioactive marker whose presence and location in a subject can be detected by standard imaging techniques.

NOVX Recombinant Expression Vectors and Host Cells

Another aspect of the invention pertains to vectors, preferably expression vectors, containing a nucleic acid encoding an NOVX protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g. replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g. NOVX proteins, mutant forms of NOVX proteins, fusion proteins, etc.).

The recombinant expression vectors of the invention can be designed for expression of NOVX proteins in prokaryotic or eukaryotic cells. For example, NOVX proteins can be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111–2118). Such alteration of nucleic acid sequences of the invention can be carried out by standard DNA synthesis techniques.

In another embodiment, the NOVX expression vector is a yeast expression vector. Examples of vectors for expression in yeast *Saccharomyces cerivisae* include pYepSec1 (Baldari, et al., 1987. *EMBO J.* 6: 229–234), pMFa (Kurjan and Herskowitz, 1982. *Cell* 30: 933–943), pJRY88 (Schultz et al., 1987. *Gene* 54: 113–123), pYES2 (Invitrogen Corporation, San Diego, Calif.), and picZ (InVitrogen Corp, San Diego, Calif.).

Alternatively, NOVX can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156–2165) and the pVL series (Lucklow and Summers, 1989. *Virology* 170: 31–39).

In yet another embodiment, a nucleic acid of the invention is expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187–195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268–277), lymphoid-specific promoters (Calame and Eaton, 1988. *Adv. Immunol.* 43: 235–275), in particular promoters of T cell receptors (Winoto and Baltimore, 1989. *EMBO J.* 8: 729–733) and immunoglobulins (Banerji, et al., 1983. *Cell* 33: 729–740; Queen and Baltimore, 1983. *Cell* 33: 741–748), neuron-specific promoters (e.g., the neurofilament promoter; Byrne and Ruddle, 1989. *Proc. Natl. Acad. Sci. USA* 86: 5473–5477), pancreas-specific promoters (Edlund, et al., 1985. *Science* 230: 912–916), and mammary gland-specific promoters (e.g., milk whey promoter; U.S. Pat. No. 4,873, 316 and European Application Publication No. 264,166). Developmentally-regulated promoters are also encompassed, e.g., the murine hox promoters (Kessel and Gruss, 1990. *Science* 249: 374–379) and the α-fetoprotein promoter (Campes and Tilghman, 1989. *Genes Dev.* 3: 537–546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to NOVX mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," *Reviews-Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, NOVX protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding NOVX or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) NOVX protein. Accordingly, the invention further provides methods for producing NOVX protein using the host cells of the invention. In one embodiment, the method comprises culturing the host cell of invention (into which a recombinant expression vector encoding NOVX protein has been introduced) in a suitable medium such that NOVX protein is produced. In another embodiment, the method further comprises isolating NOVX protein from the medium or the host cell.

Transgenic NOVX Animals

The host cells of the invention can also be used to produce non-human transgenic animals. For example, in one embodiment, a host cell of the invention is a fertilized oocyte or an embryonic stem cell into which NOVX protein-coding sequences have been introduced. Such host cells can then be used to create non-human transgenic animals in which exogenous NOVX sequences have been introduced into their genome or homologous recombinant animals in which endogenous NOVX sequences have been altered. Such animals are useful for studying the function and/or activity of NOVX protein and for identifying and/or evaluating modulators of NOVX protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous NOVX gene has been altered by homologous recombination between the endogenous gene and an exogenous DNA molecule introduced into a cell of the animal, e.g., an embryonic cell of the animal, prior to development of the animal.

A transgenic animal of the invention can be created by introducing NOVX-encoding nucleic acid into the male pronuclei of a fertilized oocyte (e.g., by microinjection, retroviral infection) and allowing the oocyte to develop in a pseudopregnant female foster animal. The human NOVX cDNA sequences SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93 can be introduced as a transgene into the genome of a non-human animal. Alternatively, a non-human homologue of the human NOVX gene, such as a mouse NOVX gene, can be isolated based on hybridization to the human NOVX cDNA (described further supra) and used as a transgene. Intronic sequences and polyadenylation signals can also be included in the transgene to increase the efficiency of expression of the transgene. A tissue-specific regulatory sequence(s) can be operably-linked to the NOVX transgene to direct expression of NOVX protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan, 1986. In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the NOVX transgene in its genome and/or expression of NOVX mRNA in tissues or cells of the animals. A transgenic founder animal can then be used to breed additional animals carrying the transgene. Moreover, transgenic animals carrying a transgene-encoding NOVX protein can further be bred to other transgenic animals carrying other transgenes.

To create a homologous recombinant animal, a vector is prepared which contains at least a portion of an NOVX gene into which a deletion, addition or substitution has been introduced to thereby alter, e.g., functionally disrupt, the NOVX gene. The NOVX gene can be a human gene (e.g., the cDNA of SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93), but more preferably, is a non-human homologue of a human NOVX gene. For example, a mouse homologue of human NOVX gene of SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93 can be used to construct a homologous recombination vector suitable for altering an endogenous NOVX gene in the mouse genome. In one embodiment, the vector is designed such that, upon homologous recombination, the endogenous NOVX gene is functionally disrupted (i.e., no longer encodes a functional protein; also referred to as a "knock out" vector).

Alternatively, the vector can be designed such that, upon homologous recombination, the endogenous NOVX gene is mutated or otherwise altered but still encodes functional protein (e.g., the upstream regulatory region can be altered to thereby alter the expression of the endogenous NOVX protein). In the homologous recombination vector, the altered portion of the NOVX gene is flanked at its 5'- and 3'-termini by additional nucleic acid of the NOVX gene to allow for homologous recombination to occur between the exogenous NOVX gene carried by the vector and an endogenous NOVX gene in an embryonic stem cell. The additional flanking NOVX nucleic acid is of sufficient length for successful homologous recombination with the endogenous gene. Typically, several kilobases of flanking DNA (both at the 5'- and 3'-termini) are included in the vector. See, e.g., Thomas, et al., 1987. *Cell* 51: 503 for a description of homologous recombination vectors. The vector is ten introduced into an embryonic stem cell line (e.g., by electroporation) and cells in which the introduced NOVX gene has homologously-recombined with the endogenous NOVX gene are selected. See, e.g., Li, et al., 1992. *Cell* 69: 915.

The selected cells are then injected into a blastocyst of an animal (e.g., a mouse) to form aggregation chimeras. See, e.g., Bradley, 1987. In: TERATOCARCINOMAS AND EMBRYONIC STEM CELLS: A PRACTICAL APPROACH, Robertson, ed. IRL, Oxford, pp. 113–152. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described further in Bradley, 1991. *Curr. Opin. Biotechnol.* 2: 823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, See, e.g., Lakso, et al., 1992. *Proc. Natl. Acad. Sci. USA* 89: 6232–6236. Another example of a recombinase system is the FLP recombinase system of *Saccharomyces cerevisiae*. See, O'Gorman, et al., 1991. *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, et al., 1997. *Nature* 385: 810–813. In brief, a cell (e.g., a somatic cell) from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

Pharmaceutical Compositions

The NOVX nucleic acid molecules, NOVX proteins, and anti-NOVX antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an NOVX protein or anti-NOVX antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci. USA* 91: 3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Screening and Detection Methods

The isolated nucleic acid molecules of the invention can be used to express NOVX protein (e.g., via a recombinant expression vector in a host cell in gene therapy applications), to detect NOVX mRNA (e.g., in a biological sample) or a genetic lesion in an NOVX gene, and to modulate NOVX activity, as described further, below. In addition, the NOVX proteins can be used to screen drugs or compounds that modulate the NOVX protein activity or expression as well as to treat disorders characterized by insufficient or excessive production of NOVX protein or production of NOVX protein forms that have decreased or aberrant activity compared to NOVX wild-type protein (e.g.; diabetes (regulates insulin release); obesity (binds and transport lipids); metabolic disturbances associated with obesity, the metabolic syndrome X as well as anorexia and wasting disorders associated with chronic diseases and various cancers, and infectious disease(possesses anti-microbial activity) and the various dyslipidemias. In addition, the anti-NOVX antibodies of the invention can be used to detect and isolate NOVX proteins and modulate NOVX activity. In yet a further aspect, the invention can be used in methods to influence appetite, absorption of nutrients and the disposition of metabolic substrates in both a positive and negative fashion.

The invention further pertains to novel agents identified by the screening assays described herein and uses thereof for treatments as described, supra.

Screening Assays

The invention provides a method (also referred to herein as a "screening assay") for identifying modulators, i.e., candidate or test compounds or agents (e.g., peptides, peptidomimetics, small molecules or other drugs) that bind to NOVX proteins or have a stimulatory or inhibitory effect on, e.g., NOVX protein expression or NOVX protein activity. The invention also includes compounds identified in the screening assays described herein.

In one embodiment, the invention provides assays for screening candidate or test compounds which bind to or modulate the activity of the membrane-bound form of an NOVX protein or polypeptide or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. *Anticancer Drug Design* 12: 145.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. *Proc. Natl. Acad. Sci. U.S.A.* 90: 6909; Erb, et al., 1994. *Proc. Natl. Acad. Sci. U.S.A.* 91: 11422; Zuckermann, et al., 1994. *J. Med. Chem.* 37: 2678; Cho, et al., 1993. *Science* 261: 1303; Carrell, et al., 1994. *Angew. Chem. Int. Ed. Engl.* 33: 2059; Carell, et al., 1994. *Angew. Chem. Int. Ed. Engl.* 33: 2061; and Gallop, et al., 1994. *J. Med. Chem.* 37:1233.

Libraries of compounds may be presented in solution (e.g., Houghten, 1992. *Biotechniques* 13: 412–421), or on beads (Lam, 1991. *Nature* 354: 82–84), on chips (Fodor, 1993. *Nature* 364: 555–556), bacteria (Ladner, U.S. Pat. No. 5,223,409), spores (Ladner, U.S. Pat. No. 5,233,409), plasmids (Cull, et al., 1992. *Proc. Natl. Acad. Sci. USA* 89: 1865–1869) or on phage (Scott and Smith, 1990. *Science* 249: 386–390; Devlin, 1990. *Science* 249: 404–406; Cwirla, et al., 1990. *Proc. Natl. Acad. Sci. U.S.A.* 87: 6378–6382; Felici, 1991. *J. Mol. Biol.* 222: 301–310; Ladner, U.S. Pat. No. 5,233,409.).

In one embodiment, an assay is a cell-based assay in which a cell which expresses a membrane-bound form of NOVX protein, or a biologically-active portion thereof, on the cell surface is contacted with a test compound and the ability of the test compound to bind to an NOVX protein determined. The cell, for example, can of mammalian origin or a yeast cell. Determining the ability of the test compound to bind to the NOVX protein can be accomplished, for example, by coupling the test compound with a radioisotope or enzymatic label such that binding of the test compound to the NOVX protein or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of NOVX protein, or a biologically-active portion thereof, on the cell surface with a known compound which binds NOVX to form an assay mixture, contacting the assay mixture with a test compound, and determining the ability of the test compound to interact with an NOVX protein, wherein determining the ability of the test compound to interact with an NOVX protein comprises determining the ability of the test compound to preferentially bind t o NOVX protein or a biologically-active portion thereof as compared to the known compound.

In another embodiment, an assay is a cell-based assay comprising contacting a cell expressing a membrane-bound form of NOVX protein, or a biologically-active portion thereof, on the cell surface with a test compound and determining the ability of the test compound to modulate (e.g., stimulate or inhibit) the activity of the NOVX protein or biologically-active portion thereof. Determining the ability of the test compound to modulate the activity of NOVX or a biologically-active portion thereof can be accomplished, for example, by determining the ability of the NOVX protein to bind to or interact with an NOVX target molecule. As used herein, a "target molecule" is a molecule with which an NOVX protein binds or interacts in nature, for example, a molecule on the surface of a cell which expresses an NOVX interacting protein, a molecule on the surface of a second cell, a molecule in the extracellular milieu, a molecule associated with the internal surface of a cell membrane or a cytoplasmic molecule. An NOVX target molecule can be a non-NOVX molecule or an NOVX protein or polypeptide of the invention. In one embodiment, an NOVX target molecule is a component of a signal transduction pathway that facilitates transduction of an extracellular signal (e.g. a signal generated by binding of a compound to a membrane-bound NOVX molecule) through the cell membrane and into the cell. The target, for example, can be a second intercellular protein that has catalytic activity or a protein that facilitates the association of downstream signaling molecules with NOVX.

Determining the ability of the NOVX protein to bind to or interact with an NOVX target molecule can be accomplished by one of the methods described above for determining direct binding. In one embodiment, determining the ability of the NOVX protein to bind to or interact with an NOVX target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising an NOVX-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting an NOVX protein or biologically-active portion thereof with a test compound and determining the ability of the test compound to bind to the NOVX protein or biologically-active portion thereof. Binding of the test compound to the NOVX protein can be determined either directly or indirectly as described above. In one such embodiment, the assay comprises contacting the NOVX protein or biologically-active portion thereof with a known compound which binds NOVX to form an assay mixture, contacting the assay mixture with a test compound, and determining the ability of the test compound to interact with an NOVX protein, wherein determining the ability of the test compound to interact with an NOVX protein comprises determining the ability of the test compound to preferentially bind to NOVX or biologically-active portion thereof as compared to the known compound.

In still another embodiment, an assay is a cell-free assay comprising contacting NOVX protein or biologically-active portion thereof with a test compound and determining the ability of the test compound to modulate (e.g. stimulate or inhibit) the activity of the NOVX protein or biologically-active portion thereof. Determining the ability of the test compound to modulate the activity of NOVX can be accomplished, for example, by determining the ability of the NOVX protein to bind to an NOVX target molecule by one of the methods described above for determining direct binding. In an alternative embodiment, determining the ability of the test compound to modulate the activity of NOVX protein can be accomplished by determining the ability of the NOVX protein further modulate an NOVX target molecule. For example, the catalytic/enzymatic activity of the target molecule on an appropriate substrate can be determined as described, supra.

In yet another embodiment, the cell-free assay comprises contacting the NOVX protein or biologically-active portion thereof with a known compound which binds NOVX protein to form an assay mixture, contacting the assay mixture with a test compound, and determining the ability of the test compound to interact with an NOVX protein, wherein determining the ability of the test compound to interact with an NOVX protein comprises determining the ability of the NOVX protein to preferentially bind to or modulate the activity of an NOVX target molecule.

The cell-free assays of the invention are amenable to use of both the soluble form or the membrane-bound form of NOVX protein. In the case of cell-free assays comprising the membrane-bound form of NOVX protein, it may be desirable to utilize a solubilizing agent such that the membrane-bound form of NOVX protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl) dimethylamminiol-2-hydroxy-1-propane sulfonate (CHAPSO).

In more than one embodiment of the above assay methods of the invention, it may be desirable to immobilize either NOVX protein or its target molecule to facilitate separation of complexed from uncomplexed forms of one or both of the proteins, as well as to accommodate automation of the assay. Binding of a test compound to NOVX protein, or interaction of NOVX protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-NOVX fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or NOVX protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of NOVX protein binding or activity determined using standard techniques.

Other techniques for immobilizing proteins on matrices can also be used in the screening assays of the invention. For example, either the NOVX protein or its target molecule can be immobilized utilizing conjugation of biotin and streptavidin. Biotinylated NOVX protein or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with NOVX protein or target molecules, but which do not interfere with binding of the NOVX protein to its target molecule, can be derivatized to the wells of the plate, and unbound target or NOVX protein trapped in the wells by antibody conjugation. Methods for detecting such complexes, in addition to those described above for the GST-immobilized complexes, include immunodetection of complexes using antibodies reactive with the NOVX protein or target molecule, as well as enzyme-linked assays that rely on detecting an enzymatic activity associated with the NOVX protein or target molecule.

In another embodiment, modulators of NOVX protein expression are identified in a method wherein a cell is contacted with a candidate compound and the expression of NOVX mRNA or protein in the cell is determined. The level of expression of NOVX mRNA or protein in the presence of the candidate compound is compared to the level of expression of NOVX mRNA or protein in the absence of the candidate compound. The candidate compound can then be identified as a modulator of NOVX mRNA or protein expression based upon this comparison. For example, when expression of NOVX mRNA or protein is greater (i.e., statistically significantly greater) in the presence of the candidate compound than in its absence, the candidate compound is identified as a stimulator of NOVX mRNA or protein expression. Alternatively, when expression of NOVX mRNA or protein is less (statistically significantly less) in the presence of the candidate compound than in its absence, the candidate compound is identified as an inhibitor of NOVX mRNA or protein expression. The level of NOVX mRNA or protein expression in the cells can be determined by methods described herein for detecting NOVX mRNA or protein.

In yet another aspect of the invention, the NOVX proteins can be used as "bait proteins" in a two-hybrid assay or three hybrid assay (see, e.g., U.S. Pat. No. 5,283,317; Zervos, et al., 1993. *Cell* 72: 223–232; Madura, et al., 1993. *J. Biol. Chem.* 268: 12046–12054; Bartel, et al., 1993. *Biotechniques* 14: 920–924; Iwabuchi, et al., 1993. *Oncogene* 8: 1693–1696; and Brent WO 94/10300), to identify other proteins that bind to or interact with NOVX ("NOVX-binding proteins" or "NOVX-bp") and modulate NOVX activity. Such NOVX-binding proteins are also likely to be involved in the propagation of signals by the NOVX proteins as, for example, upstream or downstream elements of the NOVX pathway.

The two-hybrid system is based on the modular nature of most transcription factors, which consist of separable DNA-binding and activation domains. Briefly, the assay utilizes two different DNA constructs. In one construct, the gene that codes for NOVX is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an NOVX-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with NOVX.

The invention further pertains to novel agents identified by the aforementioned screening assays and uses thereof for treatments as described herein.

Detection Assays

Portions or fragments of the cDNA sequences identified herein (and the corresponding complete gene sequences) can be used in numerous ways as polynucleotide reagents. By way of example, and not of limitation, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. Some of these applications are described in the subsections, below.

Chromosome Mapping

Once the sequence (or a portion of the sequence) of a gene has been isolated, this sequence can be used to map the location of the gene on a chromosome. This process is called chromosome mapping. Accordingly, portions or fragments of the NOVX sequences, SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93, or fragments or derivatives thereof, can be used to map the location of the NOVX genes, respectively, on a chromosome. The mapping of the NOVX sequences to chromosomes is an important first step in correlating these sequences with genes associated with disease.

Briefly, NOVX genes can be mapped to chromosomes by preparing PCR primers (preferably 15–25 bp in length) from the NOVX sequences. Computer analysis of the NOVX, sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the NOVX sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. See, e.g., D'Eustachio, et al., 1983. *Science* 220: 919–924. Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the NOVX sequences to design oligonucleotide primers, sub-localization can be achieved with panels of fragments from specific chromosomes.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases, will suffice to get good results at a reasonable amount of time. For a review of this technique, see, Verma, et al., HUMAN CHROMOSOMES: A MANUAL OF BASIC TECHNIQUES (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. Such data are found, e.g., in McKusick, MENDELIAN INHERITANCE IN MAN, available on-line through Johns Hopkins University Welch Medical Library). The relationship between genes and disease, mapped to the same chromosomal region, can then be identified through linkage analysis (co-inheritance of physically adjacent genes), described in, e.g., Egeland, et al., 1987. *Nature*, 325: 783–787.

Moreover, differences in the DNA sequences between individuals affected and unaffected with a disease associated with the NOVX gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The NOVX sequences of the invention can also be used to identify individuals from minute biological samples. In this technique, an individual's genomic DNA is digested with one or more restriction enzymes, and probed on a Southern blot to yield unique bands for identification. The sequences of the invention are useful as additional DNA markers for RFLP ("restriction fragment length polymorphisms," described in U.S. Pat. No. 5,272,057).

Furthermore, the sequences of the invention can be used to provide an alternative technique that determines the actual base-by-base DNA sequence of selected portions of an individual's genome. Thus, the NOVX sequences described herein can be used to prepare two PCR primers from the 5'- and 3'-termini of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the invention can be used to obtain such identification sequences from individuals and from tissue. The NOVX sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences can comfortably provide positive individual identification with a panel of perhaps 10 to 1,000 primers that each yield a noncoding amplified sequence of 100 bases. If predicted coding sequences, such as those in SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93 are used, a more appropriate number of primers for positive individual identification would be 500–2,000.

Predictive Medicine

The invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the invention relates to diagnostic assays for determining NOVX protein and/or nucleic acid expression as well as NOVX activity, in the context of a biological sample (e.g., blood, serum, cells, tissue) to thereby determine whether an individual is afflicted with a disease or disorder, or is at risk of developing a disorder, associated with aberrant NOVX expression or activity. The disorders include metabolic disorders, diabetes, obesity, infectious disease, anorexia, cancer-associated cachexia, cancer, neurodegenerative disorders, Alzheimer's Disease, Parkinson's Disorder, immune disorders, and hematopoietic disorders, and the various dyslipidemias, metabolic disturbances associated with obesity, the metabolic syndrome X and wasting disorders associated with chronic diseases and various cancers. The invention also provides for prognostic (or predictive) assays for determining whether an individual is at risk of developing a disorder associated with NOVX protein, nucleic acid expression or activity. For example, mutations in an NOVX gene can be assayed in a biological sample. Such assays can be used for prognostic or predictive purpose to thereby prophylactically treat an individual prior to the onset of a disorder characterized by or associated with NOVX protein, nucleic acid expression, or biological activity.

Another aspect of the invention provides methods for determining NOVX protein, nucleic acid expression or activity in an individual to thereby select appropriate therapeutic or prophylactic agents for that individual (referred to herein as "pharmacogenomics"). Pharmacogenomics allows for the selection of agents (e.g. drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs, compounds) on the expression or activity of NOVX in clinical trials.

These and other agents are described in further detail in the following sections.

Diagnostic Assays

An exemplary method for detecting the presence or absence of NOVX in a biological sample involves obtaining a biological sample from a test subject and contacting the biological sample with a compound or an agent capable of detecting NOVX protein or nucleic acid (e.g., mRNA, genomic DNA) that encodes NOVX protein such that the presence of NOVX is detected in the biological sample. An agent for detecting NOVX mRNA or genomic DNA is a labeled nucleic acid probe capable of hybridizing to NOVX mRNA or genomic DNA. The nucleic acid probe can be, for example, a full-length NOVX nucleic acid, such as the nucleic acid of SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91 and 93, or a portion thereof, such as an oligonucleotide of at least 15, 30, 50, 100, 250 or 500 nucleotides in length and sufficient to specifically hybridize under stringent conditions to NOVX mRNA or genomic DNA. Other suitable probes for use in the diagnostic assays of the invention are described herein.

An agent for detecting NOVX protein is an antibody capable of binding to NOVX protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect NOVX mRNA, protein, or genomic DNA in a biological sample in vitro as well as in vivo. For example, in vitro techniques for detection of NOVX mRNA include Northern hybridizations and in situ hybridizations. In vitro techniques for detection of NOVX protein include enzyme linked immunosorbent assays (ELISAs), Western blots, immunoprecipitations, and immunofluorescence. In vitro techniques for detection of NOVX genomic DNA include Southern hybridizations. Furthermore, in vivo techniques for detection of NOVX protein include introducing into a subject a labeled anti-NOVX antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting NOVX protein, mRNA, or genomic DNA, such that the presence of NOVX protein, mRNA or genomic DNA is detected in the biological sample, and comparing the presence of NOVX protein, mRNA or genomic DNA in the control sample with the presence of NOVX protein, mRNA or genomic DNA in the test sample.

The invention also encompasses kits for detecting the presence of NOVX in a biological sample. For example, the kit can comprise: a labeled compound or agent capable of detecting NOVX protein or mRNA in a biological sample; means for determining the amount of NOVX in the sample; and means for comparing the amount of NOVX in the sample with a standard. The compound or agent can be packaged in a suitable container. The kit can further comprise instructions for using the kit to detect NOVX protein or nucleic acid.

Prognostic Assays

The diagnostic methods described herein can furthermore be utilized to identify subjects having or at risk of developing a disease or disorder associated with aberrant NOVX expression or activity. For example, the assays described herein, such as the preceding diagnostic assays or the following assays, can be utilized to identify a subject having or at risk of developing a disorder associated with NOVX protein, nucleic acid expression or activity. Alternatively, the prognostic assays can be utilized to identify a subject having or at risk for developing a disease or disorder. Thus, the invention provides a method for identifying a disease or disorder associated with aberrant NOVX expression or activity in which a test sample is obtained from a subject and NOVX protein or nucleic acid (e.g., mRNA, genomic DNA) is detected, wherein the presence of NOVX protein or nucleic acid is diagnostic for a subject having or at risk of developing a disease or disorder associated with aberrant NOVX expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant NOVX expression or activity. For example, such methods can be used to determine whether a subject can be effectively treated with an agent for a disorder. Thus, the invention provides methods for determining whether a subject can be effectively treated with an agent for a disorder associated with aberrant NOVX expression or activity in which a test sample is obtained and NOVX protein or nucleic acid is detected (e.g., wherein the presence of NOVX protein or nucleic acid is diagnostic for a subject that can be administered the agent to treat a disorder associated with aberrant NOVX expression or activity).

The methods of the invention can also be used to detect genetic lesions in an NOVX gene, thereby determining if a subject with the lesioned gene is at risk for a disorder characterized by aberrant cell proliferation and/or differentiation. In various embodiments, the methods include detecting, in a sample of cells from the subject, the presence or absence of a genetic lesion characterized by at least one of an alteration affecting the integrity of a gene encoding an NOVX-protein, or the misexpression of the NOVX gene. For example, such genetic lesions can be detected by ascertaining the existence of at least one of: (i) a deletion of one or more nucleotides from an NOVX gene; (ii) an addition of one or more nucleotides to an NOVX gene; (iii) a substitution of one or more nucleotides of an NOVX gene, (iv) a chromosomal rearrangement of an NOVX gene; (v) an alteration in the level of a messenger RNA transcript of an NOVX gene, (vi) aberrant modification of an NOVX gene, such as of the methylation pattern of the genomic DNA, (vii) the presence of a non-wild-type splicing pattern of a messenger RNA transcript of an NOVX gene, (viii) a non-wild-type level of an NOVX protein, (ix) allelic loss of an NOVX gene, and (x) inappropriate post-translational modification of an NOVX protein. As described herein, there are a large number of assay techniques known in the art which can be used for detecting lesions in an NOVX gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR or, alternatively, in a ligation chain reaction (LCR) (see, e.g., Landegran, et al., 1988. *Science* 241: 1077–1080; and Nakazawa, et al., 1994. *Proc. Natl. Acad. Sci. USA* 91: 360–364), the latter of which can be particularly useful for detecting point mutations in the NOVX-gene (see, Abravaya, et al., 1995. *Nucl. Acids Res.* 23: 675–682). This method can include the steps of collecting a sample of cells from a patient, isolating nucleic acid (e.g., genomic, mRNA or both) from the cells of the sample, contacting the nucleic acid sample with one or more primers that specifically hybridize to an NOVX gene under conditions such that hybridization and amplification of the NOVX gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (see, Guatelli, et al., 1990. *Proc. Natl. Acad. Sci. USA* 87: 1874–1878), transcriptional amplification system (see, Kwoh, et al., 1989. *Proc. Natl. Acad. Sci. USA* 86: 1173–1177); Qβ Replicase (see, Lizardi, et al, 1988. *BioTechnology* 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an NOVX gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,493,531) can be used to score for the presence of specific mutations by development or loss of a ribozyme cleavage site.

In other embodiments, genetic mutations in NOVX can be identified by hybridizing a sample and control nucleic acids, e.g., DNA or RNA, to high-density arrays containing hundreds or thousands of oligonucleotides probes. See, e.g., Cronin, et al., 1996. *Human Mutation* 7: 244–255; Kozal, et al., 1996. *Nat. Med.* 2: 753–759. For example, genetic mutations in NOVX can be identified in two dimensional arrays containing light-generated DNA probes as described in Cronin, et al., supra. Briefly, a first hybridization array of probes can be used to scan through long stretches of DNA in a sample and control to identify base changes between the sequences by making linear arrays of sequential overlapping probes. This step allows the identification of point mutations. This is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the NOVX gene and detect mutations by comparing the sequence of the sample NOVX with the corresponding wild-type (control) sequence. Examples of sequencing reactions include those based on techniques developed by Maxim and Gilbert, 1977. *Proc. Natl. Acad. Sci. USA* 74: 560 or Sanger, 1977. *Proc. Natl. Acad. Sci. USA* 74: 5463. It is also contemplated that any of a variety of automated sequencing procedures can be utilized when performing the diagnostic assays (see, e.g., Naeve, et al., 1995. *Biotechniques* 19: 448), including sequencing by mass spectrometry (see, e.g., PCT International Publication No. WO 94/16101; Cohen, et al., 1996. *Adv. Chromatography* 36: 127–162; and Griffin, et al., 1993. *Appl. Biochem. Biotechnol.* 38: 147–159).

Other methods for detecting mutations in the NOVX gene include methods in which protection from cleavage agents is used to detect mismatched bases in RNA/RNA or RNA/DNA heteroduplexes. See, e.g., Myers, et al., 1985. *Science* 230: 1242. In general, the art technique of "mismatch cleavage" starts by providing heteroduplexes of formed by hybridizing (labeled) RNA or DNA containing the wild-type NOVX sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with $S_1$ nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton, et al., 1988. *Proc. Natl. Acad. Sci. USA* 85: 4397; Saleeba, et al., 1992. *Methods Enzymol.* 217: 286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in NOVX cDNAs obtained from samples of cells. For example, the mutY enzyme of *E. coli* cleaves A at G/A mismatches and the thymidine DNA glycosylase from HeLa cells cleaves T at G/T mismatches. See, e.g., Hsu, et al., 1994. *Carcinogenesis* 15: 1657–1662. According to an exemplary embodiment, a probe based on an NOVX sequence, e.g. a wild-type NOVX sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in NOVX genes. For example, single strand conformation polymorphism (SSCP) may be used to detect differences in electrophoretic mobility between mutant and wild type nucleic acids. See, e.g., Orita, et al., 1989. *Proc. Natl. Acad. Sci. USA:* 86: 2766; Cotton, 1993. *Mutat. Res.* 285: 125–144; Hayashi, 1992. *Genet. Anal. Tech. Appl.* 9: 73–79. Single-stranded DNA fragments of sample and control NOVX nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility. See, e.g., Keen, et al., 1991. *Trends Genet.* 7: 5.

In yet another embodiment, the movement of mutant or wild-type fragments in polyacrylamide gels containing a gradient of denaturant is assayed using denaturing gradient gel electrophoresis (DGGE). See, e.g., Myers, et al., 1985. *Nature* 313: 495. When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA. See, e.g., Rosenbaum and Reissner, 1987. *Biophys. Chem.* 265: 12753.

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found. See, e.g., Saiki, et al., 1986. *Nature* 324: 163; Saiki, et al., 1989. *Proc. Natl. Acad. Sci. USA* 86: 6230. Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization; see, e.g., Gibbs, et al., 1989. *Nucl. Acids Res.* 17: 2437–2448) or at the extreme 3'-terminus of one primer where, under appropriate conditions, mismatch can prevent, or reduce polymerase extension (see, e.g., Prossner, 1993. *Tibtech.* 11: 238). In addition it may be desirable to introduce a novel restriction site in the region of the mutation to create cleavage-based detection. See, e.g., Gasparini, et al., 1992. *Mol. Cell Probes* 6: 1. It is anticipated that in certain embodiments amplification may also be performed using Taq ligase for amplification. See, e.g., Barany, 1991. *Proc. Natl. Acad. Sci. USA* 88: 189. In such cases, ligation will occur only if there is a perfect match at the 3'-terminus of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an NOVX gene.

Furthermore, any cell type or tissue, preferably peripheral blood leukocytes, in which NOVX is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on NOVX activity (e.g., NOVX gene expression), as identified by a screening assay described herein can be administered to individuals to treat (prophylactically or therapeutically) disorders (The disorders include metabolic disorders, diabetes, obesity, infectious disease, anorexia, cancer-associated cachexia, cancer, neurodegenerative disorders, Alzheimer's Disease, Parkinson's Disorder, immune disorders, and hematopoietic disorders, and the various dyslipidemias, metabolic disturbances associated with obesity, the metabolic syndrome X and wasting disorders associated with chronic diseases and various cancers.) In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of NOVX protein, expression of NOVX nucleic acid, or mutation content of NOVX genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, 1996. *Clin. Exp. Pharmacol. Physiol.,* 23: 983–985; Linder, 1997. *Clin. Chem.,* 43: 254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. At the other extreme are the so called ultra-rapid metabolizers who do not respond to standard doses. Recently, the molecular basis of ultra-rapid metabolism has been identified to be due to CYP2D6 gene amplification.

Thus, the activity of NOVX protein, expression of NOVX nucleic acid, or mutation content of NOVX genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an NOVX modulator, such as a modulator identified by one of the exemplary screening assays described herein.

Monitoring of Effects During Clinical Trials

Monitoring the influence of agents (e.g., drugs, compounds) on the expression or activity of NOVX (e.g., the ability to modulate aberrant cell proliferation and/or differentiation) can be applied not only in basic drug screening, but also in clinical trials. For example, the effectiveness of an agent determined by a screening assay as described herein to increase NOVX gene expression, protein levels, or upregulate NOVX activity, can be monitored in clinical trails of subjects exhibiting decreased NOVX gene expression, protein levels, or downregulated NOVX activity. Alternatively, the effectiveness of an agent determined by a screening assay to decrease NOVX gene expression, protein levels, or downregulate NOVX activity, can be monitored in clinical trails of subjects exhibiting increased NOVX gene expression, protein levels, or upregulated NOVX activity. In such clinical trials, the expression or activity of NOVX and, preferably, other genes that have been implicated in, for example, a cellular proliferation or immune disorder can be used as a "read out" or markers of the immune responsiveness of a particular cell.

By way of example, and not of limitation, genes, including NOVX, that are modulated in cells by treatment with an agent (e.g., compound, drug or small molecule) that modulates NOVX activity (e.g., identified in a screening assay as described herein) can be identified. Thus, to study the effect of agents on cellular proliferation disorders, for example, in a clinical trial, cells can be isolated and RNA prepared and analyzed for the levels of expression of NOVX and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of NOVX or other genes. In this manner, the gene expression pattern can serve as a marker, indicative of the physiological response of the cells to the agent. Accordingly, this response state may be determined before, and at various points during, treatment of the individual with the agent.

In one embodiment, the invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of an NOVX protein, mRNA, or genomic DNA in the preadministration sample; (iii) obtaining one or more post-administration samples from the subject; (iv) detecting the level of expression or activity of the NOVX protein, mRNA, or genomic DNA in the post-administration samples; (v) comparing the level of expression or activity of the NOVX protein, mRNA, or genomic DNA in the pre-administration sample with the NOVX protein, mRNA, or genomic DNA in the post administration sample or samples; and (vi) altering the administration of the agent to the subject accordingly. For example, increased administration of the agent may be desirable to increase the expression or activity of NOVX to higher levels than detected, i.e., to increase the effectiveness of the agent. Alternatively, decreased administration of the agent may be desirable to decrease expression or activity of NOVX to lower levels than detected, i.e., to decrease the effectiveness of the agent.

Methods of Treatment

The invention provides for both prophylactic and therapeutic methods of treating a subject at risk of (or susceptible to) a disorder or having a disorder associated with aberrant NOVX expression or activity. The disorders include cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, tuberous sclerosis, scleroderma, obesity, transplantation, adrenoleukodystrophy, congenital adrenal hyperplasia, prostate cancer, neoplasm; adenocarcinoma, lymphoma, uterus cancer, fertility, hemophilia, hypercoagulation, idiopathic thrombocytopenic purpura, immunodeficiencies, graft versus host disease, AIDS, bronchial asthma, Crohn's disease; multiple sclerosis, treatment of Albright Hereditary Ostoeodystrophy, and other diseases, disorders and conditions of the like.

These methods of treatment will be discussed more fully, below.

Disease and Disorders

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to: (i) an aforementioned peptide, or analogs, derivatives, fragments or homologs thereof; (ii) antibodies to an aforementioned peptide; (iii) nucleic acids encoding an aforementioned peptide; (iv) administration of antisense nucleic acid and nucleic acids that are "dysfunctional" (i.e., due to a heterologous insertion within the coding sequences of coding sequences to an aforementioned peptide) that are utilized to "knockout" endogenous function of an aforementioned peptide by homologous recombination (see, e.g., Capecchi, 1989. *Science* 244: 1288–1292); or (v) modulators (i.e., inhibitors, agonists and antagonists, including additional peptide mimetic of the invention or antibodies specific to a peptide of the invention) that alter the interaction between an aforementioned peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, an aforementioned peptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

Prophylactic Methods

In one aspect, the invention provides a method for preventing, in a subject, a disease or condition associated with an aberrant NOVX expression or activity, by administering to the subject an agent that modulates NOVX expression or at least one NOVX activity. Subjects at risk for a disease that is caused or contributed to by aberrant NOVX expression or activity can be identified by, for example, any or a combination of diagnostic or prognostic assays as described herein. Administration of a prophylactic agent can occur prior to the manifestation of symptoms characteristic of the NOVX aberrancy, such that a disease or disorder is prevented or, alternatively, delayed in its progression. Depending upon the type of NOVX aberrancy, for example, an NOVX agonist or NOVX antagonist agent can be used for treating the subject. The appropriate agent can be determined based on screening assays described herein. The prophylactic methods of the invention are further discussed in the following subsections.

Therapeutic Methods

Another aspect of the invention pertains to methods of modulating NOVX expression or activity for therapeutic purposes. The modulatory method of the invention involves contacting a cell with an agent that modulates one or more of the activities of NOVX protein activity associated with the cell. An agent that modulates NOVX protein activity can be an agent as described herein, such as a nucleic acid or a protein, a naturally-occurring cognate ligand of an NOVX protein, a peptide, an NOVX peptidomimetic, or other small molecule. In one embodiment, the agent stimulates one or more NOVX protein activity. Examples of such stimulatory agents include active NOVX protein and a nucleic acid molecule encoding NOVX that has been introduced into the cell. In another embodiment, the agent inhibits one or more NOVX protein activity. Examples of such inhibitory agents include antisense NOVX nucleic acid molecules and anti-NOVX antibodies. These modulatory methods can be performed in vitro (e.g., by culturing the cell with the agent) or, alternatively, in vivo (e.g. by administering the agent to a subject). As such, the invention provides methods of treating an individual afflicted with a disease or disorder characterized by aberrant expression or activity of an NOVX protein or nucleic acid molecule. In one embodiment, the method involves administering an agent (e.g., an agent identified by a screening assay described herein), or combination of agents that modulates (e.g., up-regulates or down-regulates) NOVX expression or activity. In another embodiment, the method involves administering an NOVX protein or nucleic acid molecule as therapy to compensate for reduced or aberrant NOVX expression or activity.

Stimulation of NOVX activity is desirable in situations in which NOVX is abnormally downregulated and/or in which increased NOVX activity is likely to have a beneficial effect. One example of such a situation is where a subject has a disorder characterized by aberrant cell proliferation and/or differentiation (e.g., cancer or immune associated disorders). Another example of such a situation is where the subject has a gestational disease (e.g., preclampsia).

Determination of the Biological Effect of the Therapeutic

In various embodiments of the invention, suitable in vitro or in vivo assays are performed to determine the effect of a specific Therapeutic and whether its administration is indicated for treatment of the affected tissue.

In various specific embodiments, in vitro assays may be performed with representative cells of the type(s) involved in the patient's disorder, to determine if a given Therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

Prophylactic and Therapeutic Uses of the Compositions of the Invention

The NOVX nucleic acids and proteins of the invention are useful in potential prophylactic and therapeutic applications implicated in a variety of disorders including, but not limited to: metabolic disorders, diabetes, obesity, infectious disease, anorexia, cancer-associated cancer, neurodegenerative disorders, Alzheimer's Disease, Parkinson's Disorder, immune disorders, hematopoietic disorders, and the various dyslipidemias, metabolic disturbances associated with obesity, the metabolic syndrome X and wasting disorders associated with chronic diseases and various cancers.

As an example, a cDNA encoding the NOVX protein of the invention may be useful in gene therapy, and the protein may be useful when administered to a subject in need thereof. By way of non-limiting example, the compositions of the invention will have efficacy for treatment of patients suffering from: metabolic disorders, diabetes, obesity, infectious disease, anorexia, cancer-associated cachexia, cancer, neurodegenerative disorders, Alzheimer's Disease, Parkinson's Disorder, immune disorders, hematopoietic disorders, and the various dyslipidemias.

Both the novel nucleic acid encoding the NOVX protein, and the NOVX protein of the invention, or fragments thereof, may also be useful in diagnostic applications, wherein the presence or amount of the nucleic acid or the protein are to be assessed. A further use could be as an anti-bacterial molecule (i.e., some peptides have been found to possess anti-bacterial properties). These materials are further useful in the generation of antibodies, which immunospecifically-bind to the novel substances of the invention for use in therapeutic or diagnostic methods.

The invention will be further described in the following examples, which do not limit the scope of the invention described in the claims.

EXAMPLES

Example 1

Identification of NOVX Nucleic Acids

TblastN using CuraGen Corporation's sequence file for polypeptides or homologs was run against the Genomic Daily Files made available by GenBank or from files downloaded from the individual sequencing centers. Exons were predicted by homology and the intron/exon boundaries were determined using standard genetic rules. Exons were further selected and refined by means of similarity determination using multiple BLAST (for example, tBlastN, BlastX, and BlastN) searches, and, in some instances, GeneScan and Grail. Expressed sequences from both public and proprietary databases were also added when available to further define and complete the gene sequence. The DNA sequence was then manually corrected for apparent inconsistencies thereby obtaining the sequences encoding the full-length protein.

The novel NOVX target sequences identified in the present invention were subjected to the exon linking process to confirm the sequence. PCR primers were designed by starting at the most upstream sequence available, for the forward primer, and at the most downstream sequence available for the reverse primer. PCR primer sequences were used for obtaining different clones. In each case, the sequence was examined, walking inward from the respective termini toward the coding sequence, until a suitable sequence that is either unique or highly selective was encountered, or, in the case of the reverse primer, until the stop codon was reached. Such primers were designed based on in silico predictions for the full length cDNA, part (one or more exons) of the DNA or protein sequence of the target sequence, or by translated homology of the predicted exons to closely related human sequences from other species. These primers were then employed in PCR amplification based on the following pool of human cDNAs: adrenal gland, bone marrow, brain—amygdala, brain—cerebellum, brain—hippocampus, brain—substantia nigra, brain—thalamus, brain—whole, fetal brain, fetal kidney, fetal liver, fetal lung, heart, kidney, lymphoma—Raji, mammary gland, pancreas, pituitary gland, placenta, prostate, salivary gland, skeletal muscle, small intestine, spinal cord, spleen, stomach, testis, thyroid, trachea, uterus. Usually the resulting amplicons were gel purified, cloned and sequenced to high redundancy. The PCR product derived from exon linking was cloned into the pCR2.1 vector from Invitrogen. The resulting bacterial clone has an insert covering the entire open reading frame cloned into the pCR2.1 vector. The resulting sequences from all clones were assembled with themselves, with other fragments in CuraGen Corporation's database and with public ESTs. Fragments and ESTs were included as components for an assembly when the extent of their identity with another component of the assembly was at least 95% over 50 bp. In addition, sequence traces were evaluated manually and edited for corrections if appropriate. These procedures provide the sequence reported herein.

Physical clone: Exons were predicted by homology and the intron/exon boundaries were determined using standard genetic rules. Exons were further selected and refined by means of similarity determination using multiple BLAST (for example, tBlastN, BlastX, and BlastN) searches, and, in some instances, GeneScan and Grail. Expressed sequences from both public and proprietary databases were also added when available to further define and complete the gene sequence. The DNA sequence was then manually corrected for apparent inconsistencies thereby obtaining the sequences encoding the full-length protein.

Example 2

Identification of Single Nucleotide Polymorphisms in NOVX Nucleic Acid Sequences Variant sequences are also included in this application. A variant sequence can include a single nucleotide polymorphism (SNP). A SNP can, in some instances, be referred to as a "cSNP" to denote that the nucleotide sequence containing the SNP originates as a cDNA. A SNP can arise in several ways. For example, a SNP may be due to a substitution of one nucleotide for another at the polymorphic site. Such a substitution can be either a transition or a transversion. A SNP can also arise from a deletion of a nucleotide or an insertion of a nucleotide, relative to a reference allele. In this case, the polymorphic site is a site at which one allele bears a gap with respect to a particular nucleotide in another allele. SNPs occurring within genes may result in an alteration of the amino acid encoded by the gene at the position of the SNP. Intragenic SNPs may also be silent, when a codon including a SNP encodes the same amino acid as a result of the redundancy of the genetic code. SNPs occurring outside the region of a gene, or in an intron within a gene, do not result in changes in any amino acid sequence of a protein but may result in altered regulation of the expression pattern. Examples include alteration in temporal expression, physiological response regulation, cell type expression regulation, intensity of expression, and stability of transcribed message.

SeqCalling assemblies produced by the exon linking process were selected and extended using the following criteria. Genomic clones having regions with 98% identity to all or part of the initial or extended sequence were identified by BLASTN searches using the relevant sequence to query human genomic databases. The genomic clones that resulted were selected for further analysis because this identity indicates that these clones contain the genomic locus for these SeqCalling assemblies. These sequences were analyzed for putative coding regions as well as for similarity to the known DNA and protein sequences. Programs used for these analyses include Grail, Genscan, BLAST, HMMER, FASTA, Hybrid and other relevant programs.

Some additional genomic regions may have also been identified because selected SeqCalling assemblies map to those regions. Such SeqCalling sequences may have overlapped with regions defined by homology or exon prediction. They may also be included because the location of the fragment was in the vicinity of genomic regions identified by similarity or exon prediction that had been included in the original predicted sequence. The sequence so identified was manually assembled and then may have been extended using one or more additional sequences taken from CuraGen Corporation's human SeqCalling database. SeqCalling fragments suitable for inclusion were identified by the CuraTools™ program SeqExtend or by identifying SeqCalling fragments mapping to the appropriate regions of the genomic clones analyzed.

The regions defined by the procedures described above were then manually integrated and corrected for apparent inconsistencies that may have arisen, for example, from miscalled bases in the original fragments or from discrepancies between predicted exon junctions, EST locations and regions of sequence similarity, to derive the final sequence disclosed herein. When necessary, the process to identify and analyze SeqCalling assemblies and genomic clones was reiterated to derive the full length sequence (Alderborn et al., Determination of Single Nucleotide Polymorphisms by Real-time Pyrophosphate DNA Sequencing. Genome Research. 10 (8) 1249–1265, 2000).

Example 3

Quantitative Expression Analysis of Clones in Various Cells and Tissues

The quantitative expression of various clones was assessed using microtiter plates containing RNA samples from a variety of normal and pathology-derived cells, cell lines and tissues using real time quantitative PCR (RTQ PCR). RTQ PCR was performed on an Applied Biosystems ABI PRISM® 7700 or an ABI PRISM® 7900 HT Sequence Detection System. Various collections of samples are assembled on the plates, and referred to as Panel 1 (containing normal tissues and cancer cell lines), Panel 2 (containing samples derived from tissues from normal and cancer sources), Panel 3 (containing cancer cell lines), Panel 4 (containing cells and cell lines from normal tissues and cells related to inflammatory conditions), Panel 5D/5I (containing human tissues and cell lines with an emphasis on metabolic diseases), AI_comprehensive_panel (containing normal tissue and samples from autoimmune diseases), Panel CNSD0.01 (containing central nervous system samples from normal and diseased brains) and CNS_neurodegeneration_panel (containing samples from normal and Alzheimer's diseased brains).

RNA integrity from all samples is controlled for quality by visual assessment of agarose gel electropherograms using 28S and 18S ribosomal RNA staining intensity ratio as a guide (2:1 to 2.5:1 28s:18s) and the absence of low molecular weight RNAs that would be indicative of degradation products. Samples are controlled against genomic DNA contamination by RTQ PCR reactions run in the absence of reverse transcriptase using probe and primer sets designed to amplify across the span of a single exon.

First, the RNA samples were normalized to reference nucleic acids such as constitutively expressed genes (for example, β-actin and GAPDH). Normalized RNA (5 ul) was converted to cDNA and analyzed by RTQ-PCR using One Step RT-PCR Master Mix Reagents (Applied Biosystems; Catalog No. 4309169) and gene-specific primers according to the manufacturer's instructions.

In other cases, non-normalized RNA samples were converted to single strand cDNA (sscDNA) using Superscript II (Invitrogen Corporation; Catalog No. 18064-147) and random hexamers according to the manufacturer's instructions. Reactions containing up to 10 μg of total RNA were performed in a volume of 20 μl and incubated for 60 minutes at 42° C. This reaction can be scaled up to 50 μg of total RNA in a final volume of 100 μl. sscDNA samples are then normalized to reference nucleic acids as described previously, using 1×TaqMan® Universal Master mix (Applied Biosystems; catalog No. 4324020), following the manufacturer's instructions.

Probes and primers were designed for each assay according to Applied Biosystems Primer Express Software package (version I for Apple Computer's Macintosh Power PC) or a similar algorithm using the target sequence as input. Default settings were used for reaction conditions and the following parameters were set before selecting primers: primer concentration=250 nM, primer melting temperature (Tm) range=58°–60° C., primer optimal Tm=59° C., maximum primer difference=2° C., probe does not have 5'G, probe Tm must be 10° C. greater than primer Tm, amplicon size 75 bp to 100 bp. The probes and primers selected (see below) were synthesized by Synthegen (Houston, Tex., USA). Probes were double purified by HPLC to remove uncoupled dye and evaluated by mass spectroscopy to verify coupling of reporter and quencher dyes to the 5' and 3' ends of the probe, respectively. Their final concentrations were: forward and reverse primers, 900 nM each, and probe, 200 nM.

PCR conditions: When working with RNA samples, normalized RNA from each tissue and each cell line was spotted in each well of either a 96 well or a 384-well PCR plate (Applied Biosystems). PCR cocktails included either a single gene specific probe and primers set, or two multiplexed probe and primers sets (a set specific for the target clone and another gene-specific set multiplexed with the target probe). PCR reactions were set up using TaqMan® One-Step RT-PCR Master Mix (Applied Biosystems, Catalog No. 4313803) following manufacturer's instructions. Reverse transcription was performed at 48° C. for 30 minutes followed by amplification/PCR cycles as follows: 95° C. 10 min, then 40 cycles of 95° C. for 15 seconds, 60° C. for 1 minute. Results were recorded as CT values (cycle at which a given sample crosses a threshold level of fluorescence) using a log scale, with the difference in RNA concentration between a given sample and the sample with the lowest CT value being represented as 2 to the power of delta CT. The percent relative expression is then obtained by taking the reciprocal of this RNA difference and multiplying by 100.

When working with sscDNA samples, normalized sscDNA was used as described previously for RNA samples. PCR reactions containing one or two sets of probe and primers were set up as described previously, using 1×TaqMan® Universal Master mix (Applied Biosystems; catalog No. 4324020), following the manufacturer's instructions. PCR amplification was performed as follows: 95° C. 10 min, then 40 cycles of 95° C. for 15 seconds, 60° C. for 1 minute. Results were analyzed and processed as described previously.

Panels 1, 1.1, 1.2, and 1.3D

The plates for Panels 1, 1.1, 1.2 and 1.3D include 2 control wells (genomic DNA control and chemistry control) and 94 wells containing cDNA from various samples. The samples in these panels are broken into 2 classes: samples derived from cultured cell lines and samples derived from primary normal tissues. The cell lines are derived from cancers of the following types: lung cancer, breast cancer, melanoma, colon cancer, prostate cancer, CNS cancer, squamous cell carcinoma, ovarian cancer, liver cancer, renal cancer, gastric cancer and pancreatic cancer. Cell lines used in these panels are widely available through the American Type Culture Collection (ATCC), a repository for cultured cell lines, and were cultured using the conditions recommended by the ATCC. The normal tissues found on these panels are comprised of samples derived from all major organ systems from single adult individuals or fetuses. These samples are derived from the following organs: adult skeletal muscle, fetal skeletal muscle, adult heart, fetal heart, adult kidney, fetal kidney, adult liver, fetal liver, adult lung, fetal lung, various regions of the brain, the spleen, bone marrow, lymph node, pancreas, salivary gland, pituitary gland, adrenal gland, spinal cord, thymus, stomach, small intestine, colon, bladder, trachea, breast, ovary, uterus, placenta, prostate, testis and adipose.

In the results for Panels 1, 1.1, 1.2 and 1.3D, the following abbreviations are used:
ca.=carcinoma,
*=established from metastasis,
met=metastasis,
s cell var=small cell variant,
non-s=non-sm=non-small,
squam=squamous,
pl. eff=pl effusion=pleural effusion,
glio=glioma,
astro=astrocytoma, and
neuro=neuroblastoma.

General_screening_panel_v1.4

The plates for Panel 1.4 include 2 control wells (genomic DNA control and chemistry control) and 94 wells containing cDNA from various samples. The samples in Panel 1.4 are broken into 2 classes: samples derived from cultured cell lines and samples derived from primary normal tissues. The cell lines are derived from cancers of the following types: lung cancer, breast cancer, melanoma, colon cancer, prostate cancer, CNS cancer, squamous cell carcinoma, ovarian cancer, liver cancer, renal cancer, gastric cancer and pancreatic cancer. Cell lines used in Panel 1.4 are widely available through the American Type Culture Collection (ATCC), a repository for cultured cell lines, and were cultured using the conditions recommended by the ATCC. The normal tissues found on Panel 1.4 are comprised of pools of samples derived from all major organ systems from 2 to 5 different adult individuals or fetuses. These samples are derived from the following organs: adult skeletal muscle, fetal skeletal muscle, adult heart, fetal heart, adult kidney, fetal kidney, adult liver, fetal liver, adult lung, fetal lung, various regions of the brain, the spleen, bone marrow, lymph node, pancreas, salivary gland, pituitary gland, adrenal gland, spinal cord, thymus, stomach, small intestine, colon, bladder, trachea, breast, ovary, uterus, placenta, prostate, testis and adipose. Abbreviations are as described for Panels 1, 1.1, 1.2, and 1.3D.

Panels 2D and 2.2

The plates for Panels 2D and 2.2 generally include 2 control wells and 94 test samples composed of RNA or cDNA isolated from human tissue procured by surgeons working in close cooperation with the National Cancer Institute's Cooperative Human Tissue Network (CHTN) or the National Disease Research Initiative (NDRI). The tissues are derived from human malignancies and in cases where indicated many malignant tissues have "matched margins" obtained from noncancerous tissue just adjacent to the tumor. These are termed normal adjacent tissues and are denoted "NAT" in the results below. The tumor tissue and the "matched margins" are evaluated by two independent pathologists (the surgical pathologists and again by a pathologist at NDRI or CHTN). This analysis provides a gross histopathological assessment of tumor differentiation grade. Moreover, most samples include the original surgical pathology report that provides information regarding the clinical stage of the patient. These matched margins are taken from the tissue surrounding (i.e. immediately proximal) to the zone of surgery (designated "NAT", for normal adjacent tissue, in Table RR). In addition, RNA and cDNA samples were obtained from various human tissues derived from autopsies performed on elderly people or sudden death victims (accidents, etc.). These tissues were ascertained to be free of disease and were purchased from various commercial sources such as Clontech (Palo Alto, Calif.), Research Genetics, and Invitrogen.

Panel 3D

The plates of Panel 3D are comprised of 94 cDNA samples and two control samples. Specifically, 92 of these samples are derived from cultured human cancer cell lines, 2 samples of human primary cerebellar tissue and 2 controls. The human cell lines are generally obtained from ATCC (American Type Culture Collection), NCI or the German tumor cell bank and fall into the following tissue groups: Squamous cell carcinoma of the tongue, breast cancer, prostate cancer, melanoma, epidermoid carcinoma, sarcomas, bladder carcinomas, pancreatic cancers, kidney cancers, leukemias/lymphomas, ovarian/uterine/cervical, gastric, colon, lung and CNS cancer cell lines. In addition, there are two independent samples of cerebellum. These cells are all cultured under standard recommended conditions and RNA extracted using the standard procedures. The cell lines in panel 3D and 1.3D are of the most common cell lines used in the scientific literature.

Panels 4D, 4R, and 4.1D

Panel 4 includes samples on a 96 well plate (2 control wells, 94 test samples) composed of RNA (Panel 4R) or cDNA (Panels 4D/4.1D) isolated from various human cell lines or tissues related to inflammatory conditions. Total RNA from control normal tissues such as colon and lung (Stratagene, La Jolla, Calif.) and thymus and kidney (Clontech) was employed. Total RNA from liver tissue from cirrhosis patients and kidney from lupus patients was obtained from BioChain (Biochain Institute, Inc., Hayward, Calif.). Intestinal tissue for RNA preparation from patients diagnosed as having Crohn's disease and ulcerative colitis was obtained from the National Disease Research Interchange (NDRI) (Philadelphia, Pa.).

Astrocytes, lung fibroblasts, dermal fibroblasts, coronary artery smooth muscle cells, small airway epithelium, bronchial epithelium, microvascular dermal endothelial cells, microvascular lung endothelial cells, human pulmonary aortic endothelial cells, human umbilical vein endothelial cells were all purchased from Clonetics (Walkersville, Md.) and grown in the media supplied for these cell types by Clonetics. These primary cell types were activated with various cytokines or combinations of cytokines for 6 and/or 12–14 hours, as indicated. The following cytokines were used; IL-1 beta at approximately 1–5 ng/ml, TNF alpha at approximately 5–10 ng/ml, IFN gamma at approximately 20–50 ng/ml, IL-4 at approximately 5–10 ng/ml, IL-9 at approximately 5–10 ng/ml, IL-13 at approximately 5–10 ng/ml. Endothelial cells were sometimes starved for various times by culture in the basal media from Clonetics with 0.1% serum.

Mononuclear cells were prepared from blood of employees at CuraGen Corporation, using Ficoll. LAK cells were prepared from these cells by culture in DMEM 5% FCS (Hyclone), 100 µM non essential amino acids (Gibco/Life Technologies, Rockville, Md.), 1 mM sodium pyruvate (Gibco), mercaptoethanol $5.5 \times 10^{-5}$M (Gibco), and 10 mM Hepes (Gibco) and Interleukin 2 for 4–6 days. Cells were then either activated with 10–20 ng/ml PMA and 1–2 µg/ml ionomycin, IL-12 at 5–10 ng/ml, IFN gamma at 20–50 ng/ml and IL-18 at 5–10 ng/ml for 6 hours. In some cases, mononuclear cells were cultured for 4–5 days in DMEM 5% FCS (Hyclone), 100 µM non essential amino acids (Gibco), 1 mM sodium pyruvate (Gibco), mercaptoethanol $5.5 \times 10^{-5}$M (Gibco), and 10 mM Hepes (Gibco) with PHA (phytohemagglutinin) or PWM (pokeweed mitogen) at approximately 5 µg/ml. Samples were taken at 24, 48 and 72 hours for RNA preparation. MLR (mixed lymphocyte reaction) samples were obtained by taking blood from two donors, isolating the mononuclear cells using Ficoll and mixing the isolated mononuclear cells 1:1 at a final concentration of approximately $2 \times 10^6$ cells/ml in DMEM 5% FCS (Hyclone), 100 µM non essential amino acids (Gibco), 1 mM sodium pyruvate (Gibco), mercaptoethanol ($5.5 \times 10^{-5}$M) (Gibco), and 10 mM Hepes (Gibco). The MLR was cultured and samples taken at various time points ranging from 1–7 days for RNA preparation.

Monocytes were isolated from mononuclear cells using CD14 Miltenyi Beads, +ve VS selection columns and a Vario Magnet according to the manufacturer's instructions. Monocytes were differentiated into dendritic cells by culture in DMEM 5% fetal calf serum (FCS) (Hyclone, Logan, Utah), 100 µM non essential amino acids (Gibco), 1 mM sodium pyruvate (Gibco), mercaptoethanol $5.5 \times 10^{-5}$M (Gibco), and 10 mM Hepes (Gibco), 50 ng/ml GMCSF and 5 ng/ml IL-4 for 5–7 days. Macrophages were prepared by culture of monocytes for 5–7 days in DMEM 5% FCS (Hyclone), 100 µM non essential amino acids (Gibco), 1 mM sodium pyruvate (Gibco), mercaptoethanol $5.5 \times 10^{-5}$M (Gibco), 10 mM Hepes (Gibco) and 10% AB Human Serum or MCSF at approximately 50 ng/ml. Monocytes, macrophages and dendritic cells were stimulated for 6 and 12–14 hours with lipopolysaccharide (LPS) at 100 ng/ml. Dendritic cells were also stimulated with anti-CD40 monoclonal antibody (Pharmingen) at 10 µg/ml for 6 and 12–14 hours.

CD4 lymphocytes, CD8 lymphocytes and NK cells were also isolated from mononuclear cells using CD4, CD8 and CD56 Miltenyi beads, positive VS selection columns and a Vario Magnet according to the manufacturer's instructions. CD45RA and CD45RO CD4 lymphocytes were isolated by depleting mononuclear cells of CD8, CD56, CD14 and CD19 cells using CD8, CD56, CD14 and CD19 Miltenyi beads and positive selection. CD45RO beads were then used to isolate the CD45RO CD4 lymphocytes with the remaining cells being CD45RA CD4 lymphocytes. CD45RA CD4, CD45RO CD4 and CD8 lymphocytes were placed in DMEM 5% FCS (Hyclone), 100 µM non essential amino acids (Gibco), 1 mM sodium pyruvate (Gibco), mercaptoethanol $5.5 \times 10^{-5}$M (Gibco), and 10 mM Hepes (Gibco) and plated at $10^6$ cells/ml onto Falcon 6 well tissue culture plates that had been coated overnight with 0.5 µg/ml anti-CD28 (Pharmingen) and 3 ug/ml anti-CD3 (OKT3, ATCC) in PBS. After 6 and 24 hours, the cells were harvested for RNA preparation. To prepare chronically activated CD8 lymphocytes, we activated the isolated CD8 lymphocytes for 4 days on anti-CD28 and anti-CD3 coated plates and then harvested the cells and expanded them in DMEM 5% FCS (Hyclone), 100 µM non essential amino acids (Gibco), 1 mM sodium pyruvate (Gibco), mercaptoethanol $5.5 \times 10^{-5}$M (Gibco), and 10 mM Hepes (Gibco) and IL-2. The expanded CD8 cells were then activated again with plate bound anti-CD3 and anti-CD28 for 4 days and expanded as before. RNA was isolated 6 and 24 hours after the second activation and after 4 days of the second expansion culture. The isolated NK cells were cultured in DMEM 5% FCS (Hyclone), 100 µM non essential amino acids (Gibco), 1 mM sodium pyruvate (Gibco), mercaptoethanol $5.5 \times 10^{-5}$M (Gibco), and 10 mM Hepes (Gibco) and IL-2 for 4–6 days before RNA was prepared.

To obtain B cells, tonsils were procured from NDRI. The tonsil was cut up with sterile dissecting scissors and then passed through a sieve. Tonsil cells were then spun down and resupended at $10^6$ cells/ml in DMEM 5% FCS (Hyclone), 100 µM non essential amino acids (Gibco), 1 mM sodium pyruvate (Gibco), mercaptoethanol $5.5 \times 10^{-5}$M (Gibco), and 10 mM Hepes (Gibco). To activate the cells, we used PWM at 5 µg/ml or anti-CD40 (Pharmingen) at approximately 10 µg/ml and IL-4 at 5–10 ng/ml. Cells were harvested for RNA preparation at 24, 48 and 72 hours.

To prepare the primary and secondary Th1/Th2 and Tr1 cells, six-well Falcon plates were coated overnight with 10 µg/ml anti-CD28 (Pharmingen) and 2 µg/ml OKT3 (ATCC), and then washed twice with PBS. Umbilical cord blood CD4 lymphocytes (Poietic Systems, German Town, Md.) were cultured at $10^{5-10^6}$ cells/ml in DMEM 5% FCS (Hyclone), 100 µM non essential amino acids (Gibco), 1 mM sodium pyruvate (Gibco), mercaptoethanol $5.5 \times 10^{-5}$M (Gibco), 10 mM Hepes (Gibco) and IL-2 (4 ng/ml). IL-12 (5 ng/ml) and anti-IL4 (1 µg/ml) were used to direct to Th1, while IL-4 (5 ng/ml) and anti-IFN gamma (1 µg/ml) were used to direct to Th2 and IL-10 at 5 ng/ml was used to direct to Tr1. After 4–5 days, the activated Th1, Th2 and Tr1 lymphocytes were washed once in DMEM and expanded for 4–7 days in DMEM 5% FCS (Hyclone), 100 µM non essential amino acids (Gibco), 1 mM sodium pyruvate (Gibco), mercaptoethanol $5.5 \times 10^{-5}$M (Gibco), 10 mM Hepes (Gibco) and IL-2 (1 ng/ml). Following this, the activated Th1, Th2 and Tr1 lymphocytes were re-stimulated for 5 days with anti-CD28/OKT3 and cytokines as described above, but with the addition of anti-CD95L (1 µg/ml) to prevent apoptosis. After 4–5 days, the Th1, Th2 and Tr1 lymphocytes were washed and then expanded again with IL-2 for 4–7 days. Activated Th1 and Th2 lymphocytes were maintained in this way for a maximum of three cycles. RNA was prepared from primary and secondary Th1, Th2 and Tr1 after 6 and 24 hours following the second and third activations with plate bound anti-CD3 and anti-CD28 mAbs and 4 days into the second and third expansion cultures in Interleukin 2.

The following leukocyte cells lines were obtained from the ATCC: Ramos, EOL-1, KU-812. EOL cells were further differentiated by culture in 0.1 mM dbcAMP at $5\times10^5$ cells/ml for 8 days, changing the media every 3 days and adjusting the cell concentration to $5\times10^5$ cells/ml. For the culture of these cells, we used DMEM or RPMI (as recommended by the ATCC), with the addition of 5% FCS (Hyclone), 100 µM non essential amino acids (Gibco), 1 mM sodium pyruvate (Gibco), mercaptoethanol $5.5\times10^{-5}$M (Gibco), 10 mM Hepes (Gibco). RNA was either prepared from resting cells or cells activated with PMA at 10 ng/ml and ionomycin at 1 µg/ml for 6 and 14 hours. Keratinocyte line CCD106 and an airway epithelial tumor line NCI-H292 were also obtained from the ATCC. Both were cultured in DMEM 5% FCS (Hyclone), 100 µM non essential amino acids (Gibco), 1 mM sodium pyruvate (Gibco), mercaptoethanol $5.5\times10^{-5}$M (Gibco), and 10 mM Hepes (Gibco). CCD1106 cells were activated for 6 and 14 hours with approximately 5 ng/ml TNF alpha and 1 ng/ml IL-1 beta, while NCI-H292 cells were activated for 6 and 14 hours with the following cytokines: 5 ng/ml IL-4, 5 ng/ml IL-9, 5 ng/ml IL-13 and 25 ng/ml IFN gamma.

For these cell lines and blood cells, RNA was prepared by lysing approximately $10^7$ cells/ml using Trizol (Gibco BRL). Briefly, 1/10 volume of bromochloropropane (Molecular Research Corporation) was added to the RNA sample, vortexed and after 10 minutes at room temperature, the tubes were spun at 14,000 rpm in a Sorvall SS34 rotor. The aqueous phase was removed and placed in a 15 ml Falcon Tube. An equal volume of isopropanol was added and left at −20° C. overnight. The precipitated RNA was spun down at 9,000 rpm for 15 min in a Sorvall SS34 rotor and washed in 70% ethanol. The pellet was redissolved in 300 µl of RNAse-free water and 35 µl buffer (Promega) 5 µl DTT, 7 µl RNAsin and 8 µl DNAse were added. The tube was incubated at 37° C. for 30 minutes to remove contaminating genomic DNA, extracted once with phenol chloroform and re-precipitated with 1/10 volume of 3M sodium acetate and 2 volumes of 100% ethanol. The RNA was spun down and placed in RNAse free water. RNA was stored at −80° C.

AI_comprehensive panel_v1.0

The plates for AI_comprehensive panel_v1.0 include two control wells and 89 test samples comprised of cDNA isolated from surgical and postmortem human tissues obtained from the Backus Hospital and Clinomics (Frederick, Md.). Total RNA was extracted from tissue samples from the Backus Hospital in the Facility at CuraGen. Total RNA from other tissues was obtained from Clinomics.

Joint tissues including synovial fluid, synovium, bone and cartilage were obtained from patients undergoing total knee or hip replacement surgery at the Backus Hospital. Tissue samples were immediately snap frozen in liquid nitrogen to ensure that isolated RNA was of optimal quality and not degraded. Additional samples of osteoarthritis and rheumatoid arthritis joint tissues were obtained from Clinomics. Normal control tissues were supplied by Clinomics and were obtained during autopsy of trauma victims.

Surgical specimens of psoriatic tissues and adjacent matched tissues were provided as total RNA by Clinomics. Two male and two female patients were selected between the ages of 25 and 47. None of the patients were taking prescription drugs at the time samples were isolated.

Surgical specimens of diseased colon from patients with ulcerative colitis and Crohns disease and adjacent matched tissues were obtained from Clinomics. Bowel tissue from three female and three male Crohn's patients between the ages of 41–69 were used. Two patients were not on prescription medication while the others were taking dexamethasone, phenobarbital, or tylenol. Ulcerative colitis tissue was from three male and four female patients. Four of the patients were taking lebvid and two were on phenobarbital.

Total RNA from post mortem lung tissue from trauma victims with no disease or with emphysema, asthma or COPD was purchased from Clinomics. Emphysema patients ranged in age from 40–70 and all were smokers, this age range was chosen to focus on patients with cigarette-linked emphysema and to avoid those patients with alpha-1 antitrypsin deficiencies. Asthma patients ranged in age from 36–75, and excluded smokers to prevent those patients that could also have COPD. COPD patients ranged in age from 35–80 and included both smokers and non-smokers. Most patients were taking corticosteroids, and bronchodilators.

In the labels employed to identify tissues in the AI_comprehensive panel_v1.0 panel, the following abbreviations are used:

AI=Autoimmunity
Syn=Synovial
Normal=No apparent disease
Rep22 /Rep20=individual patients
RA=Rheumatoid arthritis
Backus=From Backus Hospital
OA=Osteoarthritis
(SS) (BA) (MF)=Individual patients
Adj=Adjacent tissue
Match control=adjacent tissues
-M=Male
-F=Female
COPD=Chronic obstructive pulmonary disease Panels 5D and 5I The plates for Panel 5D and 5I include two control wells and a variety of cDNAs isolated from human tissues and cell lines with an emphasis on metabolic diseases. Metabolic tissues were obtained from patients enrolled in the Gestational Diabetes study. Cells were obtained during different stages in the differentiation of adipocytes from human mesenchymal stem cells. Human pancreatic islets were also obtained.

In the Gestational Diabetes study subjects are young (18–40 years), otherwise healthy women with and without gestational diabetes undergoing routine (elective) Caesarean section. After delivery of the infant, when the surgical incisions were being repaired/closed, the obstetrician removed a small sample (<1 cc) of the exposed metabolic tissues during the closure of each surgical level. The biopsy material was rinsed in sterile saline, blotted and fast frozen within 5 minutes from the time of removal. The tissue was then flash frozen in liquid nitrogen and stored, individually, in sterile screw-top tubes and kept on dry ice for shipment to or to be picked up by CuraGen. The metabolic tissues of interest include uterine wall (smooth muscle), visceral adipose, skeletal muscle (rectus) and subcutaneous adipose. Patient descriptions are as follows:

| | |
|---|---|
| Patient 2 | Diabetic Hispanic, overweight, not on insulin |
| Patient 7–9 | Nondiabetic Caucasian and obese (BMI > 30) |
| Patient 10 | Diabetic Hispanic, overweight, on insulin |
| Patient 11 | Nondiabetic African American and overweight |
| Patient 12 | Diabetic Hispanic on insulin |

Adipocyte differentiation was induced in donor progenitor cells obtained from Osirus (a division of Clonetics/ BioWhittaker) in triplicate, except for Donor 3U which had only two replicates. Scientists at Clonetics isolated, grew and differentiated human mesenchymal stem cells (HuMSCs) for CuraGen based on the published protocol found in Mark F. Pittenger, et al., Multilineage Potential of Adult Human Mesenchymal Stem Cells Science Apr. 2, 1999: 143–147. Clonetics provided Trizol lysates or frozen pellets suitable for mRNA isolation and ds cDNA production. A general description of each donor is as follows:

Donor 2 and 3 U: Mesenchymal Stem cells, Undifferentiated Adipose

Donor 2 and 3 AM: Adipose, AdiposeMidway Differentiated

Donor 2 and 3 AD: Adipose, Adipose Differentiated

Human cell lines were generally obtained from ATCC (American Type Culture Collection), NCI or the German tumor cell bank and fall into the following tissue groups: kidney proximal convoluted tubule, uterine smooth muscle cells, small intestine, liver HepG2 cancer cells, heart primary stromal cells, and adrenal cortical adenoma cells. These cells are all cultured under standard recommended conditions and RNA extracted using the standard procedures. All samples were processed at CuraGen to produce single stranded cDNA.

Panel 5I contains all samples previously described with the addition of pancreatic islets from a 58 year old female patient obtained from the Diabetes Research Institute at the University of Miami School of Medicine. Islet tissue was processed to total RNA at an outside source and delivered to CuraGen for addition to panel 5I.

In the labels employed to identify tissues in the 5D and 5I panels, the following abbreviations are used:

GO Adipose=Greater Omentum Adipose

SK=Skeletal Muscle

UT=Uterus

PL=Placenta

AD=Adipose Differentiated

AM=Adipose Midway Differentiated

U=Undifferentiated Stem Cells

Panel CNSD0.01

The plates for Panel CNSD0.01 include two control wells and 94 test samples comprised of cDNA isolated from postmortem human brain tissue obtained from the Harvard Brain Tissue Resource Center. Brains are removed from calvaria of donors between 4 and 24 hours after death, sectioned by neuroanatomists, and frozen at −80° C. in liquid nitrogen vapor. All brains are sectioned and examined by neuropathologists to confirm diagnoses with clear associated neuropathology.

Disease diagnoses are taken from patient records. The panel contains two brains from each of the following diagnoses: Alzheimer's disease, Parkinson's disease, Huntington's disease, Progressive Supernuclear Palsy, Depression, and "Normal controls". Within each of these brains, the following regions are represented: cingulate gyrus, temporal pole, globus palladus, substantia nigra, Brodman Area 4 (primary motor strip), Brodman Area 7 (parietal cortex), Brodman Area 9 (prefrontal cortex), and Brodman area 17 (occipital cortex). Not all brain regions are represented in all cases; e.g., Huntington's disease is characterized in part by neurodegeneration in the globus palladus, thus this region is impossible to obtain from confirmed Huntington's cases. Likewise Parkinson's disease is characterized by degeneration of the substantia nigra making this region more difficult to obtain. Normal control brains were examined for neuropathology and found to be free of any pathology consistent with neurodegeneration.

In the labels employed to identify tissues in the CNS panel, the following abbreviations are used:

PSP=Progressive supranuclear palsy

Sub Nigra=Substantia nigra

Glob Palladus=Globus palladus

Temp Pole=Temporal pole

Cing Gyr=Cingulate gyrus

BA 4=Brodman Area 4

Panel CNS_Neurodegeneration_V1.0

The plates for Panel CNS_Neurodegeneration_V1.0 include two control wells and 47 test samples comprised of cDNA isolated from postmortem human brain tissue obtained from the Harvard Brain Tissue Resource Center (McLean Hospital) and the Human Brain and Spinal Fluid Resource Center (VA Greater Los Angeles Healthcare System). Brains are removed from calvaria of donors between 4 and 24 hours after death, sectioned by neuroanatomists, and frozen at −80° C. in liquid nitrogen vapor. All brains are sectioned and examined by neuropathologists to confirm diagnoses with clear associated neuropathology.

Disease diagnoses are taken from patient records. The panel contains six brains from Alzheimer's disease (AD) patients, and eight brains from "Normal controls" who showed no evidence of dementia prior to death. The eight normal control brains are divided into two categories: Controls with no dementia and no Alzheimer's like pathology (Controls) and controls with no dementia but evidence of severe Alzheimer's like pathology, (specifically senile plaque load rated as level 3 on a scale of 0–3; 0=no evidence of plaques, 3=severe AD senile plaque load). Within each of these brains, the following regions are represented: hippocampus, temporal cortex (Brodman Area 21), parietal cortex (Brodman area 7), and occipital cortex (Brodman area 17). These regions were chosen to encompass all levels of neurodegeneration in AD. The hippocampus is a region of early and severe neuronal loss in AD; the temporal cortex is known to show neurodegeneration in AD after the hippocampus; the parietal cortex shows moderate neuronal death in the late stages of the disease; the occipital cortex is spared in AD and therefore acts as a "control" region within AD patients. Not all brain regions are represented in all cases.

In the labels employed to identify tissues in the CNS_Neurodegeneration_V1.0 panel, the following abbreviations are used:

AD=Alzheimer's disease brain; patient was demented and showed AD-like pathology upon autopsy Control=Control brains; patient not demented, showing no neuropathology Control (Path)=Control brains; pateint not demented but showing sever AD-like pathology SupTemporal Ctx=Superior Temporal Cortex Inf Temporal Ctx=Inferior Temporal Cortex A. NOV1: Androgen-Regulated Short-Chain Dehydrogenase/Reductase Expression of gene CG57413-01 was assessed using the primer-probe set Ag3230, described in Table AA. Results of the RTQ-PCR runs are shown in Tables AB, AC, AD and AE.

TABLE AA

Probe Name Ag3230

| Primers | Sequences | | Length | Start Position |
|---|---|---|---|---|
| Forward | 5'-gatggtacgtgatgctcttgtt-3' | (SEQ ID NO:293) | 22 | 10 |
| Probe | TET-5'-cccttgccgataggaagttctttgct-3'-TAMRA | (SEQ ID NO:294) | 26 | 33 |
| Reverse | 5'-aggaagctgcacatttgttcta-3' | (SEQ ID NO:295) | 22 | 70 |

TABLE AB

CNS_neurodegeneration_v1.0

| Tissue Name | Rel. Exp. (%) Ag3230, Run 206533576 | Tissue Name | Rel. Exp. (%) Ag3230, Run 206533576 |
|---|---|---|---|
| AD 1 Hippo | 0.0 | Control (Path) 3 Temporal Ctx | 0.0 |
| AD 2 Hippo | 0.0 | Control (Path) 4 Temporal Ctx | 54.7 |
| AD 3 Hippo | 8.7 | AD 1 Occipital Ctx | 18.2 |
| AD 4 Hippo | 0.0 | AD 2 Occipital Ctx (Missing) | 0.0 |
| AD 5 hippo | 32.1 | AD 3 Occipital Ctx | 0.0 |
| AD 6 Hippo | 95.3 | AD 4 Occipital Ctx | 8.5 |
| Control 2 Hippo | 0.0 | AD 5 Occipital Ctx | 6.6 |
| Control 4 Hippo | 9.4 | AD 6 Occipital Ctx | 22.8 |
| Control (Path) 3 Hippo | 21.6 | Control 1 Occipital Ctx | 0.0 |
| AD 1 Temporal Ctx | 8.2 | Control 2 Occipital Ctx | 36.3 |
| AD 2 Temporal Ctx | 4.3 | Control 3 Occipital Ctx | 0.0 |
| AD 3 Temporal Ctx | 0.0 | Control 4 Occipital Ctx | 0.0 |
| AD 4 Temporal Ctx | 8.2 | Control (Path) 1 Occipital Ctx | 100.0 |
| AD 5 Inf Temporal Ctx | 32.5 | Control (Path) 2 Occipital Ctx | 15.3 |
| AD 5 SupTemporal Ctx | 15.2 | Control (Path) 3 Occipital Ctx | 0.0 |
| AD 6 Inf Temporal Ctx | 66.9 | Control (Path) 4 Occipital Ctx | 25.5 |
| AD 6 Sup Temporal Ctx | 67.8 | Control 1 Parietal Ctx | 0.0 |
| Control 1 Temporal Ctx | 0.0 | Control 2 Parietal Ctx | 5.6 |
| Control 2 Temporal Ctx | 18.0 | Control 3 Parietal Ctx | 20.4 |
| Control 3 Temporal Ctx | 8.1 | Control (Path) 1 Parietal Ctx | 37.9 |
| Control 4 Temporal Ctx | 17.7 | Control (Path) 2 Parietal Ctx | 7.5 |
| Control (Path) 1 Temporal Ctx | 14.8 | Control (Path) 3 Parietal Ctx | 0.0 |
| Control (Path) 2 Temporal Ctx | 34.2 | Control (Path) 4 Parietal Ctx | 43.8 |

TABLE AC

Panel 1.3D

| Tissue Name | Rel. Exp. (%) Ag3230, Run 165524130 | Tissue Name | Rel. Exp. (%) Ag3230, Run 165524130 |
|---|---|---|---|
| Liver adenocarcinoma | 0.0 | Kidney (fetal) | 0.0 |
| Pancreas | 0.0 | Renal ca. 786-0 | 9.8 |
| Pancreatic ca. CAPAN 2 | 0.0 | Renal ca. A498 | 0.0 |
| Adrenal gland | 0.0 | Renal ca. RXF 393 | 0.0 |
| Thyroid | 0.0 | Renal ca. ACHN | 0.0 |
| Salivary gland | 0.0 | Renal ca. UO-31 | 0.0 |
| Pituitary gland | 11.1 | Renal ca. TK-10 | 0.0 |
| Brain (fetal) | 0.0 | Liver | 0.0 |
| Brain (whole) | 20.0 | Liver (fetal) | 0.0 |
| Brain (amygdala) | 33.9 | Liver ca. (hepatoblast) HepG2 | 18.0 |
| Brain (cerebellum) | 0.0 | Lung | 0.0 |

TABLE AC-continued

Panel 1.3D

| Tissue Name | Rel. Exp. (%) Ag3230, Run 165524130 | Tissue Name | Rel. Exp. (%) Ag3230, Run 165524130 |
|---|---|---|---|
| Brain (hippocampus) | 16.4 | Lung (fetal) | 0.0 |
| Brain (substantia nigra) | 14.1 | Lung ca. (small cell) LX-1 | 17.9 |
| Brain (thalamus) | 0.0 | Lung ca. (small cell) NCI-H69 | 0.0 |
| Cerebral Cortex | 22.2 | Lung ca. (s. cell var.) SHP-77 | 0.0 |
| Spinal cord | 0.0 | Lung ca. (large cell) NCI-H460 | 0.0 |
| glio/astro U87-MG | 0.0 | Lung ca. (non-sm. cell) A549 | 0.0 |
| glio/astro U-118-MG | 0.0 | Lung ca. (non-s. cell) NCI-H23 | 0.0 |
| astrocytoma SW1783 | 0.0 | Lung ca. (non-s. cell) HOP-62 | 0.0 |
| neuro*; met SK-N-AS | 0.0 | Lung ca. (non-s. cl) NCI-H522 | 0.0 |
| astrocytoma SF-539 | 0.0 | Lung ca. (squam.) SW 900 | 0.0 |
| astrocytoma SNB-75 | 13.8 | Lung ca. (squam.) NCI-H596 | 0.0 |
| glioma SNB-19 | 0.0 | Mammary gland | 0.0 |
| glioma U251 | 100.0 | Breast ca.* (pl. ef) MCF-7 | 12.7 |
| glioma SF-295 | 0.0 | Breast ca.* (pl. ef) MDA-MB-231 | 0.0 |
| Heart (fetal) | 0.0 | Breast ca.* (pl. ef) T47D | 0.0 |
| Heart | 0.0 | Breast ca. BT-549 | 0.0 |
| Skeletal muscle (fetal) | 0.0 | Breast ca. MDA-N | 0.0 |
| Skeletal muscle | 0.0 | Ovary | 0.0 |
| Bone marrow | 0.0 | Ovarian ca. OVCAR-3 | 0.0 |
| Thymus | 0.0 | Ovarian ca. OVCAR-4 | 0.0 |
| Spleen | 0.0 | Ovarian ca. OVCAR-5 | 0.0 |
| Lymph node | 39.5 | Ovarian ca. OVCAR-8 | 0.0 |
| Colorectal | 43.2 | Ovarian ca. IGROV-1 | 0.0 |
| Stomach | 43.5 | Ovarian ca.* (ascites) SK-OV-3 | 36.6 |
| Small intestine | 38.7 | Uterus | 57.8 |
| Colon ca. SW480 | 0.0 | Placenta | 0.0 |
| Colon ca.* SW620 (SW480 met) | 0.0 | Prostate | 38.2 |
| Colon ca. HT29 | 0.0 | Prostate ca.* (bone met) PC-3 | 0.0 |
| Colon ca. HCT-116 | 0.0 | Testis | 17.9 |
| Colon ca. CaCo-2 | 13.4 | Melanoma Hs688 (A).T | 0.0 |
| Colon ca. tissue (ODO3866) | 0.0 | Melanoma* (met) Hs688 (B).T | 0.0 |
| Colon ca. HCC-2998 | 14.3 | Melanoma UACC-62 | 0.0 |
| Gastric ca.* (liver met) NCI-N87 | 79.6 | Melanoma M14 | 18.6 |
| Bladder | 26.8 | Melanoma LOX IMVI | 0.0 |
| Trachea | 0.0 | Melanoma* (met) SK-MEL-5 | 0.0 |
| Kidney | 0.0 | Adipose | 0.0 |

TABLE AD

Panel 2.2

| Tissue Name | Rel. Exp. (%) Ag3230, Run 174442812 | Tissue Name | Rel. Exp. (%) Ag3230, Run 174442812 |
|---|---|---|---|
| Normal Colon | 18.2 | Kidney Margin (OD04348) | 38.4 |
| Colon cancer (OD06064) | 0.0 | Kidney malignant cancer (OD06204B) | 23.2 |
| Colon Margin (OD06064) | 0.0 | Kidney normal adjacent tissue (OD06204E) | 0.0 |
| Colon cancer (OD06159) | 0.0 | Kidney Cancer (OD04450-01) | 0.0 |
| Colon Margin (OD06159) | 0.0 | Kidney Margin (OD04450-03) | 0.0 |

TABLE AD-continued

Panel 2.2

| Tissue Name | Rel. Exp. (%) Ag3230, Run 174442812 | Tissue Name | Rel. Exp. (%) Ag3230, Run 174442812 |
|---|---|---|---|
| Colon cancer (OD06297-04) | 0.0 | Kidney Cancer 8120613 | 22.7 |
| Colon Margin (OD06297-05) | 17.9 | Kidney Margin 8120614 | 0.0 |
| CC Gr. 2 ascend colon (OD03921) | 0.0 | Kidney Cancer 9010320 | 0.0 |
| CC Margin (OD03921) | 9.0 | Kidney Margin 9010321 | 0.0 |
| Colon cancer metastasis (OD06104) | 0.0 | Kidney Cancer 8120607 | 0.0 |
| Lung Margin (OD06104) | 0.0 | Kidney Margin 8120608 | 20.3 |
| Colon mets to lung (OD04451-01) | 41.5 | Normal Uterus | 12.6 |
| Lung Margin (OD04451-02) | 19.9 | Uterine Cancer 064011 | 0.0 |
| Normal Prostate | 0.0 | Normal Thyroid | 0.0 |
| Prostate Cancer (OD04410) | 12.6 | Thyroid Cancer 064010 | 0.0 |
| Prostate Margin (OD04410) | 20.0 | Thyroid Cancer A302152 | 0.0 |
| Normal Ovary | 0.0 | Thyroid Margin A302153 | 0.0 |
| Ovarian cancer (OD06283-03) | 0.0 | Normal Breast | 44.4 |
| Ovarian Margin (OD06283-07) | 0.0 | Breast Cancer (OD04566) | 0.0 |
| Ovarian Cancer 064008 | 41.8 | Breast Cancer 1024 | 18.9 |
| Ovarian cancer (OD06145) | 0.0 | Breast Cancer (OD04590-01) | 0.0 |
| Ovarian Margin (OD06145) | 4.7 | Breast Cancer Mets (OD04590-03) | 0.0 |
| Ovarian cancer (OD06455-03) | 0.0 | Breast Cancer Metastasis (OD04655-05) | 38.2 |
| Ovarian Margin (OD06455-07) | 0.0 | Breast Cancer 064006 | 15.7 |
| Normal Lung | 32.1 | Breast Cancer 9100266 | 0.0 |
| Invasive poor diff. lung adeno (OD04945-01 | 0.0 | Breast Margin 9100265 | 0.0 |
| Lung Margin (OD04945-03) | 0.0 | Breast Cancer A209073 | 0.0 |
| Lung Malignant Cancer (OD03126) | 0.0 | Breast Margin A2090734 | 20.4 |
| Lung Margin (OD03126) | 0.0 | Breast cancer (OD06083) | 39.0 |
| Lung Cancer (OD05014A) | 0.0 | Breast cancer node metastasis (OD06083) | 45.1 |
| Lung Margin (OD05014B) | 100.0 | Normal Liver | 6.0 |
| Lung cancer (OD06081) | 0.0 | Liver Cancer 1026 | 0.0 |
| Lung Margin (OD06081) | 0.0 | Liver Cancer 1025 | 27.9 |
| Lung Cancer (OD04237-01) | 0.0 | Liver Cancer 6004-T | 20.0 |
| Lung Margin (OD04237-02) | 0.0 | Liver Tissue 6004-N | 0.0 |
| Ocular Melanoma Metastasis | 12.1 | Liver Cancer 6005-T | 0.0 |
| Ocular Melanoma Margin (Liver) | 0.0 | Liver Tissue 6005-N | 0.0 |
| Melanoma Metastasis | 18.8 | Liver Cancer 064003 | 19.2 |
| Melanoma Margin (Lung) | 0.0 | Normal Bladder | 0.0 |
| Normal Kidney | 20.4 | Bladder Cancer 1023 | 0.0 |
| Kidney Ca, Nuclear grade 2 (OD04338) | 82.4 | Bladder Cancer A302173 | 0.0 |
| Kidney Margin (OD04338) | 9.0 | Normal Stomach | 44.4 |
| Kidney Ca Nuclear grade 1/2 (OD04339) | 53.2 | Gastric Cancer 9060397 | 0.0 |
| Kidney Margin (OD04339) | 18.3 | Stomach Margin 9060396 | 18.7 |
| Kidney Ca, Clear cell type (OD04340) | 38.2 | Gastric Cancer 9060395 | 33.0 |
| Kidney Margin (OD04340) | 0.0 | Stomach Margin 9060394 | 21.0 |
| Kidney Ca, Nuclear grade 3 (OD04348) | 0.0 | Gastric Cancer 064005 | 0.0 |

TABLE AE

Panel 4D

| Tissue Name | Rel. Exp. (%) Ag3230, Run 164532020 | Tissue Name | Rel. Exp. (%) Ag3230, Run 164532020 |
|---|---|---|---|
| Secondary Th1 act | 0.0 | HUVEC IL-1beta | 7.9 |
| Secondary Th2 act | 0.0 | HUVEC IFN gamma | 9.2 |
| Secondary Tr1 act | 11.1 | HUVEC TNF alpha + IFN gamma | 0.0 |

TABLE AE-continued

Panel 4D

| Tissue Name | Rel. Exp. (%) Ag3230, Run 164532020 | Tissue Name | Rel. Exp. (%) Ag3230, Run 164532020 |
|---|---|---|---|
| Secondary Th1 rest | 0.0 | HUVEC TNF alpha + IL4 | 0.0 |
| Secondary Th2 rest | 13.9 | HUVEC IL-11 | 4.0 |
| Secondary Tr1 rest | 12.2 | Lung Microvascular EC none | 15.2 |
| Primary Th1 act | 7.1 | Lung Microvascular EC TNF alpha + IL-1beta | 15.2 |
| Primary Th2 act | 17.7 | Microvascular Dermal EC none | 9.2 |
| Primary Tr1 act | 0.0 | Microsvascular Dermal EC TNF alpha + IL-1beta | 7.2 |
| Primary Th1 rest | 57.0 | Bronchial epithelium TNF alpha + IL1beta | 15.9 |
| Primary Th2 rest | 11.5 | Small airway epithelium none | 22.4 |
| Primary Tr1 rest | 7.9 | Small airway epithelium TNF alpha + IL-1beta | 100.0 |
| CD45RA CD4 lymphocyte act | 1.9 | Coronery artery SMC rest | 0.0 |
| CD45RO CD4 lymphocyte act | 25.2 | Coronery artery SMC TNF alpha + IL-1beta | 0.0 |
| CD8 lymphocyte act | 7.1 | Astrocytes rest | 0.0 |
| Secondary CD8 lymphocyte rest | 53.6 | Astrocytes TNF alpha + IL-1beta | 0.0 |
| Secondary CD8 lymphocyte act | 0.0 | KU-812 (Basophil) rest | 0.0 |
| CD4 lymphocyte none | 41.8 | KU-812 (Basophil) PMA/ionomycin | 58.2 |
| 2ry Th1/Th2/Tr1_anti-CD95 CH11 | 7.0 | CCD1106 (Keratinocytes) none | 0.0 |
| LAK cells rest | 24.8 | CCD1106 (Keratinocytes) TNF alpha + IL-1beta | 0.0 |
| LAK cells IL-2 | 32.5 | Liver cirrhosis | 51.1 |
| LAK cells IL-2 + IL-12 | 22.2 | Lupus kidney | 0.0 |
| LAK cells IL-2 + IFN gamma | 27.4 | NCI-H292 none | 0.0 |
| LAK cells IL-2 + IL-18 | 15.3 | NCI-H292 IL-4 | 31.9 |
| LAK cells PMA/ionomycin | 0.0 | NCI-H292 IL-9 | 12.3 |
| NK Cells IL-2 rest | 12.8 | NCI-H292 IL-13 | 0.0 |
| Two Way MLR 3 day | 28.9 | NCI-H292 IFN gamma | 0.0 |
| Two Way MLR 5 day | 0.0 | HPAEC none | 0.0 |
| Two Way MLR 7 day | 27.5 | HPAEC TNF alpha + IL-1beta | 3.2 |
| PBMC rest | 9.4 | Lung fibroblast none | 20.9 |
| PBMC PWM | 21.8 | Lung fibroblast TNF alpha + IL-1beta | 14.9 |
| PBMC PHA-L | 7.9 | Lung fibroblast IL-4 | 13.2 |
| Ramos (B cell) none | 0.0 | Lung fibroblast IL-9 | 0.0 |
| Ramos (B cell) ionomycin | 0.0 | Lung fibroblast IL-13 | 0.0 |
| B lymphocytes PWM | 25.9 | Lung fibroblast IFN gamma | 0.0 |
| B lymphocytes CD40L and IL-4 | 30.8 | Dermal fibroblast CCD1070 rest | 0.0 |
| EOL-1 dbcAMP | 0.0 | Dermal fibroblast CCD1070 TNF alpha | 0.0 |
| EOL-1 dbcAMP PMA/ionomycin | 0.0 | Dermal fibroblast CCD1070 IL-1beta | 0.0 |
| Dendritic cells none | 59.5 | Dermal fibroblast IFN gamma | 0.0 |
| Dendritic cells LPS | 0.0 | Dermal fibroblast IL-4 | 7.7 |
| Dendritic cells anti-CD40 | 54.3 | IBD Colitis 2 | 0.0 |
| Monocytes rest | 49.7 | IBD Crohn's | 7.1 |
| Monocytes LPS | 8.7 | Colon | 14.4 |
| Macrophages rest | 21.6 | Lung | 16.2 |
| Macrophages LPS | 8.0 | Thymus | 92.7 |
| HUVEC none | 0.0 | Kidney | 0.0 |
| HUVEC starved | 0.0 | | |

CNS_neurodegeneration_v1.0 Summary: Ag3230 This panel does not show differential expression of the CG57413-01 gene in Alzheimer's disease. However, this expression profile confirms the presence of this gene in the brain. This gene encodes a homolog of an androgen regulated short chain dehydrogenase. Members of this family are known to function in the processing of hormones in the brain. Brain hormone regulation mediates numerous clinically significant conditions, including psychiatric disorders such as anxiety, overeating and memory disorders. Therefore, agents that modulate the activity of this gene product have potential utility in the treatment of these disorders. In addition, steroid treatment is used in a number of clinical conditions including Alzheimer's disease (estrogen), menopause associated symptoms (estrogen), multiple sclerosis (glucocorticoids), and spinal cord injury (methylprednisolone). Treatment with an antagonist of this gene product, or reduction of the levels of this gene product could slow steroid degradation and lower the necessary amount given for therapeutic effect, thus reducing peripheral side effects (Biswas and Russell, J Biol Chem 1997 June 20;272(25):15959–66; Matsumoto et al., Spine 2001 February 15;26(4):426–30; Holinka, Ann N Y Acad Sci 2001 September;943:89–108; Burkman et al., Am J Obstet Gynecol 2001 August;185(2 Suppl):S13–23; Gaillard et al., Neuroreport 2001 July 20;12(10):2189–93; Penning et al., Biochem J 2000 October 1;351(Pt 1):67–77).

Panel 1.3D Summary: Ag3230 Expression of the CG57413-01 gene is restricted to a sample derived from a brain cancer cell line (CT=34.8). Thus, expression of this gene could be used to differentiate between this sample and other samples on this panel and as a marker to detect the presence of brain cancer. Furthermore, therapeutic modulation of the expression or function of this gene may be effective in the treatment of brain cancer.

Panel 2.2 Summary: Ag3230 Expression of the CG57413-01 gene is restricted to a sample derived from a normal lung tissue (CT=34.95). Thus, expression of this gene could be used to differentiate between this sample and other samples on this panel and as a marker of normal lung tissue.

Panel 4D Summary: Ag3230 Highest expression of the CG57413-01 gene is seen in Small airway epithelium stimulated with TNFalpha+IL-1 beta (CT=33.4). Significant expression is also seen in the basophil cell line KU-812 stimulated with PMA/ionomycin. This cell line constitutes a reasonable model for the inflammatory cells that take part in various inflammatory lung diseases. This expression profile in combination with the exclusive expression in normal lung seen in Panel 2D suggests that the protein encoded by this gene may be involved in the proliferation or activation of airway epithelium. Therefore, theraputics designed with the protein encoded by this transcript could be important in the treatment of pathological and inflammatory lung disorders, including emphysema, allergies, asthma and COPD.

Panel 5 Islet Summary: Ag3230 Expression of the CG57413-01 gene is low/undetectable in all samples on this panel (CTs>35).

B. NOV2a and NOV2b: Aryl-Acylamidase

Expression of gene CG57391-01 and variant CG57391-02 was assessed using the primer-probe sets Ag3053 and Ag3224, described in Tables BA and BB. Results of the RTQ-PCR runs are shown in Table BC.

TABLE BC

| | Panel 1.3D | |
|---|---|---|
| Tissue Name | Rel. Exp.(%) Ag3053, Run 167985386 | Rel. Exp.(%) Ag3224, Run 165524086 |
| Liver adenocarcinoma | 0.0 | 0.0 |
| Pancreas | 0.0 | 0.0 |
| Pancreatic ca. CAPAN 2 | 0.0 | 0.0 |
| Adrenal gland | 0.0 | 0.0 |
| Thyroid | 11.3 | 0.0 |
| Salivary gland | 0.0 | 0.0 |
| Pituitary gland | 66.0 | 12.4 |
| Brain (fetal) | 0.0 | 0.0 |
| Brain (whole) | 0.0 | 0.0 |
| Brain (amygdala) | 0.0 | 0.0 |
| Brain (cerebellum) | 0.0 | 0.0 |
| Brain (hippocampus) | 0.0 | 0.0 |
| Brain (substantia nigra) | 0.0 | 0.0 |
| Brain (thalamus) | 0.0 | 0.0 |
| Cerebral Cortex | 0.0 | 0.0 |
| Spinal Cord | 0.0 | 4.8 |
| glio/astro U87-MG | 0.0 | 0.0 |
| glio/astro U-118 MG | 0.0 | 0.0 |
| astrocytoma SW1783 | 0.0 | 0.0 |
| neuro*; met SK-N-AS | 0.0 | 0.0 |
| astrocytoma SF-539 | 0.0 | 4.6 |
| astrocytoma SNB-57 | 57.0 | 0.0 |
| glioma SNB-19 | 0.0 | 0.0 |
| glioma U251 | 0.0 | 11.8 |
| glioma SF-295 | 0.0 | 0.0 |
| Heart (fetal) | 0.0 | 0.0 |
| Heart | 0.0 | 0.0 |
| Skeletal muscle (fetal) | 0.0 | 0.0 |
| Skeletal muscle | 0.0 | 0.0 |
| Bone marrow | 0.0 | 0.0 |
| Thymus | 7.7 | 0.0 |
| Spleen | 0.0 | 0.0 |
| Lymph node | 8.4 | 13.0 |

TABLE BA

Probe Name Ag3053

| Primers | Sequences | | Length | Start Position |
|---|---|---|---|---|
| Forward | 5'-accagggatgtagccataaaac-3' | (SEQ ID NO:296) | 22 | 547 |
| Probe | TET-5'-tttcaccaaggatgaagcacttccct-3'-TAMRA | (SEQ ID NO:297) | 26 | 508 |
| Reverse | 5'-gcatgtgttggtttcttctcat-3' | (SEQ ID NO:298) | 22 | 481 |

TABLE BB

Probe Name Ag3224

| Primers | Sequences | | Length | Start Position |
|---|---|---|---|---|
| Forward | 5'-accagggatgtagccataaaac-3' | (SEQ ID NO:299) | 22 | 547 |
| Probe | TET-5'-tttcaccaaggatgaagcacttccct-3'-TAMRA | (SEQ ID NO:300) | 26 | 508 |
| Reverse | 5'-gcatgtgttggtttcttctcat-3' | (SEQ ID NO:301) | 221 | 481 |

TABLE BC-continued

Panel 1.3D

| Tissue Name | Rel. Exp.(%) Ag3053, Run 167985386 | Rel. Exp.(%) Ag3224, Run 165524086 |
|---|---|---|
| Colorectal | 0.0 | 0.0 |
| Stomach | 0.0 | 6.8 |
| Small intestine | 42.9 | 100.0 |
| Colon ca. SW480 | 0.0 | 0.0 |
| Colon ca* SW620 (SW480 met) | 0.0 | 0.0 |
| Colon ca. HT29 | 0.0 | 0.0 |
| Colon ca. HCT-116 | 0.0 | 0.0 |
| Colon ca. CaCo-2 | 7.9 | 0.0 |
| Colon ca. tissue (ODO3866) | 5.9 | 0.0 |
| Colon ca. HCC-2998 | 0.0 | 5.9 |
| Gastric ca.* (liver met) NCI-N87 | 11.4 | 4.9 |
| Bladder | 0.0 | 0.0 |
| Trachea | 24.8 | 9.6 |
| Kidney | 0.0 | 0.0 |
| Kidney (fetal) | 24.8 | 0.0 |
| Renal ca. 786-0 | 0.0 | 0.0 |
| Renal ca. A498 | 22.4 | 6.1 |
| Renal ca. RXF | 0.0 | 0.0 |
| Renal ca. ACHN | 0.0 | 0.0 |
| Renal ca. UO-31 | 0.0 | 0.0 |
| Renal ca. TK-10 | 0.0 | 0.0 |
| Liver | 0.0 | 0.0 |
| Liver (fetal) | 0.0 | 0.0 |
| Liver ca. (hepatoblast) HepG2 | 0.0 | 0.0 |
| Lung | 0.0 | 0.0 |
| Lung (fetal) | 27.5 | 0.0 |
| Lung ca. (small cell) LX-1 | 9.5 | 0.0 |
| Lung ca. (small cell) NCI-H69 | 0.0 | 0.0 |
| Lung ca (s. cell var.) SHP-77 | 0.0 | 0.0 |
| Lung ca. (large cell)NCI-H460 | 0.0 | 0.0 |
| Lung ca. (non-sm. cell) A549 | 100.0 | 5.8 |
| Lung ca. (non-s. cell) NCI-H23 | 9.3 | 0.0 |
| Lung ca. (non s. cell) HOP-62 | 17.0 | 0.0 |
| Lung ca. (non-s. cl) NCI-H522 | 10.7 | 0.0 |
| Lung ca. (squam.) SW 900 | 36.3 | 21.9 |
| Lung ca. (squam.) NCI-H596 | 0.0 | 0.0 |
| Mammary gland | 0.0 | 0.0 |
| Breast ca.* (pl. ef) MCF-7 | 0.0 | 0.0 |
| Breast ca.* (pl. ef) MDA-MB-231 | 0.0 | 0.0 |
| Breast ca.* (pl. ef) T47D | 0.0 | 0.0 |
| Breast ca. BT-549 | 0.0 | 4.0 |
| Breast ca. MDA-N | 0.0 | 0.0 |
| Ovary | 0.0 | 0.0 |
| Ovarian ca. OVCAR-3 | 12.8 | 10.4 |
| Ovarian ca. OVCAR-4 | 0.0 | 0.0 |
| Ovarian ca. OVCAR-8 | 20.4 | 0.0 |
| Ovarian ca. IGROV-1 | 0.0 | 0.0 |
| Ovarian ca.* (ascites) SK-OV-3 | 0.0 | 0.0 |
| Uterus | 0.0 | 10.7 |
| Placenta | 9.7 | 18.2 |
| Prostate | 0.0 | 0.0 |
| Prostate ca.* (bone met) PC-3 | 0.0 | 0.0 |
| Testis | 9.5 | 4.7 |
| Melanoma Hs688 (A).T | 0.0 | 0.0 |
| Melanoma* (met) Hs688 (B).T | 0.0 | 0.0 |
| Melanoma UACC-62 | 0.0 | 0.0 |
| Melanoma LOX IMVI | 0.0 | 0.0 |
| Melanoma* (met) SK-MEL-5 | 0.0 | 0.0 |
| Adipose | 57.8 | 20.9 |

Panel 1.3D Summary: Ag3053/Ag3224 Two experiments with the same probe and primer set show expression of the CG57391-01 gene restricted to samples derived from the small intestine and a lung cancer cell line (CTs=33–35). Thus, expression of this gene could be used to differentiate between these samples and other samples on this panel and as a marker for intestinal tissue and lung cancer.

Panel 4D Summary: Ag3053 Expression of the CG57391-01 gene is low/undetectable in all samples on this panel (CTs>35). (Data not shown.)

C. NOV3a: Insulysin

Expression of gene CG57433-01 was assessed using the primer-probe set Ag3225, described in Table CA. Results of the RTQ-PCR runs are shown in Tables CB, CC and CD.

TABLE CA

Probe Name Ag3225

| Primers | Sequences | | Length | Start Position |
|---|---|---|---|---|
| Forward | 5'-gggtgtttaggattccctgtag-3' | (SEQ ID NO:302) | 22 | 677 |

TABLE CA-continued

Probe Name Ag3225

| Primers | Sequences | Length | Start Position |
|---|---|---|---|
| Probe | TET-5'-ccaattgaaagagtctccaggcatca-3'-TAMRA (SEQ ID NO:303) | 26 | 645 |
| Reverse | 5'-tgcagttgattcagaacatgag-3' (SEQ ID NO:304) | 22 | 609 |

TABLE CB

Panel 1.3D

| Tissue Name | Rel. Exp. (%) Ag3225, Run 165524115 | Tissue Name | Rel. Exp. (%) Ag3225, Run 165524115 |
|---|---|---|---|
| Liver adenocarcinoma | 29.9 | Kidney (fetal) | 6.7 |
| Pancreas | 7.2 | Renal ca. 786-0 | 27.2 |
| Pancreatic ca. CAPAN 2 | 31.0 | Renal ca. A498 | 23.5 |
| Adrenal gland | 8.7 | Renal ca. RXF 393 | 23.3 |
| Thyroid | 10.2 | Renal ca. ACHN | 20.9 |
| Salivary gland | 7.1 | Renal ca. UO-31 | 28.5 |
| Pituitary gland | 10.3 | Renal ca. TK-10 | 7.1 |
| Brain (fetal) | 12.2 | Liver | 3.3 |
| Brain (whole) | 24.1 | Liver (fetal) | 22.2 |
| Brain (amygdala) | 7.7 | Liver ca. (hepatoblast) HepG2 | 47.0 |
| Brain (cerebellum) | 21.5 | Lung | 8.2 |
| Brain (hippocampus) | 11.0 | Lung (fetal) | 2.7 |
| Brain (substantia nigra) | 7.2 | Lung ca. (small cell) LX-1 | 37.1 |
| Brain (thalamus) | 20.6 | Lung ca. (small cell) NCI-H69 | 5.0 |
| Cerebral Cortex | 13.5 | Lung ca. (s. cell var.) SHP-77 | 16.6 |
| Spinal cord | 14.3 | Lung ca. (large cell) NCI-H460 | 100.0 |
| glio/astro U87-MG | 30.1 | Lung ca. (non-sm. cell) A549 | 35.6 |
| glio/astro U-118-MG | 50.3 | Lung ca. (non-s. cell) NCI-H23 | 23.3 |
| astrocytoma SW1783 | 31.0 | Lung ca. (non-s. cell) HOP-62 | 30.1 |
| neuro*; met SK-N-AS | 31.2 | Lung ca. (non-s. cl) NCI-H522 | 13.1 |
| astrocytoma SF-539 | 25.5 | Lung ca. (squam.) SW 900 | 19.9 |
| astrocytoma SNB-75 | 34.6 | Lung ca. (squam.) NCI-H596 | 14.2 |
| glioma SNB-19 | 28.7 | Mammary gland | 12.7 |
| glioma U251 | 92.7 | Breast ca.* (pl. ef) MCF-7 | 31.0 |
| glioma SF-295 | 24.7 | Breast ca.* (pl. ef) MDA-MB-231 | 62.9 |
| Heart (fetal) | 5.1 | Breast ca.* (pl. ef) T47D | 13.9 |
| Heart | 14.2 | Breast ca. BT-549 | 61.1 |
| Skeletal muscle (fetal) | 2.2 | Breast ca. MDA-N | 5.7 |
| Skeletal muscle | 90.1 | Ovary | 2.8 |
| Bone marrow | 7.5 | Ovarian ca. OVCAR-3 | 27.2 |
| Thymus | 7.0 | Ovarian ca. OVCAR-4 | 23.8 |
| Spleen | 12.2 | Ovarian ca. OVCAR-5 | 18.0 |
| Lymph node | 20.3 | Ovarian ca. OVCAR-8 | 8.6 |
| Colorectal | 7.5 | Ovarian ca. IGROV-1 | 10.2 |
| Stomach | 17.6 | Ovarian ca.* (ascites) SK-OV-3 | 20.0 |
| Small intestine | 17.4 | Uterus | 17.8 |
| Colon ca. SW480 | 18.9 | Placenta | 7.1 |
| Colon ca.* SW620 (SW480 met) | 25.7 | Prostate | 7.9 |
| Colon ca. HT29 | 9.7 | Prostate ca.* (bone met) PC-3 | 16.6 |
| Colon ca. HCT-116 | 30.6 | Testis | 10.2 |
| Colon ca. CaCo-2 | 29.9 | Melanoma Hs688 (A).T | 9.6 |
| Colon ca. tissue (ODO3866) | 24.5 | Melanoma* (met) Hs688 (B).T | 10.9 |
| Colon ca. HCC-2998 | 14.3 | Melanoma UACC-62 | 8.0 |
| Gastric ca.* (liver met) NCI-N87 | 36.1 | Melanoma M14 | 47.0 |
| Bladder | 17.4 | Melanoma LOX IMVI | 3.4 |

TABLE CB-continued

Panel 1.3D

| Tissue Name | Rel. Exp. (%) Ag3225, Run 165524115 | Tissue Name | Rel. Exp. (%) Ag3225, Run 165524115 |
|---|---|---|---|
| Trachea | 7.5 | Melanoma* (met) SK-MEL-5 | 9.2 |
| Kidney | 7.0 | Adipose | 9.2 |

TABLE CC

Panel 5 Islet

| Tissue Name | Rel. Exp. (%) Ag3225, Run 223846465 | Tissue Name | Rel. Exp. (%) Ag3225, Run 223846465 |
|---|---|---|---|
| 97457_Patient-02go_adipose | 12.2 | 94709_Donor 2 AM - A_adipose | 32.5 |
| 97476_Patient-07sk_skeletal muscle | 13.6 | 94710_Donor 2 AM - B_adipose | 16.5 |
| 97477_Patient-07ut_uterus | 10.5 | 94711_Donor 2 AM - C_adipose | 15.8 |
| 97478_Patient-07pl_placenta | 15.5 | 94712_Donor 2 AD - A_adipose | 37.9 |
| 99167_Bayer Patient 1 | 9.7 | 94713_Donor 2 AD - B_adipose | 37.4 |
| 97482_Patient-08ut_uterus | 7.8 | 94714_Donor 2 AD - C_adipose | 41.5 |
| 97483_Patient-08pl_placenta | 13.3 | 94742_Donor 3 U - A_Mesenchymal Stem Cells | 5.7 |
| 97486_Patient-09sk_skeletal muscle | 4.0 | 94743_Donor 3 U - B_Mesenchymal Stem Cells | 25.7 |
| 97487_Patient-09ut_uterus | 18.4 | 94730_Donor 3 AM - A_adipose | 42.0 |
| 97488_Patient-09pl_placenta | 6.9 | 94731_Donor 3 AM - B_adipose | 16.4 |
| 97492_Patient-10ut_uterus | 28.5 | 94732_Donor 3 AM - C_adipose | 26.4 |
| 97493_Patient-10pl_placenta | 23.0 | 94733_Donor 3 AD - A_adipose | 59.5 |
| 97495_Patient-11go_adipose | 8.9 | 94734_Donor 3 AD - B_adipose | 11.7 |
| 97496_Patient-11sk_skeletal muscle | 20.7 | 94735_Donor 3 AD - C_adipose | 35.4 |
| 97497_Patient-11ut_uterus | 23.5 | 77138_Liver_HepG2untreated | 100.0 |
| 97498_Patient-11pl_placenta | 17.0 | 73556_Heart_Cardiac stromal cells (primary) | 10.8 |
| 97500 Patient-12go_adipose | 18.3 | 81735_Small Intestine | 26.8 |
| 97501_Patient-12sk_skeletal muscle | 49.3 | 72409_Kidney_Proximal Convoluted Tubule | 12.1 |
| 97502_Patient-12ut_uterus | 29.7 | 82685_Small intestine_Duodenum | 10.4 |
| 97503_Patient-12pl_placenta | 12.9 | 90650_Adrenal_Adrenocortical adenoma | 9.8 |
| 94721_Donor 2 U - A_Mesenchymal Stem Cells | 14.3 | 72410_Kidney_HRCE | 38.4 |
| 94722_Donor 2 U - B_Mesenchymal Stem Cells | 12.3 | 72411_Kidney_HRE | 32.3 |
| 94723_Donor 2 U - C_Mesenchymal Stem Cells | 23.5 | 73139_Uterus_Uterine smooth muscle cells | 11.0 |

TABLE CD

Panel 5D

| Tissue Name | Rel. Exp. (%) Ag3225, Run 169271478 | Tissue Name | Rel. Exp. (%) Ag3225, Run 169271478 |
|---|---|---|---|
| 97457_Patient-02go_adipose | 9.7 | 94709_Donor 2 AM - A_adipose | 26.2 |
| 97476_Patient-07sk_skeletal muscle | 7.1 | 94710_Donor 2 AM - B_adipose | 19.2 |
| 97477_Patient-07ut_uterus | 9.7 | 94711_Donor 2 AM - C_adipose | 18.4 |
| 97478_Patient-07pl_placenta | 13.9 | 94712_Donor 2 AD - A_adipose | 35.1 |
| 97481_Patient-08sk_skeletal muscle | 7.7 | 94713_Donor 2 AD - B_adipose | 37.9 |

TABLE CD-continued

Panel 5D

| Tissue Name | Rel. Exp. (%) Ag3225, Run 169271478 | Tissue Name | Rel. Exp. (%) Ag3225, Run 169271478 |
|---|---|---|---|
| 97482_Patient-08ut_uterus | 10.2 | 94714_Donor 2 AD - C_adipose | 38.4 |
| 97483_Patient-08pl_placenta | 7.9 | 94742_Donor 3 U - A_Mesenchymal Stem Cells | 18.9 |
| 97486_Patient-09sk_skeletal muscle | 7.7 | 94743_Donor 3 U - B_Mesenchymal Stem Cells | 25.7 |
| 97487_Patient-09ut_uterus | 12.4 | 94730_Donor 3 AM - A_adipose | 40.1 |
| 97488_Patient-09pl_placenta | 8.4 | 94731_Donor 3 AM - B_adipose | 20.7 |
| 97492_Patient-10ut_uterus | 16.0 | 94732_Donor 3 AM - C_adipose | 30.1 |
| 97493_Patient-10pl_placenta | 24.5 | 94733_Donor 3 AD - A_adipose | 43.2 |
| 97495_Patient-11go_adipose | 6.7 | 94734_Donor 3 AD - B_adipose | 27.2 |
| 97496_Patient-11sk_skeletal muscle | 22.5 | 94735_Donor 3 AD - C_adipose | 37.9 |
| 97497_Patient-11ut_uterus | 22.4 | 77138_Liver_HepG2untreated | 100.0 |
| 97498_Patient-11pl_placenta | 8.2 | 73556_Heart_Cardiac stromal cells (primary) | 9.7 |
| 97500_Patient-12go_adipose | 9.3 | 81735_Small Intestine | 16.5 |
| 97501_Patient-12sk_skeletal muscle | 43.2 | 72409_Kidney_Proximal Convoluted Tubule | 10.2 |
| 97502_Patient-12ut_uterus | 25.2 | 82685_Small intestine_Duodenum | 13.6 |
| 97503_Patient-12pl_placenta | 9.6 | 90650_Adrenal_Adrenocortical adenoma | 8.5 |
| 94721_Donor 2 U - A_Mesenchymal Stem Cells | 15.6 | 72410_Kidney_HRCE | 26.8 |
| 94722_Donor 2 U - B_Mesenchymal Stem Cells | 12.6 | 72411_Kidney_HRE | 27.2 |
| 94723_Donor 2 U - C_Mesenchymal Stem Cells | 13.3 | 73139_Uterus_Uterine smooth muscle cells | 11.0 |

Panel 1.3D Summary: 3225 The expression of the CG57433-01 gene appears to be highest in a sample derived from a lung cancer cell line (H460 (CT=29.5). In addition, there appears to be substantial expression in other samples derived from lung cancer cell lines, brain cancer cell lines, kidney cancer cell lines, colon cancer cell lines and breast cancer cell lines. Of note, is the apparent overexpression of this gene in skeletal muscle (CT=30) in comparison to fetal skeletal muscle (CT=35). Thus, the expression of this gene could be used to distinguish H460 cells from other samples in this panel. In addition, the expression of this gene could be used to distinguish adult skeletal muscle and fetal skeletal muscle. Moreover, therapeutic modulation of this gene, through the use of small molecule drugs, protein therapeutics, or antibodies could be of benefit in the treatment of lung, brain, kidney, colon or breast cancer.

Among metabolic tissues, this gene has low levels of expression in pancreas, adrenal, thyroid, pituitary, heart, liver and adipose. Inhibition of this insulin-degrading enzyme may increase insulin signalling and action and thus be a treatment for the prevention and treatment of Type 2 diabetes. This gene product may also be a small molecule target for the treatment of metabolic and endocrine disease, including thyroidopathies, Type 1 diabetes, and obesity.

This gene is also expressed throughout the brain at low levels, indicating a role in CNS processes. Insulysin (also known as Insulin-degrading enyzme) has been shown to rapidly remove the beta-amyloid precursor protein intracellular domain (AICD) and eliminate proteins with amyloidogenic potential, which are thought to mediate of the pathological features of Alzheimer's disease. Potentiation of this process is a likely means of addressing Alzneimer's disease pathology. Therefore, agents that increase the physiological activity of this gene product are likely to have utility as clinically therapeutic treatments for Alzheimer's disease, and potentially other neurodegenerative diseases involving protein aggregation (Edbauer et al., Biol Chem 2002 Jan. 23; [epub ahead of print]; Kurochkin, Trends Biochem Sci 2001 July;26(7):421–5).

Panel 5 Islet and 5D Summary: Ag3225 The CG57433-01 gene is expressed at low levels in islets of Langerhans and mesenchymal stem cells that differentiate in vitro into adipocytes, chondrocytes and osteocytes. Therefore, therapeutic modulation of this enzyme may be a treatment for diseases of bone and cartilage as well as Types 1 and 2 diabetes.

D. NOV5: Membrane Protein

Expression of gene CG57360-01 was assessed using the primer-probe set Ag3215, described in Table DA. Results of the RTQ-PCR runs are shown in Tables DB, DC, DD and DE.

TABLE DA

Probe Name Ag3215

| Primers | Sequences | | Length | Start Position |
|---|---|---|---|---|
| Forward | 5'-ttgctctcatgaggtcagagat-3' | (SEQ ID NO:305) | 22 | 43 |
| Probe | TET-5'-ccataggatgagtcttctgttcttaaaccg-3'-TAMRA | (SEQ ID NO:306) | 30 | 73 |
| Reverse | 5'-ccgacagccttatccttacact-3' | (SEQ ID NO:307) | 22 | 103 |

TABLE DB

CNS_neurodegeneration_v1.0

| Tissue Name | Rel. Exp. (%) Ag3215, Run 209861782 | Tissue Name | Rel. Exp. (%) Ag3215, Run 209861782 |
|---|---|---|---|
| AD 1 Hippo | 5.3 | Control (Path) 3 Temporal Ctx | 3.7 |
| AD 2 Hippo | 21.8 | Control (Path) 4 Temporal Ctx | 37.6 |
| AD 3 Hippo | 0.0 | AD 1 Occipital Ctx | 8.1 |
| AD 4 Hippo | 15.5 | AD 2 Occipital Ctx (Missing) | 0.0 |
| AD 5 hippo | 42.0 | AD 3 Occipital Ctx | 2.0 |
| AD 6 Hippo | 51.8 | AD 4 Occipital Ctx | 20.3 |
| Control 2 Hippo | 25.2 | AD 5 Occipital Ctx | 4.1 |
| Control 4 Hippo | 11.8 | AD 6 Occipital Ctx | 33.4 |
| Control (Path) 3 Hippo | 1.3 | Control 1 Occipital Ctx | 5.8 |
| AD 1 Temporal Ctx | 7.5 | Control 2 Occipital Ctx | 62.9 |
| AD 2 Temporal Ctx | 33.0 | Control 3 Occipital Ctx | 14.2 |
| AD 3 Temporal Ctx | 2.7 | Control 4 Occipital Ctx | 6.9 |
| AD 4 Temporal Ctx | 27.2 | Control (Path) 1 Occipital Ctx | 100.0 |
| AD 5 Inf Temporal Ctx | 41.8 | Control (Path) 2 Occipital Ctx | 22.8 |
| AD 5 SupTemporal Ctx | 36.3 | Control (Path) 3 Occipital Ctx | 3.3 |
| AD 6 Inf Temporal Ctx | 56.6 | Control (Path) 4 Occipital Ctx | 20.3 |
| AD 6 Sup Temporal Ctx | 73.2 | Control 1 Parietal Ctx | 4.2 |
| Control 1 Temporal Ctx | 1.5 | Control 2 Parietal Ctx | 25.9 |
| Control 2 Temporal Ctx | 8.7 | Control 3 Parietal Ctx | 20.6 |
| Control 3 Temporal Ctx | 19.5 | Control (Path) 1 Parietal Ctx | 60.7 |
| Control 4 Temporal Ctx | 14.5 | Control (Path) 2 Parietal Ctx | 17.3 |
| Control (Path) 1 Temporal Ctx | 59.5 | Control (Path) 3 Parietal Ctx | 1.5 |
| Control (Path) 2 Temporal Ctx | 54.3 | Control (Path) 4 Parietal Ctx | 33.0 |

TABLE DC

Panel 1.3D

| Tissue Name | Rel. Exp. (%) Ag3215, Run 168012859 | Tissue Name | Rel. Exp. (%) Ag3215, Run 168012859 |
|---|---|---|---|
| Liver adenocarcinoma | 64.6 | Kidney (fetal) | 80.7 |
| Pancreas | 22.4 | Renal ca. 786-0 | 0.0 |
| Pancreatic ca. CAPAN 2 | 79.6 | Renal ca. A498 | 4.3 |
| Adrenal gland | 24.0 | Renal ca. RXF 393 | 20.7 |
| Thyroid | 17.3 | Renal ca. ACHN | 15.8 |
| Salivary gland | 1.6 | Renal ca. UO-31 | 1.6 |
| Pituitary gland | 26.1 | Renal ca. TK-10 | 4.3 |
| Brain (fetal) | 86.5 | Liver | 26.1 |
| Brain (whole) | 55.5 | Liver (fetal) | 20.7 |
| Brain (amygdala) | 69.7 | Liver ca. (hepatoblast) HepG2 | 18.9 |
| Brain (cerebellum) | 37.9 | Lung | 15.1 |
| Brain (hippocampus) | 20.7 | Lung (fetal) | 38.7 |
| Brain (substantia nigra) | 46.3 | Lung ca. (small cell) LX-1 | 6.0 |

TABLE DC-continued

Panel 1.3D

| Tissue Name | Rel. Exp. (%) Ag3215, Run 168012859 | Tissue Name | Rel. Exp. (%) Ag3215, Run 168012859 |
|---|---|---|---|
| Brain (thalamus) | 23.8 | Lung ca. (small cell) NCI-H69 | 5.5 |
| Cerebral Cortex | 17.6 | Lung ca. (s. cell var.) SHP-77 | 35.4 |
| Spinal cord | 19.3 | Lung ca. (large cell) NCI-H460 | 4.5 |
| glio/astro U87-MG | 20.0 | Lung ca. (non-sm. cell) A549 | 7.6 |
| glio/astro U-118-MG | 27.7 | Lung ca. (non-s. cell) NCI-H23 | 39.0 |
| astrocytoma SW1783 | 28.5 | Lung ca. (non-s. cell) HOP-62 | 29.7 |
| neuro*; met SK-N-AS | 15.2 | Lung ca. (non-s. cl) NCI-H522 | 46.3 |
| astrocytoma SF-539 | 13.8 | Lung ca. (squam.) SW 900 | 17.7 |
| astrocytoma SNB-75 | 13.5 | Lung ca. (squam.) NCI-H596 | 12.7 |
| glioma SNB-19 | 2.3 | Mammary gland | 42.0 |
| glioma U251 | 18.4 | Breast ca.* (pl. ef) MCF-7 | 0.0 |
| glioma SF-295 | 36.6 | Breast ca.* (pl. ef) MDA-MB-231 | 18.7 |
| Heart (fetal) | 2.2 | Breast ca.* (pl. ef) T47D | 15.2 |
| Heart | 2.3 | Breast ca. BT-549 | 13.6 |
| Skeletal muscle (fetal) | 12.8 | Breast ca. MDA-N | 4.2 |
| Skeletal muscle | 4.2 | Ovary | 15.0 |
| Bone marrow | 11.7 | Ovarian ca. OVCAR-3 | 6.0 |
| Thymus | 14.5 | Ovarian ca. OVCAR-4 | 12.2 |
| Spleen | 19.2 | Ovarian ca. OVCAR-5 | 39.5 |
| Lymph node | 17.2 | Ovarian ca. OVCAR-8 | 3.8 |
| Colorectal | 4.4 | Ovarian ca. IGROV-1 | 41.2 |
| Stomach | 26.2 | Ovarian ca.* (ascites) SK-OV-3 | 14.7 |
| Small intestine | 8.8 | Uterus | 24.7 |
| Colon ca. SW480 | 19.3 | Placenta | 100.0 |
| Colon ca.* SW620 (SW480 met) | 19.8 | Prostate | 8.0 |
| Colon ca. HT29 | 4.1 | Prostate ca.* (bone met) PC-3 | 11.1 |
| Colon ca. HCT-116 | 7.9 | Testis | 49.3 |
| Colon ca. CaCo-2 | 29.7 | Melanoma Hs688 (A).T | 5.7 |
| Colon ca. tissue (ODO3866) | 9.1 | Melanoma* (met) Hs688 (B).T | 7.9 |
| Colon ca. HCC-2998 | 9.9 | Melanoma UACC-62 | 4.0 |
| Gastric ca.* (liver met) NCI-N87 | 28.5 | Melanoma M14 | 2.9 |
| Bladder | 14.0 | Melanoma LOX IMVI | 15.8 |
| Trachea | 9.3 | Melanoma* (met) SK-MEL-5 | 2.0 |
| Kidney | 43.8 | Adipose | 8.4 |

TABLE DD

Panel 2.2

| Tissue Name | Rel. Exp. (%) Ag3215, Run 174416485 | Tissue Name | Rel. Exp. (%) Ag3215, Run 174416485 |
|---|---|---|---|
| Normal Colon | 4.4 | Kidney Margin (OD04348) | 100.0 |
| Colon cancer (OD06064) | 10.4 | Kidney malignant cancer (OD06204B) | 47.6 |
| Colon Margin (OD06064) | 2.9 | Kidney normal adjacent tissue (OD06204E) | 29.9 |
| Colon cancer (OD06159) | 0.0 | Kidney Cancer (OD04450-01) | 27.7 |
| Colon Margin (OD06159) | 4.7 | Kidney Margin (OD04450-03) | 31.2 |
| Colon cancer (OD06297-04) | 0.0 | Kidney Cancer 8120613 | 0.0 |
| Colon Margin (OD06297-05) | 4.6 | Kidney Margin 8120614 | 36.6 |
| CC Gr. 2 ascend colon (ODO3921) | 21.8 | Kidney Cancer 9010320 | 10.7 |

TABLE DD-continued

Panel 2.2

| Tissue Name | Rel. Exp. (%) Ag3215, Run 174416485 | Tissue Name | Rel. Exp. (%) Ag3215, Run 174416485 |
|---|---|---|---|
| CC Margin (ODO3921) | 0.0 | Kidney Margin 9010321 | 12.3 |
| Colon cancer metastasis (OD06104) | 0.0 | Kidney Cancer 8120607 | 27.9 |
| Lung Margin (OD06104) | 0.0 | Kidney Margin 8120608 | 4.5 |
| Colon mets to lung (OD04451-01) | 7.9 | Normal Uterus | 21.0 |
| Lung Margin (OD04451-02) | 19.2 | Uterine Cancer 064011 | 18.8 |
| Normal Prostate | 14.6 | Normal Thyroid | 0.0 |
| Prostate Cancer (OD04410) | 2.1 | Thyroid Cancer 064010 | 0.0 |
| Prostate Margin (OD04410) | 9.6 | Thyroid Cancer A302152 | 49.7 |
| Normal Ovary | 18.4 | Thyroid Margin A302153 | 0.0 |
| Ovarian cancer (OD06283-03) | 18.9 | Normal Breast | 0.0 |
| Ovarian Margin (OD06283-07) | 23.5 | Breast Cancer (OD04566) | 0.0 |
| Ovarian Cancer 064008 | 14.4 | Breast Cancer 1024 | 79.0 |
| Ovarian cancer (OD06145) | 5.8 | Breast Cancer (OD04590-01) | 33.7 |
| Ovarian Margin (OD06145) | 39.5 | Breast Cancer Mets (OD04590-03) | 17.2 |
| Ovarian cancer (OD06455-03) | 59.9 | Breast Cancer Metastasis (OD04655-05) | 49.0 |
| Ovarian Margin (OD06455-07) | 0.0 | Breast Cancer 064006 | 27.4 |
| Normal Lung | 14.8 | Breast Cancer 9100266 | 3.8 |
| Invasive poor diff. lung adeno (ODO4945-01) | 3.5 | Breast Margin 9100265 | 10.4 |
| Lung Margin (ODO4945-03) | 3.6 | Breast Cancer A209073 | 0.0 |
| Lung Malignant Cancer (OD03126) | 0.0 | Breast Margin A2090734 | 54.7 |
| Lung Margin (OD03126) | 10.8 | Breast cancer (OD06083) | 17.7 |
| Lung Cancer (OD05014A) | 15.7 | Breast cancer node metastasis (OD06083) | 76.3 |
| Lung Margin (OD05014B) | 2.0 | Normal Liver | 18.3 |
| Lung cancer (OD06081) | 12.4 | Liver Cancer 1026 | 0.0 |
| Lung Margin (OD06081) | 4.4 | Liver Cancer 1025 | 19.6 |
| Lung Cancer (OD04237-01) | 5.6 | Liver Cancer 6004-T | 0.0 |
| Lung Margin (OD04237-02) | 0.0 | Liver Tissue 6004-N | 0.0 |
| Ocular Melanoma Metastasis | 8.4 | Liver Cancer 6005-T | 0.0 |
| Ocular Melanoma Margin (Liver) | 0.0 | Liver Tissue 6005-N | 0.0 |
| Melanoma Metastasis | 0.0 | Liver Cancer 064003 | 18.9 |
| Melanoma Margin (Lung) | 0.0 | Normal Bladder | 33.7 |
| Normal Kidney | 37.4 | Bladder Cancer 1023 | 4.0 |
| Kidney Ca, Nuclear grade 2 (OD04338) | 82.9 | Bladder Cancer A302173 | 20.0 |
| Kidney Margin (OD04338) | 7.6 | Normal Stomach | 20.7 |
| Kidney Ca Nuclear grade 1/2 (OD04339) | 94.6 | Gastric Cancer 9060397 | 0.0 |
| Kidney Margin (OD04339) | 19.1 | Stomach Margin 9060396 | 6.0 |
| Kidney Ca, Clear cell type (OD04340) | 0.0 | Gastric Cancer 9060395 | 6.0 |
| Kidney Margin (OD04340) | 28.7 | Stomach Margin 9060394 | 4.0 |
| Kidney Ca, Nuclear grade 3 (OD04348) | 0.0 | Gastric Cancer 064005 | 11.9 |

TABLE DE

Panel 4D

| Tissue Name | Rel. Exp. (%) Ag3215, Run 164682514 | Tissue Name | Rel. Exp. (%) Ag3215, Run 164682514 |
|---|---|---|---|
| Secondary Th1 act | 6.8 | HUVEC IL-1beta | 5.8 |
| Secondary Th2 act | 7.4 | HUVEC IFN gamma | 29.5 |
| Secondary Tr1 act | 8.7 | HUVEC TNF alpha + IFN gamma | 6.0 |
| Secondary Th1 rest | 2.8 | HUVEC TNF alpha + IL4 | 17.6 |
| Secondary Th2 rest | 4.0 | HUVEC IL-11 | 11.5 |
| Secondary Tr1 rest | 6.3 | Lung Microvascular EC none | 34.4 |
| Primary Th1 act | 12.7 | Lung Microvascular EC | 42.3 |

TABLE DE-continued

Panel 4D

| Tissue Name | Rel. Exp. (%) Ag3215, Run 164682514 | Tissue Name | Rel. Exp. (%) Ag3215, Run 164682514 |
|---|---|---|---|
| Primary Th2 act | 12.5 | Microvascular Dermal EC none | 14.1 |
| Primary Tr1 act | 11.1 | Microsvascular Dermal EC TNF alpha + IL-1beta | 13.9 |
| Primary Th1 rest | 12.8 | Bronchial epithelium TNF alpha + IL1beta | 100.0 |
| Primary Th2 rest | 5.7 | Small airway epithelium none | 28.1 |
| Primary Tr1 rest | 2.4 | Small airway epithelium TNF alpha + IL-1beta | 74.2 |
| CD45RA CD4 lymphocyte act | 7.9 | Coronery artery SMC rest | 26.8 |
| CD45RO CD4 lymphocyte act | 12.0 | Coronery artery SMC TNF alpha + IL-1beta | 2.8 |
| CD8 lymphocyte act | 19.3 | Astrocytes rest | 17.3 |
| Secondary CD8 lymphocyte rest | 13.5 | Astrocytes TNF alpha + IL-1beta | 2.9 |
| Secondary CD8 lymphocyte act | 10.1 | KU-812 (Basophil) rest | 9.0 |
| CD4 lymphocyte none | 1.6 | KU-812 (Basophil) PMA/ionomycin | 6.3 |
| 2ry Th1/Th2/Tr1_anti-CD95 CH11 | 5.1 | CCD1106 (Keratinocytes) none | 25.2 |
| LAK cells rest | 1.0 | CCD1106 (Keratinocytes) TNF alpha + IL-1beta | 26.2 |
| LAK cells IL-2 | 12.3 | Liver cirrhosis | 13.2 |
| LAK cells IL-2 + IL-12 | 5.7 | Lupus kidney | 8.4 |
| LAK cells IL-2 + IFN gamma | 5.8 | NCI-H292 none | 31.6 |
| LAK cells IL-2 + IL-18 | 7.2 | NCI-H292 IL-4 | 22.2 |
| LAK cells PMA/ionomycin | 2.9 | NCI-H292 IL-9 | 57.4 |
| NK Cells IL-2 rest | 9.2 | NCI-H292 IL-13 | 26.4 |
| Two Way MLR 3 day | 14.4 | NCI-H292 IFN gamma | 35.1 |
| Two Way MLR 5 day | 1.9 | HPAEC none | 15.0 |
| Two Way MLR 7 day | 12.9 | HPAEC TNF alpha + IL-1beta | 6.9 |
| PBMC rest | 7.1 | Lung fibroblast none | 17.6 |
| PBMC PWM | 12.5 | Lung fibroblast TNF alpha + IL-1beta | 12.2 |
| PBMC PHA-L | 18.9 | Lung fibroblast IL-4 | 21.9 |
| Ramos (B cell) none | 2.3 | Lung fibroblast IL-9 | 17.0 |
| Ramos (B cell) ionomycin | 0.0 | Lung fibroblast IL-13 | 16.7 |
| B lymphocytes PWM | 20.3 | Lung fibroblast IFN gamma | 18.8 |
| B lymphocytes CD40L and IL-4 | 8.7 | Dermal fibroblast CCD1070 rest | 44.8 |
| EOL-1 dbcAMP | 0.0 | Dermal fibroblast CCD1070 TNF alpha | 30.1 |
| EOL-1 dbcAMP PMA/ionomycin | 0.0 | Dermal fibroblast CCD1070 IL-1beta | 25.3 |
| Dendritic cells none | 8.8 | Dermal fibroblast IFN gamma | 13.3 |
| Dendritic cells LPS | 0.0 | Dermal fibroblast IL-4 | 14.1 |
| Dendritic cells anti-CD40 | 6.0 | IBD Colitis 2 | 2.6 |
| Monocytes rest | 25.2 | IBD Crohn's | 11.1 |
| Monocytes LPS | 3.3 | Colon | 26.2 |
| Macrophages rest | 11.1 | Lung | 19.3 |
| Macrophages LPS | 6.7 | Thymus | 56.3 |
| HUVEC none | 37.9 | Kidney | 18.9 |
| HUVEC starved | 11.3 | | |

CNS_neurodegeneration_v1.0 Summary: Ag3215 This panel does not show differential expression of the CG57360-01 gene in Alzheimer's disease. However, this expression profile confirms the presence of this gene in the brain. Please see Panel 1.3D for discussion of utility of this gene in the central nervous system.

Panel 1.3D Summary: Ag3215 Highest expression of the CG57360-01 gene is seen in the placenta (CT=31.7). Significant expression is also seen in samples derived from pancreatic cancer, liver cancer, lung cancer, ovarian cancer, brain cancer, and colon cancer. Thus, expression of this gene could be used to differentiate these samples from other samples on this panel and as a marker to detect the presence of these cancers. Furthermore, therapeutic modulation of the expression or function of this gene may be effective in the treatment of these cancers.

Among tissues with metabolic function, this gene is expressed in fetal and adult liver, pancreas, and the adrenal and thyroid glands. This widespread expression of the gene in these tissues suggests that its protein product may play a role in normal metabolic function. This gene product may also be useful in the treatment of metabolic disorders, including obesity and diabetes.

In addition, this molecule is expressed at moderate to low levels in the CNS and may be useful for the treatment of neurologic diseases.

Panel 2.2 Summary: Ag 3215 The expression of the CG57360-01 gene appears to be highest in a sample derived from a normal kidney tissue (CT=33.8). In addition, there appears to be substantial expression in other samples derived from kidney cancers and breast cancers. Thus, the expression of this gene could be used to distinguish normal kidney tissue from other samples in the panel. Moreover, therapeutic modulation of this gene, through the use of small molecule drugs, protein therapeutics, or antibodies could be of benefit in the treatment of kidney or breast cancer.

Panel 4D Summary: Ag3215 Highest expression of the CG57360-01 gene is seen in bronchial epithelium treated with TNF-alpha+IL-1 beta (CT=31.2). Significant expression is also seen in TNF-alpha/IL-1 beta stimulated small airway epithelium, IL-4, IL-9, IL-13, IFN gamma activated-NCI-H292 mucoepidermoid cells as well as untreated NCI-H292 cells, IL-4, IL-9, IL-13 and IFN gamma activated lung fibroblasts, and both treated and untreated lung microvascular endothelial cells The expression of this gene in cells derived from or within the lung suggests that this gene may be involved in normal conditions as well as pathological and inflammatory lung disorders, including chronic obstructive pulmonary disease, asthma, allergy and emphysema.

E. NOV6: BCSC-1

Expression of gene CG57362-01 was assessed using the primer-probe set Ag3217, described in Table EA. Results of the RTQ-PCR runs are shown in Tables EB, EC, ED, EE and EF.

TABLE EA

Probe Name Ag3217

| Primers | Sequences | | Length | Start Position |
|---|---|---|---|---|
| Forward | 5'-actgggaacaggcactgtct-3' | (SEQ ID NO:308) | 20 | 1327 |
| Probe | TET-5'-cagcagaactgtccagcccatgg-3'-TAMRA | (SEQ ID NO:309) | 23 | 1347 |
| Reverse | 5'-gggtctgtcagagcatcagtac-3' | (SEQ ID NO:310) | 22 | 1395 |

TABLE EB

CNS_neurodegeneration_v1.0

| Tissue Name | Rel. Exp. (%) Ag3217, Run 209861783 | Rel. Exp. (%) Ag3217, Run 224079666 | Tissue Name | Rel. Exp. (%) Ag3217, Run 209861783 | Rel. Exp. (%) Ag3217, Run 224079666 |
|---|---|---|---|---|---|
| AD 1 Hippo | 18.3 | 24.8 | Control (Path) 3 Temporal Ctx | 15.6 | 17.7 |
| AD 2 Hippo | 30.4 | 42.6 | Control (Path) 4 Temporal Ctx | 72.2 | 81.8 |
| AD 3 Hippo | 20.2 | 18.3 | AD 1 Occipital Ctx | 25.2 | 32.5 |
| AD 4 Hippo | 21.3 | 22.2 | AD 2 Occipital Ctx (Missing) | 0.0 | 0.0 |
| AD 5 Hippo | 82.9 | 78.5 | AD 3 Occipital Ctx | 7.2 | 7.4 |
| AD 6 Hippo | 29.9 | 33.2 | AD 4 Occipital Ctx | 52.1 | 36.6 |
| Control 2 Hippo | 43.2 | 45.1 | AD 5 Occipital Ctx | 46.3 | 38.4 |
| Control 4 Hippo | 26.2 | 17.7 | AD 6 Occipital Ctx | 17.2 | 17.9 |
| Control (Path) 3 Hippo | 24.3 | 12.8 | Control 1 Occipital Ctx | 5.1 | 8.0 |
| AD 1 Temporal Ctx | 12.6 | 15.3 | Control 2 Occipital Ctx | 51.8 | 75.8 |
| AD2 Temporal Ctx | 51.8 | 33.4 | Control 3 Occipital Ctx | 71.7 | 85.9 |
| AD 3 Temporal Ctx | 12.3 | 13.3 | Control 4 Occipital Ctx | 14.4 | 17.6 |
| AD 4 Temporal Ctx | 45.4 | 46.7 | Control (Path) 1 Occipital Ctx | 100.0 | 100.0 |
| AD 5 Inf Temporal Ctx | 56.6 | 51.4 | Control (Path) 2 Occipital Ctx | 46.3 | 53.2 |
| AD 5 Sup Temporal Ctx | 43.8 | 33.2 | Control (Path) 3 Occipital Ctx | 5.9 | 6.3 |
| AD 6 Inf Temporal Ctx | 40.3 | 33.7 | Control (Path) 4 Occipital Ctx | 50.7 | 58.6 |
| AD 6 Sup Temporal Ctx | 38.4 | 46.3 | Control 1 Parietal Ctx | 10.6 | 10.4 |
| Control 1 Temporal Ctx | 12.9 | 11.0 | Control 2 Parietal Ctx | 34.4 | 43.2 |
| Control 2 Temporal Ctx | 45.7 | 41.8 | Control 3 Parietal Ctx | 49.7 | 37.1 |

TABLE EB-continued

CNS_neurodegeneration_v1.0

| Tissue Name | Rel. Exp. (%) Ag3217, Run 209861783 | Rel. Exp. (%) Ag3217, Run 224079666 | Tissue Name | Rel. Exp. (%) Ag3217, Run 209861783 | Rel. Exp. (%) Ag3217, Run 224079666 |
|---|---|---|---|---|---|
| Control 3 Temporal Ctx | 57.4 | 71.7 | Control (Path) 1 Parietal Ctx | 82.4 | 86.5 |
| Control 3 Temporal Ctx | 42.3 | 37.1 | Control (Path) 2 Parietal Ctx | 55.5 | 63.7 |
| Control 3 1 Temporal Ctx | 87.1 | 99.3 | Control (Path) 3 Parietal Ctx | 12.9 | 9.3 |
| Control (Path) 2 Temporal Ctx | 92.0 | 97.3 | Control (Path) 4 Parietal Ctx | 90.1 | 95.9 |

TABLE EC

Panel 1.3D

| Tissue Name | Rel. Exp. (%) Ag3217, Run 168012860 | Tissue Name | Rel. Exp. (%) Ag3217, Run 168012860 |
|---|---|---|---|
| Liver adenocarcinoma | 3.9 | Kidney (fetal) | 2.6 |
| Pancreas | 8.1 | Renal ca. 786-0 | 0.4 |
| Pancreatic ca. CAPAN 2 | 0.0 | Renal ca. A498 | 0.0 |
| Adrenal gland | 24.3 | Renal ca. RXF 393 | 0.0 |
| Thyroid | 0.0 | Renal ca. ACHN | 0.0 |
| Salivary gland | 5.4 | Renal ca. UO-31 | 0.1 |
| Pituitary gland | 12.9 | Renal ca. TK-10 | 1.2 |
| Brain (fetal) | 10.2 | Liver | 0.9 |
| Brain (whole) | 31.6 | Liver (fetal) | 0.0 |
| Brain (amygdala) | 72.2 | Liver ca. (hepatoblast) HepG2 | 0.0 |
| Brain (cerebellum) | 21.5 | Lung | 0.0 |
| Brain (hippocampus) | 39.5 | Lung (fetal) | 1.4 |
| Brain (substantia nigra) | 11.3 | Lung ca. (small cell) LX-1 | 1.7 |
| Brain (thalamus) | 31.6 | Lung ca. (small cell) NCI-H69 | 6.6 |
| Cerebral Cortex | 39.8 | Lung ca. (s. cell var.) SHP-77 | 27.7 |
| Spinal cord | 1.4 | Lung ca. (large cell) NCI-H460 | 0.0 |
| glio/astro U87-MG | 0.0 | Lung ca. (non-sm. cell) A549 | 4.4 |
| glio/astro U-118-MG | 0.0 | Lung ca. (non-s. cell) NCI-H23 | 0.4 |
| astrocytoma SW1783 | 0.0 | Lung ca. (non-s. cell) HOP-62 | 0.0 |
| neuro*; met SK-N-AS | 0.3 | Lung ca. (non-s. cl) NCI-H522 | 2.9 |
| astrocytoma SF-539 | 0.1 | Lung ca. (squam.) SW 900 | 1.0 |
| astrocytoma SNB-75 | 0.0 | Lung ca. (squam.) NCI-H596 | 100.0 |
| glioma SNB-19 | 2.4 | Mammary gland | 0.0 |
| glioma U251 | 3.4 | Breast ca.* (pl. ef) MCF-7 | 0.0 |
| glioma SF-295 | 0.8 | Breast ca.* (pl. ef)MDA-MB-231 | 0.0 |
| Heart (fetal) | 0.0 | Breast ca.* (pl. ef) T47D | 4.6 |
| Heart | 0.0 | Breast ca. BT-549 | 0.0 |
| Skeletal muscle (fetal) | 1.1 | Breast ca. MDA-N | 0.2 |
| Skeletal muscle | 0.0 | Ovary | 1.4 |
| Bone marrow | 1.4 | Ovarian ca. OVCAR-3 | 0.0 |
| Thymus | 0.0 | Ovarian ca. OVCAR-4 | 0.8 |
| Spleen | 0.4 | Ovarian ca. OVCAR-5 | 3.2 |
| Lymph node | 0.0 | Ovarian ca. OVCAR-8 | 0.8 |
| Colorectal | 2.6 | Ovarian ca. IGROV-1 | 0.0 |
| Stomach | 3.2 | Ovarian ca.* (ascites) SK-OV-3 | 0.3 |
| Small intestine | 1.3 | Uterus | 0.0 |
| Colon ca. SW480 | 1.5 | Placenta | 0.0 |
| Colon ca.* SW620(SW480 met) | 11.9 | Prostate | 1.6 |
| Colon ca. HT29 | 0.0 | Prostate ca.* (bone met) PC-3 | 0.4 |

TABLE EC-continued

Panel 1.3D

| Tissue Name | Rel. Exp. (%) Ag3217, Run 168012860 | Tissue Name | Rel. Exp. (%) Ag3217, Run 168012860 |
|---|---|---|---|
| Colon ca. HCT-116 | 2.9 | Testis | 2.6 |
| Colon ca. CaCo-2 | 0.0 | Melanoma Hs688(A).T | 0.0 |
| Colon ca. tissue (ODO3866) | 0.0 | Melanoma* (met) Hs688(B).T | 0.0 |
| Colon ca. HCC-2998 | 0.0 | Melanoma UACC-62 | 0.0 |
| Gastric ca.* (liver met) NCI-N87 | 0.0 | Melanoma M14 | 0.0 |
| Bladder | 0.8 | Melanoma LOX IMVI | 0.0 |
| Trachea | 0.0 | Melanoma* (met) SK-MEL-5 | 0.0 |
| Kidney | 0.0 | Adipose | 0.0 |

TABLE ED

Panel 2.2

| Tissue Name | Rel. Exp. (%) Ag3217, Run 174416493 | Tissue Name | Rel. Exp. (%) Ag3217, Run 174416493 |
|---|---|---|---|
| Normal Colon | 11.9 | Kidney Margin (OD04348) | 9.9 |
| Colon cancer (OD06064) | 0.0 | Kidney malignant cancer (OD06204B) | 0.0 |
| Colon Margin (OD06064) | 0.0 | Kidney normal adjacent tissue (OD06204E) | 0.0 |
| Colon cancer (OD06159) | 0.0 | Kidney Cancer (OD04450-01) | 3.9 |
| Colon Margin (OD06159) | 6.3 | Kidney Margin (OD04450-03) | 0.0 |
| Colon cancer (OD06297-04) | 0.0 | Kidney Cancer 8120613 | 0.0 |
| Colon Margin (OD06297-05) | 0.0 | Kidney Margin 8120614 | 0.0 |
| CC Gr. 2 ascend colon (ODO3921) | 0.0 | Kidney Cancer 9010320 | 47.6 |
| CC Margin (ODO3921) | 0.0 | Kidney Margin 9010321 | 0.0 |
| Colon cancer metastasis (OD06104) | 0.0 | Kidney Cancer 8120607 | 3.7 |
| Lung Margin (OD06104) | 0.0 | Kidney Margin 8120608 | 0.0 |
| Colon mets to lung (OD04451-01) | 0.0 | Normal Uterus | 0.0 |
| Lung Margin (OD04451-02) | 0.0 | Uterine Cancer 064011 | 12.7 |
| Normal Prostate | 22.4 | Normal Thyroid | 13.6 |
| Prostate Cancer (OD04410) | 8.4 | Thyroid Cancer 064010 | 0.0 |
| Prostate Margin (OD04410) | 0.0 | Thyroid Cancer A30152 | 0.0 |
| Normal Ovary | 0.0 | Thyroid Margin A302153 | 7.6 |
| Ovarian cancer (OD06283-03) | 0.0 | Normal Breast | 0.0 |
| Ovarian Margin (OD06283-07) | 0.0 | Breast Cancer (OD04566) | 0.0 |
| Ovarian Cancer 064008 | 9.5 | Breast Cancer 1024 | 0.0 |
| Ovarian cancer (OD06145) | 0.0 | Breast Cancer (OD04590-01) | 19.3 |
| Ovarian Margin (OD06145) | 100.0 | Breast Cancer Mets (OD04590-03) | 35.8 |
| Ovarian cancer (OD06455-03) | 0.0 | Breast Cancer Metastasis (OD04655-05) | 24.5 |
| Ovarian Margin (OD06455-07) | 0.0 | Breast Cancer 064006 | 0.0 |
| Normal Lung | 0.0 | Breast Cancer 9100266 | 10.0 |
| Invasive poor diff. lung adeno (ODO4945-01 | 0.0 | Breast Margin 9100265 | 0.0 |
| Lung Margin (ODO4945-03) | 0.0 | Breast Cancer A209073 | 0.0 |
| Lung Malignant Cancer (OD03126) | 17.4 | Breast Margin A2090734 | 9.1 |
| Lung Margin (OD03126) | 8.8 | Breast cancer (OD06083) | 0.0 |
| Lung Cancer (OD05014A) | 0.0 | Breast cancer node metastasis (OD06083) | 5.1 |
| Lung Margin (OD05014B) | 0.0 | Normal Liver | 6.7 |
| Lung cancer (OD06081) | 12.9 | Liver Cancer 1026 | 5.6 |
| Lung Margin (OD06081) | 0.0 | Liver Cancer 1025 | 8.5 |
| Lung Cancer (OD04237-01) | 0.0 | Liver Cancer 6004-T | 0.0 |
| Lung Margin (OD04237-02) | 0.0 | Liver Tissue 6004-N | 6.0 |
| Ocular Melanoma Metastasis | 0.0 | Liver Cancer 6005-T | 0.0 |

TABLE ED-continued

Panel 2.2

| Tissue Name | Rel. Exp. (%) Ag3217, Run 174416493 | Tissue Name | Rel. Exp. (%) Ag3217, Run 174416493 |
|---|---|---|---|
| Ocular Melanoma Margin (Liver) | 0.0 | Liver Tissue 6005-N | 0.0 |
| Melanoma Metastasis | 0.0 | Liver Cancer 064003 | 0.0 |
| Melanoma Margin (Lung) | 0.0 | Normal Bladder | 8.4 |
| Normal Kidney | 0.0 | Bladder Cancer 1023 | 0.0 |
| Kidney Ca, Nuclear grade 2 (OD04338) | 22.1 | Bladder Cancer A302173 | 8.7 |
| Kidney Margin (OD04338) | 0.0 | Normal Stomach | 0.0 |
| Kidney Ca Nuclear grade 1/2 (OD04339) | 40.9 | Gastric Cancer 9060397 | 0.0 |
| Kidney Margin (OD04339) | 0.0 | Stomach Margin 9060396 | 12.4 |
| Kidney Ca, Clear cell type (OD04340) | 0.0 | Gastric Cancer 9060395 | 6.4 |
| Kidney Margin (OD04340) | 0.0 | Stomach Margin 9060394 | 9.3 |
| Kidney Ca, Nuclear grade 3 (OD04348) | 0.0 | Gastric Cancer 064005 | 0.0 |

TABLE EE

Panel 4D

| Tissue Name | Rel. Exp. (%) Ag3217, Run 164682517 | Tissue Name | Rel. Exp. (%) Ag3217, Run 164682517 |
|---|---|---|---|
| Secondary Th1 act | 0.0 | HUVEC IL-1beta | 0.0 |
| Secondary Th2 act | 0.0 | HUVEC IFN gamma | 0.0 |
| Secondary Tr1 act | 0.0 | HUVEC TNF alpha + IFN gamma | 0.0 |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 0.0 | Lung Microvascular EC none | 0.0 |
| Primary Th1 act | 0.0 | Lung Microvascular EC TNF alpha + IL-1beta | 0.0 |
| Primary Th2 act | 0.0 | Microvascular Dermal EC none | 0.0 |
| Primary Tr1 act | 0.0 | Microsvasular Dermal EC TNF alpha + IL-1beta | 0.0 |
| Primary Th1 rest | 6.9 | Bronchial epithelium TNF alpha + IL1beta | 4.1 |
| Primary Th2 rest | 0.0 | Small airway epithelium none | 8.2 |
| Primary Tr1 rest | 0.0 | Small airway epithelium TNF alpha + IL-1beta | 0.0 |
| CD45RA CD4 lymphocyte act | 0.0 | Coronery artery SMC rest | 0.0 |
| CD45RO CD4 lymphocyte act | 0.0 | Coronery artery SMC TNF alpha + IL-1beta | 0.0 |
| CD8 lymphocyte act | 3.2 | Astrocytes rest | 0.0 |
| Secondary CD8 lymphocyte rest | 0.0 | Astrocytes TNF alpha + IL-1beta | 0.0 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNF alpha + IL-1beta | 0.0 |
| LAK cells IL-2 | 0.0 | Liver cirrhosis | 6.9 |
| LAK cells IL-2 + IL-12 | 0.0 | Lupus kidney | 0.0 |
| LAK cells IL-2 + IFN gamma | 0.0 | NCI-H292 none | 5.3 |
| LAK cells IL-2 + IL-18 | 0.0 | NCI-H292 IL-4 | 0.0 |
| LAK cells PMA/ionomycin | 22.7 | NCI-H292 IL-9 | 16.8 |
| NK Cells IL-2 rest | 0.0 | NCI-H292 IL-13 | 0.0 |
| Two Way MLR 3 day | 5.6 | NCI-H292 IFN gamma | 0.0 |
| Two Way MLR 5 day | 0.0 | HPAEC none | 8.5 |
| Two Way MLR 7 day | 0.0 | HPAEC TNF alpha + IL-1beta | 0.0 |
| PBMC rest | 0.0 | Lung fibroblast none | 0.0 |
| PBMC PWM | 3.8 | Lung fibroblast TNF alpha + IL-1beta | 0.0 |
| PBMC PHA-L | 0.0 | Lung fibroblast IL-4 | 0.0 |

TABLE EE-continued

Panel 4D

| Tissue Name | Rel. Exp. (%) Ag3217, Run 164682517 | Tissue Name | Rel. Exp. (%) Ag3217, Run 164682517 |
|---|---|---|---|
| Ramos (B cell) none | 0.0 | Lung fibroblast IL-9 | 0.0 |
| Ramos (B cell) ionomycin | 0.0 | Lung fibroblast IL-13 | 0.0 |
| B lymphocytes PWM | 7.2 | Lung fibroblast IFN gamma | 0.0 |
| B lymphocytes CD40L and IL-4 | 0.0 | Dermal fibroblast CCD1070 rest | 5.4 |
| EOL-1 dbcAMP | 5.3 | Dermal fibroblast CCD1070 TNF alpha | 0.0 |
| EOL-1 dbcAMP PMA/ionomycin | 0.0 | Dermal fibroblast CCD1070 IL-1beta | 0.0 |
| Dendritic cells none | 0.0 | Dermal fibroblast IFN gamma | 0.0 |
| Dendritic cells LPS | 0.0 | Dermal fibroblast IL-4 | 0.0 |
| Dendritic cells anti-CD40 | 0.0 | IBD Colitis 2 | 8.3 |
| Monocytes rest | 0.0 | IBD Crohn's | 20.6 |
| Monocytes LPS | 0.0 | Colon | 100.0 |
| Macrophages rest | 0.0 | Lung | 47.6 |
| Macrophages LPS | 0.0 | Thymus | 19.3 |
| HUVEC none | 0.0 | Kidney | 0.0 |
| HUVEC starved | 0.0 | | |

TABLE EF

Panel CNS_1

| Tissue Name | Rel. Exp. (%) Ag3217, Run 171694584 | Tissue Name | Rel. Exp. (%) Ag3217, Run 171694584 |
|---|---|---|---|
| BA4 Control | 21.0 | BA17 PSP | 14.3 |
| BA4 Control2 | 23.3 | BA17 PSP2 | 27.2 |
| BA4 Alzheimer's2 | 9.9 | Sub Nigra Control | 16.6 |
| BA4 Parkinson's | 57.4 | Sub Nigra Control2 | 8.1 |
| BA4 Parkinson's2 | 52.5 | Sub Nigra Alzheimer's2 | 9.2 |
| BA4 Huntington's | 11.9 | Sub Nigra Parkinson's2 | 10.9 |
| BA4 Huntington's2 | 24.1 | Sub Nigra Huntington's | 5.3 |
| BA4 PSP | 3.6 | Sub Nigra Huntington's2 | 17.9 |
| BA4 PSP2 | 8.5 | Sub Nigra PSP2 | 1.9 |
| BA4 Depression | 20.0 | Sub Nigra Depression | 0.0 |
| BA4 Depression2 | 9.7 | Sub Nigra Depression2 | 4.1 |
| BA7 Control | 28.9 | Glob Palladus Control | 5.6 |
| BA7 Control2 | 31.0 | Glob Palladus Control2 | 4.6 |
| BA7 Alzheimer's2 | 15.7 | Glob Palladus Alzheimer's | 5.3 |
| BA7 Parkinson's | 31.0 | Glob Palladus Alzheimer's2 | 4.7 |
| BA7 Parkinson's2 | 26.2 | Glob Palladus Parkinson's | 29.5 |
| BA7 Huntington's | 19.9 | Glob Palladus Parkinson's2 | 8.5 |
| BA7 Huntington's2 | 55.9 | Glob Palladus PSP | 2.6 |
| BA7 PSP | 15.5 | Glob Palladus PSP2 | 4.0 |
| BA7 PSP2 | 12.3 | Glob Palladus Depression | 4.0 |
| BA7 Depression | 13.5 | Temp Pole Control | 13.1 |
| BA9 Control | 15.3 | Temp Pole Control2 | 31.4 |
| BA9 Control2 | 31.6 | Temp Pole Alzheimer's | 8.0 |
| BA9 Alzheimer's | 9.4 | Temp Pole Alzheimer's2 | 8.0 |
| BA9 Alzheimer's2 | 10.4 | Temp Pole Parkinson's | 33.2 |
| BA9 Parkinson's | 42.6 | Temp Pole Parkinson's2 | 26.1 |
| BA9 Parkinson's2 | 25.9 | Temp Pole Huntington's | 22.2 |
| BA9 Huntington's | 11.6 | Temp Pole PSP | 6.0 |
| BA9 Huntington's2 | 29.9 | Temp Pole PSP2 | 2.3 |
| BA9 PSP | 11.0 | Temp Pole Depression2 | 15.1 |
| BA9 PSP2 | 9.5 | Cing Gyr Control | 34.2 |
| BA9 Depression | 16.4 | Cing Gyr Control2 | 13.2 |
| BA9 Depression2 | 12.8 | Cing Gyr Alzheimer's | 3.2 |
| BA17 Control | 68.3 | Cing Gyr Alzheimer's2 | 6.9 |
| BA17 Control2 | 28.3 | Cing Gyr Parkinson's | 17.9 |
| BA17 | 18.7 | Cing Gyr Parkinson's2 | 14.8 |

TABLE EF-continued

Panel CNS_1

| Tissue Name | Rel. Exp. (%) Ag3217, Run 171694584 | Tissue Name | Rel. Exp. (%) Ag3217, Run 171694584 |
|---|---|---|---|
| Alzheimer's2 | | | |
| BA17 Parkinson's | 48.3 | Cing Gyr Huntington's | 6.6 |
| BA17 Parkinson's2 | 100.0 | Cing Gyr Huntington's2 | 9.7 |
| BA17 Huntington's | 29.5 | Cing Gyr PSP | 2.2 |
| BA17 Huntington's2 | 32.3 | Cing Gyr PSP2 | 6.1 |
| BA17 Depression | 21.0 | Cing Gyr Depression | 5.2 |
| BA17 Depression2 | 53.2 | Cing Gyr Depression2 | 8.8 |

CNS_neurodegeneration_v1.0 Summary: Ag3217 Two experiments with the same probe and primer set show that the CG57362-01 gene exhibits decreased expression in the temporal cortex of brains suffering from Alzheimer's disease (p Panel 1.3D Summary: Ag3217 Highest expression of the CG57362-01 gene is seen in a lung cancer cell line (CT=30.1). Significant expression is also seen in a cluster of lung cancer cell lines and samples derived from the brain. Thus, expression of this gene could be used to differentiate between brain-derived samples, the lung cancer cell lines and the other samples on this panel. Furthermore, therapeutic modulation of the expression or function of this gene may be effective in the treatment of lung cancer.

Among tissues with metabolic function, this gene is expressed in the adrenal and pituitary glands, and the pancreas. Thus, this gene product may be useful in the diagnosis and/or treatment of metabolic disease, including obesity and diabetes.

In addition, brain-preferential expression of thsi gene indicates that drugs that target this potential mediator of Alzheimer's disease, as seen in CNS_neurodegeneration_V1.0, are likely to have brain-specific action, a desireable feature of effective drugs.

Panel 2.2 Summary: Ag3217 Expression of the CG57362-01 gene is restricted to a sample derived from ovarian tissue (CT=34.9). Thus, expression of this gene could be used to differentiate between this sample and other samples on this panel.

Panel 4D Summary: Ag3217 Expression of the CG57362-01 gene is restricted to a sample derived from the colon (CT=34.8). Therefore, expression of this gene may be used to distinguish colon from the other tissues on this panel. Furthermore, expression of this gene is decreased in colon samples from patients with IBD colitis and Crohn's disease relative to normal colon. Therefore, therapeutic modulation of the activity of the GPCR encoded by this gene may be useful in the treatment of inflammatory bowel disease Panel CNS_1 Summary: Ag3217 Expression in this panel confirms the presence of the CG57362-01 gene in the brain. Please see Panels 1.3D and CNS_neurodegeneration_v1.0 for discussion of utility of this gene in the central nervous system.

F. NOV7a and NOV7b: Amino Acid Transporter

Expression of gene CG57387-01 and variant CG57387-02 was assessed using the primer-probe sets Ag3222 and Ag4965, described in Tables FA and FB.

TABLE FA

Probe Name Ag3222

| Primers | Sequences | | Length | Start Position |
|---|---|---|---|---|
| Forward | 5'-tgcaatttggagctaatatcca-3' | (SEQ ID NO:311) | 22 | 1020 |
| Probe | TET-5'-taaccctcaacctgcccttgtaccag-3'-TAMRA | (SEQ ID NO:312) | 26 | 1050 |
| Reverse | 5'-cgatggagtacagcagcttaac-3' | (SEQ ID NO:313) | 22 | 1079 |

TABLE FB

Probe Name Ag4965

| Primers | Sequences | | Length | Start Position |
|---|---|---|---|---|
| Forward | 5'-ggaaaacaaaatgaaggatcct-3' | (SEQ ID NO:314) | 22 | 919 |
| Probe | TET-5'-cggaagttcccactcatcctgtacct-3'-TAMRA | (SEQ ID NO:315) | 26 | 941 |
| Reverse | 5'-atgtagaggatggtgacgatga-3' | (SEQ ID NO:316) | 22 | 975 |

CNS_neurodegeneration_v1.0 Summary: Ag3222 Expression of the CG57387-01 gene is low/undetectable in all samples on this panel (CTs>35). (Data not shown.)

General_screening_panel_v1.4 Summary: Ag4965 Expression of the CG57387-01 gene is low/undetectable in all samples on this panel (CTs>35). (Data not shown.) The amp plot indicates that there is a high probability of a probe failure.

Panel 1.3D Summary: Ag3222 Expression of the CG57387-01 gene is low/undetectable in all samples on this panel (CTs>35). (Data not shown.)

Panel 2.2 Summary: Ag3222 Results from one experiment with the CG57387-01 gene are not included. The amp plot indicates that there were experimental difficulties with this run.

Panel 4D Summary: Ag3222 Expression of the CG57387-01 gene is low/undetectable in all samples on this panel (CTs>35). (Data not shown.)

G. NOV7c: Amino Acid Transporter Like

Expression of gene CG57387-03 was assessed using the primer-probe set Ag5127, described in Table GA. Results of the RTQ-PCR runs are shown in Tables GB, GC and GD. This probe/primer set recognizes a distinct portion of this gene and shows a distinctive expression pattern when compared to expression seen using probe and primer sets Ag3222 and Ag4965 that recognize variants CG57387-01 and CG57387-02. This observation may indicate that the probe/primer sets can distinguish splice variants of this gene. In contrast to the results obtained with Ag3222 and Ag4965 which show no expression of the CG57387-01 and CG57387-02 genes, the CG57387-03 gene produces a distinct expression profile. Please see below for presentation of the results and more complete discussion of the expression profile.

TABLE GA

Probe Name Ag5127

| Primers | Sequences | | Length | Start Position |
|---|---|---|---|---|
| Forward | 5'-cagaccaaggtcttccaca-3' | (SEQ ID NO:317) | 19 | 815 |
| Probe | TET-5'-agagcaggttcctctctgtcttcagca-3'-TAMRA | (SEQ ID NO:318) | 27 | 835 |
| Reverse | 5'-actgttccatttgagactcca-3' | (SEQ ID NO:319) | 21 | 864 |

TABLE GB

CNS_neurodegeneration_v1.0

| Tissue Name | Rel. Exp. (%) Ag5127, Run 226203927 | Tissue Name | Rel. Exp. (%) Ag5127, Run 226203927 |
|---|---|---|---|
| AD 1 Hippo | 4.1 | Control (Path) 3 Temporal Ctx | 4.0 |
| AD 2 Hippo | 13.4 | Control (Path) 4 Temporal Ctx | 22.1 |
| AD 3 Hippo | 1.4 | AD 1 Occipital Ctx | 6.0 |
| AD 4 Hippo | 3.1 | AD 2 Occipital Ctx (Missing) | 0.0 |
| AD 5 Hippo | 69.3 | AD 3 Occipital Ctx | 6.0 |
| AD 6 Hippo | 33.0 | AD 4 Occipital Ctx | 11.9 |
| Control 2 Hippo | 22.4 | AD 5 Occipital Ctx | 25.7 |
| Control 4 Hippo | 3.5 | AD 6 Occipital Ctx | 9.5 |
| Control (Path) 3 Hippo | 1.8 | Control 1 Occipital Ctx | 1.8 |
| AD 1 Temporal Ctx | 4.7 | Control 2 Occipital Ctx | 69.3 |
| AD 2 Temporal Ctx | 14.5 | Control 3 Occipital Ctx | 12.1 |
| AD 3 Temporal Ctx | 1.6 | Control 4 Occipital Ctx | 2.2 |
| AD 4 Temporal Ctx | 11.6 | Control (Path) 1 Occipital Ctx | 100.0 |
| AD 5 Inf Temporal Ctx | 75.8 | Control (Path) 2 Occipital Ctx | 17.8 |
| AD 5 Sup Temporal Ctx | 21.5 | Control (Path) 3 Occipital Ctx | 1.0 |
| AD 6 Inf Temporal Ctx | 33.4 | Control (Path) 4 Occipital Ctx | 12.3 |
| AD 6 Sup Temporal Ctx | 38.2 | Control 1 Parietal Ctx | 1.6 |
| Control 1 Temporal Ctx | 0.5 | Control 2 Parietal Ctx | 22.2 |
| Control 2 Temporal Ctx | 31.0 | Control 3 Parietal Ctx | 6.5 |
| Control 3 Temporal Ctx | 2.4 | Control (Path) 1 Parietal Ctx | 64.6 |
| Control 3 Temporal Ctx | 3.8 | Control (Path) 2 Parietal Ctx | 48.6 |
| Control (Path) 1 Temporal Ctx | 55.9 | Control (Path) 3 Parietal Ctx | 1.5 |
| Control (Path) 2 Temporal Ctx | 46.7 | Control (Path) 4 Parietal Ctx | 37.9 |

TABLE GC

General_screening_panel_v1.5

| Tissue Name | Rel. Exp. (%) Ag5127, Run 228783308 | Tissue Name | Rel. Exp. (%) Ag5127, Run 228783308 |
|---|---|---|---|
| Adipose | 5.2 | Renal ca. TK-10 | 8.1 |
| Melanoma* Hs688 (A).T | 2.5 | Bladder | 12.6 |
| Melanoma* Hs688 (B).T | 2.0 | Gastric ca. (liver met.) NCI-N87 | 9.9 |
| Melanoma* M14 | 7.4 | Gastric ca. KATO III | 3.6 |
| Melanoma* LOXIMVI | 3.4 | Colon ca. SW-948 | 2.6 |
| Melanoma* SK-MEL-5 | 6.1 | Colon ca. SW480 | 8.0 |
| Squamous Cell carcinoma SCC-4 | 4.4 | Colon ca.* (SW480 met) SW620 | 3.6 |
| Testis Pool | 2.3 | Colon ca. HT29 | 1.7 |
| Prostate ca.* (bone met) PC-3 | 0.6 | Colon ca. HCT-116 | 7.3 |
| Prostate Pool | 6.8 | Colon ca. CaCo-2 | 42.0 |
| Placenta | 1.0 | Colon cancer tissue | 1.9 |
| Uterus Pool | 4.0 | Colon ca. SW1116 | 2.4 |
| Ovarian ca. OVCAR-3 | 6.2 | Colon ca. Colo-205 | 0.7 |
| Ovarian ca. SK-OV-3 | 17.2 | Colon ca. SW-48 | 0.9 |
| Ovarian ca. OVCAR-4 | 4.7 | Colon Pool | 6.1 |
| Ovarian ca. OVCAR-5 | 15.9 | Small Intestine Pool | 2.5 |
| Ovarian ca. IGROV-1 | 1.2 | Stomach Pool | 2.8 |
| Ovarian ca. OVCAR-8 | 3.0 | Bone Marrow Pool | 5.3 |
| Ovary | 1.6 | Fetal Heart | 1.6 |
| Breast ca. MCF-7 | 9.6 | Heart Pool | 0.6 |
| Breast ca. MDA-MB-231 | 10.6 | Lymph Node Pool | 9.9 |
| Breast ca. BT 549 | 9.8 | Fetal Skeletal Muscle | 2.5 |
| Breast ca. T47D | 2.6 | Skeletal Muscle Pool | 12.3 |
| Breast ca. MDA-N | 4.5 | Spleen Pool | 3.2 |
| Breast Pool | 5.6 | Thymus Pool | 9.5 |
| Trachea | 3.5 | CNS cancer (glio/astro) U87-MG | 13.7 |
| Lung | 1.4 | CNS cancer (glio/astro) U-118-MG | 9.9 |
| Fetal Lung | 4.9 | CNS cancer (neuro;met) SK-N-AS | 9.7 |
| Lung ca. NCI-N417 | 0.3 | CNS cancer (astro) SF-539 | 1.5 |
| Lung ca. LX-1 | 4.0 | CNS cancer (astro) SNB-75 | 28.7 |
| Lung ca. NCI-H146 | 0.2 | CNS cancer (glio) SNB-19 | 1.4 |
| Lung ca. SHP-77 | 3.8 | CNS cancer (glio) SF-295 | 11.3 |
| Lung ca. A549 | 8.4 | Brain (Amygdala) Pool | 3.9 |
| Lung ca. NCI-H526 | 1.0 | Brain (cerebellum) | 100.0 |
| Lung ca. NCI-H23 | 15.9 | Brain (fetal) | 17.9 |
| Lung ca. NCI-H460 | 10.3 | Brain (Hippocampus) Pool | 3.2 |
| Lung ca. HOP-62 | 3.9 | Cerebral Cortex Pool | 4.2 |
| Lung ca. NCI-H522 | 9.5 | Brain (Substantia nigra) Pool | 2.4 |
| Liver | 0.2 | Brain (Thalamus) Pool | 6.0 |
| Fetal Liver | 41.8 | Brain (whole) | 8.4 |
| Liver ca. HepG2 | 3.3 | Spinal Cord Pool | 3.3 |
| Kidney Pool | 6.3 | Adrenal Gland | 5.2 |
| Fetal Kidney | 1.0 | Pituitary gland Pool | 0.9 |
| Renal ca. 786-0 | 5.0 | Salivary Gland | 2.0 |
| Renal ca. A498 | 1.6 | Thyroid (female) | 0.2 |
| Renal ca. ACHN | 5.0 | Pancreatic ca. CAPAN2 | 2.8 |
| Renal ca. UO-31 | 7.0 | Pancreas Pool | 5.3 |

TABLE GD

Panel 4.1D

| Tissue Name | Rel. Exp. (%) Ag5127, Run 225784356 | Tissue Name | Rel. Exp. (%) Ag5127, Run 225784356 |
|---|---|---|---|
| Secondary Th1 act | 5.4 | HUVEC IL-1beta | 3.6 |
| Secondary Th2 act | 18.8 | HUVEC IFN gamma | 12.8 |
| Secondary Tr1 act | 19.1 | HUVEC TNF alpha + IFN gamma | 7.8 |
| Secondary Th1 rest | 5.4 | HUVEC TNF alpha + IL4 | 5.0 |
| Secondary Th2 rest | 4.2 | HUVEC IL-11 | 4.5 |
| Secondary Tr1 rest | 6.0 | Lung Microvascular EC none | 19.6 |
| Primary Th1 act | 8.2 | Lung Microvascular EC | 12.8 |

TABLE GD-continued

Panel 4.1D

| Tissue Name | Rel. Exp. (%) Ag5127, Run 225784356 | Tissue Name | Rel. Exp. (%) Ag5127, Run 225784356 |
|---|---|---|---|
| Primary Th2 act | 8.7 | TNF alpha + IL-1beta Microvascular Dermal EC none | 10.8 |
| Primary Tr1 act | 13.4 | Microsvasular Dermal EC TNF alpha + IL-1beta | 4.2 |
| Primary Th1 rest | 9.5 | Bronchial epithelium TNF alpha + IL1beta | 5.7 |
| Primary Th2 rest | 9.0 | Small airway epithelium none | 7.3 |
| Primary Tr1 rest | 22.7 | Small airway epithelium TNF alpha + IL-1beta | 8.5 |
| CD45RA CD4 lymphocyte act | 10.4 | Coronery artery SMC rest | 5.1 |
| CD45RO CD4 lymphocyte act | 21.8 | Coronery artery SMC TNF alpha + IL-1beta | 1.5 |
| CD8 lymphocyte act | 17.2 | Astrocytes rest | 2.6 |
| Secondary CD8 lymphocyte rest | 16.8 | Astrocytes TNF alpha + IL-1beta | 1.2 |
| Secondary CD8 lymphocyte act | 5.5 | KU-812 (Basophil) rest | 16.7 |
| CD4 lymphocyte none | 5.2 | KU-812 (Basophil) PMA/ionomycin | 33.4 |
| 2ry Th1/Th2/Tr1_anti-CD95 CH11 | 21.9 | CCD1106 (Keratinocytes) none | 14.9 |
| LAK cells rest | 42.0 | CCD1106 (Keratinocytes) TNF alpha + IL-1beta | 22.1 |
| LAK cells IL-2 | 14.5 | Liver cirrhosis | 2.8 |
| LAK cells IL-2 + IL-12 | 10.4 | NCI-H292 none | 6.5 |
| LAK cells IL-2 + IFN gamma | 10.0 | NCI-H292 IL-4 | 10.1 |
| LAK cells IL-2 + IL-18 | 15.6 | NCI-H292 IL-9 | 13.7 |
| LAK cells PMA/ionomycin | 19.3 | NCI-H292 IL-13 | 11.2 |
| NK Cells IL-2 rest | 24.8 | NCI-H292 IFN gamma | 8.4 |
| Two Way MLR 3 day | 25.9 | HPAEC none | 3.6 |
| Two Way MLR 5 day | 13.0 | HPAEC TNF alpha + IL-1beta | 12.8 |
| Two Way MLR 7 day | 10.7 | Lung fibroblast none | 19.1 |
| PBMC rest | 6.8 | Lung fibroblast TNF alpha + IL-1beta | 11.3 |
| PBMC PWM | 3.6 | Lung fibroblast IL-4 | 27.0 |
| PBMC PHA-L | 10.3 | Lung fibroblast IL-9 | 48.3 |
| Ramos (B cell) none | 11.3 | Lung fibroblast IL-13 | 22.7 |
| Ramos (B cell) ionomycin | 8.7 | Lung fibroblast IFN gamma | 22.1 |
| B lymphocytes PWM | 8.9 | Dermal fibroblast CCD1070 rest | 17.3 |
| B lymphocytes CD40L and IL-4 | 18.9 | Dermal fibroblast CCD1070 TNF alpha | 20.7 |
| EOL-1 dbcAMP | 84.1 | Dermal fibroblast CCD1070 IL-1beta | 5.4 |
| EOL-1 dbcAMP PMA/ionomycin | 30.6 | Dermal fibroblast IFN gamma | 6.4 |
| Dendritic cells none | 36.6 | Dermal fibroblast IL-4 | 9.8 |
| Dendritic cells LPS | 21.3 | Dermal Fibroblasts rest | 15.1 |
| Dendritic cells anti-CD40 | 45.1 | Neutrophils TNFa + LPS | 14.7 |
| Monocytes rest | 84.1 | Neutrophils rest | 62.0 |
| Monocytes LPS | 66.4 | Colon | 11.7 |
| Macrophages rest | 73.7 | Lung | 4.9 |
| Macrophages LPS | 4.8 | Thymus | 51.4 |
| HUVEC none | 5.7 | Kidney | 100.0 |
| HUVEC starved | 7.0 | | |

CNS_neurodegeneration_v1.0 Summary: Ag5127 This panel does not show differential expression of the CG57387-03 gene in Alzheimer's disease. However, this expression profile confirms the presence of this gene in the brain. Please see Panel 1.3D for discussion of utility of this gene in the central nervous system.

General_screening_panel_v1.5 Summary: Ag5127 Highest expression of the CG57387-03 gene is seen in the cerebellum (CT=27.7). This high level of expression in the cerebellum among all tissues examined indicates a specific role for this gene product in this brain region. Given the role of amino acid transporters in lysosomal storage disorders and the role of lysosomal disorders in CNS disease, this gene product may play an important role in CNS disease. Therefore, pharmacologic modulators of the activity of this gene product may have utility in treatment of neurodegenerative disorders such as Niemann-Pick type C disease and other diseases such as Alzheimer's disease, Parkinson's disease, and huntington's disease. In particular, spinocerebellar ataxias may benefit from the modulation of this gene, since they typically involve cerebellar dysfunction.

Significant expression is also seen in a colon cancer cell line and two ovarian cancer cell lines. Thus, expression of this gene could be used to differentiate between these samples and other samples on this panel and as a marker of cerebellar tissue and ovarian and colon cancer. Furthermore, therapeutic modulation of the expression or function of this gene may be effective in the treatment of colon or ovarian cancer.

Among tissues with metabolic function, this gene is expressed at moderate to low levels in adipose, adrenal gland, pancreas, fetal heart, and adult and fetal skeletal muscle and liver. This widespread expression among these tissues suggests that this gene product may be useful for the diagnosis and/or treatment of metabolic disease, including obesity and diabetes.

In addition, this gene is expressed at much higher levels in fetal liver(CT=29) than adult liver (CT=37). Thus, expression of this gene could be used to differentiate between the two sources of this tissue (German et al., Neuroscience 2002 February 14;109(3):437–50; Sagne et al., Proc Natl Acad Sci U S A 2001 June 19;98(13):7206–11).

Panel 4.1D Summary: Ag5127 Highest expression of the CG57387-03 gene is seen in the kidney (CT=29.9). This gene is also expressed at moderate levels in a wide range of cell types of significance in the immune response in health and disease. These cells include members of the T-cell, B-cell, endothelial cell, macrophage/monocyte, and peripheral blood mononuclear cell family, as well as epithelial and fibroblast cell types from lung and skin, and normal tissues represented by colon, lung, thymus and kidney. This ubiquitous pattern of expression suggests that this gene product may be involved in homeostatic processes for these and other cell types and tissues. This pattern is in agreement with the expression profile in General_screening_panel_v1.5 and also suggests a role for the gene product in cell survival and proliferation. Therefore, modulation of the gene product with a functional therapeutic may lead to the alteration of functions associated with these cell types and lead to improvement of the symptoms of patients suffering from autoimmune and inflammatory diseases such as asthma, allergies, inflammatory bowel disease, lupus erythematosus, psoriasis, rheumatoid arthritis, and osteoarthritis.

H. NOV8a and NOV8c: Lymphocyte Antigen Precursor

Expression of gene CG56417-01 and variant CG56417-03 was assessed using the primer-probe set Ag2917, described in Table HA. Results of the RTQ-PCR runs are shown in Tables HB, HC, HD, and HE.

TABLE HA

Probe Name Ag2917

| Primers | Sequences | | Length | Start Position |
|---|---|---|---|---|
| Forward | 5'-cagtctccaggccatgaag-3' | (SEQ ID NO:320) | 19 | 36 |
| Probe | TET-5'-accttgtccctggtcctgctggt-3'-TAMRA | (SEQ ID NO:321) | 23 | 55 |
| Reverse | 5'-agaccctgagctctctccat-3' | (SEQ ID NO:322) | 20 | 91 |

TABLE HB

CNS_neurodegeneration_v1.0

| Tissue Name | Rel. Exp. (%) Ag2917, Run 209735957 | Tissue Name | Rel. Exp. (%) Ag2917, Run 209735957 |
|---|---|---|---|
| AD 1 Hippo | 1.8 | Control (Path) 3 Temporal Ctx | 0.0 |
| AD 2 Hippo | 12.7 | Control (Path) 4 Temporal Ctx | 6.6 |
| AD 3 Hippo | 0.0 | AD 1 Occipital Ctx | 6.6 |
| AD 4 Hippo | 0.0 | AD 2 Occipital Ctx (Missing) | 0.0 |
| AD 5 hippo | 51.8 | AD 3 Occipital Ctx | 5.3 |
| AD 6 Hippo | 3.7 | AD 4 Occipital Ctx | 3.6 |
| Control 2 Hippo | 0.0 | AD 5 Occipital Ctx | 36.3 |
| Control 4 Hippo | 6.9 | AD 6 Occipital Ctx | 29.9 |
| Control (Path) 3 Hippo | 5.4 | Control 1 Occipital Ctx | 0.0 |
| AD 1 Temporal Ctx | 1.1 | Control 2 Occipital Ctx | 12.7 |
| AD 2 Temporal Ctx | 7.3 | Control 3 Occipital Ctx | 4.5 |
| AD 3 Temporal Ctx | 0.0 | Control 4 Occipital Ctx | 0.0 |
| AD 4 Temporal Ctx | 6.7 | Control (Path) 1 Occipital Ctx | 15.5 |
| AD 5 Inf Temporal Ctx | 100.0 | Control (Path) 2 Occipital Ctx | 0.0 |
| AD 5 Sup Temporal Ctx | 7.7 | Control (Path) 3 Occipital Ctx | 4.5 |
| AD 6 Inf Temporal Ctx | 9.4 | Control (Path) 4 Occipital Ctx | 16.6 |
| AD 6 Sup Temporal Ctx | 0.0 | Control 1 Parietal Ctx | 0.0 |
| Control 1 Temporal Ctx | 0.0 | Control 2 Parietal Ctx | 17.0 |
| Control 2 Temporal Ctx | 8.9 | Control 3 Parietal Ctx | 9.5 |
| Control 3 Temporal Ctx | 19.8 | Control (Path) 1 Parietal Ctx | 19.5 |
| Control 4 Temporal Ctx | 0.0 | Control (Path) 2 Parietal Ctx | 1.6 |
| Control (Path) 1 Temporal Ctx | 31.2 | Control (Path) 3 Parietal Ctx | 4.5 |

TABLE IIB-continued

CNS_neurodegeneration_v1.0

| Tissue Name | Rel. Exp. (%) Ag2917, Run 209735957 | Tissue Name | Rel. Exp. (%) Ag2917, Run 209735957 |
|---|---|---|---|
| Control (Path) 2 Temporal Ctx | 13.5 | Control (Path) 4 Parietal Ctx | 19.5 |

TABLE IIC

Panel 1.3D

| Tissue Name | Rel. Exp. (%) Ag2917, Run 161411861 | Rel. Exp. (%) Ag2917, Run 165721698 | Tissue Name | Rel. Exp. (%) Ag2917, Run 161411861 | Rel. Exp. (%) Ag2917, Run 165721698 |
|---|---|---|---|---|---|
| Liver adenocarcinoma | 0.0 | 0.0 | Kidney (fetal) | 0.0 | 0.0 |
| Pancreas | 0.0 | 0.0 | Renal ca. 786-0 | 0.0 | 0.0 |
| Pancreatic ca. CAPAN 2 | 2.5 | 25.2 | Renal ca. A498 | 6.5 | 18.7 |
| Adrenal gland | 0.0 | 0.0 | Renal ca. RXF 393 | 0.0 | 0.0 |
| Thyroid | 0.0 | 0.0 | Renal ca. ACHN | 0.4 | 0.0 |
| Salivary gland | 0.0 | 0.0 | Renal ca. UO-31 | 0.0 | 0.0 |
| Pituitary gland | 0.0 | 0.0 | Renal ca. TK-10 | 0.0 | 0.0 |
| Brain (fetal) | 0.0 | 0.0 | Liver | 0.0 | 0.0 |
| Brain (whole) | 0.0 | 100.0 | Liver (fetal) | 0.0 | 0.0 |
| Brain (amygdala) | 5.6 | 10.9 | Liver ca. (hepatoblast) HepG2 | 0.0 | 0.0 |
| Brain (cerebellum) | 6.5 | 2.5 | Lung | 0.0 | 0.0 |
| Brain (hippocampus) | 0.6 | 41.2 | Lung (fetal) | 0.0 | 6.7 |
| Brain (substantia nigra) | 0.0 | 0.0 | Lung ca. (small cell) LX-1 | 0.0 | 0.0 |
| Brain (thalamus) | 6.6 | 0.0 | Lung ca. (small cell) NCI-H69 | 0.0 | 0.0 |
| Cerebral Cortex | 100.0 | 17.1 | Lung ca. (s. cell var.) SHP-77 | 0.0 | 0.0 |
| Spinal cord | 12.9 | 26.2 | Lung ca. (large cell) NCI-H460 | 0.0 | 0.0 |
| glio/astro U87-MG | 1.7 | 0.0 | Lung ca. (non-sm. cell) A549 | 0.0 | 0.0 |
| glio/astro U-118-MG | 0.0 | 0.0 | Lung ca. (non-s. cell) NCI-H23 | 0.0 | 0.0 |
| astrocytoma SW1783 | 6.4 | 0.0 | Lung ca. (non-s. cell) HOP-62 | 0.0 | 0.0 |
| neuro*; met SK-N-AS | 0.5 | 13.4 | Lung ca. (non-s. cl) NCI-H522 | 0.3 | 0.0 |
| astrocytoma SF-539 | 0.0 | 0.0 | Lung ca. (squam.) SW 900 | 0.0 | 0.0 |
| astrocytoma SNB-75 | 0.0 | 0.0 | Lung ca. (squam.) NCI-H596 | 0.0 | 0.0 |
| glioma SNB-19 | 0.0 | 0.0 | Mammary gland | 0.0 | 0.0 |
| glioma U251 | 0.0 | 0.0 | Breast ca.* (pl. ef) MCF-7 | 0.0 | 0.0 |
| glioma SF-295 | 0.0 | 0.0 | Breast ca.* (pl. ef) MDA-MB-231 | 0.0 | 0.0 |
| Heart (fetal) | 2.1 | 0.0 | Breast ca.* (pl. ef) T47D | 0.0 | 0.0 |
| Heart | 0.0 | 12.6 | Breast ca. BT-549 | 0.0 | 0.0 |
| Skeletal muscle (fetal) | 9.0 | 0.0 | Breast ca. MDA-N | 5.5 | 0.0 |
| Skeletal muscle | 0.4 | 38.4 | Ovary | 9.8 | 0.0 |
| Bone marrow | 0.0 | 0.0 | Ovarian ca. OVCAR-3 | 0.0 | 0.0 |
| Thymus | 7.4 | 0.0 | Ovarian ca. OVCAR-4 | 0.0 | 0.0 |
| Spleen | 13.4 | 37.6 | Ovarian ca. OVCAR-5 | 0.4 | 10.3 |
| Lymph node | 0.0 | 0.0 | Ovarian ca. OVCAR-8 | 0.8 | 17.0 |
| Colorectal | 0.0 | 0.0 | Ovarian ca. IGROV-1 | 6.3 | 15.0 |

TABLE HC-continued

Panel 1.3D

| Tissue Name | Rel. Exp. (%) Ag2917, Run 161411861 | Rel. Exp. (%) Ag2917, Run 165721698 | Tissue Name | Rel. Exp. (%) Ag2917, Run 161411861 | Rel. Exp. (%) Ag2917, Run 165721698 |
|---|---|---|---|---|---|
| Stomach | 0.0 | 0.0 | Ovarian ca.* (ascites) SK-OV-3 | 0.0 | 0.0 |
| Small intestine | 0.0 | 0.0 | Uterus | 0.0 | 0.0 |
| Colon ca. SW480 | 0.0 | 7.7 | Placenta | 0.0 | 0.0 |
| Colon ca.* SW620 (SW480 met) | 0.0 | 0.0 | Prostate | 0.0 | 0.0 |
| Colon ca. HT29 | 0.0 | 0.0 | Prostate ca.* (bone met)PC-3 | 0.0 | 0.0 |
| Colon ca. HCT-116 | 0.0 | 0.0 | Testis | 18.0 | 0.0 |
| Colon ca. CaCo-2 | 7.8 | 0.0 | Melanoma Hs688 (A).T | 0.0 | 0.0 |
| Colon ca. tissue (ODO3866) | 0.0 | 0.0 | Melanoma* (met) Hs688 (B).T | 1.2 | 0.0 |
| Colon ca. HCC-2998 | 0.0 | 0.0 | Melanoma UACC-62 | 0.0 | 0.0 |
| Gastric ca.* (liver met) NCI-N87 | 44.1 | 71.7 | Melanoma M14 | 0.0 | 0.0 |
| Bladder | 2.0 | 0.0 | Melanoma LOX IMVI | 0.0 | 0.0 |
| Trachea | 10.9 | 4.8 | Melanoma* (met) SK-MEL-5 | 0.0 | 0.0 |
| Kidney | 0.0 | 0.0 | Adipose | 9.2 | 0.0 |

TABLE HD

Panel 2D

| Tissue Name | Rel. Exp. (%) Ag2917, Run 161463558 | Tissue Name | Rel. Exp. (%) Ag2917, Run 161463558 |
|---|---|---|---|
| Normal Colon | 3.2 | Kidney Margin 8120608 | 0.0 |
| CC Well to Mod Diff (ODO3866) | 0.0 | Kidney Cancer 8120613 | 0.0 |
| CC Margin (ODO3866) | 0.0 | Kidney Margin 8120614 | 0.0 |
| CC Gr. 2 rectosigmoid (ODO3868) | 0.0 | Kidney Cancer 9010320 | 0.0 |
| CC Margin (ODO3868) | 0.8 | Kidney Margin 9010321 | 0.9 |
| CC Mod Diff (ODO3920) | 0.0 | Normal Uterus | 0.0 |
| CC Margin (ODO3920) | 2.0 | Uterus Cancer 064011 | 1.7 |
| CC Gr. 2 ascend colon (ODO3921) | 0.2 | Normal Thyroid | 3.8 |
| CC Margin (ODO3921) | 0.0 | Thyroid Cancer 064010 | 0.1 |
| CC from Partial Hepatectomy (ODO4309) Mets | 0.0 | Thyroid Cancer A302152 | 0.0 |
| Liver Margin (ODO4309) | 0.0 | Thyroid Margin A302153 | 6.0 |
| Colon mets to lung (OD04451-01) | 0.0 | Normal Breast | 0.0 |
| Lung Margin (OD04451-02) | 0.0 | Breast Cancer (OD04566) | 0.0 |
| Normal Prostate 6546-1 | 1.6 | Breast Cancer (OD04590-01) | 0.0 |
| Prostate Cancer (OD04410) | 0.2 | Breast Cancer Mets (OD04590-03) | 0.0 |
| Prostate Margin (OD04410) | 0.8 | Breast Cancer Metastasis (OD04655-05) | 0.0 |
| Prostate Cancer (OD04720-01) | 0.5 | Breast Cancer 064006 | 0.9 |
| Prostate Margin (OD04720-02) | 0.8 | Breast Cancer 1024 | 1.4 |
| Normal Lung 061010 | 0.0 | Breast Cancer 9100266 | 0.1 |
| Lung Met to Muscle (ODO4286) | 1.7 | Breast Margin 9100265 | 0.0 |
| Muscle Margin (ODO4286) | 2.0 | Breast Cancer A209073 | 1.8 |
| Lung Malignant Cancer (OD03126) | 4.2 | Breast Margin A209073 | 1.2 |
| Lung Margin (OD03126) | 1.7 | Normal Liver | 0.0 |
| Lung Cancer (OD04404) | 0.0 | Liver Cancer 064003 | 0.0 |
| Lung Margin (OD04404) | 0.1 | Liver Cancer 1025 | 0.0 |
| Lung Cancer (OD04565) | 0.9 | Liver Cancer 1026 | 0.0 |
| Lung Margin (OD04565) | 0.0 | Liver Cancer 6004-T | 0.4 |
| Lung Cancer (OD04237-01) | 0.0 | Liver Tissue 6004-N | 1.4 |
| Lung Margin (OD04237-02) | 0.0 | Liver Cancer 6005-T | 0.0 |

TABLE HD-continued

Panel 2D

| Tissue Name | Rel. Exp. (%) Ag2917, Run 161463558 | Tissue Name | Rel. Exp. (%) Ag2917, Run 161463558 |
|---|---|---|---|
| Ocular Mel Met to Liver (ODO4310) | 0.0 | Liver Tissue 6005-N | 0.0 |
| Liver Margin (ODO4310) | 0.0 | Normal Bladder | 0.0 |
| Melanoma Mets to Lung (OD04321) | 0.0 | Bladder Cancer 1023 | 0.0 |
| Lung Margin (OD04321) | 0.9 | Bladder Cancer A302173 | 0.0 |
| Normal Kidney | 0.5 | Bladder Cancer (OD04718-01) | 100.0 |
| Kidney Ca, Nuclear grade 2 (OD04338) | 0.0 | Bladder Normal Adjacent (OD04718-03) | 0.0 |
| Kidney Margin (OD04338) | 0.0 | Normal Ovary | 0.0 |
| Kidney Ca Nuclear grade 1/2 (OD04339) | 0.0 | Ovarian Cancer 064008 | 0.8 |
| Kidney Margin (OD04339) | 1.2 | Ovarian Cancer (OD04768-07) | 0.0 |
| Kidney Ca, Clear cell type (OD04340) | 0.0 | Ovary Margin (OD04768-08) | 1.6 |
| Kidney Margin (OD04340) | 0.1 | Normal Stomach | 0.0 |
| Kidney Ca, Nuclear grade 3 (OD04348) | 0.0 | Gastric Cancer 9060358 | 0.0 |
| Kidney Margin (OD04348) | 0.3 | Stomach Margin 9060359 | 0.0 |
| Kidney Cancer (OD04622-01) | 0.0 | Gastric Cancer 9060395 | 1.8 |
| Kidney Margin (OD04622-03) | 0.4 | Stomach Margin 9060394 | 14.5 |
| Kidney Cancer (OD04450-01) | 0.0 | Gastric Cancer 9060397 | 0.0 |
| Kidney Margin (OD04450-03) | 0.0 | Stomach Margin 9060396 | 0.0 |
| Kidney Cancer 8120607 | 0.0 | Gastric Cancer 064005 | 31.6 |

TABLE HE

Panel 3D

| Tissue Name | Rel. Exp. (%) Ag2917, Run 164629842 | Tissue Name | Rel. Exp. (%) Ag2917, Run 164629842 |
|---|---|---|---|
| Daoy-Medulloblastoma | 0.0 | Ca Ski-Cervical epidermoid carcinoma (metastasis) | 0.0 |
| TE671-Medulloblastoma | 0.0 | ES-2-Ovarian clear cell carcinoma | 0.0 |
| D283 Med-Medulloblastoma | 0.0 | Ramos-Stimulated with PMA/ionomycin 6h | 0.0 |
| PFSK-1-Primitive Neuroectodermal | 0.0 | Ramos-Stimulated with PMA/ionomycin 14h | 0.0 |
| XF-498-CNS | 0.0 | MEG-01-Chronic myelogenous leukemia (megokaryoblast) | 0.0 |
| SNB-78-Glioma | 0.0 | Raji-Burkitt's lymphoma | 0.0 |
| SF-268-Glioblastoma | 0.0 | Daudi-Burkitt's lymphoma | 0.0 |
| T98G-Glioblastoma | 0.0 | U266-B-cell plasmacytoma | 0.0 |
| SK-N-SH-Neuroblastoma (metastasis) | 0.0 | CA46-Burkitt's lymphoma | 0.0 |
| SF-295-Glioblastoma | 0.0 | RL-non-Hodgkin's B-cell lymphoma | 0.0 |
| Cerebellum | 7.5 | JM1-pre-B-cell lymphoma | 0.0 |
| Cerebellum | 0.0 | Jurkat-T cell leukemia | 0.0 |
| NCI-H292-Mucoepidermoid lung carcinoma | 0.0 | TF-1-Erythroleukemia | 0.0 |
| DMS-114-Small cell lung cancer | 0.0 | HUT 78-T-cell lymphoma | 0.0 |
| DMS-79-Small cell lung cancer | 10.3 | U937-Histiocytic lymphoma | 4.3 |
| NCI-H146-Small cell lung cancer | 5.7 | KU-812-Myelogenous leukemia | 0.0 |
| NCI-H526-Small cell lung cancer | 0.0 | 769-P-Clear cell renal carcinoma | 0.0 |
| NCI-N417-Small cell lung cancer | 0.0 | Caki-2-Clear cell renal carcinoma | 2.5 |
| NCI-H82-Small cell lung cancer | 0.0 | SW 839-Clear cell renal carcinoma | 0.0 |
| NCI-H157-Squamous cell lung cancer (metastasis) | 0.0 | G401-Wilms' tumor | 0.0 |
| NCI-H1155-Large cell lung cancer | 0.0 | Hs766T-Pancreatic carcinoma (LN metastasis) | 42.9 |

TABLE HE-continued

Panel 3D

| Tissue Name | Rel. Exp. (%) Ag2917, Run 164629842 | Tissue Name | Rel. Exp. (%) Ag2917, Run 164629842 |
|---|---|---|---|
| NCI-H1299-Large cell lung cancer | 0.0 | CAPAN-1-Pancreatic adenocarcinoma (liver metastasis) | 0.0 |
| NCI-H727-Lung carcinoid | 0.0 | SU86.86-Pancreatic carcinoma (liver metastasis) | 0.6 |
| NCI-UMC-11-Lung carcinoid | 0.0 | BxPC-3-Pancreatic adenocarcinoma | 18.7 |
| LX-1-Small cell lung cancer | 0.0 | HPAC-Pancreatic adenocarcinoma | 92.0 |
| Colo-205-Colon cancer | 0.0 | MIA PaCa-2-Pancreatic carcinoma | 0.0 |
| KM12-Colon cancer | 6.3 | CFPAC-1-Pancreatic ductal adenocarcinoma | 3.3 |
| KM20L2-Colon cancer | 0.0 | PANC-1-Pancreatic epithelioid ductal carcinoma | 0.0 |
| NCI-H716-Colon cancer | 0.0 | T24-Bladder carcinma (transitional cell) | 0.0 |
| SW-48-Colon adenocarcinoma | 0.0 | 5637-Bladder carcinoma | 0.0 |
| SW1116-Colon adenocarcinoma | 0.0 | HT-1197-Bladder carcinoma | 13.6 |
| LS 174T-Colon adenocarcinoma | 0.0 | UM-UC-3-Bladder carcinma (transitional cell) | 0.0 |
| SW-948-Colon adenocarcinoma | 0.0 | A204-Rhabdomyosarcoma | 0.0 |
| SW-480-Colon adenocarcinoma | 0.0 | HT-1080-Fibrosarcoma | 0.0 |
| NCI-SNU-5-Gastric carcinoma | 0.0 | MG-63-Osteosarcoma | 0.0 |
| KATO III-Gastric carcinoma | 100.0 | SK-LMS-1-Leiomyosarcoma (vulva) | 0.0 |
| NCI-SNU-16-Gastric carcinoma | 0.0 | SJRH30-Rhabdomyosarcoma (met to bone marrow) | 0.0 |
| NCI-SNU-1-Gastric carcinoma | 0.0 | A431-Epidermoid carcinoma | 0.0 |
| RF-1-Gastric adenocarcinoma | 0.0 | WM266-4-Melanoma | 0.0 |
| RF-48-Gastric adenocarcinoma | 0.0 | DU 145-Prostate carcinoma (brain metastasis) | 0.0 |
| MKN-45-Gastric carcinoma | 0.0 | MDA-MB-468-Breast adenocarcinoma | 12.2 |
| NCI-N87-Gastric carcinoma | 4.0 | SCC-4-Squamous cell carcinoma of tongue | 0.0 |
| OVCAR-5-Ovarian carcinoma | 3.4 | SCC-9-Squamous cell carcinoma of tongue | 0.0 |
| RL95-2-Uterine carcinoma | 3.0 | SCC-15-Squamous cell carcinoma of tongue | 0.0 |
| HelaS3-Cervical adenocarcinoma | 0.0 | CAL 27-Squamous cell carcinoma of tongue | 0.0 |

CNS_neurodegeneration_v1.0 Summary: Ag2917 This panel does not show differential expression of the CG56417-01 gene in Alzheimer's disease. However, this expression profile confirms the presence of this gene in the brain. Please see Panel 1.3D for discussion of utility of this gene in the central nervous system.

Panel 1.3D Summary: Ag2917 Two experiments with the same probe and primer set both show highest expression of the CG56417-01 gene, a putative lymphocyte antigen, in regions of the brain (CTs=32–34). Preferential expression in the cerebral cortex indicates a role for this gene product in CNS processes. Lymphocytes are involved in the inflammatory response to brain pathologies such as trauma. Therefore, targeting this gene product with drugs or directing toxins to cells that specifically express this gene product may have utility in countering the inflammation that is thought to be part of the pathologic etiology of numerous CNS pathologies, such as stroke, trauma, and neurodegenerative disorders such as Alzheimer's, Parkinson's and Huntington's diseases.

Significant expression is also seen in a gastric cancer cell line. Thus, expression of this gene could be used to differentiate samples from the brain and the cancer cell line from other samples on this panel and as a marker for brain tissue and gastric cancer (Holmin et al., Neurosurgery 1998 February;42(2):291–8).

Panel 2D Summary: Ag2917 Highest expression of the CG56417-01 gene is seen in a bladder cancer (CT=29.4). Significant expression is also seen in a gastric cancer and normal thyroid. Thus, expression of this gene could be used to differentiate between these samples and other samples on this panel and as a marker for the presence of these cancers. Furthermore, therapeutic modulation of the expression or function of this gene may be effective in the treatment of bladder, gastric, or thyroid cancer.

Panel 3D Summary: Ag2917 Expression of the CG56417-01 gene is limited to cell lines derived from gastric cancer, pancreatic cancer, and bladder cancer (CTs=32–35). This expression is consistent with expression in Panel 2D. Thus, expression of this gene could be used to differentiate between these samples and other samples on this panel.

Panel 4.1D Summary: Ag2917 Expression of the CG56417-01 gene is low/undetectable in all samples on this panel (CTs>35). (Data not shown.)

Panel 4D Summary: Ag2917 Results from one experiment with the CG56417-01 gene are not included. The amp plot indicates that there were experimental difficulties with this run.

I. NOV8b and NOV8d: Lymphocyte Antigen Like

Expression of gene CG56417-02 and variant CG56417-04 was assessed using the primer-probe set Ag4251, described in Table IA.

TABLE IA

Probe Name Ag4251

| Primers | Sequences | | Length | Start Position |
|---|---|---|---|---|
| Forward | 5'-gtgttgctaggaagcatgttct-3' | (SEQ ID NO:323) | 22 | 87 |
| Probe | TET-5'-acacgtgcagtagctgcacctgctt-3'-TAMRA | (SEQ ID NO:324) | 25 | 128 |
| Reverse | 5'-atgacacatgcgacgtatgag-3' | (SEQ ID NO:325) | 21 | 154 |

CNS_neurodegeneration_v1.0 Summary: Ag4251 Expression of the CG56417-02 gene is low/undetectable in all samples on this panel (CTs>35). (Data not shown.) The amp plot indicates that there is a high probability of a probe failure.

General_screening_panel_v1.4 Summary: Ag4251 Expression of the CG56417-02 gene is low/undetectable in all samples on this panel (CTs>35). (Data not shown.) The amp plot indicates that there is a high probability of a probe failure.

Panel 4.1D Summary: Ag4251 Expression of the CG56417-02 gene is low/undetectable in all samples on this panel (CTs>35). (Data not shown.) The amp plot indicates that there is a high probability of a probe failure.

J. NOV9a and NOV9b: Early B-Cell Factor

Expression of gene CG57480-01 and variant CG57480-02 was assessed using the primer-probe set Ag3253, described in Table JA. Results of the RTQ-PCR runs are shown in Tables JB, JC and JD.

TABLE JA

Probe Name Ag3253

| Primers | Sequences | | Length | Start Position |
|---|---|---|---|---|
| Forward | 5'-ctttgtctacaccgcccttaat-3' | (SEQ ID NO:326) | 22 | 1050 |
| Probe | TET-5'-ccaaccatagattacggctttcagagg-3'-TAMRA | (SEQ ID NO:327) | 27 | 1075 |
| Reverse | 5'-gatgtcttgggatcactttctg-3' | (SEQ ID NO:328) | 22 | 1105 |

TABLE JB

CNS_neurodegeneration_v1.0

| Tissue Name | Rel. Exp. (%) Ag3253, Run 206533590 | Tissue Name | Rel. Exp. (%) Ag3253, Run 206533590 |
|---|---|---|---|
| AD 1 Hippo | 0.0 | Control (Path) 3 Temporal Ctx | 0.0 |
| AD 2 Hippo | 7.9 | Control (Path) 4 Temporal Ctx | 100.0 |
| AD 3 Hippo | 0.0 | AD 1 Occipital Ctx | 0.0 |
| AD 4 Hippo | 0.0 | AD 2 Occipital Ctx (Missing) | 0.0 |
| AD 5 hippo | 45.7 | AD 3 Occipital Ctx | 0.0 |
| AD 6 Hippo | 94.6 | AD 4 Occipital Ctx | 23.0 |
| Control 2 Hippo | 23.5 | AD 5 Occipital Ctx | 15.6 |
| Control 4 Hippo | 0.0 | AD 6 Occipital Ctx | 0.0 |
| Control (Path) 3 Hippo | 0.0 | Control 1 Occipital Ctx | 37.9 |
| AD 1 Temporal Ctx | 51.4 | Control 2 occipital Ctx | 0.0 |
| AD 2 Temporal Ctx | 0.0 | Control 3 Occipital Ctx | 0.0 |
| AD 3 Temporal Ctx | 39.8 | Control 4 Occipital Ctx | 55.1 |
| AD 4 Temporal Ctx | 21.2 | Control (Path) 1 Occipital Ctx | 42.0 |

TABLE JB-continued

CNS_neurodegeneration_v1.0

| Tissue Name | Rel. Exp. (%) Ag3253, Run 206533590 | Tissue Name | Rel. Exp. (%) Ag3253, Run 206533590 |
|---|---|---|---|
| AD 5 Inf Temporal Ctx | 37.1 | Control (Path) 2 Occipital Ctx | 22.4 |
| AD 5 SupTemporal Ctx | 87.1 | Control (Path) 3 Occipital Ctx | 0.0 |
| AD 6 Inf Temporal Ctx | 76.8 | Control (Path) 4 Occipital Ctx | 70.7 |
| AD 6 Sup Temporal Ctx | 41.2 | Control 1 Parietal Ctx | 0.0 |
| Control 1 Temporal Ctx | 11.0 | Control 2 Parietal Ctx | 45.1 |
| Control 2 Temporal Ctx | 21.8 | Control 3 Parietal Ctx | 15.2 |
| Control 3 Temporal Ctx | 50.0 | Control (Path) 1 Parietal Ctx | 19.8 |
| Control 4 Temporal Ctx | 0.0 | Control (Path) 2 Parietal Ctx | 34.6 |
| Control (Path) 1 Temporal Ctx | 54.0 | Control (Path) 3 Parietal Ctx | 17.7 |
| Control (Path) 2 Temporal Ctx | 40.6 | Control (Path) 4 Parietal Ctx | 0.0 |

TABLE JC

Panel 1.3D

| Tissue Name | Rel. Exp. (%) Ag3253, Run 165524927 | Tissue Name | Rel. Exp. (%) Ag3253, Run 165524927 |
|---|---|---|---|
| Liver adenocarcinoma | 0.0 | Kidney (fetal) | 0.7 |
| Pancreas | 3.3 | Renal ca. 786-0 | 0.0 |
| Pancreatic ca. CAPAN 2 | 0.0 | Renal ca. A498 | 0.8 |
| Adrenal gland | 1.2 | Renal ca. RXF 393 | 0.0 |
| Thyroid | 5.1 | Renal ca. ACHN | 20.9 |
| Salivary gland | 7.9 | Renal ca. UO-31 | 13.6 |
| Pituitary gland | 1.0 | Renal ca. TK-10 | 0.0 |
| Brain (fetal) | 0.0 | Liver | 0.7 |
| Brain (whole) | 3.8 | Liver (fetal) | 0.6 |
| Brain (amygdala) | 0.0 | Liver ca. (hepatoblast) HepG2 | 0.0 |
| Brain (cerebellum) | 8.8 | Lung | 0.0 |
| Brain (hippocampus) | 1.8 | Lung (fetal) | 0.8 |
| Brain (substantia nigra) | 81.8 | Lung ca. (small cell) LX-1 | 0.0 |
| Brain (thalamus) | 0.0 | Lung ca. (small cell) NCI-H69 | 5.9 |
| Cerebral Cortex | 0.0 | Lung ca. (s. cell var.) SHP-77 | 0.0 |
| Spinal cord | 17.4 | Lung ca. (large cell)NCI-H460 | 0.0 |
| glio/astro U87-MG | 0.0 | Lung ca. (non-sm. cell) A549 | 2.1 |
| glio/astro U-118-MG | 0.0 | Lung ca. (non-s. cell) NCI-H23 | 0.0 |
| astrocytoma SW1783 | 0.0 | Lung ca. (non-s. cell) HOP-62 | 0.0 |
| neuro*; met SK-N-AS | 75.8 | Lung ca. (non-s. cl) NCI-H522 | 0.0 |
| astrocytoma SF-539 | 0.0 | Lung ca. (squam.) SW 900 | 2.4 |
| astrocytoma SNB-75 | 0.0 | Lung ca. (squam.) NCI-H596 | 67.4 |
| glioma SNB-19 | 0.0 | Mammary gland | 29.1 |
| glioma U251 | 0.0 | Breast ca.* (pl. ef) MCF-7 | 0.0 |
| glioma SF-295 | 0.0 | Breast ca.* (pl. ef) MDA-MB-231 | 0.0 |
| Heart (fetal) | 22.5 | Breast ca.* (pl. ef) T47D | 0.0 |
| Heart | 23.3 | Breast ca. BT-549 | 0.0 |
| Skeletal muscle (fetal) | 57.0 | Breast ca. MDA-N | 0.0 |
| Skeletal muscle | 100.0 | Ovary | 3.3 |
| Bone marrow | 9.5 | Ovarian ca. OVCAR-3 | 0.0 |
| Thymus | 6.0 | Ovarian ca. OVCAR-4 | 0.0 |
| Spleen | 0.0 | Ovarian ca. OVCAR-5 | 1.0 |
| Lymph node | 98.6 | Ovarian ca. OVCAR-8 | 0.0 |
| Colorectal | 4.3 | Ovarian ca. IGROV-1 | 0.0 |

TABLE JC-continued

Panel 1.3D

| Tissue Name | Rel. Exp. (%) Ag3253, Run 165524927 | Tissue Name | Rel. Exp. (%) Ag3253, Run 165524927 |
|---|---|---|---|
| Stomach | 4.7 | Ovarian ca.* (ascites) SK-OV-3 | 0.0 |
| Small intestine | 6.4 | Uterus | 25.0 |
| Colon ca. SW480 | 1.6 | Placenta | 11.0 |
| Colon ca.* SW620 (SW480 met) | 0.0 | Prostate | 2.5 |
| Colon ca. HT29 | 0.0 | Prostate ca.* (bone met)PC-3 | 0.0 |
| Colon ca. HCT-116 | 0.7 | Testis | 11.0 |
| Colon ca. CaCo-2 | 2.8 | Melanoma Hs688 (A).T | 0.7 |
| Colon ca. tissue (ODO3866) | 9.3 | Melanoma* (met) Hs688 (B).T | 24.0 |
| Colon ca. HCC-2998 | 0.0 | Melanoma UACC-62 | 47.6 |
| Gastric ca.* (liver met) NCI-N87 | 0.0 | Melanoma M14 | 2.0 |
| Bladder | 2.3 | Melanoma LOX IMVI | 0.0 |
| Trachea | 14.8 | Melanoma* (met) SK-MEL-5 | 17.9 |
| Kidney | 0.0 | Adipose | 58.6 |

TABLE JD

Panel 4D

| Tissue Name | Rel. Exp. (%) Ag3253, Run 164391363 | Tissue Name | Rel. Exp. (%) Ag3253, Run 164391363 |
|---|---|---|---|
| Secondary Th1 act | 0.0 | HUVEC IL-1beta | 0.2 |
| Secondary Th2 act | 0.0 | HUVEC IFN gamma | 2.2 |
| Secondary Tr1 act | 0.0 | HUVEC TNF alpha + IFN gamma | 0.6 |
| Secondary Th1 rest | 0.0 | HUVEC TNF alpha + IL4 | 1.7 |
| Secondary Th2 rest | 0.0 | HUVEC IL-11 | 2.6 |
| Secondary Tr1 rest | 0.0 | Lung Microvascular EC none | 0.8 |
| Primary Th1 act | 0.0 | Lung Microvascular EC TNF alpha + IL-1beta | 0.1 |
| Primary Th2 act | 0.0 | Microvascular Dermal EC none | 0.9 |
| Primary Tr1 act | 0.0 | Microsvasular Dermal EC TNF alpha + IL-1beta | 0.5 |
| Primary Th1 rest | 0.0 | Bronchial epithelium TNF alpha + IL1beta | 0.0 |
| Primary Th2 rest | 0.0 | Small airway epithelium none | 0.0 |
| Primary Tr1 rest | 0.0 | Small airway epithelium TNF alpha + IL-1beta | 0.0 |
| CD45RA CD4 lymphocyte act | 3.0 | Coronery artery SMC rest | 36.1 |
| CD45RO CD4 lymphocyte act | 0.0 | Coronery artery SMC TNF alpha + IL-1beta | 17.6 |
| CD8 lymphocyte act | 0.0 | Astrocytes rest | 0.0 |
| Secondary CD8 lymphocyte rest | 0.0 | Astrocytes TNF alpha + IL-1beta | 0.1 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.2 | CCD1106 (Keratinocytes) none | 0.0 |
| LAK cells rest | 0.0 | CCD1106 (Keratinocytes) TNF alpha + IL-1beta | 0.0 |
| LAK cells IL-2 | 0.0 | Liver cirrhosis | 0.2 |
| LAK cells IL-2 + IL-12 | 0.0 | Lupus kidney | 0.3 |
| LAK cells IL-2 + IFN gamma | 0.0 | NCI-H292 none | 0.0 |
| LAK cells IL-2 + IL-18 | 0.0 | NCI-H292 IL-4 | 0.0 |
| LAK cells PMA/ionomycin | 0.0 | NCI-H292 IL-9 | 0.0 |
| NK Cells IL-2 rest | 0.0 | NCI-H292 IL-13 | 0.0 |
| Two Way MLR 3 day | 0.0 | NCI-H292 IFN gamma | 0.0 |
| Two Way MLR 5 day | 0.0 | HPAEC none | 0.0 |
| Two Way MLR 7 day | 0.0 | HPAEC TNF alpha + IL-1beta | 0.0 |

TABLE JD-continued

Panel 4D

| Tissue Name | Rel. Exp. (%) Ag3253, Run 164391363 | Tissue Name | Rel. Exp. (%) Ag3253, Run 164391363 |
|---|---|---|---|
| PBMC rest | 0.0 | Lung fibroblast none | 0.5 |
| PBMC PWM | 0.0 | Lung fibroblast TNF alpha + IL-1beta | 0.5 |
| PBMC PHA-L | 0.0 | Lung fibroblast IL-4 | 1.0 |
| Ramos (B cell) none | 0.0 | Lung fibroblast IL-9 | 0.3 |
| Ramos (B cell) ionomycin | 0.0 | Lung fibroblast IL-13 | 0.8 |
| B lymphocytes PWM | 0.4 | Lung fibroblast IFN gamma | 2.2 |
| B lymphocytes CD40L and IL-4 | 0.0 | Dermal fibroblast CCD1070 rest | 15.3 |
| EOL-1 dbcAMP | 40.1 | Dermal fibroblast CCD1070 TNF alpha | 8.5 |
| EOL-1 dbcAMP PMA/ionomycin | 7.6 | Dermal fibroblast CCD1070 IL-1beta | 6.4 |
| Dendritic cells none | 0.0 | Dermal fibroblast IFN gamma | 100.0 |
| Dendritic cells LPS | 0.0 | Dermal fibroblast IL-4 | 36.1 |
| Dendritic cells anti-CD40 | 0.0 | IBD Colitis 2 | 0.2 |
| Monocytes rest | 0.0 | IBD Crohn's | 0.3 |
| Monocytes LPS | 0.1 | Colon | 2.2 |
| Macrophages rest | 0.0 | Lung | 3.5 |
| Macrophages LPS | 0.0 | Thymus | 0.9 |
| HUVEC none | 3.3 | Kidney | 3.3 |
| HUVEC starved | 8.8 | | |

CNS_neurodegeneration_v1.0 Summary: Ag3253 Expression of the CG57480-01 gene is low/undetectable in all samples on this panel (CTs>35). (Data not shown.)

Panel 1.3D Summary: Ag3253 Highest expression of the CG57480-01 gene is seen in skeletal muscle (CT=29). Significant expression is also seen in fetal skeletal muscle, adipose, fetal and adult heart, pancreas, and adrenal gland. This widespread expression among tissues with metabolic function suggests that this gene product may be important for the pathogenesis and/or treatment of disease involving these tissues, including obesity and diabetes.

Significant expression is also seen in cell lines derived from melanoma, lung cancer, renal cancer and brain cancer. Thus, expression of this gene could be used as a marker for the presence of these cancers.

Low but significant expression of this putative neuronal transcription factor is also seen in the substantia nigra, indicating a specific role for this gene product in this brain region. The substantia nigra is specifically vulnerable to neurodegeneration in Parkinson's disease. Neurodegeneration is known to involve gene regulation that is under the control of transcription factors. Therefore, drugs or treatments that modulate the activity of this gene product are potentially useful for the treatment of Parkinson's disease.

Panel 4D Summary: Ag3253 Highest expression of the CG57480-01 gene is seen in dermal fibroblasts treated with IFN-gamma (CT=28.6). Significant expression is also seen in a cluster of treated dermal fibroblast samples. This expression profile suggests that this gene product may be involved in skin disorders, including psoriasis.

The transcript is also expressed in differentiated EOL-1 cells, and is downregulated after activation suggesting that it may be important in eosinophil differentiation. Regulating the transcript with antisense strategies or the protein product with small molecule therapeutics may be usefue in the treatment of hematopoietic disorders involving eosinphils, parasitic infections and asthma.

K. NOV10: High-Affinity CAMP-Specific and IBMX-Insensitive

Expression of gene CG57389-01 was assessed using the primer-probe set Ag3223, described in Table KA. Results of the RTQ-PCR runs are shown in Table KB.

TABLE KA

Probe Name Ag3223

| Primers | Sequences | | Length | Start Position |
|---|---|---|---|---|
| Forward | 5'-attcttacactgctccgagtca-3' | (SEQ ID NO:329) | 22 | 1723 |
| Probe | TET-5'-tcatggttacaaattatcgaagccaa-3'-TAMRA | (SEQ ID NO:330) | 26 | 1754 |
| Reverse | 5'-ggtagggattggaggaatgata-3' | (SEQ ID NO:331) | 22 | 1781 |

TABLE KB

Panel 1.3D

| Tissue Name | Rel. Exp. (%) Ag3223, Run 165527086 | Tissue Name | Rel. Exp. (%) Ag3223, Run 165527086 |
|---|---|---|---|
| Liver adenocarcinoma | 44.4 | Kidney (fetal) | 21.8 |
| Pancreas | 14.1 | Renal ca. 786-0 | 13.2 |
| Pancreatic ca. CAPAN 2 | 33.7 | Renal ca. A498 | 23.7 |
| Adrenal gland | 42.9 | Renal ca. RXF 393 | 35.8 |
| Thyroid | 11.0 | Renal ca. ACHN | 6.6 |
| Salivary gland | 8.0 | Renal ca. UO-31 | 8.8 |
| Pituitary gland | 18.2 | Renal ca. TK-10 | 6.7 |
| Brain (fetal) | 7.9 | Liver | 14.0 |
| Brain (whole) | 100.0 | Liver (fetal) | 13.8 |
| Brain (amygdala) | 32.5 | Liver ca. (hepatoblast) HepG2 | 44.8 |
| Brain (cerebellum) | 21.2 | Lung | 13.8 |
| Brain (hippocampus) | 55.9 | Lung (fetal) | 9.8 |
| Brain (substantia nigra) | 80.1 | Lung ca. (small cell) LX-1 | 26.4 |
| Brain (thalamus) | 98.6 | Lung ca. (small cell) NCI-H69 | 4.0 |
| Cerebral Cortex | 67.4 | Lung ca. (s. cell var.) SHP-77 | 17.7 |
| Spinal cord | 58.6 | Lung ca. (large cell)NCI-H460 | 64.2 |
| glio/astro U87-MG | 32.5 | Lung ca. (non-sm. cell) A549 | 47.6 |
| glio/astro U-118-MG | 63.3 | Lung ca. (non-s. cell) NCI-H23 | 31.2 |
| astrocytoma SW1783 | 18.6 | Lung ca. (non-s. cell) HOP-62 | 15.5 |
| neuro*; met SK-N-AS | 13.1 | Lung ca. (non-s. cl) NCI-H522 | 6.7 |
| astrocytoma SF-539 | 34.4 | Lung ca. (squam.) SW 900 | 11.1 |
| astrocytoma SNB-75 | 19.3 | Lung ca. (squam.) NCI-H596 | 7.7 |
| glioma SNB-19 | 32.3 | Mammary gland | 18.2 |
| glioma U251 | 64.2 | Breast ca.* (pl. ef) MCF-7 | 30.4 |
| glioma SF-295 | 9.3 | Breast ca.* (pl. ef) MDA-MB-231 | 37.1 |
| Heart (fetal) | 26.6 | Breast ca.* (pl. ef) T47D | 7.4 |
| Heart | 10.8 | Breast ca. BT-549 | 28.5 |
| Skeletal muscle (fetal) | 16.2 | Breast ca. MDA-N | 10.8 |
| Skeletal muscle | 18.3 | Ovary | 18.9 |
| Bone marrow | 4.2 | Ovarian ca. OVCAR-3 | 15.7 |
| Thymus | 7.3 | Ovarian ca. OVCAR-4 | 6.8 |
| Spleen | 14.9 | Ovarian ca. OVCAR-5 | 33.7 |
| Lymph node | 35.1 | Ovarian ca. OVCAR-8 | 3.6 |
| Colorectal | 43.5 | Ovarian ca. IGROV-1 | 7.7 |
| Stomach | 19.5 | Ovarian ca.* (ascites) SK-OV-3 | 18.2 |
| Small intestine | 49.0 | Uterus | 26.8 |
| Colon ca. SW480 | 29.7 | Placenta | 7.5 |
| Colon ca.* SW620 (SW480 met) | 31.6 | Prostate | 6.5 |
| Colon ca. HT29 | 8.1 | Prostate ca.* (bone met) PC-3 | 19.2 |
| Colon ca. HCT-116 | 22.8 | Testis | 25.3 |
| Colon ca. CaCo-2 | 10.1 | Melanoma Hs688 (A).T | 4.8 |
| Colon ca. tissue (ODO3866) | 20.2 | Melanoma* (met) Hs688 (B).T | 9.0 |
| Colon ca. HCC-2998 | 13.1 | Melanoma UACC-62 | 12.4 |
| Gastric ca.* (liver met) NCI-N87 | 74.7 | Melanoma M14 | 74.2 |
| Bladder | 19.9 | Melanoma LOX IMVI | 3.3 |
| Trachea | 7.3 | Melanoma* (met) SK-MEL-5 | 12.3 |
| Kidney | 25.2 | Adipose | 17.1 |

Panel 1.3D Summary: Ag3223 The expression of the CG57389-01 gene, a nucleotide phosphodiesterase homolog, appears to be highest in a sample derived from a normal brain tissue. In addition, this gene is expressed in all CNS regions examined. Nucleotide phosphodiesterases are involved in a wide range of processes in the CNS. Therefore, this gene may be useful as a drug target in neurodegenerative diseases such as Alzheimer's, Parkinson's, Huntington's, stroke, head or spinal cord trauma, or neuropsychiatric disease.

In addition, there appears to be substantial expression in other samples derived from brain cancer cell lines, lung cancer cell lines and colon cancer cell lines. Thus, the expression of this gene could be used to distinguish normal brain tissue from other samples in the panel. Moreover, therapeutic modulation of this gene, through the use of small molecule drugs, protein therapeutics, or antibodies could be of benefit in the treatment of brain, lung or colon cancer.

Among metabolic tissues, this gene is expressed at low levels in pancreas, adrenal, thyroid, pituitary, heart, liver, adipose and skeletal muscle. Regulation of cyclic nucleotide levels is believed to be important for insulin secretion, which is dysregulated or impaired in diabetes. Thus, this gene product may be a small molecule target for the treatment of metabolic and endocrine disease, specifically Types 1 and 2 diabetes and obesity.

L. NOV12a, NOV12b, NOV12c and NOV13: TWIK-3 and TASK-4

Expression of gene CG57220-01 and variants CG57220-02, CG57220-03 and CG57220-04 was assessed using the primer-probe sets Ag4293 and Ag937, described in Tables LA and LB. Results of the RTQ-PCR runs are shown in Tables LC, LD and LE. Please note that only variants CG57220-02 and CG57220-04 match the probe and primer set Ag937.

TABLE LA

Probe Name Ag4293

| Primers | Sequences | | Length | Start Position |
|---|---|---|---|---|
| Forward | 5'-gaggtacccactgtggtacaag-3' | (SEQ ID NO:332) | 22 | 733 |
| Probe | TET-5'-acatggtgtccctgtggatcctctt-3'-TAMRA | (SEQ ID NO:333) | 26 | 756 |
| Reverse | 5'-gggagaggatgagtttgatgat-3' | (SEQ ID NO:334) | 22 | 803 |

TABLE LB

Probe Name Ag937

| Primers | Sequences | | Length | Start Position |
|---|---|---|---|---|
| Forward | 5'-ggctccttcttcttttctgtgt-3' | (SEQ ID NO:335) | 22 | 341 |
| Probe | TET-5'-atcaccaccattggctatggcaacct-3'-TAMRA | (SEQ ID NO:336) | 26 | 368 |
| Reverse | 5'-ggcaaagaagatgcagaagag-3' | (SEQ ID NO:337) | 21 | 419 |

TABLE LC

CNS_neurodegeneration_v1.0

| Tissue Name | Rel. Exp. (%) Ag4293, Run 224073647 | Tissue Name | Rel. Exp. (%) Ag4293, Run 224073647 |
|---|---|---|---|
| AD 1 Hippo | 19.5 | Control (Path) 3 Temporal Ctx | 0.0 |
| AD 2 Hippo | 52.9 | Control (Path) 4 Temporal Ctx | 24.0 |
| AD 3 Hippo | 0.0 | AD 1 Occipital Ctx | 18.8 |
| AD 4 Hippo | 10.6 | AD 2 Occipital Ctx (Missing) | 0.0 |
| AD 5 Hippo | 26.4 | AD 3 Occipital Ctx | 0.0 |
| AD 6 Hippo | 82.4 | AD 4 Occipital Ctx | 11.4 |
| Control 2 Hippo | 50.7 | AD 5 Occipital Ctx | 33.4 |
| Control 4 Hippo | 49.0 | AD 6 Occipital Ctx | 23.3 |
| Control (Path) 3 Hippo | 11.7 | Control 1 Occipital Ctx | 8.5 |
| AD 1 Temporal Ctx | 20.9 | Control 2 Occipital Ctx | 52.5 |
| AD 2 Temporal Ctx | 47.6 | Control 3 Occipital Ctx | 0.0 |
| AD 3 Temporal Ctx | 0.0 | Control 4 Occipital Ctx | 0.0 |
| AD 4 Temporal Ctx | 3.2 | Control (Path) 1 Occipital Ctx | 27.9 |
| AD 5 Inf Temporal Ctx | 49.3 | Control (Path) 2 Occipital Ctx | 42.3 |
| AD 5 Sup Temporal Ctx | 27.5 | Control (Path) 3 Occipital Ctx | 17.9 |
| AD 6 Inf Temporal Ctx | 12.4 | Control (Path) 4 Occipital Ctx | 35.6 |
| AD 6 Sup Temporal Ctx | 13.6 | Control 1 Parietal Ctx | 10.0 |
| Control 1 Temporal Ctx | 12.7 | Control 2 Parietal Ctx | 0.0 |
| Control 2 Temporal Ctx | 3.1 | Control 3 Parietal Ctx | 0.0 |

TABLE LC-continued

CNS_neurodegeneration_v1.0

| Tissue Name | Rel. Exp. (%) Ag4293, Run 224073647 | Tissue Name | Rel. Exp. (%) Ag4293, Run 224073647 |
|---|---|---|---|
| Control 3 Temporal Ctx | 0.0 | Control (Path) 1 Parietal Ctx | 24.7 |
| Control 3 Temporal Ctx | 0.0 | Control (Path) 2 Parietal Ctx | 53.2 |
| Control (Path) 1 Temporal Ctx | 100.0 | Control (Path) 3 Parietal Ctx | 10.8 |
| Control (Path) 2 Temporal Ctx | 52.5 | Control (Path) 4 Parietal Ctx | 56.6 |

TABLE LD

General_screening_panel_v1.4

| Tissue Name | Rel. Exp. (%) Ag4293, Run 222182574 | Tissue Name | Rel. Exp. (%) Ag4293, Run 222182574 |
|---|---|---|---|
| Adipose | 3.0 | Renal ca. TK-10 | 0.0 |
| Melanoma* Hs688 (A).T | 0.0 | Bladder | 5.9 |
| Melanoma* Hs688 (B).T | 0.0 | Gastric ca. (liver met.) NCI-N87 | 0.0 |
| Melanoma* M14 | 0.0 | Gastric ca. KATO III | 0.0 |
| Melanoma* LOXIMVI | 0.0 | Colon ca. SW-948 | 0.0 |
| Melanoma* SK-MEL-5 | 0.0 | Colon ca. SW480 | 0.0 |
| Squamous cell carcinoma SCC-4 | 0.0 | Colon ca.* (SW480 met) SW620 | 0.0 |
| Testis Pool | 3.3 | Colon ca. HT29 | 0.0 |
| Prostate ca.* (bone met) PC-3 | 0.0 | Colon ca. HCT-116 | 0.0 |
| Prostate Pool | 1.5 | Colon ca. CaCo-2 | 0.0 |
| Placenta | 7.5 | Colon cancer tissue | 2.1 |
| Uterus Pool | 2.5 | Colon ca. SW1116 | 0.0 |
| Ovarian ca. OVCAR-3 | 0.2 | Colon ca. Colo-205 | 0.0 |
| Ovarian ca. SK-OV-3 | 0.1 | Colon ca. SW-48 | 0.0 |
| Ovarian ca. OVCAR-4 | 0.2 | Colon Pool | 7.6 |
| Ovarian ca. OVCAR-5 | 0.5 | Small Intestine Pool | 3.1 |
| Ovarian ca. IGROV-1 | 0.0 | Stomach Pool | 4.2 |
| Ovarian ca. OVCAR-8 | 0.0 | Bone Marrow Pool | 1.2 |
| Ovary | 0.5 | Fetal Heart | 3.2 |
| Breast ca. MCF-7 | 0.2 | Heart Pool | 5.8 |
| Breast ca. MDA-MB-231 | 0.0 | Lymph Node Pool | 4.0 |
| Breast ca. BT 549 | 0.0 | Fetal Skeletal Muscle | 4.6 |
| Breast ca. T47D | 0.6 | Skeletal Muscle Pool | 0.0 |
| Breast ca. MDA-N | 0.4 | Spleen Pool | 0.7 |
| Breast Pool | 3.1 | Thymus Pool | 7.4 |
| Trachea | 1.2 | CNS cancer (glio/astro) U87-MG | 0.0 |
| Lung | 2.0 | CNS cancer (glio/astro) U-118-MG | 0.0 |
| Fetal Lung | 100.0 | CNS cancer (neuro; met) SK-N-AS | 0.0 |
| Lung ca. NCI-N417 | 0.0 | CNS cancer (astro) SF-539 | 0.0 |
| Lung ca. LX-1 | 0.0 | CNS cancer (astro) SNB-75 | 0.0 |
| Lung ca. NCI-H146 | 71.2 | CNS cancer (glio) SNB-19 | 0.2 |
| Lung ca. SHP-77 | 0.0 | CNS cancer (glio) SF-295 | 0.0 |
| Lung ca. A549 | 0.0 | Brain (Amygdala) Pool | 1.5 |
| Lung ca. NCI-H526 | 0.0 | Brain (cerebellum) | 1.7 |
| Lung ca. NCI-H23 | 0.2 | Brain (fetal) | 0.2 |
| Lung ca. NCI-H460 | 0.0 | Brain (Hippocampus) Pool | 1.6 |
| Lung ca. HOP-62 | 0.0 | Cerebral Cortex Pool | 1.1 |
| Lung ca. NCI-H522 | 0.0 | Brain (Substantia nigra) Pool | 0.8 |
| Liver | 1.0 | Brain (Thalamus) Pool | 0.5 |
| Fetal Liver | 1.3 | Brain (whole) | 1.4 |
| Liver ca. HepG2 | 0.0 | Spinal Cord Pool | 2.0 |
| Kidney Pool | 10.2 | Adrenal Gland | 0.6 |
| Fetal Kidney | 1.9 | Pituitary gland Pool | 1.2 |
| Renal ca. 786-0 | 0.0 | Salivary Gland | 0.4 |
| Renal ca. A498 | 0.0 | Thyroid (female) | 6.0 |
| Renal ca. ACHN | 0.0 | Pancreatic ca. CAPAN2 | 0.0 |
| Renal ca. UO-31 | 0.0 | Pancreas Pool | 3.1 |

TABLE LE

Panel 4.1D

| Tissue Name | Rel. Exp. (%) Ag4293, Run 181981932 | Tissue Name | Rel. Exp. (%) Ag4293, Run 181981932 |
|---|---|---|---|
| Secondary Th1 act | 0.0 | HUVEC IL-1beta | 0.0 |
| Secondary Th2 act | 0.0 | HUVEC IFN gamma | 0.0 |
| Secondary Tr1 act | 0.0 | HUVEC TNF alpha + IFN gamma | 0.0 |
| Secondary Th1 rest | 0.0 | HUVEC TNF alpha + IL4 | 0.0 |
| Secondary Th2 rest | 2.8 | HUVEC IL-11 | 0.0 |
| Secondary Tr1 rest | 0.0 | Lung Microvascular EC none | 0.0 |
| Primary Th1 act | 0.0 | Lung Microvascular EC TNF alpha + IL-1beta | 0.0 |
| Primary Th2 act | 0.0 | Microvascular Dermal EC none | 0.0 |
| Primary Tr1 act | 0.0 | Microsvascular Dermal EC TNF alpha + IL-beta | 0.0 |
| Primary Th1 rest | 0.0 | Bronchial epithelium TNF alpha + IL1beta | 0.0 |
| Primary Th2 rest | 1.8 | Small airway epithelium none | 0.0 |
| Primary Tr1 rest | 0.0 | Small airway epithelium TNF alpha + IL-1beta | 0.0 |
| CD45RA CD4 lymphocyte act | 0.0 | Coronery artery SMC rest | 0.0 |
| CD45RO CD4 lymphocyte act | 0.0 | Coronery artery SMC TNF alpha + IL-1beta | 0.0 |
| CD8 lymphocyte act | 0.0 | Astrocytes rest | 0.0 |
| Secondary CD8 lymphocyte rest | 0.0 | Astrocytes TNF alpha + IL-1beta | 0.0 |
| Secondary CD8 lymphocyte act | 0.0 | KU-812 (Basophil) rest | 1.0 |
| CD4 lymphocyte none | 2.0 | KU-812 (Basophil) PMA/ionomycin | 0.0 |
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNF alpha + IL-1beta | 0.0 |
| LAK cells IL-2 | 0.0 | Liver cirrhosis | 0.9 |
| LAK cells IL-2 + IL-12 | 0.0 | NCI-H292 none | 6.7 |
| LAK cells IL-2 + IFN gamma | 0.0 | NCI-H292 IL-4 | 20.2 |
| LAK cells IL-2 + IL-18 | 0.0 | NCI-H292 IL-9 | 10.7 |
| LAK cells PMA/ionomycin | 0.0 | NCI-H292 IL-13 | 29.1 |
| NK Cells IL-2 rest | 4.9 | NCI-H292 IFN gamma | 12.9 |
| Two Way MLR 3 day | 0.8 | HPAEC none | 0.0 |
| Two Way MLR 5 day | 0.0 | HPAEC TNF alpha + IL-1beta | 0.0 |
| Two Way MLR 7 day | 0.0 | Lung fibroblast none | 0.0 |
| PBMC rest | 2.1 | Lung fibroblast TNF alpha + IL-1beta | 0.0 |
| PBMC PWM | 0.0 | Lung fibroblast IL-4 | 0.0 |
| PBMC PHA-L | 0.0 | Lung fibroblast IL-9 | 0.0 |
| Ramos (B cell) none | 0.0 | Lung fibroblast IL-13 | 0.0 |
| Ramos (B cell) ionomycin | 0.0 | Lung fibroblast IFN gamma | 0.0 |
| B lymphocytes PWM | 0.0 | Dermal fibroblast CCD1070 rest | 0.0 |
| B lymphocytes CD40L and IL-4 | 0.0 | Dermal fibroblast CCD1070 TNF alpha | 0.7 |
| EOL-1 dbcAMP | 8.1 | Dermal fibroblast CCD1070 IL-1beta | 1.0 |
| EOL-1 dbcAMP PMA/ionomycin | 0.0 | Dermal fibroblast IFN gamma | 0.0 |
| Dendritic cells none | 0.0 | Dermal fibroblast IL-4 | 0.0 |
| Dendritic cells LPS | 0.0 | Dermal Fibroblasts rest | 0.0 |
| Dendritic cells anti-CD40 | 0.0 | Neutrophils TNFa + LPS | 0.0 |
| Monocytes rest | 0.0 | Neutrophils rest | 4.0 |
| Monocytes LPS | 0.0 | Colon | 4.8 |
| Macrophages rest | 0.0 | Lung | 100.0 |
| Macrophages LPS | 0.0 | Thymus | 24.0 |
| HUVEC none | 0.0 | Kidney | 77.9 |
| HUVEC starved | 0.0 | | |

CNS_neurodegeneration_v1.0 Summary: Ag4293 No change is detected in the expression of the CG57220-01 gene in the postmortem Alzheimer's diseased brain when compared to controls. However this panel confirms the expression of this gene in the CNS in an independent group of patients. Thus, therapeutic modulation of the expression or function of this gene product may be useful in the treatment of neurologic disease. A second experiment with the probe primer set Ag937 showed low/undetectable levels of expression in all the samples on this panel (CTs>35). (Data not shown.)

General_screening_panel_v1.4 Summary: Ag4293 Highest expression of the CG57220-01 gene is seen in the fetal lung (CT=29) and a lung cancer cell line. In addition, this gene appears to be expressed at much higher levels in the fetal tissue than in the adult (CT=34.7). Higher levels of expression are also seen in fetal skeletal muscle C(T=33) than in adult skeletal muscle. Thus, expression of this gene could be used to differentiate between the two lung derived samples and other samples on this panel and as a marker to detect the presence of lung cancer. In addition, expression of this gene could be used to differentiate between the two sources of lung and skeletal muscle tissue. Furthermore, therapeutic modulation of the expression or function of this gene may be effective in the treatment of lung cancer.

Among tissues with metabolic function, this gene is expressed at low but significant levels in adipose, thyroid, pancreas, and adult and fetal heart. This widespread expression among these tissues suggests that this gene product may be useful for the diagnosis and/or treatment of metabolic disease, including obesity and diabetes.

Panel 4.1D Summary: Ag4293 Highest expression of the CG57220-01 gene is seen in the lung (CT=31). Significant levels of expression are also seen in a cluster of treated and untreated samples derived from the muco-epidermoid cell line NCI-H292, often used as a model for airway epithelium. The prominent expression in lung derived samples, both in this panel and General_screening_panel v1.4 suggests that this gene may be involved in normal lung homeostasis as well as pathological and inflammatory lung conditions. Therefore, therapeutic modulation of this gene product may resuce symptoms associated with chronic obstructive pulmonary disease, asthma, allergy and emphysema.

Panel CNS_1 Summary: Ag937 Expression of the CG57220-02 gene is low/undetectable in all samples on this panel (CTs>35). (Data not shown.)

M. NOV15: Cytokeratin

Expression of gene CG57454-01 was assessed using the primer-probe set Ag3244, described in Table MA. Results of the RTQ-PCR runs are shown in Tables MB, MC, MD and ME.

TABLE MA

Probe Name Ag3244

| Primers | Sequences | | Length | Start Position |
|---|---|---|---|---|
| Forward | 5'-gctatgcaggtggtctgagtt-3' | (SEQ ID NO:338) | 21 | 1267 |
| Probe | TET-5'-ctcacaagccctggcctcagctat-3'-TAMRA | (SEQ ID NO:339) | 24 | 1302 |
| Reverse | 5'-agagccaaagctggagctta-3' | (SEQ ID NO:340) | 20 | 1330 |

TABLE MB

CNS_neurodegeneration_v1.0

| Tissue Name | Rel. Exp. (%) Ag3244, Run 206533582 | Tissue Name | Rel. Exp. (%) Ag3244, Run 206533582 |
|---|---|---|---|
| AD 1 Hippo | 18.7 | Control (Path) 3 Temporal Ctx | 0.0 |
| AD 2 Hippo | 23.0 | Control (Path) 4 Temporal Ctx | 19.6 |
| AD 3 Hippo | 2.3 | AD 1 Occipital Ctx | 9.6 |
| AD 4 Hippo | 9.9 | AD 2 Occipital Ctx (Missing) | 0.0 |
| AD 5 hippo | 71.7 | AD 3 Occipital Ctx | 6.0 |
| AD 6 Hippo | 42.0 | AD 4 Occipital Ctx | 31.6 |
| Control 2 Hippo | 29.1 | AD 5 Occipital Ctx | 4.2 |
| Control 4 Hippo | 22.8 | AD 6 Occipital Ctx | 34.4 |
| Control (Path) 3 Hippo | 0.4 | Control 1 Occipital Ctx | 2.7 |
| AD 1 Temporal Ctx | 69.3 | Control 2 Occipital Ctx | 30.6 |
| AD 2 Temporal Ctx | 23.0 | Control 3 Occipital Ctx | 33.0 |
| AD 3 Temporal Ctx | 4.4 | Control 4 Occipital Ctx | 12.9 |
| AD 4 Temporal Ctx | 33.4 | Control (Path) 1 Occipital Ctx | 88.3 |
| AD 5 InfTemporal Ctx | 100.0 | Control (Path) 2 Occipital Ctx | 9.0 |
| AD 5 SupTemporal Ctx | 23.8 | Control (Path) 3 Occipital Ctx | 0.0 |
| AD 6 InfTemporal Ctx | 57.0 | Control (Path) 4 Occipital Ctx | 11.7 |
| AD 6 Sup Temporal Ctx | 42.0 | Control 1 Parietal Ctx | 24.5 |
| Control 1 Temporal Ctx | 4.4 | Control 2 Parietal Ctx | 59.5 |
| Control 2 Temporal Ctx | 28.7 | Control 3 Parietal Ctx | 4.5 |
| Control 3 Temporal Ctx | 15.5 | Control (Path) 1 Parietal Ctx | 59.0 |
| Control 4 Temporal Ctx | 5.3 | Control (Path) 2 Parietal Ctx | 23.2 |
| Control (Path) 1 Temporal Ctx | 28.7 | Control (Path) 3 Parietal Ctx | 0.0 |
| Control (Path) 2 Temporal Ctx | 32.5 | Control (Path) 4 Parietal Ctx | 37.6 |

TABLE MC

Panel 1.3D

| Tissue Name | Rel. Exp. (%) Ag3244, Run 165524419 | Tissue Name | Rel. Exp. (%) Ag3244, Run 165524419 |
|---|---|---|---|
| Liver adenocarcinoma | 91.4 | Kidney (fetal) | 10.6 |
| Pancreas | 3.4 | Renal ca. 786-0 | 8.3 |
| Pancreatic ca. CAPAN 2 | 23.7 | Renal ca. A498 | 29.1 |
| Adrenal gland | 0.0 | Renal ca. RXF 393 | 1.7 |
| Thyroid | 13.4 | Renal ca. ACHN | 10.9 |
| Salivary gland | 4.1 | Renal ca. UO-31 | 42.3 |
| Pituitary gland | 57.0 | Renal ca. TK-10 | 9.4 |
| Brain (fetal) | 0.0 | Liver | 5.4 |
| Brain (whole) | 48.3 | Liver (fetal) | 12.5 |
| Brain (amygdala) | 82.9 | Liver ca. (hepatoblast) HepG2 | 18.3 |
| Brain (cerebellum) | 36.3 | Lung | 9.4 |
| Brain (hippocampus) | 88.3 | Lung (fetal) | 1.7 |
| Brain (substantia nigra) | 63.3 | Lung ca. (small cell) LX-1 | 52.5 |
| Brain (thalamus) | 41.8 | Lung ca. (small cell) NCI-H69 | 1.7 |
| Cerebral Cortex | 7.1 | Lung ca. (s. cell var.) SHP-77 | 19.3 |
| Spinal cord | 60.7 | Lung ca. (large cell) NCI-H460 | 9.5 |
| glio/astro U87-MG | 0.0 | Lung ca. (non-sm. cell) A549 | 20.6 |
| glio/astro U-118-MG | 0.0 | Lung ca. (non-s. cell) NCI-H23 | 0.0 |
| astrocytoma SW1783 | 0.0 | Lung ca. (non-s. cell) HOP-62 | 10.2 |
| neuro*; met SK-N-AS | 7.4 | Lung ca. (non-s. cl) NCI-H522 | 0.0 |
| astrocytoma SF-539 | 0.0 | Lung ca. (squam.) SW 900 | 7.4 |
| astrocytoma SNB-75 | 17.1 | Lung ca. (squam.) NCI-H596 | 10.6 |
| glioma SNB-19 | 2.4 | Mammary gland | 7.0 |
| glioma U251 | 2.6 | Breast ca.* (pl. ef) MCF-7 | 80.7 |
| glioma SF-295 | 0.0 | Breast ca.* (pl. ef) MDA-MB-231 | 34.9 |
| Heart (fetal) | 3.1 | Breast ca.* (pl. ef) T47D | 21.8 |
| Heart | 2.7 | Breast ca. BT-549 | 0.0 |
| Skeletal muscle (fetal) | 0.0 | Breast ca. MDA-N | 0.0 |
| Skeletal muscle | 0.0 | Ovary | 6.0 |
| Bone marrow | 0.0 | Ovarian ca. OVCAR-3 | 37.6 |
| Thymus | 0.0 | Ovarian ca. OVCAR-4 | 22.5 |
| Spleen | 0.0 | Ovarian ca. OVCAR-5 | 98.6 |
| Lymph node | 0.0 | Ovarian ca. OVCAR-8 | 5.2 |
| Colorectal | 9.3 | Ovarian ca. IGROV-1 | 6.0 |
| Stomach | 15.1 | Ovarian ca.* (ascites) SK-OV-3 | 5.2 |
| Small intestine | 39.8 | Uterus | 0.0 |
| Colon ca. SW480 | 70.7 | Placenta | 52.1 |
| Colon ca.* SW620 (SW480 met) | 9.2 | Prostate | 19.1 |
| Colon ca. HT29 | 27.2 | Prostate ca.* (bone met) PC-3 | 0.0 |
| Colon ca. HCT-116 | 23.5 | Testis | 20.4 |
| Colon ca. CaCo-2 | 22.7 | Melanoma Hs688 (A).T | 0.0 |
| Colon ca. tissue (ODO3866) | 85.9 | Melanoma* (met) Hs688 (B).T | 0.0 |
| Colon ca. HCC-2998 | 17.8 | Melanoma UACC-62 | 0.0 |
| Gastric ca.* (liver met) NCI-N87 | 100.0 | Melanoma M14 | 0.0 |
| Bladder | 9.5 | Melanoma LOX IMVI | 0.0 |
| Trachea | 19.9 | Melanoma* (met) SK-MEL-5 | 0.0 |
| Kidney | 8.1 | Adipose | 3.8 |

TABLE MD

Panel 2.2

| Tissue Name | Rel. Exp. (%) Ag3244, Run 174441100 | Tissue Name | Rel. Exp. (%) Ag3244, Run 174441100 |
|---|---|---|---|
| Normal Colon | 31.0 | Kidney Margin (OD04348) | 12.8 |
| Colon cancer (OD06064) | 59.0 | Kidney malignant cancer (OD06204B) | 25.0 |
| Colon Margin (OD06064) | 8.0 | Kidney normal adjacent tissue (OD06204E) | 6.5 |
| Colon cancer (OD06159) | 100.0 | Kidney Cancer (OD04450-01) | 39.5 |
| Colon Margin (OD06159) | 43.2 | Kidney Margin (OD04450-03) | 2.2 |
| Colon cancer (OD06297-04) | 16.0 | Kidney Cancer 8120613 | 6.3 |
| Colon Margin (OD06297-05) | 38.7 | Kidney Margin 8120614 | 11.3 |
| CC Gr. 2 ascend colon (ODO3921) | 23.5 | Kidney Cancer 9010320 | 2.0 |
| CC Margin (ODO3921) | 20.7 | Kidney Margin 9010321 | 20.9 |
| Colon cancer metastasis (OD06104) | 12.9 | Kidney Cancer 8120607 | 17.1 |
| Lung Margin (OD06104) | 30.1 | Kidney Margin 8120608 | 4.4 |
| Colon mets to lung (OD04451-01) | 45.4 | Normal Uterus | 0.0 |
| Lung Margin (OD04451-02) | 3.3 | Uterine Cancer 064011 | 0.0 |
| Normal Prostate | 9.4 | Normal Thyroid | 8.1 |
| Prostate Cancer (OD04410) | 3.8 | Thyroid Cancer 064010 | 16.4 |
| Prostate Margin (OD04410) | 1.5 | Thyroid Cancer A302152 | 9.3 |
| Normal Ovary | 2.6 | Thyroid Margin A302153 | 4.5 |
| Ovarian cancer (OD06283-03) | 7.5 | Normal Breast | 58.6 |
| Ovarian Margin (OD06283-07) | 1.3 | Breast Cancer (OD04566) | 16.0 |
| Ovarian Cancer 064008 | 3.0 | Breast Cancer 1024 | 17.4 |
| Ovarian cancer (OD06145) | 8.0 | Breast Cancer (OD04590-01) | 59.0 |
| Ovarian Margin (OD06145) | 3.2 | Breast Cancer Mets (OD04590-03) | 24.7 |
| Ovarian cancer (OD06455-03) | 10.4 | Breast Cancer Metastasis (OD04655-05) | 21.6 |
| Ovarian Margin (OD06455-07) | 0.0 | Breast Cancer 064006 | 12.8 |
| Normal Lung | 1.4 | Breast Cancer 9100266 | 10.0 |
| Invasive poor diff. lung adeno (ODO4945-01 | 14.2 | Breast Margin 9100265 | 1.4 |
| Lung Margin (ODO4945-03) | 2.5 | Breast Cancer A209073 | 7.6 |
| Lung Malignant Cancer (OD03126) | 25.3 | Breast Margin A2090734 | 24.7 |
| Lung Margin (OD03126) | 3.7 | Breast cancer (OD06083) | 46.0 |
| Lung Cancer (OD05014A) | 6.7 | Breast cancer node metastasis (OD06083) | 22.7 |
| Lung Margin (OD05014B) | 1.3 | Normal Liver | 5.5 |
| Lung cancer (OD06081) | 1.0 | Liver Cancer 1026 | 22.7 |
| Lung Margin (OD06081) | 1.1 | Liver Cancer 1025 | 68.3 |
| Lung Cancer (OD04237-01) | 18.6 | Liver Cancer 6004-T | 19.8 |
| Lung Margin (OD04237-02) | 16.3 | Liver Tissue 6004-N | 11.6 |
| Ocular Melanoma Metastasis | 0.0 | Liver Cancer 6005-T | 62.4 |
| Ocular Melanoma Margin (Liver) | 10.0 | Liver Tissue 6005-N | 31.4 |
| Melanoma Metastasis | 11.3 | Liver Cancer 064003 | 7.4 |
| Melanoma Margin (Lung) | 4.1 | Normal Bladder | 31.2 |
| Normal Kidney | 7.3 | Bladder Cancer 1023 | 20.2 |
| Kidney Ca, Nuclear grade 2 (OD04338) | 12.0 | Bladder Cancer A302173 | 20.6 |
| Kidney Margin (OD04338) | 16.2 | Normal Stomach | 51.1 |
| Kidney Ca Nuclear grade 1/2 (OD04339) | 22.5 | Gastric Cancer 9060397 | 49.0 |
| Kidney Margin (OD04339) | 3.6 | Stomach Margin 9060396 | 50.3 |
| Kidney Ca, Clear cell type (OD04340) | 11.7 | Gastric Cancer 9060395 | 52.1 |
| Kidney Margin (OD04340) | 3.7 | Stomach Margin 9060394 | 39.5 |
| Kidney Ca, Nuclear grade 3 (OD04348) | 1.1 | Gastric Cancer 064005 | 46.3 |

TABLE ME

Panel 4D

| Tissue Name | Rel. Exp. (%) Ag3244, Run 164390753 | Tissue Name | Rel. Exp. (%) Ag3244, Run 164390753 |
|---|---|---|---|
| Secondary Th1 act | 0.0 | HUVEC IL-1beta | 0.0 |
| Secondary Th2 act | 0.0 | HUVEC IFN gamma | 3.9 |
| Secondary Tr1 act | 0.0 | HUVEC TNF alpha + IFN gamma | 3.1 |
| Secondary Th1 rest | 0.0 | HUVEC TNF alpha + IL4 | 0.0 |
| Secondary Th2 rest | 0.0 | HUVEC IL-11 | 5.1 |
| Secondary Tr1 rest | 0.0 | Lung Microvascular EC none | 27.5 |
| Primary Th1 act | 0.0 | Lung Microvascular EC TNF alpha + IL-1beta | 39.5 |
| Primary Th2 act | 0.0 | Microvascular Dermal EC none | 0.0 |
| Primary Tr1 act | 0.0 | Microsvascular Dermal EC TNF alpha + IL-1beta | 6.3 |
| Primary Th1 rest | 0.0 | Bronchial epithelium TNF alpha + IL1beta | 18.3 |
| Primary Th2 rest | 0.0 | Small airway epithelium none | 7.6 |
| Primary Tr1 rest | 0.0 | Small airway epithelium TNF alpha + IL-1beta | 23.7 |
| CD45RA CD4 lymphocyte act | 2.8 | Coronery artery SMC rest | 0.0 |
| CD45RO CD4 lymphocyte act | 0.0 | Coronery artery SMC TNF alpha + IL-1beta | 0.0 |
| CD8 lymphocyte act | 3.1 | Astrocytes rest | 0.6 |
| Secondary CD8 lymphocyte rest | 0.0 | Astrocytes TNF alpha + IL-1beta | 1.3 |
| Secondary CD8 lymphocyte act | 0.0 | KU-812 (Basophil) rest | 0.0 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 16.2 |
| LAK cells rest | 0.0 | CCD1106 (Keratinocytes) TNF alpha + IL-1beta | 25.0 |
| LAK cells IL-2 | 0.7 | Liver cirrhosis | 40.1 |
| LAK cells IL-2 + IL-12 | 0.0 | Lupus kidney | 2.5 |
| LAK cells IL-2 + IFN gamma | 0.0 | NCI-H292 none | 38.4 |
| LAK cells IL-2 + IL-18 | 0.0 | NCI-H292 IL-4 | 100.0 |
| LAK cells PMA/ionomycin | 0.0 | NCI-H292 IL-9 | 58.2 |
| NK Cells IL-2 rest | 3.3 | NCI-H292 IL-13 | 59.0 |
| Two Way MLR 3 day | 0.0 | NCI-H292 IFN gamma | 87.7 |
| Two Way MLR 5 day | 0.0 | HPAEC none | 3.7 |
| Two Way MLR 7 day | 0.0 | HPAEC TNF alpha + IL-1beta | 0.0 |
| PBMC rest | 0.0 | Lung fibroblast none | 2.4 |
| PBMC PWM | 0.0 | Lung fibroblast TNF alpha + IL-1beta | 0.0 |
| PBMC PHA-L | 0.0 | Lung fibroblast IL-4 | 27.7 |
| Ramos (B cell) none | 0.0 | Lung fibroblast IL-9 | 13.8 |
| Ramos (B cell) ionomycin | 0.0 | Lung fibroblast IL-13 | 11.1 |
| B lymphocytes PWM | 0.0 | Lung fibroblast IFN gamma | 15.4 |
| B lymphocytes CD40L and IL-4 | 0.0 | Dermal fibroblast CCD1070 rest | 1.0 |
| EOL-1 dbcAMP | 0.0 | Dermal fibroblast CCD1070 TNF alpha | 7.8 |
| EOL-1 dbcAMP PMA/ionomycin | 0.0 | Dermal fibroblast CCD1070 IL-1beta | 0.0 |
| Dendritic cells none | 3.2 | Dermal fibroblast IFN gamma | 80.1 |
| Dendritic cells LPS | 0.0 | Dermal fibroblast IL-4 | 98.6 |
| Dendritic cells anti-CD40 | 0.8 | IBD Colitis 2 | 3.5 |
| Monocytes rest | 0.0 | IBD Crohn's | 3.8 |
| Monocytes LPS | 0.0 | Colon | 51.4 |
| Macrophages rest | 0.0 | Lung | 17.9 |
| Macrophages LPS | 0.0 | Thymus | 9.3 |
| HUVEC none | 10.0 | Kidney | 1.5 |
| HUVEC starved | 4.7 | | |

CNS_neurodegeneration_v1.0 Summary: Ag3244 No change is detected in the expression of the CG57454-01 gene in the postmortem Alzheimer's diseased brain when compared to controls. See panel 1.3 for discussion of utility.

Panel 1.3D Summary: Ag3244 The expression of the CG57454-01 gene appears to be highest in a sample derived from a gastric cancer cell line (NCI-N87)(CT=33.9). In addition, there appears to be substantial expression in samples derived from ovarian cancer cell lines and colon cancer cell lines. Thus, the expression of this gene could be used to distinguish NCI-N87 cells from other samples in the panel. Moreover, therapeutic modulation of this gene, through the use of small molecule drugs, protein therapeutics or antibodies could be of benefit in the treatment of gastric cancer, colon cancer or ovarian cancer.

Panel 2.2 Summary: Ag3244 The expression of the CG57454-01 gene appears to be highest in a sample derived from a colon cancer sample (CT=33.1). In addition there appears to be substantial expression in other samples derived from colon cancers. Thus, the expression of this gene could be used to distinguish colon cancer from other samples in the panel. Moreover, therapeutic modulation of this gene, through the use of small molecule drugs, protein therapeutics or antibodies could be of benefit in the treatment of colon cancer.

Panel 4D Summary: Ag3244 The CG57454-01 transcript is expressed in dermal fibroblasts, lung fibroblasts, NCI-H292 cells and lung microvascular cells. The transcript is also expressed in normal colon but not in colitis samples. Thus, the transcript or the protein it encodes could be used to differentiate these cells and tissues from other samples on this panel that do not express this gene. Therapeutically, the protein encoded by this transcript could be used to design treatments for colitis, psoriasis, arthritis, asthma and emphysema.

N. NOV16a: Protocadherin 10

Expression of gene CG57448-01 was assessed using the primer-probe sets Ag1096, Ag3242 and Ag704, described in Tables NA, NB and NC. Results of the RTQ-PCR runs are shown in Tables ND, NE, NF, NG and NH.

TABLE NA

Probe Name Ag1096

| Primers | Sequences | | Length | Start Position |
|---|---|---|---|---|
| Forward | 5'-actttggaagaggcattgct-3' | (SEQ ID NO:341) | 20 | 2455 |
| Probe | TET-5'-cagacagattatgggctccatcgctt-3'-TAMRA | (SEQ ID NO:342) | 26 | 2476 |
| Reverse | 5'-ctcgggataaccatgatcact-3' | (SEQ ID NO:343) | 21 | 2515 |

TABLE NB

Probe Name Ag3242

| Primers | Sequences | | Length | Start Position |
|---|---|---|---|---|
| Forward | 5'-gggaccaatgctcaaattactt-3' | (SEQ ID NO:344) | 22 | 1090 |
| Probe | TET-5'-tcagaaagttccacaagcatctaagga-3'-TAMRA | (SEQ ID NO:345) | 27 | 1122 |
| Reverse | 5'-atgactccagtgttttcatcca-3' | (SEQ ID NO:346) | 22 | 1160 |

TABLE NC

Probe Name Ag704

| Primers | Sequences | | Length | Start Position |
|---|---|---|---|---|
| Forward | 5'-agacttggggaccaatgct-3' | (SEQ ID NO:347) | 19 | 1083 |
| Probe | TET-5'-tcagaaagttccacaagcatctaagga-3'-TAMRA | (SEQ ID NO:348) | 27 | 1122 |
| Reverse | 5'-tgactccagtgttttcatcca-3' | (SEQ ID NO:349) | 21 | 1160 |

TABLE ND

CNS_neurodegeneration_v1.0

| Tissue Name | Rel. Exp. (%) Ag1096, Run 206231465 | Rel. Exp. (%) Ag3242, Run 206533581 | Tissue Name | Rel. Exp. (%) Ag1096, Run 206231465 | Rel. Exp. (%) Ag3242, Run 206533581 |
|---|---|---|---|---|---|
| AD 1 Hippo | 27.0 | 16.5 | Control (Path) 3 Temporal Ctx | 0.9 | 1.4 |
| AD 2 Hippo | 11.5 | 16.8 | Control (Path) 4 Temporal Ctx | 11.8 | 4.9 |
| AD 3 Hippo | 8.8 | 5.3 | AD 1 Occipital Ctx | 6.2 | 2.9 |

TABLE ND-continued

CNS_neurodegeneration_v1.0

| Tissue Name | Rel. Exp. (%) Ag1096, Run 206231465 | Rel. Exp. (%) Ag3242, Run 206533581 | Tissue Name | Rel. Exp. (%) Ag1096, Run 206231465 | Rel. Exp. (%) Ag3242, Run 206533581 |
|---|---|---|---|---|---|
| AD 4 Hippo | 2.0 | 1.9 | AD 2 Occipital Ctx (Missing) | 0.0 | 0.0 |
| AD 5 Hippo | 46.7 | 36.6 | AD 3 Occipital Ctx | 5.6 | 2.8 |
| AD 6 Hippo | 100.0 | 100.0 | AD 4 Occipital Ctx | 6.3 | 4.1 |
| Control 2 Hippo | 51.1 | 35.1 | AD 5 Occipital Ctx | 25.0 | 16.8 |
| Control 4 Hippo | 5.3 | 4.0 | AD 6 Occipital Ctx | 5.3 | 1.0 |
| Control (Path) 3 Hippo | 4.6 | 1.0 | Control 1 Occipital Ctx | 0.8 | 0.3 |
| AD 1 Temporal Ctx | 3.6 | 2.7 | Control 2 Occipital Ctx | 17.1 | 19.5 |
| AD 2 Temporal Ctx | 12.5 | 7.5 | Control 3 Occipital Ctx | 3.1 | 3.5 |
| AD 3 Temporal Ctx | 2.5 | 1.0 | Control 4 Occipital Ctx | 1.4 | 0.8 |
| AD 4 Temporal Ctx | 6.3 | 3.3 | Control (Path) 1 Occipital Ctx | 34.6 | 30.1 |
| AD 5 Inf Temporal Ctx | 74.7 | 59.5 | Control (Path) 2 Occipital Ctx | 2.2 | 0.6 |
| AD 5 Sup Temporal Ctx | 66.0 | 61.6 | Control (Path) 3 Occipital Ctx | 0.7 | 0.4 |
| AD 6 Inf Temporal Ctx | 12.2 | 12.2 | Control (Path) 4 Occipital Ctx | 3.2 | 1.4 |
| AD 6 Sup Temporal Ctx | 14.7 | 12.3 | Control 1 Parietal Ctx | 1.3 | 1.4 |
| Control 1 Temporal Ctx | 1.9 | 2.2 | Control 2 Parietal Ctx | 21.8 | 19.6 |
| Control 2 Temporal Ctx | 21.8 | 22.2 | Control 3 Parietal Ctx | 5.9 | 5.7 |
| Control 3 Temporal Ctx | 5.9 | 4.6 | Control (Path) 1 Parietal Ctx | 38.7 | 38.7 |
| Control 3 Temporal Ctx | 1.7 | 0.9 | Control (Path) 2 Parietal Ctx | 9.5 | 4.3 |
| Control (Path) 1 Temporal Ctx | 33.9 | 28.7 | Control (Path) 3 Parietal Ctx | 1.4 | 0.5 |
| Control (Path) 2 Temporal Ctx | 17.3 | 12.3 | Control (Path) 4 Parietal Ctx | 16.8 | 15.5 |

TABLE NE

Panel 1.2

| Tissue Name | Rel. Exp. (%) Ag1096, Run 125094875 | Rel. Exp. (%) Ag1096, Run 134204525 | Tissue Name | Rel. Exp. (%) Ag1096, Run 125094875 | Rel. Exp. (%) Ag1096, Run 134204525 |
|---|---|---|---|---|---|
| Endothelial cells | 0.0 | 0.0 | Renal ca. 786-0 | 0.0 | 0.0 |
| Heart (Fetal) | 4.5 | 5.6 | Renal ca. A498 | 0.0 | 0.0 |
| Pancreas | 0.2 | 0.3 | Renal ca. RXF 393 | 0.1 | 0.1 |
| Pancreatic ca. CAPAN 2 | 0.0 | 0.0 | Renal ca. ACHN | 31.4 | 80.1 |
| Adrenal Gland | 1.6 | 2.8 | Renal ca. UO-31 | 0.0 | 0.0 |
| Thyroid | 0.1 | 0.4 | Renal ca.TK-10 | 1.0 | 1.3 |
| Salivary gland | 3.0 | 4.8 | Liver | 1.9 | 5.3 |
| Pituitary gland | 2.7 | 6.7 | Liver (fetal) | 0.8 | 1.7 |
| Brain (fetal) | 2.1 | 7.9 | Liver ca. (hepatoblast) HepG2 | 0.0 | 0.0 |
| Brain (whole) | 9.9 | 39.8 | Lung | 1.7 | 5.9 |
| Brain (amygdala) | 15.0 | 34.2 | Lung (fetal) | 1.8 | 9.9 |
| Brain (cerebellum) | 0.8 | 1.9 | Lung ca. (small cell) LX-1 | 0.4 | 1.2 |
| Brain (hippocampus) | 39.0 | 73.2 | Lung ca. (small cell) NCI-H69 | 0.2 | 0.5 |

TABLE NE-continued

Panel 1.2

| Tissue Name | Rel. Exp. (%) Ag1096, Run 125094875 | Rel. Exp. (%) Ag1096, Run 134204525 | Tissue Name | Rel. Exp. (%) Ag1096, Run 125094875 | Rel. Exp. (%) Ag1096, Run 134204525 |
|---|---|---|---|---|---|
| Brain (thalamus) | 2.5 | 9.2 | Lung ca. (s. cell var.) SHP-77 | 2.3 | 2.6 |
| Cerebral Cortex | 27.0 | 56.3 | Lung ca. (large cell) NCI-H460 | 50.7 | 100.0 |
| Spinal cord | 2.2 | 4.8 | Lung ca. (non-sm. cell) A549 | 0.1 | 0.0 |
| glio/astro U87-MG | 0.1 | 0.2 | Lung ca. (non-s. cell) NCI-H23 | 5.4 | 4.0 |
| glio/astro U-118-MG | 0.1 | 0.2 | Lung ca. (non-s. cell) HOP-62 | 15.3 | 33.2 |
| astrocytoma SW1783 | 0.0 | 0.0 | Lung ca. (non-s. cl) NCI-H522 | 0.0 | 0.0 |
| neuro*; met SK-N-AS | 6.9 | 7.3 | Lung ca. (squam.) SW 900 | 5.4 | 12.5 |
| astrocytoma SF-539 | 0.0 | 0.0 | Lung ca. (squam.) NCI-H596 | 0.0 | 0.1 |
| astrocytoma SNB-75 | 7.0 | 6.8 | Mammary gland | 0.6 | 2.7 |
| glioma SNB-19 | 2.4 | 2.2 | Breast ca.* (pl. ef) MCF-7 | 0.0 | 0.0 |
| glioma U251 | 5.5 | 11.6 | Breast ca.* (pl. ef) MDA-MB-231 | 0.0 | 0.0 |
| glioma SF-295 | 0.0 | 0.0 | Breast ca.* (pl. ef) T47D | 0.9 | 1.1 |
| Heart | 13.2 | 15.5 | Breast ca. BT-549 | 0.7 | 0.7 |
| Skeletal Muscle | 1.1 | 1.2 | Breast ca. MDA-N | 0.0 | 0.0 |
| Bone marrow | 0.0 | 0.1 | Ovary | 0.6 | 0.4 |
| Thymus | 0.5 | 1.7 | Ovarian ca. OVCAR-3 | 0.5 | 0.3 |
| Spleen | 0.4 | 0.8 | Ovarian ca. OVCAR-4 | 0.0 | 0.1 |
| Lymph node | 0.2 | 0.2 | Ovarian ca. OVCAR-5 | 15.4 | 15.2 |
| Colorectal Tissue | 4.3 | 8.1 | Ovarian ca. OVCAR-8 | 0.4 | 1.2 |
| Stomach | 3.9 | 8.8 | Ovarian ca. IGROV-1 | 0.1 | 0.0 |
| Small intestine | 1.9 | 3.7 | Ovarian ca. (ascites) SK-OV-3 | 1.9 | 1.3 |
| Colon ca. SW480 | 0.0 | 0.1 | Uterus | 2.2 | 10.6 |
| Colon ca.* SW620 (SW480 met) | 0.1 | 0.2 | Placenta | 8.2 | 10.1 |
| Colon ca. HT29 | 0.0 | 0.1 | Prostate | 3.4 | 3.5 |
| Colon ca. HCT-116 | 0.0 | 0.0 | Prostate ca.* (bone met) PC-3 | 2.6 | 3.5 |
| Colon ca. CaCo-2 | 0.0 | 0.0 | Testis | 1.3 | 2.1 |
| Colon ca. Tissue (ODO3866) | 0.3 | 1.1 | Melanoma Hs688(A).T | 0.0 | 0.0 |
| Colon ca. HCC-2998 | 2.9 | 4.3 | Melanoma* (met) Hs688(B).T | 0.0 | 0.1 |
| Gastric ca.* (liver met) NCI-N87 | 0.0 | 0.0 | Melanoma UACC-62 | 0.0 | 0.0 |
| Bladder | 0.4 | 0.7 | Melanoma M14 | 0.5 | 0.1 |
| Trachea | 3.6 | 16.5 | Melanoma LOX IMVI | 0.1 | 0.0 |
| Kidney | 13.2 | 2.7 | Melanoma* (met) SK-MEL-5 | 100.0 | 86.5 |
| Kidney (fetal) | 7.2 | 10.3 | | | |

TABLE NF

Panel 1.3D

| Tissue Name | Rel. Exp. (%) Ag3242, Run 165524415 | Tissue Name | Rel. Exp. (%) Ag3242, Run 165524415 |
|---|---|---|---|
| Liver adenocarcinoma | 0.0 | Kidney (fetal) | 2.7 |
| Pancreas | 1.0 | Renal ca. 786-0 | 0.0 |

TABLE NF-continued

Panel 1.3D

| Tissue Name | Rel. Exp. (%) Ag3242, Run 165524415 | Tissue Name | Rel. Exp. (%) Ag3242, Run 165524415 |
|---|---|---|---|
| Pancreatic ca. CAPAN 2 | 0.0 | Renal ca. A498 | 0.0 |
| Adrenal gland | 0.3 | Renal ca. RXF 393 | 0.4 |
| Thyroid | 0.0 | Renal ca. ACHN | 100.0 |
| Salivary gland | 0.6 | Renal ca. UO-31 | 0.0 |
| Pituitary gland | 4.8 | Renal ca. TK-10 | 1.1 |
| Brain (fetal) | 11.8 | Liver | 1.0 |
| Brain (whole) | 40.6 | Liver (fetal) | 0.0 |
| Brain (amygdala) | 31.6 | Liver ca. (hepatoblast) HepG2 | 0.0 |
| Brain (cerebellum) | 3.0 | Lung | 4.8 |
| Brain (hippocampus) | 76.3 | Lung (fetal) | 2.2 |
| Brain (substantia nigra) | 2.1 | Lung ca. (small cell) LX-1 | 3.7 |
| Brain (thalamus) | 6.3 | Lung ca. (small cell) NCI-H69 | 0.0 |
| Cerebral Cortex | 27.7 | Lung ca. (s. cell var.) SHP-77 | 16.0 |
| Spinal cord | 7.7 | Lung ca. (large cell) NCI-H460 | 46.0 |
| glio/astro U87-MG | 0.6 | Lung ca (non-sm. cell) A549 | 0.0 |
| glio/astro U-118-MG | 0.5 | Lung ca. (non-s. cell) NCI-H23 | 8.0 |
| astrocytoma SW1783 | 0.0 | Lung ca. (non-s. cell) HOP-62 | 13.6 |
| neuro*; met SK-N-AS | 7.5 | Lung ca. (non-s. cl) NCI-H522 | 0.0 |
| astrocytoma SF-539 | 0.0 | Lung ca. (squam.) SW 900 | 18.8 |
| astrocytoma SNB-75 | 8.4 | Lung ca. (squam.) NCI-H596 | 0.0 |
| glioma SNB-19 | 3.0 | Mammary gland | 1.4 |
| glioma U251 | 66.4 | Breast ca.* (pl. ef) MCF-7 | 0.0 |
| glioma SF-295 | 0.6 | Breast ca.* (pl. ef) MDA-MB-231 | 0.0 |
| Heart (fetal) | 3.7 | Breast ca.* (pl. ef) T47D | 1.4 |
| Heart | 1.7 | Breast ca. BT-549 | 1.6 |
| Skeletal muscle (fetal) | 6.9 | Breast ca. MDA-N | 0.0 |
| Skeletal muscle | 1.9 | Ovary | 1.5 |
| Bone marrow | 0.0 | Ovarian ca. OVCAR-3 | 1.4 |
| Thymus | 0.4 | Ovarian ca. OVCAR-4 | 0.0 |
| Spleen | 0.0 | Ovarian ca. OVCAR-5 | 24.8 |
| Lymph node | 0.0 | Ovarian ca. OVCAR-8 | 0.6 |
| Colorectal | 3.5 | Ovarian ca. IGROV-1 | 0.0 |
| Stomach | 2.5 | Ovarian ca.* (ascites) SK-OV-3 | 5.4 |
| Small intestine | 7.2 | Uterus | 15.5 |
| Colon ca. SW480 | 0.0 | Placenta | 1.1 |
| Colon ca.* SW620 (SW480 met) | 0.0 | Prostate | 1.4 |
| Colon ca. HT29 | 0.0 | Prostate ca.* (bone met) PC-3 | 0.4 |
| Colon ca. HCT-116 | 0.0 | Testis | 2.3 |
| Colon ca. CaCo-2 | 0.0 | Melanoma Hs688 (A).T | 0.0 |
| Colon ca. tissue (ODO3866) | 0.0 | Melanoma* (met) Hs688 (B).T | 0.0 |
| Colon ca. HCC-2998 | 2.1 | Melanoma UACC-62 | 0.0 |
| Gastric ca.* (liver met) NCI-N87 | 0.0 | Melanoma M14 | 1.6 |
| Bladder | 0.0 | Melanoma LOX IMVI | 0.0 |
| Trachea | 9.0 | Melanoma* (met) SK-MEL-5 | 58.6 |
| Kidney | 1.5 | Adipose | 1.5 |

TABLE NG

Panel 2.2

| Tissue Name | Rel. Exp. (%) Ag3242, Run 174443348 | Tissue Name | Rel. Exp. (%) Ag3242, Run 174443348 |
|---|---|---|---|
| Normal Colon | 4.4 | Kidney Margin (OD04348) | 1.0 |
| Colon cancer (OD06064) | 1.8 | Kidney malignant cancer (OD06204B) | 0.4 |
| Colon Margin (OD06064) | 8.9 | Kidney normal adjacent tissue (OD06204E) | 1.8 |
| Colon cancer (OD06159) | 2.0 | Kidney Cancer (OD04450-01) | 2.3 |
| Colon Margin (OD06159) | 7.1 | Kidney Margin (OD04450-03) | 0.9 |
| Colon cancer (OD06297-04) | 2.4 | Kidney Cancer 8120613 | 0.0 |
| Colon Margin (OD06297-05) | 2.2 | Kidney Margin 8120614 | 0.4 |
| CC Gr. 2 ascend colon (ODO3921) | 0.9 | Kidney Cancer 9010320 | 1.4 |
| CC Margin (ODO3921) | 3.8 | Kidney Margin 9010321 | 1.3 |
| Colon cancer metastasis (OD06104) | 0.7 | Kidney Cancer 8120607 | 0.8 |
| Lung Margin (OD06104) | 0.0 | Kidney Margin 8120608 | 0.2 |
| Colon mets to lung (OD04451-01) | 1.7 | Normal Uterus | 5.3 |
| Lung Margin (OD04451-02) | 10.1 | Uterine Cancer 064011 | 0.5 |
| Normal Prostate | 0.4 | Normal Thyroid | 0.0 |
| Prostate Cancer (OD04410) | 0.3 | Thyroid Cancer 064010 | 0.7 |
| Prostate Margin (OD04410) | 0.0 | Thyroid Cancer A302152 | 0.9 |
| Normal Ovary | 0.0 | Thyroid Margin A302153 | 0.0 |
| Ovarian cancer (OD06283-03 | 0.0 | Normal Breast | 0.6 |
| Ovarian Margin (OD06283-07) | 0.0 | Breast Cancer (OD04566) | 0.0 |
| Ovarian Cancer 064008 | 1.9 | Breast Cancer 1024 | 2.1 |
| Ovarian cancer (OD06145) | 0.0 | Breast Cancer (OD04590-01) | 0.0 |
| Ovarian Margin (OD06145) | 0.0 | Breast Cancer Mets (OD04590-03) | 0.0 |
| Ovarian cancer (OD06455-03) | 0.0 | Breast Cancer Metastasis (OD04655-05) | 0.4 |
| Ovarian Margin (OD06455-07) | 1.2 | Breast Cancer 064006 | 0.7 |
| Normal Lung | 2.3 | Breast Cancer 9100266 | 0.7 |
| Invasive poor diff. lung adeno (ODO4945-01) | 1.1 | Breast Margin 9100265 | 0.2 |
| Lung Margin (ODO4945-03) | 1.6 | Breast Cancer A209073 | 0.0 |
| Lung Malignant Cancer (OD03126) | 0.7 | Breast Margin A2090734 | 0.0 |
| Lung Margin (OD03126) | 1.2 | Breast cancer (OD06083) | 0.4 |
| Lung Cancer (OD05014A) | 1.2 | Breast cancer node metastasis (OD06083) | 0.9 |
| Lung Margin (OD05014B) | 4.4 | Normal Liver | 1.3 |
| Lung cancer (OD06081) | 0.8 | Liver Cancer 1026 | 0.3 |
| Lung Margin (OD06081) | 2.8 | Liver Cancer 1025 | 0.0 |
| Lung Cancer (OD04237-01) | 0.0 | Liver Cancer 6004-T | 0.0 |
| Lung Margin (OD04237-02) | 6.0 | Liver Tissue 6004-N | 0.0 |
| Ocular Melanoma Metastasis | 100.0 | Liver Cancer 6005-T | 2.7 |
| Ocular Melanoma Margin (Liver) | 0.7 | Liver Tissue 6005-N | 3.3 |
| Melanoma Metastasis | 1.2 | Liver Cancer 064003 | 7.1 |
| Melanoma Margin (Lung) | 4.9 | Normal Bladder | 0.0 |
| Normal Kidney | 0.0 | Bladder Cancer 1023 | 0.0 |
| Kidney Ca, Nuclear grade 2 (OD04338) | 1.3 | Bladder Cancer A302173 | 0.3 |
| Kidney Margin (OD04338) | 0.4 | Normal Stomach | 5.8 |
| Kidney Ca Nuclear grade 1/2 (OD04339) | 0.6 | Gastric Cancer 9060397 | 0.0 |
| Kidney Margin (OD04339) | 1.6 | Stomach Margin 9060396 | 2.6 |
| Kidney Ca, Clear cell type (OD04340) | 0.0 | Gastric Cancer 9060395 | 2.2 |
| Kidney Margin (OD04340) | 1.1 | Stomach Margin 9060394 | 3.4 |
| Kidney Ca, Nuclear grade 3 (OD04348) | 0.0 | Gastric Cancer 064005 | 0.3 |

TABLE NH

Panel 4D

| Tissue Name | Rel. Exp. (%) Ag1096, Run 160353275 | Rel. Exp. (%) Ag3242, Run 164390548 | Tissue Name | Rel. Exp. (%) Ag1096, Run 160353275 | Rel. Exp. (%) Ag3242, Run 164390548 |
|---|---|---|---|---|---|
| Secondary Th1 act | 0.0 | 0.0 | HUVEC IL-1beta | 0.0 | 0.0 |
| Secondary Th2 act | 0.0 | 0.0 | HUVEC IFN gamma | 0.4 | 0.0 |
| Secondary Tr1 act | 0.0 | 0.0 | HUVEC TNF alpha + IFN gamma | 0.0 | 0.0 |
| Secondary Th1 rest | 0.0 | 0.0 | HUVEC TNF alpha + IL4 | 2.0 | 0.0 |
| Secondary Th2 rest | 0.0 | 0.0 | HUVEC IL-11 | 0.0 | 0.0 |
| Secondary Tr1 rest | 0.0 | 0.0 | Lung Microvascular EC none | 0.0 | 0.0 |
| Primary Th1 act | 0.0 | 0.0 | Lung Microvascular EC TNFalpha + IL-1beta | 0.0 | 0.0 |
| Primary Th2 act | 0.0 | 0.0 | Microvascular Dermal EC none | 0.0 | 0.0 |
| Primary Tr1 act | 0.0 | 0.0 | Microsvascular Dermal EC TNFalpha + IL-1beta | 0.0 | 0.0 |
| Primary Th1 rest | 0.0 | 0.0 | Bronchial epithelium TNFalpha+ IL1beta | 0.0 | 0.0 |
| Primary Th2 rest | 0.0 | 0.0 | Small airway epithelium none | 0.0 | 0.0 |
| Primary Tr1 rest | 0.0 | 0.0 | Small airway epithelium TNFalpha + IL-1beta | 6.5 | 11.7 |
| CD45RA CD4 lymphocyte act | 0.0 | 0.0 | Coronery artery SMC rest | 0.7 | 0.0 |
| CD45RO CD4 lymphocyte act | 0.0 | 0.0 | Coronery artery SMC TNFalpha + IL-1beta | 0.0 | 0.0 |
| CD8 lymphocyte act | 1.3 | 0.0 | Astrocytes rest | 13.9 | 16.8 |
| Secondary CD8 lymphocyte rest | 0.7 | 0.0 | Astrocytes TNFalpha + IL-1beta | 3.6 | 5.3 |
| Secondary CD8 lymphocyte act | 0.0 | 0.0 | KU-812 (Basophil) rest | 0.9 | 1.0 |
| CD4 lymphocyte none | 0.0 | 0.0 | KU-812 (Basophil) PMA/ionomycin | 100.0 | 100.0 |
| 2ry Th1/Th2/Tr1_anti-CD95 CH11 | 0.0 | 0.0 | CCD1106 (Keratinocytes) none | 0.0 | 0.0 |
| LAK cells rest | 0.0 | 0.0 | CCD1106 (Keratinocytes) TNFalpha + IL-1beta | 0.0 | 0.0 |
| LAK cells IL-2 | 0.0 | 0.0 | Liver cirrhosis | 1.9 | 3.8 |
| LAK cells IL-2 + IL-12 | 0.0 | 0.0 | Lupus kidney | 1.3 | 1.4 |
| LAK cells IL-2 + IFN gamma | 0.8 | 0.0 | NCI-H292 none | 42.9 | 48.0 |
| LAK cells IL-2 + IL-18 | 0.0 | 0.0 | NCI-H292 IL-4 | 14.7 | 14.8 |
| LAK cells PMA/ionomycin | 0.0 | 0.0 | NCI-H292 IL-9 | 40.6 | 36.6 |
| NK Cells IL-2 rest | 0.8 | 0.0 | NCI-H292 IL-13 | 12.2 | 7.4 |
| Two Way MLR 3 day | 0.0 | 0.0 | NCI-H292 IFN gamma | 16.8 | 10.9 |
| Two Way MLR 5 day | 0.0 | 0.0 | HPAEC none | 0.0 | 0.0 |
| Two Way MLR 7 day | 1.5 | 0.0 | HPAEC TNF alpha + IL-1 beta | 0.0 | 0.0 |
| PBMC rest | 0.0 | 0.0 | Lung fibroblast none | 0.0 | 1.7 |
| PBMC PWM | 0.0 | 0.0 | Lung fibroblast TNF alpha + IL-1 beta | 0.0 | 0.0 |
| PBMC PHA-L | 0.0 | 0.0 | Lung fibroblast IL-4 | 1.7 | 0.0 |
| Ramos (B cell) none | 0.0 | 0.0 | Lung fibroblast IL-9 | 0.0 | 0.0 |
| Ramos (B cell) ionomycin | 0.0 | 0.0 | Lung fibroblast IL-13 | 0.7 | 0.0 |
| B lymphocytes PWM | 0.0 | 0.0 | Lung fibroblast IFN gamma | 0.0 | 0.0 |
| B lymphocytes CD40L and IL-4 | 0.0 | 0.0 | Dermal fibroblast CCD1070 rest | 0.0 | 0.0 |
| EOL-1 dbcAMP | 0.0 | 0.0 | Dermal fibroblast CCD1070 TNF alpha | 0.0 | 0.0 |
| EOL-1 dbcAMP PMA/ionomycin | 0.0 | 0.0 | Dermal fibroblast CCD1070 IL-1 beta | 0.9 | 0.0 |

TABLE NH-continued

Panel 4D

| Tissue Name | Rel. Exp. (%) Ag1096, Run 160353275 | Rel. Exp. (%) Ag3242, Run 164390548 | Tissue Name | Rel. Exp. (%) Ag1096, Run 160353275 | Rel. Exp. (%) Ag3242, Run 164390548 |
|---|---|---|---|---|---|
| Dendritic cells none | 0.0 | 0.0 | Dermal fibroblast IFN gamma | 0.0 | 0.0 |
| Dendritic cells LPS | 0.0 | 0.0 | Dermal fibroblast IL-4 | 0.0 | 0.0 |
| Dendritic cells anti-CD40 | 0.0 | 0.0 | IBD Colitis 2 | 0.8 | 2.6 |
| Monocytes rest | 0.0 | 0.0 | IBD Crohn's | 0.0 | 2.0 |
| Monocytes LPS | 1.7 | 0.0 | Colon | 28.1 | 23.2 |
| Macrophages rest | 0.0 | 0.0 | Lung | 34.9 | 51.4 |
| Macrophages LPS | 0.0 | 0.0 | Thymus | 35.1 | 28.3 |
| HUVEC none | 0.0 | 0.0 | Kidney | 8.2 | 7.4 |
| HUVEC starved | 0.0 | 0.0 | | | |

CNS_neurodegeneration_v1.0 Summary: Ag1096/Ag3242 Two experiments with two different probe and primer sets produce results that are in excellent agreement, with highest expression of the CG57448-01 gene in the hippocampus of a patient with Alzheimer's disease. No change is detected in the expression of this gene in the postmortem Alzheimer's diseased brain when compared to controls; however this panel confirms the expression of this gene in the CNS in an independent group of patients. See panel 1.2 for a discussion of utility. A third experiment with the probe and primer set Ag704 shows low/undetectable levels of expression (CTs>35). (Data not shown.) The data suggest that there is a probability of a probe failure.

Panel 1.2 Summary: Ag1096/Ag3242 Two experiments with two different probe and primer sets produce results that are in excellent agreement, with highest expression of the CG57448-01 gene in cancer cell lines derived from lung cancer and melanoma (CTs=24–25). Significant levels of expression are also seen in a renal cancer cell line, ovarian cancer cell lines and brain cancer cell lines. Thus, expression of this gene could be used to differentiate between these samples and other samples on this panel and as a diagnostic marker for the presence of these cancers. This gene encodes a protein that is homologous to cadherin, a cell-adhesion molecule. Therefore, therapeutic modulation of the expression or function of this gene may be effective in the treatment of lung, renal and melanoma cancers.

Expression of this gene is also high in many regions of the brain, including the amygdala, thalamus, cerebellum, and cerebral cortex, with highest expression in the hippocampus. Expression is also detected in the spinal cord. Cadherins can act as axon guidance and cell adhesion proteins, specifically during development and in the response to injury (ref 1). Therefore, manipulation of levels of this protein may be of use in inducing a compensatory synaptogenic response to neuronal death in Alzheimer's disease, Parkinson's disease, Huntington's disease, spinocerebellar ataxia, progressive supranuclear palsy, ALS, head trauma, stroke, or any other disease/condition associated with neuronal loss.

Among tissues with metabolic function, this gene is moderately expressed in pituitary gland, adrenal gland, thyroid, pancreas, skeletal muscle, and liver, reflecting the widespread role of cadherins in cell-cell adhesion. This expression suggests that this gene product may play a role in normal metabolic and neuroendocrine function and that dysregulated expression of this gene may contribute to metabolic diseases (such as obesity and diabetes) or neuroendocrine disorders (Ranscht, Int. J. Dev. Neurosci. 18: 643–651, 2000).

Panel 1.3D Summary: Ag3242 Highest expression of the CG57448-01 gene is seen in a renal cancer cell line (CT=31.1). Significant expression is also seen in cell lines derived from ovarian cancer, lung cancer, brain cancer and melanoma. This is in concordance with the results in the previous panel. Please see Panel 1.2 for discussion of utility of this gene in the treatment of cancer.

As in the previous panel, this gene is also highly expressed in the central nervous system. Please see Panel 1.2 for a fuller discussion of utility of this gene in the central nervous system.

Results from a second experiment with the probe primer set Ag704 are not included. The amp plot indicates that there is a high probability of a probe failure.

Panel 2.2 Summary: Ag3242 Highest expression of the CG57448-01 gene is seen in a sample derived from an ocular melanoma metastasis (CT=29). Thus, expression of this gene could be used to differentiate between this sample and other samples on this pane.

Panel 2D Summary: Ag704 Results from one experiment with the CG57448-01 gene are not included. The amp plot indicates that there were experimental difficulties with this run.

Panel 4D Summary: Ag1096/Ag3242 Two experiments with two different probe and primer sets produce results that are in excellent agreement, with highest expression of the CG57448-01 gene in the basophil cell line (KU-812) treated with PMA/ionomycin (CTs=30–32). Significant expression is also seen in a cluster of treated and untreated samples derived from the muco-epidermoid cell line NCI-H292. Thus, this gene, which encodes a cadherin homolog, is expressed in both a cell line that is often used as a model of airway epithelium (NCI-H292) and a cell line that is a reasonable model for the inflammatory cells that contribute to various inflammatory lung diseases. This suggests that suggest that therapeutic modulation of this gene product may reduce or eliminate the symptoms of patients suffering from pathological and inflammatory lung disorders, including chronic obstructive pulmonary disease, asthma, allergy and emphysema.

Low but significant levels of expression are also seen in the samples derived from normal colon, kidney, lung and thymus. This suggests that this gene product may play a role in the homeostasis of these tissues. Therefore, therapeutic modulation of the expression or function of this gene product may be important for maintaining or restoring normal function to these organs during inflammation.Results from a third experiment with the probe primer set Ag704 are not included. The amp plot indicates that there is a high probability of a probe failure.

O. NOV16b: Protocadherin

Expression of gene CG57446-01 was assessed using the primer-probe set Ag3241, described in Table OA. Results of the RTQ-PCR runs are shown in Table OB.

TABLE OA

Probe Name Ag3241

| Primers | Sequences | | Length | Start Position |
|---|---|---|---|---|
| Forward | 5'-cttgtgctagtgatcgacatca-3' | (SEQ ID NO:350) | 22 | 1251 |
| Probe | TET-5'-ccccttattctcaatcctcctactacg-3'-TAMRA | (SEQ ID NO:351) | 27 | 1285 |
| Reverse | 5'-ccgttgttttcgtttacgtaaa-3' | (SEQ ID NO:352) | 22 | 1312 |

TABLE OB

Panel 1.3D

| Tissue Name | Rel. Exp. (%) Ag3241, Run 165524414 | Tissue Name | Rel. Exp. (%) Ag3241, Run 165524414 |
|---|---|---|---|
| Liver adenocarcinoma | 0.0 | Kidney (fetal) | 0.0 |
| Pancreas | 0.0 | Renal ca. 786-0 | 0.0 |
| Pancreatic ca. CAPAN 2 | 0.0 | Renal ca. A498 | 0.0 |
| Adrenal gland | 0.0 | Renal ca. RXF 393 | 0.0 |
| Thyroid | 0.0 | Renal ca. ACHN | 0.0 |
| Salivary gland | 0.0 | Renal ca. UO-31 | 0.0 |
| Pituitary gland | 0.0 | Renal ca. TK-10 | 0.0 |
| Brain (fetal) | 0.0 | Liver | 0.0 |
| Brain (whole) | 0.0 | Liver (fetal) | 0.0 |
| Brain (amygdala) | 0.0 | Liver ca. (hepatoblast) HepG2 | 0.0 |
| Brain (cerebellum) | 0.0 | Lung | 0.0 |
| Brain (hippocampus) | 0.0 | Lung (fetal) | 0.0 |
| Brain (substantia nigra) | 0.0 | Lung ca. (small cell) LX-1 | 0.0 |
| Brain (thalamus) | 0.0 | Lung ca. (small cell) NCI-H69 | 0.0 |
| Cerebral Cortex | 0.0 | Lung ca. (s. cell var.) SHP-77 | 0.0 |
| Spinal cord | 0.0 | Lung ca. (large cell)NCI-H460 | 0.0 |
| glio/astro U87-MG | 0.0 | Lung ca. (non-sm. cell) A549 | 0.0 |
| glio/astro U-118-MG | 0.0 | Lung ca. (non-s. cell) NCI-H23 | 0.0 |
| astrocytoma SW1783 | 0.0 | Lung ca. (non-s. cell) HOP-62 | 0.0 |
| neuro*; met SK-N-AS | 0.0 | Lung ca. (non-s. cl) NCI-H522 | 0.0 |
| astrocytoma SF-539 | 0.0 | Lung ca. (squam.) SW 900 | 0.0 |
| astrocytoma SNB-75 | 0.0 | Lung ca. (squam.) NCI-H596 | 0.0 |
| glioma SNB-19 | 0.0 | Mammary gland | 0.0 |
| glioma U251 | 0.0 | Breast ca.* (pl. ef) MCF-7 | 0.0 |
| glioma SF-295 | 0.0 | Breast ca.* (pl. ef) MDA-MB-231 | 0.0 |
| Heart (fetal) | 0.0 | Breast ca.* (pl. ef) T47D | 0.0 |
| Heart | 0.0 | Breast ca. BT-549 | 0.0 |
| Skeletal muscle (fetal) | 100.0 | Breast ca. MDA-N | 0.0 |
| Skeletal muscle | 0.0 | Ovary | 0.0 |
| Bone marrow | 0.0 | Ovarian ca. OVCAR-3 | 0.0 |
| Thymus | 0.0 | Ovarian ca. OVCAR-4 | 0.0 |
| Spleen | 0.0 | Ovarian ca. OVCAR-5 | 0.0 |
| Lymph node | 0.0 | Ovarian ca. OVCAR-8 | 0.0 |
| Colorectal | 0.0 | Ovarian ca. IGROV-1 | 0.0 |
| Stomach | 0.0 | Ovarian ca.* (ascites) SK-OV-3 | 0.0 |
| Small intestine | 0.0 | Uterus | 0.0 |
| Colon ca. SW480 | 0.0 | Placenta | 0.0 |
| Colon ca.* SW620 (SW480 met) | 0.0 | Prostate | 0.0 |
| Colon ca. HT29 | 0.0 | Prostate ca.* (bone met)PC-3 | 0.0 |

TABLE OB-continued

Panel 1.3D

| Tissue Name | Rel. Exp. (%) Ag3241, Run 165524414 | Tissue Name | Rel. Exp. (%) Ag3241, Run 165524414 |
|---|---|---|---|
| Colon ca. HCT-116 | 0.0 | Testis | 0.0 |
| Colon ca. CaCo-2 | 0.0 | Melanoma Hs688 (A).T | 0.0 |
| Colon ca. tissue (ODO3866) | 0.0 | Melanoma* (met) Hs688 (B).T | 0.0 |
| Colon ca. HCC-2998 | 0.0 | Melanoma UACC-62 | 0.0 |
| Gastric ca.* (liver met) NCI-N87 | 0.0 | Melanoma M14 | 0.0 |
| Bladder | 0.0 | Melanoma LOX IMVI | 0.0 |
| Trachea | 0.0 | Melanoma* (met) SK-MEL-5 | 0.0 |
| Kidney | 0.0 | Adipose | 0.0 |

Panel 1.3D Summary: Ag3241 Expression of the CG57446-01 gene is restricted to fetal skeletal muscle (CT=33.8). Thus, expression of this gene could be used to differentiate between fetal and adult skeletal muscle (CT= 40). This gene encodes a protein that is homologous to cadherin, a cell adhesion molecule that has been implicated in muscle differentiation. Thus, the relative overexpression of this gene in fetal skeletal muscle suggests that the protein product may enhance muscular growth or development in the fetus and may also act in a regenerative capacity in the adult. Therefore, therapeutic modulation of the protein encoded by this gene could be useful in treatment of muscle related diseases. More specifically, treatment of weak or dystrophic muscle with the protein encoded by this gene could restore muscle mass or function (Goichberg et al., J Cell Sci 2001 April;114(Pt 7):1309–19).

Panel 2.2 Summary: Ag3241 Expression of the CG57446-01 gene is low/undetectable in all samples on this panel (CTs>35). (Data not shown.) The amp plot indicates that there is a possibility of a probe failure.

Panel 4D Summary: Ag3241 Expression of the CG57446-01 gene is low/undetectable in all samples on this panel (CTs>35). (Data not shown.) The amp plot indicates that there is a possibility of a probe failure.

Panel CNS_1 Summary: Ag3241 Expression of the CG57446-01 gene is low/undetectable in all samples on this panel (CTs>35). (Data not shown.) The amp plot indicates that there is a possibility of a probe failure.

P. NOV16c: Protocadherin

Expression of gene CG57444-01 was assessed using the primer-probe set Ag3240, described in Table PA. Results of the RTQ-PCR runs are shown in Tables PB, PC, PD, PE and PF.

TABLE PA

Probe Name Ag3240

| Primers | Sequences |  | Length | Start Position |
|---|---|---|---|---|
| Forward | 5'-ggagactgctttgagtcagttc-3' | (SEQ ID NO:353) | 22 | 2184 |
| Probe | TET-5'-tctgctccaagtccggacctgtg-3'-TAMRA | (SEQ ID NO:354) | 23 | 2206 |
| Reverse | 5'-aattataggcatagggcaacgt-3' | (SEQ ID NO:355) | 22 | 2253 |

TABLE PB

CNS_neurodegeneration_v1.0

| Tissue Name | Rel. Exp. (%) Ag3240, Run 210037849 | Tissue Name | Rel. Exp. (%) Ag3240, Run 210037849 |
|---|---|---|---|
| AD 1 Hippo | 17.7 | Control (Path) 3 Temporal Ctx | 6.9 |
| AD 2 Hippo | 37.9 | Control (Path) 4 Temporal Ctx | 28.1 |
| AD 3 Hippo | 6.8 | AD 1 Occipital Ctx | 13.7 |
| AD 4 Hippo | 8.3 | AD 2 Occipital Ctx (Missing) | 0.0 |
| AD 5 Hippo | 55.1 | AD 3 Occipital Ctx | 8.7 |
| AD 6 Hippo | 100.0 | AD 4 Occipital Ctx | 21.8 |
| Control 2 Hippo | 23.5 | AD 5 Occipital Ctx | 8.4 |
| Control 4 Hippo | 23.5 | AD 6 Occipital Ctx | 17.6 |
| Control (Path) 3 Hippo | 8.4 | Control 1 Occipital Ctx | 4.3 |
| AD 1 Temporal Ctx | 18.3 | Control 2 Occipital Ctx | 24.0 |
| AD 2 Temporal Ctx | 32.5 | Control 3 Occipital Ctx | 14.2 |
| AD 3 Temporal Ctx | 6.3 | Control 4 Occipital Ctx | 13.0 |

TABLE PB-continued

CNS_neurodegeneration_v1.0

| Tissue Name | Rel. Exp. (%) Ag3240, Run 210037849 | Tissue Name | Rel. Exp. (%) Ag3240, Run 210037849 |
|---|---|---|---|
| AD 4 Temporal Ctx | 24.7 | Control (Path) 1 Occipital Ctx | 51.4 |
| AD 5 Inf Temporal Ctx | 59.0 | Control (Path) 2 Occipital Ctx | 8.7 |
| AD 5 Sup Temporal Ctx | 53.6 | Control (Path) 3 Occipital Ctx | 4.9 |
| AD 6 Inf Temporal Ctx | 43.8 | Control (Path) 4 Occipital Ctx | 15.4 |
| AD 6 Sup Temporal Ctx | 56.6 | Control 1 Parietal Ctx | 11.6 |
| Control 1 Temporal Ctx | 9.6 | Control 2 Parietal Ctx | 37.1 |
| Control 2 Temporal Ctx | 14.6 | Control 3 Parietal Ctx | 15.5 |
| Control 3 Temporal Ctx | 8.9 | Control (Path) 1 Parietal Ctx | 36.3 |
| Control 3 Temporal Ctx | 9.0 | Control (Path) 2 Parietal Ctx | 22.7 |
| Control (Path) 1 Temporal Ctx | 34.9 | Control (Path) 3 Parietal Ctx | 5.8 |
| Control (Path) 2 Temporal Ctx | 19.3 | Control (Path) 4 Parietal Ctx | 37.1 |

TABLE PC

Panel 1.3D

| Tissue Name | Rel. Exp. (%) Ag3240, Run 165524271 | Tissue Name | Rel. Exp. (%) Ag3240, Run 165524271 |
|---|---|---|---|
| Liver adenocarcinoma | 2.5 | Kidney (fetal) | 6.0 |
| Pancreas | 1.7 | Renal ca. 786-0 | 3.2 |
| Pancreatic ca. CAPAN 2 | 3.5 | Renal ca. A498 | 3.7 |
| Adrenal gland | 6.6 | Renal ca. RXF 393 | 6.7 |
| Thyroid | 3.9 | Renal ca. ACHN | 2.0 |
| Salivary gland | 3.7 | Renal ca. UO-31 | 0.4 |
| Pituitary gland | 14.0 | Renal ca. TK-10 | 0.2 |
| Brain (fetal) | 23.3 | Liver | 1.9 |
| Brain (whole) | 19.3 | Liver (fetal) | 2.8 |
| Brain (amygdala) | 21.9 | Liver ca. (hepatoblast) HepG2 | 0.4 |
| Brain (cerebellum) | 48.6 | Lung | 5.9 |
| Brain (hippocampus) | 23.3 | Lung (fetal) | 2.3 |
| Brain (substantia nigra) | 9.5 | Lung ca. (small cell) LX-1 | 1.0 |
| Brain (thalamus) | 17.8 | Lung ca. (small cell) NCI-H69 | 0.4 |
| Cerebral Cortex | 10.2 | Lung ca. (s. cell var.) SHP-77 | 0.6 |
| Spinal cord | 29.7 | Lung ca. (large cell) NCI-H460 | 3.5 |
| glio/astro U87-MG | 1.0 | Lung ca. (non-sm. cell) A549 | 0.1 |
| glio/astro U-118-MG | 100.0 | Lung ca. (non-s. cell) NCI-H23 | 11.5 |
| astrocytoma SW1783 | 4.2 | Lung ca. (non-s. cell) HOP-62 | 5.2 |
| neuro*; met SK-N-AS | 34.6 | Lung ca. (non-s. cl) NCI-H522 | 2.4 |
| astrocytoma SF-539 | 3.9 | Lung ca. (squam.) SW 900 | 5.8 |
| astrocytoma SNB-75 | 6.6 | Lung ca. (squam.) NCI-H596 | 0.9 |
| glioma SNB-19 | 8.1 | Mammary gland | 14.7 |
| glioma U251 | 9.4 | Breast ca.* (pl. ef) MCF-7 | 4.8 |
| glioma SF-295 | 3.2 | Breast ca.* (pl. ef) MDA-MB-231 | 4.9 |
| Heart (fetal) | 3.6 | Breast ca.* (pl. ef) T47D | 3.9 |
| Heart | 8.7 | Breast ca. BT-549 | 5.8 |
| Skeletal muscle (fetal) | 11.0 | Breast ca. MDA-N | 2.5 |
| Skeletal muscle | 8.1 | Ovary | 31.2 |
| Bone marrow | 1.4 | Ovarian ca. OVCAR-3 | 1.5 |
| Thymus | 1.5 | Ovarian ca. OVCAR-4 | 0.5 |
| Spleen | 5.8 | Ovarian ca. OVCAR-5 | 11.2 |

TABLE PC-continued

Panel 1.3D

| Tissue Name | Rel. Exp. (%) Ag3240, Run 165524271 | Tissue Name | Rel. Exp. (%) Ag3240, Run 165524271 |
|---|---|---|---|
| Lymph node | 7.5 | Ovarian ca. OVCAR-8 | 0.5 |
| Colorectal | 6.2 | Ovarian ca. IGROV-1 | 5.7 |
| Stomach | 3.3 | Ovarian ca.* (ascites) SK-OV-3 | 6.9 |
| Small intestine | 12.4 | Uterus | 15.8 |
| Colon ca. SW480 | 0.1 | Placenta | 4.3 |
| Colon ca.* SW620 (SW480 met) | 0.2 | Prostate | 5.3 |
| Colon ca. HT29 | 0.2 | Prostate ca.* (bone met) PC-3 | 4.1 |
| Colon ca. HCT-116 | 1.0 | Testis | 4.2 |
| Colon ca. CaCo-2 | 0.8 | Melanoma Hs688 (A).T | 6.3 |
| Colon ca. tissue (ODO3866) | 3.2 | Melanoma* (met) Hs688 (B).T | 8.0 |
| Colon ca. HCC-2998 | 5.1 | Melanoma UACC-62 | 2.8 |
| Gastric ca.* (liver met) NCI-N87 | 8.9 | Melanoma M14 | 5.1 |
| Bladder | 13.3 | Melanoma LOX IMVI | 0.4 |
| Trachea | 5.5 | Melanoma* (met) SK-MEL-5 | 3.0 |
| Kidney | 6.7 | Adipose | 3.8 |

TABLE PD

Panel 2.2

| Tissue Name | Rel. Exp. (%) Ag3240, Run 174443262 | Tissue Name | Rel. Exp. (%) Ag3240, Run 174443262 |
|---|---|---|---|
| Normal Colon | 13.7 | Kidney Margin (OD04348) | 40.9 |
| Colon cancer (OD06064) | 12.9 | Kidney malignant cancer (OD06204B) | 1.2 |
| Colon Margin (OD06064) | 20.3 | Kidney normal adjacent tissue (OD06204E) | 11.7 |
| Colon cancer (OD06159) | 0.4 | Kidney Cancer (OD04450-01) | 9.0 |
| Colon Margin (OD06159) | 18.7 | Kidney Margin (OD04450-03) | 9.5 |
| Colon cancer (OD06297-04) | 5.6 | Kidney Cancer 8120613 | 1.4 |
| Colon Margin (OD06297-05) | 34.2 | Kidney Margin 8120614 | 14.1 |
| CC Gr. 2 ascend colon (ODO3921) | 0.9 | Kidney Cancer 9010320 | 3.4 |
| CC Margin (ODO3921) | 4.6 | Kidney Margin 9010321 | 5.5 |
| Colon cancer metastasis (OD06104) | 0.8 | Kidney Cancer 8120607 | 7.0 |
| Lung Margin (OD06104) | 2.5 | Kidney Margin 8120608 | 9.5 |
| Colon mets to lung (OD04451-01) | 1.8 | Normal Uterus | 52.9 |
| Lung Margin (OD04451-02) | 10.9 | Uterine Cancer 064011 | 17.9 |
| Normal Prostate | 15.7 | Normal Thyroid | 2.7 |
| Prostate Cancer (OD04410) | 17.3 | Thyroid Cancer 064010 | 13.7 |
| Prostate Margin (OD04410) | 4.9 | Thyroid Cancer A302152 | 17.0 |
| Normal Ovary | 48.3 | Thyroid Margin A302153 | 8.4 |
| Ovarian cancer (OD06283-03) | 1.9 | Normal Breast | 42.6 |
| Ovarian Margin (OD06283-07) | 14.1 | Breast Cancer (OD04566) | 1.7 |
| Ovarian Cancer 064008 | 10.1 | Breast Cancer 1024 | 40.3 |
| Ovarian cancer (OD06145) | 41.2 | Breast Cancer (OD04590-01) | 8.4 |
| Ovarian Margin (OD06145) | 37.1 | Breast Cancer Mets (OD04590-03) | 9.4 |
| Ovarian cancer (OD06455-03) | 2.6 | Breast Cancer Metastasis (OD04655-05) | 8.9 |
| Ovarian Margin (OD06455-07) | 41.8 | Breast Cancer 064006 | 4.3 |
| Normal Lung | 23.8 | Breast Cancer 9100266 | 16.4 |
| Invasive poor diff. lung adeno (ODO4945-01 | 1.8 | Breast Margin 9100265 | 18.4 |
| Lung Margin (ODO4945-03) | 21.3 | Breast Cancer A209073 | 4.1 |

TABLE PD-continued

Panel 2.2

| Tissue Name | Rel. Exp. (%) Ag3240, Run 174443262 | Tissue Name | Rel. Exp. (%) Ag3240, Run 174443262 |
|---|---|---|---|
| Lung Malignant Cancer (OD03126) | 10.4 | Breast Margin A2090734 | 16.4 |
| Lung Margin (OD03126) | 13.7 | Breast cancer (OD06083) | 34.2 |
| Lung Cancer (OD05014A) | 3.7 | Breast cancer node metastasis (OD06083) | 26.6 |
| Lung Margin (OD05014B) | 33.0 | Normal Liver | 9.7 |
| Lung cancer (OD06081) | 0.0 | Liver Cancer 1026 | 1.6 |
| Lung Margin (OD06081) | 15.3 | Liver Cancer 1025 | 9.2 |
| Lung Cancer (OD04237-01) | 1.1 | Liver Cancer 6004-T | 7.5 |
| Lung Margin (OD04237-02) | 31.6 | Liver Tissue 6004-N | 1.6 |
| Ocular Melanoma Metastasis | 0.6 | Liver Cancer 6005-T | 5.8 |
| Ocular Melanoma Margin (Liver) | 4.5 | Liver Tissue 6005-N | 17.1 |
| Melanoma Metastasis | 0.5 | Liver Cancer 064003 | 7.4 |
| Melanoma Margin (Lung) | 33.9 | Normal Bladder | 8.0 |
| Normal Kidney | 8.0 | Bladder Cancer 1023 | 4.6 |
| Kidney Ca, Nuclear grade 2 (OD04338) | 19.3 | Bladder Cancer A302173 | 3.3 |
| Kidney Margin (OD04338) | 54.7 | Normal Stomach | 32.5 |
| Kidney Ca Nuclear grade 1/2 (OD04339) | 100.0 | Gastric Cancer 9060397 | 0.0 |
| Kidney Margin (OD04339) | 18.3 | Stomach Margin 9060396 | 6.1 |
| Kidney Ca, Clear cell type (OD04340) | 6.7 | Gastric Cancer 9060395 | 6.9 |
| Kidney Margin (OD04340) | 9.5 | Stomach Margin 9060394 | 22.2 |
| Kidney Ca, Nuclear grade 3 (OD04348) | 8.7 | Gastric Cancer 064005 | 6.1 |

TABLE PE

Panel 4D

| Tissue Name | Rel. Exp. (%) Ag3240, Run 164389761 | Tissue Name | Rel. Exp. (%) Ag3240, Run 164389761 |
|---|---|---|---|
| Secondary Th1 act | 0.0 | HUVEC IL-1beta | 16.7 |
| Secondary Th2 act | 0.0 | HUVEC IFN gamma | 33.2 |
| Secondary Tr1 act | 0.0 | HUVEC TNF alpha + IFN gamma | 13.4 |
| Secondary Th1 rest | 0.0 | HUVEC TNF alpha + IL4 | 17.1 |
| Secondary Th2 rest | 0.0 | HUVEC IL-11 | 13.5 |
| Secondary Tr1 rest | 0.0 | Lung Microvascular EC none | 25.9 |
| Primary Th1 act | 0.0 | Lung Microvascular EC TNF alpha + IL-1beta | 23.5 |
| Primary Th2 act | 0.0 | Microvascular Dermal EC none | 35.6 |
| Primary Tr1 act | 0.0 | Microsvascular Dermal EC TNF alpha + IL-1beta | 21.6 |
| Primary Th1 rest | 0.0 | Bronchial epithelium TNF alpha + IL1beta | 27.7 |
| Primary Th2 rest | 0.4 | Small airway epithelium none | 9.4 |
| Primary Tr1 rest | 0.0 | Small airway epithelium TNF alpha + IL-1beta | 27.0 |
| CD45RA CD4 lymphocyte act | 8.5 | Coronery artery SMC rest | 31.6 |
| CD45RO CD4 lymphocyte act | 0.2 | Coronery artery SMC TNF alpha + IL-1beta | 11.0 |
| CD8 lymphocyte act | 0.0 | Astrocytes rest | 35.4 |
| Secondary CD8 lymphocyte rest | 0.2 | Astrocytes TNF alpha + IL-1beta | 19.9 |
| Secondary CD8 lymphocyte act | 0.0 | KU-812 (Basophil) rest | 2.9 |
| CD4 lymphocyte none | 0.1 | KU-812 (Basophil) PMA/ionomycin | 8.2 |
| 2ry Th1/Th2/Tr1_anti-CD95 CH11 | 0.0 | CCD1106 (Keratinocytes) none | 3.5 |
| LAK cells rest | 1.5 | CCD1106 (Keratinocytes) TNF alpha + IL-1beta | 0.9 |
| LAK cells IL-2 | 0.9 | Liver cirrhosis | 6.5 |
| LAK cells IL-2 + IL-12 | 0.4 | Lupus kidney | 6.6 |
| LAK cells IL-2 + IFN gamma | 1.9 | NCI-H292 none | 71.7 |

TABLE PE-continued

Panel 4D

| Tissue Name | Rel. Exp. (%) Ag3240, Run 164389761 | Tissue Name | Rel. Exp. (%) Ag3240, Run 164389761 |
|---|---|---|---|
| LAK cells IL-2 + IL-18 | 1.1 | NCI-H292 IL-4 | 55.9 |
| LAK cells PMA/ionomycin | 0.6 | NCI-H292 IL-9 | 87.7 |
| NK Cells IL-2 rest | 0.0 | NCI-H292 IL-13 | 28.7 |
| Two Way MLR 3 day | 1.6 | NCI-H292 IFN gamma | 43.2 |
| Two Way MLR 5 day | 0.4 | HPAEC none | 19.6 |
| Two Way MLR 7 day | 0.0 | HPAEC TNF alpha + IL-1beta | 15.4 |
| PBMC rest | 0.4 | Lung fibroblast none | 49.7 |
| PBMC PWM | 1.4 | Lung fibroblast TNF alpha + IL-1beta | 16.8 |
| PBMC PHA-L | 0.2 | Lung fibroblast IL-4 | 84.7 |
| Ramos (B cell) none | 7.6 | Lung fibroblast IL-9 | 59.0 |
| Ramos (B cell) ionomycin | 26.6 | Lung fibroblast IL-13 | 55.9 |
| B lymphocytes PWM | 3.7 | Lung fibroblast IFN gamma | 100.0 |
| B lymphocytes CD40L and IL-4 | 3.9 | Dermal fibroblast CCD1070 rest | 51.4 |
| EOL-1 dbcAMP | 5.1 | Dermal fibroblast CCD1070 TNF alpha | 33.2 |
| EOL-1 dbcAMP PMA/ionomycin | 5.7 | Dermal fibroblast CCD1070 IL-1beta | 20.0 |
| Dendritic cells none | 0.7 | Dermal fibroblast IFN gamma | 36.6 |
| Dendritic cells LPS | 1.2 | Dermal fibroblast IL-4 | 52.5 |
| Dendritic cells anti-CD40 | 0.7 | IBD Colitis 2 | 2.8 |
| Monocytes rest | 0.0 | IBD Crohn's | 2.6 |
| Monocytes LPS | 0.2 | Colon | 24.8 |
| Macrophages rest | 0.2 | Lung | 59.5 |
| Macrophages LPS | 1.2 | Thymus | 42.9 |
| HUVEC none | 20.4 | Kidney | 17.3 |
| HUVEC starved | 51.4 | | |

TABLE PF

Panel CNS_1

| Tissue Name | Rel. Exp. (%) Ag3240, Run 171694589 | Tissue Name | Rel. Exp. (%) Ag3240, Run 171694589 |
|---|---|---|---|
| BA4 Control | 13.0 | BA17 PSP | 28.7 |
| BA4 Control2 | 21.6 | BA17 PSP2 | 6.7 |
| BA4 Alzheimer's2 | 4.8 | Sub Nigra Control | 41.8 |
| BA4 Parkinson's | 59.9 | Sub Nigra Control2 | 36.9 |
| BA4 Parkinson's2 | 34.6 | Sub Nigra Alzheimer's2 | 18.7 |
| BA4 Huntington's | 18.8 | Sub Nigra Parkinson's2 | 58.2 |
| BA4 Huntington's2 | 5.0 | Sub Nigra Huntington's | 85.3 |
| BA4 PSP | 2.7 | Sub Nigra Huntington's2 | 23.8 |
| BA4 PSP2 | 23.3 | Sub Nigra PSP2 | 11.6 |
| BA4 Depression | 19.2 | Sub Nigra Depression | 13.9 |
| BA4 Depression2 | 17.4 | Sub Nigra Depression2 | 11.4 |
| BA7 Control | 27.0 | Glob Palladus Control | 22.8 |
| BA7 Control2 | 15.9 | Glob Palladus Control2 | 17.9 |
| BA7 Alzheimer's2 | 13.5 | Glob Palladus Alzheimer's | 17.2 |
| BA7 Parkinson's | 34.2 | Glob Palladus Alzheimer's2 | 9.8 |
| BA7 Parkinson's2 | 26.8 | Glob Palladus Parkinson's | 100.0 |
| BA7 Huntington's | 43.5 | Glob Palladus Parkinson's2 | 10.5 |
| BA7 Huntington's2 | 40.9 | Glob Palladus PSP | 17.2 |
| BA7 PSP | 48.3 | Glob Palladus PSP2 | 7.4 |
| BA7 PSP2 | 17.1 | Glob Palladus Depression | 9.3 |
| BA7 Depression | 27.0 | Temp Pole Control | 11.8 |
| BA9 Control | 11.1 | Temp Pole Control2 | 33.4 |
| BA9 Control2 | 39.5 | Temp Pole Alzheimer's | 1.5 |
| BA9 Alzheimer's | 4.7 | Temp Pole Alzheimer's2 | 5.7 |
| BA9 Alzheimer's2 | 18.7 | Temp Pole Parkinson's | 39.8 |
| BA9 Parkinson's | 26.8 | Temp Pole Parkinson's2 | 12.9 |

TABLE PF-continued

Panel CNS_1

| Tissue Name | Rel. Exp. (%) Ag3240, Run 171694589 | Tissue Name | Rel. Exp. (%) Ag3240, Run 171694589 |
| --- | --- | --- | --- |
| BA9 Parkinson's2 | 41.5 | Temp Pole Huntington's | 19.6 |
| BA9 Huntington's | 54.7 | Temp Pole PSP | 6.8 |
| BA9 Huntington's2 | 8.8 | Temp Pole PSP2 | 0.7 |
| BA9 PSP | 24.5 | Temp Pole Depression2 | 10.9 |
| BA9 PSP2 | 7.1 | Cing Gyr Control | 42.3 |
| BA9 Depression | 6.1 | Cing Gyr Control2 | 20.9 |
| BA9 Depression2 | 5.0 | Cing Gyr Alzheimer's | 23.3 |
| BA17 Control | 40.3 | Cing Gyr Alzheimer's2 | 7.9 |
| BA17 Control2 | 26.1 | Cing Gyr Parkinson's | 38.2 |
| BA17 Alzheimer's2 | 6.0 | Cing Gyr Parkinson's2 | 51.1 |
| BA17 Parkinson's | 52.1 | Cing Gyr Huntington's | 59.0 |
| BA17 Parkinson's2 | 32.1 | Cing Gyr Huntington's2 | 19.6 |
| BA17 Huntington's | 21.0 | Cing Gyr PSP | 51.1 |
| BA17 Huntington's2 | 15.4 | Cing Gyr PSP2 | 13.6 |
| BA17 Depression | 25.7 | Cing Gyr Depression | 18.3 |
| BA17 Depression2 | 10.2 | Cing Gyr Depression2 | 15.0 |

CNS_neurodegeneration_v1.0 Summary: Ag3240 Highest expression of the CG57444-01 gene is seen in the hippocampus of a patient with Alzheimer's disease (CT=27.6). This panel suggests a slight upregulation of this gene in the AD temporal cortex that falls short of significance (p=0.051). Thus, this gene product may be a drug target for the treatment of Alzheimer's disease; specifically, it may be involved in compensatory synaptogenesis in response to neuronal loss.

Panel 1.3D Summary: Ag3240 The CG57444-01 gene, a cadherin homolog, is expressed in many samples in this panel, reflecting the widespread role of cadherins in cell-cell adhesion. Highest expression is seen in a brain cancer cell line (CT=28.6). Thus, expression of this gene could be used to differentiate between this sample and other samples on this panel. Overall, however, expression appears to be associated with normal tissues rather than cancer cell lines. This can be seen in the samples from normal ovarian and breast tissue, which show higher levels of expression than the cell lines derived from breast and ovarian cancers. Loss of function of the related E-cadherin protein has been described in many tumors, along with an increased invasiveness and a decreased prognosis of many carcinomas, including tumors of endocrine glands and their target systems (ref 1). Thus, this gene product might similarly be useful as a protein therapeutic to treat a variety of tumors.

In addition, this gene is moderately expressed in pituitary gland, adrenal gland, thyroid, pancreas, and fetal and adult skeletal muscle, heart and liver, again reflecting the widespread role of this cadherin homolog. This observation may suggest that this gene product plays a role in normal metabolic and neuroendocrine function and that disregulated expression of this gene may contribute to metabolic diseases (such as obesity and diabetes) or neuroendocrine disorders.

Expression of this gene is also high in many regions of the brain, including the amygdala, thalamus, cerebellum, cerebral cortex, hippocampus, and substantia nigra. Expression is also detected in the spinal cord. Cadherins can act as axon guidance and cell adhesion proteins, specifically during development and in the response to injury (ref 2). Manipulation of levels of this protein may be of use in inducing a compensatory synaptogenic response to neuronal death in Alzheimer's disease, Parkinson's disease, Huntington's disease, spinocerebellar ataxia, progressive supranuclear palsy, ALS, head trauma, stroke, or any other disease/condition associated with neuronal loss (Potter et al., Endocr. Rev. 20: 207–239, 1999; Ranscht, Int. J. Dev. Neurosci. 18: 643–651, 2000).

Panel 2.2 Summary: Ag3240 Highest expression of the CG57444-01 gene is seen in a kidney cancer (CT=29.7). Overall, however, expression appears to be associated with normal tissues, as seen in Panel 1.3D. Thus, higher levels of expression are seen in normal colon, ovary, lung and stomach, when compared to adjacent tumors. Thus, absence of expression of this gene could be used as a diagnostic marker of these cancers. Furthermore, therapeutic modulation of the expression or function of this gene could be effective in the treatment of colon, ovarian, lung and stomach cancers.

Panel 4D Summary: Ag3240 The CG57444-01 transcript is expressed in endothelium, fibroblasts and NCI-H292 cells. This gene is also expressed in normal colon, kidney, thymus, and lung. This transcript encodes a putative protocadherin family member. Protocadherins mediate cell:cell interactions and signalling. Since this gene product is expressed in endothelium, it may also be involved in normal blood cell recirculation through the tissues. Alternatively, the protein encoded by this gene may be important for regulating tissue or organ organization and normal function since it is expressed on fibroblasts and epithelium.

Panel CNS_1 Summary: Ag3240 Results from this experiment confirm expression of the CG57444-01 gene in the brain. Please see Panel 1.3D for discussion of utility of this gene in the central nervous system.

Q. NOV17a and NOV17b: Cadherin 23

Expression of gene CG57429-01 and variant CG57429-02 was assessed using the primer-probe sets Ag3234, Ag3279 and Ag616, described in Tables QA, QB and QC. Results of the RTQ-PCR runs are shown in Tables QD, QE, QF, QG, QH, QI, QJ and QK.

TABLE QA

Probe Name Ag3234

| Primers | Sequences | | Length | Start Position |
|---|---|---|---|---|
| Forward | 5'-gcaaaatcgtcgtctctgttac-3' | (SEQ ID NO:356) | 22 | 668 |
| Probe | TET-5'-ccctctgaaagccaccagcagtg-3'-TAMRA | (SEQ ID NO:357) | 23 | 705 |
| Reverse | 5'-ccaagaggttcacaaacactgt-3' | (SEQ ID NO:358) | 22 | 730 |

TABLE QB

Probe Name Ag3279

| Primers | Sequences | | Length | Start Position |
|---|---|---|---|---|
| Forward | 5'-gcaaaatcgtcgtctctgttac-3' | (SEQ ID NO:359) | 22 | 668 |
| Probe | TET-5'-ccctctgaaagccaccagcagtg-3'-TAMRA | (SEQ ID NO:360) | 23 | 705 |
| Reverse | 5'-ccaagaggttcacaaacactgt-3' | (SEQ ID NO:361) | 22 | 730 |

TABLE QC

Probe Name Ag616

| Primers | Sequences | | Length | Start Position |
|---|---|---|---|---|
| Forward | 5'-tcgttgtccgtgcagttcag-3' | (SEQ ID NO:362) | 20 | 1156 |
| Probe | TET-5'-cagaccacccggaactcgcgtg-3'-TAMRA | (SEQ ID NO:363) | 22 | 1133 |
| Reverse | 5'-cggccgtgtacaatgtgtct-3' | (SEQ ID NO:364) | 20 | 1097 |

TABLE QD

CNS_neurodegeneration_v1.0

| Tissue Name | Rel. Exp. (%) Ag3234, Run 209862304 | Rel. Exp. (%) Ag3279, Run 210060481 | Tissue Name | Rel. Exp. (%) Ag3234, Run 209862304 | Rel. Exp. (%) Ag3279, Run 210060481 |
|---|---|---|---|---|---|
| AD 1 Hippo | 16.3 | 21.8 | Control (Path) 3 Temporal Ctx | 14.6 | 16.2 |
| AD 2 Hippo | 23.8 | 32.3 | Control (Path) 4 Temporal Ctx | 26.4 | 31.2 |
| AD 3 Hippo | 13.2 | 14.1 | AD 1 Occipital Ctx | 17.1 | 19.2 |
| AD 4 Hippo | 19.8 | 22.5 | AD 2 Occipital Ctx (Missing) | 0.0 | 0.0 |
| AD 5 hippo | 58.2 | 49.7 | AD 3 Occipital Ctx | 23.5 | 22.4 |
| AD 6 Hippo | 58.6 | 100.0 | AD 4 Occipital Ctx | 18.3 | 21.2 |
| Control 2 Hippo | 19.8 | 24.5 | AD 5 Occipital Ctx | 31.9 | 38.4 |
| Control 4 Hippo | 29.1 | 23.5 | AD 6 Occipital Ctx | 24.1 | 37.9 |
| Control (Path) 3 Hippo | 11.7 | 7.1 | Control 1 Occipital Ctx | 19.8 | 26.1 |
| AD 1 Temporal Ctx | 28.1 | 28.7 | Control 2 Occipital Ctx | 31.0 | 33.7 |
| AD 2 Temporal Ctx | 18.7 | 28.9 | Control 3 Occipital Ctx | 21.8 | 22.7 |
| AD 3 Temporal Ctx | 15.5 | 15.7 | Control 4 Occipital Ctx | 13.3 | 20.7 |

TABLE QD-continued

CNS_neurodegeneration_v1.0

| Tissue Name | Rel. Exp. (%) Ag3234, Run 209862304 | Rel. Exp. (%) Ag3279, Run 210060481 | Tissue Name | Rel. Exp. (%) Ag3234, Run 209862304 | Rel. Exp. (%) Ag3279, Run 210060481 |
|---|---|---|---|---|---|
| AD 4 Temporal Ctx | 27.7 | 25.5 | Control (Path) 1 Occipital Ctx | 37.1 | 32.5 |
| AD 5 Inf Temporal Ctx | 38.2 | 52.1 | Control (Path) 2 Occipital Ctx | 14.7 | 12.6 |
| AD 5 SupTemporal Ctx | 45.7 | 49.7 | Control (Path) 3 Occipital Ctx | 20.3 | 19.2 |
| AD 6 Inf Temporal Ctx | 81.8 | 67.8 | Control (Path) 4 Occipital Ctx | 20.4 | 26.1 |
| AD 6 Sup Temporal Ctx | 100.0 | 94.6 | Control 1 Parietal Ctx | 14.2 | 22.4 |
| Control 1 Temporal Ctx | 10.1 | 14.2 | Control 2 Parietal Ctx | 35.8 | 44.4 |
| Control 2 Temporal Ctx | 15.0 | 11.9 | Control 3 Parietal Ctx | 5.5 | 12.8 |
| Control 3 Temporal Ctx | 8.6 | 14.7 | Control (Path) 1 Parietal Ctx | 17.7 | 21.9 |
| Control 4 Temporal Ctx | 8.9 | 12.1 | Control (Path) 2 Parietal Ctx | 19.2 | 25.3 |
| Control (Path) 1 Temporal Ctx | 23.7 | 31.0 | Control (Path) 3 Parietal Ctx | 13.0 | 17.9 |
| Control (Path) 2 Temporal Ctx | 14.3 | 16.6 | Control (Path) 4 Parietal Ctx | 32.3 | 33.0 |

TABLE QE

General_screening_panel_v1.4

| Tissue Name | Rel. Exp. (%) Ag3279, Run 216512994 | Tissue Name | Rel. Exp. (%) Ag3279, Run 216512994 |
|---|---|---|---|
| Adipose | 35.8 | Renal ca. TK-10 | 0.0 |
| Melanoma* Hs688 (A).T | 0.0 | Bladder | 9.4 |
| Melanoma* Hs688 (B).T | 0.0 | Gastric ca. (liver met.) NCI-N87 | 0.4 |
| Melanoma* M14 | 0.0 | Gastric ca. KATO III | 0.0 |
| Melanoma* LOXIMVI | 0.0 | Colon ca. SW-948 | 0.0 |
| Melanoma* SK-MEL-5 | 0.1 | Colon ca. SW480 | 2.1 |
| Squamous cell carcinoma SCC-4 | 0.0 | Colon ca.* (SW480 met) SW620 | 0.7 |
| Testis Pool | 11.0 | Colon ca. HT29 | 0.0 |
| Prostate ca.* (bone met) PC-3 | 0.1 | Colon ca. HCT-116 | 0.2 |
| Prostate Pool | 3.8 | Colon ca. CaCo-2 | 1.0 |
| Placenta | 0.6 | Colon cancer tissue | 0.8 |
| Uterus Pool | 3.1 | Colon ca. SW1116 | 0.0 |
| Ovarian ca. OVCAR-3 | 10.4 | Colon ca. Colo-205 | 0.0 |
| Ovarian ca. SK-OV-3 | 1.4 | Colon ca. SW-48 | 0.0 |
| Ovarian ca. OVCAR-4 | 0.0 | Colon Pool | 8.0 |
| Ovarian ca. OVCAR-5 | 4.0 | Small Intestine Pool | 12.1 |
| Ovarian ca. IGROV-1 | 2.4 | Stomach Pool | 6.1 |
| Ovarian ca. OVCAR-8 | 1.4 | Bone Marrow Pool | 8.4 |
| Ovary | 37.4 | Fetal Heart | 15.6 |
| Breast ca. MCF-7 | 0.1 | Heart Pool | 9.4 |
| Breast ca. MDA-MB-231 | 0.0 | Lymph Node Pool | 13.7 |
| Breast ca. BT 549 | 0.0 | Fetal Skeletal Muscle | 4.7 |
| Breast ca. T47D | 5.8 | Skeletal Muscle Pool | 4.9 |
| Breast ca. MDA-N | 0.0 | Spleen Pool | 5.8 |
| Breast Pool | 7.0 | Thymus Pool | 13.0 |
| Trachea | 4.3 | CNS cancer (glio/astro) U87-MG | 0.2 |
| Lung | 16.0 | CNS cancer (glio/astro) U-118-MG | 0.0 |
| Fetal Lung | 24.5 | CNS cancer (neuro;met) SK-N-AS | 0.0 |
| Lung ca. NCI-N417 | 2.2 | CNS cancer (astro) SF-539 | 0.0 |
| Lung ca. LX-1 | 0.3 | CNS cancer (astro) SNB-75 | 0.1 |
| Lung ca. NCI-H146 | 0.3 | CNS cancer (glio) SNB-19 | 1.8 |
| Lung ca. SHP-77 | 0.0 | CNS cancer (glio) SF-295 | 0.8 |
| Lung ca. A549 | 4.2 | Brain (Amygdala) Pool | 9.7 |

TABLE QE-continued

General_screening_panel_v1.4

| Tissue Name | Rel. Exp. (%) Ag3279, Run 216512994 | Tissue Name | Rel. Exp. (%) Ag3279, Run 216512994 |
|---|---|---|---|
| Lung ca. NCI-H526 | 10.2 | Brain (cerebellum) | 100.0 |
| Lung ca. NCI-H23 | 12.0 | Brain (fetal) | 8.2 |
| Lung ca. NCI-H460 | 0.1 | Brain (Hippocampus) Pool | 10.2 |
| Lung ca. HOP-62 | 0.0 | Cerebral Cortex Pool | 7.9 |
| Lung ca. NCI-H522 | 6.0 | Brain (Substantia nigra) Pool | 6.0 |
| Liver | 9.1 | Brain (Thalamus) Pool | 10.9 |
| Fetal Liver | 3.5 | Brain (whole) | 16.0 |
| Liver ca. HepG2 | 0.0 | Spinal Cord Pool | 8.9 |
| Kidney Pool | 34.2 | Adrenal Gland | 3.9 |
| Fetal Kidney | 5.0 | Pituitary gland Pool | 0.6 |
| Renal ca. 786-0 | 0.0 | Salivary Gland | 2.5 |
| Renal ca. A498 | 1.1 | Thyroid (female) | 1.4 |
| Renal ca. ACHN | 0.0 | Pancreatic ca. CAPAN2 | 0.0 |
| Renal ca. UO-31 | 0.1 | Pancreas Pool | 9.5 |

TABLE QF

Panel 1.1

| Tissue Name | Rel. Exp. (%) Ag616, Run 111162134 | Tissue Name | Rel. Exp. (%) Ag616, Run 111162134 |
|---|---|---|---|
| Adrenal gland | 3.7 | Renal ca. UO-31 | 0.0 |
| Bladder | 11.7 | Renal ca. RXF 393 | 0.0 |
| Brain (amygdala) | 0.2 | Liver | 26.2 |
| Brain (cerebellum) | 76.8 | Liver (fetal) | 0.1 |
| Brain (hippocampus) | 7.4 | Liver ca. (hepatoblast) HepG2 | 0.0 |
| Brain (substantia nigra) | 76.3 | Lung | 4.2 |
| Brain (thalamus) | 16.2 | Lung (fetal) | 3.8 |
| Cerebral Cortex | 6.0 | Lung ca. (non-s. cell) HOP-62 | 0.0 |
| Brain (fetal) | 2.2 | Lung ca. (large cell) NCI-H460 | 0.0 |
| Brain (whole) | 31.0 | Lung ca. (non-s. cell) NCI-H23 | 6.0 |
| glio/astro U-118-MG | 0.0 | Lung ca. (non-s. cl) NCI-H522 | 18.6 |
| astrocytoma SF-539 | 0.0 | Lung ca. (non-sm. cell) A549 | 6.2 |
| astrocytoma SNB-75 | 0.0 | Lung ca. (s. cell var.) SHP-77 | 0.0 |
| astrocytoma SW1783 | 0.0 | Lung ca. (small cell) LX-1 | 0.0 |
| glioma U251 | 0.0 | Lung ca. (small cell) NCI-H69 | 1.5 |
| glioma SF-295 | 0.0 | Lung ca. (squam.) SW 900 | 0.0 |
| glioma SNB-19 | 0.0 | Lung ca. (squam.) NCI-H596 | 18.4 |
| glio/astro U87-MG | 0.0 | Lymph node | 3.4 |
| neuro*; met SK-N-AS | 0.0 | Spleen | 2.9 |
| Mammary gland | 25.0 | Thymus | 5.6 |
| Breast ca. BT-549 | 0.0 | Ovary | 47.3 |
| Breast ca. MDA-N | 0.0 | Ovarian ca. IGROV-1 | 8.6 |
| Breast ca.* (pl. ef) T47D | 0.0 | Ovarian ca. OVCAR-3 | 13.5 |
| Breast ca.* (pl. ef) MCF-7 | 0.0 | Ovarian ca. OVCAR-4 | 0.0 |
| Breast ca.* (pl. ef) MDA-MB-231 | 0.0 | Ovarian ca. OVCAR-5 | 6.8 |
| Small intestine | 2.4 | Ovarian ca. OVCAR-8 | 0.2 |
| Colorectal | 0.0 | Ovarian ca.* (ascites) SK-OV-3 | 0.1 |
| Colon ca. HT29 | 0.0 | Pancreas | 100.0 |
| Colon ca. CaCo-2 | 0.0 | Pancreatic ca. CAPAN 2 | 0.0 |
| Colon ca. HCT-15 | 0.0 | Pituitary gland | 0.0 |
| Colon ca. HCT-116 | 0.0 | Placenta | 0.5 |
| Colon ca. HCC-2998 | 0.0 | Prostate | 0.7 |
| Colon ca. SW480 | 0.0 | Prostate ca.* (bone met) PC-3 | 0.0 |
| Colon ca.* SW620 (SW480 met) | 0.0 | Salivary gland | 1.8 |

TABLE QF-continued

Panel 1.1

| Tissue Name | Rel. Exp. (%) Ag616, Run 111162134 | Tissue Name | Rel. Exp. (%) Ag616, Run 111162134 |
|---|---|---|---|
| Stomach | 3.4 | Trachea | 1.0 |
| Gastric ca. (liver met) NCI-N87 | 0.0 | Spinal cord | 10.4 |
| Heart | 46.3 | Testis | 10.2 |
| Skeletal muscle (Fetal) | 19.2 | Thyroid | 0.7 |
| Skeletal muscle | 19.2 | Uterus | 7.6 |
| Endothelial cells | 0.0 | Melanoma M14 | 0.0 |
| Heart (Fetal) | 4.1 | Melanoma LOX IMVI | 0.0 |
| Kidney | 0.6 | Melanoma UACC-62 | 0.0 |
| Kidney (fetal) | 0.2 | Melanoma SK-MEL-28 | 0.0 |
| Renal ca. 786-0 | 0.0 | Melanoma* (met) SK-MEL-5 | 0.0 |
| Renal ca. A498 | 0.0 | Melanoma Hs688 (A).T | 0.0 |
| Renal ca. ACHN | 0.0 | Melanoma* (met) Hs688 (B).T | 0.0 |
| Renal ca. TK-10 | 0.0 | | |

TABLE QG

Panel 1.2

| Tissue Name | Rel. Exp. (%) Ag616, Run 118515000 | Tissue Name | Rel. Exp. (%) Ag616, Run 118515000 |
|---|---|---|---|
| Endothelial cells | 0.0 | Renal ca. 786-0 | 0.0 |
| Heart (Fetal) | 8.5 | Renal ca. A498 | 0.1 |
| Pancreas | 100.0 | Renal ca. RXF 393 | 0.0 |
| Pancreatic ca. CAPAN 2 | 0.0 | Renal ca. ACHN | 0.0 |
| Adrenal Gland | 25.5 | Renal ca. UO-31 | 0.0 |
| Thyroid | 8.5 | Renal ca. TK-10 | 0.0 |
| Salivary gland | 8.1 | Liver | 69.7 |
| Pituitary gland | 6.2 | Liver (fetal) | 6.6 |
| Brain (fetal) | 17.8 | Liver ca. (hepatoblast) HepG2 | 0.0 |
| Brain (whole) | 52.9 | Lung | 21.5 |
| Brain (amygdala) | 23.5 | Lung (fetal) | 12.0 |
| Brain (cerebellum) | 66.4 | Lung ca. (small cell) LX-1 | 0.8 |
| Brain (hippocampus) | 21.2 | Lung ca. (small cell) NCI-H69 | 8.4 |
| Brain (thalamus) | 23.3 | Lung ca. (s. cell var.) SHP-77 | 0.0 |
| Cerebral Cortex | 0.0 | Lung ca. (large cell) NCI-H460 | 0.0 |
| Spinal cord | 19.3 | Lung ca. (non-sm. cell) A549 | 12.8 |
| glio/astro U87-MG | 0.0 | Lung ca. (non-s. cell) NCI-H23 | 11.2 |
| glio/astro U-118-MG | 0.0 | Lung ca. (non-s. cell) HOP-62 | 0.1 |
| astrocytoma SW1783 | 0.0 | Lung ca. (non-s. cl) NCI-H522 | 36.3 |
| neuro*; met SK-N-AS | 0.0 | Lung ca. (squam.) SW 900 | 1.6 |
| astrocytoma SF-539 | 0.0 | Lung ca. (squam.) NCI-H596 | 29.5 |
| astrocytoma SNB-75 | 0.0 | Mammary gland | 44.1 |
| glioma SNB-19 | 0.1 | Breast ca.* (pl. ef) MCF-7 | 0.0 |
| glioma U251 | 0.0 | Breast ca.* (pl. ef) MDA-MB-231 | 0.0 |
| glioma SF-295 | 0.0 | Breast ca.* (pl. ef) T47D | 0.1 |
| Heart | 69.7 | Breast ca. BT-549 | 0.0 |
| Skeletal Muscle | 32.1 | Breast ca. MDA-N | 0.0 |
| Bone marrow | 6.6 | Ovary | 53.2 |
| Thymus | 17.4 | Ovarian ca. OVCAR-3 | 18.9 |
| Spleen | 15.6 | Ovarian ca. OVCAR-4 | 0.4 |
| Lymph node | 15.9 | Ovarian ca. OVCAR-5 | 10.5 |
| Colorectal Tissue | 0.0 | Ovarian ca. OVCAR-8 | 3.6 |
| Stomach | 11.8 | Ovarian ca. IGROV-1 | 18.8 |
| Small intestine | 15.9 | Ovarian ca. (ascites) SK-OV-3 | 1.9 |
| Colon ca. SW480 | 0.4 | Uterus | 22.7 |

TABLE QG-continued

Panel 1.2

| Tissue Name | Rel. Exp. (%) Ag616, Run 118515000 | Tissue Name | Rel. Exp. (%) Ag616, Run 118515000 |
|---|---|---|---|
| Colon ca.* SW620 (SW480 met) | 0.2 | Placenta | 6.7 |
| Colon ca. HT29 | 1.0 | Prostate | 6.5 |
| Colon ca. HCT-116 | 0.0 | Prostate ca.* (bone met) PC-3 | 0.0 |
| Colon ca. CaCo-2 | 0.7 | Testis | 50.3 |
| Colon ca. Tissue (ODO3866) | 0.3 | Melanoma Hs688 (A).T | 0.0 |
| Colon ca. HCC-2998 | 0.6 | Melanoma* (met) Hs688 (B).T | 0.0 |
| Gastric ca.* (liver met) NCI-N87 | 0.2 | Melanoma UACC-62 | 0.0 |
| Bladder | 28.3 | Melanoma M14 | 0.0 |
| Trachea | 7.0 | Melanoma LOX IMVI | 0.0 |
| Kidney | 2.8 | Melanoma* (met) SK-MEL-5 | 0.0 |
| Kidney (fetal) | 5.3 | | |

TABLE QH

Panel 1.3D

| Tissue Name | Rel. Exp. (%) Ag3234, Run 165524160 | Tissue Name | Rel. Exp. (%) Ag3234, Run 165524160 |
|---|---|---|---|
| Liver adenocarcinoma | 5.8 | Kidney (fetal) | 2.4 |
| Pancreas | 43.2 | Renal ca. 786-0 | 0.0 |
| Pancreatic ca. CAPAN 2 | 0.0 | Renal ca. A498 | 0.0 |
| Adrenal gland | 4.5 | Renal ca. RXF 393 | 0.0 |
| Thyroid | 0.0 | Renal ca. ACHN | 0.0 |
| Salivary gland | 6.3 | Renal ca. UO-31 | 0.0 |
| Pituitary gland | 1.4 | Renal ca. TK-10 | 0.0 |
| Brain (fetal) | 5.8 | Liver | 6.3 |
| Brain (whole) | 45.4 | Liver (fetal) | 2.9 |
| Brain (amygdala) | 27.2 | Liver ca. (hepatoblast) HepG2 | 0.0 |
| Brain (cerebellum) | 100.0 | Lung | 12.2 |
| Brain (hippocampus) | 21.3 | Lung (fetal) | 6.5 |
| Brain (substantia nigra) | 21.0 | Lung ca. (small cell) LX-1 | 1.4 |
| Brain (thalamus) | 27.2 | Lung ca. (small cell) NCI-H69 | 1.2 |
| Cerebral Cortex | 14.3 | Lung ca. (s. cell var.) SHP-77 | 0.0 |
| Spinal cord | 35.4 | Lung ca. (large cell) NCI-H460 | 2.0 |
| glio/astro U87-MG | 0.0 | Lung ca. (non-sm. cell) A549 | 4.9 |
| glio/astro U-118-MG | 0.0 | Lung ca. (non-s. cell) NCI-H23 | 6.2 |
| astrocytoma SW1783 | 0.0 | Lung ca. (non-s. cell) HOP-62 | 0.0 |
| neuro*; met SK-N-AS | 1.6 | Lung ca. (non-s. cl) NCI-H522 | 0.6 |
| astrocytoma SF-539 | 0.0 | Lung ca. (squam.) SW 900 | 0.7 |
| astrocytoma SNB-75 | 0.0 | Lung ca. (squam.) NCI-H596 | 7.4 |
| glioma SNB-19 | 0.0 | Mammary gland | 28.9 |
| glioma U251 | 0.0 | Breast ca.* (pl. ef) MCF-7 | 0.0 |
| glioma SF-295 | 0.0 | Breast ca.* (pl. ef) MDA-MB-231 | 0.0 |
| Heart (fetal) | 15.2 | Breast ca.* (pl. ef) T47D | 0.0 |
| Heart | 13.3 | Breast ca. BT-549 | 0.0 |
| Skeletal muscle (fetal) | 9.9 | Breast ca. MDA-N | 0.0 |
| Skeletal muscle | 11.2 | Ovary | 50.7 |
| Bone marrow | 6.2 | Ovarian ca. OVCAR-3 | 7.1 |
| Thymus | 18.6 | Ovarian ca. OVCAR-4 | 1.3 |
| Spleen | 8.0 | Ovarian ca. OVCAR-5 | 6.0 |
| Lymph node | 14.4 | Ovarian ca. OVCAR-8 | 3.0 |
| Colorectal | 7.4 | Ovarian ca. IGROV-1 | 1.6 |

TABLE QH-continued

Panel 1.3D

| Tissue Name | Rel. Exp. (%) Ag3234, Run 165524160 | Tissue Name | Rel. Exp. (%) Ag3234, Run 165524160 |
|---|---|---|---|
| Stomach | 4.5 | Ovarian ca.* (ascites) SK-OV-3 | 1.2 |
| Small intestine | 16.6 | Uterus | 42.6 |
| Colon ca. SW480 | 0.0 | Placenta | 1.7 |
| Colon ca.* SW620(SW480 met) | 0.0 | Prostate | 3.4 |
| Colon ca. HT29 | 0.0 | Prostate ca.* (bone met) PC-3 | 0.0 |
| Colon ca. HCT-116 | 0.0 | Testis | 15.6 |
| Colon ca. CaCo-2 | 0.0 | Melanoma Hs688 (A).T | 0.0 |
| Colon ca. tissue(ODO3866) | 1.4 | Melanoma* (met) Hs688 (B).T | 0.0 |
| Colon ca. HCC-2998 | 0.0 | Melanoma UACC-62 | 0.0 |
| Gastric ca.* (liver met) NCI-N87 | 0.0 | Melanoma M14 | 0.0 |
| Bladder | 5.2 | Melanoma LOX IMVI | 0.0 |
| Trachea | 4.1 | Melanoma* (met) SK-MEL-5 | 0.0 |
| Kidney | 0.0 | Adipose | 28.1 |

TABLE QI

Panel 2.2

| Tissue Name | Rel. Exp. (%) Ag3234, Run 174442923 | Tissue Name | Rel. Exp. (%) Ag3234, Run 174442923 |
|---|---|---|---|
| Normal Colon | 7.1 | Kidney Margin (OD04348) | 4.8 |
| Colon cancer (OD06064) | 6.7 | Kidney malignant cancer (OD06204B) | 22.2 |
| Colon Margin (OD06064) | 5.6 | Kidney normal adjacent tissue (OD06204E) | 3.4 |
| Colon cancer (OD06159) | 0.0 | Kidney Cancer (OD04450-01) | 0.0 |
| Colon Margin (OD06159) | 5.9 | Kidney Margin (OD04450-03) | 1.8 |
| Colon cancer (OD06297-04) | 0.0 | Kidney Cancer 8120613 | 0.0 |
| Colon Margin (OD06297-05) | 2.9 | Kidney Margin 8120614 | 1.4 |
| CC Gr.2 ascend colon (ODO3921) | 1.8 | Kidney Cancer 9010320 | 0.0 |
| CC Margin (ODO3921) | 0.0 | Kidney Margin 9010321 | 1.3 |
| Colon cancer metastasis (OD06104) | 1.2 | Kidney Cancer 8120607 | 1.9 |
| Lung Margin (OD06104) | 0.7 | Kidney Margin 8120608 | 1.5 |
| Colon mets to lung (OD04451-01) | 0.0 | Normal Uterus | 33.9 |
| Lung Margin (OD04451-02) | 57.4 | Uterine Cancer 064011 | 6.7 |
| Normal Prostate | 2.6 | Normal Thyroid | 1.3 |
| Prostate Cancer (OD04410) | 0.0 | Thyroid Cancer 064010 | 0.0 |
| Prostate Margin (OD04410) | 7.7 | Thyroid Cancer A302152 | 1.8 |
| Normal Ovary | 100.0 | Thyroid Margin A302153 | 0.8 |
| Ovarian cancer (OD06283-03) | 5.4 | Normal Breast | 22.5 |
| Ovarian Margin (OD06283-07) | 27.9 | Breast Cancer (OD04566) | 3.9 |
| Ovarian Cancer 064008 | 12.9 | Breast Cancer 1024 | 11.4 |
| Ovarian cancer (OD06145) | 12.7 | Breast Cancer (OD04590-01) | 20.0 |
| Ovarian Margin (OD06145) | 19.3 | Breast Cancer Mets (OD04590-03) | 17.2 |
| Ovarian cancer (OD06455-03) | 8.1 | Breast Cancer Metastasis (OD04655-05) | 31.0 |
| Ovarian Margin (OD06455-07) | 25.9 | Breast Cancer 064006 | 3.9 |
| Normal Lung | 14.8 | Breast Cancer 9100266 | 10.0 |
| Invasive poor diff. lung adeno (ODO4945-01) | 0.5 | Breast Margin 9100265 | 16.8 |
| Lung Margin (ODO4945-03) | 28.7 | Breast Cancer A209073 | 10.4 |
| Lung Malignant Cancer (OD03126) | 7.0 | Breast Margin A2090734 | 28.1 |
| Lung Margin (OD03126) | 3.2 | Breast cancer (OD06083) | 12.6 |

TABLE QI-continued

Panel 2.2

| Tissue Name | Rel. Exp. (%) Ag3234, Run 174442923 | Tissue Name | Rel. Exp. (%) Ag3234, Run 174442923 |
|---|---|---|---|
| Lung Cancer (OD05014A) | 3.8 | Breast cancer node metastasis (OD06083) | 13.7 |
| Lung Margin (OD05014B) | 28.5 | Normal Liver | 41.5 |
| Lung cancer (OD06081) | 3.1 | Liver Cancer 1026 | 10.5 |
| Lung Margin (OD06081) | 18.2 | Liver Cancer 1025 | 40.1 |
| Lung Cancer (OD04237-01) | 2.7 | Liver Cancer 6004-T | 21.0 |
| Lung Margin (OD04237-02) | 12.2 | Liver Tissue 6004-N | 3.4 |
| Ocular Melanoma Metastasis | 0.0 | Liver Cancer 6005-T | 59.9 |
| Ocular Melanoma Margin (Liver) | 22.2 | Liver Tissue 6005-N | 59.5 |
| Melanoma Metastasis | 0.0 | Liver Cancer 064003 | 10.4 |
| Melanoma Margin (Lung) | 18.4 | Normal Bladder | 7.6 |
| Normal Kidney | 1.2 | Bladder Cancer 1023 | 2.5 |
| Kidney Ca, Nuclear grade 2 (OD04338) | 6.7 | Bladder Cancer A302173 | 1.4 |
| Kidney Margin (OD04338) | 1.7 | Normal Stomach | 12.3 |
| Kidney Ca Nuclear grade 1/2 (OD04339) | 22.1 | Gastric Cancer 9060397 | 1.0 |
| Kidney Margin (OD04339) | 5.0 | Stomach Margin 9060396 | 1.6 |
| Kidney Ca, Clear cell type (OD04340) | 3.5 | Gastric Cancer 9060395 | 1.3 |
| Kidney Margin (OD04340) | 3.7 | Stomach Margin 9060394 | 3.1 |
| Kidney Ca, Nuclear grade 3 (OD04348) | 0.8 | Gastric Cancer 064005 | 0.0 |

TABLE QJ

Panel 4D

| Tissue Name | Rel. Exp. (%) Ag3234, Run 164328482 | Rel. Exp. (%) Ag3279, Run 164634320 | Tissue Name | Rel. Exp. (%) Ag3234, Run 164328482 | Rel. Exp. (%) Ag3279, Run 164634320 |
|---|---|---|---|---|---|
| Secondary Th1 act | 0.0 | 0.0 | HUVEC IL-1beta | 0.0 | 0.0 |
| Secondary Th2 act | 0.2 | 0.0 | HUVEC IFN gamma | 0.0 | 0.0 |
| Secondary Tr1 act | 0.0 | 0.0 | HUVEC TNF alpha + IFN gamma | 0.0 | 0.0 |
| Secondary Th1 rest | 0.6 | 0.2 | HUVEC TNF alpha + IL4 | 0.0 | 0.0 |
| Secondary Th2 rest | 0.0 | 0.0 | HUVEC IL-11 | 0.0 | 0.0 |
| Secondary Tr1 rest | 0.3 | 0.1 | Lung Microvascular EC none | 0.0 | 0.0 |
| Primary Th1 act | 0.2 | 0.1 | Lung Microvascular EC TNFalpha + IL-1beta | 0.0 | 0.0 |
| Primary Th2 act | 0.0 | 0.0 | Microvascular Dermal EC none | 0.0 | 0.0 |
| Primary Tr1 act | 0.0 | 0.9 | Microvasular Dermal EC TNFalpha + IL-1beta | 0.0 | 0.0 |
| Primary Th1 rest | 0.7 | 0.9 | Bronchial epithelium TNFalpha + IL1beta | 0.0 | 0.0 |
| Primary Th2 rest | 0.2 | 0.2 | Small airway epithelium none | 0.0 | 0.0 |
| Primary Tr1 rest | 0.8 | 0.2 | Small airway epithelium TNFalpha + IL-1beta | 0.0 | 0.0 |
| CD45RA CD4 lymphocyte act | 0.0 | 0.0 | Coronery artery SMC rest | 0.0 | 0.0 |
| CD45RO CD4 lymphocyte act | 0.0 | 0.0 | Coronery artery SMC TNFalpha + IL-1beta | 0.0 | 0.0 |
| CD8 lymphocyte act | 0.0 | 0.0 | Astrocytes rest | 0.0 | 0.0 |
| Secondary CD8 lymphocyte rest | 0.0 | 0.0 | Astrocytes TNFalpha + IL-1beta | 0.0 | 0.0 |
| Secondary CD8 lymphocyte act | 0.0 | 0.0 | KU-812 (Basophil) rest | 0.5 | 0.0 |
| CD4 lymphocyte none | 0.2 | 0.7 | KU-812 (Basophil) PMA/ionomycin | 0.2 | 0.3 |
| 2ry Th1/Th2/Tr1_anti-CD95 CH11 | 0.2 | 0.0 | CCD1106 (Keratinocytes) none | 0.0 | 0.0 |

TABLE QJ-continued

Panel 4D

| Tissue Name | Rel. Exp. (%) Ag3234, Run 164328482 | Rel. Exp. (%) Ag3279, Run 164634320 | Tissue Name | Rel. Exp. (%) Ag3234, Run 164328482 | Rel. Exp. (%) Ag3279, Run 164634320 |
|---|---|---|---|---|---|
| LAK cells rest | 6.2 | 7.6 | CCD1106 (Keratinocytes) TNFalpha + IL-1beta | 0.0 | 0.0 |
| LAK cells IL-2 | 0.0 | 0.0 | Liver cirrhosis | 1.4 | 1.2 |
| LAK cells IL-2 + IL-12 | 0.0 | 0.0 | Lupus kidney | 0.4 | 0.2 |
| LAK cells IL-2 + IFN gamma | 0.1 | 0.4 | NCI-H292 none | 0.0 | 0.2 |
| LAK cells IL-2 + IL-18 | 0.4 | 0.0 | NCI-H292 IL-4 | 0.0 | 0.0 |
| LAK cells PMA/ionomycin | 1.3 | 2.7 | NCI-H292 IL-9 | 0.0 | 0.0 |
| NK Cells IL-2 rest | 0.0 | 0.0 | NCI-H292 IL-13 | 0.0 | 0.0 |
| Two Way MLR 3 day | 1.1 | 1.3 | NCI-H292 IFN gamma | 0.0 | 0.2 |
| Two Way MLR 5 day | 1.3 | 0.6 | HPAEC none | 0.0 | 0.0 |
| Two Way MLR 7 day | 0.8 | 0.4 | HPAEC TNF alpha + IL-1beta | 0.0 | 0.0 |
| PBMC rest | 3.3 | 3.1 | Lung fibroblast none | 0.0 | 0.0 |
| PBMC PWM | 0.0 | 0.1 | Lung fibroblast TNF alpha + IL-1 beta | 0.0 | 0.0 |
| PBMC PHA-L | 0.1 | 0.0 | Lung fibroblast IL-4 | 0.0 | 0.0 |
| Ramos (B cell) none | 0.0 | 0.0 | Lung fibroblast IL-9 | 0.0 | 0.0 |
| Ramos (B cell) ionomycin | 0.0 | 0.0 | Lung fibroblast IL-13 | 0.0 | 0.0 |
| B lymphocytes PWM | 0.0 | 0.0 | Lung fibroblast IFN gamma | 0.0 | 0.0 |
| B lymphocytes CD40L and IL-4 | 0.0 | 0.3 | Dermal fibroblast CCD1070 rest | 0.0 | 0.0 |
| EOL-1 dbcAMP | 0.0 | 0.2 | Dermal fibroblast CCD1070 TNF alpha | 0.2 | 0.6 |
| EOL-1 dbcAMP PMA/ionomycin | 0.1 | 0.0 | Dermal fibroblast CCD1070 IL-1 beta | 0.0 | 0.0 |
| Dendritic cells none | 25.9 | 49.0 | Dermal fibroblast IFN gamma | 0.0 | 0.2 |
| Dendritic cells LPS | 61.1 | 92.0 | Dermal fibroblast IL-4 | 0.2 | 0.0 |
| Dendritic cells anti-CD40 | 100.0 | 94.6 | IBD Colitis 2 | 0.0 | 0.7 |
| Monocytes rest | 12.2 | 23.0 | IBD Crohn's | 0.3 | 0.7 |
| Monocytes LPS | 2.6 | 2.5 | Colon | 3.0 | 2.8 |
| Macrophages rest | 92.0 | 100.0 | Lung | 7.4 | 9.7 |
| Macrophages LPS | 10.4 | 18.0 | Thymus | 1.2 | 3.7 |
| HUVEC none | 0.0 | 0.0 | Kidney | 35.4 | 33.4 |
| HUVEC starved | 0.0 | 0.0 | | | |

TABLE QK

Panel CNS_1

| Tissue Name | Rel. Exp. (%) Ag3279, Run 171694591 | Tissue Name | Rel. Exp. (%) Ag3279, Run 171694591 |
|---|---|---|---|
| BA4 Control | 3.2 | BA17 PSP | 13.4 |
| BA4 Control2 | 10.0 | BA17 PSP2 | 5.3 |
| BA4 Alzheimer's2 | 3.8 | Sub Nigra Control | 58.6 |
| BA4 Parkinson's | 6.5 | Sub Nigra Control2 | 21.3 |
| BA4 Parkinson's2 | 11.7 | Sub Nigra Alzheimer's2 | 12.2 |
| BA4 Huntington's | 7.6 | Sub Nigra Parkinson's2 | 63.3 |
| BA4 Huntington's2 | 4.5 | Sub Nigra Huntington's | 100.0 |
| BA4 PSP | 5.1 | Sub Nigra Huntington's2 | 87.1 |
| BA4 PSP2 | 8.8 | Sub Nigra PSP2 | 16.8 |
| BA4 Depression | 6.7 | Sub Nigra Depression | 7.9 |
| BA4 Depression2 | 7.4 | Sub Nigra Depression2 | 24.3 |
| BA7 Control | 4.5 | Glob Palladus Control | 24.3 |
| BA7 Control2 | 1.9 | Glob Palladus Control2 | 8.1 |

TABLE QK-continued

Panel CNS_1

| Tissue Name | Rel. Exp. (%) Ag3279, Run 171694591 | Tissue Name | Rel. Exp. (%) Ag3279, Run 171694591 |
|---|---|---|---|
| BA7 Alzheimer's2 | 1.0 | Glob Palladus Alzheimer's | 14.9 |
| BA7 Parkinson's | 24.1 | Glob Palladus Alzheimer's2 | 1.2 |
| BA7 Parkinson's2 | 17.4 | Glob Palladus Parkinson's | 33.0 |
| BA7 Huntington's | 6.3 | Glob Palladus Parkinson's2 | 2.0 |
| BA7 Huntington's2 | 28.5 | Glob Palladus PSP | 3.0 |
| BA7 PSP | 18.9 | Glob Palladus PSP2 | 6.0 |
| BA7 PSP2 | 3.8 | Glob Palladus Depression | 8.8 |
| BA7 Depression | 1.7 | Temp Pole Control | 5.9 |
| BA9 Control | 5.3 | Temp Pole Control2 | 11.7 |
| BA9 Control2 | 4.1 | Temp Pole Alzheimer's | 7.4 |
| BA9 Alzheimer's | 3.6 | Temp Pole Alzheimer's2 | 3.0 |
| BA9 Alzheimer's2 | 8.8 | Temp Pole Parkinson's | 11.9 |
| BA9 Parkinson's | 18.6 | Temp Pole Parkinson's2 | 7.9 |
| BA9 Parkinson's2 | 20.4 | Temp Pole Huntington's | 8.8 |
| BA9 Huntington's | 15.0 | Temp Pole PSP | 4.7 |
| BA9 Huntington's2 | 7.4 | Temp Pole PSP2 | 0.0 |
| BA9 PSP | 5.3 | Temp Pole Depression2 | 12.6 |
| BA9 PSP2 | 1.6 | Cing Gyr Control | 18.0 |
| BA9 Depression | 4.7 | Cing Gyr Control2 | 20.2 |
| BA9 Depression2 | 4.5 | Cing Gyr Alzheimer's | 8.6 |
| BA17 Control | 20.2 | Cing Gyr Alzheimer's2 | 4.2 |
| BA17 Control2 | 7.9 | Cing Gyr Parkinson's | 12.2 |
| BA17 Alzheimer's2 | 3.2 | Cing Gyr Parkinson's2 | 15.3 |
| BA17 Parkinson's | 14.1 | Cing Gyr Huntington's | 28.1 |
| BA17 Parkinson's2 | 8.7 | Cing Gyr Huntington's2 | 4.7 |
| BA17 Huntington's | 22.2 | Cing Gyr PSP | 7.8 |
| BA17 Huntington's2 | 18.2 | Cing Gyr PSP2 | 11.2 |
| BA17 Depression | 4.9 | Cing Gyr Depression | 2.9 |
| BA17 Depression2 | 19.9 | Cing Gyr Depression2 | 8.7 |

CNS_neurodegeneration_v1.0 Summary: Ag3234/Ag3279 Two experiments with the same probe and primer set produce results that are in excellent agreement. Both experiments show a difference in expression of the CG57429-01 gene between Alzheimer's diseased postmortem brains and controls for this gene. Expression is increased in the temporal cortex of patients with AD ($p=0.016$ for ag3234 and $p=0.024$ for ag3279) and in the hippocampus. Both the temporal cortex and hippocampus are regions that show severe neurodegeneration in AD. In contrast, expression in the occipital cortex, a region that does not degenerate in Alzheimer's disease, is not disregulated. Together, these data suggest that the CG57429-01 protein product may be involved in the pathology or response to Alzheimer's disease. Therefore, this may be a useful drug target for the treatment of this disease.

General_screening_panel_v1.4 Summary: Ag3279 Highest expression of the CG57429-01 gene is in the cerebellum. Significant levels of expression are also seen in other regions of the brain including the amygdala, hippocampus, cerebral cortex, substantia nigra, and thalamus. Cadherins can act as axon guidance and cell adhesion proteins, specifically during development and in the response to injury (ref 1). Manipulation of levels of this protein may be of use in inducing a compensatory synaptogenic response to neuronal death in Alzheimer's disease, Parkinson's disease, Huntington's disease, spinocerebellar ataxia, progressive supranuclear palsy, ALS, head trauma, stroke, or any other disease/condition associated with neuronal loss.

In addition, this gene is highly expressed in pituitary gland, adrenal gland, thyroid, pancreas, adult and fetal skeletal muscle, heart and liver, reflecting the widespread role of cadherins in cell-cell adhesion. This observation may suggest that this gene plays a role in normal metabolic and neuroendocrine function and that disregulated expression of this gene may contribute to metabolic diseases (such as obesity and diabetes) or neuroendocrine disorders.

Overall, gene expression is associated with normal tissues rather than cancer cell lines. Loss of function of the related E-cadherin protein has been described in many tumors, along with an increased invasiveness and a decreased prognosis of many carcinomas, including tumors of endocrine glands and their target systems (ref 1). Thus, this gene product might similarly be useful as a protein therapeutic to treat a variety of tumors, since it is found in normal cells but missing from cancer cells (Potter et al., Endocr. Rev. 20: 207–239, 1999; Ranscht, Int. J. Dev. Neurosci. 18: 643–651, 2000).

Panel 1.1 and 1.2 Summary: Ag616 Highest expression of the CG57429-01 gene, a cadherin homolog, is seen in pancreas (CT=23.2). Significant expression is also seen in adrenal gland, fetal and adult skeletal muscle, liver and heart. This widespread expression among tissues with metabolic function is consistent with expression seen in General_screening_panel_v1.4. Please see that panel for further discussion of utility of this gene in metabolic disorders.

In addition, there is higher expression in adult liver (CT=27) when compared to experession in fetal liver (CT= 34.8). Thus, expression of this gene could be used to differentiate between fetal and adult liver.

Overall, expression in this panel is in agreement with expression in the previous panel. Please see that panel for further discussion of utility of this gene.

Panel 1.3D Summary: Ag3234 Results from this experiment produce a similar profile to Panel 1.4. Please see that Panel for further discussion of expression and utility of this gene.

Panel 2.2 Summary: Ag3234 The expression of the CG57429-01 gene appears to be highest in a sample derived from a normal ovarian tissue (CT=32.3). In addition, there appears to be substantial expression in other samples derived from liver cancers. Furthermore, there appears to be expression specific to normal lung tissue when compared to malignant lung tissue. Thus, the expression of this gene could be used to distinguish normal ovarian tissue from other samples in the panel. Moreover, therapeutic modulation of this gene, through the use of small molecule drugs, protein therapeutics or antibodies could be of benefit in the treatment of liver cancer, ovarian cancer or lung cancer.

Panel 4D Summary: Ag3234/Ag3279 The CG57429-01 gene, a cadherin 23-like molecule, is expressed selectively at moderate levels (CTs=28.1–30.1) in resting and activated dendritic cells, and in resting and activated macrophages. Thus, small molecule antagonists or therapeutic antibodies that block the function of the CG57429-01 gene product may be useful in the reduction or elimination of the symptoms in patients with autoimmune and inflammatory diseases in which dendritic cells and macrophages play an important role in antigen presentation and other functions, such as, but not limited to, including Crohn's disease, ulcerative colitis, multiple sclerosis, chronic obstructive pulmonary disease, asthma, emphysema, rheumatoid arthritis, lupus erythematosus, or psoriasis.

Panel CNS_1 Summary: Ag3279 This panel confirms expression of the CG57429-01 gene in the brain. Please see Panel 1.3D for discussion of utility of this gene in the central nervous system. Results from a second experiment with Ag3234 are not included. The amp plot indicates that there were experimental difficulties with this run.

R. NOV21: Platelet Glycoprotein V

Expression of gene CG57436-01 was assessed using the primer-probe set Ag3236, described in Table SA. Results of the RTQ-PCR runs are shown in Tables RB, RC, RD and RE.

TABLE RA

Probe Name Ag3236

| Primers | Sequences | | Length | Start Position |
|---|---|---|---|---|
| Forward | 5'-gaggtgtgactcagacatcctt-3' | (SEQ ID NO:365) | 22 | 1409 |
| Probe | TET-5'-aactggctcctgctcaaccagcct-3'-TAMRA | (SEQ ID NO:366) | 24 | 1440 |
| Reverse | 5'-gtacagtgtccgtccctaacct-3' | (SEQ ID NO:367) | 22 | 1464 |

TABLE RB

General_screening_panel_v1.4

| Tissue Name | Rel. Exp. (%) Ag3236, Run 214693630 | Tissue Name | Rel. Exp. (%) Ag3236, Run 214693630 |
|---|---|---|---|
| Adipose | 0.5 | Renal ca. TK-10 | 0.0 |
| Melanoma* Hs688 (A).T | 38.2 | Bladder | 0.6 |
| Melanoma* Hs688 (B).T | 9.4 | Gastric ca. (liver met.) NCI-N87 | 0.0 |
| Melanoma* M14 | 0.0 | Gastric ca. KATO III | 0.0 |
| Melanoma* LOXIMVI | 0.7 | Colon ca. SW-948 | 0.0 |
| Melanoma* SK-MEL-5 | 0.0 | Colon ca. SW480 | 0.0 |
| Squamous cell carcinoma SCC-4 | 0.0 | Colon ca.* (SW480 met) SW620 | 0.0 |
| Testis Pool | 0.0 | Colon ca. HT29 | 0.0 |
| Prostate ca.* (bone met) PC-3 | 0.0 | Colon ca. HCT-116 | 0.0 |
| Prostate Pool | 0.1 | Colon ca. CaCo-2 | 0.0 |
| Placenta | 0.6 | Colon cancer tissue | 1.9 |
| Uterus Pool | 0.2 | Colon ca. SW1116 | 0.0 |
| Ovarian ca. OVCAR-3 | 0.0 | Colon ca. Colo-205 | 0.0 |
| Ovarian ca. SK-OV-3 | 0.0 | Colon ca. SW-48 | 0.0 |
| Ovarian ca. OVCAR-4 | 0.0 | Colon Pool | 0.3 |
| Ovarian ca. OVCAR-5 | 0.1 | Small Intestine Pool | 0.0 |
| Ovarian ca. IGROV-1 | 0.0 | Stomach Pool | 0.2 |
| Ovarian ca. OVCAR-8 | 0.0 | Bone Marrow Pool | 0.3 |
| Ovary | 0.2 | Fetal Heart | 0.0 |
| Breast ca. MCF-7 | 0.0 | Heart Pool | 0.1 |

TABLE RB-continued

General_screening_panel_v1.4

| Tissue Name | Rel. Exp. (%) Ag3236, Run 214693630 | Tissue Name | Rel. Exp. (%) Ag3236, Run 214693630 |
| --- | --- | --- | --- |
| Breast ca. MDA-MB-231 | 0.5 | Lymph Node Pool | 0.2 |
| Breast ca. BT 549 | 0.0 | Fetal Skeletal Muscle | 0.1 |
| Breast ca. T47D | 0.3 | Skeletal Muscle Pool | 0.1 |
| Breast ca. MDA-N | 0.0 | Spleen Pool | 0.1 |
| Breast Pool | 0.2 | Thymus Pool | 0.0 |
| Trachea | 0.2 | CNS cancer (glio/astro) U87-MG | 14.8 |
| Lung | 0.0 | CNS cancer (glio/astro) U-118-MG | 100.0 |
| Fetal Lung | 0.0 | CNS cancer (neuro; met) SK-N-AS | 0.0 |
| Lung ca. NCI-N417 | 0.0 | CNS cancer (astro) SF-539 | 13.2 |
| Lung ca. LX-1 | 0.0 | CNS cancer (astro) SNB-75 | 5.3 |
| Lung ca. NCI-H146 | 0.0 | CNS cancer (glio) SNB-19 | 0.0 |
| Lung ca. SHP-77 | 0.0 | CNS cancer (glio) SF-295 | 0.3 |
| Lung ca. A549 | 0.0 | Brain (Amygdala) Pool | 0.0 |
| Lung ca. NCI-H526 | 0.0 | Brain (cerebellum) | 0.0 |
| Lung ca. NCI-H23 | 0.0 | Brain (fetal) | 0.0 |
| Lung ca. NCI-H460 | 0.0 | Brain (Hippocampus) Pool | 0.0 |
| Lung ca. HOP-62 | 0.0 | Cerebral Cortex Pool | 0.0 |
| Lung ca. NCI-H522 | 0.0 | Brain (Substantia nigra) Pool | 0.0 |
| Liver | 0.0 | Brain (Thalamus) Pool | 0.0 |
| Fetal Liver | 0.0 | Brain (whole) | 0.0 |
| Liver ca. HepG2 | 0.0 | Spinal Cord Pool | 0.0 |
| Kidney Pool | 0.2 | Adrenal Gland | 0.1 |
| Fetal Kidney | 0.0 | Pituitary gland Pool | 0.0 |
| Renal ca. 786-0 | 0.1 | Salivary Gland | 0.0 |
| Renal ca. A498 | 0.1 | Thyroid (female) | 0.6 |
| Renal ca. ACHN | 0.0 | Pancreatic ca. CAPAN2 | 0.0 |
| Renal ca. UO-31 | 0.4 | Pancreas Pool | 0.1 |

TABLE RC

Panel 2.2

| Tissue Name | Rel. Exp. (%) Ag3236, Run 174442924 | Tissue Name | Rel. Exp. (%) Ag3236, Run 174442924 |
| --- | --- | --- | --- |
| Normal Colon | 0.2 | Kidney Margin (OD04348) | 0.5 |
| Colon cancer (OD06064) | 7.3 | Kidney malignant cancer (OD06204B) | 0.8 |
| Colon Margin (OD06064) | 0.2 | Kidney normal adjacent tissue (OD06204E) | 0.0 |
| Colon cancer (OD06159) | 0.3 | Kidney Cancer (OD04450-01) | 0.0 |
| Colon Margin (OD06159) | 0.6 | Kidney Margin (OD04450-03) | 0.2 |
| Colon cancer (OD06297-04) | 1.7 | Kidney Cancer 8120613 | 0.0 |
| Colon Margin (OD06297-05) | 2.4 | Kidney Margin 8120614 | 0.0 |
| CC Gr.2 ascend colon (OD03921) | 1.6 | Kidney Cancer 9010320 | 1.1 |
| CC Margin (OD03921) | 1.9 | Kidney Margin 9010321 | 1.1 |
| Colon cancer metastasis (OD06104) | 0.3 | Kidney Cancer 8120607 | 4.7 |
| Lung Margin (OD06104) | 0.6 | Kidney Margin 8120608 | 0.2 |
| Colon mets to lung (OD04451-01) | 0.6 | Normal Uterus | 1.4 |
| Lung Margin (OD04451-02) | 0.3 | Uterine Cancer 064011 | 0.0 |
| Normal Prostate | 0.0 | Normal Thyroid | 0.5 |
| Prostate Cancer (OD04410) | 0.3 | Thyroid Cancer 064010 | 1.0 |
| Prostate Margin (OD04410) | 0.0 | Thyroid Cancer A302152 | 11.9 |
| Normal Ovary | 2.7 | Thyroid Margin A302153 | 0.0 |
| Ovarian cancer (OD06283-03) | 13.9 | Normal Breast | 0.7 |
| Ovarian Margin (OD06283-07) | 1.0 | Breast Cancer (OD04566) | 3.7 |
| Ovarian Cancer 064008 | 27.0 | Breast Cancer 1024 | 3.4 |
| Ovarian cancer (OD06145) | 0.7 | Breast Cancer (OD04590-01) | 8.4 |

TABLE RC-continued

Panel 2.2

| Tissue Name | Rel. Exp. (%) Ag3236, Run 174442924 | Tissue Name | Rel. Exp. (%) Ag3236, Run 174442924 |
| --- | --- | --- | --- |
| Ovarian Margin (OD06145) | 1.1 | Breast Cancer Mets (OD04590-03) | 9.9 |
| Ovarian cancer (OD06455-03) | 0.0 | Breast Cancer Metastasis (OD04655-05) | 0.5 |
| Ovarian Margin (OD06455-07) | 0.0 | Breast Cancer 064006 | 31.2 |
| Normal Lung | 0.0 | Breast Cancer 9100266 | 14.3 |
| Invasive poor diff. lung adeno (ODO4945-01) | 4.6 | Breast Margin 9100265 | 19.1 |
| Lung Margin (ODO4945-03) | 2.1 | Breast Cancer A209073 | 5.8 |
| Lung Malignant Cancer (OD03126) | 6.4 | Breast Margin A2090734 | 0.4 |
| Lung Margin (OD03126) | 0.5 | Breast cancer (OD06083) | 15.7 |
| Lung Cancer (OD05014A) | 0.5 | Breast cancer node metastasis (OD06083) | 100.0 |
| Lung Margin (OD05014B) | 0.0 | Normal Liver | 0.2 |
| Lung cancer (OD06081) | 0.8 | Liver Cancer 1026 | 0.3 |
| Lung Margin (OD06081) | 0.0 | Liver Cancer 1025 | 1.9 |
| Lung Cancer (OD04237-01) | 0.8 | Liver Cancer 6004-T | 0.0 |
| Lung Margin (OD04237-02) | 8.5 | Liver Tissue 6004-N | 0.0 |
| Ocular Melanoma Metastasis | 0.0 | Liver Cancer 6005-T | 0.8 |
| Ocular Melanoma Margin (Liver) | 0.0 | Liver Tissue 6005-N | 0.0 |
| Melanoma Metastasis | 0.0 | Liver Cancer 064003 | 0.0 |
| Melanoma Margin (Lung) | 1.9 | Normal Bladder | 1.8 |
| Normal Kidney | 0.0 | Bladder Cancer 1023 | 8.4 |
| Kidney Ca, Nuclear grade 2 (OD04338) | 0.2 | Bladder Cancer A302173 | 6.7 |
| Kidney Margin (OD04338) | 0.0 | Normal Stomach | 1.6 |
| Kidney Ca Nuclear grade 1/2 (OD04339) | 0.0 | Gastric Cancer 9060397 | 2.4 |
| Kidney Margin (OD04339) | 0.0 | Stomach Margin 9060396 | 0.8 |
| Kidney Ca, Clear cell type (OD04340) | 0.0 | Gastric Cancer 9060395 | 0.3 |
| Kidney Margin (OD04340) | 0.0 | Stomach Margin 9060394 | 0.9 |
| Kidney Ca, Nuclear grade 3 (OD04348) | 0.0 | Gastric Cancer 064005 | 0.0 |

TABLE RD

Panel 3D

| Tissue Name | Rel. Exp. (%) Ag3236, Run 182114365 | Tissue Name | Rel. Exp. (%) Ag3236, Run 182114365 |
| --- | --- | --- | --- |
| Daoy-Medulloblastoma | 0.6 | Ca Ski-Cervical epidermoid carcinoma (metastasis) | 0.0 |
| TE671-Medulloblastoma | 0.0 | ES-2-Ovarian clear cell carcinoma | 0.0 |
| D283 Med-Medulloblastoma | 0.0 | Ramos-Stimulated with PMA/ionomycin 6 h | 0.0 |
| PFSK-1-Primitive Neuroectodermal | 0.2 | Ramos-Stimulated with PMA/ionomycin 14 h | 0.0 |
| XF-498-CNS | 100.0 | MEG-01-Chronic myelogenous leukemia (megokaryoblast) | 0.0 |
| SNB-78-Glioma | 32.5 | Raji-Burkitt's lymphoma | 0.0 |
| SF-268-Glioblastoma | 0.3 | Daudi-Burkitt's lymphoma | 0.0 |
| T98G-Glioblastoma | 0.2 | U266-B-cell plasmacytoma | 0.2 |
| SK-N-SH-Neuroblastoma (metastasis) | 0.0 | CA46-Burkitt's lymphoma | 0.0 |
| SF-295-Glioblastoma | 6.3 | RL-non-Hodgkin's B-cell lymphoma | 0.0 |
| Cerebellum | 0.0 | JM1-pre-B-cell lymphoma | 0.0 |
| Cerebellum | 0.0 | Jurkat-T cell leukemia | 0.0 |
| NCI-H292-Mucoepidermoid lung carcinoma | 0.0 | TF-1-Erythroleukemia | 0.2 |
| DMS-114-Small cell lung cancer | 0.0 | HUT 78-T-cell lymphoma | 0.2 |
| DMS-79-Small cell lung cancer | 0.0 | U937-Histiocytic lymphoma | 0.0 |

TABLE RD-continued

Panel 3D

| Tissue Name | Rel. Exp. (%) Ag3236, Run 182114365 | Tissue Name | Rel. Exp. (%) Ag3236, Run 182114365 |
|---|---|---|---|
| NCI-H146-Small cell lung cancer | 0.0 | KU-812-Myelogenous leukemia | 0.0 |
| NCI-H526-Small cell lung cancer | 0.0 | 769-P-Clear cell renal carcinoma | 0.0 |
| NCI-N417-Small cell lung cancer | 0.0 | Caki-2-Clear cell renal carcinoma | 0.0 |
| NCI-H82-Small cell lung cancer | 0.0 | SW 839-Clear cell renal carcinoma | 0.0 |
| NCI-H157-Squamous cell lung cancer (metastasis) | 0.0 | G401-Wilms' tumor | 0.5 |
| NCI-H1155-Large cell lung cancer | 0.0 | Hs766T-Pancreatic carcinoma (LN metastasis) | 0.7 |
| NCI-H1299-Large cell lung cancer | 0.0 | CAPAN-1-Pancreatic adenocarcinoma (liver metastasis) | 0.0 |
| NCI-H727-Lung carcinoid | 0.0 | SU86.86-Pancreatic carcinoma (liver metastasis) | 0.2 |
| NCI-UMC-11-Lung carcinoid | 0.0 | BxPC-3-Pancreatic adenocarcinoma | 0.0 |
| LX-1-Small cell lung cancer | 0.0 | HPAC-Pancreatic adenocarcinoma | 0.0 |
| Colo-205-Colon cancer | 0.0 | MIA PaCa-2-Pancreatic carcinoma | 0.0 |
| KM12-Colon cancer | 0.0 | CFPAC-1-Pancreatic ductal adenocarcinoma | 0.0 |
| KM20L2-Colon cancer | 0.0 | PANC-1-Pancreatic epithelioid ductal carcinoma | 1.6 |
| NCI-H716-Colon cancer | 0.0 | T24-Bladder carcinma (transitional cell) | 0.0 |
| SW-48-Colon adenocarcinoma | 0.0 | 5637-Bladder carcinoma | 0.0 |
| SW1116-Colon adenocarcinoma | 0.0 | HT-1197-Bladder carcinoma | 0.1 |
| LS 174T-Colon adenocarcinoma | 0.0 | UM-UC-3-Bladder carcinma (transitional cell) | 0.0 |
| SW-948-Colon adenocarcinoma | 0.0 | A204-Rhabdomyosarcoma | 0.9 |
| SW-480-Colon adenocarcinoma | 0.0 | HT-1080-Fibrosarcoma | 0.3 |
| NCI-SNU-5-Gastric carcinoma | 0.0 | MG-63-Osteosarcoma | 0.0 |
| KATO III-Gastric carcinoma | 0.0 | SK-LMS-1-Leiomyosarcoma (vulva) | 0.0 |
| NCI-SNU-16-Gastric carcinoma | 4.4 | SJRH30-Rhabdomyosarcoma (met to bone marrow) | 0.0 |
| NCI-SNU-1-Gastric carcinoma | 0.0 | A431-Epidermoid carcinoma | 0.0 |
| RF-1-Gastric adenocarcinoma | 0.0 | WM266-4-Melanoma | 0.7 |
| RF-48-Gastric adenocarcinoma | 0.0 | DU 145-Prostate carcinoma (brain metastasis) | 0.0 |
| MKN-45-Gastric carcinoma | 0.0 | MDA-MB-468-Breast adenocarcinoma | 0.0 |
| NCI-N87-Gastric carcinoma | 0.0 | SCC-4-Squamous cell carcinoma of tongue | 0.0 |
| OVCAR-5-Ovarian carcinoma | 0.0 | SCC-9-Squamous cell carcinoma of tongue | 0.0 |
| RL95-2-Uterine carcinoma | 0.0 | SCC-15-Squamous cell carcinoma of tongue | 0.0 |
| HelaS3-Cervical adenocarcinoma | 0.0 | CAL 27-Squamous cell carcinoma of tongue | 0.0 |

TABLE RE

Panel 4D

| Tissue Name | Rel. Exp. (%) Ag3236, Run 164328488 | Tissue Name | Rel. Exp. (%) Ag3236, Run 164328488 |
|---|---|---|---|
| Secondary Th1 act | 0.0 | HUVEC IL-1 beta | 0.0 |
| Secondary Th2 act | 0.0 | HUVEC IFN gamma | 0.0 |
| Secondary Tr1 act | 0.0 | HUVEC TNF alpha + IFN gamma | 0.0 |

TABLE RE-continued

Panel 4D

| Tissue Name | Rel. Exp. (%) Ag3236, Run 164328488 | Tissue Name | Rel. Exp. (%) Ag3236, Run 164328488 |
| --- | --- | --- | --- |
| Secondary Th1 rest | 0.0 | HUVEC TNF alpha + IL4 | 0.0 |
| Secondary Th2 rest | 0.0 | HUVEC IL-11 | 0.0 |
| Secondary Tr1 rest | 0.7 | Lung Microvascular EC none | 0.0 |
| Primary Th1 act | 0.0 | Lung Microvascular EC TNF alpha + IL-1 beta | 0.6 |
| Primary Th2 act | 0.0 | Microvascular Dermal EC none | 0.6 |
| Primary Tr1 act | 0.0 | Microsvascular Dermal EC TNF alpha + IL-1 beta | 0.0 |
| Primary Th1 rest | 0.0 | Bronchial epithelium TNF alpha + IL1 beta | 1.1 |
| Primary Th2 rest | 0.0 | Small airway epithelium none | 3.2 |
| Primary Tr1 rest | 0.0 | Small airway epithelium TNF alpha + IL-1 beta | 0.0 |
| CD45RA CD4 lymphocyte act | 4.6 | Coronery artery SMC rest | 41.5 |
| CD45RO CD4 lymphocyte act | 1.2 | Coronery artery SMC TNF alpha + IL-1 beta | 54.3 |
| CD8 lymphocyte act | 0.0 | Astrocytes rest | 17.1 |
| Secondary CD8 lymphocyte rest | 0.0 | Astrocytes TNF alpha + IL-1 beta | 17.4 |
| Secondary CD8 lymphocyte act | 0.0 | KU-812 (Basophil) rest | 0.5 |
| CD4 lymphocyte none | 0.0 | KU-812 (Basophil) PMA/ionomycin | 0.0 |
| 2ry Th1/Th2/Tr1_anti-CD95 CH11 | 0.0 | CCD1106 (Keratinocytes) none | 0.0 |
| LAK cells rest | 0.0 | CCD1106 (Keratinocytes) TNF alpha + IL-1 beta | 0.7 |
| LAK cells IL-2 | 0.0 | Liver cirrhosis | 5.2 |
| LAK cells IL-2 + IL-12 | 0.0 | Lupus kidney | 0.0 |
| LAK cells IL-2 + IFN gamma | 0.0 | NCI-H292 none | 0.0 |
| LAK cells IL-2 + IL-18 | 0.0 | NCI-H292 IL-4 | 0.7 |
| LAK cells PMA/ionomycin | 0.0 | NCI-H292 IL-9 | 0.0 |
| NK Cells IL-2 rest | 0.0 | NCI-H292 IL-13 | 0.0 |
| Two Way MLR 3 day | 0.0 | NCI-H292 IFN gamma | 0.0 |
| Two Way MLR 5 day | 0.0 | HPAEC none | 0.0 |
| Two Way MLR 7 day | 0.0 | HPAEC TNF alpha + IL-1 beta | 1.7 |
| PBMC rest | 0.0 | Lung fibroblast none | 15.9 |
| PBMC PWM | 0.0 | Lung fibroblast TNF alpha + IL-1 beta | 100.0 |
| PBMC PHA-L | 0.0 | Lung fibroblast IL-4 | 24.1 |
| Ramos (B cell) none | 0.0 | Lung fibroblast IL-9 | 26.6 |
| Ramos (B cell) ionomycin | 0.0 | Lung fibroblast IL-13 | 6.6 |
| B lymphocytes PWM | 0.0 | Lung fibroblast IFN gamma | 28.3 |
| B lymphocytes CD40L and IL-4 | 0.7 | Dermal fibroblast CCD1070 rest | 46.3 |
| EOL-1 dbcAMP | 0.0 | Dermal fibroblast CCD1070 TNF alpha | 34.6 |
| EOL-1 dbcAMP PMA/ionomycin | 0.0 | Dermal fibroblast CCD1070 IL-1 beta | 74.2 |
| Dendritic cells none | 0.0 | Dermal fibroblast IFN gamma | 81.2 |
| Dendritic cells LPS | 0.0 | Dermal fibroblast IL-4 | 82.9 |
| Dendritic cells anti-CD40 | 0.0 | IBD Colitis 2 | 0.7 |
| Monocytes rest | 0.0 | IBD Crohn's | 1.3 |
| Monocytes LPS | 0.0 | Colon | 5.0 |
| Macrophages rest | 0.0 | Lung | 35.4 |
| Macrophages LPS | 0.0 | Thymus | 0.0 |
| HUVEC none | 0.0 | Kidney | 4.2 |
| HUVEC starved | 0.0 | | |

CNS_neurodegeneration_v1.0 Summary: Ag3236 Expression of the CG57436-01 is low/undetectable in all samples on this panel (CTs>35). (Data not shown.)

General_screening_panel_v1.4 Summary: Ag3236 Highest expression of the CG57436-01 gene is seen in a brain cancer cell line (CT=23.6). Significant levels of expression are also seen in a cluster of cell lines derived from brain cancer and melanoma. Thus, expression of this gene could be used to differentiate between these samples and other samples on this panel and as a diagnostic marker for the presence of these cancers. Furthermore, therapeutic modulation of the expression or function of this gene or gene product may be effective in the treatment of brain cancer or melanoma.

Among tissues with metabolic function, this gene is expressed at moderate/low levels in pancreas, adrenal gland, adipose, adult and fetal skeletal muscle and adult heart. This widespread expression suggests that this gene may play a role in normal metabolic function and that dysregulated expression of this gene may contribute to metabolic diseases, such as obesity and diabetes.

Panel 2.2 Summary: Ag3236 Highest expression of the CG57436-01 gene is seen in a breast cancer metastasis (CT=29). Significant expression is also seen in a cluster fo breast cancer samples. This is in concordance with the expression in General_screening_panel_v1.4, where expression is predominantly in cancer cell lines. Thus, expression of this gene could be used to differentiate between these sample and other samples on this panel and as a marker to detect the presence of breast cancer. Furthermore, therapeutic modulation of the expression or function of this gene may be effective in the treatment of breast cancer.

Panel 3D Summary: Ag3236 Highest expression of the CG57436-01 gene is seen in brain cancer cell lines, consistent with General_screening_panel_v1.4. Thus, expression of this gene could be used to differentiate between this sample and other samples on this panel.

Panel 4D Summary: Ag3236 Highest expression of the CG57436-01 gene is seen in a cluster of treated and untreated samples derived from lung and dermal fibroblasts, with highest expression in TNF-alpha and IL-1 beta treated lung fibroblasts (CT=29.8). Therefore, therapeutic antibody antagonists that block the binding of von Willebrand factor or other proteins to the CG57436-01 gene product may be useful in the treatment of disorders that involve activation of the coagulation cascade or binding by other ligands, including clotting disorders, atherosclerosis, cardiovascular disease, and autoimmune and inflammatory diseases, such as Crohn's disease, ulcerative colitis, multiple sclerosis, chronic obstructive pulmonary disease, asthma, emphysema, rheumatoid arthritis, lupus erythematosus, or psoriasis.

S. NOV22: GARPIN-like

Expression of gene CG57529-01 was assessed using the primer-probe set Ag3276, described in Table SA. Results of the RTQ-PCR runs are shown in Tables SB, SC and SD.

TABLE SA

Probe Name Ag3276

| Primers | Sequences | | Length | Start Position |
|---|---|---|---|---|
| Forward | 5'-acatgagccacaatcagatctc-3' | (SEQ ID NO:368) | 22 | 1274 |
| Probe | TET-5'-actttgtccctgccagctgcct-3'-TAMRA | (SEQ ID NO:369) | 23 | 1296 |
| Reverse | 5'-attcctgaaatccacacagcta-3' | (SEQ ID NO:370) | 22 | 1338 |

TABLE SB

CNS_neurodegeneration_v1.0

| Tissue Name | Rel. Exp. (%) Ag3276, Run 206533680 | Tissue Name | Rel. Exp. (%) Ag3276, Run 206533680 |
|---|---|---|---|
| AD 1 Hippo | 27.4 | Control (Path) 3 Temporal Ctx | 6.7 |
| AD 2 Hippo | 57.0 | Control (Path) 4 Temporal Ctx | 18.9 |
| AD 3 Hippo | 4.2 | AD 1 Occipital Ctx | 20.7 |
| AD 4 Hippo | 4.4 | AD 2 Occipital Ctx (Missing) | 0.0 |
| AD 5 hippo | 88.3 | AD 3 Occipital Ctx | 12.4 |
| AD 6 Hippo | 97.9 | AD 4 Occipital Ctx | 8.7 |
| Control 2 Hippo | 38.4 | AD 5 Occipital Ctx | 10.5 |
| Control 4 Hippo | 42.9 | AD 6 Occipital Ctx | 46.3 |
| Control (Path) 3 Hippo | 2.8 | Control 1 Occipital Ctx | 5.5 |
| AD 1 Temporal Ctx | 6.3 | Control 2 Occipital Ctx | 48.0 |
| AD 2 Temporal Ctx | 27.2 | Control 3 Occipital Ctx | 9.8 |
| AD 3 Temporal Ctx | 6.4 | Control 4 Occipital Ctx | 8.8 |
| AD 4 Temporal Ctx | 15.5 | Control (Path) 1 Occipital Ctx | 66.9 |
| AD 5 Inf Temporal Ctx | 66.0 | Control (Path) 2 Occipital Ctx | 6.0 |
| AD 5 SupTemporal Ctx | 100.0 | Control (Path) 3 Occipital Ctx | 2.6 |
| AD 6 Inf Temporal Ctx | 98.6 | Control (Path) 4 Occipital Ctx | 24.7 |
| AD 6 Sup Temporal Ctx | 99.3 | Control 1 Parietal Ctx | 6.4 |
| Control 1 Temporal Ctx | 6.7 | Control 2 Parietal Ctx | 33.9 |
| Control 2 Temporal Ctx | 29.3 | Control 3 Parietal Ctx | 14.3 |
| Control 3 Temporal Ctx | 5.3 | Control (Path) 1 Parietal Ctx | 60.7 |
| Control 4 Temporal Ctx | 14.9 | Control (Path) 2 Parietal Ctx | 21.6 |
| Control (Path) 1 Temporal Ctx | 53.2 | Control (Path) 3 Parietal Ctx | 2.4 |
| Control (Path) 2 Temporal Ctx | 24.0 | Control (Path) 4 Parietal Ctx | 32.1 |

TABLE SC

Panel 1.3D

| Tissue Name | Rel. Exp. (%) Ag3276, Run 165524215 | Tissue Name | Rel. Exp. (%) Ag3276, Run 165524215 |
|---|---|---|---|
| Liver adenocarcinoma | 0.5 | Kidney (fetal) | 2.6 |
| Pancreas | 1.6 | Renal ca. 786-0 | 0.0 |
| Pancreatic ca. CAPAN 2 | 0.4 | Renal ca. A498 | 0.3 |
| Adrenal gland | 9.0 | Renal ca. RXF 393 | 0.0 |
| Thyroid | 6.0 | Renal ca. ACHN | 0.4 |
| Salivary gland | 4.3 | Renal ca. UO-31 | 0.4 |
| Pituitary gland | 4.2 | Renal ca. TK-10 | 0.7 |
| Brain (fetal) | 1.7 | Liver | 4.0 |
| Brain (whole) | 8.5 | Liver (fetal) | 25.7 |
| Brain (amygdala) | 9.8 | Liver ca. (hepatoblast) HepG2 | 0.0 |
| Brain (cerebellum) | 7.3 | Lung | 15.2 |
| Brain (hippocampus) | 8.8 | Lung (fetal) | 7.3 |
| Brain (substantia nigra) | 7.3 | Lung ca. (small cell) LX-1 | 0.4 |
| Brain (thalamus) | 5.3 | Lung ca. (small cell) NCI-H69 | 0.0 |
| Cerebral Cortex | 4.0 | Lung ca. (s. cell var.) SHP-77 | 3.5 |
| Spinal cord | 16.6 | Lung ca. (large cell) NCI-H460 | 1.3 |
| glio/astro U87-MG | 9.0 | Lung ca. (non-sm. cell) A549 | 0.5 |
| glio/astro U-118-MG | 7.7 | Lung ca. (non-s. cell) NCI-H23 | 1.4 |
| astrocytoma SW1783 | 0.7 | Lung ca. (non-s. cell) HOP-62 | 0.2 |
| neuro*; met SK-N-AS | 0.7 | Lung ca. (non-s. cl) NCI-H522 | 0.0 |
| astrocytoma SF-539 | 3.1 | Lung ca. (squam.) SW 900 | 4.4 |
| astrocytoma SNB-75 | 1.8 | Lung ca. (squam.) NCI-H596 | 0.0 |
| glioma SNB-19 | 0.8 | Mammary gland | 17.4 |
| glioma U251 | 1.6 | Breast ca.* (pl. ef) MCF-7 | 0.0 |
| glioma SF-295 | 0.0 | Breast ca.* (pl. ef) MDA-MB-231 | 4.5 |
| Heart (fetal) | 3.8 | Breast ca.* (pl. ef) T47D | 0.0 |
| Heart | 5.2 | Breast ca. BT-549 | 15.7 |
| Skeletal muscle (fetal) | 7.7 | Breast ca. MDA-N | 21.6 |
| Skeletal muscle | 2.9 | Ovary | 5.7 |
| Bone marrow | 33.9 | Ovarian ca. OVCAR-3 | 2.2 |
| Thymus | 7.3 | Ovarian ca. OVCAR-4 | 0.0 |
| Spleen | 42.6 | Ovarian ca. OVCAR-5 | 0.8 |
| Lymph node | 37.4 | Ovarian ca. OVCAR-8 | 0.0 |
| Colorectal | 1.1 | Ovarian ca. IGROV-1 | 1.7 |
| Stomach | 7.5 | Ovarian ca.* (ascites) SK-OV-3 | 0.4 |
| Small intestine | 18.9 | Uterus | 14.3 |
| Colon ca. SW480 | 1.5 | Placenta | 8.6 |
| Colon ca.* SW620 (SW480 met) | 1.5 | Prostate | 4.2 |
| Colon ca. HT29 | 0.4 | Prostate ca.* (bone met) PC-3 | 0.4 |
| Colon ca. HCT-116 | 0.0 | Testis | 3.1 |
| Colon ca. CaCo-2 | 1.2 | Melanoma Hs688 (A).T | 0.4 |
| Colon ca. tissue (ODO3866) | 4.7 | Melanoma* (met) Hs688 (B).T | 0.0 |
| Colon ca. HCC-2998 | 0.6 | Melanoma UACC-62 | 25.0 |
| Gastric ca.* (liver met) NCI-N87 | 0.8 | Melanoma M14 | 100.0 |
| Bladder | 4.0 | Melanoma LOX IMVI | 0.0 |
| Trachea | 5.5 | Melanoma* (met) SK-MEL-5 | 4.4 |
| Kidney | 1.8 | Adipose | 5.0 |

TABLE SD

Panel 4D

| Tissue Name | Rel. Exp. (%) Ag3276, Run 164635082 | Tissue Name | Rel. Exp. (%) Ag3276, Run 164635082 |
|---|---|---|---|
| Secondary Th1 act | 34.6 | HUVEC IL-1 beta | 1.9 |
| Secondary Th2 act | 26.2 | HUVEC IFN gamma | 5.3 |
| Secondary Tr1 act | 23.3 | HUVEC TNF alpha + IFN gamma | 0.7 |
| Secondary Th1 rest | 4.9 | HUVEC TNF alpha + IL4 | 0.9 |
| Secondary Th2 rest | 12.0 | HUVEC IL-11 | 3.8 |
| Secondary Tr1 rest | 15.3 | Lung Microvascular EC none | 2.3 |
| Primary Th1 act | 18.9 | Lung Microvascular EC TNF alpha + IL-1 beta | 0.2 |
| Primary Th2 act | 17.0 | Microsvasular Dermal EC none | 1.4 |
| Primary Tr1 act | 27.0 | Microvascular Dermal EC TNF alpha + IL-1 beta | 0.5 |
| Primary Th1 rest | 67.8 | Bronchial epithelium TNF alpha + IL1 beta | 0.4 |
| Primary Th2 rest | 40.9 | Small airway epithelium none | 0.2 |
| Primary Tr1 rest | 18.8 | Small airway epithelium TNF alpha + IL-1 beta | 0.0 |
| CD45RA CD4 lymphocyte act | 12.7 | Coronery artery SMC rest | 0.2 |
| CD45RO CD4 lymphocyte act | 26.1 | Coronery artery SMC TNF alpha + IL-1 beta | 0.0 |
| CD8 lymphocyte act | 18.0 | Astrocytes rest | 0.0 |
| Secondary CD8 lymphocyte rest | 19.2 | Astrocytes TNF alpha + IL-1 beta | 0.1 |
| Secondary CD8 lymphocyte act | 21.9 | KU-812 (Basophil) rest | 34.2 |
| CD4 lymphocyte none | 2.6 | KU-812 (Basophil) PMA/ionomycin | 66.0 |
| 2ry Th1/Th2/Tr1_anti-CD95 CH11 | 10.2 | CCD1106 (Keratinocytes) none | 0.3 |
| LAK cells rest | 62.9 | CCD1106 (Keratinocytes) TNF alpha + IL-1 beta | 0.2 |
| LAK cells IL-2 | 30.8 | Liver cirrhosis | 1.1 |
| LAK cells IL-2 + IL-12 | 20.2 | Lupus kidney | 0.6 |
| LAK cells IL-2 + IFN gamma | 30.1 | NCI-H292 none | 0.1 |
| LAK cells IL-2 + IL-18 | 18.2 | NCI-H292 IL-4 | 0.0 |
| LAK cells PMA/ionomycin | 12.9 | NCI-H292 IL-9 | 0.1 |
| NK Cells IL-2 rest | 24.3 | NCI-H292 IL-13 | 0.2 |
| Two Way MLR 3 day | 40.3 | NCI-H292 IFN gamma | 0.0 |
| Two Way MLR 5 day | 21.9 | HPAEC none | 2.7 |
| Two Way MLR 7 day | 17.8 | HPAEC TNF alpha + IL-1 beta | 0.6 |
| PBMC rest | 13.7 | Lung fibroblast none | 0.3 |
| PBMC PWM | 46.7 | Lung fibroblast TNF alpha + IL-1 beta | 1.3 |
| PBMC PHA-L | 22.1 | Lung fibroblast IL-4 | 1.4 |
| Ramos (B cell) none | 0.5 | Lung fibroblast IL-9 | 1.5 |
| Ramos (B cell) ionomycin | 5.4 | Lung fibroblast IL-13 | 1.5 |
| B lymphocytes PWM | 50.3 | Lung fibroblast IFN gamma | 1.8 |
| B lymphocytes CD40L and IL-4 | 7.4 | Dermal fibroblast CCD1070 rest | 0.3 |
| EOL-1 dbcAMP | 46.0 | Dermal fibroblast CCD1070 TNF alpha | 45.7 |
| EOL-1 dbcAMP PMA/ionomycin | 34.4 | Dermal fibroblast CCD1070 IL-1 beta | 0.0 |
| Dendritic cells none | 76.3 | Dermal fibroblast IFN gamma | 0.8 |
| Dendritic cells LPS | 30.6 | Dermal fibroblast IL-4 | 0.8 |
| Dendritic cells anti-CD40 | 69.7 | IBD Colitis 2 | 0.3 |
| Monocytes rest | 60.7 | IBD Crohn's | 0.2 |
| Monocytes LPS | 20.6 | Colon | 2.9 |
| Macrophages rest | 100.0 | Lung | 7.6 |
| Macrophages LPS | 34.9 | Thymus | 1.0 |
| HUVEC none | 3.6 | Kidney | 10.8 |
| HUVEC starved | 7.8 | | |

CNS_neurodegeneration_v1.0 Summary: Ag3276 This panel does not show differential expression of the CG57529-01 gene in Alzheimer's disease. However, this expression profile confirms the presence of this gene in the brain. Please see Panel 1.3D for discussion of utility of this gene in the central nervous system.

Panel 1.3D Summary: Ag3276 Highest expression of the CG57529-01 gene is seen in a melanoma cell line (CT= 28.5). Significant expression is also seen in a cluster of breast cancer and melanoma cell lines. Thus, expression of this gene could be used to differentiate between these samples and other samples on this panel and as a diagnostic marker for the presence of these cancers. Furthermore, therapeutic modulation of the expression or function of this gene may be effective in the treatment of breast cancer or melanoma.

This gene encodes a type 1 membrane protein with several leucine-rich-repeat domains, indicating that this gene product may be involved in extracellular signalling and/or interactions with the extracellular matrix. Among metabolically relevant tissues, this gene is expressed at low but significant levels in the adrenal gland, thyroid, pancreas, adipose, and fetal and adult heart, skeletal muscle and liver. As a potential extracellular signalling molecule, the this gene product may serve as an antibody target for diseases involving any or all of these tissues, including obesity and diabetes.

This gene is also detected in several regions of the CNS including amygdala, cerebellum, substantia nigra, hippocampus, thalamus, cerebral cortex and spinal cord. In *Drosophilia*, the LRR region of axon guidance proteins has been shown to be critical for function (especially in axon repulsion) (ref. 1). Since this gene encodes a leucine-rich-repeat protein that is expressed across all brain regions, it is an excellent candidate neuronal guidance protein for axons, dendrites and/or growth cones in general. Therefore, therapeutic modulation of the levels of this protein, or possible signaling via this protein, may be of utility in enhancing/directing compensatory synaptogenesis and fiber growth in the CNS in response to neuronal death (stroke, head trauma), axon lesion (spinal cord injury), or neurodegeneration (Alzheimer's, Parkinson's, Huntington's, vascular dementia or any neurodegenerative disease) (Battye et al., J. Neurosci. 21: 4290–4298, 2001).

Panel 4D Summary: Ag3276 Highest expression of the CG57529_01 transcript is found in resting macrophages and dendritic cells (CTs=25–27), cells that play a crucial role in antigen presentation that acts to activate or tolerize T cells. Significant expression of this transcript is also found in most of the cell types across this panel. This expression in cells that play a role in linking innate immunity to adaptive immunity suggests a role for this gene product in initiating inflammatory reactions. Therefore, modulation of the expression or activity of this gene may reduce or prevent early stages of inflammation and reduce the severity of inflammatory diseases such as psoriasis, asthma, inflammatory bowel disease, rheumatoid arthritis, osteoarthritis and other lung inflammatory diseases.

T. NOV23: Centaurin Beta-2

Expression of gene CG57351-01 was assessed using the primer-probe set Ag3208, described in Table TA. Results of the RTQ-PCR runs are shown in Tables TB, TC, TD and TE.

TABLE TA

Probe Name Ag3208

| Primers | Sequences | | Length | Start Position |
|---|---|---|---|---|
| Forward | 5'-cagcaacgctttcaagacat-3' | (SEQ ID NO:371) | 20 | 848 |
| Probe | TET-5'-ttctccattcagaacagccagctggt-3'-TAMRA | (SEQ ID NO:372) | 26 | 882 |
| Reverse | 5'-catccttgagcttcttctggta-3' | (SEQ ID NO:373) | 22 | 909 |

TABLE TB

CNS_neurodegeneration_v1.0

| Tissue Name | Rel. Exp. (%) Ag3208, Run 209861777 | Tissue Name | Rel. Exp. (%) Ag3208, Run 209861777 |
|---|---|---|---|
| AD 1 Hippo | 19.5 | Control (Path) 3 Temporal Ctx | 3.1 |
| AD 2 Hippo | 29.5 | Control (Path) 4 Temporal Ctx | 34.4 |
| AD 3 Hippo | 8.1 | AD 1 Occipital Ctx | 12.2 |
| AD 4 Hippo | 7.3 | AD 2 Occipital Ctx (Missing) | 0.0 |
| AD 5 hippo | 93.3 | AD 3 Occipital Ctx | 3.8 |
| AD 6 Hippo | 42.9 | AD 4 Occipital Ctx | 18.2 |
| Control 2 Hippo | 32.3 | AD 5 Occipital Ctx | 16.7 |
| Control 4 Hippo | 12.2 | AD 6 Occipital Ctx | 42.3 |
| Control (Path) 3 Hippo | 5.2 | Control 1 Occipital Ctx | 3.1 |
| AD 1 Temporal Ctx | 14.4 | Control 2 Occipital Ctx | 79.0 |
| AD 2 Temporal Ctx | 33.7 | Control 3 Occipital Ctx | 13.9 |
| AD 3 Temporal Ctx | 6.7 | Control 4 Occipital Ctx | 2.8 |
| AD 4 Temporal Ctx | 26.8 | Control (Path) 1 Occipital Ctx | 90.8 |
| AD 5 Inf Temporal Ctx | 100.0 | Control (Path) 2 Occipital Ctx | 14.3 |
| AD 5 SupTemporal Ctx | 58.6 | Control (Path) 3 Occipital Ctx | 1.5 |
| AD 6 Inf Temporal Ctx | 41.5 | Control (Path) 4 Occipital Ctx | 21.9 |
| AD 6 Sup Temporal Ctx | 44.1 | Control 1 Parietal Ctx | 7.3 |
| Control 1 Temporal Ctx | 5.0 | Control 2 Parietal Ctx | 52.5 |
| Control 2 Temporal Ctx | 61.6 | Control 3 Parietal Ctx | 22.7 |

TABLE TB-continued

CNS_neurodegeneration_v1.0

| Tissue Name | Rel. Exp. (%) Ag3208, Run 209861777 | Tissue Name | Rel. Exp. (%) Ag3208, Run 209861777 |
|---|---|---|---|
| Control 3 Temporal Ctx | 15.1 | Control (Path) 1 Parietal Ctx | 87.1 |
| Control 4 Temporal Ctx | 11.7 | Control (Path) 2 Parietal Ctx | 20.6 |
| Control (Path) 1 Temporal Ctx | 72.7 | Control (Path) 3 Parietal Ctx | 3.6 |
| Control (Path) 2 Temporal Ctx | 46.0 | Control (Path) 4 Parietal Ctx | 43.2 |

TABLE TC

Panel 1.3D

| Tissue Name | Rel. Exp. (%) Ag3208, Run 168012842 | Tissue Name | Rel. Exp. (%) Ag3208, Run 168012842 |
|---|---|---|---|
| Liver adenocarcinoma | 10.2 | Kidney (fetal) | 15.3 |
| Pancreas | 7.2 | Renal ca. 786-0 | 5.0 |
| Pancreatic ca. CAPAN 2 | 3.9 | Renal ca. A498 | 6.8 |
| Adrenal gland | 4.9 | Renal ca. RXF 393 | 10.4 |
| Thyroid | 4.7 | Renal ca. ACHN | 3.8 |
| Salivary gland | 11.0 | Renal ca. UO-31 | 5.9 |
| Pituitary gland | 20.3 | Renal ca. TK-10 | 2.0 |
| Brain (fetal) | 73.2 | Liver | 5.3 |
| Brain (whole) | 99.3 | Liver (fetal) | 5.2 |
| Brain (amygdala) | 35.8 | Liver ca. (hepatoblast) HepG2 | 10.2 |
| Brain (cerebellum) | 100.0 | Lung | 8.5 |
| Brain (hippocampus) | 21.8 | Lung (fetal) | 14.8 |
| Brain (substantia nigra) | 20.6 | Lung ca. (small cell) LX-1 | 18.0 |
| Brain (thalamus) | 29.1 | Lung ca. (small cell) NCI-H69 | 5.7 |
| Cerebral Cortex | 50.3 | Lung ca. (s. cell var.) SHP-77 | 42.3 |
| Spinal cord | 14.7 | Lung ca. (large cell) NCI-H460 | 0.6 |
| glio/astro U87-MG | 6.7 | Lung ca. (non-sm. cell) A549 | 7.1 |
| glio/astro U-118-MG | 9.7 | Lung ca. (non-s. cell) NCI-H23 | 3.7 |
| astrocytoma SW1783 | 6.7 | Lung ca. (non-s. cell) HOP-62 | 5.6 |
| neuro*; met SK-N-AS | 7.7 | Lung ca. (non-s. cl) NCI-H522 | 6.0 |
| astrocytoma SF-539 | 11.7 | Lung ca. (squam.) SW 900 | 7.2 |
| astrocytoma SNB-75 | 13.9 | Lung ca. (squam.) NCI-H596 | 11.7 |
| glioma SNB-19 | 3.1 | Mammary gland | 16.7 |
| glioma U251 | 19.6 | Breast ca.* (pl. ef) MCF-7 | 8.5 |
| glioma SF-295 | 9.8 | Breast ca.* (pl. ef) MDA-MB-231 | 8.7 |
| Heart (fetal) | 37.1 | Breast ca.* (pl. ef) T47D | 9.7 |
| Heart | 9.0 | Breast ca. BT-549 | 5.2 |
| Skeletal muscle (fetal) | 12.8 | Breast ca. MDA-N | 5.5 |
| Skeletal muscle | 10.2 | Ovary | 4.9 |
| Bone marrow | 4.7 | Ovarian ca. OVCAR-3 | 4.3 |
| Thymus | 16.6 | Ovarian ca. OVCAR-4 | 5.0 |
| Spleen | 4.8 | Ovarian ca. OVCAR-5 | 16.5 |
| Lymph node | 6.5 | Ovarian ca. OVCAR-8 | 1.1 |
| Colorectal | 1.2 | Ovarian ca. IGROV-1 | 1.4 |
| Stomach | 6.7 | Ovarian ca.* (ascites) SK-OV-3 | 14.3 |
| Small intestine | 7.7 | Uterus | 10.5 |
| Colon ca. SW480 | 5.3 | Placenta | 2.6 |
| Colon ca.* SW620 (SW480 met) | 19.9 | Prostate | 3.4 |
| Colon ca. HT29 | 4.1 | Prostate ca.* (bone met)PC-3 | 4.2 |
| Colon ca. HCT-116 | 3.9 | Testis | 3.3 |
| Colon ca. CaCo-2 | 8.5 | Melanoma Hs688 (A).T | 3.9 |

TABLE TC-continued

Panel 1.3D

| Tissue Name | Rel. Exp. (%) Ag3208, Run 168012842 | Tissue Name | Rel. Exp. (%) Ag3208, Run 168012842 |
| --- | --- | --- | --- |
| Colon ca. tissue (ODO3866) | 3.3 | Melanoma* (met) Hs688 (B).T | 3.7 |
| Colon ca. HCC-2998 | 21.5 | Melanoma UACC-62 | 9.8 |
| Gastric ca.* (liver met) NCI-N87 | 4.6 | Melanoma M14 | 3.3 |
| Bladder | 2.0 | Melanoma LOX IMVI | 4.2 |
| Trachea | 4.7 | Melanoma* (met) SK-MEL-5 | 2.5 |
| Kidney | 9.9 | Adipose | 6.8 |

TABLE TD

Panel 4D

| Tissue Name | Rel. Exp. (%) Ag3208, Run 164531754 | Tissue Name | Rel. Exp. (%) Ag3208, Run 164531754 |
| --- | --- | --- | --- |
| Secondary Th1 act | 32.5 | HUVEC IL-1beta | 3.5 |
| Secondary Th2 act | 47.6 | HUVEC IFN gamma | 22.8 |
| Secondary Tr1 act | 53.6 | HUVEC TNF alpha + IFN gamma | 10.9 |
| Secondary Th1 rest | 14.3 | HUVEC TNF alpha + IL4 | 21.6 |
| Secondary Th2 rest | 25.2 | HUVEC IL-11 | 17.9 |
| Secondary Tr1 rest | 17.7 | Lung Microvascular EC none | 33.9 |
| Primary Th1 act | 28.5 | Lung Microvascular EC TNF alpha + IL-1beta | 37.1 |
| Primary Th2 act | 28.9 | Microvascular Dermal EC none | 48.6 |
| Primary Tr1 act | 33.0 | Microvasular Dermal EC TNF alpha + IL-1beta | 18.8 |
| Primary Th1 rest | 59.0 | Bronchial epithelium TNF alpha + IL-1beta | 43.8 |
| Primary Th2 rest | 33.7 | Small airway epithelium none | 21.5 |
| Primary Tr1 rest | 32.3 | Small airway epithelium TNF alpha + IL-1beta | 61.6 |
| CD45RA CD4 lymphocyte act | 33.0 | Coronery artery SMC rest | 21.6 |
| CD45RO CD4 lymphocyte act | 24.7 | Coronery artery SMC TNF alpha + IL-1beta | 13.7 |
| CD8 lymphocyte act | 30.1 | Astrocytes rest | 45.7 |
| Secondary CD8 lymphocyte rest | 29.7 | Astrocytes TNF alpha + IL-1beta | 32.8 |
| Secondary CD8 lymphocyte act | 30.6 | KU-812 (Basophil) rest | 24.5 |
| CD4 lymphocyte none | 13.5 | KU-812 (Basophil) PMA/ionomycin | 29.7 |
| 2ry Th1/Th2/Tr1_anti-CD95 CH11 | 36.3 | CCD1106 (Keratinocytes) none | 39.8 |
| LAK cells rest | 25.0 | CCD1106 (Keratinocytes) TNF alpha + IL-1beta | 25.0 |
| LAK cells IL-2 | 31.9 | Liver cirrhosis | 2.6 |
| LAK cells IL-2 + IL-12 | 19.9 | Lupus kidney | 5.8 |
| LAK cells IL-2 + IFN gamma | 26.2 | NCI-H292 none | 15.8 |
| LAK cells IL-2 + IL-18 | 29.7 | NCI-H292 IL-4 | 16.0 |
| LAK cells PMA/ionomycin | 19.8 | NCI-H292 IL-9 | 17.6 |
| NK Cells IL-2 rest | 28.3 | NCI-H292 IL-13 | 18.6 |
| Two Way MLR 3 day | 32.5 | NCI-H292 IFN gamma | 12.9 |
| Two Way MLR 5 day | 29.1 | HPAEC none | 20.0 |
| Two Way MLR 7 day | 15.4 | HPAEC TNF alpha + IL-1beta | 17.1 |
| PBMC rest | 23.8 | Lung fibroblast none | 59.0 |
| PBMC PWM | 44.4 | Lung fibroblast TNF alpha + IL-1beta | 20.3 |
| PBMC PHA-L | 44.8 | Lung fibroblast IL-4 | 73.2 |
| Ramos (B cell) none | 29.5 | Lung fibroblast IL-9 | 62.4 |
| Ramos (B cell) ionomycin | 67.8 | Lung fibroblast IL-13 | 65.1 |
| B lymphocytes PWM | 42.6 | Lung fibroblast IFN gamma | 55.1 |
| B lymphocytes CD40L and IL-4 | 31.9 | Dermal fibroblast CCD1070 rest | 89.5 |
| EOL-1 dbcAMP | 49.3 | Dermal fibroblast CCD1070 TNF alpha | 72.7 |

TABLE TD-continued

Panel 4D

| Tissue Name | Rel. Exp. (%) Ag3208, Run 164531754 | Tissue Name | Rel. Exp. (%) Ag3208, Run 164531754 |
| --- | --- | --- | --- |
| EOL-1 dbcAMP PMA/ionomycin | 42.3 | Dermal fibroblast CCD1070 IL-1beta | 43.2 |
| Dendritic cells none | 31.6 | Dermal fibroblast IFN gamma | 39.5 |
| Dendritic cells LPS | 21.2 | Dermal fibroblast IL-4 | 73.7 |
| Dendritic cells anti-CD40 | 33.0 | IBD Colitis 2 | 5.0 |
| Monocytes rest | 57.4 | IBD Crohn's | 3.4 |
| Monocytes LPS | 11.0 | Colon | 36.6 |
| Macrophages rest | 51.1 | Lung | 23.2 |
| Macrophages LPS | 5.8 | Thymus | 59.0 |
| HUVEC none | 28.3 | Kidney | 100.0 |
| HUVEC starved | 32.1 | | |

TABLE TE

Panel CNS_1

| Tissue Name | Rel. Exp. (%) Ag3208, Run 171694583 | Tissue Name | Rel. Exp. (%) Ag3208, Run 171694583 |
| --- | --- | --- | --- |
| BA4 Control | 17.9 | BA17 PSP | 9.7 |
| BA4 Control2 | 44.1 | BA17 PSP2 | 11.0 |
| BA4 Alzheimer's2 | 5.3 | Sub Nigra Control | 26.6 |
| BA4 Parkinson's | 37.6 | Sub Nigra Control2 | 23.5 |
| BA4 Parkinson's2 | 61.1 | Sub Nigra Alzheimer's2 | 10.7 |
| BA4 Huntington's | 32.8 | Sub Nigra Parkinson's2 | 31.2 |
| BA4 Huntington's2 | 14.5 | Sub Nigra Huntington's | 37.9 |
| BA4 PSP | 7.3 | Sub Nigra Huntington's2 | 24.0 |
| BA4 PSP2 | 20.4 | Sub Nigra PSP2 | 0.9 |
| BA4 Depression | 17.0 | Sub Nigra Depression | 3.4 |
| BA4 Depression2 | 3.8 | Sub Nigra Depression2 | 2.9 |
| BA7 Control | 38.2 | Glob Palladus Control | 23.5 |
| BA7 Control2 | 69.3 | Glob Palladus Control2 | 17.9 |
| BA7 Alzheimer's2 | 9.3 | Glob Palladus Alzheimer's | 4.9 |
| BA7 Parkinson's | 26.8 | Glob Palladus Alzheimer's2 | 6.9 |
| BA7 Parkinson's2 | 38.2 | Glob Palladus Parkinson's | 100.0 |
| BA7 Huntington's | 56.6 | Glob Palladus Parkinson's2 | 15.1 |
| BA7 Huntington's2 | 50.3 | Glob Palladus PSP | 2.2 |
| BA7 PSP | 22.4 | Glob Palladus PSP2 | 4.5 |
| BA7 PSP2 | 25.2 | Glob Palladus Depression | 7.5 |
| BA7 Depression | 7.7 | Temp Pole Control | 19.3 |
| BA9 Control | 27.7 | Temp Pole Control2 | 66.4 |
| BA9 Control2 | 99.3 | Temp Pole Alzheimer's | 8.2 |
| BA9 Alzheimer's | 2.2 | Temp Pole Alzheimer's2 | 7.4 |
| BA9 Alzheimer's2 | 11.0 | Temp Pole Parkinson's | 36.1 |
| BA9 Parkinson's | 37.1 | Temp Pole Parkinson's2 | 42.3 |
| BA9 Parkinson's2 | 43.2 | Temp Pole Huntington's | 39.8 |
| BA9 Huntington's | 50.3 | Temp Pole PSP | 2.5 |
| BA9 Huntington's2 | 27.2 | Temp Pole PSP2 | 5.6 |
| BA9 PSP | 8.4 | Temp Pole Depression2 | 7.5 |
| BA9 PSP2 | 1.7 | Cing Gyr Control | 50.7 |
| BA9 Depression | 6.4 | Cing Gyr Control2 | 41.2 |
| BA9 Depression2 | 12.3 | Cing Gyr Alzheimer's | 14.5 |
| BA17 Control | 52.1 | Cing Gyr Alzheimer's2 | 10.5 |
| BA17 Control2 | 57.0 | Cing Gyr Parkinson's | 30.6 |
| BA17 Alzheimer's2 | 3.3 | Cing Gyr Parkinson's2 | 33.2 |
| BA17 Parkinson's | 37.4 | Cing Gyr Huntington's | 61.6 |
| BA17 Parkinson's2 | 45.1 | Cing Gyr Huntington's2 | 23.8 |
| BA17 Huntington's | 52.1 | Cing Gry PSP | 9.4 |

TABLE TE-continued

Panel CNS_1

| Tissue Name | Rel. Exp. (%) Ag3208, Run 171694583 | Tissue Name | Rel. Exp. (%) Ag3208, Run 171694583 |
|---|---|---|---|
| BA17 Huntington's2 | 22.1 | Cing Gyr PSP2 | 5.0 |
| BA17 Depression | 8.4 | Cing Gry Depression | 3.6 |
| BA17 Depression2 | 27.5 | Cing Gyr Depression2 | 15.8 |

CNS_neurodegeneration_v1.0 Summary: Ag3208 This panel does not show differential expression of the CG57351-01 gene in Alzheimer's disease. However, this expression profile confirms the presence of this gene in the brain. Please see Panel 1.3D for discussion of utility of this gene in the central nervous system.

Panel 1.3D Summary: Ag3208 The CG57351-01 gene, a centaurin homolog, shows a brain-preferential expression pattern. Thus, the expression of this gene could be used to distinguish normal brain tissue from other samples in the panel. Because centaurins play a role in vesicular trafficking, they may be involved in synaptic vesicle movement/release. Therefore, this gene may be a drug target for the treatment of any disorder involving neurotransmission (epilepsy, bipolar disorder, schizophrenia, mania, depression, obsessive-compulsive disorder or any neuropsychiatric condition.

In addition, there appears to be substantial expression in samples derived from lung cancer cell lines and colon cancer cell lines. Moreover, therapeutic modulation of this gene, through the use of small molecule drugs, protein therapeutics or antibodies could be of benefit in the treatment of lung or colon cancer.

Among metabolic tissues, this gene is expressed at moderate levels in pancreas, adrenal, thyroid, pituitary, heart, liver, adipose and skeletal muscle. The role of centaurins in vesicular trafficking suggests that this gene may be involved in endocrine secretory processes. Therefore, this widespread expression in metabolic tissues suggests that this gene product may be important for the pathogenesis, diagnosis and/or treatment of metabolic and endocrine disease, including Types 1 and 2 diabetes and obesity.

Panel 4D Summary: Ag3208 The CG57351-01 transcript is expressed at high to moderate levels in a wide range of cell types of significance in the immune response and tissue response in health and disease. Therefore, targeting of this gene product with a small molecule drug or antibody therapeutic may modulate the functions of cells of the immune system as well as resident tissue cells and lead to improvement of the symptoms of patients suffering from autoimmune and inflammatory diseases such as COPD, emphysema, asthma, allergies, inflammatory bowel disease, lupus erythematosus, and arthritis, including osteoarthritis and rheumatoid arthritis Panel CNS_1 Summary: Ag3208 This expression profile further confirms the presence of the CG57351-01 gene in the brain. Please see Panel 1.3D for discussion of utility of this gene in the central nervous system.

U. NOV24: Sorting Nexin 9

Expression of gene CG57515-01 was assessed using the primer-probe set Ag3262, described in Table UA. Results of the RTQ-PCR runs are shown in Tables UB and UC.

TABLE UA

Probe Name Ag3262

| Primers | Sequences | | Length | Start Position |
|---|---|---|---|---|
| Forward | 5'-tccatcaaattcgagtgagaga-3' | (SEQ ID NO:374) | 22 | 1782 |
| Probe | TET-5'-tcacagatgcagcatttcttacaacaaca-3'-TAMRA | (SEQ ID NO:375) | 29 | 1811 |
| Reverse | 5'-gcttcttccaacttctgggtaa-3' | (SEQ ID NO:376) | 22 | 1860 |

TABLE UB

CNS_neurodegeneration_v1.0

| Tissue Name | Rel. Exp. (%) Ag3262, Run 210038237 | Tissue Name | Rel. Exp. (%) Ag3262, Run 210038237 |
|---|---|---|---|
| AD 1 Hippo | 12.3 | Control (Path) 3 Temporal Ctx | 7.7 |
| AD 2 Hippo | 40.6 | Control (Path) 4 Temporal Ctx | 34.9 |
| AD 3 Hippo | 14.3 | AD 1 Occipital Ctx | 26.1 |
| AD 4 Hippo | 9.5 | AD 2 Occipital Ctx (Missing) | 0.0 |
| AD 5 hippo | 84.1 | AD 3 Occipital Ctx | 15.9 |
| AD 6 Hippo | 71.2 | AD 4 Occipital Ctx | 20.3 |
| Control 2 Hippo | 30.4 | AD 5 Occipital Ctx | 21.2 |

TABLE UB-continued

CNS_neurodegeneration_v1.0

| Tissue Name | Rel. Exp. (%) Ag3262, Run 210038237 | Tissue Name | Rel. Exp. (%) Ag3262, Run 210038237 |
| --- | --- | --- | --- |
| Control 4 Hippo | 21.3 | AD 6 Occipital Ctx | 43.5 |
| Control (Path) 3 Hippo | 10.9 | Control 1 Occipital Ctx | 9.2 |
| AD 1 Temporal Ctx | 29.9 | Control 2 Occipital Ctx | 51.1 |
| AD 2 Temporal Ctx | 40.1 | Control 3 Occipital Ctx | 23.3 |
| AD 3 Temporal Ctx | 10.2 | Control 4 Occipital Ctx | 10.7 |
| AD 4 Temporal Ctx | 18.9 | Control (Path) 1 Occipital Ctx | 86.5 |
| AD 5 Inf Temporal Ctx | 100.0 | Control (Path) 2 Occipital Ctx | 10.7 |
| AD 5 SupTemporal Ctx | 74.7 | Control (Path) 3 Occipital Ctx | 5.1 |
| AD 6 Inf Temporal Ctx | 85.3 | Control (Path) 4 Occipital Ctx | 18.2 |
| AD 6 Sup Temporal Ctx | 76.8 | Control 1 Parietal Ctx | 12.2 |
| Control 1 Temporal Ctx | 14.6 | Control 2 Parietal Ctx | 69.3 |
| Control 2 Temporal Ctx | 32.5 | Control 3 Parietal Ctx | 16.3 |
| Control 3 Temporal Ctx | 17.8 | Control (Path) 1 Parietal Ctx | 72.2 |
| Control 4 Temporal Ctx | 7.8 | Control (Path) 2 Parietal Ctx | 42.3 |
| Control (Path) 1 Temporal Ctx | 62.4 | Control (Path) 3 Parietal Ctx | 12.1 |
| Control (Path) 2 Temporal Ctx | 33.9 | Control (Path) 4 Parietal Ctx | 41.8 |

TABLE UC

Panel 4D

| Tissue Name | Rel. Exp. (%) Ag3262, Run164634869 | Tissue Name | Rel. Exp. (%) Ag3262, Run 164634869 |
| --- | --- | --- | --- |
| Secondary Th1 act | 15.2 | HUVEC IL-1beta | 7.1 |
| Secondary Th2 act | 11.7 | HUVEC IFN gamma | 7.6 |
| Secondary Tr1 act | 15.3 | HUVEC TNF alpha + IFN gamma | 3.6 |
| Secondary Th1 rest | 5.2 | HUVEC TNF alpha + IL4 | 6.6 |
| Secondary Th2 rest | 5.4 | HUVEC IL-11 | 3.4 |
| Secondary Tr1 rest | 5.4 | Lung Microvascular EC none | 5.1 |
| Primary Th1 act | 2.5 | Lung Microvascular EC TNF alpha + IL-1beta | 3.5 |
| Primary Th2 act | 2.2 | Microvascular Dermal EC none | 5.7 |
| Primary Tr1 act | 3.3 | Microsvasular Dermal EC TNF alpha + IL-1beta | 2.2 |
| Primary Th1 rest | 30.6 | Bronchial epithelium TNF alpha + IL1beta | 14.4 |
| Primary Th2 rest | 18.2 | Small airway epithelium none | 5.7 |
| Primary Tr1 rest | 6.7 | Small airway epithelium TNF alpha + IL-1beta | 17.9 |
| CD45RA CD4 lymphocyte act | 15.1 | Coronery artery SMC rest | 9.8 |
| CD45RO CD4 lymphocyte act | 15.9 | Coronery artery SMC TNF alpha + IL-1beta | 7.3 |
| CD8 lymphocyte act | 11.5 | Astrocytes rest | 26.6 |
| Secondary CD8 lymphocyte rest | 5.2 | Astrocytes TNF alpha + IL-1beta | 11.0 |
| Secondary CD8 lymphocyte act | 20.0 | KU-812 (Basophil) rest | 1.4 |
| CD4 lymphocyte none | 4.3 | KU-812 (Basophil) PMA/ionomycin | 7.5 |
| 2ry Th1/Th2/Tr1 anti-CD95 CH11 | 13.2 | CCD1106 (Keratinocytes) none | 13.7 |
| LAK cells rest | 16.3 | CCD1106 (Keratinocytes) TNF alpha + IL-1beta | 6.0 |
| LAK cells IL-2 | 45.1 | Liver cirrhosis | 1.7 |
| LAK cells IL-2 + IL-12 | 13.3 | Lupus kidney | 1.4 |
| LAK cells IL-2 + IFN gamma | 18.9 | NCI-H292 none | 13.8 |
| LAK cells IL-2 + IL-18 | 14.1 | NCI-H292 IL-4 | 15.1 |
| LAK cells PMA/ionomycin | 3.5 | NCI-H292 IL-9 | 19.1 |

TABLE UC-continued

Panel 4D

| Tissue Name | Rel. Exp. (%) Ag3262, Run164634869 | Tissue Name | Rel. Exp. (%) Ag3262, Run 164634869 |
|---|---|---|---|
| NK Cells IL-2 rest | 16.8 | NCI-H292 IL-13 | 11.7 |
| Two Way MLR 3 day | 11.5 | NCI-H292 IFN gamma | 16.7 |
| Two Way MLR 5 day | 8.0 | HPAEC none | 7.3 |
| Two Way MLR 7 day | 12.0 | HPAEC TNF alpha + IL-1beta | 3.7 |
| PBMC rest | 7.4 | Lung fibroblast none | 24.7 |
| PBMC PWM | 25.7 | Lung fibroblast TNF alpha + IL-1beta | 14.1 |
| PBMC PHA-L | 6.6 | Lung fibroblast IL-4 | 100.0 |
| Ramos (B cell) none | 0.4 | Lung fibroblast IL-9 | 49.0 |
| Ramos (B cell) ionomycin | 2.2 | Lung fibroblast IL-13 | 51.8 |
| B lymphocytes PWM | 25.3 | Lung fibroblast IFN gamma | 93.3 |
| B lymphocytes CD40L and IL-4 | 17.2 | Dermal fibroblast CCD1070 rest | 30.6 |
| EOL-1 dbcAMP | 7.1 | Dermal fibroblast CCD1070 TNF alpha | 73.7 |
| EOL-1 dbcAMP PMA/ionomycin | 4.0 | Dermal fibroblast CCD1070 IL-1beta | 19.3 |
| Dendritic cells none | 11.5 | Dermal fibroblast IFN gamma | 28.9 |
| Dendritic cells LPS | 5.6 | Dermal fibroblast IL-4 | 26.2 |
| Dendritic cells anti-CD40 | 7.9 | IBD Colitis 2 | 0.8 |
| Monocytes rest | 31.9 | IBD Crohn's | 1.0 |
| Monocytes LPS | 13.8 | Colon | 10.2 |
| Macrophages rest | 14.0 | Lung | 12.4 |
| Macrophages LPS | 10.9 | Thymus | 15.9 |
| HUVEC none | 12.7 | Kidney | 4.2 |
| HUVEC starved | 16.6 | | |

CNS_neurodegeneration_v1.0 Summary: Ag3262 This panel does not show differential expression of the CG57515-01 gene in Alzheimer's disease. However, this expression profile confirms the presence of this gene, a sorting nexin homolog, in the brain. Sorting nexins have been implicated in axonal guidance; Therefore, this gene may serve as a useful drug target in diseases/clinical conditions where neurons have degenerated/died and compensatory sprouting and/or synaptogenesis is desireable (spinal cord/head trauma, stroke, Huntington's, Parkinson's, or Alzheimer's diseases) (Worby et al., J Biol Chem 2001)

General_screening_panel_v1.4 Summary: Ag3262 Results from one experiment with the CG57515-01 gene are not included. The amp plot indicates that there were experimental difficulties with this run.

Panel 4D Summary: Ag3262 Highest expression of the CG57515-01 transcript is found in lung fibroblasts treated with either Il-4 or IFNg (CT 25.5). It is also observed at high levels in dermal fibroblasts. In addition, this transcript is expressed at high to moderate levels in a wide range of cell types of significance in the immune response and tissue response in health and disease. This transcript encodes a sorting nexin 9 like (SH3PX1) protein. This protein interacts with metalloprotease disintegrins, cysteine-rich proteins that may possess diverse biological functions such as cytokine and protein processing. This interaction is consistent with the expression profile of this gene product. Therefore, this gene may be a useful target for treatment of diseases such as osteoarthritis and rheumatoid arythritis, psoriasis, asthma and chronic obstructive pulmonary diseases (Howard et al., J Biol Chem 1999 October 29;274(44):31693–9).

V. NOV26: Calpain

Expression of gene CG57509-01 was assessed using the primer-probe set Ag2073, described in Table VA. Results of the RTQ-PCR runs are shown in Tables VB and VC.

TABLE VA

Probe Name Ag2073

| Primers | Sequences | | Length | Start Position |
|---|---|---|---|---|
| Forward | 5'-acccaagtggcatctattcag-3' | (SEQ ID NO:377) | 21 | 2234 |
| Probe | TET-5'-tcagccgcaattttcctattatcgga-3'-TAMRA | (SEQ ID NO:378) | 26 | 2202 |
| Reverse | 5'-gtgaagttgctcgaatgtcttc-3' | (SEQ ID NO:379) | 22 | 2172 |

TABLE VB

Panel 1.3D

| Tissue Name | Rel. Exp. (%) Ag2073, Run 165627447 | Tissue Name | Rel. Exp. (%) Ag2073, Run 165627447 |
|---|---|---|---|
| Liver adenocarcinoma | 0.0 | Kidney (fetal) | 0.1 |
| Pancreas | 0.1 | Renal ca. 786-0 | 0.1 |
| Pancreatic ca. CAPAN 2 | 0.0 | Renal ca. A498 | 0.1 |
| Adrenal gland | 0.1 | Renal ca. RXF 393 | 0.0 |
| Thyroid | 0.5 | Renal ca. ACHN | 0.0 |
| Salivary gland | 0.3 | Renal ca. UO-31 | 0.0 |
| Pituitary gland | 0.3 | Renal ca. TK-10 | 0.1 |
| Brain (fetal) | 0.0 | Liver | 0.3 |
| Brain (whole) | 0.7 | Liver (fetal) | 0.3 |
| Brain (amygdala) | 0.4 | Liver ca. (hepatoblast) HepG2 | 0.0 |
| Brain (cerebellum) | 0.5 | Lung | 0.4 |
| Brain (hippocampus) | 0.8 | Lung (fetal) | 0.4 |
| Brain (substantia nigra) | 0.3 | Lung ca. (small cell) LX-1 | 0.2 |
| Brain (thalamus) | 0.5 | Lung ca. (small cell) NCI-H69 | 0.0 |
| Cerebral Cortex | 0.2 | Lung ca. (s. cell var.) SHP-77 | 0.0 |
| Spinal cord | 0.6 | Lung ca. (large cell) NCI-H460 | 0.0 |
| glio/astro U87-MG | 0.0 | Lung ca. (non-sm. cell) A549 | 0.0 |
| glio/astro U-118-MG | 0.2 | Lung ca. (non-s. cell) NCI-H23 | 0.1 |
| astrocytoma SW1783 | 0.0 | Lung ca. (non-s. cell) HOP-62 | 0.0 |
| neuro*; met SK-N-AS | 0.0 | Lung ca. (non-s. cl) NCI-H522 | 0.0 |
| astrocytoma SF-539 | 0.0 | Lung ca. (squam.) SW 900 | 0.0 |
| astrocytoma SNB-75 | 0.0 | Lung ca. (squam.) NCI-H596 | 0.0 |
| glioma SNB-19 | 0.1 | Mammary gland | 0.3 |
| glioma U251 | 0.4 | Breast ca.* (pl. ef) MCF-7 | 0.0 |
| glioma SF-295 | 0.0 | Breast ca.* (pl. ef) MDA-MB-231 | 0.1 |
| Heart (fetal) | 0.1 | Breast ca.* (pl. ef) T47D | 0.0 |
| Heart | 0.3 | Breast ca. BT-549 | 0.1 |
| Skeletal muscle (fetal) | 7.7 | Breast ca. MDA-N | 0.0 |
| Skeletal muscle | 100.0 | Ovary | 0.0 |
| Bone marrow | 2.0 | Ovarian ca. OVCAR-3 | 0.1 |
| Thymus | 0.2 | Ovarian ca. OVCAR-4 | 0.0 |
| Spleen | 0.4 | Ovarian ca. OVCAR-5 | 0.1 |
| Lymph node | 1.0 | Ovarian ca. OVCAR-8 | 0.0 |
| Colorectal | 0.2 | Ovarian ca. IGROV-1 | 0.0 |
| Stomach | 0.4 | Ovarian ca.* (ascites) SK-OV-3 | 0.2 |
| Small intestine | 0.9 | Uterus | 0.6 |
| Colon ca. SW480 | 0.0 | Placenta | 0.1 |
| Colon ca.* SW620 (SW480 met) | 0.0 | Prostate | 0.3 |
| Colon ca. HT29 | 0.0 | Prostate ca.* (bone met)PC-3 | 0.1 |
| Colon ca. HCT-116 | 0.0 | Testis | 0.8 |
| Colon ca. CaCo-2 | 0.0 | Melanoma Hs688 (A).T | 0.0 |
| Colon ca. tissue (ODO3866) | 0.0 | Melanoma* (met) Hs688 (B).T | 0.0 |
| Colon ca. HCC-2998 | 0.0 | Melanoma UACC-62 | 0.1 |
| Gastric ca.* (liver met) NCI-N87 | 0.8 | Melanoma M14 | 0.1 |
| Bladder | 0.1 | Melanoma LOX IMVI | 0.0 |
| Trachea | 0.3 | Melanoma* (met) SK-MEL-5 | 0.0 |
| Kidney | 0.5 | Adipose | 0.5 |

TABLE VC

Panel 5D

| Tissue Name | Rel. Exp. (%) Ag2073, Run 169269384 | Tissue Name | Rel. Exp. (%) Ag2073, Run 169269384 |
|---|---|---|---|
| 97457_Patient-02go_adipose | 0.7 | 94709_Donor 2 AM - A_adipose | 0.2 |
| 97476_Patient-07sk_skeletal muscle | 7.9 | 94710_Donor 2 AM - B_adipose | 0.1 |
| 97477_Patient-07ut_uterus | 0.0 | 94711_Donor 2 AM - C_adipose | 0.0 |
| 97478_Patient-07pl_placenta | 0.2 | 94712_Donor 2 AD - A_adipose | 0.0 |
| 97481_Patient-08sk_skeletal muscle | 8.7 | 94713_Donor 2 AD - B_adipose | 0.7 |
| 97482_Patient-08ut_uterus | 0.1 | 94714_Donor 2 AD - C_adipose | 0.3 |
| 97483_Patient-08pl_placenta | 0.1 | 94742_Donor 3 U - A_Mesenchymal Stem Cells | 0.0 |
| 97486_Patient-09sk_skeletal muscle | 14.1 | 94743_Donor 3 U - B_Mesenchymal Stem Cells | 0.0 |
| 97487_Patient-09ut_uterus | 0.1 | 94730_Donor 3 AM - A_adipose | 0.1 |
| 97488_Patient-09pl_placenta | 0.1 | 94731_Donor 3 AM - B_adipose | 0.2 |
| 97492_Patient-10ut_uterus | 0.3 | 94732_Donor 3 AM - C_adipose | 0.2 |
| 97493_Patient-10pl_placenta | 0.1 | 94733_Donor 3 AD - A_adipose | 0.2 |
| 97495_Patient-11go_adipose | 0.2 | 94734_Donor 3 AD - B_adipose | 0.0 |
| 97496_Patient-11sk_skeletal muscle | 82.9 | 94735_Donor 3 AD - C_adipose | 0.2 |
| 97497_Patient-11ut_uterus | 0.1 | 77138_Liver_HepG2untreated | 0.0 |
| 97498_Patient-11pl_placenta | 0.3 | 73556_Heart_Cardiac stromal cells (primary) | 0.2 |
| 97500_Patient-12go_adipose | 0.5 | 81735_Small Intestine | 0.4 |
| 97501_Patient-12sk_skeletal muscle | 100.0 | 72409_Kidney_Proximal Convoluted Tubule | 0.2 |
| 97502_Patient-12ut_uterus | 0.3 | 82685_Small intestine_Duodenum | 0.4 |
| 97503_Patient-12pl_placenta | 0.1 | 90650_Adrenal_Adrenocortical adenoma | 0.1 |
| 94721_Donor 2 U - A_Mesenchymal Stem Cells | 0.2 | 72410_Kidney_HRCE | 0.3 |
| 94722_Donor 2 U - B_Mesenchymal Stem Cells | 0.0 | 72411_Kidney_HRE | 0.1 |
| 94723_Donor 2 U - C_Mesenchymal Stem Cells | 0.4 | 73139_Uterus_Uterine smooth muscle cells | 0.1 |

Panel 1.3D Summary: Ag2073 The CG57909-01 gene, a calpain homolog, has low levels of expression in thyroid, pituitary, heart, adipose and liver. Calpain 10 was recently identified as a susceptibility gene for type 2 diabetes. Thus, this gene product may be a small molecule target for the treatment of endocrine and metabolic disease, including the thyroidopathies, Types 1 and 2 diabetes and obesity. In addition, this gene is highly expressed in skeletal muscle. Mutations in the calpain 3 gene have been proven to be responsible for limb-girdle muscular dystrophy (LGMD) type 2A. Thus, therapeutic modulation of this gene product may be a treatment for LGMD type 2A (Chae et al., Neuromuscul Disord. 2001 September;11(6–7):547–55; Huang and Wang, Trends Mol Med. 2001 August;7(8): 355–62).

Panel 4D Summary: Ag2073 Results from one experiment with the CG56003-01 gene are not included. The amp plot indicates that there were experimental difficulties with this run.

Panel 5D Summary: Ag2073 Expression of the CG57509-01 gene is restricted to skeletal muscle, confirming the results from Panel 1.3D. Please see Panel 1.3D for discussion of utility of this gene in metabolic disease.

W. NOV27: Kerratin 18

Expression of gene CG57484-01 was assessed using the primer-probe set Ag1597, described in Table WA. Results of the RTQ-PCR runs are shown in Table WB.

TABLE WA

Probe Name Ag1597

| Primers | Sequences | | Length | Start Position |
|---|---|---|---|---|
| Forward | 5'-gactgaggagagcaccacagt-3' | (SEQ ID NO:380) | 21 | 810 |
| Probe | TET-5'-acactctgccaaggtcagagctgct-3'-TAMRA | (SEQ ID NO:381) | 25 | 840 |
| Reverse | 5'-gtctcagctccgttgtcatct-3' | (SEQ ID NO:382) | 21 | 866 |

TABLE WB

Panel 2D

| Tissue Name | Rel. Exp. (%) Ag1597, Run 164988404 | Tissue Name | Rel. Exp. (%) Ag1597, Run 164988404 |
|---|---|---|---|
| Normal Colon | 2.3 | Kidney Margin 8120608 | 0.0 |
| CC Well to Mod Diff (ODO3866) | 0.0 | Kidney Cancer 8120613 | 0.0 |
| CC Margin (ODO3866) | 0.0 | Kidney Margin 8120614 | 0.0 |
| CC Gr.2 rectosigmoid (ODO3868) | 0.0 | Kidney Cancer 9010320 | 0.0 |
| CC Margin (ODO3868) | 0.0 | Kidney Margin 9010321 | 0.0 |
| CC Mod Diff (ODO3920) | 0.0 | Normal Uterus | 0.0 |
| CC Margin (ODO3920) | 0.0 | Uterus Cancer 064011 | 9.3 |
| CC Gr.2 ascend colon (ODO3921) | 0.0 | Normal Thyroid | 0.0 |
| CC Margin (ODO3921) | 0.0 | Thyroid Cancer 064010 | 2.5 |
| CC from Partial Hepatectomy (ODO4309) Mets | 0.0 | Thyroid Cancer A302152 | 0.0 |
| Liver Margin (ODO4309) | 0.0 | Thyroid Margin A302153 | 0.0 |
| Colon mets to lung (OD04451-01) | 0.0 | Normal Breast | 2.4 |
| Lung Margin (OD04451-02) | 1.4 | Breast Cancer (OD04566) | 3.5 |
| Normal Prostate 6546-1 | 10.0 | Breast Cancer (OD04590-01) | 0.0 |
| Prostate Cancer (OD04410) | 7.7 | Breast Cancer Mets (OD04590-03) | 30.4 |
| Prostate Margin (OD04410) | 2.6 | Breast Cancer Metastasis (OD04655-05) | 74.7 |
| Prostate Cancer (OD04720-01) | 22.4 | Breast Cancer 064006 | 14.0 |
| Prostate Margin (OD04720-02) | 10.8 | Breast Cancer 1024 | 39.2 |
| Normal Lung 061010 | 9.3 | Breast Cancer 9100266 | 0.0 |
| Lung Met to Muscle (ODO4286) | 7.7 | Breast Margin 9100265 | 3.1 |
| Muscle Margin (ODO4286) | 0.0 | Breast Cancer A209073 | 23.2 |
| Lung Malignant Cancer (OD03126) | 21.0 | Breast Margin A209073 | 30.1 |
| Lung Margin (OD03126) | 6.1 | Normal Liver | 16.7 |
| Lung Cancer (OD04404) | 2.9 | Liver Cancer 064003 | 0.0 |
| Lung Margin (OD04404) | 0.0 | Liver Cancer 1025 | 27.0 |
| Lung Cancer (OD04565) | 0.0 | Liver Cancer 1026 | 0.0 |
| Lung Margin (OD04565) | 0.0 | Liver Cancer 6004-T | 0.0 |
| Lung Cancer (OD04237-01) | 100.0 | Liver Tissue 6004-N | 0.0 |
| Lung Margin (OD04237-02) | 10.9 | Liver Cancer 6005-T | 0.0 |
| Ocular Mel Met to Liver (ODO4310) | 2.9 | Liver Tissue 6005-N | 0.0 |
| Liver Margin (ODO4310) | 0.0 | Normal Bladder | 0.0 |
| Melanoma Mets to Lung (OD04321) | 2.0 | Bladder Cancer 1023 | 0.0 |
| Lung Margin (OD04321) | 0.0 | Bladder Cancer A302173 | 0.0 |
| Normal Kidney | 55.1 | Bladder Cancer (OD04718-01) | 0.0 |
| Kidney Ca, Nuclear grade 2 (OD04338) | 14.3 | Bladder Normal Adjacent (OD04718-03) | 0.0 |
| Kidney Margin (OD04338) | 0.0 | Normal Ovary | 0.0 |
| Kidney Ca Nuclear grade 1/2 (OD04339) | 0.0 | Ovarian Cancer 064008 | 0.0 |
| Kidney Margin (OD04339) | 0.0 | Ovarian Cancer (OD04768-07) | 0.0 |
| Kidney Ca, Clear cell type (OD04340) | 0.0 | Ovary Margin (OD04768-08) | 0.0 |
| Kidney Margin (OD04340) | 0.0 | Normal Stomach | 13.4 |
| Kidney Ca, Nuclear grade 3 (OD04348) | 0.0 | Gastric Cancer 9060358 | 0.0 |
| Kidney Margin (OD04348) | 36.9 | Stomach Margin 9060359 | 0.0 |
| Kidney Cancer (OD04622-01) | 0.0 | Gastric Cancer 9060395 | 0.0 |
| Kidney Margin (OD04622-03) | 4.7 | Stomach Margin 9060394 | 3.0 |
| Kidney Cancer (OD04450-01) | 0.0 | Gastric Cancer 9060397 | 0.0 |
| Kidney Margin (OD04450-03) | 0.0 | Stomach Margin 9060396 | 0.0 |
| Kidney Cancer 8120607 | 0.0 | Gastric Cancer 064005 | 0.0 |

Panel 2D Summary: Ag1597 Expression of the CG57484-01 gene is limited to samples derived from breast cancer and lung cancer (CTs=33). Thus, expression of this gene could be used to differentiate between these samples and other samples on this panel and as a marker to detect the presence of breast and lung cancers. This gene encodes a protein that is homologous to keratin 18. Expression of keratin 18 has been shown in both lung and breast cancers. Therefore, therapeutic modulation of the expression or function of this gene may be effective in the treatment of breast and lung cancers (Chu et al., Selection of invasive and metastatic subpopulations from a human lung adenocarcinoma cell line. Am J Respir Cell Mol Biol 1997 September;17(3): 353–60).

X. NOV29: Cholinephosphate Cytidylyltransferase

Expression of gene CG57589-01 was assessed using the primer-probe set Ag4146, described in Table XA. Results of the RTQ-PCR runs are shown in Tables XB and XC.

TABLE XA

Probe Name Ag4146

| Primers | Sequences | | Length | Start Position |
|---|---|---|---|---|
| Forward | 5'-catcttccgtcagattgacagt-3' | (SEQ ID NO:383) | 22 | 975 |
| Probe | TET-5'-agcaacctcaccacagacctcatcgt-3'-TAMRA | (SEQ ID NO:384) | 26 | 1000 |
| Reverse | 5'-atactccaacctgttggtgatg-3' | (SEQ ID NO:385) | 22 | 1035 |

TABLE XB

General_screening_panel_v1.4

| Tissue Name | Rel. Exp. (%) Ag4146, Run 221290908 | Tissue Name | Rel. Exp. (%) Ag4146, Run 221290908 |
|---|---|---|---|
| Adipose | 0.8 | Renal ca. TK-10 | 19.3 |
| Melanoma* Hs688 (A).T | 4.7 | Bladder | 4.2 |
| Melanoma* Hs688 (B).T | 4.8 | Gastric ca. (liver met.) NCI-N87 | 22.7 |
| Melanoma* M14 | 11.1 | Gastric ca. KATO III | 49.3 |
| Melanoma* LOXIMVI | 5.0 | Colon ca. SW-948 | 16.2 |
| Melanoma* SK-MEL-5 | 21.5 | Colon ca. SW480 | 24.1 |
| Squamous cell carcinoma SCC-4 | 4.7 | Colon ca.* (SW480 met) SW620 | 12.2 |
| Testis Pool | 27.9 | Colon ca. HT29 | 13.8 |
| Prostate ca.* (bone met) PC-3 | 3.3 | Colon ca. HCT-116 | 25.0 |
| Prostate Pool | 2.3 | Colon ca. CaCo-2 | 26.2 |
| Placenta | 2.7 | Colon cancer tissue | 2.2 |
| Uterus Pool | 0.4 | Colon ca. SW1116 | 4.9 |
| Ovarian ca. OVCAR-3 | 15.4 | Colon ca. Colo-205 | 12.0 |
| Ovarian ca. SK-OV-3 | 11.4 | Colon ca. SW-48 | 6.5 |
| Ovarian ca. OVCAR-4 | 12.4 | Colon Pool | 1.8 |
| Ovarian ca. OVCAR-5 | 32.3 | Small Intestine Pool | 0.9 |
| Ovarian ca. IGROV-1 | 11.0 | Stomach Pool | 1.0 |
| Ovarian ca. OVCAR-8 | 5.1 | Bone Marrow Pool | 0.6 |
| Ovary | 2.3 | Fetal Heart | 2.9 |
| Breast ca. MCF-7 | 14.0 | Heart Pool | 1.7 |
| Breast ca. MDA-MB-231 | 21.9 | Lymph Node Pool | 2.1 |
| Breast ca. BT 549 | 11.5 | Fetal Skeletal Muscle | 0.8 |
| Breast ca. T47D | 100.0 | Skeletal Muscle Pool | 3.7 |
| Breast ca. MDA-N | 10.9 | Spleen Pool | 0.8 |
| Breast Pool | 1.6 | Thymus Pool | 1.6 |
| Trachea | 4.1 | CNS cancer (glio/astro) U87-MG | 26.8 |
| Lung | 0.4 | CNS cancer (glio/astro) U-118-MG | 15.0 |
| Fetal Lung | 3.9 | CNS cancer (neuro; met) SK-N-AS | 12.5 |
| Lung ca. NCI-N417 | 2.6 | CNS cancer (astro) SF-539 | 22.4 |
| Lung ca. LX-1 | 13.7 | CNS cancer (astro) SNB-75 | 17.6 |
| Lung ca. NCI-H146 | 1.8 | CNS cancer (glio) SNB-19 | 12.2 |
| Lung ca. SHP-77 | 7.4 | CNS cancer (glio) SF-295 | 10.9 |
| Lung ca. A549 | 5.4 | Brain (Amygdala) Pool | 6.1 |
| Lung ca. NCI-H526 | 5.5 | Brain (cerebellum) | 12.6 |
| Lung ca. NCI-H23 | 2.2 | Brain (fetal) | 7.1 |
| Lung ca. NCI-H460 | 1.2 | Brain (Hippocampus) Pool | 6.2 |
| Lung ca. HOP-62 | 5.8 | Cerebral Cortex Pool | 6.8 |
| Lung ca. NCI-H522 | 6.3 | Brain (Substantia nigra) Pool | 10.1 |
| Liver | 7.3 | Brain (Thalamus) Pool | 10.4 |
| Fetal Liver | 14.2 | Brain (whole) | 8.9 |
| Liver ca. HepG2 | 29.5 | Spinal Cord Pool | 5.3 |
| Kidney Pool | 2.8 | Adrenal Gland | 3.1 |
| Fetal Kidney | 3.3 | Pituitary gland Pool | 0.7 |
| Renal ca. 786-0 | 11.3 | Salivary Gland | 1.8 |
| Renal ca. A498 | 4.9 | Thyroid (female) | 2.0 |

TABLE XB-continued

General_screening_panel_v1.4

| Tissue Name | Rel. Exp. (%) Ag4146, Run 221290908 | Tissue Name | Rel. Exp. (%) Ag4146, Run 221290908 |
|---|---|---|---|
| Renal ca. ACHN | 9.9 | Pancreatic ca. CAPAN2 | 12.5 |
| Renal ca. UO-31 | 4.2 | Pancreas Pool | 2.8 |

TABLE XC

Panel 5 Islet

| Tissue Name | Rel. Exp. (%) Ag4146, Run 242413200 |
|---|---|
| 97457_Patient-02go_adipose | 4.0 |
| 97476_Patient-07sk_skeletal muscle | 1.2 |
| 97477_Patient-07ut_uterus | 5.4 |
| 97478_Patient-07pl_placenta | 6.0 |
| 99167_Bayer Patient 1 | 10.9 |
| 97482_Patient-08ut_uterus | 4.0 |
| 97483_Patient-08pl_placenta | 1.3 |
| 97486_Patient-09sk_skeletal muscle | 0.7 |
| 97487_Patient-09ut_uterus | 1.1 |
| 97488_Patient-09pl_placenta | 2.4 |
| 97492_Patient-10ut_uterus | 4.4 |
| 97493_Patient-10pl_placenta | 8.0 |
| 97495_Patient-11go_adipose | 1.8 |
| 97496_Patient-11sk_skeletal muscle | 3.7 |
| 97497_Patient-11ut uterus | 5.3 |
| 97498_Patient-11pl_placenta | 3.7 |
| 97500_Patient-12go_adipose | 9.3 |
| 97501_Patient-12sk_skeletal muscle | 11.7 |
| 97502 Patient-12ut_uterus | 7.0 |
| 97503_Patient-12pl_placenta | 6.5 |
| 94721_Donor 2 U-A_Mesenchymal Stem Cells | 5.8 |
| 94722_Donor 2 U-B_Mesenchymal Stem Cells | 7.5 |
| 94723_Donor 2 U-C_Mesenchymal Stem Cells | 14.1 |
| 94709_Donor 2 AM - A_adipose | 18.0 |
| 94710_Donor 2 AM - B_adipose | 8.0 |
| 94711_Donor 2 AM - C_adipose | 4.7 |
| 94712_Donor 2 AD - A_adipose | 13.6 |
| 94713_Donor 2 AD - B_adipose | 15.3 |
| 94714_Donor 2 AD - C_adipose | 14.4 |
| 94742_Donor 3 U - A_Mesenchymal Stem Cells | 8.2 |
| 94743_Donor 3 U - B_Mesenchymal Stem Cells | 6.0 |
| 94730_Donor 3 AM - A_adipose | 8.9 |
| 94731_Donor 3 AM - B_adipose | 8.6 |
| 94732_Donor 3 AM - C_adipose | 5.9 |
| 94733_Donor 3 AD - A_adipose | 17.6 |
| 94734_Donor 3 AD - B_adipose | 4.8 |
| 94735_Donor 3 AD - C_adipose | 8.8 |
| 77138_Liver_HepG2untreated | 100.0 |
| 73556_Heart_Cardiac stromal cells (primary) | 3.7 |
| 81735_Small Intestine | 13.1 |
| 72409_Kidney_Proximal Convoluted Tubule | 4.1 |
| 82685_Small intestine_Duodenum | 3.9 |
| 90650_Adrenal_Adrenocortical adenoma | 2.6 |
| 72410_Kidney_HRCE | 37.1 |
| 72411_Kidney_HRE | 6.0 |
| 73139_Uterus_Uterine smooth muscle cells | 4.5 |

General_screening_panel_v1.4 Summary: Ag4146 The expression of the CG57589-01 gene appears to be highest in a sample derived from a breast cancer cell line (T47D)(CT=27.2). In addition, there appears to be substantial expression in other samples derived from breast cancer cell lines, ovarian cancer cell lines, brain cancer cell lines and colon cancer cell lines. Thus, the expression of this gene could be used to distinguish T47D cells from other samples in the panel. Moreover, therapeutic modulation of this gene, through the use of small molecule drugs, protein therapeutics or antibodies could be of benefit in the treatment of breast, ovarian, brain or colon cancer.

Among metabolic tissue, this gene has low levels of expression in adipose, heart, skeletal muscle, adrenal, pituitary, thyroid, and pancreas. Dysregulated levels of phosphatidylcholine may be involved in the pathogenesis of disease in these tissues. Therefore, this gene may be a small molecule target for the treatment of metabolic and endocrine disease, including Types 1 and 2 diabetes and obesity.

This gene, a cholinephosphate cytidylyltransferase homolog, is also expressed at moderate levels in all CNS regions examined. This protein has been shown to be upregulated in the brain during triethyltin-induced cerebral edema. Therefore this gene may be a drug target for the treatment of cerebral edema (Mages et al., Pharmacol Toxicol 1989 October;65(4):302–5).

Panel 5 Islet Summary: Ag4146 The CG57589-01 is expressed at a low level in the islets of Langerhans, with highest expression in a liver derived sample (CT=30.5). Thus, expression of this gene could be used to differentiate between this sample and other samples on this panel.

Y. NOV30: mac25/IGFBP-7

Expression of gene CG57558-01 was assessed using the primer-probe set Ag3285, described in Table YA.

TABLE YA

Probe Name Ag3285

| Primers | Sequences | | Length | Start Position |
|---|---|---|---|---|
| Forward | 5'-gacaacaaacaagcaaacacaa-3' | (SEQ ID NO:386) | 22 | 11 |
| Probe | TET-5'-accttccacttccttctggtcctgct-3'-TAMRA | (SEQ ID NO:387) | 26 | 62 |
| Reverse | 5'-gcaggagaggaggaagaagag-3' | (SEQ ID NO:388) | 21 | 89 |

CNS_neurodegeneration_v1.0 Summary: Ag3285 Expression of this gene is low/undetectable (CTs>35) across all of the samples on this panel.

Panel 1.3D Summary: Ag3285 Expression of this gene is low/undetectable (CTs>35) across all of the samples on this panel.

Panel 4D Summary: Ag3285 Expression of this gene is low/undetectable (CTs>35) across all of the samples on this panel.

OTHER EMBODIMENTS

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. The choice of nucleic acid starting material, clone of interest, or library type is believed to be a matter of routine for a person of ordinary skill in the art with knowledge of the embodiments described herein. Other aspects, advantages, and modifications considered to be within the scope of the following claims.

What is claimed is:

1. An isolated nucleic acid molecule comprising a nucleic acid sequence encoding a polypeptide comprising an amino acid sequence, SEQ ID NO: 26.

2. A nucleic acid molecule of claim 1, wherein said nucleic acid molecule comprises SEQ ID NO: 25.

3. A vector comprising the nucleic acid molecule of claim 1.

4. The vector of claim 3, further comprising a promotor operably-linked to said nucleic acid molecule.

5. A cell comprising the vector of claim 3.

6. An isolated nucleic acid molecule comprising the complement of the nucleic acid molecule of claim 1.

* * * * *